US012642270B2

(12) United States Patent
Dufour et al.
(10) Patent No.: US 12,642,270 B2
(45) Date of Patent: Jun. 2, 2026

(54) SUBSTITUTED THIOPHENE CARBOXAMIDES, THIOPHENE CARBOXYLIC ACIDS AND DERIVATIVES THEREOF

(71) Applicant: Bayer Aktiengesellschaft, Leverkusen (DE)

(72) Inventors: Jeremy Dufour, Lyons (FR); Lionel Nicolas, Lyons (FR); Tomoki Tsuchiya, Lyons (FR); Thomas Knobloch, Charnay (FR); Stephane Brunet, St. Andre de Corcy (FR); Sybille Lamprecht, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 885 days.

(21) Appl. No.: 17/786,151

(22) PCT Filed: Dec. 17, 2020

(86) PCT No.: PCT/EP2020/086870
§ 371 (c)(1),
(2) Date: Jun. 16, 2022

(87) PCT Pub. No.: WO2021/123051
PCT Pub. Date: Jun. 24, 2021

(65) Prior Publication Data

US 2023/0046892 A1 Feb. 16, 2023

(30) Foreign Application Priority Data

Dec. 20, 2019 (EP) .................................... 19218698

(51) Int. Cl.

| | |
|---|---|
| ***A01N 43/10*** | (2006.01) |
| ***A01N 43/38*** | (2006.01) |
| ***A01N 43/40*** | (2006.01) |
| ***A01N 43/46*** | (2006.01) |
| ***A01N 43/50*** | (2006.01) |
| ***C07D 333/40*** | (2006.01) |
| ***C07D 409/12*** | (2006.01) |

(52) U.S. Cl.
CPC ............. *A01N 43/10* (2013.01); *A01N 43/38* (2013.01); *A01N 43/40* (2013.01); *A01N 43/46* (2013.01); *A01N 43/50* (2013.01); *C07D 333/40* (2013.01); *C07D 409/12* (2013.01); *C07B 2200/07* (2013.01)

(58) Field of Classification Search
CPC .............................. A01N 43/10; C07D 333/40
See application file for complete search history.

(56) References Cited

U.S. PATENT DOCUMENTS

| | | | |
|---|---|---|---|
| 5,534,541 | A | 7/1996 | Drauz |
| 5,789,437 | A | 8/1998 | Elbe et al. |
| 2003/0134748 | A1 | 7/2003 | Hegde et al. |

FOREIGN PATENT DOCUMENTS

| | | | |
|---|---|---|---|
| CN | 108997305 | A | 12/2018 |
| DE | 4412331 | A1 | 10/1995 |
| DE | 4412333 | A1 | 10/1995 |
| EP | 0450355 | A1 | 10/1991 |
| FR | 3052451 | A1 | 12/2017 |
| JP | 2009078991 | A | 4/2009 |
| WO | 2004024692 | A1 | 3/2004 |
| WO | 2020007902 | A1 | 1/2020 |
| WO | 2020007904 | A1 | 1/2020 |
| WO | 2020007905 | A1 | 1/2020 |
| WO | 2020079205 | A1 | 4/2020 |

OTHER PUBLICATIONS

STN/CAPLUS Registry # 774589-17-2 ED: Nov. 4, 2004.*
STN/CAPLUS Registry # 2390033-72-2 ED: Dec. 12, 2019.*
STN/CAPLUS Registry # 1332623-35-4 ED: Sep. 16, 2011.*
STN/CAPLUS Registry # 2393420-08-9 ED: Dec. 18, 2019.*
Cudworth, D.P. et al (Sep. 1, 2007). "Structure-Activity Relationship Development of Dihaloaryl Triazole Compounds as Insecticides and Acaricides. 1. Phenyl Thiophen-2-yl Triazoles", Journal of Agricultural and Food Chemistry, 55(18): 7517-7526, XP055691403.
Hull, J.W. et al. (Sep. 4, 2007). "Development of potential manufacturing routes for substituted thiophenes—Preparation of halogenated 2-thiophenecarboxylic acid derivatives as building blocks for a new family of 2,6-dihaloaryl 1,2,4-triazoleinsecticides", Beilstein Journal of Organic Chemistry, 3(23): 1-6; XP021041099.
International Search Report mailed Mar. 31, 2021 for PCT Application No. PCT/EP2020/086870, filed Dec. 17, 2020, 7 pages.

(Continued)

*Primary Examiner* — Valerie Rodriguez-Garcia
(74) *Attorney, Agent, or Firm* — Harness, Dickey & Pierce, P.L.C.

(57) ABSTRACT

The present disclosure relates to substituted thiophene carboxamides derivatives of formula (I) and (II), their use for controlling phytopathogenic microorganisms and compositions comprising thereof.

(I)

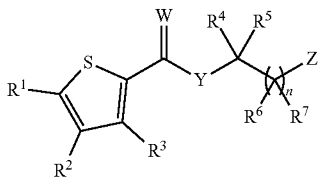

(II)

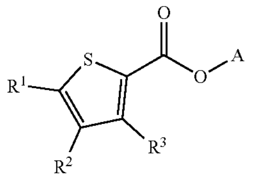

15 Claims, No Drawings

(56) References Cited

OTHER PUBLICATIONS

Kochanny et al. (Jan. 31, 2007). “Substituted thiophene-anthranilamides as potent inhibitors of human factor Xa”, Bioorganic & Medicinal Chemistry, 15(5): 2127-2146.
Steinkopf, W. et al (1937). “Thiophene series. XXXVII. lodine derivatives of 3-thiotolene”, Justus Liebigs Annalen Der Chemie, Verlag Chemie Gmbh, DE, 532: 236-249.

* cited by examiner

SUBSTITUTED THIOPHENE CARBOXAMIDES, THIOPHENE CARBOXYLIC ACIDS AND DERIVATIVES THEREOF

CROSS REFERENCE TO RELATED APPLICATIONS

This application is a national stage application under 35 U.S.C. § 371 of International Application No. PCT/EP2020/086870, filed internationally on Dec. 17, 2020, which claims the benefit of priority to European Application No. 19218698.9, filed Dec. 20, 2019.

TECHNICAL FIELD

The present invention relates to substituted thiophene carboxamide derivatives, their use for controlling phytopathogenic microorganisms and compositions comprising thereof.

BACKGROUND

Though numerous microbicidal agents have been developed until now, the need remains for the development of new microbicidal compounds in order to address the ever increasing environmental and economic requirements imposed on modern-day crop protection agents and compositions. This includes, for example, improvement to the spectrum of action, safety profile, selectivity, application rate, formation of residues, and favourable preparation ability. It may also be desired to have new compounds to prevent the emergence of resistance.

The present invention provides new compounds which have advantages over known compounds and compositions in at least some of these aspects.

EP 450355 and JP 2009078991 disclose thiophenecarboxamide derivatives that are useful for protecting plants from attacks by plant-damaging microorganisms.

WO 2004/024692 discloses heterocyclic carboxylic acid derivatives and their use as fungicides and bactericides for protection of plants or materials such as wood.

SUMMARY

The present invention relates compounds of the formula (I) and formula (II) as recited herein as well as their isomers, polymorphs, salts, N-oxides and solvates.

The present invention relates to a composition comprising at least one compound of formula (I) or (II) or as defined herein and at least one agriculturally suitable carrier.

The present invention relates to processes for preparing compounds of formula (I) or (II) as described herein and intermediates thereof.

The present invention relates to a method for controlling phytopathogenic microorganisms which comprises the step of applying at least one compound of formula (I) or (II) as defined herein or a composition as defined herein to the plants, plant parts, seeds, fruits or to the soil in which the plants grow.

Definitions

The term "alkyl" as used herein in the context of alkyl or alkylsulfonyl, alkylsulfinyl, alkylthio, alkylamino, for example, is to be understood as preferably meaning branched and unbranched alkyl, meaning e.g. methyl, ethyl, n-propyl, iso-propyl, n-butyl, iso-butyl, tert-butyl, sec-butyl, pentyl, isopentyl, hexyl, heptyl, octyl, nonyl and decyl and the isomers thereof.

The term "alkenyl" as used herein is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group.

The term "alkynyl" as used herein is to be understood as preferably meaning branched and unbranched alkynyl, e.g. an ethynyl, prop-1-yn-1-yl, but-1-yn-1-yl, but-2-yn-1-yl, or but-3-yn-1-yl group.

The term "halogen" or "Hal" as used herein is to be understood as meaning fluorine, chlorine, bromine or iodine.

The term "halo" or "halogeno" (e.g. haloalkyl, "$C_1$-$C_6$-haloalkyl" or "$C_1$-$C_8$-halogenoalkyl") designates the optional presence of one or more halogen substituents that may the same or different.

The term "haloalkyl" as used herein is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "haloalkenyl" as used herein is to be understood as preferably meaning branched and unbranched alkenyl, as defined supra, in which one or more of the hydrogen substituents is replaced in the same way or differently with halogen.

The term "haloalkynyl" as used herein is to be understood as preferably meaning branched and unbranched alkynyl, as defined supra, in which one or more of the hydrogen substituents is replaced in the same way or differently with halogen.

The term "alkoxy" as used herein refers to a group of formula (alkyl)-O—, in which the term "alkyl" is as defined herein. Examples of $C_1$-$C_6$-alkoxy include but are not limited to methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, n-hexyloxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

The term "halogenalkoxy" as used herein refers to a alkoxy group as defined above in which one or more hydrogen atoms are replaced with one or more halogen atoms that may be the same or different. Examples of $C_1$-$C_8$-halogenoalkoxy include but are not limited to chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy.

The term "alkylsulfanyl" as used herein refers to a saturated, linear or branched group of formula (alkyl)-S—, in which the term "alkyl" is as defined herein. Examples of $C_1$-$C_8$-alkylsulfanyl include but are not limited to methyl-sulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "halogenoalkylsulfanyl" as used herein refers to a alkylsulfanyl as defined above in which one or more hydrogen atoms are replaced with one or more halogen atoms that may be the same or different.

The term "alkylsulfinyl" as used herein refers to a saturated, linear or branched group of formula (alkyl)-S(═O)—, in which the term "alkyl" is as defined herein. Examples of $C_1$-$C_8$-alkylsulfinyl include but are not limited to saturated, straight-chain or branched alkylsulfinyl radicals having 1 to 8, preferably 1 to 6 and more preferably 1 to 4 carbon atoms, for example (but not limited to) methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

The term "halogenoalkylsulfinyl" as used herein refers to a alkylsulfinyl as defined above in which one or more hydrogen atoms are replaced with one or more halogen atoms that may be the same or different.

The term "alkylsulfonyl" s used herein refers to a saturated, linear or branched group of formula (alkyl)-S(═O)$_2$—, in which the term "alkyl" is as defined herein. Examples of $C_1$-$C_8$-alkylsulfonyl include but are not limited to methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

The term "halogenoalkylsulfonyl" as used herein refers to a $C_1$-$C_8$-alkylsulfonyl as defined above in which one or more hydrogen atoms are replaced with one or more halogen atoms that may be the same or different.

The term "alkylcarbonyl" as used herein refers to a saturated, linear or branched group of formula (alkyl)-C(═O)—, in which the term "alkyl" is as defined herein.

The term "halogenoalkylcarbonyl" as used herein refers to a alkylcarbonyl as defined above in which one or more hydrogen atoms are replaced with one or more halogen atoms that may be the same or different.

The term "alkoxycarbonyl" as used herein refers to a saturated, linear or branched group of formula (alkoxy)-C(═O)—, in which the term "alkoxy" is as defined herein.

The term "haloalkoxycarbonyl" as used herein refers to an alkoxycarbonyl as defined above in which one or more hydrogen atoms are replaced with one or more halogen atoms that may be the same or different.

The term "cycloalkyl" as used herein refers to a non-aromatic monocyclic carbon containing ring, having 3 to 8 carbon atoms. Examples of saturated cycloalkyl include but are not limited to cyclopropyl, cyclobutyl, cyclopentyl, cyclohexyl, cycloheptyl, cyclooctyl, cyclononyl and cyclodecyl group.

The term "heterocyclyl" as used herein refers to four-, five- or six-membered, saturated or partially unsaturated heterocycles containing one to four heteroatoms independently selected from the group of oxygen, nitrogen and sulfur. If the ring contains more than one oxygen atom, they are not directly adjacent.

The term "aryl" as used herein refers to an aromatic, hydrocarbon, ring system, comprising from 6 to 15 carbon atoms, or from 6 to 12 carbon atoms, preferably from 6 to 10 carbon atoms. The ring system may be monocyclic or fused polycyclic (e.g. bicyclic or tricyclic) aromatic ring system. Examples of aryl include but are not limited to phenyl, azulenyl, naphthyl and fluorenyl. It is further understood that when said aryl group is substituted with one or more substituents, said substituent(s) may be at any positions on said aryl ring(s). Particularly, in the case of aryl being a phenyl group, said substituent(s) may occupy one or both ortho positions, one or both meta positions, or the para position, or any combination of these positions. This definition also applies to aryl as part of a composite substituent (e.g. aryloxy).

The term "aralkyl" as used herein refers to a $C_1$-$C_6$-alkyl substituted by an aryl as defined herein. Example of aralkyl includes the benzyl group (—$CH_2$—$C_6H_5$).

The term "aromatic 5- to 14-membered heterocycle" or "heteroaryl" as used herein refers to an aromatic ring system comprising 1 to 4 heteroatoms independently selected from the group consisting of oxygen, nitrogen and sulfur. Aromatic heterocycles include aromatic 5- or 6-membered monocyclic heterocycles and 6- to 14-membered polycyclic (e.g. bicyclic or tricyclic) aromatic heterocycles. The 5- to 14-membered aromatic heterocycle can be connected to the parent molecular moiety through any carbon atom or nitrogen atom contained within the heterocycle.

As used herein, the term "$C_1$-$C_6$", e.g. in the context of the definition of "$C_1$-$C_6$-alkyl", or "$C_1$-$C_6$-alkoxy", is to be understood as meaning a group having a finite number of carbon atoms of 1 to 6, i.e. 1, 2, 3, 4, 5, or 6 carbon atoms.

As used herein, the term "$C_1$-$C_8$", e.g. in the context of the definition of "$C_1$-$C_8$-alkyl", or "$C_1$-$C_8$-alkoxy", is to be understood as meaning a group having a finite number of carbon atoms of 1 to 8, i.e. 1, 2, 3, 4, 5, 6, 7 or 8 carbon atoms.

The term "oxo" as used herein refers to an oxygen atom which is bound to a carbon atom or sulfur atom via a double bound.

The term "leaving group" as used herein is to be understood as meaning a group which is displaced from a compound in a substitution or an elimination reaction, for example a halogen atom, a trifluoromethanesulfonate ("triflate") group, alkoxy, methanesulfonate, p-toluenesulfonate, etc.

DETAILED DESCRIPTION

The present invention relates to a compound of formula (I):

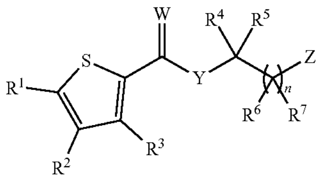

(I)

wherein $R^1$ and $R^2$ are selected independently from one another from the group consisting of halogen, cyano, $C_1$-$C_6$-alkyl or $C_1$-$C_6$-haloalkyl, wherein at least one of $R^1$ or $R^2$ is halogen;

$R^3$ is selected from the group consisting of hydrogen, halogen, cyano, $C_1$-$C_6$-alkyl or $C_1$-$C_6$-haloalkyl;

$R^4$ and $R^5$ are selected independently from one another from the group consisting of hydrogen, halogen, cyano, hydroxyl, $C_1$-$C_6$-alkyl, $C_1$-$C_6$-hydroxyalkyl, $C_1$-$C_6$-alkoxy, $C_1$-$C_6$-haloalkyl, —O—C(═O)—$C_1$-$C_6$-alkyl, $C_3$-$C_6$-carbocycle, 4-, 5- or 6-membered non-aromatic heterocyclyl, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, aryl, 5- to 9-membered heteroaryl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-4-, 5- or 6-membered non-aromatic heterocyclyl, —$C_1$-$C_6$-alkyl-aryl, —$C_1$-$C_6$-alkyl-hydroxyaryl, —$C_1$-$C_6$-alkyl-5- to 9-membered heteroaryl, —$C_1$-$C_6$-alkyl-S—$C_1$-$C_6$-alkyl, —$C_1$-$C_6$-alkyl-S—C(═O)—$C_1$-$C_6$-alkyl, —$C_1$-$C_6$-alkyl-O—(C═O)—$C_1$-$C_6$-alkyl, —$C_1$-$C_6$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—OH, —$C_1$-$C_6$-alkyl-C(═O)—O—$C_1$-$C_6$-alkyl, —$C_1$-$C_6$-alkyl-NH—C(═NH)—$NH_2$, —S—$C_1$-$C_6$-alkyl, —S—C(═O)—$C_1$-$C_6$-alkyl, —S—C(═O)—O—$C_1$-$C_6$-alkyl, —S—C(═S)—O—$C_1$-$C_6$-alkyl, —S—C(═O)—S—$C_1$-$C_6$-alkyl, —S—C(═O)—$NH_2$, —S—C(═O)—NH($C_1$-$C_6$-alkyl), —S—C(═O)—NH($C_1$-$C_6$-alkyl)$_2$, —S—C(═S)—$NH_2$, —S—C(═S)—NH($C_1$-$C_6$-alkyl), —S—C(═S)—NH($C_1$-$C_6$-alkyl)$_2$, —$C_1$-$C_6$-alkyl-S—C(═O)—O—$C_1$-$C_6$-alkyl, —$C_1$-$C_6$-alkyl-S—C(═O)—S—$C_1$-$C_6$-alkyl, —$C_1$-$C_6$-alkyl-S—C(═O)—$NH_2$, —$C_1$-$C_6$-alkyl-S—C(═O)—NH($C_1$-$C_6$-alkyl), —$C_1$-$C_6$-alkyl-S—C(═O)—NH($C_1$-$C_6$-alkyl)$_2$, —$C_1$-$C_6$-alkyl-S—C(═S)—$NH_2$, —$C_1$-$C_6$-alkyl-S—C(═S)—NH($C_1$-$C_6$-alkyl), —$C_1$-$C_6$-alkyl-S—C(═S)—NH($C_1$-$C_6$-alkyl)$_2$, wherein acyclic $R_4$, $R_5$ radicals may be substituted with one or more $R^w$ substituents, wherein cyclic $R_4$, $R_5$ radicals may be substituted with one or more $R^x$ substituents, wherein at least one of $R^4$ and $R^5$ is hydrogen, $C_1$-$C_6$-alkyl or $C_3$-$C_6$-carbocycle, or $R^4$ and $R^5$ form together with the carbon atom to which they are attached a $C_3$-$C_6$-carbocycle or a 3- to 6-membered heterocycle, wherein said $C_3$-$C_6$-carbocycle and 3- to 6-membered heterocycle may be substituted with one or more $R^x$ substituents, wherein $R^w$ is independently selected from the group consisting of nitro, hydroxyl, cyano, carboxyl, amino, sulfanyl, pentafluoro-$\lambda^6$-sulfanyl, formyl, carbamoyl, carbamate, $C_3$-$C_7$-cycloalkyl, $C_3$-$C_7$-halogenocycloalkyl having 1 to 5 halogen atoms, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl, wherein $R^x$ is independently selected from the group consisting of halogen, nitro, hydroxyl, cyano, carboxyl, amino, sulfanyl, pentafluoro-$\lambda^6$-sulfanyl, formyl, carbamoyl, carbamate, $C_1$-$C_8$-alkyl, $C_3$-$C_7$-cycloalkyl, $C_1$-$C_8$-halogenoalkyl having 1 to 5 halogen atoms, $C_3$-$C_7$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl;

$R^6$ and $R^7$ are independently selected from the group consisting of hydrogen, $C_1$-$C_6$-alkyl, $C_3$-$C_6$-carbocycle, or $R^6$ and $R^7$ form together with the carbon atom to which they are attached a $C_3$-$C_6$-carbocycle or a 3- to 6-membered heterocycle;

n is 0 or 1;

W is oxygen or sulfur;

Y is $NR^8$, wherein $R^8$ is selected from the group consisting of hydrogen, $C_1$-$C_6$-alkyl, $C_1$-$C_6$-haloalkyl, $C_1$-$C_6$-cyanoalkyl, hydroxy, $C_1$-$C_6$-alkoxy or $C_3$-$C_6$-carbocycle;

Z is selected from the group consisting of cyano, —C(═O)—$OR^a$, —C(═O)—$SR^a$, —C(═O)—$NR^b$ RI, —C(═S)—$NR^bR^c$ or —C(═O)—NH—$CR^dR^e$—C(═O)—$OR^a$, wherein $R^a$ is selected from the group consisting of hydrogen, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered non-aromatic heterocyclyl, —$C_1$-$C_6$-alkyl-Si($C_1$-$C_6$-alkyl)$_3$, —$C_1$-$C_6$-alkyl-$C_3$-$C_8$-cycloalkyl, 5- to 9-membered heteroaryl and —$C_1$-$C_6$-alkyl-5- to 9-membered heteroaryl, or $R^a$ can form together with $R_4$ and with the atoms to which they are attached, a 4- to 7-membered heterocycle, wherein $R^b$ and $R^c$ are independently selected from the group consisting of hydrogen, $C_1$-$C_6$-alkyl, hydroxyl, $C_1$-$C_6$-alkoxy, cyano, $C_1$-$C_6$-cyanoalkyl, or $R^b$ can form together with $R_4$ and with the atoms to which they are attached, a 4- to 7-membered heterocycle, wherein $R^d$ and $R^e$ are independently selected from the group consisting of hydrogen, cyano, hydroxyl, $C_1$-$C_6$-alkyl, $C_1$-$C_6$-hydroxyalkyl, $C_1$-$C_6$-alkoxy, —O—C(═O)—$C_1$-$C_6$-alkyl, $C_3$-$C_6$-carbocycle, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, aryl, 5- to 9-membered heteroaryl, —$C_1$-$C_6$-alkyl-$C_1$-$C_6$-alkoxy, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-5- to 9-membered heteroaryl, —$C_1$-$C_6$-alkyl-S—$C_1$-$C_6$-alkyl, —$C_1$-$C_6$-alkyl-S—C(═O)—$C_1$-$C_6$-alkyl, —$C_1$-$C_6$-alkyl-O—(C═O)—$C_1$-$C_6$-alkyl, —$C_1$-$C_8$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—OH, —$C_1$-$C_6$-alkyl-C(═O)—O—$C_1$-$C_6$-alkyl, —$C_1$-$C_6$-alkyl-NH—C(═NH)—$NH_2$, wherein at least one of $R^d$ and $R^e$ is hydrogen, $C_1$-$C_6$-alkyl or $C_3$-$C_6$-carbocycle, or $R^d$ and $R^e$ form together with the carbon atom to which they are attached a carbonyl, $C_3$-$C_6$-carbocycle, or a 3- to 6-membered heterocycle;

provided that compounds of formula (I) with the following combinations of $R^1$, $R^2$ and $R^3$

| $R^1$ | $R^2$ | $R^3$ |
|---|---|---|
| Cl | Cl | Cl |
| Br | Me | H |
| Br | Br | Br |
| Cl | Cl | methyl |
| Br | Br | methyl |
| Br | Br | H |
| Cl | Cl | H |

are excluded;

provided that compounds of formula (I) with the following combinations of $R^1$, $R^2$ and $R^3$

| $R^1$ | $R^2$ | $R^3$ |
|---|---|---|
| Cl | Cl | halogen |
| Br | Br | halogen |

are excluded, if $R^4$ and $R^5$ form together with the carbon atom to which they are attached a cyclopropyl, and n is 0, and W is oxygen, and Y is NH, and Z is —C(═O)—$OR^a$;

provided that compounds of formula (I) with the following combinations of $R^1$, $R^2$ and $R^3$

| $R^1$ | $R^2$ | $R^3$ |
|---|---|---|
| Cl | Cl | Br |
| Cl | Cl | I |
| Br | Br | I |

are excluded, if $R^4$ is selected from the group consisting of hydrogen, $C_1$-$C_6$-alkyl, —$C_1$-$C_6$-alkyl-aryl, —$C_1$-$C_6$-alkyl-hydroxyaryl, —$C_1$-$C_6$-alkyl-S—$C_1$-$C_6$-alkyl and $R^5$ is hydrogen, and n is 0, and W is oxygen, and Y is NH and Z is —C(═O)—$OR^a$;

provided that N-[(4-bromo-5-methyl-2-thienyl)carbonyl]-N-propylglycine [2193740-02-0] and 4-bromo-N-(1-cyano-2,2-dimethylcyclopropyl)-5-methylthiophene-2-carboxamide [2192630-99-0] are excluded from the compounds of formula (I).

It is preferred if $R^1$ is $C_1$-$C_6$-haloalkyl or $R^2$ is $C_1$-$C_6$-haloalkyl and $R^4$ is selected from the group consisting of hydrogen, $C_1$-$C_6$-alkyl and $R^5$ is selected from the group consisting of hydrogen, $C_1$-$C_6$-alkyl, and n is 0, and W is oxygen, then Z is selected from the group consisting of cyano, —C(═O)—$SR^a$, —C(═O)—$NR^bR^c$, —C(═S)—$NR^bR^c$ or —C(═O)—NH—$CR^dR^e$—C(═O)—$OR^a$.

It is also preferred that compounds of formula (I) are excluded wherein $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

It is preferred that $R^4$ and $R^5$ are selected independently from one another from the group consisting of hydrogen, halogen, cyano, hydroxyl, $C_1$-$C_6$-alkyl, $C_1$-$C_6$-hydroxyalkyl, $C_1$-$C_6$-alkoxy, $C_1$-$C_6$-haloalkyl, —O—C(═O)—$C_1$-$C_6$-alkyl, $C_3$-$C_6$-carbocycle, 4-, 5- or 6-membered non-aromatic heterocyclyl, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, aryl, 5- to 9-membered heteroaryl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-4-, 5- or 6-membered non-aromatic heterocyclyl, —$C_1$-$C_6$-alkyl-aryl, —$C_1$-$C_6$-alkyl-hydroxyaryl, —$C_1$-$C_6$-alkyl-5- to 9-membered heteroaryl, —$C_1$-$C_6$-alkyl-S—$C_1$-$C_6$-alkyl, —$C_1$-$C_6$-alkyl-S—C(═O)—$C_1$-$C_6$-alkyl, —$C_1$-$C_6$-alkyl-O—(C═O)—$C_1$-$C_6$-alkyl, —$C_1$-$C_6$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—OH, —$C_1$-$C_6$-alkyl-C(═O)—O—$C_1$-$C_6$-alkyl, —$C_1$-$C_6$-alkyl-NH—C(═NH)—$NH_2$, —S—$C_1$-$C_6$-alkyl, —S—C(═O)—$C_1$-$C_6$-alkyl, —S—C(═O)—O—$C_1$-$C_6$-alkyl, —S—C(═S)—O—$C_1$-$C_6$-alkyl, —S—C(═O)—S—$C_1$-$C_6$-alkyl, —S—C(═O)—$NH_2$, —S—C(═O)—NH($C_1$-$C_6$-alkyl), —S—C(═O)—NH($C_1$-$C_6$-alkyl)$_2$, —S—C(═S)—$NH_2$, —S—C(═S)—NH($C_1$-$C_6$-alkyl), —S—C(═S)—NH($C_1$-$C_6$-alkyl)$_2$, —$C_1$-$C_6$-alkyl-S—C(═O)—O—$C_1$-$C_6$-alkyl, —$C_1$-$C_6$-alkyl-S—C(═O)—S—$C_1$-$C_6$-alkyl, —$C_1$-$C_6$-alkyl-S—C(═O)—$NH_2$, —$C_1$-$C_6$-alkyl-S—C(═O)—NH($C_1$-$C_6$-alkyl), —$C_1$-$C_6$-alkyl-S—C(═O)—NH($C_1$-$C_6$-alkyl)$_2$, —$C_1$-$C_6$-alkyl-S—C(═S)—$NH_2$, —$C_1$-$C_6$-alkyl-S—C(═S)—NH($C_1$-$C_6$-alkyl), —$C_1$-$C_6$-alkyl-S—C(═S)—NH($C_1$-$C_6$-alkyl)$_2$, wherein acyclic $R_4$, $R_5$ radicals may be substituted with one or more $R^w$ substituents, wherein cyclic $R_4$, $R_5$ radicals may be substituted with one or more $R^x$ substituents, wherein at least one of $R^4$ and $R^5$ is hydrogen, $C_1$-$C_6$-alkyl or $C_3$-$C_6$-carbocycle, or $R^4$ and $R^5$ form together with the carbon atom to which they are attached a $C_4$-$C_6$-carbocycle or a 3- to 6-membered heterocycle, wherein said $C_4$-$C_6$-carbocycle and 3- to 6-membered heterocycle may be substituted with one or more $R^x$ substituents, wherein $R^w$ is independently selected from the group consisting of nitro, hydroxyl, cyano, carboxyl, amino, sulfanyl, pentafluoro-$\lambda^6$-sulfanyl, formyl, carbamoyl, carbamate, $C_3$-$C_7$-cycloalkyl, $C_3$-$C_7$-halogenocycloalkyl having 1 to 5 halogen atoms, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$- halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl, wherein $R^x$ is independently selected from the group consisting of halogen, nitro, hydroxyl, cyano, carboxyl, amino, sulfanyl, pentafluoro-$\lambda^6$-sulfanyl, formyl, carbamoyl, carbamate, $C_1$-$C_8$-alkyl, $C_3$-$C_7$-cycloalkyl, $C_1$-$C_8$-halogenoalkyl having 1 to 5 halogen atoms, $C_3$-$C_7$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl.

It is also preferred that $R^4$ and $R^5$ are selected independently from one another from the group consisting of hydrogen, halogen, cyano, hydroxyl, $C_1$-$C_6$-alkyl, $C_1$-$C_6$-hydroxyalkyl, $C_1$-$C_6$-alkoxy, $C_1$-$C_6$-haloalkyl, —O—C(═O)—$C_1$-$C_6$-alkyl, $C_3$-$C_6$-carbocycle, 4-, 5- or 6-membered non-aromatic heterocyclyl, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, aryl, 5- to 9-membered heteroaryl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-4-, 5- or 6-membered non-aromatic heterocyclyl, —$C_1$-$C_6$-alkyl-aryl, —$C_1$-$C_6$-alkyl-hydroxyaryl, —$C_1$-$C_6$-alkyl-5- to 9-membered heteroaryl, —$C_1$-$C_6$-alkyl-S—$C_1$-$C_6$-alkyl, —$C_1$-$C_6$-alkyl-S—C(═O)—$C_1$-$C_6$-alkyl, —$C_1$-$C_6$-alkyl-O—(C═O)—$C_1$-$C_6$-alkyl, —$C_1$-$C_6$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—OH, —$C_1$-$C_6$-alkyl-C(═O)—O—$C_1$-$C_6$-alkyl, —$C_1$-$C_6$-alkyl-NH—C(═NH)—$NH_2$, —S—$C_1$-$C_6$-alkyl, —S—C(═O)—$C_1$-$C_6$-alkyl, —S—C(═O)—O—$C_1$-$C_6$-alkyl, —S—C(═S)—O—$C_1$-$C_6$-alkyl, —S—C(═O)—S—$C_1$-$C_6$-alkyl, —S—C(═O)—$NH_2$, —S—C(═O)—NH($C_1$-$C_6$-alkyl), —S—C(═O)—NH($C_1$-$C_6$-alkyl)$_2$, —S—C(═S)—$NH_2$, —S—C(═S)—NH($C_1$-$C_6$-alkyl), —S—C(═S)—NH($C_1$-$C_6$-alkyl)$_2$, —$C_1$-$C_6$-alkyl-S—C(═O)—O—$C_1$-$C_6$-alkyl, —$C_1$-$C_6$-alkyl-S—C(═O)—S—$C_1$-$C_6$-alkyl, —$C_1$-$C_6$-alkyl-S—C(═O)—$NH_2$, —$C_1$-$C_6$-alkyl-S—C(═O)—NH($C_1$-$C_6$-alkyl), —$C_1$-$C_6$-alkyl-S—C(═O)—NH($C_1$-$C_6$-alkyl)$_2$, —$C_1$-$C_6$-alkyl-S—C(═S)—$NH_2$, —$C_1$-$C_6$-alkyl-S—C(═S)—NH($C_1$-$C_6$-alkyl), —$C_1$-$C_6$-alkyl-S—C(═S)—NH($C_1$-$C_6$-alkyl)$_2$, wherein acyclic $R_4$, $R_5$ radicals may be substituted with one or more $R^w$ substituents, wherein cyclic $R_4$, $R_5$ radicals may be substituted with one or more $R^x$ substituents, wherein at least one of $R^4$ and $R^5$ is hydrogen, $C_1$-$C_6$-alkyl or $C_3$-$C_6$-carbocycle, or $R^4$ and $R^5$ form together with the carbon atom to which they are attached a 3- to 6-membered heterocycle, wherein 3- to 6-membered heterocycle may be substituted with one or more $R^x$ substituents, wherein $R^w$ is independently selected from the group consisting of nitro, hydroxyl, cyano, carboxyl, amino, sulfanyl, pentafluoro-$\lambda^6$-sulfanyl, formyl, carbamoyl, carbamate, $C_3$-$C_7$-cycloalkyl, $C_3$-$C_7$-halogenocycloalkyl having 1 to 5 halogen atoms, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl, wherein $R^x$ is independently selected from the group consisting of halogen, nitro, hydroxyl, cyano, carboxyl, amino, sulfanyl, pentafluoro-$\lambda^6$-sulfanyl, formyl, carbamoyl, carbamate, $C_1$-$C_8$-alkyl, $C_3$-$C_7$-cycloalkyl, $C_1$-$C_8$-halogenoalkyl having 1 to 5 halogen atoms, $C_3$-$C_7$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl.

It is also preferred that compounds are excluded, where $R^4$ and $R^5$ form together with the carbon atom to which they are attached a cyclopropyl.

Also preferred is, if $R^4$ and $R^5$ are selected independently from one another from the group consisting of hydrogen, $C_1$-$C_6$-alkyl, $C_1$-$C_6$-hydroxyalkyl, $C_3$-$C_6$-carbocycle, aryl, —$C_1$-$C_6$-alkyl-$C_1$-$C_6$-alkoxy, —$C_1$-$C_6$-alkyl-$C_3$-$C_6$-carbocycle, $C_1$-$C_6$-alkyl-O—(C═O)—$C_1$-$C_6$-alkyl, —$C_1$-$C_6$-alkyl-C(═O)—OH; —$C_1$-$C_6$-alkyl-aryl, —$C_1$-$C_6$-alkyl-S—$C_1$-$C_6$-alkyl, wherein at least one of $R^4$ and $R^5$ is hydrogen, $C_1$-$C_6$-alkyl or $C_3$-$C_6$-carbocycle, and n is 0 and W is oxygen, and Y is $NR^8$, wherein $R^8$ is selected from the group consisting of hydrogen, $C_1$-$C_6$-alkyl, then Z is selected from the group consisting of cyano, —C(═O)—$SR^a$, —C(═S)—$NR^bR^c$ or —C(═O)—NH—$CR^dR^e$—C(═O)—$OR^a$.

According to a further embodiment it is preferred, if $R^1$ and $R^2$ are selected independently from one another from the group consisting of F, Cl, Br, I, Cyano, $CH_3$ and are preferably selected independently from one another from the group consisting of F, Cl, Br, I.

According to a further embodiment it is preferred, if $R^1$ is selected from the group consisting of CN, Br, Cl, F, $CHF_2$, $CF_3$ is preferably selected from the group consisting of CN, Br, Cl, F.

According to a further embodiment it is preferred, if $R^2$ is selected from the group consisting of Br, Cl, F, $CHF_2$, $CF_3$.

In still another preferred embodiment $R^3$ is selected from the group consisting of Hydrogen, F, Cl, Br, I, Cyano, $CH_3$, $CHF_2$, $CF_3$ and is preferably selected from the group consisting of Hydrogen, F, Cl, Br, I, Cyano, $CH_3$.

In still another preferred embodiment $R^3$ is selected from the group consisting of Br, Cl, F, CN, Me, $CHF_2$, $CF_3$.

Also preferred is a compound according to formula (I) with the following combinations of $R^1$, $R^2$ and $R^3$

| $R^1$ | $R^2$ | $R^3$ |
|---|---|---|
| Halogen | Halogen | Halogen |
| Halogen | Halogen | CN |
| CN | Halogen | Halogen |
| Halogen | CN | Halogen |
| Halogen | Halogen | Me, $CF_3$ or $CHF_2$ |

It is also preferred, if $R^3$ is not hydrogen.

Also preferred are compounds of formula (I) wherein $R^3$ is not hydrogen and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

It is also preferred if at least one of $R^1$, $R^2$ and $R^3$ is cyano.

In another preferred embodiment $R^4$ selected from the group consisting of hydrogen, $C_1$-$C_6$-alkyl, $C_1$-$C_8$-hydroxyalkyl, $C_3$-$C_6$-carbocycle, C(═O)—OH, —C(═O)—O—$C_1$-$C_6$-alkyl, —$C_1$-$C_8$-alkyl-$C_1$-$C_8$-alkoxy, —$C_1$-$C_8$-alkyl-$C_1$-$C_8$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, —$C_1$-$C_6$-alkyl-C(═O)—$NH_2$, —$C_1$-$C_6$-alkyl-C(═O)—OH, —$C_1$-$C_6$-alkyl-C(═O)—O—$C_1$-$C_6$-alkyl, $R_5$ selected from the group consisting of hydrogen, $C_1$-$C_6$-alkyl or $C_3$-$C_6$-carbocycle; or $R^4$ and $R^5$ form together with the carbon atom to which they are attached a $C_3$-$C_6$-carbocycle.

It is also preferred if $R^6$ and $R^7$ are independently selected from the group consisting of hydrogen, $C_1$-$C_3$-alkyl, $C_3$-$C_6$-carbocycle.

In still another preferred embodiment n is 0.

Also preferred are compounds of formula (I) wherein n is 0 and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

Also preferred is, if W is oxygen.

Also preferred are compounds of formula (I) wherein W is oxygen and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

Further preferred is, if Y is selected from the group consisting of NH, N—$OCH^3$, N—OH, and most preferably is NH.

Also preferred are compounds of formula (I) wherein Y is NH and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

According to another embodiment Z is selected from the group consisting of cyano, —C(═O)—$OR^a$, —C(═O)—$SR^a$, —C(═O)—$NR^bR^c$, —C(═S)—$NR^bR^c$ or —C(═O)—NH—$CR^dR^e$—C(═O)—$OR^a$, and preferably is —C(═O)—$OR^a$.

According to another embodiment Z is selected from the group consisting of cyano, —C(═O)—$OR^a$, —C(═O)—$SR^a$, —C(═O)—$NR^bR^c$, —C(═S)—$NR^bR^c$.

In another preferred embodiment $R^1$ and $R^2$ are selected independently from one another from the group consisting of F, Cl, Br, I, Cyano, $CH_3$ and are preferably selected independently from one another from the group consisting of F, Cl, Br, I;

$R^3$ is selected from the group consisting of Hydrogen, F, Cl, Br, I, Cyano, $CH_3$, $CHF_2$, $CF_3$ and is preferably selected from the group consisting of Hydrogen, F, Cl, Br, I, Cyano, $CH_3$, $R^4$ selected from the group consisting of hydrogen, $C_1$-$C_6$-alkyl, $C_1$-$C_6$-hydroxyalkyl, $C_3$-$C_6$-carbocycle, C(═O)—OH, —C(═O)—O—$C_1$-$C_6$-alkyl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, —$C_1$-$C_6$-alkyl-C(═O)—$NH_2$, —$C_1$-$C_6$-alkyl-C(═O)—OH, —$C_1$-$C_6$-alkyl-C(═O)—O—$C_1$—$C_6$-alkyl, $R_5$ selected from the group consisting of is hydrogen, $C_1$-$C_6$-alkyl or $C_3$-$C_6$-carbocycle; or $R^4$ and $R^5$ form together with the carbon atom to which they are attached a $C_3$-$C_6$-carbocycle;

$R^6$ and $R^7$ are independently selected from the group consisting of hydrogen, $C_1$-$C_6$-alkyl, $C_3$-$C_6$-carbocycle, or $R^6$ and $R^7$ form together with the carbon atom to which they are attached a $C_3$-$C_6$-carbocycle or a 3- to 6-membered heterocycle;

n is 0;

W is oxygen;

Y is selected from the group consisting of NH, N—$OCH_3$, N—OH, and preferably is NH;

Z is selected from the group consisting of cyano, —C(═O)—$OR^a$, —C(═O)—$SR^a$, —C(═O)—$NR^bR^c$, —C(═S)—$NR^bR^c$ or —C(═O)—NH—$CR^dR^e$—C(═O)—$OR^a$, and preferably is —C(═O)—$OR^a$.

In another preferred embodiment $R^1$ and $R^2$ are selected independently from one another from the group consisting of F, Cl, Br, I;

$R^3$ is selected from the group consisting of Hydrogen, F, Cl, Br, I, Cyano, $CH_3$, $R^4$ selected from the group consisting of hydrogen, $C_1$-$C_6$-alkyl, $C_1$-$C_6$-hydroxyalkyl, $C_3$-$C_6$-carbocycle, C(═O)—OH, —C(═O)—O—$C_1$-$C_6$-alkyl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, —$C_1$-$C_6$-alkyl-C(═O)—$NH_2$, —$C_1$-$C_6$-alkyl-C(═O)—OH, —$C_1$-$C_6$-alkyl-C(═O)—O—$C_1$-$C_6$-alkyl, $R_5$ selected from the group consisting of hydrogen, $C_1$-$C_6$-alkyl or $C_3$-$C_6$-carbocycle; or $R^4$ and $R^5$ form together with the carbon atom to which they are attached a $C_3$-$C_6$-carbocycle;

$R^6$ and $R^7$ are independently selected from the group consisting of hydrogen, $C_1$-$C_6$-alkyl, $C_3$-$C_6$-carbocycle, or $R^6$ and $R^7$ form together with the carbon atom to which they are attached a $C_3$-$C_6$-carbocycle or a 3- to 6-membered heterocycle;

n is 0;

W is oxygen;

Y is NH;

Z is —C(═O)—$OR^a$.

In still another embodiment a compound according to formula (I) is preferred, wherein $R^1$, $R^2$ and $R^3$ are the following combinations

| $R^1$ | $R^2$ | $R^3$ |
|---|---|---|
| Halogen | Halogen | Halogen |
| Halogen | Halogen | CN |
| CN | Halogen | Halogen |
| Halogen | CN | Halogen |
| Halogen | Halogen | Me, $CF_3$ or $CHF_2$ |

$R^4$ is selected from the group consisting of hydrogen, $C_1$-$C_8$-alkyl, $C_1$-$C_8$-hydroxyalkyl, $C_3$-$C_6$-carbocycle, C(═O)—OH, —C(═O)—O—$C_1$-$C_6$-alkyl, —$C_1$-$C_6$-alkyl-$C_1$-$C_6$-alkoxy, —$C_1$-$C_8$-alkyl-$C_1$-$C_8$-haloalkyl, —$C_1$-$C_6$-alkyl-$C_3$-$C_6$-carbocycle, —$C_1$-$C_8$-alkyl-aryl, —$C_1$-$C_8$-alkyl-hydroxyaryl, —$C_1$-$C_6$-alkyl-S—$C_1$-$C_6$-alkyl-, —$C_1$-$C_6$-alkyl-C(═O)—$NH_2$, —$C_1$-$C_6$-alkyl-C(═O)—OH, —$C_1$-$C_6$-alkyl-C(═O)—O—$C_1$-$C_6$-alkyl, $R_5$ selected from the group consisting of hydrogen, $C_1$-$C_6$-alkyl or $C_3$-$C_6$-carbocycle; or $R^4$ and $R^5$ form together with the carbon atom to which they are attached a $C_3$-$C_6$-carbocycle.

$R^6$ and $R^7$ are independently selected from the group consisting of hydrogen, $C_1$-$C_6$-alkyl, $C_3$-$C_6$-carbocycle, or $R^6$ and $R^7$ form together with the carbon atom to which they are attached a $C_3$-$C_6$-carbocycle or a 3- to 6-membered heterocycle;

n is 0;

W is oxygen;

Y is selected from the group consisting of NH, N—$OCH_3$, N—OH, and preferably is NH;

Z is selected from the group consisting of cyano, —C(═O)—$OR^a$, —C(═O)—$SR^a$, —C(═O)—$NR^bR^c$, —C(═S)—$NR^bR^c$ or —C(═O)—NH—$CR^dR^e$—C(═O)—$OR^a$, and preferably is —C(═O)—$OR^a$.

In another embodiment, if $R^1$=halogen, then $R^2$=cyano, $C_1$-$C_6$-alkyl or $C_1$-$C_6$-haloalkyl and $R^3$=cyano, $C_1$-$C_6$-alkyl or $C_1$-$C_6$-haloalkyl. In another embodiments, if $R^1$=halogen, then $R^2$=cyano, $C_1$-$C_6$-alkyl or $C_1$-$C_6$-haloalkyl and $R^3$=hydrogen or halogen. In another embodiment, if $R^2$=halogen, then $R^1$=cyano, $C_1$-$C_6$-alkyl or $C_1$-$C_6$-haloalkyl and $R^3$=cyano, $C_1$-$C_6$-alkyl or $C_1$-$C_6$-haloalkyl. In another embodiment, if $R^2$=halogen, then $R^1$=cyano, $C_1$-$C_6$-alkyl or $C_1$-$C_6$-haloalkyl and $R^3$=hydrogen or halogen. In another embodiment, if $R^1$ and $R^2$=halogen, $R^2$ is different from $R^1$, and $R^3$=hydrogen or halogen. In another embodiment, if $R^1$ and $R^2$=halogen, $R^2$ is different from $R^1$ and $R^3$=cyano, $C_1$-$C_6$-alkyl or $C_1$-$C_6$-haloalkyl. In another embodiment, if $R^1$ and $R^2$=halogen, $R^3$=cyano, $C_1$-$C_6$-alkyl or $C_1$-$C_6$-haloalkyl. In another embodiment, if $R^1$ and $R^2$=halogen, $R^3$=hydrogen or halogen.

In another embodiment, if $R^1$ and $R^2$=halogen, $R^3$=hydrogen. In another embodiment, if $R^1$ and $R^2$=halogen, $R^3$=halogen.

In another embodiment, $R^1$ is halogen, cyano, $C_1$-$C_6$-alkyl or $C_1$-$C_6$-haloalkyl. In another embodiment, $R^1$ is halogen, cyano, $C_1$-$C_3$-alkyl or $C_1$-$C_3$-haloalkyl. In another embodiment, $R^1$ is halogen, cyano or $C_1$-$C_3$-alkyl. In another embodiment, $R^1$ is $C_1$-$C_3$-haloalkyl. In another embodiment, $R^1$ is halogen, cyano, methyl, trifluoromethyl or difluoromethyl. In another embodiment, $R^1$ is halogen, cyano or methyl. In another embodiment, $R^1$ is trifluoromethyl or difluoromethyl.

In another embodiment, $R^2$ is halogen, cyano, $C_1$-$C_6$-alkyl or $C_1$-$C_6$-haloalkyl. In another embodiment, $R^2$ is halogen, cyano, $C_1$-$C_3$-alkyl or $C_1$-$C_3$-haloalkyl. In another embodiment, $R^2$ is halogen, cyano or $C_1$-$C_3$-alkyl. In another embodiment, $R^2$ is $C_1$-$C_3$-haloalkyl. In another embodiment, $R^2$ is halogen, cyano, methyl, trifluoromethyl or difluoromethyl. In another embodiment, $R^2$ is halogen, cyano or methyl. In another embodiment, $R^2$ is trifluoromethyl or difluoromethyl.

In another embodiment, $R^3$ is hydrogen, halogen, cyano, $C_1$-$C_6$-alkyl or $C_1$-$C_6$-haloalkyl. In another embodiment, $R^3$ is hydrogen, halogen, cyano, $C_1$-$C_3$-alkyl or $C_1$-$C_3$-haloalkyl. In another embodiment, $R^3$ is hydrogen, halogen, cyano, methyl, trifluoromethyl or difluoromethyl.

In another embodiment, $R^4$ and $R^5$ are selected independently from one another from the group consisting of halogen, cyano, hydroxyl, $C_1$-$C_6$-alkoxy, $C_1$-$C_6$-haloalkyl, —O—C(═O)—$C_1$-$C_6$-alkyl, 4-, 5- or 6-membered non-aromatic heterocyclyl, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, 5- to 9-membered heteroaryl, —$C_1$-$C_6$-alkyl-$C_1$-$C_6$-haloalkyl, —$C_1$-$C_6$-alkyl-4-, 5- or 6-membered non-aromatic heterocyclyl, —$C_1$-$C_6$-alkyl-hydroxyaryl, —$C_1$-$C_6$-alkyl-5- to 9-membered heteroaryl, —$C_1$-$C_6$-alkyl-S—C(═O)—$C_1$-$C_6$-alkyl, —$C_1$-$C_6$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—O—$C_1$-$C_6$-alkyl, —$C_1$-$C_6$-alkyl-NH—C(═NH)—$NH_2$, —S—$C_1$-$C_6$-alkyl, —S—C(═O)—$C_1$-$C_6$-alkyl, —S—C(═O)—O—$C_1$-$C_6$-alkyl, —S—C(═S)—O—$C_1$-$C_6$-alkyl, —S—C(═O)—S—$C_1$-$C_6$-alkyl, —S—C(═O)—$NH_2$, —S—C(═O)—NH($C_1$-$C_6$-alkyl), —S—C(═O)—NH($C_1$-$C_6$-alkyl)$_2$, —S—C(═S)—$NH_2$, —S—C(═S)—NH($C_1$-$C_6$-alkyl), —S—C(═S)—NH($C_1$-$C_6$-alkyl)$_2$, —$C_1$-$C_6$-alkyl-S—C(═O)—O—$C_1$-$C_6$-alkyl, —$C_1$-$C_6$-alkyl-S—C(═O)—S—$C_1$-$C_6$-alkyl, —$C_1$-$C_6$-alkyl-S—C(═O)—$NH_2$, —$C_1$-$C_6$-alkyl-S—C(═O)—NH($C_1$-$C_6$-alkyl), —$C_1$-$C_6$-alkyl-S—C(═O)—NH($C_1$-$C_6$-alkyl)$_2$, —$C_1$-$C_6$-alkyl-S—C(═S)—$NH_2$, —$C_1$-$C_6$-alkyl-S—C(═S)—NH($C_1$-$C_6$-alkyl), —$C_1$-$C_6$-alkyl-S—C(═S)—NH($C_1$-$C_6$-alkyl)$_2$; wherein acyclic $R^4$, $R^5$ radicals may be substituted with one or more $R^w$ substituents, wherein cyclic $R_4$, $R_5$ radicals may be substituted with one or more $R^x$ substituents, wherein at least one of $R^4$ and $R^5$ is hydrogen, $C_1$-$C_6$-alkyl or $C_3$-$C_6$-carbocycle. In another embodiment, $R^4$ and $R^5$ are selected independently from one another from the group consisting of hydrogen, $C_1$-$C_6$-alkyl, $C_1$-$C_6$-hydroxyalkyl, $C_3$-$C_6$-carbocycle, aryl, —$C_1$-$C_6$-alkyl-$C_1$-$C_6$-alkoxy, —$C_1$-$C_6$-alkyl-$C_3$-$C_6$-carbocycle, $C_1$-$C_6$-alkyl-O—(C═O)—$C_1$-$C_6$-alkyl, —$C_1$-$C_6$-alkyl-C(═O)—OH; —$C_1$-$C_6$-alkyl-aryl, —$C_1$-$C_6$-alkyl-S—$C_1$-$C_6$-alkyl, wherein acyclic $R^4$, $R^5$ radicals may be substituted with one or more $R^w$ substituents, wherein cyclic $R_4$, $R_5$ radicals may be substituted with one or more $R^x$ substituents, wherein at least one of $R^4$ and $R^5$ is hydrogen, $C_1$-$C_6$-alkyl or $C_3$-$C_6$-carbocycle; or $R^4$ and $R^5$ form together with the carbon atom to which they are attached a $C_3$-$C_6$-carbocycle or a 3- to 6-membered heterocycle, wherein said $C_3$-$C_6$-carbocycle and 3- to 6-membered heterocycle may be substituted with one or more $R^x$ substituents. In another embodiment, $R^4$ is hydrogen, $C_1$-$C_6$-alkyl, $C_1$-$C_6$-hydroxyalkyl, $C_3$-$C_6$-carbocycle, C(═O)—OH, —C(═O)—O—$C_1$-$C_6$-alkyl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, —$C_1$-$C_6$-alkyl-C(═O)—$NH_2$, —$C_1$-$C_6$-alkyl-C(═O)—OH, —$C_1$-$C_6$-alkyl-C(═O)—O—$C_1$-$C_6$-alkyl, $R_5$ is hydrogen, $C_1$-$C_6$-alkyl or $C_3$-$C_6$-carbocycle; or $R^4$ and $R^5$ form together with the carbon atom to which they are attached a $C_3$-$C_6$-carbocycle. In another embodiment, $R^4$ is hydrogen, $C_1$-$C_6$-alkyl, $C_3$-$C_6$-carbocycle, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, $R_5$ is hydrogen or $C_1$-$C_6$-alkyl; or $R^4$ and $R^5$ form together with the carbon atom to which they are attached a $C_3$-$C_6$-carbocycle. In another embodiment, $R^4$ is hydrogen, $C_1$-$C_6$-alkyl, $C_3$-$C_6$-carbocycle, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, $R_5$ is hydrogen or $C_1$-$C_6$-alkyl. In another embodiment, $R^4$ and $R^5$ form together with the carbon atom to which they are attached a $C_3$-$C_6$-carbocycle or 3- to 6-membered heterocycle. In another embodiment, $R^4$ and $R^5$ form together with the carbon atom to which they are attached a $C_3$-$C_6$-carbocycle. In another embodiment, $R^4$ and $R^5$ form together with the carbon atom to which they are attached a cyclopropyl or cyclobutyl.

In another embodiment n is 0. In another embodiment n is 1.

In another embodiment W is oxygen. In another embodiment W is sulfur.

In another embodiment n is 0 and W is oxygen.

Also preferred are compounds of formula (I) wherein n is 0 and W is oxygen and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen and $R^8$ is H.

Also preferred are compounds of formula (I) wherein n is 0, W is oxygen and $R^8$ is H and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H and $R^3$ is not H.

Also preferred are compounds of formula (I) wherein n is 0, W is oxygen, $R^8$ is H and $R^3$ is not H and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H and $R^3$ is selected from the group consisting of Br, Cl, F, CN, Me, $CHF_2$, $CF_3$.

Also preferred are compounds of formula (I) wherein n is 0, W is oxygen, $R^8$ is H and $R^3$ is selected from the group consisting of Br, Cl, F, CN, Me, $CHF_2$, $CF_3$ and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H and $R^1$ is selected from the group consisting of CN, Br, Cl, F, $CHF_2$, $CF_3$.

Also preferred are compounds of formula (I) wherein n is 0, W is oxygen, $R^8$ is H and $R^1$ is selected from the group consisting of CN, Br, Cl, F, $CHF_2$, $CF_3$ and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H and $R^1$ is selected from the group consisting of CN, Br, C, F.

Also preferred are compounds of formula (I) wherein n is 0, W is oxygen, $R^8$ is H and $R^1$ is selected from the group consisting of CN, Br, C, F and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H and $R^2$ is selected from the group consisting of Br, Cl, F, $CHF_2$, $CF_3$.

Also preferred are compounds of formula (I) wherein n is 0, W is oxygen, $R^8$ is H and $R^2$ is selected from the group consisting of Br, Cl, F, $CHF_2$, $CF_3$ and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H and at least one of $R^1$, $R^2$ and $R^3$ is cyano.

In another embodiment n is 0, W is oxygen, $R^8$ is H, $R^3$ is selected from the group consisting of Br, Cl, F, CN, Me, $CHF_2$, $CF_3$ and $R^1$ is selected from the group consisting of CN, Br, Cl, F, $CHF_2$, $CF_3$, Me.

Also preferred are compounds of formula (I) wherein n is 0, W is oxygen, $R^8$ is H and $R^3$ is selected from the group consisting of Br, Cl, F, CN, Me, $CHF_2$, $CF_3$ and $R^1$ is selected from the group consisting of CN, Br, Cl, F, $CHF_2$, $CF_3$, Me and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H, $R^3$ is selected from the group consisting of Br, C, F, CN, Me, $CHF_2$, $CF_3$ and $R^2$ is selected from the group consisting of Br, C, F, $CHF_2$, $CF_3$, Me.

Also preferred are compounds of formula (I) wherein n is 0, W is oxygen, $R^8$ is H and $R^3$ is selected from the group consisting of Br, C, F, CN, Me, $CHF_2$, $CF_3$ and $R^2$ is selected from the group consisting of Br, C, F, $CHF_2$, $CF_3$, Me and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment n is 0, W is oxygen, $R^8$ is H, $R^3$ is selected from the group consisting of Br, C, F, CN, Me, $CHF_2$, $CF_3$, $R^2$ is selected from the group consisting of Br, C, F, $CHF_2$, $CF_3$ and $R^1$ is selected from the group consisting of CN, Br, C, F, $CHF_2$, $CF_3$, Me.

Also preferred are compounds of formula (I) wherein n is 0, W is oxygen, $R^8$ is H and $R^3$ is selected from the group consisting of Br, C, F, CN, Me, $CHF_2$, $CF_3$, $R^2$ is selected from the group consisting of Br, C, F, $CHF_2$, $CF_3$ and $R^1$ is selected from the group consisting of CN, Br, Cl, F, $CHF_2$, $CF_3$, Me and wherein compounds are excluded when $R^1$, $R^2$ and $R^3$ are independently selected from the group consisting of halogen and $C_1$-$C_6$-alkyl; W is oxygen; Y is NH; $R^4$ and $R^5$ form together with the carbon atom to which they are attached a cyclopropyl; n is 0; and Z is selected from the group consisting of —C(═O)—$OR^a$, —C(═O)—$NR^bR^c$.

In another embodiment, Y is $NR^8$ with $R^8$ being hydrogen. In another embodiment Y is $NR^8$ with $R^8$ being $C_1$-$C_8$-alkyl, $C_1$-$C_8$-haloalkyl, $C_1$-$C_6$-cyanoalkyl, hydroxy, $C_1$-$C_6$-alkoxy or $C_3$-$C_6$-carbocycle.

In another embodiment Z is selected from the group consisting of cyano, —C(═O)—$SR^a$, —C(═O)—$NR^bR^c$, —C(═S)—$NR^bR^c$ or —C(═O)—NH—$CR^dR^e$—C(═O)—$OR^a$. In another embodiment Z is —C(═O)—$OR^a$.

In another embodiment, if $R^1$ is $C_1$-$C_6$-haloalkyl or $R^2$ is $C_1$-$C_6$-haloalkyl and $R^4$ is selected from the group consisting of hydrogen, $C_1$-$C_6$-alkyl and $R^5$ is selected from the group consisting of hydrogen, $C_1$-$C_6$-alkyl, and n is 0, and W is oxygen, then Z is selected from the group consisting of cyano, —C(═O)—$SR^a$, —C(═O)—$NR^bR^c$, —C(═S)—$NR^bR^c$ or —C(═O)—NH—$CR^dR^e$—C(═O)—$OR^a$.

In another embodiment, if $R^4$ and $R^5$ are selected independently from one another from the group consisting of hydrogen, $C_1$-$C_6$-alkyl, $C_1$-$C_6$-hydroxyalkyl, $C_3$-$C_6$-carbocycle, aryl, —$C_1$-$C_6$-alkyl-$C_1$-$C_6$-alkoxy, —$C_1$-$C_6$-alkyl-$C_3$-$C_6$-carbocycle, $C_1$-$C_6$-alkyl-O—(C═O)—$C_1$-$C_6$-alkyl, —$C_1$-$C_6$-alkyl-C(═O)—OH; —$C_1$-$C_6$-alkyl-aryl, —$C_1$-$C_6$-alkyl-S—$C_1$-$C_6$-alkyl, wherein at least one of $R^4$ and $R^5$ is hydrogen, $C_1$-$C_6$-alkyl or $C_3$-$C_6$-carbocycle, and n is 0, and W is oxygen, and Y is $NR^8$, wherein $R^8$ is selected from the group consisting of hydrogen, $C_1$-$C_6$-alkyl, then Z is selected from the group consisting of cyano, —C(═O)—$SR^a$, —C(═S)—$NR^bR^c$ or —C(═O)—NH—$CR^dR^e$—C(═O)—$OR^a$.

In another embodiment, if $R^1$, $R^2$ and $R^3$ are the following combinations

| $R^1$ | $R^2$ | $R^3$ |
|---|---|---|
| Cl | Cl | halogen |
| Br | Br | halogen |

and $R^4$ and $R^5$ form together with the carbon atom to which they are attached a cyclopropyl, and n is 0, and W is oxygen, and Y is NH, then Z is selected from the group consisting of cyano, —C(═O)—$SR^a$, —C(═O)—$NR^bR^c$, —C(═S)—$NR^bR^c$ or —C(═O)—NH—$CR^dR^e$—C(═O)—$OR^a$.

In another embodiment, if $R^1$, $R^2$ and $R^3$ are the following combinations

| $R^1$ | $R^2$ | $R^3$ |
|---|---|---|
| Cl | Cl | Br |
| Cl | Cl | I |
| Br | Br | I |

and $R^4$ is selected from the group consisting of hydrogen, $C_1$-$C_6$-alkyl, —$C_1$-$C_6$-alkyl-aryl, —$C_1$-$C_6$-alkyl-hydroxyaryl, —$C_1$-$C_6$-alkyl-S—$C_1$-$C_6$-alkyl and $R^5$ is hydrogen, and n is 0, and W is oxygen, and Y is NH then Z is selected from the group consisting of cyano, —C(═O)—$SR^a$, —C(═O)—$NR^bR^c$, —C(═S)—$NR^bR^c$ or —C(═O)—NH—$CR^dR^e$—C(═O)—$OR^a$.

Also preferred are the compounds I.0001 to I.1070 disclosed in tables I.1 and I.2 in the experimental section.

Another aspect of the present invention relates to a composition comprising at least one compound of formula (I) according to the invention and at least one agriculturally suitable auxiliary.

Another aspect of the present invention relates to a method for controlling bacterial and/or fungal diseases comprising the step of applying at least one compound of formula (I) according to the invention or a composition according to the invention to the plants, plant parts, seeds, fruits or to the soil in which the plants grow.

Another aspect of the present invention relates to the use of a compound according to the invention or a composition according to the invention to control bacterial and/or fungal diseases on plants or plant parts. Preferably they are used to control fungal diseases on plants or plant parts.

Another aspect of the present invention relates to the use of a compound according to the invention or a composition according to the invention to control nematodes on plants or plant parts.

Another aspect of the present invention relates to the use of a compound according to the invention or a composition according to the invention to control viruses on plants or plant parts.

Preferably the compound or composition according to the invention is used against: Diseases caused by powdery mildew pathogens, such as *Podosphaera* species (e.g. *Podosphaera leucotricha*), Sphaerotheca species (e.g. Sphaerotheca *fuliginea*); diseases caused by rust disease pathogens, such as *Uromyces* species (e.g. *Uromyces appendiculatus*); diseases caused by pathogens from the group of the Oomycetes, such as *Peronospora* species (e.g. *Peronospora parasitica*), *Phytophthora* species (e.g. *Phytophthora infestans*), *Plasmopara* species (e.g. *Plasmopara viticola*), *Pseudoperonospora* species (e.g. *Pseudoperonospora humuli* or *Pseudoperonospora cubensis*), *Pythium* species (e.g. *Pythium ultimum*); leaf blotch diseases and leaf wilt diseases caused, for example, by *Alternaria* species (e.g. *Alternaria solani*), *Cercospora* species (e.g. *Cercospora beticola*), *Colletotrichum* species (e.g. *Colletotrichum lindemuthanium*), *Venturia* species (e.g. *Venturia inaequalis*); diseases caused by bacterial pathogens, for example *Xanthomonas* species (e.g. *Xanthomonas campestris* pv. *campestris*), *Pseudomonas* species (e.g. *Pseudomonas syringae* pv. tomato), *Erwinia* species (e.g. *Erwinia amylovora*), Liberibacter species (e.g. Liberibacter Candidatus), *Ralstonia* species (e.g. *Ralstonia solanacearum*).

According to further aspect of the present invention the compound or composition according to the invention is used plant defense activator. A plant defense inducer according to the invention is a compound or composition which stimulates the plants' own defense system.

The present invention also relates to the use of a compound of formula (II) in crop protection (II)

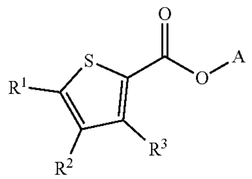

wherein $R^1$ and $R^2$ are selected independently from another from the group consisting of halogen, cyano, $C_1$-$C_3$-alkyl or $C_1$-$C_3$-haloalkyl, wherein at least one of $R^1$ or $R^2$ is halogen;

$R^3$ is selected from the group consisting of hydrogen, halogen, cyano, $C_1$-$C_3$-alkyl or $C_1$-$C_3$-haloalkyl;

A is selected from the group consisting of hydrogen and $C_1$-$C_6$-alkyl;

provided that compounds of formula (II) with the following combinations of $R^1$, $R^2$ and $R^3$

| $R^1$ | $R^2$ | $R^3$ |
|---|---|---|
| Cl | Cl | halogen |
| Br | Br | halogen |
| Br | Me | H |
| Cl | Cl | methyl |
| Br | Br | methyl |
| Br | Br | H |
| Cl | Cl | H |
| $CF_3$ | Cl | H |
| Cl | $CF_3$ | H |

are excluded.

In an embodiment, $R^1$ is halogen, cyano, $C_1$-$C_3$-alkyl or $C_1$-$C_3$-haloalkyl. In an embodiment, $R^1$ is halogen, cyano or $C_1$-$C_3$-alkyl. In an embodiment, $R^1$ is $C_1$-$C_3$-haloalkyl. In an embodiment, $R^1$ is halogen, cyano, methyl, trifluoromethyl or difluoromethyl. In an embodiment, $R^1$ is halogen, cyano or methyl. In an embodiment, $R^1$ is trifluoromethyl or difluoromethyl.

In an embodiment, $R^2$ is halogen, cyano, $C_1$-$C_3$-alkyl or $C_1$-$C_3$-haloalkyl. In an embodiment, $R^2$ is halogen, cyano or $C_1$-$C_3$-alkyl. In an embodiment, $R^2$ is $C_1$-$C_3$-haloalkyl. In an embodiment, $R^2$ is halogen, cyano, methyl, trifluoromethyl or difluoromethyl. In an embodiment, $R^2$ is halogen, cyano or methyl. In an embodiment, $R^2$ is trifluoromethyl or difluoromethyl.

In an embodiment, $R^3$ is hydrogen, halogen, cyano, $C_1$-$C_3$-alkyl or $C_1$-$C_3$-haloalkyl. In an embodiment, $R^3$ is hydrogen, halogen, cyano, methyl, trifluoromethyl or difluoromethyl.

In an embodiment, A is hydrogen. In an embodiment, A is hydrogen or $C_1$-$C_6$-alkyl. In an embodiment, A is hydrogen or $C_1$-$C_3$-alkyl. In an embodiment, A is hydrogen, methyl, ethyl or propyl.

In a preferred embodiment $R^1$ and $R^2$ are selected independently from another from the group consisting of halogen, cyano or $C_1$-$C_3$-alkyl, wherein at least one of $R_1$ or $R_2$ is halogen.

Also preferred are the compounds 11.001 to 11.104 disclosed in table II.1 in the experimental section.

It is also preferred when the compound of formula (II) is used to control phytopathogenic fungi and/or bacteria on plants or plant parts. Most preferably the compound of formula (II) is used to control fungal diseases on plants or plant parts.

It is also preferred when the compound of formula (II) is used to control nematodes on plants or plant parts.

It is also preferred when the compound of formula (II) is used to control viruses on plants or plant parts.

Preferably the compound according to the invention is used against: Diseases caused by powdery mildew pathogens, such as *Podosphaera* species (e.g. *Podosphaera leucotricha*), Sphaerotheca species (e.g. Sphaerotheca *fuliginea*); diseases caused by rust disease pathogens, such as *Uromyces* species (e.g. *Uromyces appendiculatus*); diseases caused by pathogens from the group of the Oomycetes, such as *Peronospora* species (e.g. *Peronospora parasitica*), *Phytophthora* species (e.g. *Phytophthora infestans*), *Plasmopara* species (e.g. *Plasmopara viticola*), *Pseudoperonospora* species (e.g. *Pseudoperonospora humuli* or *Pseudoperonospora cubensis*), *Pythium* species (e.g. *Pythium ultimum*); leaf blotch diseases and leaf wilt diseases caused, for example, by *Alternaria* species (e.g. *Alternaria solani*), *Cercospora* species (e.g. *Cercospora beticola*), *Colletotrichum* species (e.g. *Colletotrichum lindemuthanium*), *Venturia* species (e.g. *Venturia inaequalis*); diseases caused by bacterial pathogens, for example *Xanthomonas* species (e.g. *Xanthomonas campestris* pv. *campestris*), *Pseudomonas* species (e.g. *Pseudomonas syringae* pv. tomato), *Erwinia* species (e.g. *Erwinia amylovora*), Liberibacter species (e.g. Liberibacter Candidatus), *Ralstonia* species (e.g. *Ralstonia solanacearum*).

According to further aspect of the present invention the compound of formula (II) according to the invention is used plant defense activator. A plant defense inducer according to the invention is a compound or composition which stimulates the plants' own defense system.

The present invention also relates to a compound of formula (II-A):

(II-A)

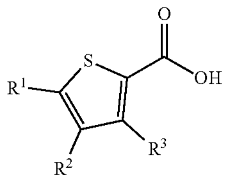

wherein $R^1$ is selected from the group consisting of halogen, cyano, methyl or $C_1$-$C_2$-haloalkyl;

$R^2$ is selected from the group consisting halogen, cyano or $C_1$-$C_2$-haloalkyl;

$R^3$ is selected from the group consisting of halogen, cyano, methyl or $C_1$-$C_2$-haloalkyl;

wherein at least two of $R^1$, $R^2$ or $R^3$ are halogen;

provided that compounds of formula (II-A) with the following combinations of $R^1$, $R^2$ and $R^3$

| $R^1$ | $R^2$ | $R^3$ |
|---|---|---|
| Cl | Cl | halogen |
| Br | Br | halogen |
| Cl | Cl | methyl |

-continued

| $R^1$ | $R^2$ | $R^3$ |
|---|---|---|
| Br | Br | methyl |
| Cl | I | F |
| Br | I | I |
| I | I | F |
| I | I | methyl |
| I | I | I |
| methyl | I | F |
| methyl | Br | Br |
| methyl | I | I |
| Br | cyano | Br |
| I | cyano | I |
| F | Br | methyl |
| Cl | Br | F |

are excluded.

WO 2020/079205 discloses 3-fluoro-5-iodothiophene-2-carboxylic acid and 5-bromo-4-chloro-3-fluorothiophene-2-carboxylic acid; FR 3 052 451 discloses 5-chloro-3-fluoro-4-methylthiophene-2-carboxylic acid and 4,5-dichloro-3-fluorothiophene-2-carboxylic acid; HULL JOHN W J R ET AL: "Development of potential manufacturing routes for substituted thiophenes—Preparation of halogenated 2-thiophenecarboxylic acid derivatives as building blocks for a new family of 2,6-dihaloaryl 1,2,4-triazole insecticides", BEILSTEIN JOURNAL OF ORGANIC CHEMISTRY, BIOMED CENTRAL, LONDON, GB, vol. 3, no. 1, 4 Sep. 2007 (2007-09-04), page 23, XP021041099, ISSN: 1860-5397 discloses 3,5-dibromo-4-methylthiophene-2-carboxylic acid; KOCHANNY ET AL: "Substituted thiophene-anthranilamides as potent inhibitors of human factor Xa", BIOORGANIC & MEDICINAL CHEMISTRY: A TETRAHEDRON PUBLICATION FOR THE RAPID DISSEMINATION OF FULL ORIGINAL RESEARCH PAPERS AND CRITICAL REVIEWS ON BIOMOLECULAR CHEMISTRY, MEDICINAL CHEMISTRY AND RELATED DISCIPLINES, ELSEVIER, NL, vol. 15, no. 5, 31 Jan. 2007 (2007-01-31), pages 2127-2146, XP005867178, ISSN: 0968-0896, DOI: 10.1016/J.BMC.2006.12.019 discloses 3-chloro-5-(chloromethyl)-4-methylthiophene-2-carboxylic acid and STEINKOPF W ET AL: "Thiophene series. XXXVII. Iodine derivatives of 3-thiotolene", JUSTUS LIEBIGS ANNALEN DER CHEMIE, VERLAG CHEMIE GMBH, DE, vol. 532, 1 Jan. 1937 (1937-01-01), pages 236-249, XP009107181, ISSN: 0075-4617, DOI: 10.1002/JLAC.19375320120 discloses 4,5-diiodo-3-methylthiophene-2-carboxylic acid. However, none of the aforementioned prior art compounds falls within the scope of the present invention as they are all excluded by the proviso.

In an embodiment, $R^1$ is halogen, cyano, methyl or $C_1$-$C_2$-haloalkyl. In an embodiment, $R^1$ is halogen, cyano, methyl, trifluoromethyl or difluoromethyl. In an embodiment, $R^1$ is halogen, cyano or methyl.

In an embodiment, $R^1$ is halogen or cyano. In an embodiment, $R^1$ is $C_1$-$C_2$-haloalkyl. In an embodiment, $R^1$ is trifluoromethyl or difluoromethyl.

In an embodiment, $R^2$ is halogen, cyano or $C_1$-$C_2$-haloalkyl. In an embodiment, $R^2$ is halogen, cyano, trifluoromethyl or difluoromethyl. In an embodiment, $R^1$ is halogen or cyano. In an embodiment, $R^2$ is $C_1$-$C_2$-haloalkyl. In an embodiment, $R^2$ is trifluoromethyl or difluoromethyl.

In an embodiment, $R^3$ is halogen, cyano, methyl or $C_1$-$C_2$-haloalkyl. In an embodiment, $R^3$ is halogen, cyano, methyl, trifluoromethyl or difluoromethyl. Not encompassed herein are compounds resulting from combinations which are against natural laws and which the person skilled in the art would therefore exclude based on his/her expert knowledge. For instance, ring structures having three or more adjacent oxygen atoms are excluded.

Depending on the nature of the substituents, the compound of formula (I) or (II) may be present in the form of different stereoisomers. These stereoisomers are, for example, enantiomers, diastereomers, atropisomers or geometric isomers. Accordingly, the invention encompasses both pure stereoisomers and any mixture of these isomers. Where a compound can be present in two or more tautomer forms in equilibrium, reference to the compound by means of one tautomeric description is to be considered to include all tautomer forms.

Any of the compounds of the present invention can also exist in one or more geometric isomer forms depending on the number of double bonds in the compound. Geometric isomers by nature of substituents about a double bond or a ring may be present in cis (=Z-) or trans (=E-) form. The invention thus relates equally to all geometric isomers and to all possible mixtures, in all proportions.

The compound of formula (I) or (II) can suitably be in its free form, salt form, N-oxide form or solvate form (e.g. hydrate).

Depending on the nature of the substituents, the compound of formula (I) or (II) may be present in the form of the free compound and/or a salt thereof, such as an agrochemically active salt.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulfuric monoesters, alkylsulfonic acids (sulfonic acids having straight-chain or branched alkyl radicals having 1 to 20 carbon atoms), arylsulfonic acids or aryldisulfonic acids (aromatic radicals, such as phenyl and naphthyl, which bear one or two sulfonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulfonic acid, salicylic acid, p-aminosalicylic acid, 2-phenoxybenzoic acid, 2-acetoxybenzoic acid, etc.

Solvates of the compounds of formula (I) or (II) or their salts are stoichiometric compositions of the compounds with solvents.

The compounds of formula (I) or (II) may exist in multiple crystalline and/or amorphous forms.

Crystalline forms include unsolvated crystalline forms, solvates and hydrates.

Processes for the Preparation of Compounds of Formula (I)

The present invention relates to processes for the preparation of compounds of formula (I). The compounds of formula (I) can be prepared by various routes in analogy to known processes (see references therein), and by one or more of the following synthetic routes described herein below and in the experimental part.

General Synthetic Routes to the Compounds of Formula (I)

Unless indicated otherwise, in the following, $R^1$, $R^2$, $R^3$, $R^4$, $R^5$, $R^6$, $R^7$, W, Y, Z and n have the same meaning as given above for compounds of formula (I).

Process A1

Compounds of formula (Ia) can be prepared by a process A1 which comprises the step of reacting a compound of formula (III) or one of its salts with a compound of formula (IV) or one of its salts as illustrated by the following reaction scheme:

Process A1

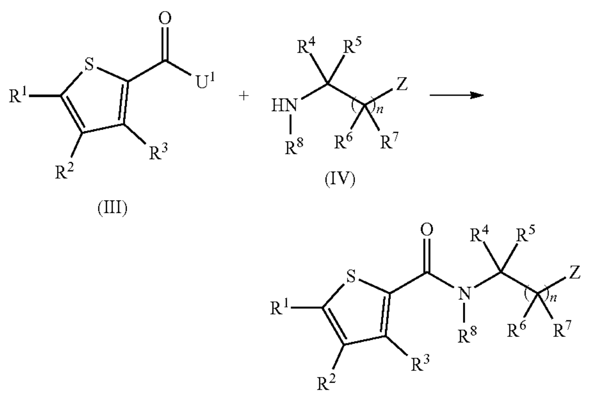

(III) (IV) (Ia)

wherein $U^1$ is halogen, hydroxy or $C_1$-$C_6$-alkoxy.

When $U^1$ represents hydroxy, process A1 is advantageously conducted in the presence of a condensing agent. Suitable condensing agents may be selected in the non-limited list consisting of acid halide former, such as phosgene, phosphorous tribromide, phosphorous trichloride, phosphorous pentachloride, phosphorous trichloride oxide, oxalyl chloride or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC), N-(3-Dimethylaminopropyl)-N'-ethylcarbodiimide hydrochloride (EDC) or other customary condensing agents, such as phosphorous pentoxide, polyphosphoric acid, bis(2-oxo-3-oxazolidinyl)phosphinic chloride, 1-[bis(dimethylamino)methylene]-1H-1,2,3-triazolo[4,5-b]pyridinium 3-oxid hexafluorophosphate (HATU), 2-(1H-Benzotriazole-1-yl)-1,1,3,3-tetramethylaminium tetrafluoroborate (TBTU), (1-cyano-2-ethoxy-2-oxoethylidenaminooxy)dimethylamino-morpholino-carbenium hexafluorophosphate, N,N'-carbonyl-diimidazole, 2-ethoxy-N-ethoxycarbonyl-1,2-dihydroquinoline (EEDQ), triphenylphosphine/tetrachloro-methane, 4-(4,6-dimethoxy[1.3.5]-triazin-2-yl)-4-methylmorpholinium chloride hydrate, bis(2-oxo-3-oxazolidinyl)phosphinic chloride (BOP-Cl), bromo-tripyrrolidinophosphoniumhexafluorophosphate (PyBroP), 2-chloro-1,3-dimethylimidazolinium chloride (DMC), propanephosphonic anhydride (T3P) and 3-(diethoxyphosphoryloxy)-1,2,3-benzotriazin-4(3H)-one (DEPBT).

When $U^1$ represents halogen, process A1 is advantageously conducted in the presence of an acid binder. Suitable acid binders for carrying out process A1 are in each case all inorganic and organic bases that are customary for such reactions. Preference is given to alkali metal carbonates, such as cesium carbonate, sodium carbonate, potassium carbonate, potassium bicarbonate, sodium bicarbonate, alkaline earth metal acetates, such as sodium acetate, potassium acetate, calcium acetate and also tertiary amines, such as trimethylamine, triethylamine, diisopropylethylamine, tributylamine, N,N-dimethylaniline, N-methylpiperidine, N,N-dimethylpyridin-4-amine, diazabicyclooctane (DABCO), diazabicyclo-nonene (DBN) or diazabicycloundecene (DBU), or aromatic bases such as pyridine.

When $U^1$ represents $C_1$-$C_6$-alkoxy, process A1 can be conducted with an excess of the amine component, optionally in the presence of a Lewis acid such as trimethylaluminium.

If appropriate, process A1 can be performed in the presence of a base and if appropriate, in the presence of a solvent, preferably under anhydrous conditions.

Suitable solvents for carrying out process A1 are not particularly limited. They can be customary inert organic solvents as long as it is not dissolving the compound to react therewith or exhibit any particular interaction therewith. Preference is given to using optionally halogenated, aliphatic, alicyclic or aromatic hydrocarbons, such as petroleum ether, pentane, hexane, heptane, cyclohexane, methylcyclohexane, benzene, toluene, xylene, decalin, ISOPAR™ E or ISOPAR™ G, chlorobenzene, dichlorobenzene, dichloromethane, chloroform, carbon tetrachloride, 1,2-dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

Process A1 may be performed in an inert atmosphere such as argon or nitrogen atmosphere. When carrying out process A1, 1 mole or an excess of compound of formula (IV) and from 1 to 5 moles of base can be employed per mole of compound of formula (III). It is also possible to employ the reaction components in other ratios. Work-up is carried out by known methods.

Compounds of formula (IV) are commercially available or can be prepared by well-known processes (J. Med. Chem. 2018, 61, 8670-8692; Tetrahedron, 44(1), 195-202; 1988, WO2009070485; WO2019086142; Chem. Res. Toxicol. 1990, 3, 118-124; JP49035334; JP49000223; Journal of Organic Chemistry (1989), 54(12), 2940-2949).

Compounds of formula (IIIa) wherein $U^1$ represents hydroxy are commercially available, can be prepared from compounds of formula (IIIb) wherein $U^1$ represents $C_1$-$C_6$-alkoxy by well-known processes such as basic hydrolysis or can be prepared by known processes (Beilstein *J. Org. Chem.* 2007, 3, No. 23)

Compounds of formula (IIIc) wherein $U^1$ represents halogen are commercially available or can be prepared from compounds of formula (IIIa) wherein $U^1$ represents hydroxy by well-known processes.

Compounds of formula (IIIb) wherein $U^1$ represents $C_1$-$C_6$-alkoxy can be prepared from compounds of formula (IIIa) wherein $U^1$ represents hydroxy by well-known processes.

Process B1

Compounds of formula (Ib), wherein $R^1$ is $C_1$-$C_6$-alkyl, (Ic) wherein $R^2$ is $C_1$-$C_6$-alkyl and (Id) wherein $R^3$ is $C_1$-$C_6$-alkyl can be prepared by a process B1 which comprises the step of reacting a compound of formula (Va), (Vb) or (Vc) or one of its salts with a compound of formula (VIa), (VIb) or (VIc) or one of its salts as illustrated by the following reaction scheme:

Process B1

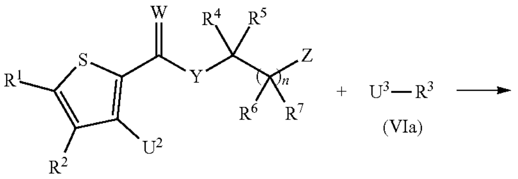

(Va)

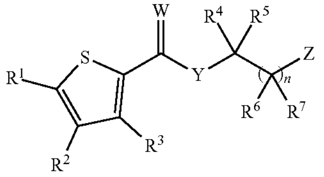

(Ib)

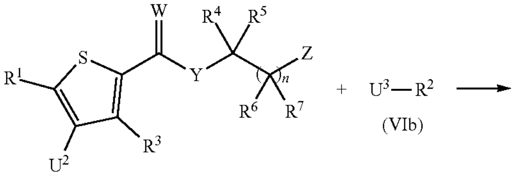

(Vb)

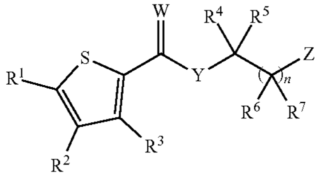

(Ic)

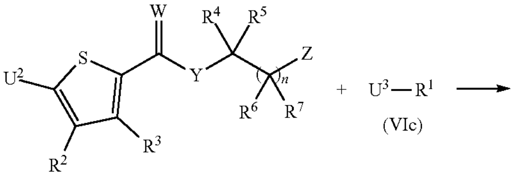

(Vb)

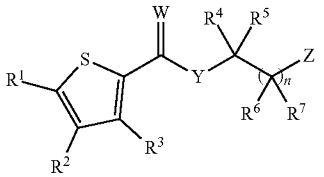

(Id)

wherein $U^3$ is a boron derivative such as a boronic acid, a boronic ester derivative, a potassium trifluoroborate derivative or a halogenometal that can be complexed by 1 to 2 ligands such as a halogenomagnesium or a halogenozinc, and wherein:

for (Va), $U^2$ is bromine, iodine, a mesylate group, a tosylate group or a triflate group provided that:

$R^1$ or $R^2$ is not iodine when $R^1$ or $R^2$ is bromine, $U^2$ is not bromine for (Vb), $U^2$ is bromine, iodine, a mesylate group, a tosylate group or a triflate group provided that:

$R^1$ or $R^3$ is not iodine when $R^1$ or $R^3$ is bromine, $U^2$ is not bromine for (Vc), $U^2$ is bromine, iodine, a mesylate group, a tosylate group or a triflate group provided that:

$R^2$ or $R^3$ is not iodine when $R^2$ or $R^3$ are bromine, $U^2$ is not bromine.

Process B1 can be performed in the presence of a transition metal catalyst such as palladium and if appropriate, in the presence of a phosphine ligand or a N-heterocyclic carbene ligand, if appropriate, in the presence of a base and if appropriate, in the presence of a solvent according to known processes (WO2012054721, Angew. Chem. Int. Ed. 2017, 56, 1581, Angew. Chem. Int. Ed. 2017, 56, 7078, and cited references therein).

Process B1 can be carried out in the presence of a catalyst, such as a metal salt or complex. Suitable metal derivatives for this purpose are transition metal catalysts such as palladium. Suitable metal salts or complexes for this purpose are for example, palladium chloride, palladium acetate, tetrakis(triphenylphosphine)palladium(0), bis(dibenzylideneacetone)palladium(0), tris(dibenzylideneacetone)dipalladium(0), bis(triphenylphosphine)palladium(II) dichloride, [1,1'-bis(diphenylphosphino)ferrocene]dichloropalladium (II), bis(cinnamyl)dichlorodipalladium(II), bis(allyl)-dichlorodipalladium(II), [1,1'-bis(di-tert-butylphosphino)ferrocene]dichloropalladium(II), di-μ-iodobis(tri-tert-butylphosphino)dipalladium(I) or di-μ-bromobis(tri-tert-butylphosphino)dipalladium(I).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenyl-phosphine, tris-(o-tolyl)phosphine, sodium 3-(diphenylphosphino)benzenesulfonate, tris-2-(methoxy-phenyl)phosphine, 2,2'-bis(diphenylphosphino)-1,1'-binaphthyl, 1,4-bis (diphenylphosphino)butane, 1,2-bis(diphenylphosphino) ethane, 1,4-bis(dicyclohexylphosphino)butane, 1,2-bis(dicyclohexylphosphino)-ethane, 2-(dicyclohexylphosphino)-2'-(N,N-dimethylamino)-biphenyl, 1,1'-bis(diphenylphosphino)-ferrocene, (R)-(−)-1-[(S)-2-diphenyl-phosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Suitable bases for carrying out process B1 can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkaline earth metal, alkali metal or ammonium fluorides such as potassium fluoride, cesium fluoride or tetrabutylammonium fluoride; alkaline earth metal or alkali metal carbonates, such as sodium carbonate, potassium carbonate, potassium bicarbonate, sodium bicarbonate or cesium carbonate; alkali metal or alkaline earth metal acetates, such as sodium acetate, lithium acetate, potassium acetate or calcium acetate; alkali metal or alkaline earth metal phosphate, such as tripotassium phosphate alkali; alkali metal alcoholates, such as potassium tert-butoxide or sodium tert-butoxide; tertiary amines, such as trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN) or diazabicycloundecene (DBU); and also aromatic bases, such as pyridine, picolines, lutidines or collidines.

Suitable solvents for carrying out process B1 can be customary inert organic solvents. Preference is given to using optionally halogen atomated aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

It can also be advantageous to carry out process B1 with a co-solvent such as water or an alcohol such as methanol, ethanol, propanol, isopropanol or tert-butanol.

Process B1 may be performed in an inert atmosphere such as argon or nitrogen atmosphere. When carrying out process B1, 1 mole or an excess of compound of formula (VIa), (VIb) or (VIc) and from 1 to 5 moles of base and from 0.01 to 20 mole percent of a palladium complex can be employed per mole of compound of formula (Va), (Vb) or (Vc). It is also possible to employ the reaction components in other ratios. Work-up is carried out by known methods.

Compounds of formula (VIa), (VIb) or (VIc) are commercially available or can be prepared by well-known processes.

Compounds of formula (Va), (Vb) or (Vc) wherein W is oxygen can be prepared by reacting a compound of formula (VIIa), (VIIb) or (VIIc) with a compound of formula (IV) in the conditions as described in connection with process A1:

(VIIa)

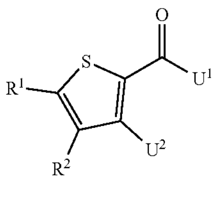

-continued (VIIb)

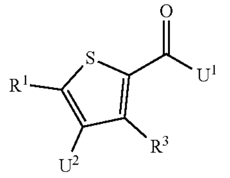

(VIIc)

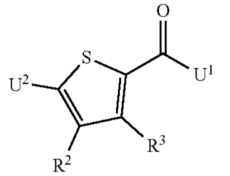

wherein $U^2$ and $U^1$ are as herein-defined.

Compounds of formula (VIIa), (VIIb) or (VIIc) wherein $U^2$ is chlorine, bromine or iodine are commercially available or can be prepared by well-known processes with the similar reaction conditions than the ones disclosed to prepare compounds of formula (III).

Compounds of formula (VIIa), (VIIb) or (VIIc) wherein $U^2$ is a mesylate group, a tosylate group or a triflate group can be prepared by well-known processes from the corresponding compound bearing a hydroxy group at the $U_2$ position.

Process C1

Compounds of formula (Ie) can be prepared by a process C1 from a compound of formula (Ia) by performing a thionation reaction as illustrated in the following reaction scheme:

Process C1

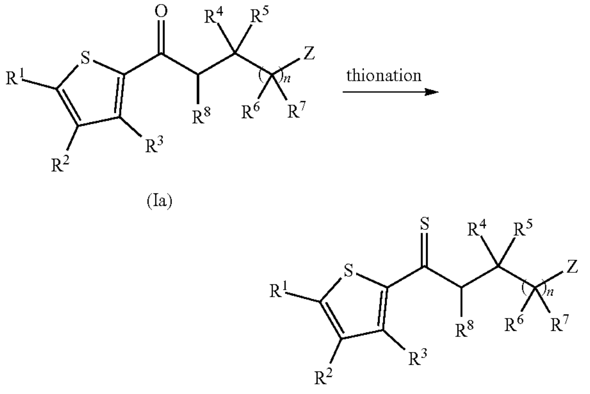

(Ia)

(Ie)

Process C1 according to the invention is performed in the presence of a thionating agent.

Suitable thionating agents for carrying out process C1 according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide ($(AlEt_2)_2S$), ammonium sulfide ($(NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358, in the optionally presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylpyridin-4-amine or N-methyl-piperidine.

Suitable solvents for carrying out process C1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichloroethane or trichloroethane, ethers, such as diethyl ether, diisopropyl ether, methyl t-butyl ether, methyl t-amyl ether, dioxane, tetrahydrofuran, 1,2-dimethoxyethane or 1,2-diethoxyethane, nitriles, such as acetonitrile, propionitrile, n- or i-butyronitrile or benzonitrile, sulfurous solvents, such as sulfolane or carbon disulfide.

When carrying out process C1 according to the invention, 1 mole or an excess of the sulfur equivalent of the thionating agent and from 1 to 3 moles of the base can be employed per mole of the amide reactant (Ia).

It is also possible to employ the reaction components in other ratios. Work-up is carried out by known methods.

Process D1

Compounds of formula (If, wherein $R^1$ is cyano, (Ig) wherein $R^2$ is cyano and (Ih) wherein $R^3$ is cyano can be prepared by a process D1 which comprises the step of reacting a compound of formula (Va), (Vb) or (Vc) or one of its salts with cyanation reagent according to known processes (Chem. Rev. 1987, 87, 4, 779-794; Chem. Soc. Rev., 2011, 40, 5049-5067; WO2012123471 and cited references therein).

Process D1 can be performed in the presence of a transition metal catalyst such as a metal salt or complex, and if appropriate in the presence of a ligand; if appropriate in the presence of a base and if appropriate in the presence of a solvent. Suitable metal derivatives for this purpose are transition metal such as palladium or copper. Suitable solvents for carrying out process D1 are not particularly limited. They can be customary inert organic solvents as long as it is not dissolving the compound to react therewith or exhibit any particular interaction therewith. Suitable solvents can be for instance the solvents disclosed in connection with process A1. Examples of cyanation agents include potassium ferrocyanide, copper cyanide, zinc cyanide, sodium cyanide, potassium cyanide.

Process E1

Compounds of formula (I) as herein defined can be prepared by a process E1 from a compound of formula (VIII) or one of its salts by performing a halogenation reaction as illustrated in the following reaction scheme:

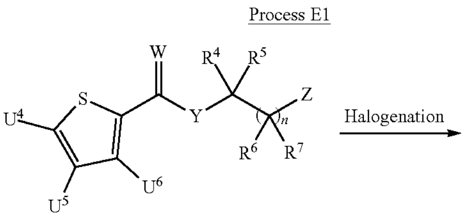

(VIII)

-continued

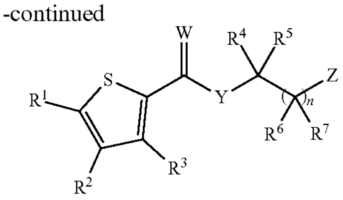

(I)

wherein $U^4$, $U^5$ and $U^6$ are independently selected from the list consisting of hydrogen, halogen, cyano, $C_1$-$C_6$-alkyl or $C_1$-$C_6$-haloalkyl provided that one of $U^4$, $U^5$ or $U^6$ is at least hydrogen.

Process E1 can be carried out according to known processes (Angewandte Chemie, International Edition, 52(16), 4440-4444; 2013; ACS Catalysis, 6(11), 7839-7843; 2016; Journal of the American Chemical Society, 2017, 139, 888; Angewandte Chemie, International Edition, 2014, 53, 7928; Journal of the American Chemical Society, 2018, 140, 2789; WO2008156879; WO2012114285; WO2008109786; WO2007098356).

Process E1 is performed in the presence of a halogenation agent and if appropriate, in the presence of a solvent.

Suitable halogenation agents for carrying out process E1 are not particularly limited provided they are used for bromination, chlorination, iodination or fluorination. Examples of bromination agents include bromine, N-bromosuccinimide, 1,2-dibromotetrachloroethane and 1,3-dibromo-5,5-dimethyl-2,4-imidazolidinedione. Examples of chlorination agents include N-chlorosuccinimide, hexachloroethane, sulfuryl chloride and 1,3-dichloro-5,5-dimethyl-2,4-imidazolidinedione. Examples of iodination agents include iodine, N-iodosuccinimide, iodine chloride and 1,3-diiodo-5,5-dimethyl-2,4-imidazolidinedione. Examples of fluorination agents include N-fluorobenzenesulfonimide and 1-chloromethyl-4-fluoro-1,4-diazoniabicyclo[2.2.2]octane bis(tetrafluoroborate.

Suitable solvents for carrying out process E1 are not particularly limited. They can be customary inert organic solvents as long as it is not dissolving the compound to react therewith or exhibit any particular interaction therewith. Suitable solvents can be for instance the solvents disclosed in connection with process A1. To carry out process E1, it can also be advantageous to use an organic acid such as acetic acid or trifluoroacetic acid as a solvent or a co-solvent. To carry out process E1, it can also be advantageous to use a Lewis acid such as zinc chloride (II) as catalyst. To carry out process E1, it can also be advantageous to use transition metal catalysts such as palladium catalysts. To carry out process E1, it can also be advantageous to use an appropriate organometallic reagent such as n-butyllithium. To carry out process E1, according to known process (WO2020079205), it can also be advantageous to use an appropriate base prior to halogenation, such as n-butyllithium, lithium di-isopropylamine, lithium tetramethylpiperidide, lithium bis(trimethylsilyl)amine, methyllithium or chloro-(2,2,6,6-tetramethyl-1-piperidyl)magnesium and the like, preferably under anhydrous conditions. Optionally lithium chloride can be used in pre-formed combination with these reagents.

Process F1

Compounds of formula (Ii) as herein-defined wherein $R^3$ is halogen, cyano, $C_1$-$C_6$-alkyl or $C_1$-$C_6$-haloalkyl can be prepared by a process F1 comprising the step of performing a diazotation of a compound of formula (IX) or one of its salts followed by an aromatic substitution to provide a compound of formula (Ii) as illustrated in the following reaction scheme:

Process F1

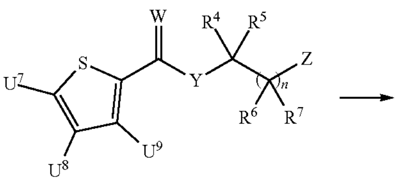

(IX)

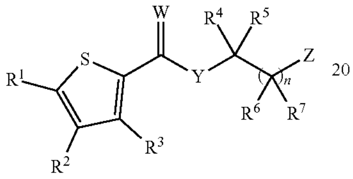

(Ii)

wherein $U^7$, $U^8$ and $U^9$ are independently selected from the list consisting of amino group, halogen, cyano, $C_1$-$C_6$-alkyl or $C_1$-$C_6$-haloalkyl provided that one of $U^7$, $U^8$ or $U^9$ is at least an amino group.

Process F1 can be carried out according to known processes (The Chemistry of diazonium and diazo groups; Saul Patai; Wiley-Interscience; 1978; 288-280 and 645-657; Account of Chemical Research (2018), 51, 496 and cited references therein).

Compounds of formula (IX) or one of its salts as herein-defined can be prepared by a process comprising the step of reducing a nitro group according to well-known methods (Science of Synthesis: Catalytic Reduction in Organic Synthesis 2; J. G. de Vries, 2018, chapter 2.7: Reduction of Nitro Compounds to Amines, Azo Compounds, Hydroxylamines, and Oximes, and Reduction of N-Oxides to Amines, and references therein) or deprotecting a protected amino group according to well-known methods.

Examples of protecting groups of the amino group include a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl, an allyloxycarbonyl, an acetyl group or a trifluoroacetyl group.

The deprotection process can be carried out according to known processes for removing protecting groups (Greene's Protective Groups in Organic Synthesis; Peter G. M. Wuts; Wiley; Fifth Edition; 2014; 895-1194). For example, tert-butoxycarbonyl and benzyloxycarbonyl protecting groups can be removed in an acidic medium (for example with hydrochloric acid or trifluoroacetic acid). Benzylic protecting groups can be removed hydrogenolytically with hydrogen in the presence of a catalyst (for example palladium on activated carbon). Trifluoroacetyl group can be removed in a basic medium (for example with potassium carbonate or lithium hydroxide).

Compounds of formula (Ij) wherein Z is —C(═O)—$OR^a$, wherein $R^a$ is selected from the group consisting of $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered non-aromatic heterocyclyl, —$C_1$-$C_6$-alkyl-Si($C_1$-$C_6$-alkyl)$_3$, —$C_1$-$C_6$-alkyl-$C_3$-$C_8$-cycloalkyl, 5- to 9-membered heteroaryl and —$C_1$-$C_6$-alkyl-5- to 9-membered heteroaryl can be prepared from compounds of formula (Ik) wherein Z is —C(═O)—$OR^a$, wherein $R^a$ is hydrogen and corresponding alcohols or one of their salts by well-known coupling processes in the conditions as described in connection with process A1.

Compounds of formula (Ik) wherein Z is —C(═O)—$OR^a$, wherein $R^a$ is hydrogen can be prepared from compounds of formula (Ij) wherein Z is —C(═O)—$OR^a$, wherein $R^a$ is selected from the group consisting of $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered non-aromatic heterocyclyl, —$C_1$-$C_6$-alkyl-Si($C_1$-$C_6$-alkyl)$_3$, —$C_1$-$C_6$-alkyl-$C_3$-$C_8$-cycloalkyl, 5- to 9-membered heteroaryl and —$C_1$-$C_6$-alkyl-5- to 9-membered heteroaryl by well-known processes such as hydrolysis. Examples of hydrolysis reagents include lithium hydroxide, potassium hydroxide, sodium hydroxide, trimethyltin hydroxide. Hydrolysis may be performed as described in WO2008157844; WO2006002099; WO20050256107; Angewandte Chemie, International Edition (2005), 44(9), 1378-1382.

Compounds of formula (Im) wherein Z is —C(═O)—$SR^a$, —C(═O)—$NR^bR^c$ or —C(═O)—NH—$CR^dR^e$—C(═O)—$OR^a$ can be prepared from compounds of formula (Ik) wherein Z is —C(═O)—$OR^a$, wherein $R^a$ is hydrogen and corresponding thiols, amines or one of their salts by well-known coupling processes in the conditions as described in connection with process A1.

Processes for the Preparation of Compounds of Formula (II)

The present invention relates to processes for the preparation of compounds of formula (II). The compounds of formula (II) can be prepared by various routes in analogy to known processes (see references therein), and by one or more of the following synthetic routes described herein below and in the experimental part.

General Synthetic Routes to the Compounds of Formula (II)

The present invention relates to processes for the preparation of compounds of formula (II). The compounds of formula (II) can be prepared by various routes in analogy to known processes described in Beilstein Journal of Organic Chemistry (2007), 3, No. 23; WO2008109786; Justus Liebigs Annalen der Chemie (1937), 532, 236-49; Justus Liebigs Annalen der Chemie (1938), 536, 135-42; WO2017212010; WO2012021696; WO2003024961; Tetrahedron Letters (1997), 38(6), 1049-1052; WO200302496; Journal of Agricultural and Food Chemistry (2007), 55(18), 7517-7526, WO2020079205 and other references therein, or by one or more of the following synthetic routes described herein below and in the experimental part.

The compounds of formula (II) can be prepared by various routes applying successively the processes described below in various orders.

Unless indicated otherwise, in the following, $R^1$, $R^2$, $R^3$ and A have the same meaning as given above for compounds of formula (II).

Process A2

Compounds of formula (IIa), wherein $R^1$ is a $C_1$-$C_3$-alkyl, (IIb) wherein $R^2$ is a $C_1$-$C_3$-alkyl and (IIc) wherein $R^3$ is a $C_1$-$C_3$-alkyl can be prepared by a process A2 which comprises the step of reacting a compound of formula (Xa), (Xb) or (Xc) or one of its salts with a compound of formula (VIa), (VIb) or (VIc) or one of its salts as illustrated by the following reaction scheme:

Process A2

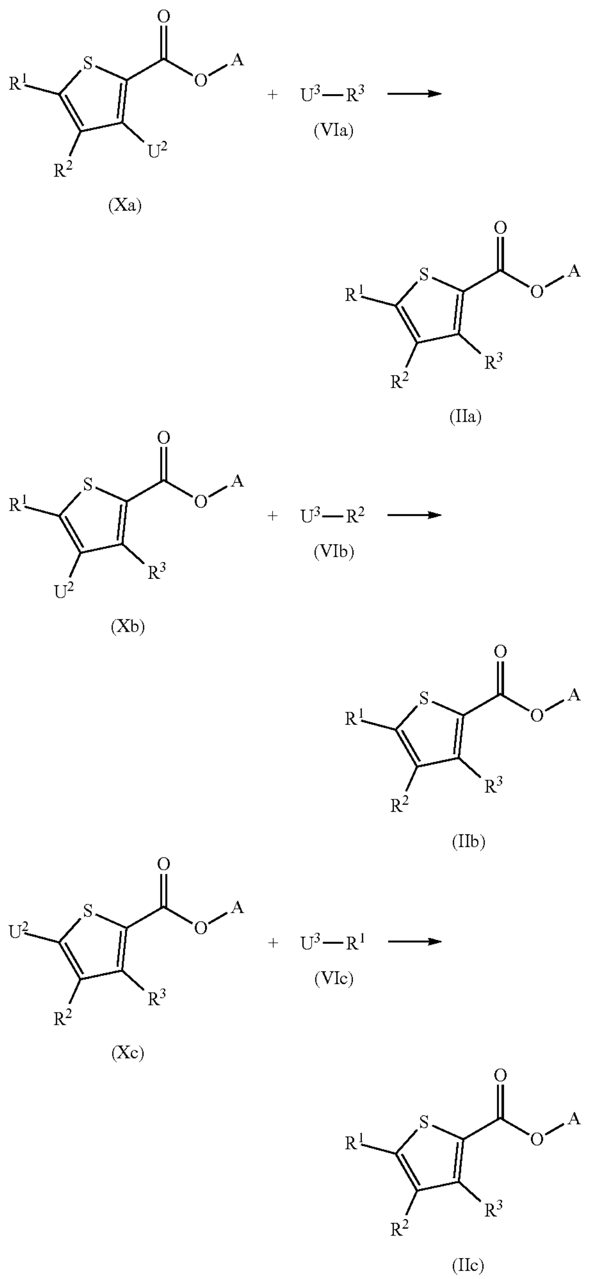

(Xa) (VIa) (IIa) (Xb) (VIb) (IIb) (Xc) (VIc) (IIc)

wherein $U^3$ is a boron derivative such as a boronic acid, a boronic ester derivative, a potassium trifluoroborate derivative or a halogenometal that can be complexed by 1 to 2 ligands such as a halogenomagnesium or a halogenozinc, and wherein:

for (Xa), $U^2$ is bromine, iodine, a mesylate group, a tosylate group or a triflate group provided that:

$R^1$ or $R^2$ is not iodine when $R^1$ or $R^2$ is bromine, $U^2$ is not bromine for (Xb), $U^2$ is bromine, iodine, a mesylate group, a tosylate group or a triflate group provided that:

$R^1$ or $R^3$ is not iodine when $R^1$ or $R^3$ is bromine, $U^2$ is not bromine for (Xc), $U^2$ is bromine, iodine, a mesylate group, a tosylate group or a triflate group provided that:

$R^2$ or $R^3$ is not iodine when $R^2$ or $R^3$ is bromine, $U^2$ is not bromine.

Process A2 can be performed in the presence of a transition metal catalyst such as palladium and if appropriate, in the presence of a phosphine ligand or a N-heterocyclic carbene ligand, if appropriate, in the presence of a base and if appropriate, in the presence of a solvent according to known processes (WO2012054721, *Angew. Chem. Int. Ed.* 2017, 56, 1581, *Angew. Chem. Int. Ed.* 2017, 56, 7078, and cited references therein).

Process A2 can be carried out in the presence of a catalyst, such as a metal salt or complex. Suitable metal derivatives for this purpose are transition metal catalysts such as palladium. Suitable metal salts or complexes for this purpose are for example, palladium chloride, palladium acetate, tetrakis(triphenylphosphine)palladium(0), bis(dibenzylideneacetone)palladium(0), tris(dibenzylideneacetone)dipalladium(0), bis(triphenylphosphine)palladium(II) dichloride, [1,1'-bis(diphenylphosphino)ferrocene]dichloropalladium (II), bis(cinnamyl)dichlorodipalladium(II), bis(allyl)-dichlorodipalladium(II), [1,1'-Bis(di-tert-butylphosphino)ferrocene]dichloropalladium(II), di-μ-iodobis(tri-tert-butylphosphino)dipalladium(I) or di-μ-bromobis(tri-tert-butylphosphino)dipalladium(I).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-2-(methoxy-phenyl) phosphine, 2,2'-bis(diphenylphosphino)-1,1'-binaphthyl, 1,4-bis(diphenylphosphino)butane, 1,2-bis(diphenylphosphino) ethane, 1,4-bis(dicyclohexylphosphino)butane, 1,2-bis(dicyclohexylphosphino)-ethane, 2-(dicyclohexylphosphino)-2'-(N,N-dimethylamino)-biphenyl, 1,1'-bis (diphenylphosphino)-ferrocene, (R)-(−)-1-[(S)-2-diphenylphosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl) imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Suitable bases for carrying out process A2 can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkaline earth metal, alkali metal or ammonium fluorides such as potassium fluoride, cesium fluoride or tetrabutylammonium fluoride; alkaline earth metal or alkali metal carbonates, such as sodium carbonate, potassium carbonate, potassium bicarbonate, sodium bicarbonate or cesium carbonate; alkali metal or alkaline earth metal acetates, such as sodium acetate, lithium acetate, potassium acetate or calcium acetate; alkali metal or alkaline earth metal phosphate, such as tripotassium phosphate alkali; alkali metal alcoholates, such as potassium tert-butoxide or sodium tert-butoxide; tertiary amines, such as trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN) or diazabicycloundecene (DBU); and also aromatic bases, such as pyridine, picolines, lutidines or collidines.

Suitable solvents for carrying out process A2 can be customary inert organic solvents. Preference is given to using optionally halogen atomated aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

It can also be advantageous to carry out process A2 with a co-solvent such as water or an alcohol such as methanol, ethanol, propanol, isopropanol or tert-butanol.

Process A2 may be performed in an inert atmosphere such as argon or nitrogen atmosphere. When carrying out process A, 1 mole or an excess of compound of formula (VIa), (Vib) or (Vic) and from 1 to 5 moles of base and from 0.01 to 20 mole percent of a palladium complex can be employed per mole of compound of formula (Xa), (Xb) or (Vc). It is also possible to employ the reaction components in other ratios. Work-up is carried out by known methods.

Compounds of formula (VIa), (Vib) or (VIc) are commercially available or can be prepared by well-known processes.

Compounds of formula (Xa), (Xb) or (Xc) are commercially available or can be prepared by well-known processes.

Process B2

Compounds of formula (IId), wherein $R^1$ is a cyano, (IIe) wherein $R^2$ is a cyano and (IIf) wherein $R^3$ is a is a cyano can be prepared by a process B2 which comprises the step of reacting a compound of formula (Xa), (Xb) or (Xc) or one of its salts with cyanation reagent according to known processes (Chem. Rev. 1987, 87, 4, 779-794; Chem. Soc. Rev., 2011, 40, 5049-5067; WO2012123471 and cited references therein).

Process B2 can be performed in the presence of a transition metal catalyst such as a metal salt or complex, and if appropriate in the presence of a ligand; if appropriate in the presence of a base and if appropriate in the presence of a solvent. Suitable metal derivatives for this purpose are transition metal such as palladium or copper. Suitable solvents for carrying out process B2 are not particularly limited. They can be customary inert organic solvents as long as it is not dissolving the compound to react therewith or exhibit any particular interaction therewith. Suitable solvents can be for instance the solvents disclosed in connection with process A2. Examples of cyanation agents include potassium ferrocyanide, copper cyanide, zinc cyanide, sodium cyanide, potassium cyanide.

Process C2

Compounds of formula (II) as herein defined can be prepared by a process C2 from a compound of formula (XI) or one of its salts by performing a halogenation reaction as illustrated in the following reaction scheme:

Process C2

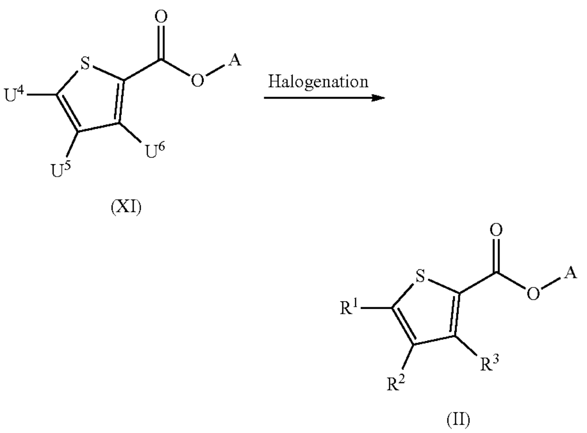

wherein $U^4$, $U^5$ and $U^6$ are independently selected from the list consisting of hydrogen, halogen, cyano, $C_1$-$C_3$-alkyl or $C_1$-$C_3$-haloalkyl provided that one of $U^4$, $U^5$ or $U^6$ is at least hydrogen.

Process C2 can be carried out according to known processes (Angewandte Chemie, International Edition, 52(16), 4440-4444; 2013; ACS Catalysis, 6(11), 7839-7843; 2016; Journal of the American Chemical Society, 2017, 139, 888; Angewandte Chemie, International Edition, 2014, 53, 7928; Journal of the American Chemical Society, 2018, 140, 2789; WO2008156879; WO2012114285; WO2008109786; WO2007098356).

Process C2 is performed in the presence of a halogenation agent and if appropriate, in the presence of a solvent.

Suitable halogenation agents for carrying out process C2 are not particularly limited provided they are used for bromination, chlorination, iodination or fluorination. Examples of bromination agents include bromine, N-bromosuccinimide, 1,2-dibromotetrachloroethane and 1,3-dibromo-5,5-dimethyl-2,4-imidazolidinedione. Examples of chlorination agents include N-chlorosuccinimide, sulfuryl chloride, hexachloroethane and 1,3-dichloro-5,5-dimethyl-2,4-imidazolidinedione. Examples of iodination agents include iodine, N-iodosuccinimide, iodine chloride and 1,3-diiodo-5,5-dimethyl-2,4-imidazolidinedione. Examples of fluorination agents include N-fluorobenzenesulfonimide and 1-chloromethyl-4-fluoro-1,4-diazoniabicyclo[2.2.2]octane bis(tetrafluoroborate.

Suitable solvents for carrying out process C2 are not particularly limited. They can be customary inert organic solvents as long as it is not dissolving the compound to react therewith or exhibit any particular interaction therewith.

Suitable solvents can be for instance the solvents disclosed in connection with process A2. To carry out process C2, it can also be advantageous to use an organic acid such as acetic acid or trifluoroacetic acid as a solvent or a co-solvent. To carry out process C2, it can also be advantageous to use a Lewis acid such as zinc chloride (II) as catalyst. To carry out process C2, it can also be advantageous to use transition metal catalysts such as palladium catalysts.

To carry out process C2, it can also be advantageous to use an appropriate organometallic reagent such as n-butyllithium. To carry out process C2, according to known process (WO2020079205), it can also be advantageous to use an appropriate base prior to halogenation, such as n-butyllithium, lithium di-isopropylamine, lithium tetramethylpiperidide, lithium bis(trimethylsilyl)amine, methyllithium or chloro-(2,2,6,6-tetramethyl-1-piperidyl)magnesium and the like, preferably under anhydrous conditions. Optionally lithium chloride can be used in pre-formed combination with these reagents.

Process D2

Compounds of formula (II) as herein-defined can be prepared by a process D2 comprising the step of performing a diazotation of a compound of formula (XII) or one of its salts followed by an aromatic substitution to provide a compound of formula (II) as illustrated in the following reaction scheme:

Process D2

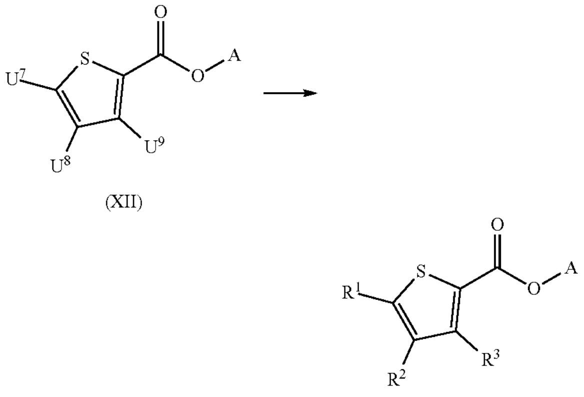

(XII)

(II)

wherein $U^7$, $U^8$ and $U^9$ are independently selected from the list consisting of amino group, halogen, cyano, $C_1$-$C_3$-alkyl or $C_1$-$C_3$-haloalkyl provided that one of $U^7$, $U^8$ or $U^9$ is at least an amino group.

Process D2 can be carried out according to known processes (The Chemistry of diazonium and diazo groups; Saul Patai; Wiley-Interscience; 1978; 288-280 and 645-657; Account of Chemical Research (2018), 51, 496 and cited references therein; Journal of Medicinal Chemistry, 46(18), 3914-3929; 2003; WO2012123471; Bioorganic & Medicinal Chemistry, 15(5), 2127-2146; 2007; WO2016092556; Advanced Synthesis & Catalysis, 356(10), 2343-2348; 2014).

Compounds of formula (XII) or one of its salts as herein-defined can be prepared by a process comprising the step of reducing a nitro group according to well-known methods (Science of Synthesis: Catalytic Reduction in Organic Synthesis 2; J. G. de Vries, 2018, chapter 2.7: Reduction of Nitro Compounds to Amines, Azo Compounds, Hydroxylamines, and Oximes, and Reduction of N-Oxides to Amines, and references therein) or deprotecting a protected amino group according to well-known methods.

Examples of protecting groups of the amino group include a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl, an allyloxycarbonyl, an acetyl group or a trifluoroacetyl group.

The deprotection process can be carried out according to known processes for removing protecting groups (Greene's Protective Groups in Organic Synthesis; Peter G. M. Wuts; Wiley; Fifth Edition; 2014; 895-1194). For example, tert-butoxycarbonyl and benzyloxycarbonyl protecting groups can be removed in an acidic medium (for example with hydrochloric acid or trifluoroacetic acid). Benzylic protecting groups can be removed hydrogenolytically with hydrogen in the presence of a catalyst (for example palladium on activated carbon). Trifluoroacetyl group can be removed in a basic medium (for example with potassium carbonate or lithium hydroxide).

Process E2

Compounds of formula (IIg) as herein-defined wherein $R^1$, $R^2$ or $R^3$ is at least respectively $C_1$-$C_3$-difluoroalkyl or $C_1$-$C_3$-fluoroalkyl can be prepared by a process E2 comprising the step of fluorination of corresponding compounds (XIII) as illustrated in the following reaction scheme:

Process E2

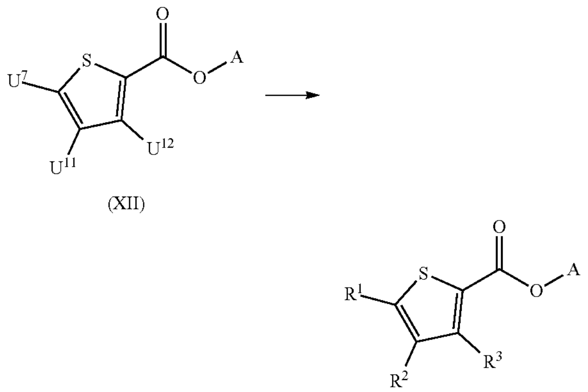

(XII)

(IIg)

wherein $U^{10}$, $U^{11}$ and $U^{12}$ are independently selected from the list consisting of respectively $C_1$-$C_3$-oxoalkylalkyl or $C_1$-$C_3$-hydroxyalkyl, halogen, cyano, $C_1$-$C_3$-alkyl or $C_1$-$C_3$-haloalkyl provided that one of corresponding $U^{10}$, $U^{11}$ or $U^{12}$ is at least respectively $C_1$-$C_3$-oxoalkylalkyl or $C_1$-$C_3$-hydroxyalkyl.

Suitable fluorinating agents for carrying out process E2 are not particularly limited provided they are used for fluorination. Examples of fluorinating agents include sulfur fluorides such as sulfur tetrafluoride, diethylaminosulfurtrifluoride, morpholinosulfur trifluoride, bis(2-methoxyethyl) aminosulfur trifluoride or 4-tert-butyl-2,6-dimethylphenylsulfur trifluoride, Process E2 may be performed as described in WO1998042347; WO2015005489; European Journal of Medicinal Chemistry, 159, 23-34; 2018.

Process F2

Compounds of formula (II) as herein-defined can be prepared by a process E2 comprising the step of hydrolysis of from compounds (XIV) as illustrated in the following reaction scheme:

Process F2

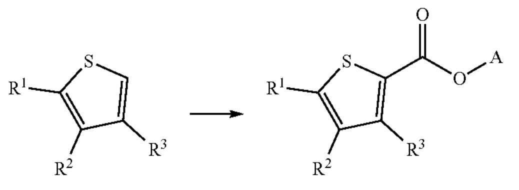

(XIV) (II)

Process F2 may be performed as described in WO2006086488; WO2013170112; WO2000021928; J. Org. Chem. 2019, 84, 16, 9869-9896; Comprehensive Organic Functional Group Transformations, Volume 5, 1995, chapter 5.02.1.2, Carbonation of Organometallic Reagents, 27-28 and references therein.

Process G2

Compounds of formula (IIh) as herein-defined provided that $R^1$, $R^2$ and $R^3$ are not cyano can be prepared by a process G2 comprising the step of hydrolysis of corresponding compounds (XV) as illustrated in the following reaction scheme:

Process F2

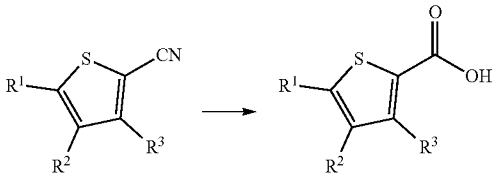

(XV) (IIh)

Process G2 may be performed as described in Beilstein Journal of Organic Chemistry, 3, No. 23, 2007; WO2012075678.

Compounds of formula (XV) are known or can be prepared by known processes.

Compounds of formula (IIi) wherein A is hydrogen can be prepared from compounds of formula (IIj) wherein A is $C_1$-$C_6$-alkyl by well-known processes such as hydrolysis. Examples of hydrolysis reagents include lithium hydroxide, potassium hydroxide, sodium hydroxide, trimethyltin hydroxide. Hydrolysis may be performed as described in WO2015043364; WO2017212010; WO2014140078; WO2003024961; WO2009154741; Angewandte Chemie, International Edition (2005), 44(9), 1378-1382.

Compounds of formula (IIj) wherein A is $C_1$-$C_6$-alkyl can be prepared from compounds of formula (IIi) wherein A is hydrogen by well-known processes such as esterification. Such processes may be performed as described in WO2017202291; Chemical Communications (Cambridge, United Kingdom), 53(8), 1370-1373; 2017; WO2010083145.

Process H2

Compounds of formula (IIi) as herein-defined can be prepared by a process H2 comprising the step of reacting a compound (XVI) as herein-defined and wherein M represents an alkali metal such as lithium that can be complexed by 1 to 2 ligands or a halogenomagnesium that can be complexed by 1 to 2 ligands with carbon dioxide as illustrated in the following reaction scheme:

Process H2

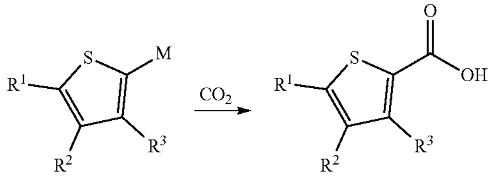

(XVI) (IIi)

Process I2

Compounds of formula (XVI) as herein-defined can be prepared by a process H2 comprising the step of metallation of a compound (XVII) wherein $U^{13}$ is selected from the list consisting of chlorine, bromine or iodine, as illustrated in the following reaction scheme:

Process G2

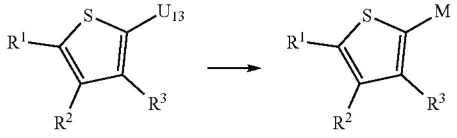

(XVII) (XVI)

Process I2 may be performed using magnesium metal or lithium metal, or by halogen/metal exchange using an alkyllithium reagent or a Grignard reagent or a manufactured complex prepared from an alkyllithium reagent or a Grignard reagent preferably under anhydrous conditions. Optionally lithium chloride can be used in pre-formed combination with these reagents.

Process I2 may be performed as described in WO2019209759, Angewandte Chemie, International Edition, 58(45), 16210-16216; 2019, New Journal of Chemistry, 41(19), 10929-10934; 2017, CN106518840, WO2014090918 or WO2013089087 and references therein.

Examples of alkyllithium reagents used in the lithiation process include methyllithium, phenyllithium, n-butyllithium, sec-butyllithium, iso-butyllithium, tert-butyllithium, and the like.

Examples of Grignard reagents used in the magnesium complexation process include methylmagnesium chloride, ethylmagnesium chloride, n-butylmagnesium chloride, isopropylmagnesium chloride, chloro-(2,2,6,6-tetramethyl-1-piperidyl)magnesium and the like. A manufactured complex prepared from n-butylmagnesium chloride and n-butyllithium may also be used.

Examples of ligands used in the lithiation process or magnesium complexation process include tetramethylethylenediamine, hexamethylphosphotriamide, (+) or (−)-sparteine or 1,3-dimethyl-3,4,5,6-tetrahydro-2(1H)-pyrimidinone.

A solvent used in the lithiation or magnesium complexation is not particularly limited as long as it forms an anhydrous reaction system without dissolving the compound to react therewith or exhibit any particular interaction therewith. Preference is given to using non-halogenated aliphatic, alicyclic or aromatic hydrocarbons, such as petroleum ether, pentane, hexane, heptane, cyclohexane, methylcyclohexane, benzene, toluene, xylene, decalin, ISOPAR (registered trademark) E or ISOPAR (registered trademark) G; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane or 1,2-diethoxyethane; and a mixture thereof.

The lithiation or magnesium complexation may be performed in an inert atmosphere and prepared at a temperature of 0° C. to −78° C.

Compounds of formula (XVII) are known or can be prepared by known processes.

Process J2

Alternatively, compounds of formula (XVI) as herein-defined can be prepared by a process J2 comprising the step of metallation of a compound (XVIII), as illustrated in the following reaction scheme:

Process J2

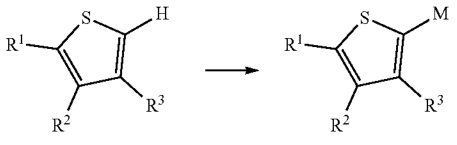

(XVIII) (XVI)

Process J2 may be performed using a base such as n-butyllithium, lithium di-isopropylamine, lithium tetramethylpiperidide, lithium bis(trimethylsilyl)amine, methyllithium or chloro-(2,2,6,6-tetramethyl-1-piperidyl)magnesium and the like, preferably under anhydrous conditions. Optionally lithium chloride can be used in pre-formed combination with these reagents.

The solvent used in the reaction of compounds (XVIII) with a base is not particularly limited as long as it forms an anhydrous reaction system without dissolving the compound to react therewith or exhibit any particular interaction therewith. Preference is given to using non-halogenated aliphatic, alicyclic or aromatic hydrocarbons, such as petroleum ether, pentane, hexane, heptane, cyclohexane, methylcyclohexane, benzene, toluene, xylene, decalin, ISOPAR (registered trademark) E or ISOPAR (registered trademark) G; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane or 1,2-diethoxyethane; and a mixture thereof.

The reaction may be performed in an inert atmosphere and prepared at a temperature of 0° C. to −78° C.

Process J2 may be performed as described in WO2006086488; WO2013170112; WO2000021928; J. Org. Chem. 2019, 84, 16, 9869-9896; Comprehensive Organic Functional Group Transformations, Volume 5, 1995, chapter 5.02.1.2, Carbonation of Organometallic Reagents, 27-28 and references therein.

Compounds of formula (XVIII) are known or can be prepared by known processes.

Alternatively, compounds of formula (IIj) wherein A is $C_1$-$C_6$-alkyl can be prepared from compounds of formula (XVII) by known processes such as photocatalytic carboxylation with carbon tetrabromide and a $C_1$-$C_6$-alkyl alcohols as described in Journal of Organic Chemistry, 84(16), 9869-9896; 2019 or direct alkoxycarbonylation via Cu-mediated trichloromethylation and in situ alcoholysis as described in organic Letters, 22(5), 2093-2098; 2020 or metalation followed by reaction with $C_1$-$C_6$-alkyl chloroformate as described in MedChemComm, 9(3), 583-589; 2018.

Intermediates for the Preparation of Compounds of Formula (I)

The present invention relates to intermediates for the preparation of compounds of formula (I) Unless indicated otherwise, in the following, $R^1$, $R^2$, $R^3$, $R^4$, $R^5$, $R^6$, $R^7$, n, W, Y and Z have the same meaning as given above for compounds of formula (I).

Compounds of formula (Va), (Vb) and (Vc) are provided:

(Va)

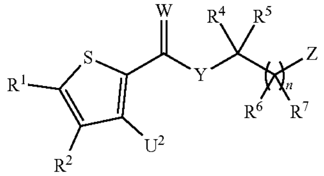

(Vb)

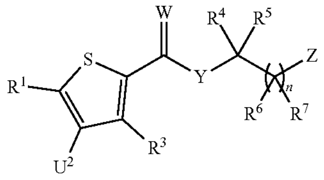

(Vc)

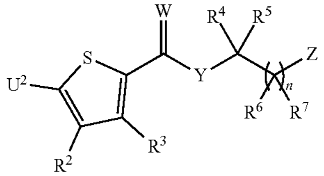

wherein for (Va), $U^2$ is bromine, iodine, a mesylate group, a tosylate group or a triflate group provided that:

$R^1$ or $R^2$ is not iodine when $R^1$ or $R^2$ is bromine, $U^2$ is not bromine for (Vb), $U^2$ is bromine, iodine, a mesylate group, a tosylate group or a triflate group provided that:

$R^1$ or $R^3$ is not iodine when $R^1$ or $R^3$ is bromine, $U^2$ is not bromine for (Vc), $U^2$ is bromine, iodine, a mesylate group, a tosylate group or a triflate group provided that:

$R^2$ or $R^3$ is not iodine when $R^2$ or $R^3$ is bromine, $U^2$ is not bromine Compounds of formula (VIII) are provided:

(VIII)

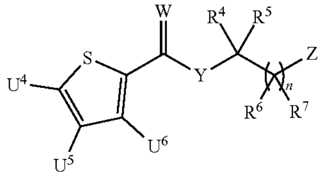

wherein $U^4$, $U^5$ and $U^6$ are independently selected from the list consisting of hydrogen, halogen, cyano, $C_1$-$C_6$-alkyl or $C_1$-$C_6$-haloalkyl provided that one of $U^4$, $U^5$ or $U^6$ is at least hydrogen.

Compounds of formula (IX) are provided:

(IX)

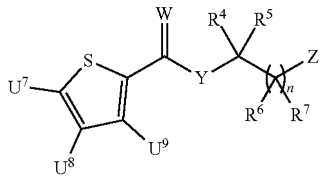

wherein $U^7$, $U^8$ and $U^9$ are independently selected from the list consisting of amino group, halogen, cyano, $C_1$-$C_6$-alkyl or $C_1$-$C_6$-haloalkyl provided that one of $U^7$, $U^8$ or $U^9$ is at least an amino group Compositions and Formulations The present invention further relates to a composition, in particular a composition for controlling unwanted microorganisms, comprising one or more compounds of formula (I) or (II). The composition is preferably is a fungicidal composition.

The composition typically comprises one or more compounds of formula (I) or (II) and one or more acceptable carriers, in particular one or more agriculturally acceptable carriers.

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, natural rock flours, such as kaolins, clays, talc, chalk, quartz, attapulgite, montmorillonite and diatomaceous earth, and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide), lactams (such as N-alkylpyrrolidones) and lactones, sulfones and sulfoxides (such as dimethyl sulfoxide). The carrier may also be a liquefied gaseous extender, i.e. liquid which is gaseous at standard temperature and under standard pressure, for example aerosol propellants such as halohydrocarbons, butane, propane, nitrogen and carbon dioxide. The amount of carrier typically ranges from 1 to 99.99%, preferably from 5 to 99.9%, more preferably from 10 to 99.5%, and most preferably from 20 to 99% by weight of the composition.

The composition may further comprise one or more acceptable auxiliaries which are customary for formulating compositions (e.g. agrochemical compositions), such as one or more surfactants.

The surfactant can be an ionic (cationic or anionic) or non-ionic surfactant, such as ionic or non-ionic emulsifier (s), foam former(s), dispersant(s), wetting agent(s) and any mixtures thereof. Examples of suitable surfactants include, but are not limited to, salts of polyacrylic acid, salts of lignosulfonic acid, salts of phenolsulfonic acid or naphthalenesulfonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulfosuccinic esters, taurine derivatives (preferably alkyl taurates), phosphoric esters of polyethoxylated alcohols or phenols, fatty esters of polyols and derivatives of compounds containing sulfates, sulfonates, phosphates (for example, alkylsulfonates, alkyl sulfates, arylsulfonates) and protein hydrolysates, lignosulfite waste liquors and methylcellulose. A surfactant is typically used when the compound of the formula (I) or (II) and/or the carrier is insoluble in water and the application is made with water. Then, the amount of surfactants typically ranges from 5 to 40% by weight of the composition.

Further examples of auxiliaries which are customary for formulating agrochemical compositions include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone, polyvinyl acetate, polyvinyl alcohol and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue, organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries is related to the intended mode of application of the compound of the formula (I) or (II) and/or on the physical properties. Furthermore, the auxiliaries may be chosen to impart particular properties (technical, physical and/or biological properties) to the compositions or use forms prepared therefrom. The choice of auxiliaries may allow customizing the compositions to specific needs.

The composition may be in any customary form, such as solutions (e.g. aqueous solutions), emulsions, wettable powders, water- and oil-based suspensions, powders, dusts, pastes, soluble powders, soluble granules, granules for broadcasting, suspoemulsion concentrates, natural or synthetic products impregnated with the compound of the invention, fertilizers and also microencapsulations in polymeric substances. The compound of formula (I) or (II) may be present in a suspended, emulsified or dissolved form.

The composition may be provided to the end user as ready-for-use formulation, i.e. the compositions may be directly applied to the plants or seeds by a suitable device, such as a spraying or dusting device. Alternatively, the composition may be provided to the end user in the form of concentrates which have to be diluted, preferably with water, prior to use.

The composition can be prepared in conventional manners, for example by mixing the compound formula (I) or (II) with one or more suitable auxiliaries, such as disclosed herein above.

The composition contains generally from 0.01 to 99% by weight, from 0.05 to 98% by weight, preferably from 0.1 to 95% by weight, more preferably from 0.5 to 90% by weight, most preferably from 1 to 80% by weight of the compound of formula (I) or (II).

The compound(s) and composition(s) comprising thereof can be mixed with other active ingredients like fungicides, bactericides, acaricides, nematicides, insecticides, herbicides, fertilizers, growth regulators, safeners or semiochemicals. This may allow to broaden the activity spectrum or to prevent development of resistance. Examples of known fungicides, insecticides, acaricides, nematicides and bactericides are disclosed in the Pesticide Manual, 17th Edition.

The active ingredients specified herein by their Common Name are known and described, for example, in The Pesticide Manual ($16^{th}$ Ed. British Crop Protection Council) or can be searched in the internet (e.g. www.alanwood.net/pesticides).

Where a compound (A) or a compound (B) can be present in tautomeric form, such a compound is understood herein above and herein below also to include, where applicable, corresponding tautomeric forms, even when these are not specifically mentioned in each case.

Examples of fungicides which could be mixed with the compound(s) of formula (I) or (II) and the composition of the invention are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) ipfentrifluconazole, (1.082) 2-[4-(4-chlorophenoxy)-2-(trifluoromethyl)phenyl]-1-(1H-1,2,4-triazol-1-yl)propan-2-ol, (1.083) 2-[6-(4-bromophenoxy)-2-(trifluoromethyl)-3-pyridyl]-1-(1,2,4-triazol-1-yl)propan-2-ol, (1.084) 2-[6-(4-chlorophenoxy)-2-(trifluoromethyl)-3-pyridyl]-1-(1,2,4-triazol-1-yl)propan-2-ol, (1.085) 3-[2-(1-chlorocyclopropyl)-3-(3-chloro-2-fluoro-phenyl)-2-hydroxy-propyl]imidazole-4-carbonitrile, (1.086) 4-[[6-[rac-(2R)-2-(2,4-difluorophenyl)-1,1-difluoro-2-hydroxy-3-(5-thioxo-4H-1,2,4-triazol-1-yl)propyl]-3-pyridyl]oxy]benzonitrile, (1.087) N-isopropyl-N'-[5-methoxy-2-methyl-4-(2,2,2-trifluoro-1-hydroxy-1-phenylethyl)phenyl]-N-methylimidoformamide, (1.088) N'-{5-bromo-2-methyl-6-[(1-propoxypropan-2-yl)oxy]pyridin-3-yl}-N-ethyl-N-methylimidoformamide.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1 RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) inpyrfluxam, (2.029) 3-(difluoromethyl)-1-methyl-N-[(3S)-1,1,3-trimethyl-2,3-dihydro-1H-inden-4-yl]-1H-pyrazole-4-carboxamide, (2.030) fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052)

N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne, (2.058) N-[rac-(1S,2S)-2-(2,4-dichlorophenyl)cyclobutyl]-2-(trifluoromethyl)nicotinamide, (2.059) N-[(1S,2S)-2-(2,4-dichlorophenyl)cyclobutyl]-2-(trifluoromethyl)nicotinamide.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) fenpicoxamid, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) pyridachlometyl, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine, (4.026) fluopimomide.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) tolprocarb.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further fungicides selected from the group consisting of (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, (15.033) 2-(6-benzylpyridin-2-yl) quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl] quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenyl methanesulfonate, (15.041) ipflufenoquin, (15.042) 2-{2-fluoro-6-[(8-fluoro-2-methylquinolin-3-yl)oxy]phenyl}propan-2-ol, (15.043) fluoxapiprolin, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one, (15.063) aminopyrifen, (15.064) (N'-[2-chloro-4-(2-fluorophenoxy)-5-methylphenyl]-N-ethyl-N-methylimidoformamide), (15.065) (N'-(2-chloro-5-methyl-4-phenoxyphenyl)-N-ethyl-N-methylimidoformamide), (15.066) (2-{2-[(7,8-difluoro-2-methylquinolin-3-yl)oxy]-6-fluorophenyl}propan-2-ol), (15.067) (5-bromo-1-(5,6-dimethylpyridin-3-yl)-3,3-dimethyl-3,4-dihydroisoquinoline), (15.068) (3-(4,4-difluoro-5,5-dimethyl-4,5-dihydrothieno[2,3-c]pyridin-7-yl) quinoline), (15.069) (1-(4,5-dimethyl-1H-benzimidazol-1-yl)-4,4-difluoro-3,3-dimethyl-3,4-dihydroisoquinoline), (15.070) 8-fluoro-3-(5-fluoro-3,3-dimethyl-3,4-dihydroisoquinolin-1-yl)quinolone, (15.071) 8-fluoro-3-(5-fluoro-3,3,4,4-tetramethyl-3,4-dihydroisoquinolin-1-yl)quinolone, (15.072) 3-(4,4-difluoro-3,3-dimethyl-3,4-dihydroisoquinolin-1-yl)-8-fluoroquinoline, (15.073) (N-methyl-N-phenyl-4-[5-(trifluoromethyl)-1,2,4-oxadiazol-3-yl]benzamide), (15.074) methyl {4-[5-(trifluoromethyl)-1,2,4-oxadiazol-3-yl]phenyl}carbamate, (15.075) (N-{4-[5-(trifluoromethyl)-1,2,4-oxadiazol-3-yl]benzyl}cyclo- propanecarboxamide), (15.076) N-methyl-4-(5-(trifluoromethyl)-1,2,4-oxadiazol-3-yl]benzamide, (15.077) N-[(E)-methoxyiminomethyl]-4-[5-(trifluoromethyl)-1,2,4-oxadiazol-3-yl]benzamide, (15.078) N-[(Z)-methoxyiminomethyl]-4-[5-(trifluoromethyl)-1,2,4-oxadiazol-3-yl]benzamide, (15.079) N-[4-[5-(trifluoromethyl)-1,2,4-oxadiazol-3-yl]phenyl]cyclopropanecarboxamide, (15.080) N-(2-fluorophenyl)-4-[5-(trifluoromethyl)-1,2,4-oxadiazol-3-yl]benzamide, (15.081) 2,2-difluoro-N-methyl-2-[4-[5-(trifluoromethyl)-1,2,4-oxadiazol-3-yl]phenyl]-acetamide, (15.082) N-allyl-N-[[4-[5-(trifluoromethyl)-1,2,4-oxadiazol-3-yl)phenyl]methyl]acetamide, (15.083) N-[(E)-N-methoxy-C-methyl-carbonimidoyl]-4-(5-(trifluoromethyl)-1,2,4-oxadiazol-3-yl]-benzamide, (15.084) N-[(Z)-N-methoxy-C-methyl-carbonimidoyl]-4-[5-(trifluoromethyl)-1,2,4-oxadiazol-3-yl]benzamide, (15.085) N-allyl-N-[[4-[5-(trifluoromethyl)-1,2,4-oxadiazol-3-yl]phenyl]methyl]-propanamide, (15.086) 4,4-dimethyl-1-[[4-[5-(trifluoromethyl)-1,2,4-oxadiazol-3-yl]phenyl]methyl]-pyrrolidin-2-one, (15.087) N-methyl-4-[5-(trifluoromethyl)-1,2,4-oxadiazol-3-yl] benzenecarbothioamide, (15.088) 5-methyl-1-[[4-[5-(trifluoromethyl)-1,2,4-oxadiazol-3-yl]phenyl]methyl] pyrrolidin-2-one, (15.089) N-((2,3-difluoro-4-[5-(trifluoromethyl)-1,2,4-oxadiazol-3-yl]phenyl] methyl]-3,3,3-trifluoro-propanamide, (15.090) 1-methoxy-1-methyl-3-[[4-[5-(trifluoromethyl}-1,2,4-oxadiazol-3-yl]phenyl]-methyl]urea, (15.091) 1,1-diethyl-3-[[4-[5-(trifluoromethyl}-1,2,4-oxadiazol-3-yl] phenyl]methyl]urea, (15.092) N-[[4-[5-(trifluoromethyl)-1,2,4-oxadiazol-3-yl]phenyl]methyl] propanamide, (15.093) N-methoxy-N-[[4-[5-(trifluoromethyl)-1,2,4-oxadiazol-3-yl]phenyl]methyl] cyclopropanecarboxamide, (15.094) 1-methoxy-3-methyl-1-[[4-[5-(trifluoromethyl)-1,2,4-oxadiazol-3-yl]phenyl]methyl]urea, (15.095) N-methoxy-N-[[4-[5-(trifluoromethyl)-1,2,4-oxadiazol-3-yl]phenyl]methyl] cyclopropanecarboxamide, (15.096) N,2-dimethoxy-N-[[4-[5-(trifluoromethyl)-1,2,4-oxadiazol-3-yl] phenyl]methyl]-propanamide, (15.097) N-ethyl-2-methyl-N-[[4-[5-(trifluoromethyl)-1,2,4-oxadiazol-3-yl]phenyl]methyl]-propanamide, (15.098) 1-methoxy-3-methyl-1-[[4-[5-(trifluoromethyl)-1,2,4-oxadiazol-3-yl]phenyl]-methyl]urea, (15.099) 1,3-dimethoxy-1-[[4-[5-(trifluoromethyl)-1,2,4-oxadiazol-3-yl]phenyl] methyl]urea, (15.100) 3-ethyl-1-methoxy-1-[[4-[5-(trifluoromethyl)-1,2,4-oxadiazol-3-yl]phenyl]methyl] urea, (15.101) 1-[[4-[5-(trifluoromethyl)-1,2,4-oxadiazol-3-yl]phenyl]methyl]piperidin-2-one, (15.102) 4,4-dimethyl-2-[[4-[5-(trifluoromethyl)-1,2, 4-oxadiazol-3-yl]phenyl]methyl]isooxazolidin-3-one, (15.103) 5,5-dimethyl-2-[[4-[5-(trifluoromethyl)-1,2,4-oxadiazol-3-yl]phenyl]methyl]isoxazolidin-3-one, (15.104) 3,3-dimethyl-1-[[4-[5-(trifluoromethyl)-1,2,4-oxadiazol-3-yl]phenyl]methyl]piperidin-2-one, (15.105) 1-[[3-fluoro-4-(5-(trifluoromethyl)-1,2,4-oxadiazol-3-yl]phenyl]methyl]azepan-2-one, (15.106) 4,4-dimethyl-2-[[4-(5-(trifluoromethyl)-1,2,4-oxadiazol-3-yl]phenyl]methyl]isoxazolidin-3-one, (15.107) 5,5-dimethyl-2-[[4-[5-(trifluoromethyl)-1,2,4-oxadiazol-3-yl]phenyl]methyl]isoxazolidin-3-one, (15.108) ethyl 1-{4-[5-(trifluoromethyl)-1,2,4-oxadiazol-3-yl]benzyl}-1H-pyrazole-4-carboxylate, (15.109) N,N-dimethyl-1-{4-[5-(trifluoromethyl)-1,2,4-oxadiazol-3-yl]benzyl}-1H-1,2,4-triazol-3-amine, (15.110) N-{2,3-difluoro-4-[5-(trifluoromethyl)-1,2,4-oxadiazol-3-yl]benzyl}butanamide, (15.111) N-(1-methylcyclopropyl)-4-[5-(trifluoromethyl)-1,2,4-oxadiazol-3-yl]benzamide, (15.112) N-(2,4-difluorophenyl)-4-[5-(trifluoromethyl)-1,2,4-oxadiazol-3-yl]benzamide, (15.113) 1-(5,6-dimethylpyridin-3-yl)-4,4-difluoro-3,3-dimethyl-3,4-dihydroisoquinoline, (15.114) 1-(6-(difluoromethyl)-5-methyl-pyridin-3-yl)-4,4-difluoro-3,3-dimethyl-3,4-dihydroisoquinoline, (15.115) 1-(5-(fluoromethyl)-6-methyl-pyridin-3-yl)-4,4-difluoro-3,3-dimethyl-3,4-dihydroisoquinoline, (15.116) 1-(6-(difluoromethyl)-5-methoxy-pyridin-3-yl)-4,4-difluoro-3,3-dimethyl-3,4-dihydroisoquinoline, (15.117) 4-[5-(trifluoromethyl)-1,2,4-oxadiazol-3-yl]phenyl dimethylcarbamate, (15.118) N-{4-[5-(trifluoromethyl)-1,2,4-oxadiazol-3-yl]phenyl}propanamide, (15.119) 3-[2-(1-{[5-methyl-3-(trifluoromethyl)-1H-pyrazol-1-yl]acetyl}piperidin-4-yl)-1,3-thiazol-4-yl]-1,5-dihydro-2,4-benzodioxepin-6-yl methanesulfonate, (15.120) 9-fluoro-3-[2-(1-{[5-methyl-3-(trifluoromethyl)-1H-pyrazol-1-yl]acetyl}piperidin-4-yl)-1,3-thiazol-4-yl]-1,5-dihydro-2,4-benzodioxepin-6-yl methanesulfonate, (15.121) 3-[2-(1-{[3,5-bis(difluoromethyl)-1H-pyrazol-1-yl]acetyl}piperidin-4-yl)-1,3-thiazol-4-yl]-1,5-dihydro-2,4-benzodioxepin-6-yl methanesulfonate, (15.122) 3-[2-(1-{[3,5-bis(difluoromethyl)-1H-pyrazol-1-yl]acetyl}piperidin-4-yl)-1,3-thiazol-4-yl]-9-fluoro-1,5-dihydro-2,4-benzodioxepin-6-yl methanesulfonate, (15.123) 1-(6,7-dimethylpyrazolo[1,5-a]pyridin-3-yl)-4,4-difluoro-3,3-dimethyl-3,4-dihydroisoquinoline, (15.124) 8-fluoro-N-(4,4,4-trifluoro-2-methyl-1-phenylbutan-2-yl)quinoline-3-carboxamide, (15.125) 8-fluoro-N-[(2S)-4,4,4-trifluoro-2-methyl-1-phenylbutan-2-yl]quinoline-3-carboxamide, (15.126) N-(2,4-dimethyl-1-phenylpentan-2-yl)-8-fluoroquinoline-3-carboxamide and (15.127) N-[(2S)-2,4-dimethyl-1-phenylpentan-2-yl]-8-fluoroquinoline-3-carboxamide.

All named mixing partners of the classes (1) to (15) can, if their functional groups enable this, optionally form salts with suitable bases or acids.

Another aspect of the present invention relates to one or more of the following compound combinations:

(I.0001)+(I.001), (I.0001)+(I.002), (I.0001)+(I.003), (I.0001)+(I.004), (I.0001)+(I.005), (I.0001)+(I.006), (I.0001)+(I.007), (I.0001)+(I.008), (I.0001)+(I.009), (I.0001)+(I.010), (I.0001)+(I.011), (I.0001)+(I.012), (I.0001)+(I.013), (I.0001)+(I.014), (I.0001)+(I.015), (I.0001)+(I.016), (I.0001)+(I.017), (I.0001)+(I.018), (I.0001)+(I.019), (I.0001)+(I.020), (I.0001)+(I.021), (I.0001)+(I.022), (I.0001)+(I.023), (I.0001)+(I.024), (I.0001)+(I.025), (I.0001)+(I.026), (I.0001)+(I.027), (I.0001)+(I.028), (I.0001)+(I.029), (I.0001)+(I.030), (I.0001)+(I.031), (I.0001)+(I.032), (I.0001)+(I.033), (I.0001)+(I.034), (I.0001)+(I.035), (I.0001)+(I.036), (I.0001)+(I.037), (I.0001)+(I.038), (I.0001)+(I.039), (I.0001)+(I.040), (I.0001)+(I.041), (I.0001)+(I.042), (I.0001)+(I.043), (I.0001)+(I.044), (I.0001)+(I.045), (I.0001)+(I.046), (I.0001)+(I.047), (I.0001)+(I.048), (I.0001)+(I.049), (I.0001)+(I.050), (I.0001)+(I.051), (I.0001)+(I.052), (I.0001)+(I.053), (I.0001)+(I.054), (I.0001)+(I.055), (I.0001)+(I.056), (I.0001)+(I.057), (I.0001)+(I.058), (I.0001)+(I.059), (I.0001)+(I.060), (I.0001)+(I.061), (I.0001)+(I.062), (I.0001)+(I.063), (I.0001)+(I.064), (I.0001)+(I.065), (I.0001)+(I.066), (I.0001)+(I.067), (I.0001)+(I.068), (I.0001)+(I.069), (I.0001)+(I.070), (I.0001)+(I.071), (I.0001)+(I.072), (I.0001)+(I.073), (I.0001)+(I.074), (I.0001)+(I.075), (I.0001)+(I.076), (I.0001)+(I.077), (I.0001)+(I.078), (I.0001)+(I.079), (I.0001)+(I.080), (I.0001)+(I.081), (I.0001)+(I.082), (I.0001)+(I.083), (I.0001)+(I.084), (I.0001)+(I.085), (I.0001)+(I.086), (I.0001)+(I.087), (I.0001)+(I.088), (I.0001)+(I.089), (I.0001)+(I.090), (I.0001)+(I.091), (I.0001)+(2.001), (I.0001)+(2.002), (I.0001)+(2.003), (I.0001)+(2.004), (I.0001)+(2.005), (I.0001)+(2.006), (I.0001)+(2.007), (I.0001)+(2.008), (I.0001)+(2.009), (I.0001)+(2.010), (I.0001)+(2.011), (I.0001)+(2.012), (I.0001)+(2.013), (I.0001)+(2.014), (I.0001)+(2.015), (I.0001)+(2.016), (I.0001)+(2.017), (I.0001)+(2.018), (I.0001)+(2.019), (I.0001)+(2.020), (I.0001)+(2.021), (I.0001)+(2.022), (I.0001)+(2.023), (I.0001)+(2.024), (I.0001)+(2.025), (I.0001)+(2.026), (I.0001)+(2.027), (I.0001)+(2.028), (I.0001)+(2.029), (I.0001)+(2.030), (I.0001)+(2.031), (I.0001)+(2.032), (I.0001)+(2.033), (I.0001)+(2.034), (I.0001)+(2.035), (I.0001)+(2.036), (I.0001)+(2.037), (I.0001)+(2.038), (I.0001)+(2.039), (I.0001)+(2.040), (I.0001)+(2.041), (I.0001)+(2.042), (I.0001)+(2.043), (I.0001)+(2.044), (I.0001)+(2.045), (I.0001)+(2.046), (I.0001)+(2.047), (I.0001)+(2.048), (I.0001)+(2.049), (I.0001)+(2.050), (I.0001)+(2.051), (I.0001)+(2.052), (I.0001)+(2.053), (I.0001)+(2.054), (I.0001)+(2.055), (I.0001)+(2.056), (I.0001)+(2.057), (I.0001)+(2.058), (I.0001)+(2.059), (I.0001)+(3.001), (I.0001)+(3.002), (I.0001)+(3.003), (I.0001)+(3.004), (I.0001)+(3.005), (I.0001)+(3.006), (I.0001)+(3.007), (I.0001)+(3.008), (I.0001)+(3.009), (I.0001)+(3.010), (I.0001)+(3.011), (I.0001)+(3.012), (I.0001)+(3.013), (I.0001)+(3.014), (I.0001)+(3.015), (I.0001)+(3.016), (I.0001)+(3.017), (I.0001)+(3.018), (I.0001)+(3.019), (I.0001)+(3.020), (I.0001)+(3.021), (I.0001)+(3.022), (I.0001)+(3.023), (I.0001)+(3.024), (I.0001)+(3.025), (I.0001)+(3.026), (I.0001)+(3.027), (I.0001)+(3.028), (I.0001)+(3.029), (I.0001)+(3.030), (I.0001)+(3.031), (I.0001)+(4.001), (I.0001)+(4.002), (I.0001)+(4.003), (I.0001)+(4.004), (I.0001)+(4.005), (I.0001)+(4.006), (I.0001)+(4.007), (I.0001)+(4.008), (I.0001)+(4.009), (I.0001)+(4.010), (I.0001)+(4.011), (I.0001)+(4.012), (I.0001)+(4.013), (I.0001)+(4.014), (I.0001)+(4.015), (I.0001)+(4.016), (I.0001)+(4.017), (I.0001)+(4.018), (I.0001)+(4.019), (I.0001)+(4.020), (I.0001)+(4.021), (I.0001)+(4.022), (I.0001)+(4.023), (I.0001)+(4.024), (I.0001)+(4.025), (I.0001)+(4.026), (I.0001)+(5.001), (I.0001)+(5.002), (I.0001)+(5.003), (I.0001)+(5.004), (I.0001)+(5.005), (I.0001)+(5.006), (I.0001)+(5.007), (I.0001)+(5.008), (I.0001)+(5.009), (I.0001)+(5.010), (I.0001)+(5.011), (I.0001)+(5.012), (I.0001)+(5.013), (I.0001)+(5.014), (I.0001)+(5.015), (I.0001)+(5.016), (I.0001)+(5.017), (I.0001)+(5.018), (I.0001)+(5.019), (I.0001)+(5.020), (I.0001)+(5.021), (I.0001)+(5.022), (I.0001)+(5.023), (I.0001)+(6.001), (I.0001)+(6.002), (I.0001)+(6.003), (I.0001)+(6.004), (I.0001)+(7.001), (I.0001)+(7.002), (I.0001)+(7.003), (I.0001)+(7.004), (I.0001)+(7.005), (I.0001)+(7.006), (I.0001)+(8.001), (I.0001)+(9.001), (I.0001)+(9.002), (I.0001)+(9.003), (I.0001)+(9.004), (I.0001)+(9.005), (I.0001)+(9.006), (I.0001)+(9.007), (I.0001)+(9.008), (I.0001)+(9.009), (I.0001)+(10.001), (I.0001)+(10.002), (I.0001)+(10.003), (I.0001)+(11.001), (I.0001)+(11.002), (I.0001)+(12.001), (I.0001)+(12.002), (I.0001)+(12.003), (I.0001)+(12.004), (I.0001)+(13.001), (I.0001)+(13.002), (I.0001)+(13.003), (I.0001)+(13.004), (I.0001)+(13.005), (I.0001)+(13.006), (I.0001)+(14.001), (I.0001)+(14.002), (I.0001)+(15.001), (I.0001)+(15.002), (I.0001)+(15.003), (I.0001)+(15.004), (I.0001)+(15.005), (I.0001)+(15.006), (I.0001)+(15.007), (I.0001)+(15.008), (I.0001)+(15.009), (I.0001)+(15.010), (I.0001)+(15.011), (I.0001)+(15.012), (I.0001)+(15.013), (I.0001)+(15.014), (I.0001)+(15.015), (I.0001)+(15.016), (I.0001)+(15.017), (I.0001)+(15.018), (I.0001)+(15.019), (I.0001)+(15.020), (I.0001)+(15.021), (I.0001)+(15.022), (I.0001)+(15.023), (I.0001)+(15.024), (I.0001)+(15.025), (I.0001)+(15.026), (I.0001)+(15.027), (I.0001)+(15.028), (I.0001)+(15.029), (I.0001)+(15.030), (I.0001)+(15.031), (I.0001)+(15.032), (I.0001)+(15.033), (I.0001)+(15.034), (I.0001)+(15.035), (I.0001)+(15.036), (I.0001)+(15.037), (I.0001)+(15.038), (I.0001)+(15.039), (I.0001)+(15.040), (I.0001)+(15.041), (I.0001)+(15.042), (I.0001)+(15.043), (I.0001)+(15.044), (I.0001)+(15.045), (I.0001)+(15.046), (I.0001)+(15.047), (I.0001)+(15.048), (I.0001)+(15.049), (I.0001)+(15.050), (I.0001)+(15.051), (I.0001)+(15.052), (I.0001)+(15.053), (I.0001)+(15.054), (I.0001)+(15.055), (I.0001)+(15.056), (I.0001)+(15.057), (I.0001)+(15.058), (I.0001)+(15.059), (I.0001)+(15.060), (I.0001)+(15.061), (I.0001)+(15.062). (I.0001)+(15.063). (I.0001)+(15.064). (I.0001)+(15.065), (I.0001)+15.066), (I.0001)+(15.067), (I.0001)+(15.068), (I.0001)+(15.069), (I.0001)+(15.070), (I.0001)+(15.071), (I.0001)+(15.072), (I.0001)+(15.073), (I.0001)+(15.074), (I.0001)+(15.075), (I.0001)+(15.076), (I.0001), (I.0001)+(15.077), (I.0001)+(15.078), (I.0001)+(15.079), (I.0001)+(15.080), (I.0001)+(15.081), (I.0001)+(15.082), (I.0001)+(15.083), (I.0001)+(15.084), (I.0001)+(15.085), (I.0001)+(15.086), (I.0001)+(15.087), (I.0001)+(15.088), (I.0001)+(15.089), (I.0001)+(15.090), (I.0001)+(15.091), (I.0001)+(15.092), (I.0001)+(15.093), (I.0001)+(15.094), (I.0001)+(15.095), (I.0001)+(15.096), (I.0001)+(15.097), (I.0001)+(15.098), (I.0001)+(15.099), (I.0001)+(15.100), (I.0001)+(15.101), (I.0001)+(15.102), (I.0001)+(15.103), (I.0001)+(15.104), (I.0001)+(15.105), (I.0001)+(15.106), (I.0001)+(15.107), (I.0001)+(15.108), (I.0001)+(15.109), (I.0001)+(15.110), (I.0001)+(15.111), (I.0001)+(15.112), (I.0001)+(15.113), (I.0001)+(15.114), (I.0001)+(15.115), (I.0001)+(15.116), (I.0001)+(15.117), (I.0001)+(15.118), (I.0001)+(15.119), (I.0001)+(15.120), (I.0001)+(15.121), (I.0001)+(15.122), (I.0001)+(15.123), (I.0001)+(15.124), (I.0001)+(15.125), (I.0001)+(15.126), (I.0001)+(15.127).

In these combinations, the first component is a compound of formula (I) as defined in tables 1.1 and 1.2 (e.g. I.0001) and the second component is a fungicide chosen in groups 1 to 15 as defined herein. For instance, the combination (I.0001)+(1.001) corresponds to a combination comprising compound 1.0001 in tables I.1 and I.2 and cyproconazole (1.001).

In some other embodiments, the compound combinations correspond to the above described combinations wherein compound (1.0001) is replaced with any one of the compounds recited in in tables I.1 and I.2.

The compounds of formula (I), and the fungicide selected from groups (1) to (15), can be present in a weight ratio ranging from 100:1 to 1:100 (compound of formula (I): fungicide selected from the groups (1) to (15)), or ranging from 50:1 to 1:50, or ranging from 20:1 to 1:20. Further examples of weight ratio ranges include 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

A further fungicide chosen in groups 1 to 15 as defined herein may be added to the compound combinations.

Another aspect of the present invention relates to one or more of the following compound combinations:

(II.001)+(1.001), (II.001)+(1.002), (II.001)+(1.003), (II.001)+(1.004), (II.001)+(1.005), (II.001)+(1.006), (II.001)+(1.007), (II.001)+(1.008), (II.001)+(1.009), (II.001)+(1.010), (II.001)+(1.011), (II.001)+(1.012), (II.001)+(1.013), (II.001)+(1.014), (II.001)+(1.015), (II.001)+(1.016), (II.001)+(1.017), (II.001)+(1.018), (II.001)+(1.019), (II.001)+(1.020), (II.001)+(1.021), (II.001)+(1.022), (II.001)+(1.023), (II.001)+(1.024), (II.001)+(1.025), (II.001)+(1.026), (II.001)+(1.027), (II.001)+(1.028), (II.001)+(1.029), (II.001)+(1.030), (II.001)+(1.031), (II.001)+(1.032), (II.001)+(1.033), (II.001)+(1.034), (II.001)+(1.035), (II.001)+(1.036), (II.001)+(1.037), (II.001)+(1.038), (II.001)+(1.039), (II.001)+(1.040), (II.001)+(1.041), (II.001)+(1.042), (II.001)+(1.043), (II.001)+(1.044), (II.001)+(1.045), (II.001)+(1.046), (II.001)+(1.047), (II.001)+(1.048), (II.001)+(1.049), (II.001)+(1.050), (II.001)+(1.051), (II.001)+(1.052), (II.001)+(1.053), (II.001)+(1.054), (II.001)+(1.055), (II.001)+(1.056), (II.001)+(1.057), (II.001)+(1.058), (II.001)+(1.059), (II.001)+(1.060), (II.001)+(1.061), (II.001)+(1.062), (II.001)+(1.063), (II.001)+(1.064), (II.001)+(1.065), (II.001)+(1.066), (II.001)+(1.067), (II.001)+(1.068), (II.001)+(1.069), (II.001)+(1.070), (II.001)+(1.071), (II.001)+(1.072), (II.001)+(1.073), (II.001)+(1.074), (II.001)+(1.075), (II.001)+(1.076), (II.001)+(1.077), (II.001)+(1.078), (II.001)+(1.079), (II.001)+(1.080), (II.001)+(1.081), (II.001)+(1.082), (II.001)+(1.083), (II.001)+(1.084), (II.001)+(1.085), (II.001)+(1.086), (II.001)+(1.087), (II.001)+(1.088), (II.001)+(1.089), (II.001)+(1.090), (II.001)+(1.091), (II.001)+(2.001), (II.001)+(2.002), (II.001)+(2.003), (II.001)+(2.004), (II.001)+(2.005), (II.001)+(2.006), (II.001)+(2.007), (II.001)+(2.008), (II.001)+(2.009), (II.001)+(2.010), (II.001)+(2.011), (II.001)+(2.012), (II.001)+(2.013), (II.001)+(2.014), (II.001)+(2.015), (II.001)+(2.016), (II.001)+(2.017), (II.001)+(2.018), (II.001)+(2.019), (1.001)+(2.020), (1.001)+(2.021), (1.001)+(2.022), (1.001)+(2.023), (1.001)+(2.024), (1.001)+(2.025), (1.001)+(2.026), (II.001)+(2.027), (II.001)+(2.028), (II.001)+(2.029), (II.001)+(2.030), (II.001)+(2.031), (II.001)+(2.032), (II.001)+(2.033), (II.001)+(2.034), (II.001)+(2.035), (II.001)+(2.036), (II.001)+(2.037), (II.001)+(2.038), (II.001)+(2.039), (II.001)+(2.040), (II.001)+(2.041), (II.001)+(2.042), (II.001)+(2.043), (II.001)+(2.044), (II.001)+(2.045), (II.001)+(2.046), (II.001)+(2.047), (II.001)+(2.048), (II.001)+(2.049), (II.001)+(2.050), (II.001)+(2.051), (II.001)+(2.052), (II.001)+(2.053), (II.001)+(2.054), (II.001)+(2.055), (II.001)+(2.056), (II.001)+(2.057), (II.001)+(2.058), (II.001)+(2.059), (II.001)+(3.001), (II.001)+(3.002), (II.001)+(3.003), (II.001)+(3.004), (II.001)+(3.005), (II.001)+(3.006), (II.001)+(3.007), (II.001)+(3.008), (II.001)+(3.009), (II.001)+(3.010), (II.001)+(3.011), (II.001)+(3.012), (II.001)+(3.013), (II.001)+(3.014), (II.001)+(3.015), (II.001)+(3.016), (II.001)+(3.017), (II.001)+(3.018), (II.001)+(3.019), (II.001)+(3.020), (II.001)+(3.021), (II.001)+(3.022), (II.001)+(3.023), (II.001)+(3.024), (II.001)+(3.025), (II.001)+(3.026), (II.001)+(3.027), (II.001)+(3.028), (II.001)+(3.029), (II.001)+(3.030), (II.001)+(3.031), (II.001)+(4.001), (II.001)+(4.002), (II.001)+(4.003), (II.001)+(4.004), (II.001)+(4.005), (II.001)+(4.006), (II.001)+(4.007), (II.001)+(4.008), (II.001)+(4.009), (II.001)+(4.010), (II.001)+(4.011), (II.001)+(4.012), (II.001)+(4.013), (II.001)+(4.014), (II.001)+(4.015), (II.001)+(4.016), (II.001)+(4.017), (II.001)+(4.018), (II.001)+(4.019), (II.001)+(4.020), (II.001)+(4.021), (II.001)+(4.022), (II.001)+(4.023), (II.001)+(4.024), (II.001)+(4.025), (II.001)+(4.026), (II.001)+(5.001), (II.001)+(5.002), (II.001)+(5.003), (II.001)+(5.004), (II.001)+(5.005), (II.001)+(5.006), (II.001)+(5.007), (II.001)+(5.008), (II.001)+(5.009), (II.001)+(5.010), (II.001)+(5.011), (II.001)+(5.012), (II.001)+(5.013), (II.001)+(5.014), (II.001)+(5.015), (II.001)+(5.016), (II.001)+(5.017), (II.001)+(5.018), (II.001)+(5.019), (II.001)+(5.020), (II.001)+(5.021), (II.001)+(5.022), (II.001)+(5.023), (II.001)+(6.001), (II.001)+(6.002), (II.001)+(6.003), (II.001)+(6.004), (II.001)+(7.001), (II.001)+(7.002), (II.001)+(7.003), (II.001)+(7.004), (II.001)+(7.005), (II.001)+(7.006), (II.001)+(8.001), (II.001)+(9.001), (II.001)+(9.002), (II.001)+(9.003), (II.001)+(9.004), (II.001)+(9.005), (II.001)+(9.006), (II.001)+(9.007), (II.001)+(9.008), (II.001)+(9.009), (II.001)+(10.001), (II.001)+(10.002), (II.001)+(10.003), (II.001)+(II.001), (II.001)+(II.002), (II.001)+(12.001), (II.001)+(12.002), (II.001)+(12.003), (II.001)+(12.004), (II.001)+(13.001), (II.001)+(13.002), (II.001)+(13.003), (II.001)+(13.004), (II.001)+(13.005), (II.001)+(13.006), (II.001)+(14.001), (II.001)+(14.002), (II.001)+(15.001), (II.001)+(15.002), (II.001)+(15.003), (II.001)+(15.004), (II.001)+(15.005), (II.001)+(15.006), (II.001)+(15.007), (II.001)+(15.008), (II.001)+(15.009), (II.001)+(15.010), (II.001)+(15.011), (II.001)+(15.012), (II.001)+(15.013), (II.001)+(15.014), (II.001)+(15.015), (II.001)+(15.016), (II.001)+(15.017), (II.001)+(15.018), (II.001)+(15.019), (II.001)+(15.020), (II.001)+(15.021), (II.001)+(15.022), (II.001)+(15.023), (II.001)+(15.024), (II.001)+(15.025), (II.001)+(15.026), (II.001)+(15.027), (II.001)+(15.028), (II.001)+(15.029), (II.001)+(15.030), (II.001)+(15.031), (II.001)+(15.032), (II.001)+(15.033), (II.001)+(15.034), (II.001)+(15.035), (II.001)+(15.036), (II.001)+(15.037), (II.001)+(15.038), (II.001)+(15.039), (II.001)+(15.040), (II.001)+(15.041), (II.001)+(15.042), (II.001)+(15.043), (II.001)+(15.044), (II.001)+(15.045), (II.001)+(15.046), (II.001)+(15.047), (II.001)+(15.048), (II.001)+(15.049), (II.001)+(15.050), (II.001)+(15.051), (II.001)+(15.052), (II.001)+(15.053), (II.001)+(15.054), (II.001)+(15.055), (II.001)+(15.056), (II.001)+(15.057), (II.001)+(15.058), (II.001)+(15.059), (II.001)+(15.060), (II.001)+(15.061), (II.001)+(15.062). (II.001)+(15.063). (II.001)+(15.064). (II.001)+(15.065), (II.001)+15.066), (II.001)+(15.067), (II.001)+(15.068), (II.001)+(15.069), (II.001)+(15.070), (II.001)+(15.071), (II.001)+(15.072), (II.001)+(15.073), (II.001)+(15.074), (II.001)+(15.075), (II.001)+(15.076), (II.001), (II.001)+(15.077), (II.001)+(15.078), (II.001)+(15.079), (II.001)+(15.080), (II.001)+(15.081), (1.001)+(15.082), (1.001)+(15.083), (1.001)+(15.084), (1.001)+(15.085), (1.001)+(15.086), (1.001)+(15.087), (1.001)+(15.088), (1.001)+(15.089), (1.001)+(15.090), (1.001)+(15.091), (1.001)+(15.092), (1.001)+(15.093), (II.001)+(15.094), (II.001)+(15.095), (II.001)+(15.096), (II.001)+(15.097), (II.001)+(15.098), (II.001)+(15.099), (II.001)+(15.100), (II.001)+(15.101), (II.001)+(15.102), (II.001)+(15.103), (II.001)+(15.104), (II.001)+(15.105), (II.001)+(15.106), (II.001)+(15.107), (II.001)+(15.108), (II.001)+(15.109), (II.001)+(15.110), (II.001)+(15.111), (II.001)+(15.112), (II.001)+(15.113), (II.001)+(15.114), (II.001)+(15.115), (II.001)+(15.116), (II.001)+(15.117), (II.001)+(15.118), (II.001)+(15.119), (II.001)+(15.120), (II.001)+(15.121), (II.001)+(15.122), (II.001)+(15.123), (II.001)+(15.124), (II.001)+(15.125), (II.001)+(15.126), (II.001)+(15.127).

In these combinations, the first component is a compound of formula (II) as defined in table II.1 (e.g. II.001) and the second component is a fungicide chosen in groups 1 to 15 as defined herein. For instance, the combination (II.001)+(1.001) corresponds to a combination comprising compound II.001 in table II.1 and cyproconazole (1.001).

In some other embodiments, the compound combinations correspond to the above described combinations wherein compound (II.001) is replaced with any one of the compounds recited in table II.1.

The compounds of formula (II), and the fungicide selected from groups (1) to (15), can be present in a weight ratio ranging from 100:1 to 1:100 (compound of formula (II): fungicide selected from the groups (1) to (15)), or ranging from 50:1 to 1:50, or ranging from 20:1 to 1:20. Further examples of weight ratio ranges include 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

A further fungicide chosen in groups 1 to 15 as defined herein may be added to the compound combinations.

The compounds of formula (I) or (II) and compositions comprising thereof may be combined with one or more biological control agents.

Examples of biological control agents which may be combined with the compounds of formula (I) or (II) and compositions comprising thereof are:

(A) Antibacterial agents selected from the group of:

(A1) bacteria, such as (A1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (A1.2) *Bacillus amyloliquefaciens*, in particular strain D747 (available as Double Nickel™ from Certis, US, having accession number FERM BP-8234 and disclosed in U.S. Pat. No. 7,094,592); (A1.3) *Bacillus pumilus*, in particular strain BU F-33 (having NRRL Accession No. 50185); (A1.4) *Bacillus subtilis* var. *amyloliquefaciens* strain FZB24 (available as Taegro® from Novozymes, US); (A1.5) a *Paenibacillus* sp. strain having Accession No. NRRL B-50972 or Accession No. NRRL B-67129 and described in International Patent Publication No. WO 2016/154297; and (A2) fungi, such as (A2.1) *Aureobasidium pullulans*, in particular blastospores of strain DSM14940; (A2.2) *Aureobasidium pullulans* blastospores of strain DSM 14941; (A2.3) *Aureobasidium pullulans*, in particular mixtures of blastospores of strains DSM14940 and DSM14941;

(B) Fungicides selected from the group of:

(B1) bacteria, for example (B1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (B1.2) *Bacillus pumilus*, in particular strain QST2808 (available as SONATA® from Bayer CropScience LP, US, having Accession No. NRRL B-30087 and described in U.S. Pat. No. 6,245,551); (B11.3) *Bacillus pumilus*, in particular strain GB34 (available as Yield Shield® from Bayer AG, DE); (B11.4) *Bacillus pumilus*, in particular strain BU F-33 (having NRRL Accession No. 50185); (B11.5) *Bacillus amyloliquefaciens*, in particular strain D747 (available as Double Nickel™ from Certis, US, having accession number FERM BP-8234 and disclosed in U.S. Pat. No. 7,094,592); (B11.6) *Bacillus subtilis* Y1336 (available as BIOBAC® WP from Bion-Tech, Taiwan, registered as a biological fungicide in Taiwan under Registration Nos. 4764, 5454, 5096 and 5277); (B11.7) *Bacillus amyloliquefaciens* strain MBI 600 (available as SUBTILEX from BASF SE); (B11.8) *Bacillus subtilis* strain GB03 (available as Kodiak® from Bayer AG, DE); (B11.9) *Bacillus subtilis* var. *amyloliquefaciens* strain FZB24 (available from Novozymes Biologicals Inc., Salem, Virginia or Syngenta Crop Protection, LLC, Greensboro, North Carolina as the fungicide TAEGRO® or TAEGRO® ECO (EPA Registration No. 70127-5); (B1.10) *Bacillus mycoides*, isolate J (available as BmJ TGAI or WG from Certis USA); (B11.11) *Bacillus licheniformis*, in particular strain SB3086 (available as EcoGuard™ Biofungicide and Green Releaf from Novozymes); (B11.12) a *Paenibacillus* sp. strain having Accession No. NRRL B-50972 or Accession No. NRRL B-67129 and described in International Patent Publication No. WO 2016/154297.

In some embodiments, the biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., "*Bacillus* Lipopeptides: Versatile Weapons for Plant Disease Biocontrol," Trends in Microbiology, Vol 16, No. 3, March 2008, pp. 115-125. *Bacillus* strains capable of producing lipopeptides include *Bacillus subtilis* QST713 (available as SERENADE OPTI or SERENADE ASO from Bayer CropScience LP, US, having NRRL Accession No. B21661 and described in U.S. Pat. No. 6,060,051), *Bacillus amyloliquefaciens* strain D747 (available as Double Nickel™ from Certis, US, having accession number FERM BP-8234 and disclosed in U.S. Pat. No. 7,094,592); *Bacillus subtilis* MB1600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABiTEP, DE); and *Bacillus subtilis* var. *amyloliquefaciens* FZB24 (available from Novozymes Biologicals Inc., Salem, Virginia or Syngenta Crop Protection, LLC, Greensboro, North Carolina as the fungicide TAEGRO® or TAEGRO® ECO (EPA Registration No. 70127-5); and (B2) fungi, for example: (B2.1) *Coniothyrium minitans*, in particular strain CON/M/91-8 (Accession No. DSM-9660; e.g. Contans® from Bayer); (B2.2) Metschnikowia fructicola, in particular strain NRRL Y-30752 (e.g. Shemer®); (B2.3) Microsphaeropsis *ochracea* (e.g. Microx® from Prophyta); (B2.5) *Trichoderma* spp., including *Trichoderma atroviride*, strain SC1 described in International Application No. PCT/IT2008/000196); (B2.6) *Trichoderma harzianum* rifai strain KRL-AG2 (also known as strain T-22, /ATCC 208479, e.g. PLANTSHIELD T-22G, Rootshield®, and TurfShield from BioWorks, US); (B2.14) *Gliocladium roseum*, strain 321U from W.F. Stoneman Company LLC; (B2.35) *Talaromyces flavus*, strain V117b; (B2.36) *Trichoderma asperellum*, strain ICC 012 from Isagro; (B2.37) *Trichoderma asperellum*, strain SKT-1 (e.g. ECO-HOPE® from Kumiai Chemical Industry); (B2.38) *Trichoderma atroviride*, strain CNCM I-1237 (e.g. Esquive® WP from Agrauxine, FR); (B2.39) *Trichoderma atroviride*, strain no. V08/002387; (B2.40) *Trichoderma atroviride*, strain NMI no. V08/002388; (B2.41) *Trichoderma atroviride*, strain NMI no. V08/002389; (B2.42) *Trichoderma atroviride*, strain NMI no. V08/002390; (B2.43) *Trichoderma atroviride*, strain LC52 (e.g. Tenet by Agrimm Technologies Limited); (B2.44) *Trichoderma atroviride*, strain ATCC 20476 (IMI 206040); (B2.45) *Trichoderma atroviride*, strain T11 (IM1352941/CECT20498); (B2.46) *Trichoderma* harmatum; (B2.47) *Trichoderma harzianum*; (B2.48) *Trichoderma harzianum* rifai T39 (e.g. Trichodex® from Makhteshim, US); (B2.49) *Trichoderma harzianum*, in particular, strain KD (e.g. Trichoplus from Biological Control Products, SA (acquired by Becker Underwood)); (B2.50) *Trichoderma harzianum*, strain ITEM 908 (e.g. Trianum-P from Koppert); (B2.51) *Trichoderma harzianum*, strain TH35 (e.g. Root-Pro by Mycontrol); (B2.52) *Trichoderma virens* (also known as *Gliocladium virens*), in particular strain GL-21 (e.g. SoilGard 12G by Certis, US); (B2.53) *Trichoderma viride*, strain TV1 (e.g. Trianum-P by Koppert); (B2.54) *Ampelomyces quisqualis*, in particular strain AQ 10 (e.g. AQ 10® by IntrachemBio Italia); (B2.56) *Aureobasidium pullulans*, in particular blastospores of strain DSM14940; (B2.57) *Aureobasidium pullulans*, in particular blastospores of strain DSM 14941; (B2.58) *Aureobasidium pullulans*, in particular mixtures of blastospores of strains DSM14940 and DSM 14941 (e.g. Botector® by bio-ferm, CH); (B2.64) *Cladosporium cladosporioides*, strain H39 (by Stichting Dienst Landbouwkundig Onderzoek); (B2.69) *Gliocladium catenulatum* (Synonym: Clonostachys *rosea* f. *catenulate*) strain J1446 (e.g. Prestop® by AgBio Inc. and also e.g. Primastop® by Kemira Agro Oy); (B2.70)

Lecanicillium lecanii (formerly known as *Verticillium* lecanii) conidia of strain KV01 (e.g. Vertalec® by Koppert/Arysta); (B2.71) *Penicillium vermiculatum*; (B2.72) *Pichia anomala*, strain WRL-076 (NRRL Y-30842); (B2.75) *Trichoderma atroviride*, strain SKT-1 (FERM P-16510); (B2.76) *Trichoderma atroviride*, strain SKT-2 (FERM P-16511); (B2.77) *Trichoderma atroviride*, strain SKT-3 (FERM P-17021); (B2.78) *Trichoderma gamsii* (formerly *T. viride*), strain ICC080 (IMI CC 392151 CABI, e.g. BioDerma by AGROBIOSOL DE MEXICO, S.A. DE C.V.); (B2.79) *Trichoderma harzianum*, strain DB 103 (e.g., T-Gro 7456 by Dagutat Biolab); (B2.80) *Trichoderma polysporum*, strain IMI 206039 (e.g. Binab TF WP by BINAB Bio-Innovation AB, Sweden); (B2.81) *Trichoderma* stromaticum (e.g. Tricovab by Ceplac, Brazil); (B2.83) Ulocladium oudemansii, in particular strain HRU3 (e.g. Botry-Zen® by Botry-Zen Ltd, NZ); (B2.84) *Verticillium albo-atrum* (formerly *V. dahliae*), strain WCS850 (CBS 276.92; e.g. Dutch Trig by Tree Care Innovations); (B2.86) *Verticillium chlamydosporium*; (B2.87) mixtures of *Trichoderma asperellum* strain ICC 012 and *Trichoderma gamsii* strain ICC 080 (product known as e.g. BIO-TAM™ from Bayer CropScience LP, US).

Further examples of biological control agents which may be combined with the compounds of formula (I) or (II) and compositions comprising thereof are:

bacteria selected from the group consisting of *Bacillus cereus*, in particular *B. cereus* strain CNCM I-1562 and *Bacillus firmus*, strain I-1582 (Accession number CNCM I-1582), *Bacillus subtilis* strain OST 30002 (Accession No. NRRL B-50421), *Bacillus thuringiensis*, in particular *B. thuringiensis* subspecies *israelensis* (serotype H-14), strain AM65-52 (Accession No. ATCC 1276), *B. thuringiensis* subsp. *aizawai*, in particular strain ABTS-1857 (SD-1372), *B. thuringiensis* subsp. *kurstaki* strain HD-1, *B. thuringiensis* subsp. *tenebrionis* strain NB 176 (SD-5428), Pasteuria *penetrans*, Pasteuria spp. (*Rotylenchulus reniformis* nematode)-PR3 (Accession Number ATCC SD-5834), *Streptomyces microflavus* strain AQ6121 (=QRD 31.013, NRRL B-50550), and *Streptomyces galbus* strain AQ 6047 (Acession Number NRRL 30232);

fungi and yeasts selected from the group consisting of *Beauveria bassiana*, in particular strain ATCC 74040, Lecanicillium spp., in particular strain HRO LEC 12, Metarhizium anisopliae, in particular strain F52 (DSM3884 or ATCC 90448), *Paecilomyces* fumosoroseus (now: lsaria fumosorosea), in particular strain IFPC 200613, or strain Apopka 97 (Accesion No. ATCC 20874), and *Paecilomyces lilacinus*, in particular *P. lilacinus* strain 251 (AGAL 89/030550);

viruses selected from the group consisting of *Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, and *Spodoptera littoralis* (African cotton leafworm) NPV.

bacteria and fungi which can be added as 'inoculant' to plants or plant parts or plant organs and which, by virtue of their particular properties, promote plant growth and plant health. Examples are: *Agrobacterium* spp., *Azorhizobium caulinodans*, Azospirillum spp., *Azotobacter* spp., *Bradyrhizobium* spp., *Burkholderia* spp., in particular *Burkholderia cepacia* (formerly known as *Pseudomonas cepacia*), Gigaspora spp., or Gigaspora *monosporum, Glomus* spp., Laccaria spp., *Lactobacillus buchneri*, Paraglomus spp., Pisolithus tinctorus, *Pseudomonas* spp., *Rhizobium* spp., in particular *Rhizobium trifolii*, Rhizopogon spp., Scleroderma spp., Suillus spp., and *Streptomyces* spp.

plant extracts and products formed by microorganisms including proteins and secondary metabolites which can be used as biological control agents, such as *Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), *Pyrethrum/Pyrethrins, Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica, Veratrin, Viscum album, Brassicaceae* extract, in particular oilseed rape powder or mustard powder.

Examples of insecticides, acaricides and nematicides, respectively, which could be mixed with the compounds of formula (I) or (II) and compositions comprising thereof are:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(8) Miscellaneous non-specific (multi-site) inhibitors, such as, for example, alkyl halides, e.g. methyl bromide and other alkyl halides; or chloropicrine or sulfuryl fluoride or borax or tartar emetic or methyl isocyanate generators, e.g. diazomet and metam.

(9) Modulators of Chordotonal Organs, such as, for example pymetrozine or flonicamid.

(10) Mite growth inhibitors, such as, for example clofentezine, hexythiazox and diflovidazin or etoxazole.

(11) Microbial disruptors of the insect gut membrane, such as, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and B.t. plant proteins: Cry1Ab, Cry1Ac, Cry1Fa, Cry1A.105, Cry2Ab, Vip3A, mCry3A, Cry3Ab, Cry3Bb, Cry34Ab1/35Ab1.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(24) Mitochondrial complex IV electron transport inhibitors, such as, for example, phosphines, e.g. aluminium phosphide, calcium phosphide, phosphine and zinc phosphide or cyanides, e.g. calcium cyanide, potassium cyanide and sodium cyanide.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active compounds such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tigolaner, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2- methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3, 3,3-trifluoropropyl)sulfinyl]-propanamide, (+)-N-[3-chloro-1-(3-pyridinyl)-1H-pyrazol-4-yl]-N-ethyl-3-[(3, 3,3-trifluoropropyl) sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl) amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(2)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1, 8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(2)]-N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Examples of safeners which could be mixed with the compounds of formula (I) or (II) and compositions comprising thereof are, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr
(-diethyl), naphthalic anhydride, oxabetrinil, 2-methoxy-N-({4-[(methylcarbamoyl)amino]phenyl}-sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Examples of herbicides which could be mixed with the compounds of formula (I) or (II) and compositions comprising thereof are:

Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammonium, and -trolamine, 2,4-DB, 2,4-DB-butyl, -dimethylammonium, -isooctyl, -potassium, and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, etha-metsulfuron-methyl, ethiozin, ethofumesate, ethoxyfen, ethoxyfen-ethyl, ethoxysulfuron, etobenzanid, F-9600, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i. e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium, and -trimesium, H-9201, i.e. O-(2,4-dimethyl-6-nitrophenyl) O-ethyl isopropylphosphoramidothioate, halauxifen, halauxifen-methyl halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl-(2,4-dichlorophenoxy) acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethyl and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thien-carbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

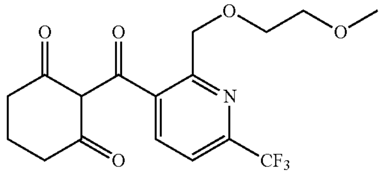

-continued

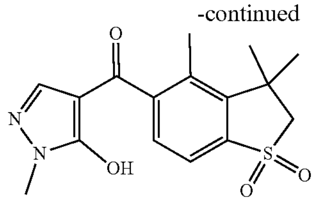

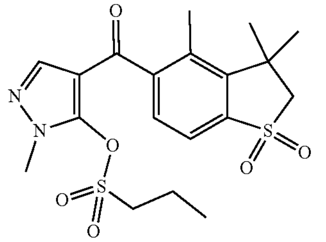

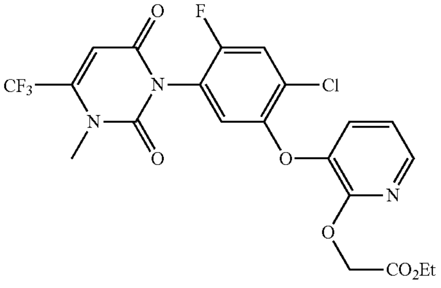

Examples for plant growth regulators are:

Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono (N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methyl-cyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Methods and Uses

The compounds of formula (I) or (II) and the compositions comprising thereof have potent microbicidal activity. They can be used for controlling unwanted microorganisms, such as unwanted fungi and bacteria. They can be particularly useful in crop protection (they control microorganisms that cause plants diseases) or for protecting materials (e.g. industrial materials, timber, storage goods) as described in more details herein below. More specifically, the compounds of formula (I) or (II) and the compositions comprising thereof can be used to protect seeds, germinating seeds, emerged seedlings, plants, plant parts, fruits, harvest goods and/or the soil in which the plants grow from unwanted microorganisms.

Control or controlling as used herein encompasses protective, curative and eradicative treatment of unwanted microorganisms. Unwanted microorganisms may be pathogenic bacteria, pathogenic virus, pathogenic oomycetes or pathogenic fungi, more specifically phytopathogenic bacteria phytopathogenic virus, phytopathogenic oomycetes or phytopathogenic fungi. As detailed herein below, these phytopathogenic microorganims are the causal agents of a broad spectrum of plants diseases.

More specifically, the compounds of formula (I) or (II) and compositions comprising thereof can be used as fungicides. For the purpose of the specification, the term "fungicide" refers to a compound or composition that can be used in crop protection for the control of unwanted fungi, such as Plasmodiophoromycetes, Chytridiomycetes, Zygomycetes, Ascomycetes, Basidiomycetes and Deuteromycetes and/or for the control of Oomycetes, more preferably for the control of Basidiomycetes (causing rust diseases).

The present invention also relates to a method for controlling unwanted microorganisms, such as phytopathogenic fungi, oomycetes and bacteria, comprising the step of applying at least one compound of formula (I) or (II) or at least one composition comprising thereof to the microorganisms and/or their habitat (to the plants, plant parts, seeds, fruits or to the soil in which the plants grow).

Typically, when the compound and the composition of the invention are used in curative or protective methods for controlling phytopathogenic fungi and/or phytopathogenic oomycetes, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the crop growth stage, the climatic conditions and the respective compound or composition of the invention used. This amount can be determined by systematic field trials that are within the capabilities of a person skilled in the art.

Plants and Plant Parts

The compounds of formula (I) and compositions comprising thereof may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which may be treated in accordance with the methods of the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

In some preferred embodiments, wild plant species and plant cultivars, or those obtained by conventional biological breeding methods, such as crossing or protoplast fusion, and also parts thereof, are treated in accordance with the methods of the invention.

In some other preferred embodiments, transgenic plants and plant cultivars obtained by genetic engineering methods, if appropriate in combination with conventional methods (Genetically Modified Organisms), and parts thereof are treated in accordance with the methods of the invention. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The methods according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which can be treated by the above disclosed methods include all plants which have genetic material which impart particularly advantageous, useful traits to these plants (whether obtained by breeding and/or biotechnological means).

Plants and plant cultivars which can be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which can be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which can be treated by the above disclosed methods include those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance.

Further yield traits include seed composition, such as carbohydrate content and composition for example cotton or starch, protein content, oil content and composition, nutritional value, reduction in anti-nutritional compounds, improved processability and better storage stability.

Plants and plant cultivars which can be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which can be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which can be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which can be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which can be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which can be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which can be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which can be treated by the above disclosed methods include plants and plant cultivars, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which can be treated by the above disclosed methods include plants and plant cultivars, such as Tobacco plants, with altered post-translational protein modification patterns.

Pathogens and Diseases

The methods disclosed above can be used to control microorganisms, in particular phytopathogenic microorganisms such as phytopathogenic fungi, causing diseases, such as:

- diseases caused by powdery mildew pathogens, such as Blumeria species (e.g. Blumeria *graminis*), *Podosphaera* species (e.g. *Podosphaera leucotricha*), Sphaerotheca species (e.g. Sphaerotheca *fuliginea*), *Uncinula* species (e.g. *Uncinula necator*);
- diseases caused by rust disease pathogens, such as *Gymnosporangium* species (e.g. *Gymnosporangium sabinae*), *Hemileia* species (e.g. *Hemileia vastatrix*), *Phakopsora* species (e.g. *Phakopsora pachyrhizi* or *Phakopsora meibomiae*), *Puccinia* species (e.g. *Puccinia recondita, Puccinia graminis* or *Puccinia striiformis*), *Uromyces* species (e.g. *Uromyces appendiculatus*);
- diseases caused by pathogens from the group of the Oomycetes, such as *Albugo* species (e.g. *Albugo candida*), *Bremia* species (e.g. *Bremia lactucae*), *Peronospora* species (e.g. *Peronospora pisi* or *P. brassicae*), *Phytophthora* species (e.g. *Phytophthora infestans*), *Plasmopara* species (e.g. *Plasmopara viticola*), *Pseudoperonospora* species (e.g. *Pseudoperonospora humuli* or *Pseudoperonospora cubensis*), *Pythium* species (e.g. *Pythium ultimum*);
- leaf blotch diseases and leaf wilt diseases caused, for example, by *Alternaria* species (e.g. *Alternaria solani*), *Cercospora* species (e.g. *Cercospora beticola*), *Cladiosporium* species (e.g. *Cladiosporium cucumerinum*), *Cochliobolus* species (e.g. *Cochliobolus sativus* (conidial form: *Drechslera*, syn: *Helminthosporium*) or *Cochliobolus miyabeanus*), *Colletotrichum* species (e.g. *Colletotrichum lindemuthanium*), *Cycloconium* species (e.g. *Cycloconium oleaginum*), *Diaporthe* species (e.g. *Diaporthe citri*), *Elsinoe* species (e.g. *Elsinoe fawcettii*), *Gloeosporium* species (e.g. *Gloeosporium laeticolor*), *Glomerella* species (e.g. *Glomerella cingulate*), *Guignardia* species (e.g. *Guignardia bidwelli*), *Leptosphaeria* species (e.g. *Leptosphaeria maculans*), *Magnaporthe* species (e.g. *Magnaporthe grisea*), *Microdochium* species (e.g. *Microdochium nivale*), *Mycosphaerella* species (e.g. *Mycosphaerella graminicola, Mycosphaerella arachidicola* or *Mycosphaerella fijiensis*), Phaeosphaeria species (e.g. Phaeosphaeria *nodorum*), *Pyrenophora* species (e.g. *Pyrenophora teres* or *Pyrenophora tritici repentis*), *Ramularia* species (e.g. *Ramularia collo-cygni* or *Ramularia areola*), *Rhynchosporium* species (e.g. *Rhynchosporium secalis*), *Septoria* species (e.g. *Septoria apii* or *Septoria lycopersici*), *Stagonospora* species (e.g. *Stagonospora nodorum*), *Typhula* species (e.g. *Typhula incarnate*), *Venturia* species (e.g. *Venturia inaequalis*),
- root and stem diseases caused, for example, by *Corticium* species (e.g. *Corticium graminearum*), *Fusarium* species (e.g. *Fusarium oxysporum*), *Gaeumannomyces* species, (e.g. *Gaeumannomyces graminis*), *Plasmodiophora* species, (e.g. *Plasmodiophora brassicae*), *Rhizoctonia* species, (e.g. *Rhizoctonia solani*), *Sarocladium* species, (e.g. *Sarocladium oryzae*), *Sclerotium* species, (e.g. *Sclerotium oryzae*), *Tapesia* species, (e.g. *Tapesia acuformis*), *Thielaviopsis* species, (e.g. *Thielaviopsis basicola*);
- ear and panicle diseases (including corn cobs) caused, for example, by *Alternaria* species, (e.g. *Alternaria* spp.), *Aspergillus* species (e.g. *Aspergillus flavus*), *Cladosporium* species (e.g. *Cladosporium cladosporioides, Claviceps* species (e.g. *Claviceps purpurea*), *Fusarium* species, (e.g. *Fusarium culmorum*), *Gibberella* species (e.g. *Gibberella zeae*), *Monographella* species, (e.g. *Monographella nivalis*), *Stagnospora* species, (e.g. *Stagnospora nodorum*);
- diseases caused by smut fungi, for example *Sphacelotheca* species (e.g. *Sphacelotheca reiliana*), *Tilletia* species (e.g. *Tilletia caries* or *Tilletia controversa*), *Urocystis* species (e.g. *Urocystis occulta*), *Ustilago* species (e.g. *Ustilago nuda*);
- fruit rot caused, for example, by *Aspergillus* species (e.g. *Aspergillus flavus*), *Botrytis* species (e.g. *Botrytis cinerea*), *Penicillium* species (e.g. *Penicillium expansum* or *Penicillium purpurogenum*), *Rhizopus* species (e.g. *Rhizopus stolonifer*), *Sclerotinia* species (e.g. *Sclerotinia sclerotiorum*), *Verticilium* species (e.g. *Verticilium alboatrum*);
- seed- and soil-borne rot and wilt diseases, and also diseases of seedlings, caused, for example, by *Alternaria* species (e.g. *Alternaria brassicicola*), *Aphanomyces* species (e.g. *Aphanomyces euteiches*), *Ascochyta* species (e.g. *Ascochyta lentis*), *Aspergillus* species (e.g. *Aspergillus flavus*), *Cladosporium* species (e.g. *Cladosporium herbarum*), *Cochliobolus* species (e.g. *Cochliobolus sativus* (conidial form: *Drechslera, Bipolaris* Syn: *Helminthosporium*)), *Colletotrichum* species (e.g. *Colletotrichum coccodes*), *Fusarium* species (e.g. *Fusarium culmorum*), *Gibberella* species (e.g. *Gibberella zeae*), *Macrophomina* species (e.g. *Macrophomina phaseolina*), *Microdochium* species (e.g. *Microdochium nivale*), *Monographella* species (e.g. *Monographella nivalis*), *Penicillium* species (e.g. *Penicillium expansum*), *Phoma* species (e.g. *Phoma* lingam), *Phomopsis* species (e.g. *Phomopsis sojae*), *Phytophthora* species (e.g. *Phytophthora cactorum*), *Pyrenophora* species (e.g. *Pyrenophora graminea*), *Pyricularia* species (e.g. *Pyricularia oryzae*), *Pythium* species (e.g. *Pythium ultimum*), *Rhizoctonia* species (e.g. *Rhizoctonia solani*), *Rhizopus* species (e.g. *Rhizopus oryzae*), *Sclerotium* species (e.g. *Sclerotium rolfsii*), *Septoria* species (e.g. *Septoria nodorum*), *Typhula* species (e.g. *Typhula incarnate*), *Verticillium* species (e.g. *Verticillium* dahlia);

cancers, galls and witches' broom caused, for example, by *Nectria* species (e.g. *Nectria galligena*); wilt diseases caused, for example, by *Monilinia* species (e.g. *Monilinia laxa*);

deformations of leaves, flowers and fruits caused, for example, by *Exobasidium* species (e.g. *Exobasidium vexans*), *Taphrina* species (e.g. *Taphrina deformans*);

degenerative diseases in woody plants, caused, for example, by Esca species (e.g. *Phaeomoniella chlamydospora, Phaeoacremonium aleophilum* or *Fomitiporia mediterranea*), *Ganoderma* species (e.g. *Ganoderma boninense*);

diseases of flowers and seeds caused, for example, by *Botrytis* species (e.g. *Botrytis cinerea*); diseases of plant tubers caused, for example, by *Rhizoctonia* species (e.g. *Rhizoctonia solani*), *Helminthosporium* species (e.g. *Helminthosporium solani*);

diseases caused by bacterial pathogens, for example *Xanthomonas* species (e.g. *Xanthomonas campestris* pv. *Oryzae*), *Pseudomonas* species (e.g. *Pseudomonas syringae* pv. *Lachrymans*), *Erwinia* species (e.g. *Erwinia amylovora*).

Seed Treatment

The method for controlling unwanted microorganisms may be used to protect seeds from phytopathogenic microorganisms, such as fungi.

The term "seed(s)" as used herein include dormant seed, primed seed, pregerminated seed and seed with emerged roots and leaves.

Thus, the present invention also relates to a method for protecting seeds and/or crops from unwanted microorganisms, such as bacteria or fungi, which comprises the step of treating the seeds with one or more compounds of formula (I) or (II) or a composition comprising thereof. The treatment of seeds with the compound(s) of formula (I) or (II) or a composition comprising thereof not only protects the seeds from phytopathogenic microorganisms, but also the germinating plants, the emerged seedlings and the plants after emergence.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of compound(s) of formula (I) or (II) or a composition comprising thereof (either as such or after dilution), the seeds and the compound(s) of formula (I) or (II) or the composition comprising thereof are mixed until a homogeneous distribution on seeds is achieved. If appropriate, the seeds may then be dried.

The invention also relates to seeds treated with one or more compounds of formula (I) or (II) or a composition comprising thereof. As said before, the use of treated seeds allows not only protecting the seeds before and after sowing from unwanted microorganisms, such as phytopathogenic fungi, but also allows protecting the germinating plants and young seedlings emerging from said treated seeds.

A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant.

Therefore, the present invention also relates to a method for protecting seeds, germinating plants and emerged seedlings, more generally to a method for protecting crop from phytopathogenic microorganisms, which comprises the step of using seeds treated by one or more compounds of formula (I) or (II) or a composition comprising thereof.

Preferably, the seed is treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pregerminated seeds, or seeds sown on nursery trays, tapes or paper.

The amount of compound(s) of formula (I) or (II) or composition comprising thereof applied to the seed is typically such that the germination of the seed is not impaired, or that the resulting plant is not damaged. This must be ensured particularly in case the active ingredients would exhibit phytotoxic effects at certain application rates. The intrinsic phenotypes of transgenic plants should also be taken into consideration when determining the amount of compound(s) of formula (I) or (II) or composition comprising thereof to be applied to the seed in order to achieve optimum seed and germinating plant protection with a minimum amount of compound(s) of formula (I) or (II) or composition comprising thereof being employed.

As indicated above, the compounds of the formula (I) or (II) can be applied, as such, directly to the seeds, i.e. without the use of any other components and without having been diluted, or a composition comprising the compounds of formula (I) or (II) can be applied. Preferably, the compositions are applied to the seed in any suitable form. Examples of suitable formulations include solutions, emulsions, suspensions, powders, foams, slurries or combined with other coating compositions for seed, such as film forming materials, pelleting materials, fine iron or other metal powders, granules, coating material for inactivated seeds, and also ULV formulations. The formulations may be ready-to-use formulations or may be concentrates that need to be diluted prior to use.

These formulations are prepared in a known manner, for instance by mixing the active ingredient or mixture thereof with customary additives, for example customary extenders and solvents or diluents, dyes, wetting agents, dispersants, emulsifiers, antifoams, preservatives, secondary thickeners, adhesives, gibberellins, and also water.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1. Useful wetting agents which may be present in the seed dressing formulations are all substances which promote wetting and which are conventionally used for the formulation of active agrochemical ingredients. Usable with preference are alkylnaphthalenesulfonates, such as diisopropyl- or diisobutylnaphthalenesulfonates. Useful dispersants and/or emulsifiers which may be present in the seed dressing formulations are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulfated derivatives thereof. Suitable anionic dispersants are especially lignosulfonates, polyacrylic acid salts and arylsulfonate/formaldehyde condensates. Antifoams which may be present in the seed dressing formulations are all foam-inhibiting substances conventionally used for the formulation of active agrochemical ingredients. Silicone antifoams and magnesium stearate can be used with preference. Preservatives which may be present in the seed dressing formulations are all substances usable for such purposes in agrochemical compositions. Examples include dichlorophene and benzyl alcohol hemiformal. Secondary thickeners which may be present in the seed dressing formulations are all substances usable for such purposes in agrochemical compositions. Preferred examples include cellulose derivatives, acrylic acid derivatives, xanthan, modified clays and finely divided silica. Adhesives which may be present in the seed dressing formulations are all customary binders usable in seed dressing products. Preferred examples include polyvinylpyrrolidone, polyvinyl acetate, polyvinyl alcohol and tylose.

The compounds of the formula (I) or (II) and the compositions comprising thereof are suitable for protecting seeds of any plant variety which is used in agriculture, in greenhouses, in forests or in horticulture. More particularly, the seed is that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

The compounds of formula (I) or (II) or the compositions comprising thereof can be used for treating transgenic seeds, in particular seeds of plants capable of expressing a protein which acts against pests, herbicidal damage or abiotic stress, thereby increasing the protective effect. Synergistic effects may also occur in interaction with the substances formed by expression.

Nematodes

In the present context, the term "nematodes" comprises all species of the phylum Nematoda and here in particular species acting as parasites on plants or fungi (for example species of the order Aphelenchida, Meloidogyne, Tylenchida and others) or else on humans and animals (for example species of the orders Trichinellida, Tylenchida, Rhabditina and Spirurida) and causing damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue. Here, the efficacy of the compounds is determined by comparing mortalities, gall formation, cyst formation, nematode density per volume of soil, nematode density per root, number of nematode eggs per soil volume, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, particularly preferably 51-79% and very particularly preferably the complete kill or the complete prevention of development and growth of the nematodes by a reduction of 80 to 100%. The control of nematodes as described herein also comprises the control of proliferation of the nematodes (development of cysts and/or eggs). Compounds of the formula (I) or (II) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) or (II) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita, Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola, Anguina tritici, Aphelenchoides arachidis, Aphelenchoides fragaria*, and the stem and leaf endoparasites *Aphelenchoides* spp., *Belonolaimus gracilis, Belonolaimus longicaudatus, Belonolaimus nortoni, Bursaphelenchus cocophilus, Bursaphelenchus eremus, Bursaphelenchus xylophilus* und *Bursaphelenchus* spp., *Cacopaurus pestis, Criconemella curvata, Criconemella onoensis, Criconemella ornata, Criconemella rusium, Criconemella xenoplax* (=*Mesocriconema xenoplax*) and *Criconemella* spp., *Criconemoides ferniae, Criconemoides onoense, Criconemoides ornatum* and *Criconemoides* spp., *Ditylenchus destructor, Ditylenchus dipsaci, Ditylenchus myceliophagus* and also the stem and leaf endoparasites *Ditylenchus* spp., *Dolichodorus heterocephalus, Globodera pallida* (=*Heterodera pallida*), *Globodera rostochiensis* (yellow potato cyst nematode), *Globodera solanacearum, Globodera taba-*

*cum, Globodera virginia* and the non-migratory cyst-forming parasites *Globodera* spp., *Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp., *Hemicriconemoides, Hemicycliophora arenaria, Hemicycliophora nudata, Hemicycliophora parvana, Heterodera avenae, Heterodera cruciferae, Heterodera glycines* (soya bean cyst nematode), *Heterodera oryzae, Heterodera schachtii, Heterodera zeae* and the non-migratory cyst-forming parasites *Heterodera* spp., *Hirschmaniella gracilis, Hirschmaniella oryzae, Hirschmaniella spinicaudata* and the stem and leaf endoparasites *Hirschmaniella* spp., *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp., *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi* and the non-migratory parasites *Meloidogyne* spp., *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp., *Paratylenchus hamatus, Paratylenchus minutus, Paratylenchus projectus* and *Paratylenchus* spp., *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp., *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp., *Rotylenchulus borealis, Rotylenchulus parvus, Rotylenchulus reniformis* and *Rotylenchulus* spp., *Rotylenchus laurentinus, Rotylenchus macrodoratus, Rotylenchus robustus, Rotylenchus uniformis* and *Rotylenchus* spp., *Scutellonema brachyurum, Scutellonema bradys, Scutellonema clathricaudatum* and the migratory endoparasites *Scutellonema* spp., *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp., *Tylenchorhynchus* agri, *Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp., *Tylenchulus semipenetrans* and the semiparasites *Tylenchulus* spp., *Xiphinema americanum, Xiphinema brevicolle, Xiphinema dimorphicaudatum, Xiphinema index* and the ectoparasites *Xiphinema* spp.

Nematodes for the control of which a compound of the formula (I) or (II) may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the *chrysanthemum* root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*) and beet cyst eelworm (*Heterodera schachtii*); nematodes of the genus *Aphelenchoides* such as the rice white-tip nematode (*Aphelenchoides besseyi*), the *chrysanthemum* nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) or (II) can be used include plants such as cereals (for example rice, barley, wheat, rye, oats, maize and the like), beans (soya bean, aduki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plant for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, water melon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) or (II) are particularly suitable for controlling coffee nematodes, in particular *Pratylenchus brachyurus, Pratylenchus coffeae, Meloidogyne exigua, Meloidogyne incognita, Meloidogyne coffeicola, Helicotylenchus* spp. and also *Meloidogyne paranaensis, Rotylenchus* spp., *Xiphinema* spp., *Tylenchorhynchus* spp. and *Scutellonema* spp.

The compounds of the formula (I) or (II) are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus*

*thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) or (II) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus and Rotylenchulus reniformis.*

The compounds of the formula (I) or (II) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei.*

The compounds of the formula (I) or (II) are particularly suitable for controlling cotton nematodes, in particular *Belonolaimus longicaudatus, Meloidogyne incognita, Hoplolaimus columbus, Hoplolaimus galeatus* and *Rotylenchulus reniformis.*

The compounds of the formula (I) or (II) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae*, (*Belonolaimus gracilis*), *Belonolaimus nortoni, Longidorus breviannulatus, Meloidogyne arenaria, Meloidogyne arenaria thamesi, Meloidogyne graminis, Meloidogyne incognita, Meloidogyne incognita* acrita, *Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola.*

The compounds of the formula (I) or (II) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus*, (*Belonolaimus gracilis*), *Meloidogyne arenaria, Meloidogyne incognita, Meloidogyne javanica, Meloidogyne hapla, Hoplolaimus columbus, Hoplolaimus galeatus* and *Rotylenchulus reniformis.*

The compounds of the formula (I) or (II) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae.*

The compounds of the formula (I) or (II) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita* acrita, *Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans.*

The compounds of the formula (I) or (II) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) or (II) are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum.*

The compounds of the formula (I) or (II) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans.*

The compounds of the formula (I) or (II) are particularly suitable for controlling nematodes in tree crops—pome fruit, in particular *Pratylenchus penetrans* and also *Pratylenchus vulnus, Longidorus elongatus, Meloidogyne incognita* and *Meloidogyne hapla.*

The compounds of the formula (I) or (II) are particularly suitable for controlling nematodes in tree crops—stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus.*

The compounds of the formula (I) or (II) are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp, *Xiphinema* spp. and *Cacopaurus pestis.*

Application

The compound of formula (I) or (II) can be applied as such, or for example in the form of as ready-to-use solutions, emulsions, water- or oil-based suspensions, powders, wettable powders, pastes, soluble powders, dusts, soluble granules, granules for broadcasting, suspoemulsion concentrates, natural products impregnated with the compound of formula (I) or (II), synthetic substances impregnated with the compound of formula (I) or (II), fertilizers or microencapsulations in polymeric substances.

Application is accomplished in a customary manner, for example by watering, spraying, atomizing, broadcasting, dusting, foaming, spreading-on and the like. It is also possible to deploy the compound of formula (I) or (II) by the ultra-low volume method, via a drip irrigation system or drench application, to apply it in-furrow or to inject it into the soil stem or trunk. It is further possible to apply the compound of formula (I) or (II) by means of a wound seal, paint or other wound dressing.

The effective and plant-compatible amount of the compound of formula (I) or (II) which is applied to the plants, plant parts, fruits, seeds or soil will depend on various factors, such as the compound/composition employed, the subject of the treatment (plant, plant part, fruit, seed or soil), the type of treatment (dusting, spraying, seed dressing), the purpose of the treatment (curative and protective), the type of microorganisms, the development stage of the microorganisms, the sensitivity of the microorganisms, the crop growth stage and the environmental conditions.

When the compound of formula (I) or (II) is used as a fungicide, the application rates can vary within a relatively wide range, depending on the kind of application. For the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). For the treatment of seeds, the application rate may range from 0.1 to 200 g per 100 kg of seeds, preferably from 1 to 150 g per 100 kg of seeds, more preferably from 2.5 to 25 g per 100 kg of seeds, even more preferably from 2.5 to 12.5 g per 100 kg of seeds. For the treatment of soil, the application rate may range from 0.1 to 10 000 g/ha, preferably from 1 to 5000 g/ha.

These application rates are merely examples and are not intended to limit the scope of the present invention.

Material Protection

The compound and the composition of the invention may also be used in the protection of materials, especially for the protection of industrial materials against attack and destruction by unwanted microorganisms.

In addition, the compound and the composition of the invention may be used as antifouling compositions, alone or in combinations with other active ingredients.

Industrial materials in the present context are understood to mean inanimate materials which have been prepared for use in industry. For example, industrial materials which are to be protected from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compound and the composition of the invention may prevent adverse effects, such as rotting, decay, discoloration, decoloration or formation of mould.

In the case of treatment of wood the compound and the composition of the invention may also be used against fungal diseases liable to grow on or inside timber.

Timber means all types of species of wood, and all types of working of this wood intended for construction, for example solid wood, high-density wood, laminated wood, and plywood. In addition, the compound and the composition of the invention may be used to protect objects which come into contact with saltwater or brackish water, especially hulls, screens, nets, buildings, moorings and signaling systems, from fouling.

The compound and the composition of the invention may also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, may be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compound and the composition of the invention may prevent adverse effects, such as rotting, decay, discoloration, decoloration or formation of mould.

Microorganisms capable of degrading or altering industrial materials include, for example, bacteria, fungi, yeasts, algae and slime organisms. The compound and the composition of the invention preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp.,

*Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae.*

Aspects of the present teaching may be further understood in light of the following examples, which should not be construed as limiting the scope of the present teaching in any way.

EXAMPLES

Synthesis of Compounds of Formula (I)

Preparation Example (I)-1: Preparation of ethyl N-[(4-bromo-5-cyano-3-methyl-2-thienyl)carbonyl] glycinate (Compound I.0024)

Step 1: Preparation of 4-bromo-5-cyano-3-methylthiophene-2-carboxylic acid

To a solution of 150 mg (0.86 mmol) of methyl 4-bromo-5-cyano-3-methylthiophene-2-carboxylate in 3.9 mL of tetrahydrofuran was added dropwise 0.7 mL of a 1.1 M aqueous lithium hydroxide solution (0.7 mmol). The reaction mixture was stirred at room temperature for 1 hour. The resulting reaction mixture was carefully acidified with a 1.0 M aqueous hydrochloric acid solution at 0° C. and extracted with ethyl acetate. Combined organic layers were dried over anhydrous magnesium sulfate, filtered and concentrated under reduced pressure to yield 142 mg (97% purity, 97% yield) of title compound as a white solid. Log P=2.05. (M+H)=246.

Step 2: Preparation of ethyl N-[(4-bromo-5-cyano-3-methyl-2-thienyl)carbonyl]glycinate (Compound I.0024)

In a 50 mL round-bottom flask vial under inert atmosphere, a solution of 402 mg (2.37 mmol) of 2-chloro-1,3-dimethylimidazolidinium chloride dissolved in 5 mL of dichloromethane was added to a solution of 450 mg (1.82 mmol) of 4-bromo-5-cyano-3-methylthiophene-2-carboxylic acid and 1.37 mL (7.86 mmol) of N,N-diisopropylethylamine dissolved in 7 mL of dichloromethane. After 5 min of stirring, 333 mg (2.37 mmol) of ethyl glycinate hydrochloride (1:1) was added and the reaction mixture was stirred at room temperature for 1 hour. The resulting reaction mixture was concentrated under reduced pressure. The residue was purified by column chromatography on silica gel (gradient n-heptane/ethyl acetate) to yield 516 mg (100% purity, 86% yield) of title compound as a yellow solid. Log P=2.40. (M+H)=331.

Preparation Example (I)-2: Preparation of N-[(4,5-dibromo-3-fluoro-2-thienyl)carbonyl]glycine (Compound I.0227)

In a first round-bottom flask, to a solution of 300 mg (0.98 mmol) of 4,5-dibromo-3-fluorothiophene-2-carboxylic acid in 6.5 mL of dry dichloromethane, were added, at room temperature, 95 μL (1.08 mmol) of oxalyl chloride and a drop of N,N-dimethylformamide. After 1 h of stirring at room temperature, the reaction mixture was concentrated under reduced pressure and dissolved in 2.3 mL of dry 1,4-dioxane to afford a solution of acyl chloride. In a second round-bottom flask, to a solution of 220 mg (0.97 mmol) of glycine hydrochloride (1:1) in 1.5 mL of water, was added 0.6 mL of a 0.5 M aqueous sodium hydroxide solution (0.3 mmol). The reaction mixture was stirred at room temperature for 3 hours and then slowly added onto the previously prepared solution of acyl chloride. The resulting reaction mixture was stirred at room temperature for 60 hours, diluted with water and carefully acidified with a 37% (w/w) aqueous hydrochloric acid solution at 0° C. The resulting precipitate was filtered off and the filtrate was concentrated under reduced pressure. Solid and filtrate were gathered and purified by preparative high performance liquid chromatography (gradient acetonitrile/aqueous solution of formic acid (1%)) to yield 100 mg (96% purity, 27% yield) of title compound as a yellow solid. Log P=1.97. (M+H)=360.

Preparation Example (I)-3: Preparation of S-ethyl 1-{[(4,5-dibromo-3-iodo-2-thienyl)carbonyl] amino}cyclopropanecarbothioate (Compound I.0139)

Under inert atmosphere, to a solution of 100 mg (2.20 mmol) of 1-{[(4,5-dibromo-3-iodo-2-thienyl)carbonyl] amino}cyclopropanecarboxylic acid in 2 mL of dry dichloromethane were added, at room temperature, 106 μL (0.60 mmol) of N,N-diisopropylethylamine followed by 115 mg (0.30 mmol) of 1-[bis(dimethylamino)methylene]-1H-1,2,3-triazolo[4,5-b]pyridinium 3-oxid hexafluorophosphate. After 15 min of stirring at room temperature, 19 mg (0.30 mmol) of ethanethiol was added and the reaction mixture was stirred at room temperature for 18 hours. A saturated aqueous sodium bicarbonate solution was added and the resulting reaction mixture was extracted twice with dichloromethane. Combined organic layers were filtered through a silica gel cartridge and concentrated under reduced pressure. The residue was purified by column chromatography on silica gel (gradient n-heptane/ethyl acetate) to yield 53 mg (100% purity, 49% yield) of title compound as a white solid. Log P=3.96. (M+H)=538.

Preparation Example (I)-4: Preparation of 1-{[(4,5-dibromo-3-fluoro-2-thienyl)carbonyl] amino}cyclobutanecarboxylic acid (Compound I.0172)

To a solution of 203 mg (0.47 mmol) of ethyl 1-{[(4,5-dibromo-3-fluoro-2-thienyl)carbonyl] amino}cyclobutanecarboxylate in 5 mL of tetrahydrofuran was added dropwise 1.04 mL of a 1 M aqueous potassium hydroxide solution (1.04 mmol). The reaction mixture was stirred at room temperature for 76 hours. The resulting reaction mixture was then carefully acidified to pH 1 with a 1.0 M aqueous hydrochloric acid solution at 0° C. and extracted three times with ethyl acetate. Combined organic layers were filtered through a Chem Elut™ cartridge and concentrated under reduced pressure. The residue was purified by preparative high performance liquid chromatography (gradient acetonitrile/aqueous solution of formic acid (1%)) to yield 115 mg (98% purity, 59% yield) of title compound as a yellow solid. Log P=2.57. (M+H)=400.

Preparation Example (I)-5: Preparation of methyl 1-{[(4,5-dibromo-3-fluoro-2-thienyl)carbonothioyl] amino}cyclopropanecarboxylate (Compound I.0328)

Step 1: Preparation of methyl 1-{[(4,5-dibromo-3-fluoro-2-thienyl)carbonyl] amino}cyclopropanecarboxylate In a 100 mL round-bottom flask vial under inert atmosphere, a solution of 733 mg (4.33 mmol) of 2-chloro-1,3- dimethylimidazolidinium chloride dissolved in 4.3 mL of dichloromethane was added to a solution of 1.0 g (3.33 mmol) of 4,5-dibromo-3-fluorothiophene-2-carboxylic acid and 2.50 mL (14.3 mmol) of N,N-diisopropylethylamine dissolved in 35 mL of dichloromethane. After 15 min of stirring, 1.0 g (6.66 mmol) of methyl 1-aminocyclopropanecarboxylate hydrochloride (1:1) was added and the reaction mixture was stirred at room temperature for 72 hours. Water was added and the resulting reaction mixture was extracted twice with dichloromethane. Combined organic layers were filtered through a Chem Elut™ cartridge and concentrated under reduced pressure. The residue was purified by column chromatography on silica gel (gradient dichloromethane/ethyl acetate) to yield 1.24 g (100% purity, 93% yield) of title compound as a white solid. Log P=2.77. (M+H)=400.

Step 2: Preparation of methyl 1-{[(4,5-dibromo-3-fluoro-2-thienyl)carbonothioyl]amino}cyclopropanecarboxylate (Compound I.0328)

To a solution of 265 mg (0.65 mmol) of methyl 1-{[(4,5-dibromo-3-fluoro-2-thienyl)carbonyl]amino}cyclopropanecarboxylate in 5 mL of 1,2-dimethoxyethane was added 267 mg (0.66 mmol) of Lawesson reagent. The reaction mixture was stirred at 50° C. for 42 hours. The resulting reaction mixture was diluted with dichloromethane, filtered through a basic Chromabond® Alumina cartridge and concentrated under reduced pressure. The residue was purified by column chromatography on silica gel (gradient n-heptane/ethyl acetate) to yield 158 mg (100% purity, 57% yield) of title compound as a yellow solid. Log P=3.91. (M+H)=416.

Preparation Example (I)-6: Preparation of 1-{[(4,5-dibromo-3-fluoro-2-thienyl)carbonothioyl]amino}cyclopropanecarboxylic acid (Compound I.0329)

To a solution of 271 mg (0.47 mmol) of methyl 1-{[(4,5-dibromo-3-fluoro-2-thienyl)carbonothioyl]amino}cyclopropanecarboxylate in 7 mL of 1,2-dichloroethane was added 203 mg (0.47 mmol) of trimethyltin hydroxide. The reaction mixture was stirred at 60° C. for 18 hours.

The resulting reaction mixture was concentrated under reduced pressure, dissolved in acetyl acetate and washed three times with a 1.0 M aqueous hydrochloric acid solution. Combined organic layers were filtered through a Chem Elut™ cartridge and concentrated under reduced pressure. The residue was purified by preparative high performance liquid chromatography (gradient acetonitrile/aqueous solution of formic acid (1%)) to yield 135 mg (100% purity, 54% yield) of title compound as a yellow solid. Log P=2.95. (M+H)=402.

Preparation Example (I)-7: Preparation of ethyl N-[(4,5-dichloro-3-cyano-2-thienyl)carbonyl]leucinate (Compound I.0279)

Step 1: Preparation of ethyl N-[(4,5-dichloro-3-iodo-2-thienyl)carbonyl]leucinate In a 5 mL microwave vial under inert atmosphere, a solution of 102 mg (0.60 mmol) of 2-chloro-1,3-dimethylimidazolidinium chloride dissolved in 1 mL of dichloromethane was added to a solution of 150 mg (0.46 mmol) of 4,5-dichloro-3-iodothiophene-2-carboxylic acid and 0.35 mL (2.00 mmol) of N,N-diisopropylethylamine dissolved in 2 mL of dichloromethane. After 5 min of stirring, 118 mg (0.60 mmol) of DL-ethyl leucinate hydrochloride (1:1) was added and the reaction mixture was stirred at room temperature for 2 hours. The resulting reaction mixture was concentrated under reduced pressure. The residue was purified by column chromatography on silica gel (gradient n-heptane/ethyl acetate) to yield 183 mg (100% purity, 85% yield) of title compound as a white solid. Log P=5.04. (M+H)=464.

Step 2: Preparation of ethyl N-[(4,5-dichloro-3-cyano-2-thienyl)carbonyl]leucinate (Compound I.0279)

In a 5 mL microwave vial under inert atmosphere, 183 mg (0.39 mmol) of ethyl N-[(4,5-dichloro-3-iodo-2-thienyl)carbonyl]leucinate and 42 mg (0.47 mmol) of copper(I) cyanide were successively added followed by degassed N,N-dimethylformamide (1.3 mL). The vial was sealed and the reaction mixture was stirred at 110° C. for 5 hours. The resulting reaction mixture was quenched with a saturated aqueous sodium bicarbonate solution and extracted with acetyl acetate. Combined organic layers were filtered through a Chem Elut™ cartridge and concentrated under reduced pressure. The residue was dissolved in dichloromethane, filtered through a silica gel cartridge and concentrated under reduced pressure to yield 125 mg (98% purity, 85% yield) of title compound as a colorless oil. Log P=4.05. (M+H)=363.

Preparation Example (I)-8: Preparation of ethyl N-[(4,5-dibromo-3-fluoro-2-thienyl)carbonyl]glycinate (Compound I.0449)

To a solution of 226 mg (0.72 mmol) of ethyl N-[(4-bromo-3-fluoro-2-thienyl)carbonyl]glycinate in 6 mL of acetic acid was added 0.23 mL (4.37 mmol) of bromine. The reaction mixture was stirred at 70° C. for 2.5 hours. The resulting reaction mixture was quenched at 0° C. with ice followed by addition of a saturated aqueous sodium thiosulfate solution and extracted twice with dichloromethane. Combined organic layers were filtered through a Chem Elut™ cartridge and concentrated under reduced pressure. The residue was purified by column chromatography on silica gel (gradient n-heptane/ethyl acetate) to yield 102 mg (100% purity, 36% yield) of title compound as a yellow solid. Log P=2.97. (M+H)=388.

Preparation Example (I)-9: Preparation of ethyl N-[(4-chloro-3-fluoro-5-methyl-2-thienyl)carbonyl]glycinate (Compound I.0793)

To a solution of 50 mg (0.14 mmol) of ethyl N-[(5-bromo-4-chloro-3-fluoro-2-thienyl)carbonyl]glycinate in 1.5 mL of degassed 1,4-dioxane were added 25 mg (0.41 mmol) of trimethylboroxine, 71 mg (0.22 mmol) of cesium carbonate and 5.9 mg (7.2 μmol) of [1,1'-bis(diphenylphosphino)ferrocene]dichloropalladium(II), (1:1) complex with dichloromethane. The reaction mixture was stirred at 100° C. for 5 hours. The reaction mixture was diluted with water and extracted with ethyl acetate. Combined organic layers were washed with brine, filtered through a Chem Elut™ cartridge and concentrated under reduced pressure. The residue was purified by column chromatography on silica gel (gradient n-heptane/ethyl acetate) to yield 40 mg (100% purity, 98% yield) of title compound as a white solid. Log P=2.54. (M+H)=280.

Preparation Example (I)-10: Preparation of N-(2-amino-2-oxoethyl)-4,5-dibromo-3-fluorothiophene-2-carboxamide (Compound I.0894)

Under inert atmosphere, to a solution of 600 mg (1.66 mmol) of N-[(4,5-dibromo-3-fluoro-2-thienyl)carbonyl]glycine in 30 mL of N,N-dimethylformamide were added, at room temperature, 133 mg (2.49 mmol) of ammonium chloride, 478 mg (2.49 mmol) of 1-(3-dimethylaminopropyl)-3-ethylcarbodiimide hydrochloride, 225 mg (1.66 mmol) of 1-hydroxybenzotriazole and 406 mg (3.32 mmol) of 4-(dimethylamino)pyridine. The reaction mixture was stirred at room temperature for 2 hours. The resulting reaction mixture was extracted with ethyl acetate. Combined organic layers were washed with brine, dried over anhydrous sodium sulfate, filtered and concentrated under reduced pressure. The residue was purified by preparative high performance liquid chromatography (gradient acetonitrile/aqueous solution of ammonium bicarbonate [10 mmol/L]) to yield 260 mg (99% purity, 43% yield) of title compound as a white solid. Log P=1.69. (M+H)=359.

Preparation Example (I)-11: N-(2-amino-2-sulfanylideneethyl)-4,5-dibromo-3-fluorothiophene-2-carboxamide (Compound I.0896)

Under inert atmosphere, to a solution of 200 mg (0.56 mmol) of N-(2-amino-2-oxoethyl)-4,5-dibromo-3-fluorothiophene-2-carboxamide in 10 mL of toluene was added 270 mg (0.67 mmol) of Lawesson reagent. The reaction mixture was stirred at 60° C. for 5 hours. The resulting reaction mixture was concentrated under reduced pressure, diluted with water and extracted with ethyl acetate. Combined organic layers were washed with brine, dried over anhydrous sodium sulfate, filtered and concentrated under reduced pressure. The residue was purified by preparative high performance liquid chromatography (gradient acetonitrile/aqueous solution of formic acid (0.1%)) to yield 80 mg (99% purity, 38% yield) of title compound as a white solid. Log P=2.25. (M+H)=375.

Preparation Example (I)-12: ethyl N-[(3-bromo-4,5-dichloro-2-thienyl)carbonyl]-2-methylalaninate (Compound I.1062)

Step 1: Preparation of ethyl N-[(3-amino-4,5-dichloro-2-thienyl)carbonyl]-2-methylalaninate A solution of 160 mg (0.94 mmol) of 2-chloro-1,3-dimethylimidazolidinium chloride dissolved in 2 mL of dichloromethane was added to a solution of 154 mg (0.72 mmol) of 3-amino-4,5-dichlorothiophene-2-carboxylic acid and 0.55 mL (3.13 mmol) of N,N-diisopropylethylamine dissolved in 5 mL of dichloromethane. After 5 min of stirring, 1.0 g (6.66 mmol) of ethyl 2-methylalaninate hydrochloride (1:1) was added and the reaction mixture was stirred at room temperature for 48 hours. Water was added and the resulting reaction mixture was extracted twice with dichloromethane. Combined organic layers were filtered through a Chem Elut™ cartridge and concentrated under reduced pressure. The residue was purified by column chromatography on silica gel (gradient heptane/ethyl acetate) to yield 205 mg (100% purity, 87% yield) of title compound as a white solid. Log P=3.09. (M+H)=325.

Step 2: Preparation of ethyl N-[(3-bromo-4,5-dichloro-2-thienyl)carbonyl]-2-methylalaninate (Compound I.1062)

To a solution of copper(I) bromide (114 mg, 0.79 mmol) in 7 mL of anhydrous acetonitrile was added dropwise tert-butyl nitrite (105 μL, 0.79 mmol) at 0° C. The mixture was allowed to warm to room temperature and 173 mg (0.53 mmol) of ethyl N-[(3-amino-4,5-dichloro-2-thienyl)carbonyl]-2-methylalaninate was added portion wise. The reaction mixture was stirred at room temperature for 3 hours. The reaction mixture was diluted with dichloromethane and carefully acidified with a 1 M aqueous hydrochloric acid solution. The aqueous layer was extracted twice with dichloromethane. Combined organic layers were dried over anhydrous magnesium sulfate, filtered and concentrated under reduced pressure. The residue was purified by column chromatography on silica gel (gradient n-heptane/ethyl acetate) to yield 63 mg (100% purity, 30% yield) of title compound as a white solid. Log P=4.24. (M+H)=388.

Synthesis of Compounds of Formula (II)

Preparation Example (II)-1: Preparation of methyl 5-chloro-4-cyano-3-methylthiophene-2-carboxylate (Compound II.028)

To a solution of copper(I) chloride (1.89 g, 19.1 mmol) in 45 mL of anhydrous acetonitrile was added dropwise tert-butyl nitrite (2.27 mL, 19.1 mmol) at 0° C. After 5 minutes of stirring at 0° C., 2.50 g (12.7 mmol) of methyl 5-amino-4-cyano-3-methylthiophene-2-carboxylate was added portion wise. The reaction mixture was allowed to warm to room temperature and was stirred for 18 hours. The reaction mixture was diluted with dichloromethane and carefully acidified with a 1 M aqueous hydrochloric acid solution. The aqueous layer was extracted twice with dichloromethane. Combined organic layers were dried over anhydrous magnesium sulfate, filtered and concentrated under reduced pressure. The residue was purified by column chromatography on silica gel (gradient n-heptane/ethyl acetate) to yield 1.15 g (100% purity, 42% yield) of title compound as a white solid. Log P=3.01. (M+H)=216.

Preparation Example (II)-2: Preparation of 4-bromo-5-cyano-3-methylthiophene-2-carboxylic acid (Compound II.042)

To a solution of 150 mg (0.86 mmol) of methyl 4-bromo-5-cyano-3-methylthiophene-2-carboxylate in 3.9 mL of tetrahydrofuran was added dropwise 0.7 mL of a 1.1 M aqueous lithium hydroxide solution (0.7 mmol). The reaction mixture was stirred at room temperature for 1 hour. The resulting reaction mixture was carefully acidified with a 1.0 M aqueous hydrochloric acid solution at 0° C. and extracted with ethyl acetate. Combined organic layers were dried over anhydrous magnesium sulfate, filtered and concentrated under reduced pressure to yield 142 mg (97% purity, 97% yield) of title compound as a white solid. Log P=2.05. (M+H)=246.

Preparation Example (II)-3: Preparation of methyl 4-chloro-5-cyanothiophene-2-carboxylate (Compound II.046)

In a microwave vial, to a solution of 100 mg (0.53 mmol) of 4-chloro-5-cyanothiophene-2-carboxylic acid in 3 mL of dry dichloromethane, were added, at room temperature, 60 μL (0.69 mmol) of oxalyl chloride and a drop of N,N-dimethylformamide. After 2 hours of stirring, 0.86 mL (21.3 mmol) of methanol was added and the reaction mixture was stirred at room temperature for 16 hours. The resulting mixture was filtered through a silica gel cartridge and concentrated under reduced pressure. The resulting reaction mixture was stirred at room temperature for 60 hours, diluted with water and carefully acidified with a 37% (w/w) aqueous hydrochloric acid solution at 0° C. The resulting precipitate was filtered off and the filtrate was concentrated under reduced pressure. The residue was purified by column chromatography on silica gel (gradient n-heptane/ethyl acetate) to yield 86 mg (99% purity, 79% yield) of title compound as a white solid. Log P=2.52. (M)=201.

Preparation Example (II)-4: Preparation of methyl 4,5-dibromo-3-(difluoromethyl)thiophene-2-carboxylate (Compound II.055)

To a solution of 57 g (182 mmol) of methyl 4,5-dibromo-3-methylthiophene-2-carboxylate in 500 mL of carbon tetrachloride were added 2.7 g (11 mmol) of dibenzoyl peroxide and 35.7 g (200 mmol) of N-bromosuccinimide 35.7 g in portions at room temperature. The reaction mixture was heated to reflux for 18 hours. The precipitate was filtered off. The organic layer was washed with warm water, saturated aqueous sodium bicarbonate solution and brine dried over anhydrous sodium sulfate and filtered. The filtrate was concentrated under reduced pressure to afford 71 g of the corresponding bromomethyl compound as yellow solid. To a solution of latter (71 g, 181 mmol) in 500 mL of dry acetonitrile was added in portions 63.4 g (540 mmol) of 4-methylmorpholine N-oxide monohydrate at 0° C. After stirring at room temperature for 16 hours, the reaction mixture was added dropwise to 2 L of a 2 N aqueous solution of hydrochloric acid and extracted with EtOAc. The organic layer washed with water, saturated aqueous sodium bicarbonate solution and brine, dried over anhydrous sodium sulfate and filtered. The filtrate was concentrated under reduced pressure to afford 23 g of the corresponding aldehyde as yellow solid. To a solution of 23 g (70 mmol) of the latter in 500 mL of dichloromethane was added dropwise 12 mL (99 mmol) of morpholinosulfur trifluoride at 0° C. The reaction mixture was stirred at room temperature for 18 hours. The reaction mixture was then carefully added to an ice: water mixture and extracted twice with dichloromethane. The organic layer was washed twice with water, twice with brine, dried over anhydrous magnesium sulfate, filtered, and concentrated under reduced pressure to give 8.9 g (14% yield) of the title compound. Log P=3.81. (M)=348.

Preparation Example (II)-5: Preparation of methyl 4,5-dichloro-3-cyanothiophene-2-carboxylate (Compound II.085)

To a solution of 10 g (44 mmol) of methyl 3-amino-4,5-dichlorothiophene-2-carboxylate in 250 mL of diethyl ether was added 11.2 mL (88 mmol) of boron trifluoride diethyl etherate at room temperature. To the stirred mixture was added 7.4 mL of isopentyl nitrite (55 mmol) leading to a slow formation of a grey precipitate. The precipitate was then filtered off and washed with diethyl ether. The resulting solid was added in portions to a stirred solution of 27.4 g (42 mmol) of potassium cyanide and 8.3 g (93 mmol) of copper(I) cyanide in 300 mL of water at 15° C. The reaction mixture was stirred at room temperature for 16 hours. Ethyl acetate was poured into the stirred reaction mixture and the organic layer was separated. The aqueous layer was extracted twice with ethyl acetate. The combined organic layers were washed with water, dried over anhydrous magnesium sulfate, filtered and concentrated under reduced pressure. The residue was purified by column chromatography on silica gel (gradient n-heptane/ethyl acetate) to yield 2.24 g (21% yield) of title compound as a white solid. Log P=2.98. (M)=235.

Preparation Example (II)-6: Preparation of ethyl 4,5-dichloro-3-cyanothiophene-2-carboxylate (Compound II.053)

Step 1: Preparation of ethyl 4,5-dichloro-3-iodothiophene-2-carboxylate

To a solution of 225 mg (1.0 mmol) of ethyl 4,5-dichlorothiophene-2-carboxylate in 10 mL of dry tetrahydrofurane under argon was added dropwise 2.39 mL (1.3 mmol) of 2,2,6,6-Tetramethylpiperidinylmagnesium chloride lithium chloride complex solution (17% in tetrahydrofurane) at 0° C. The reaction mixture was stirred at room temperature for 20 minutes. To the stirred mixture was added dropwise a solution of 508 mg of iodine (2.0 mmol) in 5 mL of dry. The reaction mixture was stirred at room temperature for 18 hours. The resulting reaction mixture was quenched with a saturated aqueous sodium thiosulfate solution and extracted with ethyl acetate. The combined organic layers were washed with water, dried over anhydrous sodium sulfate, filtered and concentrated under reduced pressure to yield 368 mg (95% purity, 99% yield) of title compound as a solid. Log P=4.75. (M)=350.

Step 2: Preparation of ethyl 4,5-dichloro-3-cyanothiophene-2-carboxylate (Compound II.053)

In a 5 mL microwave vial under inert atmosphere, 200 mg (0.57 mmol) of ethyl 4,5-dichloro-3-iodothiophene-2-carboxylate and 61 mg (0.68 mmol) of copper(I) cyanide were successively added followed by degassed N,N-dimethylformamide (1.5 mL). The vial was sealed and the reaction mixture was stirred at 110° C. for 5 hours. The resulting reaction mixture was quenched with a saturated aqueous sodium bicarbonate solution and extracted with dichloromethane. The combined organic layers were washed with water, dried over anhydrous sodium sulfate, filtered and concentrated under reduced pressure. The residue was purified by column chromatography on silica gel (gradient n-heptane/ethyl acetate) and preparative high performance liquid chromatography (gradient acetonitrile/aqueous solution of formic acid (0.1%)) to yield 60 mg (100% purity, 42% yield) of title compound as a white solid. Log P=3.54. (M+Na)=272.

Preparation Example (II)-7: Preparation of ethyl 5-bromo-4-chloro-3-methylthiophene-2-carboxylate (Compound II.033)

Step 1: Preparation of ethyl 5-amino-4-chloro-3-methylthiophene-2-carboxylate

A solution of 500 mg (2.25 mmol) of ethyl 5-amino-3-methylthiophene-2-carboxylate hydrochloride (1:1) in an aqueous sodium bicarbonate solution was extracted twice with dichloromethane. Combined organic layers were washed with a saturated aqueous sodium bicarbonate solution, filtered through a Chem Elut™ cartridge and concentrated under reduced pressure. To a solution of the residue in 4 mL of tetrahydrofurane was added 331 mg (2.48 mmol) of N-chlorosuccinimide at room temperature. The reaction mixture was stirred at room temperature for 18 hours. The resulting reaction mixture was quenched with a saturated aqueous sodium bicarbonate solution and extracted with dichloromethane. Combined organic layers were filtered through a Chem Elut™ cartridge and concentrated under reduced pressure. The residue was purified by column chromatography on silica gel (gradient n-heptane/ethyl acetate) to yield 260 mg (99% purity, 52% yield) of title compound as a brown solid. Log P=2.67. (M+H)=220.

Step 2: Preparation of ethyl 5-bromo-4-chloro-3-methylthiophene-2-carboxylate (Compound II.033)

To a solution of copper(I) chloride (1.89 g, 19.1 mmol) in 45 mL of anhydrous acetonitrile was added dropwise tert-butyl nitrite (2.27 mL, 19.1 mmol) at 0° C. After 5 minutes of stirring at 0° C., 2.50 g (12.7 mmol) of ethyl 5-amino-4-chloro-3-methylthiophene-2-carboxylate was added portion wise. The reaction mixture was allowed to warm to room temperature and was stirred for 18 hours. The reaction mixture was diluted with dichloromethane and carefully acidified with a 1 M aqueous hydrochloric acid solution. The aqueous layer was extracted twice with dichloromethane. Combined organic layers were dried over anhydrous magnesium sulfate, filtered and concentrated under reduced pressure. The residue was purified by column chromatography on silica gel (gradient n-heptane/ethyl acetate) to yield 1.15 g (100% purity, 42% yield) of title compound as a white solid. Log P=3.01. (M+H)=216.

Preparation Example (II)-8: Preparation of 4,5-dichloro-3-cyanothiophene-2-carboxylic acid (Compound II.103)

To a solution of 500 mg (2.80 mmol) of 4,5-dichlorothiophene-3-carbonitrile in 10 mL of dry tetrahydrofurane at −78° C. was added dropwise 1.40 mL (2.80 mmol) of a solution of lithium diisopropylamide (2.0 M in tetrahydrofurane). The reaction mixture was poured into a solution of crushed dry ice in dry tetrahydrofurane. The reaction mixture was concentrated under reduced pressure. A solution of residue in water was carefully acidified to pH 1 with a 1.0 M aqueous hydrochloric acid solution at 0° C. and extracted three times with ethyl acetate. Combined organic layers were dried and concentrated under reduced pressure. The residue was purified by preparative high performance liquid chromatography (gradient acetonitrile/water) to yield 327 mg (95% purity, 50% yield) of title compound as a white solid. Log P=1.61.

Exemplary Compounds

The exemplary compounds according to the invention as shown in tables I.1, I.2 and II.1 were prepared in analogy with the examples provided above and/or in accordance with the general description of the processes herein disclosed.

The following tables I.1 and I.2 illustrates in a non-limiting manner examples of compounds according to formula (I).

(I)

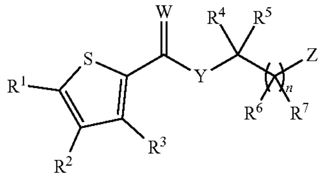

TABLE 1.1

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0001 | $CH_3$ | Br | F | O | NH | H | H | 0 | — | — | ethoxycarbonyl | 2.69[a] | | |
| 1.0002 | Cl | $CH_3$ | H | O | NH | isopropyl | H | 0 | — | — | ethoxycarbonyl | 3.48[a] | | |
| 1.0003 | Br | F | H | O | NH | isopropyl | H | 0 | — | — | ethoxycarbonyl | 3.46[a] | | |
| 1.0004 | Br | F | H | O | NH | 2,2-difluoroethyl | H | 0 | — | — | methoxycarbonyl | 2.68[a] | | |
| 1.0005 | Cl | Br | H | O | NH | 2-methylsulfanylethyl | H | 0 | — | — | carboxy | 2.58[a] | | |
| 1.0008 | Br | Br | F | O | NH | $—CH_2—CH(CH{=}CH_2)—$ | | 0 | — | — | methoxycarbonyl | 3.37[a] | (*) | |
| 1.0009 | Br | Br | F | O | NH | $—CH_2—CH_2—O—CH_2—$ | | 0 | — | — | methoxycarbonyl | 2.76[a] | | |
| 1.0010 | Br | Br | F | O | NH | $—CH_2—CH_2—CF_2—CH_2—CH_2—$ | | 0 | — | — | methoxycarbonyl | 3.74[a] | | |
| 1.0011 | Br | Br | F | O | NH | $—CH_2—CH_2—O—CH_2—CH_2—$ | | 0 | — | — | ethoxycarbonyl | 3.13[a] | | |
| 1.0012 | Br | Br | F | O | NH | $CH_2—OH$ | H | 0 | — | — | ethoxycarbonyl | 2.51[a] | | |
| 1.0013 | Br | Br | F | O | NH | 2-methylpropyl | H | 0 | — | — | ethylsulfanylcarbonyl | 5.05[a] | | |
| 1.0014 | Br | Br | F | O | NH | isopropyl | H | 0 | — | — | ethylsulfanylcarbonyl | 4.87[a] | | |
| 1.0015 | Br | Br | F | O | NH | H | H | 0 | — | — | benzylsulfanylcarbonyl | 4.15[a] | | |
| 1.0016 | Br | Br | F | O | NH | H | H | 0 | — | — | phenylsulfanylcarbonyl | 3.89[a] | | |
| 1.0018 | Cl | Br | $CH_3$ | O | NH | $—CH_2—CH_2—O—CH_2—CH_2—$ | | 0 | — | — | ethoxycarbonyl | 3.15[a] | | |
| 1.0019 | Cl | Br | $CH_3$ | O | NH | $CH_2—OH$ | H | 0 | — | — | ethoxycarbonyl | 2.54[a] | | |
| 1.0020 | Cl | Br | $CH_3$ | O | NH | 2-methylpropyl | H | 0 | — | — | ethylsulfanylcarbonyl | 5.03[a] | | |
| 1.0021 | Cl | Br | $CH_3$ | O | NH | isopropyl | H | 0 | — | — | ethylsulfanylcarbonyl | 4.74[a] | | |
| 1.0022 | Cl | Br | $CH_3$ | O | NH | H | H | 0 | — | — | benzylsulfanylcarbonyl | 4.37[a] | | |
| 1.0024 | CN | Br | $CH_3$ | O | NH | H | H | 0 | — | — | ethoxycarbonyl | 2.46[a] | | |
| 1.0025 | CN | Br | $CH_3$ | O | NH | H | H | 1 | H | H | ethoxycarbonyl | 2.52[a] | | |
| 1.0026 | CN | Br | $CH_3$ | O | NH | $—CH_2—CH_2—$ | | 0 | — | — | ethoxycarbonyl | 2.58[a] | | |
| 1.0027 | CN | Br | $CH_3$ | O | NH | isopropyl | H | 0 | — | — | ethoxycarbonyl | 3.52[a] | | |
| 1.0028 | CN | Br | $CH_3$ | O | NH | benzyl | H | 0 | — | — | ethoxycarbonyl | 3.74[a] | | |
| 1.0029 | Cl | Br | H | O | NH | benzyl | H | 0 | — | — | ethoxycarbonyl | 4.06[a] | | |
| 1.0030 | Br | F | H | O | NH | benzyl | H | 0 | — | — | ethoxycarbonyl | 3.69[a] | | |
| 1.0031 | Cl | $CH_3$ | H | O | NH | benzyl | H | 0 | — | — | ethoxycarbonyl | 3.73[a] | | |
| 1.0032 | Cl | Br | $CH_3$ | O | NH | $—CH_2—CH_2—$ | | 1 | H | H | methoxycarbonyl | 3.04[a] | | |
| 1.0033 | Cl | Br | $CH_3$ | O | NH | H | H | 1 | $—CH_2—CH_2—$ | | ethoxycarbonyl | 3.79[a] | | |
| 1.0034 | Cl | Br | $CH_3$ | O | NH | $—CH_2—O—CH_2—$ | | 0 | — | — | ethoxycarbonyl | 2.88[a] | | |
| 1.0035 | Cl | Br | $CH_3$ | O | NH | $—CH_2—S—CH_2—$ | | 0 | — | — | methoxycarbonyl | 3.29[a] | | |
| 1.0036 | Cl | Br | $CH_3$ | O | NH | 2-amino-2-oxoethyl | H | 0 | — | — | ethoxycarbonyl | 2.25[a] | | |
| 1.0037 | Cl | Br | $CH_3$ | O | NH | $—CH_2—CH_2—$ | | 1 | $—CH_2—CH_2—$ | | ethoxycarbonyl | 4.37[a] | | |
| 1.0038 | Cl | Br | $CH_3$ | O | NH | 2,2,2-trifluoroethyl | H | 0 | — | — | ethoxycarbonyl | 3.99[a] | | |
| 1.0039 | Br | Cl | $CH_3$ | O | NH | $—CH_2—CH_2—$ | | 1 | — | — | methoxycarbonyl | 3.01[a] | | |
| 1.0040 | Br | Cl | $CH_3$ | O | NH | H | H | 1 | $—CH_2—CH_2—$ | | ethoxycarbonyl | 3.75[a] | | |
| 1.0041 | Br | Cl | $CH_3$ | O | NH | $—CH_2—O—CH_2—$ | | 0 | — | — | ethoxycarbonyl | 2.84[a] | | |
| 1.0042 | Br | Cl | $CH_3$ | O | NH | $—CH_2—S—CH_2—$ | | 0 | — | — | methoxycarbonyl | 3.25[a] | | |
| 1.0043 | Br | Cl | $CH_3$ | O | NH | 2-amino-2-oxoethyl | H | 0 | — | — | ethoxycarbonyl | 2.22[a] | | |
| 1.0044 | Br | Cl | $CH_3$ | O | NH | $—CH_2—CH_2—$ | | 1 | $—CH_2—CH_2—$ | | ethoxycarbonyl | 4.32[a] | | |
| 1.0045 | Br | Cl | $CH_3$ | O | NH | 2,2,2-trifluoroethyl | H | 0 | — | — | ethoxycarbonyl | 3.94[a] | | |
| 1.0046 | Br | Br | F | O | NH | $—CH_2—O—CH_2—$ | | 0 | — | — | ethoxycarbonyl | 2.77[a] | | |
| 1.0047 | Br | Br | F | O | NH | $—CH_2—S—CH_2—$ | | 0 | — | — | methoxycarbonyl | 3.19[a] | | |
| 1.0048 | Br | Br | F | O | NH | 2-amino-2-oxoethyl | H | 0 | — | — | ethoxycarbonyl | 2.17[a] | | |
| 1.0049 | Br | Br | F | O | NH | $—CH_2—CH_2—$ | | 1 | $—CH_2—CH_2—$ | | ethoxycarbonyl | 4.41[a] | | |
| 1.0050 | Br | Br | F | O | NH | 2,2,2-trifluoroethyl | H | 0 | — | — | ethoxycarbonyl | 3.88[a] | | |
| 1.0051 | Br | Br | F | O | NH | benzyl | H | 0 | — | — | ethoxycarbonyl | 4.55[a] | | |
| 1.0052 | CN | Br | H | O | NH | H | H | 0 | — | — | ethoxycarbonyl | 2.16[a] | | |
| 1.0053 | CN | Br | H | O | NH | $—CH_2—CH_2—$ | | 0 | — | — | ethoxycarbonyl | 2.45[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0054 | CN | Br | H | O | NH | isopropyl | H | 0 | — | — | ethoxycarbonyl | 3.27[a] | | |
| 1.0055 | CN | Br | H | O | NH | benzyl | H | 0 | — | — | ethoxycarbonyl | 3.50[a] | | |
| 1.0056 | Cl | Br | $CH_3$ | O | NH | $—CH_2—CH_2—$ | | 1 | $—CH_2—CH_2—$ | | isopropyloxycarbonyl | 4.87[a] | | |
| 1.0057 | Br | Cl | $CH_3$ | O | NH | $—CH_2—CH_2—$ | | 1 | $—CH_2—CH_2—$ | | isopropyloxycarbonyl | 4.82[a] | | |
| 1.0058 | Br | Br | F | O | NH | $—CH_2—CH_2—$ | | 1 | $—CH_2—CH_2—$ | | isopropyloxycarbonyl | 4.90[a] | | |
| 1.0059 | Cl | Cl | Br | S | NH | H | H | 0 | — | — | ethoxycarbonyl | 4.61[a] | | |
| 1.0062 | Br | Br | F | O | NH | 2-methylpropyl | H | 0 | — | — | ethoxycarbonyl | 4.67[a] | | |
| 1.0063 | Cl | Br | $CH_3$ | O | NH | H | H | 0 | — | — | ethoxycarbonyl | 2.98[a] | | |
| 1.0064 | Cl | Br | $CH_3$ | O | NH | H | H | 1 | H | H | ethoxycarbonyl | 3.15[a] | | |
| 1.0065 | Cl | Br | $CH_3$ | O | NH | $—CH_2—CH_2—$ | | 0 | — | — | ethoxycarbonyl | 3.17[a] | | |
| 1.0066 | Cl | Br | $CH_3$ | O | NH | $—CH_2—CH_2—CH_2—$ | | 0 | — | — | ethoxycarbonyl | 3.71[a] | | |
| 1.0067 | Cl | Br | $CH_3$ | O | NH | isopropyl | H | 0 | — | — | ethoxycarbonyl | 4.30[a] | | |
| 1.0068 | Cl | Br | $CH_3$ | O | NH | 2,2-difluoroethyl | H | 0 | — | — | methoxycarbonyl | 3.33[a] | | |
| 1.0069 | Cl | Br | $CH_3$ | O | NH | 2-methylpropyl | H | 0 | — | — | ethoxycarbonyl | 4.58[a] | | |
| 1.0070 | Cl | Br | $CH_3$ | O | NH | 2-methylsulfanylethyl | H | 0 | — | — | ethoxycarbonyl | 3.99[a] | | |
| 1.0071 | Cl | Br | $CH_3$ | O | NH | benzyl | H | 0 | — | — | ethoxycarbonyl | 4.51[a] | | |
| 1.0072 | Br | Cl | $CH_3$ | O | NH | H | H | 0 | — | — | ethoxycarbonyl | 2.94[a] | | |
| 1.0073 | Br | Cl | $CH_3$ | O | NH | H | H | 1 | H | H | ethoxycarbonyl | 3.11[a] | | |
| 1.0074 | Br | Cl | $CH_3$ | O | NH | $—CH_2—CH_2—$ | | 0 | — | — | ethoxycarbonyl | 3.13[a] | | |
| 1.0075 | Br | Cl | $CH_3$ | O | NH | $—CH_2—CH_2—CH_2—$ | | 0 | — | — | ethoxycarbonyl | 3.67[a] | | |
| 1.0076 | Br | Cl | $CH_3$ | O | NH | isopropyl | H | 0 | — | — | ethoxycarbonyl | 4.25[a] | | |
| 1.0077 | Br | Cl | $CH_3$ | O | NH | 2,2-difluoroethyl | H | 0 | — | — | methoxycarbonyl | 3.29[a] | | |
| 1.0078 | Br | Cl | $CH_3$ | O | NH | 2-methylpropyl | H | 0 | — | — | ethoxycarbonyl | 4.53[a] | | |
| 1.0079 | Br | Cl | $CH_3$ | O | NH | 2-methylsulfanylethyl | H | 0 | — | — | ethoxycarbonyl | 3.94[a] | | |
| 1.0080 | Br | Cl | $CH_3$ | O | NH | benzyl | H | 0 | — | — | ethoxycarbonyl | 4.46[a] | | |
| 1.0081 | Br | Br | I | O | NH | H | H | 1 | H | H | ethoxycarbonyl | 3.48[a] | | |
| 1.0082 | Br | Br | I | O | NH | $—CH_2—CH_2—CH_2—$ | | 0 | — | — | ethoxycarbonyl | 4.08[a] | | |
| 1.0083 | Br | Br | I | O | NH | 2,2-difluoroethyl | H | 0 | — | — | methoxycarbonyl | 3.60[a] | | |
| 1.0084 | Cl | Cl | Br | O | NH | H | H | 1 | H | H | ethoxycarbonyl | 3.50[a] | | |
| 1.0085 | Cl | Cl | Br | O | NH | $—CH_2—CH_2—CH_2—$ | | 0 | — | — | ethoxycarbonyl | 4.23[a] | | |
| 1.0086 | Cl | Cl | Br | O | NH | 2,2-difluoroethyl | H | 0 | — | — | methoxycarbonyl | 3.60[a] | | |
| 1.0087 | Br | I | $CH_3$ | O | NH | H | H | 0 | — | — | ethoxycarbonyl | 3.09[a] | | |
| 1.0088 | Br | I | $CH_3$ | O | NH | H | H | 1 | H | H | ethoxycarbonyl | 3.23[a] | | |
| 1.0089 | Br | I | $CH_3$ | O | NH | $—CH_2—CH_2—$ | | 0 | — | — | ethoxycarbonyl | 3.25[a] | | |
| 1.0090 | Br | I | $CH_3$ | O | NH | $—CH_2—CH_2—CH_2—$ | | 0 | — | — | ethoxycarbonyl | 3.77[a] | | |
| 1.0091 | Br | I | $CH_3$ | O | NH | isopropyl | H | 0 | — | — | ethoxycarbonyl | 4.37[a] | | |
| 1.0092 | Br | I | $CH_3$ | O | NH | 2,2-difluoroethyl | H | 0 | — | — | methoxycarbonyl | 3.39[a] | | |
| 1.0093 | Br | I | $CH_3$ | O | NH | 2-methylpropyl | H | 0 | — | — | ethoxycarbonyl | 4.66[a] | | |
| 1.0094 | Br | I | $CH_3$ | O | NH | 2-methylsulfanylethyl | H | 0 | — | — | ethoxycarbonyl | 4.03[a] | | |
| 1.0095 | Br | I | $CH_3$ | O | NH | benzyl | H | 0 | — | — | ethoxycarbonyl | 4.53[a] | | |
| 1.0096 | I | Br | $CH_3$ | O | NH | H | H | 0 | — | — | ethoxycarbonyl | 3.02[a] | | |
| 1.0097 | I | Br | $CH_3$ | O | NH | H | H | 1 | H | H | ethoxycarbonyl | 3.17[a] | | |
| 1.0098 | I | Br | $CH_3$ | O | NH | $—CH_2—CH_2—$ | | 0 | — | — | ethoxycarbonyl | 3.19[a] | | |
| 1.0099 | I | Br | $CH_3$ | O | NH | $—CH_2—CH_2—CH_2—$ | | 0 | — | — | ethoxycarbonyl | 3.71[a] | | |
| 1.0100 | I | Br | $CH_3$ | O | NH | isopropyl | H | 0 | — | — | ethoxycarbonyl | 4.30[a] | | |
| 1.0101 | I | Br | $CH_3$ | O | NH | 2,2-difluoroethyl | H | 0 | — | — | methoxycarbonyl | 3.33[a] | | |
| 1.0102 | I | Br | $CH_3$ | O | NH | 2-methylpropyl | H | 0 | — | — | ethoxycarbonyl | 4.56[a] | | |
| 1.0103 | I | Br | $CH_3$ | O | NH | 2-methylsulfanylethyl | H | 0 | — | — | ethoxycarbonyl | 3.96[a] | | |
| 1.0104 | I | Br | $CH_3$ | O | NH | benzyl | H | 0 | — | — | ethoxycarbonyl | 4.46[a] | | |
| 1.0105 | Cl | Br | $CH_3$ | O | NH | H | H | 0 | — | — | cyano | 2.58[a] | | |
| 1.0106 | Cl | Br | $CH_3$ | O | NH | $—CH_2—CH_2—$ | | 0 | — | — | cyano | 2.78[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0107 | Cl | Br | $CH_3$ | O | NH | $—CH_2—CH_2—CH_2—$ | | 0 | — | — | cyano | 4.53[a] | | |
| 1.0108 | Cl | Br | $CH_3$ | O | NH | isopropyl | H | 0 | — | — | cyano | 3.63[a] | | |
| 1.0109 | Cl | Br | $CH_3$ | O | NH | phenyl | H | 0 | — | — | cyano | 3.85[a] | | |
| 1.0110 | Cl | Br | $CH_3$ | O | NH | benzyl | H | 0 | — | — | cyano | 3.99[a] | | |
| 1.0111 | Br | Cl | $CH_3$ | O | NH | H | H | 0 | — | — | cyano | 2.54[a] | | |
| 1.0112 | Br | Cl | $CH_3$ | O | NH | $—CH_2—CH_2—$ | | 0 | — | — | cyano | 2.75[a] | | |
| 1.0113 | Br | Cl | $CH_3$ | O | NH | phenyl | H | 0 | — | — | cyano | 3.81[a] | | |
| 1.0114 | Br | Cl | $CH_3$ | O | NH | benzyl | H | 0 | — | — | cyano | 3.92[a] | | |
| 1.0115 | Br | Br | F | O | NH | $—CH_2—CH_2—$ | | 0 | — | — | cyano | 2.64[a] | | |
| 1.0116 | Br | Br | F | O | NH | $—CH_2—CH_2—CH_2—$ | | 0 | — | — | cyano | 3.11[a] | | |
| 1.0117 | Br | Br | F | O | NH | phenyl | H | 0 | — | — | cyano | 3.65[a] | | |
| 1.0118 | Br | Br | F | O | NH | benzyl | H | 0 | — | — | cyano | 3.81[a] | | |
| 1.0119 | Cl | Br | $CH_3$ | O | NH | cyclopropyl | H | 0 | — | — | methoxycarbonyl | 3.39[a] | | |
| 1.0120 | Br | Cl | $CH_3$ | O | NH | cyclopropyl | H | 0 | — | — | methoxycarbonyl | 3.35[a] | | |
| 1.0121 | Br | Br | F | O | NH | cyclopropyl | H | 0 | — | — | methoxycarbonyl | 3.43[a] | | |
| 1.0122 | Cl | Br | $CH_3$ | O | NH | $CH_3$ | H | 0 | — | — | ethoxycarbonyl | 3.37[a] | | |
| 1.0124 | Cl | Br | $CH_3$ | O | NH | 1H-imidazol-4-ylmethyl | H | 0 | — | — | methoxycarbonyl | 1.48[a] | | |
| 1.0125 | Cl | Br | $CH_3$ | O | NH | methoxymethyl | H | 0 | — | — | ethoxycarbonyl | 3.44[a] | | |
| 1.0126 | Cl | Br | $CH_3$ | O | NH | (4-hydroxyphenyl)methyl | H | 0 | — | — | ethoxycarbonyl | 3.33[a] | | |
| 1.0127 | Cl | Br | $CH_3$ | O | NH | 3-carbamimidamidopropyl | H | 0 | — | — | methoxycarbonyl | 1,66[a] | (S) | −9.3° (c = 1.07, DMSO, 25° C.) |
| 1.0128 | Cl | Br | $CH_3$ | O | NH | 1H-indol-3-ylmethyl | H | 0 | — | — | ethoxycarbonyl | 4.15[a] | | |
| 1.0129 | Br | Cl | $CH_3$ | O | NH | 1H-imidazol-4-ylmethyl | H | 0 | — | — | methoxycarbonyl | 1.47[a] | | |
| 1.0130 | Br | Cl | $CH_3$ | O | NH | (4-hydroxyphenyl)methyl | H | 0 | — | — | ethoxycarbonyl | 3.29[a] | | |
| 1.0131 | Br | Cl | $CH_3$ | O | NH | 3-carbamimidamidopropyl | H | 0 | — | — | methoxycarbonyl | 1.71[a] | (S) | −1.5° (c = 1.35, DMSO, 25° C) |
| 1.0132 | Br | Cl | $CH_3$ | O | NH | 1H-indol-3-ylmethyl | H | 0 | — | — | ethoxycarbonyl | 4.11[a] | | |
| 1.0133 | Br | Br | F | O | NH | $CH_3$ | H | 0 | — | — | ethoxycarbonyl | 3.41[a] | | |
| 1.0134 | Br | Br | F | O | NH | 1H-imidazol-4-ylmethyl | H | 0 | — | — | methoxycarbonyl | 1.39[a] | | |
| 1.0135 | Br | Br | F | O | NH | methoxymethyl | H | 0 | — | — | ethoxycarbonyl | 3.46[a] | | |
| 1.0136 | Br | Br | F | O | NH | (4-hydroxyphenyl)methyl | H | 0 | — | — | ethoxycarbonyl | 3.31[a] | | |
| 1.0137 | Br | Br | F | O | NH | 1H-indol-3-ylmethyl | H | 0 | — | — | ethoxycarbonyl | 4.08[a] | | |
| 1.0138 | Br | Cl | $CH_3$ | O | NH | methoxymethyl | H | 0 | — | — | ethoxycarbonyl | 3.42[a] | | |
| 1.0139 | Br | Br | I | O | NH | $—CH_2—CH_2—$ | | 0 | — | — | ethylsulfanylcarbonyl | 3.96[a] | | |
| 1.0140 | Br | Cl | $CH_3$ | O | NH | $CH_3$ | H | 0 | — | — | ethoxycarbonyl | 3.35[a] | | |
| 1.0142 | Br | Br | Cl | O | NH | H | H | 0 | — | — | ethoxycarbonyl | 3.30[a] | | |
| 1.0143 | Br | Br | Cl | O | NH | H | H | 1 | H | H | ethoxycarbonyl | 3.53[a] | | |
| 1.0144 | Br | Br | Cl | O | NH | $—CH_2—CH_2—CH_2—$ | | 0 | — | — | ethoxycarbonyl | 4.27[a] | | |
| 1.0145 | Br | Br | Cl | O | NH | isopropyl | H | 0 | — | — | ethoxycarbonyl | 4.92[a] | | |
| 1.0146 | Br | Br | Cl | O | NH | 2,2-difluoroethyl | H | 0 | — | — | methoxycarbonyl | 3.62[a] | | |
| 1.0147 | Br | Br | Cl | O | NH | 2-methylpropyl | H | 0 | — | — | ethoxycarbonyl | 5.19[a] | | |
| 1.0148 | Br | Br | Cl | O | NH | 2-methylsulfanylethyl | H | 0 | — | — | ethoxycarbonyl | 4.46[a] | | |
| 1.0149 | Br | Br | Cl | O | NH | benzyl | H | 0 | — | — | ethoxycarbonyl | 5.00[a] | | |
| 1.0150 | Br | Br | I | S | NH | $—CH_2—CH_2—$ | | 0 | — | — | methoxycarbonyl | 3.99[a] | | |
| 1.0151 | Br | Br | F | O | NH | isopropyl | H | 0 | — | — | ethoxycarbonyl | 4.47[a] | | +34° (c = 1, CDLCl3, 25° C.) |
| 1.0152 | Br | Br | F | O | NH | propan-2-yl | H | 0 | — | — | ethoxycarbonyl | 4.47[a] | (R) | −32° (c = 1, CDCl3, 25° C.) |
| 1.0153 | Br | Br | F | O | NH | benzyl | H | 0 | — | — | ethoxycarbonyl | 4.55[a] | (R) | −85.7° (c = 1.26, MeOH, 25° C.) |
| 1.0154 | Br | Br | F | O | NH | benzyl | H | 0 | — | — | ethoxycarbonyl | 4.55[a] | (S) | +62° (c = 1, CDCl3, 25° C.) |
| 1.0155 | Br | Br | F | O | NH | benzyl | H | 0 | — | — | methoxycarbonyl | 4.12[a] | (S) | −9.8° (c = 1.02, MeOH, 25° C.) |
| 1.0156 | Br | Br | F | O | NH | 2-methylpropyl | H | 0 | — | — | ethoxycarbonyl | 4.78[a] | (R) | +2.1° (c = 0.96, CH3CN, 25"C) |
| 1.0157 | Br | Br | F | O | NH | 2-methylpropyl | H | 0 | — | — | ethoxycarbonyl | 4.78[a] | (S) | −2.1° (c = 0.97, CH3CN, 25° C.) |
| 1.0158 | Br | Br | F | O | NH | 2-methylsulfanylethyl | H | 0 | — | — | methoxycarbonyl | 3.62[a] | (R) | −29.1° (c = 0.9, CDCl3, 25° C.) |
| 1.0159 | Br | Br | F | O | NH | 2-methylsulfanylethyl | H | 0 | — | — | methoxycarbonyl | 3.62[a] | (S) | +32.2° (c = 1.06, CDCl3, 25° C.) |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0160 | Br | Br | F | O | NH | 2-amino-2-oxoethyl | H | 0 | — | — | methoxycarbonyl | 1.94[a] | (R) | |
| 1.0161 | Br | Br | F | O | NH | 2-amino-2-oxoethyl | H | 0 | — | — | methoxycarbonyl | 1.98[a] | (S) | +6.8° (c = 0.88, MeOH, 25° C.) |
| 1.0162 | Br | Cl | H | O | NH | $—CH_2—CH_2—$ | | 0 | — | — | methoxycarbonyl | 2.48[a] | | |
| 1.0163 | Br | Cl | $CH_3$ | O | NH | $—CH_2—CH_2—$ | | 0 | — | — | methoxycarbonyl | 2.76[a] | | |
| 1.0164 | Cl | Br | H | O | NH | $—CH_2—CH_2—$ | | 0 | — | — | methoxycarbonyl | 2.51[a] | | |
| 1.0165 | Cl | Br | $CH_3$ | O | NH | $—CH_2—CH_2—$ | | 0 | — | — | methoxycarbonyl | 2.80[a] | | |
| 1.0166 | Br | Br | F | O | NH | $—CH_2—CH_2—CH_2—$ | | 0 | — | — | ethoxycarbonyl | 3.78[a] | | |
| 1.0167 | Br | Br | F | O | $N—CH_3$ | H | H | 0 | — | — | ethoxycarbonyl | 3.09[a] | | |
| 1.0168 | Br | Cl | $CH_3$ | O | NH | $—CH_2—CH_2—$ | | 0 | — | — | carboxy | 2.20[a] | | |
| 1.0169 | Cl | Br | H | O | NH | $—CH_2—CH_2—$ | | 0 | — | — | carboxy | 2.02[a] | | |
| 1.0170 | Cl | Br | $CH_3$ | O | NH | $—CH_2—CH_2—$ | | 0 | — | — | carboxy | 2.21[a] | | |
| 1.0171 | Br | Br | F | O | $N—CH_3$ | isopropyl | H | 0 | — | — | ethoxycarbonyl | 4.39[a] | | |
| 1.0172 | Br | Br | F | O | NH | $—CH_2—CH_2—CH_2—$ | | 0 | — | — | carboxy | 2.62[a] | | |
| 1.0173 | Br | Br | I | S | NH | $—CH_2—CH_2—$ | | 0 | — | — | carboxy | 3.09[a] | | |
| 1.0174 | Br | Br | F | O | NH | $—CH_2—CH_2—$ | | 0 | — | — | aminocarbonyl | 1.94[a] | | |
| 1.0175 | Br | Br | F | O | NH | phenyl | H | 0 | — | — | ethoxycarbonyl | 4.47[a] | | |
| 1.0176 | Cl | Br | Cl | O | NH | H | H | 0 | — | — | cyano | 2.70[a] | | |
| 1.0177 | Cl | Br | Cl | O | NH | H | H | 0 | — | — | methoxycarbonyl | 2.85[a] | | |
| 1.0178 | Cl | Br | Cl | O | NH | H | H | 0 | — | — | ethoxycarbonyl | 3.37[a] | | |
| 1.0179 | Cl | Br | Cl | O | NH | H | H | 1 | H | H | ethoxycarbonyl | 3.54[a] | | |
| 1.0180 | Cl | Br | Cl | O | NH | $—CH_2—CH_2—$ | | 0 | — | — | ethoxycarbonyl | 3.47[a] | | |
| 1.0181 | Cl | Br | Cl | O | NH | cyclopropyl | H | 0 | — | — | methoxycarbonyl | 3.91[a] | | |
| 1.0182 | Cl | Br | Cl | O | NH | $—CH_2—CH_2—CH_2—$ | | 0 | — | — | ethoxycarbonyl | 4.33[a] | | |
| 1.0183 | Cl | Br | Cl | O | NH | isopropyl | H | 0 | — | — | ethoxycarbonyl | 4.97[a] | | |
| 1.0184 | Cl | Br | Cl | O | NH | 2,2-difluoroethyl | H | 0 | — | — | methoxycarbonyl | 3.64[a] | | |
| 1.0185 | Cl | Br | Cl | O | NH | 2-methylpropyl | H | 0 | — | — | ethoxycarbonyl | 5.20[a] | | |
| 1.0186 | Cl | Br | Cl | O | NH | 2-methylsulfanylettiyl | H | 0 | — | — | ethoxycarbonyl | 4.47[a] | | |
| 1.0187 | Cl | Br | Cl | O | NH | benzyl | H | 0 | — | — | ethoxycarbonyl | 5.04[a] | | |
| 1.0188 | Cl | Cl | I | O | NH | H | H | 0 | — | — | cyano | 2.72[a] | | |
| 1.0189 | Cl | Cl | I | O | NH | H | H | 1 | H | H | ethoxycarbonyl | 3.47[a] | | |
| 1.0190 | Cl | Cl | I | O | NH | cyclopropyl | H | 0 | — | — | methoxycarbonyl | 3.84[a] | | |
| 1.0191 | Cl | Cl | I | O | NH | $—CH_2—CH_2—CH_2—$ | | 0 | — | — | ethoxycarbonyl | 4.12[a] | | |
| 1.0192 | Cl | Cl | I | O | NH | 2,2-difluoroethyl | H | 0 | — | — | methoxycarbonyl | 3.64[a] | | |
| 1.0193 | Br | Cl | Cl | O | NH | H | H | 0 | — | — | cyano | 2.67[a] | | |
| 1.0194 | Br | Cl | Cl | O | NH | H | H | 0 | — | — | methoxycarbonyl | 2.86[a] | | |
| 1.0195 | Br | Cl | Cl | O | NH | H | H | 0 | — | — | ethoxycarbonyl | 3.28[a] | | |
| 1.0196 | Br | Cl | Cl | O | NH | H | H | 1 | H | H | ethoxycarbonyl | 3.47[a] | | |
| 1.0197 | Br | Cl | Cl | O | NH | $—CH_2—CH_2—$ | | 0 | — | — | ethoxycarbonyl | 3.47[a] | | |
| 1.0198 | Br | Cl | Cl | O | NH | cyclopropyl | H | 0 | — | — | methoxycarbonyl | 3.87[a] | | |
| 1.0199 | Br | Cl | Cl | O | NH | $—CH_2—CH_2—CH_2—$ | | 0 | — | — | ethoxycarbonyl | 4.26[a] | | |
| 1.0200 | Br | Cl | Cl | O | NH | isopropyl | H | 0 | — | — | ethoxycarbonyl | 4.89[a] | | |
| 1.0201 | Br | Cl | Cl | O | NH | 2,2-difluoroethyl | H | 0 | — | — | methoxycarbonyl | 3.60[a] | | |
| 1.0202 | Br | Cl | Cl | O | NH | 2-methylpropyl | H | 0 | — | — | ethoxycarbonyl | 5.16[a] | | |
| 1.0203 | Br | Cl | Cl | O | NH | 2-methylsulfanylethyl | H | 0 | — | — | ethoxycarbonyl | 4.44[a] | | |
| 1.0204 | Br | Cl | Cl | O | NH | benzyl | H | 0 | — | — | ethoxycarbonyl | 5.00[a] | | |
| 1.0205 | Br | Br | F | O | NH | H | H | 0 | — | — | cyano | 2.41[a] | | |
| 1.0206 | Cl | Br | Br | O | NH | H | H | 0 | — | — | cyano | 2.72[a] | | |
| 1.0207 | Cl | Br | Br | O | NH | H | H | 0 | — | — | methoxycarbonyl | 2.91[a] | | |
| 1.0208 | Cl | Br | Br | O | NH | H | H | 0 | — | — | ethoxycarbonyl | 3.35[a] | | |
| 1.0209 | Cl | Br | Br | O | NH | H | H | 1 | H | H | ethoxycarbonyl | 3.57[a] | | |
| 1.0210 | Cl | Br | Br | O | NH | $—CH_2—CH_2—$ | | 0 | — | — | ethoxycarbonyl | 3.48[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0211 | Cl | Br | Br | O | NH | cyclopropyl | H | 0 | — | — | methoxycarbonyl | 3.89[a] | | |
| 1.0212 | Cl | Br | Br | O | NH | $—CH_2—CH_2—CH_2—$ | | 0 | — | — | ethoxycarbonyl | 4.24[a] | | |
| 1.0213 | Cl | Br | Br | O | NH | isopropyl | H | 0 | — | — | ethoxycarbonyl | 4.89[a] | | |
| 1.0214 | Cl | Br | Br | O | NH | 2,2-difluoroethyl | H | 0 | — | — | methoxycarbonyl | 3.64[a] | | |
| 1.0215 | Cl | Br | Br | O | NH | 2-methylpropyl | H | 0 | — | — | ethoxycarbonyl | 5.18[a] | | |
| 1.0216 | Cl | Br | Br | O | NH | 2-methylsulfanylethyl | H | 0 | — | — | ethoxycarbonyl | 4.40[a] | | |
| 1.0217 | Cl | Br | Br | O | NH | benzyl | H | 0 | — | — | ethoxycarbonyl | 5.04[a] | | |
| 1.0226 | Br | Br | F | O | NH | benzyl | H | 0 | — | — | carboxy | 3.22[a] | | |
| 1.0227 | Br | Br | F | O | NH | H | H | 0 | — | — | carboxy | 2.01[a] | | |
| 1.0228 | Br | Br | F | O | NH | $CH_2—OH$ | H | 0 | — | — | carboxy | 1.77[a] | | |
| 1.0229 | Br | Br | F | O | NH | 2-methylpropyl | H | 0 | — | — | carboxy | 3.34[a] | | |
| 1.0230 | Br | Br | F | O | NH | 3-amino-3-oxopropyl | H | 0 | — | — | carboxy | 1.65[a] | | |
| 1.0231 | Br | Br | F | O | NH | 1H-indol-3-ylmethyl | H | 0 | — | — | carboxy | 3.05[a] | | |
| 1.0232 | Cl | Cl | CN | O | NH | $—CH_2—CH_2—$ | | 0 | — | — | ethoxycarbonyl | 2.72[a] | | |
| 1.0233 | Br | Br | F | O | NH | $CH_3$ | H | 0 | — | — | carboxy | 2.28[a] | | |
| 1.0234 | Br | Br | F | O | NH | isopropyl | H | 0 | — | — | carboxy | 2.97[a] | | |
| 1.0236 | Cl | Cl | CN | O | NH | H | H | 0 | — | — | ethoxycarbonyl | 2.52[a] | | |
| 1.0237 | Br | Cl | H | O | NH | 2-methylsulfanylethyl | H | 0 | — | — | ethoxycarbonyl | 3.59[a] | | |
| 1.0238 | Cl | Br | H | O | NH | 2-methylsulfanylethyl | H | 0 | — | — | ethoxycarbonyl | 3.65[a] | | |
| 1.0239 | Br | Cl | H | O | NH | H | H | 0 | — | — | methoxycarbonyl | 2.23[a] | | |
| 1.0240 | Cl | Br | H | O | NH | H | H | 0 | — | — | methoxycarbonyl | 2.36[a] | | |
| 1.0241 | CN | Br | $CH_3$ | O | NH | H | H | 0 | — | — | methoxycarbonyl | 2.14[a] | | |
| 1.0242 | CN | Br | $CH_3$ | O | NH | 2-methylsulfanylethyl | H | 0 | — | — | ethoxycarbonyl | 3.34[a] | | |
| 1.0243 | CN | Br | $CH_3$ | O | NH | $—CH_2—CH_2—$ | | 0 | — | — | methoxycarbonyl | 2.26[a] | | |
| 1.0244 | CN | Br | $CH_3$ | O | NH | $—CH_2—CH_2—CH_2—$ | | 0 | — | — | ethoxycarbonyl | 3.07[a] | | |
| 1.0245 | CN | Br | $CH_3$ | O | NH | 2-methylpropyl | H | 0 | — | — | ethoxycarbonyl | 3.85[a] | | |
| 1.0246 | CN | Br | $CH_3$ | O | NH | 2,2-difluoroethyl | H | 0 | — | — | methoxycarbonyl | 2.75[a] | | |
| 1.0247 | Br | Cl | H | O | NH | H | H | 0 | — | — | carboxy | 1.79[a] | | |
| 1.0248 | Cl | Br | H | O | NH | H | H | 0 | — | — | carboxy | 1.81[a] | | |
| 1.0249 | CN | Br | $CH_3$ | O | NH | H | H | 0 | — | — | carboxy | 1.61[a] | | |
| 1.0250 | CN | Br | $CH_3$ | O | NH | $—CH_2—CH_2—$ | | 0 | — | — | carboxy | 1.84[a] | | |
| 1.0251 | Cl | Cl | $CH_3$ | O | NH | $—CH_2—CH_2—$ | | 0 | — | — | ethylsulfanylcarbonyl | 4.08[a] | | |
| 1.0252 | Br | Cl | $CH_3$ | O | NH | $—CH_2—CH_2—$ | | 0 | — | — | ethylsulfanylcarbonyl | 3.74[a] | | |
| 1.0253 | Cl | Br | $CH_3$ | O | NH | $—CH_2—CH_2—$ | | 0 | — | — | ethylsulfanylcarbonyl | 3.77[a] | | |
| 1.0254 | Br | Cl | $CH_3$ | O | NH | cyclopropyl | H | 0 | — | — | carboxy | 2.64[a] | | |
| 1.0255 | Cl | Br | $CH_3$ | O | NH | cyclopropyl | H | 0 | — | — | carboxy | 2.67[a] | | |
| 1.0256 | Br | Br | F | O | NH | 2-amino-2-oxoethyl | H | 0 | — | — | carboxy | 1.66[a] | | |
| 1.0257 | Br | Br | F | O | NH | CN | H | 0 | — | — | ethoxycarbonyl | 3.07[a] | | |
| 1.0258 | CN | Cl | $CH_3$ | O | NH | $—CH_2—CH_2—$ | | 0 | — | — | ethoxycarbonyl | 2.57[a] | | |
| 1.0259 | Br | Cl | H | O | NH | cyclopropyl | H | 0 | — | — | methoxycarbonyl | 3.01[a] | | |
| 1.0260 | Cl | Br | H | O | NH | cyclopropyl | H | 0 | — | — | methoxycarbonyl | 3.07[a] | | |
| 1.0261 | CN | Br | $CH_3$ | O | NH | cyclopropyl | H | 0 | — | — | methoxycarbonyl | 2.75[a] | | |
| 1.0262 | Br | Br | I | O | NH | cyclopropyl | H | 0 | — | — | methoxycarbonyl | 3.81[a] | | |
| 1.0263 | Cl | Cl | Br | O | NH | cyclopropyl | H | 0 | — | — | methoxycarbonyl | 3.84[a] | | |
| 1.0264 | Br | Br | Cl | O | NH | cyclopropyl | H | 0 | — | — | methoxycarbonyl | 3.84[a] | | |
| 1.0265 | Cl | Br | Br | O | NH | $—CH_2—CH_2—$ | | 0 | — | — | carboxy | 2.41[a] | | |
| 1.0266 | Cl | Br | $CH_3$ | O | NH | cyclopropyl | H | 0 | — | — | ethoxycarbonyl | 3.81[a] | | |
| 1.0267 | Cl | Br | $CH_3$ | O | NH | methoxycarbonyl | H | 0 | — | — | methoxycarbonyl | 3.07[a] | | |
| 1.0268 | Cl | Br | $CH_3$ | O | NH | cyclopropylmethyl | H | 0 | — | — | ethoxycarbonyl | 4.30[a] | | |
| 1.0269 | Cl | Br | $CH_3$ | O | NH | cyclopropyl | cyclopropyl | 0 | — | — | methoxycarbonyl | 3.98[a] | | |
| 1.0270 | Cl | Br | $CH_3$ | O | NH | ethoxycarbonyl | H | 0 | — | — | ethoxycarbonyl | 3.87[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0271 | Cl | Br | $CH_3$ | O | NH | $—CH_2—N(Boc)—CH_2—$ | | 0 | — | — | ethoxycarbonyl | 4.23[a] | | |
| 1.0272 | Br | Cl | $CH_3$ | O | NH | cyclopropyl | H | 0 | — | — | ethoxycarbonyl | 3.77[a] | | |
| 1.0273 | Br | Cl | $CH_3$ | O | NH | methoxycarbonyl | H | 0 | — | — | methoxycarbonyl | 3.04[a] | | |
| 1.0274 | Br | Cl | $CH_3$ | O | NH | cyclopropylmethyl | H | 0 | — | — | ethoxycarbonyl | 4.26[a] | | |
| 1.0275 | Br | Cl | $CH_3$ | O | NH | cyclopropyl | cyclopropyl | 0 | — | — | methoxycarbonyl | 3.94[a] | | |
| 1.0276 | Br | Cl | $CH_3$ | O | NH | ethoxycarbonyl | H | 0 | — | — | ethoxycarbonyl | 3.84[a] | | |
| 1.0277 | Br | Cl | $CH_3$ | O | NH | $—CH_2—N(Boc)—CH_2—$ | | 0 | — | — | ethoxycarbonyl | 4.19[a] | | |
| 1.0278 | Br | Br | F | O | NH | 3-carbamimidamidopropyl | H | 0 | — | — | methoxycarbonyl | 1.66[a] | (S) | −7.5° (c = 1.33, DMSO, 25° C.) |
| 1.0279 | Cl | Cl | CN | O | NH | 2-methylpropyl | H | 0 | — | — | ethoxycarbonyl | 4.05[a] | | |
| 1.0280 | Cl | Cl | CN | O | NH | isopropyl | H | 0 | — | — | ethoxycarbonyl | 3.77[a] | | |
| 1.0281 | CN | Br | H | O | NH | $—CH_2—CH_2—$ | | 0 | — | — | methoxycarbonyl | 2.10[a] | | |
| 1.0282 | CN | Br | H | O | NH | $—CH_2—CH_2—$ | | 0 | — | — | carboxy | 1.70[a] | | |
| 1.0283 | CN | Cl | $CH_3$ | O | NH | $—CH_2—CH_2—$ | | 0 | — | — | methoxycarbonyl | 2.21[a] | | |
| 1.0284 | Br | Cl | H | O | NH | cyclopropyl | H | 0 | — | — | carboxy | 2.41[a] | | |
| 1.0285 | Cl | Br | H | O | NH | cyclopropyl | H | 0 | — | — | carboxy | 2.44[a] | | |
| 1.0286 | CN | Br | $CH_3$ | O | NH | cyclopropyl | H | 0 | — | — | carboxy | 2.19[a] | | |
| 1.0287 | Cl | Cl | Br | O | NH | cyclopropyl | H | 0 | — | — | carboxy | 2.95[a] | | |
| 1.0288 | Cl | Br | H | O | NH | cyclopropyl | H | 0 | — | — | [[carboxy(cyclopropyl)methyl] amino]carbonyl | 2.49[a] | | |
| 1.0289 | Cl | Cl | Br | O | NH | cyclopropyl | H | 0 | — | — | [[carboxy(cyclopropyl)methyl] amino]carbonyl | 2.97[a] | | |
| 1.0290 | CN | Cl | $CH_3$ | S | NH | $—CH_2—CH_2—$ | | 0 | — | — | methoxycarbonyl | 3.04[a] | | |
| 1.0291 | CN | Cl | $CH_3$ | O | NH | $—CH_2—CH_2—$ | | 0 | — | — | carboxy | 1.79[a] | | |
| 1.0292 | Br | Br | I | O | NH | cyclopropyl | H | 0 | — | — | carboxy | 2.97[a] | | |
| 1.0293 | Br | Br | Cl | O | NH | cyclopropyl | H | 0 | — | — | carboxy | 2.94[a] | | |
| 1.0294 | Br | Br | F | O | NH | cyclopropyl | H | 0 | — | — | carboxy | 2.64[a] | | |
| 1.0295 | F | Br | H | O | NH | H | H | 0 | — | — | methoxycarbonyl | 2.01[a] | | |
| 1.0296 | F | Cl | $CH_3$ | O | NH | H | H | 0 | — | — | methoxycarbonyl | 2.23[a] | | |
| 1.0297 | F | Cl | $CH_3$ | O | NH | H | H | 0 | — | — | ethoxycarbonyl | 2.59[a] | | |
| 1.0298 | F | Cl | $CH_3$ | O | NH | $—CH_2—CH_2—$ | | 0 | — | — | ethoxycarbonyl | 2.77[a] | | |
| 1.0299 | F | Cl | $CH_3$ | O | NH | isopropyl | H | 0 | — | — | ethoxycarbonyl | 3.87[a] | | |
| 1.0300 | F | Cl | $CH_3$ | O | NH | 2-methylsulfanylethyl | H | 0 | — | — | ethoxycarbonyl | 3.64[a] | | |
| 1.0301 | F | Cl | $CH_3$ | O | NH | benzyl | H | 0 | — | — | ethoxycarbonyl | 4.15[a] | | |
| 1.0302 | CN | Cl | $CH_3$ | O | NH | H | H | 0 | — | — | methoxycarbonyl | 2.03[a] | | |
| 1.0303 | CN | Cl | $CH_3$ | O | NH | H | H | 0 | — | — | ethoxycarbonyl | 2.39[a] | | |
| 1.0304 | CN | Cl | $CH_3$ | O | NH | isopropyl | H | 0 | — | — | ethoxycarbonyl | 3.47[a] | | |
| 1.0305 | CN | Cl | $CH_3$ | O | NH | 2-methylsulfanylethy | H | 0 | — | — | ethoxycarbonyl | 3.28[a] | | |
| 1.0306 | CN | Cl | $CH_3$ | O | NH | benzyl | H | 0 | — | — | ethoxycarbonyl | 3.77[a] | | |
| 1.0307 | Cl | F | H | O | NH | H | H | 0 | — | — | methoxycarbonyl | 1.94[a] | | |
| 1.0308 | Cl | F | H | O | NH | $—CH_2—CH_2—$ | | 0 | — | — | ethoxycarbonyl | 2.49[a] | | |
| 1.0309 | Cl | F | H | O | NH | isopropyl | H | 0 | — | — | ethoxycarbonyl | 3.44[a] | | |
| 1.0310 | Cl | F | H | O | NH | 2-methylsulfanylethyl | H | 0 | — | — | ethoxycarbonyl | 3.25[a] | | |
| 1.0311 | F | Br | H | O | NH | H | H | 0 | — | — | ethoxycarbonyl | 2.33[a] | | |
| 1.0312 | F | Br | H | O | NH | $—CH_2—CH_2—$ | | 0 | — | — | ethoxycarbonyl | 2.57[a] | | |
| 1.0313 | F | Br | H | O | NH | isopropyl | H | 0 | — | — | ethoxycarbonyl | 3.54[a] | | |
| 1.0314 | F | Br | H | O | NH | 2-methylsulfanylethyl | H | 0 | — | — | ethoxycarbonyl | 3.31[a] | | |
| 1.0315 | F | Br | H | O | NH | benzyl | H | 0 | — | — | ethoxycarbonyl | 3.77[a] | | |
| 1.0316 | F | Br | $CH_3$ | O | NH | H | H | 0 | — | — | methoxycarbonyl | 2.31[a] | | |
| 1.0317 | F | Br | $CH_3$ | O | NH | H | H | 0 | — | — | ethoxycarbonyl | 2.67[a] | | |
| 1.0318 | F | Br | $CH_3$ | O | NH | $—CH_2—CH_2—$ | | 0 | — | — | ethoxycarbonyl | 2.83[a] | | |
| 1.0319 | F | Br | $CH_3$ | O | NH | isopropyl | H | 0 | — | — | ethoxycarbonyl | 3.94[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0320 | F | Br | $CH_3$ | O | NH | 2-methylsulfanylethyl | H | 0 | — | — | ethoxycarbonyl | 3.67[a] | | |
| 1.0321 | F | Br | $CH_3$ | O | NH | benzyl | H | 0 | — | — | ethoxycarbonyl | 4.23[a] | | |
| 1.0323 | Cl | Cl | Br | S | NH | $—CH_2—CH_2—$ | | 0 | — | — | ethoxycarbonyl | 4.51[a] | | |
| 1.0324 | Cl | Br | Cl | O | NH | $—CH_2—CH_2—$ | | 0 | — | — | carboxy | 2.41[a] | | |
| 1.0325 | Cl | Br | Cl | S | NH | $—CH_2—CH_2—$ | | 0 | — | — | ethoxycarbonyl | 4.55[a] | | |
| 1.0327 | Br | Br | F | O | $N—OCH_3$ | H | H | 0 | — | — | ethoxycarbonyl | 3.37[a] | | |
| 1.0328 | Br | Br | F | S | NH | $—CH_2—CH_2—$ | | 0 | — | — | methoxycarbonyl | 3.91[a] | | |
| 1.0329 | Br | Br | F | S | NH | $—CH_2—CH_2—$ | | 0 | — | — | carboxy | 2.95[a] | | |
| 1.0330 | Br | Br | F | O | NH | 2-carboxyethyl | H | 0 | — | — | methoxycarbonyl | 2.36[a] | (S) | +5.5° (c = 1.1, CDCl3, 25° C.) |
| 1.0331 | Br | Br | F | S | NH | $—CH_2—CH_2—CH_2—$ | | 0 | — | — | ethoxycarbonyl | 4.74[a] | | |
| 1.0332 | Cl | Br | $CH_3$ | S | NH | $—CH_2—CH_2—$ | | 0 | — | — | methoxycarbonyl | 3.71[a] | | |
| 1.0333 | Br | Br | Cl | S | NH | $—CH_2—CH_2—$ | | 0 | — | — | methoxycarbonyl | 4.11[a] | | |
| 1.0334 | Cl | Cl | Br | S | NH | $—CH_2—CH_2—$ | | 0 | — | — | methoxycarbonyl | 4.06[a] | | |
| 1.0335 | CN | Br | $CH_3$ | S | NH | $—CH_2—CH_2—$ | | 0 | — | — | methoxycarbonyl | 3.10[a] | | |
| 1.0336 | CN | Br | H | S | NH | $—CH_2—CH_2—$ | | 0 | — | — | methoxycarbonyl | 3.03[a] | | |
| 1.0337 | Cl | Cl | Br | O | NH | 2,2-difluoroethyl | H | 0 | — | — | carboxy | 2.81[a] | | |
| 1.0341 | Br | Br | $CHF_2$ | O | NH | $—CH_2—CH_2—$ | | 0 | — | — | ethoxycarbonyl | 3.20[a] | | |
| 1.0342 | Cl | Cl | F | O | NH | H | H | 0 | — | — | cyano | 2.30[a] | | |
| 1.0343 | Cl | Cl | F | O | NH | H | H | 0 | — | — | methoxycarbonyl | 2.43[a] | | |
| 1.0344 | Cl | Cl | F | O | NH | H | H | 0 | — | — | ethoxycarbonyl | 2.83[a] | | |
| 1.0345 | Cl | Cl | F | O | NH | $CH_3$ | H | 0 | — | — | ethoxycarbonyl | 3.34[a] | | |
| 1.0346 | Cl | Cl | F | O | NH | cyclopropyl | H | 0 | — | — | methoxycarbonyl | 3.36[a] | | |
| 1.0347 | Cl | Cl | F | O | NH | $—CH_2—CH_2—CH_2—$ | | 0 | — | — | ethoxycarbonyl | 3.70[a] | | |
| 1.0348 | Cl | Cl | F | O | NH | isopropyl | H | 0 | — | — | ethoxycarbonyl | 4.37[a] | | |
| 1.0349 | Cl | Cl | F | O | NH | 2,2-difluoroethyl | H | 0 | — | — | methoxycarbonyl | 3.19[a] | | |
| 1.0350 | Cl | Cl | F | O | NH | 2-methylpropyl | H | 0 | — | — | ethoxycarbonyl | 4.63[a] | | |
| 1.0351 | Cl | Cl | F | O | NH | 2-methylsulfanylethyl | H | 0 | — | — | ethoxycarbonyl | 3.95[a] | | |
| 1.0352 | Cl | Cl | F | O | NH | benzyl | H | 0 | — | — | ethoxycarbonyl | 4.47[a] | | |
| 1.0353 | Br | Br | $CHF_2$ | O | NH | H | H | 0 | — | — | cyano | 2.54[a] | | |
| 1.0354 | Br | Br | $CHF_2$ | O | NH | H | H | 0 | — | — | methoxycarbonyl | 2.66[a] | | |
| 1.0355 | Br | Br | $CHF_2$ | O | NH | H | H | 0 | — | — | ethoxycarbonyl | 3.01[a] | | |
| 1.0356 | Br | Br | $CHF_2$ | O | NH | $—CH_2—CH_2—$ | | 0 | — | — | methoxycarbonyl | 2.86[a] | | |
| 1.0357 | Br | Br | $CHF_2$ | O | NH | $CH_3$ | H | 0 | — | — | ethoxycarbonyl | 3.35[a] | | |
| 1.0358 | Br | Br | $CHF_2$ | O | NH | cyclopropyl | H | 0 | — | — | methoxycarbonyl | 3.37[a] | | |
| 1.0359 | Br | Br | $CHF_2$ | O | NH | $—CH_2—CH_2—CH_2—$ | | 0 | — | — | ethoxycarbonyl | 3.67[a] | | |
| 1.0360 | Br | Br | $CHF_2$ | O | NH | isopropyl | H | 0 | — | — | ethoxycarbonyl | 4.16[a] | | |
| 1.0361 | Br | Br | $CHF_2$ | O | NH | 2,2-difluoroethyl | H | 0 | — | — | methoxycarbonyl | 3.28[a] | | |
| 1.0362 | Br | Br | $CHF_2$ | O | NH | 2-methylpropyl | H | 0 | — | — | ethoxycarbonyl | 4.45[a] | | |
| 1.0363 | Br | Br | $CHF_2$ | O | NH | 2-methylsulfanylethyl | H | 0 | — | — | ethoxycarbonyl | 3.89[a] | | |
| 1.0364 | Br | Br | $CHF_2$ | O | NH | benzyl | H | 0 | — | — | ethoxycarbonyl | 4.34[a] | | |
| 1.0365 | Br | Br | $CF_3$ | O | NH | H | H | 0 | — | — | cyano | 2.61[a] | | |
| 1.0366 | Br | Br | $CF_3$ | O | NH | H | H | 0 | — | — | methoxycarbonyl | 2.71[a] | | |
| 1.0367 | Br | Br | $CF_3$ | O | NH | H | H | 0 | — | — | ethoxycarbonyl | 3.05[a] | | |
| 1.0368 | Br | Br | $CF_3$ | O | NH | $—CH_2—CH_2—$ | | 0 | — | — | methoxycarbonyl | 2.93[a] | | |
| 1.0369 | Br | Br | $CF_3$ | O | NH | $CH_3$ | H | 0 | — | — | ethoxycarbonyl | 3.35[a] | | |
| 1.0370 | Br | Br | $CF_3$ | O | NH | $—CH_2—CH_2—$ | | 0 | — | — | ethoxycarbonyl | 3.26[a] | | |
| 1.0371 | Br | Br | $CF_3$ | O | NH | cyclopropyl | H | 0 | — | — | methoxycarbonyl | 3.37[a] | | |
| 1.0372 | Br | Br | $CF_3$ | O | NH | $—CH_2—CH_2—CH_2—$ | | 0 | — | — | ethoxycarbonyl | 3.67[a] | | |
| 1.0373 | Br | Br | $CF_3$ | O | NH | isopropyl | H | 0 | — | — | ethoxycarbonyl | 4.09[a] | | |
| 1.0374 | Br | Br | $CF_3$ | O | NH | 2,2-difluoroethyl | H | 0 | — | — | methoxycarbonyl | 3.31[a] | | |
| 1.0375 | Br | Br | $CF_3$ | O | NH | 2-methylpropyl | H | 0 | — | — | ethoxycarbonyl | 4.38[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0376 | Br | Br | $CF_3$ | O | NH | 2-methylsulfanylethyl | H | 0 | — | — | ethoxycarbonyl | 3.87[a] | | |
| 1.0377 | Br | Br | $CF_3$ | O | NH | benzyl | H | 0 | — | — | ethoxycarbonyl | 4.31[a] | | |
| 1.0378 | Cl | CN | H | O | NH | H | H | 0 | — | — | methoxycarbonyl | 1.75[a] | | |
| 1.0379 | Cl | CN | H | O | NH | H | H | 0 | — | — | ethoxycarbonyl | 2.08[a] | | |
| 1.0380 | Cl | CN | H | O | NH | $—CH_2—CH_2—$ | | 0 | — | — | ethoxycarbonyl | 2.28[a] | | |
| 1.0381 | Cl | CN | H | O | NH | cyclopropyl | H | 0 | — | — | methoxycarbonyl | 2.47[a] | | |
| 1.0382 | Cl | CN | H | O | NH | isopropyl | H | 0 | — | — | ethoxycarbonyl | 3.20[a] | | |
| 1.0383 | Cl | CN | H | O | NH | 2-methylsulfanylethyl | H | 0 | — | — | ethoxycarbonyl | 3.01[a] | | |
| 1.0384 | Cl | CN | H | O | NH | benzyl | H | 0 | — | — | ethoxycarbonyl | 3.47[a] | | |
| 1.0385 | CN | Cl | H | O | NH | H | H | 0 | — | — | methoxycarbonyl | 1.77[a] | | |
| 1.0386 | CN | Cl | H | O | NH | H | H | 0 | — | — | ethoxycarbonyl | 2.10[a] | | |
| 1.0387 | CN | Cl | H | O | NH | $—CH_2—CH_2—$ | | 0 | — | — | ethoxycarbonyl | 2.32[a] | | |
| 1.0388 | CN | Cl | H | O | NH | cyclopropyl | H | 0 | — | — | methoxycarbonyl | 2.50[a] | | |
| 1.0389 | CN | Cl | H | O | NH | isopropyl | H | 0 | — | — | ethoxycarbonyl | 3.22[a] | | |
| 1.0390 | CN | Cl | H | O | NH | 2-methylsulfanylethyl | H | 0 | — | — | ethoxycarbonyl | 3.03[a] | | |
| 1.0391 | CN | Cl | H | O | NH | benzyl | H | 0 | — | — | ethoxycarbonyl | 3.48[a] | | |
| 1.0392 | Cl | CN | Cl | O | NH | H | H | 0 | — | — | methoxycarbonyl | 2.16[a] | | |
| 1.0393 | Cl | CN | Cl | O | NH | H | H | 0 | — | — | ethoxycarbonyl | 2.54[a] | | |
| 1.0394 | Cl | CN | Cl | O | NH | $—CH_2—CH_2—$ | | 0 | — | — | ethoxycarbonyl | 2.69[a] | | |
| 1.0395 | Cl | CN | Cl | O | NH | cyclopropyl | H | 0 | — | — | methoxycarbonyl | 2.97[a] | | |
| 1.0396 | Cl | CN | Cl | O | NH | isopropyl | H | 0 | — | — | ethoxycarbonyl | 3.81[a] | | |
| 1.0397 | Cl | CN | Cl | O | NH | 2-methylsulfanylethyl | H | 0 | — | — | ethoxycarbonyl | 3.52[a] | | |
| 1.0398 | Cl | CN | Cl | O | NH | benzyl | H | 0 | — | — | ethoxycarbonyl | 4.05[a] | | |
| 1.0399 | Br | CN | H | O | NH | H | H | 0 | — | — | methoxycarbonyl | 1.79[a] | | |
| 1.0400 | Br | CN | H | O | NH | H | H | 0 | — | — | ethoxycarbonyl | 2.11[a] | | |
| 1.0401 | Br | CN | H | O | NH | $—CH_2—CH_2—$ | | 0 | — | — | ethoxycarbonyl | 2.30[a] | | |
| 1.0402 | Br | CN | H | O | NH | cyclopropyl | H | 0 | — | — | methoxycarbonyl | 2.50[a] | | |
| 1.0403 | Br | CN | H | O | NH | isopropyl | H | 0 | — | — | ethoxycarbonyl | 3.22[a] | | |
| 1.0404 | Br | CN | H | O | NH | 2-methylsulfanylethyl | H | 0 | — | — | ethoxycarbonyl | 3.03[a] | | |
| 1.0405 | Br | CN | H | O | NH | benzyl | H | 0 | — | — | ethoxycarbonyl | 3.48[a] | | |
| 1.0406 | Br | CN | Br | O | NH | H | H | 0 | — | — | methoxycarbonyl | 2.22[a] | | |
| 1.0407 | Br | CN | Br | O | NH | H | H | 0 | — | — | ethoxycarbonyl | 2.61[a] | | |
| 1.0408 | Br | CN | Br | O | NH | $—CH_2—CH_2—$ | | 0 | — | — | ethoxycarbonyl | 2.71[a] | | |
| 1.0409 | Br | CN | Br | O | NH | cyclopropyl | H | 0 | — | — | methoxycarbonyl | 3.02[a] | | |
| 1.0410 | Br | CN | Br | O | NH | isopropyl | H | 0 | — | — | ethoxycarbonyl | 3.84[a] | | |
| 1.0411 | Br | CN | Br | O | NH | 2-methylsulfanylethyl | H | 0 | — | — | ethoxycarbonyl | 3.55[a] | | |
| 1.0412 | Br | CN | Br | O | NH | benzyl | H | 0 | — | — | ethoxycarbonyl | 4.08[a] | | |
| 1.0413 | Br | Br | F | O | N—OH | cyclopropyl | H | 0 | — | — | methoxycarbonyl | 2.77[a] | | |
| 1.0414 | Cl | Cl | $CHF_2$ | O | NH | $—CH_2—CH_2—$ | | 0 | — | — | ethoxycarbonyl | 3.17[a] | | |
| 1.0415 | Cl | Cl | $CHF_2$ | O | NH | H | H | 0 | — | — | methoxycarbonyl | 2.61[a] | | |
| 1.0416 | Cl | Cl | $CHF_2$ | O | NH | H | H | 0 | — | — | ethoxycarbonyl | 2.97[a] | | |
| 1.0417 | Cl | Cl | $CHF_2$ | O | NH | cyclopropyl | H | 0 | — | — | methoxycarbonyl | 3.33[a] | | |
| 1.0418 | Cl | Cl | $CHF_2$ | O | NH | isopropyl | H | 0 | — | — | ethoxycarbonyl | 4.13[a] | | |
| 1.0419 | Cl | Cl | $CHF_2$ | O | NH | 2-methylsulfanylethyl | H | 0 | — | — | ethoxycarbonyl | 3.86[a] | | |
| 1.0420 | Cl | Cl | $CHF_2$ | O | NH | benzyl | H | 0 | — | — | ethoxycarbonyl | 4.33[a] | | |
| 1.0421 | Br | Cl | F | O | NH | H | H | 0 | — | — | cyano | 2.33[a] | | |
| 1.0422 | Br | Cl | F | O | NH | H | H | 0 | — | — | methoxycarbonyl | 2.47[a] | | |
| 1.0423 | Br | Cl | F | O | NH | H | H | 0 | — | — | ethoxycarbonyl | 2.92[a] | | |
| 1.0424 | Br | Cl | F | O | NH | $—CH_2—CH_2—$ | | 0 | — | — | methoxycarbonyl | 2.72[a] | | |
| 1.0425 | Br | Cl | F | O | NH | $CH_3$ | H | 0 | — | — | ethoxycarbonyl | 3.38[a] | | |
| 1.0426 | Br | Cl | F | O | NH | $—CH_2—CH_2—$ | | 0 | — | — | ethoxycarbonyl | 3.09[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0427 | Br | Cl | F | O | NH | cyclopropyl | H | 0 | — | — | methoxycarbonyl | 3.38[a] | | |
| 1.0428 | Br | Cl | F | O | NH | $—CH_2—CH_2—CH_2—$ | | 0 | — | — | ethoxycarbonyl | 3.73[a] | | |
| 1.0429 | Br | Cl | F | O | NH | isopropyl | H | 0 | — | — | ethoxycarbonyl | 4.38[a] | | |
| 1.0430 | Br | Cl | F | O | NH | 2,2-difluoroethyl | H | 0 | — | — | methoxycarbonyl | 3.21[a] | | |
| 1.0431 | Br | Cl | F | O | NH | 2-methylpropyl | H | 0 | — | — | ethoxycarbonyl | 4.64[a] | | |
| 1.0432 | Br | Cl | F | O | NH | 2-methylsulfanylethyl | H | 0 | — | — | ethoxycarbonyl | 3.96[a] | | |
| 1.0433 | Br | Cl | F | O | NH | benzyl | H | 0 | — | — | ethoxycarbonyl | 4.48[a] | | |
| 1.0434 | Br | Br | F | O | NH | 2-methylsulfanylethyl | H | 0 | — | — | methoxycarbonyl | 3.57[a] | | |
| 1.0435 | Br | F | H | O | NH | 2-methylpropyl | H | 0 | — | — | ethoxycarbonyl | 3.80[a] | | |
| 1.0436 | Cl | Br | H | O | NH | 2-methylpropyl | H | 0 | — | — | ethoxycarbonyl | 4.23[a] | | |
| 1.0437 | Cl | Br | H | O | NH | isopropyl | H | 0 | — | — | ethoxycarbonyl | 3.87[a] | | |
| 1.0438 | Cl | Br | H | O | NH | 2,2-difluoroethyl | H | 0 | — | — | methoxycarbonyl | 3.07[a] | | |
| 1.0439 | Cl | Br | H | O | NH | $—CH_2—CH_2—CH_2—$ | | 0 | — | — | ethoxycarbonyl | 3.44[a] | | |
| 1.0440 | Br | Br | F | O | NH | 2,2-difluoroethyl | H | 0 | — | — | methoxycarbonyl | 3.23[a] | | |
| 1.0441 | Br | Cl | H | O | NH | isopropyl | H | 0 | — | — | ethoxycarbonyl | 3.85[a] | | |
| 1.0442 | Br | Cl | H | O | NH | 2,2-difluoroethyl | H | 0 | — | — | methoxycarbonyl | 2.96[a] | | |
| 1.0443 | Br | Cl | H | O | NH | benzyl | H | 0 | — | — | ethoxycarbonyl | 4.01[a] | | |
| 1.0444 | Br | Cl | H | O | NH | 2-methylpropyl | H | 0 | — | — | ethoxycarbonyl | 4.19[a] | | |
| 1.0445 | Br | Br | F | O | NH | H | H | 1 | $—CH_2—CH_2—$ | | ethoxycarbonyl | 3.86[a] | | |
| 1.0446 | Br | Br | F | O | NH | $—CH_2—CH_2—CH_2—CH_2—$ | | 0 | — | — | ethoxycarbonyl | 4.21[a] | | |
| 1.0447 | Br | Br | F | O | NH | $—CH_2—CH_2—O—CH_2—CH_2—$ | | 0 | — | — | methoxycarbonyl | 2.77[a] | | |
| 1.0448 | Br | Br | F | O | NH | $CH_3$ | H | 1 | H | H | methoxycarbonyl | 3.14[a] | | |
| 1.0449 | Br | Br | F | O | NH | H | H | 0 | — | — | ethoxycarbonyl | 2.97[a] | | |
| 1.0450 | Br | Br | F | O | NH | H | H | 1 | H | H | ethoxycarbonyl | 3.11[a] | | |
| 1.0451 | Br | Br | F | O | NH | isopropyl | H | 0 | — | — | ethoxycarbonyl | 2.63[a] | | |
| 1.0452 | Br | Cl | H | O | NH | $—CH_2—CH_2—CH_2—$ | | 0 | — | — | ethoxycarbonyl | 3.29[a] | | |
| 1.0453 | Cl | Br | H | O | NH | H | H | 1 | H | H | ethoxycarbonyl | 2.80[a] | | |
| 1.0454 | Br | Cl | H | O | NH | $—CH_2—CH_2—$ | | 0 | — | — | ethoxycarbonyl | 2.80[a] | | |
| 1.0455 | Br | Cl | H | O | NH | $—CH_2—CH_2—$ | | 0 | — | — | carboxy | 1.99[a] | | |
| 1.0456 | Br | F | H | O | NH | H | H | 1 | H | H | ethoxycarbonyl | 2.47[a] | | |
| 1.0457 | Cl | Br | H | O | NH | H | H | 0 | — | — | ethoxycarbonyl | 2.63[a] | | |
| 1.0458 | Cl | Br | H | O | NH | $—CH_2—CH_2—$ | | 0 | — | — | ethoxycarbonyl | 3.43[a] | | |
| 1.0459 | Br | F | H | O | NH | $—CH_2—CH_2—CH_2—$ | | 0 | — | — | ethoxycarbonyl | 2.98[a] | | |
| 1.0460 | Br | F | H | O | NH | $—CH_2—CH_2—$ | | 0 | — | — | ethoxycarbonyl | 2.51[a] | | |
| 1.0461 | Br | Cl | H | O | NH | H | H | 0 | — | — | ethoxycarbonyl | 2.59[a] | | |
| 1.0462 | Br | Cl | H | O | NH | H | H | 1 | H | H | ethoxycarbonyl | 2.77[a] | | |
| 1.0463 | $CH_3$ | Br | F | O | NH | $—CH_2—CH_2—$ | | 0 | — | — | ethoxycarbonyl | 2.80[a] | | |
| 1.0464 | Cl | $CH_3$ | H | O | NH | H | H | 0 | — | — | ethoxycarbonyl | 2.33[a] | | |
| 1.0465 | Cl | $CH_3$ | H | O | NH | H | H | 1 | H | H | ethoxycarbonyl | 2.49[a] | | |
| 1.0466 | Cl | $CH_3$ | H | O | NH | $—CH_2—CH_2—$ | | 0 | — | — | ethoxycarbonyl | 2.52[a] | | |
| 1.0467 | Br | F | H | O | NH | H | H | 0 | — | — | ethoxycarbonyl | 2.28[a] | | |
| 1.0468 | I | I | H | O | NH | $—CH_2—CH_2—$ | | 0 | — | — | ethoxycarbonyl | 2.98[a] | | |
| 1.0469 | I | I | H | O | NH | $—CH_2—CH_2—$ | | 0 | — | — | carboxy | 2.08[a] | | |
| 1.0470 | I | I | H | O | NH | $—CH_2—CH_2—$ | | 0 | — | — | [[1-(aminocarbonyl)cyclopropyl] amino]carbonyl | 1.88[a] | | |
| 1.0471 | I | I | H | O | NH | H | H | 0 | — | — | carboxy | 1.87[a] | | |
| 1.0472 | Br | Br | F | O | NH | benzyl | H | 0 | — | — | methoxycarbonyl | 4.06[a] | | |
| 1.0473 | Br | Br | F | O | NH | 2-methylsulfanylethyl | H | 0 | — | — | carboxy | 2.75[a] | | |
| 1.0474 | I | I | H | O | NH | H | H | 0 | — | — | (carboxymethylamino)carbonyl | 1.63[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0475 | I | I | H | O | NH | $—CH_2—CH_2—$ | | 0 | — | — | aminocarbonyl | 1.87[a] | | |
| 1.0476 | I | I | H | O | NH | $—CH_2—CH_2—$ | | 0 | — | — | [[1-(ethoxycarbonyl)cyclopropyl] amino]carbonyl | 2.59[a] | | |
| 1.0477 | I | I | H | O | NH | $—CH_2—CH_2—$ | | 0 | — | — | methylsulfanylcarbonyl | 3.04[a] | | |
| 1.0478 | I | I | H | O | NH | $—CH_2—CH_2—$ | | 0 | — | — | [(1-carboxycyclopropyl)amino] carbonyl | 1.53[a] | | |
| 1.0479 | Br | Cl | H | S | NH | $—CH_2—CH_2—$ | | 0 | — | — | ethoxycarbonyl | 3.92[a] | | |
| 1.0480 | I | I | H | O | NH | $—CH_2—CH_2—$ | | 0 | — | — | ethylsulfanylcarbonyl | 3.39[a] | | |
| 1.0481 | $CH_3$ | Br | F | O | NH | H | H | 1 | H | H | ethoxycarbonyl | 2.78[a] | | |
| 1.0482 | Cl | Br | Br | O | NH | $CH_3$ | H | 0 | — | — | ethoxycarbonyl | 3.91[a] | | |
| 1.0483 | Cl | Br | Br | O | NH | $—CH_2—CH_2—$ | | 0 | — | — | methoxycarbonyl | 3.08[a] | | |
| 1.0484 | Cl | Br | Cl | S | NH | H | H | 0 | — | — | ethoxycarbonyl | 4.59[a] | | |
| 1.0485 | Cl | Br | Cl | S | NH | H | H | 0 | — | — | methoxycarbonyl | 4.08[a] | | |
| 1.0486 | Cl | Br | Cl | O | NH | $—CH_2—CH_2—CH_2—$ | | 0 | — | — | carboxy | 2.95[a] | | |
| 1.0489 | Br | Br | F | O | NH | $—CH_2—O—CH_2—$ | | 0 | — | — | carboxy | 1.98[a] | | |
| 1.0490 | Br | Br | Cl | O | NH | $—CH_2—CH_2—CH_2—$ | | 0 | — | — | carboxy | 2.92[a] | | |
| 1.0491 | Cl | Cl | Br | O | N—OH | H | H | 0 | — | — | ethoxycarbonyl | 2.95[a] | | |
| 1.0492 | Br | Br | Cl | O | NH | H | H | 0 | — | — | methoxycarbonyl | 2.92[a] | | |
| 1.0493 | Br | Br | Cl | S | NH | H | H | 0 | — | — | ethoxycarbonyl | 4.58[a] | | |
| 1.0494 | Br | Br | Cl | O | NH | H | H | 0 | — | — | carboxy | 2.28[a] | | |
| 1.0495 | Br | Br | F | O | NH | cyclopropyl | H | 0 | — | — | ethoxycarbonyl | 3.98[a] | | |
| 1.0496 | Br | Br | F | S | NH | cyclopropyl | H | 0 | — | — | methoxycarbonyl | 4.62[a] | | |
| 1.0497 | Br | Br | F | S | NH | benzyl | H | 0 | — | — | methoxycarbonyl | 5.32[a] | | |
| 1.0498 | Br | Br | Cl | O | NH | 3-methoxy-3-oxopropyl | H | 0 | — | — | methoxycarbonyl | 3.40[a] | (S) | +17.2° (c = 1.05, CHCl3, 25° C.) |
| 1.0499 | Cl | Cl | I | S | NH | H | H | 0 | — | — | methoxycarbonyl | 4.12[a] | | |
| 1.0500 | Cl | Br | Cl | S | NH | H | H | 0 | — | — | carboxy | 3.10[a] | | |
| 1.0502 | Br | $CHF_2$ | Br | O | NH | isopropyl | H | 0 | — | — | ethoxycarbonyl | 4.21[a] | | |
| 1.0503 | Br | $CHF_2$ | Br | O | NH | cyclopropyl | H | 0 | — | — | methoxycarbonyl | 3.37[a] | | |
| 1.0504 | Br | $CHF_2$ | Br | O | NH | benzyl | H | 0 | — | — | ethoxycarbonyl | 4.40[a] | | |
| 1.0505 | Br | $CHF_2$ | Br | O | NH | $—CH_2—CH_2—CH_2—$ | | 0 | — | — | methoxycarbonyl | 3.25[a] | | |
| 1.0506 | Br | $CHF_2$ | Br | O | NH | $—CH_2—CH_2—CH_2—$ | | 0 | — | — | ethoxycarbonyl | 3.66[a] | | |
| 1.0507 | Br | $CHF_2$ | Br | O | NH | $—CH_2—CH_2—$ | | 0 | — | — | propoxycarbonyl | 3.42[a] | | |
| 1.0508 | Br | $CHF_2$ | Br | O | NH | $—CH_2—CH_2—$ | | 0 | — | — | cyclobutyloxycarbonyl | 3.57[a] | | |
| 1.0509 | Br | $CHF_2$ | Br | O | NH | H | H | 0 | — | — | cyano | 2.37[a] | | |
| 1.0510 | $CHF_2$ | Br | Br | O | NH | H | H | 0 | — | — | ethoxycarbonyl | 3.02[a] | | |
| 1.0511 | $CHF_2$ | Br | Br | O | NH | H | H | 0 | — | — | methoxycarbonyl | 2.64[a] | | |
| 1.0512 | $CHF_2$ | Br | Br | O | NH | $—CH_2—CH_2—$ | | 0 | — | — | methoxycarbonyl | 2.79[a] | | |
| 1.0513 | $CHF_2$ | Br | Br | O | NH | CH, | $CH_3$ | 0 | — | — | methoxycarbonyl | 3.32[a] | | |
| 1.0514 | $CHF_2$ | Br | Br | O | NH | isopropyl | H | 0 | — | — | ethoxycarbonyl | 4.30[a] | | |
| 1.0515 | $CHF_2$ | Br | Br | O | NH | cyclopropyl | H | 0 | — | — | methoxycarbonyl | 3.46[a] | | |
| 1.0516 | $CHF_2$ | Br | Br | O | NH | benzyl | H | 0 | — | — | ethoxycarbonyl | 4.48[a] | | |
| 1.0517 | $CHF_2$ | Br | Br | O | NH | $—CH_2—CH_2—CH_2—$ | | 0 | — | — | methoxycarbonyl | 3.35[a] | | |
| 1.0518 | $CHF_2$ | Br | Br | O | NH | $—CH_2—CH_2—CH_2—$ | | 0 | — | — | ethoxycarbonyl | 3.75[a] | | |
| 1.0519 | $CHF_2$ | Br | Br | O | NH | $—CH_2—CH_2—$ | | 0 | — | — | propoxycarbonyl | 3.51[a] | | |
| 1.0520 | $CHF_2$ | Br | Br | O | NH | $—CH_2—CH_2—$ | | 0 | — | — | cyclobutyloxycarbonyl | 3.67[a] | | |
| 1.0521 | $CHF_2$ | Br | Br | O | NH | H | H | 0 | — | — | cyano | 2.45[a] | | |
| 1.0522 | $CHF_2$ | Br | Br | O | NH | $—CH_2—CH_2—$ | | 0 | — | — | ethoxycarbonyl | 3.14[a] | | |
| 1.0523 | Br | Br | F | O | NH | CH, | $CH_3$ | 0 | — | — | carboxy | 2.54[a] | | |
| 1.0524 | Cl | Cl | Br | O | NH | cyclopropyl | H | 0 | — | — | ethoxycarbonyl | 4.35[a] | | |
| 1.0526 | Br | Cl | $CH_3$ | S | NH | $—CH_2—CH_2—$ | | 0 | — | — | methoxycarbonyl | 3.67[a] | | |
| 1.0527 | Br | Br | F | O | NH | H | H | 0 | — | — | methoxycarbonyl | 2.52[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0528 | Br | Br | Cl | O | NH | 2-tert-butoxy-2-oxoethyl | H | 0 | — | — | methoxycarbonyl | 4.55[a] | | |
| 1.0529 | Cl | Cl | Br | O | NH | [(dimethylaminocarbonyl)thio]methyl | H | 0 | — | — | methoxycarbonyl | 3.58[a] | (R) | +6.7° (c = 0.89, CHCl3, 25° C.) |
| 1.0530 | Cl | Cl | Br | O | NH | (ethylcarbamoylthio)methyl | H | 0 | — | — | methoxycarbonyl | 3.39[a] | (R) | +21.4 (c = 0.93, CHCl3, 25° C.) |
| 1.0531 | Cl | Cl | Br | O | NH | (methylcarbamothioylthio)methyl | H | 0 | — | — | methoxycarbonyl | 3.56[a] | (R) | +7.1° (c = 0.85, CHCl3, 25° C.) |
| 1.0532 | Br | Br | Cl | O | NH | 3-ethoxy-3-oxopropyl | H | 0 | — | — | ethoxycarbonyl | 4.23[a] | (S) | +18.1 (c = 0.99, CHCl3, 25° C.) |
| 1.0533 | Br | Br | F | O | NH | [(dimethylaminocarbonyl)thio]methyl | H | 0 | — | — | methoxycarbonyl | 3.27[a] | (R) | −9.2° (c = 1.08, CHCl3, 25° C.) |
| 1.0534 | Br | Br | F | O | NH | (methylcarbamothioylthio)methyl | H | 0 | — | — | methoxycarbonyl | 3.24[a] | (R) | +1.7 (c = 1.2, CHCl3, 25° C.) |
| 1.0535 | Br | Br | Cl | O | NH | [(dimethylaminocarbonyl)thio]methyl | H | 0 | — | — | methoxycarbonyl | 3.59[a] | | |
| 1.0536 | Br | Br | Cl | O | NH | (ethylcarbamoylthio)methyl | H | 0 | — | — | methoxycarbonyl | 3.38[a] | | |
| 1.0537 | Br | Br | Cl | O | NH | (methylcarbamothioylthio)methyl | H | 0 | — | — | methoxycarbonyl | 3.54[a] | (R) | +6.5° (c = 1.23, CHCl3, 25° C.) |
| 1.0538 | Br | Br | F | S | NH | H | H | 0 | — | — | methoxycarbonyl | 3.74[a] | | |
| 1.0539 | Br | Br | F | O | NH | $—CH_2—CH_2—$ | | 0 | — | — | methoxycarbonyl | 2.09[a] | | |
| 1.0540 | Br | Br | F | O | NH | $CH_3$ | $CH_3$ | 0 | — | — | methoxycarbonyl | 3.34[a] | | |
| 1.0541 | Br | Br | F | O | NH | $—CH_2—O—CH_2—$ | | 0 | — | — | methoxycarbonyl | 2.49[a] | | |
| 1.0542 | Br | Br | F | O | N—OH | H | H | 0 | — | — | ethoxycarbonyl | 2.54[a] | | |
| 1.0543 | Br | Br | F | O | NH | (ethylcarbamoylthio)methyl | H | 0 | — | — | methoxycarbonyl | 3.10[a] | (R) | +4.6° (c = 0.87, CHCl3, 25° C.) |
| 1.0544 | Cl | Cl | Br | O | N—OH | cyclopropyl | H | 0 | — | — | methoxycarbonyl | 3.05[a] | | |
| 1.0545 | Br | Br | Cl | O | NH | 2-ethoxy-2-oxoethyl | H | 0 | — | — | ethoxycarbonyl | 4.15[a] | (S) | +43.2° (c = 0.97, CHCl3, 25° C.) |
| 1.0546 | Br | Br | Cl | O | NH | 2-methoxy-2-oxoethyl | H | 0 | — | — | methoxycarbonyl | 3.33[a] | (S) | +47.9° (c = 1.17, CHCl3, 25° C.) |
| 1.0547 | Cl | Cl | Br | O | NH | (acetylthio)methyl | H | 0 | — | — | ethoxycarbonyl | 3.46[a] | | |
| 1.0548 | Cl | Cl | Br | O | NH | 2-methoxy-2-oxoethyl | H | 0 | — | — | methoxycarbonyl | 3.33[a] | (S) | +62.7° (c = 0.93, CHCl3, 25° C.) |
| 1.0549 | Cl | Cl | Br | O | NH | 3-methoxy-3-oxopropyl | H | 0 | — | — | methoxycarbonyl | 3.41[a] | (S) | +21.7° (c = 1.01, CHCl3, 25° C.) |
| 1.0550 | Br | Br | Cl | O | NH | methylsulfanylmethyl | H | 0 | — | — | ethoxycarbonyl | 4.32[a] | | |
| 1.0551 | Cl | Cl | Br | O | NH | 2-ethoxy-2-oxoethyl | H | 0 | — | — | ethoxycarbonyl | 4.17[a] | (S) | +54.4° (c = 0.96, CHCl3, 25° C.) |
| 1.0552 | Cl | Cl | Br | O | NH | 2-tert-butoxy-2-oxoethyl | H | 0 | — | — | methoxycarbonyl | 4.59[a] | (S) | +53.4° (c = 1.2, CHCl3, 25° C.) |
| 1.0553 | Br | Br | F | O | NH | 2-(acetylthio)ethyl | H | 0 | — | — | methoxycarbonyl | 3.13[a] | | |
| 1.0554 | Br | Br | F | O | NH | (acetylthio)methyl | H | 0 | — | — | ethoxycarbonyl | 3.18[a] | | |
| 1.0555 | Br | Br | F | O | NH | 2-methoxy-2-oxoethyl | H | 0 | — | — | methoxycarbonyl | 2.99[a] | (S) | +34.1° (c = 1, CHCl3, 25° C.) |
| 1.0556 | Br | Br | F | O | NH | methylsulfanylmethyl | H | 0 | — | — | ethoxycarbonyl | 3.87[a] | | |
| 1.0557 | Br | Br | F | O | NH | 3-methoxy-3-oxopropyl | H | 0 | — | — | methoxycarbonyl | 3.07[a] | (S) | +11° (c = 0.91, CHCl3, 25° C.) |
| 1.0558 | Br | Br | F | O | NH | 2-ethoxy-2-oxoethyl | H | 0 | — | — | ethoxycarbonyl | 3.76[a] | (S) | +30.5° (c = 1.18, CHCl3, 25° C.) |
| 1.0559 | Br | Br | F | O | NH | 3-ethoxy-3-oxopropyl | H | 0 | — | — | ethoxycarbonyl | 3.84[a] | (S) | +13° (c = 1.08, CHCl3, 25° C.) |
| 1.0560 | Br | Br | F | O | NH | 2-tert-butoxy-2-oxoethyl | H | 0 | — | — | methoxycarbonyl | 4.12[a] | (S) | +26.9° (c = 1.04, CHCl3, 25° C.) |
| 1.0561 | Br | Br | Cl | O | NH | (acetylthio)methyl | H | 0 | — | — | ethoxycarbonyl | 3.44[a] | | |
| 1.0562 | Cl | Cl | Br | O | NH | 3-ethoxy-3-oxopropyl | H | 0 | — | — | ethoxycarbonyl | 4.25[a] | (S) | +22.5° (c = 1.07, CHCl3, 25° C.) |
| 1.0563 | Br | Br | F | O | NH | H | H | 0 | — | — | (cyanoamino)carbonyl | 2.17[a] | | |
| 1.0564 | $CH_3$ | Cl | Cl | O | NH | H | H | 0 | — | — | methoxycarbonyl | 2.45[a] | | |
| 1.0565 | CN | Br | Cl | O | NH | $—CH_2—CH_2—CH_2—$ | | 0 | — | — | methoxycarbonyl | 2.98[a] | | |
| 1.0566 | CN | Br | Cl | O | NH | $—CH_2—CH_2—CH_2—$ | | 0 | — | — | ethoxycarbonyl | 3.38[a] | | |
| 1.0567 | CN | Br | Cl | O | NH | $—CH_2—CH_2—$ | | 0 | — | — | propoxycarbonyl | 3.18[a] | | |
| 1.0568 | CN | Br | Cl | O | NH | $—CH_2—CH_2—$ | | 0 | — | — | cyclobutyloxycarbonyl | 3.32[a] | | |
| 1.0569 | CN | Br | Cl | O | NH | H | H | 0 | — | — | cyano | 2.08[a] | | |
| 1.0570 | CN | Cl | Cl | O | NH | H | H | 0 | — | — | ethoxycarbonyl | 2.60[a] | | |
| 1.0571 | CN | Cl | Cl | O | NH | H | H | 0 | — | — | methoxycarbonyl | 2.20[a] | | |
| 1.0572 | CN | Cl | Cl | O | NH | $—CH_2—CH_2—$ | | 0 | — | — | ethoxycarbonyl | 2.76[a] | | |
| 1.0573 | CN | Cl | Cl | O | NH | $—CH_2—CH_2—$ | | 0 | — | — | methoxycarbonyl | 2.40[a] | | |
| 1.0574 | CN | Cl | Cl | O | NH | $CH_3$ | $CH_3$ | 0 | — | — | methoxycarbonyl | 2.90[a] | | |
| 1.0575 | CN | Cl | Cl | O | NH | isopropyl | H | 0 | — | — | ethoxycarbonyl | 3.89[a] | | |
| 1.0576 | CN | Cl | Cl | O | NH | cyclopropyl | H | 0 | — | — | methoxycarbonyl | 3.05[a] | | |
| 1.0577 | CN | Cl | Cl | O | NH | benzyl | H | 0 | — | — | ethoxycarbonyl | 4.11[a] | | |
| 1.0578 | CN | Cl | Cl | O | NH | $—CH_2—CH_2—CH_2—$ | | 0 | — | — | methoxycarbonyl | 2.94[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0579 | CN | Cl | Cl | O | NH | $—CH_2—CH_2—CH_2—$ | | 0 | — | — | ethoxycarbonyl | 3.35[a] | | |
| 1.0580 | CN | Cl | Cl | O | NH | $—CH_2—CH_2—$ | | 0 | — | — | propoxycarbonyl | 3.15[a] | | |
| 1.0581 | CN | Cl | Cl | O | NH | $—CH_2—CH_2—$ | | 0 | — | — | cyclobutyloxycarbonyl | 3.30[a] | | |
| 1.0582 | CN | Cl | Cl | O | NH | H | H | 0 | — | — | cyano | 2.04[a] | | |
| 1.0583 | Cl | Br | CN | O | NH | H | H | 0 | — | — | ethoxycarbonyl | 2.56[a] | | |
| 1.0584 | Cl | Br | CN | O | NH | H | H | 0 | — | — | methoxycarbonyl | 2.20[a] | | |
| 1.0585 | Cl | Br | CN | O | NH | $—CH_2—CH_2—$ | | 0 | — | — | ethoxycarbonyl | 2.70[a] | | |
| 1.0586 | CN | Br | Cl | O | NH | benzyl | H | 0 | — | — | ethoxycarbonyl | 4.13[a] | | |
| 1.0587 | CN | Br | Cl | O | NH | cyclopropyl | H | 0 | — | — | methoxycarbonyl | 3.08[a] | | |
| 1.0588 | CN | Br | Cl | O | NH | isopropyl | H | 0 | — | — | ethoxycarbonyl | 3.92[a] | | |
| 1.0589 | CN | Br | Cl | O | NH | $CH_3$ | $CH_3$ | 0 | — | — | methoxycarbonyl | 2.93[a] | | |
| 1.0590 | Cl | Br | $CH_3$ | O | NH | $—CH_2—CH_2—$ | | 0 | — | — | cyclobutyloxycarbonyl | 3.81[a] | | |
| 1.0591 | Br | Cl | F | O | NH | $—CH_2—CH_2—$ | | 0 | — | — | propoxycarbonyl | 3.56[a] | | |
| 1.0592 | Br | Cl | F | O | NH | $—CH_2—CH_2—$ | | 0 | — | — | cyclobutyloxycarbonyl | 3.72[a] | | |
| 1.0593 | Cl | Br | Br | O | NH | $—CH_2—CH_2—$ | | 0 | — | — | propoxycarbonyl | 3.98[a] | | |
| 1.0594 | Cl | Br | Br | O | NH | $—CH_2—CH_2—$ | | 0 | — | — | cyclobutyloxycarbonyl | 4.20[a] | | |
| 1.0595 | Cl | Br | Cl | O | NH | $—CH_2—CH_2—$ | | 0 | — | — | methoxycarbonyl | 3.11[a] | | |
| 1.0596 | Cl | Br | Cl | O | NH | $—CH_2—CH_2—$ | | 0 | — | — | propoxycarbonyl | 3.98[a] | | |
| 1.0597 | Cl | Br | Cl | O | NH | $—CH_2—CH_2—$ | | 0 | — | — | cyclobutyloxycarbonyl | 4.15[a] | | |
| 1.0598 | Br | Cl | H | O | NH | $—CH_2—CH_2—$ | | 0 | — | — | propoxycarbonyl | 3.28[a] | | |
| 1.0599 | Br | Cl | H | O | NH | $—CH_2—CH_2—$ | | 0 | — | — | cyclobutyloxycarbonyl | 3.43[a] | | |
| 1.0600 | Cl | Br | CN | O | NH | $—CH_2—CH_2—$ | | 0 | — | — | methoxycarbonyl | 2.36[a] | | |
| 1.0601 | Cl | Br | H | O | NH | $—CH_2—CH_2—$ | | 0 | — | — | propoxycarbonyl | 3.43[a] | | |
| 1.0602 | CN | Br | Cl | O | NH | $—CH_2—CH_2—$ | | 0 | — | — | methoxycarbonyl | 2.44[a] | | |
| 1.0603 | Cl | Br | F | O | NH | $—CH_2—CH_2—$ | | 0 | — | — | methoxycarbonyl | 2.70[a] | | |
| 1.0604 | CN | Br | Cl | O | NH | H | H | 0 | — | — | ethoxycarbonyl | 2.63[a] | | |
| 1.0605 | CN | Br | Cl | O | NH | H | H | 0 | — | — | methoxycarbonyl | 2.24[a] | | |
| 1.0606 | CN | Br | Cl | O | NH | $—CH_2—CH_2—$ | | 0 | — | — | ethoxycarbonyl | 2.79[a] | | |
| 1.0607 | Cl | Br | H | O | NH | $—CH_2—CH_2—$ | | 0 | — | — | cyclobutyloxycarbonyl | 3.46[a] | | |
| 1.0608 | Cl | Br | CN | O | NH | $CH_3$ | $CH_3$ | 0 | — | — | methoxycarbonyl | 2.77[a] | | |
| 1.0609 | Cl | Br | CN | O | NH | isopropyl | H | 0 | — | — | ethoxycarbonyl | 3.81[a] | | |
| 1.0610 | Cl | Br | CN | O | NH | cyclopropyl | H | 0 | — | — | methoxycarbonyl | 2.93[a] | | |
| 1.0611 | Cl | Cl | Br | O | NH | $—CH_2—CH_2—CH_2—$ | | 0 | — | — | isopropyloxycarbonyl | 4.69[a] | | |
| 1.0612 | Cl | Cl | Br | O | NH | $—CH_2—C(CH_3)_2—CH_2—$ | | 0 | — | — | methoxycarbonyl | 4.50[a] | | |
| 1.0613 | Cl | Cl | Br | O | NH | $—CH_2—CH_2—CH_2—$ | | 0 | — | — | methoxycarbonyl | 3.67[a] | | |
| 1.0614 | Cl | Cl | Br | O | NH | $—CH_2—CF_2—CH_2—$ | | 0 | — | — | tert-butoxycarbonyl | 4.83[a] | | |
| 1.0615 | Br | Br | Cl | O | NH | cyclopropyl | H | 0 | — | — | phenylmethoxycarbonyl | 5.07[a] | | |
| 1.0616 | Br | Br | Cl | O | NH | $—CH_2—CH_2—CH_2—$ | | 0 | — | — | isopropyloxycarbonyl | 4.71[a] | | |
| 1.0617 | Cl | Cl | Br | O | NH | cyclopropyl | H | 0 | — | — | phenylmethoxycarbonyl | 5.10[a] | | |
| 1.0618 | Br | Br | Cl | O | NH | $—CH_2—C(CH_3)_2—CH_2—$ | | 0 | — | — | methoxycarbonyl | 4.52[a] | | |
| 1.0619 | Br | Br | F | O | NH | cyclopropyl | H | 0 | — | — | phenylmethoxycarbonyl | 4.63[a] | | |
| 1.0620 | Br | Br | F | O | NH | $—CH_2—CH_2—CH_2—$ | | 0 | — | — | isopropyloxycarbonyl | 4.23[a] | | |
| 1.0621 | Br | Br | F | O | NH | $—CH_2—C(CH_3)_2—CH_2—$ | | 0 | — | — | methoxycarbonyl | 4.12[a] | | |
| 1.0622 | Br | Br | F | O | NH | $—CH_2—CF_2—CH_2—$ | | 0 | — | — | methoxycarbonyl | 3.37[a] | | |
| 1.0623 | Br | Br | F | O | NH | $—CH_2—CF_2—CH_2—$ | | 0 | — | — | tert-butoxycarbonyl | 4.46[a] | | |
| 1.0624 | Br | Br | Cl | O | NH | $—CH_2—CF_2—CH_2—$ | | 0 | — | — | methoxycarbonyl | 3.69[a] | | |
| 1.0625 | Cl | Br | $CH_3$ | O | NH | $—CH_2—CH_2—$ | | 0 | — | — | propoxycarbonyl | 3.62[a] | | |
| 1.0626 | Cl | Cl | Br | O | NH | H | H | 0 | — | — | aminocarbonyl | 1.98[a] | | |
| 1.0627 | Br | $CHF_2$ | Br | O | NH | $CH_3$ | $CH_3$ | 0 | — | — | methoxycarbonyl | 3.22[a] | | |
| 1.0628 | Cl | Br | CN | O | NH | benzyl | H | 0 | — | — | ethoxycarbonyl | 4.00[a] | | |
| 1.0629 | Cl | Br | CN | O | NH | $—CH_2—CH_2—CH_2—$ | | 0 | — | — | methoxycarbonyl | 2.82[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0630 | Cl | Br | CN | O | NH | $-CH_2-CH_2-CH_2-$ | | 0 | — | — | ethoxycarbonyl | 3.20[a] | | |
| 1.0631 | Cl | Br | CN | O | NH | $-CH_2-CH_2-$ | | 0 | — | — | propoxycarbonyl | 3.06[a] | | |
| 1.0632 | Cl | Br | CN | O | NH | $-CH_2-CH_2-$ | | 0 | — | — | cyclobutyloxycarbonyl | 3.21[a] | | |
| 1.0633 | Cl | Br | CN | O | NH | H | H | 0 | — | — | cyano | 2.07[a] | | |
| 1.0634 | Cl | Br | F | O | NH | H | H | 0 | — | — | ethoxycarbonyl | 2.88[a] | | |
| 1.0635 | Cl | Br | F | O | NH | H | H | 0 | — | — | methoxycarbonyl | 2.49[a] | | |
| 1.0636 | Cl | Br | F | O | NH | $-CH_2-CH_2-$ | | 0 | — | — | ethoxycarbonyl | 3.10[a] | | |
| 1.0637 | Cl | Br | F | O | NH | $CH_3$ | $CH_3$ | 0 | — | — | methoxycarbonyl | 3.27[a] | | |
| 1.0638 | Br | Br | Cl | O | NH | H | H | 0 | — | — | aminocarbonyl | 1.98[a] | | |
| 1.0639 | Cl | Br | F | O | NH | isopropyl | H | 0 | — | — | ethoxycarbonyl | 4.40[a] | | |
| 1.0640 | Cl | Br | F | O | NH | benzyl | H | 0 | — | — | ethoxycarbonyl | 4.50[a] | | |
| 1.0641 | Cl | Br | F | O | NH | $-CH_2-CH_2-CH_2-$ | | 0 | — | — | methoxycarbonyl | 3.29[a] | | |
| 1.0642 | Cl | Br | F | O | NH | $-CH_2-CH_2-CH_2-$ | | 0 | — | — | ethoxycarbonyl | 3.75[a] | | |
| 1.0643 | Cl | Br | F | O | NH | $-CH_2-CH_2-$ | | 0 | — | — | propoxycarbonyl | 3.52[a] | | |
| 1.0644 | Cl | Br | F | O | NH | $-CH_2-CH_2-$ | | 0 | — | — | cyclobutyloxycarbonyl | 3.69[a] | | |
| 1.0645 | Cl | Br | F | O | NH | H | H | 0 | — | — | cyano | 2.36[a] | | |
| 1.0646 | Br | $CHF_2$ | Br | O | NH | H | H | 0 | — | — | ethoxycarbonyl | 2.92[a] | | |
| 1.0647 | Br | $CHF_2$ | Br | O | NH | H | H | 0 | — | — | methoxycarbonyl | 2.56[a] | | |
| 1.0648 | Br | $CHF_2$ | Br | O | NH | $-CH_2-CH_2-$ | | 0 | — | — | ethoxycarbonyl | 3.05[a] | | |
| 1.0649 | Br | $CHF_2$ | Br | O | NH | $-CH_2-CH_2-$ | | 0 | — | — | methoxycarbonyl | 2.70[a] | | |
| 1.0650 | Cl | Br | F | O | NH | cyclopropyl | H | 0 | — | — | methoxycarbonyl | 3.41[a] | | |
| 1.0651 | Br | Cl | $CH_3$ | O | NH | $-CH_2-CH_2-$ | | 0 | — | — | cyclobutyloxycarbonyl | 3.78[a] | | |
| 1.0652 | Br | CN | Cl | O | NH | H | H | 0 | — | — | cyano | 2.03[a] | | |
| 1.0653 | Cl | CN | Br | O | NH | H | H | 0 | — | — | ethoxycarbonyl | 2.58[a] | | |
| 1.0654 | Cl | CN | Br | O | NH | H | H | 0 | — | — | methoxycarbonyl | 2.21[a] | | |
| 1.0655 | Cl | CN | Br | O | NH | $-CH_2-CH_2-$ | | 0 | — | — | ethoxycarbonyl | 2.69[a] | | |
| 1.0656 | Cl | CN | Br | O | NH | $-CH_2-CH_2-$ | | 0 | — | — | methoxycarbonyl | 2.34[a] | | |
| 1.0657 | Cl | CN | Br | O | NH | $CH_3$ | $CH_3$ | 0 | — | — | methoxycarbonyl | 2.83[a] | | |
| 1.0658 | Cl | CN | Br | O | NH | isopropyl | H | 0 | — | — | ethoxycarbonyl | 3.83[a] | | |
| 1.0659 | Cl | CN | Br | O | NH | cyclopropyl | H | 0 | — | — | methoxycarbonyl | 3.00[a] | | |
| 1.0660 | Cl | CN | Br | O | NH | benzyl | H | 0 | — | — | ethoxycarbonyl | 4.09[a] | | |
| 1.0661 | Cl | CN | Br | O | NH | $-CH_2-CH_2-CH_2-$ | | 0 | — | — | methoxycarbonyl | 2.87[a] | | |
| 1.0662 | Cl | CN | Br | O | NH | $-CH_2-CH_2-CH_2-$ | | 0 | — | — | ethoxycarbonyl | 3.28[a] | | |
| 1.0663 | Cl | CN | Br | O | NH | H | H | 0 | — | — | cyano | 2.03[a] | | |
| 1.0664 | CN | Cl | Br | O | NH | H | H | 0 | — | — | ethoxycarbonyl | 2.64[a] | | |
| 1.0665 | CN | Cl | Br | O | NH | H | H | 0 | — | — | methoxycarbonyl | 2.25[a] | | |
| 1.0666 | CN | Cl | Br | O | NH | $-CH_2-CH_2-$ | | 0 | — | — | ethoxycarbonyl | 2.76[a] | | |
| 1.0667 | CN | Cl | Br | O | NH | $-CH_2-CH_2-$ | | 0 | — | — | methoxycarbonyl | 2.42[a] | | |
| 1.0668 | CN | Cl | Br | O | NH | $CH_3$ | $CH_3$ | 0 | — | — | methoxycarbonyl | 2.90[a] | | |
| 1.0669 | CN | Cl | Br | O | NH | isopropyl | H | 0 | — | — | ethoxycarbonyl | 3.90[a] | | |
| 1.0670 | CN | Cl | Br | O | NH | cyclopropyl | H | 0 | — | — | methoxycarbonyl | 3.07[a] | | |
| 1.0671 | CN | Cl | Br | O | NH | benzyl | H | 0 | — | — | ethoxycarbonyl | 4.14[a] | | |
| 1.0672 | CN | Cl | Br | O | NH | $-CH_2-CH_2-CH_2-$ | | 0 | — | — | methoxycarbonyl | 2.96[a] | | |
| 1.0673 | Br | CN | Cl | O | NH | $-CH_2-CH_2-CH_2-$ | | 0 | — | — | ethoxycarbonyl | 3.30[a] | | |
| 1.0674 | Br | CN | Cl | O | NH | $-CH_2-CH_2-CH_2-$ | | 0 | — | — | methoxycarbonyl | 2.89[a] | | |
| 1.0675 | Br | CN | Cl | O | NH | benzyl | H | 0 | — | — | ethoxycarbonyl | 4.06[a] | | |
| 1.0676 | Br | CN | Cl | O | NH | cyclopropyl | H | 0 | — | — | methoxycarbonyl | 2.99[a] | | |
| 1.0677 | Br | Br | Cl | O | NH | H | H | 0 | — | — | oxolan-3-yloxycarbonyl | 2.84[a] | | |
| 1.0678 | Br | Br | F | O | NH | H | H | 0 | — | — | oxolan-3-yloxycarbonyl | 2.53[a] | | |
| 1.0679 | CN | Br | $CH_3$ | O | NH | H | H | 0 | — | — | oxolan-3-yloxycarbonyl | 2.12[a] | | |
| 1.0680 | CN | Br | $CH_3$ | O | NH | $-CH_2-CH_2-CH_2-$ | | 0 | — | — | methoxycarbonyl | 2.71[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0681 | Cl | Cl | CN | O | NH | H | H | 0 | — | — | methoxycarbonyl | 2.17[a] | | |
| 1.0682 | Cl | Cl | CN | O | NH | —$CH_2$—$CH_2$— | | 0 | — | — | methoxycarbonyl | 2.33[a] | | |
| 1.0683 | CN | Cl | Br | O | NH | —$CH_2$—$CH_2$—$CH_2$— | | 0 | — | — | ethoxycarbonyl | 3.34[a] | | |
| 1.0684 | Cl | Cl | CN | O | NH | $CH_3$ | $CH_3$ | 0 | — | — | methoxycarbonyl | 2.73[a] | | |
| 1.0685 | Cl | Cl | CN | O | NH | benzyl | H | 0 | — | — | ethoxycarbonyl | 3.98[a] | | |
| 1.0686 | Cl | Cl | CN | O | NH | —$CH_2$—$CH_2$—$CH_2$— | | 0 | — | — | methoxycarbonyl | 2.79[a] | | |
| 1.0687 | Cl | Cl | CN | O | NH | —$CH_2$—$CH_2$—$CH_2$— | | 0 | — | — | ethoxycarbonyl | 3.16[a] | | |
| 1.0688 | Cl | Cl | CN | O | NH | H | H | 0 | — | — | cyano | 2.04[a] | | |
| 1.0689 | Br | CN | Cl | O | NH | H | H | 0 | — | — | ethoxycarbonyl | 2.57[a] | | |
| 1.0690 | Br | CN | Cl | O | NH | H | H | 0 | — | — | methoxycarbonyl | 2.19[a] | | |
| 1.0691 | Br | CN | Cl | O | NH | —$CH_2$—$CH_2$— | | 0 | — | — | ethoxycarbonyl | 2.71[a] | | |
| 1.0692 | Br | CN | Cl | O | NH | —$CH_2$—$CH_2$— | | 0 | — | — | methoxycarbonyl | 2.37[a] | | |
| 1.0693 | Br | CN | Cl | O | NH | $CH_3$ | $CH_3$ | 0 | — | — | methoxycarbonyl | 2.84[a] | | |
| 1.0694 | Br | CN | Cl | O | NH | isopropyl | H | 0 | — | — | ethoxycarbonyl | 3.83[a] | | |
| 1.0695 | Cl | Cl | CN | O | NH | cyclopropyl | H | 0 | — | — | methoxycarbonyl | 2.89[a] | | |
| 1.0696 | CN | Cl | Br | O | NH | H | H | 0 | — | — | cyano | 2.08[a] | | |
| 1.0697 | F | Br | Br | O | NH | H | H | 0 | — | — | ethoxycarbonyl | 3.01[a] | | |
| 1.0698 | F | Br | Br | O | NH | H | H | 0 | — | — | methoxycarbonyl | 2.60[a] | | |
| 1.0700 | $CF_3$ | Br | H | O | NH | —$CH_2$—$CH_2$— | | 0 | — | — | carboxy | 2.44[a] | | |
| 1.0701 | Cl | Br | Br | O | NH | $CH_3$ | $CH_3$ | 0 | — | — | ethoxycarbonyl | 4.30[a] | | |
| 1.0702 | Cl | Br | F | O | NH | —$CH_2$—$CH_2$— | | 0 | — | — | carboxy | 2.15[a] | | |
| 1.0703 | Br | Cl | F | O | NH | —$CH_2$—$CH_2$— | | 0 | — | — | carboxy | 2.14[a] | | |
| 1.0704 | Br | Cl | $CH_3$ | O | NH | —$CH_2$—$CH_2$— | | 0 | — | — | propoxycarbonyl | 3.62[a] | | |
| 1.0705 | Br | Cl | $CH_3$ | O | NH | —$CH_2$—$CH_2$—$CH_2$— | | 0 | — | — | cyclobutyloxycarbonyl | 4.33[a] | | |
| 1.0706 | F | Br | Br | O | NH | —$CH_2$—$CH_2$— | | 0 | — | — | ethoxycarbonyl | 3.17[a] | | |
| 1.0707 | F | Br | Br | O | NH | —$CH_2$—$CH_2$— | | 0 | — | — | methoxycarbonyl | 2.76[a] | | |
| 1.0708 | F | Br | Br | O | NH | $CH_3$ | $CH_3$ | 0 | — | — | methoxycarbonyl | 3.38[a] | | |
| 1.0709 | F | Br | Br | O | NH | isopropyl | H | 0 | — | — | ethoxycarbonyl | 4.48[a] | | |
| 1.0710 | F | Br | Br | O | NH | cyclopropyl | H | 0 | — | — | methoxycarbonyl | 3.55[a] | | |
| 1.0711 | F | Br | Br | O | NH | benzyl | H | 0 | — | — | ethoxycarbonyl | 4.67[a] | | |
| 1.0712 | F | Br | Br | O | NH | —$CH_2$—$CH_2$—$CH_2$— | | 0 | — | — | methoxycarbonyl | 3.41[a] | | |
| 1.0713 | F | Br | Br | O | NH | —$CH_2$—$CH_2$—$CH_2$— | | 0 | — | — | ethoxycarbonyl | 3.88[a] | | |
| 1.0714 | F | Br | Br | O | NH | H | H | 0 | — | — | cyano | 2.39[a] | | |
| 1.0715 | $CF_3$ | Br | H | O | NH | H | H | 0 | — | — | ethoxycarbonyl | 3.00[a] | | |
| 1.0716 | $CF_3$ | Br | H | O | NH | H | H | 0 | — | — | methoxycarbonyl | 2.65[a] | | |
| 1.0717 | $CF_3$ | Br | H | O | NH | —$CH_2$—$CH_2$— | | 0 | — | — | methoxycarbonyl | 2.87[a] | | |
| 1.0718 | $CF_3$ | Br | H | O | NH | $CH_3$ | $CH_3$ | 0 | — | — | methoxycarbonyl | 3.23[a] | | |
| 1.0719 | $CF_3$ | Br | H | O | NH | isopropyl | H | 0 | — | — | ethoxycarbonyl | 4.18[a] | | |
| 1.0720 | $CF_3$ | Br | H | O | NH | cyclopropyl | H | 0 | — | — | methoxycarbonyl | 3.41[a] | | |
| 1.0721 | $CF_3$ | Br | H | O | NH | benzyl | H | 0 | — | — | ethoxycarbonyl | 4.36[a] | | |
| 1.0722 | $CF_3$ | Br | H | O | NH | —$CH_2$—$CH_2$—$CH_2$— | | 0 | — | — | methoxycarbonyl | 3.33[a] | | |
| 1.0723 | $CF_3$ | Br | H | O | NH | —$CH_2$—$CH_2$—$CH_2$— | | 0 | — | — | ethoxycarbonyl | 3.70[a] | | |
| 1.0724 | $CF_3$ | Br | H | O | NH | H | H | 0 | — | — | cyano | 2.61[a] | | |
| 1.0725 | Cl | Br | $CH_3$ | O | NH | —$CH_2$—$CH_2$—$CH_2$— | | 0 | — | — | cyclobutyloxycarbonyl | 4.37[a] | | |
| 1.0726 | $CF_3$ | Br | H | O | NH | —$CH_2$—$CH_2$— | | 0 | — | — | ethoxycarbonyl | 3.22[a] | | |
| 1.0727 | Cl | Cl | Br | O | NH | —$CH_2$—S—$CH_2$— | | 0 | — | — | ethoxycarbonyl | 3.95[a] | | |
| 1.0728 | Br | Br | Cl | O | NH | —$CH_2$—S—$CH_2$— | | 0 | — | — | ethoxycarbonyl | 3.97[a] | | |
| 1.0729 | CN | Br | $CH_3$ | O | NH | 2-methylsulfanylethyl | H | 0 | — | — | methoxycarbonyl | 3.03[a] | (S) | +20,7° (c = 1.35, CDCl3, 25° C.) |
| 1.0730 | CN | Cl | $CH_3$ | O | NH | 2-methylsulfanylethyl | H | 0 | — | — | methoxycarbonyl | 2.97[a] | (S) | +26° (c = 1, CDCl3, 25° C.) |
| 1.0731 | CN | Br | Br | O | NH | $CH_2$—OH | H | 0 | — | — | ethoxycarbonyl | 2.62[a] | | |
| 1.0732 | CN | Br | Br | O | NH | 2-methylsulfanylethyl | H | 0 | — | — | ethoxycarbonyl | 3.81[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0733 | CN | Br | Br | O | NH | 2-methylsulfanylethyl | H | 0 | — | — | methoxycarbonyl | 3.23[a] | | |
| 1.0734 | CN | Br | Br | O | NH | 2-methylsulfanylethyl | H | 0 | — | — | methoxycarbonyl | 3.40[a] | (S) | +29.3° (c = 1.5, CDCl3, 25° C.) |
| 1.0735 | Cl | Br | $CH_3$ | O | NH | 2-methylsulfanylethyl | H | 0 | — | — | methoxycarbonyl | 3.63[a] | | |
| 1.0736 | Cl | Br | $CH_3$ | O | NH | 2-methylsulfanylethyl | H | 0 | — | — | ethoxycarbonyl | 4.02[a] | (S) | −15.4° (c = 2,08, DMSO, 25° C.) |
| 1.0737 | Br | Br | F | O | NH | H | H | 0 | — | — | methylcarbamoyl | 1.81[a] | | |
| 1.0738 | Cl | Cl | Br | O | NH | H | H | 0 | — | — | methylcarbamoyl | 2.08[a] | | |
| 1.0739 | CN | Br | Br | O | NH | H | H | 0 | — | — | ethoxycarbonyl | 2.75[a] | | |
| 1.0740 | CN | Br | Br | O | NH | $—CH_2—CH_2—$ | | 0 | — | — | ethoxycarbonyl | 3.02[a] | | |
| 1.0741 | Br | Br | Cl | O | NH | CN | H | 0 | — | — | ethoxycarbonyl | 3.34[a] | | |
| 1.0742 | CN | Br | $CH_3$ | O | NH | CN | H | 0 | — | — | ethoxycarbonyl | 2.66[a] | | |
| 1.0743 | Cl | Cl | Br | O | NH | CN | H | 0 | — | — | ethoxycarbonyl | 3.35[a] | | |
| 1.0744 | Cl | Br | Br | O | NH | CN | H | 0 | — | — | ethoxycarbonyl | 3.38[a] | | |
| 1.0745 | Cl | Cl | $CHF_2$ | O | NH | H | H | 0 | — | — | cyano | 2.50[a] | | |
| 1.0746 | Cl | Cl | $CHF_2$ | O | NH | $CH_3$ | $CH_3$ | 0 | — | — | ethoxycarbonyl | 3.55[a] | | |
| 1.0748 | Cl | Cl | $CHF_2$ | O | NH | methoxycarbonyl | H | 0 | — | — | methoxycarbonyl | 3.00[a] | | |
| 1.0749 | CN | Br | $CH_3$ | O | $N—OCH_3$ | H | H | 0 | — | — | ethoxycarbonyl | 3.23[a] | | |
| 1.0750 | Br | Br | Cl | O | NH | 2-methylsulfanylethyl | H | 0 | — | — | methoxycarbonyl | 4.04[a] | (S) | +25° (c = 0.8, CDCl3, 25° C.) |
| 1.0751 | CN | Br | $CH_3$ | O | NH | 2-methylsulfanylethyl | H | 0 | — | — | methoxycarbonyl | 3.06[a] | | |
| 1.0752 | CN | Cl | Cl | O | NH | methylsulfanylmethyl | H | 0 | — | — | ethoxycarbonyl | 3.54[a] | | |
| 1.0753 | Cl | Br | $CH_3$ | O | NH | methylsulfanylmethyl | H | 0 | — | — | ethoxycarbonyl | 3.97[a] | | |
| 1.0754 | Cl | Cl | CN | O | NH | methylsulfanylmethyl | H | 0 | — | — | ethoxycarbonyl | 3.37[a] | | |
| 1.0755 | Br | Br | CN | O | NH | methylsulfanylmethyl | H | 0 | — | — | ethoxycarbonyl | 3.40[a] | | |
| 1.0756 | Br | Cl | $CH_3$ | O | NH | methylsulfanylmethyl | H | 0 | — | — | ethoxycarbonyl | 3.94[a] | | |
| 1.0757 | Br | Br | Cl | O | NH | $—CH_2—CF_2—CH_2—$ | | 0 | — | — | tert-butoxycarbonyl | 4.89[a] | | |
| 1.0758 | Cl | Cl | $CH_3$ | O | NH | CN | H | 0 | — | — | ethoxycarbonyl | 3.23[a] | | |
| 1.0759 | Br | Cl | $CH_3$ | O | NH | 2-methylsulfanylethyl | H | 0 | — | — | methoxycarbonyl | 3.64[a] | | |
| 1.0760 | Cl | Br | $CH_3$ | O | NH | $CH_3$ | $CH_3$ | 0 | — | — | ethoxycarbonyl | 3.66[a] | | |
| 1.0764 | Br | Cl | $CH_3$ | O | NH | $CH_3$ | $CH_3$ | 0 | — | — | ethoxycarbonyl | 3.71[a] | | |
| 1.0765 | Br | Cl | $CH_3$ | O | NH | 2-methylsulfanylethyl | H | 0 | — | — | ethoxycarbonyl | 4.01[a] | (S) | −14° (c = 1.29, DMSO, 25° C.) |
| 1.0766 | Br | Br | Cl | O | NH | 2-methylsulfanylethyl | H | 0 | — | — | methoxycarbonyl | 4.04[a] | | |
| 1.0767 | Cl | Br | $CH_3$ | O | NH | 2-methylsulfanylethyl | H | 0 | — | — | methoxycarbonyl | 3.74[a] | (S) | −19.8° (c = 1.01, DMSO, 25° C.) |
| 1.0768 | Br | Cl | $CH_3$ | O | NH | 2-methylsulfanylethyl | H | 0 | — | — | methoxycarbonyl | 3.60[a] | (S) | −18.2° (c = 1.1, DMSO, 25° C.) |
| 1.0769 | CN | Br | $CH_3$ | O | NH | methylsulfanylmethyl | H | 0 | — | — | ethoxycarbonyl | 3.26[a] | | |
| 1.0770 | Cl | Cl | CN | O | NH | 2-methylsulfanylethyl | H | 0 | — | — | methoxycarbonyl | 3.14[a] | | |
| 1.0771 | CN | Cl | $CH_3$ | O | NH | ethoxycarbonyl | H | 0 | — | — | ethoxycarbonyl | 3.20[a] | | |
| 1.0772 | Br | Br | F | O | NH | ethoxycarbonyl | H | 0 | — | — | ethoxycarbonyl | 3.91[a] | | |
| 1.0773 | CN | Br | $CH_3$ | O | NH | ethoxycarbonyl | H | 0 | — | — | ethoxycarbonyl | 3.23[a] | | |
| 1.0774 | Cl | Cl | CN | O | NH | ethoxycarbonyl | H | 0 | — | — | ethoxycarbonyl | 3.40[a] | | |
| 1.0775 | Cl | Cl | Br | O | NH | ethoxycarbonyl | H | 0 | — | — | ethoxycarbonyl | 4.30[a] | | |
| 1.0776 | Br | Br | Cl | O | NH | methoxymethyl | H | 0 | — | — | ethoxycarbonyl | 3.91[a] | | |
| 1.0777 | Cl | Cl | Br | O | NH | methoxymethyl | H | 0 | — | — | ethoxycarbonyl | 3.94[a] | | |
| 1.0778 | Br | Br | CN | O | NH | 2-methylsulfanylethyl | H | 0 | — | — | methoxycarbonyl | 3.37[a] | | |
| 1.0779 | Br | Br | Cl | O | NH | $CH_2—OH$ | H | 0 | — | — | ethoxycarbonyl | 2.89[a] | | |
| 1.0780 | Cl | Cl | Br | O | NH | $CH_2—OH$ | H | 0 | — | — | ethoxycarbonyl | 3.06[a] | | |
| 1.0781 | Br | Cl | Br | O | NH | H | H | 0 | — | — | ethoxycarbonyl | 3.40[a] | | |
| 1.0782 | Br | Cl | Br | O | NH | $—CH_2—CH_2—$ | | 0 | — | — | ethoxycarbonyl | 3.56[a] | | |
| 1.0783 | Br | Br | Cl | O | NH | ethoxycarbonyl | H | 0 | — | — | ethoxycarbonyl | 4.33[a] | | |
| 1.0784 | CN | Cl | Cl | O | NH | $—CH_2—CH_2—$ | | 0 | — | — | prop-2-ynoxycarbonyl | 2.73[a] | | |
| 1.0785 | Cl | Cl | CN | O | NH | $—CH_2—CH_2—$ | | 0 | — | — | prop-2-ynoxycarbonyl | 2.65[a] | | |
| 1.0786 | Cl | Cl | Br | O | NH | $—CH_2—CH_2—$ | | 0 | — | — | aminocarbonyl | 2.08[a] | | |
| 1.0787 | Br | Br | Cl | O | NH | $—CH_2—CH_2—$ | | 0 | — | — | aminocarbonyl | 2.10[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0788 | CN | Cl | Cl | O | NH | $—CH_2—CH_2—$ | | 0 | — | — | aminocarbonyl | 1.67[a] | | |
| 1.0789 | CN | Br | $CH_3$ | O | NH | $—CH_2—CH_2—$ | | 0 | — | — | aminocarbonyl | 1.61[a] | | |
| 1.0790 | Cl | Cl | Br | O | $N—OCH_3$ | H | H | 0 | — | — | ethoxycarbonyl | 3.71[a] | | |
| 1.0791 | CN | Cl | Cl | O | NH | 2-methylsulfanylethyl | H | 0 | — | — | methoxycarbonyl | 3.26[a] | | |
| 1.0792 | CN | Br | $CH_3$ | O | NH | methoxymethyl | H | 0 | — | — | ethoxycarbonyl | 2.80[a] | | |
| 1.0793 | $CH_3$ | Cl | F | O | NH | H | H | 0 | — | — | ethoxycarbonyl | 2.54[a] | | |
| 1.0794 | Br | Br | CN | O | NH | 2-methylsulfanylethyl | H | 0 | — | — | ethoxycarbonyl | 3.51[a] | | |
| 1.0795 | Br | Br | F | O | NH | $—CH_2—S—CH_2—$ | | 0 | — | — | ethoxycarbonyl | 3.59[a] | | |
| 1.0796 | CN | Cl | Cl | O | NH | H | H | 0 | — | — | aminocarbonyl | 1.48[a] | | |
| 1.0797 | Br | Br | CN | O | NH | H | H | 0 | — | — | ethoxycarbonyl | 2.59[a] | | |
| 1.0798 | Br | Br | CN | O | NH | H | H | 0 | — | — | methoxycarbonyl | 2.24[a] | | |
| 1.0799 | Br | Br | CN | O | NH | $—CH_2—CH_2—$ | | 0 | — | — | ethoxycarbonyl | 2.73[a] | | |
| 1.0800 | Br | Br | CN | O | NH | $—CH_2—CH_2—$ | | 0 | — | — | methoxycarbonyl | 2.40[a] | | |
| 1.0801 | Br | Br | CN | O | NH | $CH_3$ | $CH_3$ | 0 | — | — | methoxycarbonyl | 2.81[a] | | |
| 1.0802 | Br | Br | CN | O | NH | H | H | 0 | — | — | cyano | 2.11[a] | | |
| 1.0803 | Br | Br | CN | O | NH | $CH_2—OH$ | H | 0 | — | — | ethoxycarbonyl | 2.29[a] | (S) | |
| 1.0804 | Br | Br | Cl | O | $N—OCH_3$ | H | H | 0 | — | — | ethoxycarbonyl | 3.67[a] | | |
| 1.0805 | Br | Br | CN | O | NH | ethoxycarbonyl | H | 0 | — | — | ethoxycarbonyl | 3.39[a] | | |
| 1.0806 | Br | Br | CN | O | NH | $—CH_2—CH_2—CH_2—$ | | 0 | — | — | methoxycarbonyl | 2.87[a] | | |
| 1.0807 | Cl | Cl | CN | O | NH | $—CH_2—CH_2—$ | | 0 | — | — | aminocarbonyl | 1.71[a] | | |
| 1.0809 | CN | Cl | Cl | O | NH | $CH_2—OH$ | H | 0 | — | — | ethoxycarbonyl | 2.33[a] | | |
| 1.0810 | Cl | Cl | CN | O | NH | $CH_2—OH$ | H | 0 | — | — | ethoxycarbonyl | 2.23[a] | | |
| 1.0811 | Br | Br | CN | O | NH | $CH_2—OH$ | H | 0 | — | — | ethoxycarbonyl | 2.29[a] | | |
| 1.0812 | Br | Br | F | O | NH | 2-methylsulfanylethyl | H | 0 | — | — | ethoxycarbonyl | 4.05[a] | | |
| 1.0813 | CN | Cl | Cl | O | NH | 2-methylsulfanylethyl | H | 0 | — | — | ethoxycarbonyl | 3.60[a] | | |
| 1.0814 | Cl | Cl | CN | O | NH | 2-methylsulfanylethyl | H | 0 | — | — | ethoxycarbonyl | 3.46[a] | | |
| 1.0815 | Br | Br | CN | O | NH | $—CH_2—CH_2—CH_2—$ | | 0 | — | — | ethoxycarbonyl | 3.23[a] | | |
| 1.0816 | Cl | Cl | Br | O | NH | $CH_2—OH$ | H | 0 | — | — | ethoxycarbonyl | 2.84[a] | (S) | +30.6° (c = 1.05, MeOH, 25° C.) |
| 1.0817 | Br | Br | Cl | O | NH | $CH_2—OH$ | H | 0 | — | — | ethoxycarbonyl | 2.84[a] | (S) | +20.3° (c = 0.99, MeOH, 25° C.) |
| 1.0823 | CN | Br | $CH_3$ | O | NH | $CH_3$ | H | 0 | — | — | ethoxycarbonyl | 2.80[a] | | |
| 1.0824 | Br | Br | Cl | O | NH | $CH_3$ | H | 0 | — | — | ethoxycarbonyl | 4.01[a] | | |
| 1.0826 | I | Cl | Cl | O | NH | H | H | 0 | — | — | methoxycarbonyl | 2.82[a] | | |
| 1.0827 | I | Cl | Cl | O | NH | H | H | 0 | — | — | ethoxycarbonyl | 3.24[a] | | |
| 1.0828 | I | Cl | Cl | O | NH | $—CH_2—CH_2—$ | | 0 | — | — | methoxycarbonyl | 3.01[a] | | |
| 1.0830 | Cl | Cl | CN | O | NH | $CH_2—OH$ | H | 0 | — | — | ethoxycarbonyl | 2.22[a] | (S) | +13° (c = 0.77, MeOH, 25° C.) |
| 1.0831 | CN | Cl | Cl | O | NH | $CH_2—OH$ | H | 0 | — | — | ethoxycarbonyl | 2.26[a] | (S) | +27.9° (c = 0.86, MeOH, 25° C.) |
| 1.0832 | Br | Br | F | O | NH | $CH_2—OH$ | H | 0 | — | — | ethoxycarbonyl | 2.54[a] | (S) | +21° (c = 1.05, MeOH, 25° C.) |
| 1.0833 | CN | Cl | $CH_3$ | O | NH | $CH_2—OH$ | H | 0 | — | — | ethoxycarbonyl | 2.07[a] | (S) | +18.3° (c = 0.99, MeOH, 25° C.) |
| 1.0834 | CN | Br | $CH_3$ | O | NH | $CH_2—OH$ | H | 0 | — | — | ethoxycarbonyl | 2.16[a] | | |
| 1.0835 | CN | Cl | $CH_3$ | O | NH | $CH_2—OH$ | H | 0 | — | — | ethoxycarbonyl | 2.12[a] | | |
| 1.0836 | CN | Cl | $CH_3$ | O | NH | 2-methylsulfanylethyl | H | 0 | — | — | methoxycarbonyl | 3.03[a] | | |
| 1.0837 | Br | Cl | Br | O | NH | H | H | 0 | — | — | cyano | 2.75[a] | | |
| 1.0838 | Br | Cl | Br | O | NH | 2-methylsulfanylethyl | H | 0 | — | — | ethoxycarbonyl | 4.55[a] | | |
| 1.0840 | Br | Cl | Br | O | NH | $CH_3$ | $CH_3$ | 0 | — | — | methoxycarbonyl | 3.81[a] | | |
| 1.0841 | Br | Cl | $CH_3$ | O | NH | $CH_2—OH$ | H | 0 | — | — | ethoxycarbonyl | 2.59[a] | (S) | +42.3° (c = 1.22, CDCl3, 25° C.) |
| 1.0842 | Cl | Br | $CH_3$ | O | NH | $CH_2—OH$ | H | 0 | — | — | ethoxycarbonyl | 2.62[a] | (S) | +39.4° (c = 1.42, CDCl3, 25° C.) |
| 1.0843 | Br | Br | $CH_3$ | O | NH | $CH_2—OH$ | H | 0 | — | — | ethoxycarbonyl | 2.64[a] | (S) | +42.1° (c = 1.33, CDCl3, 25° C.) |
| 1.0844 | Br | Cl | $CH_3$ | O | NH | $CH_2—OH$ | H | 0 | — | — | ethoxycarbonyl | 2.60[a] | | |
| 1.0845 | CN | Cl | Cl | O | $N—OCH_3$ | H | H | 0 | — | — | ethoxycarbonyl | 3.06[a] | | |
| 1.0846 | CN | Br | $CH_3$ | O | NH | $CH_2—OH$ | H | 0 | — | — | ethoxycarbonyl | 2.11[a] | (S) | +14.4° (c = 1.11, MeOH, 25° C.) |
| 1.0847 | Br | Cl | Br | O | NH | $CH_2—OH$ | H | 0 | — | — | ethoxycarbonyl | 2.89[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0848 | $CH_3$ | Cl | Cl | O | NH | H | H | 0 | — | — | ethoxycarbonyl | 2.82[a] | | |
| 1.0849 | Br | Br | Cl | O | NH | $—CH_2—CH_2—CH_2—$ | | 0 | — | — | methoxycarbonyl | 3.75[a] | | |
| 1.0850 | Br | Br | Cl | O | NH | H | H | 0 | — | — | cyano | 2.67[a] | | |
| 1.0851 | Cl | Cl | Br | S | NH | H | H | 0 | — | — | methoxycarbonyl | 4.09[a] | | |
| 1.0852 | Br | Br | Cl | S | NH | H | H | 0 | — | — | methoxycarbonyl | 4.07[a] | | |
| 1.0853 | Cl | Br | Cl | S | NH | $—CH_2—CH_2—CH_2—$ | | 0 | — | — | ethoxycarbonyl | 5.04[a] | | |
| 1.0854 | Cl | Cl | Br | S | NH | H | H | 0 | — | — | carboxy | 3.11[a] | | |
| 1.0855 | Br | Br | F | O | NH | H | H | 0 | — | — | prop-2-ynoxycarbonyl | 2.87[a] | | |
| 1.0856 | Br | Br | F | O | NH | H | H | 0 | — | — | cyclopropyloxycarbonyl | 3.02[a] | | |
| 1.0857 | Br | Br | F | O | NH | H | H | 0 | — | — | allyloxycarbonyl | 3.13[a] | | |
| 1.0858 | Br | Br | F | O | NH | H | H | 0 | — | — | 2-cyanoethoxycarbonyl | 2.48[a] | | |
| 1.0859 | Br | Br | F | O | NH | H | H | 0 | — | — | cyclopropylmethoxycarbonyl | 3.39[a] | | |
| 1.0860 | Br | Br | F | O | NH | H | H | 0 | — | — | butoxycarbonyl | 3.79[a] | | |
| 1.0861 | Br | Br | Cl | S | NH | H | H | 0 | — | — | carboxy | 3.08[a] | | |
| 1.0862 | Br | Br | F | O | NH | H | H | 0 | — | — | cyclopentyloxycarbonyl | 3.84[a] | | |
| 1.0863 | Br | Br | F | O | NH | H | H | 0 | — | — | phenoxycarbonyl | 3.58[a] | | |
| 1.0864 | CN | Br | $CH_3$ | S | NH | H | H | 0 | — | — | methoxycarbonyl | 2.92[a] | | |
| 1.0865 | Br | Br | F | S | NH | cyclopropyl | H | 0 | — | — | ethoxycarbonyl | 4.99[a] | | |
| 1.0868 | Br | Br | Cl | O | NH | $—CH_2—CH_2—S—CH_2—CH_2—$ | | 0 | — | — | cyano | 3.71[a] | | |
| 1.0871 | Br | Br | F | O | NH | $—CH_2—CH_2—S—CH_2—CH_2—$ | | 0 | — | — | cyano | 3.40[a] | | |
| 1.0872 | Br | Br | F | O | NH | cyclopropyl | $CH_3$ | 0 | — | — | cyano | 3.47[a] | | |
| 1.0873 | Br | Br | Cl | O | NH | $—CH_2—CH_2—CH_2—$ | | 0 | — | — | cyano | 3.35[a] | | |
| 1.0874 | Br | Br | Cl | O | NH | isopropyl | H | 0 | — | — | cyano | 3.88[a] | | |
| 1.0875 | Cl | Br | Cl | O | NH | H | H | 0 | — | — | carboxy | 2.18[a] | | |
| 1.0876 | Br | Br | F | S | NH | benzyl | H | 0 | — | — | carboxy | 4.17[a] | | |
| 1.0877 | CN | Br | $CH_3$ | S | NH | H | H | 0 | — | — | ethoxycarbonyl | 3.30[a] | | |
| 1.0878 | Cl | Br | H | S | NH | H | H | 0 | — | — | methoxycarbonyl | 3.35[a] | | |
| 1.0879 | Cl | Cl | Br | O | NH | $—CH_2—CH_2—CH_2—$ | | 0 | — | — | propoxycarbonyl | 4.74[a] | | |
| 1.0880 | Cl | Cl | Br | O | NH | $—CH_2—CH_2—CH_2—$ | | 0 | — | — | cyclohexyloxycarbonyl | 5.89[a] | | |
| 1.0881 | Cl | Cl | Br | O | NH | $—CH_2—CH_2—$ | | 0 | — | — | carbamothioyl | 2.77[a] | | |
| 1.0882 | Cl | Cl | Br | O | NH | $—CH_2—CH_2—$ | | 0 | — | — | methylcarbamoyl | 2.28[a] | | |
| 1.0883 | Br | Br | Cl | O | NH | H | H | 0 | — | — | oxan-4-yloxycarbonyl | 3.14[a] | | |
| 1.0884 | Br | Br | Cl | O | NH | cyclopropyl | H | 0 | — | — | tert-butoxycarbonyl | 5.36[a] | | |
| 1.0885 | Br | Br | Cl | O | NH | cyclopropyl | H | 0 | — | — | cyclobutyloxycarbonyl | 5.08[a] | | |
| 1.0886 | Br | Br | Cl | O | NH | cyclopropyl | H | 0 | — | — | isopropyloxycarbonyl | 4.89[a] | | |
| 1.0887 | Br | Br | Cl | O | NH | $—CH_2—CH_2—CH_2—$ | | 0 | — | — | cyclopropylmethoxycarbonyl | 4.81[a] | | |
| 1.0888 | Cl | Cl | Br | O | NH | $—CH_2—CH_2—CH_2—$ | | 0 | — | — | phenylmethoxycarbonyl | 5.00[a] | | |
| 1.0889 | Cl | Cl | Br | O | NH | $—CH_2—CH_2—CH_2—$ | | 0 | — | — | cyclobutyloxycarbonyl | 4.93[a] | | |
| 1.0890 | Cl | Cl | Br | O | NH | $—CH_2—CH_2—CH_2—$ | | 0 | — | — | butoxycarbonyl | 5.20[a] | | |
| 1.0891 | Cl | Cl | Br | O | NH | $—CH_2—CH_2—CH_2—$ | | 0 | — | — | tert-butoxycarbonyl | 5.28[a] | | |
| 1.0892 | Cl | $CH_3$ | Cl | O | NH | H | H | 0 | — | — | methoxycarbonyl | 2.64[a] | | |
| 1.0893 | Cl | $CH_3$ | Cl | O | NH | H | H | 0 | — | — | ethoxycarbonyl | 3.07[a] | | |
| 1.0894 | Br | Br | F | O | NH | H | H | 0 | — | — | aminocarbonyl | 1.69[a] | | |
| 1.0895 | Br | Br | F | O | NH | $—CH_2—CH_2—$ | | 0 | — | — | (cyanoamino)carbonyl | 2.38[a] | | |
| 1.0896 | Br | Br | F | O | NH | H | H | 0 | — | — | carbamothioyl | 2.25[a] | | |
| 1.0897 | $CH_3$ | Cl | Cl | O | NH | $—CH_2—CH_2—$ | | 0 | — | — | methoxycarbonyl | 2.67[a] | | |
| 1.0898 | Br | Br | Cl | O | NH | $—CH_2—CH_2—$ | | 0 | — | — | tert-butoxycarbonyl | 5.28[a] | | |
| 1.0899 | F | Cl | H | O | NH | H | H | 0 | — | — | ethoxycarbonyl | 2.23[a] | | |
| 1.0900 | Br | Br | F | O | NH | $—CH_2—CH_2—$ | | 0 | — | — | carbamothioyl | 2.42[a] | | |
| 1.0901 | F | Cl | H | O | NH | $—CH_2—CH_2—$ | | 0 | — | — | methoxycarbonyl | 2.13[a] | | |
| 1.0902 | Cl | Cl | Br | O | NH | cyclopropyl | H | 0 | — | — | tert-butoxycarbonyl | 5.41[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0903 | Cl | Cl | Br | O | NH | cyclopropyl | H | 0 | — | — | cyclobutyloxycarbonyl | 5.08[a] | | |
| 1.0904 | Cl | Cl | Br | O | NH | cyclopropyl | H | 0 | — | — | isopropyloxycarbonyl | 4.89[a] | | |
| 1.0905 | Cl | Cl | Br | O | NH | —$CH_2$—$CH_2$—$CH_2$— | | 0 | — | — | cyclopropylmethoxycarbonyl | 4.78[a] | | |
| 1.0906 | F | Cl | H | O | NH | H | H | 0 | — | — | methoxycarbonyl | 1.90[a] | | |
| 1.0907 | Br | Br | Cl | O | NH | —$CH_2$—$CH_2$—$CH_2$— | | 0 | — | — | butoxycarbonyl | 5.20[a] | | |
| 1.0908 | Br | Br | Cl | O | NH | —$CH_2$—$CH_2$—$CH_2$— | | 0 | — | — | cyclobutyloxycarbonyl | 4.97[a] | | |
| 1.0909 | Br | Br | Cl | O | NH | —$CH_2$—$CH_2$—$CH_2$— | | 0 | — | — | phenylmethoxycarbonyl | 5.00[a] | | |
| 1.0910 | Cl | Cl | CN | O | NH | H | H | 0 | — | — | prop-2-ynoxycarbonyl | 2.58[a] | | |
| 1.0911 | CN | Cl | Cl | O | NH | H | H | 0 | — | — | prop-2-ynoxycarbonyl | 2.63[a] | | |
| 1.0912 | CN | Cl | Cl | O | NH | —$CH_2$—$CH_2$— | | 0 | — | — | allyloxycarbonyl | 3.00[a] | | |
| 1.0913 | Cl | Cl | CN | O | NH | —$CH_2$—$CH_2$— | | 0 | — | — | allyloxycarbonyl | 2.91[a] | | |
| 1.0914 | CN | Cl | $CH_3$ | O | NH | H | H | 0 | — | — | aminocarbonyl | 1.34[a] | | |
| 1.0915 | CN | Br | $CH_3$ | O | NH | H | H | 0 | — | — | aminocarbonyl | 1.38[a] | | |
| 1.0916 | Cl | Cl | CN | O | NH | H | H | 0 | — | — | aminocarbonyl | 1.47[a] | | |
| 1.0917 | Br | Br | Cl | O | NH | —$CH_2$—$CH_2$—$CH_2$— | | 0 | — | — | propoxycarbonyl | 4.78[a] | | |
| 1.0918 | Br | Br | Cl | O | NH | —$CH_2$—$CH_2$—$CH_2$— | | 0 | — | — | cyclohexyloxycarbonyl | 5.89[a] | | |
| 1.0919 | Br | Br | Cl | O | NH | —$CH_2$—$CH_2$— | | 0 | — | — | carbamothioyl | 2.80[a] | | |
| 1.0920 | Br | Br | Cl | O | NH | —$CH_2$—$CH_2$— | | 0 | — | — | methylcarbamoyl | 2.31[a] | | |
| 1.0921 | Br | Br | F | O | NH | cyclopropyl | H | 0 | — | — | tert-butoxycarbonyl | 4.89[a] | | |
| 1.0922 | Br | Br | F | O | NH | cyclopropyl | H | 0 | — | — | cyclobutyloxycarbonyl | 4.59[a] | | |
| 1.0923 | Br | Br | F | O | NH | cyclopropyl | H | 0 | — | — | isopropyloxycarbonyl | 4.40[a] | | |
| 1.0924 | Br | Br | F | O | NH | —$CH_2$—$CH_2$—$CH_2$— | | 0 | — | — | cyclopropylmethoxycarbonyl | 4.33[a] | | |
| 1.0925 | Br | Br | F | O | NH | —$CH_2$—$CH_2$—$CH_2$— | | 0 | — | — | tert-butoxycarbonyl | 4.78[a] | | |
| 1.0926 | Br | Br | F | O | NH | —$CH_2$—$CH_2$—$CH_2$— | | 0 | — | — | butoxycarbonyl | 4.74[a] | | |
| 1.0927 | Br | Br | F | O | NH | —$CH_2$—$CH_2$—$CH_2$— | | 0 | — | — | phenylmethoxycarbonyl | 4.59[a] | | |
| 1.0928 | Br | Br | F | O | NH | —$CH_2$—$CH_2$—$CH_2$— | | 0 | — | — | propoxycarbonyl | 4.30[a] | | |
| 1.0929 | Br | Br | F | O | NH | —$CH_2$—$CH_2$—$CH_2$— | | 0 | — | — | cyclohexyloxycarbonyl | 5.28[a] | | |
| 1.0930 | Br | Br | F | O | NH | —$CH_2$—$CH_2$—$CH_2$— | | 0 | — | — | cyclobutyloxycarbonyl | 4.47[a] | | |
| 1.0933 | Cl | Br | Cl | S | NH | —$CH_2$—$CH_2$—$CH_2$— | | 0 | — | — | methoxycarbonyl | 4.66[a] | | |
| 1.0934 | Cl | Br | Cl | S | NH | —$CH_2$—$CH_2$—$CH_2$— | | 0 | — | — | carboxy | 3.56[a] | | |
| 1.0935 | Br | Br | Cl | O | N—cPr | H | H | 0 | — | — | ethoxycarbonyl | 3.81[a] | | |
| 1.0936 | Cl | Br | Cl | O | N—cPr | H | H | 0 | — | — | ethoxycarbonyl | 3.80[a] | | |
| 1.0937 | Cl | Cl | Br | O | N—cPr | H | H | 0 | — | — | ethoxycarbonyl | 3.81[a] | | |
| 1.0938 | Br | Br | F | O | N—cPr | H | H | 0 | — | — | ethoxycarbonyl | 3.64[a] | | |
| 1.0940 | Br | Br | Cl | O | NH | (4-chlorophenyl)methyl | H | 0 | — | — | methoxycarbonyl | 4.95[a] | | |
| 1.0941 | Br | Br | Cl | O | NH | benzyl | $CH_3$ | 0 | — | — | methoxycarbonyl | 5.12[a] | | |
| 1.0942 | Br | Br | Cl | O | NH | thiophen-2-yl | H | 0 | — | — | methoxycarbonyl | 4.25[a] | | |
| 1.0943 | Br | Br | Cl | O | NH | $CF_3$ | H | 0 | — | — | ethoxycarbonyl | 4.50[a] | | |
| 1.0946 | Cl | Cl | Br | O | NH | $CF_3$ | H | 0 | — | — | ethoxycarbonyl | 4.52[a] | | |
| 1.0947 | Cl | Cl | Br | O | NH | thiophen-2-yl | H | 0 | — | — | methoxycarbonyl | 4.26[a] | | |
| 1.0948 | Cl | Cl | Br | O | NH | benzyl | $CH_3$ | 0 | — | — | methoxycarbonyl | 5.15[a] | | |
| 1.0952 | Br | Br | F | O | NH | $CF_3$ | H | 0 | — | — | ethoxycarbonyl | 4.08[a] | | |
| 1.0953 | Br | Br | F | O | NH | thiophen-2-yl | H | 0 | — | — | methoxycarbonyl | 3.84[a] | | |
| 1.0954 | Br | Br | F | O | NH | benzyl | $CH_3$ | 0 | — | — | methoxycarbonyl | 4.64[a] | | |
| 1.0955 | Br | Br | F | O | NH | (4-chlorophenyl)methyl | H | 0 | — | — | methoxycarbonyl | 4.52[a] | | |
| 1.0959 | Br | Br | Cl | O | NH | H | H | 0 | — | — | prop-2-ynoxycarbonyl | 3.20[a] | | |
| 1.0960 | Br | Br | Cl | O | NH | H | H | 0 | — | — | cyclopropyloxycarbonyl | 3.39[a] | | |
| 1.0961 | Br | Br | Cl | O | NH | H | H | 0 | — | — | allyloxycarbonyl | 3.50[a] | | |
| 1.0962 | CN | Br | $CH_3$ | O | NH | —$CH_2$—$CH_2$— | | 0 | — | — | allyloxycarbonyl | 2.81[a] | | |
| 1.0963 | CN | Br | $CH_3$ | O | NH | —$CH_2$—$CH_2$— | | 0 | — | — | prop-2-ynoxycarbonyl | 2.61[a] | | |
| 1.0964 | CN | Br | $CH_3$ | O | NH | —$CH_2$—$CH_2$— | | 0 | — | — | isopropyloxycarbonyl | 2.93[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.0965 | CN | Br | $CH_3$ | O | NH | H | H | 0 | — | — | cyclopentyloxycarbonyl | 3.24[a] | | |
| 1.0966 | CN | Br | $CH_3$ | O | NH | $—CH_2—CH_2—$ | | 0 | — | — | propoxycarbonyl | 2.98[a] | | |
| 1.0967 | CN | Br | $CH_3$ | O | NH | H | H | 0 | — | — | phenoxycarbonyl | 3.10[a] | | |
| 1.0968 | CN | Br | $CH_3$ | O | NH | $—CH_2—CH_2—$ | | 0 | — | — | cyclobutyloxycarbonyl | 3.13[a] | | |
| 1.0969 | CN | Br | $CH_3$ | O | NH | $—CH_2—CH_2—$ | | 0 | — | — | butoxycarbonyl | 3.36[a] | | |
| 1.0970 | CN | Br | $CH_3$ | O | NH | $—CH_2—CH_2—$ | | 0 | — | — | 2-methylpropoxycarbonyl | 3.33[a] | | |
| 1.0971 | CN | Br | $CH_3$ | O | NH | $—CH_2—CH_2—$ | | 0 | — | — | tert-butoxycarbonyl | 3.28[a] | | |
| 1.0972 | CN | Br | $CH_3$ | O | NH | H | H | 0 | — | — | butoxycarbonyl | 3.23[a] | | |
| 1.0973 | CN | Br | $CH_3$ | O | NH | H | H | 0 | — | — | phenylmethoxycarbonyl | 3.26[a] | | |
| 1.0974 | CN | Br | $CH_3$ | O | NH | cyclopropyl | H | 0 | — | — | ethoxycarbonyl | 3.15[a] | | |
| 1.0975 | CN | Br | $CH_3$ | O | NH | $—CH_2—CH_2—$ | | 0 | — | — | phenylmethoxycarbonyl | 3.39[a] | | |
| 1.0976 | Br | Br | F | O | NH | $—CH_2—CH_2—$ | | 0 | — | — | methylcarbamothioyl | 2.82[a] | | |
| 1.0977 | Br | Br | F | O | NH | $—CH_2—CH_2—$ | | 0 | — | — | dimethylcarbamothioyl | 2.93[a] | | |
| 1.0978 | Cl | $CH_3$ | Cl | O | NH | $—CH_2—CH_2—$ | | 0 | — | — | methoxycarbonyl | 2.86[a] | | |
| 1.0979 | Br | Br | F | O | NH | $—CH_2—CH_2—CH_2—$ | | 0 | — | — | methoxycarbonyl | 3.32[a] | | |
| 1.0980 | CN | Br | $CH_3$ | O | NH | $—CH_2—CH_2—$ | | 0 | — | — | cyclopentyloxycarbonyl | 3.36[a] | | |
| 1.0981 | CN | Br | $CH_3$ | O | NH | H | H | 0 | — | — | tert-butoxycarbonyl | 3.14[a] | | |
| 1.0982 | CN | Br | $CH_3$ | O | NH | H | H | 0 | — | — | cyclopropylmethoxycarbonyl | 2.86[a] | | |
| 1.0983 | Br | Br | Cl | O | NH | H | H | 0 | — | — | propoxycarbonyl | 3.76[a] | | |
| 1.0984 | Br | Br | Cl | O | NH | H | H | 0 | — | — | 2-cyanoethoxycarbonyl | 2.76[a] | | |
| 1.0985 | Br | Br | Cl | O | NH | H | H | 0 | — | — | cyclopropylmethoxycarbonyl | 3.79[a] | | |
| 1.0986 | Br | Br | Cl | O | NH | H | H | 0 | — | — | tert-butoxycarbonyl | 4.20[a] | | |
| 1.0987 | Br | Br | Cl | O | NH | H | H | 0 | — | — | butoxycarbonyl | 4.22[a] | | |
| 1.0988 | Br | Br | Cl | O | NH | H | H | 0 | — | — | cyclopentyloxycarbonyl | 4.28[a] | | |
| 1.0989 | Br | Br | Cl | O | NH | H | H | 0 | — | — | phenoxycarbonyl | 3.93[a] | | |
| 1.0990 | Br | Br | Cl | O | NH | H | H | 0 | — | — | phenylmethoxycarbonyl | 4.15[a] | | |
| 1.0991 | Br | Br | Cl | O | NH | cyclopropyl | H | 0 | — | — | ethoxycarbonyl | 4.34[a] | | |
| 1.0992 | CN | Br | $CH_3$ | O | NH | H | H | 0 | — | — | prop-2-ynoxycarbonyl | 2.43[a] | | |
| 1.0993 | CN | Br | $CH_3$ | O | NH | H | H | 0 | — | — | cyclopropyloxycarbonyl | 2.54[a] | | |
| 1.0994 | CN | Br | $CH_3$ | O | NH | H | H | 0 | — | — | allyloxycarbonyl | 2.65[a] | | |
| 1.0995 | CN | Br | $CH_3$ | O | NH | H | H | 0 | — | — | propoxycarbonyl | 2.81[a] | | |
| 1.0996 | CN | Br | $CH_3$ | O | NH | H | H | 0 | — | — | 2-cyanoethoxycarbonyl | 2.09[a] | | |
| 1.0997 | Br | Br | Cl | O | NH | H | H | 0 | — | — | benzylsulfanylcarbonyl | 4.62[a] | | |
| 1.0998 | Br | Br | Cl | O | NH | isopropyl | H | 0 | — | — | ethylsulfanylcarbonyl | 5.45[a] | | |
| 1.0999 | Br | Br | F | S | NH | H | H | 0 | — | — | ethoxycarbonyl | 4.23[a] | | |
| 1.1000 | Br | Br | F | O | NH | H | H | 0 | — | — | 2-methylpropoxycarbonyl | 3.88[a] | | |
| 1.1001 | Br | Br | F | O | NH | H | H | 0 | — | — | methylcarbamothioyl | 2.56[a] | | |
| 1.1002 | Br | Br | F | O | NH | H | H | 0 | — | — | dimethylcarbamothioyl | 3.19[a] | | |
| 1.1003 | Cl | Br | Cl | O | NH | $—CH_2—CH_2—CH_2—$ | | 0 | — | — | methoxycarbonyl | 3.74[a] | | |
| 1.1004 | Cl | Cl | Br | O | NH | $—CH_2—CH_2—CH_2—$ | | 0 | — | — | methoxycarbonyl | 3.85[a] | | |
| 1.1007 | Br | Br | F | O | NH | H | H | 0 | — | — | thietan-3-yloxycarbonyl | 3.37[a] | | |
| 1.1008 | Br | Br | F | O | NH | H | H | 0 | — | — | cyanomethoxycarbonyl | 2.67[a] | | |
| 1.1010 | Br | Br | F | O | NH | isopropyl | H | 0 | — | — | cyano | 3.54[a] | | |
| 1.1013 | Cl | Cl | Br | O | NH | isopropyl | H | 0 | — | — | cyano | 3.84[a] | | |
| 1.1014 | Cl | Cl | Br | O | NH | $—CH_2—CH_2—CH_2—$ | | 0 | — | — | cyano | 3.37[a] | | |
| 1.1015 | CN | Br | $CH_3$ | O | NH | $—CH_2—CH_2—CH_2—$ | | 0 | — | — | cyano | 2.64[a] | | |
| 1.1016 | CN | Br | $CH_3$ | O | NH | isopropyl | H | 0 | — | — | cyano | 3.03[a] | | |
| 1.1017 | Cl | Cl | Br | O | NH | $—CH_2—CH_2—CH_2—$ | | 0 | — | — | carboxy | 2.95[a] | | |
| 1.1018 | Br | Br | F | O | NH | H | H | 0 | — | — | oxan-4-yloxycarbonyl | 2.80[a] | | |
| 1.1019 | Cl | Br | Cl | O | NH | $CH_3$ | $CH_3$ | 0 | — | — | methoxycarbonyl | 3.73[a] | | |
| 1.1020 | Br | Br | Cl | O | NH | $CH_3$ | $CH_3$ | 0 | — | — | methoxycarbonyl | 3.75[a] | | |

TABLE 1.1-continued

| Ex. No | $R^1$ | $R^2$ | $R^3$ | W | Y | $R^4$ | $R^5$ | n | $R^6$ | $R^7$ | Z | LogP | Enanitomer | Optical Rotation |
|---|---|---|---|---|---|---|---|---|---|---|---|---|---|---|
| 1.1021 | Cl | Cl | Br | O | NH | $CH_3$ | $CH_3$ | 0 | — | — | methoxycarbonyl | 3.71[a] | | |
| 1.1022 | Cl | Br | Cl | O | NH | $CH_3$ | $CH_3$ | 0 | — | — | carboxy | 2.80[a] | | |
| 1.1023 | Br | Br | Cl | O | NH | $CH_3$ | $CH_3$ | 0 | — | — | carboxy | 2.81[a] | | |
| 1.1024 | Cl | Cl | Br | O | NH | $CH_3$ | $CH_3$ | 0 | — | — | carboxy | 2.80[a] | | |
| 1.1025 | Br | Br | Cl | O | NH | 2-(acetylthio)ethyl | H | 0 | — | — | methoxycarbonyl | 3.98[a] | | |
| 1.1026 | Br | Br | F | O | NH | H | H | 0 | — | — | 2,2,2-trifluoroethoxycarbonyl | 3.40[a] | | |
| 1.1027 | Br | Br | F | O | NH | H | H | 0 | — | — | trimethylsilylmethoxycarbonyl | 4.40[a] | | |
| 1.1028 | Cl | Cl | Br | O | NH | 2-(acetylthio)ethyl | H | 0 | — | — | methoxycarbonyl | 3.98[a] | | |
| 1.1029 | Br | Br | F | S | NH | cyclopropyl | H | 0 | — | — | carboxy | 3.45[a] | | |
| 1.1030 | Cl | Cl | I | S | NH | H | H | 0 | — | — | carboxy | 3.13[a] | | |
| 1.1032 | CN | Br | $CH_3$ | S | NH | H | H | 0 | — | — | carboxy | 2.23[a] | | |
| 1.1033 | CN | Br | $CH_3$ | O | NH | H | H | 0 | — | — | benzylsulfanylcarbonyl | 3.78[a] | | |
| 1.1035 | Cl | Br | H | S | NH | H | H | 0 | — | — | carboxy | 2.59[a] | | |
| 1.1036 | CN | Br | $CH_3$ | O | NH | H | H | 0 | — | — | methylcarbamoyl | 1.53[a] | | |
| 1.1037 | CN | Br | $CH_3$ | O | NH | $-CH_2-S-CH_2-$ | | 0 | — | — | ethoxycarbonyl | 3.07[a] | | |
| 1.1038 | CN | Br | $CH_3$ | O | NH | 2-carboxyethyl | H | 0 | — | — | methoxycarbonyl | 2.01[a] | (3) | −15.5° (c = 1.42, MeOH, 25° C.) |
| 1.1039 | CN | Br | $CH_3$ | O | NH | 2-amino-2-oxoethyl | H | 0 | — | — | methoxycarbonyl | 1.67[a] | (S) | +12° (c = 1.01, MeOH, 25° C.) |
| 1.1040 | CN | Br | $CH_3$ | O | NH | 3-amino-3-oxopropyl | H | 0 | — | — | methoxycarbonyl | 1.77[a] | (S) | −7.7° (c = 1.05, DMSO, 25° C.) |
| 1.1041 | CN | Cl | Cl | O | NH | $-CH_2-S-CH_2-$ | | 0 | — | — | ethoxycarbonyl | 3.23[a] | | |
| 1.1042 | CN | Br | $CH_3$ | O | NH | carboxymethyl | H | 0 | — | — | methoxycarbonyl | 1.96[a] | (S) | +10.8° (c = 0.93, MeOH, 25° C.) |
| 1.1043 | Br | Br | F | O | NH | carboxymethyl | H | 0 | — | — | methoxycarbonyl | 2.28[a] | (S) | +2° (c = 1.02, MeOH, 25° C.) |
| 1.1044 | Cl | Cl | Br | O | NH | carboxymethyl | H | 0 | — | — | methoxycarbonyl | 2.58[a] | (S) | +31.8° (c = 1.01, MeOH, 25° C.) |
| 1.1045 | Br | Br | Cl | O | NH | H | H | 0 | — | — | methylcarbamoyl | 2.07[a] | | |
| 1.1046 | Br | Cl | Cl | O | NH | $-CH_2-S-CH_2-$ | | 0 | — | — | ethoxycarbonyl | 3.94[a] | | |
| 1.1047 | Cl | Cl | Br | O | NH | 2-amino-2-oxoethyl | H | 0 | — | — | methoxycarbonyl | 2.23[a] | (S) | +27.8° (c = 0.94, MeOH, 25° C.) |
| 1.1048 | Br | Br | F | O | NH | 3-amino-3-oxopropyl | H | 0 | — | — | methoxycarbonyl | 2.05[a] | (S) | −10° (c = 1.01, DMSO, 25° C.) |
| 1.1049 | Cl | Cl | Br | O | NH | 3-amino-3-oxopropyl | H | 0 | — | — | methoxycarbonyl | 2.25[a] | (S) | −9.9° (c = 1.02, DMSO, 25° C.) |
| 1.1050 | Cl | Cl | Br | O | NH | 2-carboxyethyl | H | 0 | — | — | methoxycarbonyl | 2.68[a] | (S) | −4.3° (c = 1.41, MeOH, 25° C.) |
| 1.1051 | Br | Br | CN | O | NH | $-CH_2-S-CH_2-$ | | 0 | — | — | ethoxycarbonyl | 3.15[a] | | |
| 1.1052 | Br | Br | $CHF_2$ | O | NH | $-CH_2-S-CH_2-$ | | 0 | — | — | ethoxycarbonyl | 3.58[a] | | |
| 1.1053 | CN | Br | Br | O | NH | $CH_3$ | $CH_3$ | 0 | — | — | methoxycarbonyl | 3.34[a] | | |
| 1.1054 | Cl | Cl | CN | O | NH | $-CH_2-S-CH_2-$ | | 0 | — | — | ethoxycarbonyl | 3.05[a] | | |
| 1.1055 | Br | Br | Cl | O | NH | $-CH_2-S-CH_2-CH_2-CH_2-$ | | 0 | — | — | cyano | 3.85[a] | | |
| 1.1056 | Br | Br | F | O | NH | $-CH_2-S-CH_2-CH_2-CH_2-$ | | 0 | — | — | cyano | 3.41[a] | | |
| 1.1057 | Cl | Br | $CH_3$ | O | NH | $-CH_2-S-CH_2-$ | | 0 | — | — | ethoxycarbonyl | 3.66[a] | | |
| 1.1058 | CN | Br | Br | O | NH | H | H | 0 | — | — | cyano | 2.12[a] | | |
| 1.1059 | Cl | Cl | $CHF_2$ | O | NH | $-CH_2-S-CH_2-$ | | 0 | — | — | ethoxycarbonyl | 3.55[a] | | |
| 1.1060 | Cl | Br | Br | O | NH | $-CH_2-S-CH_2-$ | | 0 | — | — | ethoxycarbonyl | 3.91[a] | | |
| 1.1061 | Br | Br | $CHF_2$ | O | NH | $CH_3$ | $CH_3$ | 0 | — | — | methoxycarbonyl | 3.21[a] | | |
| 1.1062 | Cl | Cl | Br | O | NH | $CH_3$ | $CH_3$ | 0 | — | — | ethoxycarbonyl | 4.24[a] | | |
| 1.1063 | Br | Cl | $CH_3$ | O | NH | $-CH_2-S-CH_2-$ | | 0 | — | — | ethoxycarbonyl | 3.62[a] | | |
| 1.1064 | Br | Br | $CHF_2$ | O | NH | $CH_2-OH$ | H | 0 | — | — | ethoxycarbonyl | 2.63[a] | | |
| 1.1065 | Br | Br | $CHF_2$ | O | NH | 2-methylsulfanylethyl | H | 0 | — | — | methoxycarbonyl | 3.55[a] | | |
| 1.1067 | Br | Br | $CHF_2$ | O | NH | methoxycarbonyl | H | 0 | — | — | methoxycarbonyl | 3.05[a] | | |
| 1.1068 | Cl | Cl | $CHF_2$ | O | NH | $CH_2-OH$ | H | 0 | — | — | ethoxycarbonyl | 2.67[a] | | |
| 1.1069 | Cl | Cl | $CHF_2$ | O | NH | 2-methylsulfanylethyl | H | 0 | — | — | methoxycarbonyl | 3.52[a] | | |
| 1.1070 | Cl | Cl | $CHF_2$ | O | NH | $CH_3$ | $CH_3$ | 0 | — | — | methoxycarbonyl | 3.16[a] | | |

Note:
Optical rotation concentration c is expressed in g/100 mL; (*) Mixture of stereoisomers; Boc means tert-butyloxycarbonyl; cPr means cyclopropyl

TABLE I.2

| Ex. No | $R^1$ | $R^2$ | $R^3$ | W | Y | 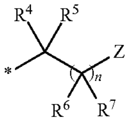 | LogP | Optical Rotation |
|---|---|---|---|---|---|---|---|---|
| 1.0006 | Br | Br | F | O | NH | 2-oxothiolan-3-yl | 2.84[a] | |
| 1.0007 | Br | Br | F | O | NH | 2,2-dimethyl-4-oxothietan-3-yl | 3.72[a] | |
| 1.0017 | Br | Br | F | O | NH | (3S)-2-oxothiolan-3-yl | 2.89[a] | −14.5° (c = 0.97, DMSO, 25° C.) |
| 1.0023 | Cl | Br | $CH_3$ | O | NH | (3S)-2-oxothiolan-3-yl | 2.99[a] | +50.3° (c = 1, CDCl3, 25° C.) |
| 1.0060 | Br | Br | F | O | NH | 2-oxooxolan-3-yl | 2.25[a] | |
| 1.0061 | Br | Br | F | O | NH | 2-oxopiperidin-3-yl | 2.01[a] | |
| 1.0123 | Cl | Br | $CH_3$ | O | NH | (2S,3S)-1-methoxy-3-methyl-1-oxopentan-2-yl | 4.27[a] | +29.3° (c = 1.03, CDCl3, 20° C.) |
| 1.0141 | Br | Br | F | O | NH | (2S,3S)-1-methoxy-3-methyl-1-oxopentan-2-yl | 4.37[a] | +7.4° (c = 1.08, CDCl3, 20° C.) |
| 1.0218 | Br | Cl | H | O | NH | 2-oxopyrrolidin-3-yl | 1.71[a] | |
| 1.0219 | Br | Cl | H | O | NH | 2-oxopiperidin-4-yl | 1.77[a] | |
| 1.0220 | Br | Cl | H | O | NH | 2-oxooxolan-3-yl | 2.09[a] | |
| 1.0221 | Br | Cl | H | O | NH | 5-oxopyrrolidin-3-yl | 1.71[a] | |
| 1.0222 | Cl | Br | H | O | NH | 2-oxopyrrolidin-3-yl | 1.73[a] | |
| 1.0223 | Cl | Br | H | O | NH | 2-oxopiperidin-4-yl | 1.80[a] | |
| 1.0224 | Cl | Br | H | O | NH | 2-oxooxolan-3-yl | 2.14[a] | |
| 1.0225 | Cl | Br | H | O | NH | 5-oxopyrrolidin-3-yl | 1.73[a] | |
| 1.0235 | Br | Br | F | O | NH | (1S,2S)-1-carboxy-2-methylbutyl | 3.40[a] | +19.4° (c = 1.55, CDCl3, 20° C.) |
| 1.0322 | Br | Cl | $CH_3$ | O | NH | (2S,3S)-1-methoxy-3-methyl-1-oxopentan-2-yl | 4.25[a] | +31.2° (c = 1.00, CDCl3, 20° C.) |
| 1.0338 | Br | Br | F | O | NH | (2S)-3-carboxy-1-oxo-1-[[(2S)-1-methoxy-1-oxo-3-phenylpropan-2-yl] amino]propan-2-yl | 2.98[a] | +12.5° (c = 0.80, CDCl3, 25° C.) |
| 1.0339 | Br | Cl | $CH_3$ | O | NH | (2S)-3-carboxy-1-oxo-1-[[(2S)-1-methoxy-1-oxo-3-phenylpropan-2-yl] amino]propan-2-yl | 3.09[a] | −8.3° (c = 1.2, DMSO, 25° C.) |
| 1.0340 | Cl | Br | $CH_3$ | O | NH | (2S)-3-carboxy-1-oxo-1-[[(2S)-1-methoxy-1-oxo-3-phenylpropan-2-yl] amino]propan-2-yl | 3.13[a] | −9.5° (c = 1.05, DMSO, 25° C.) |
| 1.0487 | Cl | Cl | Br | O | NH | (2S)-3-carboxy-1-oxo-1-[[(2S)-1-methoxy-1-oxo-3-phenylpropan-2-yl] amino]propan-2-yl | 3.23[a] | +6° (c = 1, DMSO, 25° C.) |
| 1.0488 | Br | Br | Cl | O | NH | (2S)-3-carboxy-1-oxo-1-[[(2S)-1-methoxy-1-oxo-3-phenylpropan-2-yl] amino]propan-2-yl | 3.20[a] | +3.5° (c = 1.15, DMSO, 25° C.) |
| 1.0501 | CN | Br | $CH_3$ | O | NH | (2S)-3-carboxy-1-oxo-1-[[(2S)-1-methoxy-1-oxo-3-phenylpropan-2-yl] amino]propan-2-yl | 2.70[a] | −7.6° (c = 1.05, DMSO, 25° C.) |
| 1.0525 | Cl | Br | Cl | O | NH | (3S)-2-oxothiolan-3-yl | 3.28[a] | −12.8° (c = 1.1, DMSO, 25° C.) |
| 1.0699 | Cl | Br | Br | O | NH | 1-[(1-ethoxy-2-methyl-1-oxopropan-2-yl)amino]-2-methyl-1-oxopropan-2-yl | 3.94[a] | |
| 1.0747 | Cl | Cl | $CHF_2$ | O | NH | 2-oxooxolan-3-yl | 2.40[a] | |
| 1.0761 | CN | Br | $CH_3$ | O | NH | (3S)-2-oxooxolan-3-yl | 1.94[a] | −19.5° (c = 1.03, DMSO, 25° C.) |
| 1.0762 | Cl | Br | $CH_3$ | O | NH | (3S)-2-oxooxolan-3-yl | 2.45[a] | −16.4° (c = 0.98, DMSO, 25°C.) |
| 1.0763 | Br | Cl | $CH_3$ | O | NH | (3S)-2-oxooxolan-3-yl | 2.42[a] | −14° (c = 1, DMSO, 25° C.) |
| 1.0808 | Cl | Cl | Br | O | NH | (3S)-2-oxoazetidin-3-yl | 2.03[a] | −7.6° (c = 1.06, DMSO, 25° C.) |
| 1.0818 | Cl | Cl | CN | O | NH | 2-oxooxolan-3-yl | 2.02[a] | |
| 1.0819 | CN | Cl | Cl | O | NH | 2-oxooxolan-3-yl | 2.05[a] | |
| 1.0820 | Cl | Br | $CH_3$ | O | NH | 2-oxooxolan-3-yl | 2.48[a] | |
| 1.0821 | Cl | Br | $CH_3$ | O | NH | 2-oxothiolan-3-yl | 3.03[a] | |
| 1.0822 | Br | Cl | $CH_3$ | O | NH | 2-oxothiolan-3-yl | 3.46[a] | |
| 1.0825 | Br | Cl | $CH_3$ | O | NH | 2-oxooxolan-3-yl | 2.45[a] | |
| 1.0829 | CN | Br | $CH_3$ | O | NH | 2-oxothiolan-3-yl | 2.45[a] | |
| 1.0839 | Cl | Cl | Br | O | NH | 2-oxooxolan-3-yl | 2.63[a] | |
| 1.0866 | CN | Br | $CH_3$ | O | NH | (3S)-2-oxothiolan-3-yl | 2.39[a] | −15° (c = 1.07, DMSO, 25° C.) |
| 1.0867 | Br | Br | Cl | O | NH | (3S)-2-oxothiolan-3-yl | 3.24[a] | +41.6° (c = 1.11, CDCl3, 25° C.) |
| 1.0869 | Br | Br | Cl | O | NH | 1-cyano-4-cyclohexylcyclohexyl | 6.46[a] | |
| 1.0870 | Br | Br | Cl | O | NH | 1-cyano-4-phenylcyclohexyl | 4.97[a] | |
| 1.0931 | Cl | Cl | Br | O | NH | (3S)-2-oxooxolan-3-yl | 2.59[a] | +51.3° (c = 0.98, CDCl3, 25° C.) |
| 1.0932 | Br | Br | Cl | O | NH | (3S)-2-oxooxolan-3-yl | 2.62[a] | +33.0° (c = 0.97, CDCl3, 25° C.) |
| 1.0939 | Cl | Br | Cl | O | NH | (3S)-2-oxopiperidin-3-yl | 2.29[a] | +78° (c = 1, CDCl3, 25° C.) |
| 1.0944 | Cl | Cl | Br | O | NH | (3S)-2-oxopiperidin-3-yl | 2.30[a] | +85.2° (c = 1.15, CDCl3, 25° C.) |
| 1.0945 | Cl | Cl | Br | O | NH | 2-oxoazepan-3-yl | 2.99[a] | |
| 1.0949 | Cl | Br | Cl | O | NH | 2-oxooxolan-3-yl | 2.56[a] | |
| 1.0950 | Br | Br | F | O | NH | (3S)-2-oxopiperidin-3-yl | 2.05[a] | +45.9° (c = 1.35, CDCl3, 25° C.) |
| 1.0951 | Br | Br | F | O | NH | 2-oxoazepan-3-yl | 2.68[a] | |
| 1.0956 | Br | Br | Cl | O | NH | (3S)-2-oxopiperidin-3-yl | 2.31[a] | +7.3° (c = 1.1, MeOH, 25° C.) |
| 1.0957 | Br | Br | Cl | O | NH | 2-oxoazepan-3-yl | 2.99[a] | |
| 1.0958 | Br | Br | F | O | NH | (3S)-2-oxooxolan-3-yl | 2.28[a] | +106.4° (c = 0.51, MeOH, 25° C.) |
| 1.1005 | Br | Br | Cl | O | NH | 2-oxothiolan-3-yl | 3.25[a] | |
| 1.1006 | Cl | Cl | Br | O | NH | 2-oxothiolan-3-yl | 3.25[a] | |
| 1.1009 | Br | Br | F | O | NH | 1-cyano-4-phenylcyclohexyl | 4.78[a] | |
| 1.1011 | Cl | Cl | Br | O | NH | (3S)-2-oxothiolan-3-yl | 3.24[a] | +50.5° (c = 1.11, CDCl3, 25° C.) |
| 1.1012 | Br | Br | F | O | NH | 1-cyano-4-cyclohexyl cyclohexyl | 6.13[a] | |
| 1.1031 | Br | Br | Cl | O | NH | 2-oxooxolan-3-yl | 2.58[a] | |
| 1.1034 | CN | Br | $CH_3$ | O | NH | 2-oxooxolan-3-yl | 1.92[a] | |
| 1.1066 | Br | Br | $CHF_2$ | O | NH | 2-oxooxolan-3-yl | 2.46[a] | |

Note:
"*" is linked to Y.

The following table II.1 illustrates in a non-limiting manner examples of compounds according to formula (II).

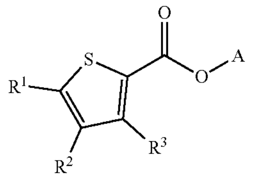

(II)

TABLE II.1

| Ex No | $R^1$ | $R^2$ | $R^3$ | A | LogP |
|---|---|---|---|---|---|
| II.001 | Br | CN | Cl | H | 1.66[a] |
| II.002 | Cl | CN | Cl | H | 1.59[a] |
| II.003 | Cl | Cl | $CHF_2$ | H | 2.39[a] |
| II.004 | Br | Br | $CF_3$ | H | 2.44[a] |
| II.005 | Cl | Br | F | H | 2.14[a] |
| II.006 | Br | Br | $CHF_2$ | H | 2.46[a] |
| II.007 | Br | CN | methyl | H | 2.03[a] |
| II.008 | Cl | CN | methyl | H | 1.94[a] |
| II.009 | Br | Cl | F | H | 2.18[a] |
| II.010 | Br | Cl | Cl | H | 2.51[a] |
| II.011 | Cl | Br | Br | H | 2.57[a] |
| II.012 | Cl | Br | Cl | H | 2.44[a] |
| II.013 | methyl | Br | F | H | 2.08[a] |
| II.014 | Cl | Br | methyl | H | 2.80[a] |
| II.015 | Br | Cl | methyl | H | 2.75[a] |
| II.016 | CN | Cl | methyl | H | 1.95[a] |
| II.017 | I | Br | methyl | H | 2.86[a] |
| II.018 | Br | I | methyl | H | 2.92[a] |
| II.019 | Br | Br | $CF_3$ | methyl | 4.08[a] |
| II.020 | Br | Cl | F | methyl | 3.47[a] |
| II.021 | Br | CN | Cl | methyl | 2.87[a] |
| II.022 | Cl | CN | Cl | methyl | 2.82[a] |
| II.023 | Cl | Cl | $CHF_2$ | methyl | 3.77[a] |
| II.024 | methyl | Br | F | 2-methylpropyl | 4.77[a] |
| II.025 | Cl | Br | F | methyl | 3.47[a] |
| II.026 | Cl | Br | Br | methyl | 4.02[a] |
| II.027 | Cl | Br | Cl | methyl | 3.94[a] |
| II.028 | Cl | CN | methyl | methyl | 2.98[a] |
| II.029 | Br | CN | methyl | methyl | 3.06[a] |
| II.030 | I | Br | methyl | ethyl | 5.03[a] |
| II.031 | Br | I | methyl | ethyl | 5.03[a] |
| II.032 | Cl | Br | methyl | ethyl | 5.00[a] |
| II.033 | Br | Cl | methyl | ethyl | 4.83[a] |
| II.034 | CN | Cl | H | H | 1.33[a] |
| II.035 | F | Br | H | H | 1.94[a] |
| II.036 | CN | Br | H | H | 1.41[a] |
| II.037 | Cl | F | H | H | 1.89[a] |
| II.038 | Cl | methyl | H | H | 2.16[a] |
| II.039 | Br | F | H | H | 1.02[a] |
| II.040 | Br | Cl | H | H | 2.23[a] |
| II.041 | Cl | CN | H | H | 1.44[a] |
| II.042 | CN | Br | methyl | H | 2.01[a] |
| II.043 | Cl | Br | H | H | 2.28[a] |
| II.044 | Br | CN | Br | H | 1.73[a] |
| II.045 | Cl | CN | H | methyl | 2.44[a] |
| II.046 | CN | Cl | H | methyl | 2.52[a] |
| II.047 | Br | Cl | H | methyl | 3.29[a] |
| II.048 | Cl | Br | H | ethyl | 4.21[a] |
| II.049 | Br | F | H | methyl | 3.04[a] |
| II.050 | Br | Cl | H | 2-methylpropyl | 5.28[a] |
| II.051 | CN | Br | methyl | methyl | 3.19[a] |
| II.052 | CN | Br | H | methyl | 2.63[a] |
| II.053 | Cl | Cl | CN | ethyl | 3.54[a] |
| II.054 | CN | Br | Br | methyl | 3.07[a] |
| II.055 | Br | Br | $CHF_2$ | methyl | 3.81[a] |
| II.056 | I | Cl | Cl | ethyl | 4.57[a] |
| II.057 | I | Cl | Cl | H | 3.01[a] |
| II.058 | methyl | Cl | Cl | methyl | 3.49[a] |
| II.059 | F | Br | Cl | methyl | 3.44[a] |
| II.060 | Cl | Br | F | 2-methylpropyl | 5.28[a] |
| II.061 | CN | Br | Br | H | 1.66[a] |

TABLE II.1-continued

| Ex No | $R^1$ | $R^2$ | $R^3$ | A | LogP |
|---|---|---|---|---|---|
| II.062 | F | Cl | H | ethyl | 3.63[a] |
| II.063 | methyl | Cl | Cl | ethyl | 4.03[a] |
| II.064 | F | Cl | H | H | 2.16[a] |
| II.065 | methyl | Cl | Cl | H | 2.49[a] |
| II.066 | F | Br | Cl | ethyl | 4.02[a] |
| II.067 | Cl | Br | F | ethyl | 4.08[a] |
| II.068 | CN | Cl | Cl | ethyl | 3.50[a] |
| II.069 | Br | Br | CN | methyl | 3.26[a] |
| II.070 | Br | Cl | Br | H | 2.41[a] |
| II.071 | Br | Cl | Br | methyl | 4.01[a] |
| II.072 | CN | Cl | H | ethyl | 3.10[a] |
| II.073 | Cl | methyl | Cl | ethyl | 4.59[a] |
| II.074 | Cl | methyl | Cl | H | 2.76[a] |
| II.075 | Br | $CHF_2$ | Br | methyl | 3.54[a] |
| II.076 | F | Br | Cl | H | 2.19[a] |
| II.077 | Cl | Br | CN | methyl | 2.99[a] |
| II.078 | Br | $CHF_2$ | Br | H | 2.26[a] |
| II.079 | CN | Cl | Cl | methyl | 2.99[a] |
| II.080 | CN | Br | Cl | methyl | 3.02[a] |
| II.081 | $CF_3$ | Br | H | H | 2.46[a] |
| II.082 | $CF_3$ | Br | H | ethyl | 4.40[a] |
| II.083 | Cl | Br | CN | H | 1.70[a] |
| II.084 | methyl | Br | F | methyl | 3.15[a] |
| II.085 | Cl | Cl | CN | methyl | 2.98[a] |
| II.086 | F | Br | Br | methyl | 3.56[a] |
| II.087 | CN | Br | Cl | H | 1.55[a] |
| II.088 | CN | Cl | Cl | H | 1.51[a] |
| II.089 | Cl | Br | Cl | ethyl | 4.62[a] |
| II.090 | Cl | CN | H | ethyl | 3.01[a] |
| II.091 | Br | CN | Cl | ethyl | 3.44[a] |
| II.092 | CN | Cl | Br | ethyl | 3.56[a] |
| II.093 | Cl | CN | Br | ethyl | 3.46[a] |
| II.094 | F | Br | Br | H | 2.26[a] |
| II.095 | Cl | CN | Br | methyl | 2.92[a] |
| II.096 | CN | Cl | Br | methyl | 3.04[a] |
| II.097 | CN | Cl | Br | H | 1.64[a] |
| II.098 | Cl | CN | Br | H | 1.68[a] |
| II.099 | $CHF_2$ | Br | Br | H | 2.51[a] |
| II.100 | Br | CN | H | H | 1.48[a] |
| II.101 | F | Cl | methyl | H | 2.45[a] |
| II.102 | F | Br | methyl | H | 2.53[a] |
| II.103 | Cl | Cl | CN | H | 1.61[a] |
| II.104 | Br | Br | CN | H | 1.71[a] |

In the above tables, measurement of Log P values was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

[c] Log P value is determined by measurement of LC-UV, in an acidic range, with 0.1% phosphoric acid and acetonitrile as eluent (linear gradient from 10% acetonitrile to 95% acetonitrile).

If more than one Log P value is available within the same method, all the values are given and separated by "+".

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists

Table A-(I) provides the NMR data ($^1H$) of according to formula (I) disclosed in the above tables.

Table A-(II) provides the NMR data ($^{1}H$ and $^{13}C$) of according to formula (II) disclosed in the above tables.

$^{1}H$-NMR data of selected examples are written in form of $^{1}H$-NMR-peak lists. To each signal peak are listed the 6-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^{1}H$ spectra, we use tetramethylsilane and/or the chemical shift of the solvent used, especially in the case of spectra measured in DMSO. Therefore, in NMR peak lists, tetramethylsilane peak can occur but not necessarily.

The $^{1}H$-NMR peak lists are similar to classical $^{1}H$-NMR prints and contains therefore usually all peaks, which are listed at classical NMR-interpretation.

Additionally they can show like classical $^{1}H$-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^{1}H$-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore, their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^{1}H$-NMR interpretation.

$^{13}C$-NMR data are displayed analogous to $^{1}H$-NMR data as peak lists from broadband decoupled $^{13}C$-NMR spectra. $^{13}C$-NMR solvent signals and tetramethylsilane are excluded from the relative intensity calibration as these signals can have very high intensities.

Further details of NMR-data description with peak lists you find in the publication "Citation of NMR Peaklist Data within Patent Applications" of the Research Disclosure Database Number 564025.

TABLE A-(I)

| NMR peak lists of compounds according to formula (I) |
|---|
| I.0001: $^{1}H$-NMR(300.2 MHz, CDCl3): |
| δ = 7.2984 (3.8); 6.8217 (0.4); 4.3287 (1.2); 4.3049 (3.7); 4.2811 (3.8); 4.2572 (1.5); 4.2495 (3.1); 4.2469 (3.1); 4.2322 (3.0); 2.4557 (16.0); 1.6195 (2.4); 1.4673 (0.4); 1.3684 (4.7); 1.3446 (9.2); 1.3208 (4.6); 1.2905 (0.6); 0.1055 (0.9); 0.0351 (3.6) |
| I.0002: $^{1}H$-NMR(400.2 MHz, $d_6$-DMSO): |
| δ = 8.6296 (1.3); 8.6099 (1.3); 7.8508 (5.2); 4.2384 (1.3); 4.2193 (2.4); 4.2002 (1.4); 4.1701 (0.6); 4.1608 (0.6); 4.1523 (0.6); 4.1430 (1.9); 4.1251 (2.1); 4.1218 (2.3); 4.1121 (0.4); 4.1040 (2.0); 4.0946 (0.6); 4.0862 (0.6); 4.0768 (0.6); 3.3313 (19.7); 2.5123 (7.1); 2.5083 (14.1); 2.5038 (18.5); 2.4994 (14.0); 2.1766 (16.0); 2.1522 (1.2); 2.1348 (1.1); 2.1176 (0.7); 1.2589 (0.5); 1.2392 (1.7); 1.2147 (4.9); 1.1970 (10.0); 1.1792 (4.8); 0.9674 (7.1); 0.9505 (7.0); 0.9313 (6.8); 0.9143 (6.6); 0.8533 (0.4); −0.0002 (0.7) |
| I.0003: $^{1}H$-NMR(400.2 MHz, $d_6$-DMSO): |
| δ = 8.7787 (2.7); 8.7589 (2.8); 8.0065 (9.7); 5.6265 (0.6); 4.2713 (2.2); 4.2521 (4.0); 4.2333 (2.3); 4.1821 (1.0); 4.1729 (1.0); 4.1644 (1.1); 4.1550 (3.3); 4.1371 (3.7); 4.1340 (4.2); 4.1157 (3.5); 4.1062 (1.2); 4.0979 (1.1); 4.0884 (1.1); 4.0706 (0.4); 3.3387 (58.3); 2.5099 (27.8); 2.5060 (36.5); 2.1891 (0.4); 2.1716 (1.2); 2.1546 (2.0); 2.1374 (2.1); 2.1203 (1.3); 2.1034 (0.5); 1.2994 (0.5); 1.2603 (1.0); 1.2383 (2.6); 1.2210 (8.1); 1.2033 (16.0); 1.1855 (7.8); 0.9712 (13.0); 0.9543 (12.9); 0.9375 (12.7); 0.9205 (12.2); 0.8537 (0.5); −0.0002 (1.0) |
| I.0004: $^{1}H$-NMR(400.2 MHz, $d_6$-DMSO): |
| δ = 9.1663 (0.7); 9.1598 (0.6); 9.1497 (0.6); 7.9534 (0.5); 7.7724 (2.7); 7.7705 (2.7); 6.1902 (0.5); 6.1823 (0.5); 4.6441 (0.4); 4.6315 (0.5); 4.6226 (0.7); 4.6109 (0.7); 4.6020 (0.6); 4.5893 (0.4); 3.6806 (16.0); 3.3545 (20.9); 3.3433 (16.4); 3.3378 (17.5); 3.3349 (16.7); 2.8970 (3.2); 2.7387 (2.6); 2.5291 (0.5); 2.5159 (8.4); 2.5116 (16.6); 2.5071 (21.7); 2.5026 (16.2); 2.4982 (8.5); 2.4695 (0.3); 2.4572 (0.5); 2.4430 (0.4); 2.4309 (0.5); 2.4180 (0.7); 2.4067 (0.6); 2.3910 (0.4); 2.3815 (0.5); 2.3756 (0.5); 2.3569 (0.4); 2.3453 (0.3); 2.3331 (0.4); 1.3006 (0.3); 1.2627 (0.6); 1.2410 (1.7); 1.1923 (0.5); 0.9350 (0.4); 0.9196 (0.4); 0.8789 (0.4); 0.8632 (0.4); 0.8559 (0.4); −0.0002 (0.6) |
| I.0005: $^{1}H$-NMR(499.9 MHz, $d_6$-DMSO): |
| δ = 12.8407 (2.5); 8.8449 (3.3); 7.9775 (4.3); 4.4737 (3.0); 3.5811 (0.5); 3.3402 (2.2); 2.5801 (3.6); 2.5210 (4.9); 2.0685 (16.0) |
| I.0006: $^{1}H$-NMR(400.2 MHz, $d_6$-DMSO): |
| δ = 8.4954 (15.7); 8.4757 (16.0); 8.3037 (1.5); 7.9520 (2.1); 7.7937 (0.4); 4.8029 (7.4); 4.7836 (13.3); 4.7711 (10.5); 4.7651 (10.2); 4.7518 (14.1); 4.7331 (7.8); 3.5726 (0.4); 3.4707 (7.7); 3.4571 (9.7); 3.4414 (18.7); 3.4277 (20.8); 3.4132 (24.0); 3.3741 (893.9); 3.3375 (25.5); 3.3199 (22.2); 3.3100 (15.4); 3.2930 (12.2); 3.2040 (0.8); 3.1653 (0.5); 3.1330 (0.5); 3.0851 (0.3); 2.8957 (11.7); 2.7362 (11.0); 2.7141 (0.4); 2.6769 (1.6); 2.6339 (0.5); 2.5901 (0.3); 2.5726 (0.5); 2.5123 (204.7); 2.5082 (263.6); 2.4717 (9.9); 2.4560 (15.1); 2.4414 (14.5); 2.4255 (8.7); 2.4055 (5.6); 2.3883 (6.4); 2.3749 (12.2); 2.3572 (12.9); 2.3442 (11.2); 2.3267 (10.9); 2.3139 (3.8); 2.2963 (3.0); 1.4342 (0.3); 1.2983 (0.5); 1.2602 (1.0); 1.2380 (4.2); 0.8698 (0.4); 0.8541 (0.8); 0.8365 (0.4); −0.0001 (2.0) |
| I.0007: $^{1}H$-NMR(400.2 MHz, $d_6$-DMSO): |
| δ = 9.2738 (1.5); 9.2529 (1.5); 5.7420 (3.3); 5.7211 (3.3); 3.3394 (10.0); 3.1617 (0.7); 2.9814 (0.4); 2.8957 (1.4); 2.8756 (0.7); 2.8624 (0.4); 2.8582 (0.5); 2.7367 (1.2); 2.5107 (21.8); 2.5064 (27.0); 2.5021 (19.7); 2.3423 (2.7); 2.2495 (2.8); 1.7701 (16.0); 1.7167 (0.4); 1.6772 (0.5); 1.6563 (15.2); 1.4766 (0.7); 1.4634 (0.7); 1.4142 (0.5); 1.4047 (0.6); 1.3744 (0.5); 1.2371 (0.4); −0.0002 (0.8) |
| I.0008: $^{1}H$-NMR(400.2 MHz, $d_6$-DMSO): |
| δ = 8.9539 (2.2); 5.7194 (0.5); 5.6942 (0.8); 5.6764 (0.8); 5.6717 (0.8); 5.6536 (0.9); 5.6514 (0.9); 5.6285 (0.7); 5.3442 (1.5); 5.3398 (1.6); 5.3013 (1.2); 5.2968 (1.2); 5.1459 (1.5); 5.1414 (1.4); 5.1203 (1.3); 5.1156 (1.4); 3.6134 (16.0); 3.3417 (15.2); 3.3372 (15.5); 2.8946 (0.5); 2.7356 (0.5); 2.5095 (14.5); 2.5054 (18.4); 2.5012 (14.0); 2.3738 (0.5); 2.3517 (1.3); 2.3299 (1.4); 2.3079 (0.6); 1.7269 (1.2); 1.7135 (1.3); 1.7068 (1.3); 1.6934 (1.2); 1.4762 (1.2); 1.4630 (1.2); 1.4526 (1.3); 1.4394 (1.0); −0.0009 (0.4) |

TABLE A-(I)-continued

| NMR peak lists of compounds according to formula (I) |
|---|
| I.0009: $^1$H-NMR(300.2 MHz, CDCl3):<br>δ = 7.3001 (1.3); 7.2981 (1.4); 6.4811 (0.9); 6.4558 (0.9); 3.9495 (0.8); 3.9353 (1.7); 3.9208 (0.9); 3.9091 (1.2); 3.8948 (2.5); 3.8806 (1.2); 3.7960 (15.7); 3.7943 (16.0); 3.7518 (1.3); 3.7432 (1.4); 3.7180 (1.5); 3.7105 (2.2); 3.6782 (1.0); 3.6696 (1.0); 2.3812 (0.9); 2.3669 (0.9); 2.3479 (0.9); 2.3341 (1.9); 2.3202 (1.2); 2.3012 (1.2); 2.2869 (1.1); 2.0805 (1.8); 2.0405 (1.4); 2.0341 (1.4); 0.0321 (1.3); 0.0301 (1.4) |
| I.0010: $^1$H-NMR(400.2 MHz, $d_6$-DMSO):<br>δ = 8.6518 (2.2); 3.6371 (16.0); 3.3717 (68.8); 2.5122 (15.2); 2.5079 (19.8); 2.5035 (15.4); 2.2420 (1.4); 2.0373 (1.4); 2.0069 (2.4); 1.9938 (1.6); 1.9761 (2.1); 1.9524 (1.9); 1.9331 (0.6) |
| I.0011: $^1$H-NMR(600.4 MHz, $d_6$-DMSO):<br>δ = 8.6128 (3.8); 4.1120 (2.3); 4.1002 (7.4); 4.0884 (7.4); 4.0766 (2.4); 3.7370 (1.2); 3.7305 (2.6); 3.7238 (1.5); 3.7173 (1.8); 3.7107 (3.5); 3.7043 (1.6); 3.5904 (1.5); 3.5832 (1.5); 3.5756 (1.8); 3.5691 (2.3); 3.5635 (1.3); 3.5561 (1.4); 3.5486 (1.2); 3.4011 (24.1); 3.3967 (29.6); 3.3898 (59.5); 3.3863 (42.4); 3.3819 (94.1); 3.3788 (160.4); 2.8962 (0.5); 2.7370 (0.4); 2.5292 (0.4); 2.5261 (0.5); 2.5230 (0.5); 2.5143 (10.0); 2.5114 (22.1); 2.5083 (31.0); 2.5052 (22.2); 2.5022 (10.1); 2.0014 (0.5); 1.9945 (0.6); 1.9849 (4.9); 1.9784 (7.0); 1.9708 (4.0); 1.9628 (2.4); 1.9471 (0.5); 1.9398 (0.4); 1.1628 (7.7); 1.1510 (16.0); 1.1392 (7.5) |
| I.0012: $^1$H-NMR(600.4 MHz, $d_6$-DMSO):<br>δ = 7.9592 (1.0); 7.9537 (1.1); 7.9469 (1.1); 7.9415 (1.0); 5.1821 (1.2); 5.1725 (2.0); 5.1626 (1.1); 4.5051 (0.8); 4.4976 (1.3); 4.4923 (1.1); 4.4904 (1.0); 4.4853 (1.4); 4.4775 (0.8); 4.1515 (2.3); 4.1397 (7.2); 4.1279 (7.4); 4.1161 (2.4); 3.8392 (0.7); 3.8305 (0.8); 3.8288 (0.8); 3.8203 (2.0); 3.8116 (1.6); 3.8100 (1.7); 3.8013 (1.3); 3.7879 (1.3); 3.7810 (1.6); 3.7790 (1.6); 3.7720 (1.5); 3.7692 (0.9); 3.7623 (0.8); 3.7601 (0.8); 3.7533 (0.7); 3.3622 (1.8); 3.3337 (8.7); 3.3313 (11.1); 3.3298 (15.5); 3.3280 (12.5); 3.3252 (24.3); 3.3242 (23.2); 3.3225 (31.3); 2.8941 (0.4); 2.5222 (0.3); 2.5104 (6.9); 2.5073 (15.3); 2.5043 (21.6); 2.5012 (15.4); 2.4982 (7.1); 1.2130 (7.7); 1.2012 (16.0); 1.1894 (7.5); −0.0002 (0.4) |
| I.0013: $^1$H-NMR(600.4 MHz, $d_6$-DMSO):<br>δ = 8.7417 (1.4); 8.7285 (1.4); 4.5568 (0.7); 4.5501 (0.8); 4.5436 (0.8); 4.5374 (1.2); 4.5319 (0.8); 4.5253 (0.8); 4.5186 (0.7); 3.3598 (2.8); 3.3433 (8.0); 3.3396 (9.9); 3.3367 (11.7); 3.3346 (13.4); 3.3304 (21.7); 3.3278 (25.9); 3.3254 (41.3); 2.8950 (1.8); 2.8270 (1.9); 2.8147 (6.2); 2.8024 (6.5); 2.7901 (2.2); 2.7361 (1.5); 2.5263 (0.3); 2.5232 (0.4); 2.5201 (0.4); 2.5114 (7.9); 2.5084 (17.7); 2.5053 (25.0); 2.5022 (17.7); 2.4991 (8.0); 1.8035 (0.6); 1.7966 (0.7); 1.7851 (0.7); 1.7813 (1.0); 1.7783 (1.0); 1.7745 (0.9); 1.7630 (0.8); 1.7560 (0.8); 1.6688 (0.4); 1.6646 (0.5); 1.6597 (0.6); 1.6529 (0.7); 1.6489 (0.7); 1.6419 (0.7); 1.6381 (0.6); 1.6312 (0.5); 1.6082 (1.2); 1.6014 (1.2); 1.5923 (0.6); 1.5859 (1.6); 1.5792 (0.9); 1.5702 (0.6); 1.5633 (0.6); 1.2392 (0.4); 1.1687 (7.5); 1.1565 (16.0); 1.1441 (7.4); 0.9097 (10.4); 0.8989 (10.4); 0.8632 (10.0); 0.8525 (10.3); −0.0002 (0.5) |
| I.0014: $^1$H-NMR(600.4 MHz, $d_6$-DMSO):<br>δ = 8.5249 (1.6); 8.5113 (1.6); 4.3663 (1.6); 4.3531 (2.4); 4.3413 (1.7); 3.3853 (2.9); 3.3505 (16.7); 3.3493 (17.1); 3.3450 (22.6); 3.3416 (37.8); 3.3404 (40.2); 3.3382 (61.0); 2.8953 (0.4); 2.8530 (2.2); 2.8407 (7.1); 2.8284 (7.2); 2.8161 (2.3); 2.7363 (0.3); 2.5269 (0.4); 2.5238 (0.4); 2.5207 (0.4); 2.5121 (8.7); 2.5090 (19.4); 2.5060 (27.2); 2.5029 (19.5); 2.4999 (8.8); 2.2708 (0.3); 2.2596 (1.0); 2.2482 (1.8); 2.2369 (1.8); 2.2256 (1.1); 2.2142 (0.4); 1.1770 (7.6); 1.1648 (16.0); 1.1525 (7.5); 0.9452 (11.0); 0.9390 (12.4); 0.9339 (11.6); 0.9277 (11.7); −0.0002 (0.4) |
| I.0015: $^1$H-NMR(600.4 MHz, $d_6$-DMSO):<br>δ = 8.7730 (1.2); 8.7639 (0.7); 7.9533 (0.4); 7.3175 (0.6); 7.3159 (0.8); 7.3132 (0.4); 7.3068 (1.4); 7.3031 (4.8); 7.2964 (5.3); 7.2925 (16.0); 7.2848 (0.9); 7.2823 (1.4); 7.2548 (1.2); 7.2511 (1.3); 7.2453 (1.4); 7.2404 (1.6); 7.2380 (0.8); 7.2349 (1.0); 7.2302 (0.8); 7.2261 (0.4); 4.1946 (5.6); 4.1847 (5.8); 4.1266 (13.5); 3.3485 (48.4); 2.8942 (3.4); 2.7366 (2.5); 2.7360 (2.7); 2.5243 (0.4); 2.5125 (6.9); 2.5095 (15.6); 2.5064 (21.8); 2.5034 (15.6); 2.5003 (6.9); −0.0002 (0.3) |
| I.0016: $^1$H-NMR(600.4 MHz, $d_6$-DMSO):<br>δ = 8.8565 (2.7); 8.8479 (1.5); 7.9531 (0.7); 7.5316 (0.3); 7.5195 (0.3); 7.5177 (0.4); 7.4858 (1.3); 7.4814 (4.5); 7.4793 (16.0); 7.4744 (15.0); 7.4684 (14.9); 7.4644 (4.1); 7.4618 (2.2); 7.4537 (0.5); 7.4515 (0.5); 7.4198 (1.0); 7.4171 (1.5); 7.4130 (9.0); 7.4105 (4.9); 7.4088 (8.2); 7.4055 (5.5); 7.4030 (8.0); 7.4008 (3.5); 7.3993 (3.6); 7.3970 (5.8); 7.3909 (0.9); 4.2942 (13.5); 4.2843 (14.0); 3.9134 (0.9); 3.9037 (1.0); 3.3608 (84.6); 2.9750 (0.7); 2.8949 (6.1); 2.8666 (0.6); 2.7365 (4.8); 2.6195 (0.4); 2.5285 (0.8); 2.5254 (0.9); 2.5223 (0.8); 2.5136 (18.0); 2.5106 (40.9); 2.5075 (57.7); 2.5044 (41.6); 2.5014 (18.8); 2.3914 (0.4); 1.2605 (0.4); 1.2379 (0.8); −0.0002 (0.8) |
| I.0017: $^1$H-NMR(400.1 MHz, $d_6$-DMSO):<br>δ = 8.6496 (0.3); 8.6281 (0.3); 8.6142 (0.4); 8.4898 (16.0); 8.4697 (15.3); 7.9520 (2.8); 7.7955 (0.4); 6.5206 (0.8); 4.8036 (6.9); 4.7843 (12.3); 4.7718 (10.2); 4.7664 (10.2); 4.7525 (12.6); 4.7340 (6.9); 4.7098 (0.4); 3.9246 (0.8); 3.5906 (0.3); 3.5414 (0.3); 3.5205 (0.4); 3.4951 (0.8); 3.4698 (5.5); 3.4563 (6.9); 3.4406 (13.8); 3.4274 (13.9); 3.4125 (11.2); 3.3989 (9.5); 3.3367 (19.3); 3.3175 (248.2); 3.2945 (13.8); 2.9511 (0.3); 2.8907 (15.6); 2.7311 (13.9); 2.6715 (1.0); 2.5543 (0.5); 2.5015 (128.0); 2.4978 (110.5); 2.4671 (11.1); 2.4512 (15.2); 2.4367 (14.4); 2.4220 (8.4); 2.3983 (5.4); 2.3808 (6.0); 2.3679 (11.2); 2.3500 (11.8); 2.3372 (10.2); 2.3193 (9.7); 2.3069 (3.7); 2.2891 (2.9); 2.2664 (0.6); 1.2362 (0.6); −0.0002 (28.5); −0.0460 (0.3) |
| I.0018: $^1$H-NMR(600.4 MHz, $d_6$-DMSO):<br>δ = 8.7315 (2.5); 4.1148 (1.4); 4.1030 (4.5); 4.0912 (4.6); 4.0794 (1.5); 3.7505 (0.8); 3.7441 (1.6); 3.7376 (0.9); 3.7309 (1.1); 3.7244 (2.2); 3.7181 (1.0); 3.5951 (0.9); 3.5872 (0.9); 3.5808 (1.1); 3.5734 (1.4); 3.5672 (0.8); 3.5615 (0.9); 3.5531 (0.8); 3.4233 (5.3); 3.3946 (26.4); 3.3911 (35.1); 3.3854 (57.1); 3.3806 (81.9); 3.3782 (118.0); 2.5281 (0.3); 2.5250 (0.4); 2.5219 (0.4); 2.5132 (8.3); 2.5102 (18.2); 2.5072 (25.5); 2.5041 (18.3); 2.5011 (8.4); 2.4158 (16.0); 2.3993 (0.6); 1.9819 (3.2); 1.9751 (4.5); 1.9682 (2.9); 1.9609 (1.6); 1.1753 (4.6); 1.1635 (9.5); 1.1517 (4.5) |
| I.0019: $^1$H-NMR(600.4 MHz, $d_6$-DMSO):<br>δ = 8.3705 (1.0); 8.3580 (1.0); 5.0904 (0.8); 5.0806 (1.6); 5.0706 (0.7); 4.4728 (0.5); 4.4644 (1.0); 4.4603 (0.6); 4.4555 (0.6); 4.4519 (1.0); 4.4430 (0.5); 4.1450 (0.6); 4.1426 (0.7); 4.1332 (2.2); 4.1308 (2.2); 4.1213 (2.3); 4.1190 (2.2); 4.1094 (0.8); 4.1072 (0.7); 3.7866 (1.2); 3.7850 (1.2); 3.7766 (2.7); 3.7672 (1.8); 3.4026 (3.4); 3.3869 (36.4); 3.3848 (65.6); 3.3834 (118.5); 2.5136 (3.9); 2.5106 (8.6); 2.5075 (12.1); 2.5045 (8.6); 2.5014 (3.9); 2.4200 (16.0); 2.4023 (0.4); 1.2141 (4.7); 1.2023 (10.0); 1.1904 (4.5) |
| I.0020: $^1$H-NMR(600.4 MHz, $d_6$-DMSO):<br>δ = 8.8434 (0.9); 8.8305 (1.0); 4.5449 (0.4); 4.5380 (0.5); 4.5319 (0.5); 4.5254 (0.7); 4.5198 (0.5); 4.5140 (0.5); 4.5069 (0.4); 3.3820 (2.4); 3.3576 (18.0); 3.3559 (18.8); 3.3535 (33.5); 3.3513 (51.6); 3.3498 (65.3); 2.8947 (0.7); 2.8343 (1.2); 2.8220 (4.0); 2.8097 (4.1); 2.7974 (1.3); 2.7356 (0.5); 2.5119 (5.1); 2.5089 (11.4); 2.5058 (15.9); 2.5027 (11.4); 2.4997 (5.1); 2.4216 (16.0); 2.4049 (0.7); 2.3948 (0.4); 1.7466 (0.4); 1.7393 (0.4); 1.7284 (0.4); 1.7245 (0.6); 1.7211 (0.6); 1.7172 (0.6); 1.7065 (0.4); 1.6991 (0.6); 1.6683 (0.4); 1.6640 (0.3); 1.6567 (0.4); 1.6531 (0.4); 1.6456 (0.4); 1.6422 (0.3); 1.6000 (0.7); 1.5928 (0.7); 1.5845 (0.4); 1.5777 (0.9); 1.5708 (0.5); 1.5624 (0.4); 1.5555 (0.4); 1.1715 (4.5); 1.1592 (9.7); 1.1469 (4.4); 0.9335 (0.3); 0.9221 (0.6); 0.9173 (6.3); 0.9064 (6.2); 0.8773 (6.0); 0.8665 (6.0); −0.0002 (0.4) |

TABLE A-(I)-continued

| NMR peak lists of compounds according to formula (I) |
|---|
| I.0021: $^1$H-NMR(600.4 MHz, $d_6$-DMSO): δ = 8.7566 (1.0); 8.7435 (1.1); 4.3511 (1.0); 4.3384 (1.6); 4.3263 (1.0); 3.3934 (2.4); 3.3674 (27.8); 3.3641 (50.5); 3.3625 (65.5); 3.3608 (94.6); 2.8557 (1.3); 2.8434 (4.1); 2.8312 (4.2); 2.8189 (1.4); 2.5121 (5.1); 2.5091 (11.3); 2.5061 (15.7); 2.5030 (11.2); 2.5000 (5.1); 2.4028 (16.0); 2.3870 (0.8); 2.2323 (0.6); 2.2209 (1.0); 2.2095 (1.0); 2.1981 (0.6); 1.1783 (4.6); 1.1660 (9.7); 1.1537 (4.5); 1.0977 (0.4); 1.0862 (0.4); 0.9530 (7.2); 0.9496 (7.1); 0.9417 (7.2); 0.9383 (6.9) |
| I.0022: $^1$H-NMR(400.1 MHz, CDCl3): δ = 7.3232 (0.6); 7.3191 (0.4); 7.3035 (2.2); 7.2886 (11.3); 7.2724 (2.1); 7.2679 (1.4); 7.2589 (2.2); 7.2506 (1.1); 7.2416 (0.4); 7.2360 (0.4); 6.4263 (0.9); 4.3708 (5.2); 4.3570 (5.1); 4.1825 (9.8); 2.5220 (16.0); 2.4930 (0.7); 1.6180 (1.5); −0.0002 (1.5) |
| I.0023: $^1$H-NMR(600.2 MHz, $d_6$-DMSO): δ = 8.6133 (3.2); 8.5995 (3.3); 4.8038 (1.5); 4.7916 (2.1); 4.7825 (1.9); 4.7783 (1.8); 4.7691 (2.2); 4.7570 (1.5); 3.4731 (1.5); 3.4641 (1.9); 3.4546 (2.8); 3.4533 (2.6); 3.4456 (2.7); 3.4443 (2.5); 3.4347 (2.7); 3.4257 (2.1); 3.3472 (2.6); 3.3371 (3.0); 3.3351 (3.0); 3.3310 (16.0); 3.3188 (2.0); 3.1775 (0.4); 3.1687 (0.4); 2.5185 (0.5); 2.5142 (3.2); 2.5112 (7.0); 2.5081 (10.2); 2.5051 (8.0); 2.5021 (3.5); 2.4979 (1.6); 2.4955 (2.0); 2.4932 (1.5); 2.4864 (2.5); 2.4844 (2.5); 2.4774 (1.6); 2.4752 (2.2); 2.4730 (1.7); 2.4658 (1.3); 2.4640 (1.2); 2.4123 (56.8); 2.3950 (0.7); 2.3179 (0.9); 2.3062 (1.2); 2.3022 (0.6); 2.2975 (2.4); 2.2856 (2.5); 2.2767 (2.3); 2.2648 (2.3); 2.2562 (0.9); 2.2445 (0.8) |
| I.0024: $^1$H-NMR(600.2 MHz, $d_6$-DMSO): δ = 9.0165 (1.0); 9.0070 (1.9); 8.9974 (1.0); 4.1576 (2.3); 4.1458 (7.1); 4.1339 (7.2); 4.1221 (2.4); 4.0211 (7.3); 4.0113 (7.3); 3.3232 (6.9); 2.5135 (2.6); 2.5106 (5.3); 2.5076 (7.2); 2.5046 (5.3); 2.5017 (2.6); 2.4188 (27.3); 2.4008 (0.7); 1.2277 (7.9); 1.2159 (16.0); 1.2040 (7.8) |
| I.0025: $^1$H-NMR(400.2 MHz, $d_6$-DMSO): δ = 8.6541 (0.7); 8.3150 (1.8); 4.0985 (1.4); 4.0808 (4.4); 4.0630 (4.4); 4.0452 (1.4); 3.4899 (0.8); 3.4739 (1.5); 3.4575 (0.8); 3.3282 (18.2); 3.3043 (0.6); 2.5920 (2.0); 2.5750 (4.3); 2.5580 (1.9); 2.5255 (0.4); 2.5206 (0.6); 2.5121 (6.8); 2.5076 (13.9); 2.5031 (18.2); 2.4984 (13.1); 2.4939 (6.3); 2.3593 (16.0); 1.2028 (4.9); 1.1850 (9.9); 1.1672 (4.7); −0.0002 (2.0) |
| I.0026: $^1$H-NMR(400.2 MHz, $d_6$-DMSO): δ = 9.2441 (2.0); 8.3149 (0.8); 4.1049 (1.4); 4.0872 (4.6); 4.0695 (4.6); 4.0517 (1.4); 3.3293 (19.3); 2.8919 (0.5); 2.7319 (0.4); 2.5207 (0.4); 2.5120 (6.1); 2.5075 (12.5); 2.5029 (16.5); 2.4983 (11.9); 2.4938 (5.8); 2.3827 (16.0); 1.4613 (1.2); 1.4491 (2.9); 1.4407 (3.3); 1.4298 (1.4); 1.2061 (1.5); 1.1951 (3.2); 1.1868 (3.2); 1.1779 (5.1); 1.1602 (10.0); 1.1424 (4.7); −0.0002 (1.7) |
| I.0027: $^1$H-NMR(300.2 MHz, CDCl3): δ = 7.2986 (15.4); 6.5162 (0.4); 6.4900 (0.4); 5.3379 (1.6); 4.7602 (1.0); 4.7456 (1.0); 4.7324 (1.0); 4.7178 (1.0); 4.3388 (0.5); 4.3259 (0.6); 4.3149 (1.4); 4.3017 (1.5); 4.2910 (1.5); 4.2779 (1.5); 4.2669 (0.6); 4.2542 (0.5); 2.5784 (14.1); 2.3733 (0.4); 2.3588 (0.5); 2.3502 (0.6); 2.3356 (0.5); 2.3272 (0.4); 2.3125 (0.4); 1.5866 (16.0); 1.3820 (3.7); 1.3582 (7.5); 1.3344 (3.6); 1.2918 (0.5); 1.0584 (5.7); 1.0355 (5.6); 1.0242 (5.9); 1.0011 (5.5); 0.0480 (0.3); 0.0372 (10.5); 0.0263 (0.4) |
| I.0028: $^1$H-NMR(400.2 MHz, $d_6$-DMSO): δ = 9.0654 (1.1); 9.0461 (1.1); 7.3237 (0.4); 7.3211 (0.6); 7.3072 (0.8); 7.3026 (2.5); 7.3009 (2.2); 7.2859 (7.4); 7.2724 (0.7); 7.2685 (1.0); 7.2626 (0.4); 7.2455 (0.8); 7.2406 (0.8); 7.2317 (0.7); 7.2286 (0.6); 7.2239 (1.0); 7.2154 (0.5); 7.2082 (0.4); 4.6428 (0.4); 4.6297 (0.5); 4.6235 (0.5); 4.6170 (0.6); 4.6104 (0.6); 4.6038 (0.5); 4.5977 (0.6); 4.5845 (0.4); 4.1499 (1.2); 4.1322 (4.0); 4.1145 (4.2); 4.0967 (1.3); 3.3304 (29.6); 3.2030 (0.7); 3.1898 (0.7); 3.1684 (1.1); 3.1554 (1.0); 3.0510 (1.1); 3.0250 (1.1); 3.0166 (0.8); 2.9906 (0.7); 2.5251 (0.4); 2.5204 (0.6); 2.5117 (8.6); 2.5072 (17.8); 2.5026 (23.5); 2.4980 (16.9); 2.4934 (8.2); 2.1939 (16.0); 1.1818 (5.0); 1.1640 (10.6); 1.1462 (4.8); −0.0002 (2.2) |
| I.0029: $^1$H-NMR(400.2 MHz, $d_6$-DMSO): δ = 9.0810 (1.5); 9.0616 (1.5); 7.9193 (9.2); 7.3075 (0.4); 7.3051 (0.5); 7.2913 (0.6); 7.2858 (3.8); 7.2790 (4.4); 7.2715 (16.0); 7.2621 (0.7); 7.2578 (1.1); 7.2265 (0.9); 7.2202 (1.0); 7.2105 (0.8); 7.2049 (1.1); 7.2005 (0.6); 7.1957 (0.5); 7.1904 (0.6); 4.6250 (0.6); 4.6106 (0.8); 4.6055 (0.7); 4.6007 (0.9); 4.5912 (0.8); 4.5863 (0.8); 4.5812 (0.9); 4.5669 (0.6); 4.1075 (1.7); 4.0898 (5.8); 4.0720 (5.9); 4.0543 (1.9); 3.3273 (20.9); 3.1620 (0.8); 3.1477 (0.9); 3.1275 (1.6); 3.1132 (1.4); 3.0633 (1.6); 3.0389 (1.6); 3.0289 (0.9); 3.0045 (0.9); 2.5252 (0.6); 2.5206 (0.9); 2.5118 (13.7); 2.5073 (28.4); 2.5027 (37.3); 2.4981 (26.1); 2.4935 (12.1); 1.2388 (0.4); 1.1355 (6.7); 1.1178 (14.3); 1.1000 (6.4); −0.0002 (3.5) |
| I.0030: $^1$H-NMR(400.2 MHz, $d_6$-DMSO): δ = 9.0765 (1.5); 9.0570 (1.5); 7.8079 (4.9); 7.8064 (4.9); 7.3030 (0.4); 7.3004 (0.5); 7.2867 (0.6); 7.2814 (3.8); 7.2804 (3.6); 7.2747 (4.4); 7.2670 (16.0); 7.2578 (0.7); 7.2535 (1.0); 7.2240 (0.9); 7.2178 (1.0); 7.2158 (0.8); 7.2074 (0.8); 7.2024 (1.1); 7.1980 (0.6); 7.1930 (0.5); 7.1881 (0.6); 4.6272 (0.6); 4.6127 (0.7); 4.6077 (0.7); 4.6031 (0.9); 4.5932 (0.8); 4.5885 (0.8); 4.5836 (0.8); 4.5690 (0.6); 4.1078 (1.7); 4.0901 (5.6); 4.0724 (5.8); 4.0547 (1.8); 3.3283 (22.0); 3.1640 (0.8); 3.1495 (0.9); 3.1296 (1.6); 3.1152 (1.4); 3.0666 (1.6); 3.0423 (1.5); 3.0322 (0.9); 3.0080 (0.8); 2.5252 (0.6); 2.5205 (0.8); 2.5118 (11.5); 2.5073 (24.0); 2.5027 (31.8); 2.4980 (22.4); 2.4934 (10.4); 1.2403 (0.4); 1.1345 (6.6); 1.1168 (14.3); 1.0990 (6.4); −0.0002 (2.7) |
| I.0031: $^1$H-NMR(400.2 MHz, $d_6$-DMSO): δ = 8.9176 (1.2); 8.8981 (1.2); 7.6692 (5.2); 7.2794 (5.2); 7.2679 (14.0); 7.2565 (0.7); 7.2201 (0.8); 7.2118 (0.7); 7.2092 (1.0); 7.1985 (1.1); 7.1918 (0.4); 7.1862 (0.6); 4.6023 (0.5); 4.5881 (0.6); 4.5828 (0.6); 4.5779 (0.8); 4.5686 (0.7); 4.5637 (0.6); 4.5584 (0.7); 4.5441 (0.5); 4.1027 (1.3); 4.0850 (4.4); 4.0673 (4.6); 4.0496 (1.5); 3.3282 (13.6); 3.1503 (0.6); 3.1361 (0.7); 3.1158 (1.4); 3.1017 (1.3); 3.0710 (1.4); 3.0465 (1.4); 3.0366 (0.7); 3.0121 (0.7); 2.5246 (0.4); 2.5199 (0.5); 2.5113 (8.2); 2.5068 (16.9); 2.5022 (22.1); 2.4976 (15.5); 2.4930 (7.2); 2.1645 (16.0); 1.1363 (5.5); 1.1186 (11.8); 1.1008 (5.3); −0.0002 (1.8) |
| I.0032: $^1$H-NMR(400.2 MHz, $d_6$-DMSO): δ = 8.5309 (1.9); 3.5921 (16.0); 3.3272 (11.5); 2.6240 (6.7); 2.5119 (13.0); 2.5075 (19.7); 2.5030 (22.2); 2.4984 (15.2); 2.4940 (6.9); 2.3358 (3.6); 2.3302 (15.5); 2.3146 (0.6); 0.8399 (0.6); 0.8151 (3.7); 0.7991 (3.2); 0.7948 (3.7); 0.7690 (0.4); 0.0056 (0.6); −0.0002 (3.6) |
| I.0033: $^1$H-NMR(400.2 MHz, $d_6$-DMSO): δ = 8.2556 (0.4); 8.2421 (0.8); 8.2283 (0.4); 4.0951 (1.4); 4.0774 (4.6); 4.0596 (4.6); 4.0419 (1.4); 3.4963 (3.2); 3.4822 (3.2); 3.3338 (38.3); 2.5209 (0.4); 2.5123 (5.6); 2.5078 (11.7); 2.5032 (15.7); 2.4985 (11.4); 2.4939 (5.5); 2.3640 (0.6); 2.3580 (16.0); 2.3415 (0.6); 1.1925 (4.8); 1.1748 (10.0); 1.1570 (4.6); 1.0994 (0.9); 1.0881 (2.2); 1.0808 (3.1); 1.0720 (1.3); 0.9766 (1.4); 0.9675 (3.1); 0.9602 (2.3); 0.9487 (0.9) |
| I.0034: $^1$H-NMR(400.2 MHz, $d_6$-DMSO): δ = 9.4383 (2.0); 4.8810 (3.6); 4.8639 (4.1); 4.6661 (4.0); 4.6491 (3.5); 4.2169 (1.3); 4.1992 (4.3); 4.1814 (4.3); 4.1637 (1.4); 3.3340 (29.4); 2.5210 (0.3); 2.5123 (4.8); 2.5078 (9.9); 2.5032 (13.0); 2.4986 (9.4); 2.4941 (4.4); 2.4247 (16.0); 1.2200 (4.5); 1.2023 (9.4); 1.1845 (4.4) |
| I.0035: $^1$H-NMR(400.2 MHz, $d_6$-DMSO): δ = 9.4328 (1.7); 3.6933 (16.0); 3.6634 (4.3); 3.4378 (4.0); 3.4115 (3.3); 3.3330 (21.4); 2.8921 (0.7); 2.7332 (0.5); 2.7322 (0.6); 2.5124 (4.6); 2.5080 (9.4); 2.5034 (12.5); 2.4987 (9.0); 2.4942 (4.3); 2.4640 (0.4); 2.4121 (14.8); 2.3942 (0.5) |

TABLE A-(I)-continued

NMR peak lists of compounds according to formula (I)

I.0036: $^1$H-NMR(400.2 MHz, $d_6$-DMSO):
δ = 8.6362 (1.1); 8.6171 (1.2); 7.4592 (0.9); 7.0100 (1.0); 4.7170 (0.5); 4.7031 (0.6); 4.6984 (1.1); 4.6844 (1.0); 4.6796 (0.7); 4.6657 (0.5); 4.1318 (1.3); 4.1141 (4.1); 4.0963 (4.2); 4.0786 (1.3); 3.3336 (22.7); 2.7101 (0.6); 2.6963 (0.6); 2.6711 (1.6); 2.6574 (1.4); 2.6375 (1.5); 2.6190 (1.5); 2.5984 (0.6); 2.5800 (0.6); 2.5126 (4.5); 2.5081 (9.2); 2.5035 (12.2); 2.4989 (8.8); 2.4944 (4.2); 2.3945 (16.0); 1.1969 (4.8); 1.1791 (9.9); 1.1614 (4.6)
I.0037: $^1$H-NMR(400.2 MHz, $d_6$-DMSO):
δ = 8.2416 (1.8); 4.1253 (1.4); 4.1076 (4.4); 4.0898 (4.4); 4.0721 (1.4); 3.3365 (29.4); 2.5215 (0.4); 2.5128 (5.4); 2.5083 (11.0); 2.5038 (14.4); 2.4991 (10.3); 2.4946 (4.8); 2.3990 (0.3); 2.3470 (16.0); 2.3312 (0.4); 1.2320 (4.7); 1.2143 (9.7); 1.1965 (4.5); 1.0594 (0.4); 1.0437 (1.7); 1.0364 (4.0); 1.0311 (2.0); 1.0182 (2.1); 1.0134 (4.1); 1.0060 (1.7); 0.9904 (0.4); 0.9057 (0.8); 0.8915 (2.3); 0.8869 (2.4); 0.8740 (1.1); 0.7291 (1.2); 0.7160 (2.3); 0.7115 (2.4); 0.6972 (0.8)
I.0038: $^1$H-NMR(400.2 MHz, $d_6$-DMSO):
δ = 8.9411 (1.0); 8.9214 (1.0); 4.7065 (0.4); 4.6968 (0.4); 4.6821 (0.6); 4.6770 (0.5); 4.6726 (0.5); 4.6625 (0.4); 4.6525 (0.4); 4.1815 (0.6); 4.1761 (0.7); 4.1730 (0.3); 4.1637 (2.0); 4.1584 (2.0); 4.1458 (2.1); 4.1407 (2.0); 4.1312 (0.3); 4.1281 (0.7); 4.1231 (0.6); 3.3376 (39.2); 2.9265 (0.8); 2.9166 (0.4); 2.8984 (1.1); 2.8885 (0.5); 2.8715 (0.8); 2.8601 (0.3); 2.8463 (0.5); 2.5219 (0.3); 2.5133 (5.0); 2.5088 (10.2); 2.5042 (13.5); 2.4996 (9.7); 2.4950 (4.6); 2.3998 (16.0); 2.3825 (0.8); 1.2173 (4.6); 1.1996 (9.7); 1.1818 (4.5)
I.0039: $^1$H-NMR(400.2 MHz, $d_6$-DMSO):
δ = 8.5106 (1.7); 3.5918 (16.0); 3.3273 (6.4); 2.8919 (0.4); 2.7332 (0.4); 2.7320 (0.4); 2.6230 (6.2); 2.5209 (0.4); 2.5122 (5.8); 2.5077 (11.6); 2.5031 (15.4); 2.4985 (11.3); 2.4940 (5.6); 2.3322 (15.6); 0.8396 (0.4); 0.8142 (2.9); 0.8100 (2.1); 0.7982 (2.1); 0.7937 (2.9); 0.7680 (0.4); −0.0002 (5.0)
I.0040: $^1$H-NMR(400.2 MHz, $d_6$-DMSO):
δ = 8.2322 (0.4); 8.2186 (0.8); 8.2049 (0.4); 4.0948 (1.4); 4.0770 (4.6); 4.0593 (4.6); 4.0415 (1.5); 3.4951 (3.4); 3.4810 (3.4); 3.3350 (32.0); 2.5210 (0.3); 2.5125 (4.7); 2.5080 (9.8); 2.5034 (13.2); 2.4988 (9.6); 2.4942 (4.7); 2.3589 (16.0); 1.1921 (4.8); 1.1744 (9.9); 1.1566 (4.7); 1.0983 (0.9); 1.0871 (2.4); 1.0797 (3.2); 1.0709 (1.4); 0.9752 (1.4); 0.9661 (3.2); 0.9587 (2.4); 0.9473 (1.0)
I.0041: $^1$H-NMR(400.2 MHz, $d_6$-DMSO):
δ = 9.4188 (2.0); 4.8801 (3.7); 4.8630 (4.3); 4.6660 (4.2); 4.6490 (3.6); 4.2161 (1.4); 4.1984 (4.4); 4.1806 (4.4); 4.1629 (1.4); 3.3345 (29.6); 2.5124 (4.8); 2.5079 (9.8); 2.5034 (12.9); 2.4988 (9.3); 2.4943 (4.4); 2.4221 (16.0); 1.2190 (4.6); 1.2013 (9.6); 1.1836 (4.5)
I.0042: $^1$H-NMR(400.2 MHz, $d_6$-DMSO):
δ = 9.4108 (1.8); 3.6920 (16.0); 3.6879 (4.6); 3.6614 (4.6); 3.4396 (4.1); 3.4134 (3.4); 3.3326 (22.2); 2.8920 (1.5); 2.7331 (1.2); 2.7321 (1.3); 2.5209 (0.4); 2.5123 (5.0); 2.5079 (10.3); 2.5033 (13.6); 2.4987 (9.8); 2.4942 (4.7); 2.4601 (0.4); 2.4093 (14.7)
I.0043: $^1$H-NMR(400.2 MHz, $d_6$-DMSO):
δ = 8.6127 (1.2); 8.5935 (1.2); 7.4591 (1.0); 7.0099 (1.0); 4.7153 (0.5); 4.7014 (0.6); 4.6968 (1.1); 4.6827 (1.0); 4.6780 (0.8); 4.6641 (0.5); 4.1310 (1.3); 4.1133 (4.1); 4.0956 (4.2); 4.0778 (1.3); 3.3330 (26.3); 2.8919 (0.4); 2.7092 (0.6); 2.6954 (0.6); 2.6702 (1.6); 2.6565 (1.4); 2.6377 (1.5); 2.6192 (1.5); 2.5986 (0.6); 2.5803 (0.6); 2.5212 (0.3); 2.5124 (4.9); 2.5080 (10.1); 2.5034 (13.4); 2.4988 (9.7); 2.4943 (4.6); 2.3941 (16.0); 1.1961 (4.8); 1.1784 (9.9); 1.1606 (4.5)
I.0044: $^1$H-NMR(400.2 MHz, $d_6$-DMSO):
δ = 8.2117 (1.9); 4.1250 (1.4); 4.1073 (4.4); 4.0895 (4.4); 4.0718 (1.4); 3.3377 (41.8); 2.5216 (0.4); 2.5129 (5.4); 2.5084 (11.2); 2.5038 (14.9); 2.4992 (10.7); 2.4947 (5.1); 2.3471 (16.0); 1.2315 (4.7); 1.2138 (9.8); 1.1960 (4.6); 1.0589 (0.4); 1.0431 (1.7); 1.0358 (4.1); 1.0306 (2.1); 1.0179 (2.1); 1.0131 (4.1); 1.0058 (1.7); 0.9901 (0.4); 0.9054 (0.8); 0.8912 (2.3); 0.8867 (2.4); 0.8737 (1.1); 0.7281 (1.2); 0.7149 (2.3); 0.7105 (2.4); 0.6961 (0.8)
I.0045: $^1$H-NMR(400.2 MHz, $d_6$-DMSO):
δ = 8.9211 (1.0); 8.9013 (1.1); 4.7049 (0.4); 4.6951 (0.4); 4.6805 (0.6); 4.6753 (0.5); 4.6710 (0.5); 4.6608 (0.4); 4.6508 (0.4); 4.1807 (0.6); 4.1753 (0.7); 4.1722 (0.3); 4.1629 (2.1); 4.1576 (2.1); 4.1451 (2.2); 4.1399 (2.0); 4.1272 (0.7); 4.1223 (0.6); 3.3381 (37.0); 2.9539 (0.3); 2.9258 (0.8); 2.9157 (0.5); 2.8982 (1.0); 2.8931 (0.5); 2.8877 (0.5); 2.8720 (0.8); 2.8600 (0.4); 2.8468 (0.5); 2.5219 (0.3); 2.5132 (4.7); 2.5087 (9.9); 2.5041 (13.2); 2.4995 (9.6); 2.4950 (4.6); 2.3993 (16.0); 1.2164 (4.7); 1.1986 (9.7); 1.1809 (4.5)
I.0046: $^1$H-NMR(400.2 MHz, $d_6$-DMSO):
δ = 9.2995 (2.4); 4.8520 (5.5); 4.8346 (6.6); 4.6951 (6.4); 4.6778 (5.4); 4.2211 (2.2); 4.2034 (7.0); 4.1857 (7.1); 4.1680 (2.2); 3.3333 (30.4); 2.8933 (1.0); 2.7346 (0.8); 2.7334 (0.8); 2.5222 (0.4); 2.5136 (6.1); 2.5091 (12.6); 2.5044 (16.9); 2.4998 (12.2); 2.4953 (5.8); 1.2215 (7.6); 1.2038 (16.0); 1.1861 (7.4); −0.0002 (0.4)
I.0047: $^1$H-NMR(400.2 MHz, $d_6$-DMSO):
δ = 9.3048 (1.6); 7.9534 (0.7); 3.6908 (16.0); 3.6826 (0.4); 3.6587 (3.5); 3.6324 (4.4); 3.5033 (4.4); 3.4769 (3.1); 3.3328 (21.4); 2.8932 (5.1); 2.7342 (4.3); 2.7330 (4.2); 2.5220 (0.4); 2.5134 (5.2); 2.5089 (10.5); 2.5043 (13.9); 2.4997 (10.0); 2.4952 (4.7); −0.0002 (0.4)
I.0048: $^1$H-NMR(400.2 MHz, $d_6$-DMSO):
δ = 8.4804 (1.0); 8.4718 (1.0); 8.4608 (1.1); 8.4522 (1.0); 7.5123 (1.6); 7.0377 (1.6); 4.7728 (0.6); 4.7585 (1.4); 4.7394 (1.5); 4.7249 (0.6); 4.1315 (1.1); 4.1279 (1.2); 4.1230 (0.4); 4.1137 (3.6); 4.1103 (3.7); 4.0958 (3.8); 4.0926 (3.6); 4.0832 (0.4); 4.0780 (1.3); 4.0751 (1.1); 3.3360 (42.6); 2.8931 (0.8); 2.7342 (0.8); 2.6943 (4.6); 2.6797 (4.8); 2.5271 (0.4); 2.5223 (0.5); 2.5136 (7.5); 2.5092 (15.3); 2.5046 (20.4); 2.5000 (14.7); 2.4955 (7.0); 1.1888 (7.7); 1.1710 (16.0); 1.1533 (7.4); −0.0002 (0.4)
I.0049: $^1$H-NMR(400.2 MHz, $d_6$-DMSO):
δ = 7.8439 (1.2); 7.8327 (1.2); 4.1375 (1.7); 4.1197 (5.4); 4.1020 (5.4); 4.0842 (1.7); 3.3360 (44.2); 2.5227 (0.4); 2.5141 (7.2); 2.5097 (14.6); 2.5051 (19.3); 2.5005 (13.9); 2.4960 (6.6); 1.2416 (5.5); 1.2239 (11.3); 1.2061 (5.3); 1.0186 (16.0); 0.9419 (1.1); 0.9277 (3.0); 0.9232 (3.2); 0.9102 (1.4); 0.7539 (1.4); 0.7406 (3.0); 0.7364 (3.1); 0.7219 (1.1); −0.0002 (0.4)
I.0050: $^1$H-NMR(400.2 MHz, $d_6$-DMSO):
δ = 8.7773 (1.1); 8.7571 (1.1); 4.7826 (0.6); 4.7689 (0.7); 4.7623 (1.2); 4.7489 (1.2); 4.7423 (0.8); 4.7284 (0.6); 4.1758 (2.1); 4.1581 (6.8); 4.1403 (6.8); 4.1226 (2.2); 3.3415 (50.2); 2.9746 (0.6); 2.9624 (0.3); 2.9474 (1.7); 2.9347 (0.9); 2.9253 (1.2); 2.9199 (1.9); 2.9069 (1.0); 2.8985 (1.0); 2.8926 (0.7); 2.8791 (0.3); 2.8713 (0.3); 2.5283 (0.3); 2.5235 (0.5); 2.5149 (7.4); 2.5104 (15.1); 2.5059 (20.0); 2.5013 (14.4); 2.4967 (6.8); 1.2107 (7.7); 1.1929 (16.0); 1.1752 (7.4); −0.0002 (0.3)
I.0051: $^1$H-NMR(400.1 MHz, CDCl3):
δ = 7.3232 (1.8); 7.3066 (5.8); 7.2885 (6.1); 7.2823 (3.2); 7.2779 (3.8); 7.2594 (13.4); 7.2427 (0.7); 7.1512 (6.2); 7.1345 (5.2); 6.7265 (1.0); 6.7106 (1.7); 6.6934 (1.0); 4.9849 (0.8); 4.9701 (2.3); 4.9548 (2.3); 4.9394 (0.8); 4.2274 (2.2); 4.2096 (6.7); 4.1918 (6.8); 4.1740 (2.4); 3.2539 (0.4); 3.2393 (0.4); 3.2187 (4.6); 3.2135 (4.8); 3.2045 (4.7); 3.1990 (4.5); 3.1788 (0.4); 3.1642 (0.4); 1.5464 (11.2); 1.2734 (8.0); 1.2556 (16.0); 1.2378 (7.8); −0.0002 (11.7)
I.0052: $^1$H-NMR(600.1 MHz, $d_6$-DMSO):
δ = 9.4533 (0.8); 9.4436 (1.5); 9.4339 (0.8); 8.0258 (7.9); 4.1485 (1.7); 4.1366 (5.4); 4.1248 (5.4); 4.1130 (1.8); 4.0528 (5.6); 4.0430 (5.6); 3.3363 (6.0); 3.3288 (14.9); 3.3259 (16.0); 2.8927 (0.4); 2.5068 (9.3); 2.5040 (12.5); 2.5010 (9.0); 1.2382 (0.4); 1.2176 (5.8); 1.2057 (11.9); 1.1939 (5.7)

TABLE A-(I)-continued

| NMR peak lists of compounds according to formula (I) |
|---|
| I.0053: $^{1}$H-NMR(499.9 MHz, $d_6$-DMSO):<br>δ = 9.5010 (5.3); 7.9668 (10.7); 4.0897 (2.5); 4.0756 (7.6); 4.0614 (7.6); 4.0473 (2.5); 3.3405 (255.5); 2.5046 (6.4); 2.5013 (8.8); 2.4981 (7.2); 1.4835 (2.3); 1.4738 (6.2); 1.4674 (7.0); 1.4586 (2.9); 1.2285 (0.4); 1.2259 (0.4); 1.1932 (2.7); 1.1842 (6.5); 1.1779 (6.9); 1.1682 (2.6); 1.1475 (7.9); 1.1333 (16.0); 1.1192 (7.8) |
| I.0054: $^{1}$H-NMR(600.1 MHz, $d_6$-DMSO):<br>δ = 8.2875 (1.4); 4.2854 (0.4); 4.1624 (0.4); 4.1506 (0.5); 4.1391 (0.5); 4.1273 (0.4); 3.3530 (10.0); 3.3507 (16.0); 2.5147 (1.0); 2.5118 (2.2); 2.5088 (3.0); 2.5058 (2.2); 2.5029 (1.0); 1.2192 (1.0); 1.2073 (2.1); 1.1955 (1.0); 0.9819 (1.5); 0.9706 (1.4); 0.9478 (1.4); 0.9364 (1.4) |
| I.0055: $^{1}$H-NMR(600.1 MHz, $d_6$-DMSO):<br>δ = 9.3437 (0.5); 9.3307 (0.6); 8.0727 (2.4); 7.2834 (1.4); 7.2776 (1.4); 7.2734 (4.4); 7.2179 (0.3); 7.2121 (0.4); 7.2076 (0.4); 4.1085 (0.5); 4.0967 (1.6); 4.0849 (1.6); 4.0730 (0.5); 3.3335 (3.6); 3.3302 (13.0); 3.3287 (16.0); 3.1673 (0.3); 3.1537 (0.5); 3.1443 (0.4); 3.0700 (0.5); 3.0536 (0.5); 3.0469 (0.3); 2.8919 (0.9); 2.7334 (0.8); 2.5065 (4.8); 2.5035 (6.4); 2.5005 (4.4); 1.1352 (1.8); 1.1233 (3.6); 1.1115 (1.7) |
| I.0056: $^{1}$H-NMR(300.2 MHz, CDCl3):<br>δ = 7.2989 (2.0); 7.0022 (1.2); 5.0969 (0.4); 5.0761 (1.0); 5.0552 (1.4); 5.0344 (1.1); 5.0136 (0.4); 2.5167 (15.9); 1.6651 (2.1); 1.2761 (16.0); 1.2552 (15.8); 1.2257 (0.9); 1.2088 (2.3); 1.1995 (3.5); 1.1880 (1.6); 1.1564 (0.4); 1.1386 (0.4); 1.1072 (1.6); 1.0956 (3.4); 1.0861 (2.3); 1.0799 (1.2); 1.0704 (1.7); 1.0501 (3.1); 1.0467 (3.2); 1.0278 (1.4); 0.7995 (1.3); 0.7801 (3.2); 0.7561 (1.0); 0.0326 (2.5) |
| I.0057: $^{1}$H-NMR(300.2 MHz, CDCl3):<br>δ = 7.2988 (2.6); 6.9966 (1.0); 5.0979 (0.4); 5.0771 (1.0); 5.0562 (1.4); 5.0354 (1.0); 5.0146 (0.4); 3.5231 (0.7); 2.5130 (16.0); 1.6629 (1.2); 1.2766 (15.9); 1.2557 (15.7); 1.2257 (0.8); 1.2156 (1.0); 1.2089 (2.1); 1.1994 (3.2); 1.1880 (1.4); 1.1569 (0.4); 1.1387 (0.4); 1.1079 (1.5); 1.0962 (3.1); 1.0867 (2.1); 1.0801 (1.0); 1.0708 (1.5); 1.0516 (2.5); 1.0471 (2.8); 1.0284 (1.3); 0.7999 (1.2); 0.7808 (2.6); 0.7766 (2.6); 0.7565 (0.9); 0.0332 (3.3) |
| I.0058: $^{1}$H-NMR(300.2 MHz, CDCl3):<br>δ = 7.3871 (0.6); 7.3629 (0.6); 7.2984 (2.0); 5.1294 (0.4); 5.1086 (1.0); 5.0878 (1.4); 5.0670 (1.1); 5.0462 (0.4); 1.6620 (2.2); 1.3099 (16.0); 1.2891 (16.0); 1.2174 (0.9); 1.2010 (2.3); 1.1915 (3.6); 1.1797 (1.5); 1.1356 (0.4); 1.1294 (0.4); 1.0855 (1.7); 1.0739 (4.1); 1.0636 (2.9); 1.0579 (3.8); 1.0520 (3.5); 1.0332 (1.4); 0.8124 (1.4); 0.7931 (3.0); 0.7891 (2.9); 0.7688 (1.0); 0.0317 (2.5) |
| I.0059: $^{1}$H-NMR(500.1 MHz, $d_6$-DMSO):<br>δ = 10.5634 (2.8); 4.4705 (16.0); 4.1716 (2.3); 4.1574 (7.1); 4.1432 (7.2); 4.1290 (2.4); 3.3083 (14.7); 2.5039 (7.1); 2.5005 (9.8); 2.4971 (7.2); 1.2287 (7.6); 1.2145 (15.3); 1.2003 (7.4); −0.0002 (5.9) |
| I.0060: $^{1}$H-NMR(400.2 MHz, $d_6$-DMSO):<br>δ = 8.6585 (7.7); 8.6541 (7.7); 8.6385 (7.7); 8.6342 (7.6); 8.3145 (0.4); 7.9537 (2.0); 7.7839 (0.4); 4.7999 (4.9); 4.7771 (7.9); 4.7736 (7.6); 4.7560 (7.1); 4.7526 (8.6); 4.7296 (5.2); 4.4099 (5.3); 4.4055 (5.8); 4.3880 (14.2); 4.3833 (13.6); 4.3660 (8.4); 4.3613 (7.0); 4.2892 (6.5); 4.2725 (8.5); 4.2674 (6.9); 4.2632 (9.0); 4.2505 (6.6); 4.2464 (8.7); 4.2415 (7.6); 4.2247 (5.1); 4.0284 (0.4); 4.0120 (0.8); 3.9956 (0.4); 3.3490 (0.4); 3.3292 (112.8); 2.8931 (16.0); 2.7343 (13.0); 2.7333 (13.2); 2.7119 (0.7); 2.6957 (0.4); 2.6824 (0.3); 2.6779 (0.7); 2.6734 (0.9); 2.6688 (0.7); 2.5914 (0.5); 2.5748 (0.8); 2.5584 (0.4); 2.5269 (2.7); 2.5222 (3.8); 2.5135 (54.9); 2.5090 (112.1); 2.5045 (146.8); 2.4998 (104.4); 2.4953 (49.5); 2.4782 (2.5); 2.4734 (2.7); 2.4615 (3.0); 2.4559 (4.0); 2.4486 (6.4); 2.4434 (5.5); 2.4384 (3.9); 2.4319 (6.5); 2.4257 (6.9); 2.4202 (5.2); 2.4082 (4.8); 2.4025 (6.4); 2.3789 (5.8); 2.3753 (8.0); 2.3522 (8.7); 2.3490 (7.8); 2.3459 (6.0); 2.3359 (1.2); 2.3257 (5.4); 2.3228 (5.2); 2.3187 (3.4); 2.3068 (0.4); 2.2960 (2.0); 1.2996 (0.6); 1.2876 (0.4); 1.2692 (0.6); 1.2597 (1.1); 1.2382 (5.0); 0.8697 (0.4); 0.8534 (1.4); 0.8360 (0.5); 0.0080 (0.4); −0.0002 (15.9); −0.0084 (0.5) |
| I.0061: $^{1}$H-NMR(400.2 MHz, $d_6$-DMSO):<br>δ = 8.3055 (1.2); 8.3031 (1.3); 8.3018 (1.3); 8.1843 (5.5); 8.1753 (5.7); 8.1667 (5.7); 7.9529 (1.0); 7.6943 (12.3); 4.2908 (2.0); 4.2756 (5.5); 4.2635 (3.9); 4.2572 (5.8); 4.2492 (4.5); 4.2308 (3.1); 4.0281 (0.4); 4.0117 (0.8); 3.9952 (0.4); 3.3422 (81.3); 3.3398 (79.1); 3.3303 (93.5); 3.1624 (10.9); 3.1524 (14.5); 3.1471 (14.2); 2.8961 (6.3); 2.7374 (5.3); 2.7124 (0.8); 2.6955 (0.4); 2.6798 (0.6); 2.6752 (0.9); 2.6706 (0.6); 2.5886 (0.4); 2.5721 (0.7); 2.5287 (2.3); 2.5240 (3.4); 2.5153 (53.7); 2.5108 (112.3); 2.5063 (149.2); 2.5016 (107.3); 2.4971 (51.7); 2.3421 (0.3); 2.3376 (0.7); 2.3330 (0.9); 2.3284 (0.7); 2.3241 (0.4); 2.0813 (2.6); 2.0700 (3.0); 2.0543 (5.8); 2.0082 (0.5); 1.8701 (1.4); 1.8610 (2.5); 1.8385 (7.7); 1.8302 (6.9); 1.8084 (16.0); 1.7886 (6.7); 1.7816 (7.8); 1.7700 (3.2); 1.7644 (3.2); 1.7563 (3.0); 1.7451 (1.7); 1.7378 (1.8); 1.7234 (0.8); 1.7129 (0.4); 1.7051 (0.5); 1.2998 (0.6); 1.2721 (0.7); 1.2618 (1.1); 1.2394 (5.3); 0.8716 (0.5); 0.8549 (1.5); 0.8373 (0.6); 0.0079 (0.5); −0.0002 (16.6); −0.0086 (0.5) |
| I.0062: $^{1}$H-NMR(300.2 MHz, CDCl3):<br>δ = 7.2989 (9.0); 6.7162 (0.5); 6.6914 (0.9); 6.6689 (0.6); 4.8157 (0.5); 4.8073 (0.4); 4.7930 (1.0); 4.7874 (1.1); 4.7751 (0.8); 4.7699 (0.7); 4.7659 (0.8); 4.7603 (0.7); 4.7483 (0.4); 4.2982 (2.3); 4.2744 (7.3); 4.2506 (7.4); 4.2269 (2.4); 1.8078 (1.0); 1.7900 (1.2); 1.7780 (1.6); 1.7658 (1.5); 1.7572 (2.6); 1.7492 (1.5); 1.7359 (1.8); 1.7237 (1.0); 1.7139 (1.8); 1.6980 (0.4); 1.6875 (1.2); 1.6821 (1.0); 1.6582 (0.9); 1.6022 (14.0); 1.3593 (7.9); 1.3356 (16.0); 1.3118 (7.7); 1.2920 (0.7); 1.0258 (8.4); 1.0186 (10.6); 1.0054 (9.6); 0.9981 (8.5); 0.0474 (0.3); 0.0366 (10.2); 0.0257 (0.4) |
| I.0063: $^{1}$H-NMR(400.2 MHz, $d_6$-DMSO):<br>δ = 8.6745 (0.5); 8.6602 (0.9); 8.6457 (0.5); 4.1527 (1.4); 4.1349 (4.4); 4.1171 (4.4); 4.0994 (1.4); 3.9754 (4.2); 3.9607 (4.1); 3.3320 (7.2); 2.5132 (3.4); 2.5087 (7.0); 2.5041 (9.2); 2.4995 (6.6); 2.4950 (3.2); 2.4238 (16.0); 2.4050 (0.9); 1.2254 (5.0); 1.2077 (10.0); 1.1899 (4.8) |
| I.0064: $^{1}$H-NMR(400.2 MHz, $d_6$-DMSO):<br>δ = 8.3299 (0.4); 8.3167 (0.8); 8.3038 (0.4); 4.0957 (1.4); 4.0779 (4.5); 4.0601 (4.5); 4.0423 (1.5); 3.4716 (0.9); 3.4545 (2.2); 3.4404 (2.2); 3.4234 (1.0); 3.3299 (7.5); 2.5735 (2.0); 2.5564 (4.2); 2.5392 (1.8); 2.5134 (3.7); 2.5089 (7.6); 2.5043 (10.0); 2.4997 (7.2); 2.4952 (3.4); 2.3705 (16.0); 2.3530 (0.9); 1.2011 (5.1); 1.1833 (10.3); 1.1655 (4.9) |
| I.0065: $^{1}$H-NMR(400.2 MHz, $d_6$-DMSO):<br>δ = 8.9172 (2.1); 4.0941 (1.4); 4.0764 (4.6); 4.0586 (4.7); 4.0409 (1.5); 3.3292 (8.1); 2.5214 (0.3); 2.5127 (4.2); 2.5082 (8.4); 2.5037 (10.9); 2.4990 (7.8); 2.4945 (3.6); 2.3881 (16.0); 2.3700 (0.9); 1.4417 (1.2); 1.4297 (3.0); 1.4214 (3.2); 1.4105 (1.3); 1.1708 (5.5); 1.1622 (3.3); 1.1532 (12.3); 1.1416 (1.3); 1.1353 (4.8) |
| I.0066: $^{1}$H-NMR(400.2 MHz, $d_6$-DMSO):<br>δ = 9.0462 (1.7); 4.1255 (1.4); 4.1078 (4.4); 4.0900 (4.5); 4.0723 (1.4); 3.3292 (8.7); 2.5752 (0.5); 2.5595 (0.6); 2.5537 (1.0); 2.5487 (0.6); 2.5468 (0.6); 2.5426 (0.9); 2.5381 (0.8); 2.5281 (1.1); 2.5207 (1.1); 2.5127 (4.3); 2.5081 (8.6); 2.5036 (10.8); 2.4989 (7.6); 2.4944 (3.6); 2.3942 (16.0); 2.3774 (0.9); 2.3061 (0.5); 2.2866 (0.9); 2.2832 (1.1); 2.2635 (0.8); 2.2539 (1.0); 2.2317 (0.6); 1.9719 (0.4); 1.9676 (0.5); 1.9593 (0.5); 1.9509 (0.8); 1.9445 (0.9); 1.9371 (0.4); 1.9302 (1.2); 1.9220 (0.5); 1.9087 (0.6); 1.1823 (4.7); 1.1646 (9.8); 1.1469 (4.6) |

TABLE A-(I)-continued

NMR peak lists of compounds according to formula (I)

I.0067: $^{1}$H-NMR(400.2 MHz, $d_6$-DMSO):
δ = 8.5626 (1.0); 8.5434 (1.0); 4.2164 (1.3); 4.2066 (0.3); 4.1988 (1.7); 4.1976 (1.8); 4.1890 (0.8); 4.1799 (1.8); 4.1712 (0.8); 4.1619 (1.7); 4.1442 (2.2); 4.1267 (2.2); 4.1091 (1.7); 4.0997 (0.7); 4.0913 (0.5); 4.0820 (0.7); 3.3269 (11.1); 2.8920 (1.0); 2.7324 (0.8); 2.5205 (0.4); 2.5119 (5.6); 2.5075 (11.4); 2.5029 (14.8); 2.4983 (10.7); 2.4939 (5.2); 2.3854 (16.0); 2.3697 (0.9); 2.1786 (0.6); 2.1616 (1.0); 2.1446 (1.0); 2.1276 (0.6); 1.2223 (4.8); 1.2045 (9.8); 1.1868 (4.7); 0.9684 (6.4); 0.9505 (9.7); 0.9324 (6.0)

I.0068: $^{1}$H-NMR(400.2 MHz, $d_6$-DMSO):
δ = 8.8018 (1.0); 8.7825 (1.1); 6.3296 (0.5); 6.2007 (0.5); 6.1895 (0.9); 6.1781 (0.4); 6.0495 (0.5); 4.6350 (0.4); 4.6151 (0.7); 4.6007 (0.7); 4.5804 (0.4); 3.6828 (15.5); 3.3285 (11.1); 2.5208 (0.4); 2.5122 (5.4); 2.5077 (10.9); 2.5032 (14.3); 2.4986 (10.3); 2.4941 (5.0); 2.4558 (0.4); 2.4528 (0.4); 2.4419 (0.4); 2.4271 (0.6); 2.4100 (16.0); 2.3925 (1.3); 2.3819 (0.4); 2.3778 (0.4); 2.3718 (0.4); 2.3671 (0.4); 2.3559 (0.3)

I.0069: $^{1}$H-NMR(400.2 MHz, $d_6$-DMSO):
δ = 8.6523 (1.1); 8.6331 (1.1); 4.4015 (0.4); 4.3902 (0.6); 4.3822 (0.5); 4.3761 (0.6); 4.3711 (0.7); 4.3639 (0.6); 4.3570 (0.5); 4.3447 (0.5); 4.1579 (0.4); 4.1487 (0.6); 4.1400 (0.5); 4.1368 (0.8); 4.1309 (2.0); 4.1190 (2.1); 4.1131 (2.1); 4.1013 (2.0); 4.0953 (0.8); 4.0922 (0.5); 4.0837 (0.6); 4.0743 (0.4); 3.3282 (9.0); 2.8925 (1.1); 2.7329 (0.9); 2.5212 (0.4); 2.5125 (5.1); 2.5081 (10.3); 2.5036 (13.5); 2.4990 (9.8); 2.4945 (4.8); 2.3906 (16.0); 2.3740 (0.9); 1.7633 (0.3); 1.7514 (0.5); 1.7368 (0.4); 1.7309 (0.5); 1.7248 (0.7); 1.7194 (0.7); 1.6948 (0.7); 1.6854 (0.5); 1.6693 (0.5); 1.6650 (0.5); 1.6526 (0.5); 1.6488 (0.4); 1.5890 (0.7); 1.5765 (0.5); 1.5673 (0.5); 1.5563 (0.9); 1.5450 (0.5); 1.5353 (0.4); 1.2110 (4.8); 1.1933 (9.9); 1.1755 (4.6); 0.9276 (5.9); 0.9116 (5.7); 0.8926 (5.7); 0.8766 (5.6)

I.0070: $^{1}$H-NMR(400.2 MHz, $d_6$-DMSO):
δ = 8.6841 (0.9); 8.6653 (0.9); 4.5127 (0.4); 4.4978 (0.5); 4.4928 (0.7); 4.4779 (0.6); 4.4734 (0.5); 4.4582 (0.4); 4.1601 (0.5); 4.1504 (0.7); 4.1423 (1.6); 4.1324 (1.7); 4.1245 (1.7); 4.1147 (1.6); 4.1063 (0.7); 4.0970 (0.5); 3.3283 (7.1); 2.8927 (0.7); 2.7339 (0.6); 2.7328 (0.6); 2.5809 (0.7); 2.5616 (1.0); 2.5468 (0.8); 2.5389 (1.2); 2.5257 (0.4); 2.5200 (0.9); 2.5127 (3.7); 2.5082 (7.4); 2.5037 (9.6); 2.4990 (6.7); 2.4945 (3.2); 2.4874 (0.3); 2.4002 (12.4); 2.3834 (0.8); 2.0572 (16.0); 2.0443 (1.2); 2.0404 (0.9); 2.0296 (0.8); 2.0239 (0.8); 2.0188 (0.5); 2.0108 (0.3); 2.0033 (0.4); 1.2180 (3.8); 1.2096 (0.4); 1.2002 (7.7); 1.1825 (3.6)

I.0071: $^{1}$H-NMR(400.2 MHz, $d_6$-DMSO):
δ = 8.7043 (1.3); 8.6848 (1.3); 7.3181 (0.4); 7.3157 (0.6); 7.3116 (0.4); 7.3019 (0.8); 7.2968 (3.0); 7.2874 (3.6); 7.2812 (11.1); 7.2703 (0.7); 7.2663 (1.0); 7.2392 (0.8); 7.2337 (0.9); 7.2242 (0.9); 7.2176 (1.0); 7.2093 (0.6); 7.2026 (0.5); 4.5936 (0.5); 4.5805 (0.6); 4.5743 (0.6); 4.5680 (0.7); 4.5612 (0.6); 4.5549 (0.6); 4.5487 (0.6); 4.5355 (0.5); 4.1394 (1.2); 4.1219 (3.7); 4.1041 (3.9); 4.0864 (1.3); 3.3302 (13.3); 3.1831 (0.7); 3.1699 (0.8); 3.1487 (1.2); 3.1356 (1.1); 3.0589 (1.2); 3.0331 (1.2); 3.0246 (0.8); 2.9988 (0.7); 2.8911 (0.5); 2.7330 (0.4); 2.5256 (0.3); 2.5209 (0.5); 2.5121 (6.5); 2.5077 (13.1); 2.5031 (17.1); 2.4985 (12.4); 2.4941 (6.1); 2.4447 (0.7); 2.2209 (16.0); 2.2048 (0.9); 1.1757 (5.1); 1.1579 (10.5); 1.1402 (4.9); −0.0002 (0.3)

I.0072: $^{1}$H-NMR(400.2 MHz, $d_6$-DMSO):
δ = 8.6567 (0.5); 8.6423 (1.0); 8.6279 (0.5); 4.1519 (1.4); 4.1341 (4.3); 4.1163 (4.3); 4.0985 (1.4); 3.9716 (4.0); 3.9569 (4.0); 3.3305 (7.7); 2.8925 (0.5); 2.7339 (0.4); 2.7327 (0.4); 2.5130 (3.9); 2.5085 (7.7); 2.5039 (10.0); 2.4993 (7.2); 2.4948 (3.4); 2.4219 (16.0); 1.2248 (5.1); 1.2070 (10.0); 1.1892 (4.8)

I.0073: $^{1}$H-NMR(400.2 MHz, $d_6$-DMSO):
δ = 8.3125 (0.4); 8.2993 (0.7); 8.2860 (0.4); 4.0948 (1.4); 4.0771 (4.4); 4.0593 (4.4); 4.0415 (1.4); 3.4679 (0.9); 3.4508 (2.1); 3.4367 (2.1); 3.4197 (0.9); 3.3292 (8.7); 2.5717 (1.9); 2.5546 (4.1); 2.5374 (1.8); 2.5217 (0.4); 2.5130 (4.5); 2.5085 (9.2); 2.5039 (12.1); 2.4993 (8.7); 2.4947 (4.2); 2.3707 (16.0); 1.2003 (5.0); 1.1826 (10.1); 1.1648 (4.8)

I.0074: $^{1}$H-NMR(400.2 MHz, $d_6$-DMSO):
δ = 8.8987 (2.0); 4.0933 (1.4); 4.0756 (4.6); 4.0579 (4.6); 4.0401 (1.4); 3.3291 (7.4); 2.5129 (4.0); 2.5084 (8.0); 2.5038 (10.5); 2.4992 (7.5); 2.4946 (3.6); 2.3878 (16.0); 1.4410 (1.1); 1.4289 (2.8); 1.4206 (3.1); 1.4097 (1.3); 1.1701 (5.7); 1.1604 (3.2); 1.1523 (12.4); 1.1398 (1.3); 1.1345 (4.8)

I.0075: $^{1}$H-NMR(400.2 MHz, $d_6$-DMSO):
δ = 9.0240 (2.0); 4.1250 (1.4); 4.1073 (4.4); 4.0896 (4.4); 4.0719 (1.4); 3.3289 (7.6); 2.8928 (1.0); 2.7338 (0.8); 2.5744 (0.6); 2.5698 (0.4); 2.5586 (0.7); 2.5529 (1.0); 2.5460 (0.7); 2.5418 (0.9); 2.5373 (0.9); 2.5272 (1.2); 2.5195 (1.1); 2.5128 (4.2); 2.5083 (8.2); 2.5038 (10.6); 2.4992 (7.5); 2.4947 (3.6); 2.3929 (16.0); 2.3068 (0.6); 2.2841 (1.2); 2.2642 (0.9); 2.2547 (1.1); 2.2327 (0.6); 1.9710 (0.5); 1.9668 (0.5); 1.9583 (0.5); 1.9502 (0.9); 1.9436 (0.9); 1.9361 (0.4); 1.9293 (1.3); 1.9211 (0.6); 1.9079 (0.6); 1.1816 (4.6); 1.1639 (9.3); 1.1461 (4.4)

I.0076: $^{1}$H-NMR(400.2 MHz, $d_6$-DMSO):
δ = 8.5380 (1.0); 8.5188 (1.0); 4.2138 (1.3); 4.2067 (0.4); 4.1960 (1.9); 4.1890 (0.9); 4.1775 (1.5); 4.1712 (0.8); 4.1619 (1.7); 4.1442 (2.2); 4.1267 (2.2); 4.1091 (1.7); 4.0997 (0.8); 4.0913 (0.6); 4.0820 (0.7); 3.3275 (7.7); 2.5207 (0.4); 2.5121 (4.6); 2.5078 (9.1); 2.5032 (11.8); 2.4987 (8.5); 2.4942 (4.1); 2.3858 (16.0); 2.1793 (0.6); 2.1623 (1.0); 2.1453 (1.1); 2.1282 (0.6); 1.2224 (4.9); 1.2047 (9.7); 1.1869 (4.6); 0.9683 (6.6); 0.9506 (9.1); 0.9318 (6.1)

I.0077: $^{1}$H-NMR(400.2 MHz, $d_6$-DMSO):
δ = 8.7834 (1.0); 8.7641 (1.0); 6.3285 (0.4); 6.1996 (0.4); 6.1884 (0.9); 6.1769 (0.4); 6.0484 (0.5); 4.6338 (0.4); 4.6142 (0.7); 4.5994 (0.7); 4.5792 (0.4); 3.6830 (15.1); 3.3303 (7.2); 2.5215 (0.3); 2.5129 (3.9); 2.5084 (7.9); 2.5038 (10.4); 2.4991 (7.4); 2.4946 (3.5); 2.4543 (0.4); 2.4429 (0.4); 2.4305 (0.6); 2.4278 (0.6); 2.4098 (16.0); 2.3942 (0.6); 2.3840 (0.4); 2.3795 (0.4); 2.3716 (0.4); 2.3580 (0.4)

I.0078: $^{1}$H-NMR(400.2 MHz, $d_6$-DMSO):
δ = 8.6308 (1.2); 8.6116 (1.2); 4.3992 (0.4); 4.3879 (0.6); 4.3798 (0.5); 4.3737 (0.6); 4.3688 (0.7); 4.3615 (0.6); 4.3546 (0.4); 4.3423 (0.5); 4.1572 (0.4); 4.1480 (0.6); 4.1393 (0.5); 4.1361 (0.7); 4.1302 (1.9); 4.1184 (2.0); 4.1124 (2.0); 4.1007 (1.9); 4.0946 (0.7); 4.0916 (0.5); 4.0830 (0.6); 4.0736 (0.4); 3.3279 (12.2); 2.8925 (0.6); 2.7329 (0.5); 2.5212 (0.5); 2.5125 (5.4); 2.5081 (10.9); 2.5036 (14.3); 2.4990 (10.4); 2.4945 (5.1); 2.3904 (16.0); 1.7655 (0.3); 1.7537 (0.5); 1.7390 (0.4); 1.7332 (0.5); 1.7270 (0.6); 1.7216 (0.7); 1.6968 (0.8); 1.6857 (0.5); 1.6695 (0.5); 1.6652 (0.5); 1.6528 (0.4); 1.6492 (0.4); 1.5880 (0.7); 1.5756 (0.5); 1.5662 (0.5); 1.5551 (0.9); 1.5440 (0.5); 1.5342 (0.4); 1.2106 (4.7); 1.1929 (9.6); 1.1751 (4.5); 0.9275 (5.8); 0.9115 (5.6); 0.8918 (5.6); 0.8758 (5.5)

I.0079: $^{1}$H-NMR(400.2 MHz, $d_6$-DMSO):
δ = 8.6637 (0.8); 8.6449 (0.8); 4.5103 (0.4); 4.4949 (0.6); 4.4905 (0.8); 4.4755 (0.8); 4.4557 (0.5); 4.1685 (0.5); 4.1595 (0.5); 4.1536 (0.9); 4.1497 (1.3); 4.1417 (1.6); 4.1357 (1.0); 4.1317 (2.2); 4.1238 (1.7); 4.1140 (1.7); 4.1057 (0.7); 4.0963 (0.4); 3.3289 (8.4); 2.8926 (1.1); 2.7340 (1.0); 2.7327 (1.0); 2.5808 (0.6); 2.5614 (4.2); 2.5474 (3.7); 2.5380 (1.2); 2.5128 (4.7); 2.5083 (9.7); 2.5037 (12.8); 2.4991 (9.1); 2.4945 (4.4); 2.4161 (4.1); 2.4137 (3.9); 2.3996 (12.4); 2.0570 (16.0); 2.0444 (1.2); 2.0293 (0.8); 2.0248 (0.9); 2.0200 (0.5); 2.0042 (0.4); 1.2268 (1.9); 1.2174 (3.7); 1.2090 (4.0); 1.1997 (7.6); 1.1913 (1.9); 1.1819 (3.5)

I.0080: $^{1}$H-NMR(400.2 MHz, $d_6$-DMSO):
δ = 8.6820 (1.2); 8.6626 (1.3); 7.3175 (0.4); 7.3150 (0.5); 7.3013 (0.7); 7.2961 (2.9); 7.2949 (2.7); 7.2871 (3.6); 7.2806 (10.8); 7.2700 (0.7); 7.2659 (0.9); 7.2383 (0.8); 7.2328 (0.9); 7.2230 (0.8); 7.2168 (1.0); 7.2083 (0.5); 7.2018 (0.5); 4.5919 (0.5); 4.5788 (0.6); 4.5726 (0.6); 4.5664 (0.7); 4.5594 (0.6); 4.5532 (0.6); 4.5470 (0.6); 4.5338 (0.5); 4.1389 (1.1); 4.1216 (3.5); 4.1040 (3.7);

TABLE A-(I)-continued

| NMR peak lists of compounds according to formula (I) |
| --- |
| 4.0861 (1.3); 3.3310 (10.3); 3.1823 (0.7); 3.1691 (0.8); 3.1479 (1.2); 3.1348 (1.1); 3.0618 (1.2); 3.0360 (1.2); 3.0275 (0.8); 3.0017 (0.7); 2.8910 (0.4); 2.7334 (0.3); 2.7322 (0.3); 2.5211 (0.4); 2.5124 (5.1); 2.5079 (10.4); 2.5033 (13.6); 2.4987 (9.8); 2.4942 (4.7); 2.2254 (16.0); 1.1756 (5.2); 1.1579 (10.7); 1.1401 (4.9) |
| I.0081: $^{1}$H-NMR(400.2 MHz, $d_6$-DMSO): |
| δ = 8.4460 (0.8); 8.4324 (1.5); 8.4186 (0.8); 4.1109 (2.3); 4.0931 (7.2); 4.0753 (7.2); 4.0575 (2.4); 3.5006 (1.4); 3.4838 (3.6); 3.4693 (3.7); 3.4526 (1.5); 3.3292 (13.2); 2.8932 (0.4); 2.7335 (0.4); 2.5868 (3.3); 2.5699 (6.8); 2.5529 (3.1); 2.5270 (0.4); 2.5136 (8.1); 2.5092 (16.0); 2.5047 (20.8); 2.5002 (15.2); 2.4958 (7.5); 1.2124 (7.9); 1.1946 (16.0); 1.1768 (7.7); −0.0002 (0.4) |
| I.0082: $^{1}$H-NMR(400.2 MHz, $d_6$-DMSO): |
| δ = 9.2003 (3.4); 7.9532 (0.4); 4.1343 (2.3); 4.1166 (7.5); 4.0988 (7.5); 4.0811 (2.4); 3.3283 (16.9); 2.8925 (2.8); 2.7336 (2.2); 2.7325 (2.2); 2.5892 (0.9); 2.5742 (1.0); 2.5665 (1.5); 2.5626 (1.1); 2.5568 (1.5); 2.5513 (1.4); 2.5424 (1.6); 2.5341 (1.4); 2.5261 (1.0); 2.5192 (1.8); 2.5127 (9.3); 2.5082 (18.5); 2.5036 (24.1); 2.4989 (17.2); 2.4944 (8.2); 2.3052 (0.9); 2.2867 (1.4); 2.2817 (1.7); 2.2750 (1.1); 2.2632 (1.5); 2.2555 (1.6); 2.2510 (1.2); 2.2321 (0.9); 2.0193 (0.5); 2.0089 (0.6); 2.0051 (0.7); 1.9958 (0.7); 1.9906 (0.5); 1.9813 (1.1); 1.9723 (0.5); 1.9671 (0.6); 1.9579 (1.0); 1.9371 (1.1); 1.9327 (0.8); 1.9186 (0.6); 1.9142 (0.7); 1.9094 (0.6); 1.2386 (0.4); 1.2339 (0.4); 1.2077 (7.7); 1.1900 (16.0); 1.1723 (7.5); −0.0002 (0.5) |
| I.0083: $^{1}$H-NMR(400.2 MHz, $d_6$-DMSO): |
| δ = 8.9646 (1.2); 8.9455 (1.2); 6.3490 (0.4); 6.2200 (0.5); 6.2090 (0.8); 6.1970 (0.4); 6.0690 (0.4); 4.6463 (0.4); 4.6333 (0.4); 4.6257 (0.7); 4.6132 (0.6); 4.6056 (0.5); 4.5923 (0.4); 3.6956 (16.0); 3.3286 (8.8); 2.5216 (0.5); 2.5129 (5.5); 2.5084 (11.2); 2.5038 (14.8); 2.4992 (10.6); 2.4947 (5.1); 2.4663 (0.4); 2.4610 (0.3); 2.4515 (0.3); 2.4381 (0.4); 2.4275 (0.7); 2.4241 (0.7); 2.4116 (0.6); 2.4010 (0.4); 2.3887 (0.4); 2.3847 (0.4); 2.3745 (0.4); −0.0002 (0.3) |
| I.0084: $^{1}$H-NMR(400.2 MHz, $d_6$-DMSO): |
| δ = 8.3924 (0.7); 8.3792 (1.2); 8.3659 (0.7); 4.1086 (2.4); 4.0908 (7.3); 4.0730 (7.4); 4.0552 (2.4); 3.5281 (1.5); 3.5114 (3.9); 3.4968 (3.9); 3.4800 (1.6); 3.3299 (9.4); 2.5986 (3.4); 2.5818 (7.2); 2.5648 (3.2); 2.5232 (0.4); 2.5147 (6.0); 2.5103 (11.8); 2.5057 (15.3); 2.5011 (11.0); 2.4966 (5.3); 1.2075 (8.1); 1.1898 (16.0); 1.1719 (7.8) |
| I.0085: $^{1}$H-NMR(400.2 MHz, $d_6$-DMSO): |
| δ = 9.1513 (2.7); 4.1397 (2.3); 4.1220 (7.4); 4.1042 (7.5); 4.0865 (2.4); 3.3282 (12.3); 2.5919 (0.8); 2.5872 (0.5); 2.5769 (1.0); 2.5697 (1.4); 2.5633 (1.0); 2.5593 (1.4); 2.5546 (1.3); 2.5450 (1.6); 2.5410 (0.9); 2.5369 (1.3); 2.5294 (0.6); 2.5223 (1.5); 2.5132 (6.5); 2.5087 (13.2); 2.5041 (17.2); 2.4995 (12.3); 2.4949 (5.9); 2.3297 (0.9); 2.3105 (1.4); 2.3063 (1.7); 2.2990 (1.0); 2.2869 (1.4); 2.2783 (1.6); 2.2554 (0.9); 2.0085 (0.5); 1.9985 (0.5); 1.9944 (0.7); 1.9860 (1.0); 1.9802 (0.6); 1.9706 (1.4); 1.9646 (1.0); 1.9570 (0.7); 1.9455 (1.5); 1.9331 (0.4); 1.9258 (0.7); 1.9232 (0.7); 1.9175 (0.5); 1.1990 (7.8); 1.1813 (16.0); 1.1636 (7.5); −0.0002 (0.4) |
| I.0086: $^{1}$H-NMR(400.2 MHz, $d_6$-DMSO): |
| δ = 8.8928 (1.0); 8.8737 (1.0); 6.3408 (0.4); 6.2120 (0.5); 6.2009 (0.9); 6.1891 (0.5); 6.0609 (0.5); 4.6875 (0.4); 4.6739 (0.4); 4.6674 (0.7); 4.6540 (0.7); 4.6479 (0.5); 4.6336 (0.4); 3.6950 (16.0); 3.3285 (8.4); 2.5218 (0.4); 2.5131 (4.7); 2.5086 (9.5); 2.5040 (12.4); 2.4994 (9.0); 2.4949 (4.4); 2.4804 (0.4); 2.4761 (0.3); 2.4587 (0.5); 2.4490 (0.6); 2.4426 (0.7); 2.4321 (0.6); 2.4200 (0.5); 2.4054 (0.6); 2.3941 (0.4) |
| I.0087: $^{1}$H-NMR(400.2 MHz, $d_6$-DMSO): |
| δ = 8.6417 (0.9); 8.6273 (1.8); 8.6127 (0.9); 4.1481 (2.2); 4.1304 (7.0); 4.1126 (7.1); 4.0948 (2.3); 3.9596 (6.3); 3.9449 (6.2); 3.3300 (10.4); 2.8924 (0.5); 2.7340 (0.4); 2.7329 (0.4); 2.5217 (0.5); 2.5130 (6.6); 2.5085 (13.2); 2.5040 (17.2); 2.4994 (12.4); 2.4949 (5.9); 2.4712 (24.2); 2.4586 (0.9); 2.4446 (0.6); 1.2227 (7.9); 1.2049 (16.0); 1.1871 (7.6); −0.0002 (0.4) |
| I.0088: $^{1}$H-NMR(400.2 MHz, $d_6$-DMSO): |
| δ = 8.3017 (0.5); 8.2882 (1.0); 8.2746 (0.5); 4.0926 (1.5); 4.0748 (4.8); 4.0570 (4.8); 4.0392 (1.6); 3.4584 (0.9); 3.4414 (2.2); 3.4272 (2.2); 3.4103 (1.0); 3.3300 (8.3); 2.8929 (0.7); 2.7343 (0.6); 2.7332 (0.6); 2.5632 (2.1); 2.5462 (4.4); 2.5289 (2.0); 2.5224 (0.5); 2.5134 (4.3); 2.5089 (8.8); 2.5044 (11.6); 2.4997 (8.4); 2.4952 (4.0); 2.4179 (16.0); 2.4087 (0.8); 2.3905 (0.3); 1.2379 (0.5); 1.2001 (5.3); 1.1823 (10.8); 1.1645 (5.2) |
| I.0089: $^{1}$H-NMR(400.2 MHz, $d_6$-DMSO): |
| δ = 8.8742 (2.4); 4.0889 (1.5); 4.0712 (4.8); 4.0535 (4.8); 4.0357 (1.5); 3.3283 (9.2); 2.5212 (0.4); 2.5126 (5.4); 2.5081 (10.7); 2.5035 (13.8); 2.4989 (9.8); 2.4944 (4.6); 2.4363 (16.0); 2.4246 (0.6); 2.4090 (0.4); 1.4315 (1.2); 1.4194 (3.0); 1.4112 (3.3); 1.4003 (1.4); 1.1684 (5.1); 1.1584 (1.7); 1.1506 (11.4); 1.1391 (3.3); 1.1329 (5.2); 1.1270 (1.3) |
| I.0090: $^{1}$H-NMR(400.2 MHz, $d_6$-DMSO): |
| δ = 9.0093 (2.3); 4.1186 (1.4); 4.1010 (4.6); 4.0832 (4.6); 4.0655 (1.5); 3.3288 (8.1); 2.8921 (1.1); 2.7326 (1.0); 2.5672 (0.6); 2.5512 (0.7); 2.5456 (1.0); 2.5390 (0.8); 2.5346 (1.0); 2.5300 (1.0); 2.5265 (1.0); 2.5204 (1.5); 2.5124 (5.7); 2.5080 (10.3); 2.5035 (13.6); 2.4989 (10.4); 2.4945 (5.2); 2.4372 (16.0); 2.4244 (0.6); 2.4124 (0.4); 2.2933 (0.6); 2.2708 (1.3); 2.2507 (1.0); 2.2414 (1.2); 2.2193 (0.6); 1.9630 (0.5); 1.9592 (0.6); 1.9507 (0.6); 1.9419 (0.9); 1.9360 (1.0); 1.9286 (0.5); 1.9214 (1.3); 1.9136 (0.6); 1.8998 (0.7); 1.1778 (4.8); 1.1601 (9.8); 1.1423 (4.6) |
| I.0091: $^{1}$H-NMR(400.2 MHz, $d_6$-DMSO): |
| δ = 8.5279 (1.1); 8.5087 (1.1); 4.2072 (1.3); 4.2017 (0.4); 4.1887 (1.8); 4.1839 (1.0); 4.1741 (0.8); 4.1710 (1.4); 4.1661 (0.9); 4.1567 (1.8); 4.1389 (2.4); 4.1212 (2.4); 4.1035 (1.8); 4.0942 (0.8); 4.0858 (0.6); 4.0764 (0.8); 3.3274 (8.8); 2.5205 (0.5); 2.5120 (5.3); 2.5076 (10.6); 2.5031 (13.7); 2.4985 (9.8); 2.4940 (4.6); 2.4287 (16.0); 2.4182 (0.6); 2.1685 (0.6); 2.1515 (1.1); 2.1345 (1.1); 2.1174 (0.6); 1.2193 (5.2); 1.2015 (10.4); 1.1838 (4.9); 0.9611 (6.8); 0.9437 (11.7); 0.9261 (6.2) |
| I.0092: $^{1}$H-NMR(400.2 MHz, $d_6$-DMSO): |
| δ = 8.7688 (1.2); 8.7495 (1.2); 6.3194 (0.4); 6.1905 (0.5); 6.1794 (0.9); 6.1678 (0.4); 6.0393 (0.5); 4.6199 (0.4); 4.6002 (0.8); 4.5856 (0.7); 4.5654 (0.4); 3.6788 (16.0); 3.3295 (8.3); 2.5214 (0.4); 2.5127 (4.6); 2.5082 (9.4); 2.5036 (12.3); 2.4990 (8.8); 2.4945 (4.2); 2.4568 (15.7); 2.4448 (0.9); 2.4306 (0.7); 2.4153 (0.6); 2.4033 (1.0); 2.3924 (0.6); 2.3816 (0.5); 2.3708 (0.4); 2.3666 (0.4); 2.3598 (0.4); 2.3449 (0.4) |
| I.0093: $^{1}$H-NMR(400.2 MHz, $d_6$-DMSO): |
| δ = 8.6125 (1.2); 8.5934 (1.2); 4.3906 (0.4); 4.3794 (0.6); 4.3715 (0.5); 4.3652 (0.5); 4.3604 (0.7); 4.3531 (0.6); 4.3464 (0.4); 4.3340 (0.5); 4.1531 (0.5); 4.1439 (0.6); 4.1353 (0.5); 4.1312 (0.8); 4.1261 (2.1); 4.1135 (2.2); 4.1083 (2.2); 4.0958 (2.1); 4.0905 (0.8); 4.0866 (0.6); 4.0782 (0.6); 4.0688 (0.5); 3.3284 (11.1); 2.8927 (0.8); 2.7342 (0.7); 2.7330 (0.7); 2.5216 (0.4); 2.5129 (5.2); 2.5084 (10.6); 2.5038 (13.8); 2.4992 (9.9); 2.4946 (4.7); 2.4356 (16.0); 2.4243 (0.6); 2.4098 (0.3); 1.7516 (0.3); 1.7397 (0.5); 1.7250 (0.4); 1.7193 (0.4); 1.7129 (0.7); 1.7079 (0.8); 1.6913 (0.5); 1.6811 (0.8); 1.6636 (0.5); 1.6595 (0.5); 1.6470 (0.4); 1.6435 (0.4); 1.5778 (0.6); 1.5652 (0.4); 1.5562 (0.5); 1.5451 (0.9); 1.5339 (0.5); 1.5243 (0.4); 1.2084 (5.1); 1.1907 (10.5); 1.1729 (4.9); 0.9233 (5.9); 0.9073 (5.6); 0.8888 (5.5); 0.8728 (5.4) |
| I.0094: $^{1}$H-NMR(400.2 MHz, $d_6$-DMSO): |
| δ = 8.6492 (1.0); 8.6304 (1.0); 4.4982 (0.4); 4.4784 (0.7); 4.4634 (0.7); 4.4592 (0.6); 4.4438 (0.4); 4.1546 (0.5); 4.1442 (0.7); 4.1368 (1.6); 4.1262 (1.7); 4.1190 (1.6); 4.1085 (1.6); 4.1008 (0.6); 4.0909 (0.5); 3.3282 (10.6); 2.5735 (0.7); 2.5573 (1.2); 2.5427 (0.6); 2.5389 (0.8); 2.5319 (1.3); 2.5261 (0.4); 2.5124 (5.7); 2.5079 (10.4); 2.5033 (13.4); 2.4987 (9.9); 2.4943 (4.7); 2.4612 (0.4); 2.4591 (0.4); 2.4442 (11.8); 2.4329 (0.4); 2.0539 (16.0); 2.0314 (1.3); 2.0165 (0.9); 2.0116 (1.0); 1.9979 (0.4); 1.9909 (0.4); 1.2143 (3.7); 1.2060 (0.5); 1.1966 (7.5); 1.1889 (0.3); 1.1788 (3.5) |

TABLE A-(I)-continued

| NMR peak lists of compounds according to formula (I) |
|---|
| I.0095: $^1$H-NMR(400.2 MHz, $d_6$-DMSO): δ = 8.6686 (1.3); 8.6492 (1.3); 7.3136 (0.6); 7.2995 (0.9); 7.2944 (2.8); 7.2783 (9.2); 7.2619 (1.1); 7.2548 (0.3); 7.2375 (0.8); 7.2323 (0.9); 7.2236 (0.8); 7.2159 (1.1); 7.2074 (0.6); 7.2004 (0.5); 4.5806 (0.5); 4.5675 (0.6); 4.5613 (0.6); 4.5550 (0.7); 4.5482 (0.7); 4.5418 (0.6); 4.5357 (0.6); 4.5225 (0.5); 4.1333 (1.2); 4.1157 (3.9); 4.0981 (4.1); 4.0804 (1.4); 3.3303 (9.9); 3.1707 (0.7); 3.1576 (0.8); 3.1363 (1.3); 3.1233 (1.1); 3.0479 (1.2); 3.0220 (1.2); 3.0135 (0.8); 2.9877 (0.8); 2.8905 (0.6); 2.7320 (0.6); 2.5118 (6.5); 2.5074 (13.0); 2.5029 (16.8); 2.4983 (12.0); 2.4938 (5.7); 2.2706 (16.0); 1.1719 (5.3); 1.1542 (10.9); 1.1364 (5.1) |
| I.0096: $^1$H-NMR(400.2 MHz, $d_6$-DMSO): δ = 8.6179 (0.6); 8.6035 (1.1); 8.5889 (0.5); 4.1467 (1.4); 4.1289 (4.6); 4.1111 (4.7); 4.0933 (1.5); 3.9559 (4.0); 3.9412 (4.0); 3.3295 (7.3); 2.5214 (0.4); 2.5126 (4.4); 2.5081 (8.9); 2.5035 (11.7); 2.4989 (8.4); 2.4943 (4.0); 2.4706 (0.4); 2.4582 (16.0); 1.2214 (5.4); 1.2036 (11.0); 1.1858 (5.2) |
| I.0097: $^1$H-NMR(400.2 MHz, $d_6$-DMSO): δ = 8.2781 (0.5); 8.2645 (1.0); 8.2508 (0.5); 4.0914 (1.5); 4.0736 (4.8); 4.0559 (4.8); 4.0381 (1.6); 3.4558 (0.9); 3.4386 (2.2); 3.4245 (2.2); 3.4075 (0.9); 3.3295 (9.0); 2.5615 (2.0); 2.5444 (4.2); 2.5271 (2.0); 2.5220 (0.5); 2.5131 (4.6); 2.5086 (9.4); 2.5040 (12.4); 2.4993 (8.9); 2.4948 (4.2); 2.4172 (0.6); 2.4081 (16.0); 1.1988 (5.5); 1.1810 (11.2); 1.1632 (5.3) |
| I.0098: $^1$H-NMR(400.2 MHz, $d_6$-DMSO): δ = 8.8498 (2.6); 4.0872 (1.5); 4.0694 (4.8); 4.0517 (4.9); 4.0339 (1.5); 3.3289 (9.0); 2.5212 (0.4); 2.5125 (5.2); 2.5080 (10.6); 2.5034 (13.9); 2.4988 (10.1); 2.4943 (4.9); 2.4359 (0.5); 2.4244 (16.0); 1.4302 (1.2); 1.4181 (3.0); 1.4098 (3.3); 1.3990 (1.4); 1.1660 (5.2); 1.1561 (1.7); 1.1483 (11.7); 1.1368 (3.3); 1.1305 (5.3); 1.1248 (1.4) |
| I.0099: $^1$H-NMR(400.2 MHz, $d_6$-DMSO): δ = 8.9791 (2.2); 4.1171 (1.4); 4.0994 (4.6); 4.0816 (4.7); 4.0639 (1.5); 3.3285 (8.2); 2.5656 (0.6); 2.5613 (0.4); 2.5499 (0.7); 2.5440 (1.0); 2.5373 (0.7); 2.5331 (1.0); 2.5282 (1.0); 2.5260 (1.0); 2.5181 (1.5); 2.5123 (5.8); 2.5079 (10.8); 2.5033 (14.1); 2.4987 (10.6); 2.4942 (5.3); 2.4445 (0.5); 2.4369 (0.4); 2.4242 (16.0); 2.4127 (0.4); 2.2938 (0.6); 2.2711 (1.2); 2.2512 (0.9); 2.2418 (1.1); 2.2197 (0.6); 1.9617 (0.5); 1.9579 (0.6); 1.9494 (0.5); 1.9403 (0.9); 1.9347 (0.9); 1.9272 (0.4); 1.9200 (1.2); 1.9122 (0.6); 1.8982 (0.6); 1.1757 (4.9); 1.1579 (10.1); 1.1402 (4.7) |
| I.0100: $^1$H-NMR(400.2 MHz, $d_6$-DMSO): δ = 8.4955 (1.2); 8.4762 (1.2); 4.2040 (1.2); 4.1851 (1.8); 4.1736 (0.7); 4.1676 (1.4); 4.1654 (1.2); 4.1558 (1.9); 4.1380 (2.6); 4.1203 (2.6); 4.1027 (1.9); 4.0933 (0.8); 4.0850 (0.6); 4.0756 (0.8); 3.3330 (24.3); 2.5213 (0.4); 2.5126 (5.8); 2.5081 (11.7); 2.5035 (15.3); 2.4988 (11.0); 2.4943 (5.3); 2.4285 (0.5); 2.4180 (16.0); 2.1691 (0.6); 2.1521 (1.0); 2.1351 (1.0); 2.1180 (0.6); 1.2248 (0.5); 1.2187 (5.2); 1.2071 (1.0); 1.2010 (10.7); 1.1893 (0.6); 1.1832 (5.0); 0.9601 (6.6); 0.9426 (10.6); 0.9247 (6.0) |
| I.0101: $^1$H-NMR(400.2 MHz, $d_6$-DMSO): δ = 8.7435 (1.2); 8.7241 (1.2); 6.3164 (0.4); 6.1874 (0.4); 6.1763 (0.9); 6.1648 (0.4); 6.0362 (0.5); 4.6175 (0.4); 4.5981 (0.8); 4.5828 (0.7); 4.5629 (0.4); 3.6768 (16.0); 3.3288 (9.4); 2.5209 (0.4); 2.5122 (5.6); 2.5077 (11.4); 2.5032 (14.9); 2.4985 (10.7); 2.4940 (5.1); 2.4558 (0.6); 2.4443 (15.6); 2.4299 (0.6); 2.4139 (0.6); 2.4021 (0.9); 2.3932 (0.6); 2.3818 (0.5); 2.3710 (0.5); 2.3670 (0.4); 2.3573 (0.5); 2.3449 (0.4) |
| I.0102: $^1$H-NMR(400.2 MHz, $d_6$-DMSO): δ = 8.5843 (1.2); 8.5651 (1.2); 4.3881 (0.4); 4.3770 (0.6); 4.3688 (0.5); 4.3626 (0.6); 4.3578 (0.7); 4.3506 (0.6); 4.3436 (0.5); 4.3313 (0.5); 4.1515 (0.4); 4.1423 (0.6); 4.1337 (0.5); 4.1296 (0.8); 4.1245 (2.0); 4.1120 (2.2); 4.1067 (2.2); 4.0943 (2.0); 4.0889 (0.8); 4.0851 (0.5); 4.0766 (0.6); 4.0673 (0.4); 3.3279 (8.5); 2.8922 (0.6); 2.7329 (0.5); 2.5124 (5.8); 2.5080 (11.6); 2.5035 (15.2); 2.4989 (11.0); 2.4944 (5.3); 2.4349 (0.5); 2.4240 (16.0); 2.4103 (0.4); 1.7549 (0.4); 1.7430 (0.5); 1.7282 (0.4); 1.7224 (0.5); 1.7162 (0.7); 1.7109 (0.8); 1.6912 (0.6); 1.6853 (0.7); 1.6796 (0.6); 1.6634 (0.5); 1.6593 (0.5); 1.6468 (0.5); 1.5759 (0.7); 1.5634 (0.5); 1.5542 (0.5); 1.5431 (1.0); 1.5319 (0.5); 1.5221 (0.4); 1.2070 (5.0); 1.1893 (10.2); 1.1715 (4.8); 0.9228 (6.2); 0.9068 (5.9); 0.8871 (5.8); 0.8711 (5.8) |
| I.0103: $^1$H-NMR(400.2 MHz, $d_6$-DMSO): δ = 8.6218 (0.9); 8.6030 (0.9); 4.4961 (0.3); 4.4767 (0.7); 4.4611 (0.6); 4.4417 (0.3); 4.1534 (0.4); 4.1426 (0.6); 4.1356 (1.5); 4.1249 (1.6); 4.1177 (1.6); 4.1072 (1.5); 4.0998 (0.6); 4.0895 (0.4); 3.3279 (7.7); 2.5733 (0.6); 2.5569 (1.0); 2.5502 (0.6); 2.5425 (0.5); 2.5388 (0.6); 2.5302 (1.1); 2.5209 (0.4); 2.5122 (4.9); 2.5078 (9.0); 2.5032 (11.6); 2.4985 (8.4); 2.4940 (4.0); 2.4491 (0.3); 2.4466 (0.4); 2.4441 (0.4); 2.4326 (11.2); 2.0534 (16.0); 2.0316 (1.2); 2.0127 (0.9); 1.9975 (0.3); 1.9923 (0.4); 1.2131 (3.6); 1.2048 (0.4); 1.1954 (7.4); 1.1776 (3.4) |
| I.0104: $^1$H-NMR(400.2 MHz, $d_6$-DMSO): δ = 8.6389 (1.4); 8.6195 (1.4); 7.3140 (0.4); 7.3113 (0.6); 7.3075 (0.3); 7.2975 (0.9); 7.2927 (2.9); 7.2910 (2.7); 7.2809 (3.9); 7.2762 (9.3); 7.2638 (0.7); 7.2599 (1.1); 7.2530 (0.3); 7.2358 (0.9); 7.2307 (0.9); 7.2219 (0.9); 7.2142 (1.1); 7.2057 (0.6); 7.1987 (0.5); 4.5783 (0.5); 4.5652 (0.6); 4.5589 (0.6); 4.5528 (0.7); 4.5459 (0.6); 4.5396 (0.6); 4.5334 (0.6); 4.5201 (0.5); 4.1315 (1.2); 4.1139 (3.7); 4.0966 (4.0); 4.0788 (1.3); 3.3298 (12.7); 3.1686 (0.7); 3.1554 (0.8); 3.1341 (1.2); 3.1211 (1.1); 3.0514 (1.2); 3.0256 (1.2); 3.0171 (0.8); 2.9914 (0.7); 2.5252 (0.4); 2.5206 (0.6); 2.5118 (7.5); 2.5073 (15.2); 2.5027 (20.0); 2.4981 (14.3); 2.4935 (6.8); 2.2655 (16.0); 1.1705 (5.6); 1.1528 (11.8); 1.1350 (5.4); −0.0002 (0.4) |
| I.0105: $^1$H-NMR(400.2 MHz, $d_6$-DMSO): δ = 8.9209 (0.8); 8.3152 (0.5); 4.2792 (8.9); 3.3307 (5.4); 2.5132 (4.2); 2.5086 (8.8); 2.5040 (11.6); 2.4994 (8.1); 2.4948 (3.7); 2.4357 (0.4); 2.4294 (16.0); 2.4100 (0.7); −0.0002 (1.3) |
| I.0106: $^1$H-NMR(400.2 MHz, $d_6$-DMSO): δ = 9.1818 (1.0); 8.3156 (0.3); 3.3296 (7.7); 2.5259 (0.3); 2.5211 (0.5); 2.5125 (5.6); 2.5081 (11.4); 2.5035 (14.9); 2.4989 (10.5); 2.4944 (5.0); 2.3991 (16.0); 2.3803 (0.7); 1.5764 (1.1); 1.5622 (2.6); 1.5552 (2.6); 1.5419 (1.3); 1.3012 (1.4); 1.2877 (2.5); 1.2806 (2.7); 1.2664 (1.1); −0.0002 (1.3) |
| I.0107: $^1$H-NMR(400.2 MHz, $d_6$-DMSO): δ = 8.4054 (1.0); 8.3176 (3.0); 7.9541 (0.8); 3.7352 (0.4); 3.3410 (1.2); 2.8927 (6.3); 2.7341 (5.4); 2.7327 (5.4); 2.6112 (0.4); 2.5986 (16.0); 2.5737 (0.3); 2.5269 (0.5); 2.5222 (0.8); 2.5135 (10.2); 2.5090 (21.1); 2.5044 (27.3); 2.4997 (18.9); 2.4951 (8.7); 2.4871 (1.3); 2.4787 (0.9); 2.4635 (0.9); 2.4552 (1.3); 2.4492 (3.2); 2.4402 (0.4); 2.4330 (0.6); 2.4298 (0.6); 2.4085 (0.4); 2.3697 (0.5); 2.3642 (0.4); 2.3575 (0.6); 2.3465 (0.8); 2.3394 (0.9); 2.3353 (0.9); 2.3318 (0.9); 2.3267 (1.0); 2.3166 (0.8); 2.3056 (0.7); 2.1842 (0.5); 2.1643 (0.8); 2.1599 (1.0); 2.1403 (0.9); 2.1343 (1.1); 2.1101 (0.6); 2.1024 (0.6); 2.0960 (0.4); 2.0862 (1.0); 2.0782 (0.7); 2.0693 (1.1); 2.0618 (0.9); 2.0539 (0.8); 2.0449 (0.9); 2.0382 (0.7); 2.0206 (0.6); 2.0004 (0.4); 1.8353 (0.4); 1.8237 (0.6); 1.8110 (0.5); 1.7984 (0.5); 1.7252 (0.4); 1.7085 (0.8); 1.7031 (0.8); 1.6940 (0.4); 1.6862 (1.4); 1.6674 (0.6); 1.6641 (0.7); 1.2370 (0.3); −0.0002 (2.9) |
| I.0108: $^1$H-NMR(400.2 MHz, $d_6$-DMSO): δ = 9.0629 (0.8); 8.3161 (0.3); 4.7251 (1.4); 4.7051 (1.4); 3.3279 (10.2); 2.5254 (0.4); 2.5207 (0.6); 2.5119 (8.0); 2.5074 (16.4); 2.5029 (21.3); 2.4982 (15.0); 2.4937 (7.0); 2.4070 (16.0); 2.1711 (0.4); 2.1542 (0.6); 2.1516 (0.5); 2.1373 (0.6); 2.1345 (0.6); 2.1176 (0.4); 1.0789 (5.5); 1.0621 (5.3); 0.9905 (5.6); 0.9738 (5.4); −0.0002 (2.0) |

TABLE A-(I)-continued

| NMR peak lists of compounds according to formula (I) |
| --- |
| I.0109: $^1$H-NMR(400.2 MHz, $d_6$-DMSO):<br>δ = 8.3140 (5.1); 7.5423 (1.4); 7.5251 (2.3); 7.4938 (1.2); 7.4761 (2.7); 7.4572 (1.4); 7.4406 (1.2); 7.4234 (1.2); 6.3321 (1.3); 6.3127 (1.4); 4.0109 (1.0); 3.3369 (6660.2); 2.8910 (3.5); 2.7308 (3.1); 2.7090 (1.2); 2.6806 (5.5); 2.6760 (11.6); 2.6714 (16.0); 2.6668 (11.6); 2.6622 (5.6); 2.5249 (47.1); 2.5203 (67.1); 2.5115 (928.7); 2.5070 (1922.4); 2.5024 (2524.0); 2.4978 (1757.2); 2.4932 (807.0); 2.4116 (15.4); 2.3945 (0.9); 2.3676 (2.3); 2.3384 (5.0); 2.3338 (10.9); 2.3292 (15.4); 2.3246 (10.8); 2.3200 (4.9); 1.2399 (5.5); 0.8532 (1.7); 0.8354 (0.8); −0.0001 (6.1) |
| I.0110: $^1$H-NMR(400.2 MHz, $d_6$-DMSO):<br>δ = 9.0613 (0.8); 7.3391 (7.1); 7.3281 (7.8); 7.2858 (0.7); 7.2756 (1.0); 7.2646 (1.0); 7.2545 (0.5); 5.1015 (0.3); 5.0820 (0.6); 5.0630 (0.3); 3.3311 (10.9); 3.2607 (0.4); 3.2430 (0.4); 3.2271 (1.3); 3.2091 (1.5); 3.2058 (1.5); 3.1831 (1.2); 3.1720 (0.4); 3.1495 (0.4); 2.8910 (0.5); 2.7331 (0.4); 2.7318 (0.4); 2.5211 (0.4); 2.5124 (6.2); 2.5079 (12.9); 2.5033 (16.8); 2.4987 (11.7); 2.4941 (5.4); 2.2719 (16.0); 2.2562 (0.9); −0.0002 (1.8) |
| I.0111: $^1$H-NMR(400.2 MHz, $d_6$-DMSO):<br>δ = 8.9068 (1.0); 8.3152 (0.3); 4.2759 (8.6); 3.3300 (6.0); 2.5130 (4.5); 2.5085 (9.4); 2.5039 (12.2); 2.4993 (8.5); 2.4947 (3.9); 2.4281 (16.0); 2.4220 (0.5); −0.0002 (1.3) |
| I.0112: $^1$H-NMR(400.2 MHz, $d_6$-DMSO):<br>δ = 9.1674 (1.3); 3.3293 (9.4); 2.5214 (0.4); 2.5127 (5.3); 2.5082 (10.9); 2.5036 (14.3); 2.4990 (9.9); 2.4944 (4.5); 2.3995 (16.0); 1.5756 (1.0); 1.5615 (2.4); 1.5544 (2.4); 1.5411 (1.2); 1.3001 (1.3); 1.2865 (2.3); 1.2796 (2.4); 1.2652 (1.0); −0.0002 (1.2) |
| I.0113: $^1$H-NMR(400.2 MHz, $d_6$-DMSO):<br>δ = 9.6145 (0.9); 9.5952 (0.9); 7.5494 (1.0); 7.5484 (1.0); 7.5445 (1.6); 7.5406 (0.5); 7.5289 (2.2); 7.5270 (2.6); 7.5255 (2.5); 7.5198 (0.4); 7.4973 (1.0); 7.4939 (1.4); 7.4887 (0.5); 7.4763 (3.0); 7.4721 (1.1); 7.4611 (0.7); 7.4578 (1.6); 7.4442 (0.7); 7.4402 (1.2); 7.4368 (0.7); 7.4295 (0.4); 7.4230 (1.2); 7.4049 (0.3); 6.3340 (1.4); 6.3148 (1.3); 3.3335 (23.2); 2.5208 (0.4); 2.5120 (6.0); 2.5075 (12.5); 2.5029 (16.5); 2.4983 (11.5); 2.4937 (5.3); 2.4126 (16.0) |
| I.0114: $^1$H-NMR(400.2 MHz, $d_6$-DMSO):<br>δ = 9.0454 (0.6); 7.3388 (6.9); 7.3277 (7.4); 7.3189 (0.4); 7.2856 (0.7); 7.2753 (1.0); 7.2643 (0.9); 7.2542 (0.5); 5.0832 (0.4); 5.0743 (0.4); 3.3402 (37.3); 3.2601 (0.4); 3.2424 (0.4); 3.2265 (1.3); 3.2064 (1.7); 3.1835 (1.2); 3.1723 (0.4); 3.1499 (0.4); 2.8914 (0.7); 2.7333 (0.6); 2.7319 (0.6); 2.5263 (0.3); 2.5216 (0.4); 2.5130 (6.4); 2.5084 (13.4); 2.5038 (17.6); 2.4992 (12.4); 2.4946 (5.7); 2.2761 (16.0) |
| I.0115: $^1$H-NMR(400.2 MHz, $d_6$-DMSO):<br>δ = 9.1156 (10.0); 7.9536 (0.7); 3.3291 (83.8); 2.8928 (5.6); 2.7340 (4.5); 2.7328 (4.7); 2.6776 (0.4); 2.6731 (0.6); 2.6684 (0.4); 2.5266 (1.8); 2.5219 (2.6); 2.5132 (37.9); 2.5087 (77.8); 2.5042 (101.1); 2.4995 (70.0); 2.4949 (32.0); 2.3354 (0.4); 2.3309 (0.6); 2.3263 (0.4); 1.5824 (7.0); 1.5681 (15.7); 1.5609 (15.7); 1.5475 (8.2); 1.5074 (0.7); 1.3606 (0.7); 1.3206 (8.5); 1.3069 (15.2); 1.2999 (16.0); 1.2854 (6.6); 1.2472 (0.5); 1.2386 (0.8); 0.0080 (0.3); −0.0002 (10.4) |
| I.0116: $^1$H-NMR(400.1 MHz, CDCl3):<br>δ = 18.3930 (0.4); 15.5794 (0.4); 14.3525 (0.4); 7.5187 (1.0); 7.3085 (0.5); 7.2598 (157.1); 7.2243 (1.9); 7.2063 (0.9); 6.9955 (0.9); 6.5114 (6.8); 6.4962 (7.3); 3.5783 (0.5); 3.5212 (0.4); 2.9106 (6.5); 2.9035 (5.4); 2.8980 (8.2); 2.8886 (10.4); 2.8830 (10.4); 2.8765 (16.0); 2.8649 (12.2); 2.8555 (11.1); 2.8436 (10.2); 2.6797 (1.0); 2.6648 (0.4); 2.6474 (0.4); 2.4937 (6.1); 2.4695 (14.5); 2.4484 (12.7); 2.4404 (14.7); 2.4160 (8.5); 2.3703 (0.6); 2.3559 (0.6); 2.3355 (2.2); 2.3138 (4.6); 2.3060 (3.2); 2.2930 (6.3); 2.2845 (7.6); 2.2723 (4.3); 2.2636 (10.0); 2.2511 (2.1); 2.2427 (5.8); 2.2212 (1.6); 2.1977 (2.6); 2.1857 (4.5); 2.1735 (5.7); 2.1620 (8.0); 2.1564 (4.7); 2.1504 (6.0); 2.1452 (5.1); 2.1385 (4.8); 2.1328 (5.8); 2.1209 (4.0); 2.1087 (2.6); 2.0969 (1.2); 2.0662 (0.5); 2.0055 (10.3); 1.9710 (0.6); 1.9197 (0.4); 1.5875 (0.5); 1.5400 (131.7); 1.4529 (0.8); 1.4079 (0.5); 1.2934 (1.1); 1.2784 (1.4); 1.2547 (1.8); 1.2198 (0.5); 0.1459 (0.9); −0.0002 (218.1); −0.0345 (2.8); −0.0560 (1.2); −0.1324 (0.5); −0.1491 (1.2); −3.3106 (0.4); −3.7191 (0.4) |
| I.0117: $^1$H-NMR(400.2 MHz, $d_6$-DMSO):<br>δ = 9.5827 (3.9); 9.5632 (3.9); 7.9532 (2.0); 7.9247 (0.8); 7.5450 (5.5); 7.5403 (7.9); 7.5360 (2.6); 7.5264 (6.8); 7.5243 (11.3); 7.5228 (13.2); 7.5211 (12.4); 7.5150 (1.5); 7.5006 (0.3); 7.4870 (4.6); 7.4831 (6.6); 7.4780 (2.5); 7.4657 (15.2); 7.4615 (5.1); 7.4507 (4.3); 7.4473 (8.4); 7.4408 (1.4); 7.4369 (3.8); 7.4331 (6.8); 7.4293 (3.5); 7.4224 (1.9); 7.4156 (6.0); 7.4074 (1.1); 7.4010 (0.9); 7.3976 (1.5); 7.3945 (0.7); 6.3327 (7.1); 6.3133 (7.1); 3.3297 (92.8); 2.8915 (16.0); 2.7331 (13.4); 2.7318 (13.2); 2.6767 (0.4); 2.6721 (0.6); 2.6675 (0.4); 2.5257 (1.9); 2.5210 (2.7); 2.5123 (37.8); 2.5078 (78.2); 2.5032 (102.3); 2.4986 (71.0); 2.4940 (32.3); 2.3346 (0.5); 2.3300 (0.6); 2.3254 (0.4); 1.2392 (1.1); −0.0002 (10.4) |
| I.0118: $^1$H-NMR(400.2 MHz, $d_6$-DMSO):<br>δ = 9.0017 (1.1); 8.9837 (1.1); 7.3323 (10.3); 7.3213 (16.0); 7.3113 (0.8); 7.2914 (0.4); 7.2815 (1.2); 7.2719 (1.3); 7.2699 (1.4); 7.2598 (1.6); 7.2519 (0.5); 7.2479 (0.8); 7.2385 (0.3); 5.1216 (0.4); 5.1020 (1.2); 5.0826 (1.2); 5.0632 (0.4); 3.3341 (54.5); 3.2493 (0.4); 3.2344 (2.5); 3.2282 (2.5); 3.2158 (2.2); 3.2070 (2.3); 3.1948 (0.4); 3.1735 (0.4); 2.8915 (1.1); 2.7335 (0.9); 2.7322 (1.0); 2.5263 (0.5); 2.5216 (0.8); 2.5129 (12.4); 2.5084 (26.0); 2.5039 (34.4); 2.4992 (24.3); 2.4946 (11.4); −0.0002 (0.5) |
| I.0119: $^1$H-NMR(400.2 MHz, $d_6$-DMSO):<br>δ = 8.8814 (0.9); 8.8642 (0.9); 3.7029 (1.1); 3.6857 (1.2); 3.6793 (1.4); 3.6708 (16.0); 3.6622 (1.2); 3.3349 (32.8); 2.5210 (0.4); 2.5123 (4.9); 2.5078 (9.8); 2.5032 (12.9); 2.4986 (9.2); 2.4940 (4.3); 2.3998 (15.5); 2.3935 (0.6); 2.3832 (0.5); 1.2397 (0.4); 1.2316 (0.4); 1.2280 (0.3); 1.2194 (0.6); 1.2078 (0.6); 1.1997 (0.4); 1.1959 (0.6); 1.1877 (0.3); 1.1838 (0.4); 0.6207 (0.6); 0.6115 (0.6); 0.6072 (0.5); 0.5998 (0.5); 0.5969 (0.6); 0.5913 (0.3); 0.5858 (0.4); 0.5758 (0.4); 0.5477 (0.4); 0.5440 (0.4); 0.5342 (0.6); 0.5273 (0.4); 0.5239 (0.6); 0.5139 (0.7); 0.4928 (0.4); 0.4882 (0.3); 0.4756 (0.5); 0.4656 (0.7); 0.4534 (0.8); 0.4423 (0.6); 0.3900 (0.4); 0.3787 (0.6); 0.3668 (0.7); 0.3544 (0.6); 0.3445 (0.4) |
| I.0120: $^1$H-NMR(400.2 MHz, $d_6$-DMSO):<br>δ = 8.8602 (0.9); 8.8430 (0.9); 3.7001 (1.2); 3.6829 (1.3); 3.6763 (1.7); 3.6703 (16.0); 3.6594 (1.4); 3.3358 (29.5); 2.5124 (4.0); 2.5079 (8.3); 2.5033 (11.1); 2.4988 (8.0); 2.4942 (3.8); 2.3991 (15.6); 1.2415 (0.4); 1.2335 (0.4); 1.2299 (0.4); 1.2214 (0.6); 1.2182 (0.4); 1.2096 (0.6); 1.2061 (0.4); 1.2011 (0.4); 1.1978 (0.6); 1.1880 (0.4); 1.1862 (0.4); 0.6202 (0.6); 0.6108 (0.6); 0.6064 (0.6); 0.5993 (0.5); 0.5962 (0.6); 0.5908 (0.4); 0.5852 (0.4); 0.5752 (0.4); 0.5567 (0.3); 0.5469 (0.4); 0.5431 (0.5); 0.5333 (0.6); 0.5266 (0.4); 0.5231 (0.6); 0.5129 (0.7); 0.4919 (0.4); 0.4868 (0.3); 0.4742 (0.5); 0.4642 (0.7); 0.4519 (0.8); 0.4409 (0.6); 0.3886 (0.4); 0.3773 (0.6); 0.3654 (0.7); 0.3529 (0.6); 0.3430 (0.4) |
| I.0121: $^1$H-NMR(400.2 MHz, $d_6$-DMSO):<br>δ = 8.6628 (0.7); 8.6457 (0.7); 3.7207 (0.9); 3.7032 (1.0); 3.6971 (1.0); 3.6796 (1.1); 3.6652 (16.0); 3.3376 (33.1); 2.8933 (0.7); 2.7344 (0.6); 2.7331 (0.6); 2.5136 (4.4); 2.5091 (9.1); 2.5044 (12.2); 2.4998 (8.8); 2.4953 (4.2); 1.2950 (0.3); 1.2864 (0.6); 1.2747 (0.6); 1.2661 (0.4); 1.2628 (0.6); 1.2546 (0.3); 1.2510 (0.4); 1.2426 (0.4); 0.6193 (0.6); 0.6100 (0.6); 0.6057 (0.5); 0.5986 (0.5); 0.5951 (0.6); 0.5901 (0.4); 0.5842 (0.4); 0.5741 (0.3); 0.5358 (0.4); 0.5320 (0.4); 0.5220 (0.6); 0.5155 (0.4); 0.5119 (0.6); 0.5016 (0.7); 0.4807 (0.6); 0.4674 (0.5); 0.4577 (0.7); 0.4456 (0.8); 0.4342 (0.6); 0.3742 (0.3); 0.3632 (0.5); 0.3595 (0.4); 0.3511 (0.7); 0.3382 (0.6); 0.3286 (0.4) |

TABLE A-(I)-continued

NMR peak lists of compounds according to formula (I)

I.0122: $^1$H-NMR(400.2 MHz, $d_6$-DMSO):
δ = 8.6846 (1.3); 8.6672 (1.3); 4.4099 (1.2); 4.3919 (1.9); 4.3738 (1.2); 4.1425 (0.7); 4.1356 (0.9); 4.1248 (2.1); 4.1186 (2.2); 4.1071 (2.2); 4.1009 (2.2); 4.0896 (0.9); 4.0832 (0.7); 3.3280 (11.8); 2.5029 (17.9); 2.4990 (13.7); 2.3994 (16.0); 2.3826 (0.5); 1.3802 (7.5); 1.3619 (7.4); 1.2382 (0.6); 1.2123 (4.6); 1.1947 (9.2); 1.1768 (4.5); −0.0002 (1.7)

I.0123: $^1$H-NMR(400.2 MHz, $d_6$-DMSO):
δ = 8.5956 (0.9); 8.5767 (0.9); 4.2971 (1.0); 4.2789 (1.8); 4.2606 (1.0); 3.6631 (16.0); 3.3260 (11.3); 2.5250 (0.4); 2.5204 (0.6); 2.5117 (6.7); 2.5072 (13.5); 2.5026 (17.6); 2.4980 (12.6); 2.4935 (6.0); 2.3787 (15.4); 2.3629 (0.6); 1.9348 (0.4); 1.9301 (0.3); 1.9241 (0.4); 1.9185 (0.4); 1.9129 (0.4); 1.9068 (0.3); 1.9022 (0.4); 1.4775 (0.4); 1.4666 (0.4); 1.4622 (0.5); 1.4516 (0.4); 1.4435 (0.4); 1.4329 (0.4); 1.2887 (0.4); 1.2701 (0.6); 1.2671 (0.5); 1.2544 (0.5); 1.2484 (0.6); 1.2367 (0.8); 1.2144 (0.3); 0.9014 (5.9); 0.8842 (6.1); 0.8798 (3.6); 0.8611 (6.2); 0.8425 (2.5); −0.0002 (2.6)

I.0124: $^1$H-NMR(400.2 MHz, $d_6$-DMSO):
δ = 8.8085 (1.2); 8.7897 (1.2); 8.1414 (0.5); 8.0866 (2.3); 7.9539 (0.9); 7.0959 (0.4); 7.0703 (2.9); 4.7052 (0.5); 4.6913 (0.6); 4.6852 (1.0); 4.6719 (0.9); 4.6661 (0.7); 4.6521 (0.5); 3.6512 (16.0); 3.1306 (0.3); 3.1069 (1.6); 3.0974 (1.9); 3.0774 (1.4); 3.0405 (0.3); 2.8922 (6.5); 2.7332 (5.4); 2.7322 (5.4); 2.5266 (0.5); 2.5221 (0.7); 2.5133 (8.2); 2.5089 (16.7); 2.5044 (22.0); 2.4998 (16.0); 2.4953 (7.9); 2.3453 (16.0); 2.3309 (1.0); 1.2392 (0.5); −0.0002 (3.2)

I.0125: $^1$H-NMR(400.2 MHz, $d_6$-DMSO):
δ = 8.6565 (1.3); 8.6378 (1.3); 4.6392 (0.6); 4.6280 (0.8); 4.6214 (1.2); 4.6101 (1.2); 4.6038 (0.8); 4.5925 (0.6); 4.1604 (0.7); 4.1533 (0.8); 4.1426 (2.1); 4.1362 (2.2); 4.1249 (2.2); 4.1185 (2.1); 4.1074 (0.9); 4.1008 (0.7); 3.7499 (0.8); 3.7327 (0.8); 3.7247 (1.8); 3.7077 (1.7); 3.6878 (1.7); 3.6768 (1.8); 3.6627 (0.9); 3.6516 (0.7); 3.3266 (10.8); 3.2797 (18.0); 2.5066 (16.0); 2.5024 (20.0); 2.4981 (15.0); 2.3976 (16.0); 2.3808 (0.5); 1.2137 (4.5); 1.1960 (9.2); 1.1782 (4.4); −0.0002 (2.1)

I.0126: $^1$H-NMR(400.2 MHz, $d_6$-DMSO):
δ = 9.2298 (3.8); 8.6284 (1.3); 8.6093 (1.3); 7.0662 (3.6); 7.0450 (4.0); 6.6831 (0.5); 6.6762 (4.5); 6.6551 (4.2); 4.4907 (0.4); 4.4773 (0.6); 4.4714 (0.6); 4.4656 (0.7); 4.4581 (0.6); 4.4523 (0.6); 4.4464 (0.6); 4.4330 (0.5); 4.1295 (0.8); 4.1267 (0.9); 4.1117 (2.5); 4.1091 (2.7); 4.0939 (2.7); 4.0915 (2.6); 4.0759 (1.0); 3.3294 (19.2); 3.0481 (0.6); 3.0349 (0.7); 3.0136 (1.1); 3.0006 (1.0); 2.9331 (1.1); 2.9077 (1.1); 2.8986 (0.7); 2.8732 (0.6); 2.5248 (0.6); 2.5200 (0.9); 2.5111 (12.3); 2.5069 (25.0); 2.5024 (33.1); 2.4978 (24.6); 2.4934 (12.4); 2.2471 (16.0); 2.2319 (0.7); 1.2390 (0.5); 1.1765 (4.8); 1.1587 (10.1); 1.1410 (4.7); −0.0002 (4.5)

I.0127: $^1$H-NMR(300.2 MHz, $d_6$-DMSO):
δ = 8.7180 (1.6); 8.6930 (1.6); 7.5112 (0.7); 7.4927 (1.3); 7.4742 (0.7); 4.4510 (0.4); 4.4337 (0.6); 4.4203 (0.8); 4.4087 (0.7); 4.4031 (0.6); 4.3955 (0.6); 4.3779 (0.4); 4.0597 (0.4); 4.0360 (0.4); 3.6886 (16.0); 3.3629 (14.5); 3.1704 (0.7); 3.1482 (1.8); 3.1275 (1.8); 3.1053 (0.7); 2.5340 (1.0); 2.5282 (2.2); 2.5222 (3.0); 2.5163 (2.2); 2.5106 (1.0); 2.4517 (0.4); 2.4210 (17.3); 2.4047 (0.7); 2.0086 (1.8); 1.8843 (0.4); 1.8577 (0.7); 1.8401 (0.6); 1.8142 (0.5); 1.7873 (0.5); 1.7653 (0.6); 1.7561 (0.5); 1.7371 (0.4); 1.6125 (0.4); 1.5876 (1.0); 1.5629 (1.2); 1.5399 (0.8); 1.2175 (0.5); 1.1938 (1.0); 1.1701 (0.5); 0.0183 (3.2)

I.0128: $^1$H-NMR(400.2 MHz, $d_6$-DMSO):
δ = 10.8798 (1.6); 8.6242 (1.5); 8.6055 (1.5); 8.3155 (0.7); 7.5396 (1.9); 7.5200 (2.0); 7.3531 (2.2); 7.3330 (2.6); 7.2052 (2.7); 7.1997 (2.7); 7.0891 (1.0); 7.0715 (2.0); 7.0536 (1.2); 7.0515 (1.2); 7.0059 (1.4); 7.0041 (1.4); 6.9863 (2.1); 6.9688 (0.9); 6.9669 (0.9); 4.6126 (0.5); 4.5989 (0.7); 4.5934 (0.7); 4.5895 (0.9); 4.5802 (0.8); 4.5760 (0.8); 4.5708 (0.8); 4.5571 (0.5); 4.1240 (1.2); 4.1064 (4.0); 4.0887 (4.2); 4.0710 (1.4); 3.3310 (17.4); 3.2988 (0.6); 3.2853 (0.7); 3.2623 (1.4); 3.2490 (1.3); 3.2185 (1.4); 3.1951 (1.3); 3.1821 (0.6); 3.1587 (0.6); 2.8892 (2.0); 2.7317 (1.8); 2.5239 (0.6); 2.5106 (10.2); 2.5064 (19.7); 2.5019 (25.4); 2.4974 (18.6); 2.2350 (16.0); 2.2186 (0.8); 1.2380 (0.7); 1.1555 (5.2); 1.1378 (10.8); 1.1200 (5.0); −0.0002 (2.8)

I.0129: $^1$H-NMR(400.2 MHz, $d_6$-DMSO):
δ = 8.7842 (1.4); 8.7655 (1.4); 8.0364 (2.8); 7.0494 (3.3); 4.6976 (0.5); 4.6780 (1.2); 4.6641 (1.0); 4.6592 (0.9); 4.6447 (0.5); 3.6484 (16.0); 3.1209 (0.4); 3.0976 (1.8); 3.0910 (2.0); 3.0853 (1.8); 3.0707 (1.6); 3.0337 (0.3); 2.5265 (0.5); 2.5219 (0.7); 2.5087 (17.0); 2.5043 (22.8); 2.4999 (18.0); 2.3483 (15.8); 2.3325 (0.4); 1.2385 (0.5); −0.0002 (2.6)

I.0130: $^1$H-NMR(400.2 MHz, $d_6$-DMSO):
δ = 9.2283 (5.1); 8.6060 (1.5); 8.5868 (1.5); 7.0663 (3.6); 7.0452 (4.0); 6.6829 (0.5); 6.6761 (4.5); 6.6549 (4.2); 4.4890 (0.5); 4.4758 (0.6); 4.4698 (0.6); 4.4640 (0.7); 4.4566 (0.7); 4.4509 (0.6); 4.4448 (0.6); 4.4315 (0.5); 4.1294 (0.7); 4.1265 (0.9); 4.1116 (2.5); 4.1089 (2.7); 4.0937 (2.7); 4.0913 (2.7); 4.0758 (0.9); 3.3320 (17.8); 3.0476 (0.6); 3.0344 (0.7); 3.0130 (1.1); 2.9999 (1.0); 2.9359 (1.1); 2.9106 (1.1); 2.9015 (0.7); 2.8761 (0.7); 2.5250 (0.5); 2.5115 (9.8); 2.5072 (19.6); 2.5026 (25.8); 2.4981 (19.1); 2.4938 (9.6); 2.2517 (16.0); 1.2389 (0.6); 1.1764 (4.9); 1.1586 (10.1); 1.1409 (4.7); −0.0002 (3.3)

I.0131: $^1$H-NMR(500.1 MHz, $d_6$-DMSO):
δ = 8.6645 (0.9); 8.6497 (0.9); 7.9597 (1.8); 7.4667 (0.8); 4.4063 (0.6); 4.3967 (0.5); 3.6896 (0.3); 3.6760 (9.3); 3.3190 (16.0); 3.1431 (0.6); 3.1305 (1.3); 3.1187 (1.3); 3.1061 (0.6); 2.8983 (9.2); 2.7388 (8.7); 2.5479 (0.7); 2.5093 (7.9); 2.5070 (7.7); 2.4093 (9.4); 1.8617 (0.4); 1.8476 (0.5); 1.8364 (0.4); 1.7638 (0.4); 1.7523 (0.5); 1.7453 (0.4); 1.7346 (0.4); 1.5623 (0.8); 1.5510 (0.9); 1.5325 (0.5)

I.0132: $^1$H-NMR(400.2 MHz, $d_6$-DMSO):
δ = 10.8792 (1.8); 8.6019 (1.6); 8.5834 (1.6); 8.3156 (1.0); 7.5387 (2.0); 7.5192 (2.2); 7.3520 (2.3); 7.3319 (2.6); 7.2038 (3.0); 7.1987 (2.8); 7.0886 (1.0); 7.0709 (2.1); 7.0526 (1.3); 7.0511 (1.3); 7.0035 (1.5); 6.9855 (2.2); 6.9665 (1.0); 4.6086 (0.5); 4.5948 (0.8); 4.5856 (0.9); 4.5762 (0.9); 4.5725 (0.9); 4.5672 (0.8); 4.5534 (0.6); 4.1230 (1.3); 4.1054 (4.1); 4.0877 (4.2); 4.0700 (1.4); 3.3307 (16.7); 3.3066 (0.5); 3.2975 (0.6); 3.2840 (0.7); 3.2609 (1.5); 3.2477 (1.4); 3.2188 (1.4); 3.1954 (1.4); 3.1823 (0.7); 3.1590 (0.6); 2.5057 (23.6); 2.5016 (29.7); 2.4973 (22.5); 2.2390 (16.0); 1.2379 (0.8); 1.1548 (4.9); 1.1371 (9.9); 1.1193 (4.7); −0.0002 (3.2)

I.0133: $^1$H-NMR(400.2 MHz, $d_6$-DMSO):
δ = 8.5110 (1.3); 8.4940 (1.3); 4.4515 (0.4); 4.4335 (1.6); 4.4156 (2.5); 4.3976 (1.6); 4.3796 (0.4); 4.1491 (0.3); 4.1399 (1.1); 4.1352 (1.2); 4.1315 (0.5); 4.1221 (3.6); 4.1175 (3.7); 4.1043 (3.7); 4.0998 (3.6); 4.0902 (0.5); 4.0865 (1.3); 4.0821 (1.2); 4.0727 (0.3); 3.3280 (21.6); 2.5262 (0.6); 2.5215 (0.9); 2.5127 (11.3); 2.5084 (22.5); 2.5038 (29.3); 2.4992 (21.3); 2.4948 (10.4); 1.3940 (11.3); 1.3758 (11.2); 1.2386 (1.0); 1.2061 (7.8); 1.1883 (16.0); 1.1706 (7.5); −0.0002 (3.9)

I.0134: $^1$H-NMR(400.2 MHz, $d_6$-DMSO):
δ = 8.7326 (0.8); 8.7268 (0.8); 8.7142 (0.9); 8.7089 (0.8); 8.2149 (0.5); 8.1408 (0.7); 8.1203 (2.5); 7.9539 (1.4); 7.1061 (0.8); 7.0828 (3.2); 4.7384 (0.5); 4.7221 (1.4); 4.7044 (1.4); 4.6879 (0.5); 3.6537 (0.8); 3.6389 (16.0); 3.6235 (1.3); 3.5797 (1.2); 3.1278 (3.3); 3.1118 (3.2); 2.8926 (9.3); 2.7329 (8.1); 2.5267 (0.8); 2.5092 (24.0); 2.5048 (31.0); 2.5003 (23.0); 1.2387 (0.6); −0.0002 (3.5)

I.0135: $^1$H-NMR(400.2 MHz, $d_6$-DMSO):
δ = 8.2433 (1.4); 8.2383 (1.4); 8.2252 (1.4); 8.2201 (1.4); 4.6685 (0.9); 4.6574 (1.3); 4.6520 (1.5); 4.6402 (1.6); 4.6351 (1.2); 4.6241 (0.9); 4.1752 (0.5); 4.1660 (1.2); 4.1591 (1.5); 4.1483 (3.6); 4.1418 (3.8); 4.1305 (3.8); 4.1241 (3.6); 4.1130 (1.4); 4.1065 (1.2); 4.0970 (0.4); 3.7856 (1.6); 3.7700 (1.6); 3.7604 (3.0); 3.7449 (2.8); 3.7099 (2.8); 3.6994 (3.0); 3.6847 (1.7); 3.6742 (1.4); 3.3285 (14.7); 3.2790 (31.0); 2.5083 (23.6); 2.5039 (30.1); 2.4996 (22.5); 1.2384 (0.9); 1.2104 (8.0); 1.1927 (16.0); 1.1750 (7.6); −0.0002 (3.1)

I.0136: $^1$H-NMR(400.2 MHz, $d_6$-DMSO):
δ = 9.2354 (8.5); 8.3388 (1.4); 8.3218 (1.5); 7.0449 (5.5); 7.0238 (6.2); 6.6763 (0.7); 6.6694 (6.9); 6.6482 (6.4); 4.5335 (0.7); 4.5118 (1.3); 4.4983 (1.2); 4.4924 (1.1); 4.4781 (0.7); 4.1236 (1.6); 4.1171 (0.4); 4.1060 (4.9); 4.0893 (5.0); 4.0788 (0.4); 4.0715

TABLE A-(I)-continued

NMR peak lists of compounds according to formula (I)

(1.8); 3.3334 (23.0); 3.0534 (0.6); 3.0393 (0.8); 3.0186 (2.1); 3.0044 (2.0); 2.9963 (2.2); 2.9736 (1.9); 2.9617 (0.7); 2.9389 (0.7); 2.8913 (0.7); 2.7322 (0.6); 2.5262 (0.6); 2.5215 (0.9); 2.5126 (12.4); 2.5082 (25.5); 2.5037 (33.8); 2.4992 (25.5); 2.4948 (13.1); 1.2380 (0.8); 1.1728 (7.7); 1.1550 (16.0); 1.1373 (7.4); −0.0002 (4.6)

I.0137: $^1$H-NMR(400.2 MHz, $d_6$-DMSO):
δ = 10.8988 (2.0); 8.2840 (1.2); 8.2794 (1.2); 8.2656 (1.2); 8.2614 (1.2); 7.5207 (2.4); 7.5010 (2.6); 7.3482 (2.9); 7.3280 (3.4); 7.2064 (3.5); 7.2006 (3.4); 7.0875 (1.2); 7.0850 (1.3); 7.0698 (2.1); 7.0675 (2.6); 7.0499 (1.6); 7.0472 (1.6); 6.9953 (1.8); 6.9930 (1.9); 6.9755 (2.8); 6.9735 (2.1); 6.9581 (1.3); 6.9558 (1.2); 4.6509 (0.6); 4.6316 (1.5); 4.6171 (1.3); 4.6129 (1.2); 4.5979 (0.7); 4.1163 (2.0); 4.0986 (6.6); 4.0808 (6.7); 4.0630 (2.1); 3.3322 (24.4); 3.3180 (0.4); 3.3036 (0.5); 3.2810 (2.3); 3.2725 (2.6); 3.2673 (2.4); 3.2526 (2.0); 3.2362 (0.4); 3.2161 (0.4); 2.8898 (0.5); 2.7328 (0.5); 2.7316 (0.5); 2.5252 (0.7); 2.5205 (1.0); 2.5118 (12.4); 2.5074 (24.8); 2.5028 (32.2); 2.4982 (23.0); 2.4936 (10.9); 1.2374 (0.9); 1.1549 (7.6); 1.1371 (16.0); 1.1194 (7.2); −0.0002 (4.8)

I.0138: $^1$H-NMR(300.2 MHz, CDCl3):
δ = 7.2979 (0.5); 6.6913 (0.5); 6.6655 (0.5); 4.8666 (0.5); 4.8565 (1.1); 4.8463 (0.6); 4.8403 (0.6); 4.8300 (1.1); 4.8199 (0.5); 4.3289 (0.5); 4.3201 (0.6); 4.3051 (1.7); 4.2966 (1.7); 4.2812 (1.7); 4.2729 (1.7); 4.2575 (0.6); 4.2492 (0.6); 3.9312 (1.0); 3.9214 (1.0); 3.8995 (1.4); 3.8897 (1.4); 3.7601 (1.4); 3.7495 (1.4); 3.7284 (1.0); 3.7178 (1.0); 3.3859 (16.0); 2.5495 (14.9); 1.3522 (3.9); 1.3284 (7.9); 1.3046 (3.8); 0.0206 (0.5)

I.0139: $^1$H-NMR(300.2 MHz, CDCl3):
δ = 7.6850 (1.7); 7.2985 (21.4); 2.9558 (2.3); 2.9309 (7.2); 2.9061 (7.4); 2.8814 (2.4); 1.8526 (2.0); 1.8359 (5.7); 1.8244 (5.9); 1.8090 (2.5); 1.5805 (10.5); 1.4349 (2.6); 1.4196 (5.9); 1.4081 (5.9); 1.3913 (2.1); 1.3032 (8.0); 1.2784 (16.0); 1.2536 (7.3); 0.0483 (1.0); 0.0375 (29.1); 0.0266 (1.0)

I.0140: $^1$H-NMR(300.2 MHz, CDCl3):
δ = 7.2983 (0.5); 6.5598 (0.5); 6.5377 (0.5); 4.7256 (1.1); 4.7019 (1.6); 4.6782 (1.1); 4.2994 (1.1); 4.2757 (3.4); 4.2519 (3.6); 4.2281 (1.2); 3.4910 (0.4); 2.5251 (16.0); 1.5374 (7.2); 1.5136 (7.0); 1.3527 (4.3); 1.3289 (8.6); 1.3051 (4.2); 0.0166 (0.4)

I.0141: $^1$H-NMR(400.1 MHz, $d_6$-DMSO):
δ = 8.3105 (1.7); 8.2928 (1.7); 4.3314 (1.4); 4.3132 (2.5); 4.2953 (1.3); 3.6741 (16.0); 3.3138 (69.7); 2.5105 (12.7); 1.9543 (1.2); 1.5032 (0.5); 1.4882 (0.8); 1.4725 (1.1); 1.4569 (1.0); 1.4418 (0.7); 1.2643 (0.7); 1.2457 (1.2); 1.2284 (1.1); 1.2112 (0.9); 1.1932 (0.6); 0.8996 (8.4); 0.8851 (10.1); 0.8718 (8.5); 0.8529 (3.7)

I.0142: $^1$H-NMR(500.1 MHz, $d_6$-DMSO):
δ = 8.6052 (0.6); 8.5938 (1.2); 8.5823 (0.6); 4.1487 (1.4); 4.1345 (4.3); 4.1202 (4.3); 4.1060 (1.4); 4.0287 (4.6); 4.0170 (4.6); 3.3083 (16.0); 2.5041 (7.4); 2.5006 (10.1); 2.4971 (7.5); 1.2193 (4.6); 1.2051 (9.4); 1.1909 (4.5); −0.0002 (6.5)

I.0143: $^1$H-NMR(400.2 MHz, $d_6$-DMSO):
δ = 8.3332 (0.6); 8.3204 (1.2); 8.3124 (1.0); 4.1005 (2.2); 4.0828 (7.0); 4.0650 (7.0); 4.0472 (2.3); 3.5247 (1.2); 3.5078 (3.0); 3.4933 (3.0); 3.4765 (1.2); 3.3296 (23.2); 2.5926 (3.1); 2.5756 (6.6); 2.5584 (2.9); 2.5275 (0.4); 2.5228 (0.6); 2.5141 (9.0); 2.5096 (18.3); 2.5051 (23.9); 2.5004 (17.2); 2.4959 (8.2); 1.2021 (7.9); 1.1844 (16.0); 1.1665 (7.6); −0.0002 (1.2)

I.0144: $^1$H-NMR(400.2 MHz, $d_6$-DMSO):
δ = 9.0520 (4.0); 4.1345 (2.5); 4.1168 (7.6); 4.0990 (7.6); 4.0814 (2.6); 3.9667 (0.4); 3.9489 (0.4); 3.9298 (0.3); 3.9109 (0.3); 3.3298 (42.1); 3.2005 (0.8); 3.0623 (0.5); 3.0546 (0.4); 3.0171 (0.4); 2.8936 (2.1); 2.7345 (1.9); 2.6730 (0.4); 2.6685 (0.4); 2.6313 (0.4); 2.5834 (1.5); 2.5676 (2.0); 2.5618 (2.5); 2.5505 (2.7); 2.5465 (2.7); 2.5365 (3.2); 2.5283 (3.4); 2.5086 (30.3); 2.5041 (37.8); 2.4997 (27.6); 2.3706 (2.1); 2.3386 (3.0); 2.3154 (4.0); 2.2955 (3.5); 2.2864 (3.7); 2.2641 (2.6); 2.1977 (1.2); 2.0630 (0.4); 2.0525 (0.4); 2.0430 (0.4); 2.0215 (0.4); 2.0072 (0.6); 1.9934 (1.0); 1.9796 (1.5); 1.9706 (1.5); 1.9615 (2.2); 1.9562 (2.2); 1.9411 (2.8); 1.9338 (1.5); 1.9197 (1.6); 1.8990 (0.6); 1.8929 (0.5); 1.8238 (0.3); 1.8086 (0.4); 1.7830 (0.4); 1.7710 (0.4); 1.2390 (0.3); 1.1898 (8.0); 1.1721 (16.0); 1.1544 (7.6); 1.0391 (0.6); 1.0294 (0.6); 1.0122 (0.6); 0.9943 (0.5); 0.9807 (0.4); 0.9037 (0.4); 0.8830 (0.4); 0.8721 (0.3); −0.0002 (1.1)

I.0145: $^1$H-NMR(400.2 MHz, $d_6$-DMSO):
δ = 8.4355 (1.3); 8.4160 (1.4); 8.3124 (0.4); 4.3038 (1.7); 4.2882 (2.0); 4.2842 (2.0); 4.2687 (1.8); 4.2206 (0.3); 4.2028 (1.1); 4.1936 (0.8); 4.1850 (1.1); 4.1758 (2.7); 4.1672 (0.4); 4.1627 (1.0); 4.1580 (2.8); 4.1450 (2.9); 4.1403 (1.1); 4.1358 (0.4); 4.1273 (2.8); 4.1180 (1.1); 4.1096 (0.9); 4.1003 (1.1); 4.0826 (0.4); 3.3298 (39.2); 2.5268 (0.6); 2.5221 (0.9); 2.5134 (11.6); 2.5089 (23.5); 2.5043 (30.7); 2.4997 (22.0); 2.4952 (10.5); 2.2089 (0.8); 2.1922 (1.3); 2.1758 (1.4); 2.1589 (0.9); 1.2300 (7.7); 1.2122 (16.0); 1.1945 (7.4); 0.9658 (10.1); 0.9544 (10.4); 0.9488 (10.6); 0.9373 (9.2); −0.0002 (1.2)

I.0146: $^1$H-NMR(400.2 MHz, $d_6$-DMSO):
δ = 8.7808 (1.0); 6.3228 (0.5); 6.1939 (0.5); 6.1827 (1.1); 6.1711 (0.5); 6.0427 (0.6); 4.6698 (0.6); 3.6887 (16.0); 3.3303 (17.0); 2.5274 (0.3); 2.5225 (0.5); 2.5137 (5.9); 2.5094 (12.0); 2.5049 (15.9); 2.5004 (11.7); 2.4959 (5.9); 2.4800 (0.5); 2.4696 (0.4); 2.4640 (0.7); 2.4522 (1.1); 2.4434 (0.6); 2.4324 (0.6); 2.4212 (0.5); 2.4168 (0.4); 2.4073 (0.5); 2.3953 (0.5); −0.0002 (0.5)

I.0147: $^1$H-NMR(400.2 MHz, $d_6$-DMSO):
δ = 8.6435 (1.6); 8.6246 (1.6); 4.4290 (0.6); 4.4175 (0.9); 4.4097 (0.7); 4.4044 (0.9); 4.3985 (1.0); 4.3919 (0.9); 4.3853 (0.7); 4.3729 (0.7); 4.1632 (0.6); 4.1540 (1.0); 4.1443 (1.3); 4.1362 (3.2); 4.1263 (3.5); 4.1184 (3.4); 4.1086 (3.3); 4.1003 (1.4); 4.0909 (1.0); 4.0816 (0.6); 3.3265 (26.5); 2.5264 (0.6); 2.5216 (1.0); 2.5130 (13.5); 2.5085 (27.5); 2.5039 (35.9); 2.4993 (25.8); 2.4948 (12.3); 1.7855 (0.5); 1.7735 (0.7); 1.7598 (0.6); 1.7531 (0.8); 1.7476 (1.0); 1.7416 (1.1); 1.7276 (0.5); 1.7168 (1.3); 1.7042 (0.8); 1.7008 (0.7); 1.6880 (0.8); 1.6840 (0.8); 1.6713 (0.7); 1.6678 (0.6); 1.6554 (0.5); 1.6172 (1.2); 1.6047 (0.8); 1.5958 (0.7); 1.5846 (1.4); 1.5731 (0.8); 1.5638 (0.6); 1.5527 (0.4); 1.2140 (7.7); 1.1962 (16.0); 1.1785 (7.4); 0.9262 (9.7); 0.9103 (9.3); 0.8934 (9.1); 0.8775 (9.1); −0.0002 (1.3)

I.0148: $^1$H-NMR(400.2 MHz, $d_6$-DMSO):
δ = 8.7034 (0.7); 8.6850 (0.7); 4.5372 (0.6); 4.5222 (0.5); 4.1661 (0.4); 4.1578 (0.7); 4.1483 (1.4); 4.1403 (1.6); 4.1305 (1.6); 4.1226 (1.4); 4.1129 (0.7); 4.1049 (0.4); 3.3267 (11.4); 2.5828 (0.6); 2.5645 (1.2); 2.5444 (1.2); 2.5259 (0.8); 2.5218 (0.6); 2.5129 (5.8); 2.5085 (11.2); 2.5039 (14.4); 2.4992 (10.2); 2.4947 (4.8); 2.0907 (0.5); 2.0726 (1.1); 2.0539 (16.0); 2.0393 (0.3); 2.0328 (0.4); 1.2211 (3.4); 1.2033 (7.1); 1.1856 (3.3); −0.0002 (0.4)

I.0149: $^1$H-NMR(400.2 MHz, $d_6$-DMSO):
δ = 8.5404 (1.3); 8.5220 (1.3); 8.3133 (0.4); 7.3171 (0.7); 7.3142 (1.2); 7.3103 (0.5); 7.2960 (3.6); 7.2935 (3.0); 7.2849 (1.0); 7.2788 (5.5); 7.2727 (4.2); 7.2678 (6.8); 7.2609 (0.9); 7.2515 (2.2); 7.2469 (1.1); 7.2431 (1.4); 7.2392 (1.3); 7.2331 (0.7); 7.2281 (0.8); 7.2217 (2.2); 7.2143 (0.5); 7.2100 (0.5); 7.2049 (0.7); 7.2004 (0.4); 4.6642 (0.5); 4.6504 (0.7); 4.6418 (0.9); 4.6317 (0.8); 4.6283 (0.8); 4.6232 (0.8); 4.6092 (0.5); 4.1472 (1.5); 4.1305 (4.6); 4.1295 (4.7); 4.1127 (5.0); 4.0948 (1.7); 3.3291 (27.4); 3.2003 (0.9); 3.1869 (0.9); 3.1660 (1.8); 3.1526 (1.6); 3.1101 (1.7); 3.0871 (1.7); 3.0758 (0.9); 3.0527 (0.9); 2.5265 (0.6); 2.5217 (0.9); 2.5131 (12.1); 2.5086 (24.6); 2.5040 (32.1); 2.4993 (23.0); 2.4948 (10.9); 2.0538 (0.4); 1.1850 (7.6); 1.1672 (16.0); 1.1494 (7.2); −0.0002 (1.0)

I.0150: $^1$H-NMR(300.2 MHz, CDCl3):
δ = 8.8692 (0.6); 7.2984 (9.3); 3.7649 (16.0); 2.0830 (1.0); 1.8537 (1.0); 1.8362 (2.7); 1.8258 (2.6); 1.8093 (1.2); 1.5845 (4.6); 1.4833 (1.2); 1.4671 (2.5); 1.4566 (2.6); 1.4388 (1.0); 1.2970 (0.7); 0.0480 (0.4); 0.0372 (10.6); 0.0263 (0.4)

TABLE A-(I)-continued

| NMR peak lists of compounds according to formula (I) |
|---|
| I.0151: $^1$H-NMR(400.2 MHz, $d_6$-DMSO):<br>δ = 8.2845 (1.1); 8.2656 (1.1); 4.2433 (1.5); 4.2248 (2.2); 4.2073 (1.9); 4.1898 (1.0); 4.1805 (0.9); 4.1720 (1.1); 4.1627 (2.8); 4.1544 (1.3); 4.1449 (3.0); 4.1368 (2.9); 4.1272 (1.3); 4.1191 (2.9); 4.1097 (1.1); 4.1013 (0.9); 4.0920 (1.0); 4.0743 (0.3); 3.3257 (15.7); 2.5220 (0.5); 2.5134 (7.3); 2.5089 (14.9); 2.5043 (19.6); 2.4997 (14.0); 2.4952 (6.7); 2.2000 (0.9); 2.1830 (1.6); 2.1660 (1.6); 2.1491 (1.0); 1.2381 (0.5); 1.2223 (7.8); 1.2046 (16.0); 1.1868 (7.5); 0.9519 (10.1); 0.9368 (13.0); 0.9354 (13.2); 0.9204 (9.3); −0.0002 (10.1); −0.0085 (0.4) |
| I.0152: $^1$H-NMR(400.2 MHz, $d_6$-DMSO):<br>δ = 8.2848 (1.1); 8.2658 (1.1); 4.2432 (1.5); 4.2246 (2.2); 4.2071 (1.9); 4.1896 (1.0); 4.1804 (0.9); 4.1719 (1.0); 4.1626 (2.8); 4.1543 (1.3); 4.1448 (2.9); 4.1367 (2.9); 4.1271 (1.3); 4.1190 (2.8); 4.1096 (1.1); 4.1012 (0.9); 4.0919 (1.0); 4.0741 (0.3); 3.3262 (17.9); 2.5268 (0.4); 2.5220 (0.5); 2.5134 (7.3); 2.5089 (15.0); 2.5043 (19.9); 2.4997 (14.2); 2.4951 (6.8); 2.1999 (0.9); 2.1829 (1.5); 2.1660 (1.6); 2.1490 (0.9); 1.2378 (0.6); 1.2222 (7.8); 1.2045 (16.0); 1.1867 (7.4); 0.9518 (10.0); 0.9368 (12.9); 0.9354 (13.0); 0.9203 (9.1); −0.0002 (9.0) |
| I.0153: $^1$H-NMR(400.2 MHz, $d_6$-DMSO):<br>δ = 8.4604 (1.3); 8.4414 (1.3); 7.3090 (0.8); 7.3063 (1.2); 7.3025 (0.6); 7.2913 (2.0); 7.2880 (4.0); 7.2857 (3.4); 7.2774 (1.1); 7.2694 (8.5); 7.2630 (7.8); 7.2556 (1.2); 7.2470 (2.3); 7.2422 (1.0); 7.2325 (1.4); 7.2283 (1.4); 7.2219 (0.8); 7.2176 (1.0); 7.2111 (2.2); 7.2034 (0.6); 7.2000 (0.6); 7.1945 (0.8); 7.1898 (0.4); 4.6282 (0.6); 4.6141 (0.8); 4.6053 (1.1); 4.5946 (1.0); 4.5916 (1.0); 4.5860 (1.0); 4.5719 (0.7); 4.1322 (1.7); 4.1146 (5.4); 4.0970 (5.7); 4.0793 (1.9); 3.3288 (16.6); 3.1848 (0.7); 3.1708 (0.8); 3.1503 (2.1); 3.1365 (1.9); 3.1225 (2.0); 3.0991 (1.9); 3.0882 (0.8); 3.0647 (0.8); 2.5268 (0.3); 2.5220 (0.5); 2.5134 (7.7); 2.5089 (15.8); 2.5044 (20.9); 2.4997 (14.9); 2.4952 (7.1); 1.2374 (0.9); 1.1686 (7.7); 1.1509 (16.0); 1.1331 (7.4); −0.0002 (10.7); −0.0085 (0.4) |
| I.0154: $^1$H-NMR(400.2 MHz, $d_6$-DMSO):<br>δ = 8.4610 (1.4); 8.4421 (1.4); 7.3088 (0.8); 7.3062 (1.2); 7.3024 (0.6); 7.2879 (4.1); 7.2857 (3.4); 7.2773 (1.2); 7.2694 (8.7); 7.2630 (8.0); 7.2557 (1.2); 7.2468 (2.2); 7.2324 (1.4); 7.2282 (1.5); 7.2219 (0.9); 7.2176 (1.0); 7.2111 (2.3); 7.2035 (0.6); 7.1999 (0.6); 7.1944 (0.8); 7.1898 (0.4); 4.6277 (0.7); 4.6135 (0.9); 4.6050 (1.1); 4.5940 (1.1); 4.5914 (1.0); 4.5855 (1.0); 4.5714 (0.7); 4.1320 (1.7); 4.1242 (0.3); 4.1144 (5.6); 4.0968 (5.9); 4.0790 (2.0); 3.3286 (20.4); 3.1843 (0.7); 3.1705 (0.8); 3.1500 (2.2); 3.1361 (2.0); 3.1220 (2.1); 3.0986 (2.0); 3.0877 (0.8); 3.0642 (0.8); 2.5265 (0.3); 2.5216 (0.6); 2.5131 (8.8); 2.5086 (17.7); 2.5041 (23.1); 2.4995 (16.5); 2.4951 (7.9); 1.2376 (1.0); 1.1681 (7.7); 1.1504 (16.0); 1.1326 (7.4); 0.0080 (0.4); −0.0002 (12.0); −0.0084 (0.4) |
| I.0155: $^1$H-NMR(400.2 MHz, $d_6$-DMSO):<br>δ = 8.4806 (0.8); 8.4615 (0.8); 7.3073 (0.5); 7.3045 (0.8); 7.3007 (0.4); 7.2895 (1.3); 7.2863 (2.6); 7.2840 (2.2); 7.2755 (0.7); 7.2679 (4.4); 7.2601 (4.8); 7.2532 (0.7); 7.2440 (1.4); 7.2394 (0.6); 7.2292 (0.8); 7.2250 (0.9); 7.2189 (0.6); 7.2142 (0.6); 7.2078 (1.5); 7.2003 (0.4); 7.1962 (0.3); 7.1910 (0.5); 4.6631 (0.4); 4.6504 (0.5); 4.6434 (0.5); 4.6392 (0.6); 4.6307 (0.6); 4.6266 (0.6); 4.6197 (0.6); 4.6067 (0.4); 3.6588 (16.0); 3.3294 (9.3); 3.2012 (0.6); 3.1884 (0.6); 3.1667 (1.2); 3.1540 (1.1); 3.1180 (1.2); 3.0936 (1.2); 3.0837 (0.6); 3.0592 (0.6); 2.5219 (0.3); 2.5135 (4.5); 2.5090 (9.2); 2.5044 (12.2); 2.4998 (8.8); 2.4953 (4.2); 1.2372 (0.6); −0.0002 (6.2) |
| I.0156: $^1$H-NMR(400.1 MHz, CDCl3):<br>δ = 7.2634 (3.6); 6.6742 (1.0); 6.6567 (1.7); 6.6391 (1.1); 4.7704 (0.8); 4.7515 (1.8); 4.7395 (1.6); 4.7194 (0.9); 4.2526 (2.2); 4.2348 (6.8); 4.2170 (7.0); 4.1992 (2.5); 2.0442 (0.4); 2.0066 (0.8); 1.7818 (0.4); 1.7643 (1.2); 1.7516 (1.9); 1.7381 (2.8); 1.7280 (2.9); 1.7033 (2.1); 1.6875 (1.5); 1.6783 (1.8); 1.6734 (1.9); 1.6523 (2.0); 1.6311 (1.2); 1.6083 (0.3); 1.5844 (6.9); 1.3166 (7.3); 1.2988 (14.7); 1.2810 (8.4); 1.2652 (4.4); 0.9858 (12.6); 0.9789 (16.0); 0.9723 (15.8); 0.9651 (12.8); 0.8981 (1.9); 0.8820 (3.8); 0.8646 (1.9); −0.0002 (3.8) |
| I.0157: $^1$H-NMR(400.1 MHz, CDCl3):<br>δ = 7.2604 (25.4); 6.6528 (1.7); 6.6352 (1.1); 4.7699 (0.9); 4.7508 (1.8); 4.7393 (1.6); 4.7189 (0.9); 4.2521 (2.3); 4.2343 (7.0); 4.2165 (7.1); 4.1987 (2.5); 3.7759 (0.7); 1.7803 (0.4); 1.7636 (1.2); 1.7509 (2.0); 1.7377 (2.8); 1.7282 (2.8); 1.7017 (1.9); 1.6861 (1.4); 1.6719 (1.8); 1.6502 (1.9); 1.6300 (1.2); 1.6194 (0.6); 1.5480 (54.3); 1.3162 (7.2); 1.2983 (14.5); 1.2805 (7.6); 1.2664 (1.6); 0.9856 (12.6); 0.9787 (16.0); 0.9716 (15.9); 0.9643 (12.9); 0.8999 (0.4); 0.8821 (0.8); 0.8649 (0.4); −0.0002 (27.6) |
| I.0158: $^1$H-NMR(500.1 MHz, $d_6$-DMSO):<br>δ = 8.5449 (0.8); 8.5300 (0.8); 5.7529 (1.0); 4.5792 (0.4); 4.5646 (1.0); 4.5503 (1.0); 4.5357 (0.4); 3.6647 (13.3); 3.3124 (3.5); 2.5776 (0.5); 2.5645 (0.8); 2.5510 (1.2); 2.5374 (0.6); 2.5265 (0.6); 2.5108 (1.7); 2.5076 (1.2); 2.5037 (1.5); 2.5001 (1.3); 2.4961 (1.1); 2.4842 (0.6); 2.0943 (0.8); 2.0797 (2.0); 2.0658 (1.8); 2.0484 (16.0); −0.0002 (0.9) |
| I.0159: $^1$H-NMR(500.1 MHz, $d_6$-DMSO):<br>δ = 8.5451 (0.7); 8.5301 (0.7); 5.7529 (1.1); 4.5788 (0.4); 4.5641 (0.9); 4.5499 (0.9); 4.5353 (0.4); 3.6644 (12.9); 3.3134 (6.2); 2.5772 (0.5); 2.5642 (0.8); 2.5506 (1.0); 2.5370 (0.6); 2.5261 (0.5); 2.5105 (1.6); 2.5074 (1.1); 2.5036 (1.4); 2.4998 (1.2); 2.4957 (1.0); 2.4838 (0.6); 2.0939 (0.7); 2.0792 (1.7); 2.0655 (1.6); 2.0481 (16.0); −0.0002 (0.9) |
| I.0160: $^1$H-NMR(300.2 MHz, CDCl3):<br>δ = 7.7900 (0.6); 7.7664 (0.9); 7.7423 (0.6); 7.2991 (4.4); 5.6674 (0.8); 5.5756 (0.8); 5.0322 (0.5); 5.0183 (1.0); 5.0069 (1.0); 4.9950 (1.0); 4.9813 (0.5); 3.8248 (16.0); 3.1583 (1.0); 3.1444 (1.0); 3.1036 (1.6); 3.0898 (1.6); 2.9053 (1.5); 2.8908 (1.6); 2.8506 (1.0); 2.8362 (1.0); 1.6495 (1.4); 1.2898 (0.3); 0.0351 (5.4) |
| I.0161: $^1$H-NMR(400.1 MHz, $d_6$-DMSO):<br>δ = 8.4811 (0.8); 8.4724 (0.9); 8.4616 (0.9); 8.4529 (0.8); 7.5090 (1.3); 7.0258 (1.3); 4.8133 (0.4); 4.7988 (1.1); 4.7799 (1.1); 4.7655 (0.5); 3.6375 (16.0); 3.3165 (14.9); 2.6985 (3.8); 2.6842 (3.9); 2.5060 (4.2); 2.5017 (5.6); 2.4973 (4.3); −0.0002 (6.1) |
| I.0162: $^1$H-NMR(300.2 MHz, CDCl3):<br>δ = 7.3063 (5.3); 7.2984 (3.5); 6.7186 (1.0); 3.7455 (16.0); 1.7153 (1.0); 1.6984 (2.9); 1.6876 (3.0); 1.6722 (1.2); 1.6245 (2.1); 1.3345 (1.3); 1.3192 (3.0); 1.3083 (3.0); 1.2914 (1.1); 0.0349 (4.3) |
| I.0163: $^1$H-NMR(300.2 MHz, CDCl3):<br>δ = 7.2984 (2.8); 6.3269 (0.8); 3.7465 (16.0); 2.5409 (15.0); 1.7184 (1.0); 1.7016 (2.7); 1.6908 (2.7); 1.6754 (1.2); 1.6186 (1.5); 1.3394 (1.3); 1.3240 (2.8); 1.3132 (2.8); 1.2964 (1.0); 0.0344 (3.7) |
| I.0164: $^1$H-NMR(300.2 MHz, CDCl3):<br>δ = 7.3355 (4.9); 7.2982 (4.3); 6.6509 (0.8); 3.7457 (16.0); 1.7179 (0.9); 1.7010 (2.6); 1.6903 (2.7); 1.6748 (1.1); 1.6133 (2.1); 1.3361 (1.3); 1.3208 (2.8); 1.3099 (2.8); 1.2929 (1.0); 0.0353 (5.7) |
| I.0165: $^1$H-NMR(300.2 MHz, CDCl3):<br>δ = 7.2984 (3.8); 6.3131 (0.8); 3.7479 (16.0); 2.5470 (14.7); 2.5172 (0.7); 1.7207 (1.0); 1.7039 (2.8); 1.6931 (2.8); 1.6777 (1.2); 1.6084 (2.4); 1.3409 (1.3); 1.3255 (2.8); 1.3147 (2.8); 1.2978 (1.1); 0.0352 (4.8) |
| I.0166: $^1$H-NMR(300.2 MHz, CDCl3):<br>δ = 7.2984 (9.6); 6.9937 (1.0); 6.9708 (1.0); 4.3406 (2.4); 4.3169 (7.5); 4.2931 (7.6); 4.2694 (2.5); 2.7609 (0.7); 2.7556 (0.4); 2.7397 (1.0); 2.7319 (1.3); 2.7172 (1.9); 2.7049 (1.2); 2.6941 (2.9); 2.6683 (3.1); 2.6357 (3.1); 2.6081 (2.0); 2.5982 (1.6); 2.5920 (1.0); 2.5712 (0.6); 2.5656 (0.8); 2.2086 (0.6); 2.2015 (0.6); 2.1932 (0.4); 2.1815 (2.4); 2.1695 (1.1); 2.1549 (3.1); 2.1484 (2.2); 2.1367 (0.8); 2.1274 (2.2); 2.1166 (1.0); 2.0998 (0.5); 2.0948 (0.5); 1.5985 (7.3); 1.3684 (7.9); 1.3446 (16.0); 1.3209 (7.6); 0.0464 (0.4); 0.0357 (11.6); 0.0248 (0.4) |

TABLE A-(I)-continued

NMR peak lists of compounds according to formula (I)

I.0167: $^1$H-NMR(300.2 MHz, CDCl3):
δ = 7.2982 (0.9); 4.2889 (2.0); 4.2651 (6.1); 4.2413 (6.2); 4.2173 (2.8); 4.2021 (6.2); 3.2271 (2.6); 3.1482 (0.5); 1.3400 (8.0); 1.3162 (16.0); 1.3025 (0.4); 1.2923 (7.8); 0.0171 (0.8)
I.0168: $^1$H-NMR(300.2 MHz, $d_6$-DMSO):
δ = 12.6129 (0.4); 12.5282 (1.6); 8.8073 (14.8); 4.0609 (0.9); 4.0371 (1.0); 4.0136 (0.4); 3.3472 (12.1); 3.2694 (0.9); 2.6217 (0.5); 2.5279 (27.0); 2.5220 (36.4); 2.5160 (26.9); 2.4733 (0.6); 2.4504 (0.6); 2.4283 (1.9); 2.4072 (82.8); 2.3573 (0.7); 2.3406 (0.4); 2.1891 (0.4); 2.0091 (4.0); 1.9287 (0.9); 1.4819 (0.3); 1.4307 (5.7); 1.4148 (14.4); 1.4040 (16.0); 1.3900 (7.0); 1.3371 (0.6); 1.2541 (0.5); 1.2183 (1.2); 1.1946 (2.7); 1.1709 (1.4); 1.1443 (7.2); 1.1303 (15.6); 1.1194 (14.7); 1.1034 (5.5); 1.0524 (0.4); 0.0305 (1.5); 0.0198 (32.2); 0.0088 (1.5)
I.0169: $^1$H-NMR(300.2 MHz, $d_6$-DMSO):
δ = 12.5262 (0.4); 9.1923 (2.2); 7.8313 (5.6); 3.3478 (16.0); 2.5340 (2.7); 2.5280 (5.6); 2.5219 (7.7); 2.5159 (5.5); 2.5099 (2.5); 2.0089 (1.0); 1.9288 (0.5); 1.4525 (0.9); 1.4366 (2.2); 1.4258 (2.5); 1.4117 (1.1); 1.1943 (0.6); 1.1426 (1.1); 1.1285 (2.4); 1.1177 (2.3); 1.1017 (0.8); 0.0195 (8.9); 0.0085 (0.3)
I.0170: $^1$H-NMR(300.2 MHz, $d_6$-DMSO):
δ = 12.6372 (0.4); 12.6088 (0.5); 12.5696 (0.6); 12.5472 (0.6); 12.4756 (0.4); 12.4461 (0.4); 8.8228 (14.5); 3.3477 (8.4); 2.6219 (0.5); 2.5340 (14.2); 2.5280 (30.1); 2.5219 (41.4); 2.5159 (29.6); 2.5100 (13.6); 2.4935 (1.1); 2.4735 (0.6); 2.4552 (0.4); 2.4440 (0.7); 2.4075 (91.0); 2.3898 (5.0); 2.3736 (0.6); 2.3409 (0.3); 2.1895 (0.5); 2.0091 (0.7); 1.9284 (0.6); 1.4284 (5.6); 1.4125 (14.2); 1.4016 (16.0); 1.3877 (7.0); 1.3356 (0.6); 1.2551 (0.7); 1.2438 (1.3); 1.2217 (1.3); 1.1944 (1.1); 1.1893 (1.1); 1.1707 (0.5); 1.1447 (7.2); 1.1307 (15.5); 1.1198 (14.7); 1.1037 (5.5); 1.0566 (0.4); 0.0305 (1.4); 0.0197 (39.7); 0.0089 (1.4)
I.0171: $^1$H-NMR(300.2 MHz, CDCl3):
δ = 7.2985 (2.0); 4.7588 (0.3); 4.2773 (1.1); 4.2536 (2.8); 4.2299 (2.8); 4.2063 (1.0); 3.1595 (2.8); 3.0958 (0.4); 2.3779 (0.8); 2.3645 (0.4); 2.3558 (1.1); 2.3427 (0.8); 2.3338 (0.9); 2.3206 (1.1); 2.3120 (0.5); 2.2985 (0.8); 2.2765 (0.3); 1.3431 (8.0); 1.3341 (0.8); 1.3194 (16.0); 1.2956 (7.8); 1.0781 (2.6); 1.0610 (2.8); 1.0429 (1.6); 1.0189 (1.0); 0.9981 (5.4); 0.9759 (5.2); 0.0273 (1.9)
I.0172: $^1$H-NMR(300.2 MHz, CDCl3):
δ = 8.0776 (2.2); 7.2987 (65.2); 7.2320 (0.3); 6.9603 (3.4); 6.9475 (2.3); 6.9375 (3.3); 4.3207 (0.3); 3.0075 (16.0); 2.9823 (0.4); 2.9329 (13.5); 2.8567 (1.6); 2.8109 (4.0); 2.7930 (4.1); 2.7674 (2.7); 2.5880 (1.9); 2.5568 (4.4); 2.5205 (4.0); 2.4890 (2.1); 2.4653 (0.9); 2.2219 (0.8); 2.1941 (2.6); 2.1660 (4.4); 2.1444 (3.4); 2.1160 (2.0); 2.0964 (1.1); 1.2912 (0.4); 0.0479 (1.2); 0.0368 (68.3); 0.0261 (4.4); −0.0294 (0.7); −0.1619 (0.3)
I.0173: $^1$H-NMR(300.2 MHz, $d_6$-DMSO):
δ = 10.7963 (1.2); 3.3517 (16.0); 2.5340 (1.6); 2.5280 (3.1); 2.5220 (4.2); 2.5159 (3.0); 2.5100 (1.4); 1.5907 (0.5); 1.5739 (1.2); 1.5632 (1.4); 1.5485 (0.6); 1.3014 (0.6); 1.2868 (1.3); 1.2760 (1.2); 1.2593 (0.5); 0.0198 (4.6)
I.0174: $^1$H-NMR(400.2 MHz, $d_6$-DMSO):
δ = 8.4723 (7.4); 8.4669 (7.4); 7.7811 (0.7); 7.4228 (4.7); 7.0643 (4.8); 3.9197 (0.5); 3.3313 (88.2); 2.5419 (0.5); 2.5116 (16.6); 2.5072 (34.5); 2.5026 (46.7); 2.4981 (32.8); 2.4936 (14.8); 2.0759 (0.3); 1.3132 (6.0); 1.3020 (14.5); 1.2936 (16.0); 1.2833 (6.5); 1.2434 (0.5); 1.0336 (0.5); 0.9940 (6.8); 0.9837 (15.4); 0.9753 (14.6); 0.9640 (5.8); 0.9439 (0.5); 0.9353 (0.4); 0.9257 (0.3); 0.0080 (0.4); −0.0001 (10.2); −0.0085 (0.3)
I.0175: $^1$H-NMR(300.2 MHz, CDCl3):
δ = 7.4703 (1.1); 7.4616 (1.7); 7.4487 (3.0); 7.4361 (7.7); 7.4289 (2.7); 7.4184 (7.1); 7.4158 (6.2); 7.4084 (2.8); 7.4018 (4.0); 7.3992 (3.8); 7.3932 (5.0); 7.3771 (2.2); 7.3575 (1.1); 7.2980 (2.6); 5.7161 (2.6); 5.7122 (2.4); 5.6930 (2.5); 4.3633 (0.4); 4.3394 (1.2); 4.3275 (0.9); 4.3156 (1.3); 4.3036 (2.6); 4.2918 (0.5); 4.2798 (2.7); 4.2727 (1.0); 4.2558 (1.1); 4.2488 (2.6); 4.2368 (0.5); 4.2251 (2.6); 4.2130 (1.2); 4.2014 (0.9); 4.1893 (1.2); 4.1656 (0.4); 1.6379 (0.9); 1.2929 (8.0); 1.2691 (16.0); 1.2453 (7.6); 0.0382 (2.8)
I.0176: $^1$H-NMR(400.2 MHz, $d_6$-DMSO):
δ = 8.9309 (2.7); 4.3285 (16.0); 3.3298 (30.6); 2.5265 (0.4); 2.5130 (10.0); 2.5087 (20.0); 2.5042 (26.2); 2.4997 (18.9); 2.4954 (9.2); 1.2381 (0.6); −0.0002 (4.1)
I.0177: $^1$H-NMR(400.1 MHz, CDCl3):
δ = 7.5221 (0.9); 7.2605 (7.4); 5.2993 (0.3); 4.2587 (5.3); 4.2463 (5.3); 3.8208 (16.0); 1.5454 (8.0); −0.0002 (8.4)
I.0178: $^1$H-NMR(300.2 MHz, CDCl3):
δ = 7.2988 (10.6); 4.3519 (0.7); 4.3281 (2.2); 4.3043 (2.2); 4.2814 (3.6); 4.2653 (2.9); 1.5892 (16.0); 1.3845 (2.6); 1.3607 (5.2); 1.3369 (2.5); 0.0478 (0.4); 0.0370 (11.2); 0.0260 (0.4)
I.0179: $^1$H-NMR(400.2 MHz, $d_6$-DMSO):
δ = 8.3464 (0.6); 8.3330 (1.2); 8.3192 (0.7); 8.3153 (0.8); 4.1005 (2.2); 4.0827 (6.9); 4.0649 (6.9); 4.0471 (2.3); 3.5302 (1.3); 3.5133 (3.4); 3.4987 (3.4); 3.4818 (1.4); 3.3275 (33.3); 2.5954 (3.1); 2.5784 (6.7); 2.5612 (3.0); 2.5261 (0.5); 2.5212 (0.8); 2.5127 (10.4); 2.5083 (21.1); 2.5037 (27.7); 2.4991 (19.8); 2.4946 (9.4); 1.2381 (0.6); 1.2008 (7.9); 1.1830 (16.0); 1.1652 (7.6); −0.0002 (4.5)
I.0180: $^1$H-NMR(300.2 MHz, CDCl3):
δ = 7.4320 (1.7); 7.2988 (5.0); 4.2400 (2.4); 4.2162 (7.4); 4.1924 (7.6); 4.1687 (2.5); 1.7304 (2.1); 1.7135 (5.7); 1.7028 (5.8); 1.6874 (2.6); 1.6253 (8.6); 1.3729 (2.7); 1.3576 (5.8); 1.3468 (5.9); 1.3299 (2.2); 1.2936 (8.1); 1.2699 (16.0); 1.2461 (7.6); 0.0338 (6.2)
I.0181: $^1$H-NMR(400.2 MHz, $d_6$-DMSO):
δ = 8.7605 (0.9); 8.7434 (0.9); 3.8011 (1.0); 3.7839 (1.0); 3.7782 (1.2); 3.7609 (1.0); 3.6800 (16.0); 3.3276 (23.0); 2.5207 (0.4); 2.5120 (6.6); 2.5077 (13.5); 2.5032 (18.0); 2.4986 (13.0); 2.4942 (6.3); 1.2792 (0.4); 1.2699 (0.7); 1.2586 (0.7); 1.2472 (0.7); 1.2385 (0.8); 1.2271 (0.4); 0.6233 (0.6); 0.6144 (0.6); 0.6098 (0.6); 0.5998 (0.7); 0.5949 (0.4); 0.5887 (0.4); 0.5788 (0.4); 0.5592 (0.3); 0.5494 (0.4); 0.5460 (0.5); 0.5367 (0.6); 0.5293 (0.5); 0.5258 (0.6); 0.5156 (0.7); 0.4939 (0.5); 0.4803 (0.5); 0.4708 (0.7); 0.4585 (0.9); 0.4472 (0.7); 0.4051 (0.4); 0.3936 (0.6); 0.3817 (0.7); 0.3691 (0.7); 0.3597 (0.4); −0.0002 (1.5)
I.0182: $^1$H-NMR(500.1 MHz, CDCl3):
δ = 7.6992 (1.7); 7.2621 (5.5); 4.3035 (2.5); 4.2892 (7.7); 4.2749 (7.8); 4.2607 (2.6); 2.6849 (6.1); 2.6684 (10.9); 2.6523 (8.4); 2.1659 (0.6); 2.1633 (0.6); 2.1497 (1.7); 2.1472 (1.7); 2.1371 (1.1); 2.1327 (2.8); 2.1143 (1.8); 2.0999 (0.7); 1.5621 (6.6); 1.3325 (7.9); 1.3182 (16.0); 1.3039 (7.9); −0.0002 (7.1)
I.0183: $^1$H-NMR(300.2 MHz, CDCl3):
δ = 7.5678 (0.9); 7.5408 (0.9); 7.2984 (7.6); 4.7676 (2.3); 4.7529 (2.4); 4.7397 (2.3); 4.7250 (2.3); 4.3366 (0.4); 4.3246 (1.0); 4.3149 (1.3); 4.3007 (3.3); 4.2913 (3.4); 4.2769 (3.4); 4.2676 (3.3); 4.2531 (1.2); 4.2439 (1.1); 4.2317 (0.4); 2.4026 (0.3); 2.3877 (0.4); 2.3796 (0.8); 2.3649 (0.9); 2.3567 (1.2); 2.3419 (1.2); 2.3337 (0.9); 2.3190 (0.9); 2.3109 (0.4); 2.2960 (0.4); 1.6054 (11.4); 1.3711 (7.9); 1.3473 (16.0); 1.3235 (7.6); 1.0593 (12.3); 1.0442 (13.2); 1.0364 (12.7); 1.0212 (11.9); 0.0351 (8.3)
I.0184: $^1$H-NMR(400.2 MHz, $d_6$-DMSO):
δ = 8.7933 (0.9); 6.3281 (0.5); 6.1991 (0.5); 6.1881 (1.0); 6.1766 (0.5); 6.0481 (0.5); 4.6764 (0.6); 3.6881 (16.0); 3.3266 (20.3); 2.5254 (0.4); 2.5121 (8.1); 2.5078 (15.8); 2.5033 (20.2); 2.4988 (14.6); 2.4948 (7.3); 2.4744 (0.4); 2.4683 (0.7); 2.4565 (1.0); 2.4479 (0.7); 2.4368 (0.6); 2.4256 (0.5); 2.4210 (0.4); 2.4114 (0.5); 2.3997 (0.5); −0.0002 (3.1)
I.0185: $^1$H-NMR(400.2 MHz, $d_6$-DMSO):
δ = 8.6537 (1.8); 8.6347 (1.8); 4.4347 (0.6); 4.4232 (1.0); 4.4158 (0.9); 4.4099 (1.0); 4.4042 (1.2); 4.3977 (1.0); 4.3910 (0.8); 4.3786 (0.8); 4.1643 (0.5); 4.1551 (1.0); 4.1457 (1.5); 4.1373 (3.2); 4.1277 (3.4); 4.1195 (3.4); 4.1100 (3.2); 4.1014 (1.5); 4.0923

TABLE A-(I)-continued

NMR peak lists of compounds according to formula (I)

(1.0); 4.0830 (0.6); 3.3274 (56.7); 2.5256 (0.7); 2.5122 (14.9); 2.5078 (30.1); 2.5033 (39.4); 2.4988 (28.3); 2.4944 (13.6); 1.7909 (0.5); 1.7790 (0.8); 1.7652 (0.6); 1.7585 (0.9); 1.7532 (1.1); 1.7469 (1.2); 1.7331 (0.7); 1.7215 (1.4); 1.7049 (0.8); 1.6883 (0.9); 1.6845 (0.9); 1.6717 (0.8); 1.6558 (0.6); 1.6215 (1.2); 1.6090 (1.0); 1.5999 (0.8); 1.5888 (1.5); 1.5775 (0.8); 1.5679 (0.6); 1.5567 (0.4); 1.2391 (0.6); 1.2136 (7.7); 1.1958 (16.0); 1.1781 (7.5); 1.1686 (0.4); 0.9268 (10.5); 0.9109 (10.1); 0.8940 (10.0); 0.8781 (9.8); 0.8535 (0.4); −0.0002 (6.1)

I.0186: $^1$H-NMR(400.2 MHz, $d_6$-DMSO):
δ = 8.7131 (0.8); 8.6948 (0.8); 4.5431 (0.7); 4.5274 (0.6); 4.1668 (0.5); 4.1586 (0.7); 4.1490 (1.5); 4.1412 (1.6); 4.1312 (1.6); 4.1235 (1.5); 4.1136 (0.7); 4.1058 (0.5); 3.3260 (25.0); 2.5838 (0.7); 2.5658 (1.5); 2.5459 (1.5); 2.5263 (0.9); 2.5116 (7.2); 2.5073 (14.2); 2.5029 (18.9); 2.4983 (13.9); 2.4939 (7.0); 2.0941 (0.6); 2.0762 (1.3); 2.0541 (16.0); 2.0371 (0.5); 1.2203 (3.6); 1.2026 (7.4); 1.1848 (3.4); −0.0002 (2.2)

I.0187: $^1$H-NMR(400.2 MHz, $d_6$-DMSO):
δ = 8.5494 (1.7); 8.5306 (1.7); 7.3184 (0.8); 7.3156 (1.2); 7.3118 (0.5); 7.2974 (3.8); 7.2949 (3.1); 7.2864 (1.1); 7.2801 (6.1); 7.2750 (4.7); 7.2699 (7.3); 7.2537 (2.2); 7.2441 (1.4); 7.2401 (1.4); 7.2340 (0.8); 7.2292 (0.9); 7.2228 (2.2); 7.2152 (0.5); 7.2111 (0.5); 7.2060 (0.7); 7.2015 (0.4); 4.6712 (0.6); 4.6576 (0.8); 4.6486 (1.1); 4.6387 (1.0); 4.6349 (0.9); 4.6296 (0.9); 4.6158 (0.7); 4.1484 (1.5); 4.1307 (4.8); 4.1137 (5.1); 4.0959 (1.7); 3.3289 (49.7); 3.2044 (0.8); 3.1908 (0.9); 3.1699 (1.8); 3.1565 (1.6); 3.1141 (1.8); 3.0910 (1.7); 3.0798 (1.0); 3.0567 (0.9); 2.8914 (0.9); 2.7332 (0.7); 2.7320 (0.7); 2.5256 (0.6); 2.5209 (0.9); 2.5122 (12.8); 2.5077 (26.1); 2.5032 (34.1); 2.4985 (24.0); 2.4940 (11.2); 1.2382 (0.4); 1.1846 (7.6); 1.1668 (16.0); 1.1490 (7.3); −0.0002 (5.0)

I.0188: $^1$H-NMR(400.2 MHz, $d_6$-DMSO):
δ = 9.0905 (1.8); 9.0770 (3.5); 9.0634 (1.8); 4.3368 (16.0); 4.3230 (15.9); 3.3255 (19.3); 2.8926 (0.4); 2.7332 (0.4); 2.5261 (0.9); 2.5127 (19.1); 2.5083 (39.0); 2.5038 (51.5); 2.4993 (37.6); 2.4951 (18.7); 1.2382 (0.6); −0.0002 (10.2); −0.0084 (0.4)

I.0189: $^1$H-NMR(400.2 MHz, $d_6$-DMSO):
δ = 8.4281 (0.7); 8.4146 (1.3); 8.4010 (0.7); 4.1131 (2.2); 4.0954 (6.9); 4.0776 (7.0); 4.0598 (2.3); 3.5110 (1.4); 3.4942 (3.6); 3.4797 (3.7); 3.4630 (1.5); 3.3242 (18.9); 2.5924 (3.2); 2.5756 (6.8); 2.5586 (3.0); 2.5258 (0.5); 2.5209 (0.8); 2.5124 (10.4); 2.5079 (20.9); 2.5034 (27.2); 2.4988 (19.2); 2.4944 (9.1); 1.2390 (0.4); 1.2125 (7.9); 1.1947 (16.0); 1.1769 (7.6); −0.0002 (5.3)

I.0190: $^1$H-NMR(400.2 MHz, $d_6$-DMSO):
δ = 8.8610 (1.0); 8.8438 (1.0); 3.8150 (0.9); 3.7978 (1.0); 3.7923 (1.0); 3.7752 (0.9); 3.6872 (16.0); 3.3235 (12.4); 2.5117 (6.8); 2.5073 (13.9); 2.5027 (18.5); 2.4982 (13.5); 2.4937 (6.6); 1.2450 (0.4); 1.2359 (0.8); 1.2246 (0.6); 1.2135 (0.7); 1.2017 (0.4); 0.6208 (0.5); 0.6131 (0.6); 0.6082 (0.6); 0.5992 (0.8); 0.5931 (0.4); 0.5873 (0.4); 0.5780 (0.4); 0.5740 (0.4); 0.5647 (0.4); 0.5614 (0.5); 0.5528 (0.7); 0.5445 (0.5); 0.5413 (0.6); 0.5321 (0.6); 0.5105 (0.4); 0.5048 (0.3); 0.4920 (0.5); 0.4827 (0.7); 0.4702 (0.9); 0.4598 (0.8); 0.4476 (0.3); 0.4323 (0.4); 0.4196 (0.6); 0.4093 (0.7); 0.3969 (0.6); 0.3877 (0.4); −0.0002 (3.5)

I.0191: $^1$H-NMR(400.2 MHz, $d_6$-DMSO):
δ = 9.1962 (3.7); 4.1380 (2.3); 4.1203 (7.4); 4.1026 (7.4); 4.0848 (2.4); 3.3227 (18.8); 2.8918 (0.3); 2.5935 (1.0); 2.5784 (1.2); 2.5709 (1.7); 2.5612 (1.7); 2.5556 (1.6); 2.5468 (1.9); 2.5385 (1.6); 2.5246 (1.8); 2.5115 (12.9); 2.5071 (26.3); 2.5026 (34.6); 2.4981 (25.1); 2.4937 (12.3); 2.3134 (1.0); 2.2947 (1.6); 2.2898 (2.0); 2.2833 (1.4); 2.2713 (1.7); 2.2636 (1.9); 2.2401 (1.1); 2.0367 (0.3); 2.0235 (0.6); 2.0128 (0.7); 2.0092 (0.8); 1.9999 (0.8); 1.9951 (0.6); 1.9852 (1.4); 1.9762 (0.6); 1.9711 (0.7); 1.9619 (1.3); 1.9427 (1.3); 1.9385 (0.9); 1.9238 (0.7); 1.9198 (0.8); 1.9151 (0.7); 1.2393 (0.6); 1.2091 (7.8); 1.1914 (16.0); 1.1736 (7.6); −0.0002 (7.0)

I.0192: $^1$H-NMR(400.2 MHz, $d_6$-DMSO):
δ = 8.9535 (1.1); 8.9346 (1.1); 6.3531 (0.4); 6.2241 (0.5); 6.2131 (0.9); 6.2013 (0.5); 6.0730 (0.5); 4.6593 (0.4); 4.6458 (0.5); 4.6388 (0.7); 4.6262 (0.7); 4.6193 (0.5); 4.6055 (0.4); 3.6977 (16.0); 3.3237 (10.3); 2.5249 (0.4); 2.5115 (7.4); 2.5073 (14.7); 2.5028 (19.0); 2.4983 (13.8); 2.4939 (6.8); 2.4745 (0.6); 2.4605 (0.4); 2.4481 (0.5); 2.4359 (0.8); 2.4215 (0.6); 2.4106 (0.5); 2.4054 (0.4); 2.3989 (0.5); 2.3927 (0.5); 2.3844 (0.4); −0.0002 (3.6)

I.0193: $^1$H-NMR(400.2 MHz, $d_6$-DMSO):
δ = 8.9269 (2.7); 4.3260 (16.0); 3.3260 (10.5); 2.5263 (0.4); 2.5215 (0.7); 2.5130 (9.6); 2.5085 (19.3); 2.5040 (25.1); 2.4994 (17.7); 2.4949 (8.3); −0.0002 (5.5)

I.0194: $^1$H-NMR(400.2 MHz, $d_6$-DMSO):
δ = 8.6250 (0.5); 8.6128 (1.0); 8.5994 (0.5); 4.0562 (3.2); 4.0422 (3.1); 3.6678 (16.0); 3.3241 (7.8); 2.8920 (0.4); 2.7324 (0.4); 2.5118 (6.2); 2.5077 (12.2); 2.5032 (16.0); 2.4987 (11.7); 2.4944 (5.8); −0.0002 (3.1)

I.0195: $^1$H-NMR(400.2 MHz, $d_6$-DMSO):
δ = 8.6150 (0.7); 8.6017 (1.5); 8.5881 (0.7); 4.1561 (2.1); 4.1384 (6.7); 4.1206 (6.8); 4.1028 (2.2); 4.0342 (5.0); 4.0200 (4.9); 3.3241 (16.9); 2.8921 (1.0); 2.7333 (0.8); 2.7323 (0.9); 2.5256 (0.5); 2.5122 (10.5); 2.5077 (21.1); 2.5031 (27.4); 2.4986 (19.4); 2.4940 (9.1); 1.2254 (7.7); 1.2076 (16.0); 1.1898 (7.5); −0.0002 (6.2)

I.0196: $^1$H-NMR(400.2 MHz, $d_6$-DMSO):
δ = 8.3368 (0.8); 8.3240 (1.5); 8.3163 (1.2); 4.1002 (2.3); 4.0825 (7.2); 4.0647 (7.2); 4.0469 (2.4); 3.5258 (1.4); 3.5090 (3.7); 3.4943 (3.7); 3.4776 (1.5); 3.3248 (17.1); 2.5948 (3.6); 2.5778 (7.4); 2.5607 (3.3); 2.5259 (0.5); 2.5125 (11.2); 2.5082 (22.7); 2.5038 (29.9); 2.4993 (21.7); 2.4950 (10.6); 1.2381 (0.4); 1.2005 (8.0); 1.1827 (16.0); 1.1650 (7.7); −0.0002 (5.2)

I.0197: $^1$H-NMR(400.2 MHz, $d_6$-DMSO):
δ = 8.9508 (3.2); 8.3151 (0.7); 4.0947 (2.1); 4.0770 (6.8); 4.0593 (6.9); 4.0416 (2.2); 3.3253 (27.8); 2.5255 (0.6); 2.5208 (0.9); 2.5121 (11.4); 2.5076 (23.6); 2.5031 (31.1); 2.4985 (22.3); 2.4940 (10.6); 1.4614 (1.8); 1.4492 (4.6); 1.4408 (5.0); 1.4299 (2.1); 1.2400 (0.5); 1.2016 (2.2); 1.1905 (4.9); 1.1822 (4.8); 1.1705 (9.1); 1.1529 (16.0); 1.1351 (7.4); −0.0002 (3.8)

I.0198: $^1$H-NMR(400.2 MHz, $d_6$-DMSO):
δ = 8.7611 (0.9); 8.7442 (0.9); 3.7959 (0.9); 3.7786 (1.0); 3.7729 (1.0); 3.7556 (0.9); 3.6797 (16.0); 3.3244 (15.4); 2.5252 (0.3); 2.5119 (6.8); 2.5075 (13.8); 2.5029 (18.0); 2.4984 (12.9); 2.4939 (6.2); 1.2793 (0.3); 1.2762 (0.4); 1.2672 (0.6); 1.2559 (0.6); 1.2444 (0.7); 1.2362 (0.5); 1.2328 (0.5); 0.6229 (0.6); 0.6140 (0.6); 0.6093 (0.6); 0.5993 (0.7); 0.5942 (0.4); 0.5882 (0.4); 0.5783 (0.4); 0.5493 (0.4); 0.5457 (0.5); 0.5364 (0.6); 0.5288 (0.5); 0.5256 (0.6); 0.5156 (0.7); 0.4940 (0.5); 0.4798 (0.5); 0.4703 (0.7); 0.4581 (0.9); 0.4468 (0.7); 0.4044 (0.4); 0.3930 (0.6); 0.3811 (0.7); 0.3685 (0.7); 0.3591 (0.4); −0.0002 (2.7)

I.0199: $^1$H-NMR(400.2 MHz, $d_6$-DMSO):
δ = 9.0614 (3.4); 4.1355 (2.2); 4.1178 (7.2); 4.1001 (7.2); 4.0824 (2.3); 3.3236 (21.7); 2.8916 (0.3); 2.5842 (1.0); 2.5686 (1.2); 2.5627 (1.7); 2.5558 (1.3); 2.5515 (1.7); 2.5474 (1.6); 2.5373 (2.0); 2.5295 (1.7); 2.5253 (1.3); 2.5116 (13.5); 2.5072 (26.9); 2.5027 (35.6); 2.4981 (25.9); 2.4937 (12.6); 2.3401 (1.1); 2.3294 (0.5); 2.3174 (2.1); 2.2974 (1.6); 2.2881 (1.8); 2.2658 (1.0); 1.9937 (0.5); 1.9798 (1.0); 1.9707 (1.0); 1.9616 (1.6); 1.9564 (1.6); 1.9414 (2.2); 1.9337 (1.0); 1.9197 (1.2); 1.2394 (0.4); 1.1891 (7.7); 1.1714 (16.0); 1.1537 (7.4); −0.0002 (6.4)

I.0200: $^1$H-NMR(400.2 MHz, $d_6$-DMSO):
δ = 8.4432 (1.7); 8.4237 (1.7); 4.3026 (2.0); 4.2870 (2.3); 4.2833 (2.3); 4.2675 (2.0); 4.2211 (0.3); 4.2033 (1.0); 4.1941 (0.9); 4.1855 (1.1); 4.1763 (2.7); 4.1675 (0.5); 4.1633 (1.1); 4.1585 (2.8); 4.1457 (2.8); 4.1409 (1.1); 4.1369 (0.5); 4.1280 (2.7); 4.1187 (1.1); 4.1103 (0.9); 4.1010 (1.1); 4.0832 (0.3); 3.3237 (27.5); 2.8925 (0.7); 2.7332 (0.6); 2.5253 (0.6); 2.5120 (14.0); 2.5076 (28.3); 2.5031 (37.0); 2.4986 (26.5); 2.4944 (12.9); 2.2104 (0.9); 2.1936 (1.6); 2.1770 (1.6); 2.1602 (1.0); 2.1431 (0.3); 1.2290 (7.9); 1.2112 (16.0); 1.1935 (7.6); 0.9676 (11.1); 0.9552 (12.2); 0.9507 (12.3); 0.9383 (10.4); −0.0002 (6.9)

TABLE A-(I)-continued

NMR peak lists of compounds according to formula (I)

I.0201: $^1$H-NMR(400.2 MHz, $d_6$-DMSO):
δ = 8.7995 (1.0); 8.7805 (1.0); 6.3276 (0.4); 6.1987 (0.5); 6.1876 (0.9); 6.1761 (0.4); 6.0476 (0.5); 4.6987 (0.3); 4.6793 (0.7); 4.6642 (0.7); 4.6447 (0.3); 3.6876 (16.0); 3.3243 (11.2); 2.5253 (0.4); 2.5119 (7.8); 2.5075 (15.4); 2.5029 (19.8); 2.4983 (13.9); 2.4938 (6.7); 2.4821 (0.5); 2.4716 (0.4); 2.4658 (0.6); 2.4539 (1.0); 2.4452 (0.6); 2.4343 (0.5); 2.4230 (0.5); 2.4185 (0.4); 2.4091 (0.5); 2.3970 (0.4); −0.0002 (4.0)

I.0202: $^1$H-NMR(400.2 MHz, $d_6$-DMSO):
δ = 8.6521 (1.8); 8.6330 (1.8); 4.4306 (0.6); 4.4190 (1.0); 4.4115 (0.8); 4.4058 (1.0); 4.4001 (1.1); 4.3935 (1.0); 4.3867 (0.8); 4.3743 (0.8); 4.1638 (0.6); 4.1547 (1.0); 4.1452 (1.4); 4.1369 (3.2); 4.1272 (3.4); 4.1190 (3.4); 4.1095 (3.1); 4.1009 (1.5); 4.0918 (1.0); 4.0825 (0.6); 3.6875 (0.4); 3.3233 (21.1); 2.8919 (0.6); 2.7323 (0.5); 2.5252 (0.6); 2.5118 (14.4); 2.5074 (28.8); 2.5029 (37.5); 2.4983 (26.8); 2.4938 (12.7); 1.7896 (0.5); 1.7776 (0.7); 1.7638 (0.6); 1.7571 (0.8); 1.7516 (1.0); 1.7456 (1.2); 1.7319 (0.6); 1.7201 (1.4); 1.7048 (0.8); 1.6885 (0.9); 1.6844 (0.9); 1.6718 (0.8); 1.6559 (0.6); 1.6194 (1.2); 1.6069 (0.9); 1.5979 (0.7); 1.5867 (1.4); 1.5753 (0.8); 1.5657 (0.6); 1.5549 (0.4); 1.2389 (0.4); 1.2132 (7.7); 1.1955 (16.0); 1.1777 (7.4); 0.9266 (10.1); 0.9107 (9.7); 0.8932 (9.6); 0.8773 (9.6); −0.0002 (6.5)

I.0203: $^1$H-NMR(400.2 MHz, $d_6$-DMSO):
δ = 8.7102 (0.9); 8.6915 (0.9); 4.5585 (0.3); 4.5391 (0.7); 4.5240 (0.6); 4.5202 (0.5); 4.5047 (0.3); 4.1665 (0.4); 4.1583 (0.7); 4.1488 (1.4); 4.1408 (1.6); 4.1309 (1.6); 4.1232 (1.4); 4.1134 (0.7); 4.1055 (0.4); 3.3236 (12.8); 2.5842 (0.6); 2.5660 (1.2); 2.5457 (1.3); 2.5262 (0.8); 2.5207 (0.5); 2.5118 (6.6); 2.5073 (13.0); 2.5028 (17.2); 2.4982 (12.4); 2.4937 (6.1); 2.0925 (0.6); 2.0746 (1.2); 2.0540 (16.0); 2.0417 (0.4); 2.0353 (0.4); 1.2202 (3.5); 1.2025 (7.4); 1.1847 (3.4); −0.0002 (3.4)

I.0204: $^1$H-NMR(400.2 MHz, $d_6$-DMSO):
δ = 8.5533 (1.9); 8.5343 (2.0); 7.3145 (1.2); 7.2963 (4.0); 7.2940 (3.4); 7.2781 (7.0); 7.2694 (7.9); 7.2533 (2.4); 7.2430 (1.4); 7.2390 (1.5); 7.2328 (0.8); 7.2281 (0.9); 7.2217 (2.3); 7.2141 (0.5); 7.2102 (0.5); 7.2049 (0.8); 7.2004 (0.4); 4.6655 (0.7); 4.6518 (0.9); 4.6463 (1.0); 4.6428 (1.2); 4.6327 (1.1); 4.6292 (1.1); 4.6237 (1.0); 4.6100 (0.8); 4.1472 (1.7); 4.1296 (5.4); 4.1120 (5.6); 4.0945 (1.9); 3.3263 (37.4); 3.2021 (0.9); 3.1886 (1.0); 3.1676 (2.0); 3.1542 (1.8); 3.1115 (1.9); 3.0884 (1.9); 3.0771 (1.0); 3.0540 (1.0); 2.5253 (0.6); 2.5116 (14.7); 2.5073 (29.8); 2.5027 (39.1); 2.4982 (27.8); 2.4937 (13.2); 1.2381 (0.5); 1.1832 (7.6); 1.1655 (16.0); 1.1477 (7.4); −0.0002 (5.7)

I.0205: $^1$H-NMR(400.1 MHz, CDCl3):
δ = 15.8699 (0.4); 15.3691 (0.4); 15.3184 (0.4); 12.9806 (0.4); 12.3737 (0.3); 11.2344 (0.3); 10.5593 (0.3); 7.5199 (0.6); 7.3113 (0.8); 7.2606 (115.8); 6.9960 (0.7); 6.5348 (2.3); 4.9381 (0.3); 4.4843 (0.4); 4.4731 (0.4); 4.4547 (0.3); 4.3765 (16.0); 4.3619 (15.4); 3.6302 (0.3); 2.9570 (1.0); 2.8842 (1.0); 1.8209 (0.3); 1.5442 (148.0); 0.1468 (0.3); 0.0701 (0.4); −0.0002 (57.0); −0.1494 (0.5)

I.0206: $^1$H-NMR(400.2 MHz, $d_6$-DMSO):
δ = 9.0143 (2.0); 4.3331 (16.0); 3.3272 (9.4); 2.8922 (0.7); 2.7333 (0.6); 2.7321 (0.6); 2.5262 (0.4); 2.5215 (0.6); 2.5129 (8.2); 2.5084 (17.0); 2.5038 (22.3); 2.4992 (15.7); 2.4946 (7.3); 1.2379 (0.7); −0.0002 (6.7)

I.0207: $^1$H-NMR(600.1 MHz, $d_6$-DMSO):
δ = 8.6727 (0.4); 8.6633 (0.8); 8.6538 (0.4); 4.0622 (3.9); 4.0525 (3.9); 3.6721 (16.0); 3.3221 (10.3); 2.5097 (2.8); 2.5067 (6.3); 2.5036 (8.9); 2.5006 (6.3); 2.4976 (2.9); −0.0001 (1.1)

I.0208: $^1$H-NMR(600.1 MHz, $d_6$-DMSO):
δ = 8.6623 (0.7); 8.6528 (1.3); 8.6433 (0.6); 4.1509 (2.0); 4.1390 (6.6); 4.1272 (6.6); 4.1153 (2.1); 4.0396 (5.9); 4.0299 (6.0); 3.3223 (19.6); 2.5097 (4.5); 2.5066 (10.1); 2.5036 (14.4); 2.5005 (10.2); 2.4975 (4.6); 1.2238 (7.6); 1.2120 (16.0); 1.2001 (7.4); −0.0001 (2.4)

I.0209: $^1$H-NMR(400.2 MHz, $d_6$-DMSO):
δ = 8.4042 (0.7); 8.3901 (1.2); 8.3767 (0.7); 4.1055 (2.2); 4.0877 (6.8); 4.0699 (6.8); 4.0521 (2.2); 3.5210 (1.4); 3.5042 (3.5); 3.4896 (3.6); 3.4729 (1.5); 3.3242 (10.6); 2.8922 (0.7); 2.7331 (0.6); 2.5931 (3.2); 2.5763 (6.7); 2.5593 (2.9); 2.5257 (0.4); 2.5209 (0.7); 2.5123 (9.9); 2.5078 (20.0); 2.5033 (26.0); 2.4987 (18.3); 2.4941 (8.5); 1.2383 (0.8); 1.2046 (7.8); 1.1868 (16.0); 1.1690 (7.6); −0.0002 (8.1)

I.0210: $^1$H-NMR(600.1 MHz, $d_6$-DMSO):
δ = 9.0191 (3.1); 8.3131 (1.3); 4.0898 (2.0); 4.0780 (6.5); 4.0662 (6.5); 4.0544 (2.1); 3.3228 (20.8); 3.2991 (0.5); 2.5093 (5.6); 2.5063 (12.3); 2.5033 (17.2); 2.5002 (12.2); 2.4973 (5.5); 1.4542 (1.8); 1.4462 (4.7); 1.4407 (5.2); 1.4333 (2.0); 1.1854 (2.1); 1.1779 (5.5); 1.1753 (8.6); 1.1725 (5.5); 1.1635 (16.0); 1.1517 (7.0); −0.0001 (1.6)

I.0211: $^1$H-NMR(600.1 MHz, $d_6$-DMSO):
δ = 8.7993 (0.8); 8.7879 (0.8); 3.8169 (0.8); 3.8055 (1.0); 3.8018 (0.9); 3.7903 (0.8); 3.6848 (16.0); 3.3242 (22.0); 2.5096 (3.1); 2.5065 (6.9); 2.5035 (9.7); 2.5004 (6.9); 2.4974 (3.1); 1.2413 (0.6); 1.2337 (0.5); 1.2262 (0.6); 1.2183 (0.3); 0.6169 (0.4); 0.6149 (0.3); 0.6097 (0.5); 0.6083 (0.5); 0.6030 (0.4); 0.6003 (0.5); 0.5962 (0.3); 0.5934 (0.4); 0.5510 (0.3); 0.5486 (0.4); 0.5444 (0.4); 0.5416 (0.5); 0.5353 (0.5); 0.5281 (0.5); 0.4797 (0.4); 0.4719 (0.6); 0.4640 (0.7); 0.4549 (0.6); 0.4035 (0.5); 0.3952 (0.6); 0.3866 (0.6); 0.3784 (0.4); −0.0001 (0.3)

I.0212: $^1$H-NMR(600.1 MHz, $d_6$-DMSO):
δ = 9.1434 (2.8); 4.1283 (2.2); 4.1165 (7.2); 4.1047 (7.2); 4.0929 (2.2); 3.3261 (55.9); 2.8927 (1.2); 2.7337 (0.9); 2.7329 (0.8); 2.5772 (0.8); 2.5744 (0.4); 2.5675 (0.9); 2.5621 (1.3); 2.5596 (0.9); 2.5555 (1.3); 2.5524 (1.2); 2.5460 (1.4); 2.5428 (0.7); 2.5403 (1.2); 2.5356 (0.4); 2.5309 (1.0); 2.5094 (5.9); 2.5064 (13.2); 2.5033 (18.6); 2.5002 (13.2); 2.4972 (5.9); 2.3127 (0.9); 2.3085 (0.3); 2.3002 (1.2); 2.2967 (1.6); 2.2917 (1.1); 2.2842 (1.3); 2.2789 (1.5); 2.2756 (1.1); 2.2630 (0.9); 1.9976 (0.5); 1.9907 (0.6); 1.9882 (0.6); 1.9817 (0.8); 1.9789 (0.4); 1.9722 (1.0); 1.9682 (0.4); 1.9658 (0.5); 1.9629 (0.5); 1.9560 (1.0); 1.9532 (0.7); 1.9405 (1.1); 1.9376 (0.6); 1.9346 (0.4); 1.9280 (0.6); 1.9252 (0.7); 1.9219 (0.6); 1.1917 (7.5); 1.1799 (16.0); 1.1681 (7.4); −0.0001 (0.4)

I.0213: $^1$H-NMR(600.1 MHz, $d_6$-DMSO):
δ = 8.4711 (1.3); 8.4581 (1.3); 4.3214 (1.7); 4.3114 (1.8); 4.3084 (1.8); 4.2983 (1.7); 4.2084 (0.4); 4.1965 (1.2); 4.1904 (0.8); 4.1847 (1.3); 4.1785 (2.4); 4.1729 (0.4); 4.1667 (2.5); 4.1559 (1.0); 4.1551 (1.0); 4.1442 (2.6); 4.1380 (0.4); 4.1324 (2.5); 4.1262 (1.3); 4.1206 (0.8); 4.1143 (1.3); 4.1025 (0.4); 3.3215 (32.7); 2.5094 (6.3); 2.5064 (14.1); 2.5033 (19.9); 2.5003 (14.0); 2.4972 (6.2); 2.2062 (0.8); 2.1949 (1.2); 2.1844 (1.2); 2.1732 (0.8); 1.2273 (7.6); 1.2155 (16.0); 1.2037 (7.4); 0.9752 (9.8); 0.9634 (15.4); 0.9514 (9.1); −0.0001 (2.5)

I.0214: $^1$H-NMR(600.1 MHz, $d_6$-DMSO):
δ = 8.8861 (0.8); 8.8736 (0.8); 6.2044 (0.4); 6.1970 (0.7); 6.1892 (0.4); 6.1038 (0.3); 4.6654 (0.4); 4.6601 (0.5); 4.6520 (0.5); 4.6468 (0.4); 3.6935 (16.0); 3.3223 (13.9); 2.8926 (0.4); 2.5094 (3.2); 2.5063 (7.1); 2.5033 (10.0); 2.5002 (7.2); 2.4972 (3.2); 2.4729 (0.3); 2.4477 (0.4); 2.4427 (0.5); 2.4257 (0.4); 2.4179 (0.4); 2.4085 (0.3); −0.0001 (1.2)

I.0215: $^1$H-NMR(600.1 MHz, $d_6$-DMSO):
δ = 8.7027 (1.5); 8.6901 (1.6); 4.4158 (0.5); 4.4080 (0.9); 4.4031 (0.6); 4.3995 (0.7); 4.3954 (1.0); 4.3912 (0.9); 4.3869 (0.6); 4.3785 (0.7); 4.1576 (0.9); 4.1514 (0.8); 4.1457 (0.9); 4.1396 (2.9); 4.1377 (1.3); 4.1340 (0.4); 4.1277 (3.2); 4.1258 (3.2); 4.1195 (0.4); 4.1156 (1.3); 4.1139 (3.0); 4.1077 (0.9); 4.1021 (0.9); 4.0959 (0.9); 3.3213 (17.3); 3.3203 (20.6); 2.5095 (6.1); 2.5065 (13.7); 2.5034 (19.4); 2.5003 (13.8); 2.4973 (6.2); 1.7558 (0.5); 1.7473 (0.8); 1.7388 (0.5); 1.7304 (1.6); 1.7250 (1.2); 1.7130 (1.6); 1.7041 (0.8); 1.6929 (0.4); 1.6092 (0.5); 1.6057 (0.6); 1.5965 (0.8); 1.5886 (1.6); 1.5807 (0.8); 1.5757 (0.3); 1.2131 (7.6); 1.2013 (16.0); 1.1895 (7.4); 0.9276 (8.4); 0.9170 (8.1); 0.8966 (7.9); 0.8858 (7.6); −0.0001 (2.4)

TABLE A-(I)-continued

| NMR peak lists of compounds according to formula (I) |
|---|
| I.0216: $^{1}$H-NMR(600.1 MHz, $d_6$-DMSO):<br>δ = 8.7700 (0.6); 8.7577 (0.6); 4.5334 (0.3); 4.5276 (0.4); 4.5208 (0.4); 4.5190 (0.4); 4.5150 (0.4); 4.1690 (0.4); 4.1629 (0.4); 4.1572 (0.4); 4.1510 (1.6); 4.1391 (2.6); 4.1272 (1.7); 4.1210 (0.4); 4.1153 (0.4); 4.1092 (0.4); 3.3235 (4.1); 3.3217 (8.2); 3.3208 (8.4); 2.5948 (0.6); 2.5853 (0.6); 2.5815 (0.6); 2.5756 (0.5); 2.5718 (0.5); 2.5624 (0.9); 2.5498 (0.5); 2.5094 (2.6); 2.5063 (5.9); 2.5032 (8.4); 2.5002 (6.0); 2.4971 (2.7); 2.0795 (0.3); 2.0668 (0.6); 2.0588 (16.0); 2.0452 (0.7); 2.0411 (0.3); 2.0314 (0.3); 1.2202 (3.3); 1.2084 (7.1); 1.1966 (3.3); −0.0001 (0.7) |
| I.0217: $^{1}$H-NMR(600.1 MHz, $d_6$-DMSO):<br>δ = 8.6273 (1.8); 8.6147 (1.9); 7.3116 (1.6); 7.3091 (0.7); 7.2992 (4.4); 7.2901 (1.2); 7.2871 (4.4); 7.2688 (4.0); 7.2663 (5.7); 7.2550 (2.7); 7.2403 (1.0); 7.2379 (1.5); 7.2356 (0.8); 7.2260 (2.4); 7.2225 (0.6); 7.2166 (0.5); 7.2141 (0.9); 7.2118 (0.4); 4.6626 (0.7); 4.6535 (0.8); 4.6499 (0.9); 4.6477 (1.0); 4.6408 (1.0); 4.6385 (1.0); 4.6351 (0.9); 4.6259 (0.7); 4.1389 (1.1); 4.1361 (1.2); 4.1332 (0.4); 4.1270 (3.5); 4.1243 (3.6); 4.1151 (3.6); 4.1125 (3.5); 4.1063 (0.4); 4.1032 (1.2); 4.1007 (1.1); 3.3251 (69.4); 3.1864 (1.0); 3.1773 (1.1); 3.1634 (1.6); 3.1543 (1.5); 3.0896 (1.6); 3.0744 (1.6); 3.0665 (1.1); 3.0514 (1.0); 2.5208 (0.4); 2.5177 (0.4); 2.5089 (8.2); 2.5059 (18.4); 2.5028 (26.1); 2.4998 (18.8); 2.4968 (8.6); 1.1787 (7.6); 1.1668 (16.0); 1.1550 (7.4); −0.0001 (0.9) |
| I.0218: $^{1}$H-NMR(400.2 MHz, $d_6$-DMSO):<br>δ = 8.9104 (2.5); 8.8895 (2.6); 7.9538 (0.5); 7.9278 (3.1); 7.8163 (16.0); 4.5112 (1.0); 4.4897 (2.2); 4.4857 (1.6); 4.4682 (1.6); 4.4641 (2.2); 4.4427 (1.1); 3.3291 (12.4); 3.2463 (3.1); 3.2314 (2.2); 3.2236 (3.5); 3.2084 (2.0); 3.1846 (0.3); 2.8928 (3.2); 2.7342 (2.6); 2.7331 (2.6); 2.5271 (0.4); 2.5223 (0.6); 2.5138 (8.2); 2.5093 (16.7); 2.5047 (21.8); 2.5001 (15.4); 2.4956 (7.2); 2.3916 (0.5); 2.3848 (0.5); 2.3774 (0.7); 2.3701 (1.0); 2.3617 (1.0); 2.3551 (1.2); 2.3476 (1.2); 2.3396 (1.1); 2.3322 (0.8); 2.3250 (0.7); 2.3183 (0.5); 1.9991 (0.6); 1.9760 (1.5); 1.9686 (0.7); 1.9503 (1.6); 1.9456 (1.4); 1.9271 (0.7); 1.9197 (1.3); 1.8967 (0.4); 1.2380 (0.4); −0.0002 (4.0) |
| I.0219: $^{1}$H-NMR(400.2 MHz, $d_6$-DMSO):<br>δ = 8.6432 (3.0); 8.6255 (3.0); 7.8648 (16.0); 7.5963 (3.2); 4.1705 (0.4); 4.1558 (1.1); 4.1468 (1.1); 4.1385 (1.4); 4.1341 (1.4); 4.1257 (1.1); 4.1166 (1.1); 4.1018 (0.4); 3.3316 (18.5); 3.2349 (0.3); 3.2222 (0.8); 3.2151 (0.8); 3.2036 (1.4); 3.1970 (1.4); 3.1911 (2.3); 3.1841 (2.4); 3.1782 (2.3); 3.1674 (1.8); 3.1633 (1.5); 3.1557 (1.4); 3.1523 (1.4); 3.1440 (1.6); 3.1250 (0.5); 3.1213 (0.5); 3.1131 (0.4); 2.8936 (2.1); 2.7349 (1.8); 2.7338 (1.8); 2.5278 (0.6); 2.5144 (11.6); 2.5100 (23.5); 2.5055 (30.7); 2.5010 (21.6); 2.4966 (10.8); 2.4622 (2.2); 2.4496 (2.1); 2.4476 (2.0); 2.2216 (3.1); 2.2004 (3.0); 2.1784 (2.3); 2.1571 (2.3); 1.9399 (1.1); 1.9290 (1.1); 1.9170 (1.1); 1.9074 (1.5); 1.8967 (1.4); 1.7486 (0.6); 1.7351 (0.8); 1.7258 (1.3); 1.7122 (1.5); 1.7026 (1.3); 1.6931 (1.3); 1.6798 (0.9); 1.6701 (0.6); 1.6566 (0.4); 1.2373 (0.7); −0.0002 (4.2) |
| I.0220: $^{1}$H-NMR(400.2 MHz, $d_6$-DMSO):<br>δ = 9.1971 (2.3); 9.1771 (2.3); 7.9537 (2.0); 7.7801 (16.0); 4.7959 (1.2); 4.7734 (1.7); 4.7687 (1.6); 4.7531 (1.5); 4.7484 (1.8); 4.7258 (1.2); 4.4378 (1.1); 4.4336 (1.2); 4.4158 (2.8); 4.4115 (2.8); 4.3938 (1.6); 4.3895 (1.4); 4.3035 (1.3); 4.2874 (1.7); 4.2817 (1.3); 4.2773 (1.8); 4.2654 (1.3); 4.2610 (1.7); 4.2555 (1.5); 4.2392 (1.1); 3.3293 (21.5); 2.8927 (14.6); 2.7341 (12.0); 2.7329 (12.2); 2.5266 (0.5); 2.5134 (9.7); 2.5089 (19.6); 2.5043 (26.4); 2.4997 (19.2); 2.4951 (9.3); 2.4850 (1.3); 2.4809 (1.0); 2.4759 (1.0); 2.4734 (1.1); 2.4672 (1.1); 2.4622 (0.9); 2.4503 (0.8); 2.4461 (0.7); 2.3423 (0.7); 2.3197 (1.0); 2.3156 (1.4); 2.2926 (1.6); 2.2890 (1.5); 2.2855 (1.3); 2.2657 (0.9); 2.2626 (1.1); 2.2584 (0.8); 2.2357 (0.5); 1.2392 (0.7); −0.0002 (4.5) |
| I.0221: $^{1}$H-NMR(400.2 MHz, $d_6$-DMSO):<br>δ = 8.9625 (2.4); 8.9456 (2.5); 7.9546 (0.8); 7.8586 (16.0); 7.7100 (3.1); 4.5372 (0.6); 4.5275 (1.0); 4.5194 (1.3); 4.5101 (1.5); 4.5007 (1.3); 4.4929 (1.0); 4.4896 (0.8); 4.4828 (0.6); 3.5928 (2.2); 3.5749 (2.3); 3.5677 (2.7); 3.5500 (2.3); 3.3321 (14.6); 3.1451 (2.2); 3.1358 (2.2); 3.1197 (2.0); 3.1105 (2.0); 2.8938 (5.6); 2.7351 (4.8); 2.7339 (4.7); 2.5836 (2.6); 2.5626 (2.8); 2.5414 (3.4); 2.5202 (4.3); 2.5149 (9.3); 2.5105 (18.3); 2.5059 (23.9); 2.5013 (17.2); 2.4968 (8.3); 2.1864 (3.1); 2.1750 (3.1); 2.1442 (2.5); 2.1328 (2.5); 1.2375 (0.6); −0.0002 (4.0) |
| I.0222: $^{1}$H-NMR(400.2 MHz, $d_6$-DMSO):<br>δ = 8.9213 (2.5); 8.9003 (2.5); 7.9540 (0.9); 7.9278 (3.1); 7.8558 (16.0); 4.5149 (1.1); 4.4934 (2.2); 4.4893 (1.7); 4.4718 (1.6); 4.4678 (2.3); 4.4463 (1.1); 3.3295 (14.8); 3.2670 (0.3); 3.2644 (0.3); 3.2462 (3.2); 3.2311 (2.4); 3.2236 (3.6); 3.2082 (2.1); 3.1844 (0.3); 2.8928 (5.6); 2.7343 (4.9); 2.7329 (4.7); 2.5271 (0.5); 2.5224 (0.8); 2.5138 (9.0); 2.5093 (18.0); 2.5048 (23.4); 2.5002 (16.7); 2.4956 (7.9); 2.3912 (0.5); 2.3844 (0.6); 2.3769 (0.7); 2.3697 (1.0); 2.3613 (1.1); 2.3547 (1.3); 2.3471 (1.2); 2.3392 (1.2); 2.3320 (0.8); 2.3246 (0.8); 2.3178 (0.6); 1.9983 (0.6); 1.9753 (1.6); 1.9678 (0.8); 1.9495 (1.6); 1.9448 (1.5); 1.9264 (0.8); 1.9189 (1.3); 1.8959 (0.5); 1.2382 (0.6); −0.0002 (4.1) |
| I.0223: $^{1}$H-NMR(400.2 MHz, $d_6$-DMSO):<br>δ = 8.6589 (2.5); 8.6411 (2.5); 7.9042 (16.0); 7.5973 (2.6); 4.1760 (0.3); 4.1610 (0.9); 4.1522 (0.8); 4.1439 (1.1); 4.1395 (1.2); 4.1312 (0.9); 4.1222 (0.9); 4.1074 (0.3); 3.3317 (12.4); 3.2238 (0.6); 3.2168 (0.7); 3.2054 (1.1); 3.1988 (1.1); 3.1927 (1.8); 3.1858 (1.9); 3.1792 (1.7); 3.1741 (1.6); 3.1676 (1.3); 3.1635 (1.2); 3.1564 (1.1); 3.1527 (1.1); 3.1445 (1.3); 3.1258 (0.4); 3.1218 (0.4); 3.1141 (0.4); 2.8939 (1.3); 2.7344 (1.1); 2.5283 (0.4); 2.5236 (0.7); 2.5149 (8.7); 2.5105 (18.5); 2.5060 (24.3); 2.5014 (16.9); 2.4968 (8.5); 2.4633 (1.8); 2.4507 (1.7); 2.4487 (1.7); 2.2219 (2.6); 2.2008 (2.5); 2.1787 (1.9); 2.1576 (1.9); 1.9479 (0.4); 1.9387 (0.9); 1.9278 (0.9); 1.9164 (0.9); 1.9064 (1.2); 1.8956 (1.2); 1.7505 (0.5); 1.7372 (0.6); 1.7279 (1.1); 1.7144 (1.2); 1.7048 (1.1); 1.6951 (1.0); 1.6818 (0.8); 1.6722 (0.5); 1.6588 (0.4); 1.2372 (0.5); −0.0002 (3.8) |
| I.0224: $^{1}$H-NMR(400.2 MHz, $d_6$-DMSO):<br>δ = 9.2080 (2.1); 9.1883 (2.1); 7.8195 (16.0); 4.8026 (0.9); 4.7802 (1.5); 4.7756 (1.4); 4.7597 (1.3); 4.7551 (1.6); 4.7327 (0.9); 4.4386 (1.1); 4.4345 (1.2); 4.4166 (2.9); 4.4124 (2.9); 4.3946 (1.7); 4.3904 (1.5); 4.3043 (1.3); 4.2881 (1.7); 4.2823 (1.4); 4.2780 (1.8); 4.2661 (1.4); 4.2618 (1.7); 4.2561 (1.4); 4.2400 (1.1); 3.3286 (11.8); 2.8932 (1.1); 2.7344 (0.9); 2.5270 (0.5); 2.5138 (8.5); 2.5093 (16.8); 2.5048 (22.3); 2.5002 (16.2); 2.4957 (7.9); 2.4859 (1.3); 2.4819 (1.0); 2.4766 (1.0); 2.4744 (1.1); 2.4688 (1.2); 2.4632 (1.0); 2.4513 (0.8); 2.4472 (0.7); 2.3417 (0.7); 2.3190 (1.0); 2.3150 (1.5); 2.2920 (1.6); 2.2885 (1.6); 2.2850 (1.4); 2.2623 (1.1); 2.2578 (0.8); 2.2351 (0.5); 1.2385 (0.5); −0.0002 (3.7) |
| I.0225: $^{1}$H-NMR(400.2 MHz, $d_6$-DMSO):<br>δ = 8.9756 (2.2); 8.9587 (2.2); 7.9547 (0.6); 7.8981 (16.0); 7.7099 (2.8); 4.5404 (0.5); 4.5337 (0.7); 4.5307 (0.9); 4.5228 (1.2); 4.5134 (1.4); 4.5039 (1.2); 4.4961 (0.9); 4.4929 (0.8); 4.4861 (0.6); 3.5923 (2.1); 3.5744 (2.2); 3.5670 (2.6); 3.5494 (2.2); 3.3306 (13.8); 3.1449 (2.1); 3.1355 (2.1); 3.1194 (1.9); 3.1103 (1.9); 2.8936 (4.4); 2.7350 (3.6); 2.7338 (3.6); 2.5837 (2.6); 2.5627 (2.7); 2.5415 (3.4); 2.5279 (0.6); 2.5204 (3.9); 2.5147 (8.9); 2.5102 (17.9); 2.5056 (23.6); 2.5010 (16.8); 2.4965 (7.9); 2.1845 (3.1); 2.1732 (3.0); 2.1423 (2.5); 2.1310 (2.5); 1.2376 (0.6); −0.0002 (4.4) |
| I.0226: $^{1}$H-NMR(400.1 MHz, $d_6$-DMSO):<br>δ = 8.2304 (2.5); 8.2108 (2.4); 7.9598 (2.3); 7.3027 (1.9); 7.2847 (6.1); 7.2666 (16.0); 7.2493 (3.3); 7.2248 (2.3); 7.2070 (2.7); 4.5734 (2.0); 4.5630 (2.0); 4.5422 (1.0); 3.6143 (0.4); 3.6082 (0.4); 3.5770 (0.5); 3.3302 (64.3); 3.2149 (3.0); 3.2040 (2.8); 3.1795 (3.6); 3.1692 (3.2); 3.1146 (2.7); 3.0904 (2.7); 3.0570 (1.5); 3.0093 (0.3); 2.8989 (10.4); 2.7400 (9.9); 2.5105 (19.5) |
| I.0227: $^{1}$H-NMR(400.2 MHz, $d_6$-DMSO):<br>δ = 8.3737 (3.4); 8.3676 (3.3); 3.9052 (15.8); 3.8907 (16.0); 2.8934 (1.7); 2.7340 (1.4); 2.5487 (0.8); 2.5277 (0.8); 2.5143 (17.9); 2.5099 (35.8); 2.5054 (46.6); 2.5008 (33.5); 2.4964 (16.1); 1.2378 (1.2); 0.0079 (1.1); −0.0002 (33.5); −0.0085 (1.2) |

TABLE A-(I)-continued

| NMR peak lists of compounds according to formula (I) |
|---|
| I.0228: $^1$H-NMR(400.1 MHz, $d_6$-DMSO):<br>δ = 7.9598 (3.6); 7.7847 (1.4); 4.4377 (1.4); 4.4293 (1.4); 3.8505 (0.8); 3.8382 (0.8); 3.8223 (1.8); 3.8111 (1.8); 3.7892 (1.9); 3.7810 (1.9); 3.7612 (0.9); 3.7530 (0.8); 3.3319 (21.6); 3.0683 (0.3); 2.8987 (16.0); 2.7396 (15.2); 2.5096 (8.6) |
| I.0229: $^1$H-NMR(400.2 MHz, $d_6$-DMSO):<br>δ = 8.3152 (2.3); 8.2953 (2.2); 7.9545 (1.7); 4.3843 (1.1); 4.3735 (1.3); 4.3644 (1.3); 4.3578 (1.7); 4.3540 (1.8); 4.3479 (1.3); 4.3386 (1.3); 4.3279 (1.1); 2.8937 (12.5); 2.7350 (10.1); 2.7340 (10.6); 2.5481 (1.6); 2.5277 (0.6); 2.5229 (1.0); 2.5143 (14.0); 2.5098 (28.9); 2.5052 (38.2); 2.5007 (27.7); 2.4961 (13.4); 1.7974 (0.8); 1.7870 (1.2); 1.7711 (1.0); 1.7655 (1.7); 1.7607 (1.7); 1.7554 (1.5); 1.7396 (1.2); 1.7288 (1.5); 1.6903 (0.6); 1.6846 (0.5); 1.6739 (1.0); 1.6683 (1.0); 1.6568 (1.3); 1.6519 (1.4); 1.6409 (1.3); 1.6358 (1.1); 1.6257 (1.1); 1.6143 (2.1); 1.6036 (2.2); 1.5921 (0.9); 1.5824 (2.1); 1.5718 (1.3); 1.5603 (0.9); 1.5494 (0.8); 1.3889 (0.6); 1.3707 (0.6); 1.2389 (0.7); 0.9145 (16.0); 0.8986 (15.5); 0.8785 (15.5); 0.8628 (15.8); 0.8370 (0.4); 0.0080 (0.8); −0.0002 (23.6); −0.0085 (0.8) |
| I.0230: $^1$H-NMR(400.1 MHz, $d_6$-DMSO):<br>δ = 8.4896 (6.4); 8.4733 (6.3); 7.9596 (1.3); 7.3451 (7.1); 6.8449 (7.2); 4.3199 (5.2); 3.7679 (0.4); 3.7295 (0.4); 3.7145 (0.5); 3.7013 (0.5); 3.6873 (0.5); 3.5437 (1.3); 3.5126 (1.8); 3.3311 (130.5); 3.0041 (0.6); 2.9943 (0.5); 2.9868 (0.5); 2.8988 (5.7); 2.7401 (5.4); 2.6783 (0.5); 2.6393 (0.3); 2.5106 (39.7); 2.3389 (0.4); 2.2773 (0.4); 2.2174 (7.3); 2.2003 (16.0); 2.1829 (10.0); 2.1048 (2.6); 2.0874 (3.7); 2.0699 (4.2); 2.0568 (3.5); 1.9934 (1.9); 1.9751 (3.8); 1.9558 (4.3); 1.9392 (3.3); 1.9206 (2.2); 1.9043 (0.9); 1.2432 (0.4) |
| I.0231: $^1$H-NMR(400.2 MHz, $d_6$-DMSO):<br>δ = 10.8791 (1.4); 8.0432 (0.7); 8.0366 (0.8); 8.0246 (0.8); 8.0179 (0.8); 7.9528 (2.4); 7.5458 (1.6); 7.5262 (1.7); 7.3409 (1.8); 7.3207 (2.2); 7.1879 (2.3); 7.1825 (2.3); 7.0772 (0.9); 7.0595 (1.7); 7.0417 (1.0); 7.0396 (1.0); 6.9805 (1.2); 6.9788 (1.2); 6.9610 (1.8); 6.9433 (0.8); 4.6265 (0.4); 4.6068 (0.9); 4.5946 (0.8); 4.5881 (0.6); 4.5748 (0.4); 3.3331 (0.7); 3.3204 (0.8); 3.2961 (1.4); 3.2838 (1.4); 3.2758 (1.4); 3.2549 (1.2); 3.2388 (0.4); 3.2182 (0.4); 2.8898 (16.0); 2.7325 (13.7); 2.5415 (0.5); 2.5249 (0.4); 2.5116 (8.1); 2.5073 (16.0); 2.5028 (20.8); 2.4983 (15.1); 2.4940 (7.4); 1.2383 (0.5); 0.0079 (0.5); −0.0002 (11.6); −0.0085 (0.4) |
| I.0232: $^1$H-NMR(300.2 MHz, CDCl3):<br>δ = 7.2980 (1.5); 7.1670 (2.0); 5.3287 (4.2); 4.2392 (2.4); 4.2154 (7.5); 4.1916 (7.6); 4.1679 (2.5); 1.7375 (2.1); 1.7203 (5.8); 1.7097 (6.0); 1.6938 (2.6); 1.3763 (2.6); 1.3607 (5.8); 1.3500 (5.8); 1.3326 (2.2); 1.2928 (8.0); 1.2690 (16.0); 1.2453 (7.6); 0.0238 (1.6) |
| I.0233: $^1$H-NMR(300.2 MHz, $d_6$-DMSO):<br>δ = 8.3272 (2.6); 8.3096 (2.6); 4.4132 (0.6); 4.3894 (2.1); 4.3656 (3.2); 4.3418 (2.2); 4.3185 (0.6); 3.4705 (0.3); 3.2373 (0.4); 3.1875 (1.4); 2.5338 (2.7); 2.5279 (5.7); 2.5219 (7.8); 2.5159 (5.7); 2.5102 (2.8); 1.4062 (16.0); 1.3823 (15.7); 1.0739 (0.4); 0.0158 (2.0) |
| I.0234: $^1$H-NMR(300.2 MHz, $d_6$-DMSO):<br>δ = 8.0345 (1.4); 8.0154 (1.3); 4.2522 (1.3); 4.2305 (1.8); 4.2065 (1.3); 3.3698 (0.5); 3.3520 (0.5); 2.5337 (3.2); 2.5279 (6.8); 2.5219 (9.2); 2.5159 (6.7); 2.5102 (3.2); 2.2308 (0.8); 2.2085 (1.2); 2.1869 (1.3); 2.1649 (0.8); 1.2769 (1.0); 1.2548 (1.1); 0.9580 (16.0); 0.9356 (15.6); 0.0179 (4.7) |
| I.0235: $^1$H-NMR(499.9 MHz, CDCl3):<br>δ = 7.2628 (6.4); 6.6857 (1.2); 6.6712 (1.9); 6.6566 (1.2); 5.3000 (2.1); 4.8591 (1.9); 4.8476 (1.9); 2.1121 (1.5); 1.5111 (0.7); 1.4972 (1.2); 1.4834 (1.6); 1.4695 (1.5); 1.4557 (1.0); 1.4422 (0.4); 1.3234 (0.4); 1.3088 (1.0); 1.2942 (1.6); 1.2802 (1.8); 1.2661 (1.8); 1.2543 (2.3); 0.9927 (7.6); 0.9849 (12.8); 0.9791 (16.0); 0.9724 (13.2); 0.8799 (0.3); 0.0699 (0.4); −0.0002 (6.1) |
| I.0236: $^1$H-NMR(400.2 MHz, $d_6$-DMSO):<br>δ = 9.3465 (2.0); 4.1670 (2.2); 4.1492 (7.0); 4.1314 (7.1); 4.1137 (2.3); 4.0233 (9.4); 3.3330 (14.5); 2.8938 (0.4); 2.7345 (0.3); 2.5136 (7.2); 2.5093 (13.4); 2.5048 (16.8); 2.5003 (11.8); 2.4959 (5.4); 1.2342 (7.9); 1.2164 (16.0); 1.1986 (7.7); −0.0002 (4.3) |
| I.0237: $^1$H-NMR(400.1 MHz, CDCl3):<br>δ = 7.3025 (4.9); 7.2596 (9.9); 6.7849 (1.3); 6.7675 (1.3); 4.8424 (0.7); 4.8268 (1.6); 4.8098 (1.5); 4.7959 (0.6); 4.2833 (1.3); 4.2659 (3.7); 4.2481 (3.6); 4.2302 (1.3); 2.9538 (0.4); 2.8830 (0.4); 2.5886 (2.0); 2.5707 (4.2); 2.5531 (2.5); 2.2840 (0.7); 2.2657 (1.0); 2.2476 (1.2); 2.2319 (0.9); 2.2149 (0.4); 2.1492 (0.6); 2.1312 (1.6); 2.1169 (16.0); 2.0986 (1.2); 2.0801 (0.7); 1.5428 (9.1); 1.3314 (3.9); 1.3133 (7.5); 1.2958 (3.8); −0.0002 (11.5) |
| I.0238: $^1$H-NMR(400.1 MHz, CDCl3):<br>δ = 7.3362 (4.8); 7.2601 (6.6); 6.7901 (1.3); 6.7728 (1.3); 4.8455 (0.7); 4.8301 (1.6); 4.8140 (1.5); 4.7979 (0.6); 4.2844 (1.3); 4.2667 (3.7); 4.2489 (3.7); 4.2314 (1.2); 2.9553 (0.5); 2.8837 (0.5); 2.5893 (1.9); 2.5714 (4.1); 2.5533 (2.5); 2.2987 (0.3); 2.2830 (0.7); 2.2653 (1.0); 2.2475 (1.2); 2.2307 (0.9); 2.2151 (0.4); 2.1488 (0.6); 2.1172 (16.0); 2.0959 (1.2); 2.0786 (0.7); 1.5524 (6.3); 1.3319 (4.0); 1.3141 (7.6); 1.2964 (3.8); −0.0002 (7.8) |
| I.0239: $^1$H-NMR(400.1 MHz, CDCl3):<br>δ = 8.0189 (0.4); 7.3029 (5.2); 7.2600 (6.9); 6.4164 (1.3); 4.1996 (5.7); 4.1884 (5.5); 3.8099 (16.0); 2.9565 (1.8); 2.8831 (1.8); 1.5545 (6.8); −0.0002 (8.2) |
| I.0240: $^1$H-NMR(500.1 MHz, CDCl3):<br>δ = 7.3366 (3.9); 7.2599 (11.3); 4.2040 (3.1); 4.1939 (3.1); 3.8176 (0.4); 3.8116 (10.5); 1.5454 (16.0); 0.0062 (0.4); −0.0002 (13.1); −0.0068 (0.5) |
| I.0241: $^1$H-NMR(400.1 MHz, CDCl3):<br>δ = 7.2637 (2.7); 6.4812 (0.7); 4.2321 (5.0); 4.2196 (5.1); 3.8257 (15.9); 2.5388 (16.0); 2.5111 (0.4); 1.5840 (5.2); −0.0002 (3.1) |
| I.0242: $^1$H-NMR(400.1 MHz, CDCl3):<br>δ = 7.2601 (7.4); 6.8824 (1.3); 6.8655 (1.3); 4.8683 (0.7); 4.8543 (1.7); 4.8381 (1.6); 4.8231 (0.6); 4.2983 (1.4); 4.2811 (3.9); 4.2634 (3.9); 4.2457 (1.3); 2.5978 (2.4); 2.5803 (5.1); 2.5625 (3.1); 2.5440 (14.7); 2.3118 (0.7); 2.2937 (1.1); 2.2755 (1.3); 2.2585 (1.0); 2.2441 (0.4); 2.1909 (0.5); 2.1733 (1.3); 2.1567 (1.5); 2.1378 (1.4); 2.1213 (16.0); 1.5419 (7.2); 1.3425 (4.0); 1.3247 (7.7); 1.3070 (3.8); −0.0002 (8.6) |
| I.0243: $^1$H-NMR(400.1 MHz, CDCl3):<br>δ = 7.2597 (9.1); 6.3824 (2.1); 3.7234 (16.0); 2.5196 (15.3); 1.7037 (1.5); 1.6893 (4.9); 1.6747 (1.8); 1.5393 (8.5); 1.3182 (4.9); 1.3026 (1.5); −0.0002 (10.6) |
| I.0244: $^1$H-NMR(400.1 MHz, CDCl3):<br>δ = 7.2601 (7.4); 6.6897 (2.2); 4.3173 (1.5); 4.3004 (4.2); 4.2829 (4.2); 4.2646 (1.4); 2.9556 (0.5); 2.8799 (0.5); 2.7240 (0.5); 2.6939 (2.5); 2.6720 (5.5); 2.6628 (5.1); 2.6477 (4.5); 2.6154 (0.3); 2.5205 (16.0); 2.1834 (0.7); 2.1641 (2.0); 2.1438 (2.8); 2.1246 (2.0); 2.1037 (0.6); 1.5424 (7.6); 1.3466 (4.4); 1.3289 (8.4); 1.3113 (4.2); −0.0002 (8.8) |
| I.0245: $^1$H-NMR(400.1 MHz, CDCl3):<br>δ = 7.2603 (6.3); 6.3726 (1.4); 6.3540 (1.4); 4.7858 (0.8); 4.7680 (1.6); 4.7529 (1.4); 4.7342 (0.7); 4.2697 (1.5); 4.2521 (4.1); 4.2344 (4.1); 4.2167 (1.4); 2.5265 (16.0); 1.8021 (0.4); 1.7881 (1.0); 1.7739 (1.3); 1.7576 (1.5); 1.7436 (2.0); 1.7288 (1.3); 1.7133 (1.4); 1.6973 (1.3); 1.6803 (1.8); 1.6494 (1.3); 1.6308 (0.8); 1.5464 (6.1); 1.3311 (4.4); 1.3132 (8.4); 1.2955 (4.2); 1.0017 (8.4); 0.9870 (15.2); 0.9719 (8.1); −0.0002 (7.1) |

TABLE A-(I)-continued

| NMR peak lists of compounds according to formula (I) |
| --- |
| I.0246: $^{1}$H-NMR(400.1 MHz, CDCl3): δ = 7.2598 (7.3); 6.7064 (1.2); 6.6925 (1.2); 6.1410 (0.4); 6.1336 (0.7); 6.1236 (0.4); 5.9948 (1.4); 5.9851 (0.8); 5.8560 (0.7); 5.8457 (0.4); 4.9375 (0.7); 4.9227 (1.7); 4.9071 (1.7); 4.8925 (0.7); 3.8482 (16.0); 2.6337 (0.8); 2.5929 (1.1); 2.5533 (1.2); 2.5364 (15.9); 2.5078 (0.5); 2.4949 (0.6); 2.4803 (0.9); 2.4677 (0.6); 2.4540 (0.6); 2.4418 (0.8); 2.4273 (0.5); 1.5404 (6.9); −0.0002 (8.5) |
| I.0247: $^{1}$H-NMR(400.1 MHz, $d_6$-DMSO): δ = 9.0527 (6.2); 7.8247 (16.0); 3.9279 (15.6); 3.9140 (15.3); 3.5778 (0.4); 3.5668 (0.4); 3.5569 (0.4); 3.3174 (24.7); 3.1244 (0.6); 2.8986 (0.7); 2.7405 (0.7); 2.5105 (34.6) |
| I.0248: $^{1}$H-NMR(400.1 MHz, $d_6$-DMSO): δ = 9.0789 (3.5); 9.0657 (6.2); 7.9606 (2.9); 7.8641 (16.0); 3.9325 (15.4); 3.9184 (15.2); 3.5755 (0.4); 3.3195 (14.0); 3.1230 (0.6); 2.8996 (12.6); 2.7403 (11.9); 2.5102 (26.0) |
| I.0249: $^{1}$H-NMR(400.1 MHz, $d_6$-DMSO): δ = 8.8666 (6.2); 7.9594 (1.1); 3.9381 (16.0); 3.9243 (15.9); 3.5930 (0.5); 3.5465 (0.7); 3.3210 (9.6); 3.0768 (0.6); 2.9982 (0.4); 2.8998 (4.6); 2.7405 (4.4); 2.5873 (0.6); 2.5522 (0.9); 2.5105 (27.5); 2.4257 (47.5); 2.2599 (0.3); 1.2597 (0.5); 1.2438 (0.6) |
| I.0250: $^{1}$H-NMR(400.1 MHz, $d_6$-DMSO): δ = 9.1211 (4.3); 3.3170 (14.4); 2.8998 (0.4); 2.7404 (0.4); 2.5104 (9.5); 2.3885 (16.0); 1.4200 (5.3); 1.1472 (5.3) |
| I.0251: $^{1}$H-NMR(300.2 MHz, CDCl3): δ = 7.7408 (2.0); 7.2987 (2.0); 2.9432 (2.3); 2.9183 (7.4); 2.8935 (7.6); 2.8687 (2.5); 1.8432 (2.2); 1.8264 (6.1); 1.8149 (6.3); 1.7996 (2.6); 1.6603 (0.4); 1.4225 (2.7); 1.4071 (6.3); 1.3956 (6.2); 1.3788 (2.2); 1.2913 (7.9); 1.2665 (16.0); 1.2417 (7.4); 0.0281 (2.5) |
| I.0252: $^{1}$H-NMR(300.2 MHz, CDCl3): δ = 7.2987 (1.3); 6.4929 (1.2); 2.9410 (1.2); 2.9162 (3.8); 2.8914 (3.9); 2.8666 (1.3); 2.5722 (16.0); 1.8186 (1.1); 1.8020 (3.1); 1.7904 (3.3); 1.7752 (1.4); 1.6709 (0.5); 1.3946 (1.4); 1.3793 (3.3); 1.3678 (3.2); 1.3511 (1.2); 1.2878 (4.1); 1.2631 (8.3); 1.2383 (3.8); 0.0294 (1.4) |
| I.0253: $^{1}$H-NMR(300.2 MHz, CDCl3): δ = 7.2985 (1.7); 6.4720 (1.1); 2.9440 (1.2); 2.9192 (3.9); 2.8944 (4.0); 2.8696 (1.3); 2.5805 (16.0); 2.5518 (0.7); 1.8226 (1.2); 1.8060 (3.1); 1.7945 (3.2); 1.7792 (1.3); 1.6532 (0.5); 1.3959 (1.4); 1.3806 (3.2); 1.3690 (3.1); 1.3523 (1.2); 1.2902 (4.3); 1.2655 (8.6); 1.2406 (3.9); 0.0308 (2.0) |
| I.0254: $^{1}$H-NMR(300.2 MHz, $d_6$-DMSO): δ = 12.6595 (11.7); 8.7188 (15.8); 8.6949 (16.0); 4.1249 (0.6); 3.6846 (13.0); 3.6605 (14.6); 3.6538 (15.1); 3.6298 (13.3); 3.3573 (6.4); 3.1879 (6.3); 2.6344 (1.0); 2.5338 (8.6); 2.5280 (17.6); 2.5220 (23.8); 2.5160 (17.4); 2.5101 (8.4); 2.4850 (1.0); 2.4199 (194.4); 2.3675 (0.5); 2.3526 (1.4); 2.2017 (1.0); 2.0952 (1.6); 1.2803 (1.4); 1.2639 (3.4); 1.2493 (4.5); 1.2370 (7.1); 1.2218 (6.9); 1.2069 (7.1); 1.1910 (4.3); 1.1801 (3.7); 1.1637 (1.8); 0.6762 (0.7); 0.6507 (4.6); 0.6442 (4.0); 0.6339 (6.8); 0.6156 (9.1); 0.6047 (9.1); 0.5874 (5.6); 0.5770 (4.5); 0.5587 (4.0); 0.5464 (4.7); 0.5411 (6.2); 0.5296 (8.9); 0.5127 (14.2); 0.5050 (14.1); 0.4875 (15.5); 0.4711 (10.7); 0.4588 (7.9); 0.4417 (3.5); 0.4144 (1.0); 0.3986 (4.7); 0.3866 (6.1); 0.3832 (6.1); 0.3697 (10.3); 0.3523 (9.1); 0.3429 (5.2); 0.3353 (3.4); 0.3120 (1.1); 0.0291 (0.8); 0.0182 (19.5); 0.0073 (0.9) |
| I.0255: $^{1}$H-NMR(300.2 MHz, $d_6$-DMSO): δ = 8.3896 (0.6); 8.0872 (3.7); 8.0688 (3.6); 7.9543 (0.4); 7.9030 (0.4); 7.8757 (0.4); 7.8569 (0.4); 7.8287 (0.4); 7.7462 (0.4); 7.7061 (0.3); 7.6917 (0.3); 4.5740 (2.0); 3.7999 (3.3); 3.7790 (5.6); 3.7578 (3.3); 3.4700 (0.9); 3.4467 (0.9); 3.4235 (0.3); 3.1865 (6.5); 2.6593 (0.4); 2.5338 (4.6); 2.5281 (9.7); 2.5222 (13.3); 2.5162 (9.9); 2.4451 (92.0); 2.4300 (3.3); 2.4171 (1.3); 2.3784 (0.6); 2.2272 (0.4); 2.0955 (0.7); 1.9185 (16.0); 1.2421 (0.9); 1.2245 (1.7); 1.2166 (2.3); 1.2086 (1.7); 1.1986 (4.2); 1.1740 (4.6); 1.1552 (2.5); 1.1310 (1.0); 1.0964 (1.0); 1.0731 (1.8); 1.0498 (0.9); 0.4907 (0.9); 0.4839 (1.3); 0.4725 (2.5); 0.4643 (2.8); 0.4470 (5.7); 0.4199 (5.7); 0.3962 (6.2); 0.3812 (9.6); 0.3683 (12.8); 0.3549 (11.9); 0.3462 (11.3); 0.3316 (5.1); 0.3174 (2.4); 0.0163 (8.9); 0.0055 (0.4) |
| I.0256: $^{1}$H-NMR(400.1 MHz, $d_6$-DMSO): δ = 8.3624 (3.7); 8.3522 (3.6); 7.9602 (3.6); 7.5018 (5.6); 7.0050 (5.7); 4.6922 (4.0); 4.6754 (3.9); 3.6775 (0.3); 3.6730 (0.3); 3.3300 (118.1); 3.0661 (0.5); 3.0411 (0.4); 2.8990 (15.6); 2.8338 (0.3); 2.7400 (16.0); 2.7029 (5.6); 2.6856 (8.0); 2.6703 (5.4); 2.6439 (1.5); 2.6303 (1.3); 2.5104 (28.1) |
| I.0257: $^{1}$H-NMR(400.1 MHz, $d_6$-DMSO): δ = 9.4228 (3.7); 9.4054 (3.6); 7.9595 (1.2); 5.9268 (5.1); 5.9087 (4.9); 4.2619 (3.0); 4.2447 (7.9); 4.2269 (7.9); 4.2097 (2.9); 3.3272 (281.7); 2.8993 (5.2); 2.7400 (5.0); 2.5102 (18.4); 2.4760 (0.3); 1.2496 (8.7); 1.2321 (16.0); 1.2147 (8.1) |
| I.0258: $^{1}$H-NMR(400.2 MHz, $d_6$-DMSO): δ = 9.2449 (2.2); 4.1058 (1.4); 4.0881 (4.5); 4.0703 (4.5); 4.0526 (1.4); 3.3352 (27.9); 2.8924 (0.3); 2.5259 (0.4); 2.5211 (0.5); 2.5125 (5.4); 2.5080 (10.7); 2.5035 (14.0); 2.4989 (10.2); 2.4944 (5.0); 2.3647 (16.0); 1.4638 (1.2); 1.4516 (3.1); 1.4433 (3.4); 1.4324 (1.4); 1.2092 (1.5); 1.1982 (3.3); 1.1899 (3.2); 1.1781 (5.8); 1.1604 (9.9); 1.1426 (4.7) |
| I.0259: $^{1}$H-NMR(400.1 MHz, CDCl3): δ = 8.0163 (0.4); 7.3082 (5.3); 7.2597 (7.5); 6.4459 (1.4); 6.4303 (1.4); 4.1818 (1.3); 4.1624 (2.5); 4.1430 (1.3); 3.7974 (16.0); 2.9547 (1.7); 2.8823 (1.6); 1.5513 (6.4); 1.1442 (1.3); 1.1303 (1.2); 0.6683 (0.7); 0.6397 (1.8); 0.6176 (1.7); 0.6022 (1.4); 0.5952 (1.5); 0.5814 (2.1); 0.5642 (2.1); 0.5521 (1.7); 0.5029 (1.6); 0.4861 (1.3); −0.0002 (9.5) |
| I.0260: $^{1}$H-NMR(400.1 MHz, CDCl3): δ = 7.3404 (5.1); 7.2596 (7.5); 6.4469 (1.1); 6.4314 (1.1); 4.1860 (1.3); 4.1657 (2.5); 4.1460 (1.3); 3.7982 (16.0); 1.5478 (5.5); 1.1601 (0.7); 1.1472 (1.1); 1.1385 (1.0); 1.1278 (1.1); 1.1177 (0.7); 0.6709 (0.6); 0.6587 (0.9); 0.6388 (1.5); 0.6188 (1.4); 0.6005 (1.2); 0.5832 (1.8); 0.5660 (1.8); 0.5526 (1.6); 0.5414 (1.4); 0.5199 (0.9); 0.5019 (1.4); 0.4868 (1.2); −0.0002 (9.6) |
| I.0261: $^{1}$H-NMR(400.1 MHz, CDCl3): δ = 7.2596 (8.2); 6.4784 (1.1); 6.4632 (1.1); 4.2223 (1.3); 4.2021 (2.4); 4.1825 (1.2); 3.8151 (16.0); 2.9532 (0.6); 2.8811 (0.6); 2.5291 (15.5); 1.5398 (7.3); 1.1803 (0.7); 1.1689 (1.1); 1.1591 (0.9); 1.1494 (1.1); 1.1383 (0.6); 0.6964 (0.5); 0.6811 (1.1); 0.6641 (1.4); 0.6444 (1.4); 0.6252 (1.1); 0.6159 (1.2); 0.6058 (1.2); 0.5906 (1.3); 0.5810 (1.3); 0.5659 (1.5); 0.5557 (1.4); 0.5412 (1.1); 0.5252 (1.4); 0.5211 (1.3); 0.5053 (1.1); −0.0002 (10.4) |
| I.0262: $^{1}$H-NMR(400.1 MHz, CDCl3): δ = 7.6054 (1.3); 7.5924 (1.3); 7.2593 (9.7); 4.3244 (1.4); 4.3047 (2.5); 4.2851 (1.3); 3.8099 (16.0); 1.5345 (8.1); 1.2386 (1.3); 1.2306 (1.1); 1.2232 (1.2); 0.6570 (1.8); 0.6357 (3.0); 0.6154 (2.1); 0.5889 (1.2); 0.5754 (1.2); 0.5558 (3.5); 0.5462 (3.8); −0.0002 (12.6) |
| I.0263: $^{1}$H-NMR(400.1 MHz, CDCl3): δ = 7.6595 (1.2); 7.6454 (1.2); 7.2593 (8.4); 4.2871 (1.3); 4.2681 (2.5); 4.2489 (1.3); 3.8092 (16.0); 1.5346 (6.2); 1.2345 (0.7); 1.2220 (1.1); 1.2146 (1.0); 1.2045 (1.2); 1.1937 (0.7); 0.6515 (1.5); 0.6346 (2.4); 0.6151 (1.7); 0.5865 (1.1); 0.5703 (1.0); 0.5431 (3.0); −0.0002 (10.8) |
| I.0264: $^{1}$H-NMR(400.1 MHz, CDCl3): δ = 7.5132 (1.2); 7.4959 (1.1); 7.2596 (9.2); 4.2604 (1.3); 4.2407 (2.4); 4.2214 (1.3); 3.8058 (16.0); 1.5345 (6.9); 1.2248 (0.7); 1.2116 (1.2); 1.2033 (1.1); 1.1922 (1.1); 1.1841 (0.7); 0.6566 (1.3); 0.6498 (1.4); 0.6437 (1.4); 0.6294 (2.1); 0.6141 (1.5); 0.5828 (1.2); 0.5682 (1.1); 0.5512 (1.8); 0.5391 (2.0); 0.5231 (1.7); −0.0002 (11.8) |

TABLE A-(I)-continued

| NMR peak lists of compounds according to formula (I) |
| --- |
| I.0265: $^1$H-NMR(400.1 MHz, $d_6$-DMSO): δ = 12.5583 (3.7); 12.4946 (0.4); 8.8782 (12.8); 3.3108 (43.7); 2.6785 (0.5); 2.5112 (65.6); 2.3382 (0.5); 1.9981 (0.3); 1.4701 (0.5); 1.4215 (15.8); 1.3675 (0.6); 1.2481 (0.4); 1.1951 (1.0); 1.1434 (16.0) |
| I.0266: $^1$H-NMR(400.1 MHz, $d_6$-DMSO): δ = 8.8833 (1.3); 8.8663 (1.3); 4.1765 (0.6); 4.1672 (0.6); 4.1587 (0.6); 4.1494 (1.8); 4.1442 (0.8); 4.1316 (1.9); 4.1263 (1.9); 4.1137 (0.8); 4.1086 (1.7); 4.0993 (0.6); 4.0908 (0.6); 4.0816 (0.6); 3.6636 (1.2); 3.6464 (1.3); 3.6400 (1.3); 3.6229 (1.2); 3.3322 (74.0); 2.5065 (10.3); 2.5021 (13.6); 2.4978 (10.0); 2.3971 (16.0); 2.3810 (0.8); 1.2387 (0.4); 1.2182 (4.9); 1.2005 (9.7); 1.1828 (5.0); 1.1635 (0.4); 0.6245 (0.3); 0.6166 (0.7); 0.6075 (0.7); 0.6030 (0.7); 0.5932 (0.8); 0.5817 (0.5); 0.5720 (0.4); 0.5548 (0.4); 0.5414 (0.6); 0.5318 (0.7); 0.5213 (0.7); 0.5113 (0.8); 0.4992 (0.4); 0.4901 (0.7); 0.4770 (0.6); 0.4671 (0.8); 0.4548 (1.0); 0.4438 (0.7); 0.3931 (0.4); 0.3816 (0.7); 0.3702 (0.9); 0.3578 (0.8); 0.3479 (0.5); 0.0079 (0.5); −0.0002 (9.3) |
| I.0267: $^1$H-NMR(400.2 MHz, $d_6$-DMSO): δ = 9.2015 (0.7); 9.1831 (0.7); 5.3025 (1.5); 5.2840 (1.5); 3.7380 (16.0); 3.3263 (3.9); 2.5116 (3.2); 2.5072 (6.4); 2.5027 (8.4); 2.4981 (6.2); 2.4937 (3.1); 2.4206 (8.8); 2.4032 (0.3); −0.0002 (2.4) |
| I.0268: $^1$H-NMR(400.2 MHz, $d_6$-DMSO): δ = 8.6607 (1.2); 8.6422 (1.2); 4.4117 (0.5); 4.3981 (0.7); 4.3928 (0.7); 4.3895 (0.7); 4.3796 (0.8); 4.3761 (0.7); 4.3710 (0.6); 4.3573 (0.5); 4.1403 (0.7); 4.1359 (0.8); 4.1226 (2.2); 4.1182 (2.3); 4.1047 (2.3); 4.1006 (2.3); 4.0869 (0.8); 4.0829 (0.7); 3.3260 (15.4); 2.5249 (0.5); 2.5114 (10.2); 2.5071 (20.4); 2.5026 (26.9); 2.4980 (20.1); 2.4937 (10.2); 2.4034 (16.0); 2.3871 (0.8); 1.7769 (0.4); 1.7599 (0.4); 1.7545 (0.4); 1.7418 (0.7); 1.7249 (0.7); 1.7197 (0.7); 1.7025 (0.6); 1.6519 (0.6); 1.6380 (0.8); 1.6342 (0.8); 1.6198 (0.8); 1.6029 (0.4); 1.5991 (0.5); 1.5853 (0.4); 1.2123 (4.6); 1.1945 (9.5); 1.1768 (4.6); 0.8213 (0.4); 0.8156 (0.4); 0.8032 (0.7); 0.7911 (0.4); 0.7848 (0.5); 0.4581 (0.5); 0.4487 (0.8); 0.4457 (0.7); 0.4377 (1.3); 0.4287 (1.2); 0.4177 (1.4); 0.4073 (0.8); 0.3974 (0.6); 0.1919 (0.6); 0.1827 (0.6); 0.1791 (0.7); 0.1684 (0.8); 0.1610 (0.6); 0.1505 (0.4); 0.0815 (0.4); 0.0710 (0.7); 0.0626 (0.8); 0.0523 (0.7); 0.0398 (0.6); −0.0002 (6.4) |
| I.0269: $^1$H-NMR(400.2 MHz, $d_6$-DMSO): δ = 8.3039 (2.0); 3.5849 (16.0); 3.3259 (14.8); 2.5247 (0.4); 2.5199 (0.6); 2.5113 (8.1); 2.5068 (16.4); 2.5022 (21.8); 2.4976 (16.1); 2.4931 (8.0); 2.3521 (15.6); 2.3363 (0.6); 1.3238 (0.4); 1.3101 (1.0); 1.3026 (1.0); 1.2965 (0.7); 1.2890 (2.1); 1.2814 (0.7); 1.2752 (1.1); 1.2678 (1.1); 1.2540 (0.6); 0.5398 (0.3); 0.5347 (0.6); 0.5300 (0.6); 0.5255 (0.9); 0.5210 (0.7); 0.5115 (1.2); 0.5062 (1.1); 0.4997 (0.8); 0.4975 (0.8); 0.4926 (0.9); 0.4819 (0.3); 0.4682 (0.6); 0.4459 (2.2); 0.4430 (2.6); 0.4390 (2.7); 0.4218 (2.4); 0.4176 (2.8); 0.3941 (0.6); 0.3808 (0.4); 0.3699 (1.0); 0.3656 (0.9); 0.3563 (1.0); 0.3516 (1.3); 0.3461 (0.8); 0.3423 (0.7); 0.3377 (0.9); 0.3324 (0.7); 0.3287 (0.6); 0.3229 (0.4); −0.0002 (5.5) |
| I.0270: $^1$H-NMR(400.2 MHz, $d_6$-DMSO): δ = 9.1705 (1.0); 9.1521 (1.0); 5.2283 (2.3); 5.2098 (2.3); 4.2471 (0.9); 4.2379 (0.9); 4.2293 (0.9); 4.2200 (3.8); 4.2117 (0.5); 4.2021 (5.8); 4.1927 (0.4); 4.1842 (3.9); 4.1748 (1.0); 4.1664 (1.0); 4.1571 (0.9); 3.3262 (7.1); 2.5251 (0.3); 2.5203 (0.5); 2.5116 (6.5); 2.5071 (13.4); 2.5025 (17.7); 2.4979 (13.1); 2.4935 (6.5); 2.4194 (14.1); 2.4023 (0.8); 1.2386 (8.0); 1.2209 (16.0); 1.2031 (7.6); −0.0002 (5.1) |
| I.0271: $^1$H-NMR(400.2 MHz, $d_6$-DMSO): δ = 9.3608 (1.2); 4.1916 (0.6); 4.1739 (1.8); 4.1561 (1.8); 4.1384 (0.6); 4.0137 (0.8); 3.9908 (0.7); 3.3296 (17.6); 2.5203 (0.4); 2.5117 (5.5); 2.5073 (11.1); 2.5027 (14.6); 2.4981 (10.7); 2.4937 (5.3); 2.4114 (7.1); 2.3939 (0.3); 1.3945 (16.0); 1.2005 (1.9); 1.1827 (4.1); 1.1650 (1.9); −0.0002 (2.9) |
| I.0272: $^1$H-NMR(400.1 MHz, $d_6$-DMSO): δ = 8.8615 (1.3); 8.8444 (1.3); 4.1760 (0.6); 4.1667 (0.6); 4.1582 (0.7); 4.1489 (1.8); 4.1435 (0.8); 4.1311 (1.9); 4.1257 (1.8); 4.1133 (0.8); 4.1080 (1.7); 4.0987 (0.6); 4.0903 (0.6); 4.0809 (0.6); 3.6603 (1.1); 3.6433 (1.2); 3.6368 (1.3); 3.6196 (1.2); 3.3363 (42.9); 2.5067 (8.8); 2.5023 (11.6); 2.4979 (8.5); 2.4159 (0.4); 2.3965 (16.0); 1.2402 (0.4); 1.2291 (0.5); 1.2178 (4.9); 1.2001 (9.6); 1.1824 (4.6); 1.1652 (0.4); 0.6242 (0.3); 0.6159 (0.6); 0.6069 (0.7); 0.6026 (0.7); 0.5925 (0.7); 0.5814 (0.4); 0.5714 (0.4); 0.5541 (0.4); 0.5405 (0.6); 0.5310 (0.7); 0.5205 (0.7); 0.5105 (0.8); 0.4985 (0.4); 0.4892 (0.6); 0.4754 (0.6); 0.4657 (0.8); 0.4534 (1.0); 0.4425 (0.7); 0.4300 (0.3); 0.3916 (0.4); 0.3804 (0.7); 0.3686 (0.9); 0.3561 (0.8); 0.3462 (0.5); 0.0079 (0.4); −0.0002 (8.7) |
| I.0273: $^1$H-NMR(400.2 MHz, $d_6$-DMSO): δ = 9.1808 (0.7); 9.1623 (0.7); 5.2989 (1.4); 5.2804 (1.4); 3.7372 (16.0); 3.3279 (4.0); 2.8914 (0.4); 2.5115 (3.8); 2.5071 (7.5); 2.5025 (9.8); 2.4980 (7.2); 2.4935 (3.6); 2.4192 (8.7); −0.0002 (2.8) |
| I.0274: $^1$H-NMR(400.2 MHz, $d_6$-DMSO): δ = 8.6388 (1.1); 8.6202 (1.1); 4.4098 (0.4); 4.3964 (0.6); 4.3911 (0.6); 4.3874 (0.6); 4.3778 (0.7); 4.3740 (0.6); 4.3689 (0.6); 4.3553 (0.4); 4.1398 (0.6); 4.1352 (0.7); 4.1220 (2.1); 4.1175 (2.2); 4.1042 (2.2); 4.0998 (2.1); 4.0903 (0.3); 4.0863 (0.8); 4.0822 (0.7); 3.3285 (29.1); 2.8916 (0.9); 2.7327 (0.8); 2.7316 (0.8); 2.5251 (0.5); 2.5204 (0.8); 2.5117 (10.0); 2.5072 (20.2); 2.5026 (26.6); 2.4980 (19.5); 2.4935 (9.5); 2.4029 (16.0); 1.7616 (0.4); 1.7561 (0.4); 1.7436 (0.6); 1.7396 (0.5); 1.7266 (0.6); 1.7213 (0.6); 1.7042 (0.6); 1.6509 (0.5); 1.6372 (0.6); 1.6330 (0.6); 1.6190 (0.7); 1.6022 (0.4); 1.5979 (0.4); 1.5843 (0.4); 1.2117 (4.6); 1.1940 (9.6); 1.1762 (4.4); 0.8207 (0.4); 0.8143 (0.4); 0.8022 (0.6); 0.7902 (0.4); 0.7836 (0.4); 0.4575 (0.5); 0.4484 (0.6); 0.4449 (0.6); 0.4372 (1.1); 0.4284 (1.0); 0.4256 (0.9); 0.4170 (1.2); 0.4065 (0.7); 0.3969 (0.5); 0.1918 (0.5); 0.1827 (0.5); 0.1790 (0.6); 0.1687 (0.6); 0.1606 (0.5); 0.1568 (0.4); 0.0701 (0.6); 0.0615 (0.7); 0.0515 (0.6); 0.0486 (0.6); 0.0389 (0.5); −0.0002 (6.4) |
| I.0275: $^1$H-NMR(400.2 MHz, $d_6$-DMSO): δ = 8.2769 (2.2); 3.5840 (16.0); 3.3260 (15.2); 2.8912 (0.4); 2.7314 (0.3); 2.5246 (0.5); 2.5109 (9.4); 2.5066 (18.8); 2.5021 (24.8); 2.4976 (18.5); 2.4932 (9.4); 2.3511 (15.6); 1.3230 (0.5); 1.3093 (1.0); 1.3018 (1.1); 1.2958 (0.8); 1.2882 (2.2); 1.2807 (0.8); 1.2744 (1.2); 1.2670 (1.2); 1.2532 (0.6); 0.5333 (0.6); 0.5287 (0.7); 0.5243 (1.0); 0.5197 (0.8); 0.5103 (1.3); 0.5047 (1.2); 0.4990 (0.9); 0.4963 (0.9); 0.4911 (1.0); 0.4805 (0.4); 0.4669 (0.7); 0.4451 (2.4); 0.4417 (2.8); 0.4378 (2.9); 0.4205 (2.7); 0.4164 (3.0); 0.3926 (0.6); 0.3799 (0.4); 0.3691 (1.0); 0.3647 (1.0); 0.3555 (1.1); 0.3504 (1.4); 0.3415 (0.8); 0.3366 (1.0); 0.3315 (0.7); 0.3279 (0.7); 0.3224 (0.4); −0.0002 (6.4) |
| I.0276: $^1$H-NMR(400.2 MHz, $d_6$-DMSO): δ = 9.1477 (1.1); 9.1293 (1.1); 5.2247 (2.5); 5.2063 (2.5); 4.2466 (0.9); 4.2374 (0.9); 4.2288 (1.0); 4.2195 (3.8); 4.2111 (0.4); 4.2015 (5.8); 4.1919 (0.4); 4.1836 (3.9); 4.1742 (0.9); 4.1657 (1.0); 4.1565 (0.9); 3.3262 (12.7); 2.8914 (1.7); 2.7316 (1.5); 2.5250 (0.4); 2.5203 (0.5); 2.5116 (6.9); 2.5071 (14.0); 2.5025 (18.5); 2.4979 (13.6); 2.4934 (6.7); 2.4184 (14.1); 1.2383 (8.0); 1.2206 (16.0); 1.2028 (7.6); −0.0002 (5.1) |
| I.0277: $^1$H-NMR(400.2 MHz, $d_6$-DMSO): δ = 9.3408 (1.3); 4.1910 (0.7); 4.1733 (1.8); 4.1556 (1.8); 4.1378 (0.6); 4.0136 (0.9); 3.9907 (0.7); 3.3282 (11.9); 2.8918 (0.3); 2.5204 (0.4); 2.5117 (5.0); 2.5074 (9.9); 2.5028 (12.9); 2.4983 (9.5); 2.4939 (4.7); 2.4096 (6.9); 1.3946 (16.0); 1.1997 (1.9); 1.1820 (4.0); 1.1642 (1.9); −0.0002 (2.5) |
| I.0278: $^1$H-NMR(499.9 MHz, $d_6$-DMSO): δ = 8.5261 (0.4); 7.4984 (0.5); 4.4376 (0.7); 4.4285 (0.8); 4.4206 (0.8); 4.4114 (0.6); 3.6630 (16.0); 3.3225 (2.9); 3.1211 (1.4); 3.1076 (2.3); 3.0940 (1.2); 2.5058 (3.7); 2.5024 (4.8); 2.4990 (3.6); 1.8937 (0.4); 1.8781 (0.6); 1.8645 (0.7); 1.8553 (0.6); 1.8478 (0.5); 1.8365 (0.4); 1.8143 (0.4); 1.8022 (0.4); 1.7955 (0.7); 1.7839 (0.7); 1.7764 (0.6); 1.7664 (0.6); 1.7569 (0.4); 1.7449 (0.8); 1.5618 (0.5); 1.5483 (0.9); 1.5374 (1.3); 1.5299 (1.1); 1.5240 (1.2); 1.5189 (1.1); 1.5053 (0.7); 1.4919 (0.3); −0.0002 (1.9) |

TABLE A-(I)-continued

| NMR peak lists of compounds according to formula (I) |
|---|
| I.0279: $^1$H-NMR(300.2 MHz, CDCl3):<br>δ = 7.2986 (2.1); 7.1250 (1.0); 7.0996 (1.1); 5.3323 (0.6); 4.7965 (0.7); 4.7882 (0.4); 4.7823 (0.4); 4.7688 (1.8); 4.7508 (0.9); 4.7426 (1.3); 4.7334 (0.4); 4.7249 (0.6); 4.3127 (2.3); 4.2889 (7.2); 4.2651 (7.5); 4.2414 (2.6); 1.8458 (0.9); 1.8279 (1.2); 1.8162 (1.3); 1.7968 (4.3); 1.7838 (1.5); 1.7746 (2.7); 1.7581 (0.9); 1.7438 (1.0); 1.7379 (0.9); 1.7154 (0.9); 1.6784 (3.1); 1.3632 (8.0); 1.3394 (16.0); 1.3156 (7.7); 1.2927 (0.4); 1.2841 (0.4); 1.2691 (0.5); 1.0484 (0.6); 1.0269 (14.5); 1.0067 (13.9); 0.9826 (0.9); 0.9766 (0.8); 0.9507 (0.7); 0.9252 (0.5); 0.0285 (2.1) |
| I.0280: $^1$H-NMR(400.2 MHz, $d_6$-DMSO):<br>δ = 9.1757 (1.6); 9.1565 (1.6); 4.2652 (1.7); 4.2477 (2.5); 4.2290 (1.7); 4.1996 (0.8); 4.1904 (0.8); 4.1819 (0.9); 4.1726 (2.3); 4.1647 (1.1); 4.1548 (2.4); 4.1471 (2.4); 4.1372 (1.1); 4.1294 (2.3); 4.1200 (0.9); 4.1117 (0.8); 4.1023 (0.8); 3.3324 (19.6); 2.8937 (0.7); 2.7342 (0.6); 2.5088 (13.1); 2.5045 (16.7); 2.5000 (12.5); 2.2031 (0.8); 2.1861 (1.4); 2.1691 (1.5); 2.1521 (0.9); 1.2322 (6.2); 1.2144 (12.3); 1.1967 (5.9); 0.9862 (9.0); 0.9690 (16.0); 0.9515 (8.2); −0.0002 (3.8) |
| I.0281: $^1$H-NMR(300.2 MHz, CDCl3):<br>δ = 7.4555 (5.2); 7.2987 (3.6); 6.8695 (1.0); 3.7573 (16.0); 1.7479 (1.0); 1.7308 (2.7); 1.7201 (2.7); 1.7044 (1.2); 1.6300 (2.8); 1.3646 (1.4); 1.3489 (2.8); 1.3382 (2.8); 1.3210 (1.1); 0.0344 (4.5) |
| I.0282: $^1$H-NMR(300.2 MHz, $d_6$-DMSO):<br>δ = 12.6485 (1.1); 9.4509 (6.9); 7.9894 (16.0); 3.8695 (0.4); 3.3541 (11.8); 2.5342 (3.3); 2.5283 (6.7); 2.5223 (9.1); 2.5163 (6.6); 2.5104 (3.2); 1.4767 (2.7); 1.4607 (6.6); 1.4499 (7.4); 1.4359 (3.3); 1.1718 (3.4); 1.1576 (7.2); 1.1469 (6.8); 1.1307 (2.6); 0.0292 (0.4); 0.0185 (9.0); 0.0074 (0.4) |
| I.0283: $^1$H-NMR(300.2 MHz, CDCl3):<br>δ = 7.2990 (3.2); 6.4674 (1.0); 3.7593 (16.0); 2.5265 (15.3); 1.7492 (1.1); 1.7320 (3.2); 1.7213 (3.3); 1.7057 (1.4); 1.6516 (0.4); 1.3760 (1.4); 1.3603 (3.3); 1.3496 (3.3); 1.3325 (1.1); 0.0347 (4.0) |
| I.0284: $^1$H-NMR(300.2 MHz, $d_6$-DMSO):<br>δ = 8.7405 (2.2); 8.7154 (1.8); 8.0205 (14.8); 4.5748 (0.4); 3.7718 (1.8); 3.7465 (3.2); 3.7209 (1.6); 2.5285 (5.9); 2.5225 (7.8); 2.5166 (5.6); 2.0952 (0.8); 1.9175 (16.0); 1.2476 (0.4); 1.2209 (1.0); 1.2032 (1.9); 1.1874 (1.4); 1.1772 (2.0); 1.1600 (1.1); 1.1513 (0.8); 1.1335 (0.4); 0.5263 (0.8); 0.5188 (0.9); 0.5111 (1.2); 0.5015 (1.6); 0.4908 (2.5); 0.4644 (1.8); 0.4202 (2.0); 0.3906 (4.1); 0.3673 (8.0); 0.3526 (4.8); 0.3119 (0.5); 0.0174 (3.8) |
| I.0285: $^1$H-NMR(300.2 MHz, $d_6$-DMSO):<br>δ = 9.0720 (3.3); 9.0484 (3.4); 8.0655 (16.0); 3.7003 (2.8); 3.6766 (3.2); 3.6696 (3.3); 3.6458 (2.9); 3.4290 (0.3); 3.4038 (0.3); 3.1883 (0.4); 2.5342 (1.6); 2.5285 (3.3); 2.5224 (4.6); 2.5164 (3.4); 2.5107 (1.7); 1.2627 (0.4); 1.2471 (0.9); 1.2320 (1.0); 1.2194 (1.6); 1.2045 (1.6); 1.1896 (1.6); 1.1740 (1.0); 1.1628 (0.8); 1.1466 (0.4); 0.6680 (0.4); 0.6591 (0.6); 0.6534 (0.7); 0.6416 (1.4); 0.6336 (1.3); 0.6246 (1.6); 0.6126 (2.1); 0.5965 (1.1); 0.5848 (1.3); 0.5785 (1.1); 0.5654 (1.2); 0.5610 (1.3); 0.5486 (1.9); 0.5338 (1.7); 0.5223 (2.4); 0.5134 (1.5); 0.5043 (1.8); 0.4992 (1.9); 0.4945 (1.8); 0.4869 (2.2); 0.4700 (2.4); 0.4570 (1.8); 0.4406 (0.8); 0.3956 (1.0); 0.3796 (1.6); 0.3662 (2.1); 0.3497 (2.0); 0.3380 (1.2); 0.3317 (0.9); 0.0161 (3.7) |
| I.0286: $^1$H-NMR(300.2 MHz, $d_6$-DMSO):<br>δ = 8.2766 (0.7); 8.2666 (0.7); 3.8110 (3.4); 3.7883 (3.8); 3.1869 (2.0); 2.5342 (1.4); 2.5282 (5.5); 2.5221 (9.2); 2.5161 (7.4); 2.5103 (4.2); 2.4444 (53.9); 2.3774 (0.8); 1.9132 (16.0); 1.2092 (0.8); 1.2005 (0.4); 1.1892 (2.2); 1.1663 (2.7); 1.1452 (1.7); 1.1226 (0.7); 0.4546 (0.6); 0.4414 (0.5); 0.4238 (3.4); 0.4090 (3.2); 0.3996 (3.6); 0.3929 (3.8); 0.3722 (2.6); 0.3636 (3.9); 0.3535 (5.8); 0.3306 (5.9); 0.3170 (3.6); 0.3062 (2.7); 0.0171 (8.3); 0.0064 (0.9) |
| I.0287: $^1$H-NMR(300.2 MHz, $d_6$-DMSO):<br>δ = 8.4390 (7.8); 8.4167 (7.3); 7.9733 (0.6); 7.6823 (0.4); 7.6619 (0.4); 7.6028 (0.4); 7.5848 (0.4); 7.5548 (0.4); 7.4932 (0.4); 7.4776 (0.5); 7.4395 (0.5); 7.3999 (0.5); 7.2786 (0.5); 7.2339 (0.5); 7.1436 (0.4); 7.0895 (0.4); 7.0616 (0.4); 6.9743 (0.4); 6.8971 (0.3); 6.8654 (0.3); 4.8591 (0.3); 4.8332 (0.3); 4.7536 (0.4); 4.7204 (0.4); 4.7105 (0.4); 4.6761 (0.4); 4.6144 (0.5); 4.5787 (0.7); 4.4201 (0.6); 4.3460 (0.7); 4.2472 (0.8); 4.1445 (1.0); 3.9733 (1.2); 3.9293 (7.6); 3.9071 (13.5); 3.8847 (7.4); 3.8049 (0.9); 3.7216 (0.8); 3.6930 (0.8); 3.5879 (0.6); 3.5617 (0.6); 3.5228 (0.6); 3.5019 (0.6); 3.4706 (0.5); 3.4262 (0.5); 3.4094 (0.5); 3.3736 (0.4); 3.2711 (0.3); 2.9103 (3.8); 2.7510 (3.2); 2.5345 (9.8); 2.5286 (20.0); 2.5226 (27.2); 2.5166 (19.9); 2.5108 (9.6); 2.4574 (0.3); 1.2635 (1.4); 1.2462 (3.6); 1.2376 (3.9); 1.2303 (2.9); 1.2193 (6.6); 1.2023 (4.8); 1.1942 (7.2); 1.1788 (4.0); 1.1703 (3.6); 1.1527 (1.7); 0.8888 (0.5); 0.8698 (0.4); 0.5154 (0.4); 0.4988 (1.6); 0.4880 (3.6); 0.4778 (3.5); 0.4600 (14.3); 0.4511 (10.2); 0.4418 (12.6); 0.4261 (15.7); 0.4184 (16.0); 0.4076 (9.9); 0.3909 (14.4); 0.3767 (12.0); 0.3642 (11.2); 0.3599 (10.6); 0.3513 (7.2); 0.3419 (5.0); 0.3338 (5.7); 0.3098 (1.4); 0.0273 (0.6); 0.0165 (18.1); 0.0056 (1.0) |
| I.0288: $^1$H-NMR(499.9 MHz, $d_6$-DMSO):<br>δ = 8.9031 (3.9); 8.8867 (7.6); 8.8708 (4.2); 8.5250 (1.2); 8.5117 (1.2); 8.2902 (3.0); 8.2742 (3.3); 8.2495 (3.5); 8.2346 (3.4); 8.1009 (14.3); 8.0922 (16.0); 7.6653 (0.4); 7.6445 (0.5); 3.9528 (4.6); 3.9438 (4.0); 3.9366 (9.1); 3.9269 (5.6); 3.9206 (5.6); 3.9109 (3.4); 3.8900 (0.4); 3.8399 (1.0); 3.8246 (1.7); 3.8097 (1.0); 3.7474 (2.9); 3.7318 (5.3); 3.7162 (3.0); 3.6641 (0.4); 3.5773 (0.4); 3.5581 (0.3); 3.5115 (0.6); 3.3223 (38.0); 3.2014 (0.8); 2.6396 (0.4); 2.6319 (0.4); 2.5078 (42.8); 2.5045 (58.8); 2.5011 (45.8); 2.3656 (0.4); 1.3958 (0.4); 1.3853 (0.4); 1.3334 (0.5); 1.3255 (0.5); 1.3008 (0.5); 1.2383 (3.1); 1.2256 (1.6); 1.2163 (1.3); 1.2089 (1.6); 1.1997 (1.3); 1.1930 (1.2); 1.1775 (0.8); 1.1596 (2.4); 1.1440 (4.9); 1.1386 (5.2); 1.1297 (5.8); 1.1221 (5.2); 1.1151 (5.0); 1.1056 (3.5); 1.0992 (3.1); 1.0895 (1.8); 1.0830 (1.3); 1.0729 (0.7); 0.8565 (0.6); 0.8425 (0.6); 0.8310 (0.4); 0.6487 (2.2); 0.6390 (4.0); 0.6293 (4.2); 0.6195 (2.8); 0.6124 (2.2); 0.6035 (1.2); 0.5436 (1.1); 0.5250 (1.4); 0.5073 (3.6); 0.4887 (9.8); 0.4805 (12.5); 0.4729 (10.4); 0.4648 (11.7); 0.4471 (4.4); 0.4398 (3.8); 0.4301 (3.4); 0.4197 (3.6); 0.4136 (4.3); 0.4029 (5.1); 0.3943 (4.1); 0.3842 (4.0); 0.3742 (3.9); 0.3686 (3.3); 0.3565 (1.8); 0.3473 (2.2); 0.3392 (3.7); 0.3302 (5.4); 0.3202 (6.9); 0.3146 (6.7); 0.3091 (7.0); 0.2979 (5.9); 0.2878 (5.1); 0.2793 (4.5) |
| I.0289: $^1$H-NMR(499.9 MHz, $d_6$-DMSO):<br>δ = 8.2088 (1.1); 8.1964 (0.8); 8.1074 (1.4); 8.0930 (1.7); 8.0801 (1.0); 4.0492 (0.8); 4.0337 (1.5); 4.0255 (0.8); 4.0183 (1.0); 4.0093 (1.2); 3.9933 (0.6); 3.7617 (0.6); 3.7464 (1.0); 3.7314 (0.6); 3.5851 (0.7); 3.5697 (1.3); 3.5544 (0.8); 3.1447 (3.6); 2.3302 (11.7); 2.3269 (16.0); 2.3236 (12.8); 1.0605 (1.0); 0.9977 (0.6); 0.9899 (1.2); 0.9810 (1.3); 0.9743 (1.5); 0.9647 (1.4); 0.9567 (1.3); 0.9487 (1.1); 0.9402 (1.1); 0.9308 (0.8); 0.9240 (0.8); 0.9145 (0.6); 0.9083 (0.4); 0.4156 (0.4); 0.4084 (0.5); 0.3987 (0.6); 0.3875 (0.5); 0.3830 (0.5); 0.3709 (0.6); 0.3609 (0.8); 0.3499 (0.7); 0.3342 (0.7); 0.3227 (1.2); 0.3158 (1.7); 0.3109 (1.7); 0.3057 (2.0); 0.2998 (2.0); 0.2938 (2.3); 0.2893 (2.5); 0.2832 (2.3); 0.2775 (3.3); 0.2659 (3.1); 0.2554 (2.0); 0.2496 (1.9); 0.2456 (1.8); 0.2303 (1.6); 0.2230 (1.4); 0.2120 (1.4); 0.2042 (1.3); 0.1944 (1.2); 0.1846 (1.3); 0.1765 (1.2); 0.1687 (1.0); 0.1582 (1.2); 0.1493 (1.6); 0.1399 (1.7); 0.1301 (1.3); 0.1015 (0.5) |
| I.0290: $^1$H-NMR(300.2 MHz, CDCl3):<br>δ = 7.9502 (0.8); 7.2988 (1.4); 3.7647 (16.0); 2.4701 (12.8); 1.8516 (0.9); 1.8336 (2.6); 1.8235 (2.6); 1.8067 (1.1); 1.4533 (1.1); 1.4366 (2.5); 1.4265 (2.5); 1.4085 (0.9); 0.1115 (0.4); 0.1091 (0.4); 0.0320 (1.2) |
| I.0291: $^1$H-NMR(300.2 MHz, $d_6$-DMSO):<br>δ = 12.6204 (0.7); 9.1564 (3.0); 3.3516 (16.0); 2.5345 (2.8); 2.5286 (5.8); 2.5225 (7.8); 2.5165 (5.7); 2.5106 (2.6); 2.3815 (18.4); 1.4570 (1.2); 1.4408 (2.9); 1.4299 (3.3); 1.4159 (1.5); 1.1811 (1.5); 1.1671 (3.2); 1.1562 (3.0); 1.1400 (1.2); 0.0202 (5.4) |

TABLE A-(I)-continued

| NMR peak lists of compounds according to formula (I) |
|---|
| I.0292: $^1$H-NMR(300.2 MHz, $d_6$-DMSO): δ = 8.5510 (7.3); 8.5276 (7.3); 8.2549 (0.6); 4.5801 (0.4); 4.4667 (0.4); 4.4402 (0.4); 4.3961 (0.4); 4.1227 (0.8); 4.0785 (0.8); 3.9060 (6.0); 3.8812 (10.3); 3.8566 (6.3); 3.7404 (1.2); 3.6974 (1.1); 3.6842 (1.2); 3.6727 (1.1); 3.5533 (1.0); 3.4705 (0.9); 3.4634 (0.9); 3.4469 (0.9); 3.4242 (0.9); 3.4163 (0.8); 3.4082 (0.8); 3.3725 (0.8); 3.1870 (7.5); 3.0669 (0.4); 3.0067 (0.3); 2.5280 (15.5); 2.5220 (21.7); 2.5161 (16.4); 1.9274 (1.2); 1.2830 (0.7); 1.2662 (1.8); 1.2562 (2.9); 1.2508 (2.9); 1.2397 (4.9); 1.2239 (3.7); 1.2133 (5.0); 1.1971 (3.2); 1.1872 (2.3); 1.1706 (1.2); 0.5664 (2.6); 0.5559 (1.5); 0.5471 (3.2); 0.5379 (7.0); 0.5200 (2.4); 0.5103 (5.1); 0.5037 (5.1); 0.4931 (3.9); 0.4865 (3.6); 0.4737 (4.7); 0.4655 (6.4); 0.4599 (5.3); 0.4530 (4.8); 0.4317 (16.0); 0.4167 (16.0); 0.2943 (0.4); 0.0166 (9.6) |
| I.0293: $^1$H-NMR(300.2 MHz, $d_6$-DMSO): δ = 8.5082 (0.5); 8.3766 (7.6); 8.3545 (6.4); 7.6905 (0.3); 7.6784 (0.3); 7.6601 (0.4); 7.6318 (0.3); 7.5796 (0.4); 7.5085 (0.4); 7.4875 (0.4); 7.4056 (0.4); 7.3825 (0.4); 7.3184 (0.4); 7.2934 (0.4); 7.2468 (0.4); 7.1851 (0.3); 4.9122 (0.3); 4.8515 (0.3); 4.8180 (0.4); 4.7937 (0.4); 4.7166 (0.4); 4.6832 (0.4); 4.6207 (0.5); 4.5788 (0.7); 4.5380 (0.5); 4.4932 (0.5); 4.4602 (0.6); 4.3618 (0.6); 4.2530 (0.6); 4.2083 (0.7); 4.1551 (0.7); 4.1049 (0.7); 4.0604 (0.7); 4.0278 (0.8); 3.9946 (0.8); 3.9809 (0.8); 3.8903 (6.7); 3.8681 (11.0); 3.8457 (5.6); 3.7841 (0.4); 3.7784 (0.4); 3.7396 (0.4); 3.6957 (0.5); 3.6529 (0.3); 3.6263 (0.4); 3.6110 (0.3); 3.4093 (0.3); 3.1868 (1.8); 2.9097 (1.0); 2.7503 (0.9); 2.5346 (8.5); 2.5288 (16.8); 2.5227 (22.1); 2.5167 (15.4); 2.5108 (6.7); 1.9257 (8.9); 1.3149 (0.3); 1.2911 (0.4); 1.2578 (1.7); 1.2410 (3.7); 1.2322 (3.8); 1.2247 (2.9); 1.2139 (6.3); 1.1898 (6.5); 1.1731 (3.6); 1.1651 (3.1); 1.1475 (1.3); 0.9117 (0.4); 0.8874 (0.8); 0.8680 (0.5); 0.8629 (0.6); 0.8461 (0.4); 0.5022 (0.6); 0.4778 (3.7); 0.4679 (3.5); 0.4608 (4.5); 0.4498 (11.8); 0.4429 (10.9); 0.4297 (11.1); 0.4189 (14.2); 0.4144 (14.8); 0.4045 (14.7); 0.3954 (8.8); 0.3781 (16.0); 0.3673 (11.4); 0.3531 (11.2); 0.3422 (6.1); 0.3276 (4.7); 0.3034 (0.9); 0.0254 (0.4); 0.0146 (11.3); 0.0036 (0.4) |
| I.0294: $^1$H-NMR(300.2 MHz, $d_6$-DMSO): δ = 7.9100 (4.8); 4.5739 (0.5); 3.8156 (3.5); 3.7962 (7.4); 3.7767 (5.0); 3.6803 (0.4); 2.9083 (0.8); 2.7477 (0.6); 2.5340 (1.8); 2.5279 (8.0); 2.5219 (14.2); 2.5159 (12.3); 2.5101 (7.4); 1.9203 (16.0); 1.2016 (1.6); 1.1798 (4.7); 1.1578 (6.3); 1.1360 (4.5); 1.1140 (1.8); 0.4269 (0.5); 0.4116 (6.6); 0.4050 (11.0); 0.3883 (11.2); 0.3791 (6.6); 0.3615 (3.4); 0.3545 (3.6); 0.3469 (8.8); 0.3398 (8.6); 0.3322 (8.5); 0.3214 (15.1); 0.3061 (10.0); 0.2957 (7.5); 0.2878 (6.0); 0.0800 (0.8); 0.0125 (7.1); −0.0453 (0.7); −0.2795 (0.4) |
| I.0295: $^1$H-NMR(400.2 MHz, $d_6$-DMSO): δ = 9.1806 (0.5); 9.1662 (1.0); 9.1516 (0.5); 7.7313 (3.0); 7.7222 (3.1); 4.0290 (4.2); 4.0142 (4.2); 3.6588 (16.0); 3.3392 (25.7); 2.5222 (0.4); 2.5134 (4.5); 2.5090 (9.2); 2.5045 (12.2); 2.4999 (9.1); 2.4955 (4.6) |
| I.0296: $^1$H-NMR(400.2 MHz, $d_6$-DMSO): δ = 8.5821 (0.4); 8.5682 (0.8); 8.5541 (0.4); 3.9889 (3.6); 3.9744 (3.5); 3.6626 (14.8); 3.3352 (17.6); 2.5127 (3.7); 2.5082 (7.6); 2.5036 (9.9); 2.4990 (7.3); 2.4945 (3.6); 2.3869 (16.0) |
| I.0297: $^1$H-NMR(400.2 MHz, $d_6$-DMSO): δ = 8.5701 (0.5); 8.5558 (1.0); 8.5416 (0.5); 4.1502 (1.3); 4.1325 (4.1); 4.1147 (4.2); 4.0969 (1.4); 3.9685 (4.2); 3.9538 (4.1); 3.3335 (16.3); 2.5124 (4.5); 2.5080 (8.8); 2.5035 (11.5); 2.4990 (8.5); 2.4947 (4.3); 2.3859 (16.0); 1.2241 (4.5); 1.2064 (9.0); 1.1885 (4.4) |
| I.0298: $^1$H-NMR(400.2 MHz, $d_6$-DMSO): δ = 8.8348 (1.9); 8.3158 (1.9); 4.0922 (1.3); 4.0745 (4.2); 4.0568 (4.2); 4.0390 (1.4); 3.3339 (18.8); 3.3103 (0.6); 2.5211 (0.4); 2.5125 (4.6); 2.5081 (9.2); 2.5035 (12.0); 2.4989 (8.7); 2.4944 (4.3); 2.3494 (16.0); 1.4392 (1.1); 1.4271 (2.9); 1.4188 (3.1); 1.4080 (1.3); 1.1684 (5.3); 1.1588 (3.2); 1.1507 (11.5); 1.1382 (1.3); 1.1329 (4.4) |
| I.0299: $^1$H-NMR(400.2 MHz, $d_6$-DMSO): δ = 8.4601 (0.9); 8.4409 (0.9); 8.3150 (0.7); 4.2054 (1.4); 4.1877 (2.3); 4.1786 (0.6); 4.1693 (1.6); 4.1608 (1.6); 4.1432 (2.0); 4.1261 (2.0); 4.1085 (1.6); 4.0992 (0.7); 4.0908 (0.5); 4.0814 (0.7); 3.3385 (36.9); 3.3147 (0.4); 2.5124 (6.1); 2.5080 (12.1); 2.5035 (15.9); 2.4989 (11.6); 2.4944 (5.7); 2.3575 (16.0); 2.1820 (0.6); 2.1649 (1.0); 2.1479 (1.0); 2.1308 (0.6); 1.2219 (4.4); 1.2042 (9.1); 1.1864 (4.3); 0.9714 (6.1); 0.9544 (6.6); 0.9496 (6.5); 0.9324 (5.7) |
| I.0300: $^1$H-NMR(400.2 MHz, $d_6$-DMSO): δ = 8.5906 (1.1); 8.5717 (1.1); 4.5103 (0.4); 4.4910 (0.9); 4.4750 (0.9); 4.4557 (0.4); 4.1583 (0.5); 4.1490 (0.8); 4.1405 (1.6); 4.1310 (1.8); 4.1226 (1.8); 4.1132 (1.6); 4.1046 (0.8); 4.0956 (0.5); 3.3439 (46.8); 2.5970 (0.4); 2.5808 (0.8); 2.5635 (1.2); 2.5561 (0.7); 2.5466 (0.8); 2.5363 (1.4); 2.5266 (0.4); 2.5130 (5.3); 2.5086 (10.3); 2.5041 (13.7); 2.4997 (10.0); 2.4955 (5.1); 2.4845 (0.4); 2.3678 (13.9); 2.0657 (1.0); 2.0564 (16.0); 2.0481 (1.9); 2.0292 (1.4); 2.0130 (0.5); 2.0090 (0.5); 1.2168 (3.8); 1.1990 (7.8); 1.1813 (3.7) |
| I.0301: $^1$H-NMR(400.2 MHz, $d_6$-DMSO): δ = 8.6000 (0.8); 8.5830 (0.8); 8.3160 (1.8); 7.3139 (0.4); 7.2949 (2.8); 7.2873 (3.4); 7.2801 (10.8); 7.2703 (0.6); 7.2661 (0.8); 7.2379 (0.7); 7.2319 (0.8); 7.2221 (0.7); 7.2163 (0.8); 7.2124 (0.5); 7.2074 (0.4); 7.2017 (0.4); 4.5688 (0.5); 4.5594 (0.5); 4.5453 (0.5); 4.1375 (1.0); 4.1198 (3.0); 4.1027 (3.2); 4.0849 (1.1); 3.3382 (30.7); 3.3144 (0.7); 3.1830 (0.6); 3.1698 (0.7); 3.1486 (1.2); 3.1354 (1.0); 3.0681 (1.2); 3.0424 (1.2); 3.0337 (0.8); 3.0081 (0.7); 2.5210 (0.5); 2.5124 (6.0); 2.5080 (12.0); 2.5034 (15.8); 2.4988 (11.5); 2.4943 (5.6); 2.1851 (16.0); 1.1748 (4.5); 1.1571 (9.5); 1.1393 (4.4) |
| I.0302: $^1$H-NMR(400.2 MHz, $d_6$-DMSO): δ = 9.0233 (0.5); 9.0097 (1.0); 8.9959 (0.5); 4.0411 (3.6); 4.0267 (3.6); 3.6753 (16.0); 3.3378 (24.2); 2.5214 (0.4); 2.5128 (4.6); 2.5085 (9.0); 2.5040 (11.7); 2.4994 (8.7); 2.4951 (4.3); 2.3965 (15.8) |
| I.0303: $^1$H-NMR(400.2 MHz, $d_6$-DMSO): δ = 8.9995 (0.9); 8.3139 (1.6); 4.1619 (1.4); 4.1441 (4.3); 4.1263 (4.3); 4.1085 (1.4); 4.0122 (8.1); 3.3362 (16.0); 3.3125 (0.6); 2.5211 (0.4); 2.5126 (4.6); 2.5082 (9.2); 2.5036 (12.2); 2.4991 (9.0); 2.4946 (4.5); 2.3958 (16.0); 1.2294 (4.8); 1.2117 (9.6); 1.1939 (4.6) |
| I.0304: $^1$H-NMR(400.2 MHz, $d_6$-DMSO): δ = 8.9135 (1.0); 8.8944 (1.0); 4.2642 (1.2); 4.2474 (1.6); 4.2454 (1.6); 4.2284 (1.2); 4.1996 (0.7); 4.1904 (0.5); 4.1819 (0.7); 4.1726 (1.7); 4.1549 (1.9); 4.1394 (1.9); 4.1217 (1.8); 4.1124 (0.8); 4.1040 (0.6); 4.0946 (0.7); 3.3339 (31.0); 2.5208 (0.5); 2.5122 (5.9); 2.5077 (11.7); 2.5031 (15.3); 2.4985 (11.2); 2.4940 (5.4); 2.3576 (16.0); 2.1920 (0.6); 2.1749 (1.0); 2.1579 (1.0); 2.1410 (0.6); 1.2279 (4.9); 1.2102 (10.0); 1.1924 (4.7); 0.9718 (6.5); 0.9586 (7.3); 0.9549 (7.5); 0.9417 (6.0) |
| I.0305: $^1$H-NMR(400.2 MHz, $d_6$-DMSO): δ = 9.0281 (1.0); 9.0094 (1.0); 4.5476 (0.4); 4.5342 (0.4); 4.5256 (0.6); 4.5153 (0.5); 4.5125 (0.5); 4.5067 (0.5); 4.4934 (0.4); 4.1702 (0.5); 4.1612 (0.8); 4.1524 (1.6); 4.1433 (1.7); 4.1346 (1.7); 4.1256 (1.6); 4.1166 (0.8); 4.1079 (0.5); 3.3402 (34.0); 2.5877 (0.7); 2.5723 (0.9); 2.5684 (1.3); 2.5500 (1.4); 2.5303 (0.7); 2.5126 (4.7); 2.5082 (9.4); 2.5037 (12.3); 2.4991 (9.2); 2.4947 (4.6); 2.3733 (12.6); 2.0782 (0.5); 2.0596 (16.0); 2.0454 (1.2); 2.0286 (0.7); 2.0086 (0.4); 1.2232 (3.7); 1.2055 (7.6); 1.1877 (3.6) |
| I.0306: $^1$H-NMR(400.2 MHz, $d_6$-DMSO): δ = 9.0632 (1.3); 9.0438 (1.3); 7.3212 (0.6); 7.3015 (2.8); 7.2857 (9.3); 7.2735 (0.8); 7.2698 (1.1); 7.2627 (0.3); 7.2454 (0.8); 7.2401 (0.9); 7.2314 (0.8); 7.2239 (1.1); 7.2154 (0.6); 7.2084 (0.5); 4.6447 (0.5); 4.6316 (0.6); 4.6253 (0.6); 4.6190 (0.7); 4.6123 |

TABLE A-(I)-continued

| NMR peak lists of compounds according to formula (I) |
|---|
| (0.7); 4.6058 (0.6); 4.5996 (0.7); 4.5864 (0.5); 4.1514 (1.3); 4.1337 (4.1); 4.1160 (4.2); 4.0983 (1.4); 3.3470 (53.8); 3.2066 (0.8); 3.1935 (0.8); 3.1721 (1.2); 3.1591 (1.1); 3.0569 (1.2); 3.0309 (1.2); 3.0225 (0.9); 2.9966 (0.8); 2.8913 (0.5); 2.7323 (0.4); 2.5125 (6.7); 2.5082 (13.5); 2.5037 (17.7); 2.4992 (13.1); 2.4948 (6.6); 2.1775 (16.0); 1.1829 (4.8); 1.1651 (9.8); 1.1473 (4.6) |
| I.0307: $^1$H-NMR(400.2 MHz, $d_6$-DMSO): |
| δ = 9.2319 (0.4); 9.2174 (0.8); 9.2027 (0.4); 7.8126 (4.4); 4.0363 (3.9); 4.0216 (3.8); 3.6601 (16.0); 3.3341 (68.5); 2.8914 (0.8); 2.7316 (0.7); 2.5252 (0.7); 2.5204 (1.1); 2.5118 (13.9); 2.5073 (28.0); 2.5028 (36.7); 2.4982 (27.0); 2.4937 (13.3) |
| I.0308: $^1$H-NMR(400.2 MHz, $d_6$-DMSO): |
| δ = 9.2917 (3.5); 7.9540 (0.3); 7.7622 (7.7); 4.0936 (2.3); 4.0760 (7.2); 4.0582 (7.2); 4.0405 (2.3); 3.3403 (35.4); 2.8933 (2.5); 2.7336 (2.1); 2.5275 (0.4); 2.5228 (0.6); 2.5142 (7.1); 2.5097 (14.4); 2.5052 (18.9); 2.5006 (13.8); 2.4961 (6.8); 1.4736 (1.9); 1.4615 (4.8); 1.4533 (5.2); 1.4423 (2.2); 1.1697 (2.3); 1.1585 (5.6); 1.1542 (9.2); 1.1506 (5.8); 1.1365 (16.0); 1.1188 (7.2) |
| I.0309: $^1$H-NMR(400.2 MHz, $d_6$-DMSO): |
| δ = 8.8068 (2.1); 8.7869 (2.2); 8.0657 (9.4); 4.2758 (2.3); 4.2567 (4.0); 4.2378 (2.3); 4.1828 (0.9); 4.1734 (1.0); 4.1650 (1.0); 4.1556 (3.2); 4.1376 (3.5); 4.1344 (3.7); 4.1165 (3.3); 4.1071 (1.0); 4.0987 (1.0); 4.0894 (1.0); 4.0716 (0.3); 3.3375 (57.6); 2.8932 (0.5); 2.7337 (0.5); 2.5093 (23.5); 2.5049 (31.0); 2.5006 (23.7); 2.1894 (0.4); 2.1724 (1.1); 2.1552 (1.9); 2.1380 (1.9); 2.1208 (1.2); 2.1038 (0.4); 1.2203 (8.0); 1.2026 (16.0); 1.1848 (7.7); 0.9720 (12.1); 0.9550 (11.8); 0.9379 (11.7); 0.9209 (11.4) |
| I.0310: $^1$H-NMR(400.2 MHz, $d_6$-DMSO): |
| δ = 8.9801 (1.0); 8.9613 (1.0); 7.9059 (4.1); 4.5448 (0.4); 4.5319 (0.5); 4.5259 (0.5); 4.5219 (0.6); 4.5131 (0.5); 4.5091 (0.5); 4.5031 (0.5); 4.4901 (0.4); 4.1551 (0.6); 4.1505 (0.6); 4.1373 (1.8); 4.1329 (1.9); 4.1195 (1.9); 4.1152 (1.8); 4.1017 (0.6); 4.0975 (0.6); 3.3392 (24.8); 2.5904 (0.7); 2.5766 (0.7); 2.5704 (0.8); 2.5573 (1.0); 2.5383 (1.1); 2.5140 (4.3); 2.5096 (8.7); 2.5050 (11.6); 2.5005 (8.4); 2.4960 (4.2); 2.0702 (0.5); 2.0572 (16.0); 2.0360 (0.8); 2.0296 (0.7); 2.0144 (0.6); 2.0060 (0.4); 1.9917 (0.4); 1.2113 (3.8); 1.1935 (7.8); 1.1758 (3.7) |
| I.0311: $^1$H-NMR(400.2 MHz, $d_6$-DMSO): |
| δ = 9.1581 (0.9); 9.1436 (1.7); 9.1290 (0.9); 7.7284 (5.0); 7.7193 (4.9); 4.1483 (2.3); 4.1306 (7.0); 4.1128 (7.1); 4.0950 (2.3); 4.0085 (6.5); 3.9937 (6.5); 3.3383 (34.8); 2.5273 (0.3); 2.5224 (0.5); 2.5138 (6.8); 2.5094 (13.5); 2.5048 (17.5); 2.5003 (12.8); 2.4958 (6.3); 1.2204 (8.0); 1.2027 (16.0); 1.1849 (7.7) |
| I.0312: $^1$H-NMR(400.2 MHz, $d_6$-DMSO): |
| δ = 9.2209 (4.0); 7.9540 (0.5); 7.6824 (4.6); 7.6734 (4.6); 4.0900 (2.3); 4.0723 (7.2); 4.0546 (7.2); 4.0369 (2.4); 3.3448 (53.0); 2.8932 (3.2); 2.7337 (2.8); 2.5277 (0.4); 2.5098 (17.4); 2.5054 (22.3); 2.5009 (16.7); 1.4643 (2.0); 1.4523 (5.2); 1.4441 (5.7); 1.4331 (2.4); 1.1624 (2.5); 1.1533 (10.8); 1.1432 (6.0); 1.1359 (16.0); 1.1181 (7.4) |
| I.0313: $^1$H-NMR(400.2 MHz, $d_6$-DMSO): |
| δ = 8.7379 (1.9); 8.7181 (1.9); 7.9990 (5.0); 7.9899 (4.9); 4.2694 (2.1); 4.2506 (3.4); 4.2317 (2.1); 4.1782 (0.9); 4.1689 (1.0); 4.1604 (1.0); 4.1510 (3.4); 4.1427 (0.5); 4.1327 (4.4); 4.1219 (0.4); 4.1138 (3.4); 4.1043 (1.0); 4.0960 (1.0); 4.0866 (0.9); 3.3439 (65.2); 2.8941 (0.4); 2.7351 (0.4); 2.5285 (0.4); 2.5150 (8.7); 2.5106 (17.4); 2.5061 (22.6); 2.5015 (16.5); 2.4971 (8.1); 2.1715 (1.0); 2.1544 (1.7); 2.1372 (1.7); 2.1200 (1.0); 2.1029 (0.4); 1.2194 (7.9); 1.2016 (16.0); 1.1839 (7.7); 0.9733 (11.0); 0.9564 (10.7); 0.9376 (10.6); 0.9206 (10.2) |
| I.0314: $^1$H-NMR(400.2 MHz, $d_6$-DMSO): |
| δ = 8.9132 (1.1); 8.8944 (1.1); 7.8394 (2.4); 7.8303 (2.4); 4.5345 (0.4); 4.5214 (0.5); 4.5155 (0.6); 4.5121 (0.6); 4.5025 (0.6); 4.4990 (0.6); 4.4933 (0.6); 4.4801 (0.4); 4.1511 (0.6); 4.1468 (0.7); 4.1334 (1.9); 4.1292 (1.9); 4.1155 (2.0); 4.1115 (1.9); 4.0977 (0.7); 4.0939 (0.6); 3.3403 (28.3); 2.5949 (0.8); 2.5807 (0.8); 2.5752 (0.8); 2.5614 (0.9); 2.5437 (1.2); 2.5243 (0.9); 2.5141 (4.9); 2.5099 (9.7); 2.5054 (12.1); 2.5008 (8.9); 2.4965 (4.5); 2.0587 (16.0); 2.0459 (0.9); 2.0405 (0.9); 2.0258 (1.1); 2.0087 (0.9); 2.0026 (0.5); 1.9881 (0.4); 1.2101 (3.8); 1.1924 (7.8); 1.1746 (3.7) |
| I.0315: $^1$H-NMR(400.2 MHz, $d_6$-DMSO): |
| δ = 9.0435 (1.7); 9.0241 (1.8); 7.7900 (3.8); 7.7810 (3.8); 7.3064 (0.5); 7.2865 (4.5); 7.2807 (4.9); 7.2729 (16.0); 7.2596 (1.2); 7.2275 (0.9); 7.2208 (1.1); 7.2111 (1.0); 7.2060 (1.2); 7.2015 (0.8); 7.1969 (0.6); 7.1917 (0.6); 7.1846 (0.3); 4.6281 (0.7); 4.6138 (0.8); 4.6086 (0.9); 4.6038 (1.0); 4.5943 (0.9); 4.5895 (0.9); 4.5843 (1.0); 4.5700 (0.7); 4.1084 (1.8); 4.0907 (5.7); 4.0730 (5.8); 4.0552 (1.9); 3.3432 (47.9); 3.1613 (0.9); 3.1470 (1.0); 3.1268 (1.8); 3.1126 (1.6); 3.0626 (1.8); 3.0382 (1.8); 3.0283 (1.0); 3.0038 (1.0); 2.8913 (0.7); 2.7329 (0.6); 2.5271 (0.3); 2.5135 (7.8); 2.5092 (15.7); 2.5047 (20.6); 2.5001 (15.3); 2.4957 (7.7); 1.1385 (6.3); 1.1207 (13.1); 1.1029 (6.1) |
| I.0316: $^1$H-NMR(400.2 MHz, $d_6$-DMSO): |
| δ = 8.5840 (0.4); 8.5716 (0.8); 8.5593 (0.4); 3.9869 (2.8); 3.9731 (2.7); 3.6623 (15.2); 3.3399 (26.1); 2.5216 (0.4); 2.5131 (3.9); 2.5087 (7.8); 2.5041 (10.1); 2.4995 (7.4); 2.4950 (3.6); 2.4007 (16.0) |
| I.0317: $^1$H-NMR(400.2 MHz, $d_6$-DMSO): |
| δ = 8.5752 (0.4); 8.5609 (0.9); 8.5466 (0.4); 4.1498 (1.3); 4.1320 (4.1); 4.1142 (4.1); 4.0964 (1.3); 3.9669 (3.7); 3.9523 (3.6); 3.3360 (20.2); 2.8924 (0.5); 2.7337 (0.4); 2.7326 (0.4); 2.5216 (0.3); 2.5129 (4.0); 2.5084 (8.0); 2.5038 (10.6); 2.4992 (7.7); 2.4947 (3.8); 2.3994 (16.0); 1.2239 (4.7); 1.2061 (9.4); 1.1883 (4.5) |
| I.0318: $^1$H-NMR(400.2 MHz, $d_6$-DMSO): |
| δ = 8.8356 (2.1); 4.0915 (1.4); 4.0738 (4.3); 4.0561 (4.3); 4.0383 (1.4); 3.3362 (23.0); 2.5218 (0.4); 2.5128 (4.6); 2.5083 (9.3); 2.5038 (12.2); 2.4992 (8.9); 2.4947 (4.4); 2.3623 (16.0); 1.4375 (1.1); 1.4254 (2.9); 1.4171 (3.2); 1.4063 (1.3); 1.1684 (5.7); 1.1567 (3.5); 1.1507 (10.5); 1.1331 (4.6) |
| I.0319: $^1$H-NMR(400.2 MHz, $d_6$-DMSO): |
| δ = 8.4654 (0.9); 8.4462 (1.0); 4.2054 (1.4); 4.1870 (2.4); 4.1778 (0.6); 4.1692 (1.9); 4.1600 (1.7); 4.1423 (2.0); 4.1251 (2.0); 4.1075 (1.6); 4.0982 (0.7); 4.0898 (0.5); 4.0804 (0.7); 3.3392 (37.7); 2.5214 (0.4); 2.5127 (5.2); 2.5082 (10.5); 2.5036 (13.8); 2.4990 (10.1); 2.4945 (4.9); 2.3685 (16.0); 2.1797 (0.6); 2.1627 (1.0); 2.1456 (1.0); 2.1286 (0.6); 1.2215 (4.6); 1.2038 (9.4); 1.1860 (4.4); 0.9702 (6.2); 0.9531 (6.8); 0.9489 (6.6); 0.9318 (5.7) |
| I.0320: $^1$H-NMR(400.2 MHz, $d_6$-DMSO): |
| δ = 8.5944 (0.9); 8.5755 (0.9); 4.5084 (0.4); 4.4889 (0.8); 4.4732 (0.7); 4.4537 (0.4); 4.1575 (0.5); 4.1480 (0.7); 4.1397 (1.6); 4.1301 (1.7); 4.1219 (1.7); 4.1123 (1.6); 4.1037 (0.7); 4.0946 (0.5); 3.3447 (34.8); 2.5795 (0.7); 2.5622 (1.0); 2.5554 (0.7); 2.5451 (0.7); 2.5356 (1.3); 2.5267 (0.3); 2.5218 (0.6); 2.5133 (4.3); 2.5088 (8.5); 2.5042 (11.2); 2.4996 (8.2); 2.4951 (4.0); 2.4835 (0.3); 2.3795 (13.2); 2.0560 (16.0); 2.0449 (1.5); 2.0259 (1.1); 2.0107 (0.4); 2.0056 (0.4); 1.2164 (3.7); 1.1987 (7.8); 1.1809 (3.6) |
| I.0321: $^1$H-NMR(400.2 MHz, $d_6$-DMSO): |
| δ = 8.6061 (1.2); 8.5868 (1.2); 8.3143 (2.2); 7.3143 (0.5); 7.2947 (3.0); 7.2868 (3.4); 7.2801 (11.1); 7.2701 (0.8); 7.2659 (1.0); 7.2381 (0.7); 7.2322 (0.8); 7.2228 (0.8); 7.2166 (0.9); 7.2083 (0.5); 7.2019 (0.5); 4.5848 (0.5); 4.5716 (0.6); 4.5655 (0.6); 4.5593 (0.7); 4.5523 (0.6); 4.5462 (0.6); 4.5401 (0.6); 4.5267 (0.5); 4.1367 (1.1); 4.1190 (3.4); 4.1014 (3.6); 4.0837 (1.2); 3.3493 (38.6); 3.3252 (1.1); 3.1812 (0.7); 3.1679 (0.8); 3.1468 (1.2); 3.1336 (1.1); 3.0646 (1.2); 3.0389 (1.2); 3.0303 (0.8); 3.0046 (0.7); 2.5131 (5.3); 2.5087 (10.8); 2.5042 (14.4); 2.4997 (10.8); 2.4953 (5.5); 2.1969 (16.0); 1.1743 (4.5); 1.1566 (9.2); 1.1388 (4.4) |
| I.0322: $^1$H-NMR(400.2 MHz, $d_6$-DMSO): |
| δ = 8.5716 (1.0); 8.5525 (1.0); 4.2936 (1.1); 4.2753 (2.0); 4.2571 (1.1); 3.6628 (16.0); 3.3264 (9.9); 2.5116 (5.7); 2.5072 (11.5); 2.5027 (15.0); 2.4982 (11.0); 2.4937 (5.4); 2.3789 (15.4); 1.9360 (0.4); 1.9314 (0.4); 1.9253 (0.5); 1.9199 (0.5); 1.9142 (0.5); |

TABLE A-(I)-continued

| NMR peak lists of compounds according to formula (I) |
|---|
| 1.9079 (0.4); 1.9035 (0.4); 1.4867 (0.3); 1.4788 (0.4); 1.4678 (0.4); 1.4635 (0.5); 1.4528 (0.4); 1.4448 (0.5); 1.4341 (0.4); 1.2872 (0.5); 1.2687 (0.6); 1.2527 (0.5); 1.2470 (0.6); 1.2351 (0.7); 1.2130 (0.4); 0.9004 (6.2); 0.8831 (6.6); 0.8609 (6.4); 0.8423 (2.7); −0.0002 (2.1) |
| I.0323: $^1$H-NMR(300.2 MHz, CDCl3): |
| δ = 9.0488 (1.5); 7.2985 (7.5); 4.2594 (2.4); 4.2356 (7.4); 4.2119 (7.5); 4.1882 (2.4); 1.8425 (2.1); 1.8251 (5.8); 1.8147 (5.8); 1.7982 (2.6); 1.6149 (3.4); 1.4392 (2.6); 1.4231 (5.6); 1.4126 (5.8); 1.3949 (2.1); 1.3000 (7.9); 1.2763 (16.0); 1.2526 (7.6); 0.0353 (7.6) |
| I.0324: $^1$H-NMR(300.2 MHz, $d_6$-DMSO): |
| δ = 12.5842 (1.0); 8.8352 (3.5); 3.3428 (16.0); 2.5352 (2.5); 2.5292 (5.4); 2.5231 (7.5); 2.5170 (5.3); 2.5110 (2.4); 1.4572 (1.4); 1.4409 (3.6); 1.4300 (4.1); 1.4159 (1.8); 1.1843 (1.9); 1.1701 (4.0); 1.1591 (3.7); 1.1427 (1.4); 0.0209 (5.9) |
| I.0325: $^1$H-NMR(300.2 MHz, CDCl3): |
| δ = 8.9681 (1.4); 7.2989 (3.1); 4.2559 (2.4); 4.2322 (7.4); 4.2084 (7.6); 4.1847 (2.4); 2.0437 (0.4); 1.8396 (2.2); 1.8221 (5.7); 1.8117 (5.6); 1.7952 (2.6); 1.4290 (2.5); 1.4127 (5.3); 1.4023 (5.6); 1.3848 (2.1); 1.2964 (7.9); 1.2727 (16.0); 1.2489 (7.6); 0.0346 (3.5) |
| I.0327: $^1$H-NMR(300.2 MHz, CDCl3): |
| δ = 7.2988 (2.7); 4.4715 (9.4); 4.2995 (1.2); 4.2756 (3.6); 4.2518 (3.6); 4.2280 (1.2); 3.8239 (16.0); 1.6247 (0.7); 1.3387 (4.1); 1.3149 (8.1); 1.2911 (4.0); 0.0343 (3.3) |
| I.0328: $^1$H-NMR(300.2 MHz, CDCl3): |
| δ = 8.2314 (0.4); 8.1960 (0.4); 7.2987 (2.5); 3.7520 (16.0); 1.8405 (1.1); 1.8229 (2.9); 1.8125 (2.8); 1.7959 (1.3); 1.6073 (3.2); 1.4209 (1.3); 1.4045 (2.7); 1.3941 (2.9); 1.3764 (1.0); 0.0352 (3.1) |
| I.0329: $^1$H-NMR(300.2 MHz, $d_6$-DMSO): |
| δ = 12.6638 (0.9); 10.3511 (3.0); 10.3429 (3.0); 3.6238 (1.1); 3.3527 (16.0); 2.5344 (3.5); 2.5284 (7.5); 2.5223 (10.2); 2.5162 (7.3); 2.5103 (3.3); 2.0949 (2.2); 1.5666 (2.1); 1.5493 (5.3); 1.5385 (5.9); 1.5237 (2.6); 1.4691 (0.4); 1.3158 (2.7); 1.3011 (5.6); 1.2903 (5.3); 1.2730 (2.0); 0.0299 (0.4); 0.0191 (12.4); 0.0082 (0.4) |
| I.0330: $^1$H-NMR(400.1 MHz, CDCl3): |
| δ = 8.0320 (0.6); 7.2602 (10.8); 7.0220 (0.6); 7.0050 (1.0); 6.9866 (0.5); 4.8165 (0.5); 4.7997 (1.0); 4.7841 (0.9); 4.7667 (0.4); 3.7989 (16.0); 2.9667 (3.7); 2.8912 (3.4); 2.5610 (0.5); 2.5370 (0.9); 2.5183 (1.8); 2.5082 (1.0); 2.4997 (1.3); 2.4913 (1.9); 2.4744 (1.0); 2.4483 (0.5); 2.4312 (0.3); 2.3748 (0.4); 2.3567 (0.6); 2.3391 (0.7); 2.3254 (0.8); 2.3211 (0.8); 2.3077 (0.7); 2.1685 (0.4); 2.1505 (0.9); 2.1320 (1.1); 2.1141 (0.9); 2.0960 (0.6); −0.0002 (13.4) |
| I.0331: $^1$H-NMR(400.1 MHz, $d_6$-DMSO): |
| δ = 10.5089 (3.7); 4.1280 (2.6); 4.1103 (7.7); 4.0927 (7.8); 4.0750 (2.6); 3.3097 (57.2); 2.8976 (1.5); 2.7386 (1.4); 2.6760 (1.5); 2.6543 (2.5); 2.6413 (3.0); 2.6253 (3.4); 2.6074 (1.8); 2.5072 (20.2); 2.4402 (1.6); 2.4179 (3.6); 2.3885 (2.9); 2.3634 (1.4); 2.3130 (0.4); 1.9978 (1.0); 1.9790 (3.1); 1.9581 (4.3); 1.9388 (2.8); 1.9176 (0.8); 1.1796 (8.1); 1.1619 (16.0); 1.1442 (7.7) |
| I.0332: $^1$H-NMR(400.1 MHz, $d_6$-DMSO): |
| δ = 10.5917 (2.0); 3.6267 (16.0); 3.3087 (23.4); 2.8978 (0.9); 2.7387 (0.8); 2.5073 (9.0); 2.3233 (15.0); 2.3075 (0.9); 1.5938 (1.2); 1.5809 (3.2); 1.5730 (3.5); 1.5614 (1.4); 1.3529 (1.5); 1.3415 (3.4); 1.3335 (3.3); 1.3206 (1.1) |
| I.0333: $^1$H-NMR(400.1 MHz, $d_6$-DMSO): |
| δ = 10.7521 (2.1); 3.6216 (16.0); 3.3087 (24.1); 2.8977 (1.8); 2.7386 (1.7); 2.5113 (7.9); 2.5074 (10.0); 1.6086 (1.2); 1.5957 (3.3); 1.5877 (3.5); 1.5760 (1.5); 1.3399 (1.5); 1.3283 (3.4); 1.3202 (3.4); 1.3075 (1.2) |
| I.0334: $^1$H-NMR(400.1 MHz, $d_6$-DMSO): |
| δ = 10.8525 (2.0); 3.6291 (16.0); 3.3081 (25.1); 2.5074 (9.6); 1.6180 (1.2); 1.6052 (3.4); 1.5972 (3.6); 1.5856 (1.5); 1.3397 (1.5); 1.3282 (3.5); 1.3202 (3.5); 1.3072 (1.2) |
| I.0335: $^1$H-NMR(400.1 MHz, $d_6$-DMSO): |
| δ = 10.9373 (2.1); 3.6370 (16.0); 3.3095 (24.7); 2.8978 (0.6); 2.7386 (0.6); 2.5073 (8.7); 2.3137 (15.3); 1.6105 (1.2); 1.5976 (3.3); 1.5896 (3.5); 1.5781 (1.5); 1.3712 (1.6); 1.3598 (3.5); 1.3519 (3.3); 1.3388 (1.1) |
| I.0336: $^1$H-NMR(400.1 MHz, $d_6$-DMSO): |
| δ = 10.9853 (2.0); 7.9592 (1.4); 7.9110 (5.6); 3.6171 (16.0); 3.3108 (18.6); 2.8976 (8.6); 2.7385 (7.8); 2.5112 (6.4); 2.5073 (8.0); 1.6210 (1.0); 1.6087 (3.0); 1.6008 (3.2); 1.5899 (1.2); 1.3685 (1.4); 1.3573 (3.0); 1.3493 (2.9); 1.3367 (1.0) |
| I.0337: $^1$H-NMR(300.2 MHz, $d_6$-DMSO): |
| δ = 13.2575 (2.8); 8.7616 (16.0); 8.7359 (16.0); 6.4078 (2.8); 6.3929 (5.3); 6.3773 (2.4); 6.2207 (5.5); 6.2058 (11.0); 6.1903 (5.3); 6.0339 (2.7); 6.0190 (5.6); 6.0034 (2.7); 4.6207 (4.8); 4.6019 (6.4); 4.5940 (9.9); 4.5762 (9.4); 4.5680 (6.7); 4.5495 (4.7); 3.5277 (0.4); 3.3547 (13.4); 3.2062 (0.4); 2.9967 (0.5); 2.5597 (1.2); 2.5282 (31.7); 2.5223 (40.4); 2.5164 (31.7); 2.4940 (4.9); 2.4731 (7.4); 2.4535 (10.8); 2.4388 (8.6); 2.4236 (6.3); 2.4166 (4.9); 2.4005 (6.6); 2.3883 (4.5); 2.3745 (4.0); 2.3600 (3.0); 2.3248 (0.8); 2.3100 (0.6); 2.2929 (0.5); 2.0951 (8.8); 1.2546 (0.5); 0.0183 (14.5) |
| I.0338: $^1$H-NMR(600.2 MHz, $d_6$-DMSO): |
| δ = 12.3867 (0.5); 8.3849 (1.3); 8.3722 (1.3); 8.2011 (0.7); 8.1963 (0.7); 8.1875 (0.7); 8.1827 (0.7); 7.2443 (0.8); 7.2414 (0.4); 7.2323 (2.1); 7.2301 (1.8); 7.2247 (0.7); 7.2205 (3.1); 7.2043 (4.6); 7.1928 (2.4); 7.1897 (1.9); 7.1838 (0.3); 7.1773 (0.4); 4.7608 (0.4); 4.7516 (0.5); 4.7480 (0.8); 4.7389 (0.8); 4.7350 (0.6); 4.7260 (0.4); 4.4716 (0.5); 4.4623 (0.6); 4.4574 (0.8); 4.4493 (0.8); 4.4445 (0.7); 4.4351 (0.5); 3.5994 (16.0); 3.3284 (4.9); 3.0416 (0.6); 3.0323 (0.7); 3.0186 (1.2); 3.0094 (1.0); 2.9722 (1.1); 2.9575 (1.1); 2.9492 (0.7); 2.9345 (0.6); 2.7548 (0.5); 2.7459 (0.6); 2.7268 (1.4); 2.7182 (1.2); 2.7009 (1.3); 2.6883 (1.4); 2.6729 (0.6); 2.6605 (0.6); 2.5136 (1.4); 2.5107 (3.2); 2.5077 (4.4); 2.5047 (3.3); 2.5017 (1.6) |
| I.0339: $^1$H-NMR(400.1 MHz, $d_6$-DMSO): |
| δ = 8.3801 (2.3); 8.3649 (2.4); 7.9526 (3.6); 7.2334 (2.9); 7.2122 (6.8); 4.7414 (1.0); 4.7288 (1.0); 4.4872 (0.5); 4.4692 (1.1); 4.4539 (1.1); 4.4351 (0.5); 3.5948 (9.4); 3.3174 (4.3); 3.0528 (0.6); 3.0390 (0.7); 3.0181 (1.4); 3.0044 (1.4); 2.9816 (1.4); 2.9596 (3.2); 2.9244 (1.0); 2.8902 (16.0); 2.7316 (15.5); 2.7110 (2.0); 2.6988 (1.6); 2.6379 (1.2); 2.6159 (1.2); 2.5969 (0.7); 2.5745 (0.7); 2.5571 (0.4); 2.5017 (5.2); 2.4786 (1.4); 2.3470 (8.8); 2.1552 (1.0); 2.0722 (0.5); −0.0002 (0.6) |
| I.0340: $^1$H-NMR(400.1 MHz, $d_6$-DMSO): |
| δ = 12.3752 (0.7); 8.4073 (2.2); 8.3871 (4.0); 8.3682 (2.1); 7.9515 (0.6); 7.2347 (3.6); 7.2213 (7.1); 7.2112 (9.5); 7.1989 (3.5); 7.1749 (0.9); 4.7605 (0.7); 4.7398 (1.4); 4.7279 (1.3); 4.7073 (0.7); 4.4850 (0.7); 4.4654 (1.4); 4.4515 (1.4); 4.4317 (0.7); 3.5932 (16.0); 3.3162 (29.2); 3.0515 (0.8); 3.0373 (0.9); 3.0166 (1.9); 3.0029 (1.7); 2.9795 (1.8); 2.9578 (1.8); 2.9452 (0.9); 2.9235 (0.8); 2.8898 (3.4); 2.7483 (1.0); 2.7307 (3.5); 2.7075 (1.8); 2.6955 (1.6); 2.6335 (1.6); 2.6115 (1.6); 2.5917 (0.9); 2.5697 (0.9); 2.5007 (14.0); 2.4733 (1.3); 2.3437 (14.4); 2.3271 (1.3); −0.0002 (1.9) |
| I.0341: $^1$H-NMR(600.1 MHz, $d_6$-DMSO): |
| δ = 9.4374 (3.4); 7.4092 (0.9); 7.3206 (2.3); 7.2319 (1.0); 4.0931 (2.1); 4.0813 (6.8); 4.0695 (6.9); 4.0576 (2.1); 3.3237 (31.6); 2.8924 (1.0); 2.7336 (0.8); 2.7330 (0.8); 2.5093 (5.6); 2.5062 (12.5); 2.5032 (17.7); 2.5001 (12.6); 2.4971 (5.6); 1.4384 (1.8); 1.4303 (4.5); 1.4248 (5.0); 1.4174 (2.0); 1.2077 (2.0); 1.2002 (4.6); 1.1947 (4.6); 1.1866 (1.6); 1.1685 (7.6); 1.1567 (16.0); 1.1449 (7.4); −0.0001 (1.4) |
| I.0342: $^1$H-NMR(600.1 MHz, $d_6$-DMSO): |
| δ = 8.8682 (2.4); 4.3321 (0.7); 4.3228 (0.7); 4.3016 (15.7); 4.2923 (16.0); 3.3323 (95.6); 2.8946 (1.0); 2.7353 (0.9); 2.5235 (0.3); 2.5116 (8.1); 2.5086 (17.9); 2.5056 (25.0); 2.5026 (17.8); 2.4996 (8.1); −0.0001 (1.6) |

TABLE A-(I)-continued

| NMR peak lists of compounds according to formula (I) |
|---|
| I.0343: $^1$H-NMR(600.1 MHz, $d_6$-DMSO): δ = 8.5748 (0.6); 4.0150 (3.6); 4.0052 (3.7); 3.6690 (0.8); 3.6604 (16.0); 3.3273 (27.3); 2.5097 (3.2); 2.5067 (7.0); 2.5037 (9.6); 2.5007 (6.7); 2.4977 (3.0) |
| I.0344: $^1$H-NMR(600.1 MHz, $d_6$-DMSO): δ = 8.5576 (1.0); 8.5484 (0.6); 4.1408 (2.1); 4.1369 (0.4); 4.1290 (6.7); 4.1252 (0.5); 4.1171 (6.8); 4.1053 (2.2); 3.9925 (5.9); 3.9828 (6.1); 3.3235 (30.0); 2.5094 (5.2); 2.5064 (11.7); 2.5033 (16.6); 2.5002 (11.8); 2.4972 (5.3); 1.2202 (0.4); 1.2146 (7.6); 1.2084 (0.9); 1.2027 (16.0); 1.1966 (0.5); 1.1909 (7.5); −0.0001 (1.7) |
| I.0345: $^1$H-NMR(600.1 MHz, $d_6$-DMSO): δ = 8.5534 (1.0); 8.5419 (1.0); 4.4515 (0.4); 4.4395 (1.5); 4.4275 (2.4); 4.4155 (1.6); 4.4034 (0.4); 4.1408 (0.6); 4.1347 (1.0); 4.1285 (1.4); 4.1229 (3.1); 4.1165 (3.3); 4.1110 (3.3); 4.1047 (3.1); 4.0990 (1.4); 4.0929 (1.0); 4.0867 (0.5); 3.3263 (49.9); 3.3253 (60.6); 2.8926 (0.4); 2.5210 (0.4); 2.5091 (7.6); 2.5061 (16.9); 2.5030 (23.7); 2.5000 (16.8); 2.4970 (7.5); 1.4066 (0.4); 1.3963 (11.3); 1.3841 (11.2); 1.2018 (7.6); 1.1900 (16.0); 1.1782 (7.5); −0.0001 (1.5) |
| I.0346: $^1$H-NMR(600.1 MHz, $d_6$-DMSO): δ = 8.7105 (0.6); 8.6987 (0.6); 3.7223 (0.9); 3.7107 (0.9); 3.7065 (0.9); 3.6949 (0.9); 3.6813 (0.6); 3.6675 (16.0); 3.3278 (34.9); 2.5096 (3.1); 2.5065 (7.0); 2.5035 (9.9); 2.5004 (7.0); 2.4974 (3.1); 1.2895 (0.5); 1.2874 (0.3); 1.2816 (0.5); 1.2760 (0.4); 1.2737 (0.5); 0.6194 (0.4); 0.6169 (0.3); 0.6121 (0.5); 0.6104 (0.5); 0.6056 (0.4); 0.6024 (0.4); 0.5957 (0.4); 0.5290 (0.4); 0.5252 (0.3); 0.5241 (0.3); 0.5219 (0.4); 0.5157 (0.5); 0.5084 (0.5); 0.4683 (0.5); 0.4607 (0.6); 0.4528 (0.7); 0.4449 (0.4); 0.4433 (0.5); 0.3598 (0.5); 0.3577 (0.4); 0.3519 (0.6); 0.3504 (0.6); 0.3439 (0.5); 0.3424 (0.5); 0.3345 (0.4) |
| I.0347: $^1$H-NMR(600.1 MHz, $d_6$-DMSO): δ = 8.9366 (3.0); 4.1233 (2.3); 4.1194 (0.4); 4.1115 (7.4); 4.0997 (7.4); 4.0879 (2.4); 3.3200 (21.6); 2.5588 (1.0); 2.5556 (0.6); 2.5483 (1.2); 2.5447 (1.7); 2.5400 (1.2); 2.5368 (1.7); 2.5346 (1.6); 2.5274 (2.0); 2.5223 (1.7); 2.5178 (0.8); 2.5091 (6.8); 2.5062 (14.4); 2.5032 (20.0); 2.5002 (14.4); 2.4973 (6.6); 2.3459 (1.1); 2.3323 (1.8); 2.3302 (2.1); 2.3247 (1.3); 2.3168 (1.6); 2.3102 (2.0); 2.2953 (1.1); 1.9658 (0.6); 1.9611 (0.6); 1.9592 (0.6); 1.9562 (0.9); 1.9473 (1.9); 1.9405 (1.6); 1.9334 (2.4); 1.9252 (0.9); 1.9194 (1.3); 1.9151 (0.7); 1.9055 (0.4); 1.1754 (7.8); 1.1636 (16.0); 1.1518 (7.5); −0.0001 (2.2) |
| I.0348: $^1$H-NMR(600.1 MHz, $d_6$-DMSO): δ = 8.3278 (1.1); 8.3142 (1.1); 4.2448 (1.6); 4.2333 (2.1); 4.2320 (2.1); 4.2205 (1.7); 4.1941 (0.4); 4.1822 (1.2); 4.1760 (0.8); 4.1704 (1.3); 4.1642 (2.5); 4.1586 (0.4); 4.1523 (2.6); 4.1454 (0.9); 4.1405 (0.9); 4.1336 (2.6); 4.1273 (0.4); 4.1218 (2.6); 4.1155 (1.3); 4.1099 (0.8); 4.1037 (1.3); 4.0919 (0.4); 3.3201 (34.0); 2.8925 (0.3); 2.5209 (0.3); 2.5178 (0.3); 2.5090 (7.0); 2.5060 (15.5); 2.5029 (21.8); 2.4998 (15.7); 2.4968 (7.1); 2.1964 (0.9); 2.1851 (1.6); 2.1737 (1.6); 2.1624 (1.0); 1.2248 (0.3); 1.2174 (7.6); 1.2130 (0.9); 1.2056 (16.0); 1.2013 (0.7); 1.1938 (7.5); 0.9677 (0.4); 0.9517 (10.2); 0.9403 (11.1); 0.9374 (10.8); 0.9260 (9.6); −0.0001 (2.9) |
| I.0349: $^1$H-NMR(600.1 MHz, $d_6$-DMSO): δ = 8.6959 (0.6); 8.6833 (0.6); 6.2628 (0.4); 6.1769 (0.4); 6.1693 (0.7); 6.1616 (0.4); 6.0759 (0.4); 4.6843 (0.3); 4.6717 (0.8); 4.6603 (0.8); 4.6476 (0.3); 3.6895 (0.8); 3.6786 (16.0); 3.3216 (12.6); 2.5095 (2.9); 2.5064 (6.6); 2.5034 (9.3); 2.5003 (6.6); 2.4973 (3.0); 2.4869 (0.4); 2.4792 (0.4); 2.4753 (0.4); 2.4675 (0.4); 2.4566 (0.5); 2.4489 (0.8); 2.4414 (0.6); 2.4304 (0.4); 2.4227 (0.4); 2.4188 (0.3); −0.0001 (1.2) |
| I.0350: $^1$H-NMR(600.1 MHz, $d_6$-DMSO): δ = 8.5398 (1.4); 8.5270 (1.4); 4.4258 (0.8); 4.4181 (0.9); 4.4130 (0.8); 4.4081 (1.0); 4.4053 (1.0); 4.4006 (0.8); 4.3954 (0.8); 4.3877 (0.8); 4.1433 (0.7); 4.1372 (1.1); 4.1314 (0.8); 4.1281 (1.2); 4.1253 (3.3); 4.1163 (3.3); 4.1135 (3.4); 4.1046 (3.1); 4.1017 (1.2); 4.0984 (0.8); 4.0928 (0.9); 4.0865 (0.7); 3.3216 (21.8); 3.3205 (25.8); 2.8932 (0.4); 2.5095 (6.8); 2.5065 (15.0); 2.5035 (21.0); 2.5004 (14.9); 2.4975 (6.7); 1.8062 (0.7); 1.7982 (0.8); 1.7886 (0.7); 1.7838 (1.0); 1.7806 (0.9); 1.7759 (1.0); 1.7663 (0.9); 1.7583 (0.9); 1.6786 (0.4); 1.6676 (0.6); 1.6635 (0.6); 1.6595 (0.5); 1.6557 (0.7); 1.6526 (0.8); 1.6489 (0.4); 1.6445 (0.7); 1.6418 (0.6); 1.6336 (0.5); 1.6009 (1.2); 1.5932 (1.2); 1.5857 (0.7); 1.5784 (1.6); 1.5709 (0.9); 1.5635 (0.7); 1.5557 (0.6); 1.2090 (0.4); 1.2006 (7.6); 1.1973 (1.0); 1.1887 (16.0); 1.1769 (7.6); 0.9260 (0.6); 0.9185 (10.8); 0.9076 (10.6); 0.8912 (0.6); 0.8795 (10.8); 0.8687 (10.5); −0.0001 (2.6) |
| I.0351: $^1$H-NMR(600.1 MHz, $d_6$-DMSO): δ = 8.5835 (0.6); 8.5708 (0.6); 4.5495 (0.4); 4.5374 (0.9); 4.5254 (0.9); 4.5132 (0.4); 4.1560 (0.3); 4.1498 (0.5); 4.1441 (0.4); 4.1413 (0.6); 4.1380 (1.5); 4.1295 (1.5); 4.1262 (1.6); 4.1177 (1.4); 4.1143 (0.5); 4.1116 (0.4); 4.1060 (0.4); 3.3232 (22.6); 2.5780 (0.5); 2.5668 (0.7); 2.5558 (0.9); 2.5441 (0.5); 2.5287 (0.5); 2.5157 (1.2); 2.5095 (3.0); 2.5065 (6.8); 2.5034 (9.7); 2.5004 (6.7); 2.4974 (3.0); 2.4935 (0.7); 2.0909 (0.7); 2.0785 (1.6); 2.0668 (1.5); 2.0549 (1.6); 2.0505 (16.0); 1.2071 (3.6); 1.2043 (0.6); 1.1953 (7.5); 1.1835 (3.5); −0.0001 (0.3) |
| I.0352: $^1$H-NMR(600.1 MHz, $d_6$-DMSO): δ = 8.5080 (1.2); 8.4950 (1.2); 7.2984 (1.3); 7.2958 (0.7); 7.2858 (4.2); 7.2777 (1.1); 7.2742 (4.9); 7.2666 (4.3); 7.2638 (6.1); 7.2598 (1.0); 7.2529 (2.2); 7.2271 (0.9); 7.2244 (1.4); 7.2216 (0.8); 7.2128 (2.2); 7.2089 (0.6); 7.2042 (0.5); 7.2012 (0.8); 7.1986 (0.4); 4.6279 (0.7); 4.6188 (0.8); 4.6150 (0.9); 4.6122 (1.0); 4.6060 (0.9); 4.6031 (0.9); 4.5993 (0.9); 4.5902 (0.8); 4.1333 (0.4); 4.1270 (1.2); 4.1250 (1.2); 4.1216 (0.4); 4.1151 (3.8); 4.1132 (3.8); 4.1032 (4.0); 4.1014 (3.7); 4.0913 (1.3); 4.0897 (1.2); 3.3288 (80.4); 3.1795 (0.9); 3.1704 (1.0); 3.1565 (1.8); 3.1475 (1.7); 3.1183 (1.8); 3.1024 (1.8); 3.0954 (1.0); 3.0794 (1.0); 2.5096 (6.8); 2.5065 (15.2); 2.5035 (21.4); 2.5004 (15.2); 2.4974 (6.8); 1.2173 (0.4); 1.2055 (1.0); 1.1937 (0.4); 1.1800 (0.4); 1.1681 (1.0); 1.1642 (7.6); 1.1561 (0.8); 1.1523 (16.0); 1.1405 (7.3); 0.9523 (0.6); 0.9409 (0.7); 0.9380 (0.6); 0.9265 (0.6); −0.0001 (0.6) |
| I.0353: $^1$H-NMR(600.1 MHz, $d_6$-DMSO): δ = 9.5054 (2.5); 7.4861 (1.2); 7.3975 (3.2); 7.3090 (1.5); 4.3058 (16.0); 3.3282 (34.9); 2.5105 (5.6); 2.5075 (12.5); 2.5045 (17.5); 2.5014 (12.5); 2.4985 (5.6); −0.0001 (1.0) |
| I.0354: $^1$H-NMR(600.1 MHz, $d_6$-DMSO): δ = 9.2865 (0.4); 9.2770 (0.8); 9.2675 (0.4); 7.4692 (0.6); 7.3806 (1.5); 7.2919 (0.7); 4.0087 (3.8); 3.9991 (3.8); 3.6735 (16.0); 3.3305 (21.2); 2.5098 (3.1); 2.5068 (7.1); 2.5037 (10.0); 2.5006 (7.2); 2.4976 (3.2) |
| I.0355: $^1$H-NMR(600.1 MHz, $d_6$-DMSO): δ = 9.2762 (1.0); 9.2666 (1.9); 9.2571 (1.0); 7.4610 (1.1); 7.3724 (2.8); 7.2837 (1.3); 4.1506 (2.3); 4.1388 (7.2); 4.1269 (7.2); 4.1151 (2.3); 3.9872 (7.3); 3.9775 (7.3); 3.3244 (26.1); 2.8927 (0.3); 2.5093 (6.5); 2.5064 (14.1); 2.5034 (19.5); 2.5005 (14.0); 2.4976 (6.5); 1.2195 (7.8); 1.2077 (16.0); 1.1958 (7.6); −0.0001 (1.7) |
| I.0356: $^1$H-NMR(600.1 MHz, $d_6$-DMSO): δ = 9.4295 (1.9); 7.4322 (0.5); 7.3436 (1.3); 7.2549 (0.6); 3.6237 (16.0); 3.3235 (16.6); 2.5092 (3.1); 2.5061 (7.0); 2.5030 (9.9); 2.5000 (7.1); 2.4969 (3.2); 1.4541 (1.1); 1.4460 (2.7); 1.4404 (3.0); 1.4330 (1.2); 1.2231 (1.2); 1.2156 (2.7); 1.2100 (2.7); 1.2019 (1.0); −0.0001 (1.4) |
| I.0357: $^1$H-NMR(600.1 MHz, $d_6$-DMSO): δ = 9.2374 (1.4); 9.2266 (1.4); 7.3830 (1.0); 7.2944 (2.4); 7.2058 (1.1); 4.4021 (1.1); 4.3904 (1.6); 4.3786 (1.1); 4.1487 (0.7); 4.1426 (0.9); 4.1368 (0.8); 4.1307 (3.1); 4.1249 (0.4); 4.1205 (3.6); 4.1189 (3.4); 4.1145 (0.4); 4.1088 (3.2); 4.1026 (0.8); 4.0970 (0.9); 4.0908 (0.7); 3.3224 (23.2); 2.8926 (0.3); 2.5092 (5.9); 2.5061 (13.0); 2.5031 (18.1); 2.5001 (12.9); 2.4971 (5.8); 1.3768 (11.1); 1.3646 (11.1); 1.2069 (7.7); 1.1951 (16.0); 1.1832 (7.5); −0.0001 (1.8) |

TABLE A-(I)-continued

| NMR peak lists of compounds according to formula (I) |
| --- |
| I.0358: $^{1}$H-NMR(600.1 MHz, $d_6$-DMSO):<br>δ = 9.4411 (0.7); 9.4303 (0.7); 7.3633 (0.4); 7.2748 (1.2); 7.1861 (0.5); 3.6960 (0.7); 3.6851 (0.8); 3.6789 (16.0); 3.6693 (0.7); 3.3252 (17.8); 2.5092 (2.9); 2.5062 (6.5); 2.5031 (9.3); 2.5000 (6.6); 2.4970 (3.0); 1.1903 (0.5); 1.1824 (0.5); 1.1768 (0.3); 1.1745 (0.5); 0.6213 (0.4); 0.6140 (0.4); 0.6126 (0.4); 0.6075 (0.4); 0.6043 (0.4); 0.5976 (0.3); 0.5440 (0.4); 0.5369 (0.4); 0.5308 (0.5); 0.5235 (0.4); 0.4763 (0.4); 0.4686 (0.6); 0.4607 (0.6); 0.4513 (0.5); 0.3832 (0.5); 0.3752 (0.5); 0.3739 (0.5); 0.3660 (0.5); 0.3579 (0.3); −0.0001 (0.9) |
| I.0359: $^{1}$H-NMR(600.1 MHz, $d_6$-DMSO):<br>δ = 9.5647 (3.3); 7.3430 (0.9); 7.2543 (2.6); 7.1656 (1.1); 4.1296 (2.2); 4.1178 (7.3); 4.1059 (7.3); 4.0941 (2.3); 3.3275 (51.8); 2.8926 (1.2); 2.7336 (0.9); 2.5605 (0.9); 2.5574 (0.5); 2.5498 (1.0); 2.5463 (1.5); 2.5429 (0.9); 2.5415 (0.9); 2.5386 (1.4); 2.5359 (1.3); 2.5290 (1.6); 2.5242 (1.5); 2.5216 (0.7); 2.5184 (0.7); 2.5142 (1.2); 2.5095 (6.2); 2.5065 (13.8); 2.5034 (19.4); 2.5003 (13.8); 2.4973 (6.2); 2.3244 (0.9); 2.3110 (1.5); 2.3088 (1.8); 2.3030 (1.1); 2.2955 (1.4); 2.2888 (1.7); 2.2741 (0.9); 1.9721 (0.5); 1.9679 (0.4); 1.9654 (0.4); 1.9623 (0.8); 1.9537 (1.5); 1.9468 (1.4); 1.9401 (2.0); 1.9315 (0.7); 1.9261 (1.1); 1.9214 (0.6); 1.1797 (7.6); 1.1679 (16.0); 1.1561 (7.4); −0.0001 (0.5) |
| I.0360: $^{1}$H-NMR(600.1 MHz, $d_6$-DMSO):<br>δ = 9.0925 (1.7); 9.0798 (1.7); 7.2772 (1.0); 7.1887 (2.5); 7.1001 (1.2); 4.2327 (1.8); 4.2205 (2.5); 4.2090 (1.8); 4.1988 (0.4); 4.1869 (1.3); 4.1807 (0.8); 4.1751 (1.4); 4.1689 (2.4); 4.1633 (0.5); 4.1570 (2.5); 4.1452 (0.8); 4.1402 (0.8); 4.1284 (2.5); 4.1222 (0.5); 4.1166 (2.5); 4.1104 (1.4); 4.1048 (0.8); 4.0986 (1.4); 4.0867 (0.4); 3.3286 (74.2); 2.8925 (0.5); 2.7331 (0.4); 2.5212 (0.3); 2.5093 (6.7); 2.5063 (15.1); 2.5033 (21.4); 2.5002 (15.4); 2.4972 (7.0); 2.1656 (0.9); 2.1543 (1.6); 2.1430 (1.6); 2.1317 (1.0); 1.2189 (7.7); 1.2070 (16.0); 1.1952 (7.5); 0.9488 (10.4); 0.9371 (13.6); 0.9243 (9.7); −0.0001 (0.3) |
| I.0361: $^{1}$H-NMR(600.1 MHz, $d_6$-DMSO):<br>δ = 9.3696 (1.0); 9.3570 (1.0); 7.4027 (0.5); 7.3142 (1.3); 7.2257 (0.6); 6.2073 (0.4); 6.1999 (0.7); 6.1922 (0.4); 6.1067 (0.3); 4.6221 (0.3); 4.6139 (0.4); 4.6075 (0.5); 4.6011 (0.5); 4.5944 (0.4); 4.5861 (0.3); 3.6916 (16.0); 3.3241 (19.8); 2.5092 (3.5); 2.5061 (7.9); 2.5031 (11.2); 2.5000 (8.0); 2.4970 (3.6); 2.4402 (0.3); 2.4149 (0.5); 2.4098 (0.4); 2.4076 (0.4); 2.3906 (0.4); 2.3851 (0.5); 2.3745 (0.3); −0.0001 (1.3) |
| I.0362: $^{1}$H-NMR(600.1 MHz, $d_6$-DMSO):<br>δ = 9.1901 (1.7); 9.1778 (1.7); 7.3607 (0.9); 7.2721 (2.5); 7.1835 (1.1); 4.3850 (0.7); 4.3773 (0.9); 4.3726 (0.8); 4.3680 (0.9); 4.3649 (1.0); 4.3598 (0.8); 4.3557 (0.8); 4.3474 (0.7); 4.1550 (0.9); 4.1489 (0.8); 4.1432 (1.0); 4.1371 (2.7); 4.1325 (1.1); 4.1252 (2.8); 4.1208 (2.9); 4.1134 (1.0); 4.1090 (2.8); 4.1027 (1.0); 4.0972 (0.8); 4.0909 (1.0); 3.3237 (34.7); 3.3233 (35.5); 2.8928 (0.6); 2.7338 (0.5); 2.5093 (6.7); 2.5063 (15.0); 2.5032 (21.2); 2.5002 (15.0); 2.4972 (6.7); 1.7308 (0.6); 1.7225 (0.7); 1.7133 (0.6); 1.7087 (0.7); 1.7049 (0.9); 1.7005 (1.0); 1.6914 (0.5); 1.6834 (1.0); 1.6698 (0.7); 1.6667 (0.6); 1.6585 (0.7); 1.6557 (0.7); 1.6472 (0.7); 1.6448 (0.6); 1.6363 (0.4); 1.5880 (1.0); 1.5797 (0.8); 1.5734 (0.7); 1.5657 (1.5); 1.5580 (0.7); 1.5515 (0.6); 1.5440 (0.4); 1.2063 (7.6); 1.1945 (16.0); 1.1827 (7.4); 0.9208 (9.6); 0.9100 (9.3); 0.8845 (9.1); 0.8738 (9.0); −0.0001 (2.2) |
| I.0363: $^{1}$H-NMR(600.1 MHz, $d_6$-DMSO):<br>δ = 9.2193 (0.8); 9.2072 (0.8); 7.3681 (0.4); 7.2795 (1.1); 7.1909 (0.5); 4.4969 (0.4); 4.4929 (0.4); 4.4898 (0.5); 4.4846 (0.4); 4.4815 (0.4); 4.4777 (0.4); 4.1650 (0.4); 4.1588 (0.4); 4.1531 (0.4); 4.1469 (1.4); 4.1350 (1.6); 4.1335 (1.6); 4.1216 (1.4); 4.1154 (0.4); 4.1098 (0.4); 4.1035 (0.4); 3.3238 (12.4); 3.3224 (15.2); 2.5722 (0.7); 2.5630 (0.6); 2.5588 (0.6); 2.5492 (0.6); 2.5461 (0.5); 2.5327 (0.9); 2.5239 (0.4); 2.5204 (0.6); 2.5092 (3.3); 2.5061 (7.0); 2.5030 (9.8); 2.5000 (7.0); 2.4970 (3.3); 2.0549 (16.0); 2.0459 (0.4); 2.0415 (0.6); 2.0330 (0.5); 2.0287 (0.6); 2.0246 (0.5); 2.0202 (0.4); 2.0148 (0.5); 1.9999 (0.4); 1.2125 (3.5); 1.2006 (7.3); 1.1888 (3.4); −0.0001 (1.0) |
| I.0364: $^{1}$H-NMR(600.1 MHz, $d_6$-DMSO):<br>δ = 9.2986 (1.6); 9.2858 (1.6); 7.3117 (1.6); 7.3092 (0.7); 7.2992 (4.4); 7.2904 (1.2); 7.2873 (4.6); 7.2724 (4.2); 7.2699 (5.8); 7.2586 (2.6); 7.2421 (1.0); 7.2396 (1.5); 7.2372 (0.8); 7.2278 (2.4); 7.2242 (0.6); 7.2186 (0.5); 7.2160 (0.8); 7.2137 (0.4); 7.1072 (0.8); 7.0186 (2.0); 6.9301 (1.0); 4.6144 (0.6); 4.6055 (0.7); 4.6017 (0.7); 4.5974 (0.8); 4.5928 (0.8); 4.5885 (0.8); 4.5847 (0.7); 4.5757 (0.6); 4.1371 (1.7); 4.1253 (5.5); 4.1136 (5.8); 4.1018 (1.9); 3.3250 (42.9); 3.1783 (1.1); 3.1694 (1.2); 3.1553 (1.5); 3.1465 (1.4); 3.0260 (1.5); 3.0088 (1.5); 3.0031 (1.2); 2.9860 (1.1); 2.5209 (0.3); 2.5090 (7.0); 2.5060 (15.6); 2.5030 (22.0); 2.4999 (15.7); 2.4969 (7.0); 1.1714 (7.6); 1.1595 (16.0); 1.1477 (7.4); −0.0001 (1.9) |
| I.0365: $^{1}$H-NMR(600.1 MHz, $d_6$-DMSO):<br>δ = 9.7109 (0.5); 4.3469 (16.0); 3.3274 (9.0); 2.5095 (4.6); 2.5064 (10.5); 2.5033 (14.8); 2.5003 (10.5); 2.4972 (4.7); −0.0001 (0.9) |
| I.0366: $^{1}$H-NMR(600.1 MHz, $d_6$-DMSO):<br>δ = 9.4262 (0.4); 9.4168 (0.8); 9.4072 (0.4); 4.0266 (3.3); 4.0168 (3.3); 3.6679 (16.0); 3.3267 (17.0); 3.3254 (17.0); 2.5089 (3.0); 2.5059 (6.7); 2.5028 (9.5); 2.4998 (6.8); 2.4968 (3.1); −0.0001 (0.3) |
| I.0367: $^{1}$H-NMR(600.1 MHz, $d_6$-DMSO):<br>δ = 9.4057 (1.2); 4.1435 (2.1); 4.1317 (6.8); 4.1198 (6.8); 4.1080 (2.2); 4.0017 (3.5); 3.9927 (3.5); 3.3293 (38.7); 3.3282 (34.1); 2.8922 (0.5); 2.7335 (0.4); 2.7327 (0.4); 2.5091 (5.5); 2.5060 (12.4); 2.5030 (17.6); 2.4999 (12.5); 2.4969 (5.6); 1.2204 (7.6); 1.2086 (16.0); 1.1967 (7.5); −0.0001 (0.4) |
| I.0368: $^{1}$H-NMR(600.1 MHz, $d_6$-DMSO):<br>δ = 9.5830 (1.5); 3.6297 (16.0); 3.3220 (16.4); 3.3211 (16.4); 2.5082 (4.3); 2.5051 (9.6); 2.5021 (13.5); 2.4990 (9.5); 2.4959 (4.2); 1.4544 (1.0); 1.4464 (2.5); 1.4409 (2.7); 1.4333 (1.0); 1.1296 (1.1); 1.1219 (2.5); 1.1165 (2.6); 1.1084 (0.9); −0.0001 (1.8) |
| I.0369: $^{1}$H-NMR(600.1 MHz, $d_6$-DMSO):<br>δ = 9.4088 (1.4); 9.3972 (1.4); 4.4022 (0.4); 4.3902 (1.7); 4.3782 (2.5); 4.3663 (1.7); 4.3542 (0.4); 4.1399 (0.5); 4.1338 (1.0); 4.1276 (1.4); 4.1219 (3.2); 4.1156 (3.4); 4.1100 (3.4); 4.1038 (3.2); 4.0980 (1.4); 4.0920 (1.0); 4.0858 (0.6); 3.3229 (24.3); 3.3223 (23.2); 2.5086 (5.5); 2.5056 (12.4); 2.5025 (17.5); 2.4994 (12.5); 2.4964 (5.6); 1.3381 (10.7); 1.3259 (10.7); 1.2111 (7.6); 1.1993 (16.0); 1.1874 (7.4); −0.0001 (2.2) |
| I.0370: $^{1}$H-NMR(600.1 MHz, $d_6$-DMSO):<br>δ = 9.5796 (3.0); 8.3127 (1.3); 4.0963 (2.3); 4.0845 (7.5); 4.0727 (7.5); 4.0608 (2.3); 3.3210 (18.2); 3.2972 (0.4); 2.5085 (6.0); 2.5055 (13.6); 2.5024 (19.1); 2.4993 (13.6); 2.4963 (6.0); 1.4390 (2.0); 1.4310 (4.9); 1.4255 (5.3); 1.4180 (2.0); 1.1919 (7.6); 1.1800 (16.0); 1.1682 (7.4); 1.1172 (2.1); 1.1096 (4.9); 1.1041 (5.1); 1.0961 (1.8); −0.0001 (2.7) |
| I.0371: $^{1}$H-NMR(600.1 MHz, $d_6$-DMSO):<br>δ = 9.5818 (0.7); 9.5710 (0.7); 3.7626 (0.6); 3.7513 (0.7); 3.7473 (0.7); 3.7361 (0.6); 3.6755 (16.0); 3.3213 (9.3); 3.3202 (10.0); 2.5084 (3.2); 2.5054 (7.2); 2.5023 (10.2); 2.4993 (7.3); 2.4962 (3.2); 1.1402 (0.6); 1.1325 (0.5); 1.1250 (0.6); 1.1170 (0.3); 0.5965 (0.4); 0.5944 (0.3); 0.5892 (0.5); 0.5879 (0.5); 0.5827 (0.4); 0.5796 (0.5); 0.5757 (0.3); 0.5729 (0.4); 0.5344 (0.3); 0.5320 (0.4); 0.5281 (0.4); 0.5267 (0.3); 0.5249 (0.5); 0.5188 (0.6); 0.5114 (0.5); 0.4587 (0.5); 0.4509 (0.6); 0.4429 (0.7); 0.4337 (0.5); 0.3505 (0.5); 0.3423 (0.6); 0.3334 (0.6); 0.3252 (0.4); −0.0001 (1.2) |
| I.0372: $^{1}$H-NMR(600.1 MHz, $d_6$-DMSO):<br>δ = 9.7437 (3.7); 4.1213 (2.3); 4.1095 (7.4); 4.0976 (7.5); 4.0858 (2.4); 3.3257 (60.6); 2.8922 (1.4); 2.7332 (1.1); 2.5678 (1.0); 2.5575 (1.2); 2.5531 (1.7); 2.5503 (1.2); 2.5462 (1.6); 2.5428 (1.6); 2.5364 (1.8); 2.5313 (1.4); 2.5213 (1.4); 2.5178 (0.6); 2.5086 |

TABLE A-(I)-continued

NMR peak lists of compounds according to formula (I)

(7.8); 2.5057 (16.7); 2.5026 (23.0); 2.4996 (16.4); 2.4967 (7.4); 2.2259 (1.0); 2.2132 (1.6); 2.2104 (1.9); 2.2053 (1.3); 2.1976 (1.6); 2.1917 (1.9); 2.1765 (1.1); 1.9661 (0.5); 1.9592 (0.6); 1.9562 (1.0); 1.9508 (0.9); 1.9466 (0.6); 1.9407 (2.2); 1.9356 (0.8); 1.9266 (1.9); 1.9140 (1.0); 1.9082 (0.5); 1.8991 (0.3); 1.2002 (7.7); 1.1883 (16.0); 1.1765 (7.5); −0.0001 (0.8)

I.0373: $^{1}$H-NMR(600.1 MHz, $d_6$-DMSO):
δ = 9.2865 (1.8); 9.2732 (1.8); 4.2648 (2.1); 4.2543 (2.3); 4.2514 (2.2); 4.2410 (2.1); 4.1861 (0.4); 4.1742 (1.2); 4.1681 (0.8); 4.1624 (1.2); 4.1562 (2.6); 4.1506 (0.4); 4.1443 (2.6); 4.1383 (0.9); 4.1325 (0.9); 4.1265 (2.6); 4.1203 (0.4); 4.1147 (2.6); 4.1085 (1.3); 4.1029 (0.8); 4.0966 (1.3); 4.0848 (0.4); 3.3258 (62.6); 2.5087 (6.8); 2.5057 (15.1); 2.5027 (21.0); 2.4996 (14.9); 2.4967 (6.7); 2.1355 (0.9); 2.1243 (1.5); 2.1132 (1.5); 2.1020 (0.9); 1.2185 (7.7); 1.2066 (16.0); 1.1948 (7.5); 0.9227 (10.2); 0.9165 (11.2); 0.9113 (10.6); 0.9051 (10.6); −0.0001 (0.7)

I.0374: $^{1}$H-NMR(600.1 MHz, $d_6$-DMSO):
δ = 9.5834 (0.7); 6.2504 (0.4); 6.1645 (0.4); 6.1571 (0.8); 6.1497 (0.4); 6.0638 (0.4); 4.6167 (0.4); 4.6096 (0.4); 4.6027 (0.4); 4.5955 (0.3); 3.6880 (16.0); 3.3285 (28.2); 2.5089 (3.5); 2.5059 (7.9); 2.5028 (11.2); 2.4998 (8.0); 2.4967 (3.6); 2.4297 (0.4); 2.4047 (0.3); 2.3984 (0.4); 2.3056 (0.3); −0.0001 (0.7)

I.0375: $^{1}$H-NMR(600.1 MHz, $d_6$-DMSO):
δ = 9.3781 (1.8); 9.3655 (1.9); 4.3737 (0.8); 4.3655 (0.7); 4.3610 (0.9); 4.3565 (1.1); 4.3529 (0.8); 4.3487 (0.7); 4.3440 (0.9); 4.3360 (0.6); 4.1469 (0.8); 4.1408 (0.9); 4.1350 (0.9); 4.1288 (3.8); 4.1232 (0.4); 4.1169 (6.0); 4.1107 (0.4); 4.1051 (3.9); 4.0989 (0.9); 4.0933 (0.9); 4.0870 (0.8); 3.3221 (42.1); 2.5204 (0.3); 2.5085 (7.4); 2.5055 (16.2); 2.5024 (22.6); 2.4994 (16.1); 2.4964 (7.2); 1.6609 (0.5); 1.6570 (0.4); 1.6498 (1.1); 1.6436 (1.3); 1.6373 (0.6); 1.6330 (1.2); 1.6281 (1.7); 1.6199 (0.8); 1.6108 (1.2); 1.6025 (0.8); 1.5733 (0.7); 1.5629 (1.0); 1.5560 (0.9); 1.5483 (1.6); 1.5406 (0.7); 1.5254 (0.4); 1.2110 (7.6); 1.1992 (16.0); 1.1873 (7.5); 0.9130 (9.1); 0.9023 (9.2); 0.8777 (8.8); 0.8670 (8.9); −0.0001 (2.4)

I.0376: $^{1}$H-NMR(600.1 MHz, $d_6$-DMSO):
δ = 9.4116 (0.8); 9.3992 (0.8); 4.4988 (0.4); 4.4940 (0.4); 4.4908 (0.4); 4.4864 (0.4); 4.4831 (0.4); 4.4783 (0.4); 4.1577 (0.3); 4.1516 (0.4); 4.1458 (0.4); 4.1398 (1.5); 4.1294 (1.6); 4.1279 (1.7); 4.1177 (1.4); 4.1115 (0.4); 4.1059 (0.4); 4.0997 (0.4); 3.3213 (10.4); 3.3200 (10.5); 2.5445 (0.7); 2.5358 (0.6); 2.5305 (0.6); 2.5206 (0.9); 2.5083 (3.8); 2.5054 (7.6); 2.5023 (10.2); 2.4992 (7.3); 2.4962 (3.5); 2.4845 (0.4); 2.0500 (16.0); 2.0288 (0.4); 2.0164 (0.4); 2.0085 (0.3); 1.9443 (0.4); 1.9290 (0.4); 1.2177 (3.5); 1.2058 (7.3); 1.1940 (3.4); −0.0001 (1.2)

I.0377: $^{1}$H-NMR(600.1 MHz, $d_6$-DMSO):
δ = 9.4562 (1.6); 9.4434 (1.6); 7.3228 (2.0); 7.3201 (0.7); 7.3090 (4.4); 7.3023 (0.9); 7.2979 (4.3); 7.2548 (8.5); 7.2427 (6.1); 7.2327 (0.6); 7.2305 (0.9); 4.6090 (0.6); 4.6001 (0.7); 4.5960 (0.8); 4.5923 (0.8); 4.5872 (0.8); 4.5833 (0.8); 4.5794 (0.8); 4.5704 (0.6); 4.1239 (1.4); 4.1131 (4.2); 4.1121 (4.4); 4.1012 (4.5); 4.1004 (4.4); 4.0892 (1.6); 3.3212 (27.4); 3.1483 (1.2); 3.1394 (1.2); 3.1252 (1.5); 3.1164 (1.4); 2.9567 (1.6); 2.9398 (1.6); 2.9337 (1.3); 2.9168 (1.2); 2.8910 (0.6); 2.7324 (0.5); 2.5199 (0.4); 2.5168 (0.3); 2.5080 (7.7); 2.5050 (17.2); 2.5020 (24.2); 2.4989 (17.2); 2.4959 (7.7); 1.1712 (7.6); 1.1593 (16.0); 1.1475 (7.4); −0.0001 (3.2)

I.0378: $^{1}$H-NMR(400.2 MHz, $d_6$-DMSO):
δ = 9.3346 (0.5); 9.3202 (1.0); 9.3057 (0.5); 8.0592 (6.8); 7.9532 (0.4); 4.0485 (3.8); 4.0338 (3.8); 3.6631 (16.0); 3.3282 (12.5); 2.8925 (3.4); 2.7337 (2.8); 2.7325 (2.7); 2.5127 (4.5); 2.5082 (8.9); 2.5036 (12.0); 2.4990 (8.9); 2.4945 (4.3); −0.0002 (0.8)

I.0379: $^{1}$H-NMR(400.2 MHz, $d_6$-DMSO):
δ = 9.3141 (1.0); 9.2996 (2.0); 9.2851 (1.0); 8.0569 (11.6); 4.1526 (2.3); 4.1348 (7.2); 4.1170 (7.4); 4.0993 (2.4); 4.0276 (7.2); 4.0129 (7.3); 3.3270 (18.1); 2.5260 (0.4); 2.5124 (8.2); 2.5081 (16.4); 2.5035 (22.3); 2.4990 (17.0); 2.4948 (8.5); 1.2216 (7.8); 1.2038 (16.0); 1.1861 (7.7); −0.0002 (1.2)

I.0380: $^{1}$H-NMR(400.2 MHz, $d_6$-DMSO):
δ = 9.3859 (4.0); 8.0024 (11.5); 7.9533 (0.5); 4.0947 (2.3); 4.0770 (7.3); 4.0593 (7.4); 4.0416 (2.4); 3.3262 (21.7); 2.8922 (3.5); 2.7334 (2.9); 2.7323 (2.9); 2.5256 (0.4); 2.5123 (9.8); 2.5078 (19.3); 2.5033 (26.0); 2.4987 (19.4); 2.4943 (9.4); 1.4802 (1.9); 1.4681 (5.0); 1.4599 (5.3); 1.4489 (2.2); 1.1762 (2.3); 1.1651 (5.3); 1.1540 (9.3); 1.1446 (2.5); 1.1362 (16.0); 1.1185 (7.4); −0.0002 (1.6)

I.0381: $^{1}$H-NMR(400.2 MHz, $d_6$-DMSO):
δ = 9.3250 (1.2); 9.3084 (1.2); 8.2221 (6.3); 3.7192 (1.1); 3.7026 (1.2); 3.6953 (1.2); 3.6785 (1.3); 3.6662 (16.0); 3.3263 (12.4); 2.8925 (1.7); 2.7331 (1.5); 2.5122 (5.3); 2.5079 (10.5); 2.5034 (14.2); 2.4989 (10.7); 2.4947 (5.3); 1.2212 (0.3); 1.2179 (0.4); 1.2095 (0.6); 1.1976 (0.6); 1.1858 (0.6); 1.1774 (0.4); 1.1741 (0.4); 0.6422 (0.6); 0.6321 (0.6); 0.6290 (0.6); 0.6189 (0.7); 0.6119 (0.4); 0.6075 (0.5); 0.5973 (0.5); 0.5944 (0.5); 0.5840 (0.5); 0.5809 (0.5); 0.5709 (0.7); 0.5611 (0.7); 0.5506 (0.6); 0.4873 (0.5); 0.4755 (0.8); 0.4634 (0.9); 0.4527 (0.7); 0.3915 (0.4); 0.3797 (0.7); 0.3686 (0.9); 0.3566 (0.8); 0.3453 (0.4); −0.0002 (0.9)

I.0382: $^{1}$H-NMR(400.2 MHz, $d_6$-DMSO):
δ = 8.8943 (2.0); 8.8746 (2.0); 8.3133 (11.3); 4.2755 (2.1); 4.2569 (3.2); 4.2380 (2.1); 4.1829 (0.9); 4.1736 (1.0); 4.1651 (1.0); 4.1557 (3.4); 4.1474 (0.5); 4.1375 (4.4); 4.1268 (0.5); 4.1186 (3.4); 4.1091 (1.0); 4.1007 (1.0); 4.0914 (0.9); 3.3266 (25.3); 2.8928 (0.7); 2.7332 (0.6); 2.5260 (0.4); 2.5128 (9.6); 2.5084 (19.1); 2.5038 (25.8); 2.4993 (19.4); 2.4949 (9.4); 2.1786 (1.0); 2.1614 (1.7); 2.1442 (1.7); 2.1271 (1.0); 2.1101 (0.4); 1.2203 (7.7); 1.2026 (16.0); 1.1849 (7.6); 0.9760 (10.6); 0.9591 (10.5); 0.9416 (10.3); 0.9246 (10.1); −0.0002 (1.0)

I.0383: $^{1}$H-NMR(400.2 MHz, $d_6$-DMSO):
δ = 9.0784 (1.1); 9.0598 (1.1); 8.1568 (5.4); 4.5416 (0.4); 4.5289 (0.5); 4.5228 (0.6); 4.5189 (0.6); 4.5102 (0.6); 4.5061 (0.6); 4.5002 (0.5); 4.4874 (0.4); 4.1557 (0.6); 4.1516 (0.6); 4.1379 (1.9); 4.1339 (1.9); 4.1201 (2.0); 4.1162 (1.8); 4.1023 (0.7); 4.0986 (0.6); 3.3273 (15.6); 2.8927 (0.4); 2.7336 (0.3); 2.5962 (0.7); 2.5823 (0.7); 2.5762 (0.7); 2.5649 (0.8); 2.5627 (0.8); 2.5460 (1.1); 2.5267 (0.9); 2.5123 (5.9); 2.5081 (10.6); 2.5035 (13.9); 2.4991 (10.5); 2.4948 (5.4); 2.0711 (0.7); 2.0577 (16.0); 2.0378 (0.9); 2.0315 (0.9); 2.0164 (0.7); 2.0081 (0.4); 1.9938 (0.4); 1.2112 (3.6); 1.1934 (7.5); 1.1757 (3.5); −0.0002 (0.4)

I.0384: $^{1}$H-NMR(400.2 MHz, $d_6$-DMSO):
δ = 9.2093 (1.7); 9.1899 (1.7); 8.1071 (8.9); 7.3061 (0.4); 7.3039 (0.4); 7.2845 (4.4); 7.2794 (4.9); 7.2709 (16.0); 7.2583 (1.0); 7.2272 (0.9); 7.2203 (1.0); 7.2184 (1.0); 7.2144 (0.8); 7.2090 (0.9); 7.2057 (1.1); 7.2006 (0.8); 7.1956 (0.5); 7.1918 (0.6); 4.6387 (0.6); 4.6242 (0.8); 4.6192 (0.8); 4.6145 (0.9); 4.6048 (0.8); 4.6001 (0.8); 4.5951 (0.8); 4.5807 (0.6); 4.1125 (1.6); 4.0947 (5.1); 4.0770 (5.3); 4.0593 (1.7); 3.3301 (36.4); 3.1718 (0.8); 3.1575 (0.9); 3.1374 (1.5); 3.1231 (1.4); 3.0687 (1.5); 3.0444 (1.5); 3.0343 (0.9); 3.0100 (0.8); 2.8913 (1.8); 2.7331 (1.5); 2.7319 (1.4); 2.5256 (0.4); 2.5122 (8.7); 2.5077 (17.2); 2.5032 (23.2); 2.4986 (17.3); 2.4942 (8.3); 1.1392 (5.7); 1.1215 (12.3); 1.1037 (5.6); −0.0002 (0.4)

I.0385: $^{1}$H-NMR(400.2 MHz, $d_6$-DMSO):
δ = 9.4794 (0.9); 8.0039 (6.8); 4.0801 (2.6); 4.0665 (2.7); 3.6688 (16.0); 3.3267 (8.4); 2.5126 (4.1); 2.5082 (8.3); 2.5036 (11.3); 2.4991 (8.5); 2.4947 (4.2); −0.0002 (0.8)

I.0386: $^{1}$H-NMR(400.2 MHz, $d_6$-DMSO):
δ = 9.4605 (1.5); 8.0018 (11.6); 4.1579 (2.2); 4.1402 (7.0); 4.1224 (7.1); 4.1046 (2.3); 4.0581 (3.8); 4.0458 (3.8); 3.3272 (21.0); 2.5260 (0.4); 2.5126 (7.3); 2.5081 (14.9); 2.5035 (20.4); 2.4990 (15.4); 2.4945 (7.5); 1.2237 (7.7); 1.2060 (16.0); 1.1882 (7.6); −0.0002 (1.5)

TABLE A-(I)-continued

| NMR peak lists of compounds according to formula (I) |
|---|
| I.0387: $^1$H-NMR(400.2 MHz, $d_6$-DMSO): δ = 9.5254 (3.9); 7.9473 (11.7); 4.1000 (2.3); 4.0823 (7.4); 4.0646 (7.4); 4.0468 (2.4); 3.3266 (24.0); 2.8924 (3.2); 2.7336 (2.6); 2.7326 (2.6); 2.5260 (0.5); 2.5126 (9.0); 2.5081 (17.8); 2.5035 (24.0); 2.4990 (18.0); 2.4945 (8.7); 1.4942 (1.9); 1.4820 (4.9); 1.4738 (5.3); 1.4628 (2.2); 1.1997 (2.3); 1.1885 (5.1); 1.1804 (5.0); 1.1681 (1.9); 1.1554 (7.7); 1.1377 (16.0); 1.1200 (7.5); −0.0002 (1.4) |
| I.0388: $^1$H-NMR(400.2 MHz, $d_6$-DMSO): δ = 9.4833 (1.1); 9.4669 (1.1); 8.1741 (6.8); 3.7466 (1.0); 3.7301 (1.1); 3.7227 (1.1); 3.7061 (1.0); 3.6721 (16.0); 3.3262 (13.0); 2.8924 (0.8); 2.7337 (0.7); 2.7325 (0.7); 2.5127 (4.9); 2.5082 (9.7); 2.5035 (13.0); 2.4990 (9.7); 2.4945 (4.6); 1.2264 (0.3); 1.2180 (0.6); 1.2144 (0.4); 1.2061 (0.6); 1.1978 (0.4); 1.1941 (0.6); 1.1860 (0.4); 1.1823 (0.3); 0.6504 (0.5); 0.6404 (0.6); 0.6365 (0.6); 0.6295 (0.5); 0.6265 (0.6); 0.6201 (0.4); 0.6154 (0.4); 0.6055 (0.4); 0.5992 (0.4); 0.5893 (0.4); 0.5857 (0.5); 0.5791 (0.5); 0.5757 (0.6); 0.5661 (0.6); 0.5557 (0.6); 0.4997 (0.5); 0.4883 (0.7); 0.4761 (0.8); 0.4654 (0.6); 0.4021 (0.3); 0.3906 (0.6); 0.3790 (0.8); 0.3669 (0.7); 0.3566 (0.4); −0.0002 (0.9) |
| I.0389: $^1$H-NMR(400.2 MHz, $d_6$-DMSO): δ = 9.0603 (2.0); 9.0406 (2.1); 8.2620 (11.9); 4.3042 (2.0); 4.2854 (3.2); 4.2667 (2.1); 4.1883 (0.9); 4.1790 (1.0); 4.1706 (1.0); 4.1611 (3.5); 4.1528 (0.5); 4.1427 (5.0); 4.1326 (0.6); 4.1246 (3.6); 4.1150 (1.0); 4.1067 (1.0); 4.0973 (0.9); 3.3267 (30.7); 2.8930 (0.8); 2.7333 (0.7); 2.5265 (0.4); 2.5130 (9.7); 2.5087 (19.3); 2.5041 (26.1); 2.4996 (19.8); 2.4952 (9.8); 2.1909 (1.0); 2.1738 (1.7); 2.1567 (1.7); 2.1395 (1.0); 2.1225 (0.3); 1.2225 (7.7); 1.2047 (16.0); 1.1870 (7.6); 0.9813 (10.6); 0.9643 (10.4); 0.9475 (10.3); 0.9304 (10.0); −0.0002 (1.5) |
| I.0390: $^1$H-NMR(400.2 MHz, $d_6$-DMSO): δ = 9.2298 (1.1); 9.2112 (1.1); 8.1014 (5.6); 4.5714 (0.4); 4.5587 (0.5); 4.5526 (0.6); 4.5485 (0.6); 4.5400 (0.6); 4.5359 (0.6); 4.5298 (0.5); 4.5171 (0.4); 4.1605 (0.6); 4.1571 (0.7); 4.1428 (1.9); 4.1394 (2.0); 4.1250 (2.0); 4.1217 (2.0); 4.1072 (0.7); 4.1042 (0.6); 3.3271 (18.7); 2.8922 (0.4); 2.7326 (0.4); 2.6028 (0.8); 2.5889 (0.7); 2.5828 (0.7); 2.5725 (0.8); 2.5692 (0.8); 2.5536 (1.1); 2.5346 (0.7); 2.5122 (5.4); 2.5080 (10.6); 2.5035 (14.3); 2.4990 (11.0); 2.4947 (5.5); 2.0839 (0.5); 2.0587 (16.0); 2.0423 (0.8); 2.0316 (0.5); 2.0267 (0.6); 2.0186 (0.4); 2.0043 (0.4); 1.2127 (3.7); 1.1950 (7.6); 1.1772 (3.6); −0.0002 (0.4) |
| I.0391: $^1$H-NMR(400.2 MHz, $d_6$-DMSO): δ = 9.3644 (1.6); 9.3450 (1.6); 8.0486 (8.5); 7.3044 (0.4); 7.2845 (4.5); 7.2802 (4.9); 7.2715 (16.0); 7.2591 (1.0); 7.2275 (0.9); 7.2204 (1.0); 7.2184 (1.0); 7.2148 (0.8); 7.2089 (0.9); 7.2059 (1.1); 7.2009 (0.8); 7.1957 (0.5); 7.1922 (0.6); 4.6723 (0.6); 4.6580 (0.8); 4.6529 (0.8); 4.6482 (0.9); 4.6386 (0.8); 4.6339 (0.8); 4.6288 (0.8); 4.6144 (0.6); 4.1188 (1.6); 4.1010 (5.2); 4.0833 (5.3); 4.0655 (1.7); 3.3309 (34.0); 3.1881 (0.8); 3.1739 (0.9); 3.1536 (1.5); 3.1394 (1.4); 3.0782 (1.5); 3.0539 (1.5); 3.0438 (0.9); 3.0194 (0.9); 2.8913 (1.9); 2.7322 (1.5); 2.5259 (0.4); 2.5125 (8.0); 2.5080 (16.2); 2.5034 (22.2); 2.4989 (16.9); 2.4945 (8.4); 1.1419 (5.7); 1.1241 (12.2); 1.1064 (5.6); −0.0002 (0.4) |
| I.0392: $^1$H-NMR(400.2 MHz, $d_6$-DMSO): δ = 8.7522 (0.6); 8.7379 (1.0); 8.7236 (0.5); 4.0586 (4.1); 4.0441 (4.2); 3.6691 (16.0); 3.3267 (11.8); 2.5120 (4.1); 2.5075 (8.0); 2.5030 (10.7); 2.4984 (8.0); 2.4940 (3.9); −0.0002 (0.8) |
| I.0393: $^1$H-NMR(400.2 MHz, $d_6$-DMSO): δ = 8.7414 (1.0); 8.7271 (1.9); 8.7129 (1.0); 4.1576 (2.2); 4.1398 (6.9); 4.1220 (7.0); 4.1043 (2.3); 4.0364 (7.0); 4.0218 (7.1); 3.3253 (19.3); 2.8922 (0.4); 2.5253 (0.4); 2.5118 (7.2); 2.5074 (14.4); 2.5028 (19.4); 2.4983 (14.7); 2.4939 (7.2); 1.2258 (7.7); 1.2080 (16.0); 1.1902 (7.6); −0.0002 (1.3) |
| I.0394: $^1$H-NMR(400.2 MHz, $d_6$-DMSO): δ = 9.0972 (3.9); 4.0990 (2.2); 4.0813 (7.2); 4.0635 (7.3); 4.0458 (2.3); 3.3253 (22.3); 2.5253 (0.4); 2.5119 (7.7); 2.5074 (15.3); 2.5029 (20.8); 2.4983 (15.7); 2.4939 (7.7); 1.4682 (1.9); 1.4558 (5.0); 1.4475 (5.4); 1.4365 (2.3); 1.2077 (2.3); 1.1965 (5.1); 1.1883 (5.0); 1.1730 (8.2); 1.1553 (16.0); 1.1376 (7.6); −0.0002 (1.5) |
| I.0395: $^1$H-NMR(400.2 MHz, $d_6$-DMSO): δ = 8.9415 (1.2); 8.9244 (1.2); 3.7830 (1.1); 3.7657 (1.2); 3.7597 (1.2); 3.7425 (1.1); 3.6804 (16.0); 3.3251 (14.6); 2.5113 (5.4); 2.5071 (10.6); 2.5026 (14.3); 2.4981 (10.9); 2.4938 (5.5); 1.2751 (0.4); 1.2722 (0.4); 1.2632 (0.7); 1.2517 (0.6); 1.2403 (0.7); 1.2315 (0.4); 1.2286 (0.4); 0.6295 (0.6); 0.6206 (0.6); 0.6159 (0.6); 0.6057 (0.7); 0.5947 (0.4); 0.5848 (0.4); 0.5630 (0.3); 0.5529 (0.4); 0.5494 (0.5); 0.5396 (0.7); 0.5327 (0.6); 0.5293 (0.7); 0.5191 (0.8); 0.5072 (0.4); 0.4988 (0.7); 0.4862 (0.6); 0.4766 (0.8); 0.4645 (0.9); 0.4532 (0.7); 0.4012 (0.4); 0.3898 (0.6); 0.3781 (0.8); 0.3655 (0.7); 0.3558 (0.4); −0.0002 (0.9) |
| I.0396: $^1$H-NMR(400.2 MHz, $d_6$-DMSO): δ = 8.6173 (1.7); 8.5978 (1.8); 4.2929 (2.0); 4.2770 (2.4); 4.2734 (2.4); 4.2576 (2.1); 4.2217 (0.4); 4.2039 (1.1); 4.1946 (0.9); 4.1861 (1.2); 4.1769 (2.9); 4.1681 (0.6); 4.1649 (1.2); 4.1591 (3.0); 4.1472 (3.0); 4.1413 (1.2); 4.1381 (0.6); 4.1295 (2.9); 4.1201 (1.2); 4.1117 (1.0); 4.1024 (1.1); 4.0846 (0.4); 3.3242 (29.4); 2.5249 (0.5); 2.5115 (10.0); 2.5071 (20.1); 2.5025 (27.5); 2.4980 (20.9); 2.4935 (10.4); 2.2083 (0.9); 2.1915 (1.6); 2.1748 (1.6); 2.1580 (1.0); 2.1412 (0.3); 1.2295 (7.8); 1.2117 (16.0); 1.1940 (7.6); 0.9679 (10.8); 0.9559 (11.8); 0.9510 (12.2); 0.9389 (10.4); −0.0002 (1.6) |
| I.0397: $^1$H-NMR(400.2 MHz, $d_6$-DMSO): δ = 8.8588 (1.0); 8.8400 (1.0); 4.5584 (0.4); 4.5440 (0.5); 4.5385 (0.7); 4.5245 (0.7); 4.5192 (0.6); 4.5046 (0.4); 4.1681 (0.5); 4.1603 (0.7); 4.1503 (1.6); 4.1429 (1.7); 4.1325 (1.7); 4.1252 (1.6); 4.1149 (0.7); 4.1075 (0.5); 3.3265 (20.9); 2.5854 (0.7); 2.5664 (1.0); 2.5506 (0.8); 2.5444 (1.2); 2.5253 (0.9); 2.5114 (5.5); 2.5072 (10.2); 2.5027 (13.5); 2.4982 (10.2); 2.4938 (5.1); 2.0939 (0.5); 2.0901 (0.5); 2.0752 (1.1); 2.0692 (1.0); 2.0544 (16.0); 2.0332 (0.5); 1.2212 (3.5); 1.2035 (7.3); 1.1857 (3.4); −0.0002 (0.4) |
| I.0398: $^1$H-NMR(400.2 MHz, $d_6$-DMSO): δ = 8.7388 (2.2); 8.7197 (2.2); 7.3160 (1.3); 7.3122 (0.6); 7.2977 (4.2); 7.2955 (3.7); 7.2790 (8.8); 7.2723 (8.7); 7.2563 (2.5); 7.2437 (1.5); 7.2395 (1.6); 7.2332 (1.0); 7.2288 (1.1); 7.2223 (2.4); 7.2147 (0.6); 7.2112 (0.6); 7.2057 (0.8); 7.2011 (0.4); 4.6620 (0.8); 4.6485 (1.0); 4.6428 (1.1); 4.6386 (1.3); 4.6294 (1.2); 4.6251 (1.1); 4.6194 (1.2); 4.6059 (0.8); 4.1489 (1.8); 4.1312 (5.9); 4.1136 (6.2); 4.1037 (0.4); 4.0959 (2.1); 3.3305 (59.3); 3.2051 (1.1); 3.1916 (1.2); 3.1706 (2.0); 3.1573 (1.8); 3.1019 (2.0); 3.0782 (1.9); 3.0676 (1.2); 3.0438 (1.1); 2.8910 (0.4); 2.7317 (0.4); 2.5248 (0.6); 2.5115 (11.6); 2.5071 (23.1); 2.5026 (31.6); 2.4980 (24.1); 2.4937 (12.1); 1.1830 (7.6); 1.1652 (16.0); 1.1474 (7.5); −0.0002 (0.4) |
| I.0399: $^1$H-NMR(400.2 MHz, $d_6$-DMSO): δ = 9.3035 (0.6); 9.2891 (1.2); 9.2745 (0.6); 8.0292 (6.5); 4.0412 (3.9); 4.0265 (3.9); 3.6622 (16.0); 3.3302 (10.9); 2.5132 (3.7); 2.5088 (7.4); 2.5043 (10.1); 2.4997 (7.7); 2.4954 (3.9); −0.0002 (0.6) |
| I.0400: $^1$H-NMR(400.2 MHz, $d_6$-DMSO): δ = 9.2843 (1.1); 9.2698 (2.2); 9.2552 (1.1); 8.0276 (11.4); 4.1513 (2.3); 4.1335 (7.2); 4.1158 (7.3); 4.0980 (2.4); 4.0201 (7.0); 4.0054 (7.0); 3.3294 (22.8); 2.8927 (0.4); 2.5129 (7.3); 2.5086 (14.6); 2.5040 (19.9); 2.4996 (15.3); 2.4953 (7.7); 1.2209 (7.8); 1.2031 (16.0); 1.1854 (7.7); −0.0002 (1.0) |
| I.0401: $^1$H-NMR(400.2 MHz, $d_6$-DMSO): δ = 9.3567 (4.5); 7.9746 (11.2); 7.9536 (0.9); 4.0928 (2.3); 4.0751 (7.3); 4.0574 (7.4); 4.0397 (2.4); 3.3285 (26.6); 2.8928 (5.7); 2.7337 (4.9); 2.5127 (9.7); 2.5084 (18.8); 2.5039 (25.2); 2.4994 (19.1); 2.4952 (9.6); 1.4769 (2.0); 1.4648 (5.1); 1.4567 (5.5); 1.4457 (2.3); 1.1735 (2.4); 1.1624 (5.6); 1.1529 (11.3); 1.1420 (2.9); 1.1350 (16.0); 1.1173 (7.4); −0.0002 (1.4) |

TABLE A-(I)-continued

| NMR peak lists of compounds according to formula (I) |
|---|
| I.0402: $^1$H-NMR(400.2 MHz, $d_6$-DMSO):<br>δ = 9.2952 (1.2); 9.2786 (1.2); 8.1929 (6.7); 7.9535 (0.4); 3.7122 (1.0); 3.6956 (1.1); 3.6883 (1.1); 3.6711 (1.9); 3.6648 (16.0); 3.3278 (14.1); 2.8926 (2.6); 2.7340 (2.1); 2.7327 (2.2); 2.5130 (4.5); 2.5085 (9.1); 2.5039 (12.4); 2.4993 (9.3); 2.4948 (4.5); 1.2153 (0.3); 1.2069 (0.6); 1.1950 (0.6); 1.1867 (0.4); 1.1832 (0.6); 1.1749 (0.4); 1.1714 (0.3); 0.6400 (0.5); 0.6301 (0.6); 0.6263 (0.6); 0.6164 (0.6); 0.6097 (0.4); 0.6052 (0.4); 0.5952 (0.4); 0.5923 (0.4); 0.5822 (0.4); 0.5788 (0.5); 0.5687 (0.6); 0.5591 (0.6); 0.5487 (0.6); 0.4845 (0.5); 0.4728 (0.7); 0.4606 (0.8); 0.4500 (0.6); 0.3903 (0.3); 0.3785 (0.6); 0.3673 (0.8); 0.3552 (0.7); 0.3429 (0.4); −0.0002 (0.9) |
| I.0403: $^1$H-NMR(400.2 MHz, $d_6$-DMSO):<br>δ = 8.8654 (2.2); 8.8457 (2.2); 8.2821 (11.6); 4.2681 (2.0); 4.2495 (3.3); 4.2306 (2.1); 4.1814 (0.9); 4.1721 (1.0); 4.1636 (1.0); 4.1542 (3.3); 4.1459 (0.6); 4.1362 (4.2); 4.1347 (4.0); 4.1248 (0.6); 4.1167 (3.3); 4.1072 (1.0); 4.0989 (1.0); 4.0895 (0.9); 3.3279 (34.3); 2.8931 (0.9); 2.7334 (0.8); 2.5266 (0.5); 2.5132 (10.2); 2.5088 (19.8); 2.5042 (26.5); 2.4997 (19.8); 2.4954 (9.7); 2.1758 (1.0); 2.1587 (1.7); 2.1415 (1.7); 2.1244 (1.0); 2.1073 (0.3); 1.2193 (7.7); 1.2015 (16.0); 1.1838 (7.6); 0.9742 (10.6); 0.9572 (10.4); 0.9400 (10.2); 0.9229 (10.0); −0.0002 (1.3) |
| I.0404: $^1$H-NMR(400.2 MHz, $d_6$-DMSO):<br>δ = 9.0500 (1.0); 9.0314 (1.0); 8.1280 (5.4); 4.5344 (0.4); 4.5216 (0.4); 4.5157 (0.5); 4.5116 (0.6); 4.5029 (0.5); 4.4988 (0.5); 4.4930 (0.5); 4.4801 (0.4); 4.1543 (0.5); 4.1499 (0.6); 4.1365 (1.7); 4.1322 (1.8); 4.1187 (1.8); 4.1145 (1.7); 4.1008 (0.6); 4.0969 (0.5); 3.3298 (19.0); 2.8928 (0.4); 2.5945 (0.7); 2.5806 (0.7); 2.5745 (0.6); 2.5691 (0.3); 2.5635 (0.7); 2.5606 (0.7); 2.5442 (1.0); 2.5256 (0.8); 2.5131 (4.6); 2.5087 (8.8); 2.5041 (11.8); 2.4995 (8.9); 2.4951 (4.4); 2.0678 (0.6); 2.0569 (16.0); 2.0354 (0.8); 2.0293 (0.8); 2.0147 (0.6); 2.0061 (0.4); 1.9917 (0.4); 1.2102 (3.6); 1.2030 (0.3); 1.1925 (7.6); 1.1748 (3.5); −0.0002 (0.4) |
| I.0405: $^1$H-NMR(400.2 MHz, $d_6$-DMSO):<br>δ = 9.1810 (1.8); 9.1616 (1.9); 8.0779 (8.2); 7.9534 (0.4); 7.3029 (0.5); 7.2830 (4.5); 7.2779 (5.1); 7.2697 (16.0); 7.2570 (1.2); 7.2260 (0.9); 7.2191 (1.1); 7.2128 (0.9); 7.2080 (1.0); 7.2045 (1.2); 7.1996 (0.8); 7.1947 (0.6); 7.1906 (0.6); 4.6308 (0.6); 4.6162 (0.8); 4.6112 (0.8); 4.6068 (1.0); 4.5969 (0.9); 4.5922 (0.9); 4.5874 (0.9); 4.5729 (0.6); 4.1106 (1.6); 4.0928 (5.0); 4.0751 (5.2); 4.0574 (1.7); 3.3342 (46.8); 3.1687 (0.8); 3.1544 (0.9); 3.1342 (1.6); 3.1200 (1.5); 3.0671 (1.6); 3.0428 (1.6); 3.0327 (1.0); 3.0084 (0.9); 2.8916 (3.0); 2.7331 (2.6); 2.5125 (8.6); 2.5083 (16.9); 2.5038 (22.8); 2.4993 (17.5); 2.4951 (9.0); 1.1377 (5.5); 1.1199 (11.5); 1.1022 (5.4); −0.0002 (0.3) |
| I.0406: $^1$H-NMR(400.2 MHz, $d_6$-DMSO):<br>δ = 8.8002 (0.6); 8.7861 (1.1); 8.7718 (0.6); 4.0543 (4.0); 4.0398 (4.0); 3.6711 (16.0); 3.3274 (11.7); 2.8925 (0.5); 2.7337 (0.4); 2.7325 (0.4); 2.5124 (4.6); 2.5080 (8.8); 2.5035 (11.7); 2.4989 (8.8); 2.4945 (4.3); −0.0002 (0.9) |
| I.0407: $^1$H-NMR(400.2 MHz, $d_6$-DMSO):<br>δ = 8.7893 (1.0); 8.7752 (1.8); 8.7610 (1.0); 4.1590 (2.2); 4.1412 (7.0); 4.1234 (7.2); 4.1056 (2.3); 4.0319 (6.8); 4.0174 (6.8); 3.3265 (17.7); 2.8928 (0.6); 2.7337 (0.5); 2.5258 (0.5); 2.5126 (7.7); 2.5082 (15.1); 2.5036 (20.3); 2.4991 (15.3); 2.4946 (7.5); 1.2289 (7.8); 1.2112 (16.0); 1.1934 (7.7); −0.0002 (1.5) |
| I.0408: $^1$H-NMR(400.2 MHz, $d_6$-DMSO):<br>δ = 9.1504 (3.9); 4.1003 (2.0); 4.0826 (6.7); 4.0649 (6.8); 4.0471 (2.1); 3.3263 (24.8); 2.5256 (0.4); 2.5122 (8.1); 2.5077 (16.3); 2.5031 (22.2); 2.4985 (16.7); 2.4941 (8.1); 1.4622 (1.8); 1.4499 (4.5); 1.4417 (4.9); 1.4307 (2.1); 1.1898 (2.3); 1.1812 (9.4); 1.1705 (5.3); 1.1635 (16.0); 1.1586 (2.8); 1.1458 (7.2); −0.0002 (1.8) |
| I.0409: $^1$H-NMR(400.2 MHz, $d_6$-DMSO):<br>δ = 8.9733 (1.1); 8.9563 (1.1); 3.7930 (1.0); 3.7759 (1.1); 3.7700 (1.1); 3.7529 (1.0); 3.6831 (16.0); 3.3267 (15.1); 2.5123 (4.7); 2.5079 (9.4); 2.5033 (12.6); 2.4988 (9.4); 2.4944 (4.6); 1.2448 (0.3); 1.2418 (0.4); 1.2328 (0.7); 1.2215 (0.6); 1.2101 (0.6); 1.2008 (0.4); 1.1983 (0.4); 0.6241 (0.6); 0.6152 (0.6); 0.6106 (0.6); 0.6008 (0.7); 0.5952 (0.4); 0.5894 (0.4); 0.5797 (0.4); 0.5681 (0.4); 0.5584 (0.4); 0.5549 (0.5); 0.5454 (0.7); 0.5381 (0.5); 0.5348 (0.6); 0.5249 (0.7); 0.5037 (0.4); 0.5000 (0.4); 0.4872 (0.5); 0.4774 (0.8); 0.4651 (0.9); 0.4544 (0.7); 0.4132 (0.4); 0.4016 (0.6); 0.3902 (0.8); 0.3778 (0.7); 0.3681 (0.4); −0.0002 (0.7) |
| I.0410: $^1$H-NMR(400.2 MHz, $d_6$-DMSO):<br>δ = 8.6246 (1.9); 8.6051 (1.9); 4.3008 (1.9); 4.2853 (2.3); 4.2813 (2.2); 4.2659 (2.0); 4.2214 (0.4); 4.2036 (1.1); 4.1944 (0.9); 4.1859 (1.2); 4.1766 (2.8); 4.1655 (1.2); 4.1588 (3.0); 4.1477 (3.0); 4.1410 (1.2); 4.1300 (2.9); 4.1207 (1.2); 4.1123 (0.9); 4.1030 (1.1); 4.0852 (0.4); 3.3268 (38.3); 2.5254 (0.5); 2.5121 (10.0); 2.5077 (19.9); 2.5031 (27.1); 2.4986 (20.5); 2.4941 (10.1); 2.2047 (0.9); 2.1879 (1.4); 2.1716 (1.5); 2.1548 (0.9); 1.2319 (7.7); 1.2142 (16.0); 1.1964 (7.5); 0.9748 (10.3); 0.9629 (11.5); 0.9579 (11.7); 0.9459 (9.9); −0.0002 (1.3) |
| I.0411: $^1$H-NMR(400.2 MHz, $d_6$-DMSO):<br>δ = 8.9041 (1.1); 8.8855 (1.1); 4.5385 (0.4); 4.5250 (0.5); 4.5177 (0.7); 4.5048 (0.6); 4.4985 (0.5); 4.4850 (0.4); 4.1691 (0.5); 4.1602 (0.8); 4.1513 (1.6); 4.1424 (1.8); 4.1335 (1.8); 4.1247 (1.6); 4.1156 (0.8); 4.1070 (0.5); 3.3290 (21.5); 2.5983 (0.7); 2.5817 (1.3); 2.5626 (1.7); 2.5430 (0.7); 2.5279 (0.4); 2.5120 (5.1); 2.5078 (10.0); 2.5033 (13.4); 2.4988 (10.1); 2.4945 (5.0); 2.0803 (0.5); 2.0579 (16.0); 2.0348 (0.8); 2.0298 (0.7); 2.0144 (0.4); 1.2249 (3.6); 1.2072 (7.6); 1.1894 (3.6); −0.0002 (0.3) |
| I.0412: $^1$H-NMR(400.2 MHz, $d_6$-DMSO):<br>δ = 8.8060 (2.3); 8.7870 (2.4); 7.3199 (1.5); 7.3017 (4.6); 7.2842 (6.7); 7.2702 (8.3); 7.2535 (3.1); 7.2459 (2.0); 7.2422 (1.9); 7.2303 (1.2); 7.2246 (2.7); 7.2178 (0.7); 7.2121 (0.6); 7.2075 (0.9); 7.2037 (0.5); 4.6531 (0.8); 4.6393 (1.1); 4.6337 (1.2); 4.6302 (1.4); 4.6201 (1.3); 4.6166 (1.2); 4.6112 (1.2); 4.5973 (0.9); 4.1441 (1.9); 4.1264 (6.1); 4.1087 (6.4); 4.0983 (0.5); 4.0910 (2.2); 3.3334 (50.2); 3.1911 (1.1); 3.1775 (1.2); 3.1567 (2.1); 3.1432 (1.9); 3.0826 (2.0); 3.0593 (2.0); 3.0483 (1.3); 3.0249 (1.1); 2.8917 (0.8); 2.7330 (0.7); 2.5256 (0.6); 2.5119 (11.8); 2.5078 (23.0); 2.5033 (31.0); 2.4988 (23.5); 2.4948 (11.9); 1.1808 (7.6); 1.1630 (16.0); 1.1453 (7.7); −0.0002 (0.7) |
| I.0413: $^1$H-NMR(300.2 MHz, $d_6$-DMSO):<br>δ = 11.0579 (3.2); 4.2464 (1.9); 4.2126 (2.0); 3.6798 (14.1); 3.3493 (16.0); 2.9110 (1.0); 2.7517 (0.9); 2.5343 (2.7); 2.5283 (5.7); 2.5223 (7.8); 2.5163 (5.6); 2.5104 (2.6); 1.3821 (0.5); 1.3734 (0.4); 1.3653 (0.5); 1.3566 (0.4); 1.3484 (0.5); 0.7359 (0.4); 0.7302 (0.4); 0.7235 (0.7); 0.7082 (0.4); 0.7030 (0.4); 0.6940 (0.5); 0.5967 (0.5); 0.5767 (1.0); 0.5668 (1.1); 0.5501 (1.5); 0.5344 (0.5); 0.3615 (0.3); 0.3547 (0.4); 0.3454 (0.7); 0.3265 (0.6); 0.3097 (0.4); 0.0199 (2.1) |
| I.0414: $^1$H-NMR(400.2 MHz, $d_6$-DMSO):<br>δ = 9.4832 (3.7); 7.4946 (1.4); 7.3620 (3.2); 7.2294 (1.6); 4.1027 (2.2); 4.0850 (7.1); 4.0673 (7.2); 4.0495 (2.3); 3.3396 (63.1); 2.8915 (0.9); 2.7317 (0.8); 2.5253 (0.8); 2.5120 (13.0); 2.5078 (25.7); 2.5033 (33.5); 2.4988 (24.6); 2.4945 (12.3); 1.4483 (1.9); 1.4360 (4.9); 1.4276 (5.5); 1.4168 (2.3); 1.2213 (2.4); 1.2104 (5.2); 1.2020 (5.0); 1.1897 (1.8); 1.1729 (7.8); 1.1552 (16.0); 1.1374 (7.4); −0.0002 (2.6) |
| I.0415: $^1$H-NMR(400.2 MHz, $d_6$-DMSO):<br>δ = 9.3399 (0.5); 9.3265 (1.0); 9.3123 (0.5); 7.5551 (0.9); 7.4224 (1.9); 7.2897 (1.0); 4.0172 (4.1); 4.0027 (4.1); 3.6744 (16.0); 3.3386 (11.8); 2.5080 (12.1); 2.5036 (15.5); 2.4991 (11.2); 2.4950 (5.5); −0.0002 (1.3) |
| I.0416: $^1$H-NMR(400.2 MHz, $d_6$-DMSO):<br>δ = 9.3288 (0.9); 9.3148 (1.7); 9.3006 (0.9); 7.5462 (1.4); 7.4136 (3.3); 7.2809 (1.7); 4.1604 (2.2); 4.1426 (7.0); 4.1248 (7.0); 4.1071 (2.3); 3.9958 (6.9); 3.9814 (6.8); 3.3427 (57.4); 2.5262 (0.6); 2.5126 (10.0); 2.5084 (19.7); 2.5039 (25.5); 2.4994 (18.5); 2.4950 (9.1); 1.2254 (7.8); 1.2076 (16.0); 1.1899 (7.6); −0.0002 (0.5) |

TABLE A-(I)-continued

| NMR peak lists of compounds according to formula (I) |
| --- |
| I.0417: $^1$H-NMR(400.2 MHz, $d_6$-DMSO):<br>δ = 9.4973 (0.9); 9.4828 (0.9); 7.4563 (0.8); 7.3239 (1.8); 7.1912 (0.9); 3.6982 (0.8); 3.6801 (16.0); 3.6593 (0.8); 3.3390 (32.4); 2.5078 (12.8); 2.5034 (16.5); 2.4989 (12.2); 1.2118 (0.3); 1.2088 (0.4); 1.2001 (0.6); 1.1884 (0.6); 1.1765 (0.6); 1.1682 (0.4); 1.1648 (0.4); 0.6311 (0.6); 0.6218 (0.6); 0.6177 (0.6); 0.6075 (0.7); 0.6020 (0.4); 0.5964 (0.4); 0.5864 (0.4); 0.5687 (0.3); 0.5585 (0.4); 0.5552 (0.5); 0.5454 (0.6); 0.5352 (0.6); 0.5249 (0.7); 0.5039 (0.4); 0.4980 (0.4); 0.4857 (0.5); 0.4754 (0.8); 0.4631 (0.9); 0.4518 (0.7); 0.4019 (0.4); 0.3904 (0.7); 0.3788 (0.8); 0.3664 (0.7); 0.3559 (0.4); −0.0002 (0.8) |
| I.0418: $^1$H-NMR(400.2 MHz, $d_6$-DMSO):<br>δ = 9.1468 (1.5); 9.1280 (1.5); 7.3728 (1.3); 7.2404 (2.9); 7.1079 (1.4); 4.2404 (1.6); 4.2223 (2.6); 4.2049 (1.7); 4.1987 (1.2); 4.1894 (0.8); 4.1808 (1.1); 4.1715 (2.4); 4.1632 (0.4); 4.1538 (3.2); 4.1360 (3.2); 4.1268 (0.4); 4.1183 (2.5); 4.1090 (1.1); 4.1006 (0.8); 4.0912 (1.1); 4.0736 (0.3); 3.3456 (57.4); 2.5081 (21.6); 2.5037 (28.1); 2.4992 (20.6); 2.4949 (10.3); 2.1789 (0.9); 2.1619 (1.5); 2.1449 (1.6); 2.1279 (1.0); 1.2251 (6.9); 1.2074 (14.2); 1.1896 (6.6); 0.9556 (9.9); 0.9393 (16.0); 0.9232 (9.1); −0.0002 (0.4) |
| I.0419: $^1$H-NMR(400.2 MHz, $d_6$-DMSO):<br>δ = 9.2695 (0.9); 9.2513 (0.9); 7.4604 (0.6); 7.3278 (1.5); 7.1953 (0.7); 4.5210 (0.4); 4.5073 (0.5); 4.5022 (0.5); 4.4992 (0.6); 4.4889 (0.5); 4.4857 (0.5); 4.4807 (0.5); 4.4671 (0.4); 4.1677 (0.5); 4.1575 (0.6); 4.1499 (1.5); 4.1396 (1.6); 4.1320 (1.6); 4.1219 (1.5); 4.1140 (0.6); 4.1042 (0.5); 3.3460 (39.8); 2.5792 (0.7); 2.5638 (0.9); 2.5592 (1.1); 2.5441 (0.8); 2.5380 (1.2); 2.5130 (6.4); 2.5086 (12.3); 2.5041 (15.9); 2.4995 (11.2); 2.4951 (5.3); 2.0559 (16.0); 2.0342 (1.1); 2.0194 (0.7); 2.0143 (0.6); 1.9987 (0.4); 1.2183 (3.6); 1.2095 (0.4); 1.2006 (7.4); 1.1828 (3.4) |
| I.0420: $^1$H-NMR(400.2 MHz, $d_6$-DMSO):<br>δ = 9.3523 (1.5); 9.3360 (1.5); 7.3212 (1.3); 7.3029 (4.2); 7.2855 (6.7); 7.2747 (8.1); 7.2582 (2.7); 7.2491 (1.7); 7.2452 (1.6); 7.2395 (0.9); 7.2340 (1.0); 7.2278 (2.4); 7.2205 (0.6); 7.2158 (0.6); 7.2109 (0.8); 7.2066 (0.5); 7.1935 (1.4); 7.0609 (3.1); 6.9285 (1.6); 4.6269 (0.5); 4.6105 (0.9); 4.6003 (1.0); 4.5868 (0.9); 4.5721 (0.5); 4.1468 (2.0); 4.1291 (6.6); 4.1114 (6.8); 4.0936 (2.2); 3.3523 (112.5); 3.1920 (1.2); 3.1785 (1.3); 3.1575 (1.9); 3.1443 (1.8); 3.0413 (1.9); 3.0155 (1.9); 3.0070 (1.4); 2.9813 (1.2); 2.8913 (0.9); 2.7326 (0.8); 2.5263 (0.8); 2.5126 (15.5); 2.5085 (30.3); 2.5041 (39.0); 2.4996 (28.4); 1.1759 (7.7); 1.1581 (16.0); 1.1404 (7.4) |
| I.0421: $^1$H-NMR(400.2 MHz, $d_6$-DMSO):<br>δ = 8.8495 (3.3); 4.2983 (15.9); 4.2846 (16.0); 3.3359 (57.3); 2.8928 (1.7); 2.7330 (1.4); 2.5269 (1.0); 2.5133 (18.8); 2.5093 (37.1); 2.5048 (48.5); 2.5003 (35.5); 2.4960 (17.7); −0.0002 (6.1) |
| I.0422: $^1$H-NMR(400.2 MHz, $d_6$-DMSO):<br>δ = 8.5598 (0.7); 4.0102 (3.6); 3.9956 (3.6); 3.6581 (16.0); 3.3359 (17.5); 2.5125 (5.5); 2.5082 (10.9); 2.5037 (14.3); 2.4991 (10.5); 2.4947 (5.2); −0.0002 (1.2) |
| I.0423: $^1$H-NMR(400.1 MHz, CDCl3):<br>δ = 7.2604 (31.4); 6.7683 (1.3); 4.2918 (2.5); 4.2739 (7.4); 4.2561 (7.6); 4.2382 (2.8); 4.2053 (8.0); 4.1928 (8.2); 2.1710 (2.1); 2.0066 (0.4); 1.5461 (47.8); 1.3309 (8.1); 1.3131 (16.0); 1.2953 (8.2); 1.2649 (0.9); 0.8821 (0.7); −0.0002 (30.3) |
| I.0424: $^1$H-NMR(400.1 MHz, CDCl3):<br>δ = 7.2642 (2.1); 6.7237 (0.9); 6.7073 (0.9); 3.7109 (16.0); 1.6935 (1.3); 1.6809 (3.8); 1.6731 (4.0); 1.6613 (1.6); 1.5956 (3.9); 1.3094 (1.7); 1.2978 (4.2); 1.2899 (4.3); 1.2772 (1.9); 1.2643 (1.3); 1.2389 (0.3); 0.8976 (0.5); 0.8817 (1.0); 0.8643 (0.5); −0.0002 (2.6) |
| I.0425: $^1$H-NMR(400.2 MHz, $d_6$-DMSO):<br>δ = 8.5464 (2.4); 8.5293 (2.4); 4.4546 (0.5); 4.4370 (2.0); 4.4190 (3.1); 4.4010 (2.1); 4.3836 (0.5); 4.1494 (0.4); 4.1403 (1.8); 4.1357 (1.6); 4.1225 (5.5); 4.1180 (4.1); 4.1047 (5.7); 4.1004 (4.0); 4.0870 (2.0); 4.0828 (1.4); 4.0734 (0.4); 3.3383 (74.8); 2.5079 (45.4); 2.5038 (48.2); 1.3954 (12.8); 1.3773 (12.6); 1.2056 (7.9); 1.1989 (1.5); 1.1878 (16.0); 1.1814 (2.2); 1.1701 (7.7); 0.0019 (1.6); −0.0002 (2.2) |
| I.0426: $^1$H-NMR(400.2 MHz, $d_6$-DMSO):<br>δ = 8.8372 (2.9); 7.9537 (0.3); 4.0874 (2.2); 4.0697 (7.1); 4.0519 (7.1); 4.0342 (2.2); 3.3436 (65.5); 2.8926 (2.3); 2.7332 (2.0); 2.7323 (1.9); 2.5265 (0.7); 2.5131 (11.2); 2.5088 (21.8); 2.5043 (28.3); 2.4998 (20.6); 2.4956 (10.1); 1.4532 (1.9); 1.4409 (4.8); 1.4326 (5.3); 1.4216 (2.2); 1.1994 (2.3); 1.1883 (5.1); 1.1800 (4.9); 1.1676 (1.9); 1.1572 (7.8); 1.1395 (16.0); 1.1218 (7.4); −0.0002 (0.9) |
| I.0427: $^1$H-NMR(400.2 MHz, $d_6$-DMSO):<br>δ = 8.7051 (0.8); 8.6883 (0.8); 3.7183 (1.0); 3.7009 (1.1); 3.6947 (1.1); 3.6772 (1.3); 3.6651 (16.0); 3.3496 (48.9); 2.5265 (0.4); 2.5132 (7.1); 2.5089 (13.8); 2.5043 (17.7); 2.4998 (12.7); 2.4954 (6.1); 1.2986 (0.3); 1.2954 (0.4); 1.2867 (0.6); 1.2751 (0.6); 1.2632 (0.6); 1.2550 (0.4); 1.2514 (0.4); 0.6213 (0.6); 0.6119 (0.6); 0.6076 (0.6); 0.6005 (0.5); 0.5972 (0.6); 0.5922 (0.4); 0.5863 (0.4); 0.5761 (0.3); 0.5374 (0.4); 0.5338 (0.5); 0.5238 (0.6); 0.5170 (0.5); 0.5137 (0.6); 0.5034 (0.7); 0.4916 (0.3); 0.4824 (0.6); 0.4694 (0.5); 0.4595 (0.8); 0.4474 (0.9); 0.4359 (0.6); 0.3737 (0.4); 0.3624 (0.6); 0.3505 (0.7); 0.3377 (0.7); 0.3279 (0.4) |
| I.0428: $^1$H-NMR(400.2 MHz, $d_6$-DMSO):<br>δ = 8.9258 (3.3); 4.1288 (2.4); 4.1111 (7.4); 4.0934 (7.4); 4.0757 (2.4); 3.3352 (50.4); 2.5671 (1.0); 2.5620 (0.7); 2.5468 (1.9); 2.5391 (1.5); 2.5339 (2.1); 2.5307 (2.0); 2.5122 (15.0); 2.5080 (26.3); 2.5036 (33.5); 2.4991 (25.0); 2.3514 (1.2); 2.3291 (2.6); 2.3079 (1.8); 2.2977 (2.2); 2.2759 (1.1); 1.9727 (0.9); 1.9582 (1.1); 1.9509 (2.4); 1.9355 (1.9); 1.9296 (2.8); 1.9217 (1.1); 1.9091 (1.5); 1.8882 (0.4); 1.1778 (7.8); 1.1601 (16.0); 1.1424 (7.5); −0.0002 (1.8) |
| I.0429: $^1$H-NMR(400.2 MHz, $d_6$-DMSO):<br>δ = 8.3270 (1.3); 8.3083 (1.3); 4.2416 (1.7); 4.2234 (2.5); 4.2054 (1.8); 4.1898 (1.0); 4.1805 (0.9); 4.1720 (1.1); 4.1627 (2.8); 4.1542 (1.3); 4.1449 (3.0); 4.1364 (2.9); 4.1271 (1.3); 4.1187 (2.8); 4.1094 (1.1); 4.1010 (0.9); 4.0916 (1.0); 4.0739 (0.3); 3.3336 (36.0); 2.5260 (0.6); 2.5125 (11.3); 2.5081 (22.6); 2.5036 (29.4); 2.4990 (21.2); 2.4946 (10.3); 2.1996 (0.9); 2.1826 (1.6); 2.1656 (1.7); 2.1487 (1.0); 2.1315 (0.3); 1.2212 (7.7); 1.2034 (16.0); 1.1857 (7.5); 0.9521 (10.6); 0.9362 (15.3); 0.9203 (9.8); −0.0002 (4.4) |
| I.0430: $^1$H-NMR(400.2 MHz, $d_6$-DMSO):<br>δ = 8.6830 (0.8); 8.6639 (0.8); 6.3092 (0.5); 6.1804 (0.5); 6.1690 (1.0); 6.1576 (0.5); 6.0289 (0.5); 4.6845 (0.4); 4.6657 (1.0); 4.6486 (1.0); 4.6298 (0.4); 3.6760 (16.0); 3.3363 (23.0); 2.5257 (0.3); 2.5124 (6.1); 2.5082 (12.0); 2.5037 (16.0); 2.4993 (11.8); 2.4949 (5.9); 2.4723 (0.5); 2.4563 (0.7); 2.4444 (1.0); 2.4328 (0.7); 2.4249 (0.4); 2.4166 (0.5); 2.4048 (0.5); 2.3989 (0.5); 2.3872 (0.4); −0.0002 (1.4) |
| I.0431: $^1$H-NMR(400.2 MHz, $d_6$-DMSO):<br>δ = 8.5336 (1.5); 8.5145 (1.5); 4.4258 (0.7); 4.4143 (0.9); 4.4066 (0.9); 4.3992 (1.1); 4.3953 (1.1); 4.3883 (0.9); 4.3804 (0.9); 4.3691 (0.7); 4.1517 (0.4); 4.1425 (1.0); 4.1354 (1.3); 4.1247 (3.4); 4.1179 (3.5); 4.1069 (3.6); 4.1002 (3.4); 4.0893 (1.3); 4.0825 (1.0); 4.0732 (0.5); 3.3357 (44.5); 2.5261 (0.7); 2.5128 (12.6); 2.5084 (25.0); 2.5039 (32.7); 2.4993 (23.8); 2.4949 (11.6); 1.8125 (0.5); 1.8016 (0.8); 1.7863 (0.7); 1.7803 (1.0); 1.7752 (1.0); 1.7694 (1.0); 1.7541 (0.8); 1.7428 (1.0); 1.6867 (0.4); 1.6702 (0.6); 1.6644 (0.6); 1.6530 (0.8); 1.6482 (0.8); 1.6366 (0.8); 1.6319 (0.7); 1.6211 (0.6); 1.6039 (1.3); 1.5923 (1.4); 1.5815 (0.6); 1.5711 (1.4); 1.5600 (0.9); 1.5490 (0.6); 1.5375 (0.6); 1.2040 (7.7); 1.1863 (16.0); 1.1685 (7.4); 0.9190 (10.3); 0.9029 (10.0); 0.8793 (10.1); 0.8634 (10.2); −0.0002 (2.6) |
| I.0432: $^1$H-NMR(400.2 MHz, $d_6$-DMSO):<br>δ = 8.5748 (0.7); 8.5563 (0.7); 4.5491 (0.4); 4.5308 (1.0); 4.5128 (1.0); 4.4946 (0.4); 4.1548 (0.5); 4.1482 (0.6); 4.1370 (1.6); 4.1306 (1.7); 4.1192 (1.7); 4.1129 (1.6); 4.1015 (0.6); 4.0953 (0.5); 3.3318 (16.9); 2.5835 (0.4); 2.5669 (0.7); 2.5504 (1.2); 2.5333 |

TABLE A-(I)-continued

NMR peak lists of compounds according to formula (I)

(0.9); 2.5121 (6.7); 2.5078 (12.8); 2.5033 (16.7); 2.4987 (12.3); 2.4944 (6.0); 2.4832 (0.6); 2.0937 (0.7); 2.0753 (1.8); 2.0574 (2.0); 2.0488 (16.0); 2.0402 (0.8); 1.2102 (3.7); 1.2012 (0.4); 1.1925 (7.6); 1.1747 (3.5); −0.0002 (2.3)

I.0433: $^1$H-NMR(400.2 MHz, $d_6$-DMSO):
δ = 8.5023 (1.6); 8.4834 (1.6); 7.3057 (1.2); 7.2872 (4.3); 7.2690 (10.4); 7.2630 (8.8); 7.2470 (2.3); 7.2322 (1.4); 7.2279 (1.6); 7.2215 (0.9); 7.2110 (2.3); 7.2033 (0.6); 7.2000 (0.6); 7.1945 (0.8); 7.1900 (0.4); 4.6251 (0.8); 4.6108 (1.0); 4.6021 (1.3); 4.5916 (1.2); 4.5885 (1.2); 4.5826 (1.2); 4.5686 (0.8); 4.1303 (1.9); 4.1128 (5.9); 4.0951 (6.2); 4.0775 (2.0); 3.3364 (140.3); 3.1834 (0.8); 3.1695 (1.0); 3.1490 (2.4); 3.1352 (2.1); 3.1182 (2.3); 3.0946 (2.2); 3.0838 (0.9); 3.0603 (0.9); 2.8908 (0.8); 2.7312 (0.8); 2.6763 (0.3); 2.6717 (0.5); 2.6676 (0.4); 2.5071 (61.8); 2.5027 (79.3); 2.4983 (58.2); 2.3340 (0.4); 2.3294 (0.5); 2.3251 (0.3); 1.1657 (7.7); 1.1479 (16.0); 1.1302 (7.4); −0.0002 (3.7)

I.0434: $^1$H-NMR(300.2 MHz, CDCl3):
δ = 7.2987 (2.1); 7.0398 (0.5); 5.3348 (1.2); 4.9223 (0.3); 4.9165 (0.6); 4.9115 (0.6); 4.8924 (0.6); 3.8343 (15.0); 2.6261 (1.0); 2.6220 (1.0); 2.6004 (2.8); 2.5752 (2.1); 2.3335 (0.4); 2.3163 (0.4); 2.3105 (0.5); 2.2931 (0.5); 2.2860 (0.8); 2.2688 (0.7); 2.2613 (0.3); 2.2049 (0.4); 2.1820 (0.8); 2.1566 (1.1); 2.1461 (16.0); 2.1341 (0.9); 2.1095 (0.4); 1.6314 (4.4); 0.0330 (2.0)

I.0435: $^1$H-NMR(400.2 MHz, $d_6$-DMSO):
δ = 8.9175 (2.4); 8.8983 (2.4); 7.8648 (8.0); 4.4409 (0.8); 4.4291 (1.3); 4.4213 (1.0); 4.4154 (1.1); 4.4100 (1.5); 4.4036 (1.3); 4.3972 (0.8); 4.3844 (1.0); 4.1421 (1.4); 4.1390 (1.5); 4.1244 (4.3); 4.1214 (4.3); 4.1066 (4.6); 4.1038 (4.4); 4.0887 (1.7); 4.0762 (0.4); 4.0122 (0.3); 3.6777 (1.0); 3.3369 (71.4); 2.5094 (31.1); 2.5051 (39.2); 2.5008 (29.0); 1.7477 (0.6); 1.7365 (0.9); 1.7164 (1.0); 1.7071 (1.7); 1.6914 (1.1); 1.6807 (1.9); 1.6635 (1.2); 1.6478 (1.1); 1.6321 (0.8); 1.6143 (1.6); 1.6010 (0.9); 1.5938 (0.9); 1.5833 (1.6); 1.5717 (1.1); 1.5631 (0.7); 1.5533 (0.5); 1.2994 (0.5); 1.2910 (0.3); 1.2595 (1.0); 1.2391 (3.0); 1.2050 (7.9); 1.1873 (16.0); 1.1695 (7.7); 1.1535 (0.4); 1.1497 (0.4); 1.1356 (0.3); 0.9324 (10.5); 0.9170 (10.0); 0.8755 (10.2); 0.8600 (10.4); 0.8363 (0.5); −0.0002 (1.1)

I.0436: $^1$H-NMR(300.2 MHz, CDCl3):
δ = 7.3494 (11.0); 7.2985 (3.8); 6.6161 (1.2); 6.5887 (1.2); 4.8238 (0.8); 4.8063 (0.7); 4.7947 (1.6); 4.7784 (1.3); 4.7666 (1.0); 4.7504 (0.7); 4.3046 (2.0); 4.2808 (6.5); 4.2570 (6.8); 4.2332 (2.3); 1.7985 (0.4); 1.7938 (0.4); 1.7767 (1.4); 1.7661 (1.0); 1.7593 (1.3); 1.7493 (2.2); 1.7325 (1.9); 1.7286 (2.0); 1.7065 (2.0); 1.6756 (1.6); 1.6687 (6.7); 1.6511 (1.1); 1.6461 (1.2); 1.6212 (0.9); 1.3680 (7.8); 1.3443 (16.0); 1.3205 (7.6); 1.0193 (9.0); 1.0071 (11.0); 0.9998 (11.0); 0.9869 (9.0); 0.0334 (4.6)

I.0437: $^1$H-NMR(400.2 MHz, $d_6$-DMSO):
δ = 8.7762 (2.0); 8.7565 (2.0); 8.1236 (10.5); 4.2700 (2.0); 4.2510 (3.3); 4.2324 (2.1); 4.1803 (0.9); 4.1710 (1.0); 4.1625 (1.0); 4.1532 (3.3); 4.1450 (0.6); 4.1352 (3.8); 4.1329 (4.0); 4.1233 (0.6); 4.1151 (3.4); 4.1057 (1.1); 4.0973 (1.0); 4.0879 (1.0); 4.0702 (0.3); 3.3382 (64.1); 2.5289 (0.6); 2.5156 (10.5); 2.5112 (21.2); 2.5067 (27.8); 2.5022 (20.6); 2.4979 (10.7); 2.1920 (0.3); 2.1751 (1.0); 2.1579 (1.8); 2.1408 (1.8); 2.1236 (1.1); 2.1065 (0.4); 1.2998 (0.5); 1.2606 (0.8); 1.2384 (2.3); 1.2215 (8.0); 1.2038 (16.0); 1.1861 (7.6); 0.9747 (11.5); 0.9578 (11.3); 0.9398 (11.0); 0.9228 (10.6); 0.8539 (0.6); −0.0002 (1.0)

I.0438: $^1$H-NMR(300.2 MHz, CDCl3):
δ = 7.3870 (5.7); 7.2989 (1.3); 6.7754 (0.6); 6.7517 (0.6); 6.1989 (0.5); 6.0283 (0.6); 6.0134 (1.0); 5.9987 (0.5); 5.8279 (0.5); 4.9614 (0.5); 4.9440 (0.6); 4.9387 (0.9); 4.9210 (0.8); 4.9154 (0.6); 4.8981 (0.5); 3.8658 (16.0); 2.6465 (0.3); 2.5912 (0.5); 2.5501 (0.4); 2.5343 (0.4); 2.4967 (0.4); 2.4805 (0.4); 2.4749 (0.4); 2.4591 (0.4); 2.4260 (0.4); 1.6965 (0.4); 0.0330 (1.6)

I.0439: $^1$H-NMR(300.2 MHz, CDCl3):
δ = 7.3351 (11.0); 7.2990 (4.9); 6.9092 (2.2); 4.3565 (2.4); 4.3327 (7.6); 4.3090 (7.7); 4.2853 (2.5); 2.7296 (0.5); 2.7083 (0.9); 2.7016 (1.1); 2.6878 (2.1); 2.6796 (1.1); 2.6629 (5.4); 2.6322 (4.6); 2.6045 (2.1); 2.5983 (1.5); 2.5631 (0.6); 2.1970 (0.6); 2.1916 (0.6); 2.1811 (0.4); 2.1702 (2.6); 2.1603 (1.2); 2.1433 (3.3); 2.1389 (2.5); 2.1284 (0.8); 2.1160 (2.2); 2.1075 (1.1); 2.0891 (0.5); 2.0845 (0.5); 1.6335 (1.8); 1.3829 (7.9); 1.3592 (16.0); 1.3355 (7.7); 1.2888 (0.4); 0.0346 (6.3)

I.0440: $^1$H-NMR(400.1 MHz, $d_6$-DMSO):
δ = 8.6499 (0.9); 8.6332 (0.9); 6.3133 (0.5); 6.1844 (0.5); 6.1731 (1.0); 6.1617 (0.5); 6.0330 (0.6); 4.6876 (0.4); 4.6694 (1.0); 4.6518 (1.0); 4.6337 (0.4); 3.6823 (16.0); 3.3262 (121.0); 2.5140 (5.9); 2.5096 (8.4); 2.5054 (6.8); 2.4774 (0.8); 2.4612 (0.9); 2.4495 (1.2); 2.4378 (0.8); 2.4213 (0.6); 2.4098 (0.6); 2.4041 (0.6); 2.3926 (0.5)

I.0441: $^1$H-NMR(300.2 MHz, CDCl3):
δ = 7.3470 (8.2); 7.2986 (2.1); 6.5206 (0.6); 6.4927 (0.6); 4.7189 (1.6); 4.7029 (1.7); 4.6904 (1.6); 4.6744 (1.6); 4.3164 (0.8); 4.3085 (0.8); 4.3048 (0.4); 4.2925 (2.4); 4.2848 (2.5); 4.2686 (2.5); 4.2610 (2.5); 4.2485 (0.4); 4.2448 (0.9); 4.2374 (0.8); 2.3184 (0.6); 2.3023 (0.6); 2.2955 (0.8); 2.2794 (0.8); 2.2726 (0.7); 2.2565 (0.6); 1.6977 (3.6); 1.3667 (5.7); 1.3429 (11.6); 1.3191 (5.5); 1.0334 (8.5); 1.0101 (16.0); 0.9867 (8.3); 0.0324 (2.6)

I.0442: $^1$H-NMR(400.2 MHz, $d_6$-DMSO):
δ = 9.1629 (0.6); 9.1558 (0.6); 9.1445 (0.7); 7.8539 (3.5); 7.8518 (2.4); 7.8491 (2.5); 6.1967 (0.6); 6.1863 (0.5); 4.6347 (0.4); 4.6219 (0.5); 4.6134 (0.7); 4.6015 (0.7); 4.5929 (0.5); 4.5798 (0.4); 3.6799 (16.0); 3.3452 (11.8); 3.3413 (13.7); 3.3385 (12.9); 2.5292 (0.3); 2.5244 (0.5); 2.5159 (5.9); 2.5114 (11.6); 2.5069 (15.1); 2.5023 (10.8); 2.4978 (5.2); 2.4487 (0.5); 2.4391 (0.3); 2.4310 (0.3); 2.4186 (0.4); 2.4076 (0.8); 2.3940 (0.6); 2.3809 (0.6); 2.3682 (0.6); 2.3554 (0.6); 2.3441 (0.3); 2.3309 (0.3)

I.0443: $^1$H-NMR(400.2 MHz, $d_6$-DMSO):
δ = 9.0705 (1.4); 9.0635 (1.5); 9.0517 (1.6); 9.0442 (1.5); 7.8777 (6.6); 7.8758 (5.6); 7.8735 (6.6); 7.3024 (0.7); 7.3002 (0.7); 7.2795 (7.9); 7.2754 (7.4); 7.2706 (16.0); 7.2674 (15.6); 7.2333 (0.4); 7.2197 (1.3); 7.2127 (1.6); 7.2091 (1.6); 7.2037 (1.7); 7.2003 (1.6); 7.1952 (1.1); 7.1903 (0.9); 7.1789 (0.3); 4.6249 (1.0); 4.6105 (1.4); 4.6053 (1.4); 4.6007 (1.7); 4.5909 (1.5); 4.5864 (1.5); 4.5813 (1.5); 4.5668 (1.1); 4.1136 (2.5); 4.0959 (8.0); 4.0782 (8.1); 4.0604 (2.7); 3.3525 (37.4); 3.3432 (35.5); 3.1650 (1.4); 3.1507 (1.5); 3.1305 (2.7); 3.1164 (2.4); 3.0662 (2.6); 3.0417 (2.6); 3.0318 (1.6); 3.0073 (1.4); 2.8974 (0.6); 2.7402 (0.5); 2.5304 (1.0); 2.5129 (26.3); 2.5086 (33.7); 2.5042 (25.2); 1.2413 (0.7); 1.1475 (6.0); 1.1426 (3.9); 1.1297 (12.2); 1.1248 (7.8); 1.1120 (5.8); 1.1071 (3.6); 0.0012 (0.5); −0.0002 (0.6)

I.0444: $^1$H-NMR(300.2 MHz, CDCl3):
δ = 7.3170 (11.3); 7.2990 (4.9); 6.5767 (1.1); 6.5490 (1.1); 5.3363 (0.6); 4.8213 (0.7); 4.8035 (0.6); 4.7923 (1.5); 4.7757 (1.2); 4.7643 (1.0); 4.7478 (0.7); 4.3042 (2.1); 4.2804 (6.8); 4.2566 (7.0); 4.2329 (2.4); 1.7808 (1.2); 1.7673 (1.3); 1.7639 (1.2); 1.7494 (2.1); 1.7371 (2.0); 1.7286 (1.8); 1.7087 (1.5); 1.6909 (0.5); 1.6780 (1.4); 1.6521 (7.6); 1.6233 (0.9); 1.3675 (7.9); 1.3438 (16.0); 1.3200 (7.6); 1.3088 (0.4); 1.0211 (8.4); 1.0086 (10.3); 1.0014 (10.2); 0.9881 (8.6); 0.0350 (6.5)

I.0445: $^1$H-NMR(400.2 MHz, $d_6$-DMSO):
δ = 7.9790 (0.9); 7.9724 (0.9); 4.1030 (2.3); 4.0853 (7.6); 4.0675 (7.6); 4.0498 (2.4); 3.5184 (4.8); 3.5038 (4.8); 3.3373 (40.0); 2.5228 (0.4); 2.5141 (7.2); 2.5096 (15.0); 2.5050 (20.1); 2.5004 (14.7); 2.4959 (7.1); 1.1981 (7.8); 1.1804 (16.0); 1.1626 (7.6); 1.1001 (1.5); 1.0888 (3.9); 1.0814 (5.4); 1.0726 (2.4); 1.0198 (0.4); 0.9823 (2.4); 0.9732 (5.3); 0.9659 (4.0); 0.9543 (1.6); −0.0002 (0.3)

I.0446: $^1$H-NMR(400.2 MHz, $d_6$-DMSO):
δ = 8.5271 (3.8); 4.0929 (2.4); 4.0753 (7.5); 4.0575 (7.6); 4.0398 (2.5); 3.3523 (41.4); 3.3444 (45.8); 2.5110 (21.4); 2.5068 (26.8); 2.5025 (19.9); 2.1263 (1.7); 2.1141 (1.5); 2.1075 (1.8); 2.0935 (2.6); 2.0771 (1.3); 2.0328 (1.3); 2.0189 (2.8); 2.0107 (2.0); 2.0035 (1.8); 1.9871 (1.8); 1.9743 (1.0); 1.7432 (0.4); 1.6963 (5.8); 1.6885 (5.1); 1.6449 (0.3); 1.2389 (0.5); 1.1537 (7.9); 1.1360 (16.0); 1.1183 (7.7); −0.0002 (0.5)

TABLE A-(I)-continued

| NMR peak lists of compounds according to formula (I) |
| --- |
| I.0447: $^1$H-NMR(400.2 MHz, $d_6$-DMSO):<br>δ = 8.6241 (2.4); 3.7416 (0.8); 3.7323 (1.6); 3.7227 (1.0); 3.7123 (1.3); 3.7029 (2.3); 3.6937 (1.2); 3.6258 (16.0); 3.5996 (1.1); 3.5891 (1.1); 3.5782 (1.3); 3.5685 (1.6); 3.5490 (0.9); 3.5377 (0.8); 3.3593 (71.4); 3.3512 (84.9); 2.8948 (0.6); 2.7359 (0.6); 2.5098 (26.8); 2.5057 (32.4); 2.0145 (0.4); 1.9903 (3.4); 1.9808 (4.9); 1.9705 (3.0); 1.9584 (1.6); 1.2406 (0.4); −0.0002 (0.5) |
| I.0448: $^1$H-NMR(500.1 MHz, CDCl3):<br>δ = 7.2816 (0.6); 7.1088 (0.3); 7.0952 (0.5); 7.0818 (0.3); 4.5225 (0.4); 4.5193 (0.5); 4.5158 (0.4); 4.5125 (0.4); 4.5091 (0.5); 4.5058 (0.6); 4.5024 (0.5); 4.4990 (0.4); 4.4956 (0.4); 4.4922 (0.5); 4.4892 (0.4); 3.7302 (16.0); 2.6814 (0.6); 2.6708 (0.6); 2.6494 (2.0); 2.6388 (2.0); 2.6257 (2.4); 2.6163 (2.4); 2.5937 (0.7); 2.5842 (0.7); 1.7826 (0.4); 1.3372 (7.6); 1.3236 (7.6); −0.0002 (0.7) |
| I.0449: $^1$H-NMR(400.1 MHz, CDCl3):<br>δ = 7.2631 (3.6); 6.7844 (1.9); 4.2902 (2.6); 4.2724 (7.6); 4.2546 (8.0); 4.2369 (3.5); 4.2036 (9.0); 4.1912 (10.3); 4.1568 (0.6); 1.5795 (3.7); 1.3302 (8.0); 1.3124 (16.0); 1.2946 (9.0); 0.0699 (0.7); −0.0002 (4.9) |
| I.0450: $^1$H-NMR(300.2 MHz, CDCl3):<br>δ = 7.2985 (5.7); 7.2796 (0.5); 7.2774 (0.6); 7.0297 (0.6); 7.0123 (0.8); 4.2598 (2.0); 4.2360 (6.2); 4.2122 (6.3); 4.1884 (2.1); 3.7658 (1.2); 3.7627 (1.3); 3.7441 (3.2); 3.7237 (3.4); 3.7126 (0.8); 3.7060 (1.4); 3.7033 (1.3); 3.6936 (0.4); 2.6774 (4.0); 2.6571 (5.4); 2.6379 (3.6); 2.3055 (0.4); 1.6513 (0.8); 1.4661 (3.4); 1.3420 (8.1); 1.3182 (16.0); 1.2944 (10.1); 1.2563 (0.8); 0.9374 (1.0); 0.9157 (3.0); 0.8923 (1.2); 0.1050 (0.4); 0.0340 (4.1) |
| I.0451: $^1$H-NMR(300.2 MHz, CDCl3):<br>δ = 7.3683 (0.9); 7.2982 (2.3); 6.8272 (0.5); 6.8020 (0.8); 6.7765 (0.5); 4.7251 (1.1); 4.7190 (1.2); 4.7097 (1.2); 4.7036 (1.3); 4.6967 (1.2); 4.6907 (1.1); 4.6859 (0.5); 4.6812 (1.1); 4.6753 (1.1); 4.3209 (0.3); 4.3089 (1.2); 4.3029 (1.2); 4.2970 (0.5); 4.2850 (3.6); 4.2791 (3.7); 4.2611 (3.7); 4.2555 (3.7); 4.2430 (0.5); 4.2373 (1.3); 4.2318 (1.2); 4.2195 (0.3); 2.3484 (0.4); 2.3411 (0.8); 2.3255 (0.9); 2.3181 (1.2); 2.3025 (1.3); 2.2952 (1.0); 2.2796 (0.9); 2.2723 (0.5); 2.2567 (0.4); 1.6876 (0.8); 1.4608 (1.6); 1.3592 (7.9); 1.3354 (16.0); 1.3117 (7.6); 1.2836 (0.4); 1.0580 (0.6); 1.0435 (11.8); 1.0313 (2.0); 1.0206 (12.1); 1.0130 (12.8); 0.9900 (11.5); 0.0284 (2.0) |
| I.0452: $^1$H-NMR(400.2 MHz, $d_6$-DMSO):<br>δ = 9.2466 (3.6); 7.8998 (10.8); 4.1202 (2.3); 4.1025 (7.4); 4.0847 (7.4); 4.0670 (2.4); 3.3396 (35.8); 2.8939 (1.0); 2.7349 (0.8); 2.5919 (1.0); 2.5870 (0.6); 2.5763 (1.2); 2.5703 (1.7); 2.5633 (1.3); 2.5591 (1.7); 2.5551 (1.6); 2.5450 (1.9); 2.5372 (1.5); 2.5231 (1.9); 2.5148 (8.5); 2.5104 (16.5); 2.5059 (21.1); 2.5013 (15.2); 2.4969 (7.3); 2.3106 (1.0); 2.2876 (2.1); 2.2677 (1.6); 2.2583 (1.9); 2.2361 (1.0); 1.9909 (0.5); 1.9803 (0.9); 1.9767 (1.0); 1.9681 (1.0); 1.9590 (1.6); 1.9535 (1.6); 1.9387 (2.2); 1.9309 (1.0); 1.9171 (1.1); 1.1660 (7.8); 1.1483 (16.0); 1.1305 (7.5); −0.0002 (0.4) |
| I.0453: $^1$H-NMR(400.2 MHz, $d_6$-DMSO):<br>δ = 8.7767 (0.9); 8.7640 (1.6); 8.7510 (0.8); 7.7962 (5.5); 7.7940 (8.5); 5.6253 (0.8); 4.0977 (2.3); 4.0799 (7.2); 4.0621 (7.2); 4.0443 (2.4); 3.6806 (0.4); 3.4793 (1.6); 3.4623 (4.0); 3.4482 (4.0); 3.4313 (1.7); 3.3395 (37.4); 2.5778 (3.5); 2.5608 (7.1); 2.5437 (3.2); 2.5300 (0.5); 2.5164 (7.7); 2.5120 (15.6); 2.5076 (20.5); 2.5030 (15.2); 2.4987 (7.9); 1.3003 (0.4); 1.2608 (0.8); 1.2375 (1.8); 1.1963 (8.0); 1.1786 (16.0); 1.1608 (7.8); 0.8538 (0.4); −0.0002 (0.7) |
| I.0454: $^1$H-NMR(400.2 MHz, $d_6$-DMSO):<br>δ = 9.2431 (3.9); 7.7753 (8.8); 4.0912 (2.3); 4.0735 (7.1); 4.0558 (7.2); 4.0380 (2.3); 3.3412 (33.6); 2.8955 (0.3); 2.5116 (14.2); 2.5072 (18.5); 2.5028 (13.9); 1.4684 (2.0); 1.4563 (5.2); 1.4481 (5.6); 1.4372 (2.3); 1.2391 (0.5); 1.1681 (2.5); 1.1559 (11.6); 1.1491 (6.0); 1.1380 (16.0); 1.1203 (7.0); −0.0002 (0.4) |
| I.0455: $^1$H-NMR(300.2 MHz, $d_6$-DMSO):<br>δ = 12.5602 (2.2); 9.1868 (6.3); 7.7948 (14.8); 4.0601 (0.4); 4.0364 (0.4); 3.3477 (16.0); 2.5335 (5.8); 2.5278 (11.7); 2.5218 (15.7); 2.5158 (11.5); 2.5101 (5.6); 2.0086 (1.8); 1.9286 (1.2); 1.4523 (2.4); 1.4364 (6.0); 1.4257 (6.7); 1.4117 (2.9); 1.2177 (0.5); 1.1940 (1.2); 1.1703 (0.6); 1.1413 (3.0); 1.1271 (6.6); 1.1164 (6.2); 1.1004 (2.3); 0.0298 (0.6); 0.0189 (13.8); 0.0080 (0.6) |
| I.0456: $^1$H-NMR(400.2 MHz, $d_6$-DMSO):<br>δ = 8.7819 (1.0); 8.7686 (1.8); 8.7553 (1.0); 7.6912 (7.1); 4.0950 (2.4); 4.0772 (7.2); 4.0594 (7.3); 4.0416 (2.4); 3.4765 (1.7); 3.4596 (4.3); 3.4452 (4.3); 3.4284 (1.8); 3.3382 (45.4); 2.8939 (0.4); 2.7346 (0.3); 2.5784 (3.8); 2.5614 (7.9); 2.5442 (3.6); 2.5282 (0.6); 2.5145 (8.9); 2.5104 (17.7); 2.5060 (23.1); 2.5015 (17.4); 1.8580 (0.4); 1.2999 (0.4); 1.2598 (0.6); 1.2380 (1.5); 1.1915 (8.0); 1.1738 (16.0); 1.1559 (7.7); −0.0002 (0.8) |
| I.0457: $^1$H-NMR(400.2 MHz, $d_6$-DMSO):<br>δ = 9.1949 (1.0); 9.1805 (2.0); 9.1659 (1.0); 7.8614 (10.4); 4.1497 (2.3); 4.1319 (7.2); 4.1142 (7.3); 4.0964 (2.4); 4.0114 (7.2); 3.9967 (7.2); 3.3388 (47.3); 2.5274 (0.5); 2.5139 (8.6); 2.5096 (17.2); 2.5052 (22.6); 2.5007 (16.9); 2.4965 (8.9); 1.2593 (0.4); 1.2379 (0.7); 1.2208 (8.0); 1.2031 (16.0); 1.1853 (7.7); −0.0002 (0.7) |
| I.0458: $^1$H-NMR(300.2 MHz, CDCl3):<br>δ = 7.3421 (9.8); 7.2988 (5.1); 6.8297 (2.4); 5.3366 (0.5); 4.2373 (2.4); 4.2135 (7.5); 4.1898 (7.6); 4.1661 (2.5); 1.6984 (2.1); 1.6816 (6.0); 1.6709 (6.4); 1.6555 (2.7); 1.6416 (3.8); 1.3198 (2.8); 1.3045 (6.8); 1.2938 (14.4); 1.2701 (16.0); 1.2463 (7.6); 0.0341 (4.7) |
| I.0459: $^1$H-NMR(400.2 MHz, $d_6$-DMSO):<br>δ = 9.2470 (3.6); 8.3017 (0.6); 7.8116 (9.2); 7.7421 (0.8); 7.4036 (0.6); 7.3823 (1.0); 7.3352 (0.9); 7.3138 (0.5); 4.4404 (0.6); 4.4260 (0.6); 4.1234 (2.7); 4.1057 (8.4); 4.0880 (8.5); 4.0703 (2.9); 4.0573 (0.4); 3.3794 (62.4); 3.3628 (50.3); 3.3484 (48.2); 3.3445 (56.5); 2.8966 (0.5); 2.7381 (0.5); 2.6758 (0.3); 2.5960 (1.2); 2.5913 (1.2); 2.5750 (2.5); 2.5700 (2.4); 2.5633 (2.6); 2.5594 (2.6); 2.5491 (3.0); 2.5421 (2.7); 2.5112 (42.4); 2.5070 (56.3); 2.5030 (45.0); 2.3336 (0.4); 2.3124 (1.4); 2.2897 (3.1); 2.2695 (2.3); 2.2597 (3.1); 2.2381 (1.6); 2.0712 (1.5); 1.9872 (0.9); 1.9772 (1.4); 1.9656 (2.6); 1.9543 (2.3); 1.9449 (3.0); 1.9325 (1.4); 1.9244 (1.7); 1.9176 (1.2); 1.9036 (0.4); 1.8967 (0.4); 1.2996 (0.5); 1.2798 (0.4); 1.2620 (1.0); 1.2404 (2.0); 1.1714 (7.6); 1.1670 (3.5); 1.1537 (16.0); 1.1495 (6.7); 1.1360 (7.7); 1.1318 (3.3); 0.8554 (0.4); −0.0002 (1.8) |
| I.0460: $^1$H-NMR(400.2 MHz, $d_6$-DMSO):<br>δ = 9.2640 (4.4); 7.9540 (0.6); 7.7076 (7.2); 7.3917 (0.3); 4.0917 (2.2); 4.0741 (6.8); 4.0563 (6.8); 4.0386 (2.3); 3.3389 (55.5); 2.8929 (3.9); 2.7336 (3.5); 2.5090 (21.7); 2.5048 (27.7); 2.5006 (20.9); 1.4706 (2.0); 1.4585 (5.3); 1.4504 (5.8); 1.4394 (2.3); 1.2993 (0.5); 1.2912 (0.3); 1.2731 (0.3); 1.2593 (0.8); 1.2387 (2.4); 1.1669 (2.7); 1.1529 (10.2); 1.1483 (7.0); 1.1351 (16.0); 1.1173 (7.0); 0.8533 (0.5); −0.0002 (0.7) |
| I.0461: $^1$H-NMR(400.2 MHz, $d_6$-DMSO):<br>δ = 9.1648 (2.0); 9.1523 (1.8); 7.8195 (7.8); 7.8158 (5.5); 7.8121 (5.3); 4.1515 (4.0); 4.1337 (12.5); 4.1160 (12.6); 4.0982 (4.1); 4.0054 (8.6); 3.9906 (8.6); 3.3449 (24.5); 3.3401 (25.2); 3.3374 (24.2); 2.5292 (0.8); 2.5161 (13.7); 2.5117 (26.2); 2.5072 (33.3); 2.5027 (23.6); 2.4982 (11.1); 1.2392 (0.9); 1.2270 (8.1); 1.2243 (7.0); 1.2093 (16.0); 1.2064 (13.7); 1.1914 (7.8); 1.1887 (6.6); −0.0002 (0.7) |
| I.0462: $^1$H-NMR(400.2 MHz, $d_6$-DMSO):<br>δ = 8.7524 (1.8); 7.7532 (8.9); 7.7492 (3.8); 7.7466 (3.6); 4.0966 (3.2); 4.0789 (9.3); 4.0611 (9.3); 4.0433 (3.1); 3.4750 (2.4); 3.4581 (5.6); 3.4439 (5.4); 3.4270 (2.3); 3.3562 (19.5); 3.3503 (25.8); 3.3439 (21.8); 3.3377 (17.1); 2.5757 (4.4); 2.5588 (8.6); 2.5416 (4.1); 2.5164 (11.8); 2.5123 (21.2); 2.5078 (26.7); 2.5034 (19.4); 2.4991 (9.6); 1.2388 (0.6); 1.1977 (8.3); 1.1800 (16.0); 1.1622 (7.7); −0.0002 (0.5) |

TABLE A-(I)-continued

NMR peak lists of compounds according to formula (I)

I.0463: $^1$H-NMR(300.2 MHz, CDCl3):
δ = 7.2982 (1.9); 6.7754 (0.6); 6.7512 (0.6); 4.2281 (1.3); 4.2043 (4.2); 4.1805 (4.2); 4.1568 (1.4); 2.4464 (16.0); 1.7051 (1.2); 1.6885 (3.3); 1.6777 (3.4); 1.6629 (2.9); 1.4635 (0.9); 1.3285 (1.6); 1.3134 (3.4); 1.3025 (3.5); 1.2849 (5.6); 1.2609 (9.0); 1.2372 (4.3); 0.1026 (0.5); 0.0313 (1.7)
I.0464: $^1$H-NMR(400.2 MHz, $d_6$-DMSO):
δ = 9.0089 (0.6); 8.9943 (1.1); 8.9798 (0.6); 7.6163 (5.2); 4.1409 (1.5); 4.1232 (4.6); 4.1054 (4.7); 4.0876 (1.5); 3.9684 (4.6); 3.9535 (4.6); 3.3319 (14.7); 2.5121 (5.0); 2.5078 (10.1); 2.5033 (13.1); 2.4988 (9.4); 2.4944 (4.6); 2.1723 (16.0); 1.2387 (0.9); 1.2167 (5.2); 1.1990 (10.4); 1.1811 (5.0); −0.0002 (0.5)
I.0465: $^1$H-NMR(400.2 MHz, $d_6$-DMSO):
δ = 8.6097 (0.6); 8.5966 (1.0); 8.5833 (0.6); 7.5466 (5.1); 4.0902 (1.5); 4.0724 (4.6); 4.0546 (4.7); 4.0368 (1.6); 3.4566 (1.0); 3.4394 (2.7); 3.4253 (2.6); 3.4082 (1.2); 3.3328 (17.3); 2.5616 (2.4); 2.5445 (5.0); 2.5271 (2.5); 2.5130 (5.4); 2.5087 (10.8); 2.5042 (14.3); 2.4997 (10.8); 2.4955 (5.8); 2.1515 (16.0); 1.2590 (0.4); 1.2388 (1.0); 1.1917 (5.1); 1.1739 (10.4); 1.1561 (5.0); -0.0002 (0.6)
I.0466: $^1$H-NMR(400.2 MHz, $d_6$-DMSO):
δ = 9.0986 (2.7); 7.5870 (5.3); 4.0808 (1.5); 4.0631 (4.6); 4.0454 (4.7); 4.0277 (1.6); 3.3313 (20.1); 2.8920 (0.9); 2.7327 (0.8); 2.5259 (0.3); 2.5124 (6.0); 2.5081 (12.1); 2.5037 (16.1); 2.4992 (12.3); 2.1590 (16.0); 1.4462 (1.3); 1.4343 (3.4); 1.4261 (3.8); 1.4152 (1.6); 1.2590 (0.4); 1.2393 (1.1); 1.1484 (5.0); 1.1405 (2.0); 1.1306 (12.6); 1.1213 (4.1); 1.1130 (5.2); −0.0002 (0.6)
I.0467: $^1$H-NMR(400.2 MHz, $d_6$-DMSO):
δ = 9.1837 (0.9); 9.1692 (1.8); 9.1547 (0.9); 7.7565 (6.0); 7.7551 (6.2); 4.1501 (2.2); 4.1324 (7.0); 4.1146 (7.1); 4.0968 (2.3); 4.0109 (6.8); 3.9961 (6.7); 3.3383 (35.4); 2.5271 (0.5); 2.5136 (7.7); 2.5092 (15.7); 2.5047 (20.7); 2.5002 (15.5); 2.4959 (8.1); 1.2593 (0.4); 1.2382 (0.7); 1.2208 (7.9); 1.2031 (16.0); 1.1853 (7.6); −0.0002 (0.7)
I.0468: $^1$H-NMR(300.2 MHz, CDCl3):
δ = 7.5809 (0.3); 7.4954 (0.3); 7.4912 (0.3); 7.3136 (9.2); 7.2987 (12.1); 7.2880 (0.5); 6.6187 (1.6); 4.2328 (2.3); 4.2090 (7.2); 4.1939 (0.8); 4.1852 (7.3); 4.1704 (1.0); 4.1615 (2.4); 4.1466 (0.8); 2.0830 (3.2); 1.6988 (1.8); 1.6821 (5.2); 1.6713 (5.0); 1.6561 (2.2); 1.6172 (10.5); 1.3435 (0.4); 1.3371 (0.5); 1.3205 (3.8); 1.3052 (6.8); 1.2949 (8.0); 1.2893 (10.1); 1.2777 (2.9); 1.2724 (2.2); 1.2655 (16.0); 1.2533 (0.8); 1.2417 (7.6); 0.9394 (0.5); 0.9175 (1.8); 0.8942 (0.6); 0.0464 (0.4); 0.0355 (10.4); 0.0245 (0.4)
I.0469: $^1$H-NMR(300.2 MHz, $d_6$-DMSO):
δ = 12.5146 (6.1); 9.0566 (7.4); 8.0163 (0.5); 8.0121 (0.5); 7.8410 (0.5); 7.8367 (0.5); 7.6950 (0.6); 7.6751 (16.0); 3.3492 (7.8); 3.1889 (0.5); 2.5341 (6.8); 2.5282 (14.3); 2.5221 (19.6); 2.5161 (14.4); 2.5103 (6.9); 1.4306 (2.8); 1.4145 (7.1); 1.4041 (7.3); 1.3902 (3.2); 1.1206 (3.7); 1.1067 (7.5); 1.0960 (6.8); 1.0801 (2.6); 0.0305 (0.7); 0.0197 (20.0); 0.0087 (0.8)
I.0470: $^1$H-NMR(300.2 MHz, CDCl3):
δ = 13.9017 (6.8); 13.4565 (7.0); 12.4735 (0.5); 12.4561 (16.0); 11.9691 (3.2); 11.6365 (3.1); 11.3585 (0.5); 8.1294 (7.8); 7.2843 (3.9); 7.2783 (8.4); 7.2722 (11.5); 7.2661 (8.3); 7.2601 (3.9); 6.8446 (12.8); 6.0944 (2.4); 6.0792 (5.8); 6.0684 (6.3); 6.0552 (2.7); 5.9945 (2.7); 5.9798 (6.1); 5.9686 (6.8); 5.9554 (3.0); 5.7529 (2.8); 5.7395 (6.1); 5.7286 (5.8); 5.7138 (2.3); 5.6651 (0.4); 5.6125 (3.0); 5.5991 (6.7); 5.5879 (6.3); 5.5733 (2.5); 4.7804 (0.3); 4.7696 (9.9); 4.7586 (0.4)
I.0471: $^1$H-NMR(300.2 MHz, $d_6$-DMSO):
δ = 8.9891 (0.5); 8.9690 (1.1); 8.9495 (0.5); 7.7153 (5.3); 3.9117 (2.6); 3.8919 (2.6); 3.3463 (16.0); 2.5341 (3.1); 2.5281 (6.5); 2.5220 (8.9); 2.5160 (6.5); 2.5100 (3.1); 2.0953 (0.7); 0.0201 (4.3)
I.0472: $^1$H-NMR(300.2 MHz, CDCl3):
δ = 7.3845 (0.4); 7.3759 (0.6); 7.3704 (0.4); 7.3553 (2.2); 7.3314 (3.3); 7.3258 (2.2); 7.3201 (1.3); 7.3142 (0.5); 7.2987 (2.1); 7.1849 (2.0); 7.1790 (2.2); 7.1587 (1.8); 7.1545 (1.6); 6.7444 (0.3); 6.7211 (0.6); 6.6985 (0.4); 5.3354 (1.6); 5.0549 (0.3); 5.0403 (0.6); 5.0352 (0.9); 5.0154 (0.9); 5.0105 (0.7); 3.7945 (16.0); 3.2638 (1.7); 3.2525 (1.9); 3.2451 (1.9); 3.2329 (1.7); 1.6261 (2.3); 0.0383 (1.9)
I.0473: $^1$H-NMR(300.2 MHz, CDCl3):
δ = 7.2988 (9.3); 7.1192 (0.4); 7.0968 (0.7); 7.0738 (0.5); 7.0146 (0.6); 5.3371 (0.4); 4.9537 (0.4); 4.9324 (0.7); 4.9121 (0.7); 4.8919 (0.4); 4.1979 (0.7); 4.1741 (2.1); 4.1502 (2.2); 4.1265 (0.8); 4.0865 (1.8); 3.8141 (0.8); 3.7920 (0.3); 2.6810 (1.3); 2.6573 (2.9); 2.6335 (1.7); 2.4911 (0.9); 2.3892 (0.3); 2.3572 (0.5); 2.3333 (0.6); 2.3081 (1.3); 2.2347 (0.6); 2.2170 (0.7); 2.2112 (0.8); 2.1869 (0.7); 2.1612 (16.0); 2.1540 (5.2); 2.0873 (9.8); 1.9319 (0.4); 1.9213 (0.4); 1.9098 (0.9); 1.8984 (0.4); 1.4683 (8.0); 1.3214 (2.8); 1.2976 (5.9); 1.2914 (2.2); 1.2738 (2.8); 1.2584 (1.4); 0.8904 (0.4); 0.8635 (0.3); 0.0360 (9.1); 0.0252 (0.4)
I.0474: $^1$H-NMR(300.2 MHz, $d_6$-DMSO):
δ = 8.9279 (0.6); 8.2861 (0.5); 7.7288 (2.5); 3.8859 (1.1); 3.8660 (1.1); 3.7877 (1.3); 3.7683 (1.3); 3.3458 (16.0); 2.5341 (2.9); 2.5281 (6.3); 2.5220 (8.6); 2.5159 (6.2); 2.5100 (3.0); 0.0202 (2.4)
I.0475: $^1$H-NMR(300.2 MHz, $d_6$-DMSO):
δ = 8.9841 (1.8); 7.6857 (4.2); 7.4063 (0.7); 7.0525 (0.7); 3.3457 (16.0); 2.5341 (3.5); 2.5282 (7.2); 2.5221 (9.7); 2.5160 (7.0); 2.5100 (3.3); 1.3256 (0.7); 1.3108 (1.7); 1.3000 (1.8); 1.2867 (0.8); 0.9607 (0.8); 0.9474 (1.8); 0.9363 (1.7); 0.9215 (0.6); 0.0312 (0.4); 0.0204 (11.5); 0.0094 (0.5)
I.0476: $^1$H-NMR(300.2 MHz, CDCl3):
δ = 7.5404 (0.6); 7.4795 (3.0); 7.4280 (1.0); 7.2983 (4.2); 4.0023 (0.4); 3.9786 (1.2); 3.9548 (1.2); 3.9311 (0.4); 2.0449 (16.0); 1.7346 (0.5); 1.7181 (1.3); 1.7076 (1.5); 1.6882 (2.9); 1.6344 (0.6); 1.6178 (1.5); 1.6071 (1.6); 1.5919 (0.6); 1.2858 (0.4); 1.2559 (0.7); 1.2407 (1.5); 1.2300 (1.5); 1.2197 (2.2); 1.2127 (1.2); 1.1960 (5.6); 1.1861 (1.6); 1.1722 (2.2); 0.0331 (4.1)
I.0477: $^1$H-NMR(300.2 MHz, CDCl3):
δ = 7.3762 (5.1); 7.2988 (7.7); 6.6169 (1.0); 2.3204 (16.0); 1.8361 (1.0); 1.8194 (3.0); 1.8079 (3.1); 1.7926 (1.2); 1.6047 (2.8); 1.4097 (1.4); 1.3944 (3.4); 1.3829 (3.3); 1.3662 (1.1)
I.0478: $^1$H-NMR(300.2 MHz, $d_6$-DMSO):
δ = 12.2531 (0.6); 12.2314 (0.5); 8.9695 (8.1); 8.4483 (8.6); 7.7353 (0.6); 7.7127 (16.0); 4.0833 (0.8); 4.0596 (2.4); 4.0359 (2.5); 4.0122 (0.8); 3.6424 (0.9); 3.6204 (2.2); 3.5985 (0.9); 3.3571 (12.7); 2.5280 (17.6); 2.5221 (23.3); 2.5161 (17.2); 2.0085 (10.6); 1.8009 (0.9); 1.7907 (1.1); 1.7790 (2.5); 1.7675 (1.0); 1.7569 (0.9); 1.3740 (0.5); 1.3332 (3.4); 1.3171 (9.5); 1.3067 (10.4); 1.3009 (10.2); 1.2906 (9.6); 1.2759 (3.7); 1.2174 (3.1); 1.1937 (5.7); 1.1700 (2.8); 1.1244 (0.4); 1.0434 (0.3); 0.9889 (3.8); 0.9754 (7.9); 0.9638 (9.1); 0.9472 (9.6); 0.9360 (7.8); 0.9205 (3.1); 0.0297 (1.0); 0.0189 (19.0); 0.0080 (1.0)
I.0479: $^1$H-NMR(300.2 MHz, CDCl3):
δ = 8.8899 (1.6); 7.3042 (13.1); 7.0002 (10.7); 4.2658 (2.4); 4.2421 (7.5); 4.2184 (7.7); 4.1946 (2.6); 1.8327 (2.2); 1.8154 (6.3); 1.8050 (6.3); 1.7886 (2.7); 1.5972 (10.4); 1.4747 (0.4); 1.4213 (2.8); 1.4054 (6.1); 1.3948 (6.3); 1.3772 (2.2); 1.3084 (8.0); 1.2846 (16.0); 1.2609 (7.7); 0.0528 (0.5); 0.0422 (12.8); 0.0313 (0.5)
I.0480: $^1$H-NMR(300.2 MHz, CDCl3):
δ = 7.4112 (0.4); 7.3734 (9.6); 7.2985 (13.8); 6.5961 (1.9); 2.9413 (2.1); 2.9165 (6.8); 2.8917 (7.0); 2.8669 (2.4); 2.0848 (0.6); 1.8228 (1.7); 1.8062 (4.9); 1.7946 (5.2); 1.7793 (2.1); 1.6070 (3.1); 1.4006 (2.5); 1.3853 (5.9); 1.3737 (5.8); 1.3570 (2.0); 1.2970 (0.9); 1.2884 (8.4); 1.2636 (16.0); 1.2387 (7.3)

TABLE A-(I)-continued

NMR peak lists of compounds according to formula (I)

I.0481: $^1$H-NMR(300.2 MHz, CDCl3):
δ = 7.2985 (3.4); 6.9754 (0.3); 6.9583 (0.3); 4.2574 (1.2); 4.2336 (3.8); 4.2097 (3.8); 4.1860 (1.3); 3.7693 (0.7); 3.7658 (0.7); 3.7474 (1.8); 3.7291 (1.8); 3.7268 (1.8); 3.7092 (0.7); 3.7060 (0.7); 2.6760 (2.2); 2.6558 (3.0); 2.6362 (2.0); 2.4420 (16.0); 1.6355 (1.4); 1.4667 (2.4); 1.3399 (4.5); 1.3161 (9.1); 1.2923 (4.9); 0.1050 (0.8); 0.0344 (3.4)
I.0482: $^1$H-NMR(600.1 MHz, $d_6$-DMSO):
δ = 8.7120 (1.4); 8.7005 (1.4); 4.4523 (0.4); 4.4403 (1.6); 4.4284 (2.4); 4.4166 (1.6); 4.4045 (0.4); 4.1570 (0.7); 4.1508 (0.9); 4.1451 (0.7); 4.1419 (1.2); 4.1390 (3.1); 4.1301 (3.3); 4.1271 (3.3); 4.1183 (3.1); 4.1153 (1.2); 4.1121 (0.8); 4.1065 (1.0); 4.1003 (0.7); 3.3222 (23.6); 2.5095 (5.5); 2.5064 (12.4); 2.5034 (17.5); 2.5003 (12.5); 2.4973 (5.7); 1.3976 (11.6); 1.3855 (11.6); 1.2170 (7.7); 1.2051 (16.0); 1.1933 (7.6); −0.0001 (1.5)
I.0483: $^1$H-NMR(600.1 MHz, $d_6$-DMSO):
δ = 9.0052 (1.7); 3.6216 (16.0); 3.3205 (10.1); 2.5092 (3.1); 2.5061 (7.0); 2.5031 (9.8); 2.5000 (7.0); 2.4970 (3.1); 1.4704 (1.1); 1.4624 (2.8); 1.4569 (3.0); 1.4493 (1.2); 1.2028 (1.3); 1.1953 (3.0); 1.1898 (3.1); 1.1817 (1.1); −0.0001 (1.4)
I.0484: $^1$H-NMR(500.1 MHz, CDCl3):
δ = 9.3384 (0.7); 7.2595 (15.3); 4.5292 (5.8); 4.5206 (5.8); 4.3457 (1.4); 4.3315 (4.3); 4.3172 (4.3); 4.3029 (1.5); 1.5331 (16.0); 1.3607 (4.6); 1.3464 (9.1); 1.3321 (4.5); −0.0002 (20.1)
I.0485: $^1$H-NMR(500.1 MHz, CDCl3):
δ = 9.3183 (0.6); 7.2595 (10.4); 4.5498 (5.2); 4.5411 (5.2); 3.8669 (16.0); 1.5335 (10.8); −0.0002 (13.8)
I.0486: $^1$H-NMR(400.1 MHz, $d_6$-DMSO):
δ = 12.6025 (0.8); 12.4794 (0.4); 12.4577 (0.3); 8.8442 (16.0); 4.0390 (0.4); 4.0216 (0.4); 3.6026 (0.4); 3.3112 (5.8); 2.5661 (3.5); 2.5479 (8.0); 2.5334 (7.9); 2.5012 (36.3); 2.4323 (0.8); 2.3928 (0.6); 2.3718 (4.7); 2.3501 (10.9); 2.3212 (9.1); 2.2975 (4.7); 2.1846 (0.4); 1.9892 (3.9); 1.9715 (9.7); 1.9514 (13.7); 1.9315 (8.4); 1.9095 (3.9); 1.7601 (0.5); 1.3562 (1.5); 1.2694 (0.5); 1.2505 (0.4); 1.2365 (0.6); 1.1930 (0.6); 1.1816 (1.0); 1.1752 (1.2); 1.1577 (0.6); −0.0002 (14.4)
I.0487: $^1$H-NMR(400.1 MHz, $d_6$-DMSO):
δ = 12.4437 (0.8); 8.4767 (3.3); 8.4568 (3.3); 7.2669 (1.3); 7.2493 (3.3); 7.2316 (5.0); 7.2137 (7.4); 7.1971 (4.0); 7.1737 (1.0); 4.7831 (0.6); 4.7650 (1.4); 4.7502 (1.3); 4.7315 (0.6); 4.5055 (0.7); 4.4858 (1.4); 4.4711 (1.4); 4.4521 (0.7); 3.5935 (16.0); 3.3149 (33.3); 3.1743 (1.1); 3.1625 (1.0); 3.0606 (0.8); 3.0465 (1.0); 3.0256 (1.8); 3.0119 (1.7); 2.9836 (1.7); 2.9623 (1.7); 2.9500 (0.9); 2.9272 (0.8); 2.8901 (0.7); 2.7608 (0.6); 2.7464 (0.6); 2.7305 (1.0); 2.7184 (2.1); 2.7047 (2.3); 2.6981 (2.3); 2.6797 (2.0); 2.6565 (0.7); 2.6379 (0.6); 2.5046 (24.2); 2.5008 (29.2); 2.3266 (0.3); −0.0002 (5.2)
I.0488: $^1$H-NMR(400.1 MHz, $d_6$-DMSO):
δ = 12.4254 (1.0); 8.4324 (2.2); 8.4113 (3.5); 8.3890 (2.2); 7.2543 (1.5); 7.2339 (3.7); 7.2192 (7.1); 7.2089 (8.9); 7.1929 (3.9); 4.7770 (0.8); 4.7605 (1.5); 4.7451 (1.4); 4.7267 (0.7); 4.4998 (0.8); 4.4793 (1.5); 4.4653 (1.5); 4.4456 (0.7); 3.5959 (16.0); 3.3131 (4.0); 3.0568 (0.8); 3.0430 (1.0); 3.0219 (1.9); 3.0086 (1.8); 2.9806 (2.0); 2.9589 (1.8); 2.9469 (1.0); 2.9245 (0.8); 2.8901 (1.2); 2.7648 (0.5); 2.7523 (0.7); 2.7236 (2.8); 2.7119 (3.8); 2.6958 (2.2); 2.6716 (0.6); 2.6541 (0.5); 2.5011 (11.5); −0.0002 (2.2)
I.0489: $^1$H-NMR(400.1 MHz, $d_6$-DMSO):
δ = 13.1920 (0.4); 13.1637 (0.4); 13.1308 (0.4); 13.1136 (0.4); 9.1426 (8.6); 4.8397 (12.9); 4.8230 (16.0); 4.6841 (15.3); 4.6673 (13.3); 3.3148 (5.9); 2.5018 (19.6); −0.0002 (11.4)
I.0490: $^1$H-NMR(500.1 MHz, $d_6$-DMSO):
δ = 12.5345 (0.5); 8.8423 (11.2); 7.4234 (0.6); 4.0375 (0.4); 4.0233 (0.4); 3.3179 (0.4); 2.5568 (2.3); 2.5532 (1.5); 2.5421 (5.0); 2.5378 (3.3); 2.5308 (4.3); 2.5277 (4.0); 2.5162 (5.2); 2.5102 (5.5); 2.5065 (11.1); 2.5028 (16.3); 2.4992 (11.2); 2.4956 (5.1); 2.3613 (2.7); 2.3440 (6.2); 2.3266 (4.1); 2.3193 (4.8); 2.3013 (2.6); 1.9892 (2.1); 1.9815 (2.0); 1.9653 (5.6); 1.9497 (9.1); 1.9332 (5.1); 1.9173 (1.6); 1.9102 (16.0); 1.9033 (0.4); 1.3565 (1.7); 1.1902 (0.6); 1.1760 (1.1); 1.1618 (0.6); −0.0002 (5.5)
I.0491: $^1$H-NMR(500.1 MHz, CDCl3):
δ = 8.0005 (0.3); 7.5403 (0.4); 7.2608 (13.5); 4.5740 (7.3); 4.2969 (2.3); 4.2826 (7.0); 4.2683 (7.1); 4.2540 (2.4); 2.9601 (2.2); 2.8788 (2.1); 1.6376 (0.5); 1.3496 (0.4); 1.3364 (8.2); 1.3221 (16.0); 1.3078 (7.8); 1.2548 (0.7); 0.0063 (0.4); −0.0002 (16.5); −0.0068 (0.7)
I.0492: $^1$H-NMR(400.1 MHz, CDCl3):
δ = 7.5146 (1.2); 7.2603 (7.0); 5.2989 (3.0); 4.2547 (5.7); 4.2426 (5.6); 3.8194 (16.0); 1.5443 (6.7); −0.0002 (8.9)
I.0493: $^1$H-NMR(500.1 MHz, CDCl3):
δ = 9.3307 (0.4); 7.2594 (16.4); 4.5228 (3.4); 4.5142 (3.4); 4.3452 (0.8); 4.3309 (2.5); 4.3166 (2.6); 4.3024 (0.9); 1.5335 (16.0); 1.3602 (2.7); 1.3459 (5.4); 1.3316 (2.7); −0.0002 (22.9)
I.0494: $^1$H-NMR(400.1 MHz, $d_6$-DMSO):
δ = 12.7561 (1.6); 8.4650 (3.1); 8.4510 (5.7); 8.4378 (3.3); 3.9614 (15.8); 3.9471 (16.0); 3.3075 (10.0); 2.5018 (20.5); 1.9881 (0.3); 1.2349 (0.4); −0.0002 (7.5)
I.0495: $^1$H-NMR(400.1 MHz, CDCl3):
δ = 7.2611 (9.7); 6.8058 (2.2); 4.3102 (0.4); 4.2828 (1.6); 4.2745 (2.3); 4.2652 (4.2); 4.2570 (4.6); 4.2474 (4.7); 4.2393 (4.4); 4.2297 (2.5); 4.2217 (1.8); 4.1845 (2.0); 4.1657 (3.8); 4.1460 (2.0); 1.5561 (17.4); 1.5161 (0.3); 1.3766 (0.4); 1.3608 (0.5); 1.3279 (8.3); 1.3101 (16.0); 1.2923 (8.2); 1.2088 (0.5); 1.1884 (1.3); 1.1762 (2.1); 1.1652 (1.9); 1.1564 (2.2); 1.1447 (1.4); 1.1363 (1.0); 1.1241 (0.5); 0.6889 (0.4); 0.6691 (1.2); 0.6561 (1.9); 0.6359 (3.3); 0.6159 (3.6); 0.6052 (2.9); 0.5907 (3.4); 0.5852 (3.6); 0.5687 (3.4); 0.5563 (3.0); 0.5478 (2.6); 0.5226 (1.8); 0.5029 (2.8); 0.4893 (2.2); −0.0002 (9.5)
I.0496: $^1$H-NMR(500.1 MHz, CDCl3):
δ = 7.2597 (11.7); 4.6581 (0.3); 4.6546 (0.3); 4.6439 (0.4); 4.6409 (0.6); 4.6376 (0.4); 4.6269 (0.3); 3.8018 (11.3); 1.5369 (16.0); 1.2931 (0.4); 1.2768 (0.4); 0.7016 (0.4); 0.6944 (0.6); 0.6852 (0.5); 0.6781 (0.6); 0.6694 (0.4); 0.6677 (0.4); 0.6600 (0.4); 0.6536 (0.4); 0.6519 (0.5); 0.6493 (0.4); 0.6410 (0.4); 0.6362 (0.4); 0.6343 (0.5); 0.6240 (0.6); 0.6166 (0.5); 0.5818 (0.3); 0.5641 (0.5); 0.5541 (0.5); 0.0063 (0.4); −0.0002 (14.2); −0.0068 (0.5)
I.0497: $^1$H-NMR(500.1 MHz, CDCl3):
δ = 7.3287 (0.4); 7.3152 (1.1); 7.3120 (0.6); 7.3007 (1.1); 7.2939 (0.4); 7.2906 (0.7); 7.2877 (0.4); 7.2767 (0.6); 7.2593 (11.0); 7.1277 (0.8); 7.1246 (1.1); 7.1114 (0.9); 5.4399 (0.4); 5.4288 (0.4); 3.7725 (7.7); 3.4511 (0.4); 3.4394 (0.4); 3.4231 (0.5); 3.4114 (0.5); 3.3042 (0.5); 3.2938 (0.5); 3.2762 (0.4); 3.2658 (0.4); 1.5357 (16.0); 0.0062 (0.4); −0.0002 (12.5); −0.0068 (0.5)
I.0498: $^1$H-NMR(400.2 MHz, $d_6$-DMSO):
δ = 8.6853 (1.1); 8.6666 (1.1); 4.4887 (0.4); 4.4758 (0.5); 4.4699 (0.6); 4.4655 (0.7); 4.4571 (0.6); 4.4527 (0.6); 4.4469 (0.6); 4.4338 (0.4); 3.6676 (15.1); 3.5892 (16.0); 3.3773 (83.8); 2.5159 (5.5); 2.5116 (10.9); 2.5071 (14.1); 2.5025 (10.2); 2.4981 (4.9); 2.4641 (1.1); 2.4459 (2.9); 2.4268 (1.7); 2.1633 (0.4); 2.1498 (0.5); 2.1341 (0.4); 2.1283 (0.7); 2.1153 (0.6); 2.0285 (0.5); 2.0225 (0.4); 2.0102 (0.5); 2.0054 (0.5); 1.9931 (0.4); 1.9869 (0.5); 1.9700 (0.3)
I.0499: $^1$H-NMR(500.1 MHz, CDCl3):
δ = 9.3007 (0.4); 7.2598 (13.8); 4.5754 (4.9); 4.5667 (4.8); 3.8725 (16.0); 1.5384 (5.6); 1.2552 (1.4); 0.0063 (0.4); −0.0002 (14.5); −0.0067 (0.5)

TABLE A-(I)-continued

| NMR peak lists of compounds according to formula (I) |
|---|
| I.0500: $^1$H-NMR(400.1 MHz, $d_6$-DMSO): δ = 10.3146 (3.4); 4.3787 (16.0); 4.0385 (0.4); 4.0210 (0.4); 3.6805 (0.5); 3.6123 (0.4); 3.5958 (0.4); 3.5851 (0.4); 3.5539 (0.4); 3.5334 (0.5); 3.4934 (0.6); 3.3224 (1.2); 3.1671 (0.6); 3.1061 (0.4); 3.1004 (0.4); 2.6665 (0.3); 2.5018 (25.4); 1.9886 (1.3); 1.2343 (0.7); 1.1927 (0.5); 1.1748 (0.8); 1.1567 (0.4); −0.0002 (6.8) |
| I.0501: $^1$H-NMR(500.1 MHz, $d_6$-DMSO): δ = 12.4336 (0.4); 8.7737 (1.4); 8.7580 (1.4); 8.4906 (1.6); 8.4757 (1.6); 7.9595 (3.1); 7.2729 (0.9); 7.2578 (2.6); 7.2435 (3.4); 7.2266 (5.0); 7.2122 (2.5); 7.2066 (1.8); 7.1923 (0.5); 4.7890 (0.4); 4.7795 (0.5); 4.7721 (0.9); 4.7631 (0.9); 4.7560 (0.6); 4.7463 (0.5); 4.4903 (0.5); 4.4743 (1.0); 4.4626 (0.9); 4.4469 (0.5); 3.6006 (13.2); 3.3190 (0.9); 3.0591 (0.6); 3.0479 (0.7); 3.0314 (1.3); 3.0202 (1.2); 2.9830 (1.2); 2.9648 (1.7); 2.9555 (0.7); 2.9376 (0.6); 2.8975 (16.0); 2.7555 (0.8); 2.7386 (15.2); 2.7218 (1.2); 2.7128 (1.1); 2.6329 (1.1); 2.6145 (1.1); 2.5994 (0.8); 2.5812 (0.7); 2.5085 (5.0); 2.3353 (11.9); 2.1790 (0.4) |
| I.0502: $^1$H-NMR(400.2 MHz, $d_6$-DMSO): δ = 8.6486 (2.2); 8.6293 (2.2); 7.1821 (1.7); 7.0521 (3.8); 6.9220 (1.9); 4.3018 (2.2); 4.2861 (2.8); 4.2826 (2.8); 4.2668 (2.2); 4.2193 (0.4); 4.2016 (1.1); 4.1924 (1.0); 4.1838 (1.2); 4.1746 (2.8); 4.1618 (1.5); 4.1568 (3.0); 4.1443 (3.1); 4.1393 (1.4); 4.1267 (2.9); 4.1173 (1.2); 4.1089 (1.0); 4.0996 (1.2); 4.0818 (0.4); 3.3441 (3.2); 3.3336 (15.9); 2.5080 (26.8); 2.5038 (31.9); 2.4996 (23.8); 2.2154 (0.4); 2.1984 (1.1); 2.1818 (1.8); 2.1653 (1.8); 2.1485 (1.1); 2.1317 (0.4); 1.2313 (8.0); 1.2135 (16.0); 1.1958 (7.6); 0.9737 (12.4); 0.9626 (13.9); 0.9568 (13.6); 0.9458 (11.3); −0.0002 (1.6) |
| I.0503: $^1$H-NMR(400.2 MHz, $d_6$-DMSO): δ = 8.9607 (1.2); 8.9439 (1.2); 7.1813 (1.0); 7.0511 (2.2); 6.9210 (1.1); 3.7990 (1.0); 3.7818 (1.2); 3.7765 (1.2); 3.7591 (1.1); 3.6822 (16.0); 3.3422 (4.5); 3.3381 (7.2); 3.3339 (7.5); 2.5077 (12.9); 2.5035 (15.7); 2.4991 (11.5); 1.2352 (0.5); 1.2252 (0.8); 1.2141 (0.7); 1.2031 (0.8); 1.1928 (0.5); 1.1828 (0.3); 0.6170 (0.7); 0.6082 (0.7); 0.6043 (0.7); 0.5948 (0.8); 0.5887 (0.5); 0.5827 (0.5); 0.5732 (0.4); 0.5640 (0.4); 0.5538 (0.6); 0.5510 (0.6); 0.5422 (0.8); 0.5308 (0.8); 0.5212 (0.8); 0.5087 (0.3); 0.4997 (0.4); 0.4954 (0.4); 0.4827 (0.6); 0.4728 (0.8); 0.4606 (1.1); 0.4497 (0.9); 0.4375 (0.4); 0.4138 (0.4); 0.4016 (0.8); 0.3909 (0.9); 0.3785 (0.8); 0.3686 (0.5); −0.0002 (0.9) |
| I.0504: $^1$H-NMR(400.2 MHz, $d_6$-DMSO): δ = 8.7897 (2.6); 8.7708 (2.6); 7.3234 (1.5); 7.3052 (5.2); 7.2876 (8.2); 7.2822 (7.5); 7.2780 (9.3); 7.2615 (3.0); 7.2477 (1.7); 7.2441 (1.9); 7.2385 (1.1); 7.2268 (2.7); 7.2196 (0.7); 7.2148 (0.7); 7.2099 (0.9); 7.1527 (1.8); 7.0225 (4.1); 6.8924 (2.0); 4.6492 (0.9); 4.6351 (1.2); 4.6262 (1.5); 4.6161 (1.4); 4.6126 (1.4); 4.6072 (1.3); 4.5932 (0.9); 4.1443 (2.0); 4.1267 (6.2); 4.1090 (6.5); 4.0912 (2.2); 3.3425 (17.3); 3.3360 (21.2); 3.1885 (1.2); 3.1750 (1.3); 3.1541 (2.2); 3.1406 (2.0); 3.0755 (2.1); 3.0520 (2.1); 3.0412 (1.4); 3.0177 (1.2); 2.5075 (27.9); 2.5034 (33.9); 2.4992 (25.5); 1.1825 (7.9); 1.1648 (16.0); 1.1470 (7.6); −0.0002 (1.7) |
| I.0505: $^1$H-NMR(400.2 MHz, $d_6$-DMSO): δ = 9.2433 (2.3); 7.1819 (1.0); 7.0517 (2.2); 6.9216 (1.1); 3.6524 (16.0); 3.3430 (8.4); 3.3406 (8.5); 3.3373 (10.6); 2.8918 (0.5); 2.7327 (0.5); 2.5962 (0.6); 2.5810 (0.7); 2.5737 (1.0); 2.5636 (1.1); 2.5588 (1.0); 2.5495 (1.2); 2.5413 (1.0); 2.5266 (1.1); 2.5211 (0.7); 2.5078 (11.7); 2.5035 (14.7); 2.4991 (10.8); 2.3204 (0.7); 2.2969 (1.3); 2.2778 (1.1); 2.2697 (1.2); 2.2465 (0.7); 2.0094 (0.4); 1.9953 (0.5); 1.9856 (0.6); 1.9817 (0.6); 1.9717 (0.8); 1.9593 (0.9); 1.9481 (0.5); 1.9400 (0.9); 1.9178 (0.5); −0.0002 (0.9) |
| I.0506: $^1$H-NMR(400.2 MHz, $d_6$-DMSO): δ = 9.2560 (4.5); 7.1812 (1.8); 7.0510 (4.1); 6.9209 (2.0); 4.1351 (2.5); 4.1173 (7.6); 4.0996 (7.6); 4.0819 (2.5); 3.3398 (23.4); 2.8920 (0.3); 2.5863 (1.2); 2.5709 (1.5); 2.5640 (2.1); 2.5537 (2.2); 2.5488 (2.1); 2.5396 (2.4); 2.5313 (2.2); 2.5081 (22.5); 2.5038 (27.7); 2.4994 (20.3); 2.3119 (1.3); 2.2886 (2.5); 2.2692 (2.1); 2.2612 (2.3); 2.2382 (1.3); 2.0173 (0.4); 2.0038 (0.7); 1.9897 (1.0); 1.9796 (1.4); 1.9660 (1.6); 1.9570 (1.7); 1.9366 (1.7); 1.9147 (1.0); 1.8950 (0.4); 1.8892 (0.4); 1.1992 (8.0); 1.1815 (16.0); 1.1638 (7.6); −0.0002 (1.5) |
| I.0507: $^1$H-NMR(400.2 MHz, $d_6$-DMSO): δ = 9.1125 (5.2); 8.3183 (0.5); 7.1740 (2.0); 7.0438 (4.5); 6.9137 (2.2); 4.0073 (4.9); 3.9913 (9.9); 3.9753 (5.0); 3.3446 (33.9); 3.3394 (28.5); 2.5077 (30.9); 2.5039 (36.5); 1.6068 (0.6); 1.5889 (2.5); 1.5721 (5.1); 1.5541 (5.2); 1.5374 (2.8); 1.5195 (0.7); 1.4550 (2.4); 1.4427 (6.6); 1.4348 (7.2); 1.4239 (3.0); 1.1892 (3.0); 1.1782 (7.1); 1.1703 (7.0); 1.1580 (2.5); 0.8906 (8.2); 0.8721 (16.0); 0.8536 (7.4); −0.0002 (1.4) |
| I.0508: $^1$H-NMR(400.2 MHz, $d_6$-DMSO): δ = 9.1119 (13.5); 7.1774 (4.5); 7.0471 (10.2); 6.9170 (5.1); 4.9405 (1.2); 4.9216 (4.8); 4.9035 (7.2); 4.8847 (4.9); 4.8666 (1.3); 3.3375 (68.6); 2.8918 (0.8); 2.7327 (0.7); 2.6724 (0.5); 2.5075 (74.5); 2.5034 (90.0); 2.4995 (67.9); 2.3302 (0.6); 2.2887 (2.0); 2.2821 (2.8); 2.2639 (6.0); 2.2584 (6.1); 2.2515 (5.5); 2.2442 (6.2); 2.2401 (6.7); 2.2341 (5.3); 2.2207 (3.4); 2.2147 (2.6); 2.0168 (1.5); 2.0100 (1.2); 1.9915 (5.7); 1.9850 (4.0); 1.9719 (6.1); 1.9671 (7.3); 1.9613 (5.6); 1.9481 (4.6); 1.9418 (5.6); 1.9239 (1.6); 1.9175 (1.8); 1.7683 (1.5); 1.7418 (4.0); 1.7167 (4.0); 1.6920 (1.4); 1.6331 (1.1); 1.6126 (2.4); 1.6084 (2.6); 1.5876 (4.8); 1.5622 (4.0); 1.5418 (1.9); 1.5365 (1.5); 1.5157 (0.6); 1.4439 (5.7); 1.4317 (14.7); 1.4237 (16.0); 1.4127 (6.6); 1.3726 (0.6); 1.2347 (0.4); 1.2153 (0.6); 1.1755 (7.0); 1.1645 (15.5); 1.1565 (15.0); 1.1441 (5.4); 1.1058 (0.3); −0.0002 (2.8) |
| I.0509: $^1$H-NMR(400.2 MHz, $d_6$-DMSO): δ = 9.1129 (2.5); 7.9545 (0.4); 7.1865 (1.7); 7.0564 (3.9); 6.9265 (2.0); 4.3305 (16.0); 3.3386 (8.9); 2.8928 (2.5); 2.7337 (2.2); 2.5273 (0.4); 2.5223 (0.6); 2.5137 (7.8); 2.5095 (15.2); 2.5050 (19.5); 2.5004 (14.2); 2.4962 (7.0); −0.0002 (1.3) |
| I.0510: $^1$H-NMR(400.2 MHz, $d_6$-DMSO): δ = 8.8898 (2.2); 7.5181 (2.1); 7.3836 (4.9); 7.2494 (2.3); 4.1652 (2.4); 4.1475 (7.4); 4.1297 (7.5); 4.1119 (2.5); 4.0510 (5.4); 4.0421 (5.2); 3.3363 (16.5); 2.5086 (21.6); 2.5044 (26.8); 2.5001 (20.4); 1.2335 (8.1); 1.2157 (16.0); 1.1979 (7.8); −0.0002 (1.3) |
| I.0511: $^1$H-NMR(400.2 MHz, $d_6$-DMSO): δ = 8.9008 (1.7); 7.5189 (1.1); 7.3845 (2.5); 7.2502 (1.2); 4.0699 (7.4); 3.6785 (16.0); 3.3371 (7.4); 2.5089 (10.9); 2.5046 (13.6); 2.5002 (10.2); −0.0002 (0.8) |
| I.0512: $^1$H-NMR(400.2 MHz, $d_6$-DMSO): δ = 9.2105 (1.9); 7.5195 (1.1); 7.3851 (2.7); 7.2508 (1.2); 3.6305 (16.0); 3.3387 (9.8); 2.5085 (10.7); 2.5040 (13.4); 2.4995 (9.8); 2.4954 (4.8); 1.4845 (1.2); 1.4722 (3.1); 1.4639 (3.3); 1.4529 (1.4); 1.2154 (1.5); 1.2042 (3.4); 1.1960 (3.2); 1.1837 (1.2); −0.0002 (0.9) |
| I.0513: $^1$H-NMR(400.2 MHz, $d_6$-DMSO): δ = 8.9117 (1.5); 7.5196 (0.8); 7.3852 (1.8); 7.2509 (0.8); 3.6307 (10.8); 3.3466 (6.0); 3.3443 (5.7); 3.3384 (10.2); 2.5075 (8.2); 2.5038 (10.0); 2.4999 (7.7); 1.4645 (16.0); −0.0002 (0.5) |
| I.0514: $^1$H-NMR(400.2 MHz, $d_6$-DMSO): δ = 8.7664 (2.0); 8.7469 (2.0); 7.5243 (1.9); 7.3898 (4.6); 7.2556 (2.1); 4.3285 (2.1); 4.3129 (2.6); 4.3091 (2.6); 4.2935 (2.1); 4.2263 (0.4); 4.2085 (1.1); 4.1993 (0.9); 4.1907 (1.2); 4.1815 (2.8); 4.1683 (1.4); 4.1637 (3.0); 4.1507 (3.1); 4.1462 (1.4); 4.1416 (0.7); 4.1330 (2.9); 4.1237 (1.2); 4.1153 (1.0); 4.1060 (1.2); 4.0883 (0.4); 3.3347 (18.3); 2.5264 (0.7); 2.5087 (24.1); 2.5042 (29.6); 2.4998 (22.0); 2.2286 (0.3); 2.2116 (1.0); 2.1949 (1.6); 2.1784 (1.7); 2.1616 (1.1); 2.1447 (0.4); 1.2355 (8.0); 1.2177 (16.0); 1.2000 (7.6); 0.9819 (12.2); 0.9735 (12.3); 0.9649 (12.5); 0.9565 (11.1); −0.0002 (1.1) |
| I.0515: $^1$H-NMR(400.2 MHz, $d_6$-DMSO): δ = 9.0815 (1.0); 9.0645 (1.0); 7.5250 (1.0); 7.3906 (2.6); 7.2563 (1.2); 3.8270 (1.0); 3.8098 (1.1); 3.8042 (1.1); 3.7870 (1.0); 3.6895 (16.0); 3.6661 (0.7); 3.3353 (9.4); 2.5216 (0.4); 2.5128 (5.6); 2.5084 (11.2); 2.5038 (14.6); 2.4993 (10.7); 2.4948 (5.3); 1.2452 (0.3); 1.2426 (0.4); 1.2333 (0.7); 1.2220 (0.6); 1.2109 (0.7); 1.1991 (0.4); 0.6239 (0.6); 0.6156 (0.6); 0.6106 (0.6); 0.6012 |

TABLE A-(I)-continued

NMR peak lists of compounds according to formula (I)

(0.8); 0.5961 (0.4); 0.5895 (0.4); 0.5802 (0.4); 0.5704 (0.4); 0.5610 (0.4); 0.5575 (0.5); 0.5484 (0.7); 0.5408 (0.5); 0.5374 (0.6); 0.5277 (0.8); 0.5153 (0.3); 0.5067 (0.7); 0.4934 (0.5); 0.4842 (0.8); 0.4718 (0.9); 0.4612 (0.8); 0.4488 (0.4); 0.4257 (0.4); 0.4140 (0.6); 0.4028 (0.8); 0.3903 (0.7); 0.3808 (0.4); −0.0002 (0.9)

I.0516: $^{1}$H-NMR(400.2 MHz, $d_6$-DMSO):
δ = 8.9177 (2.1); 8.8988 (2.1); 7.5020 (1.8); 7.3675 (4.3); 7.3229 (1.2); 7.3045 (4.3); 7.2869 (11.8); 7.2814 (9.0); 7.2655 (2.3); 7.2492 (1.5); 7.2447 (1.6); 7.2332 (3.0); 7.2280 (2.4); 7.2199 (0.7); 7.2114 (0.8); 7.2066 (0.4); 4.6773 (0.8); 4.6636 (1.0); 4.6582 (1.1); 4.6541 (1.2); 4.6445 (1.2); 4.6405 (1.1); 4.6352 (1.1); 4.6213 (0.8); 4.1500 (1.9); 4.1324 (6.0); 4.1147 (6.3); 4.0970 (2.1); 3.3377 (16.8); 3.2001 (1.1); 3.1866 (1.2); 3.1657 (2.0); 3.1522 (1.8); 3.0868 (1.9); 3.0632 (1.9); 3.0524 (1.2); 3.0288 (1.1); 2.5260 (0.6); 2.5123 (11.6); 2.5082 (22.2); 2.5037 (28.2); 2.4992 (20.6); 2.4950 (10.2); 1.1856 (7.8); 1.1679 (16.0); 1.1501 (7.5); −0.0002 (1.7)

I.0517: $^{1}$H-NMR(400.2 MHz, $d_6$-DMSO):
δ = 9.3544 (2.5); 7.5269 (1.1); 7.3923 (2.6); 7.2581 (1.2); 3.6611 (16.0); 3.3367 (10.7); 2.6097 (0.7); 2.5944 (0.8); 2.5873 (1.1); 2.5772 (1.2); 2.5722 (1.2); 2.5631 (1.3); 2.5549 (1.0); 2.5409 (0.9); 2.5083 (12.2); 2.5039 (14.8); 2.4997 (10.8); 2.3346 (0.8); 2.3111 (1.4); 2.2918 (1.2); 2.2842 (1.3); 2.2608 (0.7); 2.0198 (0.4); 2.0056 (0.6); 1.9957 (0.7); 1.9819 (0.9); 1.9726 (1.0); 1.9512 (1.0); 1.9290 (0.6); −0.0002 (0.7)

I.0518: $^{1}$H-NMR(400.2 MHz, $d_6$-DMSO):
δ = 9.3645 (3.7); 7.5257 (1.8); 7.3913 (4.4); 7.2569 (2.1); 4.1428 (2.3); 4.1251 (7.5); 4.1074 (7.6); 4.0896 (2.4); 3.3373 (16.6); 2.5997 (1.0); 2.5846 (1.2); 2.5774 (1.7); 2.5673 (1.8); 2.5623 (1.7); 2.5531 (2.0); 2.5449 (1.6); 2.5306 (1.5); 2.5216 (0.9); 2.5126 (9.7); 2.5084 (18.7); 2.5039 (23.7); 2.4994 (17.3); 2.4951 (8.5); 2.3257 (1.2); 2.3063 (1.8); 2.3024 (2.1); 2.2958 (1.4); 2.2831 (1.8); 2.2749 (2.0); 2.2519 (1.1); 2.0140 (0.6); 1.9998 (0.9); 1.9898 (1.1); 1.9762 (1.4); 1.9670 (1.4); 1.9471 (1.5); 1.9249 (0.8); 1.9194 (0.6); 1.9054 (0.3); 1.2025 (7.8); 1.1848 (16.0); 1.1671 (7.6); −0.0002 (1.5)

I.0519: $^{1}$H-NMR(400.2 MHz, $d_6$-DMSO):
δ = 9.2284 (5.2); 7.5192 (2.1); 7.3846 (4.9); 7.2504 (2.3); 4.0146 (5.0); 3.9986 (10.1); 3.9826 (5.0); 3.3391 (24.8); 2.5084 (27.7); 2.5045 (32.4); 1.6102 (0.6); 1.5926 (2.5); 1.5753 (5.1); 1.5574 (5.1); 1.5406 (2.8); 1.5230 (0.7); 1.4685 (2.4); 1.4564 (6.5); 1.4484 (7.0); 1.4374 (2.8); 1.2044 (3.0); 1.1934 (7.0); 1.1854 (6.7); 1.1731 (2.3); 0.8924 (8.2); 0.8740 (16.0); 0.8554 (7.3); −0.0002 (1.4)

I.0520: $^{1}$H-NMR(400.2 MHz, $d_6$-DMSO):
δ = 9.2246 (13.8); 7.5207 (5.1); 7.3862 (11.7); 7.2519 (5.6); 4.9469 (1.2); 4.9286 (4.9); 4.9101 (7.4); 4.8917 (5.0); 4.8730 (1.3); 3.3412 (62.7); 2.8921 (0.6); 2.7327 (0.5); 2.6733 (0.4); 2.5083 (57.9); 2.5043 (74.7); 2.5003 (58.7); 2.3312 (0.5); 2.2927 (1.8); 2.2862 (2.7); 2.2667 (5.8); 2.2627 (5.9); 2.2558 (5.2); 2.2484 (5.9); 2.2429 (6.6); 2.2248 (3.4); 2.2186 (2.6); 2.0189 (1.5); 2.0123 (1.1); 1.9942 (5.6); 1.9877 (3.9); 1.9745 (5.7); 1.9690 (7.1); 1.9642 (5.6); 1.9505 (4.4); 1.9442 (5.4); 1.9265 (1.5); 1.9196 (1.7); 1.7699 (1.5); 1.7444 (4.0); 1.7188 (3.9); 1.6935 (1.4); 1.6355 (1.1); 1.6150 (2.3); 1.6104 (2.6); 1.5899 (4.8); 1.5642 (4.1); 1.5439 (1.9); 1.5390 (1.5); 1.5183 (0.6); 1.4572 (5.4); 1.4450 (14.4); 1.4369 (16.0); 1.4259 (6.6); 1.3860 (0.6); 1.2312 (0.8); 1.1910 (6.8); 1.1799 (15.8); 1.1719 (15.5); 1.1596 (5.6); 1.1215 (0.3); −0.0002 (3.4)

I.0521: $^{1}$H-NMR(400.2 MHz, $d_6$-DMSO):
δ = 9.2372 (1.6); 7.5247 (1.8); 7.3905 (4.1); 7.2563 (2.0); 4.3605 (16.0); 3.3401 (9.8); 2.5272 (0.4); 2.5094 (16.9); 2.5052 (21.1); 2.5008 (15.5); −0.0002 (0.9)

I.0522: $^{1}$H-NMR(400.2 MHz, $d_6$-DMSO):
δ = 9.2181 (4.3); 7.5190 (2.0); 7.3846 (4.6); 7.2502 (2.2); 4.1067 (2.3); 4.0890 (7.1); 4.0713 (7.2); 4.0536 (2.4); 3.3370 (17.0); 2.5082 (20.8); 2.5042 (26.1); 1.4679 (2.1); 1.4557 (5.5); 1.4475 (6.0); 1.4365 (2.4); 1.1979 (2.8); 1.1884 (12.2); 1.1787 (6.5); 1.1710 (16.0); 1.1533 (7.5); −0.0002 (1.4)

I.0523: $^{1}$H-NMR(500.1 MHz, $d_6$-DMSO):
δ = 8.1583 (0.8); 8.1549 (0.9); 2.5100 (0.7); 2.5064 (1.7); 2.5028 (2.3); 2.4991 (1.7); 2.4955 (0.8); 1.9890 (0.7); 1.9098 (1.2); 1.5287 (0.4); 1.4604 (16.0); 1.1760 (0.4); −0.0002 (0.7)

I.0524: $^{1}$H-NMR(400.2 MHz, $d_6$-DMSO):
δ = 8.7928 (1.8); 8.7761 (1.9); 8.3170 (0.8); 4.1928 (0.9); 4.1836 (1.0); 4.1750 (1.0); 4.1657 (3.3); 4.1573 (0.5); 4.1477 (4.1); 4.1461 (3.8); 4.1361 (0.5); 4.1280 (3.3); 4.1186 (1.0); 4.1102 (1.0); 4.1009 (0.9); 3.7889 (1.7); 3.7719 (1.9); 3.7663 (2.0); 3.7493 (1.8); 3.3349 (27.9); 3.3111 (0.4); 2.5268 (0.4); 2.5131 (8.2); 2.5089 (15.6); 2.5044 (20.0); 2.4998 (14.8); 2.4955 (7.4); 1.2588 (0.6); 1.2501 (0.8); 1.2477 (0.8); 1.2380 (2.0); 1.2311 (8.5); 1.2134 (16.0); 1.1956 (8.0); 1.1838 (0.4); 0.6426 (0.3); 0.6331 (0.5); 0.6291 (0.5); 0.6204 (1.0); 0.6121 (1.2); 0.6075 (1.2); 0.5981 (1.4); 0.5922 (0.7); 0.5863 (0.8); 0.5769 (0.8); 0.5690 (0.7); 0.5595 (0.9); 0.5562 (0.9); 0.5477 (1.3); 0.5393 (1.0); 0.5361 (1.2); 0.5268 (1.2); 0.5139 (0.6); 0.5052 (0.7); 0.5002 (0.7); 0.4876 (0.9); 0.4781 (1.3); 0.4658 (1.7); 0.4549 (1.4); 0.4427 (0.6); 0.4241 (0.8); 0.4120 (1.2); 0.4011 (1.3); 0.3886 (1.2); 0.3793 (0.7); 0.3669 (0.3); −0.0002 (2.2)

I.0525: $^{1}$H-NMR(600.2 MHz, $d_6$-DMSO):
δ = 8.6153 (4.8); 8.6018 (4.9); 4.8208 (2.1); 4.8084 (3.2); 4.7996 (2.7); 4.7956 (2.6); 4.7867 (3.3); 4.7744 (2.2); 3.4750 (2.0); 3.4659 (2.4); 3.4563 (3.7); 3.4473 (3.7); 3.4463 (3.5); 3.4365 (3.5); 3.4275 (2.8); 3.3525 (3.6); 3.3425 (3.9); 3.3406 (3.8); 3.3357 (2.9); 3.3342 (3.0); 3.3246 (16.0); 3.2042 (4.5); 2.9762 (0.7); 2.6348 (6.8); 2.5140 (4.2); 2.5109 (8.0); 2.5079 (12.2); 2.5049 (9.4); 2.5020 (4.3); 2.4969 (3.6); 2.4950 (3.5); 2.4879 (2.4); 2.4857 (3.2); 2.4835 (2.5); 2.4763 (1.9); 2.4745 (1.8); 2.3777 (1.3); 2.3659 (1.5); 2.3573 (3.2); 2.3454 (3.3); 2.3366 (3.0); 2.3247 (3.0); 2.3162 (1.2); 2.3044 (1.0); 1.3612 (0.6); 1.3456 (0.6); 1.2695 (0.4); 1.2583 (0.4); 1.2386 (0.8); 1.2275 (0.4); 1.1750 (0.5)

I.0526: $^{1}$H-NMR(400.1 MHz, $d_6$-DMSO):
δ = 10.5725 (2.3); 7.9594 (0.9); 3.6262 (16.0); 3.3095 (24.0); 2.8977 (5.0); 2.7386 (4.7); 2.5073 (9.9); 2.3235 (15.3); 1.5935 (1.2); 1.5805 (3.4); 1.5726 (3.6); 1.5611 (1.5); 1.3505 (1.6); 1.3391 (3.6); 1.3312 (3.4); 1.3183 (1.2)

I.0527: $^{1}$H-NMR(400.1 MHz, CDCl3):
δ = 7.2619 (3.3); 6.7775 (0.7); 4.2228 (4.5); 4.2101 (4.5); 3.8060 (16.0); 1.5652 (4.1); −0.0002 (4.3)

I.0528: $^{1}$H-NMR(400.2 MHz, $d_6$-DMSO):
δ = 8.6203 (0.5); 8.6004 (0.6); 4.8542 (0.4); 4.8378 (0.4); 4.8351 (0.4); 3.6721 (6.2); 3.3294 (4.0); 2.8496 (0.6); 2.8353 (0.6); 2.7994 (0.6); 2.7819 (0.6); 2.5130 (2.5); 2.5087 (4.8); 2.5042 (6.3); 2.4996 (4.6); 2.4952 (2.3); 1.3901 (16.0); −0.0002 (0.8)

I.0529: $^{1}$H-NMR(400.2 MHz, $d_6$-DMSO):
δ = 8.7134 (1.3); 8.6943 (1.3); 4.6667 (0.5); 4.6550 (0.6); 4.6460 (0.9); 4.6353 (0.9); 4.6263 (0.6); 4.6145 (0.5); 3.6900 (16.0); 3.4961 (1.0); 3.4842 (1.1); 3.4610 (1.4); 3.4492 (1.2); 3.3324 (15.6); 3.2706 (1.2); 3.2490 (1.2); 3.2354 (1.0); 3.2140 (0.9); 2.9257 (6.8); 2.8927 (0.7); 2.7333 (0.5); 2.5131 (5.7); 2.5087 (11.2); 2.5042 (14.4); 2.4996 (10.3); 2.4953 (4.9); −0.0002 (1.9)

I.0530: $^{1}$H-NMR(600.1 MHz, $d_6$-DMSO):
δ = 8.6446 (1.3); 8.6320 (1.3); 8.2720 (0.6); 8.2632 (1.2); 8.2543 (0.6); 4.6543 (0.5); 4.6464 (0.6); 4.6410 (0.9); 4.6333 (0.9); 4.6280 (0.6); 4.6200 (0.5); 3.6860 (16.0); 3.4548 (0.8); 3.4469 (0.9); 3.4312 (1.1); 3.4233 (1.0); 3.3758 (5.9); 3.3734 (6.0); 3.3704 (6.5); 3.3662 (6.7); 3.3638 (6.6); 3.3607 (6.5); 3.3588 (6.3); 3.3543 (7.7); 3.3514 (11.8); 3.3447 (8.5); 3.3435 (9.7); 3.3422 (8.7); 3.3394 (16.0); 3.3366 (15.9); 3.2225 (0.9); 3.2085 (1.0); 3.1990 (0.8); 3.1850 (0.8); 3.1250 (0.9); 3.1197 (0.9); 3.1160 (1.0); 3.1111 (1.2); 3.1082 (1.1); 3.1042 (0.9); 3.0989 (1.0); 3.0867 (0.4); 2.8924 (0.4); 2.7328 (0.4); 2.5106 (5.0); 2.5076 (11.2); 2.5045 (15.7); 2.5015 (11.2); 2.4984 (5.0); 1.0156 (2.8); 1.0036 (5.6); 0.9916 (2.7); −0.0001 (0.4)

TABLE A-(I)-continued

| NMR peak lists of compounds according to formula (I) |
|---|
| I.0531: $^{1}$H-NMR(400.2 MHz, $d_6$-DMSO):<br>δ = 10.0835 (0.9); 10.0725 (0.8); 8.7927 (1.4); 8.7731 (1.5); 7.9531 (0.8); 4.7844 (0.5); 4.7726 (0.6); 4.7617 (0.8); 4.7528 (0.8); 4.7418 (0.6); 4.7299 (0.5); 3.9817 (1.0); 3.9700 (1.0); 3.9467 (1.2); 3.9349 (1.0); 3.7147 (0.4); 3.7075 (2.0); 3.6981 (16.0); 3.6903 (1.4); 3.6824 (0.7); 3.5900 (1.1); 3.5668 (1.1); 3.5548 (1.0); 3.5317 (0.9); 3.3594 (29.4); 3.2965 (0.4); 3.0247 (7.7); 3.0135 (7.6); 2.9243 (0.7); 2.9116 (0.7); 2.8927 (5.4); 2.7335 (4.6); 2.7325 (4.5); 2.5277 (0.4); 2.5143 (8.2); 2.5099 (16.2); 2.5053 (21.1); 2.5008 (15.1); 2.4963 (7.2); −0.0002 (0.7) |
| I.0532: $^{1}$H-NMR(400.2 MHz, $d_6$-DMSO):<br>δ = 8.6660 (2.0); 8.6474 (2.0); 4.4602 (0.7); 4.4472 (0.9); 4.4414 (1.0); 4.4371 (1.1); 4.4286 (1.1); 4.4241 (1.0); 4.4184 (1.0); 4.4054 (0.8); 4.1558 (1.2); 4.1527 (1.3); 4.1475 (0.5); 4.1381 (3.8); 4.1350 (3.9); 4.1202 (4.1); 4.1174 (3.8); 4.1078 (0.5); 4.1023 (1.4); 4.0998 (1.2); 4.0772 (2.2); 4.0594 (6.9); 4.0417 (7.0); 4.0239 (2.3); 3.3290 (12.3); 2.5263 (0.5); 2.5129 (9.3); 2.5086 (18.2); 2.5041 (23.6); 2.4996 (17.1); 2.4953 (8.4); 2.4490 (1.4); 2.4443 (1.4); 2.4295 (3.8); 2.4094 (2.4); 2.1687 (0.3); 2.1554 (0.4); 2.1492 (0.6); 2.1357 (1.0); 2.1145 (1.2); 2.1013 (1.0); 2.0956 (0.5); 2.0820 (0.4); 2.0353 (0.5); 2.0189 (0.8); 2.0160 (0.7); 1.9998 (0.9); 1.9959 (0.9); 1.9837 (0.6); 1.9813 (0.6); 1.9768 (0.8); 1.9605 (0.5); 1.2163 (7.3); 1.1986 (15.3); 1.1881 (8.3); 1.1808 (7.5); 1.1703 (16.0); 1.1525 (7.6); −0.0002 (3.4) |
| I.0533: $^{1}$H-NMR(400.2 MHz, $d_6$-DMSO):<br>δ = 8.5462 (0.6); 8.5275 (0.6); 4.5924 (0.4); 4.5809 (0.5); 4.5732 (0.5); 4.5617 (0.4); 4.5503 (0.3); 3.6734 (10.2); 3.4826 (0.6); 3.4712 (0.7); 3.4475 (0.9); 3.4362 (0.8); 3.3285 (4.6); 3.2703 (0.8); 3.2468 (0.8); 3.2352 (0.7); 3.2118 (0.6); 2.9239 (16.0); 2.8925 (0.4); 2.7326 (0.3); 2.5084 (8.0); 2.5041 (10.2); 2.4997 (7.6); −0.0002 (1.3) |
| I.0534: $^{1}$H-NMR(400.2 MHz, $d_6$-DMSO):<br>δ = 10.0656 (1.0); 10.0549 (1.0); 8.6180 (0.9); 8.5984 (1.0); 7.9537 (1.4); 4.7462 (0.5); 4.7345 (0.6); 4.7220 (0.7); 4.7147 (0.7); 4.7106 (0.7); 4.7018 (0.6); 4.6902 (0.5); 3.9691 (1.0); 3.9575 (1.1); 3.9341 (1.3); 3.9225 (1.1); 3.8314 (0.4); 3.8004 (0.4); 3.6901 (2.4); 3.6832 (16.0); 3.6654 (0.9); 3.6576 (0.5); 3.5780 (1.2); 3.5532 (1.5); 3.5430 (1.1); 3.5183 (1.0); 3.3309 (10.2); 3.0223 (7.8); 3.0111 (7.8); 2.9083 (0.7); 2.8921 (9.7); 2.7332 (8.2); 2.7320 (8.2); 2.5263 (0.5); 2.5126 (9.1); 2.5084 (17.7); 2.5039 (22.6); 2.4994 (16.3); 2.4950 (7.9); −0.0002 (3.5) |
| I.0535: $^{1}$H-NMR(400.2 MHz, $d_6$-DMSO):<br>δ = 8.6323 (1.4); 8.6134 (1.4); 4.6499 (0.5); 4.6385 (0.6); 4.6281 (0.9); 4.6192 (0.8); 4.6089 (0.7); 4.5974 (0.5); 3.6835 (16.0); 3.4957 (1.0); 3.4842 (1.0); 3.4605 (1.4); 3.4491 (1.2); 3.3335 (22.7); 3.2846 (1.2); 3.2623 (1.2); 3.2494 (1.0); 3.2271 (0.9); 2.9246 (11.0); 2.8923 (1.3); 2.7325 (1.0); 2.5264 (0.4); 2.5126 (6.7); 2.5085 (13.3); 2.5040 (17.5); 2.4996 (12.9); 2.4953 (6.5); −0.0002 (0.8) |
| I.0536: $^{1}$H-NMR(600.1 MHz, $d_6$-DMSO):<br>δ = 8.5469 (1.3); 8.5344 (1.3); 8.2895 (0.6); 8.2807 (1.2); 8.2719 (0.6); 4.6408 (0.5); 4.6332 (0.6); 4.6272 (0.8); 4.6199 (0.8); 4.6141 (0.6); 4.6064 (0.5); 3.6800 (16.0); 3.4548 (0.8); 3.4472 (0.9); 3.4312 (1.0); 3.4236 (1.0); 3.3753 (7.7); 3.3714 (7.9); 3.3679 (8.5); 3.3646 (7.9); 3.3609 (8.6); 3.3561 (14.1); 3.3540 (10.9); 3.3506 (13.8); 3.3454 (23.0); 3.3443 (24.9); 3.2354 (0.9); 3.2210 (0.9); 3.2118 (0.8); 3.1974 (0.7); 3.1259 (0.8); 3.1204 (0.8); 3.1169 (0.9); 3.1118 (1.1); 3.1088 (1.0); 3.1050 (0.9); 3.0995 (0.9); 3.0930 (0.4); 3.0874 (0.4); 2.8927 (1.0); 2.7331 (0.9); 2.5112 (5.2); 2.5081 (11.5); 2.5051 (16.1); 2.5020 (11.4); 2.4990 (5.1); 1.0168 (2.8); 1.0048 (5.6); 0.9927 (2.7); −0.0001 (0.4) |
| I.0537: $^{1}$H-NMR(600.1 MHz, $d_6$-DMSO):<br>δ = 10.0762 (1.0); 10.0688 (1.0); 8.6975 (0.4); 8.6906 (1.9); 8.6850 (0.4); 8.6775 (1.9); 7.9524 (1.1); 4.7713 (0.7); 4.7635 (0.8); 4.7581 (0.8); 4.7557 (0.9); 4.7504 (0.9); 4.7480 (0.8); 4.7425 (0.7); 4.7347 (0.7); 3.9774 (1.0); 3.9696 (1.1); 3.9539 (1.2); 3.9462 (1.1); 3.8212 (0.4); 3.7022 (1.5); 3.6934 (16.0); 3.6806 (1.8); 3.6751 (0.4); 3.6721 (0.4); 3.5976 (1.2); 3.5818 (1.2); 3.5742 (1.1); 3.5585 (1.1); 3.3887 (14.6); 3.3762 (18.4); 3.3738 (21.2); 3.3687 (19.5); 3.3658 (27.5); 3.3594 (38.4); 3.0224 (7.6); 3.0149 (7.7); 2.9166 (0.7); 2.9082 (0.7); 2.8929 (11.5); 2.7333 (9.2); 2.5239 (0.4); 2.5208 (0.4); 2.5122 (7.3); 2.5091 (16.6); 2.5060 (23.5); 2.5030 (16.7); 2.4999 (7.3); −0.0001 (0.4) |
| I.0538: $^{1}$H-NMR(500.1 MHz, CDCl3):<br>δ = 7.2593 (16.6); 4.5237 (2.6); 4.5147 (2.6); 3.8523 (10.0); 1.5321 (16.0); 1.2533 (0.5); −0.0002 (22.5) |
| I.0539: $^{1}$H-NMR(300.2 MHz, $d_6$-DMSO):<br>δ = 8.4844 (4.4); 8.4764 (4.3); 7.9042 (2.6); 7.8892 (2.6); 5.7781 (0.6); 3.3471 (16.0); 2.6010 (21.9); 2.5858 (21.8); 2.5343 (3.6); 2.5283 (7.4); 2.5222 (10.1); 2.5162 (7.3); 2.5103 (3.4); 1.3420 (3.4); 1.3268 (8.4); 1.3156 (9.6); 1.3020 (4.0); 1.2491 (0.4); 1.0753 (0.7); 1.0521 (0.3); 1.0191 (4.1); 1.0055 (9.3); 0.9943 (8.6); 0.9791 (3.3); 0.0193 (6.2) |
| I.0540: $^{1}$H-NMR(500.1 MHz, CDCl3):<br>δ = 7.2640 (1.0); 6.9690 (0.4); 6.9551 (0.4); 3.7866 (9.6); 1.6610 (16.0); 1.5862 (1.5); 1.2646 (0.4); 0.8816 (0.5); −0.0002 (1.2) |
| I.0541: $^{1}$H-NMR(500.1 MHz, CDCl3):<br>δ = 7.2635 (2.0); 7.0231 (0.6); 7.0098 (0.6); 5.0749 (3.7); 5.0612 (4.2); 4.8772 (4.2); 4.8635 (3.7); 3.8866 (16.0); 1.5881 (3.0); −0.0002 (2.5) |
| I.0542: $^{1}$H-NMR(500.1 MHz, CDCl3):<br>δ = 7.2614 (6.1); 4.5674 (15.5); 4.2931 (2.4); 4.2788 (7.2); 4.2645 (7.3); 4.2502 (2.4); 1.3332 (8.1); 1.3189 (16.0); 1.3046 (7.9); 1.2548 (1.0); −0.0002 (7.1); −0.0067 (0.3) |
| I.0543: $^{1}$H-NMR(400.2 MHz, $d_6$-DMSO):<br>δ = 8.4524 (0.8); 8.4480 (0.8); 8.4340 (0.8); 8.2964 (0.6); 8.2836 (1.1); 8.2703 (0.6); 7.9539 (0.6); 4.5946 (0.4); 4.5832 (0.5); 4.5731 (0.7); 4.5640 (0.7); 4.5535 (0.5); 4.5419 (0.4); 3.6688 (16.0); 3.4472 (0.8); 3.4359 (0.9); 3.4119 (1.1); 3.4007 (1.0); 3.3300 (9.3); 3.2226 (1.0); 3.1996 (1.0); 3.1873 (0.8); 3.1644 (0.8); 3.1568 (0.4); 3.1382 (0.9); 3.1278 (1.0); 3.1248 (1.0); 3.1201 (1.0); 3.1148 (1.1); 3.1103 (1.1); 3.1069 (1.0); 3.0968 (0.9); 3.0789 (0.4); 2.8923 (4.4); 2.7325 (3.6); 2.5264 (0.4); 2.5129 (6.7); 2.5085 (13.3); 2.5040 (17.3); 2.4994 (12.5); 2.4950 (6.1); 1.0269 (3.2); 1.0089 (6.4); 0.9909 (3.0); −0.0002 (2.6) |
| I.0544: $^{1}$H-NMR(500.1 MHz, CDCl3):<br>δ = 7.4921 (1.0); 7.2629 (1.8); 4.4991 (0.8); 4.4796 (0.8); 3.8279 (16.0); 2.0068 (0.4); 1.4920 (0.6); 1.4885 (0.4); 1.4822 (0.6); 1.4760 (0.5); 1.4726 (0.6); 1.4660 (0.4); 1.4628 (0.3); 0.8295 (0.4); 0.8215 (0.5); 0.8163 (0.5); 0.8124 (0.8); 0.8092 (0.5); 0.8046 (0.4); 0.8006 (0.4); 0.7949 (0.6); 0.7930 (0.5); 0.6808 (0.4); 0.6713 (0.8); 0.6625 (1.6); 0.6498 (1.6); 0.6391 (0.5); 0.6348 (0.4); 0.6299 (0.4); 0.5622 (0.4); 0.5593 (0.5); 0.5531 (0.8); 0.5503 (0.8); 0.5409 (0.8); 0.5316 (0.5); −0.0002 (2.0) |
| I.0545: $^{1}$H-NMR(400.2 MHz, $d_6$-DMSO):<br>δ = 8.6747 (1.7); 8.6550 (1.7); 4.8634 (0.6); 4.8467 (1.4); 4.8275 (1.3); 4.8120 (0.7); 4.1571 (1.6); 4.1394 (5.3); 4.1217 (5.5); 4.1147 (1.8); 4.1039 (2.0); 4.0969 (5.1); 4.0792 (5.2); 4.0614 (1.7); 3.3284 (8.0); 2.9762 (0.8); 2.9615 (0.9); 2.9349 (2.1); 2.9203 (1.9); 2.8864 (2.0); 2.8693 (2.0); 2.8451 (0.9); 2.8281 (0.8); 2.5268 (0.4); 2.5133 (6.6); 2.5089 (13.3); 2.5044 (17.6); 2.4998 (12.8); 2.4954 (6.3); 1.1981 (7.7); 1.1963 (8.1); 1.1805 (15.4); 1.1785 (16.0); 1.1626 (7.3); 1.1608 (7.7); −0.0002 (2.7) |
| I.0546: $^{1}$H-NMR(400.2 MHz, $d_6$-DMSO):<br>δ = 8.7009 (1.2); 8.6812 (1.2); 4.8940 (0.5); 4.8767 (1.0); 4.8598 (1.0); 4.8425 (0.5); 3.6679 (15.4); 3.6251 (16.0); 3.3291 (7.6); 3.0086 (0.7); 2.9940 (0.7); 2.9671 (1.5); 2.9525 (1.4); 2.9068 (1.5); 2.8895 (1.6); 2.8653 (0.7); 2.8479 (0.7); 2.7324 (0.3); 2.5124 (5.4); 2.5083 (10.7); 2.5039 (14.0); 2.4994 (10.2); 2.4951 (5.0); −0.0002 (1.8) |

TABLE A-(I)-continued

NMR peak lists of compounds according to formula (I)

I.0547: $^1$H-NMR(400.2 MHz, $d_6$-DMSO):
δ = 8.5336 (1.3); 8.5139 (1.3); 4.5286 (0.6); 4.5155 (0.7); 4.5082 (1.2); 4.4954 (1.2); 4.4881 (0.7); 4.4750 (0.6); 4.1475 (0.8); 4.1448 (0.9); 4.1298 (2.7); 4.1271 (2.6); 4.1119 (2.9); 4.1094 (2.6); 4.0999 (0.3); 4.0940 (1.0); 3.6111 (1.1); 3.5981 (1.1); 3.5769 (1.4); 3.5638 (1.3); 3.3533 (1.5); 3.3318 (5.9); 3.3191 (1.4); 3.2981 (1.1); 2.5274 (0.3); 2.5141 (5.9); 2.5098 (11.5); 2.5052 (14.8); 2.5007 (10.8); 2.4964 (5.3); 1.8559 (16.0); 1.2135 (4.9); 1.1957 (10.2); 1.1779 (4.7); −0.0002 (2.2)
I.0548: $^1$H-NMR(400.2 MHz, $d_6$-DMSO):
δ = 8.7660 (1.2); 8.7465 (1.2); 4.8990 (0.5); 4.8818 (1.0); 4.8655 (0.9); 4.8480 (0.5); 3.6763 (15.4); 3.6318 (16.0); 3.3287 (6.2); 3.0040 (0.6); 2.9897 (0.6); 2.9623 (1.6); 2.9481 (1.5); 2.9174 (1.6); 2.9001 (1.6); 2.8757 (0.6); 2.8585 (0.6); 2.5127 (5.2); 2.5084 (10.0); 2.5039 (12.7); 2.4994 (9.1); 2.4950 (4.4); −0.0002 (1.8)
I.0549: $^1$H-NMR(400.2 MHz, $d_6$-DMSO):
δ = 8.7599 (1.1); 8.7415 (1.1); 4.4920 (0.4); 4.4789 (0.6); 4.4732 (0.6); 4.4691 (0.7); 4.4603 (0.6); 4.4561 (0.6); 4.4505 (0.6); 4.4374 (0.4); 3.6736 (15.4); 3.5932 (16.0); 3.4068 (0.4); 3.3717 (76.6); 2.5149 (5.6); 2.5108 (10.9); 2.5063 (14.2); 2.5018 (10.3); 2.4976 (5.1); 2.4806 (1.2); 2.4623 (3.0); 2.4431 (1.8); 2.1604 (0.4); 2.1468 (0.6); 2.1256 (0.8); 2.1124 (0.6); 2.0216 (0.5); 2.0030 (0.5); 1.9989 (0.6); 1.9861 (0.4); 1.9803 (0.5); 1.9634 (0.4)
I.0550: $^1$H-NMR(400.2 MHz, $d_6$-DMSO):
δ = 8.6237 (1.1); 8.6048 (1.1); 4.6720 (0.5); 4.6592 (0.6); 4.6517 (0.9); 4.6395 (0.8); 4.6323 (0.6); 4.6193 (0.5); 4.1781 (0.9); 4.1605 (2.8); 4.1431 (2.9); 4.1255 (1.0); 3.3301 (7.9); 3.0435 (0.5); 3.0306 (0.6); 3.0087 (1.6); 2.9959 (1.4); 2.9788 (1.5); 2.9578 (1.4); 2.9439 (0.6); 2.9230 (0.6); 2.8924 (1.4); 2.7327 (1.2); 2.5085 (9.9); 2.5041 (12.7); 2.4996 (9.2); 2.4955 (4.6); 2.0948 (16.0); 1.2287 (4.1); 1.2109 (8.3); 1.1932 (3.9); −0.0002 (1.6)
I.0551: $^1$H-NMR(400.2 MHz, $d_6$-DMSO):
δ = 8.7411 (1.9); 8.7216 (2.0); 4.8689 (0.8); 4.8525 (1.6); 4.8338 (1.5); 4.8183 (0.8); 4.1641 (1.8); 4.1563 (0.3); 4.1464 (5.8); 4.1287 (6.1); 4.1203 (2.0); 4.1110 (2.3); 4.1027 (5.6); 4.0850 (5.8); 4.0672 (2.0); 3.3288 (11.4); 2.9722 (0.9); 2.9578 (1.0); 2.9308 (2.7); 2.9164 (2.5); 2.8955 (2.6); 2.8788 (2.6); 2.8541 (0.9); 2.8374 (0.9); 2.5260 (0.4); 2.5128 (8.8); 2.5085 (17.2); 2.5040 (22.3); 2.4995 (16.2); 2.4951 (8.0); 1.2072 (7.6); 1.2002 (8.0); 1.1895 (15.8); 1.1825 (16.0); 1.1717 (7.5); 1.1647 (7.5); −0.0002 (3.2)
I.0552: $^1$H-NMR(400.2 MHz, $d_6$-DMSO):
δ = 8.6929 (0.5); 8.6733 (0.5); 4.8610 (0.4); 4.8439 (0.4); 3.6803 (6.3); 3.3307 (5.3); 2.8462 (0.7); 2.8320 (0.6); 2.8055 (0.6); 2.7884 (0.6); 2.5128 (2.3); 2.5086 (4.6); 2.5040 (5.9); 2.4995 (4.3); 2.4951 (2.1); 1.3948 (16.0); −0.0002 (0.8)
I.0553: $^1$H-NMR(300.2 MHz, CDCl3):
δ = 7.2986 (6.4); 6.2526 (0.6); 6.2267 (0.6); 4.7740 (0.5); 4.7577 (0.6); 4.7484 (1.0); 4.7320 (1.0); 4.7227 (0.6); 4.7063 (0.5); 3.8089 (15.8); 3.1795 (0.7); 3.1596 (0.7); 3.1511 (0.8); 3.1304 (0.7); 3.1232 (0.7); 3.1014 (0.8); 3.0944 (0.8); 3.0731 (0.8); 3.0482 (0.4); 2.3246 (0.3); 2.3077 (0.6); 2.2865 (0.6); 2.2781 (0.4); 2.2695 (0.4); 2.2617 (0.4); 2.2570 (0.4); 2.1346 (0.4); 2.1120 (16.0); 2.0879 (0.8); 2.0806 (0.6); 2.0600 (0.6); 2.0411 (0.4); 1.6261 (3.9); 0.0350 (8.0)
I.0554: $^1$H-NMR(400.2 MHz, $d_6$-DMSO):
δ = 8.5074 (1.4); 8.4877 (1.4); 7.9535 (0.3); 4.5174 (0.6); 4.5043 (0.7); 4.4972 (1.2); 4.4843 (1.2); 4.4773 (0.8); 4.4641 (0.6); 4.1393 (0.8); 4.1367 (0.9); 4.1218 (2.5); 4.1190 (2.8); 4.1039 (2.7); 4.1014 (2.8); 4.0918 (0.4); 4.0860 (1.0); 4.0839 (0.9); 3.5874 (1.0); 3.5743 (1.0); 3.5529 (1.3); 3.5400 (1.2); 3.3392 (47.0); 3.3103 (1.4); 3.2965 (1.1); 3.2759 (1.0); 2.8923 (2.2); 2.7324 (1.9); 2.5086 (18.8); 2.5042 (24.6); 2.4999 (18.5); 1.8482 (16.0); 1.2049 (4.7); 1.1872 (9.7); 1.1694 (4.6); −0.0002 (1.0)
I.0555: $^1$H-NMR(600.1 MHz, $d_6$-DMSO):
δ = 8.5461 (0.7); 8.5329 (0.7); 4.8633 (0.4); 4.8513 (1.0); 4.8394 (0.9); 4.8282 (0.4); 3.6547 (14.9); 3.6208 (16.0); 3.3803 (6.3); 3.3772 (6.4); 3.3728 (6.2); 3.3623 (9.7); 3.3581 (8.1); 3.3500 (16.6); 3.3483 (21.1); 2.9891 (0.9); 2.9789 (0.9); 2.9615 (1.4); 2.9513 (1.3); 2.8730 (1.3); 2.8611 (1.3); 2.8454 (0.8); 2.8335 (0.8); 2.5117 (4.1); 2.5087 (9.1); 2.5056 (12.8); 2.5025 (9.1); 2.4995 (4.0)
I.0556: $^1$H-NMR(600.1 MHz, $d_6$-DMSO):
δ = 8.4801 (0.7); 8.4669 (0.7); 4.6243 (0.4); 4.6159 (0.5); 4.6099 (0.7); 4.6017 (0.7); 4.5967 (0.5); 4.5881 (0.4); 4.1586 (0.5); 4.1546 (0.6); 4.1468 (1.7); 4.1428 (1.8); 4.1349 (1.8); 4.1310 (1.8); 4.1231 (0.7); 4.1192 (0.6); 3.4013 (7.4); 3.3980 (8.5); 3.3934 (8.6); 3.3920 (8.6); 3.3890 (8.4); 3.3784 (14.5); 3.3756 (11.5); 3.3711 (16.7); 3.3673 (29.2); 3.3658 (33.4); 3.0186 (0.7); 3.0101 (0.8); 2.9954 (1.6); 2.9870 (1.4); 2.9658 (1.3); 2.9508 (1.3); 2.9427 (0.6); 2.9277 (0.6); 2.5128 (4.0); 2.5098 (8.9); 2.5067 (12.5); 2.5036 (8.9); 2.5006 (3.9); 2.0860 (16.0); 1.2130 (3.9); 1.2012 (8.2); 1.1894 (3.8)
I.0557: $^1$H-NMR(400.2 MHz, $d_6$-DMSO):
δ = 8.5333 (0.8); 8.5144 (0.8); 4.4683 (0.4); 4.4555 (0.5); 4.4491 (0.5); 4.4448 (0.6); 4.4367 (0.6); 4.4321 (0.6); 4.4259 (0.5); 4.4130 (0.4); 3.6543 (15.0); 3.5853 (16.0); 3.3327 (13.8); 2.5133 (5.0); 2.5089 (10.0); 2.5044 (13.2); 2.4998 (9.6); 2.4954 (4.7); 2.4419 (1.3); 2.4234 (3.2); 2.4048 (1.7); 2.1565 (0.4); 2.1412 (0.5); 2.1275 (0.4); 2.1216 (0.7); 2.1086 (0.6); 2.0365 (0.6); 2.0305 (0.4); 2.0187 (0.5); 2.0128 (0.6); 2.0014 (0.4); 1.9949 (0.5); 1.9777 (0.4); −0.0002 (1.4)
I.0558: $^1$H-NMR(600.1 MHz, $d_6$-DMSO):
δ = 8.5074 (1.4); 8.5043 (1.4); 8.4940 (1.4); 8.4911 (1.4); 4.8305 (0.8); 4.8186 (1.8); 4.8066 (1.8); 4.7954 (0.8); 4.1363 (1.1); 4.1336 (1.3); 4.1245 (3.4); 4.1219 (4.0); 4.1126 (3.6); 4.1101 (4.0); 4.1005 (2.7); 4.0902 (4.0); 4.0885 (4.9); 4.0783 (4.1); 4.0767 (4.9); 4.0703 (0.4); 4.0663 (1.4); 4.0650 (1.6); 3.3791 (8.9); 3.3768 (10.6); 3.3716 (10.9); 3.3683 (12.6); 3.3635 (11.1); 3.3616 (12.3); 3.3566 (11.4); 3.3534 (21.9); 3.3517 (16.9); 3.3480 (14.1); 3.3464 (16.2); 3.3448 (19.9); 3.3430 (15.8); 3.3406 (29.0); 3.3389 (28.2); 2.9554 (1.5); 2.9451 (1.6); 2.9280 (2.6); 2.9177 (2.4); 2.8932 (0.4); 2.8508 (2.3); 2.8391 (2.4); 2.8235 (1.5); 2.8117 (1.4); 2.5231 (0.4); 2.5200 (0.4); 2.5113 (7.7); 2.5083 (17.1); 2.5052 (24.0); 2.5021 (17.1); 2.4991 (7.7); 1.1877 (7.6); 1.1821 (7.7); 1.1758 (16.0); 1.1702 (15.8); 1.1640 (7.8); 1.1584 (7.4); −0.0001 (0.6)
I.0559: $^1$H-NMR(400.2 MHz, $d_6$-DMSO):
δ = 8.5123 (1.3); 8.4939 (1.3); 4.4399 (0.6); 4.4271 (0.8); 4.4210 (0.8); 4.4164 (1.0); 4.4083 (0.9); 4.4037 (0.8); 4.3976 (0.8); 4.3846 (0.6); 4.1453 (1.1); 4.1424 (1.2); 4.1369 (0.4); 4.1275 (3.6); 4.1247 (3.6); 4.1097 (3.9); 4.1071 (3.6); 4.0975 (0.4); 4.0918 (1.4); 4.0797 (0.4); 4.0734 (2.0); 4.0556 (6.2); 4.0378 (6.3); 4.0201 (2.1); 3.3578 (93.6); 2.8937 (0.3); 2.5283 (0.5); 2.5150 (9.2); 2.5106 (18.1); 2.5060 (23.4); 2.5015 (16.8); 2.4970 (8.0); 2.4264 (1.8); 2.4080 (4.5); 2.3892 (2.6); 2.1497 (0.4); 2.1434 (0.5); 2.1301 (0.8); 2.1086 (1.1); 2.0957 (0.9); 2.0896 (0.5); 2.0765 (0.4); 2.0472 (0.4); 2.0298 (0.8); 2.0237 (0.6); 2.0116 (0.7); 2.0061 (0.8); 1.9946 (0.6); 1.9878 (0.7); 1.9710 (0.5); 1.2072 (6.9); 1.1894 (15.4); 1.1864 (9.2); 1.1715 (8.6); 1.1685 (16.0); 1.1506 (7.1); −0.0002 (0.4)
I.0560: $^1$H-NMR(400.2 MHz, $d_6$-DMSO):
δ = 4.8293 (0.4); 4.8123 (0.4); 3.6569 (6.2); 3.3755 (34.7); 2.8645 (0.3); 2.8391 (0.6); 2.8240 (0.6); 2.7631 (0.6); 2.7449 (0.6); 2.7226 (0.3); 2.5158 (2.6); 2.5116 (5.0); 2.5071 (6.5); 2.5026 (4.7); 2.4983 (2.3); 1.3859 (16.0)
I.0561: $^1$H-NMR(400.2 MHz, $d_6$-DMSO):
δ = 8.5231 (1.4); 8.5033 (1.4); 4.5254 (0.6); 4.5123 (0.7); 4.5050 (1.2); 4.4922 (1.2); 4.4849 (0.7); 4.4719 (0.6); 4.1444 (0.8); 4.1416 (0.9); 4.1360 (0.3); 4.1266 (2.6); 4.1240 (2.7); 4.1088 (2.8); 4.1063 (2.7); 4.0909 (1.0); 3.5983 (1.1); 3.5853 (1.1); 3.5641 (1.4); 3.5510 (1.3); 3.3424 (1.6); 3.3308 (6.2); 3.3218 (1.7); 3.3082 (1.2); 3.2874 (1.1); 2.8934 (0.4); 2.7333 (0.4); 2.5139 (6.3); 2.5098 (12.2); 2.5053 (15.7); 2.5008 (11.5); 2.4966 (5.7); 1.8528 (16.0); 1.2095 (4.9); 1.1917 (10.2); 1.1740 (4.7); −0.0002 (2.2)

TABLE A-(I)-continued

NMR peak lists of compounds according to formula (I)

I.0562: $^1$H-NMR(400.2 MHz, $d_6$-DMSO):
δ = 8.7390 (2.0); 8.7206 (2.0); 4.4615 (0.8); 4.4484 (1.0); 4.4429 (1.0); 4.4386 (1.2); 4.4298 (1.1); 4.4257 (1.1); 4.4201 (1.1); 4.4069 (0.8); 4.1706 (0.3); 4.1614 (1.1); 4.1574 (1.3); 4.1531 (0.6); 4.1436 (3.7); 4.1397 (3.9); 4.1258 (3.9); 4.1220 (3.8); 4.1125 (0.6); 4.1080 (1.3); 4.1044 (1.2); 4.0950 (0.4); 4.0813 (2.3); 4.0636 (7.0); 4.0458 (7.1); 4.0280 (2.3); 3.3276 (11.2); 2.5122 (9.2); 2.5081 (18.2); 2.5037 (23.8); 2.4992 (17.6); 2.4948 (8.9); 2.4642 (1.5); 2.4592 (1.5); 2.4447 (3.8); 2.4241 (2.4); 2.1667 (0.3); 2.1537 (0.4); 2.1475 (0.7); 2.1337 (1.0); 2.1126 (1.2); 2.0993 (1.0); 2.0935 (0.6); 2.0801 (0.4); 2.0296 (0.5); 2.0131 (0.8); 2.0094 (0.8); 1.9935 (0.9); 1.9905 (1.0); 1.9779 (0.6); 1.9710 (0.8); 1.9550 (0.6); 1.2230 (7.5); 1.2052 (15.5); 1.1911 (9.0); 1.1876 (8.5); 1.1734 (16.0); 1.1556 (7.6); −0.0002 (3.1)
I.0563: $^1$H-NMR(400.2 MHz, $d_6$-DMSO):
δ = 8.5101 (5.6); 8.5038 (5.7); 4.0272 (15.0); 4.0135 (16.0); 3.9569 (0.7); 3.9481 (0.5); 3.9066 (0.4); 3.8859 (0.8); 3.8500 (0.3); 3.7999 (0.4); 3.7062 (0.4); 3.6711 (0.5); 3.6488 (0.6); 3.5822 (0.8); 3.5665 (0.9); 3.4372 (2.9); 3.3475 (115.8); 3.1979 (1.0); 3.1045 (0.6); 3.0577 (0.4); 3.0405 (0.4); 3.0205 (0.4); 2.9961 (0.3); 2.6763 (0.7); 2.6719 (0.9); 2.6670 (0.7); 2.5421 (1.2); 2.5118 (50.8); 2.5073 (108.9); 2.5028 (149.8); 2.4983 (107.1); 2.4938 (50.0); 2.4420 (0.5); 2.3345 (0.8); 2.3297 (1.0); 2.3252 (0.8); 2.0761 (1.9); 1.2319 (0.3); 0.0083 (0.6); 0.0001 (17.3); −0.0082 (0.9)
I.0564: $^1$H-NMR(300.1 MHz, $d_6$-DMSO):
δ = 8.4602 (0.7); 4.0513 (3.4); 4.0319 (3.4); 3.6669 (16.0); 3.3579 (0.6); 2.5174 (0.6); 2.5116 (1.2); 2.5057 (1.5); 2.4998 (1.1); 2.4635 (11.1)
I.0565: $^1$H-NMR(400.2 MHz, $d_6$-DMSO):
δ = 9.4335 (2.1); 3.6614 (16.0); 3.3359 (11.2); 2.8922 (0.8); 2.7327 (0.7); 2.6096 (0.6); 2.5938 (0.8); 2.5879 (1.0); 2.5768 (1.0); 2.5726 (1.0); 2.5625 (1.2); 2.5548 (0.9); 2.5405 (0.8); 2.5258 (0.5); 2.5124 (6.9); 2.5082 (12.8); 2.5037 (16.0); 2.4992 (11.6); 2.4951 (5.6); 2.3493 (0.6); 2.3295 (1.2); 2.3262 (1.4); 2.3063 (1.0); 2.2970 (1.2); 2.2747 (0.6); 2.0088 (0.3); 1.9947 (0.6); 1.9860 (0.6); 1.9767 (1.0); 1.9713 (1.0); 1.9564 (1.4); 1.9487 (0.6); 1.9349 (0.7); −0.0002 (1.1)
I.0566: $^1$H-NMR(400.2 MHz, $d_6$-DMSO):
δ = 9.4513 (4.2); 4.1450 (2.4); 4.1273 (7.6); 4.1096 (7.7); 4.0918 (2.5); 3.3335 (16.4); 2.8924 (0.5); 2.7326 (0.5); 2.5994 (1.1); 2.5832 (1.4); 2.5779 (1.9); 2.5665 (1.9); 2.5626 (1.8); 2.5524 (2.2); 2.5448 (1.8); 2.5302 (1.7); 2.5083 (21.9); 2.5038 (28.0); 2.4994 (20.7); 2.3419 (1.2); 2.3191 (2.4); 2.2990 (1.9); 2.2897 (2.2); 2.2674 (1.2); 2.0046 (0.6); 1.9945 (1.0); 1.9903 (1.1); 1.9816 (1.2); 1.9743 (1.9); 1.9671 (1.8); 1.9531 (2.6); 1.9448 (1.1); 1.9319 (1.3); 1.9115 (0.3); 1.1977 (8.0); 1.1800 (16.0); 1.1622 (7.7); −0.0002 (1.8)
I.0567: $^1$H-NMR(400.2 MHz, $d_6$-DMSO):
δ = 9.3119 (5.6); 4.0126 (4.8); 3.9966 (9.8); 3.9806 (4.9); 3.3384 (14.5); 3.3339 (16.8); 2.8929 (1.1); 2.7332 (1.0); 2.5083 (28.8); 2.5041 (34.3); 1.6009 (0.6); 1.5830 (2.4); 1.5660 (4.9); 1.5480 (5.0); 1.5313 (2.6); 1.5135 (0.7); 1.4762 (2.2); 1.4639 (6.1); 1.4559 (6.6); 1.4448 (2.7); 1.2258 (2.8); 1.2148 (6.5); 1.2067 (6.3); 1.1942 (2.2); 0.8830 (8.1); 0.8645 (16.0); 0.8460 (7.3); −0.0002 (1.7)
I.0568: $^1$H-NMR(400.2 MHz, $d_6$-DMSO):
δ = 9.3097 (13.2); 7.9529 (0.4); 4.9419 (1.2); 4.9237 (4.8); 4.9052 (7.2); 4.8868 (4.8); 4.8681 (1.3); 3.3363 (41.7); 2.8920 (2.2); 2.7321 (2.1); 2.6730 (0.4); 2.5040 (71.8); 2.5000 (56.1); 2.3309 (0.4); 2.2885 (2.0); 2.2820 (2.9); 2.2628 (6.2); 2.2584 (6.1); 2.2516 (5.6); 2.2443 (6.3); 2.2392 (6.8); 2.2207 (3.4); 2.2146 (2.6); 2.0032 (1.5); 1.9967 (1.2); 1.9785 (5.7); 1.9719 (4.1); 1.9587 (6.1); 1.9535 (7.3); 1.9484 (5.6); 1.9348 (4.7); 1.9286 (5.5); 1.9109 (1.6); 1.9039 (1.7); 1.7637 (1.6); 1.7382 (4.0); 1.7126 (4.0); 1.6877 (1.4); 1.6346 (1.0); 1.6140 (2.4); 1.6092 (2.6); 1.5888 (4.8); 1.5631 (4.0); 1.5430 (1.8); 1.5379 (1.4); 1.5173 (0.6); 1.4671 (5.8); 1.4547 (15.0); 1.4466 (15.9); 1.4356 (6.6); 1.3955 (0.6); 1.2526 (0.6); 1.2328 (0.6); 1.2127 (7.3); 1.2016 (16.0); 1.1936 (15.1); 1.1812 (5.4); −0.0001 (4.0); −0.0013 (3.2)
I.0569: $^1$H-NMR(400.2 MHz, $d_6$-DMSO):
δ = 9.2542 (2.6); 4.3696 (16.0); 3.3406 (12.2); 2.8936 (0.7); 2.7338 (0.6); 2.5277 (0.3); 2.5102 (13.8); 2.5059 (17.7); 2.5016 (13.5); −0.0002 (1.0)
I.0570: $^1$H-NMR(400.2 MHz, $d_6$-DMSO):
δ = 8.9398 (1.9); 4.1646 (2.4); 4.1468 (7.4); 4.1291 (7.5); 4.1113 (2.5); 4.0656 (4.9); 4.0570 (4.8); 3.3421 (18.3); 2.5093 (14.9); 2.5049 (18.7); 2.5006 (14.2); 1.2300 (8.2); 1.2122 (16.0); 1.1944 (7.8); −0.0002 (0.9)
I.0571: $^1$H-NMR(400.2 MHz, $d_6$-DMSO):
δ = 8.9490 (1.1); 4.0902 (3.2); 4.0769 (3.1); 3.6761 (16.0); 3.3355 (8.3); 2.8924 (0.7); 2.7331 (0.6); 2.5082 (11.5); 2.5039 (13.5); 2.4995 (9.6); −0.0002 (0.7)
I.0572: $^1$H-NMR(400.2 MHz, $d_6$-DMSO):
δ = 9.3038 (3.7); 4.1063 (2.3); 4.0885 (7.4); 4.0708 (7.4); 4.0531 (2.4); 3.3335 (9.6); 2.8926 (0.5); 2.7330 (0.4); 2.5263 (0.4); 2.5128 (8.5); 2.5084 (16.2); 2.5039 (20.3); 2.4993 (14.6); 2.4948 (7.0); 1.4800 (2.0); 1.4677 (5.0); 1.4594 (5.4); 1.4483 (2.3); 1.2238 (2.5); 1.2128 (5.4); 1.2045 (5.2); 1.1920 (2.0); 1.1796 (7.9); 1.1618 (16.0); 1.1441 (7.6); −0.0002 (1.5)
I.0573: $^1$H-NMR(400.2 MHz, $d_6$-DMSO):
δ = 9.2844 (2.4); 3.6280 (16.0); 3.3362 (5.6); 2.5082 (9.3); 2.5039 (11.5); 2.4994 (8.4); 1.4962 (1.3); 1.4838 (3.3); 1.4755 (3.5); 1.4643 (1.5); 1.2408 (1.6); 1.2297 (3.6); 1.2214 (3.3); 1.2089 (1.2); −0.0002 (0.7)
I.0574: $^1$H-NMR(400.2 MHz, $d_6$-DMSO):
δ = 8.9792 (1.5); 3.6318 (11.0); 3.3344 (6.0); 2.8926 (0.4); 2.7329 (0.4); 2.5080 (7.0); 2.5037 (8.7); 2.4994 (6.5); 1.4738 (16.0); −0.0002 (0.5)
I.0575: $^1$H-NMR(400.2 MHz, $d_6$-DMSO):
δ = 8.8812 (2.6); 8.8620 (2.6); 4.3233 (2.4); 4.3071 (3.5); 4.2882 (2.2); 4.2268 (0.4); 4.2090 (1.2); 4.1998 (1.1); 4.1912 (1.4); 4.1821 (3.0); 4.1643 (3.2); 4.1524 (3.2); 4.1468 (1.7); 4.1348 (3.0); 4.1254 (1.3); 4.1171 (1.1); 4.1077 (1.1); 4.0901 (0.3); 3.3423 (23.7); 2.5084 (26.2); 2.5045 (28.4); 2.2291 (0.4); 2.2126 (1.3); 2.1960 (2.1); 2.1792 (2.1); 2.1624 (1.3); 2.1456 (0.4); 1.2329 (8.1); 1.2151 (15.4); 1.1974 (7.5); 0.9712 (16.0); 0.9652 (15.4); 0.9543 (15.6); 0.9484 (13.6); −0.0002 (1.0)
I.0576: $^1$H-NMR(400.2 MHz, $d_6$-DMSO):
δ = 9.1836 (1.3); 9.1678 (1.3); 3.8162 (1.0); 3.7992 (1.2); 3.7938 (1.3); 3.7765 (1.0); 3.6884 (16.0); 3.3356 (11.0); 2.5041 (14.1); 1.2757 (0.3); 1.2648 (0.5); 1.2544 (0.8); 1.2438 (0.8); 1.2328 (0.9); 1.2214 (0.5); 1.2126 (0.4); 0.6419 (0.4); 0.6323 (0.8); 0.6207 (0.9); 0.6102 (1.0); 0.5992 (0.5); 0.5892 (0.4); 0.5692 (0.4); 0.5562 (0.7); 0.5465 (0.9); 0.5360 (0.9); 0.5259 (1.0); 0.5066 (0.8); 0.4971 (0.8); 0.4879 (1.0); 0.4755 (1.2); 0.4639 (0.9); 0.4521 (0.4); 0.4150 (0.5); 0.4033 (0.9); 0.3921 (1.0); 0.3798 (1.0); 0.3699 (0.6); −0.0002 (0.7)
I.0577: $^1$H-NMR(400.2 MHz, $d_6$-DMSO):
δ = 8.9938 (2.3); 8.9751 (2.3); 7.3202 (1.2); 7.3016 (5.0); 7.2851 (14.3); 7.2806 (10.9); 7.2645 (2.5); 7.2471 (1.6); 7.2427 (1.7); 7.2260 (2.4); 7.2173 (0.8); 7.2096 (0.8); 4.6898 (0.8); 4.6762 (1.2); 4.6706 (1.2); 4.6664 (1.4); 4.6572 (1.3); 4.6529 (1.3); 4.6475 (1.2); 4.6338 (0.9); 4.1553 (2.3); 4.1376 (7.1); 4.1198 (7.3); 4.1020 (2.4); 3.3519 (11.4); 3.3479 (17.8); 3.3425 (24.0); 3.2150 (1.3); 3.2016 (1.4); 3.1805 (2.3); 3.1672 (2.1); 3.0990 (2.3); 3.0750 (2.3); 3.0646 (1.5); 3.0406 (1.3); 2.5084 (21.0); 2.5043 (25.4); 2.5002 (18.6); 1.1863 (8.0); 1.1684 (16.0); 1.1508 (7.7); −0.0002 (1.3)

TABLE A-(I)-continued

| NMR peak lists of compounds according to formula (I) |
|---|
| I.0578: $^1$H-NMR(400.2 MHz, $d_6$-DMSO):<br>δ = 9.4359 (2.0); 3.6631 (16.0); 3.3342 (7.5); 2.8921 (0.7); 2.7324 (0.6); 2.6117 (0.6); 2.6071 (0.4); 2.5958 (0.7); 2.5901 (1.0); 2.5828 (0.8); 2.5788 (1.0); 2.5747 (0.9); 2.5645 (1.2); 2.5569 (0.9); 2.5492 (0.4); 2.5425 (0.8); 2.5256 (0.4); 2.5119 (6.1); 2.5079 (11.3); 2.5035 (14.2); 2.4991 (10.3); 2.3545 (0.6); 2.3315 (1.4); 2.3116 (1.0); 2.3020 (1.2); 2.2799 (0.6); 2.0104 (0.3); 2.0002 (0.5); 1.9961 (0.6); 1.9875 (0.6); 1.9798 (1.0); 1.9728 (1.0); 1.9586 (1.4); 1.9503 (0.6); 1.9374 (0.7); −0.0002 (0.9) |
| I.0579: $^1$H-NMR(400.2 MHz, $d_6$-DMSO):<br>δ = 9.4551 (4.0); 4.1464 (2.4); 4.1286 (7.6); 4.1109 (7.7); 4.0932 (2.5); 3.3325 (15.0); 2.6007 (1.1); 2.5844 (1.5); 2.5793 (2.0); 2.5678 (2.1); 2.5640 (1.9); 2.5537 (2.3); 2.5462 (1.8); 2.5317 (1.7); 2.5256 (1.2); 2.5074 (27.5); 2.5031 (34.3); 2.4988 (25.5); 2.3464 (1.2); 2.3237 (2.7); 2.3033 (2.0); 2.2939 (2.3); 2.2718 (1.2); 2.0057 (0.6); 1.9960 (1.0); 1.9914 (1.1); 1.9824 (1.3); 1.9762 (2.1); 1.9683 (1.9); 1.9549 (2.6); 1.9461 (1.1); 1.9340 (1.4); 1.9135 (0.4); 1.1980 (7.9); 1.1803 (16.0); 1.1626 (7.6); −0.0002 (2.1) |
| I.0580: $^1$H-NMR(400.2 MHz, $d_6$-DMSO):<br>δ = 9.3167 (5.9); 4.0129 (5.1); 3.9971 (10.2); 3.9810 (5.1); 3.3469 (2.1); 3.3355 (17.4); 3.3318 (16.8); 2.8915 (1.2); 2.7316 (1.1); 2.5034 (33.5); 1.5997 (0.6); 1.5822 (2.8); 1.5645 (5.4); 1.5475 (5.6); 1.5297 (3.0); 1.5129 (0.8); 1.4777 (2.5); 1.4655 (6.9); 1.4575 (7.3); 1.4466 (3.0); 1.2284 (3.2); 1.2174 (7.4); 1.2095 (6.9); 1.1972 (2.4); 0.8823 (8.4); 0.8640 (16.0); 0.8454 (7.5); −0.0002 (1.1) |
| I.0581: $^1$H-NMR(400.2 MHz, $d_6$-DMSO):<br>δ = 9.3159 (10.8); 4.9427 (1.1); 4.9250 (4.6); 4.9071 (6.6); 4.8879 (4.6); 4.8703 (1.2); 3.3360 (33.8); 2.8924 (0.9); 2.7331 (0.8); 2.7320 (0.7); 2.6728 (0.4); 2.5263 (1.4); 2.5215 (2.3); 2.5129 (27.3); 2.5084 (52.8); 2.5038 (67.0); 2.4992 (48.0); 2.4947 (22.7); 2.3353 (0.3); 2.3307 (0.4); 2.2897 (1.9); 2.2829 (2.8); 2.2756 (2.4); 2.2697 (3.8); 2.2652 (5.0); 2.2629 (5.0); 2.2592 (5.2); 2.2523 (5.0); 2.2452 (5.4); 2.2414 (5.4); 2.2392 (5.7); 2.2347 (4.4); 2.2288 (2.8); 2.2214 (3.4); 2.2150 (2.5); 2.0080 (0.7); 2.0043 (1.3); 1.9970 (1.0); 1.9834 (2.9); 1.9788 (5.7); 1.9719 (3.7); 1.9638 (2.3); 1.9594 (5.8); 1.9547 (6.1); 1.9530 (6.1); 1.9482 (4.9); 1.9356 (4.3); 1.9290 (5.1); 1.9246 (2.8); 1.9112 (1.6); 1.9050 (1.6); 1.7699 (0.8); 1.7651 (1.4); 1.7588 (0.8); 1.7385 (3.6); 1.7323 (1.9); 1.7193 (2.1); 1.7135 (3.5); 1.7061 (1.7); 1.6955 (0.8); 1.6935 (0.8); 1.6888 (1.2); 1.6868 (1.2); 1.6821 (0.7); 1.6354 (1.2); 1.6153 (2.4); 1.6111 (2.1); 1.6093 (2.2); 1.5950 (1.8); 1.5900 (4.8); 1.5847 (2.4); 1.5686 (2.4); 1.5636 (3.8); 1.5584 (1.1); 1.5441 (1.8); 1.5382 (1.4); 1.5180 (0.6); 1.4706 (6.0); 1.4583 (14.7); 1.4499 (16.0); 1.4389 (7.0); 1.3990 (0.6); 1.2572 (0.5); 1.2325 (0.4); 1.2173 (7.6); 1.2062 (15.8); 1.1979 (15.4); 1.1854 (5.9); −0.0002 (3.3) |
| I.0582: $^1$H-NMR(400.2 MHz, $d_6$-DMSO):<br>δ = 9.2535 (2.5); 4.3721 (16.0); 3.3387 (8.0); 2.8937 (0.4); 2.7341 (0.4); 2.5277 (0.3); 2.5100 (12.7); 2.5057 (15.7); 2.5012 (11.5); −0.0002 (1.0) |
| I.0583: $^1$H-NMR(400.2 MHz, $d_6$-DMSO):<br>δ = 9.3308 (2.0); 4.1655 (2.2); 4.1477 (7.0); 4.1299 (7.1); 4.1121 (2.3); 4.0213 (12.6); 3.3418 (15.5); 2.5278 (0.4); 2.5141 (8.1); 2.5099 (15.9); 2.5054 (20.6); 2.5009 (15.3); 2.4966 (7.8); 1.2326 (8.0); 1.2149 (16.0); 1.1970 (7.6); −0.0002 (0.6) |
| I.0584: $^1$H-NMR(400.2 MHz, $d_6$-DMSO):<br>δ = 9.3464 (1.2); 4.0430 (8.4); 3.6788 (16.0); 3.3449 (13.0); 2.8933 (0.5); 2.7333 (0.4); 2.5097 (10.4); 2.5057 (13.3); 2.5016 (10.4) |
| I.0585: $^1$H-NMR(400.2 MHz, $d_6$-DMSO):<br>δ = 9.5197 (5.2); 4.1091 (2.5); 4.0914 (7.8); 4.0736 (7.8); 4.0559 (2.6); 3.3395 (17.6); 3.3361 (17.4); 2.5087 (30.9); 2.5047 (35.9); 1.4823 (2.2); 1.4701 (6.2); 1.4621 (6.6); 1.4509 (2.6); 1.2014 (2.8); 1.1904 (6.6); 1.1819 (7.3); 1.1763 (9.3); 1.1584 (16.0); 1.1408 (7.7); −0.0002 (1.8) |
| I.0586: $^1$H-NMR(400.2 MHz, $d_6$-DMSO):<br>δ = 8.9944 (1.7); 8.9777 (1.7); 7.3201 (1.2); 7.3017 (4.6); 7.2841 (11.7); 7.2783 (9.3); 7.2621 (2.4); 7.2472 (1.5); 7.2428 (1.6); 7.2360 (1.0); 7.2321 (1.2); 7.2259 (2.4); 7.2178 (0.7); 7.2095 (0.8); 7.2046 (0.4); 4.6827 (0.6); 4.6660 (1.0); 4.6598 (1.1); 4.6520 (1.0); 4.6448 (1.1); 4.6286 (0.6); 4.1521 (2.1); 4.1344 (6.7); 4.1166 (6.9); 4.0989 (2.2); 3.3348 (24.2); 3.2093 (1.2); 3.1959 (1.3); 3.1748 (2.1); 3.1615 (1.9); 3.0912 (2.0); 3.0672 (2.0); 3.0568 (1.3); 3.0328 (1.2); 2.8911 (1.2); 2.7322 (1.1); 2.5252 (1.1); 2.5076 (34.5); 2.5032 (42.8); 2.4988 (30.8); 1.1839 (7.8); 1.1661 (16.0); 1.1484 (7.5); −0.0002 (2.2) |
| I.0587: $^1$H-NMR(400.2 MHz, $d_6$-DMSO):<br>δ = 9.1855 (1.4); 9.1687 (1.3); 7.9540 (1.0); 3.8172 (1.2); 3.7998 (1.4); 3.7942 (1.4); 3.7769 (1.2); 3.6875 (16.0); 3.3456 (17.5); 3.3419 (15.1); 2.8932 (5.8); 2.7337 (5.3); 2.5087 (12.2); 2.5047 (14.3); 2.5007 (10.5); 1.2705 (0.4); 1.2617 (0.5); 1.2501 (0.8); 1.2388 (0.8); 1.2277 (0.8); 1.2180 (0.5); 1.2073 (0.4); 0.6429 (0.4); 0.6394 (0.4); 0.6313 (0.8); 0.6227 (0.8); 0.6184 (0.8); 0.6082 (0.9); 0.5967 (0.5); 0.5870 (0.4); 0.5683 (0.4); 0.5549 (0.6); 0.5454 (0.8); 0.5348 (0.8); 0.5249 (1.0); 0.5070 (0.8); 0.4951 (0.7); 0.4860 (0.9); 0.4739 (1.1); 0.4626 (0.9); 0.4502 (0.4); 0.4146 (0.5); 0.4030 (0.8); 0.3919 (1.0); 0.3793 (0.9); 0.3693 (0.5); −0.0002 (0.7) |
| I.0588: $^1$H-NMR(400.2 MHz, $d_6$-DMSO):<br>δ = 8.8850 (1.8); 8.8656 (1.8); 4.3209 (2.0); 4.3051 (2.5); 4.3015 (2.4); 4.2857 (2.0); 4.2250 (0.3); 4.2072 (1.1); 4.1980 (0.9); 4.1894 (1.2); 4.1802 (2.8); 4.1681 (1.2); 4.1624 (3.0); 4.1504 (3.0); 4.1446 (1.2); 4.1327 (2.9); 4.1234 (1.2); 4.1150 (0.9); 4.1057 (1.2); 4.0879 (0.4); 3.3421 (12.7); 3.3373 (17.9); 2.5265 (0.6); 2.5130 (9.8); 2.5088 (18.6); 2.5043 (23.4); 2.4998 (17.0); 2.4955 (8.4); 2.2078 (1.0); 2.1910 (1.6); 2.1744 (1.6); 2.1576 (1.0); 2.1407 (0.4); 1.2318 (8.0); 1.2140 (16.0); 1.1963 (7.6); 0.9686 (12.3); 0.9628 (11.8); 0.9515 (12.0); 0.9457 (11.1); −0.0002 (1.4) |
| I.0589: $^1$H-NMR(400.2 MHz, $d_6$-DMSO):<br>δ = 8.9850 (1.4); 3.6305 (11.5); 3.3376 (6.9); 2.5085 (7.3); 2.5041 (8.9); 2.4996 (6.5); 1.4701 (16.0) |
| I.0590: $^1$H-NMR(400.1 MHz, $d_6$-DMSO):<br>δ = 8.6889 (3.4); 4.6974 (0.3); 4.6791 (1.3); 4.6608 (2.0); 4.6422 (1.4); 4.6239 (0.4); 3.0939 (3.6); 2.2676 (2.6); 2.1776 (2.0); 2.1564 (16.0); 2.1385 (1.8); 2.0432 (0.8); 2.0228 (1.9); 2.0200 (1.9); 2.0125 (1.8); 2.0013 (2.2); 1.9819 (1.1); 1.7483 (0.4); 1.7417 (0.4); 1.7233 (1.6); 1.6987 (2.2); 1.6737 (1.7); 1.6555 (0.6); 1.6493 (0.6); 1.5232 (0.5); 1.4972 (1.2); 1.4720 (1.2); 1.4474 (0.5); 1.3717 (0.8); 1.3500 (1.4); 1.3249 (1.2); 1.3038 (0.6); 1.1979 (1.5); 1.1856 (4.2); 1.1781 (4.6); 1.1672 (2.0); 0.9324 (1.8); 0.9215 (4.3); 0.9139 (4.3); 0.9017 (1.7) |
| I.0591: $^1$H-NMR(400.1 MHz, CDCl3):<br>δ = 7.2628 (6.5); 6.7181 (2.1); 6.7016 (2.1); 4.0852 (5.3); 4.0686 (10.7); 4.0521 (5.5); 1.6800 (2.7); 1.6675 (8.3); 1.6596 (8.5); 1.6497 (5.4); 1.6336 (6.1); 1.6158 (6.1); 1.5982 (3.4); 1.5752 (12.0); 1.3071 (3.1); 1.2953 (8.0); 1.2876 (8.0); 1.2750 (2.9); 0.9199 (8.3); 0.9014 (16.0); 0.8829 (7.8); −0.0002 (8.2) |
| I.0592: $^1$H-NMR(400.1 MHz, $d_6$-DMSO):<br>δ = 8.8403 (12.3); 4.9226 (1.2); 4.9042 (4.6); 4.8858 (7.0); 4.8672 (4.9); 4.8489 (1.4); 3.3343 (19.5); 2.5093 (9.9); 2.2728 (2.7); 2.2527 (6.6); 2.2425 (6.0); 2.2312 (7.4); 2.2118 (3.8); 1.9825 (1.4); 1.9761 (1.2); 1.9576 (5.4); 1.9330 (7.6); 1.9080 (6.0); 1.8898 (1.9); 1.8836 (2.0); 1.7557 (1.6); 1.7297 (4.2); 1.7045 (4.2); 1.6799 (1.6); 1.6295 (1.1); 1.6052 (2.7); 1.5838 (4.8); 1.5587 (4.1); 1.5381 (2.0); 1.5122 (0.7); 1.4924 (0.4); 1.4540 (5.3); 1.4416 (14.6); 1.4338 (16.0); 1.4228 (7.1); 1.3830 (0.9); 1.3640 (0.5); 1.2389 (0.7); 1.1989 (6.5); 1.1879 (15.3); 1.1801 (15.1); 1.1677 (5.8); 1.1305 (0.6) |
| I.0593: $^1$H-NMR(400.1 MHz, $d_6$-DMSO):<br>δ = 9.0479 (6.0); 4.0104 (5.0); 3.9944 (10.2); 3.9785 (5.3); 3.3345 (7.3); 2.5091 (5.2); 1.6065 (0.6); 1.5890 (2.6); 1.5718 (5.4); 1.5540 (5.5); 1.5371 (3.1); 1.5194 (0.9); 1.4649 (2.5); 1.4526 (7.0); 1.4448 (7.6); 1.4339 (3.3); 1.3943 (0.4); 1.2012 (3.1); 1.1902 (7.4); 1.1824 (7.2); 1.1701 (2.8); 0.8902 (8.1); 0.8717 (16.0); 0.8532 (7.7) |

TABLE A-(I)-continued

NMR peak lists of compounds according to formula (I)

I.0594: $^1$H-NMR(400.1 MHz, $d_6$-DMSO):
δ = 9.0495 (13.2); 4.9424 (1.1); 4.9242 (4.6); 4.9058 (7.0); 4.8873 (4.9); 4.8690 (1.4); 3.3333 (22.4); 2.5092 (17.3); 2.2856 (2.6); 2.2653 (6.4); 2.2550 (5.8); 2.2436 (7.3); 2.2243 (3.7); 2.0934 (0.4); 2.0157 (1.4); 2.0093 (1.2); 1.9908 (5.4); 1.9662 (7.5); 1.9410 (5.8); 1.9228 (1.9); 1.9164 (2.0); 1.7711 (1.5); 1.7455 (4.1); 1.7203 (4.2); 1.6953 (1.6); 1.6380 (1.0); 1.6137 (2.6); 1.5924 (4.7); 1.5674 (4.0); 1.5461 (2.0); 1.5207 (0.6); 1.4938 (0.4); 1.4554 (5.2); 1.4431 (14.5); 1.4353 (16.0); 1.4243 (7.0); 1.3852 (1.0); 1.2284 (0.6); 1.1881 (6.4); 1.1770 (15.4); 1.1692 (15.1); 1.1569 (5.8); 1.1192 (0.6)
I.0595: $^1$H-NMR(400.1 MHz, $d_6$-DMSO):
δ = 8.9455 (2.9); 3.6230 (16.0); 3.3351 (2.8); 2.5092 (2.1); 1.4833 (1.3); 1.4709 (3.6); 1.4630 (4.0); 1.4519 (1.7); 1.2280 (1.6); 1.2169 (3.9); 1.2089 (3.8); 1.1965 (1.4)
I.0596: $^1$H-NMR(400.1 MHz, $d_6$-DMSO):
δ = 8.9816 (6.0); 4.0076 (4.9); 3.9916 (10.2); 3.9757 (5.4); 3.3340 (8.2); 2.5092 (6.3); 1.5970 (0.6); 1.5793 (2.6); 1.5622 (5.3); 1.5444 (5.5); 1.5275 (3.1); 1.5097 (0.9); 1.4662 (2.5); 1.4539 (6.9); 1.4460 (7.7); 1.4350 (3.4); 1.3956 (0.4); 1.2163 (3.0); 1.2053 (7.3); 1.1974 (7.2); 1.1849 (2.9); 0.8827 (8.0); 0.8642 (16.0); 0.8457 (7.7)
I.0597: $^1$H-NMR(400.1 MHz, $d_6$-DMSO):
δ = 8.9790 (12.7); 4.9378 (1.1); 4.9193 (4.5); 4.9008 (6.9); 4.8824 (4.8); 4.8642 (1.5); 3.3339 (17.1); 2.5094 (14.4); 2.2826 (2.6); 2.2620 (6.5); 2.2521 (5.9); 2.2405 (7.4); 2.2214 (3.7); 2.0935 (0.4); 1.9988 (1.4); 1.9739 (5.3); 1.9492 (7.5); 1.9242 (5.9); 1.9066 (1.9); 1.8997 (2.0); 1.7653 (1.6); 1.7397 (4.2); 1.7144 (4.2); 1.6894 (1.6); 1.6368 (1.0); 1.6125 (2.7); 1.5907 (4.7); 1.5657 (4.0); 1.5447 (2.0); 1.5195 (0.7); 1.4987 (0.4); 1.4602 (5.1); 1.4477 (14.4); 1.4400 (16.0); 1.4291 (7.2); 1.3888 (0.9); 1.3782 (0.6); 1.2431 (0.7); 1.2037 (6.3); 1.1926 (15.1); 1.1849 (15.2); 1.1724 (5.9); 1.1344 (0.6)
I.0598: $^1$H-NMR(400.1 MHz, $d_6$-DMSO):
δ = 9.2610 (6.5); 7.7833 (11.0); 3.9984 (5.0); 3.9824 (10.4); 3.9664 (5.4); 3.3349 (7.5); 3.1817 (0.6); 3.1687 (0.6); 2.5091 (5.5); 1.5737 (0.6); 1.5561 (2.7); 1.5389 (5.4); 1.5211 (5.6); 1.5042 (3.2); 1.4863 (1.0); 1.4674 (2.6); 1.4553 (7.0); 1.4476 (7.7); 1.4367 (3.4); 1.3970 (0.4); 1.1791 (3.0); 1.1681 (7.3); 1.1604 (7.2); 1.1483 (2.8); 0.8532 (8.1); 0.8347 (16.0); 0.8162 (7.7)
I.0599: $^1$H-NMR(400.1 MHz, $d_6$-DMSO):
δ = 9.2436 (9.5); 7.7808 (16.0); 4.9203 (0.8); 4.9018 (3.1); 4.8833 (4.8); 4.8647 (3.3); 4.8466 (1.0); 3.3359 (8.3); 3.1820 (0.3); 3.1689 (0.3); 2.5092 (5.8); 2.2682 (1.8); 2.2480 (4.4); 2.2449 (4.3); 2.2376 (4.0); 2.2264 (5.0); 2.2070 (2.5); 1.9734 (0.9); 1.9669 (0.8); 1.9482 (3.6); 1.9236 (5.1); 1.8984 (4.0); 1.8803 (1.3); 1.8742 (1.4); 1.7484 (1.1); 1.7225 (2.9); 1.6973 (2.9); 1.6724 (1.1); 1.6241 (0.7); 1.6000 (1.8); 1.5784 (3.2); 1.5532 (2.7); 1.5326 (1.4); 1.5065 (0.6); 1.4672 (3.6); 1.4550 (9.9); 1.4474 (10.8); 1.4364 (4.7); 1.3967 (0.5); 1.2074 (0.4); 1.1671 (4.3); 1.1561 (10.3); 1.1484 (10.2); 1.1363 (4.0); 1.0978 (0.4)
I.0600: $^1$H-NMR(400.2 MHz, $d_6$-DMSO):
δ = 9.5238 (1.8); 3.6290 (16.0); 3.3368 (6.3); 2.5090 (12.3); 2.5047 (15.3); 2.5004 (11.3); 1.4962 (1.2); 1.4839 (3.2); 1.4757 (3.4); 1.4645 (1.4); 1.2167 (1.4); 1.2056 (3.4); 1.1974 (3.2); 1.1850 (1.2); −0.0002 (0.9)
I.0601: $^1$H-NMR(400.1 MHz, $d_6$-DMSO):
δ = 9.2688 (6.3); 7.8216 (11.0); 3.9991 (5.0); 3.9830 (10.3); 3.9670 (5.4); 3.3343 (9.6); 2.5093 (6.6); 1.5747 (0.6); 1.5570 (2.6); 1.5398 (5.4); 1.5220 (5.6); 1.5050 (3.2); 1.4873 (0.9); 1.4674 (2.6); 1.4553 (7.0); 1.4476 (7.7); 1.4368 (3.4); 1.3976 (0.4); 1.1802 (3.0); 1.1692 (7.2); 1.1615 (7.2); 1.1494 (2.8); 0.8539 (8.1); 0.8355 (16.0); 0.8170 (7.7)
I.0602: $^1$H-NMR(400.2 MHz, $d_6$-DMSO):
δ = 9.2791 (2.5); 3.6266 (16.0); 3.3350 (8.9); 2.8921 (0.5); 2.7322 (0.4); 2.5082 (11.4); 2.5038 (14.1); 2.4994 (10.2); 1.4930 (1.3); 1.4805 (3.2); 1.4723 (3.4); 1.4612 (1.4); 1.2364 (1.6); 1.2253 (3.4); 1.2170 (3.2); 1.2046 (1.2); −0.0002 (0.8)
I.0603: $^1$H-NMR(400.2 MHz, $d_6$-DMSO):
δ = 8.8597 (0.4); 3.6081 (1.7); 3.5036 (16.0); 3.4852 (5.4); 3.4522 (3.4); 3.4345 (3.3); 2.5168 (3.5); 1.4562 (0.5); 1.4487 (0.4); 1.2125 (0.5); 1.2051 (0.4)
I.0604: $^1$H-NMR(400.2 MHz, $d_6$-DMSO):
δ = 8.9444 (2.8); 4.1621 (2.4); 4.1444 (7.3); 4.1266 (7.4); 4.1088 (2.5); 4.0573 (10.2); 3.3374 (38.4); 2.8922 (0.4); 2.7327 (0.4); 2.5079 (34.2); 2.5038 (40.3); 2.4996 (29.9); 1.2281 (7.9); 1.2103 (16.0); 1.1925 (7.7); −0.0002 (0.4)
I.0605: $^1$H-NMR(400.2 MHz, $d_6$-DMSO):
δ = 8.9500 (0.9); 4.0856 (2.5); 4.0755 (2.4); 3.6749 (16.0); 3.3387 (8.0); 3.3375 (8.1); 3.3358 (8.3); 2.8923 (0.4); 2.5129 (5.8); 2.5086 (11.0); 2.5041 (13.9); 2.4995 (10.0); 2.4952 (4.8); −0.0002 (0.7)
I.0606: $^1$H-NMR(400.2 MHz, $d_6$-DMSO):
δ = 9.2978 (4.9); 4.1046 (2.4); 4.0869 (7.4); 4.0692 (7.4); 4.0514 (2.4); 3.3345 (17.7); 2.5083 (21.7); 2.5039 (27.8); 2.4994 (20.9); 1.4768 (2.1); 1.4644 (5.5); 1.4562 (6.1); 1.4451 (2.5); 1.2195 (2.6); 1.2083 (6.0); 1.2002 (5.8); 1.1877 (2.2); 1.1792 (8.1); 1.1615 (16.0); 1.1437 (7.6); −0.0002 (1.3)
I.0607: $^1$H-NMR(400.1 MHz, $d_6$-DMSO):
δ = 9.2551 (9.6); 7.8199 (16.0); 4.9203 (0.8); 4.9019 (3.2); 4.8834 (4.9); 4.8649 (3.4); 4.8463 (1.0); 3.3359 (9.9); 2.5092 (6.3); 2.2683 (1.9); 2.2482 (4.6); 2.2378 (4.2); 2.2264 (5.2); 2.2071 (2.6); 1.9743 (1.0); 1.9679 (0.9); 1.9490 (3.8); 1.9247 (5.3); 1.8994 (4.2); 1.8811 (1.4); 1.8752 (1.5); 1.7485 (1.2); 1.7226 (3.0); 1.6974 (3.0); 1.6727 (1.2); 1.6242 (0.8); 1.6002 (1.9); 1.5785 (3.4); 1.5535 (2.9); 1.5323 (1.4); 1.5066 (0.6); 1.4668 (3.8); 1.4546 (10.2); 1.4471 (11.2); 1.4362 (4.9); 1.3960 (0.6); 1.3607 (0.7); 1.2077 (0.4); 1.1683 (4.4); 1.1573 (10.7); 1.1497 (10.7); 1.1375 (4.1); 1.1000 (0.4)
I.0608: $^1$H-NMR(400.2 MHz, $d_6$-DMSO):
δ = 9.1794 (1.4); 3.6211 (11.1); 3.3370 (6.2); 2.8934 (0.6); 2.7335 (0.5); 2.5093 (7.7); 2.5049 (9.7); 2.5005 (7.2); 1.4588 (16.0); −0.0002 (0.6)
I.0609: $^1$H-NMR(400.2 MHz, $d_6$-DMSO):
δ = 9.1634 (1.1); 9.1493 (1.1); 4.2601 (0.8); 4.2440 (1.5); 4.2276 (0.8); 4.1976 (0.8); 4.1884 (0.7); 4.1799 (0.9); 4.1706 (2.3); 4.1625 (1.1); 4.1528 (2.4); 4.1449 (2.4); 4.1351 (1.1); 4.1272 (2.4); 4.1179 (0.9); 4.1095 (0.8); 4.1001 (0.8); 3.3359 (10.4); 2.5267 (0.5); 2.5132 (7.8); 2.5091 (14.8); 2.5047 (18.9); 2.5002 (13.8); 2.4961 (6.9); 2.1997 (0.8); 2.1827 (1.4); 2.1657 (1.5); 2.1487 (0.9); 1.2301 (6.3); 1.2123 (12.6); 1.1946 (6.0); 0.9849 (8.9); 0.9679 (16.0); 0.9507 (8.2); −0.0002 (0.8)
I.0610: $^1$H-NMR(400.2 MHz, $d_6$-DMSO):
δ = 9.4899 (1.9); 3.7418 (1.7); 3.7181 (1.7); 3.6840 (16.0); 3.3445 (7.9); 3.3381 (9.5); 2.8936 (0.7); 2.7340 (0.7); 2.5092 (14.2); 2.5051 (16.1); 1.2435 (0.4); 1.2328 (0.6); 1.2234 (0.8); 1.2119 (0.8); 1.2004 (0.8); 1.1915 (0.5); 1.1803 (0.4); 0.6502 (0.4); 0.6385 (0.8); 0.6296 (0.9); 0.6254 (0.8); 0.6155 (0.9); 0.6041 (0.5); 0.5944 (0.5); 0.5802 (0.4); 0.5667 (0.7); 0.5569 (0.9); 0.5468 (0.9); 0.5365 (0.9); 0.5243 (0.4); 0.5162 (0.8); 0.5038 (0.7); 0.4940 (1.0); 0.4819 (1.2); 0.4710 (0.9); 0.4584 (0.4); 0.4123 (0.5); 0.4009 (0.9); 0.3894 (1.1); 0.3774 (1.0); 0.3670 (0.6); −0.0002 (0.7)
I.0611: $^1$H-NMR(400.2 MHz, $d_6$-DMSO):
δ = 9.1694 (2.3); 7.9580 (0.6); 4.9474 (0.4); 4.9319 (1.2); 4.9163 (1.6); 4.9007 (1.2); 4.8851 (0.5); 3.3400 (31.4); 2.8960 (3.8); 2.7361 (3.5); 2.5735 (0.7); 2.5581 (0.9); 2.5514 (1.2); 2.5405 (1.4); 2.5122 (31.0); 2.5079 (39.0); 2.5037 (30.2); 2.3186 (0.7); 2.2955 (1.5); 2.2753 (1.2); 2.2675 (1.3); 2.2444 (0.7); 1.9998 (0.4); 1.9857 (0.6); 1.9771 (0.7); 1.9614 (1.2); 1.9384 (1.3); 1.9167 (0.6); 1.1915 (16.0); 1.1759 (15.9)

TABLE A-(I)-continued

NMR peak lists of compounds according to formula (I)

I.0612: $^1$H-NMR(400.2 MHz, $d_6$-DMSO):
δ = 9.2310 (2.0); 3.6403 (16.0); 3.3413 (23.0); 2.8962 (1.5); 2.7364 (1.3); 2.5302 (0.6); 2.5254 (1.0); 2.5167 (10.7); 2.5124 (20.8); 2.5078 (27.1); 2.5033 (19.8); 2.4989 (9.7); 2.4779 (2.3); 2.4440 (2.8); 2.1221 (2.7); 2.0880 (2.3); 1.2355 (10.0); 1.1361 (10.2)
I.0613: $^1$H-NMR(400.2 MHz, $d_6$-DMSO):
δ = 9.5132 (1.9); 3.7007 (16.0); 3.3861 (0.4); 3.3424 (21.4); 3.3228 (0.9); 3.3155 (1.3); 3.2842 (0.6); 3.0395 (0.5); 3.0072 (1.0); 2.9815 (0.8); 2.9781 (0.8); 2.9686 (0.6); 2.9432 (0.4); 2.8960 (2.2); 2.7360 (1.8); 2.5303 (0.6); 2.5254 (0.9); 2.5167 (10.3); 2.5123 (20.2); 2.5078 (26.2); 2.5032 (19.2); 2.4987 (9.3)
I.0614: $^1$H-NMR(400.2 MHz, $d_6$-DMSO):
δ = 9.4503 (1.1); 3.3429 (18.8); 3.2675 (0.5); 3.2303 (0.6); 2.9606 (0.5); 2.9370 (0.5); 2.8959 (0.8); 2.7364 (0.7); 2.5118 (16.2); 2.5075 (19.7); 2.5030 (14.7); 1.4135 (16.0)
I.0615: $^1$H-NMR(400.2 MHz, $d_6$-DMSO):
δ = 8.8447 (1.8); 8.8277 (1.8); 7.3891 (8.4); 7.3780 (16.0); 7.3640 (0.9); 7.3597 (0.6); 7.3546 (1.7); 7.3456 (1.7); 7.3333 (1.3); 7.3249 (0.6); 7.3207 (0.5); 5.2360 (1.8); 5.2043 (4.8); 5.1707 (4.8); 5.1391 (1.8); 3.8414 (1.4); 3.8240 (1.5); 3.8182 (1.5); 3.8010 (1.4); 3.3472 (63.8); 2.8952 (0.4); 2.7363 (0.3); 2.5299 (1.0); 2.5163 (17.5); 2.5121 (32.8); 2.5076 (41.6); 2.5031 (30.6); 2.4989 (15.2); 1.3103 (0.4); 1.3020 (0.5); 1.2993 (0.5); 1.2897 (0.8); 1.2788 (0.9); 1.2675 (0.8); 1.2557 (0.5); 1.2470 (0.4); 0.6389 (0.4); 0.6344 (0.4); 0.6218 (0.8); 0.6130 (0.9); 0.6035 (1.2); 0.5919 (0.6); 0.5831 (0.6); 0.5670 (0.4); 0.5570 (0.6); 0.5533 (0.7); 0.5440 (1.0); 0.5330 (1.0); 0.5244 (1.4); 0.5117 (1.0); 0.5078 (1.2); 0.5055 (1.2); 0.5010 (1.2); 0.4883 (1.2); 0.4781 (0.9); 0.4653 (0.4); 0.4226 (0.6); 0.4109 (0.8); 0.3999 (1.1); 0.3876 (1.1); 0.3790 (0.6); 0.3735 (0.4)
I.0616: $^1$H-NMR(400.2 MHz, $d_6$-DMSO):
δ = 9.0779 (1.9); 4.9428 (0.4); 4.9271 (1.1); 4.9115 (1.6); 4.8959 (1.2); 4.8803 (0.4); 3.3381 (26.4); 2.8961 (2.1); 2.7369 (1.8); 2.7357 (1.7); 2.5652 (0.5); 2.5601 (0.4); 2.5498 (0.7); 2.5436 (1.0); 2.5302 (1.5); 2.5255 (1.8); 2.5167 (13.9); 2.5122 (26.7); 2.5076 (34.4); 2.5030 (25.2); 2.4985 (12.4); 2.3342 (0.3); 2.3289 (0.6); 2.3050 (1.1); 2.2850 (0.8); 2.2757 (1.0); 2.2534 (0.5); 1.9748 (0.4); 1.9713 (0.5); 1.9623 (0.5); 1.9533 (0.8); 1.9479 (0.8); 1.9330 (1.2); 1.9254 (0.5); 1.9114 (0.6); 1.1823 (16.0); 1.1666 (15.9)
I.0617: $^1$H-NMR(400.2 MHz, $d_6$-DMSO):
δ = 8.8942 (1.7); 8.8773 (1.7); 7.3949 (9.6); 7.3837 (16.0); 7.3712 (0.6); 7.3662 (1.0); 7.3617 (0.7); 7.3574 (1.6); 7.3481 (1.9); 7.3437 (0.9); 7.3364 (1.5); 7.3320 (0.5); 7.3271 (0.7); 5.2416 (2.0); 5.2099 (5.4); 5.1765 (5.5); 5.1449 (2.1); 3.8632 (1.5); 3.8462 (1.7); 3.8403 (1.7); 3.8233 (1.6); 3.3397 (48.4); 2.8957 (0.4); 2.7358 (0.4); 2.6767 (0.4); 2.5300 (1.3); 2.5166 (24.8); 2.5122 (47.5); 2.5076 (61.0); 2.5030 (44.5); 2.4986 (21.5); 2.3345 (0.4); 1.2951 (0.4); 1.2866 (0.5); 1.2839 (0.6); 1.2747 (0.9); 1.2723 (0.9); 1.2633 (0.9); 1.2520 (0.9); 1.2400 (0.6); 1.2318 (0.5); 0.6413 (0.4); 0.6369 (0.4); 0.6274 (0.8); 0.6227 (0.8); 0.6154 (0.9); 0.6062 (1.2); 0.5946 (0.6); 0.5859 (0.7); 0.5764 (0.5); 0.5669 (0.6); 0.5632 (0.8); 0.5538 (1.0); 0.5473 (0.7); 0.5429 (1.0); 0.5342 (1.5); 0.5284 (0.9); 0.5212 (1.1); 0.5171 (1.1); 0.5138 (1.1); 0.5086 (1.3); 0.4958 (1.4); 0.4859 (1.0); 0.4733 (0.4); 0.4375 (0.6); 0.4257 (0.9); 0.4149 (1.2); 0.4026 (1.1); 0.3937 (0.7); 0.3889 (0.5)
I.0618: $^1$H-NMR(400.2 MHz, $d_6$-DMSO):
δ = 9.1550 (1.9); 3.6338 (16.0); 3.3396 (20.4); 2.8961 (0.6); 2.7361 (0.5); 2.5303 (0.7); 2.5255 (0.9); 2.5167 (11.6); 2.5123 (23.2); 2.5078 (30.6); 2.5032 (22.6); 2.4988 (11.1); 2.4709 (2.1); 2.4370 (2.5); 2.1266 (2.5); 2.0924 (2.1); 1.2213 (9.2); 1.1321 (9.3)
I.0619: $^1$H-NMR(400.2 MHz, $d_6$-DMSO):
δ = 8.7509 (1.2); 8.7339 (1.2); 7.3799 (5.7); 7.3700 (16.0); 7.3592 (1.5); 7.3488 (1.5); 7.3417 (1.1); 7.3374 (1.2); 7.3273 (1.1); 7.3149 (0.5); 5.2248 (1.4); 5.1930 (4.2); 5.1638 (4.2); 5.1319 (1.4); 3.7668 (1.2); 3.7496 (1.4); 3.7432 (1.4); 3.7258 (1.2); 3.3447 (64.1); 2.8955 (1.3); 2.7357 (1.1); 2.5122 (38.6); 2.5077 (48.5); 2.5033 (36.5); 1.3351 (0.3); 1.3236 (0.5); 1.3149 (0.7); 1.3116 (0.8); 1.3032 (0.8); 1.2915 (0.7); 1.2798 (0.4); 1.2713 (0.4); 0.6379 (0.4); 0.6338 (0.4); 0.6204 (0.7); 0.6122 (0.8); 0.6030 (1.0); 0.5913 (0.5); 0.5822 (0.5); 0.5591 (0.4); 0.5452 (0.6); 0.5357 (0.8); 0.5244 (0.9); 0.5158 (1.3); 0.4986 (1.2); 0.4951 (1.2); 0.4822 (1.1); 0.4719 (0.7); 0.3958 (0.5); 0.3845 (0.7); 0.3735 (1.0); 0.3612 (1.0); 0.3523 (0.6); 0.3469 (0.4)
I.0620: $^1$H-NMR(400.2 MHz, $d_6$-DMSO):
δ = 8.8928 (1.6); 4.9342 (0.4); 4.9186 (1.2); 4.9030 (1.6); 4.8874 (1.2); 4.8718 (0.4); 3.3386 (17.2); 2.8961 (0.5); 2.7370 (0.5); 2.7357 (0.5); 2.5487 (0.5); 2.5433 (0.4); 2.5283 (1.4); 2.5258 (1.4); 2.5168 (10.8); 2.5124 (20.7); 2.5077 (26.7); 2.5031 (19.8); 2.4986 (9.7); 2.4800 (0.7); 2.3437 (0.6); 2.3213 (1.1); 2.3003 (0.8); 2.2943 (0.8); 2.2899 (1.1); 2.2682 (0.5); 1.9659 (0.4); 1.9519 (0.5); 1.9443 (1.1); 1.9380 (0.4); 1.9290 (0.9); 1.9230 (1.3); 1.9153 (0.5); 1.9023 (0.7); 1.1734 (16.0); 1.1577 (15.8)
I.0621: $^1$H-NMR(400.2 MHz, $d_6$-DMSO):
δ = 9.0126 (2.5); 7.9580 (0.7); 3.6217 (16.0); 3.3385 (30.0); 2.8964 (4.5); 2.7367 (4.1); 2.5123 (25.2); 2.5080 (32.3); 2.5037 (24.6); 2.4530 (2.6); 2.4193 (3.2); 2.1438 (3.1); 2.1101 (2.6); 1.2004 (11.1); 1.1260 (11.2)
I.0622: $^1$H-NMR(400.2 MHz, $d_6$-DMSO):
δ = 9.2476 (1.8); 3.6822 (16.0); 3.3417 (16.8); 3.3250 (1.0); 3.3182 (0.8); 3.2935 (0.8); 3.2863 (1.2); 3.2550 (0.5); 3.0871 (0.5); 3.0632 (0.6); 3.0527 (1.0); 3.0284 (0.8); 3.0143 (0.5); 2.9903 (0.4); 2.8961 (0.8); 2.7368 (0.7); 2.7357 (0.6); 2.5303 (0.5); 2.5255 (0.8); 2.5168 (9.4); 2.5123 (18.6); 2.5077 (24.2); 2.5031 (17.6); 2.4986 (8.4)
I.0623: $^1$H-NMR(400.2 MHz, $d_6$-DMSO):
δ = 9.1481 (0.8); 3.3390 (9.4); 3.2402 (0.4); 3.2335 (0.4); 3.2090 (0.4); 3.2021 (0.5); 3.0087 (0.4); 2.9850 (0.4); 2.8960 (0.7); 2.7370 (0.6); 2.7358 (0.6); 2.5256 (0.4); 2.5168 (5.2); 2.5123 (10.3); 2.5077 (13.5); 2.5031 (9.8); 2.4986 (4.7); 1.3944 (16.0); 1.3840 (0.6)
I.0624: $^1$H-NMR(400.2 MHz, $d_6$-DMSO):
δ = 9.4005 (2.2); 3.6941 (16.0); 3.3769 (0.4); 3.3414 (19.2); 3.3139 (0.8); 3.3064 (1.2); 3.2751 (0.5); 3.0559 (0.5); 3.0240 (1.0); 2.9979 (0.8); 2.9856 (0.6); 2.9596 (0.4); 2.8959 (0.4); 2.5302 (0.5); 2.5254 (0.8); 2.5167 (9.5); 2.5122 (18.8); 2.5076 (24.4); 2.5030 (17.8); 2.4985 (8.5)
I.0625: $^1$H-NMR(400.1 MHz, $d_6$-DMSO):
δ = 8.9411 (3.2); 4.0067 (3.0); 3.9908 (6.2); 3.9749 (3.3); 3.3345 (5.8); 2.5092 (4.4); 2.4113 (2.0); 2.3905 (16.0); 2.3729 (1.5); 1.5962 (0.4); 1.5784 (1.6); 1.5613 (3.3); 1.5434 (3.4); 1.5265 (1.9); 1.5089 (0.6); 1.4453 (1.4); 1.4331 (4.1); 1.4254 (4.6); 1.4147 (2.1); 1.1844 (1.7); 1.1735 (4.2); 1.1658 (4.3); 1.1536 (1.7); 0.8824 (4.9); 0.8640 (9.8); 0.8455 (4.8)
I.0626: $^1$H-NMR(400.1 MHz, $d_6$-DMSO):
δ = 8.3072 (6.6); 7.4983 (6.7); 7.4339 (0.5); 7.2539 (0.4); 7.1819 (6.7); 3.8873 (15.5); 3.8767 (16.0); 3.7023 (0.3); 3.3774 (0.4); 3.3071 (36.7); 3.1979 (0.4); 3.1581 (0.4); 2.6702 (0.4); 2.5003 (46.8); 2.3593 (0.5); 2.3262 (0.7); 2.3116 (0.5); 1.2386 (0.6); 0.0487 (0.4); −0.0002 (30.1); −0.0506 (1.1); −0.0913 (0.6); −0.1452 (0.5)
I.0627: $^1$H-NMR(400.2 MHz, $d_6$-DMSO):
δ = 8.8012 (1.5); 7.1750 (0.7); 7.0449 (1.5); 6.9148 (0.8); 3.6214 (11.0); 3.3346 (8.3); 2.5077 (9.4); 2.5033 (11.8); 2.4989 (8.9); 1.4521 (16.0); −0.0002 (0.6)
I.0628: $^1$H-NMR(400.2 MHz, $d_6$-DMSO):
δ = 9.3531 (1.7); 7.3096 (0.5); 7.2900 (4.4); 7.2846 (4.8); 7.2765 (16.0); 7.2635 (1.0); 7.2362 (1.0); 7.2295 (1.1); 7.2231 (0.9); 7.2182 (0.9); 7.2146 (1.2); 7.2099 (0.8); 7.2047 (0.5); 7.2006 (0.6); 4.6269 (0.7); 4.6131 (0.8); 4.6034 (0.9); 4.5893 (0.7); 4.1358

TABLE A-(I)-continued

NMR peak lists of compounds according to formula (I)

(1.7); 4.1181 (5.4); 4.1003 (5.5); 4.0825 (1.8); 3.3429 (19.9); 3.1835 (0.9); 3.1695 (1.0); 3.1491 (1.6); 3.1351 (1.5); 3.0787 (1.6); 3.0543 (1.6); 3.0444 (1.0); 3.0200 (0.9); 2.8918 (1.4); 2.7336 (1.2); 2.7325 (1.2); 2.5274 (0.4); 2.5139 (8.4); 2.5095 (16.5); 2.5050 (21.0); 2.5004 (15.2); 2.4960 (7.3); 1.1642 (6.0); 1.1464 (12.5); 1.1287 (5.8); −0.0002 (0.8)

I.0629: $^{1}$H-NMR(400.2 MHz, $d_6$-DMSO):
δ = 9.6326 (1.1); 3.6608 (16.0); 3.3458 (14.7); 2.6117 (0.6); 2.5953 (0.8); 2.5904 (1.1); 2.5834 (0.8); 2.5788 (1.1); 2.5748 (1.0); 2.5646 (1.2); 2.5572 (1.0); 2.5426 (0.8); 2.5278 (0.4); 2.5143 (5.9); 2.5101 (10.9); 2.5056 (13.5); 2.5010 (9.8); 2.4968 (4.8); 2.3400 (0.7); 2.3173 (1.3); 2.2972 (1.0); 2.2873 (1.2); 2.2655 (0.6); 2.0066 (0.4); 1.9973 (0.4); 1.9920 (0.6); 1.9781 (1.1); 1.9691 (1.0); 1.9577 (1.3); 1.9467 (0.6); 1.9368 (0.7); 1.9312 (0.4)

I.0630: $^{1}$H-NMR(400.2 MHz, $d_6$-DMSO):
δ = 9.6280 (2.3); 4.1454 (2.3); 4.1277 (7.4); 4.1100 (7.4); 4.0923 (2.4); 3.3371 (17.3); 2.8928 (0.4); 2.6010 (1.0); 2.5845 (1.3); 2.5798 (1.7); 2.5725 (1.3); 2.5681 (1.7); 2.5642 (1.6); 2.5539 (2.0); 2.5465 (1.5); 2.5319 (1.5); 2.5271 (1.0); 2.5133 (12.4); 2.5089 (23.7); 2.5044 (29.8); 2.4998 (21.4); 2.4954 (10.2); 2.3316 (1.2); 2.3091 (2.2); 2.2889 (1.6); 2.2789 (2.0); 2.2573 (1.0); 2.0027 (0.6); 1.9965 (0.6); 1.9882 (0.9); 1.9756 (1.8); 1.9653 (1.6); 1.9550 (2.2); 1.9428 (0.8); 1.9342 (1.2); 1.9275 (0.7); 1.1943 (7.8); 1.1766 (16.0); 1.1588 (7.5); −0.0002 (1.8)

I.0631: $^{1}$H-NMR(400.2 MHz, $d_6$-DMSO):
δ = 9.5319 (3.7); 4.0137 (5.0); 3.9977 (10.4); 3.9816 (5.1); 3.3348 (16.0); 2.5267 (0.8); 2.5088 (27.3); 2.5044 (34.8); 2.5000 (26.1); 1.5966 (0.5); 1.5783 (2.3); 1.5617 (4.6); 1.5435 (4.8); 1.5270 (2.4); 1.5090 (0.7); 1.4798 (2.2); 1.4676 (5.7); 1.4594 (6.2); 1.4484 (2.6); 1.2073 (2.6); 1.1962 (6.0); 1.1880 (5.9); 1.1757 (2.1); 0.8742 (8.0); 0.8558 (16.0); 0.8372 (7.2); −0.0002 (2.0)

I.0632: $^{1}$H-NMR(400.2 MHz, $d_6$-DMSO):
δ = 9.5202 (11.4); 4.9486 (1.3); 4.9302 (4.9); 4.9119 (7.2); 4.8934 (4.9); 4.8750 (1.3); 3.3403 (35.1); 3.3373 (35.7); 2.8937 (0.6); 2.7339 (0.6); 2.6738 (0.5); 2.5083 (71.7); 2.5050 (76.2); 2.3314 (0.5); 2.2772 (3.0); 2.2569 (7.0); 2.2538 (6.8); 2.2465 (6.3); 2.2391 (7.3); 2.2357 (7.6); 2.2159 (3.6); 2.0106 (1.6); 2.0042 (1.4); 1.9853 (5.8); 1.9610 (7.9); 1.9413 (5.1); 1.9356 (5.8); 1.9175 (1.7); 1.9114 (1.8); 1.7584 (1.7); 1.7323 (4.4); 1.7071 (4.4); 1.6823 (1.6); 1.6317 (1.1); 1.6106 (2.8); 1.6074 (2.8); 1.5860 (5.0); 1.5611 (4.1); 1.5401 (2.0); 1.5141 (0.9); 1.4753 (5.9); 1.4630 (15.3); 1.4556 (15.9); 1.4444 (6.4); 1.4050 (0.6); 1.2366 (0.8); 1.1971 (7.2); 1.1862 (16.0); 1.1786 (15.0); 1.1661 (5.3); 1.1296 (0.4); −0.0006 (3.2)

I.0633: $^{1}$H-NMR(400.2 MHz, $d_6$-DMSO):
δ = 9.6221 (2.1); 4.3659 (16.0); 3.3391 (4.6); 2.8937 (0.6); 2.7338 (0.5); 2.5063 (21.4); −0.0002 (0.9)

I.0634: $^{1}$H-NMR(400.2 MHz, $d_6$-DMSO):
δ = 8.5466 (2.0); 4.1484 (2.6); 4.1307 (7.8); 4.1129 (7.8); 4.0952 (2.6); 3.9926 (8.2); 3.9781 (8.1); 3.3537 (2.2); 3.3384 (20.8); 2.8927 (0.3); 2.5049 (26.0); 1.2194 (8.3); 1.2017 (16.0); 1.1839 (7.9); −0.0002 (1.2); −0.0012 (1.2)

I.0635: $^{1}$H-NMR(400.2 MHz, $d_6$-DMSO):
δ = 8.5659 (0.9); 4.0157 (4.2); 4.0011 (4.1); 3.6602 (16.0); 3.3402 (9.7); 2.5097 (10.6); 2.5054 (12.7); 2.5010 (9.0); −0.0002 (0.7)

I.0636: $^{1}$H-NMR(400.2 MHz, $d_6$-DMSO):
δ = 8.8362 (3.9); 4.0892 (2.4); 4.0715 (7.5); 4.0538 (7.6); 4.0361 (2.5); 3.3398 (24.0); 2.5095 (21.4); 2.5056 (25.4); 1.4553 (2.2); 1.4429 (6.1); 1.4348 (6.5); 1.4237 (2.7); 1.2038 (2.7); 1.1927 (6.4); 1.1846 (6.0); 1.1721 (2.2); 1.1588 (8.1); 1.1411 (16.0); 1.1234 (7.8); −0.0002 (1.1)

I.0637: $^{1}$H-NMR(400.2 MHz, $d_6$-DMSO):
δ = 8.4169 (1.0); 3.6044 (11.7); 3.3346 (7.7); 2.5214 (0.4); 2.5128 (5.2); 2.5084 (10.0); 2.5038 (12.6); 2.4992 (9.0); 2.4947 (4.3); 1.4518 (16.0); −0.0002 (0.8)

I.0638: $^{1}$H-NMR(400.1 MHz, $d_6$-DMSO):
δ = 8.2503 (6.8); 7.4734 (6.9); 7.3912 (0.4); 7.2635 (0.3); 7.1521 (6.9); 5.7509 (0.9); 3.8634 (15.3); 3.8534 (16.0); 3.8121 (0.7); 3.6061 (0.3); 3.5835 (0.4); 3.3705 (0.5); 3.3072 (34.6); 3.2612 (0.8); 3.1425 (0.4); 2.6679 (0.5); 2.6587 (0.4); 2.6038 (0.4); 2.5003 (54.0); 2.4283 (0.9); 2.3691 (0.4); 2.3255 (0.5); 2.0691 (0.3); 1.2962 (0.3); 1.2614 (1.9); 1.2458 (1.7); −0.0002 (30.9); −0.0596 (1.3); −0.0898 (0.5); −0.1542 (0.4)

I.0639: $^{1}$H-NMR(400.2 MHz, $d_6$-DMSO):
δ = 8.3257 (1.5); 8.3068 (1.5); 4.2462 (1.5); 4.2281 (2.6); 4.2101 (1.7); 4.1910 (0.7); 4.1819 (0.7); 4.1732 (0.8); 4.1641 (2.0); 4.1557 (1.1); 4.1462 (2.2); 4.1382 (2.1); 4.1284 (1.1); 4.1205 (2.0); 4.1123 (0.8); 4.1029 (0.7); 4.0934 (0.7); 3.3375 (15.8); 2.5062 (26.0); 2.5047 (25.9); 2.2035 (0.9); 2.1865 (1.5); 2.1696 (1.5); 2.1528 (0.9); 1.2226 (5.3); 1.2048 (10.3); 1.1872 (5.0); 0.9544 (9.3); 0.9386 (16.0); 0.9225 (8.4); 0.0020 (1.1); −0.0002 (1.1)

I.0640: $^{1}$H-NMR(400.2 MHz, $d_6$-DMSO):
δ = 8.5006 (1.6); 8.4812 (1.6); 7.3083 (1.2); 7.2898 (4.6); 7.2722 (11.8); 7.2666 (9.1); 7.2506 (2.4); 7.2340 (1.5); 7.2297 (1.6); 7.2228 (1.0); 7.2191 (1.2); 7.2127 (2.3); 7.2047 (0.7); 7.2021 (0.6); 7.1962 (0.8); 7.1916 (0.4); 4.6338 (0.8); 4.6197 (1.0); 4.6109 (1.3); 4.6003 (1.2); 4.5971 (1.2); 4.5915 (1.1); 4.5775 (0.8); 4.1340 (1.9); 4.1164 (6.1); 4.0987 (6.3); 4.0885 (0.4); 4.0809 (2.1); 3.3408 (18.5); 3.3390 (18.8); 3.1884 (0.8); 3.1746 (1.0); 3.1540 (2.5); 3.1402 (2.2); 3.1254 (2.4); 3.1019 (2.3); 3.0911 (0.9); 3.0675 (0.9); 2.5268 (0.7); 2.5093 (21.6); 2.5049 (26.6); 2.5004 (19.1); 1.1688 (7.9); 1.1511 (16.0); 1.1333 (7.5); −0.0002 (1.7)

I.0641: $^{1}$H-NMR(400.2 MHz, $d_6$-DMSO):
δ = 8.9341 (2.3); 3.6401 (16.0); 3.3409 (13.0); 2.8936 (0.5); 2.7341 (0.5); 2.5778 (0.7); 2.5576 (1.4); 2.5443 (1.5); 2.5304 (1.9); 2.5231 (2.0); 2.5092 (13.4); 2.5055 (15.3); 2.3597 (0.8); 2.3373 (1.9); 2.3159 (1.3); 2.3067 (1.6); 2.2847 (0.8); 1.9752 (0.6); 1.9613 (0.8); 1.9528 (1.6); 1.9384 (1.3); 1.9314 (1.9); 1.9107 (1.0); −0.0002 (0.7)

I.0642: $^{1}$H-NMR(400.2 MHz, $d_6$-DMSO):
δ = 8.9259 (4.4); 4.1307 (2.6); 4.1130 (7.7); 4.0952 (7.7); 4.0776 (2.5); 3.3455 (26.6); 3.3408 (27.3); 2.8941 (0.4); 2.7344 (0.4); 2.5685 (1.4); 2.5485 (2.7); 2.5058 (29.6); 2.3555 (1.6); 2.3332 (3.6); 2.3026 (3.0); 2.2806 (1.4); 1.9739 (1.2); 1.9523 (3.1); 1.9366 (2.7); 1.9311 (3.6); 1.9107 (2.0); 1.8894 (0.5); 1.1796 (8.2); 1.1619 (16.0); 1.1442 (7.7); −0.0002 (1.2)

I.0643: $^{1}$H-NMR(400.2 MHz, $d_6$-DMSO):
δ = 8.8584 (3.2); 3.9933 (4.7); 3.9773 (9.8); 3.9613 (4.8); 3.3354 (17.3); 2.8927 (0.5); 2.7329 (0.4); 2.5268 (0.6); 2.5132 (12.6); 2.5090 (24.4); 2.5045 (31.2); 2.5000 (22.8); 2.4957 (11.3); 1.5775 (0.5); 1.5592 (2.1); 1.5428 (4.3); 1.5245 (4.5); 1.5080 (2.2); 1.4899 (0.7); 1.4505 (2.0); 1.4382 (5.3); 1.4299 (5.8); 1.4189 (2.4); 1.2080 (2.5); 1.1969 (5.6); 1.1886 (5.3); 1.1762 (1.9); 0.8623 (8.0); 0.8439 (16.0); 0.8252 (7.1); −0.0002 (2.1)

I.0644: $^{1}$H-NMR(400.2 MHz, $d_6$-DMSO):
δ = 8.8347 (9.8); 4.9170 (1.2); 4.8986 (4.8); 4.8801 (7.2); 4.8615 (4.9); 4.8433 (1.3); 3.3349 (49.6); 2.8927 (0.9); 2.7332 (0.8); 2.6776 (0.4); 2.6737 (0.5); 2.6687 (0.4); 2.5266 (1.9); 2.5088 (68.4); 2.5044 (84.7); 2.5000 (61.7); 2.3356 (0.4); 2.3313 (0.5); 2.2742 (1.9); 2.2676 (2.7); 2.2542 (4.1); 2.2479 (5.6); 2.2439 (5.6); 2.2370 (5.1); 2.2298 (5.8); 2.2244 (6.2); 2.2196 (4.8); 2.2062 (3.3); 2.2001 (2.5); 1.9778 (1.4); 1.9709 (1.1); 1.9525 (5.5); 1.9458 (3.8); 1.9328 (5.8); 1.9274 (6.6); 1.9222 (5.2); 1.9090 (4.4); 1.9026 (5.3); 1.8848 (1.5); 1.8783 (1.6); 1.7501 (1.5); 1.7444 (1.0); 1.7242 (4.0); 1.6990 (3.8); 1.6738 (1.3); 1.6241 (1.1); 1.6039 (2.4); 1.5992 (2.4); 1.5786 (4.8); 1.5527 (3.9); 1.5328 (1.8); 1.5271 (1.4); 1.5067 (0.6); 1.4496 (5.7); 1.4372 (14.7); 1.4290 (16.0); 1.4180 (6.6); 1.3784 (0.6); 1.2357 (0.8); 1.1964 (6.8); 1.1853 (15.3); 1.1771 (14.8); 1.1646 (5.2); −0.0002 (5.0)

TABLE A-(I)-continued

NMR peak lists of compounds according to formula (I)

I.0645: $^1$H-NMR(400.2 MHz, $d_6$-DMSO):
δ = 8.8548 (2.8); 4.2952 (16.0); 3.3388 (15.8); 2.8934 (0.8); 2.7336 (0.7); 2.5281 (0.6); 2.5146 (11.2); 2.5103 (21.9); 2.5058 (28.2); 2.5012 (20.5); 2.4968 (9.9); 1.3925 (0.6); −0.0002 (2.0)
I.0646: $^1$H-NMR(400.2 MHz, $d_6$-DMSO):
δ = 8.7637 (2.2); 7.1812 (1.7); 7.0511 (3.9); 6.9210 (1.9); 4.1579 (2.5); 4.1508 (1.2); 4.1401 (7.4); 4.1334 (1.4); 4.1224 (7.3); 4.1046 (2.4); 4.0264 (6.6); 4.0125 (5.8); 3.3473 (10.0); 3.3358 (18.9); 2.5126 (16.4); 2.5084 (24.6); 2.5039 (27.5); 2.4994 (19.1); 1.2393 (1.2); 1.2289 (8.2); 1.2220 (2.5); 1.2111 (16.0); 1.1933 (7.6); 0.0047 (0.3); −0.0002 (1.5)
I.0647: $^1$H-NMR(400.2 MHz, $d_6$-DMSO):
δ = 8.7733 (1.2); 7.1815 (1.1); 7.0514 (2.4); 6.9213 (1.2); 4.0488 (3.2); 4.0356 (3.2); 3.6710 (16.0); 3.3438 (7.2); 3.3368 (12.6); 2.5083 (12.0); 2.5040 (15.4); 2.4998 (12.0); −0.0002 (0.8)
I.0648: $^1$H-NMR(400.2 MHz, $d_6$-DMSO):
δ = 9.1031 (3.8); 7.1738 (1.5); 7.0436 (3.5); 6.9134 (1.7); 4.0996 (1.9); 4.0819 (6.1); 4.0642 (6.2); 4.0464 (2.0); 3.3372 (19.6); 2.5257 (0.5); 2.5122 (10.8); 2.5080 (20.1); 2.5035 (25.2); 2.4990 (18.6); 1.4543 (1.7); 1.4421 (4.5); 1.4339 (4.9); 1.4229 (2.0); 1.1850 (7.7); 1.1674 (16.0); 1.1497 (7.7); −0.0002 (1.5)
I.0649: $^1$H-NMR(400.2 MHz, $d_6$-DMSO):
δ = 9.0928 (2.7); 7.1738 (1.0); 7.0437 (2.3); 6.9135 (1.2); 3.6233 (16.0); 3.3408 (17.8); 2.5078 (14.0); 2.5036 (17.2); 2.4993 (13.0); 1.4708 (1.3); 1.4585 (3.3); 1.4503 (3.6); 1.4393 (1.5); 1.2004 (1.6); 1.1893 (3.6); 1.1811 (3.5); 1.1688 (1.2); −0.0002 (0.9)
I.0650: $^1$H-NMR(400.2 MHz, $d_6$-DMSO):
δ = 8.7016 (1.0); 8.6845 (1.0); 3.7238 (1.1); 3.7062 (1.2); 3.7004 (1.4); 3.6902 (1.2); 3.6827 (1.3); 3.6669 (16.0); 3.3355 (9.8); 2.8931 (0.3); 2.5091 (12.0); 2.5048 (14.9); 2.5004 (11.5); 1.3006 (0.4); 1.2919 (0.7); 1.2803 (0.8); 1.2685 (0.8); 1.2602 (0.5); 1.2568 (0.5); 1.2484 (0.4); 0.6335 (0.4); 0.6300 (0.4); 0.6223 (0.7); 0.6130 (0.8); 0.6091 (0.8); 0.5983 (0.8); 0.5875 (0.5); 0.5772 (0.4); 0.5477 (0.4); 0.5338 (0.6); 0.5238 (0.8); 0.5137 (0.8); 0.5035 (0.9); 0.4916 (0.4); 0.4835 (0.8); 0.4715 (0.7); 0.4618 (0.9); 0.4496 (1.1); 0.4380 (0.8); 0.4255 (0.3); 0.3759 (0.4); 0.3646 (0.8); 0.3529 (0.9); 0.3404 (0.8); 0.3303 (0.5); −0.0002 (0.8)
I.0651: $^1$H-NMR(400.1 MHz, $d_6$-DMSO):
δ = 8.9133 (3.5); 4.9199 (1.2); 4.9015 (1.8); 4.8829 (1.2); 4.8649 (0.4); 3.3349 (4.2); 2.5092 (3.1); 2.3977 (16.0); 2.2843 (0.7); 2.2639 (1.7); 2.2611 (1.6); 2.2536 (1.5); 2.2425 (1.9); 2.2231 (1.0); 1.9891 (0.3); 1.9637 (1.3); 1.9392 (1.9); 1.9141 (1.5); 1.8960 (0.5); 1.8899 (0.5); 1.7643 (0.4); 1.7385 (1.0); 1.7133 (1.1); 1.6888 (0.4); 1.6129 (0.7); 1.5914 (1.2); 1.5664 (1.0); 1.5450 (0.6); 1.4386 (1.3); 1.4263 (3.7); 1.4186 (4.1); 1.4078 (1.8); 1.1721 (1.7); 1.1612 (3.9); 1.1534 (3.8); 1.1413 (1.5)
I.0652: $^1$H-NMR(400.2 MHz, $d_6$-DMSO):
δ = 9.0438 (5.2); 6.5346 (0.4); 4.3354 (16.0); 4.3229 (15.4); 3.3362 (71.2); 2.8938 (0.8); 2.7347 (0.6); 2.7335 (0.6); 2.6741 (0.3); 2.5277 (1.0); 2.5229 (1.5); 2.5143 (20.3); 2.5098 (41.2); 2.5052 (53.8); 2.5006 (38.2); 2.4960 (17.7); 2.3321 (0.3); 0.0080 (0.6); −0.0002 (18.9); −0.0086 (0.5)
I.0653: $^1$H-NMR(400.2 MHz, $d_6$-DMSO):
δ = 8.7939 (0.9); 8.7798 (1.8); 8.7656 (0.9); 7.9532 (0.4); 4.1605 (2.3); 4.1427 (7.0); 4.1249 (7.1); 4.1072 (2.3); 4.0394 (7.0); 4.0321 (1.3); 4.0249 (7.0); 3.3333 (24.1); 2.8932 (2.6); 2.7339 (2.3); 2.5265 (0.4); 2.5087 (14.9); 2.5042 (19.6); 2.4998 (14.5); 1.2301 (7.9); 1.2124 (16.0); 1.1946 (7.6); −0.0002 (4.9)
I.0654: $^1$H-NMR(400.2 MHz, $d_6$-DMSO):
δ = 8.8043 (0.6); 8.7903 (1.1); 8.7760 (0.6); 4.0618 (4.3); 4.0546 (0.9); 4.0473 (4.2); 3.6729 (16.0); 3.3340 (17.8); 2.8929 (0.8); 2.7330 (0.8); 2.5086 (9.0); 2.5042 (11.8); 2.4997 (8.8); −0.0002 (3.2)
I.0655: $^1$H-NMR(400.2 MHz, $d_6$-DMSO):
δ = 9.1644 (3.4); 4.1017 (2.0); 4.0840 (6.4); 4.0663 (6.5); 4.0486 (2.1); 3.3323 (26.0); 2.8924 (0.3); 2.5258 (0.4); 2.5121 (8.3); 2.5080 (16.4); 2.5035 (21.3); 2.4990 (15.6); 2.4947 (7.7); 1.4656 (1.8); 1.4533 (4.7); 1.4451 (5.1); 1.4340 (2.1); 1.1955 (2.2); 1.1824 (10.2); 1.1762 (5.3); 1.1644 (16.0); 1.1467 (7.0); −0.0002 (5.6)
I.0656: $^1$H-NMR(400.2 MHz, $d_6$-DMSO):
δ = 9.1524 (2.4); 3.6237 (16.0); 3.3330 (23.5); 2.5079 (13.8); 2.5037 (17.2); 2.4995 (12.6); 1.4815 (1.2); 1.4692 (3.3); 1.4610 (3.5); 1.4498 (1.4); 1.2123 (1.5); 1.2011 (3.4); 1.1930 (3.3); 1.1805 (1.2); −0.0002 (3.2)
I.0657: $^1$H-NMR(400.2 MHz, $d_6$-DMSO):
δ = 8.8044 (1.3); 3.6255 (11.6); 3.3324 (18.6); 2.8921 (0.6); 2.7321 (0.5); 2.5120 (4.7); 2.5077 (9.2); 2.5031 (12.0); 2.4986 (8.7); 2.4942 (4.2); 1.4631 (16.0); −0.0002 (2.4)
I.0658: $^1$H-NMR(400.2 MHz, $d_6$-DMSO):
δ = 8.6240 (1.4); 8.6046 (1.4); 4.3087 (1.8); 4.2933 (2.0); 4.2892 (2.1); 4.2738 (1.8); 4.2242 (0.3); 4.2065 (1.0); 4.1972 (0.9); 4.1887 (1.1); 4.1794 (2.8); 4.1683 (1.0); 4.1617 (2.9); 4.1506 (2.9); 4.1439 (1.1); 4.1329 (2.8); 4.1236 (1.1); 4.1151 (0.9); 4.1058 (1.1); 4.0881 (0.3); 3.3330 (34.8); 2.8928 (0.3); 2.5263 (0.4); 2.5216 (0.6); 2.5129 (8.2); 2.5084 (16.8); 2.5038 (22.5); 2.4992 (16.3); 2.4947 (7.8); 2.2109 (0.8); 2.1941 (1.4); 2.1778 (1.4); 2.1610 (0.9); 1.2339 (7.8); 1.2161 (16.0); 1.1984 (7.5); 0.9784 (10.3); 0.9657 (11.0); 0.9614 (11.5); 0.9487 (9.5); −0.0002 (5.0)
I.0659: $^1$H-NMR(400.2 MHz, $d_6$-DMSO):
δ = 8.9804 (1.0); 8.9635 (1.0); 3.7967 (1.0); 3.7797 (1.1); 3.7738 (1.2); 3.7566 (1.0); 3.6848 (16.0); 3.3360 (24.0); 2.8928 (0.8); 2.7333 (0.7); 2.5127 (6.0); 2.5083 (11.5); 2.5038 (14.8); 2.4992 (10.7); 2.4949 (5.1); 1.2509 (0.4); 1.2483 (0.4); 1.2391 (0.7); 1.2278 (0.6); 1.2164 (0.6); 1.2071 (0.4); 1.2046 (0.4); 0.6272 (0.6); 0.6184 (0.6); 0.6139 (0.6); 0.6039 (0.7); 0.5987 (0.4); 0.5926 (0.4); 0.5828 (0.4); 0.5704 (0.4); 0.5607 (0.4); 0.5573 (0.5); 0.5478 (0.7); 0.5371 (0.7); 0.5272 (0.7); 0.5059 (0.4); 0.5034 (0.4); 0.4903 (0.5); 0.4805 (0.8); 0.4681 (0.9); 0.4573 (0.7); 0.4157 (0.4); 0.4037 (0.6); 0.3925 (0.8); 0.3801 (0.7); 0.3702 (0.4); −0.0002 (3.0)
I.0660: $^1$H-NMR(400.2 MHz, $d_6$-DMSO):
δ = 8.8072 (1.8); 8.7884 (1.8); 7.3202 (1.4); 7.3165 (0.6); 7.3019 (4.0); 7.2902 (1.2); 7.2845 (6.0); 7.2712 (7.4); 7.2548 (2.6); 7.2462 (1.6); 7.2423 (1.6); 7.2371 (0.8); 7.2309 (1.0); 7.2249 (2.5); 7.2178 (0.6); 7.2125 (0.5); 7.2078 (0.8); 7.2036 (0.4); 4.6611 (0.7); 4.6473 (0.9); 4.6418 (1.0); 4.6383 (1.2); 4.6284 (1.1); 4.6247 (1.0); 4.6193 (1.0); 4.6054 (0.8); 4.1461 (1.7); 4.1285 (5.5); 4.1110 (5.8); 4.0932 (1.9); 3.3352 (47.6); 3.1957 (1.0); 3.1820 (1.1); 3.1612 (1.8); 3.1477 (1.7); 3.0887 (1.7); 3.0655 (1.7); 3.0543 (1.1); 3.0311 (1.0); 2.8915 (1.2); 2.7328 (1.0); 2.5258 (0.5); 2.5210 (0.8); 2.5124 (11.1); 2.5079 (22.6); 2.5034 (29.7); 2.4988 (21.4); 2.4943 (10.2); 1.1828 (7.7); 1.1651 (16.0); 1.1473 (7.4); −0.0002 (6.4)
I.0661: $^1$H-NMR(400.2 MHz, $d_6$-DMSO):
δ = 9.2826 (1.8); 3.6564 (16.0); 3.3350 (27.4); 2.8924 (0.5); 2.7332 (0.4); 2.7322 (0.4); 2.6015 (0.5); 2.5863 (0.6); 2.5794 (0.9); 2.5689 (0.9); 2.5644 (0.8); 2.5545 (1.0); 2.5465 (0.8); 2.5394 (0.4); 2.5322 (0.8); 2.5264 (0.4); 2.5212 (0.4); 2.5125 (5.3); 2.5080 (10.7); 2.5035 (14.1); 2.4989 (10.2); 2.4944 (4.8); 2.3324 (0.6); 2.3264 (0.3); 2.3133 (0.9); 2.3094 (1.1); 2.3025 (0.7); 2.2900 (0.9); 2.2812 (1.0); 2.2584 (0.6); 2.0013 (0.3); 1.9973 (0.5); 1.9888 (0.6); 1.9830 (0.4); 1.9734 (1.1); 1.9595 (0.4); 1.9503 (1.1); 1.9286 (0.5); −0.0002 (3.5)
I.0662: $^1$H-NMR(400.2 MHz, $d_6$-DMSO):
δ = 9.2976 (4.0); 4.1411 (2.4); 4.1234 (7.5); 4.1057 (7.6); 4.0879 (2.4); 3.3333 (40.1); 2.8929 (1.9); 2.7333 (1.7); 2.5915 (1.1); 2.5762 (1.4); 2.5695 (1.9); 2.5589 (2.0); 2.5545 (1.9); 2.5448 (2.2); 2.5368 (1.8); 2.5220 (2.4); 2.5083 (20.9); 2.5038 (27.0);

TABLE A-(I)-continued

NMR peak lists of compounds according to formula (I)

2.4994 (20.0); 2.3259 (1.3); 2.3026 (2.4); 2.2832 (1.9); 2.2746 (2.2); 2.2519 (1.2); 2.0073 (0.6); 1.9928 (1.1); 1.9845 (1.2); 1.9694 (2.5); 1.9475 (2.2); 1.9274 (1.1); 1.9060 (0.4); 1.2007 (7.9); 1.1830 (16.0); 1.1652 (7.6); −0.0002 (6.5)

I.0663: $^1$H-NMR(400.2 MHz, $d_6$-DMSO):
δ = 9.1469 (2.4); 9.1348 (4.8); 9.1224 (2.4); 6.5343 (0.5); 4.3462 (16.0); 4.3331 (15.8); 3.3351 (70.1); 3.2648 (0.4); 2.8934 (0.4); 2.7337 (0.4); 2.5094 (34.4); 2.5051 (45.0); 2.5006 (33.3); 0.0079 (0.5); −0.0002 (14.3); −0.0085 (0.5)

I.0664: $^1$H-NMR(400.2 MHz, $d_6$-DMSO):
δ = 9.0052 (2.7); 8.9926 (1.4); 7.9537 (0.5); 4.1669 (2.6); 4.1492 (7.7); 4.1314 (7.7); 4.1136 (2.6); 4.0652 (7.9); 4.0516 (7.5); 3.3336 (35.6); 2.8934 (2.6); 2.7339 (2.4); 2.5045 (27.3); 1.2345 (8.2); 1.2168 (16.0); 1.1990 (7.8); −0.0002 (4.8)

I.0665: $^1$H-NMR(400.2 MHz, $d_6$-DMSO):
δ = 9.0153 (1.4); 4.0891 (4.1); 4.0758 (4.0); 3.6809 (16.0); 3.3366 (26.7); 2.8941 (0.9); 2.7344 (0.8); 2.5058 (15.2); −0.0002 (2.4)

I.0666: $^1$H-NMR(400.2 MHz, $d_6$-DMSO):
δ = 9.3629 (4.2); 4.1108 (2.3); 4.0931 (7.2); 4.0753 (7.2); 4.0576 (2.3); 3.3358 (33.8); 2.5264 (0.4); 2.5085 (16.8); 2.5041 (22.1); 2.4998 (16.7); 1.4778 (2.0); 1.4655 (5.2); 1.4573 (5.8); 1.4463 (2.4); 1.2102 (2.5); 1.1991 (5.9); 1.1915 (12.7); 1.1739 (16.0); 1.1561 (7.5); −0.0002 (4.7)

I.0667: $^1$H-NMR(400.2 MHz, $d_6$-DMSO):
δ = 9.3531 (2.7); 3.6336 (16.0); 3.3345 (23.1); 2.8929 (0.8); 2.7336 (0.7); 2.5081 (12.0); 2.5039 (14.7); 2.4998 (10.8); 1.4944 (1.3); 1.4821 (3.4); 1.4739 (3.6); 1.4627 (1.5); 1.2270 (1.6); 1.2159 (3.6); 1.2077 (3.4); 1.1952 (1.2); −0.0002 (3.0)

I.0668: $^1$H-NMR(400.2 MHz, $d_6$-DMSO):
δ = 9.0476 (1.2); 3.6359 (11.3); 3.3336 (13.5); 2.8925 (0.4); 2.7328 (0.3); 2.5123 (3.4); 2.5081 (6.7); 2.5036 (8.8); 2.4991 (6.5); 2.4947 (3.2); 1.4698 (16.0); −0.0002 (1.9)

I.0669: $^1$H-NMR(400.2 MHz, $d_6$-DMSO):
δ = 8.8955 (1.7); 8.8759 (1.7); 4.3335 (1.9); 4.3181 (2.2); 4.3140 (2.2); 4.2985 (2.0); 4.2277 (0.3); 4.2100 (1.1); 4.2007 (0.9); 4.1922 (1.1); 4.1829 (2.8); 4.1726 (1.2); 4.1652 (2.9); 4.1548 (3.0); 4.1472 (1.1); 4.1371 (2.9); 4.1278 (1.1); 4.1193 (0.9); 4.1100 (1.1); 4.0923 (0.3); 3.3347 (38.0); 2.8928 (0.8); 2.7329 (0.6); 2.5262 (0.4); 2.5128 (8.3); 2.5084 (17.0); 2.5039 (22.4); 2.4993 (16.2); 2.4948 (7.7); 2.2129 (0.9); 2.1961 (1.5); 2.1797 (1.5); 2.1629 (1.0); 2.1460 (0.3); 1.2371 (7.9); 1.2193 (16.0); 1.2015 (7.6); 0.9798 (11.7); 0.9741 (11.3); 0.9627 (11.5); 0.9570 (10.7); −0.0002 (5.8)

I.0670: $^1$H-NMR(400.2 MHz, $d_6$-DMSO):
δ = 9.2261 (0.9); 9.2093 (0.9); 3.8276 (0.9); 3.8106 (1.0); 3.8048 (1.0); 3.7877 (0.9); 3.6917 (16.0); 3.3330 (19.8); 2.8926 (0.4); 2.5213 (0.4); 2.5126 (5.2); 2.5082 (10.4); 2.5036 (13.4); 2.4990 (9.6); 2.4945 (4.5); 1.2443 (0.3); 1.2413 (0.3); 1.2323 (0.6); 1.2210 (0.6); 1.2097 (0.6); 1.2005 (0.3); 1.1979 (0.4); 0.6303 (0.6); 0.6220 (0.6); 0.6169 (0.6); 0.6072 (0.7); 0.6027 (0.4); 0.5957 (0.4); 0.5863 (0.4); 0.5755 (0.4); 0.5659 (0.4); 0.5623 (0.5); 0.5528 (0.6); 0.5457 (0.5); 0.5421 (0.6); 0.5323 (0.8); 0.5201 (0.3); 0.5128 (0.6); 0.5044 (0.4); 0.5011 (0.5); 0.4920 (0.8); 0.4797 (0.9); 0.4691 (0.7); 0.4274 (0.4); 0.4160 (0.6); 0.4046 (0.7); 0.3998 (0.4); 0.3921 (0.7); 0.3825 (0.4); −0.0002 (3.9)

I.0671: $^1$H-NMR(400.2 MHz, $d_6$-DMSO):
δ = 9.0666 (2.1); 9.0477 (2.2); 7.3247 (1.4); 7.3063 (4.6); 7.2886 (7.1); 7.2825 (6.2); 7.2783 (8.6); 7.2618 (2.7); 7.2492 (1.5); 7.2451 (1.8); 7.2399 (1.1); 7.2280 (2.6); 7.2210 (0.7); 7.2161 (0.6); 7.2111 (0.8); 4.6826 (0.8); 4.6689 (1.1); 4.6632 (1.2); 4.6596 (1.4); 4.6496 (1.2); 4.6459 (1.2); 4.6405 (1.2); 4.6266 (0.8); 4.1511 (2.1); 4.1334 (6.5); 4.1157 (6.7); 4.0979 (2.2); 3.3358 (59.2); 3.2022 (1.2); 3.1887 (1.3); 3.1678 (2.0); 3.1543 (1.9); 3.0839 (2.0); 3.0604 (2.0); 3.0496 (1.3); 3.0260 (1.2); 2.8914 (1.1); 2.7325 (1.0); 2.5078 (24.2); 2.5033 (31.6); 2.4989 (23.8); 1.1860 (7.8); 1.1683 (16.0); 1.1505 (7.5); −0.0002 (5.6)

I.0672: $^1$H-NMR(400.2 MHz, $d_6$-DMSO):
δ = 9.5049 (2.4); 7.9524 (0.5); 3.6670 (16.0); 3.3369 (38.1); 2.8924 (2.9); 2.7326 (2.7); 2.6153 (0.6); 2.5994 (0.8); 2.5931 (1.1); 2.5828 (1.1); 2.5780 (1.1); 2.5685 (1.3); 2.5605 (1.0); 2.5461 (0.9); 2.5080 (11.8); 2.5037 (15.4); 2.4994 (11.7); 2.3392 (0.7); 2.3163 (1.4); 2.2966 (1.1); 2.2888 (1.3); 2.2656 (0.7); 2.0230 (0.4); 2.0089 (0.6); 2.0002 (0.8); 1.9845 (1.1); 1.9601 (1.2); 1.9380 (0.6); −0.0002 (2.9)

I.0673: $^1$H-NMR(400.2 MHz, $d_6$-DMSO):
δ = 9.2177 (3.2); 4.1377 (2.3); 4.1200 (7.3); 4.1022 (7.4); 4.0845 (2.3); 3.3332 (34.9); 2.5850 (0.9); 2.5805 (0.6); 2.5690 (1.2); 2.5636 (1.7); 2.5565 (1.3); 2.5521 (1.7); 2.5482 (1.6); 2.5379 (2.0); 2.5302 (1.6); 2.5128 (9.4); 2.5084 (18.1); 2.5038 (23.8); 2.4992 (17.4); 2.4948 (8.4); 2.3354 (1.1); 2.3126 (2.1); 2.2925 (1.6); 2.2827 (1.8); 2.2607 (1.0); 1.9942 (0.6); 1.9851 (0.7); 1.9799 (0.9); 1.9653 (1.8); 1.9568 (1.5); 1.9443 (2.2); 1.9345 (0.9); 1.9235 (1.1); 1.1920 (7.8); 1.1743 (16.0); 1.1565 (7.5); −0.0002 (5.7)

I.0674: $^1$H-NMR(400.2 MHz, $d_6$-DMSO):
δ = 9.2002 (1.9); 7.9528 (0.4); 3.6522 (16.0); 3.3347 (19.8); 2.8927 (2.6); 2.7329 (2.2); 2.5951 (0.5); 2.5906 (0.3); 2.5793 (0.7); 2.5737 (0.9); 2.5669 (0.7); 2.5623 (0.9); 2.5583 (0.9); 2.5480 (1.1); 2.5404 (0.9); 2.5260 (0.9); 2.5128 (4.8); 2.5084 (9.7); 2.5039 (12.8); 2.4993 (9.3); 2.4949 (4.5); 2.3420 (0.6); 2.3192 (1.2); 2.2992 (0.9); 2.2894 (1.0); 2.2673 (0.6); 1.9879 (0.4); 1.9832 (0.5); 1.9746 (0.6); 1.9679 (1.0); 1.9600 (0.9); 1.9466 (1.2); 1.9376 (0.5); 1.9256 (0.6); −0.0002 (2.9)

I.0675: $^1$H-NMR(400.2 MHz, $d_6$-DMSO):
δ = 8.7404 (2.1); 8.7213 (2.1); 7.3156 (1.3); 7.2973 (4.3); 7.2792 (8.1); 7.2714 (8.5); 7.2551 (2.5); 7.2433 (1.5); 7.2391 (1.6); 7.2332 (0.9); 7.2284 (1.0); 7.2221 (2.4); 7.2145 (0.6); 7.2107 (0.6); 7.2054 (0.8); 7.2009 (0.4); 4.6533 (0.8); 4.6398 (1.0); 4.6343 (1.0); 4.6301 (1.3); 4.6208 (1.2); 4.6168 (1.1); 4.6110 (1.1); 4.5973 (0.8); 4.1468 (1.9); 4.1293 (5.9); 4.1116 (6.2); 4.1015 (0.3); 4.0938 (2.0); 3.3353 (47.8); 3.1999 (1.1); 3.1865 (1.1); 3.1655 (2.0); 3.1521 (1.8); 3.0955 (1.8); 3.0717 (1.9); 3.0612 (1.1); 3.0374 (1.0); 2.8917 (1.8); 2.7330 (1.5); 2.5258 (0.5); 2.5125 (11.2); 2.5081 (22.4); 2.5036 (29.2); 2.4991 (21.4); 2.4948 (10.5); 1.1815 (7.8); 1.1637 (16.0); 1.1460 (7.4); −0.0002 (6.0)

I.0676: $^1$H-NMR(400.2 MHz, $d_6$-DMSO):
δ = 8.9396 (0.9); 8.9225 (0.9); 3.7765 (1.0); 3.7593 (1.1); 3.7533 (1.1); 3.7361 (1.0); 3.6795 (16.0); 3.3327 (16.7); 2.8929 (0.6); 2.7331 (0.5); 2.5128 (5.1); 2.5083 (10.1); 2.5038 (13.1); 2.4992 (9.4); 2.4948 (4.5); 1.2673 (0.3); 1.2643 (0.4); 1.2554 (0.6); 1.2440 (0.6); 1.2326 (0.6); 1.2236 (0.3); 1.2207 (0.4); 0.6268 (0.6); 0.6177 (0.6); 0.6131 (0.6); 0.6059 (0.5); 0.6029 (0.6); 0.5980 (0.4); 0.5919 (0.4); 0.5820 (0.4); 0.5619 (0.3); 0.5518 (0.4); 0.5482 (0.5); 0.5385 (0.6); 0.5316 (0.5); 0.5281 (0.6); 0.5180 (0.7); 0.5060 (0.3); 0.4970 (0.6); 0.4839 (0.5); 0.4741 (0.8); 0.4620 (0.9); 0.4508 (0.6); 0.3999 (0.4); 0.3886 (0.6); 0.3767 (0.8); 0.3642 (0.7); 0.3543 (0.4); −0.0002 (3.3)

I.0677: $^1$H-NMR(400.2 MHz, $d_6$-DMSO):
δ = 8.6551 (2.9); 8.6410 (5.8); 8.6265 (2.8); 7.9511 (0.5); 6.5496 (0.8); 5.2928 (3.2); 5.2811 (4.9); 5.2774 (5.1); 5.2659 (3.2); 4.0642 (0.4); 4.0345 (16.0); 4.0200 (15.5); 3.9903 (0.4); 3.8073 (4.7); 3.7999 (2.5); 3.7960 (5.1); 3.7809 (12.9); 3.7699 (7.8); 3.7623 (6.9); 3.7415 (6.7); 3.7294 (4.3); 3.7199 (6.0); 3.7084 (6.3); 3.6989 (10.2); 3.6878 (2.2); 3.6726 (5.0); 3.6397 (0.5); 3.4800 (0.4); 3.3395 (1126.4); 2.8906 (3.4); 2.7472 (0.4); 2.7309 (3.1); 2.6757 (2.2); 2.6714 (3.0); 2.6670 (2.2); 2.5068 (373.2); 2.5024 (483.2); 2.4981 (360.4); 2.3802 (0.4); 2.3335 (2.1); 2.3293 (2.9); 2.3251 (2.2); 2.1996 (1.2); 2.1832 (1.5); 2.1789 (2.7); 2.1634 (3.5); 2.1445 (3.9); 2.1288 (3.3); 2.1081 (1.5); 1.9239 (1.8); 1.9099 (2.9); 1.8930 (2.6); 1.8759 (2.2); 1.8627 (1.3); 1.2343 (0.7); 0.0075 (1.4); −0.0004 (30.4)

TABLE A-(I)-continued

| NMR peak lists of compounds according to formula (I) |
| --- |
| I.0678: $^1$H-NMR(400.2 MHz, $d_6$-DMSO): δ = 8.5507 (3.6); 8.5453 (3.6); 7.9527 (0.7); 5.2829 (3.2); 5.2784 (2.6); 5.2714 (4.9); 5.2674 (5.0); 5.2628 (2.6); 5.2559 (3.2); 4.0191 (0.3); 3.9899 (16.0); 3.9753 (15.7); 3.8027 (5.4); 3.7978 (2.5); 3.7913 (5.6); 3.7767 (14.4); 3.7652 (8.6); 3.7595 (7.2); 3.7381 (6.1); 3.7256 (4.4); 3.7162 (6.4); 3.7047 (6.5); 3.6945 (8.0); 3.6922 (8.3); 3.6843 (2.5); 3.6659 (4.9); 3.3448 (329.7); 2.8915 (5.3); 2.7320 (4.5); 2.6814 (0.4); 2.6770 (0.8); 2.6724 (1.1); 2.6679 (0.8); 2.6635 (0.4); 2.5257 (3.3); 2.5124 (70.0); 2.5079 (139.4); 2.5034 (182.2); 2.4988 (131.5); 2.4944 (62.9); 2.3393 (0.4); 2.3347 (0.8); 2.3302 (1.1); 2.3257 (0.8); 2.1972 (1.3); 2.1810 (1.6); 2.1765 (2.9); 2.1607 (3.6); 2.1559 (1.6); 2.1468 (2.1); 2.1421 (4.2); 2.1263 (3.6); 2.1217 (2.0); 2.1057 (1.6); 1.9162 (1.6); 1.9025 (2.8); 1.8858 (2.5); 1.8681 (2.1); 1.8549 (1.2); 1.2345 (0.4); 0.0079 (0.6); −0.0002 (16.6); −0.0085 (0.5) |
| I.0679: $^1$H-NMR(400.2 MHz, $d_6$-DMSO): δ = 9.0555 (0.5); 9.0414 (1.1); 9.0272 (0.5); 5.3018 (0.6); 5.2974 (0.5); 5.2954 (0.5); 5.2904 (1.0); 5.2864 (1.0); 5.2748 (0.6); 4.0234 (3.8); 4.0088 (3.7); 3.8101 (1.1); 3.8037 (0.5); 3.7987 (1.1); 3.7838 (2.8); 3.7726 (1.7); 3.7656 (1.4); 3.7439 (1.2); 3.7314 (0.9); 3.7221 (1.3); 3.7105 (1.4); 3.7017 (2.0); 3.6897 (0.4); 3.6759 (1.0); 3.3347 (28.4); 2.8907 (2.2); 2.7307 (1.8); 2.5249 (0.7); 2.5201 (1.1); 2.5114 (17.3); 2.5069 (35.6); 2.5024 (47.3); 2.4978 (34.6); 2.4933 (16.8); 2.4760 (1.7); 2.4078 (16.0); 2.1863 (0.6); 2.1706 (0.7); 2.1657 (0.3); 2.1565 (0.4); 2.1519 (0.8); 2.1361 (0.7); 2.1315 (0.4); 1.9250 (0.3); 1.9107 (0.6); 1.8949 (0.5); 1.8764 (0.4); −0.0002 (6.3) |
| I.0680: $^1$H-NMR(400.2 MHz, $d_6$-DMSO): δ = 9.3948 (2.2); 7.9525 (0.7); 3.6548 (16.0); 3.3365 (68.1); 2.8911 (4.3); 2.7316 (3.8); 2.6002 (0.6); 2.5790 (1.1); 2.5677 (1.1); 2.5634 (1.0); 2.5532 (1.3); 2.5459 (1.0); 2.5311 (1.0); 2.5250 (0.9); 2.5069 (30.4); 2.5026 (38.2); 2.4982 (28.0); 2.3867 (15.5); 2.3305 (0.8); 2.3082 (1.3); 2.2881 (1.0); 2.2784 (1.2); 2.2567 (0.7); 1.9986 (0.3); 1.9894 (0.4); 1.9842 (0.6); 1.9702 (1.1); 1.9613 (0.9); 1.9495 (1.3); 1.9289 (0.7); −0.0002 (3.1) |
| I.0681: $^1$H-NMR(400.2 MHz, $d_6$-DMSO): δ = 9.3645 (1.6); 4.0452 (8.6); 3.6802 (16.0); 3.3342 (7.2); 2.8940 (0.7); 2.7345 (0.7); 2.5091 (8.2); 2.5051 (10.2); 2.5010 (7.4); −0.0002 (2.6) |
| I.0682: $^1$H-NMR(400.2 MHz, $d_6$-DMSO): δ = 9.5403 (1.5); 3.6306 (16.0); 3.3334 (7.4); 2.5138 (3.5); 2.5093 (7.2); 2.5047 (9.4); 2.5001 (6.7); 2.4955 (3.2); 1.4992 (1.1); 1.4870 (2.8); 1.4786 (3.0); 1.4675 (1.3); 1.2191 (1.3); 1.2080 (2.9); 1.1996 (2.8); 1.1872 (1.0); −0.0002 (3.4) |
| I.0683: $^1$H-NMR(400.2 MHz, $d_6$-DMSO): δ = 9.5176 (2.8); 7.9527 (0.4); 4.1483 (2.2); 4.1306 (7.2); 4.1128 (7.3); 4.0951 (2.3); 3.3358 (66.8); 2.8923 (3.4); 2.7332 (2.8); 2.7319 (2.7); 2.6047 (0.8); 2.6000 (0.5); 2.5895 (1.0); 2.5825 (1.4); 2.5721 (1.4); 2.5674 (1.3); 2.5577 (1.6); 2.5497 (1.3); 2.5421 (0.6); 2.5354 (1.2); 2.5258 (0.6); 2.5210 (0.9); 2.5124 (13.7); 2.5079 (28.1); 2.5033 (37.0); 2.4986 (26.4); 2.4941 (12.4); 2.3304 (1.0); 2.3254 (0.6); 2.3118 (1.4); 2.3078 (1.7); 2.3006 (1.0); 2.2884 (1.4); 2.2795 (1.5); 2.2568 (0.9); 2.0169 (0.4); 2.0067 (0.5); 2.0026 (0.7); 1.9942 (0.8); 1.9883 (0.6); 1.9789 (1.7); 1.9651 (0.7); 1.9559 (1.7); 1.9361 (0.7); 1.9280 (0.5); 1.2074 (7.5); 1.1989 (0.4); 1.1897 (16.0); 1.1720 (7.3); 1.1591 (0.5); −0.0002 (8.4) |
| I.0684: $^1$H-NMR(400.2 MHz, $d_6$-DMSO): δ = 9.1863 (1.4); 3.6222 (11.8); 3.3358 (11.5); 2.8936 (1.1); 2.7341 (1.0); 2.5134 (3.2); 2.5091 (6.3); 2.5046 (8.1); 2.5000 (5.9); 2.4957 (2.8); 1.4614 (16.0); −0.0002 (1.4) |
| I.0685: $^1$H-NMR(400.2 MHz, $d_6$-DMSO): δ = 9.3750 (1.4); 9.3562 (1.4); 7.3092 (0.4); 7.2893 (4.6); 7.2850 (5.0); 7.2764 (16.0); 7.2639 (1.0); 7.2354 (1.0); 7.2269 (1.0); 7.2232 (0.9); 7.2140 (1.1); 7.2091 (0.8); 7.2003 (0.6); 4.6394 (0.5); 4.6251 (0.7); 4.6205 (0.8); 4.6152 (0.9); 4.6063 (0.8); 4.6011 (0.8); 4.5964 (0.8); 4.5823 (0.6); 4.1379 (1.7); 4.1202 (5.6); 4.1025 (5.6); 4.0847 (1.8); 3.3351 (22.9); 3.1864 (0.9); 3.1724 (1.0); 3.1520 (1.7); 3.1381 (1.5); 3.0812 (1.7); 3.0567 (1.6); 3.0468 (1.0); 3.0224 (0.9); 2.8920 (1.4); 2.7332 (1.2); 2.5265 (0.4); 2.5130 (7.1); 2.5087 (14.2); 2.5042 (18.6); 2.4997 (13.5); 2.4953 (6.5); 1.1665 (6.1); 1.1488 (12.6); 1.1310 (5.8); −0.0002 (4.0) |
| I.0686: $^1$H-NMR(400.2 MHz, $d_6$-DMSO): δ = 9.6426 (2.2); 7.9529 (0.4); 3.6623 (16.0); 3.3345 (14.8); 2.8932 (2.6); 2.7334 (2.4); 2.6133 (0.6); 2.5925 (1.2); 2.5852 (0.9); 2.5805 (1.2); 2.5770 (1.1); 2.5662 (1.4); 2.5592 (1.1); 2.5443 (0.9); 2.5086 (9.7); 2.5045 (13.0); 2.5003 (10.6); 2.3439 (0.7); 2.3216 (1.6); 2.3008 (1.1); 2.2910 (1.5); 2.2694 (0.7); 2.0023 (0.4); 1.9917 (0.6); 1.9808 (1.3); 1.9688 (1.1); 1.9599 (1.5); 1.9465 (0.6); 1.9390 (0.8); 1.9318 (0.5); −0.0002 (2.3) |
| I.0687: $^1$H-NMR(400.2 MHz, $d_6$-DMSO): δ = 9.6394 (3.8); 7.9537 (0.5); 4.1483 (2.4); 4.1306 (7.5); 4.1128 (7.6); 4.0951 (2.4); 3.3340 (24.6); 2.8936 (3.2); 2.7339 (2.7); 2.6037 (1.0); 2.5990 (0.6); 2.5869 (1.4); 2.5829 (1.8); 2.5756 (1.3); 2.5708 (1.8); 2.5670 (1.6); 2.5565 (2.1); 2.5494 (1.6); 2.5347 (1.4); 2.5275 (0.5); 2.5135 (8.0); 2.5091 (15.7); 2.5046 (20.4); 2.5001 (14.7); 2.4957 (7.1); 2.3371 (1.2); 2.3147 (2.3); 2.2943 (1.7); 2.2840 (2.2); 2.2626 (1.1); 2.0035 (0.7); 1.9893 (1.0); 1.9797 (2.0); 1.9665 (1.7); 1.9585 (2.4); 1.9522 (1.2); 1.9442 (0.9); 1.9377 (1.3); 1.9301 (0.6); 1.9170 (0.3); 1.1971 (7.9); 1.1794 (16.0); 1.1617 (7.6); −0.0002 (4.8) |
| I.0688: $^1$H-NMR(400.2 MHz, $d_6$-DMSO): δ = 9.6398 (1.2); 4.3676 (16.0); 3.3378 (5.6); 2.8946 (0.4); 2.5152 (4.4); 2.5108 (9.0); 2.5062 (11.9); 2.5016 (8.6); 2.4971 (4.1); −0.0002 (3.4) |
| I.0689: $^1$H-NMR(400.2 MHz, $d_6$-DMSO): δ = 8.7346 (1.0); 8.7207 (1.9); 8.7064 (1.0); 4.1563 (2.3); 4.1385 (7.1); 4.1207 (7.1); 4.1030 (2.3); 4.0298 (7.1); 4.0152 (7.0); 3.3332 (25.3); 2.5127 (7.6); 2.5085 (14.6); 2.5040 (18.9); 2.4995 (13.9); 1.2254 (8.0); 1.2076 (16.0); 1.1898 (7.7); −0.0002 (4.5) |
| I.0690: $^1$H-NMR(400.2 MHz, $d_6$-DMSO): δ = 8.7437 (0.6); 8.7300 (1.1); 8.7161 (0.6); 4.0518 (4.3); 4.0372 (4.2); 3.6681 (16.0); 3.3331 (11.7); 2.8928 (0.4); 2.7332 (0.3); 2.5082 (7.7); 2.5039 (10.1); 2.4995 (7.5); −0.0002 (2.4); −0.0012 (2.3) |
| I.0691: $^1$H-NMR(400.2 MHz, $d_6$-DMSO): δ = 9.0902 (4.1); 4.0975 (2.3); 4.0798 (7.2); 4.0620 (7.2); 4.0443 (2.3); 3.3343 (30.2); 2.8932 (0.3); 2.5265 (0.4); 2.5086 (16.8); 2.5042 (21.8); 2.4998 (16.1); 1.4651 (2.0); 1.4528 (5.2); 1.4446 (5.6); 1.4335 (2.3); 1.2023 (2.4); 1.1912 (5.4); 1.1830 (5.3); 1.1725 (9.0); 1.1549 (16.0); 1.1372 (7.6); −0.0002 (5.3) |
| I.0692: $^1$H-NMR(400.2 MHz, $d_6$-DMSO): δ = 9.0724 (3.0); 3.6187 (16.0); 3.3330 (18.5); 2.5081 (10.8); 2.5041 (13.9); 1.4797 (1.2); 1.4672 (3.4); 1.4591 (3.7); 1.4480 (1.5); 1.2188 (1.5); 1.2075 (3.5); 1.1994 (3.4); 1.1870 (1.2); −0.0002 (2.7) |
| I.0693: $^1$H-NMR(400.2 MHz, $d_6$-DMSO): δ = 8.7288 (1.2); 3.6201 (12.5); 3.3320 (11.7); 2.8926 (0.8); 2.7335 (0.7); 2.7325 (0.7); 2.5126 (3.7); 2.5081 (7.4); 2.5035 (9.7); 2.4989 (6.9); 2.4943 (3.2); 1.4612 (16.0); −0.0002 (2.6) |
| I.0694: $^1$H-NMR(400.2 MHz, $d_6$-DMSO): δ = 8.6191 (2.6); 8.5997 (2.6); 4.2849 (2.0); 4.2665 (3.2); 4.2498 (2.0); 4.2193 (0.4); 4.2014 (1.1); 4.1921 (0.9); 4.1837 (1.2); 4.1743 (2.8); 4.1567 (3.1); 4.1443 (2.9); 4.1266 (2.8); 4.1174 (1.2); 4.1090 (1.0); 4.0996 (1.1); 4.0816 (0.4); 3.3306 (67.0); 2.8916 (0.3); 2.7319 (0.3); 2.5031 (43.0); 2.4993 (36.8); 2.2188 (0.4); 2.2019 (1.1); 2.1849 (1.9); 2.1682 (1.9); 2.1513 (1.2); 2.1342 (0.4); 1.2280 (8.0); 1.2104 (16.0); 1.1925 (7.7); 0.9644 (12.6); 0.9521 (14.6); 0.9481 (15.6); 0.9358 (12.1); −0.0002 (6.8); −0.0014 (5.9) |

TABLE A-(I)-continued

NMR peak lists of compounds according to formula (I)

I.0695: $^1$H-NMR(400.2 MHz, $d_6$-DMSO):
δ = 9.5127 (0.9); 9.4974 (0.9); 3.7491 (0.8); 3.7330 (0.8); 3.7254 (0.9); 3.7094 (0.8); 3.6850 (16.0); 3.3332 (15.7); 2.8931 (0.5); 2.7332 (0.4); 2.5131 (4.6); 2.5088 (9.2); 2.5043 (12.0); 2.4997 (8.6); 2.4953 (4.2); 1.2387 (0.3); 1.2355 (0.4); 1.2269 (0.6); 1.2151 (0.6); 1.2034 (0.6); 1.1952 (0.4); 1.1917 (0.4); 0.6410 (0.6); 0.6321 (0.6); 0.6272 (0.6); 0.6172 (0.7); 0.6126 (0.4); 0.6061 (0.4); 0.5963 (0.4); 0.5818 (0.4); 0.5716 (0.4); 0.5682 (0.5); 0.5582 (0.6); 0.5515 (0.5); 0.5481 (0.6); 0.5378 (0.8); 0.5260 (0.3); 0.5177 (0.7); 0.5053 (0.6); 0.4957 (0.8); 0.4834 (0.9); 0.4724 (0.6); 0.4112 (0.4); 0.4002 (0.6); 0.3883 (0.8); 0.3758 (0.7); 0.3657 (0.4); −0.0002 (3.0)
I.0696: $^1$H-NMR(400.2 MHz, $d_6$-DMSO):
δ = 9.3501 (1.8); 4.3734 (16.0); 3.3379 (20.6); 2.5141 (5.7); 2.5097 (11.6); 2.5052 (15.1); 2.5006 (10.8); 2.4961 (5.1); −0.0002 (4.3)
I.0697: $^1$H-NMR(400.2 MHz, $d_6$-DMSO):
δ = 8.5643 (1.0); 8.5502 (2.0); 8.5363 (1.0); 4.1579 (2.3); 4.1401 (7.1); 4.1224 (7.2); 4.1046 (2.4); 4.0440 (7.6); 4.0295 (7.5); 3.3344 (46.9); 2.8927 (1.6); 2.7333 (1.4); 2.5085 (21.1); 2.5040 (27.4); 2.4996 (20.6); 1.2285 (7.9); 1.2107 (16.0); 1.1929 (7.7); −0.0002 (5.9)
I.0698: $^1$H-NMR(400.2 MHz, $d_6$-DMSO):
δ = 8.5758 (0.4); 8.5618 (0.8); 8.5477 (0.4); 4.0666 (4.1); 4.0522 (4.1); 3.6701 (16.0); 3.3352 (15.9); 2.8929 (0.9); 2.7341 (0.7); 2.7329 (0.8); 2.5134 (3.8); 2.5089 (7.9); 2.5043 (10.5); 2.4997 (7.5); 2.4952 (3.6); −0.0002 (3.8)
I.0699: $^1$H-NMR(600.2 MHz, CDCl3):
δ = 8.0543 (0.8); 7.2649 (1.9); 6.8558 (0.7); 4.2215 (0.8); 4.2096 (2.4); 4.1977 (2.4); 4.1858 (0.8); 3.1944 (2.5); 2.0454 (0.7); 1.7016 (15.2); 1.5907 (16.0); 1.2791 (2.6); 1.2672 (5.2); 1.2597 (0.9); 1.2554 (3.0); 1.2479 (0.4); 0.8934 (0.3); 0.8818 (0.7); 0.8698 (0.3); −0.0002 (2.1)
I.0700: $^1$H-NMR(400.1 MHz, $d_6$-DMSO):
δ = 12.5801 (3.7); 9.3923 (12.4); 9.3362 (0.4); 7.9756 (13.3); 4.0576 (0.4); 4.0398 (1.2); 4.0220 (1.3); 4.0041 (0.5); 3.3223 (17.5); 2.5035 (20.9); 1.9897 (4.7); 1.9107 (1.8); 1.4318 (16.0); 1.3804 (1.0); 1.3583 (0.8); 1.2346 (0.6); 1.1935 (1.8); 1.1763 (3.1); 1.1330 (15.8); −0.0002 (4.1)
I.0701: $^1$H-NMR(600.2 MHz, CDCl3):
δ = 7.9666 (0.7); 7.2629 (1.5); 4.2762 (0.7); 4.2643 (2.2); 4.2525 (2.2); 4.2406 (0.7); 1.6963 (16.0); 1.5691 (1.6); 1.3142 (2.3); 1.3023 (4.5); 1.2904 (2.2); −0.0002 (1.9)
I.0702: $^1$H-NMR(400.1 MHz, $d_6$-DMSO):
δ = 12.5559 (1.6); 12.4585 (0.4); 8.7244 (11.4); 4.0372 (0.3); 3.9276 (1.6); 3.6051 (0.6); 3.4470 (0.3); 3.4303 (0.4); 3.3229 (43.7); 3.2158 (0.8); 3.1883 (0.5); 3.1647 (0.4); 3.1306 (0.4); 3.0044 (0.3); 2.6692 (0.6); 2.5015 (94.8); 2.3274 (0.8); 1.9888 (1.0); 1.4423 (0.4); 1.4045 (5.3); 1.3923 (14.4); 1.3850 (16.0); 1.3743 (7.4); 1.3356 (0.9); 1.2359 (1.0); 1.2254 (0.9); 1.1948 (1.4); 1.1744 (1.1); 1.1547 (6.8); 1.1440 (15.8); 1.1363 (15.6); 1.1243 (6.2); 1.0428 (0.3); −0.0002 (43.8)
I.0703: $^1$H-NMR(400.1 MHz, $d_6$-DMSO):
δ = 12.6057 (0.6); 12.5971 (0.6); 12.5864 (0.7); 12.5438 (0.8); 12.5343 (0.8); 12.4949 (0.7); 12.4889 (0.6); 12.4034 (0.3); 8.7297 (11.5); 8.3050 (0.4); 3.9436 (1.9); 3.6066 (0.4); 3.3290 (72.6); 3.1960 (0.9); 3.1528 (0.5); 3.0999 (0.4); 3.0619 (0.3); 3.0216 (0.3); 2.6700 (0.5); 2.5020 (73.8); 2.3282 (0.7); 1.9895 (1.0); 1.9089 (0.4); 1.4451 (0.4); 1.4071 (5.3); 1.3952 (14.6); 1.3876 (16.0); 1.3771 (7.1); 1.3367 (0.8); 1.2911 (0.4); 1.2348 (1.2); 1.1907 (1.3); 1.1755 (1.0); 1.1508 (6.8); 1.1400 (15.4); 1.1326 (15.0); 1.1202 (5.8); 1.0870 (0.7); −0.0002 (18.7)
I.0704: $^1$H-NMR(400.1 MHz, $d_6$-DMSO):
δ = 8.9241 (3.3); 4.0057 (2.7); 3.9898 (5.5); 3.9739 (2.8); 3.3348 (5.5); 2.5094 (4.2); 2.3902 (16.0); 1.5771 (1.4); 1.5602 (2.8); 1.5423 (2.9); 1.5254 (1.6); 1.5078 (0.4); 1.4443 (1.4); 1.4322 (3.7); 1.4243 (4.0); 1.4135 (1.7); 1.1826 (1.7); 1.1717 (3.9); 1.1639 (3.8); 1.1517 (1.4); 0.8817 (4.3); 0.8633 (8.5); 0.8448 (4.0)
I.0705: $^1$H-NMR(400.1 MHz, CDCl3):
δ = 7.2632 (1.8); 6.5264 (1.8); 5.1002 (1.0); 5.0817 (1.6); 5.0631 (1.1); 5.0448 (0.3); 2.6548 (4.2); 2.6343 (7.7); 2.6144 (4.9); 2.5028 (16.0); 2.4355 (0.5); 2.4290 (0.7); 2.4103 (1.5); 2.4046 (1.5); 2.3980 (1.4); 2.3910 (1.6); 2.3853 (1.7); 2.3668 (0.9); 2.3606 (0.7); 2.1547 (0.8); 2.1307 (2.2); 2.1209 (2.5); 2.1145 (2.6); 2.1112 (2.6); 2.1041 (2.7); 2.0993 (2.6); 2.0862 (1.6); 2.0795 (1.8); 2.0619 (0.6); 2.0550 (0.6); 1.8725 (0.4); 1.8457 (0.9); 1.8201 (1.0); 1.7949 (0.4); 1.6994 (0.6); 1.6957 (0.6); 1.6745 (1.1); 1.6487 (0.9); 1.6273 (0.5); 1.5878 (2.6); −0.0002 (2.4)
I.0706: $^1$H-NMR(400.2 MHz, $d_6$-DMSO):
δ = 8.9195 (3.4); 4.0959 (2.2); 4.0782 (6.8); 4.0604 (6.9); 4.0427 (2.2); 3.3325 (30.7); 2.8927 (1.6); 2.7333 (1.4); 2.5261 (0.4); 2.5126 (8.8); 2.5083 (17.6); 2.5038 (23.1); 2.4993 (16.8); 2.4950 (8.2); 1.4585 (1.9); 1.4463 (4.9); 1.4380 (5.3); 1.4270 (2.2); 1.1923 (2.3); 1.1809 (5.9); 1.1772 (9.0); 1.1731 (5.6); 1.1595 (16.0); 1.1417 (7.1); −0.0002 (5.9)
I.0707: $^1$H-NMR(400.2 MHz, $d_6$-DMSO):
δ = 8.9056 (1.9); 3.6184 (16.0); 3.3344 (20.0); 2.5215 (0.3); 2.5129 (4.4); 2.5085 (9.0); 2.5039 (11.8); 2.4993 (8.6); 2.4948 (4.1); 1.4745 (1.1); 1.4622 (3.0); 1.4539 (3.2); 1.4428 (1.3); 1.2099 (1.4); 1.1988 (3.1); 1.1905 (3.0); 1.1781 (1.1); −0.0002 (3.8)
I.0708: $^1$H-NMR(400.2 MHz, $d_6$-DMSO):
δ = 8.5458 (1.1); 3.6241 (11.9); 3.3373 (25.3); 2.5127 (4.2); 2.5082 (8.5); 2.5037 (11.2); 2.4991 (8.1); 2.4946 (3.9); 1.4703 (16.0); −0.0002 (2.7)
I.0709: $^1$H-NMR(400.2 MHz, $d_6$-DMSO):
δ = 8.3273 (1.7); 8.3078 (1.7); 4.3418 (1.9); 4.3270 (2.1); 4.3225 (2.1); 4.3076 (1.9); 4.2080 (1.0); 4.1987 (0.9); 4.1902 (1.1); 4.1810 (2.7); 4.1700 (1.1); 4.1632 (2.8); 4.1522 (2.8); 4.1453 (1.1); 4.1345 (2.7); 4.1252 (1.0); 4.1168 (0.9); 4.1075 (1.0); 4.0896 (0.3); 3.3358 (55.8); 2.8929 (0.4); 2.7332 (0.4); 2.5087 (22.6); 2.5042 (29.6); 2.4998 (21.7); 2.2236 (0.9); 2.2068 (1.5); 2.1907 (1.5); 2.1743 (1.0); 2.1573 (0.3); 1.2336 (7.5); 1.2159 (15.1); 1.1981 (7.2); 0.9801 (11.1); 0.9641 (16.0); 0.9485 (10.4); −0.0002 (6.7)
I.0710: $^1$H-NMR(400.2 MHz, $d_6$-DMSO):
δ = 8.6671 (0.9); 8.6502 (0.9); 3.8270 (1.1); 3.8098 (1.2); 3.8043 (1.2); 3.7871 (1.1); 3.6837 (16.0); 3.3363 (24.8); 2.8922 (0.4); 2.7326 (0.4); 2.5081 (10.0); 2.5037 (13.2); 2.4993 (9.8); 1.2661 (0.4); 1.2566 (0.7); 1.2454 (0.6); 1.2345 (0.7); 1.2227 (0.4); 1.2142 (0.3); 0.6220 (0.6); 0.6128 (0.6); 0.6085 (0.6); 0.5988 (0.7); 0.5929 (0.4); 0.5873 (0.4); 0.5777 (0.4); 0.5668 (0.4); 0.5573 (0.4); 0.5541 (0.5); 0.5461 (0.6); 0.5339 (0.6); 0.5230 (0.7); 0.5027 (0.4); 0.4942 (0.3); 0.4819 (0.5); 0.4719 (0.6); 0.4593 (0.8); 0.4486 (0.8); 0.4365 (0.4); 0.4185 (0.4); 0.4060 (0.7); 0.3967 (0.8); 0.3826 (0.6); 0.3731 (0.4); −0.0002 (2.7)
I.0711: $^1$H-NMR(400.2 MHz, $d_6$-DMSO):
δ = 8.4846 (1.9); 8.4660 (2.0); 7.3179 (1.4); 7.2998 (4.2); 7.2873 (1.3); 7.2819 (5.6); 7.2651 (7.3); 7.2469 (3.3); 7.2305 (1.0); 7.2246 (2.5); 7.2177 (0.5); 7.2118 (0.5); 7.2074 (0.8); 4.6827 (0.8); 4.6688 (1.0); 4.6611 (1.3); 4.6497 (1.2); 4.6478 (1.2); 4.6422 (1.1); 4.6283 (0.8); 4.1460 (1.5); 4.1394 (0.4); 4.1299 (4.5); 4.1283 (4.6); 4.1121 (4.8); 4.1108 (4.7); 4.1008 (0.4); 4.0941 (1.6); 3.3365 (55.4); 3.1993 (1.0); 3.1856 (1.0); 3.1649 (2.1); 3.1512 (1.9); 3.1118 (2.0); 3.0897 (2.0); 3.0774 (1.0); 3.0553 (1.0); 2.5259 (0.6); 2.5123 (13.2); 2.5080 (26.5); 2.5035 (34.7); 2.4990 (25.2); 2.4946 (12.2); 1.1854 (7.7); 1.1677 (16.0); 1.1499 (7.4); −0.0002 (7.2)
I.0712: $^1$H-NMR(400.2 MHz, $d_6$-DMSO):
δ = 9.0169 (1.6); 3.6517 (16.0); 3.3359 (23.5); 2.8925 (0.4); 2.5979 (0.5); 2.5830 (0.6); 2.5755 (0.8); 2.5690 (0.6); 2.5653 (0.8); 2.5606 (0.8); 2.5510 (0.9); 2.5467 (0.5); 2.5428 (0.8); 2.5354 (0.3); 2.5284 (0.8); 2.5218 (0.4); 2.5129 (4.4); 2.5084 (9.1); 2.5039

TABLE A-(I)-continued

| NMR peak lists of compounds according to formula (I) |
|---|
| (12.0); 2.4992 (8.6); 2.4947 (4.0); 2.3357 (0.6); 2.3169 (0.8); 2.3125 (1.0); 2.3053 (0.6); 2.2933 (0.8); 2.2849 (0.9); 2.2618 (0.5); 1.9970 (0.4); 1.9871 (0.6); 1.9734 (0.7); 1.9642 (0.7); 1.9595 (0.4); 1.9445 (0.8); 1.9358 (0.3); 1.9251 (0.4); 1.9221 (0.4); −0.0002 (3.9) |
| I.0713: $^{1}$H-NMR(400.2 MHz, $d_6$-DMSO):<br>δ = 9.0333 (2.9); 4.1366 (2.3); 4.1189 (7.4); 4.1011 (7.5); 4.0834 (2.4); 3.3351 (37.5); 2.8928 (0.7); 2.7336 (0.6); 2.5868 (0.9); 2.5820 (0.6); 2.5718 (1.0); 2.5645 (1.5); 2.5583 (1.1); 2.5542 (1.5); 2.5495 (1.4); 2.5400 (1.7); 2.5318 (1.5); 2.5263 (0.8); 2.5130 (8.0); 2.5085 (15.8); 2.5040 (21.0); 2.4994 (15.2); 2.4949 (7.3); 2.3303 (1.1); 2.3110 (1.5); 2.3068 (1.8); 2.2996 (1.2); 2.2875 (1.5); 2.2790 (1.7); 2.2560 (1.0); 2.0062 (0.5); 1.9961 (0.6); 1.9921 (0.8); 1.9832 (1.1); 1.9781 (0.6); 1.9683 (1.4); 1.9641 (1.1); 1.9608 (1.2); 1.9550 (0.8); 1.9419 (1.5); 1.9222 (0.7); 1.9196 (0.7); 1.9140 (0.6); 1.1954 (7.8); 1.1776 (16.0); 1.1599 (7.6); −0.0002 (5.2) |
| I.0714: $^{1}$H-NMR(400.2 MHz, $d_6$-DMSO):<br>δ = 8.9171 (2.0); 8.9047 (3.9); 8.8923 (2.0); 4.3328 (16.0); 4.3193 (15.7); 3.3377 (77.1); 3.3212 (0.4); 2.8937 (0.5); 2.7349 (0.4); 2.5280 (0.7); 2.5233 (1.1); 2.5145 (16.4); 2.5100 (33.7); 2.5054 (44.5); 2.5008 (31.9); 2.4963 (15.0); 0.0080 (0.5); −0.0002 (15.9); −0.0086 (0.5) |
| I.0715: $^{1}$H-NMR(400.2 MHz, $d_6$-DMSO):<br>δ = 9.4282 (0.9); 9.4137 (1.9); 9.3991 (1.0); 8.0264 (4.1); 8.0235 (4.3); 4.1598 (2.3); 4.1421 (7.2); 4.1243 (7.3); 4.1065 (2.4); 4.0560 (6.8); 4.0413 (6.9); 3.3407 (43.4); 2.8938 (0.6); 2.7344 (0.5); 2.5147 (7.4); 2.5104 (15.2); 2.5060 (20.3); 2.5014 (15.1); 2.4972 (7.5); 1.2265 (7.9); 1.2088 (16.0); 1.1909 (7.7); −0.0002 (3.4) |
| I.0716: $^{1}$H-NMR(400.2 MHz, $d_6$-DMSO):<br>δ = 9.4479 (0.6); 9.4337 (1.1); 9.4192 (0.6); 8.0300 (2.6); 8.0267 (2.7); 4.0782 (4.2); 4.0634 (4.1); 3.6718 (16.0); 3.3420 (21.8); 2.8946 (1.2); 2.7350 (1.0); 2.5155 (4.1); 2.5113 (8.1); 2.5068 (10.7); 2.5023 (7.9); −0.0002 (2.0) |
| I.0717: $^{1}$H-NMR(400.2 MHz, $d_6$-DMSO):<br>δ = 9.4890 (1.9); 7.9813 (2.3); 7.9779 (2.4); 7.9744 (1.0); 3.6169 (16.0); 3.3412 (22.2); 2.8942 (2.1); 2.7355 (1.8); 2.7343 (1.8); 2.5153 (3.9); 2.5108 (8.0); 2.5062 (10.6); 2.5016 (7.6); 2.4970 (3.6); 1.4999 (1.1); 1.4877 (2.7); 1.4794 (3.0); 1.4684 (1.3); 1.2160 (1.3); 1.2049 (2.8); 1.1966 (2.8); 1.1844 (1.0); −0.0002 (2.4) |
| I.0718: $^{1}$H-NMR(400.2 MHz, $d_6$-DMSO):<br>δ = 9.0342 (1.3); 8.1363 (1.8); 8.1329 (1.8); 8.1294 (0.7); 3.5984 (12.5); 3.3411 (15.1); 2.5159 (2.9); 2.5114 (6.0); 2.5068 (7.8); 2.5022 (5.6); 2.4977 (2.6); 1.4689 (16.0); −0.0002 (2.4) |
| I.0719: $^{1}$H-NMR(400.2 MHz, $d_6$-DMSO):<br>δ = 9.0151 (1.7); 8.9953 (1.7); 8.2829 (3.9); 8.2795 (4.0); 8.2762 (1.6); 4.3088 (2.0); 4.2900 (2.9); 4.2712 (2.0); 4.1905 (0.9); 4.1812 (0.9); 4.1727 (1.0); 4.1634 (3.1); 4.1550 (0.4); 4.1455 (3.5); 4.1430 (3.4); 4.1334 (0.4); 4.1252 (3.1); 4.1158 (1.0); 4.1075 (0.9); 4.0981 (0.9); 3.3404 (52.9); 2.8946 (1.8); 2.7349 (1.5); 2.5290 (0.4); 2.5241 (0.7); 2.5156 (8.7); 2.5111 (17.6); 2.5066 (23.0); 2.5020 (16.6); 2.4974 (7.8); 2.1961 (0.9); 2.1789 (1.6); 2.1617 (1.6); 2.1446 (1.0); 1.2249 (7.8); 1.2072 (16.0); 1.1894 (7.5); 0.9864 (10.2); 0.9694 (9.9); 0.9510 (9.7); 0.9339 (9.3); −0.0002 (4.7) |
| I.0720: $^{1}$H-NMR(400.2 MHz, $d_6$-DMSO):<br>δ = 9.4337 (1.1); 9.4172 (1.1); 8.2002 (2.5); 8.1968 (2.5); 3.7506 (1.1); 3.7340 (1.1); 3.7266 (1.2); 3.7101 (1.1); 3.6746 (16.0); 3.3405 (22.1); 2.5155 (4.4); 2.5111 (8.8); 2.5066 (11.5); 2.5020 (8.4); 2.4976 (4.1); 1.2349 (0.4); 1.2319 (0.4); 1.2233 (0.6); 1.2115 (0.6); 1.1996 (0.6); 1.1912 (0.4); 1.1879 (0.4); 0.6508 (0.6); 0.6409 (0.6); 0.6376 (0.6); 0.6274 (0.7); 0.6207 (0.4); 0.6161 (0.5); 0.6061 (0.4); 0.6015 (0.4); 0.5914 (0.5); 0.5881 (0.5); 0.5781 (0.7); 0.5684 (0.7); 0.5579 (0.6); 0.4994 (0.5); 0.4880 (0.8); 0.4758 (0.9); 0.4651 (0.7); 0.4075 (0.4); 0.3958 (0.7); 0.3845 (0.9); 0.3724 (0.8); 0.3599 (0.4); −0.0002 (2.3) |
| I.0721: $^{1}$H-NMR(400.2 MHz, $d_6$-DMSO):<br>δ = 9.3184 (1.5); 9.2990 (1.5); 8.0766 (3.1); 8.0732 (3.2); 8.0697 (1.3); 7.2899 (5.9); 7.2882 (5.7); 7.2782 (16.0); 7.2667 (0.8); 7.2303 (0.9); 7.2194 (1.1); 7.2087 (1.2); 7.2023 (0.5); 7.1962 (0.7); 4.6729 (0.6); 4.6585 (0.7); 4.6534 (0.7); 4.6486 (0.8); 4.6391 (0.8); 4.6343 (0.7); 4.6292 (0.8); 4.6148 (0.6); 4.1215 (1.6); 4.1037 (5.4); 4.0860 (5.5); 4.0682 (1.8); 3.3456 (47.8); 3.1902 (0.8); 3.1759 (0.9); 3.1557 (1.5); 3.1415 (1.4); 3.0856 (1.5); 3.0611 (1.5); 3.0511 (0.9); 3.0266 (0.8); 2.8931 (2.0); 2.7355 (1.6); 2.7342 (1.6); 2.5242 (0.4); 2.5155 (6.5); 2.5110 (13.4); 2.5064 (17.8); 2.5018 (12.8); 2.4972 (6.0); 1.1455 (6.2); 1.1277 (13.2); 1.1100 (6.0); −0.0002 (3.3) |
| I.0722: $^{1}$H-NMR(400.2 MHz, $d_6$-DMSO):<br>δ = 9.5038 (2.1); 8.1096 (2.5); 8.1062 (2.5); 3.6401 (16.0); 3.3421 (24.5); 2.8952 (0.6); 2.7363 (0.5); 2.6231 (0.6); 2.6073 (0.7); 2.6014 (1.0); 2.5947 (0.8); 2.5903 (1.0); 2.5862 (1.0); 2.5761 (1.2); 2.5683 (0.9); 2.5608 (0.4); 2.5540 (0.8); 2.5159 (4.6); 2.5116 (8.8); 2.5071 (11.4); 2.5026 (8.4); 2.4985 (4.1); 2.3462 (0.6); 2.3234 (1.3); 2.3034 (1.0); 2.2940 (1.2); 2.2718 (0.6); 2.0108 (0.3); 1.9967 (0.6); 1.9879 (0.6); 1.9786 (1.0); 1.9734 (1.0); 1.9584 (1.3); 1.9507 (0.7); 1.9366 (0.7); −0.0002 (1.8) |
| I.0723: $^{1}$H-NMR(400.2 MHz, $d_6$-DMSO):<br>δ = 9.4871 (3.4); 8.1017 (4.1); 8.0983 (4.1); 8.0949 (1.6); 4.1310 (2.3); 4.1133 (7.4); 4.0956 (7.5); 4.0778 (2.4); 3.3417 (51.0); 2.6124 (0.9); 2.6075 (0.6); 2.5968 (1.1); 2.5908 (1.6); 2.5842 (1.1); 2.5797 (1.5); 2.5756 (1.4); 2.5654 (1.8); 2.5577 (1.4); 2.5502 (0.6); 2.5435 (1.2); 2.5287 (0.4); 2.5240 (0.6); 2.5153 (8.2); 2.5109 (16.7); 2.5063 (21.9); 2.5017 (15.6); 2.4972 (7.3); 2.3388 (1.0); 2.3332 (0.6); 2.3189 (1.7); 2.3159 (2.0); 2.2960 (1.5); 2.2864 (1.8); 2.2643 (1.0); 2.0069 (0.5); 1.9971 (0.8); 1.9927 (0.9); 1.9841 (0.9); 1.9766 (1.5); 1.9695 (1.5); 1.9554 (2.1); 1.9471 (0.9); 1.9342 (1.0); 1.1710 (7.8); 1.1533 (16.0); 1.1356 (7.5); −0.0002 (4.2) |
| I.0724: $^{1}$H-NMR(400.2 MHz, $d_6$-DMSO):<br>δ = 9.6974 (1.9); 9.6843 (3.7); 9.6712 (1.9); 7.9952 (9.9); 7.9917 (10.1); 7.9883 (4.0); 4.4040 (16.0); 4.3905 (15.8); 3.3436 (76.9); 3.2025 (0.5); 2.8954 (0.9); 2.7358 (0.7); 2.6335 (0.8); 2.5304 (0.6); 2.5257 (0.9); 2.5170 (13.0); 2.5125 (26.7); 2.5080 (35.2); 2.5034 (25.2); 2.4988 (11.9); −0.0002 (9.4) |
| I.0725: $^{1}$H-NMR(400.1 MHz, CDCl3):<br>δ = 7.2642 (1.8); 6.5401 (2.0); 5.1179 (0.3); 5.0996 (1.3); 5.0811 (1.9); 5.0625 (1.3); 5.0443 (0.4); 2.6528 (4.6); 2.6323 (8.2); 2.6125 (4.7); 2.5338 (2.0); 2.5059 (16.0); 2.4768 (1.4); 2.4353 (0.6); 2.4289 (0.8); 2.4100 (1.7); 2.4045 (1.8); 2.3979 (1.6); 2.3909 (1.8); 2.3852 (2.0); 2.3667 (1.0); 2.3606 (0.8); 2.1538 (0.9); 2.1304 (2.7); 2.1193 (2.9); 2.1132 (3.1); 2.1041 (3.1); 2.0994 (3.1); 2.0865 (1.8); 2.0796 (2.0); 2.0621 (0.5); 2.0551 (0.5); 1.8725 (0.4); 1.8458 (1.1); 1.8202 (1.1); 1.7948 (0.4); 1.6957 (0.7); 1.6745 (1.2); 1.6488 (1.1); 1.6274 (0.5); 1.6003 (2.0); −0.0002 (2.4) |
| I.0726: $^{1}$H-NMR(400.2 MHz, $d_6$-DMSO):<br>δ = 9.4748 (3.9); 7.9752 (4.2); 7.9719 (4.4); 7.9686 (1.8); 7.9550 (0.7); 4.1001 (2.4); 4.0824 (7.5); 4.0647 (7.5); 4.0470 (2.4); 3.3409 (51.2); 2.8943 (5.4); 2.7347 (4.5); 2.5285 (0.4); 2.5236 (0.8); 2.5152 (8.4); 2.5108 (16.9); 2.5062 (22.2); 2.5016 (16.0); 2.4971 (7.7); 1.4901 (2.0); 1.4780 (5.1); 1.4698 (5.5); 1.4588 (2.3); 1.1995 (2.4); 1.1885 (5.3); 1.1803 (5.2); 1.1681 (2.0); 1.1579 (7.9); 1.1402 (16.0); 1.1225 (7.5); −0.0002 (3.9) |
| I.0727: $^{1}$H-NMR(400.2 MHz, $d_6$-DMSO):<br>δ = 9.6090 (3.7); 4.1937 (2.3); 4.1759 (7.4); 4.1582 (7.4); 4.1405 (2.4); 3.6872 (6.7); 3.6612 (8.0); 3.4497 (7.9); 3.4236 (6.4); 3.3458 (49.3); 2.8958 (1.9); 2.7363 (1.7); 2.5299 (0.9); 2.5165 (17.6); 2.5121 (33.7); 2.5076 (43.0); 2.5030 (31.3); 2.4987 (15.1); 1.2126 (7.7); 1.1949 (16.0); 1.1772 (7.5) |

TABLE A-(I)-continued

NMR peak lists of compounds according to formula (I)

I.0728: $^{1}$H-NMR(400.2 MHz, $d_6$-DMSO):
δ = 9.5019 (3.7); 4.1883 (2.2); 4.1705 (7.3); 4.1528 (7.4); 4.1351 (2.3); 3.6781 (6.2); 3.6520 (7.6); 3.4634 (7.4); 3.4373 (5.9); 3.3431 (50.5); 2.8960 (2.1); 2.7364 (1.8); 2.6768 (0.3); 2.5303 (1.1); 2.5256 (1.7); 2.5169 (20.3); 2.5124 (40.3); 2.5078 (52.5); 2.5032 (38.2); 2.4987 (18.3); 1.2016 (7.6); 1.1839 (16.0); 1.1661 (7.5)
I.0729: $^{1}$H-NMR(400.1 MHz, CDCl3):
δ = 7.2643 (2.4); 6.9058 (0.8); 6.8885 (0.8); 4.8977 (0.6); 4.8807 (1.1); 4.8674 (1.1); 4.8633 (0.9); 4.8502 (0.6); 3.8187 (16.0); 2.5993 (1.3); 2.5818 (2.7); 2.5641 (1.7); 2.5435 (15.8); 2.3164 (0.3); 2.3113 (0.5); 2.2983 (0.6); 2.2932 (0.7); 2.2803 (0.7); 2.2752 (0.9); 2.2624 (0.8); 2.2573 (0.5); 2.2443 (0.4); 2.1959 (0.4); 2.1790 (1.1); 2.1619 (1.2); 2.1431 (1.1); 2.1226 (10.3); 1.5831 (1.9); −0.0002 (2.9)
I.0730: $^{1}$H-NMR(400.1 MHz, CDCl3):
δ = 7.2610 (7.8); 6.8952 (0.7); 6.8769 (0.7); 4.8993 (0.6); 4.8824 (1.0); 4.8691 (1.0); 4.8650 (0.8); 4.8519 (0.6); 3.8199 (16.0); 2.5986 (1.7); 2.5810 (3.9); 2.5633 (2.1); 2.5168 (15.8); 2.3129 (0.4); 2.3000 (0.5); 2.2946 (0.7); 2.2819 (0.7); 2.2768 (0.8); 2.2639 (0.7); 2.2586 (0.4); 2.2459 (0.3); 2.1982 (0.4); 2.1813 (1.1); 2.1642 (1.2); 2.1455 (0.9); 2.1223 (14.5); 1.5514 (7.5); −0.0002 (9.5)
I.0731: $^{1}$H-NMR(400.1 MHz, CDCl3):
δ = 8.2125 (1.2); 8.1961 (1.2); 7.2611 (17.6); 5.2994 (0.9); 4.8377 (1.1); 4.8295 (2.4); 4.8209 (2.2); 4.8122 (2.4); 4.8040 (1.2); 4.3444 (2.3); 4.3266 (7.2); 4.3087 (7.3); 4.2909 (2.5); 4.1682 (0.6); 4.1598 (0.7); 4.1546 (0.7); 4.1458 (0.8); 4.1402 (1.4); 4.1317 (1.7); 4.1265 (1.7); 4.1179 (1.4); 4.1023 (1.3); 4.0941 (1.6); 4.0879 (1.6); 4.0796 (1.4); 4.0660 (0.7); 4.0596 (0.7); 4.0515 (0.6); 2.9862 (0.4); 2.1223 (1.4); 2.1079 (2.7); 2.0935 (1.4); 2.0437 (0.6); 1.5586 (24.4); 1.4825 (0.4); 1.3582 (7.9); 1.3404 (16.0); 1.3225 (7.8); 1.2587 (0.5); 0.0078 (0.8); −0.0002 (21.6)
I.0732: $^{1}$H-NMR(400.1 MHz, CDCl3):
δ = 7.9890 (0.8); 7.9715 (0.8); 7.2630 (3.5); 4.9099 (0.5); 4.8942 (1.1); 4.8791 (1.1); 4.8630 (0.6); 4.3132 (1.2); 4.2953 (3.8); 4.2775 (3.8); 4.2597 (1.3); 2.6203 (0.3); 2.6034 (0.8); 2.5868 (1.1); 2.5822 (1.3); 2.5785 (1.0); 2.5654 (1.3); 2.5620 (1.4); 2.5578 (1.1); 2.5416 (1.0); 2.5244 (0.3); 2.3480 (0.4); 2.3262 (0.7); 2.3118 (0.8); 2.3056 (0.5); 2.2961 (0.5); 2.2920 (0.6); 2.2206 (0.4); 2.2046 (0.8); 2.1994 (0.5); 2.1883 (0.6); 2.1839 (0.9); 2.1684 (0.8); 2.1527 (0.3); 2.1479 (0.5); 2.1107 (16.0); 1.5659 (2.2); 1.3521 (4.0); 1.3343 (8.0); 1.3164 (3.9); 1.2558 (0.4); −0.0002 (4.4)
I.0733: $^{1}$H-NMR(400.1 MHz, CDCl3):
δ = 7.9689 (0.7); 7.9522 (0.7); 7.2626 (4.3); 5.3002 (0.3); 4.9359 (0.5); 4.9199 (1.0); 4.9051 (1.0); 4.8887 (0.5); 3.8316 (16.0); 2.6004 (0.8); 2.5810 (1.8); 2.5636 (2.0); 2.5454 (1.0); 2.3515 (0.4); 2.3480 (0.4); 2.3291 (0.6); 2.3155 (0.7); 2.3126 (0.6); 2.2988 (0.5); 2.2964 (0.6); 2.2798 (0.4); 2.2224 (0.4); 2.2062 (0.8); 2.2022 (0.5); 2.1896 (0.7); 2.1861 (0.9); 2.1700 (0.8); 2.1539 (0.4); 2.1501 (0.5); 2.1100 (15.1); 1.5609 (7.5); −0.0002 (5.1); −0.0081 (0.3)
I.0734: $^{1}$H-NMR(400.1 MHz, CDCl3):
δ = 7.9668 (0.7); 7.9496 (0.7); 7.2641 (2.5); 4.9353 (0.5); 4.9192 (1.0); 4.9045 (1.0); 4.8882 (0.5); 3.8439 (0.3); 3.8316 (16.0); 2.6005 (0.7); 2.5816 (1.6); 2.5636 (1.7); 2.5459 (0.8); 2.3513 (0.3); 2.3476 (0.4); 2.3289 (0.7); 2.3153 (0.7); 2.3124 (0.6); 2.3099 (0.6); 2.2963 (0.6); 2.2930 (0.4); 2.2795 (0.3); 2.2224 (0.4); 2.2062 (0.8); 2.2023 (0.5); 2.1896 (0.6); 2.1861 (0.9); 2.1700 (0.8); 2.1538 (0.4); 2.1501 (0.5); 2.1222 (0.4); 2.1102 (11.8); 1.5715 (1.5); −0.0002 (3.1)
I.0735: $^{1}$H-NMR(400.1 MHz, $d_6$-DMSO):
δ = 8.6798 (1.5); 8.6616 (1.7); 4.5461 (0.5); 4.5266 (1.3); 4.5101 (1.3); 4.4923 (0.6); 3.6688 (13.9); 3.3114 (3.0); 2.5934 (0.5); 2.5769 (1.1); 2.5596 (1.8); 2.5435 (1.3); 2.5321 (1.9); 2.5003 (4.3); 2.4196 (1.5); 2.4003 (11.8); 2.3850 (1.8); 2.0536 (16.0); −0.0002 (2.4)
I.0736: $^{1}$H-NMR(400.1 MHz, $d_6$-DMSO):
δ = 8.6737 (1.0); 8.6550 (1.1); 4.5107 (0.4); 4.4907 (0.9); 4.4757 (0.8); 4.4562 (0.4); 4.1582 (0.5); 4.1486 (0.8); 4.1405 (1.6); 4.1307 (1.7); 4.1227 (1.7); 4.1129 (1.6); 4.1044 (0.9); 4.0952 (0.6); 4.0861 (0.3); 3.3123 (10.5); 2.5784 (0.8); 2.5593 (1.3); 2.5433 (1.0); 2.5374 (1.5); 2.5185 (0.9); 2.5048 (3.5); 2.5010 (4.5); 2.4967 (3.5); 2.4179 (1.4); 2.3985 (11.7); 2.3820 (1.2); 2.0555 (16.0); 2.0427 (2.0); 2.0275 (1.3); 2.0219 (1.3); 2.0097 (0.6); 2.0011 (0.6); 1.2349 (0.6); 1.2153 (3.6); 1.1976 (7.4); 1.1799 (3.7); −0.0002 (5.1)
I.0737: $^{1}$H-NMR(400.1 MHz, CDCl3):
δ = 7.2619 (12.2); 7.0642 (1.2); 5.9950 (1.0); 4.0854 (7.8); 4.0726 (7.9); 3.4906 (0.6); 2.9420 (0.4); 2.9284 (0.4); 2.8781 (16.0); 2.8660 (16.0); 1.5928 (7.2); 1.2553 (0.7); −0.0002 (16.0)
I.0738: $^{1}$H-NMR(400.1 MHz, CDCl3):
δ = 7.9295 (1.5); 7.5188 (0.6); 7.2598 (105.2); 6.9961 (0.6); 5.8050 (1.0); 4.2676 (0.3); 4.1294 (9.6); 4.1175 (9.6); 3.8254 (0.9); 3.7955 (0.6); 3.4895 (0.4); 3.0846 (0.6); 2.9875 (0.6); 2.9745 (0.7); 2.9538 (1.2); 2.9406 (0.7); 2.9030 (16.0); 2.8909 (16.0); 2.5076 (0.6); 1.7043 (0.4); 1.5489 (21.9); 1.4136 (0.3); 1.4003 (0.4); 1.2551 (7.4); 1.1060 (0.4); 1.0902 (0.3); 0.8808 (0.7); 0.8551 (0.6); 0.1576 (0.3); 0.1462 (0.6); −0.0002 (139.1); −0.0223 (1.2); −0.0301 (0.6); −0.1487 (0.6)
I.0739: $^{1}$H-NMR(400.1 MHz, CDCl3):
δ = 7.8161 (1.2); 7.2658 (2.9); 5.3013 (0.4); 4.3225 (2.3); 4.3046 (7.1); 4.2868 (7.3); 4.2699 (11.4); 4.2582 (9.4); 1.5941 (0.8); 1.3521 (8.0); 1.3342 (16.0); 1.3164 (7.9); −0.0002 (3.8)
I.0740: $^{1}$H-NMR(400.1 MHz, CDCl3):
δ = 7.5981 (2.0); 7.2606 (29.3); 5.2994 (1.8); 4.2088 (2.4); 4.1910 (7.6); 4.1731 (7.7); 4.1554 (2.6); 1.7151 (2.1); 1.7024 (6.1); 1.6944 (6.3); 1.6826 (2.7); 1.5468 (46.2); 1.5181 (0.3); 1.3703 (2.6); 1.3585 (6.2); 1.3505 (6.5); 1.3378 (2.3); 1.2604 (8.0); 1.2426 (16.0); 1.2248 (7.8); −0.0002 (35.7); −0.0082 (2.1)
I.0741: $^{1}$H-NMR(400.1 MHz, $d_6$-DMSO):
δ = 9.5059 (2.9); 9.4879 (2.9); 5.9701 (4.5); 5.9520 (4.4); 5.7530 (0.3); 4.2610 (2.1); 4.2434 (6.6); 4.2256 (6.8); 4.2079 (2.3); 3.3101 (14.0); 2.5062 (5.8); 2.5020 (7.4); 2.4979 (5.7); 1.2476 (8.6); 1.2299 (16.0); 1.2121 (7.7); 0.8747 (0.4); 0.8582 (1.1); 0.8406 (0.5); −0.0002 (7.9)
I.0742: $^{1}$H-NMR(400.1 MHz, $d_6$-DMSO):
δ = 9.9154 (2.1); 9.8982 (2.2); 5.9970 (3.1); 5.9795 (3.2); 5.7539 (0.9); 4.2755 (1.6); 4.2681 (0.5); 4.2582 (5.2); 4.2405 (5.5); 4.2227 (2.0); 4.2126 (0.4); 3.3154 (5.0); 2.5067 (3.4); 2.5023 (4.6); 2.4979 (3.5); 2.4232 (29.0); 2.4045 (1.0); 2.0743 (1.5); 1.2541 (7.6); 1.2364 (16.0); 1.2187 (7.7); −0.0002 (6.0); −0.0083 (0.4)
I.0743: $^{1}$H-NMR(400.1 MHz, $d_6$-DMSO):
δ = 9.6057 (2.6); 9.5878 (2.6); 5.9935 (4.5); 5.9755 (4.5); 4.2669 (1.9); 4.2492 (5.9); 4.2315 (6.2); 4.2138 (2.1); 3.3163 (3.6); 2.5073 (3.2); 2.5029 (4.3); 2.4986 (3.2); 2.0752 (0.5); 1.2546 (7.7); 1.2369 (16.0); 1.2191 (7.5); −0.0002 (6.4)
I.0744: $^{1}$H-NMR(400.1 MHz, $d_6$-DMSO):
δ = 9.6024 (2.5); 9.5845 (2.6); 5.9881 (4.2); 5.9702 (4.2); 4.2650 (1.7); 4.2474 (5.5); 4.2297 (5.8); 4.2120 (2.0); 3.3148 (13.4); 2.5070 (3.8); 2.5026 (5.1); 2.4983 (3.8); 2.0746 (0.7); 1.2533 (7.6); 1.2355 (16.0); 1.2178 (7.6); −0.0002 (8.1)
I.0745: $^{1}$H-NMR(400.1 MHz, $d_6$-DMSO):
δ = 9.5358 (3.0); 7.5718 (1.7); 7.4393 (3.8); 7.3067 (1.9); 4.3113 (16.0); 3.3169 (5.9); 2.5075 (2.2); 2.5032 (2.9); 2.4988 (2.2); −0.0002 (4.2)

TABLE A-(I)-continued

| NMR peak lists of compounds according to formula (I) |
|---|
| I.0746: $^1$H-NMR(400.1 MHz, $d_6$-DMSO):<br>δ = 9.1704 (1.2); 7.3696 (0.6); 7.2369 (1.3); 7.1043 (0.7); 4.1048 (0.8); 4.0871 (2.6); 4.0693 (2.6); 4.0516 (0.9); 3.3163 (5.3); 2.5062 (1.4); 2.5018 (1.9); 2.4975 (1.4); 1.4349 (16.0); 1.1685 (2.6); 1.1508 (5.5); 1.1331 (2.6); −0.0002 (1.1) |
| I.0747: $^1$H-NMR(400.1 MHz, $d_6$-DMSO):<br>δ = 9.3180 (14.3); 7.5613 (7.4); 7.4286 (16.0); 7.2959 (8.1); 4.7680 (7.1); 4.7442 (10.4); 4.7414 (10.6); 4.7178 (7.5); 4.4329 (4.5); 4.4291 (4.9); 4.4109 (11.6); 4.4069 (11.4); 4.3889 (7.0); 4.3849 (6.3); 4.3021 (5.0); 4.2857 (6.5); 4.2800 (6.1); 4.2761 (7.0); 4.2635 (5.8); 4.2596 (7.0); 4.2543 (5.7); 4.2378 (4.0); 3.3090 (59.6); 2.5059 (20.2); 2.5014 (25.4); 2.4969 (20.8); 2.4819 (5.8); 2.4771 (5.1); 2.4728 (4.2); 2.4654 (5.3); 2.4595 (5.7); 2.4543 (4.4); 2.4421 (3.7); 2.4381 (3.3); 2.3793 (2.7); 2.3526 (6.4); 2.3293 (7.1); 2.3261 (7.1); 2.2997 (4.7); 2.2728 (1.8); 2.0728 (5.4); 1.9884 (0.8); 1.2452 (1.1); 1.1755 (0.4); 0.8747 (0.4); 0.8582 (1.2); 0.8403 (0.5); −0.0002 (19.4) |
| I.0748: $^1$H-NMR(400.1 MHz, $d_6$-DMSO):<br>δ = 9.8443 (0.8); 7.4531 (0.5); 7.3207 (1.0); 7.1884 (0.5); 5.3169 (1.1); 3.7473 (16.0); 3.3146 (1.8); 2.5065 (0.7); 2.5022 (1.0); 2.4979 (0.8); −0.0002 (1.3) |
| I.0749: $^1$H-NMR(400.1 MHz, CDCl3):<br>δ = 7.2619 (3.5); 4.4666 (10.3); 4.2743 (1.3); 4.2566 (4.0); 4.2388 (4.1); 4.2213 (1.4); 3.7435 (16.0); 2.5600 (15.6); 1.5588 (1.1); 1.3120 (4.1); 1.2943 (8.2); 1.2766 (4.2); −0.0002 (4.8) |
| I.0750: $^1$H-NMR(400.1 MHz, CDCl3):<br>δ = 7.6877 (1.3); 7.6713 (1.4); 7.2639 (2.0); 4.9101 (0.7); 4.8945 (1.7); 4.8789 (1.8); 4.8630 (0.8); 3.8130 (16.0); 2.6091 (0.4); 2.5938 (1.1); 2.5768 (2.5); 2.5591 (2.7); 2.5430 (1.4); 2.5278 (0.5); 2.3413 (0.3); 2.3252 (0.7); 2.3074 (1.0); 2.2904 (1.2); 2.2744 (1.0); 2.2571 (0.4); 2.1893 (0.5); 2.1722 (1.1); 2.1545 (1.4); 2.1365 (1.3); 2.1073 (13.5); 1.5769 (2.0); −0.0002 (2.7) |
| I.0751: $^1$H-NMR(400.1 MHz, CDCl3):<br>δ = 7.2664 (1.6); 6.9170 (1.2); 6.9004 (1.3); 4.8970 (0.7); 4.8804 (1.6); 4.8662 (1.6); 4.8500 (0.7); 3.8189 (16.0); 2.5991 (2.2); 2.5816 (4.9); 2.5640 (2.8); 2.5435 (15.8); 2.5175 (0.4); 2.3114 (0.6); 2.2935 (1.0); 2.2756 (1.2); 2.2616 (1.0); 2.2441 (0.4); 2.1955 (0.5); 2.1789 (1.3); 2.1616 (1.5); 2.1430 (1.2); 2.1226 (16.0); 2.0082 (0.5); 1.6091 (2.8); 1.2562 (0.4); −0.0002 (1.7) |
| I.0752: $^1$H-NMR(400.1 MHz, CDCl3):<br>δ = 7.9826 (1.2); 7.9671 (1.3); 7.2641 (2.1); 4.9838 (0.7); 4.9707 (1.6); 4.9557 (1.7); 4.9428 (0.8); 4.3187 (1.3); 4.3010 (4.0); 4.2833 (4.1); 4.2657 (1.5); 3.1730 (0.6); 3.1616 (0.7); 3.1378 (2.2); 3.1262 (2.2); 3.1108 (2.2); 3.0986 (2.2); 3.0754 (0.7); 3.0633 (0.6); 2.1416 (16.0); 1.5755 (2.7); 1.3536 (4.1); 1.3359 (8.1); 1.3183 (4.2); −0.0002 (2.4) |
| I.0753: $^1$H-NMR(400.1 MHz, CDCl3):<br>δ = 7.2641 (1.6); 6.7096 (1.3); 6.6945 (1.3); 4.9427 (0.7); 4.9294 (1.7); 4.9143 (1.7); 4.9014 (0.8); 4.2960 (1.4); 4.2784 (4.0); 4.2607 (4.1); 4.2430 (1.4); 3.1458 (0.7); 3.1342 (0.7); 3.1106 (2.1); 3.0990 (2.0); 3.0739 (2.1); 3.0619 (2.1); 3.0389 (0.8); 3.0267 (0.7); 2.5815 (1.7); 2.5546 (13.1); 2.5259 (1.0); 2.1323 (16.0); 1.5949 (1.5); 1.3421 (4.2); 1.3245 (8.1); 1.3068 (4.1); −0.0002 (2.1) |
| I.0754: $^1$H-NMR(400.1 MHz, CDCl3):<br>δ = 7.5099 (1.2); 7.4941 (1.2); 7.2627 (2.6); 4.9514 (0.7); 4.9380 (1.6); 4.9222 (1.7); 4.9089 (0.8); 4.3172 (1.3); 4.2995 (3.9); 4.2817 (4.0); 4.2640 (1.4); 3.1562 (0.5); 3.1442 (0.6); 3.1210 (2.2); 3.1087 (2.4); 3.0994 (2.5); 3.0856 (2.2); 3.0640 (0.6); 3.0502 (0.6); 2.1527 (16.0); 1.5763 (0.6); 1.3490 (4.1); 1.3313 (8.1); 1.3136 (4.2); −0.0002 (3.6) |
| I.0755: $^1$H-NMR(400.1 MHz, CDCl3):<br>δ = 7.5147 (1.2); 7.4988 (1.2); 7.2626 (3.0); 4.9497 (0.7); 4.9360 (1.6); 4.9203 (1.7); 4.9069 (0.8); 4.3155 (1.3); 4.2977 (3.9); 4.2800 (4.0); 4.2623 (1.4); 3.1554 (0.6); 3.1433 (0.6); 3.1198 (2.2); 3.1077 (2.4); 3.0976 (2.4); 3.0838 (2.2); 3.0617 (0.6); 3.0487 (0.6); 2.1522 (16.0); 1.5668 (4.0); 1.3479 (4.1); 1.3302 (8.1); 1.3125 (4.1); −0.0002 (3.7) |
| I.0756: $^1$H-NMR(400.1 MHz, CDCl3):<br>δ = 7.2635 (2.0); 6.7035 (1.2); 6.6880 (1.2); 4.9429 (0.7); 4.9299 (1.6); 4.9141 (1.6); 4.9013 (0.7); 4.2964 (1.4); 4.2787 (4.0); 4.2609 (4.1); 4.2433 (1.4); 3.1459 (0.7); 3.1341 (0.8); 3.1108 (2.1); 3.0991 (2.1); 3.0748 (2.0); 3.0626 (2.1); 3.0397 (0.8); 3.0273 (0.7); 2.5494 (15.6); 2.1326 (16.0); 1.5867 (2.6); 1.3422 (4.1); 1.3245 (8.1); 1.3068 (4.2); −0.0002 (2.5) |
| I.0757: $^1$H-NMR(400.1 MHz, CDCl3):<br>δ = 7.7313 (5.6); 7.2610 (9.8); 5.2990 (1.6); 3.3011 (0.3); 3.2650 (9.0); 3.2376 (16.0); 3.2078 (8.9); 3.1707 (0.5); 1.6694 (0.5); 1.5557 (11.4); 1.5119 (100.2); 1.3505 (0.6); 1.2927 (0.4); 1.2563 (1.2); 1.2261 (0.4); −0.0002 (11.4) |
| I.0758: $^1$H-NMR(400.1 MHz, CDCl3):<br>δ = 7.2601 (5.4); 6.5473 (1.4); 6.5313 (1.4); 5.5947 (2.6); 5.5773 (2.6); 4.4400 (1.3); 4.4222 (4.0); 4.4045 (4.1); 4.3872 (1.5); 2.5256 (16.0); 1.5535 (4.3); 1.4160 (4.2); 1.3983 (8.3); 1.3805 (4.2); 1.2641 (0.5); 0.8816 (0.3); −0.0002 (7.1) |
| I.0759: $^1$H-NMR(400.1 MHz, $d_6$-DMSO):<br>δ = 8.6564 (1.7); 8.6383 (1.7); 4.5427 (0.5); 4.5246 (1.3); 4.5076 (1.4); 4.4903 (0.6); 3.6679 (13.8); 3.3066 (5.5); 2.5930 (0.5); 2.5764 (1.1); 2.5594 (1.8); 2.5313 (1.9); 2.5000 (5.8); 2.3995 (13.6); 2.0534 (16.0); 2.0304 (2.6); −0.0002 (2.3) |
| I.0760: $^1$H-NMR(400.1 MHz, CDCl3):<br>δ = 7.2602 (3.5); 6.6344 (0.9); 4.2749 (0.7); 4.2574 (2.1); 4.2396 (2.2); 4.2217 (0.8); 2.5322 (0.8); 2.5048 (7.0); 2.4761 (0.6); 1.6737 (16.0); 1.5461 (2.3); 1.3158 (2.2); 1.2982 (4.4); 1.2804 (2.4); 1.2605 (0.6); −0.0002 (4.7) |
| I.0761: $^1$H-NMR(500.1 MHz, $d_6$-DMSO):<br>δ = 9.0478 (3.2); 4.8105 (1.4); 4.7904 (2.4); 4.7704 (1.4); 4.4320 (1.2); 4.4144 (2.8); 4.3968 (1.6); 4.3048 (0.9); 4.2899 (1.3); 4.2854 (1.5); 4.2721 (1.5); 4.2534 (0.8); 3.3154 (16.0); 2.5198 (0.7); 2.5039 (5.7); 2.4820 (1.2); 2.4648 (0.8); 2.4129 (20.3); 2.3960 (0.5); 2.3663 (0.5); 2.3451 (1.4); 2.3246 (1.7); 2.3032 (1.1); 2.2811 (0.5) |
| I.0762: $^1$H-NMR(500.1 MHz, $d_6$-DMSO):<br>δ = 8.7143 (3.5); 4.7618 (1.4); 4.7413 (2.4); 4.7217 (1.4); 4.4210 (1.4); 4.4183 (1.5); 4.4034 (3.3); 4.4006 (3.4); 4.3858 (1.9); 4.3829 (1.8); 4.2940 (1.4); 4.2808 (1.8); 4.2764 (1.7); 4.2731 (2.0); 4.2631 (1.6); 4.2599 (2.0); 4.2557 (1.7); 4.2424 (1.2); 3.3144 (16.0); 2.5087 (5.3); 2.5052 (7.2); 2.5017 (5.6); 2.4983 (3.3); 2.4838 (0.9); 2.4793 (1.2); 2.4733 (1.5); 2.4695 (1.3); 2.4656 (1.2); 2.4601 (1.5); 2.4551 (1.6); 2.4511 (1.4); 2.4450 (4.5); 2.4384 (1.4); 2.4244 (33.9); 2.4062 (2.8); 2.3534 (0.7); 2.3321 (1.8); 2.3133 (2.0); 2.3110 (2.1); 2.2900 (1.5); 2.2684 (0.5) |
| I.0763: $^1$H-NMR(500.1 MHz, $d_6$-DMSO):<br>δ = 8.6993 (2.4); 4.7584 (0.9); 4.7383 (1.7); 4.7184 (1.0); 4.4206 (1.1); 4.4175 (1.2); 4.4030 (2.6); 4.3998 (2.7); 4.3853 (1.5); 4.3821 (1.4); 4.2932 (1.2); 4.2800 (1.5); 4.2757 (1.4); 4.2723 (1.6); 4.2624 (1.3); 4.2591 (1.6); 4.2549 (1.4); 4.2417 (1.0); 3.3144 (16.0); 2.5086 (4.3); 2.5051 (5.9); 2.5015 (4.5); 2.4921 (0.8); 2.4821 (0.7); 2.4777 (0.9); 2.4715 (1.1); 2.4676 (1.0); 2.4638 (0.9); 2.4583 (1.2); 2.4536 (1.2); 2.4493 (1.0); 2.4394 (0.9); 2.4361 (1.0); 2.4233 (32.1); 2.3732 (0.6); 2.3537 (0.6); 2.3324 (1.4); 2.3137 (1.6); 2.3113 (1.6); 2.3089 (1.4); 2.2906 (1.2); 2.2687 (0.4) |
| I.0764: $^1$H-NMR(400.1 MHz, $d_6$-DMSO):<br>δ = 8.5729 (1.8); 4.0888 (0.8); 4.0712 (2.3); 4.0536 (2.4); 4.0363 (0.9); 3.3124 (4.6); 2.5006 (2.9); 2.3650 (8.6); 1.4288 (16.0); 1.1638 (2.3); 1.1463 (4.7); 1.1289 (2.5); −0.0002 (0.7) |
| I.0765: $^1$H-NMR(500.1 MHz, $d_6$-DMSO):<br>δ = 8.6517 (0.9); 8.6368 (0.9); 4.5081 (0.3); 4.4964 (0.4); 4.4918 (0.6); 4.4803 (0.6); 4.4764 (0.5); 4.4646 (0.3); 4.1654 (0.3); 4.1580 (0.4); 4.1512 (0.4); 4.1438 (1.5); 4.1322 (1.6); 4.1297 (1.7); 4.1181 (1.5); 4.1107 (0.4); 4.1040 (0.4); 4.0965 (0.3); 3.3130 |

TABLE A-(I)-continued

NMR peak lists of compounds according to formula (I)

(4.5); 2.5811 (0.7); 2.5687 (0.7); 2.5663 (0.7); 2.5545 (0.9); 2.5398 (1.1); 2.5289 (0.3); 2.5246 (0.6); 2.5126 (1.0); 2.5088 (1.5); 2.5052 (2.1); 2.5015 (1.5); 2.4980 (0.9); 2.4025 (12.8); 2.0600 (16.0); 2.0466 (1.1); 2.0415 (0.8); 2.0354 (0.8); 2.0290 (0.8); 2.0241 (0.5); 2.0203 (0.4); 2.0123 (0.4); 1.2162 (3.5); 1.2020 (7.3); 1.1878 (3.4)
I.0766: $^1$H-NMR(400.1 MHz, CDCl3):
δ = 7.6886 (1.3); 7.6716 (1.4); 7.2779 (0.4); 4.9081 (0.7); 4.8917 (1.6); 4.8766 (1.7); 4.8608 (0.8); 3.8143 (15.8); 2.6102 (0.4); 2.5951 (1.1); 2.5775 (2.8); 2.5596 (2.9); 2.5437 (1.5); 2.5274 (0.5); 2.3240 (0.6); 2.3070 (1.0); 2.2903 (1.2); 2.2741 (1.0); 2.2567 (0.4); 2.1915 (0.4); 2.1740 (1.1); 2.1556 (1.3); 2.1381 (1.2); 2.1070 (16.0); −0.0002 (0.6)
I.0767: $^1$H-NMR(400.1 MHz, $d_6$-DMSO):
δ = 8.6787 (0.9); 8.6600 (1.0); 4.5454 (0.4); 4.5252 (0.7); 4.5106 (0.7); 4.5055 (0.6); 4.4907 (0.4); 3.6681 (12.8); 3.3079 (4.4); 2.5763 (0.8); 2.5602 (0.9); 2.5507 (0.7); 2.5420 (0.7); 2.5310 (1.3); 2.5097 (2.0); 2.5051 (3.4); 2.5006 (4.7); 2.4963 (3.7); 2.4790 (0.4); 2.4194 (1.4); 2.3999 (11.6); 2.3831 (1.1); 2.0651 (0.7); 2.0533 (16.0); 2.0329 (1.1); 2.0245 (1.1); 2.0198 (0.8); 2.0039 (0.5); −0.0002 (8.3); −0.0083 (0.5)
I.0768: $^1$H-NMR(500.1 MHz, $d_6$-DMSO):
δ = 8.6606 (0.8); 8.6458 (0.8); 4.5310 (0.4); 4.5262 (0.5); 4.5149 (0.5); 4.5110 (0.4); 3.6725 (12.9); 3.3139 (6.2); 2.5793 (0.7); 2.5673 (0.7); 2.5642 (0.7); 2.5516 (0.7); 2.5497 (0.7); 2.5333 (1.1); 2.5181 (0.6); 2.5128 (0.8); 2.5091 (1.8); 2.5056 (2.6); 2.5019 (1.7); 2.4984 (0.8); 2.4041 (13.0); 2.0660 (0.6); 2.0582 (16.0); 2.0512 (1.2); 2.0440 (0.8); 2.0401 (0.9); 2.0360 (0.6); 2.0319 (0.8); 2.0266 (0.6); 2.0152 (0.4)
I.0769: $^1$H-NMR(400.1 MHz, CDCl3):
δ = 7.2628 (3.2); 6.8507 (1.2); 6.8359 (1.2); 4.9488 (0.7); 4.9357 (1.6); 4.9198 (1.6); 4.9072 (0.8); 4.3081 (1.3); 4.2904 (3.9); 4.2726 (4.0); 4.2549 (1.4); 3.1653 (0.8); 3.1541 (0.8); 3.1303 (2.0); 3.1187 (2.0); 3.0870 (2.0); 3.0748 (2.0); 3.0518 (0.8); 3.0394 (0.8); 2.5655 (15.5); 2.5387 (0.4); 2.1337 (16.0); 1.5705 (2.6); 1.3506 (4.1); 1.3329 (8.1); 1.3152 (4.2); −0.0002 (4.0)
I.0770: $^1$H-NMR(400.1 MHz, $d_6$-DMSO):
δ = 9.3216 (1.9); 4.5571 (1.1); 3.6804 (13.3); 3.3140 (10.2); 2.6216 (0.4); 2.6056 (1.0); 2.5873 (1.3); 2.5752 (1.3); 2.5586 (1.7); 2.5395 (1.0); 2.5247 (0.8); 2.5010 (9.7); 2.0865 (0.8); 2.0546 (16.0); 2.0352 (1.7); 2.0144 (0.8); −0.0002 (7.6)
I.0771: $^1$H-NMR(400.1 MHz, $d_6$-DMSO):
δ = 9.5206 (1.8); 5.2641 (2.4); 4.2551 (1.0); 4.2465 (1.3); 4.2288 (4.3); 4.2108 (6.5); 4.1930 (4.6); 4.1758 (1.6); 4.1663 (1.2); 4.1484 (0.5); 3.3103 (11.7); 2.5003 (12.8); 2.3834 (14.7); 1.2407 (8.0); 1.2229 (16.0); 1.2053 (8.4); −0.0002 (12.1)
I.0772: $^1$H-NMR(400.1 MHz, $d_6$-DMSO):
δ = 8.7263 (1.6); 8.7134 (1.6); 5.1839 (2.4); 5.1676 (2.5); 4.2681 (0.3); 4.2500 (1.1); 4.2409 (1.3); 4.2230 (3.9); 4.2044 (5.6); 4.1857 (4.1); 4.1675 (1.6); 4.1585 (1.3); 4.1399 (0.5); 3.3133 (8.3); 2.5019 (4.6); 1.2323 (8.1); 1.2147 (16.0); 1.1974 (8.4); −0.0002 (2.0)
I.0773: $^1$H-NMR(400.1 MHz, $d_6$-DMSO):
δ = 9.5250 (1.7); 5.2707 (1.9); 5.2593 (1.8); 4.2544 (1.0); 4.2455 (1.3); 4.2281 (4.4); 4.2102 (6.4); 4.1924 (4.4); 4.1752 (1.4); 4.1659 (1.1); 4.1478 (0.4); 3.3121 (7.7); 2.5009 (6.8); 2.4006 (14.4); 1.2404 (8.2); 1.2227 (16.0); 1.2051 (8.0); −0.0002 (3.9)
I.0774: $^1$H-NMR(400.1 MHz, $d_6$-DMSO):
δ = 9.8041 (2.4); 5.2850 (2.9); 4.2620 (1.0); 4.2528 (1.3); 4.2359 (4.3); 4.2181 (6.5); 4.2003 (4.6); 4.1832 (1.6); 4.1742 (1.2); 4.1561 (0.4); 3.3140 (3.7); 2.5017 (3.6); 1.2454 (7.9); 1.2279 (16.0); 1.2103 (8.5); −0.0002 (1.8)
I.0775: $^1$H-NMR(400.1 MHz, $d_6$-DMSO):
δ = 8.8834 (2.1); 5.2384 (2.4); 4.2917 (0.4); 4.2736 (1.1); 4.2648 (1.3); 4.2470 (3.4); 4.2287 (3.8); 4.2220 (3.8); 4.2041 (3.6); 4.1864 (1.5); 4.1780 (1.4); 4.1592 (0.5); 3.3118 (14.3); 2.5009 (7.5); 1.2413 (8.0); 1.2237 (16.0); 1.2061 (8.4); −0.0002 (2.9)
I.0776: $^1$H-NMR(400.1 MHz, CDCl3):
δ = 7.8338 (1.2); 7.8167 (1.2); 7.2667 (1.1); 4.8502 (1.6); 4.8408 (1.4); 4.8316 (1.6); 4.3076 (0.7); 4.2978 (1.1); 4.2902 (2.0); 4.2812 (2.3); 4.2730 (2.3); 4.2639 (2.2); 4.2561 (1.3); 4.2467 (0.8); 4.2382 (0.4); 3.9230 (1.3); 3.9175 (1.4); 3.8993 (1.8); 3.8936 (1.9); 3.7578 (1.7); 3.7514 (1.8); 3.7340 (1.4); 3.7275 (1.4); 3.3782 (16.0); 1.6255 (0.8); 1.3270 (4.1); 1.3093 (8.1); 1.2917 (4.2); −0.0002 (1.2)
I.0777: $^1$H-NMR(400.1 MHz, CDCl3):
δ = 7.9795 (1.2); 7.9621 (1.2); 7.2630 (2.4); 4.8608 (1.6); 4.8516 (1.4); 4.8424 (1.6); 4.3103 (0.8); 4.2929 (2.1); 4.2845 (2.3); 4.2755 (2.3); 4.2672 (2.2); 4.2591 (1.2); 4.2505 (0.8); 3.9266 (1.4); 3.9219 (1.4); 3.9031 (1.8); 3.8981 (1.8); 3.7617 (1.8); 3.7556 (1.8); 3.7382 (1.4); 3.7319 (1.4); 3.3830 (16.0); 1.5783 (2.6); 1.3296 (4.1); 1.3118 (8.1); 1.2941 (4.1); −0.0002 (2.8)
I.0778: $^1$H-NMR(400.1 MHz, $d_6$-DMSO):
δ = 9.2780 (1.9); 4.5443 (1.2); 3.6779 (13.6); 3.3114 (6.3); 2.6226 (0.4); 2.6050 (1.1); 2.5877 (1.5); 2.5591 (1.8); 2.5404 (1.1); 2.5235 (0.8); 2.5011 (8.7); 2.0811 (0.8); 2.0536 (16.0); 2.0309 (2.1); 2.0095 (1.0); −0.0002 (8.3)
I.0779: $^1$H-NMR(400.1 MHz, CDCl3):
δ = 7.9635 (2.6); 7.9486 (2.6); 7.2652 (2.8); 4.7937 (3.2); 4.7858 (3.3); 4.7777 (3.2); 4.3282 (2.6); 4.3105 (7.8); 4.2927 (7.9); 4.2751 (2.8); 4.0782 (7.1); 2.4714 (3.4); 1.6439 (2.7); 1.3487 (8.1); 1.3309 (16.0); 1.3133 (8.2); 1.2626 (0.7); 0.8814 (0.4); −0.0002 (3.3)
I.0780: $^1$H-NMR(400.1 MHz, CDCl3):
δ = 8.1090 (2.5); 8.0944 (2.6); 7.2657 (2.5); 4.8061 (3.1); 4.7982 (3.3); 4.7902 (3.4); 4.3318 (2.6); 4.3140 (7.8); 4.2962 (8.1); 4.2786 (3.1); 4.1237 (0.4); 4.0826 (6.8); 2.4917 (2.5); 2.4786 (3.8); 2.4650 (1.8); 1.6536 (4.6); 1.3517 (8.0); 1.3339 (16.0); 1.3163 (8.5); 1.2624 (0.4); −0.0002 (2.8)
I.0781: $^1$H-NMR(400.1 MHz, CDCl3):
δ = 7.6809 (2.5); 7.2613 (8.9); 4.3085 (2.7); 4.2908 (7.9); 4.2730 (8.1); 4.2454 (11.4); 4.2338 (11.2); 1.5605 (12.7); 1.3431 (8.2); 1.3254 (16.0); 1.3077 (8.2); −0.0002 (11.6)
I.0782: $^1$H-NMR(400.1 MHz, CDCl3):
δ = 7.4923 (4.1); 7.2609 (15.9); 4.1979 (2.7); 4.1803 (7.9); 4.1626 (8.0); 4.1452 (2.8); 1.6873 (2.9); 1.6744 (8.8); 1.6683 (9.2); 1.6570 (3.6); 1.6149 (0.4); 1.5514 (29.3); 1.3377 (3.4); 1.3263 (9.1); 1.3202 (9.0); 1.3073 (3.1); 1.2543 (8.4); 1.2367 (16.0); 1.2191 (8.1); −0.0002 (20.2)
I.0783: $^1$H-NMR(400.1 MHz, $d_6$-DMSO):
δ = 8.8334 (2.0); 8.8181 (2.1); 5.2274 (2.5); 5.2118 (2.6); 4.2840 (0.3); 4.2655 (1.1); 4.2567 (1.3); 4.2390 (3.4); 4.2186 (4.3); 4.1980 (3.8); 4.1809 (1.6); 4.1715 (1.4); 4.1536 (0.6); 3.3139 (6.8); 3.1990 (2.6); 2.6296 (3.8); 2.5023 (5.2); 1.2371 (8.0); 1.2196 (16.0); 1.2021 (8.6); −0.0002 (2.9)
I.0784: $^1$H-NMR(400.1 MHz, CDCl3):
δ = 8.0188 (0.7); 7.4481 (4.6); 7.2605 (12.9); 4.7194 (16.0); 2.9556 (3.5); 2.8827 (3.4); 2.4703 (6.4); 1.7867 (3.1); 1.7677 (9.6); 1.7556 (3.7); 1.5456 (11.9); 1.4457 (0.4); 1.4314 (0.9); 1.4060 (3.6); 1.3931 (9.4); 1.3882 (9.5); 1.3745 (3.2); −0.0002 (17.7)
I.0785: $^1$H-NMR(400.1 MHz, CDCl3):
δ = 7.2603 (13.0); 7.1082 (4.7); 4.7193 (16.0); 2.9556 (0.6); 2.8835 (0.6); 2.4702 (6.6); 1.7799 (2.9); 1.7656 (9.5); 1.7604 (9.9); 1.7485 (4.0); 1.7072 (0.4); 1.5448 (10.8); 1.4308 (0.9); 1.3878 (3.6); 1.3751 (9.7); 1.3695 (9.9); 1.3562 (3.4); 1.3169 (0.4); 1.2972 (0.3); 1.2568 (0.6); 0.8552 (0.3); −0.0002 (17.8)

TABLE A-(I)-continued

| NMR peak lists of compounds according to formula (I) |
|---|
| I.0786: $^1$H-NMR(400.1 MHz, $d_6$-DMSO):<br>δ = 8.7340 (12.1); 7.9631 (0.3); 7.4007 (5.5); 7.3336 (0.4); 7.1286 (5.6); 3.3208 (82.8); 2.8990 (1.4); 2.7412 (1.3); 2.5101 (33.3); 1.3383 (16.0); 1.2879 (1.0); 1.2695 (0.8); 1.2542 (0.6); 1.0494 (0.4); 0.9990 (15.8); 0.9947 (15.7) |
| I.0787: $^1$H-NMR(400.1 MHz, $d_6$-DMSO):<br>δ = 8.6203 (12.5); 7.9598 (0.6); 7.3925 (5.6); 7.0947 (5.7); 3.3547 (0.7); 3.3202 (96.8); 2.8998 (2.4); 2.7399 (2.3); 2.6796 (0.4); 2.5103 (38.9); 2.4095 (0.3); 2.3332 (0.3); 1.3289 (16.0); 1.2788 (1.0); 1.0463 (0.4); 0.9938 (16.0) |
| I.0788: $^1$H-NMR(400.1 MHz, $d_6$-DMSO):<br>δ = 8.9765 (12.4); 7.5150 (5.9); 7.1407 (5.9); 3.3220 (86.6); 2.8996 (1.0); 2.7401 (1.0); 2.5097 (30.2); 1.3490 (16.0); 1.2976 (0.8); 1.2675 (0.4); 1.2488 (0.4); 1.0582 (0.5); 1.0075 (15.6); 1.0030 (15.6) |
| I.0789: $^1$H-NMR(400.1 MHz, $d_6$-DMSO):<br>δ = 8.9334 (4.1); 7.9617 (1.8); 7.4102 (1.7); 7.0783 (1.7); 3.3214 (24.7); 2.8999 (8.0); 2.7404 (7.6); 2.5098 (10.9); 2.3833 (16.0); 1.3335 (5.2); 1.2821 (0.3); 0.9931 (5.1); 0.9887 (5.1) |
| I.0790: $^1$H-NMR(400.1 MHz, CDCl3):<br>δ = 7.2604 (7.0); 4.4575 (10.4); 4.2639 (1.4); 4.2463 (4.0); 4.2286 (4.0); 4.2107 (1.4); 3.7525 (16.0); 1.5409 (5.7); 1.3047 (4.2); 1.2871 (8.1); 1.2694 (4.2); −0.0002 (9.7) |
| I.0791: $^1$H-NMR(400.1 MHz, $d_6$-DMSO):<br>δ = 9.0761 (1.7); 9.0578 (1.6); 4.6193 (0.6); 4.5994 (1.2); 4.5857 (1.2); 4.5664 (0.6); 3.6842 (13.7); 3.3178 (23.4); 2.6070 (0.4); 2.5907 (1.1); 2.5719 (2.0); 2.5517 (2.1); 2.5318 (1.1); 2.5011 (6.5); 2.1042 (0.8); 2.0876 (1.7); 2.0696 (2.6); 2.0544 (16.0); −0.0002 (1.7) |
| I.0792: $^1$H-NMR(400.1 MHz, CDCl3):<br>δ = 7.2617 (5.4); 6.7858 (1.2); 6.7679 (1.2); 5.2995 (0.5); 4.8333 (1.6); 4.8235 (1.3); 4.8137 (1.6); 4.3124 (0.7); 4.2955 (2.0); 4.2784 (2.4); 4.2662 (2.1); 4.2495 (0.8); 3.9082 (1.5); 3.8848 (1.9); 3.7500 (1.8); 3.7441 (1.9); 3.7262 (1.4); 3.7202 (1.4); 3.3684 (16.0); 2.5440 (15.4); 2.5145 (0.5); 1.5608 (8.8); 1.3323 (4.0); 1.3147 (8.1); 1.2971 (4.3); −0.0002 (6.5) |
| I.0793: $^1$H-NMR(500.1 MHz, $d_6$-DMSO):<br>δ = 8.3502 (1.2); 8.3460 (1.2); 4.1429 (2.2); 4.1287 (7.0); 4.1145 (7.1); 4.1003 (2.3); 3.9789 (6.8); 3.9672 (6.9); 3.3129 (4.6); 2.5125 (1.5); 2.5090 (3.2); 2.5054 (4.5); 2.5018 (3.4); 2.4983 (1.7); 2.4289 (26.4); 1.2180 (7.8); 1.2038 (16.0); 1.1896 (7.6) |
| I.0794: $^1$H-NMR(400.1 MHz, $d_6$-DMSO):<br>δ = 9.2619 (1.9); 4.5098 (1.2); 4.1596 (1.0); 4.1438 (2.3); 4.1289 (2.5); 4.1143 (1.2); 3.3102 (11.0); 2.6240 (0.4); 2.6067 (1.0); 2.5865 (1.8); 2.5654 (1.9); 2.5460 (1.1); 2.5318 (0.7); 2.5008 (10.5); 2.0765 (0.8); 2.0560 (16.0); 2.0274 (1.9); 2.0079 (1.0); 1.2209 (3.6); 1.2033 (7.4); 1.1858 (3.9); −0.0002 (6.7) |
| I.0795: $^1$H-NMR(400.2 MHz, $d_6$-DMSO):<br>δ = 9.3170 (3.0); 4.1818 (2.2); 4.1641 (7.2); 4.1463 (7.3); 4.1286 (2.3); 3.6559 (5.6); 3.6297 (7.3); 3.4928 (7.2); 3.4666 (5.3); 3.3418 (36.9); 2.8960 (2.3); 2.7367 (1.9); 2.7355 (1.9); 2.5303 (0.8); 2.5255 (1.3); 2.5168 (15.1); 2.5123 (30.2); 2.5077 (39.5); 2.5031 (28.8); 2.4986 (13.8); 2.3955 (0.7); 1.1913 (7.6); 1.1736 (16.0); 1.1558 (7.3) |
| I.0796: $^1$H-NMR(400.1 MHz, $d_6$-DMSO):<br>δ = 8.5572 (5.9); 7.5033 (6.1); 7.1701 (6.2); 5.7532 (1.9); 3.8882 (15.2); 3.8748 (16.0); 3.3074 (28.6); 3.1527 (0.3); 2.6694 (0.4); 2.5396 (0.3); 2.5004 (51.0); 2.4411 (0.8); 2.3309 (0.4); 1.2562 (1.1); 1.2457 (1.1); −0.0002 (43.0); −0.1498 (0.3) |
| I.0797: $^1$H-NMR(400.1 MHz, $d_6$-DMSO):<br>δ = 9.2960 (4.3); 4.1715 (2.6); 4.1534 (7.8); 4.1358 (8.1); 4.1185 (3.1); 4.0221 (13.5); 3.3194 (58.3); 2.8986 (0.5); 2.7412 (0.4); 2.5098 (31.6); 1.2382 (8.0); 1.2206 (16.0); 1.2029 (8.5) |
| I.0798: $^1$H-NMR(400.1 MHz, $d_6$-DMSO):<br>δ = 9.3119 (3.0); 4.0442 (9.4); 3.6839 (16.0); 3.3203 (20.0); 2.8999 (0.6); 2.7408 (0.5); 2.5100 (13.1) |
| I.0799: $^1$H-NMR(500.1 MHz, $d_6$-DMSO):<br>δ = 9.4791 (0.9); 4.1045 (0.6); 4.0903 (1.9); 4.0761 (2.0); 4.0620 (0.6); 3.3142 (16.0); 2.5122 (1.4); 2.5089 (2.9); 2.5054 (4.0); 2.5019 (3.0); 1.4768 (0.5); 1.4671 (1.4); 1.4606 (1.5); 1.4516 (0.6); 1.1964 (0.6); 1.1874 (1.4); 1.1808 (1.5); 1.1743 (2.2); 1.1601 (4.0); 1.1459 (1.9) |
| I.0800: $^1$H-NMR(400.1 MHz, $d_6$-DMSO):<br>δ = 9.4889 (3.3); 3.6339 (16.0); 3.3195 (16.1); 2.5099 (10.8); 1.4798 (4.7); 1.2070 (4.6); 1.2017 (4.6) |
| I.0801: $^1$H-NMR(400.1 MHz, $d_6$-DMSO):<br>δ = 9.1434 (1.8); 3.6260 (8.8); 3.3220 (20.4); 2.5096 (6.5); 1.4631 (16.0) |
| I.0802: $^1$H-NMR(500.1 MHz, $d_6$-DMSO):<br>δ = 9.5839 (1.0); 4.3595 (6.4); 3.3154 (16.0); 3.3069 (0.4); 2.5126 (1.3); 2.5091 (2.7); 2.5055 (3.7); 2.5019 (2.7); 2.4984 (1.3) |
| I.0803: $^1$H-NMR(400.1 MHz, $d_6$-DMSO):<br>δ = 9.0452 (3.2); 9.0298 (3.3); 5.1302 (2.4); 5.1159 (4.9); 5.1023 (2.7); 4.4956 (3.1); 4.4813 (3.3); 4.1664 (2.7); 4.1492 (7.7); 4.1314 (8.0); 4.1138 (3.2); 3.7866 (8.2); 3.7741 (5.2); 3.3219 (55.6); 2.8997 (0.5); 2.7409 (0.5); 2.5095 (20.6); 1.2294 (8.1); 1.2119 (16.0); 1.1944 (8.5) |
| I.0804: $^1$H-NMR(400.1 MHz, CDCl3):<br>δ = 7.2601 (8.1); 4.4529 (10.4); 4.2623 (1.3); 4.2447 (4.0); 4.2269 (4.1); 4.2094 (1.5); 3.7552 (16.0); 1.5394 (6.9); 1.3030 (4.1); 1.2853 (8.1); 1.2676 (4.2); −0.0002 (11.2) |
| I.0805: $^1$H-NMR(400.1 MHz, $d_6$-DMSO):<br>δ = 9.7600 (2.4); 5.2801 (3.0); 4.2840 (0.4); 4.2571 (1.4); 4.2401 (4.4); 4.2223 (6.5); 4.2044 (4.5); 4.1873 (1.5); 4.1787 (1.2); 4.1608 (0.4); 3.3196 (21.6); 2.5096 (11.1); 1.2507 (8.0); 1.2332 (16.0); 1.2157 (8.2) |
| I.0806: $^1$H-NMR(400.1 MHz, $d_6$-DMSO):<br>δ = 9.5934 (3.4); 3.6648 (16.0); 3.3209 (24.5); 2.6149 (1.0); 2.5936 (1.9); 2.5818 (2.2); 2.5693 (2.3); 2.5486 (1.4); 2.5101 (11.0); 2.3438 (1.1); 2.3213 (2.5); 2.2936 (2.3); 2.2713 (1.1); 1.9829 (2.0); 1.9626 (2.3); 1.9414 (1.2) |
| I.0807: $^1$H-NMR(400.1 MHz, $d_6$-DMSO):<br>δ = 19.7326 (0.6); 9.3064 (0.7); 9.2782 (13.0); 7.9515 (1.0); 7.5637 (0.7); 7.5166 (6.3); 7.2054 (0.5); 7.1314 (6.4); 7.0596 (0.6); 3.6222 (0.6); 3.3060 (120.3); 3.1984 (0.6); 3.1756 (0.5); 3.1628 (0.6); 3.1463 (0.8); 3.1113 (0.7); 3.0869 (0.6); 3.0662 (0.6); 3.0394 (0.8); 3.0093 (0.9); 2.9979 (0.9); 2.9472 (0.9); 2.8905 (4.5); 2.7306 (4.2); 2.6695 (1.0); 2.4998 (143.0); 2.3850 (0.7); 2.3264 (1.2); 2.0721 (1.9); 1.3244 (16.0); 1.2585 (2.6); 1.2411 (2.5); 1.1826 (0.8); 1.1490 (0.6); 1.0258 (0.6); 0.9722 (15.3); 0.9653 (15.7); 0.9213 (1.0); 0.8883 (0.6); 0.7752 (0.5); 0.1449 (0.8); −0.0002 (116.8); −0.0452 (1.4); −0.1492 (1.0); −3.1405 (0.5) |
| I.0808: $^1$H-NMR(500.1 MHz, $d_6$-DMSO):<br>δ = 8.9904 (8.3); 8.9743 (8.4); 8.0845 (12.7); 5.7530 (0.9); 5.0014 (3.9); 4.9963 (4.8); 4.9904 (5.4); 4.9855 (7.6); 4.9806 (5.5); 4.9747 (4.9); 4.9695 (4.1); 3.4762 (7.8); 3.4654 (16.0); 3.4546 (8.4); 3.3190 (2.2); 3.2626 (9.1); 3.2572 (10.2); 3.2522 (9.6); 3.2468 (8.7); 2.5047 (7.2); 1.2795 (0.4); 1.2649 (0.7); 1.2505 (0.6) |
| I.0809: $^1$H-NMR(400.1 MHz, $d_6$-DMSO):<br>δ = 8.6230 (3.5); 8.6050 (3.5); 5.7532 (0.6); 5.2443 (2.6); 5.2305 (5.2); 5.2167 (2.7); 4.5525 (3.0); 4.5440 (2.9); 4.5360 (3.0); 4.5248 (1.5); 4.1756 (2.7); 4.1580 (7.8); 4.1404 (7.9); 4.1228 (2.7); 3.8659 (0.8); 3.8524 (1.4); 3.8384 (2.7); 3.8247 (3.6); 3.8101 |

TABLE A-(I)-continued

| NMR peak lists of compounds according to formula (I) |
|---|
| (3.8); 3.7973 (3.6); 3.7850 (2.6); 3.7696 (1.3); 3.7581 (0.8); 3.3116 (12.1); 2.5012 (9.9); 1.2281 (8.6); 1.2104 (16.0); 1.1928 (8.0); −0.0002 (3.8) |
| I.0810: $^1$H-NMR(400.1 MHz, $d_6$-DMSO): |
| δ = 9.0854 (3.2); 5.1249 (3.8); 4.4872 (3.2); 4.1607 (2.6); 4.1431 (7.7); 4.1254 (7.8); 4.1080 (2.7); 3.7834 (7.4); 3.3165 (16.1); 2.5015 (12.6); 1.2228 (8.3); 1.2051 (16.0); 1.1874 (8.0); −0.0002 (9.2) |
| I.0811: $^1$H-NMR(400.1 MHz, $d_6$-DMSO): |
| δ = 9.0450 (3.4); 9.0270 (3.5); 5.7555 (0.6); 5.1248 (2.4); 5.1109 (5.0); 5.0965 (2.7); 4.4995 (1.3); 4.4868 (3.1); 4.4719 (3.2); 4.4584 (1.4); 4.1581 (2.6); 4.1402 (7.8); 4.1226 (7.9); 4.1052 (3.0); 3.8196 (0.3); 3.7897 (4.2); 3.7780 (8.0); 3.7646 (4.9); 3.3167 (15.2); 2.5013 (18.3); 2.1934 (0.8); 1.2207 (8.0); 1.2030 (16.0); 1.1854 (8.4); −0.0002 (13.5) |
| I.0812: $^1$H-NMR(400.1 MHz, $d_6$-DMSO): |
| δ = 8.5329 (1.4); 8.5180 (1.5); 4.5436 (0.5); 4.5266 (1.3); 4.5098 (1.3); 4.4927 (0.5); 4.1458 (1.0); 4.1305 (2.4); 4.1161 (2.4); 4.1006 (1.1); 3.3126 (15.1); 2.5815 (0.6); 2.5651 (1.1); 2.5483 (1.7); 2.5331 (1.5); 2.5009 (7.3); 2.4639 (0.4); 2.0912 (1.1); 2.0732 (3.0); 2.0483 (16.0); 1.2089 (3.7); 1.1913 (7.4); 1.1737 (3.8); −0.0002 (2.4) |
| I.0813: $^1$H-NMR(400.1 MHz, $d_6$-DMSO): |
| δ = 9.0635 (1.6); 9.0454 (1.7); 4.5806 (0.6); 4.5614 (1.2); 4.5472 (1.2); 4.5292 (0.6); 4.1644 (1.0); 4.1534 (2.1); 4.1483 (2.2); 4.1369 (2.2); 4.1207 (1.1); 3.3109 (28.3); 2.6069 (0.4); 2.5905 (1.1); 2.5740 (2.3); 2.5553 (2.6); 2.5363 (1.1); 2.5002 (12.3); 2.0966 (0.8); 2.0560 (16.0); 2.0303 (0.9); 1.2233 (3.8); 1.2057 (7.5); 1.1881 (3.8); −0.0002 (8.3) |
| I.0814: $^1$H-NMR(400.1 MHz, $d_6$-DMSO): |
| δ = 9.3134 (1.6); 9.2962 (1.5); 4.5447 (0.6); 4.5270 (1.1); 4.5108 (1.1); 4.4951 (0.5); 4.1634 (1.0); 4.1468 (2.4); 4.1334 (2.4); 4.1170 (1.0); 3.3125 (25.6); 2.6236 (0.4); 2.6080 (1.1); 2.5877 (1.7); 2.5655 (1.8); 2.5460 (1.0); 2.5304 (0.7); 2.5008 (12.5); 2.0573 (16.0); 2.0321 (1.6); 2.0129 (0.8); 1.2230 (3.8); 1.2054 (7.4); 1.1878 (3.7); −0.0002 (7.0) |
| I.0815: $^1$H-NMR(400.1 MHz, $d_6$-DMSO): |
| δ = 9.5902 (6.8); 4.1506 (2.7); 4.1330 (7.8); 4.1155 (8.0); 4.0983 (2.8); 3.3201 (39.4); 2.8999 (0.4); 2.7399 (0.4); 2.6045 (1.8); 2.5842 (3.6); 2.5721 (4.1); 2.5597 (4.2); 2.5387 (2.8); 2.5099 (21.7); 2.3363 (2.1); 2.3142 (4.6); 2.2869 (4.4); 2.2637 (2.1); 1.9814 (3.8); 1.9732 (3.4); 1.9605 (4.4); 1.9394 (2.4); 1.9212 (0.7); 1.2000 (8.1); 1.1824 (16.0); 1.1650 (8.2) |
| I.0816: $^1$H-NMR(400.1 MHz, CDCl3): |
| δ = 8.1052 (2.5); 8.0918 (2.5); 8.0145 (0.8); 7.2603 (13.2); 4.8168 (3.3); 4.8107 (3.4); 4.8023 (3.2); 4.3343 (2.8); 4.3167 (7.9); 4.2991 (8.0); 4.2813 (2.8); 4.0864 (7.5); 2.9544 (3.8); 2.8806 (3.7); 2.2612 (2.2); 1.5568 (6.0); 1.4316 (0.6); 1.3525 (8.3); 1.3349 (16.0); 1.3172 (8.1); −0.0002 (18.2) |
| I.0817: $^1$H-NMR(400.1 MHz, CDCl3): |
| δ = 7.9607 (2.5); 7.9460 (2.5); 7.2602 (15.3); 4.8058 (3.3); 4.7975 (3.3); 4.7899 (3.2); 4.3311 (2.6); 4.3136 (7.9); 4.2959 (8.0); 4.2779 (2.9); 4.0833 (7.3); 3.0882 (0.4); 2.9543 (0.9); 2.8814 (0.9); 2.2544 (2.2); 1.5520 (6.7); 1.4318 (1.3); 1.3496 (8.2); 1.3320 (16.0); 1.3141 (8.1); −0.0002 (21.3) |
| I.0818: $^1$H-NMR(400.1 MHz, CDCl3): |
| δ = 7.2610 (31.6); 7.1808 (0.3); 7.1005 (8.5); 6.9960 (0.4); 4.7441 (4.4); 4.7214 (6.6); 4.6988 (6.6); 4.6791 (4.6); 4.5779 (7.1); 4.5550 (16.0); 4.5323 (9.2); 4.3887 (5.0); 4.3727 (6.1); 4.3631 (8.5); 4.3481 (8.6); 4.3391 (5.6); 4.3228 (4.3); 2.9198 (4.0); 2.8991 (5.8); 2.8861 (7.2); 2.8708 (6.5); 2.8516 (4.4); 2.4305 (2.4); 2.4015 (6.9); 2.3770 (8.4); 2.3496 (6.3); 2.3194 (2.0); 1.5934 (0.4); 1.5601 (44.4); 1.2586 (0.4); −0.0002 (41.5) |
| I.0819: $^1$H-NMR(400.1 MHz, CDCl3): |
| δ = 7.5517 (8.8); 7.2622 (31.8); 4.7184 (4.6); 4.7046 (5.2); 4.6964 (6.1); 4.6873 (7.5); 4.6763 (6.1); 4.6688 (5.5); 4.6551 (4.7); 4.5867 (7.2); 4.5640 (16.0); 4.5414 (9.3); 4.4087 (5.1); 4.3940 (6.1); 4.3827 (7.8); 4.3683 (8.0); 4.3577 (5.2); 4.3428 (4.3); 3.0213 (4.2); 3.0018 (5.6); 2.9883 (7.8); 2.9739 (6.3); 2.9546 (4.5); 2.3653 (2.4); 2.3360 (6.7); 2.3124 (7.8); 2.2834 (6.3); 2.2542 (2.1); 2.0441 (0.5); 1.5611 (71.6); 1.2556 (1.5); −0.0002 (34.6) |
| I.0820: $^1$H-NMR(400.1 MHz, CDCl3): |
| δ = 7.2629 (3.8); 6.3727 (1.7); 4.6845 (0.8); 4.6700 (1.0); 4.6620 (1.2); 4.6546 (1.4); 4.6430 (1.2); 4.6360 (1.0); 4.6213 (0.9); 4.5566 (1.3); 4.5336 (3.0); 4.5111 (1.7); 4.3798 (0.9); 4.3643 (1.2); 4.3543 (1.5); 4.3395 (1.5); 4.3298 (1.0); 4.3140 (0.8); 2.9657 (0.8); 2.9475 (1.1); 2.9325 (1.4); 2.9173 (1.2); 2.8984 (0.8); 2.5474 (2.0); 2.5189 (16.0); 2.4893 (1.4); 2.3252 (0.4); 2.2954 (1.3); 2.2715 (1.6); 2.2435 (1.2); 2.2141 (0.4); 1.5797 (8.0); −0.0002 (4.2) |
| I.0821: $^1$H-NMR(400.1 MHz, CDCl3): |
| δ = 7.2609 (6.9); 6.2473 (1.6); 4.6124 (0.8); 4.5980 (1.3); 4.5814 (1.6); 4.5658 (1.4); 4.5506 (0.9); 3.4544 (0.6); 3.4422 (0.7); 3.4253 (1.6); 3.4126 (1.7); 3.3956 (1.2); 3.3832 (1.2); 3.3426 (1.8); 3.3253 (2.0); 3.3145 (1.4); 3.2968 (1.1); 3.1174 (0.8); 3.1027 (1.3); 3.0872 (1.6); 3.0722 (1.4); 3.0578 (0.9); 2.5489 (1.9); 2.5204 (16.0); 2.4906 (1.4); 2.0672 (0.4); 2.0495 (0.5); 2.0366 (1.2); 2.0188 (1.2); 2.0054 (1.3); 1.9880 (1.2); 1.9743 (0.5); 1.9569 (0.4); 1.5507 (8.0); −0.0002 (9.5) |
| I.0822: $^1$H-NMR(400.1 MHz, CDCl3): |
| δ = 7.2612 (5.1); 6.2451 (1.4); 4.6114 (0.7); 4.5963 (1.2); 4.5808 (1.3); 4.5646 (1.2); 4.5504 (0.7); 3.4541 (0.6); 3.4412 (0.6); 3.4246 (1.4); 3.4121 (1.5); 3.3950 (1.0); 3.3827 (1.0); 3.3421 (1.6); 3.3247 (1.7); 3.3140 (1.1); 3.2967 (0.9); 3.1162 (0.7); 3.1008 (1.1); 3.0861 (1.3); 3.0708 (1.2); 3.0558 (0.7); 2.5150 (16.0); 2.0690 (0.4); 2.0503 (0.4); 2.0374 (1.1); 2.0200 (1.1); 2.0061 (1.1); 1.9888 (1.0); 1.9748 (0.4); 1.5550 (7.3); −0.0002 (6.8) |
| I.0823: $^1$H-NMR(400.1 MHz, CDCl3): |
| δ = 7.2614 (4.9); 6.6228 (1.2); 6.6088 (1.2); 4.7380 (0.4); 4.7209 (1.3); 4.7033 (2.0); 4.6858 (1.3); 4.6677 (0.4); 4.2915 (1.4); 4.2738 (4.0); 4.2561 (4.1); 4.2386 (1.4); 2.5316 (16.0); 1.5561 (6.3); 1.5419 (8.5); 1.5242 (8.2); 1.3392 (4.3); 1.3214 (8.4); 1.3039 (4.3); −0.0002 (6.5) |
| I.0824: $^1$H-NMR(400.1 MHz, CDCl3): |
| δ = 7.6558 (2.6); 7.2600 (22.8); 4.7511 (0.7); 4.7332 (2.5); 4.7165 (3.8); 4.6994 (2.8); 4.6815 (1.0); 4.2873 (2.6); 4.2695 (7.6); 4.2519 (8.0); 4.2343 (3.3); 1.5422 (40.2); 1.5315 (18.4); 1.4358 (0.5); 1.3843 (0.3); 1.3670 (0.4); 1.3338 (8.1); 1.3161 (16.0); 1.2987 (8.8); 1.2561 (0.9); 1.1706 (0.3); 1.1564 (0.4); −0.0002 (29.5) |
| I.0825: $^1$H-NMR(400.1 MHz, CDCl3): |
| δ = 7.2640 (2.1); 6.4310 (1.4); 6.4220 (1.4); 4.6944 (0.7); 4.6799 (0.8); 4.6725 (1.0); 4.6653 (1.0); 4.6594 (1.0); 4.6520 (1.0); 4.6446 (0.9); 4.6303 (0.7); 4.5545 (1.0); 4.5319 (2.4); 4.5092 (1.4); 4.3789 (0.8); 4.3640 (0.9); 4.3527 (1.2); 4.3379 (1.2); 4.3282 (0.8); 4.3130 (0.6); 2.9492 (0.6); 2.9297 (0.9); 2.9159 (1.1); 2.9019 (0.9); 2.8825 (0.6); 2.5084 (16.0); 2.4826 (0.3); 2.3353 (0.4); 2.3064 (1.0); 2.2820 (1.2); 2.2785 (1.2); 2.2537 (0.9); 1.6027 (4.7); −0.0002 (2.3) |
| I.0826: $^1$H-NMR(300.1 MHz, $d_6$-DMSO): |
| δ = 8.6125 (0.7); 8.5924 (1.2); 8.5743 (0.6); 4.0420 (3.9); 4.0226 (3.9); 3.6610 (16.0); 3.3772 (21.4); 2.7280 (0.4); 2.5140 (24.3); 2.5083 (47.8); 2.5024 (63.0); 2.4966 (43.9); 2.2724 (0.4); 2.2658 (0.3); −0.0002 (6.6) |
| I.0827: $^1$H-NMR(300.1 MHz, $d_6$-DMSO): |
| δ = 8.5946 (1.0); 8.5757 (1.9); 8.5566 (1.0); 4.1615 (2.2); 4.1378 (6.9); 4.1141 (7.0); 4.0904 (2.2); 4.0247 (6.4); 4.0053 (6.3); 3.3577 (2.5); 2.5175 (2.8); 2.5118 (5.3); 2.5059 (6.9); 2.5002 (4.8); 2.0800 (0.8); 1.2291 (7.8); 1.2055 (16.0); 1.1817 (7.2); −0.0002 (0.6) |

TABLE A-(I)-continued

| NMR peak lists of compounds according to formula (I) |
|---|
| I.0828: $^1$H-NMR(300.1 MHz, $d_6$-DMSO):<br>δ = 8.9032 (1.6); 3.6145 (16.0); 3.3630 (3.3); 2.5435 (0.7); 2.5313 (3.8); 2.5248 (5.7); 2.5191 (12.5); 2.5133 (18.6); 2.5075 (23.7); 2.5017 (17.0); 1.4764 (1.0); 1.4596 (2.7); 1.4485 (3.0); 1.4342 (1.3); 1.2137 (1.2); 1.1992 (2.7); 1.1883 (2.5); 1.1716 (1.0) |
| I.0829: $^1$H-NMR(400.1 MHz, CDCl3):<br>δ = 7.2619 (4.2); 6.3979 (1.4); 4.6276 (0.7); 4.6130 (1.2); 4.5969 (1.4); 4.5808 (1.2); 4.5658 (0.7); 3.4736 (0.5); 3.4603 (0.6); 3.4440 (1.4); 3.4318 (1.4); 3.4142 (1.0); 3.4021 (1.0); 3.3668 (1.6); 3.3494 (1.8); 3.3388 (1.1); 3.3210 (0.9); 3.1253 (0.7); 3.1111 (1.1); 3.0955 (1.3); 3.0796 (1.2); 3.0657 (0.7); 2.5292 (16.0); 2.5018 (0.4); 2.0942 (0.4); 2.0768 (0.4); 2.0631 (1.0); 2.0456 (1.1); 2.0323 (1.1); 2.0145 (1.0); 2.0015 (0.4); 1.9835 (0.3); 1.5584 (5.2); −0.0002 (5.7) |
| I.0830: $^1$H-NMR(400.1 MHz, CDCl3):<br>δ = 8.0131 (0.6); 7.5721 (2.2); 7.5565 (2.3); 7.2606 (12.4); 4.8009 (3.1); 4.7925 (3.1); 4.7835 (3.1); 4.3374 (2.6); 4.3198 (7.6); 4.3019 (7.7); 4.2842 (2.8); 4.1672 (1.9); 4.1606 (2.0); 4.1391 (3.4); 4.1326 (3.5); 4.0760 (3.3); 4.0691 (3.5); 4.0479 (1.9); 4.0408 (1.9); 2.9568 (2.9); 2.8808 (2.9); 2.1572 (0.9); 1.5711 (1.8); 1.5078 (0.4); 1.4316 (0.8); 1.3484 (8.1); 1.3307 (16.0); 1.3130 (8.2); −0.0002 (17.0) |
| I.0831: $^1$H-NMR(400.1 MHz, CDCl3):<br>δ = 8.0287 (2.4); 8.0129 (2.8); 7.2608 (12.7); 4.8210 (3.2); 4.8125 (3.2); 4.8043 (3.2); 4.3425 (2.7); 4.3248 (7.8); 4.3071 (8.0); 4.2893 (2.8); 4.1560 (1.6); 4.1289 (3.6); 4.0868 (3.5); 4.0594 (1.6); 2.9558 (2.2); 2.8799 (2.1); 2.0953 (2.0); 1.5557 (4.7); 1.4317 (1.2); 1.3560 (8.1); 1.3382 (16.0); 1.3205 (8.3); −0.0002 (17.4) |
| I.0832: $^1$H-NMR(400.1 MHz, CDCl3):<br>δ = 7.2603 (14.9); 7.2072 (2.4); 4.7800 (3.1); 4.7721 (3.0); 4.3211 (2.7); 4.3033 (7.8); 4.2856 (7.9); 4.2679 (2.8); 4.1005 (1.4); 4.0744 (3.8); 4.0478 (3.8); 4.0188 (1.3); 2.9560 (0.5); 2.8823 (0.5); 2.2046 (2.3); 1.5535 (7.6); 1.3426 (8.2); 1.3250 (16.0); 1.3073 (8.2); −0.0002 (20.4) |
| I.0833: $^1$H-NMR(400.1 MHz, CDCl3):<br>δ = 7.2609 (5.7); 6.9079 (1.2); 6.8930 (1.2); 4.7965 (1.7); 4.7880 (1.6); 4.7795 (1.6); 4.3318 (1.4); 4.3142 (4.1); 4.2963 (4.1); 4.2786 (1.4); 4.1476 (1.0); 4.1411 (1.0); 4.1194 (2.0); 4.1130 (2.0); 4.0654 (2.0); 4.0598 (2.0); 4.0378 (1.0); 4.0316 (1.0); 2.9610 (0.4); 2.8803 (0.3); 2.5280 (16.0); 2.1200 (0.4); 1.5871 (0.4); 1.3527 (4.3); 1.3350 (8.4); 1.3172 (4.3); −0.0002 (7.8) |
| I.0834: $^1$H-NMR(400.1 MHz, CDCl3):<br>δ = 7.2669 (1.4); 6.9473 (1.3); 6.9307 (1.3); 4.7876 (1.6); 4.7790 (1.6); 4.7700 (1.6); 4.3250 (1.4); 4.3072 (4.1); 4.2894 (4.2); 4.2718 (1.5); 4.1427 (0.5); 4.1329 (0.8); 4.1160 (1.2); 4.1049 (1.6); 4.0956 (1.1); 4.0622 (1.1); 4.0516 (1.4); 4.0411 (1.2); 4.0240 (0.8); 4.0145 (0.6); 2.5506 (16.0); 2.5240 (0.3); 2.3655 (1.3); 2.3518 (2.5); 2.3382 (1.3); 1.6839 (3.2); 1.3504 (4.3); 1.3326 (8.5); 1.3149 (4.3); −0.0002 (1.5) |
| I.0835: $^1$H-NMR(400.1 MHz, CDCl3):<br>δ = 7.2616 (6.9); 6.9111 (1.2); 6.8958 (1.2); 4.7980 (1.7); 4.7893 (1.7); 4.7806 (1.6); 4.3321 (1.4); 4.3144 (4.1); 4.2967 (4.2); 4.2788 (1.4); 4.1446 (0.8); 4.1165 (1.6); 4.0611 (1.5); 4.0501 (1.3); 4.0346 (0.8); 2.5283 (16.0); 2.5057 (0.5); 2.1379 (1.2); 2.1245 (2.4); 2.1113 (1.2); 1.5738 (17.6); 1.3531 (4.2); 1.3354 (8.4); 1.3177 (4.3); −0.0002 (7.1) |
| I.0836: $^1$H-NMR(400.1 MHz, CDCl3):<br>δ = 7.2634 (3.6); 6.9041 (1.2); 6.8875 (1.3); 5.3000 (0.4); 4.8981 (0.7); 4.8823 (1.6); 4.8677 (1.6); 4.8517 (0.7); 3.8197 (15.8); 2.5985 (2.3); 2.5811 (5.0); 2.5637 (2.9); 2.5164 (15.5); 2.3139 (0.6); 2.2958 (1.0); 2.2783 (1.2); 2.2626 (1.0); 2.2454 (0.4); 2.1975 (0.5); 2.1806 (1.3); 2.1636 (1.4); 2.1450 (1.2); 2.1223 (16.0); 1.5766 (10.6); −0.0002 (3.7) |
| I.0837: $^1$H-NMR(400.1 MHz, CDCl3):<br>δ = 7.3900 (3.3); 7.2616 (10.6); 4.4081 (15.8); 4.3941 (16.0); 1.5605 (23.1); 1.2638 (0.5); 0.8820 (0.4); −0.0002 (12.7) |
| I.0838: $^1$H-NMR(400.1 MHz, CDCl3):<br>δ = 7.8290 (1.4); 7.8131 (1.4); 7.2616 (6.4); 4.8934 (0.7); 4.8781 (1.7); 4.8627 (1.8); 4.8474 (0.7); 4.2990 (1.4); 4.2814 (4.0); 4.2638 (4.1); 4.2461 (1.4); 2.6180 (0.5); 2.6028 (1.1); 2.5843 (1.6); 2.5748 (1.4); 2.5657 (1.5); 2.5570 (1.7); 2.5385 (1.3); 2.5229 (0.6); 2.5041 (0.4); 2.3462 (0.3); 2.3307 (0.6); 2.3111 (1.0); 2.2957 (1.2); 2.2764 (0.9); 2.2612 (0.4); 2.1941 (0.4); 2.1779 (1.0); 2.1585 (1.2); 2.1417 (1.1); 2.1077 (16.0); 2.0062 (2.9); 1.5576 (14.0); 1.3432 (4.1); 1.3255 (8.3); 1.3077 (4.6); 1.2648 (2.4); 0.8969 (0.9); 0.8819 (1.8); 0.8649 (0.9); −0.0002 (7.6) |
| I.0839: $^1$H-NMR(400.1 MHz, CDCl3):<br>δ = 7.6679 (8.9); 7.2628 (18.5); 4.7071 (4.4); 4.6934 (5.3); 4.6850 (6.2); 4.6766 (7.5); 4.6662 (6.1); 4.6579 (5.5); 4.6442 (4.7); 4.5697 (7.1); 4.5471 (16.0); 4.5246 (9.3); 4.3916 (5.1); 4.3763 (6.1); 4.3656 (7.9); 4.3512 (8.1); 4.3414 (5.2); 4.3257 (4.3); 3.0042 (4.2); 2.9866 (5.8); 2.9713 (7.7); 2.9561 (6.4); 2.9370 (4.5); 2.3530 (2.3); 2.3241 (6.8); 2.3004 (8.0); 2.2718 (6.4); 2.2426 (2.1); 1.5726 (40.7); 1.2555 (0.5); −0.0002 (21.7) |
| I.0840: $^1$H-NMR(400.1 MHz, CDCl3):<br>δ = 7.8639 (1.0); 7.2612 (2.8); 3.7999 (8.4); 1.6932 (16.0); 1.5550 (5.7); −0.0002 (3.5) |
| I.0841: $^1$H-NMR(500.1 MHz, CDCl3):<br>δ = 7.2661 (1.2); 6.8111 (0.6); 6.7976 (0.6); 4.7701 (0.6); 4.7631 (1.2); 4.7560 (1.2); 4.7490 (1.2); 4.7420 (0.6); 4.3053 (1.1); 4.2911 (3.3); 4.2768 (3.4); 4.2626 (1.2); 4.0593 (0.9); 4.0516 (0.6); 4.0468 (0.6); 4.0391 (0.8); 2.6048 (0.6); 2.5258 (16.0); 1.7070 (0.3); 1.3376 (4.2); 1.3323 (0.4); 1.3234 (8.4); 1.3091 (4.1); −0.0002 (1.4) |
| I.0842: $^1$H-NMR(500.1 MHz, CDCl3):<br>δ = 7.2668 (1.4); 6.8206 (0.6); 6.8070 (0.6); 4.7695 (0.6); 4.7625 (1.3); 4.7554 (1.2); 4.7483 (1.2); 4.7413 (0.6); 4.3041 (1.1); 4.2898 (3.4); 4.2756 (3.5); 4.2613 (1.2); 4.0608 (0.8); 4.0553 (0.8); 4.0385 (0.8); 2.6320 (0.4); 2.5561 (2.0); 2.5290 (16.0); 2.5243 (0.8); 2.5003 (1.3); 1.3370 (4.9); 1.3228 (9.9); 1.3085 (4.8); −0.0002 (1.6) |
| I.0843: $^1$H-NMR(500.1 MHz, CDCl3):<br>δ = 7.2661 (1.2); 6.8143 (0.7); 6.8007 (0.8); 4.7688 (0.6); 4.7619 (1.3); 4.7548 (1.2); 4.7477 (1.3); 4.7407 (0.6); 4.3037 (1.1); 4.2894 (3.4); 4.2752 (3.5); 4.2609 (1.2); 4.0805 (0.4); 4.0664 (0.6); 4.0583 (1.0); 4.0495 (0.8); 4.0454 (0.7); 4.0366 (1.0); 4.0289 (0.7); 4.0147 (0.3); 2.6216 (0.5); 2.6115 (0.9); 2.6013 (0.5); 2.5569 (16.0); 1.7099 (0.6); 1.3367 (4.3); 1.3224 (8.5); 1.3082 (4.2); −0.0002 (1.3) |
| I.0844: $^1$H-NMR(400.1 MHz, $d_6$-DMSO):<br>δ = 8.3621 (3.4); 8.3438 (3.6); 5.0703 (2.4); 5.0559 (5.1); 5.0415 (2.8); 4.4727 (1.3); 4.4590 (3.1); 4.4432 (3.2); 4.4296 (1.5); 4.1480 (2.5); 4.1304 (7.5); 4.1128 (7.8); 4.0954 (2.9); 3.7829 (4.9); 3.7698 (9.1); 3.7564 (5.4); 3.3123 (14.7); 2.5008 (9.2); 2.4158 (29.4); 1.2144 (7.9); 1.1968 (16.0); 1.1794 (8.4); −0.0002 (6.6) |
| I.0845: $^1$H-NMR(400.1 MHz, CDCl3):<br>δ = 7.2606 (6.7); 4.4736 (10.3); 4.2779 (1.4); 4.2602 (4.1); 4.2424 (4.1); 4.2247 (1.4); 3.7609 (16.0); 1.5479 (3.4); 1.3148 (4.3); 1.2971 (8.2); 1.2794 (4.2); −0.0002 (9.0) |
| I.0846: $^1$H-NMR(400.1 MHz, CDCl3):<br>δ = 7.2610 (6.4); 6.9134 (1.2); 6.9002 (1.2); 4.7996 (1.6); 4.7906 (1.7); 4.7821 (1.7); 4.3319 (1.4); 4.3142 (4.1); 4.2965 (4.2); 4.2790 (1.5); 4.1479 (1.0); 4.1423 (1.1); 4.1212 (2.0); 4.1143 (2.1); 4.0656 (2.0); 4.0596 (2.1); 4.0392 (1.1); 4.0317 (1.1); 2.9680 (0.9); 2.8880 (1.0); 2.5801 (1.2); 2.5565 (16.0); 2.5281 (0.4); 2.2419 (0.3); 1.4325 (0.5); 1.3528 (4.2); 1.3350 (8.4); 1.3174 (4.4); −0.0002 (8.3) |

TABLE A-(I)-continued

| NMR peak lists of compounds according to formula (I) |
|---|
| I.0847: $^{1}$H-NMR(400.1 MHz, $d_6$-DMSO): δ = 8.3379 (3.4); 8.3197 (3.5); 5.2523 (2.4); 5.2386 (5.1); 5.2247 (2.6); 4.5417 (2.8); 4.5326 (2.8); 4.5242 (2.9); 4.5140 (1.5); 4.1747 (2.6); 4.1572 (7.7); 4.1394 (7.9); 4.1219 (2.8); 3.8657 (0.8); 3.8531 (1.4); 3.8390 (2.5); 3.8254 (3.0); 3.8131 (1.9); 3.7945 (1.9); 3.7830 (3.1); 3.7711 (2.4); 3.7557 (1.5); 3.7444 (0.9); 3.3072 (14.9); 2.5006 (17.3); 1.2295 (7.9); 1.2118 (16.0); 1.1941 (8.2); −0.0002 (15.8) |
| I.0848: $^{1}$H-NMR(300.1 MHz, $d_6$-DMSO): δ = 8.4710 (0.8); 8.4521 (1.6); 8.4329 (0.8); 4.1610 (2.2); 4.1372 (6.9); 4.1135 (7.0); 4.0899 (2.2); 4.0250 (6.9); 4.0056 (6.8); 3.3588 (1.4); 2.5148 (3.2); 2.5090 (6.2); 2.5031 (8.2); 2.4973 (5.7); 2.4644 (25.8); 2.0771 (0.4); 1.2296 (7.7); 1.2059 (16.0); 1.1822 (7.4); −0.0001 (1.6) |
| I.0849: $^{1}$H-NMR(400.2 MHz, $d_6$-DMSO): δ = 9.0481 (2.8); 3.6475 (16.0); 3.6284 (2.0); 3.3400 (103.2); 3.3240 (24.3); 2.8913 (0.8); 2.7314 (0.8); 2.6717 (0.3); 2.5913 (1.0); 2.5696 (1.8); 2.5030 (51.6); 2.3403 (1.1); 2.3177 (2.1); 2.2977 (1.8); 2.2896 (1.9); 2.2666 (1.0); 1.9951 (0.6); 1.9817 (1.1); 1.9721 (1.1); 1.9595 (1.9); 1.9409 (1.9); 1.9199 (1.2); 1.8993 (0.4); 0.0002 (2.7); −0.0192 (0.4) |
| I.0850: $^{1}$H-NMR(400.1 MHz, CDCl3): δ = 7.2598 (44.9); 7.2331 (2.6); 4.4018 (16.0); 4.3873 (15.6); 1.5360 (25.7); 1.2538 (1.3); 0.8821 (0.5); 0.1474 (0.4); −0.0002 (58.9) |
| I.0851: $^{1}$H-NMR(400.1 MHz, CDCl3): δ = 9.4476 (0.7); 7.2599 (10.1); 4.5589 (5.2); 4.5482 (5.2); 3.8703 (16.0); 1.5354 (5.6); −0.0002 (13.2) |
| I.0852: $^{1}$H-NMR(400.1 MHz, CDCl3): δ = 9.3139 (0.7); 7.2599 (10.4); 4.5447 (5.2); 4.5338 (5.0); 3.8666 (16.0); 1.5355 (6.9); −0.0002 (13.6) |
| I.0853: $^{1}$H-NMR(400.1 MHz, CDCl3): δ = 8.9317 (2.0); 7.2598 (26.7); 4.2474 (2.5); 4.2296 (7.6); 4.2118 (7.7); 4.1941 (2.7); 2.8847 (1.4); 2.8708 (1.7); 2.8614 (2.1); 2.8485 (2.7); 2.8375 (2.4); 2.8283 (2.0); 2.8149 (1.8); 2.4481 (1.4); 2.4286 (2.1); 2.4231 (2.9); 2.4038 (2.5); 2.3964 (2.8); 2.3717 (1.6); 2.2120 (0.7); 2.2059 (0.6); 2.1924 (1.0); 2.1870 (1.2); 2.1831 (1.2); 2.1638 (1.8); 2.1444 (1.4); 2.1307 (1.0); 2.1171 (1.3); 2.1053 (1.6); 2.0916 (1.3); 2.0803 (1.0); 2.0767 (1.0); 2.0652 (0.7); 2.0513 (0.4); 1.5371 (17.3); 1.2833 (8.0); 1.2655 (16.0); 1.2477 (8.0); −0.0002 (33.7) |
| I.0854: $^{1}$H-NMR(400.1 MHz, $d_6$-DMSO): δ = 10.4039 (1.7); 4.3196 (16.0); 3.3404 (1.5); 3.2535 (1.1); 3.1115 (0.4); 2.5012 (39.0); 1.9887 (0.4); 1.3556 (0.5); −0.0002 (13.2) |
| I.0855: $^{1}$H-NMR(400.2 MHz, $d_6$-DMSO): δ = 8.5812 (3.1); 4.7672 (16.0); 4.7611 (14.2); 4.0486 (11.8); 4.0341 (10.1); 3.6046 (4.3); 3.5993 (6.6); 3.5933 (3.2); 3.3375 (36.6); 2.8935 (1.2); 2.7341 (1.1); 2.5094 (27.5); 2.5052 (31.7); 1.2384 (0.4); −0.0002 (0.7) |
| I.0856: $^{1}$H-NMR(400.2 MHz, $d_6$-DMSO): δ = 8.5236 (3.7); 8.5184 (3.6); 4.1390 (1.5); 4.1312 (3.0); 4.1235 (4.3); 4.1154 (5.0); 4.1115 (3.6); 4.1081 (3.7); 4.0997 (2.9); 4.0920 (1.5); 3.9626 (15.9); 3.9480 (16.0); 3.3358 (52.9); 2.8936 (1.7); 2.7342 (1.5); 2.5096 (32.7); 2.5052 (42.2); 2.5008 (32.0); 1.2376 (0.6); 0.7317 (1.6); 0.7263 (1.4); 0.7123 (7.5); 0.6969 (9.2); 0.6935 (8.3); 0.6823 (5.9); 0.6636 (2.7); 0.6578 (4.4); 0.6501 (9.9); 0.6431 (9.7); 0.6373 (7.8); 0.6254 (2.1); 0.6179 (2.0); −0.0002 (1.2) |
| I.0857: $^{1}$H-NMR(400.2 MHz, $d_6$-DMSO): δ = 8.5644 (3.8); 8.5591 (3.7); 5.9633 (1.4); 5.9499 (2.9); 5.9368 (2.8); 5.9236 (3.5); 5.9204 (2.2); 5.9100 (2.1); 5.9068 (3.8); 5.8936 (3.3); 5.8805 (3.6); 5.8672 (1.8); 5.3546 (2.4); 5.3506 (6.3); 5.3465 (6.6); 5.3425 (2.8); 5.3115 (2.1); 5.3075 (5.5); 5.3034 (5.7); 5.2994 (2.4); 5.2445 (2.8); 5.2413 (6.3); 5.2376 (6.2); 5.2150 (5.8); 5.2113 (5.9); 4.6233 (8.6); 4.6199 (13.8); 4.6165 (9.6); 4.6101 (9.1); 4.6066 (13.6); 4.6033 (8.9); 4.0432 (15.8); 4.0286 (16.0); 3.3372 (55.4); 2.8934 (1.9); 2.7337 (1.6); 2.5097 (32.7); 2.5053 (42.6); 2.5008 (32.8); 1.2373 (0.7); −0.0002 (1.4) |
| I.0858: $^{1}$H-NMR(400.2 MHz, $d_6$-DMSO): δ = 8.5778 (3.4); 8.5725 (3.3); 7.9536 (0.8); 4.2808 (7.8); 4.2658 (15.5); 4.2508 (8.1); 4.0508 (12.8); 4.0363 (12.8); 3.3373 (54.0); 2.9168 (8.4); 2.9018 (16.0); 2.8934 (6.4); 2.8869 (8.3); 2.7341 (4.3); 2.5091 (29.5); 2.5052 (37.5); 1.2378 (0.6); −0.0003 (0.8) |
| I.0859: $^{1}$H-NMR(400.2 MHz, $d_6$-DMSO): δ = 8.5266 (3.1); 8.5214 (3.0); 7.9539 (0.3); 4.0075 (12.5); 3.9928 (12.6); 3.9344 (15.8); 3.9163 (16.0); 3.3362 (52.8); 2.8930 (2.2); 2.7333 (2.0); 2.5091 (30.6); 2.5048 (39.4); 2.5004 (30.3); 1.2370 (0.6); 1.1307 (0.6); 1.1231 (1.0); 1.1112 (1.9); 1.1044 (1.7); 1.1009 (1.5); 1.0927 (3.0); 1.0846 (1.5); 1.0807 (1.9); 1.0730 (2.1); 1.0610 (1.1); 1.0545 (0.7); 1.0426 (0.3); 0.5416 (2.2); 0.5306 (7.4); 0.5266 (7.7); 0.5158 (3.8); 0.5107 (7.6); 0.5063 (7.2); 0.4960 (2.7); 0.4793 (0.3); 0.2925 (2.7); 0.2818 (9.0); 0.2784 (8.8); 0.2701 (8.0); 0.2664 (9.1); 0.2551 (2.2); −0.0002 (1.0) |
| I.0860: $^{1}$H-NMR(400.2 MHz, $d_6$-DMSO): δ = 8.5249 (1.6); 8.5196 (1.6); 4.0931 (4.5); 4.0767 (9.2); 4.0603 (4.6); 3.9894 (6.8); 3.9748 (6.9); 3.3368 (31.9); 2.8934 (0.4); 2.7336 (0.4); 2.5274 (0.3); 2.5138 (7.9); 2.5095 (15.6); 2.5050 (20.5); 2.5005 (15.5); 2.4963 (8.0); 1.5918 (0.9); 1.5749 (2.9); 1.5685 (1.1); 1.5578 (3.8); 1.5379 (3.2); 1.5216 (1.3); 1.3721 (0.6); 1.3535 (2.3); 1.3345 (3.7); 1.3156 (3.7); 1.2974 (2.2); 1.2793 (0.6); 1.2373 (0.4); 0.8994 (8.2); 0.8811 (16.0); 0.8625 (7.0); −0.0002 (1.5) |
| I.0861: $^{1}$H-NMR(400.1 MHz, $d_6$-DMSO): δ = 10.3096 (2.4); 4.3403 (16.0); 4.0379 (0.4); 4.0204 (0.4); 3.6786 (0.4); 3.4958 (0.4); 3.4147 (0.5); 3.3622 (0.5); 3.3481 (0.5); 3.3243 (0.5); 3.2810 (0.5); 3.2696 (0.5); 3.2371 (0.4); 3.1992 (0.4); 3.1460 (0.3); 2.5019 (25.5); 1.9888 (1.6); 1.3553 (1.7); 1.2331 (0.3); 1.1928 (0.5); 1.1750 (0.9); 1.1572 (0.5); −0.0002 (8.1) |
| I.0862: $^{1}$H-NMR(400.2 MHz, $d_6$-DMSO): δ = 8.5050 (4.1); 8.4999 (4.1); 8.3168 (0.4); 7.9537 (0.7); 5.1252 (2.8); 5.1106 (5.3); 5.0959 (2.8); 3.9407 (15.8); 3.9261 (16.0); 3.3364 (71.1); 3.3136 (0.4); 2.8937 (4.2); 2.7341 (3.7); 2.5097 (37.5); 2.5054 (49.6); 2.5011 (40.1); 1.8302 (5.2); 1.8176 (4.6); 1.8036 (3.5); 1.7973 (3.4); 1.7889 (2.6); 1.6299 (13.4); 1.6211 (10.4); 1.5982 (7.4); 1.5829 (5.2); 1.5742 (4.4); 1.5668 (4.2); 1.5595 (4.4); 1.5549 (4.1); 1.5461 (5.3); 1.5386 (5.3); 1.5290 (3.2); 1.2373 (1.0); −0.0002 (1.2) |
| I.0863: $^{1}$H-NMR(400.2 MHz, $d_6$-DMSO): δ = 8.7065 (4.0); 8.7011 (4.0); 7.9545 (0.4); 7.4615 (7.3); 7.4567 (3.4); 7.4424 (13.4); 7.4413 (13.5); 7.4264 (4.6); 7.4219 (10.9); 7.4164 (2.1); 7.3013 (5.2); 7.2989 (3.7); 7.2828 (8.1); 7.2667 (2.2); 7.2643 (3.4); 7.1470 (11.6); 7.1442 (15.0); 7.1253 (12.4); 7.1233 (11.6); 4.2935 (15.5); 4.2792 (16.0); 3.3425 (92.0); 2.8922 (3.0); 2.7335 (2.5); 2.6743 (0.3); 2.5098 (39.9); 2.5053 (52.4); 2.5008 (40.3); 2.4966 (21.9); 2.3322 (0.3); 1.2374 (0.6); −0.0002 (1.3) |
| I.0864: $^{1}$H-NMR(400.1 MHz, CDCl3): δ = 8.0610 (0.5); 7.2612 (5.2); 5.2996 (0.8); 4.5391 (3.2); 4.5281 (3.2); 3.8750 (10.0); 3.8582 (0.9); 2.5325 (9.5); 2.5089 (0.4); 2.4700 (0.5); 2.1702 (16.0); 2.0065 (0.4); 1.6259 (0.6); 1.2563 (1.0); −0.0002 (5.9) |
| I.0865: $^{1}$H-NMR(500.1 MHz, CDCl3): δ = 8.2963 (1.1); 7.2604 (10.3); 4.6796 (1.5); 4.6650 (2.9); 4.6495 (1.6); 4.2861 (2.4); 4.2719 (7.3); 4.2577 (7.4); 4.2434 (2.5); 1.5453 (11.3); 1.3313 (8.0); 1.3171 (16.0); 1.3029 (8.9); 1.2933 (2.0); 1.2848 (1.3); 1.2771 (1.8); 1.2675 (1.0); 1.2612 (0.8); 1.2513 (0.4); 0.7079 (0.8); 0.6980 (1.3); 0.6872 (1.8); 0.6814 (2.5); 0.6710 (1.9); 0.6649 (2.7); 0.6564 (2.1); 0.6463 (2.8); 0.6405 (2.7); 0.6294 (2.6); 0.6196 (2.4); 0.6119 (1.9); 0.6034 (0.9); 0.5949 (1.5); 0.5848 (1.4); 0.5787 (2.2); 0.5679 (1.7); 0.5622 (0.9); −0.0002 (12.3) |

TABLE A-(I)-continued

| NMR peak lists of compounds according to formula (I) |
|---|
| I.0866: $^1$H-NMR(400.1 MHz, $d_6$-DMSO):<br>δ = 8.8986 (2.1); 4.8404 (0.8); 4.8233 (0.9); 4.8087 (0.9); 4.7917 (0.8); 3.4940 (0.4); 3.4807 (0.6); 3.4649 (1.1); 3.4517 (1.2); 3.4364 (0.9); 3.4231 (0.8); 3.3611 (1.2); 3.3436 (1.4); 3.3337 (1.1); 3.3172 (10.0); 2.8905 (0.4); 2.7309 (0.3); 2.5419 (0.5); 2.5270 (0.8); 2.5011 (10.0); 2.3941 (16.0); 2.3115 (0.4); 2.2939 (0.4); 2.2807 (0.9); 2.2628 (1.0); 2.2497 (0.9); 2.2319 (0.9); 2.2192 (0.4); −0.0002 (2.6) |
| I.0867: $^1$H-NMR(600.2 MHz, $d_6$-DMSO):<br>δ = 8.6620 (6.5); 8.6485 (6.6); 4.8698 (2.6); 4.8573 (4.1); 4.8486 (3.4); 4.8446 (3.2); 4.8358 (4.1); 4.8234 (2.7); 3.5279 (2.4); 3.5188 (2.9); 3.5091 (4.7); 3.5001 (4.6); 3.4895 (4.1); 3.4804 (3.3); 3.4056 (4.5); 3.3953 (5.0); 3.3936 (4.8); 3.3871 (4.3); 3.3803 (16.0); 2.5686 (6.8); 2.5656 (11.0); 2.5625 (15.7); 2.5595 (13.4); 2.5567 (7.2); 2.5499 (4.4); 2.5482 (4.3); 2.5388 (3.9); 2.5368 (3.0); 2.5293 (2.3); 2.4245 (1.5); 2.4127 (1.9); 2.4041 (3.9); 2.3922 (4.1); 2.3835 (3.7); 2.3715 (3.6); 2.3630 (1.4); 2.3512 (1.1); 2.0497 (0.6); 1.2357 (0.3) |
| I.0868: $^1$H-NMR(400.1 MHz, $d_6$-DMSO):<br>δ = 8.8798 (11.7); 7.9522 (1.6); 3.3159 (61.0); 3.2750 (0.6); 2.8905 (9.7); 2.8293 (3.1); 2.8219 (2.9); 2.8129 (3.2); 2.8010 (6.1); 2.7867 (7.9); 2.7780 (6.4); 2.7627 (6.6); 2.7562 (7.6); 2.7385 (7.7); 2.7313 (16.0); 2.7031 (3.4); 2.6966 (3.0); 2.6701 (0.5); 2.5263 (6.0); 2.5010 (47.6); 2.1975 (4.4); 2.1896 (4.9); 2.1738 (5.2); 2.1647 (7.5); 2.1566 (4.6); 2.1399 (4.1); 2.1320 (3.4); −0.0002 (12.6) |
| I.0869: $^1$H-NMR(400.1 MHz, CDCl3):<br>δ = 7.5191 (0.4); 7.2864 (0.5); 7.2600 (76.3); 7.0179 (0.4); 6.9816 (11.1); 2.9566 (0.7); 2.8837 (0.7); 2.6898 (8.3); 2.6645 (12.6); 2.6363 (0.5); 2.5578 (0.3); 2.3169 (0.5); 2.2856 (0.5); 1.8831 (10.2); 1.8507 (8.4); 1.7936 (1.0); 1.7439 (16.0); 1.7211 (15.9); 1.6770 (5.2); 1.6472 (4.9); 1.6170 (4.9); 1.5794 (11.6); 1.5560 (23.3); 1.5408 (24.2); 1.5023 (7.1); 1.4732 (2.4); 1.4449 (0.7); 1.4302 (0.7); 1.4105 (0.8); 1.3790 (0.7); 1.3440 (0.4); 1.3126 (0.4); 1.2696 (2.3); 1.2388 (6.5); 1.2080 (9.4); 1.1708 (13.4); 1.1510 (9.0); 1.1404 (9.4); 1.1094 (4.0); 1.0779 (1.3); 1.0168 (3.8); 0.9927 (7.6); 0.9645 (6.7); 0.9364 (2.5); 0.8797 (0.3); 0.1456 (0.5); 0.0271 (0.4); −0.0002 (108.1); −0.0338 (0.5); −0.0473 (0.4); −0.1489 (0.5) |
| I.0870: $^1$H-NMR(400.1 MHz, $d_6$-DMSO):<br>δ = 8.9311 (6.4); 7.9523 (0.3); 7.3434 (4.9); 7.3243 (13.3); 7.3062 (11.4); 7.2591 (16.0); 7.2403 (10.4); 7.2131 (8.8); 7.1951 (4.5); 3.3633 (0.4); 3.3192 (115.6); 2.8903 (1.8); 2.7308 (1.7); 2.6971 (1.9); 2.6681 (3.9); 2.6388 (2.8); 2.5814 (6.8); 2.5512 (8.2); 2.5014 (47.8); 2.4978 (41.8); 2.3653 (0.4); 2.3344 (0.5); 2.0238 (0.6); 1.9706 (5.8); 1.9389 (6.5); 1.8335 (2.9); 1.8010 (7.1); 1.7660 (7.4); 1.7526 (6.1); 1.7215 (8.3); 1.6878 (5.4); 1.6603 (1.9); 1.6320 (0.4); 1.2314 (0.4); −0.0002 (5.6) |
| I.0871: $^1$H-NMR(400.1 MHz, $d_6$-DMSO):<br>δ = 17.9456 (0.5); 17.7772 (0.4); 8.6331 (8.7); 7.9521 (2.4); 4.5533 (0.4); 3.4638 (0.4); 3.4386 (0.7); 3.3225 (93.8); 3.2135 (0.8); 3.1878 (0.6); 3.1119 (0.5); 3.0769 (0.5); 2.9978 (0.5); 2.9732 (0.6); 2.9420 (0.5); 2.8900 (14.8); 2.8012 (1.6); 2.7649 (14.5); 2.7447 (8.0); 2.7302 (16.0); 2.7092 (2.2); 2.6698 (1.6); 2.5008 (210.2); 2.4969 (172.7); 2.3275 (1.4); 2.2800 (0.5); 2.2614 (0.5); 2.1618 (3.2); 2.1511 (3.8); 2.1400 (4.0); 2.1285 (5.9); 2.1053 (3.5); 2.0962 (3.0); 0.1459 (0.6); −0.0002 (90.9); −3.6640 (0.5) |
| I.0872: $^1$H-NMR(400.1 MHz, $d_6$-DMSO):<br>δ = 8.6089 (2.8); 3.3166 (16.1); 2.8909 (1.6); 2.7317 (1.5); 2.5054 (8.6); 2.5015 (11.0); 1.6325 (16.0); 1.5406 (0.4); 1.5259 (0.8); 1.5210 (0.9); 1.5146 (0.7); 1.5068 (1.5); 1.4931 (0.9); 1.4881 (0.8); 1.4735 (0.4); 0.6582 (1.3); 0.6469 (2.1); 0.6376 (3.7); 0.6224 (2.8); 0.6179 (2.7); 0.6047 (0.9); 0.5933 (0.4); 0.5293 (0.4); 0.5080 (1.3); 0.4958 (1.2); 0.4823 (0.7); 0.4706 (0.3); −0.0002 (3.4) |
| I.0873: $^1$H-NMR(400.1 MHz, CDCl3):<br>δ = 14.6496 (0.4); 7.5176 (0.7); 7.3046 (0.5); 7.2598 (134.0); 7.2418 (13.5); 7.1435 (0.4); 6.9957 (0.8); 3.4912 (0.4); 2.9295 (6.6); 2.9168 (8.3); 2.9072 (10.5); 2.9018 (10.8); 2.8950 (16.0); 2.8835 (12.0); 2.8743 (10.2); 2.8625 (9.3); 2.5131 (6.2); 2.4889 (15.0); 2.4601 (14.7); 2.4365 (7.9); 2.3483 (1.8); 2.3268 (4.5); 2.3197 (2.8); 2.3057 (6.5); 2.2977 (7.3); 2.2847 (4.4); 2.2768 (9.6); 2.2557 (5.6); 2.2340 (1.5); 2.2151 (2.4); 2.2028 (4.2); 2.1904 (5.7); 2.1791 (7.4); 2.1670 (5.8); 2.1549 (4.5); 2.1494 (5.1); 2.1374 (3.6); 2.1255 (2.2); 2.1134 (1.1); 1.5818 (0.4); 1.5356 (75.1); 1.2545 (2.1); 0.8993 (0.5); 0.8823 (0.5); 0.8656 (0.4); 0.1475 (0.8); 0.0438 (0.4); −0.0002 (182.9); −0.1495 (1.0) |
| I.0874: $^1$H-NMR(400.1 MHz, CDCl3):<br>δ = 7.2601 (10.5); 7.2181 (1.2); 7.1970 (1.2); 4.9665 (1.8); 4.9517 (2.1); 4.9450 (2.0); 4.9302 (1.9); 2.2408 (0.3); 2.2243 (0.9); 2.2078 (1.5); 2.1915 (1.6); 2.1749 (1.1); 2.1584 (0.4); 1.5405 (4.6); 1.1835 (10.7); 1.1692 (16.0); 1.1531 (10.9); −0.0002 (14.2) |
| I.0875: $^1$H-NMR(500.1 MHz, $d_6$-DMSO):<br>δ = 12.7749 (1.0); 8.4807 (1.6); 8.4696 (3.0); 8.4583 (1.6); 3.9620 (9.4); 3.9505 (9.4); 3.3099 (16.0); 2.5015 (25.7); 2.4991 (24.9); 1.2341 (0.4); −0.0002 (11.6) |
| I.0876: $^1$H-NMR(500.1 MHz, $d_6$-DMSO):<br>δ = 13.2163 (0.6); 10.0422 (1.3); 10.0335 (1.3); 7.9597 (3.0); 7.3161 (0.9); 7.3002 (4.9); 7.2880 (16.0); 7.2769 (1.6); 7.2361 (1.4); 7.2282 (1.5); 7.2236 (1.7); 7.2114 (0.8); 5.1418 (0.7); 5.1251 (1.2); 5.1161 (1.2); 5.0993 (0.7); 3.3194 (6.3); 3.3058 (3.4); 3.2962 (2.4); 3.2633 (2.1); 3.2446 (2.0); 3.2355 (1.1); 3.2166 (1.0); 2.8976 (16.0); 2.7386 (15.0); 2.5476 (0.8); 2.5088 (11.8) |
| I.0878: $^1$H-NMR(400.1 MHz, $d_6$-DMSO):<br>δ = 10.7748 (1.4); 7.8075 (5.5); 4.4518 (8.7); 3.6650 (16.0); 3.3171 (73.6); 3.2780 (0.5); 3.2667 (0.4); 2.5010 (21.6); 2.0734 (0.6); 1.2360 (0.4); −0.0002 (7.5) |
| I.0879: $^1$H-NMR(400.2 MHz, $d_6$-DMSO):<br>δ = 9.1660 (5.3); 4.0426 (5.1); 4.0266 (10.3); 4.0106 (5.1); 3.3478 (53.0); 3.3417 (43.9); 2.5944 (1.4); 2.5723 (2.5); 2.5616 (2.7); 2.5572 (2.7); 2.5480 (3.0); 2.5398 (2.5); 2.5081 (36.1); 2.5044 (43.1); 2.3350 (1.8); 2.3119 (3.2); 2.2918 (2.6); 2.2841 (3.0); 2.2613 (1.5); 2.0263 (0.4); 2.0122 (0.8); 1.9976 (1.4); 1.9893 (1.6); 1.9743 (3.1); 1.9522 (2.9); 1.9315 (1.4); 1.9106 (0.5); 1.9050 (0.4); 1.6214 (0.6); 1.6038 (2.6); 1.5864 (5.2); 1.5688 (5.3); 1.5516 (2.8); 1.5340 (0.7); 0.8901 (8.3); 0.8717 (16.0); 0.8531 (7.4) |
| I.0880: $^1$H-NMR(400.2 MHz, $d_6$-DMSO):<br>δ = 9.1598 (16.0); 7.9534 (1.3); 4.7540 (1.5); 4.7459 (3.1); 4.7356 (4.0); 4.7262 (5.8); 4.7173 (4.4); 4.7065 (2.9); 4.6976 (1.5); 3.3553 (338.3); 2.8924 (9.5); 2.7332 (7.8); 2.7323 (8.1); 2.6830 (0.4); 2.6785 (0.7); 2.6739 (1.0); 2.6694 (0.7); 2.5778 (3.9); 2.5732 (2.7); 2.5622 (4.9); 2.5561 (7.1); 2.5497 (5.6); 2.5451 (7.3); 2.5410 (7.0); 2.5309 (9.0); 2.5275 (8.5); 2.5228 (11.3); 2.5139 (63.5); 2.5095 (125.3); 2.5049 (158.0); 2.5003 (114.1); 2.4958 (55.8); 2.3314 (5.2); 2.3083 (8.8); 2.2883 (6.9); 2.2792 (8.1); 2.2569 (4.3); 2.0315 (0.4); 2.0173 (1.0); 2.0035 (2.3); 1.9897 (4.2); 1.9806 (4.1); 1.9703 (6.7); 1.9664 (7.0); 1.9504 (8.6); 1.9436 (4.6); 1.9289 (4.9); 1.9230 (2.4); 1.9082 (1.3); 1.9014 (1.1); 1.8805 (0.4); 1.7412 (4.0); 1.7321 (4.6); 1.7136 (6.6); 1.7015 (6.0); 1.6929 (6.9); 1.6524 (3.6); 1.6278 (5.8); 1.6108 (6.2); 1.6059 (6.2); 1.4496 (5.2); 1.4379 (7.8); 1.4296 (9.4); 1.4182 (7.2); 1.4084 (8.8); 1.3826 (7.7); 1.3645 (4.7); 1.3574 (7.4); 1.3347 (6.7); 1.3273 (6.6); 1.3052 (6.9); 1.2886 (3.2); 1.2818 (3.0); 1.2673 (2.2); 1.2607 (2.2); 1.2365 (0.9); −0.0002 (0.3) |
| I.0881: $^1$H-NMR(400.2 MHz, $d_6$-DMSO):<br>δ = 9.6643 (5.6); 9.1524 (5.8); 8.8039 (14.7); 7.9534 (0.5); 3.3708 (152.7); 2.8930 (3.0); 2.7418 (0.3); 2.7333 (2.7); 2.6792 (0.7); 2.6748 (0.9); 2.5102 (107.7); 2.5060 (133.2); 2.5017 (97.4); 2.3326 (0.8); 1.8547 (6.2); 1.8442 (15.1); 1.8352 (15.9); 1.8252 (6.3); 1.7860 (0.4); 1.2763 (0.5); 1.2367 (7.1); 1.2265 (16.0); 1.2175 (15.5); 1.2069 (5.9) |

TABLE A-(I)-continued

NMR peak lists of compounds according to formula (I)

I.0882: $^1$H-NMR(400.2 MHz, $d_6$-DMSO):
δ = 8.7086 (6.1); 8.3180 (0.3); 7.8929 (2.6); 7.8827 (2.5); 3.3742 (269.0); 2.8963 (1.0); 2.7359 (0.9); 2.6788 (0.4); 2.6077 (15.7); 2.5964 (16.0); 2.5096 (71.4); 2.3361 (0.4); 1.4083 (0.3); 1.3560 (2.6); 1.3445 (7.2); 1.3368 (8.1); 1.3266 (3.3); 1.0072 (3.1); 0.9968 (7.6); 0.9890 (7.8); 0.9778 (2.8)
I.0883: $^1$H-NMR(400.2 MHz, $d_6$-DMSO):
δ = 8.6635 (2.6); 8.6496 (5.5); 8.6353 (2.6); 7.9547 (0.4); 4.9583 (1.1); 4.9482 (2.2); 4.9374 (3.3); 4.9269 (4.5); 4.9163 (3.3); 4.9055 (2.3); 4.8954 (1.1); 4.0461 (16.0); 4.0317 (15.7); 3.7961 (3.4); 3.7851 (5.7); 3.7715 (4.4); 3.7676 (4.8); 3.7550 (6.8); 3.7436 (4.0); 3.4912 (4.9); 3.4837 (5.6); 3.4691 (5.8); 3.4618 (9.6); 3.4548 (4.9); 3.4401 (5.1); 3.4326 (4.6); 3.3697 (284.5); 2.8947 (2.8); 2.7355 (2.4); 2.6813 (0.5); 2.6769 (0.6); 2.6725 (0.5); 2.5302 (2.6); 2.5253 (4.2); 2.5168 (42.5); 2.5124 (83.0); 2.5079 (106.1); 2.5033 (76.4); 2.4988 (36.6); 2.3391 (0.5); 2.3346 (0.6); 2.3301 (0.5); 1.8833 (1.8); 1.8742 (3.8); 1.8686 (3.5); 1.8646 (3.9); 1.8513 (3.5); 1.8412 (4.8); 1.8370 (4.2); 1.8317 (4.5); 1.8226 (2.0); 1.5883 (2.4); 1.5784 (2.6); 1.5666 (4.7); 1.5563 (6.4); 1.5453 (4.3); 1.5342 (6.0); 1.5240 (3.8); 1.5121 (2.1); 1.5023 (1.8); 1.4019 (0.4)
I.0884: $^1$H-NMR(400.2 MHz, $d_6$-DMSO):
δ = 8.5954 (0.5); 8.5781 (0.5); 3.6875 (0.4); 3.6699 (0.5); 3.6656 (0.6); 3.6479 (0.4); 3.3383 (4.1); 3.3346 (4.9); 2.5079 (8.9); 2.5042 (10.8); 1.4272 (16.0); 1.2113 (0.3); 1.1904 (0.3); 0.5883 (0.3); 0.5192 (0.3); 0.4981 (0.3); 0.4462 (0.4); 0.4341 (0.4); 0.4229 (0.4); 0.3819 (0.4); 0.3709 (0.4); 0.3586 (0.3); −0.0002 (0.5)
I.0885: $^1$H-NMR(400.2 MHz, $d_6$-DMSO):
δ = 8.7551 (13.9); 8.7383 (13.9); 7.8799 (1.1); 7.8493 (1.0); 6.5715 (0.4); 6.0914 (1.0); 6.0605 (1.0); 4.9904 (2.7); 4.9725 (10.9); 4.9541 (16.0); 4.9356 (11.0); 4.9178 (2.8); 4.0130 (0.4); 3.9958 (0.5); 3.9785 (0.4); 3.8463 (0.4); 3.8298 (0.5); 3.8136 (0.4); 3.7997 (0.4); 3.7904 (0.6); 3.7341 (11.7); 3.7171 (12.8); 3.7113 (13.5); 3.6943 (11.9); 3.5084 (0.4); 3.3330 (264.2); 2.8912 (1.7); 2.7318 (1.5); 2.6762 (2.5); 2.6717 (3.5); 2.6672 (2.5); 2.5251 (11.7); 2.5203 (19.2); 2.5115 (228.6); 2.5072 (450.1); 2.5027 (578.8); 2.4982 (423.4); 2.4939 (209.2); 2.4283 (0.6); 2.3299 (7.3); 2.3245 (7.0); 2.3096 (9.0); 2.3006 (12.1); 2.2929 (13.2); 2.2820 (13.4); 2.2754 (11.4); 2.2619 (6.4); 2.2551 (5.5); 2.0791 (2.2); 2.0736 (1.2); 2.0698 (0.9); 2.0541 (6.5); 2.0485 (4.7); 2.0347 (7.8); 2.0291 (9.3); 2.0235 (7.9); 2.0148 (8.9); 2.0097 (9.5); 2.0042 (9.0); 1.9956 (8.3); 1.9902 (9.1); 1.9847 (8.1); 1.9799 (4.9); 1.9706 (5.7); 1.9654 (6.6); 1.9601 (3.9); 1.9502 (1.2); 1.9458 (1.5); 1.9404 (2.5); 1.8040 (1.8); 1.7991 (3.1); 1.7927 (2.0); 1.7792 (4.9); 1.7725 (8.7); 1.7658 (5.0); 1.7544 (4.9); 1.7520 (5.1); 1.7476 (8.7); 1.7410 (4.9); 1.7277 (1.9); 1.7227 (2.9); 1.7160 (1.7); 1.6643 (2.7); 1.6441 (5.5); 1.6392 (6.5); 1.6235 (3.9); 1.6189 (11.4); 1.5987 (6.1); 1.5924 (9.0); 1.5720 (4.3); 1.5672 (3.4); 1.5468 (1.5); 1.4257 (2.4); 1.3905 (5.0); 1.2715 (1.9); 1.2622 (7.1); 1.2460 (8.9); 1.2387 (9.8); 1.2336 (10.9); 1.2280 (9.0); 1.2167 (13.5); 1.2047 (5.2); 1.1964 (4.4); 1.1843 (2.5); 1.1608 (0.7); 1.0428 (0.5); 1.0254 (0.6); 0.8449 (0.4); 0.6427 (2.3); 0.6338 (3.3); 0.6298 (3.5); 0.6215 (7.4); 0.6134 (7.3); 0.6084 (7.6); 0.5983 (8.7); 0.5871 (5.2); 0.5773 (4.4); 0.5548 (3.7); 0.5446 (5.0); 0.5412 (6.0); 0.5317 (7.8); 0.5250 (6.2); 0.5210 (7.8); 0.5112 (10.1); 0.4980 (7.1); 0.4915 (6.9); 0.4840 (7.0); 0.4756 (9.6); 0.4633 (11.1); 0.4522 (8.1); 0.4395 (3.6); 0.4035 (4.5); 0.3925 (7.6); 0.3806 (9.3); 0.3680 (8.7); 0.3585 (5.2); 0.3471 (2.5); 0.3254 (0.4); 0.0079 (1.0); −0.0003 (30.2); −0.0085 (1.0)
I.0886: $^1$H-NMR(400.2 MHz, $d_6$-DMSO):
δ = 8.7240 (1.9); 8.7073 (1.9); 4.9755 (0.8); 4.9599 (2.0); 4.9443 (2.7); 4.9287 (2.0); 4.9131 (0.8); 3.7198 (1.8); 3.7028 (2.0); 3.6972 (2.0); 3.6801 (1.8); 3.3377 (14.3); 3.3353 (15.1); 2.5261 (0.9); 2.5084 (28.4); 2.5040 (35.5); 2.4996 (25.6); 1.2504 (0.6); 1.2396 (0.8); 1.2215 (13.8); 1.2096 (16.0); 1.2061 (15.2); 1.1943 (13.1); 1.1755 (0.4); 0.6309 (0.3); 0.6209 (0.5); 0.6174 (0.5); 0.6093 (1.0); 0.6001 (1.1); 0.5958 (1.1); 0.5860 (1.3); 0.5799 (0.7); 0.5744 (0.8); 0.5649 (0.7); 0.5528 (0.6); 0.5431 (0.8); 0.5399 (0.9); 0.5319 (1.2); 0.5197 (1.1); 0.5092 (1.1); 0.4975 (0.5); 0.4887 (0.6); 0.4828 (0.6); 0.4703 (0.9); 0.4606 (1.2); 0.4486 (1.6); 0.4372 (1.4); 0.4249 (0.6); 0.4048 (0.7); 0.3927 (1.2); 0.3829 (1.4); 0.3691 (1.1); 0.3598 (0.7); 0.3473 (0.3); −0.0002 (1.6)
I.0887: $^1$H-NMR(400.2 MHz, $d_6$-DMSO):
δ = 9.0981 (7.3); 3.9259 (15.9); 3.9081 (16.0); 3.3377 (53.6); 2.8922 (0.9); 2.7328 (0.8); 2.6775 (0.3); 2.6727 (0.4); 2.5917 (1.8); 2.5756 (2.4); 2.5705 (3.3); 2.5589 (3.3); 2.5553 (3.1); 2.5448 (3.8); 2.5373 (3.2); 2.5220 (4.5); 2.5127 (28.8); 2.5083 (55.1); 2.5038 (69.5); 2.4993 (49.8); 2.4950 (24.0); 2.3464 (2.0); 2.3237 (4.2); 2.3035 (3.1); 2.2937 (3.7); 2.2719 (1.9); 2.0124 (0.4); 1.9991 (1.0); 1.9847 (1.7); 1.9708 (3.4); 1.9617 (2.9); 1.9501 (4.1); 1.9394 (1.6); 1.9293 (2.2); 1.9085 (0.6); 1.9017 (0.4); 1.1043 (0.6); 1.0983 (0.8); 1.0925 (0.5); 1.0863 (1.6); 1.0784 (1.5); 1.0748 (1.3); 1.0666 (2.8); 1.0582 (1.3); 1.0545 (1.6); 1.0467 (1.7); 1.0403 (0.5); 1.0349 (0.9); 1.0288 (0.6); 0.5047 (2.2); 0.4939 (6.8); 0.4893 (7.2); 0.4849 (3.1); 0.4788 (3.3); 0.4735 (7.1); 0.4691 (6.4); 0.4589 (2.5); 0.2676 (2.6); 0.2570 (8.1); 0.2533 (7.5); 0.2453 (7.0); 0.2414 (8.1); 0.2304 (1.9); −0.0002 (0.5)
I.0888: $^1$H-NMR(400.2 MHz, $d_6$-DMSO):
δ = 9.2325 (3.1); 7.3844 (0.5); 7.3645 (2.6); 7.3507 (16.0); 7.3366 (2.6); 7.3321 (1.6); 7.3265 (0.9); 7.3190 (0.9); 7.3151 (1.1); 7.3077 (0.4); 7.3015 (0.4); 5.1455 (11.3); 3.3400 (13.5); 3.3354 (13.2); 2.6242 (0.8); 2.6086 (0.9); 2.6019 (1.3); 2.5915 (1.4); 2.5871 (1.3); 2.5774 (1.5); 2.5693 (1.2); 2.5552 (1.0); 2.5249 (0.8); 2.5072 (23.7); 2.5029 (29.7); 2.4986 (21.7); 2.3494 (0.8); 2.3263 (1.8); 2.3068 (1.4); 2.2985 (1.5); 2.2756 (0.8); 2.0247 (0.4); 2.0105 (0.7); 2.0020 (0.9); 1.9863 (1.3); 1.9622 (1.4); 1.9406 (0.7); −0.0002 (1.5)
I.0889: $^1$H-NMR(400.2 MHz, $d_6$-DMSO):
δ = 9.1889 (15.1); 7.9533 (0.7); 6.5894 (0.5); 6.3017 (0.3); 4.9547 (1.5); 4.9362 (6.0); 4.9180 (9.0); 4.8995 (6.0); 4.8813 (1.6); 3.3341 (78.7); 2.8918 (3.6); 2.7323 (3.4); 2.6722 (1.1); 2.5758 (3.8); 2.5537 (7.0); 2.5431 (7.8); 2.5389 (7.8); 2.5033 (182.1); 2.3295 (1.4); 2.3141 (5.7); 2.3056 (5.2); 2.2923 (14.2); 2.2876 (13.9); 2.2739 (13.4); 2.2640 (16.0); 2.2435 (8.0); 2.0276 (2.3); 2.0214 (1.8); 2.0029 (8.3); 1.9974 (6.9); 1.9837 (10.8); 1.9777 (13.3); 1.9597 (12.5); 1.9539 (12.3); 1.9360 (9.1); 1.9144 (3.9); 1.8938 (1.4); 1.8877 (1.4); 1.8668 (0.4); 1.7781 (1.9); 1.7519 (5.0); 1.7267 (5.0); 1.7075 (1.2); 1.7016 (1.8); 1.6549 (1.3); 1.6302 (3.3); 1.6093 (5.9); 1.5840 (4.9); 1.5633 (2.2); 1.5377 (0.7); 1.2808 (1.3); 1.2641 (1.3); 1.2380 (1.5); 1.2216 (1.4); −0.0001 (6.6)
I.0890: $^1$H-NMR(400.2 MHz, $d_6$-DMSO):
δ = 9.1617 (3.8); 8.3193 (0.3); 4.0810 (4.4); 4.0651 (9.0); 4.0492 (4.4); 3.3339 (19.8); 2.5878 (1.1); 2.5726 (1.3); 2.5655 (1.8); 2.5551 (1.9); 2.5506 (1.8); 2.5410 (2.1); 2.5327 (1.8); 2.5255 (1.8); 2.5122 (18.4); 2.5078 (35.1); 2.5032 (44.6); 2.4986 (32.0); 2.4942 (15.4); 2.3297 (1.4); 2.3102 (1.9); 2.3063 (2.2); 2.2996 (1.4); 2.2868 (1.8); 2.2784 (2.1); 2.2554 (1.1); 2.0090 (0.6); 1.9949 (0.9); 1.9864 (1.2); 1.9709 (1.8); 1.9578 (0.9); 1.9466 (1.9); 1.9256 (0.9); 1.9187 (0.6); 1.9043 (0.3); 1.5774 (0.8); 1.5610 (2.6); 1.5540 (1.0); 1.5443 (3.3); 1.5391 (2.4); 1.5240 (2.9); 1.5082 (1.2); 1.3636 (0.6); 1.3450 (2.2); 1.3260 (3.4); 1.3072 (3.4); 1.2890 (2.0); 1.2708 (0.6); 0.8796 (8.1); 0.8612 (16.0); 0.8427 (6.8); −0.0002 (1.3)
I.0891: $^1$H-NMR(400.2 MHz, $d_6$-DMSO):
δ = 9.0705 (1.0); 3.3872 (17.0); 3.3851 (18.8); 3.3777 (26.0); 2.8925 (0.3); 2.5239 (0.8); 2.5148 (4.6); 2.5104 (8.5); 2.5059 (10.7); 2.5013 (7.9); 2.4969 (3.9); 2.4782 (0.4); 2.2769 (0.6); 2.2568 (0.4); 2.2485 (0.5); 1.9624 (0.3); 1.9396 (0.6); 1.9206 (0.5); 1.4038 (16.0)
I.0892: $^1$H-NMR(400.1 MHz, $d_6$-DMSO):
δ = 8.4737 (0.5); 8.4597 (1.0); 8.4456 (0.5); 4.0454 (4.3); 4.0309 (4.2); 3.6636 (16.0); 3.3526 (11.0); 2.5087 (2.1); 2.5043 (2.8); 2.5000 (2.0); 2.1567 (14.9); 2.0761 (0.6)
I.0893: $^1$H-NMR(300.1 MHz, $d_6$-DMSO):
δ = 8.4648 (0.5); 8.4459 (0.9); 8.4267 (0.5); 4.1601 (1.2); 4.1364 (3.9); 4.1127 (4.0); 4.0890 (1.3); 4.0242 (4.1); 4.0048 (4.1); 3.3230 (12.0); 2.5139 (1.9); 2.5080 (3.7); 2.5021 (4.9); 2.4962 (3.4); 2.4906 (1.6); 2.1577 (16.0); 1.2283 (4.4); 1.2046 (9.2); 1.1809 (4.2); 0.0000 (1.3)

TABLE A-(I)-continued

| NMR peak lists of compounds according to formula (I) |
|---|
| I.0894: $^{1}$H-NMR(300.1 MHz, $d_6$-DMSO):<br>δ = 8.1677 (1.7); 8.1493 (3.7); 8.1381 (3.7); 7.4458 (5.2); 7.1173 (5.2); 3.8016 (15.7); 3.7826 (16.0); 3.3348 (154.4); 2.5426 (0.4); 2.5093 (24.2); 2.5034 (31.8); 2.4976 (22.5); −0.0003 (4.2) |
| I.0895: $^{1}$H-NMR(300.1 MHz, $d_6$-DMSO):<br>δ = 11.4852 (0.7); 8.7056 (8.2); 8.6994 (8.2); 8.5792 (0.3); 7.7784 (0.5); 5.0995 (0.3); 3.9235 (1.0); 3.8340 (0.3); 3.8067 (0.3); 3.3439 (11.0); 3.1889 (0.4); 2.5412 (0.4); 2.5141 (15.9); 2.5085 (31.4); 2.5026 (41.5); 2.4968 (29.5); 2.0754 (1.4); 1.9767 (0.4); 1.9549 (0.4); 1.5788 (0.4); 1.5309 (5.4); 1.5140 (13.6); 1.5023 (16.0); 1.4884 (7.4); 1.4354 (0.8); 1.3604 (0.9); 1.3385 (0.6); 1.3064 (7.3); 1.2922 (15.4); 1.2804 (13.7); 1.2635 (5.2); 1.2337 (1.1); 0.9229 (0.8); 0.8986 (1.6); 0.8738 (0.7); −0.0005 (7.1) |
| I.0896: $^{1}$H-NMR(300.1 MHz, $d_6$-DMSO):<br>δ = 9.7698 (4.4); 9.2329 (4.4); 8.3587 (1.9); 8.3411 (4.2); 8.3293 (4.2); 8.3107 (2.0); 4.1430 (15.8); 4.1240 (16.0); 3.3314 (81.0); 2.5425 (0.3); 2.5150 (14.4); 2.5092 (27.9); 2.5033 (36.6); 2.4974 (25.6); 2.0759 (3.0); −0.0001 (4.9) |
| I.0897: $^{1}$H-NMR(300.1 MHz, $d_6$-DMSO):<br>δ = 8.7662 (1.8); 3.6097 (16.0); 3.3415 (13.4); 2.5141 (3.1); 2.5082 (6.0); 2.5023 (8.0); 2.4963 (5.5); 2.4906 (2.5); 2.4557 (12.8); 2.0755 (0.8); 1.4718 (1.0); 1.4552 (2.7); 1.4441 (3.0); 1.4296 (1.3); 1.2096 (1.4); 1.1951 (3.0); 1.1841 (2.7); 1.1672 (1.0); −0.0001 (1.1) |
| I.0898: $^{1}$H-NMR(400.2 MHz, $d_6$-DMSO):<br>δ = 8.9838 (1.0); 3.3437 (12.5); 2.5130 (5.2); 2.5089 (9.5); 2.5045 (11.8); 2.5001 (8.6); 2.4714 (0.4); 2.2877 (0.6); 2.2668 (0.4); 2.2575 (0.5); 1.9377 (0.5); 1.9261 (0.4); 1.9166 (0.6); 1.3970 (16.0) |
| I.0899: $^{1}$H-NMR(300.1 MHz, $d_6$-DMSO):<br>δ = 9.1824 (0.9); 9.1630 (1.8); 9.1437 (1.0); 7.7346 (4.2); 7.7222 (4.3); 4.1610 (2.3); 4.1373 (7.2); 4.1136 (7.3); 4.0899 (2.4); 4.0188 (7.3); 3.9991 (7.3); 3.3549 (7.4); 2.5198 (1.6); 2.5140 (3.1); 2.5082 (4.0); 2.5023 (2.8); 1.2291 (7.8); 1.2054 (16.0); 1.1817 (7.5) |
| I.0900: $^{1}$H-NMR(300.1 MHz, $d_6$-DMSO):<br>δ = 9.6009 (5.7); 9.1125 (5.8); 8.5011 (8.7); 8.4932 (8.6); 6.5320 (0.5); 3.3262 (189.0); 2.8909 (1.4); 2.7294 (2.5); 2.7221 (1.4); 2.5140 (124.1); 2.5081 (239.4); 2.5022 (315.6); 2.4963 (221.0); 2.4907 (103.8); 2.2781 (1.4); 2.2721 (1.9); 2.2662 (1.4); 2.0753 (8.0); 1.8363 (6.2); 1.8220 (14.8); 1.8099 (16.0); 1.7965 (6.6); 1.7445 (0.4); 1.2855 (0.4); 1.2330 (7.2); 1.2193 (15.8); 1.2071 (15.1); 1.1927 (6.0); 0.1951 (0.4); 0.0107 (3.6); −0.0001 (96.4); −0.0111 (3.5); −0.1986 (0.4) |
| I.0901: $^{1}$H-NMR(400.1 MHz, $d_6$-DMSO):<br>δ = 9.2525 (1.8); 7.6876 (2.5); 7.6783 (2.5); 3.6058 (16.0); 3.3388 (8.4); 3.3321 (8.7); 2.5110 (7.3); 2.5066 (15.0); 2.5020 (20.2); 2.4975 (14.0); 2.4930 (6.2); 1.4743 (1.1); 1.4622 (2.7); 1.4540 (2.8); 1.4430 (1.2); 1.1779 (1.3); 1.1669 (2.8); 1.1586 (2.7); 1.1465 (0.9); −0.0001 (4.3) |
| I.0902: $^{1}$H-NMR(400.2 MHz, $d_6$-DMSO):<br>δ = 8.6374 (0.4); 8.6203 (0.4); 3.7176 (0.4); 3.7002 (0.4); 3.6960 (0.5); 3.6784 (0.4); 3.3587 (5.0); 3.3531 (5.7); 3.3473 (5.8); 3.3417 (5.1); 2.5084 (8.0); 2.5039 (10.1); 2.4995 (7.4); 1.4325 (16.0); 1.1796 (0.3); 0.5915 (0.3); 0.5298 (0.3); 0.4387 (0.4); 0.4281 (0.4); 0.3952 (0.3); 0.3852 (0.4); −0.0002 (0.3) |
| I.0903: $^{1}$H-NMR(400.2 MHz, $d_6$-DMSO):<br>δ = 8.8030 (14.0); 8.7863 (13.9); 7.9551 (0.6); 7.8948 (0.8); 7.8638 (0.8); 6.5477 (1.2); 6.2124 (0.8); 6.1817 (0.7); 4.9972 (2.8); 4.9789 (10.7); 4.9604 (16.0); 4.9420 (10.7); 4.9235 (2.7); 4.0132 (0.3); 3.9963 (0.4); 3.9794 (0.3); 3.8570 (0.4); 3.8406 (0.5); 3.8239 (0.4); 3.7592 (11.0); 3.7422 (12.4); 3.7368 (13.0); 3.7198 (11.1); 3.5091 (0.4); 3.4660 (0.4); 3.4235 (0.6); 3.3470 (498.0); 2.8941 (3.6); 2.7345 (3.3); 2.6794 (1.5); 2.6751 (2.0); 2.6706 (1.5); 2.5105 (270.5); 2.5062 (341.8); 2.5018 (254.6); 2.3365 (5.4); 2.3293 (6.6); 2.3156 (9.2); 2.3069 (12.4); 2.2988 (12.9); 2.2875 (13.6); 2.2815 (11.3); 2.2679 (6.4); 2.2611 (5.4); 2.0924 (2.0); 2.0869 (1.2); 2.0674 (6.3); 2.0618 (4.6); 2.0478 (7.8); 2.0423 (9.0); 2.0368 (7.6); 2.0276 (8.8); 2.0228 (9.3); 2.0175 (8.7); 2.0084 (7.9); 2.0031 (8.9); 1.9977 (7.8); 1.9934 (5.1); 1.9833 (5.4); 1.9782 (6.2); 1.9732 (3.8); 1.9589 (1.4); 1.9531 (2.3); 1.8108 (1.9); 1.8048 (3.2); 1.7989 (2.1); 1.7791 (8.5); 1.7537 (8.5); 1.7344 (2.0); 1.7280 (3.0); 1.6687 (2.4); 1.6484 (5.2); 1.6436 (6.2); 1.6232 (10.8); 1.6026 (6.0); 1.5973 (8.9); 1.5767 (4.2); 1.5718 (3.3); 1.5512 (1.3); 1.4344 (0.6); 1.4059 (4.9); 1.3005 (0.5); 1.2828 (4.8); 1.2658 (5.4); 1.2502 (4.0); 1.2404 (9.7); 1.2292 (9.6); 1.2240 (9.2); 1.2189 (8.7); 1.2078 (8.8); 1.1962 (5.5); 1.1875 (4.4); 1.1752 (2.4); 1.1213 (0.3); 1.0424 (0.4); 1.0262 (0.5); 1.0110 (0.4); 0.6494 (2.3); 0.6402 (3.2); 0.6363 (3.6); 0.6279 (7.5); 0.6196 (7.4); 0.6149 (7.8); 0.6052 (8.8); 0.5936 (5.1); 0.5840 (4.5); 0.5692 (4.0); 0.5561 (6.1); 0.5468 (8.3); 0.5357 (7.9); 0.5260 (9.3); 0.5136 (4.4); 0.5065 (7.8); 0.4948 (6.7); 0.4857 (9.3); 0.4734 (11.3); 0.4624 (8.7); 0.4500 (3.6); 0.4379 (0.6); 0.4210 (4.8); 0.4097 (7.9); 0.3983 (9.6); 0.3857 (8.7); 0.3761 (5.0); 0.3644 (2.3); 0.0018 (0.5) |
| I.0904: $^{1}$H-NMR(400.2 MHz, $d_6$-DMSO):<br>δ = 8.7746 (1.8); 8.7583 (1.8); 4.9828 (0.8); 4.9672 (2.0); 4.9516 (2.7); 4.9360 (2.0); 4.9203 (0.8); 3.7455 (1.8); 3.7286 (2.0); 3.7230 (2.0); 3.7062 (1.8); 3.3645 (93.2); 3.3635 (93.4); 2.5127 (33.0); 2.5083 (42.1); 2.5038 (30.8); 1.2309 (13.5); 1.2185 (16.0); 1.2156 (15.7); 1.2032 (12.9); 1.1873 (0.8); 1.1786 (0.6); 0.6285 (0.4); 0.6248 (0.5); 0.6154 (0.9); 0.6074 (1.1); 0.6031 (1.1); 0.5937 (1.4); 0.5872 (0.7); 0.5818 (0.8); 0.5725 (0.8); 0.5673 (0.7); 0.5578 (0.8); 0.5547 (0.9); 0.5464 (1.3); 0.5346 (1.1); 0.5254 (1.0); 0.5122 (0.5); 0.5034 (0.6); 0.4927 (0.5); 0.4802 (0.9); 0.4706 (1.2); 0.4584 (1.6); 0.4473 (1.4); 0.4351 (0.6); 0.4206 (0.7); 0.4080 (1.3); 0.3972 (1.2); 0.3850 (1.1); 0.3756 (0.6) |
| I.0905: $^{1}$H-NMR(400.2 MHz, $d_6$-DMSO):<br>δ = 9.1973 (7.1); 3.9298 (15.9); 3.9120 (16.0); 3.3686 (210.3); 2.6792 (0.3); 2.6750 (0.4); 2.6707 (0.3); 2.6004 (1.9); 2.5850 (2.3); 2.5783 (3.3); 2.5678 (3.4); 2.5633 (3.2); 2.5537 (3.7); 2.5457 (3.0); 2.5310 (3.2); 2.5146 (29.9); 2.5105 (57.1); 2.5060 (72.0); 2.5015 (52.0); 2.4974 (25.4); 2.3372 (2.4); 2.3141 (4.1); 2.2945 (3.3); 2.2860 (3.8); 2.2633 (2.1); 2.0293 (0.5); 2.0157 (1.0); 2.0012 (1.8); 1.9929 (1.9); 1.9875 (1.4); 1.9780 (4.2); 1.9559 (3.8); 1.9361 (1.8); 1.9145 (0.6); 1.9090 (0.5); 1.1132 (0.6); 1.1070 (0.8); 1.0951 (1.6); 1.0872 (1.6); 1.0836 (1.3); 1.0754 (2.8); 1.0670 (1.3); 1.0634 (1.6); 1.0556 (1.7); 1.0438 (0.9); 1.0376 (0.6); 0.5129 (2.2); 0.5020 (6.9); 0.4975 (7.3); 0.4870 (3.3); 0.4817 (7.2); 0.4774 (6.6); 0.4670 (2.5); 0.2745 (2.6); 0.2639 (8.3); 0.2603 (7.7); 0.2522 (7.1); 0.2484 (8.2); 0.2373 (1.9) |
| I.0906: $^{1}$H-NMR(300.1 MHz, $d_6$-DMSO):<br>δ = 9.2049 (0.5); 9.1857 (1.0); 9.1663 (0.5); 7.7377 (2.9); 7.7252 (2.9); 4.0414 (3.9); 4.0217 (3.9); 3.6650 (16.0); 3.3506 (1.6); 2.5151 (0.9); 2.5093 (1.2); 2.5035 (0.8) |
| I.0907: $^{1}$H-NMR(400.2 MHz, $d_6$-DMSO):<br>δ = 9.0754 (4.3); 4.0778 (4.4); 4.0619 (9.0); 4.0460 (4.4); 3.3532 (83.4); 2.5803 (1.1); 2.5646 (1.4); 2.5588 (2.0); 2.5473 (2.1); 2.5438 (2.0); 2.5333 (2.5); 2.5246 (3.0); 2.5105 (35.4); 2.5060 (43.3); 2.5015 (31.2); 2.3391 (1.3); 2.3165 (2.5); 2.2963 (1.9); 2.2870 (2.2); 2.2649 (1.2); 1.9940 (0.6); 1.9837 (1.0); 1.9803 (1.1); 1.9712 (1.2); 1.9631 (1.9); 1.9568 (1.8); 1.9423 (2.6); 1.9348 (1.2); 1.9209 (1.4); 1.9002 (0.4); 1.5698 (0.9); 1.5534 (2.8); 1.5464 (1.0); 1.5368 (3.5); 1.5164 (3.1); 1.5007 (1.2); 1.3569 (0.6); 1.3383 (2.3); 1.3194 (3.6); 1.3005 (3.6); 1.2823 (2.1); 1.2641 (0.6); 0.8739 (8.1); 0.8555 (16.0); 0.8370 (6.9) |
| I.0908: $^{1}$H-NMR(400.2 MHz, $d_6$-DMSO):<br>δ = 9.0981 (16.0); 8.3157 (1.2); 4.9512 (1.7); 4.9334 (6.8); 4.9150 (10.1); 4.8967 (6.8); 4.8790 (1.7); 3.3616 (450.7); 2.8927 (1.6); 2.7326 (1.4); 2.6791 (0.8); 2.6745 (1.0); 2.6699 (0.8); 2.5688 (4.1); 2.5531 (5.3); 2.5471 (7.5); 2.5358 (8.1); 2.5316 (8.1); 2.5280 (9.2); 2.5142 (72.0); 2.5100 (132.0); 2.5054 (168.5); 2.5009 (125.1); 2.4966 (61.6); 2.3259 (5.0); 2.3026 (13.4); 2.2952 (9.3); 2.2895 (8.6); 2.2826 (14.6); 2.2785 (14.2); 2.2722 (15.1); 2.2650 (9.8); 2.2586 (10.4); 2.2540 (9.6); 2.2519 (9.6); 2.2410 (5.2); 2.2343 (3.7); 2.0126 (2.3); 2.0050 (1.8); 1.9911 (5.0); 1.9869 (10.1); 1.9801 (6.8); 1.9679 (10.8); 1.9622 (13.8); 1.9559 (13.0); |

TABLE A-(I)-continued

| NMR peak lists of compounds according to formula (I) |
|---|
| 1.9477 (9.7); 1.9441 (9.8); 1.9367 (12.2); 1.9328 (13.6); 1.9197 (4.0); 1.9115 (7.2); 1.8907 (1.5); 1.8836 (1.2); 1.8628 (0.4); 1.7781 (1.2); 1.7728 (2.0); 1.7665 (1.3); 1.7464 (5.3); 1.7400 (2.9); 1.7275 (3.0); 1.7214 (5.2); 1.7019 (1.2); 1.6965 (1.8); 1.6897 (1.0); 1.6539 (1.7); 1.6337 (3.5); 1.6297 (3.3); 1.6282 (3.3); 1.6086 (6.8); 1.5822 (5.3); 1.5775 (1.8); 1.5625 (2.5); 1.5570 (2.0); 1.5366 (0.8); 1.2346 (0.4); −0.0001 (0.4) |
| I.0909: $^1$H-NMR(400.2 MHz, $d_6$-DMSO): |
| δ = 9.1409 (3.2); 7.3756 (0.4); 7.3663 (0.4); 7.3609 (1.1); 7.3567 (2.4); 7.3538 (2.4); 7.3429 (16.0); 7.3328 (3.3); 7.3294 (2.5); 7.3228 (1.0); 7.3120 (1.1); 7.3011 (0.4); 7.2981 (0.4); 5.1426 (11.8); 3.3373 (14.9); 2.8908 (1.5); 2.7324 (1.2); 2.7313 (1.2); 2.6155 (0.7); 2.5999 (0.9); 2.5941 (1.3); 2.5873 (1.0); 2.5828 (1.3); 2.5788 (1.2); 2.5686 (1.5); 2.5609 (1.2); 2.5466 (1.0); 2.5258 (0.7); 2.5210 (1.0); 2.5123 (12.0); 2.5079 (24.1); 2.5033 (31.4); 2.4987 (22.7); 2.4941 (10.9); 2.3583 (0.8); 2.3353 (1.7); 2.3156 (1.2); 2.3060 (1.5); 2.2838 (0.8); 2.0080 (0.4); 1.9980 (0.6); 1.9937 (0.7); 1.9850 (0.8); 1.9776 (1.2); 1.9705 (1.2); 1.9564 (1.7); 1.9483 (0.8); 1.9351 (0.9); −0.0002 (1.4) |
| I.0910: $^1$H-NMR(400.1 MHz, CDCl3): |
| δ = 7.2617 (6.3); 7.1555 (2.7); 4.8183 (16.0); 4.8140 (15.0); 4.3112 (12.4); 4.2984 (12.5); 2.5347 (7.1); 1.5636 (7.5); 1.2630 (0.5); −0.0002 (8.2) |
| I.0911: $^1$H-NMR(400.1 MHz, CDCl3): |
| δ = 7.5758 (2.8); 7.2621 (6.7); 5.2995 (1.8); 4.8245 (16.0); 4.8203 (15.7); 4.3368 (12.7); 4.3246 (13.0); 2.5476 (7.2); 1.5573 (8.8); 1.2580 (0.7); 0.8819 (0.3); −0.0002 (8.4) |
| I.0912: $^1$H-NMR(500.1 MHz, $d_6$-DMSO): |
| δ = 9.3256 (10.3); 5.9201 (1.3); 5.9099 (2.7); 5.8993 (2.6); 5.8887 (3.1); 5.8858 (1.9); 5.8784 (1.8); 5.8754 (3.3); 5.8648 (2.9); 5.8542 (3.3); 5.8440 (1.6); 5.3224 (2.0); 5.3191 (5.6); 5.3158 (5.9); 5.3125 (2.4); 5.2878 (1.8); 5.2846 (5.0); 5.2812 (5.3); 5.2780 (2.1); 5.2117 (5.6); 5.2087 (5.6); 5.1905 (5.3); 5.1876 (5.4); 4.5925 (7.6); 4.5896 (13.2); 4.5866 (8.6); 4.5825 (8.4); 4.5794 (13.3); 4.5765 (8.0); 3.3144 (16.0); 2.5126 (2.3); 2.5092 (5.0); 2.5056 (7.0); 2.5021 (5.2); 2.4987 (2.6); 1.5111 (4.8); 1.5013 (12.9); 1.4946 (14.2); 1.4857 (5.9); 1.4537 (0.4); 1.2926 (0.4); 1.2607 (6.0); 1.2516 (14.0); 1.2450 (14.1); 1.2352 (5.2) |
| I.0913: $^1$H-NMR(400.1 MHz, CDCl3): |
| δ = 7.2638 (5.6); 7.1239 (7.6); 5.9194 (1.0); 5.9054 (2.1); 5.8927 (2.2); 5.8787 (3.2); 5.8638 (3.4); 5.8498 (2.6); 5.8368 (2.6); 5.8226 (1.4); 5.3100 (7.0); 5.2670 (6.2); 5.2425 (7.6); 5.2163 (6.8); 4.6562 (0.4); 4.6287 (15.3); 4.6155 (15.9); 1.7410 (4.8); 1.7275 (15.4); 1.7213 (16.0); 1.7097 (6.7); 1.6686 (0.5); 1.5886 (5.8); 1.4065 (0.5); 1.3654 (5.7); 1.3531 (15.8); 1.3468 (15.7); 1.3342 (5.7); 1.2940 (0.4); 1.2576 (0.8); −0.0002 (6.9) |
| I.0914: $^1$H-NMR(400.1 MHz, CDCl3): |
| δ = 15.8101 (1.7); 14.7841 (1.7); 10.3013 (1.8); 7.6526 (1.7); 7.5173 (2.2); 7.4141 (1.8); 7.2590 (328.1); 7.2216 (2.6); 6.9944 (2.4); 6.7820 (1.9); 6.7654 (2.0); 5.6387 (1.7); 5.6302 (2.1); 5.5443 (1.6); 4.1570 (6.2); 4.1458 (6.2); 4.0985 (1.8); 3.6235 (2.3); 3.5454 (2.0); 3.5220 (2.5); 3.5015 (2.2); 3.4768 (2.1); 3.4306 (1.8); 3.4008 (1.9); 2.5202 (16.0); 2.1215 (1.8); 1.5338 (486.2); 1.4927 (5.3); 1.4566 (2.0); 1.2557 (4.2); 0.8825 (2.0); 0.1545 (2.7); 0.1465 (2.6); 0.0695 (2.3); −0.0002 (422.1); −0.0388 (4.0); −0.1506 (2.5); −3.9308 (1.7) |
| I.0915: $^1$H-NMR(400.1 MHz, CDCl3): |
| δ = 18.5280 (0.4); 16.8460 (0.4); 7.5178 (0.5); 7.2602 (45.8); 7.2174 (0.6); 6.8282 (1.0); 6.1754 (0.5); 6.1545 (0.5); 6.1424 (0.7); 6.0592 (1.3); 6.0417 (1.3); 5.9725 (2.0); 5.8908 (1.3); 5.8552 (1.3); 5.7919 (0.8); 5.7376 (0.4); 5.7213 (0.4); 5.5299 (0.6); 5.5131 (0.7); 5.4453 (0.4); 4.1478 (3.2); 3.9183 (0.4); 3.8143 (0.5); 3.7337 (12.9); 3.7183 (13.2); 3.6297 (0.4); 3.5639 (0.5); 3.5066 (0.5); 3.3820 (0.4); 3.3230 (0.4); 3.2583 (0.5); 3.1851 (16.0); 3.1723 (13.1); 3.1111 (0.4); 2.9642 (0.4); 2.8866 (0.4); 2.8107 (0.8); 2.5460 (7.0); 2.0076 (3.8); 1.6916 (0.8); 1.5833 (27.3); 1.5087 (24.5); 1.4842 (90.7); 1.4692 (88.7); 1.4445 (75.4); 1.4295 (75.0); 1.3202 (2.0); 1.2970 (2.0); 1.2580 (3.6); 1.1573 (0.8); 1.0902 (0.8); 1.0648 (0.8); 1.0384 (0.7); 1.0172 (0.8); 1.0076 (0.6); 0.9659 (0.5); 0.9488 (0.4); 0.8787 (1.4); 0.8353 (3.5); 0.1466 (0.6); 0.0693 (0.7); −0.0002 (60.2); −0.1511 (0.5) |
| I.0916: $^1$H-NMR(400.1 MHz, $d_6$-DMSO): |
| δ = 9.0782 (0.4); 8.9998 (4.6); 7.4693 (6.2); 7.1292 (6.2); 3.8075 (16.0); 3.3061 (13.9); 3.1743 (0.4); 2.5007 (21.9); 2.4322 (0.4); −0.0002 (13.8) |
| I.0917: $^1$H-NMR(400.2 MHz, $d_6$-DMSO): |
| δ = 9.0764 (4.2); 4.0378 (4.7); 4.0218 (9.9); 4.0058 (4.8); 3.3407 (15.2); 3.3343 (19.9); 2.5856 (1.1); 2.5643 (2.0); 2.5528 (2.0); 2.5491 (2.0); 2.5387 (2.4); 2.5310 (2.0); 2.5263 (1.7); 2.5082 (31.8); 2.5038 (40.0); 2.4993 (29.2); 2.3432 (1.2); 2.3204 (2.6); 2.2999 (1.9); 2.2905 (2.3); 2.2686 (1.2); 1.9958 (0.6); 1.9866 (0.8); 1.9816 (1.0); 1.9674 (2.1); 1.9585 (1.8); 1.9462 (2.5); 1.9254 (1.3); 1.9046 (0.4); 1.6124 (0.5); 1.5940 (2.1); 1.5776 (4.4); 1.5593 (4.5); 1.5429 (2.3); 1.5248 (0.6); 0.8822 (7.9); 0.8638 (16.0); 0.8452 (7.1); −0.0002 (1.9) |
| I.0918: $^1$H-NMR(400.2 MHz, $d_6$-DMSO): |
| δ = 9.0739 (16.0); 7.9539 (2.3); 4.7436 (2.9); 4.7338 (3.9); 4.7242 (5.4); 4.7155 (4.2); 4.7048 (2.7); 4.6964 (1.4); 3.3354 (75.0); 2.8922 (14.0); 2.7327 (12.8); 2.6729 (0.9); 2.5694 (3.5); 2.5491 (6.9); 2.5360 (7.5); 2.5216 (13.2); 2.5082 (115.0); 2.5039 (145.2); 2.4999 (110.2); 2.3403 (4.3); 2.3184 (9.0); 2.2967 (6.5); 2.2876 (8.0); 2.2658 (3.9); 2.0019 (0.6); 1.9875 (2.9); 1.9736 (3.8); 1.9654 (8.0); 1.9510 (6.3); 1.9441 (9.1); 1.9234 (5.0); 1.9024 (1.2); 1.8957 (0.8); 1.7331 (4.0); 1.7238 (4.6); 1.7061 (6.8); 1.6935 (6.0); 1.6851 (6.9); 1.6440 (3.6); 1.6207 (5.8); 1.6035 (6.2); 1.4429 (5.6); 1.4211 (9.5); 1.4078 (7.0); 1.3998 (8.4); 1.3768 (9.4); 1.3550 (7.3); 1.3324 (6.3); 1.3252 (6.5); 1.3031 (6.8); 1.2847 (3.1); 1.2642 (2.3); 1.2576 (2.2); 1.2342 (1.0); −0.0002 (6.2) |
| I.0919: $^1$H-NMR(400.2 MHz, $d_6$-DMSO): |
| δ = 9.6384 (6.8); 9.2621 (0.4); 9.1294 (7.0); 8.6760 (15.9); 6.5416 (0.3); 3.3381 (58.2); 2.9780 (0.7); 2.8916 (1.2); 2.7318 (1.3); 2.6728 (0.8); 2.5616 (0.4); 2.5490 (0.6); 2.5040 (126.8); 2.3305 (0.7); 1.8849 (0.3); 1.8474 (5.9); 1.8367 (14.8); 1.8282 (16.0); 1.8184 (6.6); 1.7787 (0.4); 1.5872 (0.4); 1.5799 (0.4); 1.3192 (0.4); 1.3064 (0.5); 1.3001 (0.5); 1.2645 (0.5); 1.2242 (6.6); 1.2141 (15.6); 1.2055 (15.7); 1.1951 (6.1); 1.1559 (0.3); −0.0004 (1.1) |
| I.0920: $^1$H-NMR(400.2 MHz, $d_6$-DMSO): |
| δ = 8.5895 (5.7); 7.8819 (2.1); 7.8712 (2.1); 3.3527 (34.2); 3.3516 (34.4); 3.3433 (43.8); 2.8920 (0.6); 2.7326 (0.6); 2.5923 (16.0); 2.5809 (15.7); 2.5085 (39.6); 2.5041 (49.2); 2.4999 (36.4); 1.3423 (2.7); 1.3310 (7.0); 1.3228 (7.5); 1.3124 (3.0); 0.9968 (3.2); 0.9865 (7.4); 0.9782 (7.1); 0.9670 (2.6); −0.0002 (0.4) |
| I.0921: $^1$H-NMR(400.2 MHz, $d_6$-DMSO): |
| δ = 8.5002 (0.4); 8.4839 (0.4); 3.5962 (0.5); 3.5755 (0.7); 3.5559 (0.6); 3.4581 (56.6); 3.4294 (11.8); 2.5112 (10.4); 1.4187 (16.0); 1.2065 (0.3); 0.6011 (0.3); 0.5907 (0.3); 0.5036 (0.3); 0.4927 (0.3); 0.4438 (0.3); 0.4312 (0.4); 0.4192 (0.3); 0.3525 (0.3); 0.3416 (0.4); 0.3296 (0.4) |
| I.0922: $^1$H-NMR(400.2 MHz, $d_6$-DMSO): |
| δ = 8.6454 (10.7); 8.6287 (10.6); 7.9538 (1.4); 6.5520 (1.2); 4.9791 (2.7); 4.9611 (10.9); 4.9426 (16.0); 4.9242 (11.0); 4.9063 (2.8); 3.6619 (11.9); 3.6448 (13.1); 3.6385 (13.1); 3.6213 (12.2); 3.3372 (108.1); 3.3347 (113.1); 2.8922 (9.8); 2.7328 (8.2); 2.6774 (1.2); 2.6728 (1.6); 2.6684 (1.1); 2.6640 (0.5); 2.5262 (6.4); 2.5128 (106.5); 2.5084 (203.5); 2.5039 (257.4); 2.4993 (183.8); 2.4949 (87.8); 2.3306 (2.5); 2.3258 (4.7); 2.3190 (4.5); 2.3147 (5.2); 2.3060 (9.3); 2.2955 (11.9); 2.2876 (13.2); 2.2772 (13.7); 2.2695 (11.3); 2.2599 (6.4); 2.2490 (5.1); 2.2419 (1.3); 2.0675 (2.2); 2.0624 (1.2); 2.0565 (0.9); 2.0480 (3.4); 2.0425 (6.7); 2.0369 (5.4); 2.0333 (4.3); 2.0231 (7.7); 2.0173 (9.6); 2.0120 (9.7); 2.0086 (8.9); 2.0038 (6.4); 1.9976 (7.0); 1.9921 (9.6); 1.9890 |

TABLE A-(I)-continued

| NMR peak lists of compounds according to formula (I) |
| --- |
| (10.3); 1.9836 (8.8); 1.9780 (7.4); 1.9723 (3.7); 1.9676 (4.5); 1.9640 (6.1); 1.9587 (6.7); 1.9531 (3.5); 1.9447 (1.2); 1.9387 (1.6); 1.9338 (2.5); 1.7998 (1.8); 1.7945 (3.2); 1.7881 (2.0); 1.7747 (5.0); 1.7681 (8.6); 1.7613 (4.9); 1.7499 (5.1); 1.7477 (5.1); 1.7431 (8.6); 1.7364 (4.8); 1.7232 (2.0); 1.7182 (2.9); 1.7115 (1.6); 1.6611 (2.7); 1.6409 (5.7); 1.6360 (6.4); 1.6205 (4.2); 1.6158 (11.4); 1.6097 (5.8); 1.5955 (6.4); 1.5893 (9.0); 1.5843 (2.8); 1.5690 (4.4); 1.5640 (3.4); 1.5437 (1.5); 1.4185 (0.5); 1.3679 (0.4); 1.2944 (1.8); 1.2823 (4.0); 1.2738 (4.8); 1.2708 (5.2); 1.2620 (8.0); 1.2505 (7.9); 1.2388 (7.8); 1.2304 (4.5); 1.2269 (4.7); 1.2187 (4.0); 1.2066 (2.2); 1.1950 (0.6); 1.1716 (0.4); 0.6423 (2.5); 0.6336 (3.5); 0.6297 (3.6); 0.6203 (7.0); 0.6136 (7.1); 0.6083 (7.5); 0.6014 (6.7); 0.5980 (8.4); 0.5871 (4.9); 0.5769 (4.6); 0.5454 (3.7); 0.5351 (4.9); 0.5315 (6.0); 0.5216 (7.7); 0.5155 (5.8); 0.5112 (7.8); 0.5015 (11.0); 0.4904 (7.7); 0.4828 (10.0); 0.4782 (7.9); 0.4705 (9.9); 0.4583 (10.7); 0.4472 (7.4); 0.4341 (3.2); 0.4106 (0.4); 0.3780 (4.3); 0.3671 (7.9); 0.3620 (5.6); 0.3552 (9.2); 0.3424 (8.7); 0.3330 (5.5); 0.3222 (2.5); 0.3085 (0.5); 0.3031 (0.5); 0.0078 (0.5); −0.0002 (12.8); −0.0085 (0.4) |
| I.0923: $^{1}$H-NMR(400.2 MHz, $d_6$-DMSO): |
| δ = 8.6164 (2.0); 8.5997 (1.9); 4.9627 (0.9); 4.9471 (2.3); 4.9315 (3.1); 4.9159 (2.3); 4.9003 (0.9); 3.6387 (1.9); 3.6215 (2.2); 3.6155 (2.2); 3.5983 (2.0); 3.3370 (19.6); 3.3332 (27.3); 2.8920 (1.4); 2.7324 (1.2); 2.5080 (38.7); 2.5036 (48.4); 2.4992 (35.5); 1.2713 (0.6); 1.2603 (0.8); 1.2508 (1.4); 1.2394 (1.4); 1.2279 (1.5); 1.2109 (15.6); 1.2027 (15.8); 1.1953 (16.0); 1.1872 (14.8); 0.6286 (0.4); 0.6183 (0.6); 0.6152 (0.6); 0.6071 (1.3); 0.5977 (1.3); 0.5938 (1.3); 0.5836 (1.4); 0.5784 (0.9); 0.5724 (0.9); 0.5623 (0.8); 0.5430 (0.7); 0.5295 (1.0); 0.5199 (1.4); 0.5094 (1.4); 0.4993 (1.6); 0.4874 (0.7); 0.4776 (1.0); 0.4630 (1.1); 0.4530 (1.6); 0.4407 (1.9); 0.4294 (1.4); 0.4171 (0.6); 0.3783 (0.8); 0.3667 (1.4); 0.3552 (1.7); 0.3428 (1.5); 0.3328 (0.9); 0.3204 (0.4); −0.0002 (2.2) |
| I.0924: $^{1}$H-NMR(400.2 MHz, $d_6$-DMSO): |
| δ = 8.9334 (6.2); 3.9204 (15.9); 3.9027 (16.0); 3.3361 (38.4); 2.8923 (0.9); 2.7323 (0.8); 2.6730 (0.4); 2.5753 (1.7); 2.5706 (1.2); 2.5560 (3.5); 2.5482 (2.4); 2.5421 (3.3); 2.5270 (5.1); 2.5219 (5.2); 2.5130 (26.4); 2.5086 (51.6); 2.5041 (65.3); 2.4995 (46.5); 2.4950 (22.2); 2.3593 (2.0); 2.3375 (4.6); 2.3314 (3.2); 2.3159 (3.0); 2.3055 (3.7); 2.2839 (1.8); 1.9806 (1.5); 1.9598 (4.1); 1.9495 (1.6); 1.9395 (5.2); 1.9266 (1.7); 1.9190 (3.2); 1.9043 (0.7); 1.8980 (0.7); 1.2110 (0.5); 1.2029 (0.5); 1.1954 (0.5); 1.1875 (0.4); 1.0985 (0.6); 1.0924 (0.7); 1.0867 (0.5); 1.0789 (1.5); 1.0726 (1.4); 1.0691 (1.2); 1.0607 (2.7); 1.0523 (1.2); 1.0487 (1.6); 1.0408 (1.7); 1.0348 (0.5); 1.0289 (0.9); 1.0229 (0.6); 0.4944 (2.2); 0.4836 (6.8); 0.4791 (7.1); 0.4747 (3.1); 0.4687 (3.2); 0.4634 (7.1); 0.4588 (6.5); 0.4487 (2.6); 0.2583 (2.7); 0.2478 (7.9); 0.2439 (7.5); 0.2361 (6.8); 0.2320 (8.0); 0.2209 (1.9); −0.0002 (1.2) |
| I.0925: $^{1}$H-NMR(400.2 MHz, $d_6$-DMSO): |
| δ = 8.7885 (0.8); 3.3532 (5.8); 3.3510 (5.3); 3.3467 (5.7); 3.3416 (7.2); 2.5225 (0.6); 2.5135 (4.1); 2.5091 (7.9); 2.5046 (10.2); 2.5000 (7.3); 2.4956 (3.6); 2.4754 (0.5); 2.4711 (0.4); 2.4549 (0.3); 2.3053 (0.6); 2.2835 (0.4); 2.2770 (0.4); 2.2736 (0.4); 1.9318 (0.5); 1.9125 (0.8); 1.8914 (0.4); 1.3893 (16.0) |
| I.0926: $^{1}$H-NMR(400.2 MHz, $d_6$-DMSO): |
| δ = 8.9222 (4.9); 4.0692 (4.6); 4.0534 (9.5); 4.0375 (4.7); 3.3496 (107.4); 2.5613 (1.3); 2.5415 (2.6); 2.5095 (38.6); 2.5055 (47.6); 2.5017 (37.4); 2.3523 (1.4); 2.3301 (3.4); 2.3082 (2.3); 2.2992 (2.9); 2.2771 (1.4); 1.9728 (1.1); 1.9513 (3.0); 1.9302 (3.5); 1.9098 (2.0); 1.8892 (0.4); 1.5578 (1.0); 1.5414 (3.2); 1.5246 (4.2); 1.5046 (3.6); 1.4887 (1.3); 1.3413 (0.6); 1.3225 (2.5); 1.3035 (4.3); 1.2848 (4.2); 1.2666 (2.3); 1.2484 (0.6); 0.8645 (8.4); 0.8460 (16.0); 0.8276 (7.1) |
| I.0927: $^{1}$H-NMR(400.2 MHz, $d_6$-DMSO): |
| δ = 8.9920 (3.9); 7.3656 (0.8); 7.3617 (0.5); 7.3505 (2.0); 7.3429 (3.2); 7.3323 (16.0); 7.3291 (15.5); 7.3187 (3.0); 7.3143 (2.8); 7.3057 (2.0); 7.2908 (0.5); 5.1387 (15.2); 3.3653 (12.5); 3.3572 (26.3); 3.3544 (27.8); 3.3496 (19.0); 3.3432 (21.5); 2.8913 (1.4); 2.7322 (1.2); 2.5957 (1.0); 2.5758 (2.0); 2.5624 (2.0); 2.5485 (2.3); 2.5420 (1.9); 2.5267 (2.3); 2.5084 (34.4); 2.5042 (43.0); 2.4998 (32.1); 2.3731 (1.2); 2.3509 (2.6); 2.3300 (2.1); 2.3197 (2.4); 2.2980 (1.1); 1.9864 (0.9); 1.9650 (2.4); 1.9440 (2.8); 1.9234 (1.6); 1.9026 (0.4); −0.0002 (2.1) |
| I.0928: $^{1}$H-NMR(400.2 MHz, $d_6$-DMSO): |
| δ = 8.9219 (5.8); 4.0299 (4.9); 4.0140 (10.2); 3.9980 (5.1); 3.3335 (47.1); 2.8919 (1.0); 2.7318 (1.0); 2.6728 (0.4); 2.6685 (0.4); 2.5631 (1.3); 2.5472 (2.9); 2.5308 (3.2); 2.5081 (42.2); 2.5039 (60.2); 2.4996 (55.8); 2.3543 (1.6); 2.3312 (3.9); 2.3026 (3.5); 2.2806 (1.6); 1.9756 (1.2); 1.9550 (3.4); 1.9344 (4.4); 1.9139 (2.6); 1.8937 (0.6); 1.6009 (0.6); 1.5825 (2.7); 1.5645 (5.0); 1.5479 (5.5); 1.5299 (2.8); 1.5132 (0.7); 0.8685 (8.0); 0.8502 (16.0); 0.8315 (7.4); −0.0002 (1.7); −0.0021 (1.2); −0.0042 (1.0) |
| I.0929: $^{1}$H-NMR(400.2 MHz, $d_6$-DMSO): |
| δ = 8.9072 (16.0); 7.9539 (1.9); 4.7368 (3.4); 4.7272 (4.6); 4.7176 (6.2); 4.7091 (5.0); 4.6983 (3.1); 3.3352 (105.8); 2.8922 (11.9); 2.7327 (10.6); 2.6771 (1.0); 2.6727 (1.2); 2.6685 (0.9); 2.5528 (4.4); 2.5344 (10.4); 2.5260 (11.9); 2.5082 (164.2); 2.5038 (205.6); 2.4996 (157.3); 2.3554 (4.8); 2.3337 (12.0); 2.3024 (8.9); 2.2801 (4.4); 1.9749 (3.3); 1.9549 (9.8); 1.9354 (14.0); 1.9148 (8.1); 1.8953 (2.1); 1.7200 (4.8); 1.7111 (5.3); 1.6935 (8.3); 1.6802 (7.2); 1.6726 (8.2); 1.6302 (4.1); 1.6085 (7.0); 1.5878 (7.4); 1.4361 (6.6); 1.4150 (11.1); 1.3935 (10.1); 1.3723 (11.4); 1.3520 (8.8); 1.3292 (7.4); 1.3223 (7.7); 1.3004 (7.9); 1.2821 (3.8); 1.2610 (2.8); 1.2338 (1.4); −0.0003 (8.3) |
| I.0930: $^{1}$H-NMR(400.2 MHz, $d_6$-DMSO): |
| δ = 8.9151 (14.0); 7.9574 (0.4); 6.5539 (0.6); 4.9460 (1.4); 4.9275 (5.4); 4.9091 (8.2); 4.8908 (5.5); 4.8721 (1.5); 3.3637 (459.9); 2.8971 (2.4); 2.7369 (2.2); 2.6790 (1.0); 2.6749 (0.9); 2.5570 (3.4); 2.5374 (7.8); 2.5141 (125.1); 2.5100 (167.7); 2.5057 (145.0); 2.3446 (4.3); 2.3227 (9.4); 2.3087 (5.8); 2.3011 (9.6); 2.2917 (11.9); 2.2817 (8.9); 2.2776 (9.5); 2.2710 (10.5); 2.2647 (9.0); 2.2601 (8.6); 2.2582 (8.6); 2.2400 (3.9); 2.0023 (1.8); 1.9974 (1.6); 1.9784 (7.2); 1.9718 (7.7); 1.9491 (15.3); 1.9286 (16.0); 1.9079 (7.0); 1.8870 (1.4); 1.7702 (1.9); 1.7452 (4.8); 1.7188 (4.7); 1.6939 (1.7); 1.6536 (1.2); 1.6284 (3.2); 1.6076 (5.3); 1.5821 (4.7); 1.5612 (2.0); 1.5574 (2.0); 1.5333 (0.8) |
| I.0931: $^{1}$H-NMR(500.1 MHz, CDCl3): |
| δ = 7.6718 (7.1); 7.6659 (7.1); 7.3422 (0.4); 7.2623 (25.3); 5.2998 (0.8); 4.7003 (5.1); 4.6898 (5.4); 4.6832 (6.2); 4.6770 (6.6); 4.6729 (6.8); 4.6667 (6.2); 4.6600 (5.9); 4.6495 (5.3); 4.5646 (7.4); 4.5465 (16.0); 4.5284 (9.1); 4.3849 (5.8); 4.3732 (6.6); 4.3660 (6.4); 4.3627 (7.7); 4.3543 (6.5); 4.3509 (7.7); 4.3438 (5.8); 4.3320 (5.1); 2.9966 (4.2); 2.9845 (4.8); 2.9797 (5.1); 2.9702 (7.0); 2.9596 (5.3); 2.9546 (5.4); 2.9427 (4.4); 2.3424 (2.8); 2.3245 (3.6); 2.3192 (6.8); 2.3013 (7.1); 2.2948 (7.5); 2.2769 (6.6); 2.2717 (3.7); 2.2537 (2.5); 1.5716 (13.4); 1.4453 (1.0); 1.2550 (1.1); −0.0002 (26.7) |
| I.0932: $^{1}$H-NMR(500.1 MHz, CDCl3): |
| δ = 7.5097 (5.5); 7.5009 (5.6); 7.4692 (0.4); 7.2626 (35.0); 4.6988 (6.0); 4.6879 (6.0); 4.6815 (6.7); 4.6756 (6.9); 4.6707 (6.8); 4.6647 (6.6); 4.6584 (6.4); 4.6475 (6.2); 4.5624 (6.4); 4.5606 (6.7); 4.5441 (14.2); 4.5425 (14.2); 4.5261 (8.3); 4.5243 (7.8); 4.3799 (7.2); 4.3681 (8.2); 4.3612 (6.8); 4.3575 (8.4); 4.3494 (7.1); 4.3456 (8.3); 4.3388 (7.0); 4.3270 (6.3); 4.1284 (0.3); 4.1141 (0.3); 3.8617 (0.4); 3.5348 (0.8); 3.2686 (10.5); 3.1372 (1.2); 3.0235 (0.6); 3.0061 (0.6); 2.9760 (3.7); 2.9738 (3.9); 2.9642 (4.2); 2.9619 (4.1); 2.9588 (4.2); 2.9566 (4.3); 2.9508 (4.7); 2.9480 (6.2); 2.9448 (4.3); 2.9390 (4.6); 2.9367 (4.4); 2.9336 (4.6); 2.9314 (4.5); 2.9217 (4.1); 2.9196 (3.9); 2.7839 (16.0); 2.3498 (3.5); 2.3320 (4.0); 2.3270 (7.1); 2.3091 (7.3); 2.3071 (5.2); 2.3039 (5.4); 2.3020 (7.1); 2.2841 (6.4); 2.2790 (3.8); 2.2612 (3.0); 2.0439 (1.5); 1.5781 (3.4); 1.2732 (0.7); 1.2588 (1.5); 1.2546 (1.3); 1.2446 (0.6); 0.8812 (0.4); 0.0063 (1.3); −0.0002 (44.8); −0.0068 (1.8) |

TABLE A-(I)-continued

NMR peak lists of compounds according to formula (I)

I.0933: $^{1}$H-NMR(400.1 MHz, CDCl3):
δ = 8.9534 (1.0); 7.2603 (10.3); 3.7456 (16.0); 2.8972 (0.7); 2.8920 (0.5); 2.8833 (0.9); 2.8744 (1.1); 2.8612 (1.4); 2.8501 (1.3); 2.8411 (1.0); 2.8275 (0.9); 2.4347 (0.7); 2.4098 (1.5); 2.3905 (1.3); 2.3832 (1.4); 2.3581 (0.9); 2.2168 (0.4); 2.2107 (0.4); 2.1977 (0.6); 2.1888 (0.7); 2.1691 (0.9); 2.1475 (0.7); 2.1341 (0.5); 2.1208 (0.6); 2.1090 (0.9); 2.0951 (0.7); 2.0806 (0.5); 2.0693 (0.4); 1.5551 (7.6); −0.0002 (13.0)

I.0934: $^{1}$H-NMR(400.1 MHz, $d_6$-DMSO):
δ = 19.0205 (1.0); 18.5344 (1.0); 13.1095 (1.1); 12.6839 (1.2); 12.6058 (1.7); 12.5585 (2.1); 12.5065 (1.1); 12.4933 (1.1); 11.7794 (1.0); 10.7801 (7.6); 6.5790 (1.1); 4.0563 (1.3); 4.0381 (2.3); 4.0205 (1.9); 3.3060 (928.4); 3.2548 (2.3); 3.0164 (1.1); 2.9564 (1.1); 2.7671 (1.0); 2.6940 (1.0); 2.6355 (8.4); 2.6220 (9.7); 2.6075 (10.5); 2.5623 (1.8); 2.5001 (446.3); 2.4275 (7.8); 2.4155 (7.7); 2.3851 (5.2); 2.3269 (3.2); 1.9877 (16.0); 1.9687 (14.1); 1.9494 (10.6); 1.9291 (3.3); 1.9075 (4.5); 1.2707 (1.1); 1.2483 (1.1); 1.2343 (2.2); 1.1923 (2.0); 1.1745 (5.1); 1.1690 (6.3); 1.1566 (2.5); 0.4073 (1.1); 0.1461 (1.2); −0.0002 (240.2); −0.0848 (1.1); −0.1486 (1.4)

I.0935: $^{1}$H-NMR(400.1 MHz, CDCl3):
δ = 7.2599 (21.7); 4.5622 (0.4); 4.2583 (2.5); 4.2403 (8.0); 4.2253 (16.0); 4.2048 (3.0); 4.1921 (0.7); 4.1735 (0.4); 4.1211 (0.7); 3.0734 (2.0); 1.5431 (35.9); 1.3203 (7.6); 1.3024 (15.1); 1.2846 (7.8); 1.2724 (1.2); 1.2547 (0.6); 0.7648 (0.9); 0.7473 (3.7); 0.7322 (4.6); 0.7196 (3.0); 0.7017 (2.9); 0.6904 (6.6); 0.6606 (1.0); −0.0002 (25.9)

I.0936: $^{1}$H-NMR(400.1 MHz, CDCl3):
δ = 7.2599 (16.5); 4.2582 (2.5); 4.2403 (7.8); 4.2261 (16.0); 4.2048 (2.8); 3.0895 (1.5); 3.0793 (1.9); 1.5435 (26.1); 1.3203 (7.5); 1.3024 (14.7); 1.2846 (7.4); 0.7690 (0.9); 0.7516 (3.6); 0.7361 (4.4); 0.7240 (2.9); 0.7050 (2.6); 0.6939 (6.4); 0.6639 (0.9); −0.0002 (20.1)

I.0937: $^{1}$H-NMR(400.1 MHz, CDCl3):
δ = 7.2598 (16.3); 4.2615 (2.3); 4.2436 (7.1); 4.2243 (16.0); 4.2081 (3.2); 3.0745 (1.3); 3.0642 (1.7); 1.5426 (21.6); 1.3236 (7.2); 1.3058 (14.4); 1.2880 (7.3); 0.7702 (0.5); 0.7498 (3.1); 0.7326 (3.5); 0.7169 (3.7); 0.7060 (6.3); 0.6767 (0.7); −0.0002 (20.2)

I.0938: $^{1}$H-NMR(400.1 MHz, CDCl3):
δ = 7.2600 (15.8); 4.5489 (0.6); 4.2451 (2.1); 4.2272 (7.0); 4.2154 (16.0); 4.1915 (2.5); 4.1713 (0.4); 4.1103 (0.8); 3.1351 (1.4); 1.5450 (23.9); 1.3096 (6.5); 1.2918 (13.1); 1.2739 (6.7); 1.2525 (0.5); 0.8217 (0.7); 0.8045 (3.6); 0.7882 (3.6); 0.7761 (2.1); 0.7198 (4.2); 0.7116 (4.1); −0.0002 (19.4)

I.0939: $^{1}$H-NMR(400.1 MHz, CDCl3):
δ = 19.4461 (0.6); 12.8271 (0.6); 8.0192 (1.1); 7.9661 (6.2); 7.5196 (0.7); 7.2593 (160.1); 7.2256 (2.0); 6.9950 (0.7); 5.7426 (6.3); 5.6863 (0.6); 4.4457 (3.6); 4.4317 (6.1); 4.4166 (6.2); 4.4029 (6.5); 4.3891 (3.5); 3.5722 (0.6); 3.4214 (8.8); 3.4154 (9.6); 3.4006 (16.0); 3.3873 (9.1); 2.9545 (5.6); 2.8832 (5.4); 2.7799 (2.0); 2.7678 (4.5); 2.7542 (4.6); 2.7472 (3.6); 2.7356 (5.2); 2.7218 (4.8); 2.7116 (2.2); 2.0316 (3.4); 2.0126 (8.5); 2.0005 (12.2); 1.9870 (9.1); 1.9647 (2.7); 1.7045 (2.2); 1.6834 (3.3); 1.6734 (3.9); 1.6528 (5.3); 1.6430 (3.2); 1.6319 (3.2); 1.6240 (2.7); 1.6015 (1.7); 1.5812 (0.7); 1.5686 (2.3); 1.5415 (218.2); 1.5078 (4.1); 1.4707 (1.1); 1.4417 (0.6); 1.2570 (0.9); 0.1563 (0.6); 0.1461 (1.0); 0.0691 (1.3); 0.0264 (1.0); −0.0002 (205.8); −0.0319 (2.9); −0.0493 (1.7); −0.1490 (1.2); −2.5733 (0.6)

I.0940: $^{1}$H-NMR(400.2 MHz, $d_6$-DMSO):
δ = 8.6248 (1.2); 8.6055 (1.3); 7.9564 (0.4); 7.3674 (2.8); 7.3626 (1.0); 7.3514 (1.4); 7.3463 (5.9); 7.3407 (0.8); 7.3105 (0.8); 7.3050 (5.1); 7.3000 (1.3); 7.2886 (0.9); 7.2838 (2.6); 4.7064 (0.4); 4.6940 (0.5); 4.6869 (0.5); 4.6822 (0.7); 4.6745 (0.6); 4.6698 (0.6); 4.6626 (0.6); 4.6501 (0.5); 3.6789 (16.0); 3.3495 (79.7); 3.2202 (0.6); 3.2076 (0.7); 3.1857 (1.1); 3.1733 (1.0); 3.0921 (1.0); 3.0675 (1.0); 3.0576 (0.7); 3.0331 (0.6); 2.8947 (3.0); 2.7352 (2.5); 2.5296 (0.8); 2.5248 (1.1); 2.5162 (15.1); 2.5118 (30.3); 2.5072 (39.7); 2.5026 (28.7); 2.4981 (13.8)

I.0941: $^{1}$H-NMR(400.2 MHz, $d_6$-DMSO):
δ = 8.3514 (2.1); 7.9560 (0.4); 7.3189 (0.5); 7.3143 (0.8); 7.3102 (0.4); 7.2975 (2.4); 7.2933 (1.3); 7.2795 (2.4); 7.2695 (0.7); 7.2655 (1.4); 7.2618 (0.9); 7.2548 (0.4); 7.2482 (1.3); 7.1185 (1.9); 7.1145 (2.5); 7.0981 (2.1); 3.6585 (16.0); 3.3454 (55.8); 3.3099 (1.2); 3.2765 (1.8); 3.1919 (1.8); 3.1585 (1.1); 2.8943 (3.1); 2.7354 (2.5); 2.7342 (2.4); 2.5288 (0.7); 2.5241 (1.0); 2.5154 (13.1); 2.5109 (26.6); 2.5063 (35.0); 2.5017 (25.3); 2.4971 (12.1); 1.4357 (9.1)

I.0942: $^{1}$H-NMR(400.2 MHz, $d_6$-DMSO):
δ = 9.2061 (1.1); 9.1890 (1.1); 7.5599 (1.8); 7.5568 (1.9); 7.5471 (1.9); 7.5440 (1.9); 7.1987 (1.1); 7.1961 (1.5); 7.1938 (1.1); 7.1899 (1.3); 7.1876 (1.6); 7.1850 (1.2); 7.0461 (2.0); 7.0373 (1.7); 7.0334 (1.9); 7.0245 (1.7); 5.8707 (1.8); 5.8540 (1.8); 3.9115 (0.4); 3.7146 (16.0); 3.3417 (52.3); 2.8944 (1.1); 2.7355 (0.9); 2.7343 (0.9); 2.5288 (0.8); 2.5241 (1.2); 2.5154 (14.7); 2.5109 (29.7); 2.5063 (38.9); 2.5016 (28.1); 2.4971 (13.5)

I.0943: $^{1}$H-NMR(400.2 MHz, $d_6$-DMSO):
δ = 9.4882 (1.8); 9.4670 (1.8); 5.6025 (1.3); 5.5818 (2.1); 5.5608 (1.4); 5.5399 (0.4); 4.2719 (0.4); 4.2627 (1.0); 4.2564 (1.1); 4.2449 (3.3); 4.2387 (3.3); 4.2271 (3.4); 4.2210 (3.2); 4.2093 (1.2); 4.2033 (1.0); 4.1940 (0.4); 3.3357 (61.7); 2.8916 (0.5); 2.7324 (0.4); 2.6722 (0.3); 2.5257 (1.0); 2.5210 (1.4); 2.5123 (20.5); 2.5078 (41.9); 2.5032 (55.1); 2.4985 (39.8); 2.4940 (19.1); 2.3301 (0.3); 1.2428 (7.7); 1.2251 (16.0); 1.2073 (7.4)

I.0944: $^{1}$H-NMR(400.1 MHz, CDCl3):
δ = 16.4960 (0.9); 16.2195 (0.9); 14.9450 (0.9); 12.8433 (0.9); 8.0962 (6.5); 8.0187 (2.4); 7.5183 (1.4); 7.2591 (256.6); 6.9955 (1.0); 5.7268 (6.2); 5.6107 (1.0); 4.4503 (3.4); 4.4377 (6.1); 4.4238 (6.2); 4.4084 (6.0); 4.3949 (3.8); 3.4935 (1.1); 3.4174 (10.3); 3.4031 (16.0); 3.3888 (9.2); 2.9544 (14.7); 2.8828 (13.4); 2.7953 (2.2); 2.7842 (4.7); 2.7716 (5.0); 2.7534 (5.2); 2.7400 (4.9); 2.7280 (2.3); 2.0349 (3.7); 2.0145 (8.6); 2.0021 (12.3); 1.9905 (9.1); 1.9542 (0.9); 1.7010 (2.2); 1.6792 (3.2); 1.6712 (4.2); 1.6499 (5.4); 1.6296 (3.7); 1.6184 (3.2); 1.5982 (2.0); 1.5375 (360.1); 1.4935 (1.6); 1.2559 (1.0); 0.1451 (1.8); −0.0002 (329.8); −0.0413 (1.2); −0.1495 (1.7); −3.7883 (0.9)

I.0945: $^{1}$H-NMR(400.2 MHz, $d_6$-DMSO):
δ = 8.6051 (16.0); 8.5912 (16.0); 8.1345 (6.7); 8.1216 (9.2); 8.1051 (6.4); 5.7590 (10.8); 4.6098 (7.4); 4.5959 (7.6); 4.5856 (7.9); 4.5715 (7.5); 4.1080 (0.4); 4.0947 (0.4); 3.4151 (0.3); 3.3320 (712.1); 3.2838 (3.7); 3.2715 (3.7); 3.2541 (4.2); 3.2452 (7.4); 3.2343 (5.6); 3.2177 (5.4); 3.2057 (5.2); 3.1749 (3.2); 3.1617 (3.1); 3.1155 (4.0); 3.0998 (5.8); 3.0840 (5.0); 3.0641 (3.7); 3.0512 (2.6); 2.6807 (1.8); 2.6762 (3.6); 2.6717 (5.0); 2.6672 (3.6); 2.6627 (1.6); 2.5252 (16.5); 2.5204 (25.8); 2.5118 (319.9); 2.5073 (634.8); 2.5028 (818.2); 2.4982 (582.9); 2.4937 (277.0); 2.4149 (0.4); 2.3385 (1.7); 2.3341 (3.6); 2.3296 (5.0); 2.3250 (3.6); 2.3207 (1.6); 2.0237 (6.7); 1.9898 (7.4); 1.9625 (0.5); 1.9342 (5.3); 1.9004 (7.4); 1.7969 (5.3); 1.7867 (5.6); 1.7739 (3.8); 1.7609 (5.9); 1.7493 (6.8); 1.7170 (4.3); 1.7090 (6.3); 1.7008 (3.6); 1.6836 (4.4); 1.6760 (6.3); 1.6689 (3.6); 1.6514 (1.9); 1.6430 (2.6); 1.4842 (3.2); 1.4772 (3.3); 1.4508 (8.3); 1.4233 (6.4); 1.4183 (7.2); 1.3912 (2.8); 1.3857 (2.1); 1.2812 (2.4); 1.2492 (6.2); 1.2151 (5.8); 1.1854 (2.1); 0.0080 (2.1); −0.0002 (65.1); −0.0085 (2.0)

I.0946: $^{1}$H-NMR(400.2 MHz, $d_6$-DMSO):
δ = 9.5463 (1.6); 9.5253 (1.6); 5.7589 (0.9); 5.6186 (1.2); 5.5977 (1.9); 5.5769 (1.3); 5.5561 (0.4); 4.2799 (0.5); 4.2708 (1.0); 4.2624 (1.5); 4.2530 (3.2); 4.2449 (3.4); 4.2352 (3.4); 4.2271 (3.2); 4.2176 (1.5); 4.2094 (1.0); 4.2002 (0.5); 3.3296 (68.3); 2.6757 (0.5); 2.6712 (0.6); 2.6667 (0.5); 2.5246 (2.3); 2.5198 (3.5); 2.5112 (40.9); 2.5068 (81.3); 2.5022 (104.8); 2.4976 (74.7); 2.4931 (35.6); 2.3336 (0.5); 2.3291 (0.6); 2.3245 (0.4); 1.2496 (7.6); 1.2319 (16.0); 1.2141 (7.3); 0.0079 (0.3); −0.0001 (10.1)

TABLE A-(I)-continued

| NMR peak lists of compounds according to formula (I) |
| --- |
| I.0947: ${}^1$H-NMR(400.2 MHz, $d_6$-DMSO):<br>δ = 9.2275 (1.0); 9.2106 (1.0); 7.5665 (1.8); 7.5633 (1.9); 7.5537 (2.0); 7.5505 (1.9); 7.2086 (1.1); 7.2057 (1.4); 7.2036 (1.1); 7.1998 (1.3); 7.1976 (1.6); 7.1947 (1.2); 7.0493 (1.9); 7.0404 (1.7); 7.0365 (1.8); 7.0276 (1.6); 5.8761 (1.7); 5.8752 (1.7); 5.8594 (1.7); 3.7180 (16.0); 3.3325 (43.6); 2.8907 (0.6); 2.7317 (0.5); 2.7304 (0.5); 2.5248 (0.9); 2.5201 (1.3); 2.5114 (16.9); 2.5068 (34.1); 2.5022 (44.5); 2.4976 (31.9); 2.4930 (15.1) |
| I.0948: ${}^1$H-NMR(400.2 MHz, $d_6$-DMSO):<br>δ = 8.4518 (2.0); 7.3183 (0.5); 7.3139 (0.8); 7.3097 (0.4); 7.2969 (2.4); 7.2928 (1.3); 7.2789 (2.4); 7.2670 (0.7); 7.2632 (1.4); 7.2595 (0.8); 7.2521 (0.4); 7.2457 (1.3); 7.2273 (0.3); 7.1173 (1.9); 7.1134 (2.4); 7.0969 (2.1); 3.6622 (16.0); 3.3342 (52.3); 3.3156 (1.3); 3.2821 (1.8); 3.1960 (1.8); 3.1627 (1.1); 2.8908 (1.0); 2.7319 (0.8); 2.7305 (0.8); 2.5249 (0.8); 2.5202 (1.1); 2.5115 (14.4); 2.5070 (29.3); 2.5024 (38.4); 2.4977 (27.6); 2.4932 (13.2); 1.4308 (9.0) |
| I.0949: ${}^1$H-NMR(400.1 MHz, CDCl3):<br>δ = 7.4875 (5.0); 7.2940 (0.4); 7.2608 (40.6); 4.7000 (3.6); 4.6868 (3.8); 4.6786 (4.4); 4.6709 (4.7); 4.6654 (4.6); 4.6578 (4.3); 4.6496 (4.1); 4.6362 (3.7); 4.5654 (5.0); 4.5427 (11.2); 4.5203 (6.4); 4.3861 (4.2); 4.3715 (4.8); 4.3625 (4.6); 4.3583 (5.4); 4.3478 (4.7); 4.3436 (5.5); 4.3347 (3.9); 4.3201 (3.6); 3.8221 (1.5); 2.9915 (2.9); 2.9762 (3.4); 2.9718 (3.5); 2.9585 (5.0); 2.9447 (3.8); 2.9408 (3.7); 2.9243 (3.0); 2.3505 (2.2); 2.3282 (2.8); 2.3218 (4.8); 2.2992 (5.1); 2.2913 (5.1); 2.2688 (4.6); 2.2397 (1.9); 1.6371 (0.4); 1.5579 (62.4); 1.4225 (1.5); 1.4035 (0.4); 1.3351 (2.6); 1.2841 (3.0); 1.2560 (16.0); 1.1057 (0.7); 1.0721 (0.5); 0.9963 (0.3); 0.9804 (0.4); 0.8807 (2.0); 0.8639 (1.5); 0.8532 (1.5); 0.7534 (0.3); 0.7164 (0.3); −0.0002 (29.7) |
| I.0950: ${}^1$H-NMR(400.1 MHz, CDCl3):<br>δ = 15.4862 (1.4); 9.4549 (1.3); 8.0197 (2.1); 7.5176 (2.2); 7.3476 (1.2); 7.2592 (348.8); 7.2328 (8.2); 7.2210 (7.8); 6.9961 (1.9); 5.7114 (6.2); 5.6241 (1.2); 4.9884 (1.2); 4.4211 (5.4); 4.4049 (5.6); 4.3899 (5.9); 3.5911 (1.3); 3.5502 (1.2); 3.5336 (1.2); 3.4985 (1.3); 3.4062 (9.9); 3.3947 (16.0); 3.3777 (8.8); 3.3455 (1.5); 3.2854 (1.2); 2.9760 (1.3); 2.9547 (10.6); 2.8835 (9.8); 2.7036 (3.8); 2.6910 (4.2); 2.6729 (5.2); 2.6580 (4.7); 2.6467 (2.3); 2.0031 (9.1); 1.9904 (11.4); 1.9792 (9.2); 1.7106 (1.9); 1.6890 (3.4); 1.6801 (4.4); 1.6581 (5.8); 1.6374 (2.8); 1.6281 (2.9); 1.6076 (2.1); 1.5910 (2.1); 1.5373 (424.5); 1.2565 (3.6); 1.2173 (1.2); 0.7210 (1.2); 0.1462 (1.6); −0.0002 (447.6); −0.1500 (2.6) |
| I.0951: ${}^1$H-NMR(400.2 MHz, $d_6$-DMSO):<br>δ = 8.1274 (1.2); 8.1140 (1.7); 8.0978 (1.3); 7.9826 (1.5); 7.9695 (2.7); 7.9536 (3.0); 6.5534 (1.4); 4.5522 (1.3); 4.5377 (1.4); 4.5254 (1.4); 4.5112 (1.3); 3.9633 (0.4); 3.3397 (261.2); 3.2682 (0.9); 3.2565 (0.9); 3.2298 (1.5); 3.2188 (1.2); 3.2023 (1.2); 3.1904 (1.1); 3.0910 (1.2); 3.0745 (1.0); 3.0606 (0.8); 3.0422 (0.6); 2.8913 (16.0); 2.7323 (12.9); 2.7311 (13.2); 2.6813 (0.4); 2.6767 (0.8); 2.6722 (1.2); 2.6676 (0.8); 2.6629 (0.4); 2.5257 (3.6); 2.5210 (5.4); 2.5123 (70.2); 2.5078 (142.0); 2.5032 (186.7); 2.4986 (135.3); 2.4940 (65.0); 2.3392 (0.4); 2.3346 (0.9); 2.3300 (1.2); 2.3254 (0.9); 2.3210 (0.4); 1.9984 (1.3); 1.9638 (1.4); 1.9235 (1.0); 1.8888 (1.4); 1.7865 (1.0); 1.7766 (1.1); 1.7632 (0.8); 1.7511 (1.1); 1.7421 (1.2); 1.7342 (1.1); 1.6956 (1.2); 1.6698 (0.9); 1.6626 (1.2); 1.6378 (0.4); 1.6292 (0.5); 1.4843 (0.6); 1.4773 (0.7); 1.4505 (1.6); 1.4230 (1.2); 1.4177 (1.4); 1.3907 (0.6); 1.2701 (0.5); 1.2349 (1.6); 1.2033 (1.1); 1.1734 (0.4); −0.0001 (0.3) |
| I.0952: ${}^1$H-NMR(400.2 MHz, $d_6$-DMSO):<br>δ = 9.3439 (1.5); 9.3228 (1.6); 5.5683 (1.3); 5.5475 (2.0); 5.5265 (1.4); 5.5056 (0.4); 4.2621 (0.6); 4.2530 (1.0); 4.2440 (0.9); 4.2414 (1.2); 4.2352 (3.2); 4.2237 (3.3); 4.2174 (3.3); 4.2060 (3.1); 4.1995 (1.2); 4.1882 (1.0); 4.1790 (0.6); 3.3383 (78.6); 2.8947 (0.8); 2.7353 (0.6); 2.6752 (0.4); 2.5285 (1.4); 2.5152 (25.7); 2.5108 (49.8); 2.5062 (63.9); 2.5016 (46.0); 2.4972 (22.0); 2.3331 (0.4); 1.2354 (7.8); 1.2176 (16.0); 1.1998 (7.5) |
| I.0953: ${}^1$H-NMR(400.2 MHz, $d_6$-DMSO):<br>δ = 9.1203 (0.7); 9.1026 (0.7); 7.5496 (1.8); 7.5464 (1.9); 7.5368 (2.0); 7.5336 (1.9); 7.1850 (1.1); 7.1822 (1.4); 7.1800 (1.1); 7.1762 (1.3); 7.1740 (1.6); 7.1712 (1.2); 7.0380 (2.0); 7.0292 (1.8); 7.0252 (1.9); 7.0164 (1.7); 5.8407 (1.7); 5.8234 (1.7); 3.9116 (0.7); 3.7105 (0.4); 3.7013 (16.0); 3.6250 (0.5); 3.3407 (44.8); 2.8945 (1.1); 2.7356 (1.0); 2.7343 (0.9); 2.5288 (0.8); 2.5241 (1.2); 2.5154 (15.6); 2.5109 (31.7); 2.5062 (41.4); 2.5016 (29.6); 2.4970 (14.0) |
| I.0954: ${}^1$H-NMR(400.2 MHz, $d_6$-DMSO):<br>δ = 8.1584 (1.2); 7.9562 (0.3); 7.3166 (0.5); 7.3118 (0.8); 7.3077 (0.4); 7.2951 (2.4); 7.2907 (1.2); 7.2771 (2.4); 7.2684 (0.7); 7.2643 (1.4); 7.2606 (0.9); 7.2537 (0.4); 7.2471 (1.2); 7.1116 (1.9); 7.1076 (2.3); 7.0912 (2.0); 3.6272 (16.0); 3.3420 (46.1); 3.2879 (1.1); 3.2546 (1.7); 3.1533 (1.7); 3.1200 (1.1); 2.8944 (2.7); 2.7356 (2.2); 2.7344 (2.2); 2.5289 (0.7); 2.5243 (1.0); 2.5155 (13.9); 2.5110 (28.4); 2.5064 (37.5); 2.5018 (27.0); 2.4972 (12.9); 1.3993 (8.9) |
| I.0955: ${}^1$H-NMR(400.2 MHz, $d_6$-DMSO):<br>δ = 8.5415 (0.8); 8.5233 (0.8); 7.9557 (0.4); 7.3549 (2.7); 7.3499 (1.0); 7.3389 (1.3); 7.3336 (5.8); 7.3281 (0.8); 7.3002 (0.8); 7.2948 (5.0); 7.2897 (1.2); 7.2784 (0.9); 7.2735 (2.4); 4.6699 (0.4); 4.6571 (0.5); 4.6499 (0.5); 4.6449 (0.6); 4.6376 (0.6); 4.6327 (0.5); 4.6253 (0.5); 4.6126 (0.4); 3.6630 (16.0); 3.3475 (48.1); 3.3448 (59.7); 3.2042 (0.6); 3.1917 (0.6); 3.1696 (1.0); 3.1572 (0.9); 3.1042 (1.0); 3.0791 (1.0); 3.0699 (0.6); 3.0447 (0.6); 2.8940 (3.1); 2.7349 (2.5); 2.7342 (2.5); 2.5287 (0.8); 2.5240 (1.3); 2.5153 (15.9); 2.5108 (31.7); 2.5062 (41.4); 2.5016 (29.9); 2.4971 (14.4) |
| I.0956: ${}^1$H-NMR(400.1 MHz, CDCl3):<br>δ = 8.0182 (1.4); 7.9544 (6.6); 7.2618 (26.0); 5.8655 (6.6); 4.4426 (3.0); 4.4303 (5.5); 4.4155 (5.7); 4.4008 (5.6); 4.3886 (3.2); 3.4136 (9.2); 3.4015 (16.0); 2.9563 (5.9); 2.8841 (5.7); 2.7733 (1.7); 2.7628 (4.1); 2.7499 (4.6); 2.7309 (4.7); 2.7185 (4.5); 2.0292 (3.3); 1.9984 (11.6); 1.9862 (9.2); 1.7067 (1.8); 1.6763 (3.7); 1.6547 (4.9); 1.6346 (3.3); 1.6244 (3.1); 1.5820 (35.2); −0.0002 (32.7) |
| I.0957: ${}^1$H-NMR(400.2 MHz, $d_6$-DMSO):<br>δ = 8.4923 (6.0); 8.4785 (6.0); 8.1413 (2.4); 8.1244 (3.3); 8.1122 (2.4); 7.9527 (2.1); 7.9456 (0.6); 6.5483 (3.4); 6.2984 (1.0); 4.5877 (2.6); 4.5739 (2.7); 4.5634 (2.8); 4.5495 (2.6); 3.5896 (1.1); 3.3337 (456.1); 3.2789 (1.7); 3.2668 (1.6); 3.2488 (1.6); 3.2401 (2.8); 3.2297 (2.1); 3.2123 (2.0); 3.2005 (1.9); 3.1124 (1.4); 3.0972 (2.1); 3.0820 (1.8); 3.0608 (1.4); 3.0480 (1.0); 2.8908 (16.0); 2.7921 (2.1); 2.7308 (13.4); 2.6806 (0.9); 2.6760 (2.0); 2.6715 (2.8); 2.6669 (2.0); 2.6624 (0.9); 2.6458 (0.3); 2.5250 (8.3); 2.5202 (12.7); 2.5115 (173.8); 2.5071 (349.8); 2.5025 (457.8); 2.4979 (333.3); 2.4934 (162.1); 2.3383 (1.1); 2.3338 (2.2); 2.3293 (3.0); 2.3247 (2.2); 2.3203 (1.1); 2.0247 (2.4); 1.9898 (2.6); 1.9307 (1.9); 1.8962 (2.6); 1.7930 (1.9); 1.7828 (2.0); 1.7707 (1.4); 1.7572 (2.1); 1.7472 (2.3); 1.7120 (1.5); 1.7044 (2.3); 1.6963 (1.4); 1.6785 (1.6); 1.6710 (2.3); 1.6467 (0.8); 1.6380 (1.0); 1.6297 (0.6); 1.4787 (1.1); 1.4721 (1.2); 1.4457 (3.0); 1.4178 (2.2); 1.4127 (2.6); 1.3860 (1.0); 1.3801 (0.8); 1.2759 (1.0); 1.2348 (2.8); 1.2098 (2.2); 1.1810 (0.8); −0.0002 (0.9) |
| I.0958: ${}^1$H-NMR(400.2 MHz, $d_6$-DMSO):<br>δ = 8.6672 (8.7); 8.6624 (8.5); 8.6472 (8.6); 8.6424 (8.5); 7.9557 (1.6); 7.7874 (0.3); 6.5505 (0.5); 4.8008 (5.6); 4.7783 (8.7); 4.7743 (8.4); 4.7571 (8.0); 4.7535 (9.6); 4.7305 (6.0); 4.4113 (5.8); 4.4069 (6.4); 4.3893 (16.0); 4.3847 (15.1); 4.3674 (9.4); 4.3627 (7.8); 4.2900 (7.3); 4.2734 (9.5); 4.2682 (7.6); 4.2640 (9.9); 4.2514 (7.4); 4.2472 (9.6); 4.2423 (8.3); 4.2255 (5.7); 3.4528 (1.4); 3.3420 (344.8); 2.8943 (12.5); 2.7351 (10.0); 2.7343 (9.8); 2.6843 (0.6); 2.6798 (1.4); 2.6752 (2.0); 2.6706 (1.4); 2.6661 (0.6); 2.5600 (0.4); 2.5287 (6.2); 2.5240 (9.4); 2.5153 (119.4); 2.5108 (240.0); 2.5062 (313.5); 2.5016 (224.8); 2.4970 (106.6); 2.4790 (3.5); 2.4741 (3.5); 2.4622 (3.6); 2.4565 (4.6); 2.4492 (7.1); 2.4440 (6.1); 2.4390 (4.3); 2.4325 (7.2); 2.4263 (7.6); 2.4209 (5.7); 2.4088 (5.2); 2.4019 (5.9); 2.3786 (6.4); 2.3750 (8.8); 2.3519 (9.6); 2.3487 (8.5); 2.3456 (6.6); 2.3377 (2.1); 2.3330 (2.6); 2.3251 (6.0); 2.3230 (5.8); 2.3184 (3.7); 2.2957 (2.3); 1.2364 (0.7); 0.0023 (0.5) |

TABLE A-(I)-continued

| NMR peak lists of compounds according to formula (I) |
|---|
| I.0959: $^{1}$H-NMR(400.2 MHz, $d_6$-DMSO):<br>δ = 8.6838 (1.8); 8.6694 (3.7); 8.6551 (1.8); 6.5532 (0.5); 4.7742 (16.0); 4.7681 (15.9); 4.0932 (11.5); 4.0786 (11.5); 3.6105 (3.5); 3.6045 (6.8); 3.5988 (3.3); 3.3630 (117.4); 3.3581 (140.4); 3.3540 (140.7); 3.3509 (150.7); 2.8918 (0.6); 2.7322 (0.5); 2.6779 (0.4); 2.6732 (0.6); 2.6689 (0.4); 2.5265 (1.6); 2.5130 (37.4); 2.5087 (73.8); 2.5042 (95.6); 2.4997 (69.3); 2.4953 (33.5); 2.3355 (0.4); 2.3310 (0.6); 2.3266 (0.4); 0.0079 (0.5); −0.0002 (12.2); −0.0082 (0.4) |
| I.0960: $^{1}$H-NMR(400.2 MHz, $d_6$-DMSO):<br>δ = 8.6292 (2.7); 8.6151 (5.3); 8.6012 (2.8); 7.9530 (0.7); 4.1484 (1.4); 4.1406 (2.7); 4.1330 (3.9); 4.1247 (4.9); 4.1205 (4.1); 4.1092 (2.8); 4.1017 (1.5); 4.0070 (15.8); 3.9925 (16.0); 3.3431 (179.6); 3.3387 (201.2); 2.8915 (3.8); 2.7322 (3.5); 2.6720 (0.8); 2.5030 (132.7); 2.3300 (0.8); 0.7340 (1.5); 0.7299 (1.3); 0.7151 (7.5); 0.6997 (9.8); 0.6857 (5.7); 0.6612 (4.2); 0.6539 (10.2); 0.6471 (10.5); 0.6219 (2.0); −0.0003 (9.6) |
| I.0961: $^{1}$H-NMR(400.2 MHz, $d_6$-DMSO):<br>δ = 8.6660 (2.6); 8.6517 (5.3); 8.6373 (2.6); 5.9674 (1.1); 5.9554 (2.1); 5.9540 (2.4); 5.9409 (2.4); 5.9274 (2.9); 5.9125 (3.0); 5.9110 (3.0); 5.8978 (2.7); 5.8846 (2.9); 5.8712 (1.5); 5.3589 (4.4); 5.3573 (5.0); 5.3549 (5.4); 5.3534 (5.2); 5.3142 (4.3); 5.3118 (4.6); 5.3103 (4.4); 5.2453 (5.3); 5.2431 (5.6); 5.2190 (4.9); 5.2168 (5.2); 4.6265 (11.9); 4.6131 (11.7); 4.0878 (16.0); 4.0733 (16.0); 3.3493 (136.3); 3.3446 (150.2); 2.8923 (0.6); 2.7328 (0.5); 2.6731 (0.6); 2.5262 (1.6); 2.5085 (79.2); 2.5042 (104.4); 2.5005 (80.5); 2.3309 (0.6); 2.3275 (0.5); 0.0015 (8.2); −0.0001 (9.5) |
| I.0962: $^{1}$H-NMR(400.2 MHz, $d_6$-DMSO):<br>δ = 9.2925 (1.9); 5.9271 (0.4); 5.9143 (0.7); 5.9011 (0.7); 5.8879 (0.9); 5.8844 (0.6); 5.8748 (0.5); 5.8713 (1.0); 5.8580 (0.8); 5.8448 (0.9); 5.8320 (0.4); 5.3162 (1.5); 5.3121 (1.6); 5.2731 (1.3); 5.2690 (1.4); 5.2132 (1.6); 5.2096 (1.6); 5.1869 (1.4); 5.1832 (1.5); 4.5846 (3.6); 4.5811 (2.5); 4.5755 (2.3); 4.5718 (3.5); 3.3493 (20.2); 3.3401 (22.9); 2.5076 (15.0); 2.5033 (19.4); 2.4990 (14.7); 2.3762 (16.0); 2.3583 (0.3); 1.4913 (1.2); 1.4790 (3.3); 1.4707 (3.6); 1.4598 (1.5); 1.2418 (1.6); 1.2307 (3.6); 1.2225 (3.4); 1.2101 (1.2); −0.0002 (2.6) |
| I.0963: $^{1}$H-NMR(400.2 MHz, $d_6$-DMSO):<br>δ = 9.3060 (2.7); 4.7305 (5.8); 4.7285 (6.2); 4.7247 (7.1); 3.5788 (1.4); 3.5733 (3.2); 3.5700 (3.2); 3.5642 (1.5); 3.3450 (30.3); 2.5030 (21.2); 2.4992 (18.6); 2.3879 (16.0); 2.3860 (15.8); 2.3697 (0.4); 1.4951 (1.3); 1.4828 (3.6); 1.4752 (4.2); 1.4645 (1.7); 1.2629 (1.7); 1.2519 (4.0); 1.2441 (4.0); 1.2318 (1.4); −0.0002 (2.1); −0.0025 (1.9) |
| I.0964: $^{1}$H-NMR(400.2 MHz, $d_6$-DMSO):<br>δ = 9.2442 (1.8); 4.9083 (0.4); 4.8927 (1.0); 4.8771 (1.4); 4.8615 (1.1); 4.8459 (0.4); 3.3568 (23.4); 3.3483 (31.9); 2.8916 (1.5); 2.7318 (1.3); 2.5261 (0.4); 2.5212 (0.6); 2.5127 (7.8); 2.5083 (15.6); 2.5037 (20.4); 2.4992 (14.7); 2.4947 (7.0); 2.3803 (13.8); 1.4367 (1.0); 1.4245 (2.7); 1.4162 (3.0); 1.4054 (1.2); 1.1847 (1.4); 1.1736 (3.8); 1.1673 (16.0); 1.1518 (14.7); −0.0002 (1.7) |
| I.0965: $^{1}$H-NMR(400.2 MHz, $d_6$-DMSO):<br>δ = 9.0136 (0.6); 8.9991 (1.2); 8.9848 (0.6); 5.1426 (0.6); 5.1332 (0.8); 5.1278 (1.2); 5.1130 (0.6); 3.9740 (4.2); 3.9593 (4.2); 3.3528 (8.4); 3.3462 (20.1); 3.3439 (19.1); 3.3397 (24.8); 2.5256 (0.4); 2.5121 (9.1); 2.5078 (17.7); 2.5033 (22.7); 2.4987 (16.3); 2.4944 (7.8); 2.4082 (16.0); 1.8413 (1.1); 1.8268 (1.0); 1.8130 (0.7); 1.8068 (0.7); 1.7988 (0.6); 1.6360 (3.0); 1.6259 (1.9); 1.6155 (1.4); 1.6054 (1.5); 1.5976 (1.2); 1.5887 (1.0); 1.5787 (0.8); 1.5719 (0.9); 1.5637 (0.8); 1.5516 (1.1); 1.5442 (1.0); 1.5337 (0.6); -0.0002 (2.4) |
| I.0966: $^{1}$H-NMR(400.2 MHz, $d_6$-DMSO):<br>δ = 9.2609 (2.2); 4.0129 (2.6); 3.9968 (5.5); 3.9808 (2.7); 3.3492 (13.8); 3.3483 (13.8); 3.3381 (20.0); 2.8918 (0.4); 2.7324 (0.4); 2.5076 (16.7); 2.5032 (20.3); 2.4987 (14.3); 2.3792 (16.0); 1.5799 (1.2); 1.5634 (2.5); 1.5451 (2.5); 1.5287 (1.3); 1.5106 (0.3); 1.4606 (1.2); 1.4484 (3.1); 1.4402 (3.3); 1.4293 (1.4); 1.2127 (1.5); 1.2018 (3.3); 1.1935 (3.1); 1.1812 (1.1); 0.8793 (4.4); 0.8609 (8.9); 0.8423 (4.0); −0.0002 (2.9) |
| I.0967: $^{1}$H-NMR(400.2 MHz, $d_6$-DMSO):<br>δ = 9.2055 (0.7); 9.1913 (1.4); 9.1773 (0.7); 7.9527 (0.5); 7.4670 (1.7); 7.4625 (0.8); 7.4466 (3.3); 7.4320 (0.9); 7.4275 (2.6); 7.3071 (1.3); 7.3049 (1.0); 7.2885 (2.0); 7.2701 (0.8); 7.1611 (2.6); 7.1583 (3.7); 7.1394 (3.0); 7.1373 (3.0); 4.3256 (4.1); 4.3112 (4.0); 3.3546 (16.7); 3.3488 (16.3); 3.3435 (22.4); 2.8908 (3.5); 2.7312 (3.1); 2.5258 (0.4); 2.5122 (7.8); 2.5080 (16.0); 2.5035 (21.3); 2.4991 (16.0); 2.4290 (16.0); 2.4113 (0.3); −0.0002 (3.0) |
| I.0968: $^{1}$H-NMR(400.2 MHz, $d_6$-DMSO):<br>δ = 9.2527 (2.9); 4.9251 (1.1); 4.9067 (1.6); 4.8881 (1.1); 3.3475 (20.9); 3.3391 (30.3); 2.8917 (1.2); 2.7323 (1.1); 2.5075 (18.2); 2.5032 (22.1); 2.4988 (16.0); 2.3881 (16.0); 2.3696 (0.3); 2.2908 (0.4); 2.2841 (0.6); 2.2642 (1.3); 2.2605 (1.3); 2.2536 (1.2); 2.2462 (1.3); 2.2423 (1.4); 2.2362 (1.1); 2.2229 (0.8); 2.2166 (0.6); 1.9673 (1.2); 1.9605 (0.8); 1.9475 (1.3); 1.9427 (1.5); 1.9371 (1.2); 1.9237 (1.0); 1.9174 (1.2); 1.8995 (0.3); 1.8934 (0.4); 1.7630 (0.3); 1.7370 (0.9); 1.7118 (0.8); 1.6152 (0.5); 1.6108 (0.5); 1.5900 (1.0); 1.5642 (0.8); 1.5442 (0.4); 1.4529 (1.3); 1.4407 (3.3); 1.4326 (3.6); 1.4216 (1.5); 1.2012 (1.6); 1.1903 (3.5); 1.1821 (3.3); 1.1697 (1.2); −0.0002 (2.8) |
| I.0969: $^{1}$H-NMR(400.2 MHz, $d_6$-DMSO):<br>δ = 9.2571 (2.5); 4.0539 (2.5); 4.0379 (5.1); 4.0220 (2.5); 3.3503 (17.3); 3.3416 (19.4); 2.5124 (6.6); 2.5081 (13.3); 2.5036 (17.4); 2.4990 (12.6); 2.4946 (6.1); 2.3772 (16.0); 1.5554 (0.5); 1.5387 (1.5); 1.5319 (0.6); 1.5222 (1.9); 1.5171 (1.4); 1.5019 (1.7); 1.4860 (0.7); 1.4545 (1.2); 1.4422 (3.0); 1.4340 (3.4); 1.4231 (1.4); 1.3512 (0.3); 1.3326 (1.2); 1.3135 (2.0); 1.2947 (1.9); 1.2765 (1.1); 1.2085 (1.5); 1.1976 (3.3); 1.1893 (3.2); 1.1770 (1.2); 0.8809 (4.6); 0.8626 (9.0); 0.8440 (3.9); −0.0002 (2.3) |
| I.0970: $^{1}$H-NMR(400.2 MHz, $d_6$-DMSO):<br>δ = 9.2700 (2.3); 3.8434 (5.5); 3.8274 (5.5); 3.3515 (23.3); 3.3470 (20.4); 3.3431 (31.1); 2.5079 (15.0); 2.5036 (19.9); 2.4993 (15.2); 2.3784 (15.8); 1.8713 (0.5); 1.8548 (1.0); 1.8382 (1.2); 1.8217 (1.0); 1.8052 (0.5); 1.4627 (1.2); 1.4503 (3.2); 1.4421 (3.6); 1.4313 (1.5); 1.2202 (1.6); 1.2092 (3.5); 1.2010 (3.4); 1.1887 (1.2); 0.8693 (16.0); 0.8524 (15.4); −0.0002 (1.9) |
| I.0971: $^{1}$H-NMR(400.2 MHz, $d_6$-DMSO):<br>δ = 9.1773 (1.0); 3.3545 (11.2); 3.3507 (11.5); 3.3478 (13.7); 2.8920 (0.8); 2.7326 (0.7); 2.7318 (0.7); 2.5130 (3.3); 2.5086 (6.5); 2.5040 (8.4); 2.4994 (6.0); 2.4949 (2.8); 2.3752 (6.8); 1.3989 (0.6); 1.3865 (2.0); 1.3776 (16.0); 1.1329 (0.6); 1.1221 (1.3); 1.1138 (1.2); 1.1018 (0.4); −0.0002 (0.8) |
| I.0972: $^{1}$H-NMR(400.2 MHz, $d_6$-DMSO):<br>δ = 9.0294 (0.5); 9.0150 (1.0); 9.0004 (0.5); 4.1084 (2.2); 4.0921 (4.6); 4.0757 (2.2); 4.0226 (3.6); 4.0079 (3.6); 3.3498 (9.9); 3.3449 (10.2); 3.3409 (14.5); 2.8917 (1.0); 2.7329 (0.8); 2.7315 (0.8); 2.5215 (0.4); 2.5128 (5.4); 2.5083 (10.9); 2.5037 (14.3); 2.4991 (10.2); 2.4945 (4.8); 2.4111 (16.0); 1.6015 (0.4); 1.5847 (1.3); 1.5778 (0.4); 1.5674 (1.6); 1.5476 (1.4); 1.5313 (0.6); 1.3618 (1.1); 1.3427 (1.6); 1.3287 (0.7); 1.3238 (1.6); 1.3056 (1.0); 0.9043 (4.3); 0.8860 (8.7); 0.8674 (3.6); −0.0002 (3.0) |
| I.0973: $^{1}$H-NMR(400.2 MHz, $d_6$-DMSO):<br>δ = 9.0692 (0.5); 9.0548 (1.1); 9.0403 (0.5); 7.3915 (4.2); 7.3802 (12.9); 7.3713 (1.2); 7.3618 (1.3); 7.3544 (0.9); 7.3493 (0.8); 7.3403 (0.8); 7.3275 (0.3); 5.1717 (8.7); 4.0993 (3.5); 4.0846 (3.5); 3.3364 (15.5); 3.3327 (19.0); 2.8903 (0.6); 2.7314 (0.5); 2.5246 (0.6); 2.5197 (0.9); 2.5112 (11.0); 2.5067 (22.2); 2.5021 (29.2); 2.4976 (21.1); 2.4930 (10.1); 2.3879 (16.0); −0.0002 (6.9) |
| I.0974: $^{1}$H-NMR(400.2 MHz, $d_6$-DMSO):<br>δ = 9.2367 (1.1); 9.2200 (1.1); 4.1866 (0.6); 4.1773 (0.6); 4.1688 (0.6); 4.1595 (1.8); 4.1417 (2.0); 4.1382 (2.0); 4.1204 (1.8); 4.1111 (0.6); 4.1027 (0.6); 4.0934 (0.6); 3.7028 (1.0); 3.6860 (1.1); 3.6793 (1.1); 3.6624 (1.0); 3.3415 (16.7); 3.3368 (16.2); |

TABLE A-(I)-continued

| NMR peak lists of compounds according to formula (I) |
| --- |
| 3.3333 (19.8); 2.5249 (0.5); 2.5115 (11.3); 2.5071 (22.8); 2.5025 (30.0); 2.4979 (21.6); 2.4935 (10.4); 2.3864 (16.0); 1.2240 (4.8); 1.2062 (9.9); 1.1885 (5.2); 1.1770 (0.7); 1.1687 (0.4); 1.1651 (0.4); 0.6291 (0.6); 0.6206 (0.6); 0.6157 (0.6); 0.6057 (0.7); 0.5945 (0.4); 0.5847 (0.4); 0.5669 (0.3); 0.5570 (0.4); 0.5534 (0.5); 0.5437 (0.7); 0.5369 (0.5); 0.5331 (0.6); 0.5232 (0.8); 0.5111 (0.4); 0.5037 (0.6); 0.4933 (0.5); 0.4842 (0.8); 0.4719 (0.9); 0.4610 (0.7); 0.4091 (0.4); 0.3978 (0.6); 0.3863 (0.8); 0.3736 (0.7); 0.3638 (0.4); −0.0002 (5.9) |
| I.0975: $^{1}$H-NMR(400.2 MHz, $d_6$-DMSO):<br>δ = 9.2998 (2.5); 7.3937 (0.3); 7.3894 (0.7); 7.3847 (0.5); 7.3689 (2.1); 7.3546 (4.4); 7.3407 (7.0); 7.3291 (1.4); 7.3223 (2.2); 7.3111 (0.4); 7.3056 (0.3); 5.1233 (8.1); 3.3450 (26.0); 3.3359 (24.8); 2.8905 (0.8); 2.7313 (0.6); 2.5247 (0.7); 2.5113 (13.6); 2.5069 (26.8); 2.5024 (34.7); 2.4979 (25.0); 2.4935 (11.9); 2.3046 (16.0); 1.5077 (1.1); 1.4954 (2.8); 1.4871 (3.1); 1.4761 (1.3); 1.2488 (1.4); 1.2377 (3.1); 1.2295 (2.9); 1.2171 (1.1); −0.0002 (6.9) |
| I.0976: $^{1}$H-NMR(400.2 MHz, $d_6$-DMSO):<br>δ = 9.6965 (1.5); 9.6860 (1.5); 8.5107 (3.0); 8.5051 (3.1); 3.3148 (11.8); 2.9769 (16.0); 2.9656 (16.0); 2.5105 (5.8); 2.5060 (12.1); 2.5015 (16.6); 2.4969 (12.2); 2.4925 (6.0); 2.0740 (0.4); 1.8219 (2.7); 1.8112 (6.4); 1.8022 (7.0); 1.7920 (2.8); 1.5515 (0.3); 1.2341 (0.5); 1.2143 (2.9); 1.2040 (6.8); 1.1949 (6.6); 1.1842 (2.6); 0.0000 (4.5) |
| I.0977: $^{1}$H-NMR(400.2 MHz, $d_6$-DMSO):<br>δ = 8.6716 (8.2); 3.4734 (26.3); 3.3833 (0.4); 3.3511 (0.6); 3.3463 (0.6); 3.3189 (196.7); 3.2854 (27.1); 2.6752 (0.5); 2.6707 (0.6); 2.6657 (0.5); 2.5409 (2.2); 2.5238 (1.1); 2.5105 (34.0); 2.5060 (72.7); 2.5015 (100.0); 2.4969 (70.8); 2.4924 (32.6); 2.3329 (0.4); 2.3281 (0.6); 2.3239 (0.5); 2.0744 (1.2); 1.5142 (5.9); 1.5010 (14.7); 1.4935 (16.0); 1.4820 (7.6); 1.4413 (0.8); 1.3616 (0.6); 1.3210 (7.3); 1.3094 (15.0); 1.3020 (15.0); 1.2887 (5.6); 1.2512 (0.4); 0.0081 (0.8); −0.0001 (28.6); −0.0084 (1.1) |
| I.0978: $^{1}$H-NMR(400.2 MHz, $d_6$-DMSO):<br>δ = 8.7543 (1.4); 3.6108 (16.0); 3.3329 (2.7); 2.5115 (1.1); 2.5071 (2.3); 2.5026 (3.0); 2.4981 (2.2); 2.4938 (1.0); 2.1432 (5.1); 2.1386 (9.7); 1.4654 (1.2); 1.4531 (3.1); 1.4448 (3.3); 1.4338 (1.4); 1.2069 (1.4); 1.1958 (3.2); 1.1875 (3.0); 1.1751 (1.1); 0.0000 (0.5); −0.0027 (0.3) |
| I.0979: $^{1}$H-NMR(400.2 MHz, $d_6$-DMSO):<br>δ = 8.9076 (2.2); 3.6345 (16.0); 3.3335 (90.6); 2.8906 (1.8); 2.7310 (1.6); 2.6714 (0.5); 2.5721 (0.7); 2.5516 (1.4); 2.5387 (1.6); 2.5356 (1.6); 2.5060 (69.6); 2.5021 (83.8); 2.4982 (63.2); 2.3514 (0.8); 2.3288 (2.1); 2.3080 (1.2); 2.2983 (1.4); 2.2762 (0.7); 1.9710 (0.5); 1.9564 (0.7); 1.9477 (1.4); 1.9338 (1.2); 1.9264 (1.6); 1.9055 (0.9); −0.0006 (9.3) |
| I.0980: $^{1}$H-NMR(400.2 MHz, $d_6$-DMSO):<br>δ = 9.2385 (2.9); 7.9530 (0.6); 5.0941 (0.7); 5.0795 (1.3); 5.0655 (0.7); 3.3432 (23.0); 3.3403 (23.8); 3.3383 (24.0); 3.3344 (30.8); 2.8914 (4.2); 2.7316 (3.7); 2.5115 (17.0); 2.5073 (32.7); 2.5028 (42.2); 2.4984 (30.6); 2.4942 (14.9); 2.3707 (16.0); 1.7852 (1.2); 1.7702 (1.1); 1.7525 (0.8); 1.5879 (2.9); 1.5766 (2.8); 1.5705 (2.7); 1.5560 (3.0); 1.5345 (1.3); 1.5252 (1.1); 1.4258 (1.2); 1.4136 (3.2); 1.4054 (3.5); 1.3946 (1.4); 1.1781 (1.5); 1.1672 (3.5); 1.1590 (3.3); 1.1467 (1.2); −0.0002 (6.8) |
| I.0981: $^{1}$H-NMR(400.2 MHz, $d_6$-DMSO):<br>δ = 8.9328 (0.5); 3.9120 (1.7); 3.8972 (1.7); 3.3516 (6.2); 3.3497 (6.1); 3.3441 (5.3); 3.3402 (6.7); 2.8918 (0.5); 2.7322 (0.5); 2.5125 (3.0); 2.5081 (5.8); 2.5037 (7.4); 2.4992 (5.4); 2.4948 (2.6); 2.4135 (6.5); 1.4261 (16.0); −0.0002 (1.0) |
| I.0982: $^{1}$H-NMR(400.2 MHz, $d_6$-DMSO):<br>δ = 9.0356 (0.5); 9.0213 (1.0); 9.0074 (0.5); 4.0401 (3.2); 4.0256 (3.2); 3.9470 (4.7); 3.9289 (4.8); 3.3498 (15.1); 3.3464 (14.2); 3.3451 (14.3); 3.3405 (19.4); 2.5258 (0.3); 2.5210 (0.5); 2.5124 (7.4); 2.5079 (15.3); 2.5033 (20.2); 2.4986 (14.4); 2.4941 (6.7); 2.4162 (16.0); 1.1168 (0.5); 1.1096 (0.4); 1.1059 (0.4); 1.0978 (0.8); 1.0898 (0.4); 1.0859 (0.5); 1.0781 (0.6); 0.5484 (0.6); 0.5376 (2.1); 0.5331 (2.1); 0.5287 (0.9); 0.5226 (0.9); 0.5174 (2.2); 0.5129 (1.9); 0.5027 (0.8); 0.2974 (0.8); 0.2868 (2.3); 0.2829 (2.2); 0.2751 (2.0); 0.2711 (2.4); 0.2600 (0.6); −0.0002 (3.2) |
| I.0983: $^{1}$H-NMR(400.2 MHz, $d_6$-DMSO):<br>δ = 8.6358 (1.0); 8.6213 (2.0); 8.6069 (1.0); 4.0581 (4.5); 4.0420 (16.0); 4.0269 (8.8); 3.3539 (43.0); 3.3457 (49.6); 2.8916 (2.0); 2.7317 (1.8); 2.5262 (0.8); 2.5127 (17.2); 2.5083 (34.2); 2.5038 (44.7); 2.4993 (32.6); 2.4949 (15.9); 1.6401 (0.5); 1.6219 (2.2); 1.6048 (4.2); 1.5868 (4.5); 1.5694 (2.3); 1.5518 (0.6); 0.9050 (7.4); 0.8865 (14.7); 0.8679 (6.7); −0.0002 (5.1) |
| I.0984: $^{1}$H-NMR(400.2 MHz, $d_6$-DMSO):<br>δ = 8.6788 (2.0); 8.6645 (4.0); 8.6500 (1.9); 6.5501 (0.4); 4.2871 (8.1); 4.2722 (15.8); 4.2572 (8.4); 4.0974 (13.4); 4.0829 (13.3); 3.3599 (95.5); 3.3560 (90.7); 3.3490 (123.2); 2.9216 (8.6); 2.9066 (16.0); 2.8917 (9.1); 2.7328 (0.8); 2.6777 (0.4); 2.6732 (0.5); 2.6686 (0.4); 2.5267 (1.6); 2.5219 (2.4); 2.5133 (32.5); 2.5088 (65.5); 2.5042 (85.6); 2.4996 (60.8); 2.4950 (28.2); 2.3356 (0.4); 2.3310 (0.5); 2.3264 (0.4); −0.0002 (9.0) |
| I.0985: $^{1}$H-NMR(400.2 MHz, $d_6$-DMSO):<br>δ = 8.6315 (2.3); 8.6171 (4.6); 8.6025 (2.2); 7.9524 (0.5); 4.0529 (13.6); 4.0383 (13.5); 3.9418 (15.9); 3.9237 (16.0); 3.3570 (96.4); 3.3518 (93.9); 3.3467 (128.0); 2.8918 (3.5); 2.7320 (3.1); 2.6775 (0.4); 2.6729 (0.5); 2.6686 (0.4); 2.5261 (1.4); 2.5085 (62.7); 2.5040 (82.2); 2.4996 (61.3); 2.3356 (0.4); 2.3306 (0.5); 2.3264 (0.4); 1.1343 (0.6); 1.1270 (0.9); 1.1148 (1.8); 1.1080 (1.6); 1.0962 (2.9); 1.0881 (1.4); 1.0844 (1.8); 1.0767 (2.0); 1.0647 (1.1); 1.0582 (0.7); 0.5446 (2.2); 0.5337 (7.0); 0.5295 (7.8); 0.5188 (3.4); 0.5136 (7.3); 0.5093 (7.2); 0.4989 (2.6); 0.2959 (2.6); 0.2850 (8.5); 0.2819 (8.9); 0.2735 (7.3); 0.2699 (9.2); 0.2585 (2.0); −0.0002 (8.7) |
| I.0986: $^{1}$H-NMR(400.2 MHz, $d_6$-DMSO):<br>δ = 8.5251 (0.4); 3.9258 (1.6); 3.9111 (1.6); 3.3515 (10.2); 3.3480 (11.6); 3.3423 (14.5); 2.5210 (0.4); 2.5124 (4.9); 2.5080 (10.1); 2.5034 (13.3); 2.4988 (9.6); 2.4942 (4.5); 1.4218 (16.0); −0.0002 (1.8) |
| I.0987: $^{1}$H-NMR(400.2 MHz, $d_6$-DMSO):<br>δ = 8.6316 (1.1); 8.6172 (2.3); 8.6027 (1.1); 4.0997 (4.4); 4.0834 (9.2); 4.0670 (4.5); 4.0345 (7.5); 4.0199 (7.5); 3.3526 (43.2); 3.3495 (41.0); 3.3399 (59.0); 2.8913 (0.6); 2.7316 (0.5); 2.6724 (0.4); 2.5259 (1.0); 2.5211 (1.4); 2.5124 (23.2); 2.5080 (47.0); 2.5034 (61.4); 2.4988 (43.7); 2.4942 (20.5); 2.3302 (0.4); 1.5958 (0.9); 1.5790 (2.8); 1.5724 (0.9); 1.5620 (3.5); 1.5419 (3.0); 1.5257 (1.2); 1.3768 (0.6); 1.3580 (2.2); 1.3390 (3.4); 1.3202 (3.4); 1.3020 (2.0); 1.2839 (0.6); 0.9001 (8.1); 0.8817 (16.0); 0.8632 (6.8); −0.0002 (7.8) |
| I.0988: $^{1}$H-NMR(400.2 MHz, $d_6$-DMSO):<br>δ = 8.6154 (2.6); 8.6009 (5.1); 8.5866 (2.5); 5.1347 (2.5); 5.1255 (2.9); 5.1199 (4.6); 5.1053 (2.4); 3.9856 (16.0); 3.9711 (16.0); 3.3534 (129.8); 3.3462 (195.1); 2.8917 (1.1); 2.7317 (1.0); 2.6729 (0.6); 2.5083 (72.9); 2.5039 (96.3); 2.4996 (73.6); 2.3306 (0.6); 2.3265 (0.5); 1.8745 (0.4); 1.8511 (1.8); 1.8316 (4.3); 1.8181 (3.9); 1.8155 (3.9); 1.8049 (3.0); 1.7988 (2.7); 1.7906 (2.3); 1.6340 (12.5); 1.6231 (7.4); 1.6143 (5.6); 1.6036 (6.4); 1.5955 (4.8); 1.5857 (3.5); 1.5749 (3.0); 1.5684 (3.4); 1.5639 (3.2); 1.5604 (3.3); 1.5454 (4.7); 1.5399 (4.3); 1.5297 (2.5); 1.5076 (0.5); 1.2332 (0.4); 0.0079 (0.3); −0.0003 (10.7) |
| I.0989: $^{1}$H-NMR(400.2 MHz, $d_6$-DMSO):<br>δ = 8.8085 (2.1); 8.7943 (4.3); 8.7802 (2.1); 7.9528 (2.3); 7.4644 (5.6); 7.4596 (2.2); 7.4452 (10.4); 7.4291 (3.0); 7.4249 (8.4); 7.4192 (1.1); 7.3041 (3.9); 7.2855 (6.3); 7.2670 (2.5); 7.1547 (9.2); 7.1519 (11.8); 7.1469 (3.0); 7.1331 (9.6); 7.1311 (8.8); 7.1243 (1.0); 6.7584 (0.5); 6.7369 (0.5); 6.5466 (0.5); 4.3342 (14.2); 4.3198 (14.2); 3.3557 (105.1); 3.3520 (106.4); 3.3438 (138.4); 2.8910 (16.0); 2.7315 (13.8); 2.6769 (0.5); 2.6725 (0.7); 2.6681 (0.6); 2.5258 (1.9); 2.5122 (46.6); 2.5080 (93.7); 2.5036 (123.1); 2.4991 (90.1); 2.4948 (44.3); 2.3349 (0.6); 2.3304 (0.8); 2.3261 (0.6); 0.0080 (0.5); −0.0002 (17.5); −0.0085 (0.6) |

TABLE A-(I)-continued

| NMR peak lists of compounds according to formula (I) |
| --- |
| I.0990: $^1$H-NMR(400.2 MHz, $d_6$-DMSO):<br>δ = 8.6789 (0.8); 8.6648 (1.6); 8.6503 (0.8); 7.3883 (6.0); 7.3770 (16.0); 7.3589 (1.8); 7.3510 (1.4); 7.3461 (1.0); 7.3374 (1.1); 7.3308 (0.4); 7.3246 (0.4); 5.1673 (11.4); 4.1123 (5.0); 4.0977 (5.0); 3.3498 (44.6); 3.3459 (51.9); 2.8911 (0.5); 2.7324 (0.4); 2.5081 (25.3); 2.5036 (32.3); 2.4992 (24.2); −0.0002 (4.3) |
| I.0991: $^1$H-NMR(400.2 MHz, $d_6$-DMSO):<br>δ = 8.7536 (2.0); 8.7367 (2.0); 4.1841 (0.8); 4.1749 (0.9); 4.1663 (0.9); 4.1570 (3.3); 4.1490 (0.5); 4.1378 (4.5); 4.1281 (0.4); 4.1198 (3.4); 4.1105 (0.9); 4.1020 (0.9); 4.0927 (0.9); 3.7604 (1.7); 3.7433 (1.8); 3.7379 (2.0); 3.7205 (1.7); 3.3512 (71.5); 3.3436 (63.3); 3.3391 (93.4); 2.6719 (0.5); 2.5072 (64.5); 2.5029 (82.9); 2.4985 (61.5); 2.3296 (0.5); 1.2690 (0.5); 1.2583 (0.7); 1.2487 (1.2); 1.2372 (1.2); 1.2218 (8.0); 1.2040 (16.0); 1.1863 (7.4); 0.6377 (0.3); 0.6277 (0.5); 0.6243 (0.5); 0.6159 (1.0); 0.6072 (1.1); 0.6030 (1.2); 0.5930 (1.3); 0.5816 (0.8); 0.5718 (0.7); 0.5566 (0.6); 0.5434 (0.9); 0.5344 (1.2); 0.5234 (1.2); 0.5134 (1.3); 0.5012 (0.5); 0.4916 (0.9); 0.4769 (1.0); 0.4673 (1.3); 0.4551 (1.7); 0.4439 (1.3); 0.4316 (0.6); 0.4059 (0.7); 0.3940 (1.2); 0.3824 (1.4); 0.3702 (1.3); 0.3597 (0.7); 0.3482 (0.3); −0.0002 (9.0); −0.0084 (0.3) |
| I.0992: $^1$H-NMR(400.2 MHz, $d_6$-DMSO):<br>δ = 9.0795 (0.6); 9.0651 (1.2); 9.0506 (0.6); 4.7824 (5.9); 4.7763 (5.9); 4.0845 (4.0); 4.0699 (4.0); 3.6164 (1.3); 3.6105 (2.7); 3.6044 (1.3); 3.3499 (16.0); 3.3450 (14.4); 3.3399 (17.5); 2.5078 (13.9); 2.5034 (17.9); 2.4990 (13.2); 2.4152 (16.0); −0.0002 (2.6) |
| I.0993: $^1$H-NMR(400.2 MHz, $d_6$-DMSO):<br>δ = 9.0272 (0.4); 9.0137 (0.9); 8.9999 (0.4); 7.9526 (0.4); 4.1582 (0.4); 4.1504 (0.7); 4.1427 (1.0); 4.1347 (1.2); 4.1307 (0.7); 4.1270 (0.8); 4.1189 (0.7); 4.1111 (0.3); 3.9969 (3.0); 3.9828 (2.9); 3.3556 (10.6); 3.3499 (10.3); 3.3411 (14.7); 2.8918 (2.6); 2.7327 (2.1); 2.7315 (2.2); 2.5128 (6.0); 2.5083 (11.9); 2.5038 (15.4); 2.4992 (11.0); 2.4947 (5.2); 2.4073 (16.0); 0.7394 (0.4); 0.7239 (1.2); 0.7207 (1.6); 0.7153 (1.0); 0.7078 (1.6); 0.7056 (1.9); 0.7016 (1.6); 0.6902 (1.2); 0.6718 (0.6); 0.6647 (0.9); 0.6571 (1.9); 0.6547 (1.5); 0.6503 (1.9); 0.6444 (1.5); 0.6410 (0.9); 0.6331 (0.4); 0.6254 (0.4); −0.0002 (2.7) |
| I.0994: $^1$H-NMR(400.2 MHz, $d_6$-DMSO):<br>δ = 9.0639 (0.7); 9.0496 (1.3); 9.0353 (0.7); 5.9720 (0.3); 5.9584 (0.7); 5.9454 (0.7); 5.9321 (0.8); 5.9290 (0.7); 5.9154 (1.0); 5.9023 (0.8); 5.8891 (0.9); 5.8757 (0.4); 5.3669 (0.6); 5.3630 (1.5); 5.3589 (1.8); 5.3553 (0.9); 5.3199 (1.3); 5.3159 (1.5); 5.3123 (0.8); 5.2507 (1.6); 5.2471 (1.7); 5.2244 (1.4); 5.2209 (1.6); 4.6334 (3.6); 4.6301 (2.7); 4.6234 (2.3); 4.6200 (3.5); 4.6167 (2.6); 4.0753 (4.4); 4.0606 (4.4); 3.3464 (22.4); 3.3435 (25.8); 2.8918 (0.4); 2.5080 (13.7); 2.5036 (18.2); 2.4994 (14.6); 2.4116 (16.0); 2.3938 (0.3); −0.0002 (2.1) |
| I.0995: $^1$H-NMR(400.2 MHz, $d_6$-DMSO):<br>δ = 9.0349 (0.7); 9.0206 (1.3); 9.0062 (0.7); 4.0665 (2.7); 4.0501 (5.5); 4.0307 (5.3); 4.0155 (4.4); 3.3521 (23.9); 3.3454 (29.0); 2.8918 (0.3); 2.5080 (14.6); 2.5037 (18.2); 2.4994 (13.4); 2.4123 (16.0); 1.6274 (1.4); 1.6104 (2.8); 1.5922 (2.9); 1.5751 (1.5); 1.5571 (0.4); 0.9090 (4.5); 0.8906 (8.8); 0.8719 (4.0); −0.0002 (1.7) |
| I.0996: $^1$H-NMR(400.2 MHz, $d_6$-DMSO):<br>δ = 9.0821 (0.7); 9.0679 (1.3); 9.0534 (0.6); 4.2954 (2.4); 4.2805 (4.8); 4.2655 (2.5); 4.0841 (4.1); 4.0696 (4.1); 3.3487 (17.0); 2.9268 (2.7); 2.9118 (5.0); 2.8969 (2.6); 2.7314 (0.4); 2.5124 (6.9); 2.5082 (13.4); 2.5037 (17.5); 2.4992 (12.7); 2.4949 (6.1); 2.4668 (0.5); 2.4198 (16.0); −0.0002 (1.8) |
| I.0997: $^1$H-NMR(600.2 MHz, $d_6$-DMSO):<br>δ = 8.8934 (0.8); 8.8836 (1.6); 8.8738 (0.8); 7.3253 (0.4); 7.3238 (0.6); 7.3147 (0.9); 7.3107 (4.3); 7.3056 (4.8); 7.3009 (16.0); 7.2944 (0.8); 7.2915 (1.1); 7.2614 (0.9); 7.2573 (1.1); 7.2511 (1.1); 7.2470 (1.2); 7.2441 (0.7); 7.2413 (0.7); 7.2371 (0.6); 7.2327 (0.3); 4.2416 (5.0); 4.2318 (5.1); 4.1420 (11.7); 3.3265 (6.4); 2.5139 (1.3); 2.5109 (2.9); 2.5079 (4.0); 2.5048 (2.8); 2.5018 (1.3) |
| I.0998: $^1$H-NMR(600.2 MHz, $d_6$-DMSO):<br>δ = 8.7115 (1.2); 8.6980 (1.2); 4.4167 (1.3); 4.4060 (1.5); 4.4033 (1.5); 4.3925 (1.3); 3.3238 (16.0); 2.8701 (1.4); 2.8578 (4.6); 2.8456 (4.7); 2.8333 (1.5); 2.5136 (1.7); 2.5107 (3.6); 2.5077 (4.9); 2.5046 (3.5); 2.5017 (1.6); 2.2687 (0.6); 2.2575 (1.1); 2.2464 (1.1); 2.2351 (0.7); 1.1830 (5.2); 1.1707 (10.9); 1.1631 (0.5); 1.1584 (5.1); 0.9645 (7.0); 0.9542 (10.6); 0.9434 (7.2) |
| I.0999: $^1$H-NMR(400.1 MHz, CDCl3):<br>δ = 8.4557 (1.0); 7.2611 (7.0); 4.5016 (7.5); 4.4910 (7.6); 4.3385 (2.4); 4.3206 (7.4); 4.3028 (7.5); 4.2849 (2.6); 1.5498 (7.7); 1.3545 (8.0); 1.3366 (16.0); 1.3188 (8.0); 1.2550 (0.9); 0.0694 (0.4); −0.0002 (8.6) |
| I.1000: $^1$H-NMR(400.1 MHz, CDCl3):<br>δ = 7.2597 (12.2); 6.7772 (0.6); 4.2246 (3.8); 4.2118 (3.9); 3.9966 (4.9); 3.9800 (5.1); 2.0083 (0.5); 1.9915 (0.9); 1.9748 (1.2); 1.9581 (1.0); 1.9413 (0.5); 1.5400 (9.6); 0.9584 (16.0); 0.9415 (15.7); −0.0002 (17.1) |
| I.1001: $^1$H-NMR(300.1 MHz, $d_6$-DMSO):<br>δ = 9.8532 (1.8); 8.3994 (2.2); 8.3870 (2.2); 8.3676 (1.2); 4.2356 (7.2); 4.2164 (7.3); 3.3258 (44.2); 2.9964 (16.0); 2.9813 (15.9); 2.7275 (0.4); 2.5131 (23.4); 2.5074 (45.5); 2.5016 (59.2); 2.4957 (41.5); 2.2715 (0.4); 2.0754 (1.8); 1.2370 (0.4); 0.0103 (2.4); −0.0004 (51.1); −0.0114 (1.8) |
| I.1002: $^1$H-NMR(400.2 MHz, $d_6$-DMSO):<br>δ = 8.4244 (5.1); 8.4137 (5.0); 4.2984 (16.0); 4.2865 (15.8); 3.6005 (0.4); 3.5175 (0.6); 3.4280 (67.6); 3.3447 (93.0); 3.3288 (42.3); 3.2509 (0.4); 3.1673 (0.5); 2.6720 (0.4); 2.6674 (0.3); 2.5117 (25.8); 2.5073 (52.9); 2.5028 (71.0); 2.4983 (50.6); 2.4939 (23.6); 2.3345 (0.3); 2.3298 (0.4); 2.0768 (2.8); 2.0090 (0.5); 1.9899 (0.4); 1.2855 (0.3); 1.2340 (2.7); 0.8695 (0.3); 0.8538 (0.8); 0.0082 (1.5); 0.0000 (37.7); −0.0083 (1.4) |
| I.1003: $^1$H-NMR(400.1 MHz, CDCl3):<br>δ = 7.6496 (1.2); 7.2611 (3.3); 3.8191 (16.0); 2.7310 (0.5); 2.7145 (0.8); 2.7089 (1.0); 2.6983 (1.4); 2.6806 (2.1); 2.6621 (1.3); 2.6496 (1.2); 2.6276 (2.2); 2.6055 (1.4); 2.5990 (1.2); 2.5735 (0.6); 2.1767 (0.4); 2.1572 (1.7); 2.1495 (0.8); 2.1368 (2.2); 2.1248 (0.6); 2.1165 (1.6); 2.1100 (0.7); 2.0952 (0.4); 1.5543 (4.4); 0.0699 (0.4); −0.0002 (4.3) |
| I.1004: $^1$H-NMR(400.1 MHz, CDCl3):<br>δ = 7.7926 (1.2); 7.2619 (3.4); 3.8225 (16.0); 2.7323 (0.4); 2.7153 (0.8); 2.7099 (0.9); 2.6998 (1.3); 2.6818 (2.2); 2.6626 (1.9); 2.6383 (2.3); 2.6165 (1.4); 2.6103 (1.2); 2.5846 (0.5); 2.1807 (0.6); 2.1616 (1.7); 2.1406 (2.5); 2.1328 (0.6); 2.1211 (1.5); 2.1001 (0.5); 1.5640 (4.6); 1.2652 (0.5); 0.8820 (0.5); −0.0002 (4.7) |
| I.1005: $^1$H-NMR(400.1 MHz, CDCl3):<br>δ = 15.3336 (0.3); 14.5405 (0.3); 7.6326 (0.3); 7.5198 (1.0); 7.4578 (10.0); 7.3432 (0.3); 7.2992 (0.4); 7.2608 (130.7); 6.9971 (0.9); 6.3979 (0.3); 6.3869 (0.4); 4.6499 (7.6); 4.6358 (10.6); 4.6187 (13.9); 4.6038 (11.4); 4.5874 (7.7); 4.5616 (0.5); 3.5991 (0.4); 3.5861 (0.4); 3.5314 (0.4); 3.5154 (0.3); 3.4840 (0.4); 3.4637 (5.9); 3.4509 (6.6); 3.4348 (14.6); 3.4221 (15.7); 3.4048 (11.4); 3.3921 (11.4); 3.3526 (14.6); 3.3359 (16.0); 3.3247 (9.5); 3.3074 (8.3); 3.2673 (0.4); 3.2458 (0.4); 3.1207 (6.5); 3.1047 (10.0); 3.0898 (12.3); 3.0736 (10.6); 3.0599 (6.3); 3.0011 (0.3); 2.9566 (1.6); 2.8843 (1.7); 2.5303 (5.7); 2.2194 (0.3); 2.1161 (4.3); 2.0986 (4.6); 2.0851 (11.6); 2.0676 (11.6); 2.0539 (11.3); 2.0363 (10.9); 2.0225 (4.2); 2.0051 (3.8); 1.9796 (0.3); 1.5560 (77.2); 1.4775 (0.8); 1.4544 (0.6); 1.4247 (0.5); 1.3486 (0.4); 1.3294 (0.3); 1.2982 (0.3); 1.2927 (0.3); 1.2560 (1.1); 0.1460 (0.7); −0.0002 (161.5); −0.0347 (0.6); −0.0436 (0.5); −0.1499 (0.8) |
| I.1006: $^1$H-NMR(400.1 MHz, CDCl3):<br>δ = 8.0167 (1.1); 7.6240 (9.8); 7.5196 (0.6); 7.4544 (1.3); 7.2620 (60.5); 6.9980 (0.4); 4.8880 (0.4); 4.6541 (7.0); 4.6382 (10.4); 4.6232 (13.7); 4.6060 (11.2); 4.5921 (8.4); 4.5638 (0.8); 4.4966 (0.3); 4.4641 (0.3); 3.4692 (5.1); 3.4565 (6.0); 3.4397 (13.3); |

TABLE A-(I)-continued

NMR peak lists of compounds according to formula (I)

3.4272 (14.9); 3.4103 (11.0); 3.3975 (11.3); 3.3570 (14.4); 3.3398 (16.0); 3.3297 (10.4); 3.3119 (9.2); 3.1335 (5.8); 3.1192 (9.5); 3.1034 (12.4); 3.0884 (11.2); 3.0733 (7.6); 2.9748 (0.5); 2.9571 (6.2); 2.9077 (0.6); 2.8840 (6.0); 2.7838 (0.6); 2.7551 (0.5); 2.7266 (0.6); 2.6973 (0.4); 2.6782 (0.3); 2.2087 (0.6); 2.1982 (0.4); 2.1678 (0.4); 2.1166 (4.3); 2.0992 (4.8); 2.0855 (11.7); 2.0680 (12.0); 2.0543 (12.1); 2.0368 (11.6); 2.0231 (5.0); 2.0058 (4.4); 1.9525 (0.4); 1.5817 (19.4); 1.3317 (0.4); 1.3027 (0.4); 1.2537 (1.0); 1.2333 (0.4); −0.0002 (70.0); −0.1491 (0.4)

I.1007: $^1$H-NMR(400.1 MHz, CDCl3):
δ = 8.4218 (0.6); 8.4021 (0.6); 8.2574 (0.6); 8.2359 (0.8); 8.0387 (0.4); 8.0211 (0.7); 8.0031 (0.4); 7.8796 (0.4); 7.8625 (0.7); 7.2605 (44.8); 6.7139 (2.5); 6.7015 (2.5); 6.1302 (3.9); 5.7574 (1.2); 5.7375 (4.2); 5.7176 (6.5); 5.6978 (4.4); 5.6780 (1.3); 5.2991 (0.5); 4.1899 (15.9); 4.1770 (16.0); 3.8191 (0.5); 3.5492 (5.4); 3.5284 (9.9); 3.5248 (10.1); 3.5041 (6.6); 3.3438 (7.4); 3.3243 (10.6); 3.3196 (9.7); 3.3000 (5.7); 2.5008 (0.4); 2.4864 (0.5); 1.5481 (38.8); 1.5204 (1.3); 1.3121 (0.3); 1.2568 (0.5); −0.0002 (57.9); −0.1501 (0.3)

I.1008: $^1$H-NMR(400.1 MHz, CDCl3):
δ = 7.2595 (15.9); 6.7139 (0.8); 6.7016 (0.9); 4.8314 (16.0); 4.3242 (5.8); 4.3102 (5.9); 1.5401 (25.8); −0.0002 (21.0)

I.1009: $^1$H-NMR(400.1 MHz, CDCl3):
δ = 7.5199 (0.3); 7.3444 (4.3); 7.3259 (11.8); 7.3078 (10.5); 7.2588 (46.0); 7.2361 (17.1); 7.1979 (2.2); 7.1454 (0.6); 7.1099 (0.4); 7.0680 (0.3); 6.9959 (0.3); 6.2784 (4.2); 6.2583 (4.6); 5.2981 (0.7); 2.7881 (7.2); 2.7574 (8.1); 2.6841 (1.0); 2.6433 (1.2); 2.6153 (2.5); 2.6043 (3.4); 2.5913 (2.8); 2.5639 (1.5); 2.1575 (0.3); 2.1178 (0.6); 2.0457 (9.7); 2.0295 (16.0); 1.9953 (5.6); 1.9653 (2.0); 1.8727 (0.4); 1.8681 (0.4); 1.7928 (3.8); 1.7811 (3.6); 1.7617 (6.2); 1.7499 (5.8); 1.7354 (3.9); 1.7205 (3.4); 1.6610 (0.7); 1.6223 (0.6); 1.5466 (26.1); 1.4132 (0.4); 1.3823 (0.4); 1.3029 (0.4); 1.2544 (1.2); 0.8431 (0.5); 0.1455 (0.3); −0.0002 (41.6); −0.0743 (0.5); −0.1510 (0.4)

I.1010: $^1$H-NMR(400.1 MHz, CDCl3):
δ = 7.3891 (1.2); 7.3690 (1.2); 7.2606 (12.0); 4.9773 (2.5); 4.9630 (2.7); 4.9559 (2.6); 4.9415 (2.4); 2.2518 (0.4); 2.2352 (1.1); 2.2185 (1.8); 2.2032 (1.9); 2.1866 (1.3); 2.1699 (0.5); 1.5516 (6.3); 1.2535 (0.4); 1.1955 (14.3); 1.1849 (16.0); 1.1788 (15.4); 1.1680 (14.0); −0.0002 (14.9)

I.1011: $^1$H-NMR(600.2 MHz, $d_6$-DMSO):
δ = 8.6869 (3.8); 8.6735 (3.8); 4.8168 (1.6); 4.8044 (2.6); 4.7956 (2.1); 4.7917 (2.0); 4.7830 (2.7); 4.7706 (1.7); 3.4777 (1.5); 3.4687 (1.9); 3.4589 (3.1); 3.4499 (3.1); 3.4393 (2.6); 3.4303 (2.2); 3.3580 (2.9); 3.3479 (3.2); 3.3462 (3.0); 3.3412 (2.3); 3.3397 (2.3); 3.3293 (2.4); 3.3241 (16.0); 2.9761 (0.3); 2.5357 (1.2); 2.5339 (1.3); 2.5267 (1.6); 2.5245 (2.3); 2.5223 (1.7); 2.5136 (5.7); 2.5108 (7.1); 2.5076 (10.0); 2.5046 (8.8); 2.5018 (4.9); 2.4948 (1.6); 2.4931 (1.4); 2.3407 (1.0); 2.3289 (1.2); 2.3203 (2.6); 2.3084 (2.6); 2.2997 (2.4); 2.2879 (2.4); 2.2793 (0.9); 2.2675 (0.8); 1.9949 (0.4); 1.2839 (0.5); 1.2727 (0.5); 1.2401 (1.3); 1.2302 (0.6)

I.1012: $^1$H-NMR(500.1 MHz, $d_6$-DMSO):
δ = 8.5549 (2.1); 3.6050 (0.8); 3.3133 (16.0); 2.5127 (1.9); 2.5091 (4.1); 2.5054 (5.7); 2.5018 (4.1); 2.4982 (2.0); 2.4725 (1.1); 2.4466 (1.2); 2.2153 (0.7); 2.1940 (0.8); 2.1913 (0.8); 1.8004 (0.9); 1.7725 (1.1); 1.7576 (0.7); 1.7524 (0.7); 1.7165 (1.7); 1.7098 (1.8); 1.6904 (3.1); 1.6699 (1.9); 1.6557 (1.1); 1.6290 (0.9); 1.6053 (1.4); 1.6001 (1.4); 1.5790 (1.3); 1.5728 (1.2); 1.5529 (0.8); 1.5469 (0.7); 1.5246 (0.5); 1.5190 (0.5); 1.4990 (0.8); 1.4926 (0.7); 1.4726 (0.5); 1.4666 (0.5); 1.2946 (0.4); 1.2718 (0.9); 1.2442 (1.2); 1.2215 (1.2); 1.2172 (1.2); 1.2109 (1.2); 1.2045 (1.4); 1.1946 (1.6); 1.1867 (1.5); 1.1805 (1.8); 1.1749 (1.7); 1.1635 (1.4); 1.1466 (1.2); 1.1407 (1.4); 1.1351 (1.2); 1.1130 (1.4); 1.1021 (1.1); 1.0909 (1.3); 1.0844 (1.3); 1.0665 (0.6); 1.0513 (0.3); 0.9969 (0.5); 0.9903 (0.7); 0.9715 (1.2); 0.9662 (1.2); 0.9491 (1.1); 0.9424 (1.0); 0.9185 (0.4)

I.1013: $^1$H-NMR(400.1 MHz, CDCl3):
δ = 7.2606 (8.2); 6.1600 (0.6); 6.1391 (0.7); 4.9317 (1.3); 4.9160 (1.4); 4.9098 (1.3); 4.8941 (1.3); 2.5285 (16.0); 2.5009 (0.4); 2.2062 (0.6); 2.1896 (1.1); 2.1730 (1.1); 2.1563 (0.7); 1.5560 (5.5); 1.2554 (0.4); 1.1775 (7.0); 1.1607 (7.2); 1.1516 (7.5); 1.1346 (7.0); −0.0002 (10.5); −0.0082 (0.7)

I.1014: $^1$H-NMR(400.1 MHz, CDCl3):
δ = 18.9225 (0.6); 13.1930 (0.6); 7.5185 (1.3); 7.4241 (11.9); 7.2951 (1.2); 7.2596 (238.9); 7.2375 (2.6); 7.2142 (0.8); 6.9959 (1.5); 3.5489 (0.6); 3.5265 (0.7); 3.5019 (0.6); 3.4131 (0.7); 2.9317 (6.4); 2.9251 (5.4); 2.9193 (8.8); 2.9096 (10.2); 2.9048 (10.6); 2.8973 (16.0); 2.8860 (12.1); 2.8769 (10.7); 2.8647 (10.2); 2.5191 (6.7); 2.4948 (14.9); 2.4739 (12.7); 2.4663 (15.0); 2.4425 (8.4); 2.3505 (1.6); 2.3289 (4.4); 2.3083 (6.5); 2.2999 (7.7); 2.2790 (10.0); 2.2581 (5.8); 2.2376 (1.6); 2.2249 (2.6); 2.2122 (4.7); 2.1996 (5.6); 2.1883 (7.9); 2.1761 (5.9); 2.1646 (4.7); 2.1588 (5.6); 2.1469 (3.4); 2.1352 (2.1); 2.1229 (1.2); 1.5728 (1.4); 1.5369 (210.7); 1.4947 (1.4); 1.3232 (0.7); 1.2550 (1.7); 0.8796 (0.7); 0.8641 (0.7); 0.1459 (1.6); 0.0360 (1.4); −0.0002 (334.0); −0.0421 (1.2); −0.0721 (0.8); −0.1496 (1.7)

I.1015: $^1$H-NMR(400.1 MHz, CDCl3):
δ = 7.2603 (12.7); 6.2054 (1.2); 2.9247 (0.7); 2.9123 (0.9); 2.9027 (1.0); 2.8975 (1.1); 2.8907 (1.6); 2.8794 (1.2); 2.8697 (1.0); 2.8579 (1.0); 2.5395 (16.0); 2.5110 (0.4); 2.5020 (0.7); 2.4780 (1.5); 2.4568 (1.3); 2.4489 (1.4); 2.4252 (0.8); 2.3367 (0.5); 2.3161 (0.7); 2.3075 (0.8); 2.2955 (0.4); 2.2868 (1.0); 2.2660 (0.6); 2.2004 (0.5); 2.1883 (0.6); 2.1766 (0.8); 2.1708 (0.5); 2.1649 (0.6); 2.1593 (0.5); 2.1528 (0.5); 2.1471 (0.6); 2.1354 (0.4); 2.0433 (0.5); 1.5460 (10.9); 1.2588 (0.4); −0.0002 (17.5)

I.1016: $^1$H-NMR(400.1 MHz, CDCl3):
δ = 7.2600 (31.6); 6.4729 (0.8); 6.4527 (1.4); 4.9441 (1.5); 4.9402 (1.6); 4.9286 (1.8); 4.9242 (2.3); 4.9066 (1.5); 4.9028 (1.5); 2.5907 (0.4); 2.2048 (0.4); 2.1889 (1.2); 2.1718 (2.2); 2.1553 (2.2); 2.1389 (1.4); 2.1222 (0.5); 1.5497 (8.7); 1.2539 (0.5); 1.1674 (14.7); 1.1505 (15.7); 1.1440 (16.0); 1.1269 (14.3); 0.0694 (0.5); −0.0002 (41.0)

I.1017: $^1$H-NMR(400.1 MHz, $d_6$-DMSO):
δ = 12.6228 (0.8); 12.5920 (0.9); 12.5735 (0.9); 8.9295 (16.0); 4.0386 (1.0); 4.0207 (1.0); 4.0035 (0.4); 3.6164 (0.4); 3.6013 (0.9); 3.3089 (22.0); 3.0864 (0.4); 2.5713 (3.6); 2.5521 (7.8); 2.5385 (7.9); 2.5243 (10.0); 2.5181 (9.2); 2.5008 (57.6); 2.3563 (4.7); 2.3345 (10.6); 2.3042 (9.6); 2.2827 (5.0); 2.1831 (0.5); 1.9977 (3.6); 1.9877 (6.6); 1.9768 (9.8); 1.9561 (11.8); 1.9456 (5.2); 1.9361 (7.4); 1.9082 (4.0); 1.7759 (0.4); 1.7600 (1.0); 1.7451 (0.5); 1.3557 (1.7); 1.2708 (0.5); 1.2347 (0.5); 1.1928 (1.4); 1.1811 (1.6); 1.1750 (2.6); 1.1572 (1.3); 1.1369 (0.3); −0.0002 (20.3)

I.1018: $^1$H-NMR(400.2 MHz, $d_6$-DMSO):
δ = 8.5574 (4.0); 8.5530 (4.0); 4.9487 (1.1); 4.9386 (2.2); 4.9276 (3.4); 4.9172 (4.5); 4.9066 (3.4); 4.8957 (2.3); 4.8856 (1.1); 4.0016 (15.9); 3.9870 (16.0); 3.7922 (3.5); 3.7810 (6.3); 3.7639 (5.2); 3.7511 (7.5); 3.7399 (4.2); 3.4890 (4.9); 3.4818 (5.6); 3.4668 (5.9); 3.4597 (9.6); 3.4532 (5.1); 3.4378 (5.0); 3.4306 (4.5); 3.3670 (274.7); 2.8952 (0.6); 2.7355 (0.6); 2.6772 (0.6); 2.5123 (74.6); 2.5082 (93.1); 2.5041 (70.0); 2.3349 (0.6); 1.8690 (4.2); 1.8593 (4.3); 1.8467 (3.9); 1.8361 (5.3); 1.8268 (5.0); 1.5833 (2.4); 1.5734 (2.7); 1.5615 (4.8); 1.5513 (6.6); 1.5402 (4.4); 1.5291 (6.2); 1.5189 (3.8); 1.5070 (2.1); 1.4971 (1.8)

I.1019: $^1$H-NMR(400.1 MHz, CDCl3):
δ = 7.7584 (0.6); 7.2602 (3.9); 3.7990 (8.9); 1.6889 (16.0); 1.5441 (3.8); −0.0002 (5.3)

I.1020: $^1$H-NMR(400.1 MHz, CDCl3):
δ = 7.7483 (0.9); 7.2601 (8.0); 3.7979 (8.4); 1.6884 (16.0); 1.5393 (9.3); 1.2582 (0.3); −0.0002 (10.9)

I.1021: $^1$H-NMR(400.1 MHz, CDCl3):
δ = 7.8754 (0.6); 7.2606 (2.7); 3.8008 (8.9); 1.6939 (16.0); 1.5482 (2.9); −0.0002 (3.6)

TABLE A-(I)-continued

NMR peak lists of compounds according to formula (I)

I.1022: $^1$H-NMR(400.1 MHz, $d_6$-DMSO):
δ = 8.4294 (1.4); 3.3163 (1.4); 2.5014 (5.1); 1.4799 (16.0); −0.0002 (1.6)
I.1023: $^1$H-NMR(400.1 MHz, $d_6$-DMSO):
δ = 8.4229 (1.5); 3.3188 (1.4); 2.5018 (4.5); 1.9887 (0.8); 1.4748 (16.0); 1.1751 (0.5); −0.0002 (1.3)
I.1024: $^1$H-NMR(400.1 MHz, $d_6$-DMSO):
δ = 8.4918 (1.5); 4.0385 (0.8); 4.0207 (0.8); 3.3185 (1.0); 2.5019 (3.8); 1.9888 (3.3); 1.4792 (16.0); 1.1930 (0.9); 1.1752 (1.7); 1.1574 (1.0); 0.1324 (0.5); −0.0002 (1.2); −0.0102 (0.7)
I.1025: $^1$H-NMR(400.1 MHz, CDCl3):
δ = 7.6587 (1.0); 7.6417 (1.0); 7.2637 (2.7); 4.8271 (0.6); 4.8088 (1.3); 4.7961 (1.3); 4.7908 (0.8); 4.7779 (0.6); 3.8182 (15.8); 3.0072 (0.3); 2.9918 (0.4); 2.9855 (0.4); 2.9721 (1.1); 2.9573 (1.0); 2.9510 (1.0); 2.9358 (0.9); 2.9235 (0.8); 2.9064 (1.2); 2.9028 (1.1); 2.8861 (1.0); 2.8718 (0.5); 2.8679 (0.5); 2.8511 (0.4); 2.3313 (16.0); 2.3028 (0.6); 2.2993 (0.6); 2.2939 (0.5); 2.2805 (0.9); 2.2645 (0.9); 2.2588 (0.7); 2.2507 (0.6); 2.2458 (0.7); 2.2295 (0.4); 2.1441 (0.4); 2.1260 (0.7); 2.1087 (1.0); 2.0897 (0.9); 2.0734 (0.5); 1.5843 (4.5); −0.0002 (2.9)
I.1026: $^1$H-NMR(400.1 MHz, CDCl3):
δ = 7.5189 (0.4); 7.2602 (59.8); 6.7120 (2.5); 4.6028 (4.8); 4.5821 (14.1); 4.5614 (14.3); 4.5407 (4.8); 4.3362 (16.0); 4.3230 (16.0); 1.5443 (105.5); 1.2541 (0.7); 0.1455 (0.4); −0.0002 (76.8); −0.1494 (0.4)
I.1027: $^1$H-NMR(400.1 MHz, CDCl3):
δ = 7.1668 (17.1); 6.6997 (1.0); 5.2055 (1.2); 4.1156 (6.6); 4.1032 (6.6); 3.8069 (16.0); 1.4572 (31.0); 0.1474 (0.4); −0.0002 (78.7); −0.0246 (1.3); −0.0941 (21.6); −0.1512 (0.4)
I.1028: $^1$H-NMR(400.1 MHz, CDCl3):
δ = 7.7867 (0.8); 7.7694 (0.8); 7.2617 (3.0); 4.8412 (0.6); 4.8278 (0.8); 4.8232 (1.2); 4.8103 (1.3); 4.8054 (0.8); 4.7923 (0.6); 3.8231 (15.9); 2.9929 (0.4); 2.9865 (0.4); 2.9735 (1.0); 2.9585 (1.0); 2.9520 (1.0); 2.9359 (1.2); 2.9164 (1.1); 2.9120 (1.0); 2.8956 (1.0); 2.8820 (0.4); 2.8774 (0.4); 2.8608 (0.4); 2.3286 (16.0); 2.3068 (0.5); 2.3038 (0.5); 2.2979 (0.4); 2.2903 (0.4); 2.2846 (0.8); 2.2686 (0.8); 2.2628 (0.5); 2.2550 (0.5); 2.2495 (0.6); 2.2335 (0.4); 2.1509 (0.4); 2.1342 (0.7); 2.1153 (0.9); 2.0965 (0.8); 2.0784 (0.4); 1.5672 (3.4); 1.2565 (0.3); −0.0002 (3.5)
I.1029: $^1$H-NMR(400.1 MHz, $d_6$-DMSO):
δ = 13.1794 (0.4); 13.1737 (0.4); 13.1136 (0.4); 13.0778 (0.5); 13.0683 (0.5); 12.9761 (0.8); 12.9441 (1.0); 12.9238 (1.1); 12.9134 (1.2); 12.8754 (1.1); 12.8555 (1.1); 12.8389 (1.0); 12.7772 (0.8); 12.7579 (0.6); 12.7227 (0.6); 12.7124 (0.5); 12.6936 (0.5); 12.6800 (0.5); 12.6040 (0.3); 12.5376 (0.3); 12.4869 (0.3); 10.2794 (8.1); 10.2652 (8.4); 8.3871 (0.3); 7.9610 (3.1); 6.5152 (1.0); 4.2613 (7.0); 4.2399 (10.4); 4.2213 (7.8); 4.1450 (0.4); 3.7092 (0.5); 3.6712 (0.7); 3.6411 (0.3); 3.6329 (0.4); 3.6054 (0.4); 3.5949 (0.4); 3.3286 (353.0); 3.1263 (2.0); 2.9990 (1.0); 2.9880 (1.0); 2.9496 (0.8); 2.8996 (15.7); 2.8503 (0.8); 2.8133 (0.5); 2.7883 (0.5); 2.7750 (0.5); 2.7403 (14.5); 2.6792 (0.8); 2.6000 (0.4); 2.5100 (75.0); 2.3363 (0.9); 2.2691 (0.4); 2.2235 (0.3); 2.2074 (0.4); 2.1844 (0.4); 2.1609 (0.3); 1.4734 (0.3); 1.4546 (0.4); 1.4373 (1.2); 1.4136 (4.0); 1.4051 (6.3); 1.3944 (6.5); 1.3849 (6.6); 1.3518 (2.0); 1.2750 (0.7); 1.2459 (2.2); 1.1815 (0.4); 0.8610 (0.4); 0.7082 (0.9); 0.6839 (5.2); 0.6576 (8.7); 0.6416 (5.0); 0.5858 (2.8); 0.5440 (16.0); 0.5316 (14.6); 0.5216 (8.3); 0.4305 (8.4); 0.4168 (8.8); 0.3509 (0.9); 0.2780 (0.4); 0.2699 (0.4); 0.2173 (0.3); 0.1876 (0.3)
I.1030: $^1$H-NMR(400.1 MHz, $d_6$-DMSO):
δ = 10.4669 (3.0); 7.9603 (1.4); 4.3816 (16.0); 3.9521 (0.3); 3.8003 (0.4); 3.3286 (34.3); 2.8996 (6.7); 2.8067 (0.3); 2.7403 (6.2); 2.6831 (0.5); 2.6062 (0.3); 2.5102 (33.2); 2.3367 (0.3); 1.2463 (1.2)
I.1031: $^1$H-NMR(400.1 MHz, $d_6$-DMSO):
δ = 14.6571 (0.4); 13.3481 (0.3); 8.8668 (0.4); 8.7604 (14.2); 8.7410 (14.2); 8.6693 (0.3); 8.6638 (0.3); 7.9622 (0.4); 6.5217 (1.7); 5.3253 (0.3); 4.8703 (0.4); 4.8248 (5.3); 4.8008 (10.8); 4.7777 (11.1); 4.7548 (5.8); 4.6186 (0.4); 4.5961 (0.4); 4.4260 (6.7); 4.4042 (16.0); 4.3823 (10.1); 4.3367 (0.8); 4.3060 (6.2); 4.2888 (9.5); 4.2814 (10.0); 4.2638 (10.4); 4.2417 (5.3); 4.2091 (0.7); 4.1604 (0.4); 3.9722 (0.4); 3.3676 (3.2); 3.3241 (952.1); 3.2890 (25.2); 3.1838 (2.7); 3.1535 (2.0); 3.0945 (1.2); 3.0405 (0.8); 3.0279 (0.7); 2.9962 (0.7); 2.8997 (2.7); 2.8686 (0.5); 2.7404 (2.3); 2.7242 (0.3); 2.6751 (0.7); 2.5642 (0.4); 2.5099 (92.8); 2.4841 (13.2); 2.4662 (11.8); 2.4420 (7.5); 2.4098 (4.8); 2.3832 (9.8); 2.3581 (11.7); 2.3316 (8.0); 2.3027 (2.9); 2.2450 (0.7); 2.2040 (0.6); 2.1952 (0.6); 2.1699 (0.6); 2.1293 (0.4); 2.0845 (0.4); 2.0229 (0.4); 2.0024 (0.4); 1.4831 (0.4); 1.4630 (0.3); 1.3348 (0.3); 1.2446 (2.0); 1.1984 (0.3); −1.3692 (0.4); −3.3559 (0.3); −3.5736 (0.3)
I.1032: $^1$H-NMR(400.1 MHz, $d_6$-DMSO):
δ = 10.7180 (0.4); 7.9608 (3.2); 4.4257 (7.9); 3.3266 (11.6); 3.0688 (0.4); 2.8996 (16.0); 2.7403 (15.0); 2.5099 (11.2); 2.3699 (15.9)
I.1033: $^1$H-NMR(400.1 MHz, CDCl3):
δ = 7.3316 (0.5); 7.3108 (2.0); 7.2969 (9.5); 7.2824 (2.9); 7.2694 (1.2); 7.2600 (4.5); 7.2459 (0.6); 6.5480 (0.9); 4.4119 (5.1); 4.3983 (5.1); 4.2061 (9.5); 2.5346 (16.0); 2.5070 (0.4); 2.0414 (0.6); 1.5742 (2.1); 1.2573 (0.6); −0.0002 (3.7)
I.1034: $^1$H-NMR(600.2 MHz, $d_6$-DMSO):
δ = 9.0630 (3.0); 9.0498 (3.1); 5.7622 (1.0); 4.8181 (1.4); 4.8031 (2.2); 4.8000 (2.0); 4.7893 (2.0); 4.7863 (2.3); 4.7712 (1.5); 4.4327 (1.6); 4.4302 (1.8); 4.4180 (3.9); 4.4154 (3.8); 4.4032 (2.2); 4.4007 (2.0); 4.3024 (1.7); 4.2915 (2.2); 4.2878 (2.0); 4.2849 (2.2); 4.2770 (1.9); 4.2739 (2.3); 4.2703 (1.9); 4.2595 (1.5); 3.3236 (16.0); 2.5215 (0.5); 2.5137 (5.4); 2.5107 (10.4); 2.5076 (14.8); 2.5046 (11.2); 2.5020 (5.9); 2.4949 (1.6); 2.4917 (1.4); 2.4883 (1.5); 2.4870 (1.6); 2.4829 (1.6); 2.4796 (1.3); 2.4714 (1.2); 2.4688 (1.0); 2.4150 (46.1); 2.3975 (1.0); 2.3612 (0.9); 2.3457 (1.4); 2.3432 (2.0); 2.3278 (2.3); 2.3256 (2.2); 2.3235 (2.0); 2.3081 (1.7); 2.3051 (1.3); 2.2900 (0.7); 1.2412 (0.4)
I.1035: $^1$H-NMR(400.1 MHz, $d_6$-DMSO):
δ = 10.6816 (2.7); 7.9609 (2.2); 7.8076 (16.0); 7.7583 (0.4); 4.3774 (15.5); 3.6612 (0.4); 3.5534 (0.6); 3.3281 (44.0); 3.0867 (0.9); 3.0395 (0.7); 3.0276 (0.6); 2.9778 (0.5); 2.9445 (0.5); 2.8993 (11.2); 2.8383 (0.4); 2.8183 (0.3); 2.7744 (0.4); 2.7402 (10.4); 2.6798 (0.5); 2.5099 (31.2); 2.3371 (0.3); 1.2440 (0.8)
I.1036: $^1$H-NMR(400.1 MHz, $d_6$-DMSO):
δ = 8.7026 (2.3); 7.9159 (1.8); 7.9063 (1.8); 3.8313 (5.7); 3.8226 (5.9); 3.3107 (19.6); 3.1750 (0.5); 3.1618 (0.5); 2.6127 (15.7); 2.6013 (16.0); 2.5050 (13.6); 2.5007 (18.1); 2.4963 (13.6); 2.4246 (35.1); 0.0077 (0.9); −0.0002 (23.3)
I.1037: $^1$H-NMR(400.1 MHz, CDCl3):
δ = 7.2628 (3.8); 6.7860 (1.3); 4.3689 (1.3); 4.3510 (4.0); 4.3332 (4.0); 4.3154 (1.3); 3.8201 (3.8); 3.7940 (4.6); 3.5506 (4.6); 3.5245 (3.7); 2.5351 (16.0); 1.5743 (7.4); 1.3670 (4.1); 1.3492 (8.3); 1.3314 (4.0); −0.0002 (4.3)
I.1038: $^1$H-NMR(400.1 MHz, $d_6$-DMSO):
δ = 12.2193 (1.7); 9.0000 (1.4); 8.9815 (1.5); 5.7542 (0.4); 4.4753 (0.5); 4.4622 (0.6); 4.4568 (0.7); 4.4520 (0.8); 4.4439 (0.7); 4.4388 (0.7); 4.4336 (0.7); 4.4203 (0.5); 3.6715 (15.9); 3.3164 (2.2); 2.5058 (3.1); 2.5015 (4.2); 2.4971 (3.2); 2.3902 (16.0); 2.3788 (1.7); 2.3592 (3.2); 2.3402 (1.9); 2.1100 (0.4); 2.0960 (0.7); 2.0753 (0.8); 2.0619 (0.6); 1.9568 (0.5); 1.9385 (0.6); 1.9336 (0.6); 1.9216 (0.5); 1.9152 (0.6); 1.8984 (0.4); −0.0002 (4.5)

TABLE A-(I)-continued

| NMR peak lists of compounds according to formula (I) |
|---|
| I.1039: $^1$H-NMR(400.1 MHz, $d_6$-DMSO):<br>δ = 8.9827 (1.4); 8.9638 (1.5); 7.4641 (1.3); 7.0065 (1.4); 4.7845 (0.5); 4.7658 (1.2); 4.7519 (1.2); 4.7474 (0.9); 4.7331 (0.6); 3.6527 (16.0); 3.3138 (9.9); 2.7321 (0.6); 2.7185 (0.7); 2.6923 (2.0); 2.6899 (2.2); 2.6793 (1.6); 2.6522 (1.6); 2.6334 (1.6); 2.6130 (0.7); 2.5942 (0.6); 2.5052 (4.2); 2.5010 (5.7); 2.4967 (4.4); 2.4146 (0.4); 2.3804 (15.7); 2.3636 (0.5); 1.9882 (1.1); 1.1749 (0.6); −0.0002 (8.1) |
| I.1040: $^1$H-NMR(400.1 MHz, $d_6$-DMSO):<br>δ = 13.8139 (1.0); 9.0904 (1.4); 9.0727 (1.4); 8.7688 (2.5); 8.7657 (2.5); 8.7579 (2.6); 8.7547 (2.5); 8.5449 (2.6); 8.5417 (2.5); 8.5239 (2.7); 8.5207 (2.6); 7.5317 (2.6); 7.5207 (2.5); 7.5107 (2.5); 7.4997 (2.4); 7.3542 (1.1); 6.8526 (1.1); 4.4310 (0.5); 4.4185 (0.6); 4.4131 (0.7); 4.4078 (0.8); 4.4008 (0.8); 4.3955 (0.7); 4.3903 (0.7); 4.3778 (0.5); 3.6710 (16.0); 3.3173 (1.6); 2.6905 (0.5); 2.5070 (6.0); 2.5027 (8.1); 2.4983 (6.2); 2.4338 (0.3); 2.4041 (15.8); 2.3876 (0.5); 2.2304 (1.3); 2.2120 (3.4); 2.1942 (2.0); 2.0960 (0.4); 2.0796 (0.6); 2.0611 (0.8); 2.0481 (0.6); 1.9376 (0.6); 1.9199 (0.6); 1.9147 (0.7); 1.9029 (0.5); 1.8972 (0.6); 1.8797 (0.4); 1.2733 (0.5); 1.2616 (0.9); 1.2445 (1.0); 0.0078 (0.3); −0.0002 (10.3) |
| I.1041: $^1$H-NMR(400.1 MHz, CDCl3):<br>δ = 7.8871 (2.4); 7.2642 (4.5); 4.3862 (2.4); 4.3684 (7.6); 4.3506 (7.8); 4.3328 (2.6); 3.8046 (6.9); 3.7787 (9.1); 3.6356 (9.2); 3.6098 (6.7); 1.5724 (5.4); 1.3759 (7.8); 1.3581 (16.0); 1.3403 (7.8); −0.0002 (5.1) |
| I.1042: $^1$H-NMR(400.1 MHz, $d_6$-DMSO):<br>δ = 12.5568 (2.0); 9.0595 (1.5); 9.0404 (1.5); 4.7913 (0.5); 4.7774 (0.8); 4.7718 (1.2); 4.7583 (1.2); 4.7526 (0.8); 4.7388 (0.6); 3.6669 (15.8); 3.3123 (2.0); 2.8966 (0.8); 2.8831 (0.9); 2.8548 (1.6); 2.8413 (1.5); 2.7778 (1.5); 2.7576 (1.5); 2.7359 (0.8); 2.7158 (0.8); 2.5053 (3.5); 2.5010 (4.7); 2.4967 (3.6); 2.3748 (16.0); −0.0002 (5.1) |
| I.1043: $^1$H-NMR(400.1 MHz, $d_6$-DMSO):<br>δ = 12.5501 (1.3); 8.4734 (0.9); 8.4669 (0.9); 8.4537 (0.9); 8.4471 (0.9); 4.8393 (0.5); 4.8229 (1.1); 4.8050 (1.1); 4.7882 (0.5); 3.6515 (16.0); 3.3149 (1.2); 2.9080 (0.8); 2.8935 (0.8); 2.8660 (1.6); 2.8515 (1.5); 2.8027 (1.6); 2.7855 (1.6); 2.7606 (0.8); 2.7435 (0.8); 2.5065 (2.7); 2.5021 (3.6); 2.4977 (2.7); −0.0002 (4.0) |
| I.1044: $^1$H-NMR(400.1 MHz, $d_6$-DMSO):<br>δ = 12.6133 (1.1); 8.7069 (1.5); 8.6873 (1.5); 4.8713 (0.5); 4.8558 (1.1); 4.8370 (1.1); 4.8221 (0.5); 3.6726 (16.0); 3.3146 (1.2); 2.9132 (0.5); 2.8994 (0.6); 2.8708 (1.8); 2.8571 (1.8); 2.8430 (1.8); 2.8269 (1.8); 2.8005 (0.5); 2.7845 (0.5); 2.5066 (2.4); 2.5022 (3.2); 2.4978 (2.4); −0.0002 (2.8) |
| I.1045: $^1$H-NMR(400.1 MHz, $d_6$-DMSO):<br>δ = 8.3331 (1.6); 8.3196 (3.0); 8.3060 (1.6); 7.9290 (1.9); 7.9197 (1.9); 3.8730 (8.6); 3.8591 (8.6); 3.3150 (5.8); 2.6151 (15.9); 2.6036 (16.0); 2.5057 (9.2); 2.5014 (12.2); 2.4972 (9.3); 2.0738 (0.5); −0.0002 (14.7) |
| I.1046: $^1$H-NMR(400.1 MHz, CDCl3):<br>δ = 7.7496 (2.2); 7.2617 (9.2); 5.2995 (0.6); 4.3639 (2.4); 4.3461 (7.6); 4.3283 (7.7); 4.3105 (2.6); 3.8092 (5.6); 3.7836 (7.1); 3.6001 (6.7); 3.5745 (5.3); 1.5581 (15.0); 1.3580 (7.9); 1.3402 (16.0); 1.3224 (7.8); −0.0002 (9.0) |
| I.1047: $^1$H-NMR(400.1 MHz, $d_6$-DMSO):<br>δ = 8.7448 (1.4); 8.7252 (1.4); 7.5184 (1.3); 7.0224 (1.3); 4.8475 (0.5); 4.8342 (1.1); 4.8146 (1.2); 4.8013 (0.5); 3.6519 (16.0); 3.3117 (54.8); 2.7751 (0.3); 2.7611 (0.4); 2.7347 (1.8); 2.7194 (2.8); 2.7049 (1.9); 2.6779 (0.5); 2.6649 (0.5); 2.5049 (20.5); 2.5006 (27.4); 2.4962 (20.5); 1.9880 (0.6); −0.0002 (44.0) |
| I.1048: $^1$H-NMR(400.1 MHz, $d_6$-DMSO):<br>δ = 8.6875 (1.1); 8.6702 (1.1); 7.3423 (1.1); 6.8631 (1.1); 4.4186 (0.4); 4.4073 (0.6); 4.3962 (0.8); 4.3897 (0.8); 4.3844 (0.7); 4.3786 (0.7); 4.3669 (0.5); 3.6515 (16.0); 3.3109 (21.9); 2.5050 (10.2); 2.5007 (13.6); 2.4964 (10.3); 2.2107 (1.0); 2.1934 (2.6); 2.1769 (1.7); 2.0915 (0.4); 2.0744 (0.6); 2.0564 (0.7); 2.0444 (0.6); 1.9902 (0.3); 1.9730 (0.7); 1.9555 (0.6); 1.9497 (0.7); 1.9382 (0.5); 1.9325 (0.6); 1.9154 (0.4); 1.2725 (0.9); 1.2588 (1.8); 1.2438 (1.4); −0.0002 (17.6) |
| I.1049: $^1$H-NMR(400.1 MHz, $d_6$-DMSO):<br>δ = 8.7914 (1.4); 8.7736 (1.4); 7.3204 (1.0); 6.8337 (1.0); 4.4392 (0.5); 4.4267 (0.6); 4.4212 (0.7); 4.4168 (0.8); 4.4089 (0.8); 4.4044 (0.7); 4.3989 (0.7); 4.3863 (0.5); 3.6705 (16.0); 3.6346 (0.4); 3.6152 (0.4); 3.3123 (5.6); 3.1435 (0.4); 3.1263 (0.3); 2.5055 (5.2); 2.5011 (7.0); 2.4967 (5.3); 2.2363 (1.3); 2.2179 (3.4); 2.1999 (2.0); 2.1078 (0.4); 2.1032 (0.4); 2.0868 (0.6); 2.0680 (0.7); 2.0550 (0.6); 1.9529 (0.6); 1.9304 (0.7); 1.9180 (0.5); 1.9128 (0.6); 1.8954 (0.4); 1.2739 (1.8); 1.2603 (4.2); 1.2444 (3.9); 1.2262 (0.9); 0.0078 (0.3); −0.0002 (9.5) |
| I.1050: $^1$H-NMR(400.1 MHz, $d_6$-DMSO):<br>δ = 12.2042 (1.5); 8.7254 (1.4); 8.7069 (1.4); 4.4941 (0.5); 4.4811 (0.6); 4.4751 (0.7); 4.4715 (0.8); 4.4625 (0.7); 4.4583 (0.7); 4.4529 (0.7); 4.4399 (0.5); 3.6732 (16.0); 3.3094 (5.7); 2.5055 (3.6); 2.5011 (4.9); 2.4967 (3.6); 2.3866 (1.3); 2.3685 (3.4); 2.3499 (2.0); 2.1213 (0.4); 2.1071 (0.6); 2.0864 (0.8); 2.0731 (0.6); 1.9790 (0.6); 1.9608 (0.6); 1.9564 (0.7); 1.9438 (0.5); 1.9383 (0.6); 1.9212 (0.4); −0.0002 (5.8) |
| I.1051: $^1$H-NMR(400.1 MHz, CDCl3):<br>δ = 7.5053 (2.3); 7.2615 (11.1); 5.2995 (1.7); 4.3629 (2.4); 4.3451 (7.6); 4.3273 (7.7); 4.3094 (2.6); 3.8300 (6.3); 3.8038 (7.7); 3.5589 (7.5); 3.5328 (6.2); 1.5585 (18.5); 1.3550 (7.9); 1.3372 (16.0); 1.3194 (7.8); 1.2554 (0.6); 0.0078 (0.4); −0.0002 (12.0) |
| I.1052: $^1$H-NMR(400.1 MHz, CDCl3):<br>δ = 7.2604 (20.6); 7.1952 (3.3); 7.0612 (4.5); 6.9273 (2.2); 5.2989 (0.4); 4.3418 (2.5); 4.3240 (7.6); 4.3062 (7.7); 4.2884 (2.6); 3.8190 (6.1); 3.7931 (7.0); 3.5106 (7.0); 3.4847 (5.9); 1.5483 (33.6); 1.3384 (7.9); 1.3206 (16.0); 1.3028 (7.9); 1.2588 (0.5); 0.8821 (0.4); −0.0002 (21.2) |
| I.1053: $^1$H-NMR(400.1 MHz, CDCl3):<br>δ = 8.0833 (0.6); 7.2657 (0.9); 3.8215 (9.4); 1.7160 (16.0); 1.5849 (0.8); −0.0002 (1.2) |
| I.1054: $^1$H-NMR(400.1 MHz, CDCl3):<br>δ = 7.5134 (3.1); 7.2718 (1.9); 5.3039 (0.8); 4.3653 (2.4); 4.3475 (7.4); 4.3297 (7.5); 4.3119 (2.6); 3.8255 (7.1); 3.8000 (9.0); 3.5662 (9.4); 3.5404 (8.1); 1.3580 (7.9); 1.3402 (16.0); 1.3224 (8.0); −0.0002 (1.4) |
| I.1055: $^1$H-NMR(400.1 MHz, $d_6$-DMSO):<br>δ = 8.8578 (16.0); 3.3678 (8.4); 3.3332 (10.0); 3.3113 (64.5); 2.9840 (12.9); 2.9506 (11.1); 2.6698 (0.5); 2.6056 (9.2); 2.5944 (14.6); 2.5789 (10.9); 2.5544 (0.8); 2.5051 (54.0); 2.5008 (73.4); 2.4964 (55.6); 2.3279 (0.5); 2.2571 (2.8); 2.2456 (3.1); 2.2235 (3.9); 2.2110 (3.6); 2.0731 (2.6); 2.0530 (2.9); 2.0415 (3.6); 2.0335 (3.9); 2.0187 (5.9); 1.9883 (6.3); 1.9619 (3.5); 1.9564 (3.4); 1.9308 (1.5); 1.9165 (3.1); 1.8990 (3.4); 1.8912 (2.9); 1.8829 (3.0); 1.8733 (2.7); 1.8591 (1.7); 1.8400 (1.0); 1.2459 (0.6); 1.1746 (0.4); 0.8580 (0.6); 0.8417 (0.4); 0.1461 (0.5); 0.0078 (4.0); −0.0002 (111.6); −0.0083 (6.7); −0.0313 (0.5); −0.1495 (0.5) |
| I.1056: $^1$H-NMR(400.1 MHz, $d_6$-DMSO):<br>δ = 8.6263 (16.0); 3.3584 (8.1); 3.3237 (10.1); 3.3124 (48.3); 2.9638 (13.3); 2.9304 (11.5); 2.6144 (0.6); 2.5966 (9.3); 2.5855 (13.8); 2.5701 (11.4); 2.5445 (0.8); 2.5053 (41.8); 2.5009 (56.8); 2.4966 (43.0); 2.4580 (0.4); 2.3274 (0.5); 2.2696 (2.8); 2.2648 (2.8); 2.2556 (3.3); 2.2325 (4.1); 2.2218 (3.4); 2.0459 (3.1); 2.0346 (3.5); 2.0282 (3.8); 2.0104 (5.6); 1.9795 (6.0); 1.9526 (3.8); 1.9472 (3.9); 1.9275 (1.7); 1.9125 (3.0); 1.8957 (3.4); 1.8860 (2.8); 1.8791 (3.2); 1.8698 (2.9); 1.8621 (2.3); 1.8539 (1.8); 1.8359 (1.0); 1.2412 (0.4); 0.1458 (0.4); 0.0369 (0.3); 0.0077 (2.7); −0.0002 (76.9); −0.0262 (0.5); −0.1498 (0.3) |

TABLE A-(I)-continued

NMR peak lists of compounds according to formula (I)

I.1057: $^{1}$H-NMR(400.1 MHz, CDCl3):
δ = 7.2617 (4.5); 6.5736 (1.2); 5.2993 (0.5); 4.3509 (1.3); 4.3331 (3.9); 4.3153 (4.0); 4.2975 (1.3); 3.8150 (3.8); 3.7892 (4.5); 3.5225 (4.4); 3.4968 (3.7); 2.5253 (16.0); 1.5673 (1.4); 1.3523 (4.1); 1.3345 (8.3); 1.3167 (4.1); 1.2554 (1.2); −0.0002 (4.2)
I.1058: $^{1}$H-NMR(400.1 MHz, CDCl3):
δ = 7.4967 (1.7); 7.2604 (25.7); 5.2991 (5.2); 4.4376 (16.0); 4.4232 (16.0); 2.0062 (2.9); 1.5478 (29.7); 1.2552 (2.6); 0.8596 (0.4); 0.8448 (0.4); −0.0002 (26.4)
I.1059: $^{1}$H-NMR(400.1 MHz, CDCl3):
δ = 7.2611 (11.1); 7.1947 (3.7); 7.0609 (4.6); 6.9271 (2.3); 4.3444 (2.5); 4.3266 (7.7); 4.3088 (7.8); 4.2910 (2.6); 3.8179 (6.8); 3.7919 (8.0); 3.5118 (7.9); 3.4858 (6.7); 1.5561 (19.5); 1.3409 (8.0); 1.3231 (16.0); 1.3053 (7.8); −0.0002 (11.2); −0.0083 (0.6)
I.1060: $^{1}$H-NMR(400.1 MHz, CDCl3):
δ = 7.9655 (2.6); 7.2612 (12.6); 4.3644 (2.5); 4.3466 (7.7); 4.3287 (7.8); 4.3110 (2.6); 3.8124 (7.4); 3.7868 (9.3); 3.5989 (9.3); 3.5734 (7.3); 1.5503 (17.4); 1.3591 (8.0); 1.3413 (16.0); 1.3235 (7.8); −0.0002 (14.2)
I.1061: $^{1}$H-NMR(400.1 MHz, CDCl3):
δ = 7.2632 (1.2); 7.1825 (0.6); 7.0485 (1.4); 7.0265 (0.4); 6.9145 (0.7); 3.7841 (9.3); 1.6519 (16.0); 1.5780 (1.3); −0.0002 (1.3)
I.1062: $^{1}$H-NMR(400.1 MHz, CDCl3):
δ = 7.9385 (0.5); 7.2602 (4.0); 4.2858 (0.7); 4.2680 (2.2); 4.2502 (2.2); 4.2324 (0.8); 1.6979 (16.0); 1.5453 (1.5); 1.3202 (2.3); 1.3024 (4.6); 1.2846 (2.3); −0.0002 (5.2)
I.1063: $^{1}$H-NMR(400.1 MHz, CDCl3):
δ = 7.2595 (51.0); 6.5359 (1.2); 5.2986 (0.9); 4.3518 (1.3); 4.3340 (3.8); 4.3162 (3.9); 4.2984 (1.4); 3.8156 (4.0); 3.7898 (4.6); 3.5258 (4.6); 3.5000 (3.8); 2.5232 (16.0); 2.0051 (0.4); 1.5375 (77.1); 1.3522 (4.0); 1.3344 (8.2); 1.3166 (4.0); 0.0077 (2.2); −0.0002 (53.6)
I.1064: $^{1}$H-NMR(400.1 MHz, CDCl3):
δ = 7.3062 (1.2); 7.2608 (14.2); 7.2167 (2.2); 7.0827 (4.5); 6.9488 (2.2); 4.7815 (1.1); 4.7733 (2.3); 4.7645 (2.1); 4.7555 (2.2); 4.7473 (1.1); 4.3201 (2.4); 4.3022 (7.3); 4.2844 (7.4); 4.2665 (2.5); 4.1278 (0.8); 4.1190 (0.9); 4.1127 (1.0); 4.0995 (1.8); 4.0908 (1.9); 4.0845 (1.9); 4.0760 (1.7); 4.0585 (1.7); 4.0500 (1.9); 4.0439 (1.9); 4.0353 (1.8); 4.0217 (0.8); 4.0157 (0.8); 4.0071 (0.7); 2.1227 (1.9); 2.1078 (3.8); 2.0929 (1.8); 1.5607 (18.6); 1.3408 (8.0); 1.3229 (16.0); 1.3051 (7.9); −0.0002 (16.4)
I.1065: $^{1}$H-NMR(400.1 MHz, CDCl3):
δ = 7.2654 (1.5); 7.2220 (1.0); 7.1502 (0.5); 7.0881 (1.8); 6.9541 (1.0); 4.8688 (0.4); 4.8512 (0.9); 4.8381 (0.9); 4.8205 (0.4); 3.8029 (14.6); 2.5819 (1.0); 2.5764 (1.0); 2.5629 (2.1); 2.5597 (1.8); 2.5438 (1.4); 2.5411 (1.3); 2.2966 (0.4); 2.2837 (0.5); 2.2793 (0.6); 2.2663 (0.6); 2.2609 (0.7); 2.2481 (0.6); 2.2424 (0.4); 2.1599 (0.3); 2.1430 (0.8); 2.1238 (1.0); 2.1080 (16.0); 2.0881 (0.5); 1.5981 (0.8); −0.0002 (1.4)
I.1066: $^{1}$H-NMR(400.1 MHz, CDCl3):
δ = 7.2608 (43.3); 7.1920 (6.9); 7.0580 (13.2); 6.9241 (9.6); 6.9160 (4.0); 5.2996 (16.0); 4.6854 (2.9); 4.6714 (3.2); 4.6639 (3.5); 4.6564 (3.7); 4.6500 (3.7); 4.6424 (3.5); 4.6351 (3.3); 4.6211 (3.0); 4.5573 (4.2); 4.5345 (9.5); 4.5119 (5.6); 4.3766 (4.1); 4.3619 (4.6); 4.3531 (4.4); 4.3487 (5.0); 4.3384 (4.5); 4.3339 (5.0); 4.3253 (3.8); 4.3105 (3.4); 2.9638 (2.5); 2.9490 (2.8); 2.9463 (2.9); 2.9424 (2.9); 2.9289 (4.2); 2.9175 (3.2); 2.9149 (3.2); 2.9110 (3.2); 2.8959 (2.7); 2.3352 (1.9); 2.3128 (2.5); 2.3065 (4.4); 2.2842 (4.6); 2.2756 (4.3); 2.2531 (3.9); 2.2468 (2.2); 2.2244 (1.6); 2.0439 (1.3); 2.0065 (1.3); 1.6767 (1.5); 1.5863 (0.3); 1.5538 (48.4); 1.2542 (3.8); 0.8988 (0.7); 0.8820 (1.8); 0.8644 (0.8); −0.0002 (46.5)
I.1067: $^{1}$H-NMR(400.1 MHz, CDCl3):
δ = 7.2608 (3.6); 7.2294 (0.6); 7.0957 (1.1); 6.9620 (0.6); 5.2995 (0.8); 5.2771 (1.0); 5.2610 (1.0); 3.8644 (16.0); 1.5495 (3.0); −0.0002 (4.1)
I.1068: $^{1}$H-NMR(400.1 MHz, CDCl3):
δ = 7.2957 (1.1); 7.2616 (8.1); 7.2218 (2.3); 7.0881 (4.6); 6.9543 (2.4); 5.2997 (1.1); 4.7787 (1.0); 4.7703 (2.1); 4.7615 (2.0); 4.7526 (2.1); 4.7442 (1.1); 4.3202 (2.3); 4.3023 (7.1); 4.2845 (7.3); 4.2666 (2.5); 4.1283 (0.6); 4.1194 (0.7); 4.1139 (0.8); 4.1002 (1.4); 4.0914 (1.6); 4.0858 (1.6); 4.0772 (1.3); 4.0549 (1.3); 4.0463 (1.6); 4.0409 (1.6); 4.0323 (1.4); 4.0182 (0.8); 4.0129 (0.7); 4.0042 (0.6); 2.1528 (1.3); 2.1382 (2.6); 2.1235 (1.3); 1.5805 (6.4); 1.3412 (8.0); 1.3234 (16.0); 1.3055 (7.8); −0.0002 (8.4)
I.1069: $^{1}$H-NMR(400.1 MHz, CDCl3):
δ = 7.2682 (0.9); 7.2287 (1.0); 7.1495 (0.5); 7.0948 (1.9); 6.9610 (1.1); 4.8660 (0.4); 4.8484 (0.9); 4.8353 (0.8); 4.8177 (0.4); 3.8040 (14.5); 2.5818 (1.0); 2.5780 (1.1); 2.5628 (2.6); 2.5435 (1.8); 2.2939 (0.4); 2.2809 (0.6); 2.2766 (0.6); 2.2635 (0.5); 2.2581 (0.7); 2.2454 (0.6); 2.2396 (0.4); 2.1610 (0.4); 2.1439 (0.8); 2.1252 (1.0); 2.1091 (16.0); 2.0894 (0.5); 1.6270 (0.8); −0.0002 (0.9)
I.1070: $^{1}$H-NMR(400.1 MHz, CDCl3):
δ = 7.2641 (0.8); 7.1856 (0.7); 7.0518 (1.4); 7.0193 (0.4); 6.9179 (0.7); 3.7861 (9.3); 1.6524 (16.0); 1.5914 (0.5); −0.0002 (0.8)

TABLE A-(II)

NMR peak lists of compounds according to formula (II)

II.001: $^{1}$H-NMR (499.9 MHz, $d_6$-DMSO):
δ = 14.8672 (0.3); 14.8409 (0.3); 14.8165 (0.4); 14.7954 (0.4); 14.7837 (0.4); 14.7748 (0.4); 14.7701 (0.4); 14.7591 (0.4); 14.7076 (0.5); 14.6839 (0.5); 14.6483 (0.6); 14.6247 (0.6); 14.6040 (0.6); 14.5301 (0.8); 14.5000 (0.7); 14.4564 (0.8); 14.4505 (0.8); 14.4034 (0.8); 14.3672 (0.8); 14.3428 (0.9); 14.3341 (0.8); 14.2880 (0.8); 14.2718 (0.8); 14.2428 (0.8); 14.1747 (0.7); 14.1679 (0.7); 14.1332 (0.7); 14.1178 (0.7); 14.0991 (0.6); 14.0781 (0.6); 14.0557 (0.6); 14.0362 (0.6); 13.9962 (0.5); 13.9637 (0.5); 13.9417 (0.5); 13.8849 (0.4); 13.8601 (0.4); 13.8452 (0.4); 13.8345 (0.4); 13.7884 (0.4); 13.7810 (0.4); 13.7653 (0.3); 13.7486 (0.3); 8.4749 (0.5); 8.0357 (0.4); 7.1794 (0.7); 7.0765 (0.7); 6.9742 (0.7); 4.4502 (0.4); 4.4360 (1.1); 4.4222 (1.1); 4.4074 (0.5); 4.3861 (0.4); 4.3720 (1.0); 4.3580 (1.0); 4.3437 (0.5); 4.0976 (0.3); 4.0794 (1.4); 4.0633 (0.4); 4.0492 (1.6); 4.0348 (4.3); 4.0206 (4.4); 4.0064 (1.9); 3.9290 (0.4); 3.8860 (0.5); 3.8428 (0.6); 3.8081 (0.6); 3.7967 (0.7); 3.7766 (0.7); 3.7641 (0.8); 3.6748 (1.0); 3.3319 (3.7); 3.2910 (3.6); 3.1188 (1.7); 3.0393 (1.2); 3.0002 (1.0); 2.9537 (0.8); 2.8351 (0.6); 2.7644 (0.5); 2.7475 (0.4); 2.7414 (0.4); 2.7127 (0.4); 2.6752 (0.5); 2.6354 (1.1); 2.5733 (0.6); 2.5397 (13.6); 2.5004 (109.0); 2.3621 (0.6); 2.1038 (1.2); 1.9869 (16.0); 1.9072 (1.3); 1.4586 (1.0); 1.4445 (2.0); 1.4307 (1.0); 1.3273 (0.9); 1.3131 (1.6); 1.2990 (0.9); 1.2436 (0.3); 1.2319 (0.7); 1.1877 (4.4); 1.1735 (8.6); 1.1593 (4.5)
II.002: $^{1}$H-NMR (499.9 MHz, $d_6$-DMSO):
δ = 14.4288 (1.5); 8.1364 (1.5); 8.0812 (1.2); 3.3247 (17.2); 2.6403 (3.5); 2.5089 (333.4); 2.5054 (469.7); 2.5018 (363.6); 2.4985 (193.6); 2.3664 (3.0); 2.0773 (16.0); 1.9124 (2.1); 1.4493 (1.0)

TABLE A-(II)-continued

NMR peak lists of compounds according to formula (II)

II.003: $^1$H-NMR (499.9 MHz, d6-DMSO):
δ = 7.7585 (7.2); 7.6520 (16.0); 7.5453 (8.0); 2.5047 (5.5); 2.5015 (7.3); 2.4983 (5.8); 1.9838 (1.0); 1.9064 (0.5); 1.3506 (1.1); 1.1707 (0.5)
II.004: $^1$H-NMR (499.9 MHz, $d_6$-DMSO):
δ = 19.9030 (0.4); 19.7518 (0.4); 19.4121 (0.4); 19.3987 (0.4); 19.3413 (0.4); 19.1183 (0.4); 16.0300 (0.4); 15.5948 (0.4); 15.4718 (0.5); 15.4366 (0.4); 15.3556 (0.4); 15.3223 (0.5); 15.3074 (0.4); 15.2897 (0.5); 15.2433 (0.6); 15.2035 (0.7); 15.1930 (0.6); 15.1825 (0.6); 15.1600 (0.6); 15.1508 (0.6); 15.1054 (0.7); 15.0936 (0.7); 15.0697 (0.7); 15.0196 (0.8); 14.9823 (0.8); 14.9573 (0.8); 14.9391 (0.9); 14.9330 (1.0); 14.9130 (0.9); 14.8902 (0.9); 14.8676 (0.9); 14.8551 (0.9); 14.8376 (0.9); 14.8237 (1.0); 14.7786 (1.0); 14.7561 (1.0); 14.7337 (1.0); 14.7082 (1.1); 14.6405 (1.3); 14.6231 (1.1); 14.6068 (1.2); 14.5826 (1.2); 14.5473 (1.1); 14.5080 (1.2); 14.4828 (1.1); 14.4616 (1.1); 14.4353 (1.1); 14.4167 (1.0); 14.4108 (1.0); 14.3980 (1.0); 14.3845 (0.9); 14.3704 (1.0); 14.3442 (1.0); 14.2850 (0.8); 14.2541 (0.7); 14.2451 (0.7); 14.2088 (0.7); 14.1759 (0.7); 14.1513 (0.7); 14.1321 (0.8); 14.0913 (0.6); 14.0764 (0.5); 14.0572 (0.6); 14.0168 (0.6); 13.9597 (0.6); 13.9237 (0.4); 13.8220 (0.4); 13.6004 (0.4); 12.7913 (0.4); 11.5309 (0.4); 8.5079 (7.6); 8.5063 (7.6); 8.1616 (0.5); 8.1368 (2.0); 8.0362 (0.4); 4.5788 (0.4); 4.4454 (0.4); 4.3942 (0.4); 4.3314 (0.4); 4.3072 (0.4); 4.2785 (0.4); 4.2657 (0.4); 4.2400 (0.5); 4.1739 (0.5); 4.1548 (0.7); 4.1359 (0.6); 4.1071 (0.6); 4.0737 (0.6); 4.0549 (1.7); 4.0405 (4.1); 4.0264 (4.2); 4.0121 (1.9); 3.9855 (0.7); 3.9568 (0.8); 3.9255 (0.9); 3.9072 (0.9); 3.8549 (1.0); 3.844 5(1.0) ;3.7947 (1.3); 3.7286 (1.6); 3.7223 (1.6); 3.6911 (1.9); 3.6330 (2.5); 3.5528 (3.9); 3.5125 (5.6); 3.4518 (7.8); 3.3380 (13.1); 3.0881 (3.0); 3.0074 (2.0); 2.9602 (1.5); 2.9017 (1.2); 2.8734 (1.0); 2.8308 (0.9); 2.8079 (0.8); 2.7921 (0.8); 2.6827 (0.5); 2.6439 (2.8); 2.6403 (3.8); 2.6365 (3.1); 2.6057 (0.5); 2.5818 (0.5); 2.5417 (1.1); 2.5124 (197.0); 2.5089 (430.2); 2.5054 (611.2); 2.5018 (473.0); 2.4983 (253.1); 2.4197 (0.7); 2.3787 (0.6); 2.3700 (2.9); 2.3661 (3.7); 2.3409 (0.4); 2.3327 (0.4); 2.3076 (0.4); 2.2311 (0.4); 2.0855 (0.6); 2.0775 (15.9); 1.9924 (16.0); 1.9802 (0.7); 1.9126 (4.0); 1.3030 (0.4); 1.2592 (0.5); 1.2398 (2.0); 1.2133 (4.4); 1.2003 (4.3); 1.1932 (4.9); 1.1790 (9.0); 1.1647 (4.3); 1.1083 (0.4); 1.0734 (0.5); 1.0598 (0.8); 0.8575 (0.5); −2.0631 (0.4); −2.9373 (0.4); −3.6491 (0.4)
II.005: $^1$H-NMR (499.9 MHz, CDCl3):
δ = 12.4586 (16.0); 12.2227 (0.9); 12.1163 (1.0); 8.6730 (0.7); 7.2561 (6.9); 7.2528 (7.1); 5.9254 (0.3); 4.6739 (15.4); 4.5538 (0.4)
II.006: $^1$H-NMR (499.9 MHz, $d_6$-DMSO):
δ = 7.9721 (0.4); 7.8624 (7.4); 7.7553 (16.0); 7.6761 (0.4); 7.6481 (8.0); 7.5707 (0.4); 5.6747 (0.4); 5.6681 (0.4); 4.8002 (0.5); 3.9066 (0.9); 3.8972 (0.9); 2.5550 (12.9); 2.0392 (0.5); 1.4058 (1.9); 1.2781 (1.4); 1.2257 (1.7); 1.2120 (1.3); 0.9003 (0.3); 0.8089 (0.6); 0.0084 (0.4); −0.0002 (0.4)
II.007: $^1$H-NMR (600.2 MHz, $d_6$-DMSO):
δ = 14.1835 (0.4); 14.1483 (0.4); 13.9079 (0.9); 13.9000 (0.9); 13.8734 (1.0); 13.8606 (1.0); 8.7244 (2.4); 6.8746 (0.4); 4.0519 (1.3); 4.0400 (3.8); 4.0282 (3.8); 4.0163 (1.3); 3.8481 (1.3); 3.4514 (0.4); 3.4398 (0.4); 2.6724 (4.2); 2.6225 (0.5); 2.6195 (0.8); 2.6167 (0.6); 2.5939 (0.4); 2.5833 (1.7); 2.5654 (789.4); 2.5493 (3.9); 2.5437 (1.4); 2.5343 (1.0); 2.5285 (1.2); 2.5253 (1.5); 2.5221 (1.7); 2.5135 (42.2); 2.5106 (88.6); 2.5076 (122.4); 2.5046 (89.6); 2.5016 (43.0); 2.4549 (4.4); 2.3945 (0.6); 2.3915 (0.8); 2.3885 (0.6); 2.1879 (0.8); 2.1727 (0.9); 2.0913 (0.5); 1.9939 (16.0); 1.9141 (2.2); 1.3601 (5.5); 1.3242 (3.4); 1.2371 (1.0); 1.1920 (4.3); 1.1801 (8.7); 1.1683 (4.3); 1.0726 (0.4); 1.0609 (0.7); 1.0493 (0.3)
II.008: $^1$H-NMR (499.9 MHz, $d_6$-DMSO):
δ = 14.5322 (0.3); 14.4908 (0.4); 14.4435 (0.4); 14.3793 (0.6); 14.3712 (0.6); 13.9072 (4.4); 13.8983 (4.4); 13.4295 (0.7); 13.3442 (0.5); 13.3232 (0.5); 13.2959 (0.4); 13.2323 (0.4); 13.1873 (0.3); 6.8575 (1.6); 6.6099 (0.3); 5.7390 (2.5); 4.0414 (0.5); 4.0272 (1.5); 4.0129 (1.5); 3.9988 (0.5); 2.6534 (8.4); 2.6325 (1.3); 2.5245 (1382.0); 2.5040 (39.2); 2.5009 (43.9); 2.4711 (2.1); 2.4247 (0.8); 2.4199 (0.8); 2.3922 (8.1); 2.3626 (0.6); 2.3379 (0.4); 2.3113 (0.4); 2.2959 (0.4); 2.1722 (2.6); 2.0796 (0.5); 2.0680 (0.3); 1.9800 (6.1); 1.9029 (1.6); 1.3456 (16.0); 1.3182 (0.5); 1.2938 (0.3); 1.2882 (0.4); 1.2483 (0.5); 1.2092 (2.5); 1.1820 (1.8); 1.1678 (3.4); 1.1536 (1.7); 1.1172 (0.6); 1.1016 (0.6); 1.0873 (0.4); 0.8752 (0.4); 0.8391 (0.5)
II.009: $^1$H-NMR (500.1 MHz, $d_6$-DMSO):
δ = 14.5919 (0.4); 14.5845 (0.4); 14.4993 (0.5); 14.4883 (0.6); 14.0165 (16.0); 13.6188 (0.9); 13.5474 (0.7); 13.5058 (0.6); 13.4806 (0.5); 13.4366 (0.5); 13.4056 (0.4); 13.3788 (0.4); 13.3676 (0.4); 13.3486 (0.4); 13.3363 (0.4); 13.3108 (0.3); 7.4373 (2.4); 6.8675 (0.7); 3.9852 (0.4); 3.9512 (4.6); 3.8927 (0.4); 3.8671 (0.4); 3.8427 (0.5); 3.8165 (0.5); 3.8024 (0.6); 3.7924 (0.7); 3.7618 (0.6); 3.7529 (0.6); 3.6921 (0.7); 3.6134 (1.7); 3.6002 (3.2); 3.5871 (1.8); 3.5101 (1.0); 3.4924 (1.1); 3.4800 (1.1); 3.4581 (1.1); 3.4300 (1.1); 3.4190 (1.1); 3.3668 (1.2); 3.3403 (1.1); 3.3100 (1.1); 3.2831 (1.1); 3.2569 (1.2); 3.2264 (1.0); 3.1715 (0.9); 3.1250 (0.8); 3.1154 (0.7); 3.0636 (0.6); 3.0381 (0.6); 2.9732 (0.6); 2.9246 (0.5); 2.8988 (0.4); 2.8755 (0.4); 2.8362 (0.4); 2.8150 (0.4); 2.7952 (0.4); 2.7733 (0.4); 2.7577 (0.4); 2.7323 (0.4); 2.7177 (0.4); 2.6673 (0.4); 2.6400 (1.2); 2.6130 (0.5); 2.5969 (0.5); 2.5086 (102.5); 2.5052 (136.1); 2.5017 (101.1); 2.3696 (0.5); 2.3664 (0.7); 2.1819 (1.0); 2.0861 (3.5); 2.0594 (0.6); 1.7719 (1.0); 1.7656 (1.2); 1.7588 (2.8); 1.7519 (1.2); 1.7457 (1.0); 1.4895 (0.3); 1.4743 (0.5); 1.4601 (0.4); 1.4113 (0.3); 1.3695 (1.2); 1.3540 (7.4); 1.3384 (1.3); 1.3320 (1.1); 1.3124 (0.5); 1.2970 (0.6); 1.2814 (0.5); 1.2691 (0.4); 1.2342 (0.8); 1.2227 (1.2); 1.1789 (1.5); 1.1673 (0.9); 1.1262 (0.4); 0.9072 (1.0); 0.8926 (2.0); 0.8837 (0.4); 0.8779 (0.8)
II.010: $^1$H-NMR (499.9 MHz, $d_6$-DMSO):
δ = 15.1679 (0.3); 15.1303 (0.3); 15.1220 (0.4); 15.0965 (0.4); 15.0520 (0.4); 15.0439 (0.4); 14.9564 (0.6); 14.9427 (0.6); 14.9306 (0.6); 14.8856 (0.7); 14.8727 (0.7); 14.6582 (1.4); 14.6214 (1.6); 14.4855 (3.0); 14.1523 (16.0); 13.5649 (1.5); 13.5212 (1.3); 13.4974 (1.2); 13.4930 (1.2); 13.4769 (1.2); 13.4056 (1.0); 13.3639 (0.8); 13.3551 (0.8); 13.3014 (0.7); 13.2762 (0.7); 13.2671 (0.7); 13.1589 (0.6); 13.1424 (0.6); 13.1169 (0.6); 13.0074 (0.4); 12.9962 (0.4); 12.9420 (0.4); 12.9329 (0.4); 12.9123 (0.4); 12.8889 (0.4); 12.8588 (0.4); 12.8162 (0.3);8.1143 (0.4); 7.6761 (1.4); 7.4438 (6.4); 7.3784 (0.4); 4.0254 (0.8); 4.0118 (0.8); 3.9493 (0.3); 3.8880 (0.3); 3.7811 (0.4); 3.7252 (0.4); 3.7183 (0.3); 3.6723 (0.3); 3.6469 (0.4); 3.6218 (0.4); 3.5756 (0.4); 3.5412 (0.5); 3.4964 (1.2); 3.3742 (1.2); 3.3623 (1.2); 3.2916 (0.7); 3.2397 (0.5); 3.2212 (0.5); 3.1844 (0.4); 3.1244 (0.3); 2.6877 (0.6); 2.6343 (0.6); 2.5951 (0.4); 2.4985 (66.0); 2.3617 (1.5); 2.3034 (0.7); 2.1655 (0.6); 2.1172 (0.4); 2.0936 (0.3); 1.9781 (1.8); 1.9016 (0.5); 1.8972 (0.5); 1.8814 (0.4); 1.2039 (3.2); 1.1647 (1.5); 1.0782 (1.7); 1.0410 (0.5); 0.8335 (0.6); 0.7986 (0.4); 0.7925 (0.4)
II.011: $^1$H-NMR (499.9 MHz, $d_6$-DMSO):
δ = 14.5232 (0.4); 14.5008 (0.4); 14.4443 (0.6); 14.1188 (13.2); 13.7355 (0.6); 13.6987 (0.5); 13.6482 (0.4); 8.2054 (4.5); 5.7526 (3.3); 3.7901 (0.4); 3.7726 (0.3); 3.7135 (0.4); 3.5757 (0.6); 3.4897 (0.8); 3.4273 (0.8); 3.4193 (0.9); 3.3930 (0.9); 3.3575 (0.8); 3.3395 (0.8); 3.3239 (0.8); 3.3074 (0.8); 3.2473 (0.8); 3.2103 (0.7); 3.1712 (16.0); 3.0881 (0.5); 3.0304 (0.4); 2.9913 (0.4); 2.9703 (0.4); 2.6397 (1.1); 2.6357 (0.9); 2.6060 (0.3); 2.5081 (109.7); 2.5046 (148.9); 2.5011 (110.7); 2.3656 (0.8); 2.3621 (0.6); 1.2241 (0.5)
II.012: $^1$H-NMR (499.9 MHz, $d_6$-DMSO):
δ = 14.5937 (0.4); 14.5771 (0.4); 14.5249 (0.5); 14.5107 (0.5); 14.4754 (0.6); 14.3681 (0.9); 14.3493 (0.9); 14.3316 (1.0); 14.3034 (1.1); 14.2877 (1.2); 14.2798 (1.2); 14.2057 (1.4); 14.1856 (1.5); 14.1808 (1.5); 14.0345 (1.3); 13.9977 (1.2); 13.8041 (0.6); 13.7664 (0.6); 13.7338 (0.5); 13.7184 (0.5); 13.7047 (0.4); 13.6645 (0.4); 13.6228 (0.4); 13.6067 (0.3); 6.8713 (1.6); 6.6327 (0.8); 6.6267 (1.2); 4.0381 (0.5); 4.0242 (0.5); 4.0093 (0.4); 3.9730 (0.4); 3.9370 (0.4); 3.9245 (0.4); 3.8452 (0.5); 3.7866 (0.6); 3.7418 (0.7); 3.7301 (0.7); 3.7062 (0.8); 3.6369 (1.1); 3.3239 (15.9); 3.0459 (1.1); 3.0349 (1.1); 2.8346 (0.4); 2.8104 (0.4); 2.7768 (0.4); 2.7697 (0.4); 2.7355 (0.3); 2.7170 (0.4); 2.6388 (1.1); 2.5073 (107.4); 2.5040 (142.7); 2.5008 (112.7); 2.3655 (0.8); 2.1847 (2.4); 1.9902 (0.9); 1.3569 (16.0); 1.3410 (2.3); 1.3168 (0.5); 1.2713 (1.6); 1.2336 (1.1); 1.1825 (9.0); 1.1709 (2.0); 1.1291 (0.4); 1.0957 (0.4)

TABLE A-(II)-continued

| NMR peak lists of compounds according to formula (II) |
|---|
| II.013: $^{1}$H-NMR (600.2 MHz, $d_6$-DMSO): δ = 13.6095 (16.0); 8.1782 (0.5); 8.1714 (0.5); 8.0768 (0.4); 8.0742 (0.4); 7.7520 (0.6); 7.7492 (0.5); 7.6621 (3.2); 7.6111 (0.4); 6.9487 (4.0); 6.9471 (3.9); 5.8165 (0.8); 4.0955 (0.5); 4.0836 (0.5); 3.3833 (1.9); 2.9173 (0.6); 2.6781 (0.4); 2.6751 (0.6); 2.6721 (0.4); 2.5864 (4.0); 2.5809 (0.9); 2.5690 (36.6); 2.5661 (76.3); 2.5631 (104.7); 2.5601 (76.5); 2.5572 (37.0); 2.5299 (0.3); 2.5253 (0.4); 2.5189 (0.4); 2.5017 (15.1); 2.5005 (15.1); 2.4789 (739.1); 2.4729 (32.7); 2.4579 (1.7); 2.4502 (1.2); 2.4471 (1.3); 2.4441 (1.0); 2.4367 (0.5); 2.4302 (0.4); 2.4142 (0.5); 2.4067 (0.5); 2.3678 (3.8); 2.2386 (0.6); 2.1466 (0.4); 2.0580 (0.4); 2.0493 (2.1); 1.9699 (0.5); 1.4157 (0.8); 1.3586 (2.1); 1.3186 (2.8); 1.2923 (1.2); 1.2850 (0.4); 1.2472 (0.6); 1.2353 (1.1); 1.2294 (0.4); 1.2235 (0.6); −0.0002 (3.0) |
| II.014: $^{1}$H-NMR (499.9 MHz, $d_6$-DMSO): δ = 7.9519 (1.1); 5.0020 (1.1); 4.1406 (0.3); 4.1288 (0.4); 4.0498 (0.4); 4.0275 (0.4); 3.9936 (0.4); 3.9892 (0.4); 3.9211 (0.4); 3.8943 (0.4); 3.8149 (2.4); 3.7653 (0.4); 3.7221 (0.4); 3.6935 (0.4); 3.6568 (0.4); 3.6042 (0.4); 3.5929 (0.5); 3.5811 (0.4); 2.7441 (0.4); 2.5954 (9.6); 2.5074 (226.2); 2.5041 (289.1); 2.5009 (221.9); 2.4670 (2229.3); 2.4391 (124.2); 2.3685 (6.3); 2.3653 (6.5); 2.3350 (16.0); 2.3069 (3.7); 2.2671 (2.7); 2.2164 (2.0); 2.1740 (1.7); 2.1442 (1.6); 2.1368 (1.8); 2.1126 (1.3); 2.0702 (1.2); 2.0168 (1.0); 1.9682 (0.8); 1.9062 (0.8); 1.7620 (0.6); 1.7493 (0.7); 1.7357 (0.6); 1.6932 (0.5); 1.6123 (0.4); 1.5616 (0.3); 1.4501 (0.4); 1.3759 (0.4); 1.3458 (0.9); 1.2442 (0.4); 1.1993 (5.3); 1.1584 (1.3); 1.1475 (1.0); 1.0355 (0.3); 0.8473 (0.4); 0.8345 (0.8); 0.8203 (0.6); 0.7957 (0.4); −0.0186 (0.6) |
| II.015: $^{1}$H-NMR (499.9 MHz, $d_6$-DMSO): δ = 13.9443 (0.3); 13.9196 (0.3); 13.8895 (0.3); 13.8485 (0.3); 13.8386 (0.3); 13.8155 (0.3); 13.8017 (0.4); 13.7749 (0.4); 13.7348 (0.4); 13.6917 (0.4); 13.6817 (0.4); 13.6744 (0.4); 13.6505 (0.4); 13.6382 (0.4); 13.6147 (0.4); 13.6049 (0.4); 13.5894 (0.4); 13.5653 (0.4); 13.5323 (0.4); 13.4995 (0.4); 13.4947 (0.4); 13.4718 (0.4); 13.4601 (0.4); 13.4404 (0.4); 13.3959 (0.4); 13.3677 (0.4); 13.3297 (0.4); 13.3114 (0.4); 13.2876 (0.4); 13.2802 (0.3); 13.2651 (0.3); 13.2491 (0.3); 13.2342 (0.3); 13.2193 (0.3); 13.1944 (0.3); 13.1507 (0.3); 13.1412 (0.3); 7.8442 (2.3); 5.0006 (0.7); 4.6813 (0.8); 4.1820 (2.4); 4.1785 (2.6); 4.1707 (1.4); 4.0387 (0.7); 4.0245 (1.9); 4.0103 (2.0); 3.9962 (1.0); 3.8488 (0.3); 3.8294 (2.1); 3.8000 (3.3); 3.7639 (0.5); 3.6612 (0.4); 3.2420 (1.3); 2.7511 (0.8); 2.7470 (0.6); 2.6634 (16.0); 2.6428 (2.3); 2.6331 (1.6); 2.5041 (68.0); 2.4843 (14.9); 2.4520 (423.8); 2.4138 (30.4); 2.3202 (8.2); 2.2883 (4.8); 2.2538 (3.8); 2.1093 (1.9); 2.0769 (1.8); 2.0651 (1.8); 2.0327 (1.6); 2.0103 (1.5); 1.9938 (1.4); 1.9783 (7.9); 1.9063 (2.0); 1.8476 (1.2); 1.7637 (1.0); 1.7034 (0.9); 1.6624 (0.8); 1.5364 (0.7); 1.5125 (0.7); 1.4870 (0.7); 1.4732 (0.7); 1.4596 (0.7); 1.3935 (0.6); 1.3797 (0.6); 1.3587 (0.6); 1.3424 (0.6); 1.3213 (0.6); 1.3057 (0.7); 1.2975 (0.8); 1.2854 (0.7); 1.2682 (0.7); 1.2545 (0.9); 1.2409 (1.0); 1.2257 (0.9); 1.2037 (1.0); 1.1793 (2.7); 1.1650 (4.3); 1.1508 (2.9); 1.0909 (0.8); 1.0774 (0.7); 1.0715 (0.7); 1.0651 (0.8); 1.0572 (0.8); 1.0509 (0.8); 1.0375 (0.7); 0.9013 (0.4); 0.8869 (0.4); 0.8471 (0.8); 0.8335 (1.4); 0.8191 (1.1); 0.7751 (0.5); 0.6586 (0.3); 0.6501 (0.3) |
| II.016: $^{1}$H-NMR (499.9 MHz, $d_6$-DMSO): δ = 14.7483 (0.4); 14.6881 (0.4); 14.6327 (0.4); 14.6277 (0.4); 14.5935 (0.4); 14.5531 (0.4); 14.5232 (0.4); 14.5131 (0.4); 14.4891 (0.4); 14.4751 (0.4); 14.4191 (0.4); 14.4141 (0.4); 14.4038 (0.4); 14.3487 (0.4); 14.2499 (0.4); 14.2002 (0.3); 14.1884 (0.3); 8.0394 (0.3); 7.7669 (0.3); 6.9205 (0.4); 4.1024 (1.3); 4.0882 (3.8); 4.0739 (3.8); 4.0597 (1.3); 3.9370 (0.4); 3.9227 (3.0); 3.9204 (2.0); 3.9102 (1.2); 3.8653 (0.3); 3.8491 (1.0); 3.2238 (0.9); 2.6476 (1.9); 2.6405 (3.5); 2.5751 (3.9); 2.5643 (12.1); 2.5608 (26.2); 2.5573 (34.3); 2.5537 (25.6); 2.5504 (13.2); 2.5377 (7.1); 2.5117 (649.6); 2.4944 (16.1); 2.4614 (0.6); 2.4343 (1.0); 2.4217 (0.4); 2.4184 (0.4); 2.4065 (0.3); 2.3968 (0.6); 2.3793 (3.6); 2.2340 (0.7); 2.0404 (16.0); 1.9623 (1.2); 1.4066 (4.7); 1.3877 (0.5); 1.3735 (0.3); 1.3491 (0.7); 1.3227 (0.4); 1.3094 (1.0); 1.2758 (2.3); 1.2416 (4.4); 1.2274 (8.6); 1.2198 (1.3); 1.2132 (4.4); 1.1789 (0.3); 1.1091 (0.4); 0.9123 (0.4); 0.9017 (0.5) |
| II.017: $^{1}$H-NMR (600.2 MHz, $d_6$-DMSO): δ = 13.5200 (16.0); 7.9900 (0.4); 6.5840 (0.3); 4.2871 (0.4); 4.2753 (0.5); 3.3269 (5.3); 2.6408 (1.9); 2.6225 (0.4); 2.6196 (0.5); 2.6165 (0.4); 2.5569 (6.1); 2.5509 (4.0); 2.5344 (371.0); 2.5134 (28.3); 2.5105 (58.5); 2.5075 (80.1); 2.5046 (58.7); 2.5017 (28.2); 2.4865 (0.4); 2.4766 (0.5); 2.4604 (1.6); 2.4243 (2.0); 2.3945 (0.4); 2.3915 (0.5); 2.3885 (0.4); 1.9942 (1.3); 1.3604 (1.2); 1.2984 (0.6); 1.2865 (1.1); 1.2750 (0.8); 1.2372 (1.2); 1.1921 (0.5); 1.1802 (1.0); 1.1743 (2.5); 1.1684 (0.6) |
| II.018: $^{1}$H-NMR (600.2 MHz, $d_6$-DMSO): δ = 13.5453 (16.0); 5.0089 (0.4); 4.2994 (0.4); 4.2876 (1.2); 4.2758 (1.2); 4.2639 (0.4); 3.3285 (3.1); 2.6629 (2.0); 2.6227 (0.4); 2.6197 (0.5); 2.6167 (0.5); 2.5732 (6.1); 2.5566 (372.1); 2.5416 (1.6); 2.5342 (7.8); 2.5279 (5.9); 2.5136 (23.8); 2.5107 (49.3); 2.5077 (67.1); 2.5047 (49.0); 2.5018 (23.2); 2.4467 (1.9); 2.3916 (0.4); 1.9941 (1.2); 1.3603 (1.2); 1.2963 (1.3); 1.2845 (2.6); 1.2727 (1.3); 1.2361 (0.8); 1.1920 (0.5); 1.1801 (0.9); 1.1741 (2.1); 1.1684 (0.5) |
| II.019: $^{1}$H-NMR (499.9 MHz, CDCl3): δ = 7.2611 (2.2); 3.9261 (16.0); 2.0066 (0.4); 1.5515 (2.2); −0.0002 (2.7) |
| II.020: $^{1}$H-NMR (499.9 MHz, $d_6$-DMSO): δ = 3.8594 (0.3); 3.8460 (16.0); 3.3169 (4.6); 2.5060 (1.3); 2.5031 (1.1); −0.0002 (0.4) |
| II.021: $^{1}$H-NMR (600.2 MHz, CDCl3): δ = 7.2635 (3.1); 4.2128 (0.4); 4.2059 (0.4); 4.1989 (0.4); 3.9343 (16.0); 3.8544 (6.5); 3.1836 (0.5); 2.9793 (0.4); 2.6105 (0.3); 1.5666 (0.5); −0.0002 (3.7) |
| II.022: $^{1}$H-NMR (499.9 MHz, $d_6$-DMSO): δ = 3.8760 (16.0); 3.3238 (34.8); 2.5125 (0.9); 2.5090 (1.9); 2.5054 (2.8); 2.5018 (2.1); 2.4982 (1.2) |
| II.023: $^{1}$H-NMR (499.9 MHz, CDCl3): δ = 7.6708 (1.2); 7.5641 (2.4); 7.4574 (1.2); 7.2625 (1.2); 3.9234 (16.0); 3.4943 (0.7); 3.4855 (0.8); 1.5774 (4.0); −0.0002 (1.1) |
| II.024: $^{1}$H-NMR (600.2 MHz, CDCl3): δ = 7.2611 (4.1); 4.0761 (5.3); 4.0652 (5.4); 2.4225 (15.4); 2.0580 (0.5); 2.0468 (1.0); 2.0357 (1.2); 2.0246 (1.0); 2.0135 (0.5); 1.5497 (4.5); 0.9996 (16.0); 0.9884 (15.9); −0.0002 (5.0) |
| II.025: $^{1}$H-NMR (499.9 MHz, $d_6$-DMSO): δ = 4.9685 (9.5); 3.7175 (16.0); 3.3228 (17.2); 2.5116 (0.6); 2.5082 (1.0); 2.5046 (1.4); 2.5011 (1.0); 2.4977 (0.5) |
| II.026: $^{1}$H-NMR (600.2 MHz, $d_6$-DMSO): δ = 3.8596 (16.0); 3.3235 (4.6); 2.5135 (0.6); 2.5107 (1.4); 2.5077 (2.0); 2.5047 (1.5); 2.5019 (0.8) |
| II.027: $^{1}$H-NMR (499.9 MHz, CDCl3): δ = 7.2625 (1.3); 3.9117 (16.0); 1.5540 (1.1); −0.0002 (1.7) |
| II.028: $^{1}$H-NMR (600.2 MHz, CDCl3): δ = 7.2635 (1.8); 3.8916 (16.0); 2.6424 (15.6); 1.5608 (0.7); −0.0002 (2.2) |
| II.029: $^{1}$H-NMR (499.9 MHz, $d_6$-DMSO): δ = 3.8305 (16.0); 3.3621 (7.2); 2.5600 (16.0); 2.5009 (1.0) |
| II.030: $^{1}$H-NMR (499.9 MHz, $d_6$-DMSO): δ = 4.2923 (2.5); 4.2781 (7.6); 4.2639 (7.6); 4.2497 (2.4); 3.3209 (1.6); 2.5442 (0.6); 2.5217 (29.1); 2.5092 (1.3); 2.5055 (1.0); 1.3027 (7.8); 1.2884 (16.0); 1.2743 (7.8) |

TABLE A-(II)-continued

NMR peak lists of compounds according to formula (II)

II.031: $^1$H-NMR (499.9 MHz, $d_6$-DMSO):
δ = 4.2984 (2.5); 4.2842 (7.5); 4.2700 (7.5); 4.2559 (2.4); 3.3206 (5.5); 2.5563 (29.8); 2.5337 (0.6); 2.5271 (0.5); 2.5161 (0.6); 2.5125 (1.2); 2.5090 (1.6); 2.5054 (1.2); 2.5022 (0.6); 1.3008 (7.7); 1.2865 (16.0); 1.2723 (7.7)
II.032: $^1$H-NMR (499.9 MHz, CDCl3):
δ = 7.2604 (2.2); 4.3522 (1.2); 4.3380 (3.9); 4.3237 (3.9); 4.3094 (1.3); 2.5596 (16.0); 2.5260 (0.6); 2.2709 (0.5); 1.5491 (2.2); 1.4319 (4.4); 1.3776 (4.0); 1.3634 (8.1); 1.3491 (4.0); −0.0002 (2.7)
II.033: $^1$H-NMR (499.9 MHz, CDCl3):
δ = 7.2632 (0.7); 4.3522 (1.3); 4.3379 (4.0); 4.3236 (4.0); 4.3094 (1.3); 2.5497 (16.0); 1.5760 (0.6); 1.3792 (4.1); 1.3650 (8.2); 1.3507 (4.0); −0.0002 (0.9)
II.034: $^1$H-NMR (499.9 MHz, $d_6$-DMSO):
δ = 7.9164 (16.0); 2.5086 (5.4); 2.5052 (7.2); 2.5018 (5.6); 1.9910 (0.5)
II.035: $^1$H-NMR (499.9 MHz, $d_6$-DMSO):
δ = 13.7031 (0.5); 7.6216 (15.9); 7.6137 (16.0); 2.5077 (2.8); 2.5042 (3.8); 2.5007 (2.8)
II.036: $^1$H-NMR (500.1 MHz, $d_6$-DMSO):
δ = 7.9159 (16.0); 2.5075 (4.1); 1.9920 (0.4)
II.037: $^1$H-NMR (499.9 MHz, $d_6$-DMSO):
δ = 13.8781 (0.6); 7.7856 (16.0); 2.5617 (2.6); 2.5583 (3.5); 2.5549 (2.7)
II.038: $^1$H-NMR (600.2 MHz, $d_6$-DMSO):
δ = 13.3358 (1.1); 7.5775 (4.7); 2.5135 (0.6); 2.5106 (1.4); 2.5075 (1.9); 2.5045 (1.4); 2.5016 (0.6); 2.1757 (16.0)
II.039: $^1$H-NMR (600.2 MHz, $d_6$-DMSO):
δ = 13.7749 (0.4); 7.6995 (0.4); 7.6785 (15.9); 7.6772 (16.0); 2.5135 (2.1); 2.5106 (4.4); 2.5076 (6.2); 2.5046 (4.7); 2.5017 (2.3); 2.4237 (1.0); 1.9137 (0.3); 1.3589 (0.7)
II.040: $^1$H-NMR (499.9 MHz, $d_6$-DMSO):
δ = 7.6854 (16.0); 2.5076 (1.1); 2.5042 (1.5); 2.5007 (1.2)
II.041: $^1$H-NMR (499.9 MHz, $d_6$-DMSO):
δ = 8.0233 (16.0); 7.9998 (0.3); 3.1726 (0.9); 2.5088 (9.5); 2.5053 (13.3); 2.5018 (10.6); 1.2368 (0.4)
II.042: $^1$H-NMR (499.9 MHz, $d_6$-DMSO):
δ = 14.2581 (2.0); 14.1226 (0.8); 8.0485 (0.4); 6.8709 (0.3); 4.0522 (1.2); 4.0380 (3.7); 4.0238 (3.7); 4.0095 (1.3); 3.8597 (1.4); 3.8253 (8.6); 3.4302 (0.3); 3.3683 (0.3); 3.3505 (0.3); 3.3405 (0.3); 3.2577 (0.4); 2.6399 (0.6); 2.6360 (0.4); 2.6214 (3.4); 2.5849 (0.4); 2.5755 (1.8); 2.5712 (3.5); 2.5620 (2.3); 2.5565 (1.2); 2.5438 (0.6); 2.5287 (8.5); 2.5119 (44.5); 2.5084 (47.5); 2.5047 (64.7); 2.5010 (51.9); 2.4927 (615.2); 2.4711 (2.5); 2.4658 (7.7); 2.4549 (1.1); 2.3849 (0.6); 2.3656 (0.4); 2.3603 (3.3); 2.1844 (0.6); 1.9902 (16.0); 1.3716 (0.4); 1.3567 (4.4); 1.2314 (0.6); 1.1911 (4.4); 1.1768 (8.8); 1.1706 (0.6); 1.1626 (4.3)
II.043: $^1$H-NMR (499.9 MHz, $d_6$-DMSO):
δ = 13.7246 (2.4); 7.8612 (0.4); 7.8525 (0.4); 7.7485 (0.4); 7.6440 (16.0); 2.4968 (0.9)
II.044: $^1$H-NMR (499.9 MHz, $d_6$-DMSO):
δ = 20.0185 (0.4); 14.3723 (4.0); 8.1319 (0.5); 8.0700 (0.6); 8.0257 (0.6); 7.1840 (1.4); 7.0816 (1.5); 6.9795 (1.3); 4.4408 (0.4); 4.4268 (0.8); 4.4129 (0.8); 4.3720 (0.4); 4.3580 (0.4); 4.0811 (0.9); 3.5082 (0.9); 3.2617 (1.9); 3.1773 (0.9); 2.6378 (0.4); 2.5424 (47.1); 2.5065 (88.2); 2.5032 (112.7); 2.5000 (89.9); 2.3641 (1.3); 2.1057 (2.0); 2.0733 (16.0); 1.9086 (0.4); 1.7568 (0.8); 1.5689 (0.5); 1.4590 (0.8); 1.4451 (1.6); 1.4311 (0.8); 1.3296 (0.6); 1.3155 (1.1); 1.3016 (0.8); 1.2590 (0.6); 1.2454 (0.6); 1.2219 (0.9); 1.0417 (0.4); 1.0296 (0.4); 0.9498 (0.8); 0.9351 (1.5); 0.9202 (0.7)
II.045: $^1$H-NMR (499.9 MHz, CDCl3):
δ = 7.7634 (4.9); 7.2607 (0.7); 3.9197 (16.0); 1.5430 (0.4); 1.2550 (0.4); −0.0002 (5.7)
II.046: $^1$H-NMR (499.9 MHz, $d_6$-DMSO):
δ = 8.0923 (5.6); 3.9501 (16.0); 3.3765 (13.6); 2.5635 (0.6); 2.5600 (0.9); 2.5565 (0.7)
II.047: $^1$H-NMR (499.9 MHz, $d_6$-DMSO):
δ = 7.5342 (4.9); 3.8219 (16.0); 3.3148 (9.5); 2.5053 (1.2)
II.048: $^1$H-NMR (499.9 MHz, CDCl3):
δ = 7.5934 (10.4); 7.2637 (2.3); 6.9837 (0.4); 4.3671 (2.4); 4.3528 (7.4); 4.3385 (7.5); 4.3242 (2.5); 1.6266 (0.4); 1.3791 (8.0); 1.3710 (0.9); 1.3648 (16.0); 1.3505 (7.9); 1.3339 (0.4); 1.2848 (0.5); 1.2545 (0.6); −0.0002 (2.4)
II.049: $^1$H-NMR (600.2 MHz, CDCl3):
δ = 7.4203 (2.9); 7.4184 (3.0); 7.2628 (1.2); 3.8863 (16.0); 1.5670 (1.2); −0.0002 (1.4)
II.050: $^1$H-NMR (600.2 MHz, CDCl3):
δ = 7.5458 (5.7); 7.2612 (2.4); 4.0756 (5.5); 4.0645 (5.6); 2.0623 (0.5); 2.0512 (1.0); 2.0400 (1.2); 2.0288 (1.0); 2.0177 (0.5); 0.9962 (16.0); 0.9850 (15.9); −0.0002 (3.1)
II.051: $^1$H-NMR (600.2 MHz, $d_6$-DMSO):
δ = 3.8874 (16.0); 3.8285 (1.0); 3.3214 (2.5); 2.5277 (1.0); 2.5066 (17.1)
II.052: $^1$H-NMR (499.9 MHz, $d_6$-DMSO):
δ = 8.0458 (5.3); 3.8951 (16.0); 3.3467 (1.8); 2.5142 (0.7); 2.5108 (1.3); 2.5072 (1.7); 2.5037 (1.3); 2.5003 (0.6)
II.053: $^1$H-NMR (600.4 MHz, $d_6$-DMSO):
δ = 4.4072 (2.4); 4.3953 (7.6); 4.3835 (7.6); 4.3717 (2.5); 3.3060 (21.4); 2.5224 (0.5); 2.5193 (0.7); 2.5162 (0.8); 2.5074 (11.9); 2.5044 (23.3); 2.5014 (30.8); 2.4984 (22.1); 2.4954 (10.2); 1.3364 (7.8); 1.3246 (16.0); 1.3128 (7.6); −0.0001 (2.4)
II.054: $^1$H-NMR (500.1 MHz, $d_6$-DMSO):
δ = 3.9625 (16.0); 3.3693 (4.1); 2.5703 (0.7); 2.5667 (1.4); 2.5631 (2.0); 2.5595 (1.5); 2.5559 (0.7)
II.055: $^1$H-NMR (500.1 MHz, CDCl3):
δ = 7.6839 (1.1); 7.5771 (2.2); 7.4703 (1.1); 7.2606 (1.5); 3.9212 (16.0); 1.5457 (2.0); −0.0002 (1.9)
II.056: $^1$H-NMR (600.4 MHz, $d_6$-DMSO):
δ = 4.3275 (2.3); 4.3157 (7.3); 4.3039 (7.3); 4.2921 (2.3); 3.3075 (20.4); 2.5230 (0.7); 2.5199 (0.9); 2.5167 (1.0); 2.5081 (16.1); 2.5050 (32.6); 2.5019 (44.3); 2.4989 (32.0); 2.4959 (14.8); 1.3042 (7.6); 1.2923 (16.0); 1.2805 (7.4); −0.0001 (3.3)
II.057: $^1$H-NMR (600.4 MHz, $d_6$-DMSO):
δ = 14.0903 (0.6); 14.0707 (0.6); 7.8035 (0.4); 7.7892 (0.4); 7.4436 (0.4); 7.4293 (0.4); 7.2061 (2.4); 7.1216 (2.8); 7.0373 (2.4); 5.7524 (0.6); 4.7679 (0.8); 4.4368 (0.4); 4.0431 (0.5); 4.0313 (0.5); 3.9101 (0.4); 3.8445 (3.0); 3.8371 (0.5); 3.7524 (0.6); 3.5860 (1.2); 3.5113 (3.0); 3.3176 (6.3); 3.1707 (16.0); 3.1017 (1.6); 3.0899 (1.5); 3.0530 (1.1); 2.9900 (0.8); 2.7987 (0.4); 2.7658 (0.8); 2.7415 (0.4); 2.7049 (0.4); 2.6916 (0.4); 2.6687 (0.4); 2.6466 (0.4); 2.6328 (0.4); 2.6204 (3.1); 2.6175 (6.1); 2.6145 (8.2); 2.6114 (6.0); 2.6085 (3.0); 2.5923 (0.5); 2.5652 (0.7); 2.5616 (0.8); 2.5419 (1.3); 2.5387 (1.6); 2.5235 (20.0); 2.5204 (24.5); 2.5173 (24.5); 2.5085 (483.6); 2.5055 (1013.6); 2.5025 (1398.1); 2.4994 (1029.1); 2.4965 (489.2); 2.3924 (2.6); 2.3894 (5.6); 2.3864 (7.7); 2.3834 (5.5); 2.3805 (2.5); 2.0734 (0.5); 1.9097 (1.6); 1.3785 (4.0); 1.2341 (2.3); 1.1929 (0.4); 1.1808 (0.6); 1.1686 (0.4); 0.8649 (0.3); 0.8539 (0.6); 0.8422 (0.4); 0.0968 (0.4); 0.0683 (0.4); 0.0053 (2.5); −0.0001 (89.3); −0.0056 (2.9); −0.1002 (0.4)

TABLE A-(II)-continued

NMR peak lists of compounds according to formula (II)

II.058: $^1$H-NMR (600.4 MHz, $d_6$-DMSO):
δ = 3.8381 (16.0); 3.3075 (8.8); 2.5200 (0.4); 2.5169 (0.5); 2.5081 (5.7); 2.5052 (11.0); 2.5021 (14.6); 2.4991 (10.5); 2.4962 (5.0); 2.4883 (16.1); −0.0001 (1.0)
II.059: $^1$H-NMR (500.1 MHz, $d_6$-DMSO):
δ = 3.8499 (16.0); 3.3100 (2.5); 2.5105 (0.4); 2.5071 (0.9); 2.5036 (1.4); 2.5000 (1.0); −0.0002 (1.2)
II.060: $^1$H-NMR (500.1 MHz, CDCl3):
δ = 7.2614 (2.0); 4.0934 (5.2); 4.0804 (5.4); 2.0652 (0.4); 2.0518 (0.8); 2.0384 (1.1); 2.0251 (0.9); 2.0117 (0.4); 1.5539 (2.5); 1.0007 (16.0); 0.9923 (0.6); 0.9872 (15.9); −0.0002 (2.5)
II.061: $^1$H-NMR (500.1 MHz, $d_6$-DMSO):
δ = 19.9991 (0.4); 14.4664 (1.2); 8.3364 (3.2); 8.1206 (0.8); 7.9180 (3.7); 5.7520 (12.5); 4.3930 (0.3); 4.3788 (1.0); 4.3704 (0.6); 4.3646 (1.1); 4.3560 (1.8); 4.3418 (1.8); 4.3276 (0.6); 4.2211 (0.4); 2.6402 (0.6); 2.5089 (81.8); 2.5053 (115.9); 2.5018 (88.1); 2.3663 (0.8); 2.0875 (0.8); 1.5516 (2.8); 1.5359 (0.5); 1.3613 (16.0); 1.3357 (2.8); 1.3297 (1.0); 1.3215 (5.7); 1.3073 (3.0); 0.9306 (0.5); 0.9241 (0.3)
II.062: $^1$H-NMR (300.1 MHz, CDCl3):
δ = 7.4552 (5.3); 7.4419 (5.2); 7.2704 (1.1); 4.3785 (2.5); 4.3547 (7.6); 4.3309 (7.7); 4.3072 (2.6); 1.3873 (8.1); 1.3636 (16.0); 1.3497 (0.4); 1.3397 (7.8); −0.0001 (0.9)
II.063: $^1$H-NMR (600.4 MHz, $d_6$-DMSO):
δ = 4.3218 (2.4); 4.3100 (7.5); 4.2982 (7.6); 4.2864 (2.4); 3.3083 (1.2); 2.5235 (0.5); 2.5204 (0.7); 2.5172 (0.8); 2.5085 (11.4); 2.5055 (22.7); 2.5024 (30.4); 2.4994 (22.0); 2.4964 (10.4); 2.4844 (30.7); 1.3053 (7.8); 1.2935 (16.0); 1.2817 (7.7); −0.0001 (2.0)
II.064: $^1$H-NMR (600.4 MHz, $d_6$-DMSO):
δ = 7.6253 (16.0); 7.6186 (16.0); 3.3112 (0.5); 3.1710 (1.0); 2.6177 (0.6); 2.6147 (0.8); 2.6117 (0.6); 2.5338 (0.3); 2.5305 (0.4); 2.5238 (2.1); 2.5207 (2.6); 2.5176 (2.7); 2.5087 (49.0); 2.5058 (100.0); 2.5027 (135.9); 2.4997 (100.2); 2.4968 (48.1); 2.3897 (0.6); 2.3867 (0.8); 2.3837 (0.6); −0.0001 (8.0)
II.065: $^1$H-NMR (600.4 MHz, $d_6$-DMSO):
δ = 13.6953 (4.6); 5.7529 (0.3); 4.6529 (0.4); 3.7313 (0.7); 3.5103 (1.6); 3.3745 (8.2); 3.3163 (15.4); 3.1715 (16.0); 2.6181 (7.0); 2.6151 (9.5); 2.6121 (6.9); 2.6091 (3.4); 2.5757 (8.2); 2.5241 (23.5); 2.5210 (28.7); 2.5179 (28.9); 2.5091 (569.2); 2.5061 (1189.8); 2.5031 (1639.5); 2.5000 (1210.0); 2.4971 (578.2); 2.4683 (1486.8); 2.4159 (1.3); 2.3931 (3.3); 2.3901 (6.8); 2.3870 (9.4); 2.3840 (6.8); 2.3810 (3.3); 2.3571 (7.8); 2.3384 (0.5); 2.0740 (0.8); 1.9102 (2.1); 1.2337 (1.2); 0.8534 (0.4); 0.0968 (0.5); 0.0053 (3.6); −0.0001 (111.4); −0.0057 (3.4); −0.1001 (0.4)
II.066: $^1$H-NMR (500.1 MHz, $d_6$-DMSO):
δ = 4.3407 (2.5); 4.3265 (7.7); 4.3123 (7.8); 4.2981 (2.6); 3.3141 (2.4); 2.5129 (0.8); 2.5095 (1.2); 2.5061 (0.9); 1.3140 (7.9); 1.2998 (16.0); 1.2856 (7.9); −0.0002 (0.7)
II.067: $^1$H-NMR (500.1 MHz, CDCl3):
δ = 7.2628 (2.4); 4.3829 (2.4); 4.3686 (7.3); 4.3544 (7.4); 4.3401 (2.5); 1.5686 (2.6); 1.3830 (8.0); 1.3687 (16.0); 1.3544 (7.9); −0.0002 (2.8)
II.068: $^1$H-NMR (500.1 MHz, $d_6$-DMSO):
δ = 4.4564 (2.4); 4.4422 (7.6); 4.4279 (7.7); 4.4138 (2.5); 3.3641 (3.9); 2.5669 (0.5); 2.5634 (1.2); 2.5598 (1.6); 2.5562 (1.2); 2.5527 (0.6); 1.3925 (7.8); 1.3783 (16.0); 1.3641 (7.7)
II.069: $^1$H-NMR (600.4 MHz, $d_6$-DMSO):
δ = 3.9099 (16.0); 3.3066 (11.0); 2.5076 (6.2); 2.5046 (13.2); 2.5016 (18.3); 2.4985 (13.4); 2.4956 (6.4); −0.0001 (1.3)
II.070: $^1$H-NMR (500.1 MHz, $d_6$-DMSO):
δ = 20.0051 (0.4); 14.0742 (16.0); 7.6812 (12.0); 4.8089 (0.4); 4.1332 (0.6); 3.4600 (1.3); 3.4461 (2.3); 3.4321 (2.4); 3.4182 (1.4); 2.7238 (0.7); 2.6400 (1.0); 2.5082 (84.5); 2.5048 (110.8); 2.5014 (84.0); 2.3659 (0.7); 2.1935 (1.1); 1.4191 (0.4); 1.2029 (0.9); 1.0670 (1.6); 1.0530 (3.2); 1.0389 (1.7)
II.071: $^1$H-NMR (500.1 MHz, $d_6$-DMSO):
δ = 3.8579 (16.0); 3.3124 (2.9); 2.5128 (0.5); 2.5092 (1.0); 2.5056 (1.4); 2.5020 (1.0); 2.4985 (0.5)
II.072: $^1$H-NMR (500.1 MHz, $d_6$-DMSO):
δ = 8.0291 (7.7); 4.3823 (1.8); 4.3681 (5.6); 4.3538 (5.7); 4.3397 (1.8); 3.3160 (16.0); 2.5133 (0.9); 2.5096 (2.0); 2.5060 (2.8); 2.5023 (2.1); 2.4987 (1.0); 1.3298 (5.8); 1.3156 (12.3); 1.3014 (5.8); 1.2378 (0.5)
II.073: $^1$H-NMR (600.4 MHz, $d_6$-DMSO):
δ = 4.3144 (1.3); 4.3026 (4.0); 4.2908 (4.1); 4.2790 (1.3); 3.3072 (9.0); 2.5081 (5.0); 2.5051 (10.6); 2.5020 (14.7); 2.4990 (10.8); 2.4960 (5.2); 2.1633 (16.0); 1.2986 (4.2); 1.2868 (8.5); 1.2749 (4.1); −0.0001 (1.1)
II.074: $^1$H-NMR (600.4 MHz, $d_6$-DMSO):
δ = 2.5088 (6.1); 2.5059 (12.6); 2.5029 (17.2); 2.4999 (12.7); 2.4970 (6.1); 2.1530 (16.0); −0.0001 (1.0)
II.075: $^1$H-NMR (600.2 MHz, $d_6$-DMSO):
δ = 7.0483 (0.9); 6.9617 (2.0); 6.8751 (1.0); 3.7434 (16.0); 3.7015 (0.5); 3.2134 (1.5); 2.4013 (0.6); 2.3983 (0.9); 2.3953 (0.6)
II.076: $^1$H-NMR (500.1 MHz, $d_6$-DMSO):
δ = 14.0928 (2.5); 7.7869 (3.7); 7.6139 (2.7); 4.0980 (8.4); 3.0024 (0.7); 2.9880 (0.9); 2.9779 (0.9); 2.9634 (0.7); 2.5995 (0.3); 2.5689 (9.0); 2.5653 (19.9); 2.5616 (28.1); 2.5580 (20.3); 2.5543 (9.5); 2.1314 (16.0); 1.9669 (1.0); 1.4424 (0.6); 1.2369 (2.6); 1.2224 (5.4); 1.2078 (2.5); −0.0002 (5.4)
II.077: $^1$H-NMR (600.2 MHz, $d_6$-DMSO):
δ = 3.9218 (16.0); 3.3211 (1.6); 2.5136 (0.6); 2.5106 (1.2); 2.5076 (1.7); 2.5046 (1.3); 2.5017 (0.6)
II.078: $^1$H-NMR (600.2 MHz, $d_6$-DMSO):
δ = 14.0878 (0.8); 7.1365 (6.5); 7.0497 (16.0); 6.9630 (7.5); 4.0368 (0.4); 4.0250 (0.4); 2.5134 (2.6); 2.5105 (5.4); 2.5075 (7.5); 2.5046 (5.4); 2.5017 (2.6); 1.9911 (1.8); 1.9132 (0.4); 1.1888 (0.5); 1.1769 (1.0); 1.1650 (0.5)
II.079: $^1$H-NMR (600.2 MHz, $d_6$-DMSO):
δ = 3.9670 (16.0); 3.3755 (4.8); 2.5672 (0.4); 2.5642 (1.0); 2.5611 (1.4); 2.5581 (1.0); 2.5552 (0.5)
II.080: $^1$H-NMR (600.2 MHz, $d_6$-DMSO):
δ = 3.9082 (16.0); 3.3218 (3.1); 2.5106 (0.7); 2.5076 (1.0); 2.5046 (0.8); 2.5017 (0.4)
II.081: $^1$H-NMR (600.2 MHz, $d_6$-DMSO):
δ = 7.8985 (15.2); 7.8962 (16.0); 2.5136 (3.3); 2.5106 (7.1); 2.5076 (9.8); 2.5046 (7.1); 2.5017 (3.3); 2.0787 (0.6)
II.082: $^1$H-NMR (600.2 MHz, CDCl3):
δ = 7.6929 (4.1); 7.6907 (4.2); 7.2614 (3.6); 4.4058 (2.5); 4.3939 (7.7); 4.3820 (7.8); 4.3702 (2.6); 1.5503 (3.5); 1.3994 (8.1); 1.3875 (16.0); 1.3756 (8.1); −0.0002 (4.8)
II.083: $^1$H-NMR (600.2 MHz, $d_6$-DMSO):
δ = 8.6930 (2.7); 8.1907 (4.8); 7.1861 (4.6); 7.1407 (0.7); 7.1366 (0.5); 7.1009 (5.3); 7.0158 (4.5); 6.6860 (0.6); 6.6722 (0.5); 4.0485 (0.7); 4.0367 (0.6); 3.5783 (0.5); 3.5133 (0.8); 3.4627 (0.6); 3.4510 (1.4); 3.4393 (1.4); 3.4277 (0.6); 3.4217 (0.4); 3.3945 (3.1); 3.1738 (2.8); 2.5134 (31.2); 2.5104 (97.8); 2.5074 (158.8); 2.5045 (132.9); 2.5016 (78.4); 2.3944 (1.9); 2.3913 (2.2); 2.3884

TABLE A-(II)-continued

| NMR peak lists of compounds according to formula (II) |
|---|
| (2.0); 2.3156 (0.8); 2.3037 (0.8); 2.2919 (0.8); 2.2855 (0.7); 2.2823 (0.8); 2.2725 (0.9); 2.2685 (0.9); 2.2600 (1.2); 2.2476 (1.0); 2.1960 (0.5); 2.1889 (0.7); 2.1834 (0.6); 2.1716 (0.5); 2.1253 (0.6); 2.0794 (0.6); 1.4655 (0.5); 1.3575 (1.7); 1.3403 (8.9); 1.3022 (2.3); 1.2665 (0.5); 1.2626 (3.4); 1.2347 (11.1); 1.2287 (16.0); 1.1912 (1.6); 1.1848 (1.7); 1.1777 (1.6); 1.1731 (2.3); 1.1658 (2.0); 1.1612 (1.8); 1.1535 (1.6); 1.1410 (1.1); 1.1314 (0.9); 1.1191 (0.8); 1.1072 (0.7); 1.0957 (0.6); 1.0719 (1.5); 1.0603 (2.8); 1.0486 (1.7); 1.0362 (0.6); 0.8671 (0.7); 0.8566 (2.3); 0.8447 (1.7); 0.8406 (1.5); 0.8323 (2.3); 0.8291 (2.2); 0.8212 (3.1); 0.8099 (2.3); 0.7973 (1.7); 0.7540 (0.9); 0.7424 (0.9); 0.7147 (0.6); 0.6521 (0.4); 0.5985 (0.4) |
| II.084: $^1$H-NMR (600.2 MHz, $d_6$-DMSO): |
| δ = 3.8243 (16.0); 3.3228 (2.9); 2.5136 (0.6); 2.5107 (1.2); 2.5077 (1.7); 2.5047 (1.2); 2.5017 (0.6); 2.4423 (15.1) |
| II.085: $^1$H-NMR (600.2 MHz, CDCl3): |
| δ = 7.2652 (1.0); 3.9980 (16.0); 1.5699 (0.7); 1.2548 (0.5); −0.0002 (1.4) |
| II.086: $^1$H-NMR (600.2 MHz, $d_6$-DMSO): |
| δ = 3.8489 (16.0); 3.3221 (1.7); 2.5136 (0.4); 2.5106 (0.8); 2.5075 (1.2); 2.5045 (0.9); 2.5016 (0.4) |
| II.088: $^1$H-NMR (600.2 MHz, $d_6$-DMSO): |
| δ = 8.3203 (0.5); 8.3063 (0.5); 8.1382 (0.3); 2.5493 (1.3); 2.5158 (7.2); 2.5130 (22.5); 2.5100 (36.5); 2.5071 (31.1); 2.5043 (18.7); 2.4317 (0.5); 2.3969 (0.4); 2.3939 (0.5); 2.3909 (0.5); 2.1120 (0.4); 2.0801 (16.0); 1.2278 (0.4); −0.0002 (10.0); −0.0051 (1.7) |
| II.089: $^1$H-NMR (400.1 MHz, CDCl3): |
| δ = 7.2615 (2.7); 4.4011 (2.8); 4.3833 (7.9); 4.3656 (8.0); 4.3478 (3.0); 1.5469 (2.2); 1.3979 (8.3); 1.3801 (16.0); 1.3624 (8.4); −0.0002 (3.6) |
| II.090: $^1$H-NMR (600.4 MHz, $d_6$-DMSO): |
| δ = 8.1820 (9.3); 4.3456 (2.4); 4.3338 (7.5); 4.3219 (7.6); 4.3101 (2.6); 3.3065 (14.3); 2.5232 (0.4); 2.5201 (0.4); 2.5169 (0.5); 2.5082 (7.8); 2.5052 (15.8); 2.5021 (21.6); 2.4991 (15.7); 2.4961 (7.3); 1.3638 (0.7); 1.3525 (0.7); 1.3420 (0.3); 1.3096 (7.8); 1.2977 (16.0); 1.2912 (0.7); 1.2859 (7.7); −0.0001 (1.7) |
| II.091: $^1$H-NMR (600.2 MHz, $d_6$-DMSO): |
| δ = 4.3543 (2.3); 4.3424 (7.5); 4.3306 (7.5); 4.3188 (2.4); 3.3201 (2.6); 2.5135 (0.7); 2.5105 (1.6); 2.5075 (2.2); 2.5044 (1.6); 2.5014 (0.7); 1.3167 (7.7); 1.3049 (16.0); 1.2930 (7.7) |
| II.092: $^1$H-NMR (600.2 MHz, $d_6$-DMSO): |
| δ = 4.3981 (2.4); 4.3863 (7.5); 4.3744 (7.6); 4.3626 (2.5); 3.3205 (3.1); 2.5135 (0.9); 2.5105 (1.8); 2.5075 (2.5); 2.5046 (1.8); 2.5016 (0.9); 1.3397 (7.8); 1.3278 (16.0); 1.3160 (7.7) |
| II.093: $^1$H-NMR (600.2 MHz, $d_6$-DMSO): |
| δ = 4.3599 (2.4); 4.3480 (7.6); 4.3362 (7.7); 4.3244 (2.5); 3.3206 (3.4); 2.5135 (1.1); 2.5106 (2.2); 2.5076 (3.0); 2.5046 (2.2); 2.5016 (1.0); 1.3219 (7.8); 1.3100 (16.0); 1.2982 (7.8); 1.0474 (0.4); 1.0373 (0.4) |
| II.094: $^1$H-NMR (600.2 MHz, $d_6$-DMSO): |
| δ = 14.4097 (0.4); 14.3923 (0.4); 14.3334 (0.5); 14.2927 (0.7); 14.2584 (0.9); 14.0297 (4.3); 13.6920 (0.5); 13.5701 (0.3); 7.7017 (2.2); 7.2651 (0.5); 7.2626 (0.5); 7.2528 (1.0); 7.2403 (0.7); 7.1832 (0.9); 7.1712 (0.8); 7.1611 (0.4); 7.1487 (0.4); 4.0758 (10.8); 3.8483 (0.3); 3.7987 (0.6); 3.7873 (0.4); 3.7770 (0.4); 3.7670 (0.4); 3.6922 (0.6); 3.6432 (0.7); 3.6266 (0.9); 3.3385 (16.0); 3.1497 (1.5); 3.1238 (1.2); 3.0626 (0.7); 2.9304 (0.5); 2.9043 (0.4); 2.6228 (1.1); 2.6197 (1.4); 2.6167 (1.1); 2.6137 (0.6); 2.5969 (0.4); 2.5859 (0.3); 2.5470 (0.7); 2.5439 (0.8); 2.5283 (2.7); 2.5252 (3.6); 2.5136 (80.1); 2.5107 (164.4); 2.5077 (223.0); 2.5047 (161.3); 2.5018 (75.2); 2.4887 (0.5); 2.3976 (0.5); 2.3946 (0.9); 2.3916 (1.2); 2.3886 (0.9); 2.3043 (3.5); 2.0910 (0.6); 2.0234 (0.9); 1.9142 (2.3); 1.5803 (0.4); 1.4169 (0.7); 1.3564 (0.4); 1.3474 (0.8); 1.3421 (0.7); 1.3310 (1.8); 1.3191 (0.4); 1.3046 (0.4); 1.2824 (0.3); 1.2663 (0.4); 1.2531 (0.7); 1.2404 (2.1); 1.2360 (2.3); 1.2007 (0.5); 1.1834 (0.5); 1.1791 (0.5); 1.1760 (0.8); 1.1681 (0.5); 1.1527 (0.3); 1.1317 (2.8); 1.1159 (0.7); 1.1121 (0.4); 1.1026 (0.4); 1.0517 (0.4); 1.0471 (1.3); 1.0370 (1.3); 1.0242 (0.4); 0.9783 (0.3); 0.8897 (2.4); 0.8571 (0.4); 0.8245 (0.4) |
| II.095: $^1$H-NMR (500.1 MHz, CDCl3): |
| δ = 7.2639 (2.2); 3.9377 (16.0); 1.5602 (3.0); −0.0002 (2.9) |
| II.096: $^1$H-NMR (500.1 MHz, CDCl3): |
| δ = 7.2636 (2.0); 3.9758 (16.0); 1.5588 (2.5); −0.0002 (2.6) |
| II.097: $^1$H-NMR (500.1 MHz, $d_6$-DMSO): |
| δ = 14.4869 (1.5); 10.0224 (3.2); 10.0182 (0.8); 8.7273 (0.4); 8.3556 (0.6); 7.8977 (4.2); 7.1906 (1.3); 7.0884 (1.5); 6.9862 (1.3); 5.7669 (0.6); 5.0559 (0.6); 4.6994 (0.7); 4.4649 (1.1); 4.4532 (1.2); 4.0468 (1.3); 4.0326 (3.7); 4.0184 (3.8); 4.0042 (1.3); 3.9027 (10.8); 3.8845 (5.5); 3.8751 (2.5); 3.8581 (1.3); 3.8437 (8.1); 3.8334 (5.6); 3.8156 (1.6); 3.7823 (1.5); 3.7661 (0.6); 3.7240 (0.6); 3.4471 (0.4); 3.4330 (0.4); 3.1700 (0.5); 2.7007 (0.4); 2.6399 (0.5); 2.5439 (0.6); 2.5119 (28.9); 2.5084 (59.2); 2.5049 (80.4); 2.5013 (59.3); 2.4979 (29.4); 2.4543 (1.1); 2.4424 (0.9); 2.4205 (0.8); 2.4056 (0.7); 2.3934 (0.9); 2.3660 (0.6); 2.0732 (0.4); 1.9856 (16.0); 1.9086 (2.1); 1.3173 (0.5); 1.2160 (1.2); 1.1867 (4.4); 1.1725 (8.6); 1.1583 (4.3); 1.0685 (0.4); 1.0544 (0.7); 1.0405 (0.4) |
| II.098: $^1$H-NMR (500.1 MHz, $d_6$-DMSO): |
| δ = 15.1437 (0.3); 15.1006 (0.3); 15.0263 (0.4); 14.9872 (0.5); 14.8822 (0.7); 14.8323 (0.8); 14.7366 (1.1); 14.6574 (1.4); 14.6350 (1.6); 14.2900 (5.0); 14.2744 (5.1); 14.2501 (5.0); 14.2381 (4.9); 14.1687 (4.4); 13.9707 (2.3); 13.8844 (1.7); 13.8356 (1.5); 13.6966 (1.0); 13.6746 (1.0); 13.6660 (0.9); 13.6087 (0.8); 13.5265 (0.7); 13.5020 (0.6); 13.4797 (0.6); 13.4623 (0.6); 13.4379 (0.5); 13.4190 (0.5); 13.3927 (0.5); 13.3138 (0.4); 13.2826 (0.4); 13.2419 (0.4); 13.2324 (0.4); 13.2077 (0.4); 13.1892 (0.4); 13.0686 (0.3); 9.8521 (4.0); 9.7984 (0.4); 8.8342 (16.0); 7.9835 (3.4); 7.9449 (1.9); 7.8689 (3.4); 7.8545 (3.6); 7.8523 (3.4); 7.6042 (0.7); 7.5894 (1.8); 7.5744 (1.2); 7.4608 (2.3); 7.4451 (3.6); 7.4300 (2.2); 7.4150 (0.6); 7.1119 (0.5); 7.0096 (0.6); 6.9076 (0.5); 5.2665 (2.5); 5.2358 (8.0); 5.2134 (0.3); 4.6128 (1.2); 4.3435 (9.2); 4.3034 (0.3); 4.2016 (1.7); 4.1014 (1.3); 3.9526 (0.5); 3.9383 (0.6); 3.9243 (0.3); 3.8169 (0.4); 3.8012 (0.4); 3.7923 (0.4); 3.7838 (0.4); 3.7652 (0.5); 3.7555 (0.4); 3.7389 (0.4); 3.7198 (0.4); 3.7043 (0.5); 3.6914 (0.6); 3.6786 (0.4); 3.6570 (0.4); 3.6424 (0.5); 3.6275 (0.4); 3.5837 (0.8); 3.5403 (0.4); 3.5252 (1.4); 3.4538 (0.3); 3.4303 (0.3); 3.4175 (0.3); 3.3971 (0.3); 3.3897 (0.3); 3.3656 (0.4); 3.3513 (0.4); 3.3377 (0.4); 3.3054 (0.4); 3.2988 (0.4); 3.0873 (0.4); 2.7048 (7.5); 2.5559 (0.7); 2.4246 (115.9); 2.4211 (164.5); 2.4176 (129.2); 2.3371 (1.0); 2.2853 (1.2); 2.2823 (1.5); 2.2140 (0.4); 2.1695 (0.7); 2.1339 (0.4); 2.1252 (0.3); 2.1030 (0.6); 1.9909 (0.8); 1.9049 (1.9); 1.8859 (0.7); 1.8266 (0.9); 1.8077 (0.4); 1.6766 (0.3); 1.4305 (0.4); 1.1418 (2.3); 1.1063 (0.6); 1.0919 (1.0); 1.0838 (0.6); 1.0774 (0.5); 0.7670 (0.4); −0.0002 (0.8) |
| II.099: $^1$H-NMR (499.9 MHz, $d_6$-DMSO): |
| δ = 7.9887 (0.4); 7.9740 (0.4); 7.8647 (7.5); 7.7575 (16.0); 7.6778 (0.5); 7.6504 (8.1); 7.5727 (0.4); 5.6764 (0.5); 5.6698 (0.4); 4.8024 (0.5); 3.9555 (0.3); 3.9083 (1.0); 3.8996 (1.0); 2.5573 (13.4); 2.0409 (0.5); 1.4075 (1.7); 1.2794 (1.5); 1.2279 (2.5); 0.9018 (0.4); 0.8885 (0.4); 0.8165 (0.9); −0.0002 (0.6) |
| II.100: $^1$H-NMR (500.1 MHz, $d_6$-DMSO): |
| δ = 14.0085 (0.4); 8.0312 (16.0); 2.5121 (1.2); 2.5088 (2.4); 2.5053 (3.3); 2.5017 (2.4) |
| II.101: $^1$H-NMR (500.1 MHz, $d_6$-DMSO): |
| δ = 13.5779 (16.0); 4.9734 (0.5); 2.5520 (1.9); 2.5042 (12.9); 2.4235 (313.6); 2.2915 (2.0); 1.2126 (0.3) |

TABLE A-(II)-continued

| NMR peak lists of compounds according to formula (II) |
|---|
| II.102: ¹H-NMR (500.1 MHz, $d_6$-DMSO):<br>δ = 13.5655 (16.0); 7.7340 (0.4); 7.7306 (0.4); 7.3491 (0.4); 7.3449 (0.4); 7.2560 (0.5); 7.2418 (0.4); 7.1739 (0.6); 7.1696 (0.4); 7.1579 (0.4); 7.1530 (0.4); 6.9962 (0.8); 6.9921 (0.8); 6.7493 (0.4); 6.7451 (0.4); 5.7531 (0.7); 4.9088 (2.4); 4.8761 (0.3); 3.4117 (0.4); 3.4013 (0.4); 3.3834 (0.4); 2.5845 (4.2); 2.5124 (14.0); 2.5089 (30.2); 2.5054 (42.3); 2.5018 (32.0); 2.4984 (16.4); 2.4798 (1.4); 2.4766 (2.0); 2.4562 (796.1); 2.4388 (6.6); 2.4343 (3.9); 2.4307 (3.1); 2.4283 (3.1); 2.4188 (4.1); 2.3931 (0.6); 2.3699 (0.6); 2.3665 (0.6); 2.3547 (0.6); 2.3243 (4.6); 2.1836 (0.4); 1.5771 (0.4); 1.3566 (2.4); 1.3360 (0.4); 1.3208 (0.4); 1.2998 (0.3); 1.2971 (0.3); 1.2857 (0.5); 1.2712 (0.4); 1.2651 (0.6); 1.2354 (2.2); 1.2298 (3.6); 1.2127 (1.0); 1.1997 (0.5); 1.1881 (0.4); 1.1784 (0.8); 1.1685 (0.5); 1.1648 (0.7); 1.1546 (0.4); 1.1286 (0.4); 0.8651 (0.5); 0.8522 (1.0); 0.8381 (0.6) |
| II.103: ¹H-NMR (500.1 MHz, $d_6$-DMSO):<br>δ = 4.0517 (1.2); 4.0375 (3.7); 4.0233 (3.7); 4.0090 (1.2); 2.5123 (3.4); 2.5088 (7.6); 2.5052 (10.7); 2.5016 (8.0); 2.4981 (3.9); 1.9895 (16.0); 1.1910 (4.3); 1.1767 (8.5); 1.1625 (4.2) |
| II.104: ¹H-NMR (500.1 MHz, $d_6$-DMSO):<br>δ = 8.2516 (1.0); 7.9558 (1.0); 7.4158 (0.4); 7.3991 (0.4); 7.3701 (0.4); 7.2692 (0.4); 7.2517 (0.4); 7.2054 (3.0); 7.1032 (3.3); 7.0011 (2.8); 4.7508 (2.2); 4.7423 (0.4); 4.7317 (0.8); 3.6412 (0.4); 3.6278 (0.4); 3.5122 (0.8); 3.4645 (0.8); 3.4505 (2.1); 3.4365 (2.1); 3.4226 (0.7); 3.1726 (9.9); 2.9397 (0.6); 2.9287 (0.5); 2.9145 (0.4); 2.8942 (6.0); 2.8295 (2.7); 2.7346 (5.4); 2.5570 (1.0); 2.5452 (4.1); 2.5091 (80.6); 2.5059 (108.7); 2.5026 (86.7); 2.3672 (0.7); 2.1801 (0.4); 2.0760 (0.4); 1.8732 (0.5); 1.4726 (0.3); 1.4359 (0.6); 1.3542 (0.4); 1.3374 (1.1); 1.2990 (4.5); 1.2594 (6.5); 1.2288 (16.0); 1.1799 (3.3); 1.1653 (4.4); 1.1507 (2.8); 1.0722 (2.6); 1.0582 (4.7); 1.0442 (2.8); 0.9787 (0.5); 0.9291 (0.4); 0.9141 (0.4); 0.8999 (0.3); 0.8927 (0.4); 0.8521 (3.0); 0.8378 (2.5); 0.8254 (1.9); 0.6668 (0.5) |
| II.001: ¹³C-NMR (125.7 MHz, $d_6$-DMSO):<br>δ = 159.9021 (1.7); 129.9298 (1.3); 129.7010 (0.9); 116.6561 (1.6); 112.5165 (1.7); 40.4974 (15.0); 40.3303 (46.2); 40.1632 (91.6); 39.9963 (107.1); 39.8297 (91.5); 39.6627 (46.0); 39.4955 (14.6) |
| II.002: 13C-NMR (125.7 MHz, $d_6$-DMSO):<br>δ = 159.9409 (1.8); 144.3263 (1.0); 129.0108 (0.6); 128.3300 (0.4); 113.8109 (1.1); 111.4686 (1.4); 100.3081 (0.2); 40.5949 (0.6); 40.5041 (15.0); 40.4287 (1.8); 40.3370 (46.5); 40.2615 (3.5); 40.1699 (92.9); 40.0027 (109.0); 39.8358 (92.2); 39.6691 (46.2); 39.5021 (15.1) |
| II.003: ¹³C-NMR (125.7 MHz, $d_6$-DMSO):<br>δ = 161.0011 (15.0); 134.5673 (3.3); 134.3736 (7.8); 134.1782 (4.0); 133.4944 (3.3); 133.4345 (5.5); 133.3723 (2.9); 131.2402 (10.7); 123.3997 (14.5); 110.7964 (7.8); 108.9185 (13.5); 107.0403 (6.7); 40.4806 (47.0); 40.3135 (141.0); 40.1464 (278.9); 39.9793 (326.2); 39.8122 (275.7); 39.6454 (137.0); 39.4787 (45.5) |
| II.004: ¹³C-NMR (125.7 MHz, $d_6$-DMSO):<br>δ = 160.0437 (0.6); 121.2846 (0.2); 119.3458 (0.3); 119.1100 (0.2); 113.7084 (0.3); 96.5085 (0.2); 89.9694 (0.2); 40.5965 (0.6); 40.5053 (15.0); 40.4296 (1.8); 40.3381 (46.1); 40.2629 (3.5); 40.1710 (92.0); 40.0040 (107.6); 39.8373 (91.6); 39.6704 (46.2); 39.5033 (15.2) |
| II.005: ¹³C-NMR (125.7 MHz, CDCl3):<br>δ = 164.9498 (0.7); 164.9224 (0.7); 159.9425 (0.5); 157.7452 (0.5); 136.3772 (0.4); 136.3303 (0.4); 123.0205 (0.1); 122.8222 (0.1); 119.7782 (0.1); 117.4326 (0.3); 117.3499 (0.4); 109.5780 (0.1); 108.3307 (0.1); 107.9284 (0.5); 107.7126 (0.5); 106.8733 (0.1); 83.2954 (14.5); 83.0356 (15.0); 82.7758 (14.4); 45.3631 (1.4); 45.1957 (4.4); 45.0284 (8.7); 44.8610 (10.2); 44.6938 (8.7); 44.5268 (4.4); 44.3597 (1.4); 4.9314 (0.2) |
| II.006: ¹³C-NMR (125.7 MHz, $d_6$-DMSO):<br>δ = 161.0482 (12.6); 138.6053 (2.0); 136.2408 (2.2); 136.0477 (4.3); 135.8529 (1.8); 119.8181 (8.7); 113.5742 (15.0); 110.6800 (5.4); 108.8019 (10.3); 106.9248 (5.0); 40.4931 (49.0); 40.4145 (7.0); 40.3264 (149.6); 40.2499 (12.8); 40.1595 (299.2); 39.9925 (353.7); 39.8253 (301.4); 39.6582 (150.4); 39.4912 (48.3) |
| II.007: ¹³C-NMR (150.9 MHz, $d_6$-DMSO):<br>δ = 161.9937 (7.9); 146.1377 (6.9); 131.1650 (3.6); 128.6514 (4.5); 117.9119 (4.8); 113.8668 (5.6); 40.5271 (1.1); 40.4084 (30.8); 40.2696 (93.7); 40.1304 (185.0); 39.9909 (217.2); 39.8517 (187.4); 39.7127 (94.7); 39.5739 (31.0); 15.0858 (15.0) |
| II.008: ¹³C-NMR (125.7 MHz, $d_6$-DMSO):<br>δ = 161.9827 (10.7); 145.2139 (9.0); 142.9724 (7.0); 128.5399 (5.2); 114.7729 (6.5); 112.7240 (7.4); 40.4735 (7.0); 40.3064 (21.2); 40.1392 (42.2); 39.9720 (49.4); 39.8050 (41.7); 39.6383 (20.7); 39.4712 (6.7); 30.8590 (0.2); 15.0648 (15.0) |
| II.009: ¹³C-NMR (125.8 MHz, $d_6$-DMSO):<br>δ = 160.0420 (15.0); 160.0183 (13.6); 153.7111 (10.1); 151.5079 (10.4); 117.8683 (8.4); 117.6783 (8.2); 115.7053 (9.5); 115.6736 (9.6); 115.0854 (7.2); 115.0091 (7.3); 40.4909 (37.4); 40.4172 (4.8); 40.3240 (113.4); 40.2486 (8.8); 40.1574 (226.8); 39.9904 (268.7); 39.8234 (229.8); 39.6563 (115.0); 39.4890 (37.6) |
| II.010: ¹³C-NMR (125.7 MHz, $d_6$-DMSO):<br>δ = 160.2808 (14.2); 133.6011 (1.5); 129.8260 (1.2); 128.9887 (7.4); 127.6934 (11.5); 127.5864 (14.7); 118.6579 (1.0); 118.1230 (1.1); 115.7487 (15.0); 40.4860 (30.0); 40.3192 (91.4); 40.1523 (182.1); 39.9852 (214.9); 39.8181 (183.1); 39.6510 (92.1); 39.4844 (30.7) |
| II.011: ¹³C-NMR (125.7 MHz, $d_6$-DMSO):<br>δ = 160.4160 (9.0); 134.1140 (0.2); 132.0844 (4.9); 131.4222 (0.2); 130.7033 (0.2); 129.1881 (0.2); 128.5758 (4.7); 124.5141 (0.3); 121.1172 (0.3); 120.8287 (0.3); 118.7157 (5.0); 118.0870 (6.8); 117.7414 (0.3); 115.9362 (0.2); 111.1229 (0.2); 109.3338 (0.2); 108.8472 (0.2); 108.2760 (0.2); 105.9611 (0.2); 103.6653 (0.2); 40.5912 (0.6); 40.5008 (15.0); 40.4247 (1.7); 40.3340 (46.0); 40.2587 (3.3); 40.1672 (92.8); 40.0001 (110.0); 39.8330 (93.8); 39.6658 (46.9); 39.4988 (15.2) |
| II.012: ¹³C-NMR (125.7 MHz, $d_6$-DMSO):<br>δ = 160.2594 (2.0); 131.8358 (1.3); 129.7592 (1.1); 126.8913 (0.8); 115.4362 (1.5); 115.0114 (0.4); 40.5009 (15.0); 40.4254 (2.3); 40.3342 (45.1); 40.2561 (4.0); 40.1673 (90.2); 40.0003 (106.3); 39.8331 (90.3); 39.6660 (44.7); 39.4989 (14.2) |
| II.013: ¹³C-NMR (150.9MHz, $d_6$-DMSO):<br>δ = 160.7352 (3.8); 160.7122 (2.8); 155.5973 (2.5); 153.7888 (2.4); 140.6843 (3.7); 140.6628 (3.0); 111.0349 (1.8); 110.9705 (1.6); 101.1943 (2.5); 101.0213 (2.8); 40.5264 (1.6); 40.4079 (39.3); 40.2690 (118.9); 40.1296 (234.2); 39.9902 (278.4); 39.8511 (239.7); 39.7122 (120.7); 39.5733 (39.1); 16.1197 (15.0) |
| II.014: ¹³C-NMR (125.7 MHz, $d_6$-DMSO):<br>δ = 162.3982 (7.3); 143.6350 (4.9); 130.4654 (4.7); 127.1999 (3.8); 126.4694 (0.4); 116.5489 (5.7); 40.5640 (0.9); 40.4729 (4.7); 40.3963 (1.8); 40.3058 (14.7); 40.2293 (3.0); 40.1387 (29.3); 40.0619 (2.8); 39.9715 (34.5); 39.8954 (2.1); 39.8043 (29.2); 39.6374 (14.5); 39.4710 (4.7); 16.4461 (15.0); 14.7478 (0.6) |
| II.015: ¹³C-NMR (125.7 MHz, $d_6$-DMSO):<br>δ = 162.8677 (0.3); 162.4114 (9.8); 142.1930 (7.6); 129.2171 (11.7); 114.6974 (6.5); 40.5498 (0.9); 40.4577 (6.1); 40.3823 (2.5); 40.2907 (19.1); 40.2155 (4.5); 40.1235 (38.5); 39.9564 (45.4); 39.7893 (38.6); 39.6226 (19.4); 39.4557 (6.6); 14.8985 (15.0); 14.7254 (0.6); 14.5346 (0.4); 13.8684 (0.7) |

TABLE A-(II)-continued

| NMR peak lists of compounds according to formula (II) |
|---|
| II.016: $^{13}$C-NMR (125.7 MHz, $d_6$-DMSO):<br>δ = 162.0363 (2.0); 141.2924 (4.0); 137.0218 (4.6); 136.0869 (0.8); 112.5179 (6.9); 107.8735 (5.5); 60.2165 (0.4); 40.4998 (15.0); 40.4216 (2.0); 40.3329 (45.6); 40.2548 (3.5); 40.1661 (90.6); 39.9992 (107.2); 39.8321 (91.5); 39.6649 (45.8); 39.4978 (14.8); 21.2275 (0.3); 14.5545 (0.4); 13.9938 (13.8) |
| II.017: $^{13}$C-NMR (150.9 MHz, $d_6$-DMSO):<br>δ = 162.3329 (8.5); 143.9318 (7.9); 133.9216 (4.2); 125.3097 (7.5); 88.8892 (6.5); 40.5300 (2.6); 40.4102 (63.6); 40.2714 (196.7); 40.1326 (391.6); 39.9936 (456.1); 39.8543 (382.6); 39.7148 (192.5); 39.5756 (63.5); 17.0811 (15.0) |
| II.018: $^{13}$C-NMR (150.9MHz, $d_6$-DMSO):<br>δ = 162.3752 (8.8); 147.8529 (7.4); 130.2984 (4.3); 121.9164 (6.7); 99.5351 (8.8); 40.5296 (2.3); 40.4104 (49.4); 40.2716 (151.8); 40.1328 (302.1); 39.9938 (352.6); 39.8547 (295.7); 39.7151 (148.0); 39.5759 (48.6); 20.0279 (15.0) |
| II.019: 13C-NMR (125.7 MHz, CDCl3):<br>δ = 159.1507 (3.7); 135.9804 (1.8); 131.7962 (1.6); 131.5064 (1.3); 122.8446 (0.8); 120.6656 (1.8); 119.2338 (4.6); 118.4851 (2.0); 114.1254 (2.5); 77.2713 (140.0); 77.0172 (139.1); 76.7624 (137.7); 53.5183 (15.0); −0.0022 (2.3) |
| II.020: $^{13}$C-NMR (125.7 MHz, $d_6$-DMSO):<br>δ = 159.0611 (3.0); 159.0313 (2.6); 154.1957 (2.7); 151.9785 (2.9); 118.0800 (2.3); 117.8951 (2.3); 116.7104 (3.1); 116.6791 (2.9); 113.2894 (2.0); 113.2141 (1.9); 53.3332 (15.0); 40.5026 (15.0); 40.4273 (2.0); 40.3357 (46.8); 40.1686 (94.2); 40.0014 (111.0); 39.8344 (94.3); 39.6674 (47.1); 39.5007 (15.5) |
| II.021: $^{13}$C-NMR (150.9 MHz, CDCl3):<br>δ = 171.2164 (3.0); 158.8457 (6.4); 131.9519 (4.5); 128.4512 (6.7); 128.3985 (3.4); 117.5981 (4.1); 111.3306 (5.7); 77.2351 (204.0); 77.0229 (215.0); 76.8108 (202.2); 54.1964 (7.6); 53.5006 (5.7); 53.0624 (15.0); 45.7020 (8.7); 26.7752 (7.8); −0.0018 (2.1) |
| II.022: $^{13}$C-NMR (125.7 MHz, $d_6$-DMSO):<br>δ = 158.8604 (1.6); 145.1471 (1.3); 130.0648 (1.1); 125.9965 (1.4); 113.9091 (1.5); 111.3388 (2.0); 101.0344 (0.2); 95.4975 (0.1); 92.4967 (0.1); 53.7113 (4.6); 40.5904 (0.6); 40.4992 (15.0); 40.4240 (1.9); 40.3322 (46.0); 40.2593 (3.7); 40.1654 (91.4); 39.9986 (108.4); 39.8315 (92.8); 39.6644 (46.6); 39.4972 (15.2) |
| II.023: $^{13}$C-NMR (125.7 MHz, CDCl3):<br>δ = 159.9331 (3.2); 136.6395 (1.3); 136.4410 (2.4); 136.2435 (1.3); 132.6288 (2.5); 131.3835 (0.5); 130.2287 (0.5); 129.5457 (0.5); 129.0705 (1.1); 129.0119 (2.0); 128.9565 (1.0); 124.9570 (4.0); 124.7052 (0.6); 110.0932 (4.1); 108.2024 (8.3); 106.3105 (3.4); 77.2722 (71.9); 77.0184 (72.2); 76.7638 (69.2); 53.1496 (15.0); 50.8956 (1.3); −0.0102 (1.0) |
| II.024: $^{13}$C-NMR (150.9 MHz, CDCl3):<br>δ = 159.9113 (0.6); 159.8860 (0.9); 156.5155 (0.8); 154.6816 (0.7); 140.0779 (1.1); 140.0557 (1.0); 109.9068 (0.6); 109.8399 (0.6); 101.4264 (1.0); 101.2567 (0.8); 77.2275 (87.0); 77.0150 (88.0); 76.8040 (82.4); 71.3078 (7.0); 27.8225 (6.4); 19.0139 (15.0); 16.0754 (3.1); −0.0038 (1.1) |
| II.025: $^{13}$C-NMR (125.7 MHz, $d_6$-DMSO):<br>δ = 168.0735 (6.5); 158.1758 (3.9); 131.6128 (3.8); 129.7635 (2.6); 125.7596 (3.7); 122.8079 (3.1); 62.2787 (11.0); 52.7002 (10.9); 40.5002 (15.0); 40.3332 (45.1); 40.1666 (89.6); 39.9997 (105.8); 39.8326 (90.4); 39.6654 (45.2); 39.4984 (14.7) |
| II.026: $^{13}$C-NMR (150.9 MHz, $d_6$-DMSO):<br>δ = 159.3362 (8.6); 132.8462 (5.3); 126.4950 (4.6); 119.8344 (8.5); 118.4093 (7.8); 53.4665 (15.0); 40.5319 (1.4); 40.4135 (35.6); 40.2740 (109.2); 40.1349 (220.3); 39.9960 (261.6); 39.8571 (222.8); 39.7182 (110.8); 39.5790 (35.8) |
| II.027: $^{13}$C-NMR (125.7 MHz, CDCl3):<br>δ = 159.5351 (5.2); 133.0581 (4.2); 131.7211 (3.3); 124.1074 (3.9); 115.2118 (4.8); 77.2777 (74.5); 77.0228 (76.0); 76.7688 (76.9); 52.7010 (15.0); 0.0013 (1.0) |
| II.028: $^{13}$C-NMR (150.9 MHz, CDCl3):<br>δ = 160.8806 (3.9); 146.3596 (5.5); 144.1241 (4.2); 126.1227 (4.5); 115.0166 (4.4); 112.1280 (5.8); 77.2339 (114.8); 77.0225 (122.9); 76.8100 (118.6); 52.5658 (15.0); 15.1760 (10.3); −0.0039 (1.5) |
| II.029: $^{13}$C-NMR (125.7 MHz, $d_6$-DMSO):<br>δ = 160.7673 (7.0); 147.0740 (6.8); 129.5685 (5.6); 128.9325 (4.6); 117.9341 (5.8); 113.7211 (5.3); 53.2591 (15.0); 40.4132 (11.7); 40.2460 (36.0); 40.1700 (3.6); 40.0788 (71.9); 39.9119 (84.1); 39.7452 (71.2); 39.5784 (35.9); 39.4113 (11.7); 15.2619 (13.8) |
| II.030: $^{13}$C-NMR (125.7 MHz, $d_6$-DMSO):<br>δ = 160.6906 (6.7); 144.5416 (7.4); 132.2869 (4.9); 125.4387 (6.4); 89.7635 (4.8); 61.7045 (13.9); 46.2454 (0.7); 40.5241 (6.9); 40.3571 (21.0); 40.2793 (1.6); 40.1903 (42.3); 40.0232 (50.2); 39.8560 (42.7); 39.6889 (21.3); 39.5218 (6.9); 20.2100 (0.2); 17.2273 (13.8); 14.5348 (15.0) |
| II.031: $^{13}$C-NMR (125.7 MHz, $d_6$-DMSO):<br>δ = 160.7296 (6.1); 148.5946 (5.6); 128.6438 (5.2); 122.6386 (5.7); 99.7356 (4.7); 61.8030 (12.2); 61.7226 (0.4); 46.1583 (0.4); 40.5209 (10.6); 40.3538 (32.7); 40.1867 (64.8); 40.0197 (75.9); 39.8530 (64.7); 39.6861 (32.4); 39.5190 (10.6); 20.2178 (14.4); 14.5407 (15.0) |
| II.032: $^{13}$C-NMR (125.7 MHz, CDCl3):<br>δ = 161.1717 (4.5); 144.6707 (4.8); 139.5389 (0.7); 138.4676 (0.7); 136.6905 (0.8); 135.7735 (0.9); 133.8306 (0.7); 131.9330 (3.5); 129.5724 (0.7); 128.2595 (0.7); 125.5234 (1.6); 125.0396 (3.6); 116.2480 (4.8); 77.2693 (113.4); 77.0147 (114.2); 76.7606 (114.4); 61.3877 (13.1); 34.2325 (1.1); 30.3290 (5.1); 21.1880 (0.7); 16.4914 (12.3); 14.7863 (0.6); 14.2671 (15.0); −0.0029 (1.8) |
| II.033: $^{13}$C-NMR (125.7 MHz, CDCl3):<br>δ = 161.1917 (4.6); 143.1995 (5.6); 133.7833 (0.2); 129.8355 (3.9); 127.3731 (3.2); 126.0256 (0.2); 114.8630 (5.0); 77.2778 (35.2); 77.0240 (35.3); 76.7695 (33.9); 61.3513 (13.7); 29.7118 (0.4); 14.9386 (10.8); 14.2621 (15.0); −0.0038 (0.7) |
| II.034: $^{13}$C-NMR (125.7 MHz, $d_6$-DMSO):<br>δ = 161.2398 (3.7); 142.0639 (2.3); 135.7512 (3.8); 132.4717 (7.0); 112.1522 (2.6); 110.2919 (2.8); 102.5177 (0.2); 101.7440 (0.2); 99.5908 (0.2); 40.5923 (0.7); 40.5005 (15.0); 40.4258 (1.9); 40.3337 (45.8); 40.2581 (3.5); 40.1669 (92.1); 39.9999 (109.1); 39.8328 (93.0); 39.6656 (46.5); 39.4985 (15.1) |
| II.035: $^{13}$C-NMR (125.7 MHz, $d_6$-DMSO):<br>δ = 163.7525 (3.0); 162.2293 (5.0); 162.2096 (4.0); 161.4256 (3.6); 137.1146 (0.4); 132.7738 (15.0); 123.8819 (3.2); 123.8642 (3.6); 93.9505 (4.1); 93.8364 (3.8); 40.4884 (11.6); 40.3213 (35.9); 40.2441 (2.8); 40.1542 (71.7); 39.9870 (84.3); 39.8200 (71.2); 39.6532 (35.3); 39.4865 (11.5) |
| II.036: $^{13}$C-NMR (125.8 MHz, $d_6$-DMSO):<br>δ = 161.1316 (5.5); 142.6573 (3.6); 135.0417 (9.8); 122.7474 (6.0); 113.0971 (4.9); 112.5911 (4.4); 40.5044 (15.0); 40.3374 (45.9); 40.1703 (90.8); 40.0036 (106.3); 39.8369 (91.4); 39.6699 (46.1); 39.5030 (15.0) |
| II.037: $^{13}$C-NMR (125.7 MHz, $d_6$-DMSO):<br>δ = 161.8087 (7.0); 161.7875 (7.2); 154.3260 (6.3); 152.2449 (6.5); 130.0679 (4.9); 130.0145 (5.2); 122.6455 (15.0); 122.4588 (12.4); 119.8456 (0.6); 118.1683 (0.6); 115.3480 (4.6); 115.2020 (4.5); 40.4896 (25.3); 40.4133 (2.8); 40.3225 (78.9); 40.2470 (5.8); 40.1553 (157.9); 39.9883 (184.9); 39.8215 (156.3); 39.6547 (79.0); 39.4876 (25.8) |

TABLE A-(II)-continued

| NMR peak lists of compounds according to formula (II) |
| --- |
| II.038: $^{13}$C-NMR (150.9 MHz, $d_6$-DMSO):<br>δ = 162.4532 (8.5); 136.7035 (5.2); 135.3458 (13.5); 131.2422 (4.1); 130.5094 (4.2); 40.5254 (0.9); 40.4064 (22.1); 40.2670 (66.9); 40.1277 (135.3); 39.9887 (160.8); 39.8498 (137.2); 39.7109 (68.2); 39.5718 (21.9); 19.2820 (0.5); 13.7143 (15.0) |
| II.039: $^{13}$C-NMR (150.9 MHz, $d_6$-DMSO):<br>δ = 161.8567 (9.4); 161.8417 (8.3); 156.2874 (6.5); 154.5640 (7.0); 133.3086 (7.1); 133.2638 (5.1); 122.7651 (13.3); 122.6008 (15.0); 99.8196 (6.5); 99.6740 (6.3); 40.5187 (2.2); 40.4011 (43.7); 40.2624 (132.4); 40.1234 (260.4); 39.9840 (302.1); 39.8446 (260.1); 39.7055 (131.7); 39.5666 (42.9); 29.2287 (0.8) |
| II.040: $^{13}$C-NMR (125.7 MHz, $d_6$-DMSO):<br>δ = 161.6248 (8.3); 135.6229 (5.2); 132.7131 (15.0); 129.7236 (0.2); 127.4113 (6.6); 125.3529 (0.2); 116.2562 (5.1); 115.3240 (0.2); 40.4855 (7.7); 40.3187 (22.9); 40.1520 (45.8); 39.9849 (54.1); 39.8177 (46.0); 39.6506 (22.9); 39.4835 (7.4) |
| II.041: $^{13}$C-NMR (125.7 MHz, $d_6$-DMSO):<br>δ = 161.3207 (0.5); 144.5544 (0.9); 133.4622 (1.5); 112.9568 (1.6); 111.6103 (1.5); 107.0650 (0.2); 102.5634 (0.2); 40.5962 (0.6); 40.5040 (15.0); 40.4292 (1.8); 40.3369 (46.5); 40.2628 (3.7); 40.1697 (93.2); 40.0026 (109.2); 39.8356 (92.4); 39.6689 (46.3); 39.5020 (15.3) |
| II.042: $^{13}$C-NMR (125.7 MHz, $d_6$-DMSO):<br>δ = 161.9134 (3.8); 143.4920 (3.6); 135.4388 (2.2); 126.6549 (3.8); 119.7392 (0.4); 113.4438 (3.5); 110.3141 (3.5); 40.5014 (15.0); 40.4252 (1.7); 40.3348 (46.2); 40.2603 (3.4); 40.1678 (93.1); 40.0007 (110.0); 39.8335 (93.5); 39.6664 (46.6); 39.4995 (15.0); 16.7376 (0.4); 15.6592 (8.8) |
| II.043: $^{13}$C-NMR (125.7 MHz, $d_6$-DMSO):<br>δ = 162.1955 (0.1); 161.8924 (0.2); 161.8154 (0.1); 161.5027 (8.3); 134.8130 (15.0); 134.5942 (0.2); 133.6120 (6.4); 133.2880 (0.4); 133.2166 (0.4); 132.4356 (0.3); 132.3459 (0.6); 132.2641 (5.6); 131.7284 (0.1); 131.1197 (0.2); 130.1721 (0.1); 129.9287 (0.1); 128.7948 (0.2); 128.0157 (0.1); 124.7329 (0.1); 124.6324 (0.2); 122.0260 (0.1); 120.5108 (0.1); 119.1187 (0.1); 116.0174 (0.2); 112.0376 (6.8); 110.3759 (0.1); 109.9359 (0.1); 40.4027 (4.6); 40.2359 (13.2); 40.0690 (25.8); 39.9018 (30.1); 39.7348 (25.4); 39.5677 (12.8); 39.4011 (4.2) |
| II.044: $^{13}$C-NMR (125.7 MHz, $d_6$-DMSO):<br>δ = 160.1249 (5.3); 132.4631 (2.3); 130.7185 (4.9); 119.0884 (4.9); 116.8996 (4.0); 113.3215 (5.3); 40.9094 (0.4); 40.4974 (15.0); 40.4212 (2.0); 40.3302 (45.8); 40.2514 (3.5); 40.1630 (91.1); 39.9960 (106.4); 39.8292 (89.8); 39.6623 (45.1); 39.4953 (14.7) |
| II.045: $^{13}$C-NMR (125.7 MHz, CDCl3):<br>δ = 160.1223 (3.5); 145.9866 (3.4); 133.2642 (15.0); 132.6447 (4.5); 111.9775 (4.0); 111.7550 (3.9); 77.2714 (270.6); 77.0172 (268.0); 76.7624 (266.8); 53.0209 (13.0); −0.0020 (3.9) |
| II.046: $^{13}$C-NMR (125.7 MHz, $d_6$-DMSO):<br>δ = 160.2621 (6.2); 139.4989 (5.6); 135.9809 (6.8); 135.6815 (0.2); 133.3184 (0.2); 133.0903 (15.0); 111.9963 (5.2); 110.9379 (3.7); 108.3318 (0.1); 105.8185 (0.1); 104.8978 (0.1); 103.7139 (0.1); 98.7779 (0.1); 53.8651 (13.2); 40.5910 (0.6); 40.5000 (12.4); 40.4243 (1.5); 40.3330 (37.9); 40.2576 (2.9); 40.1663 (75.8); 39.9994 (89.8); 39.8322 (76.7); 39.6651 (38.4); 39.4980 (12.4) |
| II.048: $^{13}$C-NMR (125.7 MHz, CDCl3):<br>δ = 160.4075 (4.3); 140.3327 (0.3); 138.2894 (0.3); 135.5068 (0.3); 134.8948 (15.0); 133.7164 (3.6); 132.3932 (0.3); 131.4674 (4.2); 128.5447 (0.5); 111.5592 (3.8); 77.2818 (46.5); 77.0281 (48.2); 76.7743 (46.8); 61.8662 (13.0); 30.2064 (0.2); 29.7108 (0.4); 20.8391 (1.0); 14.2361 (13.2); −0.0008 (0.7) |
| II.049: $^{13}$C-NMR (150.9 MHz, CDCl3):<br>δ = 161.0596 (2.8); 161.0384 (2.2); 156.4177 (3.1); 154.6793 (3.2); 135.4601 (0.2); 131.0629 (2.0); 131.0150 (1.7); 122.2000 (7.0); 122.0340 (7.3); 100.2483 (3.0); 100.1028 (3.0); 77.2314 (69.1); 77.0206 (67.0); 76.8087 (69.9); 52.6355 (15.0); −0.0038 (1.2) |
| II.050: $^{13}$C-NMR (150.9 MHz, CDCl3):<br>δ = 160.4410 (2.0); 133.4469 (2.3); 132.5533 (5.0); 127.9928 (2.4); 116.3340 (2.0); 77.2228 (59.8); 77.0104 (59.2); 76.7998 (57.1); 71.6781 (8.0); 27.8232 (5.2); 19.0172 (15.0); −0.0039 (0.8) |
| II.051: $^{13}$C-NMR (150.9 MHz, $d_6$-DMSO):<br>δ = 161.1673 (0.3); 160.7688 (6.0); 145.1119 (0.4); 144.3538 (6.5); 133.1240 (5.0); 127.7403 (0.4); 126.8432 (5.9); 118.0114 (0.4); 113.2867 (4.3); 110.9881 (4.0); 53.5721 (9.9); 53.0008 (0.7); 40.5330 (0.8); 40.4145 (17.9); 40.2752 (53.8); 40.1358 (108.0); 39.9967 (128.8); 39.8578 (110.0); 39.7189 (55.0); 39.5799 (17.6); 16.9100 (0.6); 15.8362 (15.0) |
| II.052: $^{13}$C-NMR (125.7 MHz, $d_6$-DMSO):<br>δ = 160.1705 (3.5); 140.1190 (3.5); 135.6893 (9.4); 123.0282 (4.2); 117.4049 (0.3); 113.2259 (2.5); 112.9715 (2.9); 53.8508 (7.5); 40.5048 (15.0); 40.3377 (45.4); 40.1706 (90.0); 40.0036 (105.2); 39.8367 (89.2); 39.6698 (44.8); 39.5029 (14.8) |
| II.053: $^{13}$C-NMR (151.0 MHz, $d_6$-DMSO):<br>δ = 157.7775 (2.5); 137.6143 (2.0); 131.6154 (1.8); 126.6822 (1.8); 113.3421 (1.8); 111.4428 (2.3); 63.1532 (6.5); 40.2351 (3.0); 40.1153 (11.7); 39.9768 (34.5); 39.8380 (67.4); 39.6990 (78.8); 39.5600 (66.7); 39.4209 (33.4); 39.2819 (10.9); 13.9609 (7.0); 0.2519 (0.3) |
| II.054: $^{13}$C-NMR (125.8 MHz, $d_6$-DMSO):<br>δ = 239.9873 (0.2); 237.5861 (0.1); 159.0582 (2.4); 134.3090 (2.4); 128.3680 (3.1); 120.3007 (3.0); 112.8059 (2.8); 112.7363 (2.2); 53.9175 (7.8); 40.6043 (0.8); 40.5119 (15.0); 40.4358 (1.9); 40.3448 (45.9); 40.2697 (3.5); 40.1778 (91.3); 40.0111 (106.6); 39.8444 (91.3); 39.6774 (46.0); 39.5103 (15.0); 0.6260 (0.2) |
| II.055: $^{13}$C-NMR (125.8 MHz, CDCl3):<br>δ = 159.8646 (2.6); 138.5430 (1.3); 138.3448 (2.5); 138.1484 (1.0); 133.5260 (0.9); 133.4724 (1.8); 133.4162 (0.8); 120.5571 (3.5); 114.5088 (5.8); 109.9735 (3.5); 108.0782 (6.3); 106.1865 (2.8); 77.2734 (81.3); 77.0189 (80.3); 76.7645 (81.5); 53.1418 (15.0); −0.0038 (1.2) |
| II.056: $^{13}$C-NMR (151.0 MHz, $d_6$-DMSO):<br>δ = 158.4894 (2.6); 132.1711 (2.0); 130.7441 (2.0); 127.2778 (2.1); 87.1601 (2.1); 61.9864 (6.0); 40.2351 (4.1); 40.1152 (17.6); 39.9768 (52.1); 39.8380 (101.8); 39.6990 (119.0); 39.5599 (100.8); 39.4209 (50.5); 39.2818 (16.4); 14.1234 (7.0); 0.2534 (0.4) |
| II.057: $^{13}$C-NMR (151.0 MHz, $d_6$-DMSO):<br>δ = 170.6290 (0.4); 160.0116 (5.3); 156.4666 (0.4); 133.5839 (0.9); 133.4496 (0.6); 131.7319 (7.0); 131.3842 (0.4); 127.8332 (0.3); 125.9043 (2.1); 102.1214 (0.3); 85.5577 (2.5); 48.7493 (0.4); 40.3531 (1.6); 40.2350 (30.3); 40.1154 (174.2); 39.9768 (515.6); 39.8380 (1008.7); 39.6990 (1179.2); 39.5600 (999.4); 39.4209 (500.8); 39.2818 (163.4); 38.6830 (0.4); 34.1258 (0.4); 28.2394 (0.4); 23.4977 (0.3); 0.2579 (3.3); −2.1171 (0.4); −4.3281 (0.4) |
| II.058: $^{13}$C-NMR (151.0 MHz, $d_6$-DMSO):<br>δ = 159.6373 (2.3); 140.0288 (2.6); 128.2967 (1.5); 123.2516 (1.7); 122.1785 (1.6); 52.7203 (7.0); 40.2350 (2.8); 40.1152 (11.0); 39.9768 (32.6); 39.8380 (63.8); 39.6990 (74.5); 39.5600 (63.1); 39.4209 (31.6); 39.2818 (10.3); 14.4460 (6.6); 0.2493 (0.3) |
| II.059: $^{13}$C-NMR (125.8 MHz, $d_6$-DMSO):<br>δ = 163.3461 (2.2); 161.0062 (2.2); 159.7966 (2.1); 159.7761 (1.9); 128.9966 (2.5); 115.6822 (2.1); 98.3504 (1.4); 98.2309 (1.6); 53.3891 (11.4); 40.5112 (15.0); 40.4364 (1.9); 40.3441 (46.4); 40.2703 (3.3); 40.1771 (92.0); 40.0102 (107.7); 39.8435 (91.5); 39.6767 (46.3); 39.5096 (15.2); 0.5638 (0.8) |

TABLE A-(II)-continued

| NMR peak lists of compounds according to formula (II) |
| --- |
| II.060: $^{13}$C-NMR (125.8 MHz, CDCl3):<br>δ = 159.0371 (1.2); 159.0063 (1.1); 155.8102 (1.2); 153.5936 (1.0); 132.6088 (0.9); 132.5634 (0.9); 111.4040 (0.8); 111.3206 (0.7); 103.3760 (0.9); 103.1619 (1.0); 77.2728 (39.7); 77.0181 (40.6); 76.7641 (41.1); 71.7718 (6.3); 27.7921 (7.9); 18.9682 (15.0); −0.0038 (0.6) |
| II.061: $^{13}$C-NMR (125.8 MHz, dd$_6$-DMSO):<br>δ = 160.0684 (6.4); 136.6119 (4.8); 128.1550 (5.5); 119.2918 (5.2); 112.9293 (5.6); 112.0765 (4.3); 40.5013 (15.0); 40.4266 (1.7); 40.3344 (46.7); 40.2599 (3.3); 40.1674 (94.2); 40.0003 (111.0); 39.8332 (94.1); 39.6663 (47.0); 39.4997 (15.6) |
| II.063: $^{13}$C-NMR (151.0 MHz, d$_6$-DMSO):<br>δ = 159.1776 (2.4); 139.9028 (2.6); 128.1658 (1.6); 123.2132 (1.8); 122.4749 (1.7); 61.6278 (6.6); 40.2350 (2.6); 40.1155 (12.4); 39.9768 (36.8); 39.8380 (72.0); 39.6990 (84.3); 39.5600 (71.4); 39.4209 (35.7); 39.2819 (11.6); 14.4226 (6.5); 14.1797 (7.0); 0.2466 (0.3) |
| II.064: $^{13}$C-NMR (151.0 MHz, d$_6$-DMSO):<br>δ = 161.9376 (2.6); 161.8700 (2.4); 159.9204 (2.4); 130.2768 (7.0); 122.4460 (1.9); 107.9204 (2.9); 107.8464 (2.9); 40.2351 (8.3); 40.1154 (50.9); 39.9768 (150.4); 39.8380 (294.0); 39.6990 (343.7); 39.5600 (291.4); 39.4209 (146.1); 39.2819 (47.8); 0.2527 (1.0) |
| II.065: $^{13}$C-NMR (151.0 MHz, d$_6$-DMSO):<br>δ = 160.7077 (1.6); 139.0795 (1.5); 127.3968 (0.8); 124.1582 (0.6); 122.9330 (1.6); 40.2354 (2.5); 40.1155 (13.6); 39.9769 (40.2); 39.8381 (78.5); 39.6991 (91.8); 39.5600 (77.7); 39.4210 (38.9); 39.2819 (12.7); 14.3843 (7.0); 0.2544 (0.3) |
| II.066: $^{13}$C-NMR (125.8 MHz, d$_6$-DMSO):<br>δ = 163.2824 (2.6); 160.9433 (3.0); 159.3124 (2.6); 159.2933 (3.4); 128.8888 (4.0); 115.9414 (3.6); 98.3214 (2.2); 98.2005 (2.6); 62.4344 (14.9); 40.5133 (8.3); 40.4370 (1.1); 40.3463 (25.1); 40.2713 (1.9); 40.1796 (50.0); 40.0129 (59.3); 39.8459 (50.7); 39.6788 (25.5); 39.5117 (8.3); 14.4566 (15.0); 0.5334 (0.3) |
| II.067: $^{13}$C-NMR (125.8 MHz, CDCl3):<br>δ = 158.9502 (1.9); 158.9180 (2.2); 155.8350 (2.6); 153.6178 (2.5); 132.5728 (2.1); 132.5271 (1.8); 111.3377 (1.4); 111.2594 (1.3); 103.3567 (1.9); 103.1423 (1.8); 77.2762 (62.4); 77.0224 (61.9); 76.7676 (60.2); 61.9528 (15.0); 14.2096 (13.2); −0.0039 (1.1) |
| II.068: $^{13}$C-NMR (125.8 MHz, d$_6$-DMSO):<br>δ = 158.5064 (4.9); 135.6947 (4.6); 132.5714 (3.5); 128.8200 (3.9); 111.6660 (5.0); 110.0381 (4.6); 63.1470 (14.3); 40.6032 (0.7); 40.5128 (11.5); 40.4345 (1.6); 40.3457 (35.3); 40.2717 (2.8); 40.1789 (69.9); 40.0122 (82.5); 39.8453 (70.7); 39.6782 (35.5); 39.5111 (11.7); 14.3676 (15.0) |
| II.069: $^{13}$C-NMR (151.0 MHz, d$_6$-DMSO):<br>δ = 158.1978 (2.7); 141.2497 (2.3); 120.2501 (2.5); 118.4321 (2.4); 116.1607 (2.1); 112.2374 (2.4); 53.7394 (7.0); 40.2351 (3.6); 40.1153 (13.9); 39.9768 (40.9); 39.8380 (79.8); 39.6990 (93.3); 39.5600 (79.0); 39.4209 (39.6); 39.2819 (12.9); 0.2546 (0.4) |
| II.070: $^{13}$C-NMR (125.8 MHz, d$_6$-DMSO):<br>δ = 160.4194 (15.0); 132.7666 (0.3); 130.4326 (10.9); 129.8130 (11.4); 116.3518 (9.1); 115.9560 (11.6); 40.4887 (11.4); 40.4135 (1.6); 40.3218 (35.0); 40.2477 (2.8); 40.1547 (69.5); 39.9879 (81.3); 39.8212 (69.5); 39.6542 (35.0); 39.4872 (11.4) |
| II.071: $^{13}$C-NMR (125.8 MHz, d$_6$-DMSO):<br>δ = 159.3844 (4.5); 130.1060 (2.7); 128.4073 (3.0); 117.4255 (4.1); 116.8223 (3.6); 53.4228 (8.7); 40.5132 (15.0); 40.4376 (1.9); 40.3462 (45.6); 40.2717 (3.4); 40.1795 (90.6); 40.0128 (107.6); 39.8458 (92.2); 39.6786 (46.3); 39.5115 (15.2) |
| II.072: $^{13}$C-NMR (125.8 MHz, d$_6$-DMSO):<br>δ = 240.1260 (0.4); 159.7861 (2.2); 139.8454 (3.0); 135.9666 (2.4); 133.0089 (7.4); 112.0165 (2.2); 110.8571 (1.9); 63.0023 (7.1); 40.5081 (15.0); 40.4326 (1.8); 40.3415 (46.6); 40.2664 (3.4); 40.1745 (94.1); 40.0074 (111.1); 39.8403 (94.3); 39.6734 (47.1); 39.5066 (15.4); 14.4271 (7.1) |
| II.073: $^{13}$C-NMR (151.0 MHz, d$_6$-DMSO):<br>δ = 159.0306 (2.3); 135.5968 (2.7); 130.4340 (1.7); 130.3580 (1.8); 122.8984 (1.5); 61.6782 (6.5); 40.2352 (2.7); 40.1152 (10.7); 39.9768 (31.6); 39.8380 (61.7); 39.6990 (72.1); 39.5600 (61.1); 39.4209 (30.6); 39.2818 (10.0); 14.1790 (7.0); 12.7170 (6.5); 0.2481 (0.3) |
| II.074: $^{13}$C-NMR (151.0 MHz, d$_6$-DMSO):<br>δ = 160.5667 (2.7); 135.4516 (3.0); 129.6314 (1.3); 129.5551 (1.6); 124.6309 (0.8); 40.2352 (2.6); 40.1155 (14.1); 39.9769 (41.7); 39.8380 (81.6); 39.6990 (95.4); 39.5600 (80.8); 39.4209 (40.5); 39.2819 (13.2); 12.7621 (7.0); 0.2538 (0.3) |
| II.075: $^{13}$C-NMR (150.9 MHz, d$_6$-DMSO):<br>δ = 159.4825 (4.9); 133.9152 (1.0); 133.7550 (1.8); 133.5966 (1.0); 129.6746 (3.4); 122.6709 (0.9); 122.6377 (2.2); 122.6048 (0.9); 115.5369 (2.5); 113.3936 (2.1); 111.8229 (4.1); 110.2523 (2.0); 53.7985 (0.3); 53.3773 (15.0); 40.5309 (0.6); 40.4121 (10.7); 40.2730 (32.9); 40.1340 (66.0); 39.9951 (77.7); 39.8562 (65.6); 39.7171 (32.4); 39.5776 (10.4) |
| II.076: $^{13}$C-NMR (125.8 MHz, d$_6$-DMSO):<br>δ = 162.8911 (7.8); 160.8892 (12.7); 160.8688 (15.0); 160.5590 (8.1); 128.0053 (10.5); 117.5473 (14.7); 97.9667 (6.5); 97.8480 (7.8); 62.6581 (0.8); 41.8248 (0.8); 40.4955 (32.7); 40.4188 (4.3); 40.3284 (100.0); 40.2532 (7.6); 40.1613 (199.6); 39.9943 (233.0); 39.8275 (196.9); 39.6608 (99.0); 39.4938 (32.5); 11.4938 (0.8); 1.6200 (0.8); 0.6230 (0.8) |
| II.077: $^{13}$C-NMR (150.9 MHz, d$_6$-DMSO):<br>δ = 158.5309 (5.5); 138.8382 (4.3); 133.9747 (3.9); 116.0270 (5.2); 115.8431 (6.0); 112.5737 (4.6); 54.1124 (15.0); 40.5330 (0.9); 40.4144 (23.6); 40.2752 (71.5); 40.1358 (143.8); 39.9967 (171.4); 39.8578 (146.7); 39.7189 (73.3); 39.5799 (23.7) |
| II.078: $^{13}$C-NMR (150.9 MHz, d$_6$-DMSO):<br>δ = 160.5836 (15.0); 133.8606 (2.4); 133.7012 (4.7); 133.5434 (2.4); 131.7296 (8.4); 121.8384 (2.5); 121.8036 (4.8); 121.7714 (2.2); 114.4801 (5.4); 113.4662 (4.6); 111.8968 (9.3); 110.3272 (4.3); 40.5163 (1.0); 40.3977 (27.7); 40.2583 (85.8); 40.1192 (173.6); 39.9803 (205.6); 39.8414 (174.6); 39.7024 (86.6); 39.5631 (28.0) |
| II.079: $^{13}$C-NMR (150.9 MHz, d$_6$-DMSO):<br>δ = 158.9758 (5.9); 135.6889 (3.9); 132.2970 (4.2); 128.9024 (3.8); 111.6989 (5.8); 110.1143 (4.2); 53.9208 (15.0); 40.5316 (0.8); 40.4124 (19.2); 40.2731 (59.8); 40.1342 (120.5); 39.9953 (142.2); 39.8564 (120.1); 39.7173 (59.3); 39.5779 (19.0) |
| II.080: $^{13}$C-NMR (150.9 MHz, d$_6$-DMSO):<br>δ = 158.8848 (5.6); 132.4575 (5.1); 131.1584 (3.1); 125.6636 (6.1); 112.7113 (5.2); 112.2663 (5.5); 53.9058 (15.0); 40.5317 (0.5); 40.4135 (12.8); 40.2741 (39.1); 40.1350 (79.2); 39.9960 (94.1); 39.8572 (80.1); 39.7182 (39.8); 39.5790 (12.8) |
| II.081: $^{13}$C-NMR (150.9 MHz, d$_6$-DMSO):<br>δ = 161.4272 (7.5); 142.4443 (0.2); 138.6969 (2.8); 136.9306 (15.0); 130.0004 (0.4); 129.7559 (1.2); 129.5123 (1.3); 129.2688 (0.4); 124.2456 (0.6); 122.4537 (1.9); 120.6616 (1.7); 118.8698 (0.5); 113.4900 (0.7); 113.4695 (2.0); 113.4494 (1.8); 113.4309 (0.7); 40.5177 (0.6); 40.3990 (19.9); 40.2598 (60.2); 40.1203 (121.4); 39.9813 (144.6); 39.8424 (123.6); 39.7035 (61.6); 39.5645 (19.9) |
| II.082: $^{13}$C-NMR (150.9 MHz, CDCl3):<br>δ = 160.1863 (4.4); 136.6988 (11.0); 136.0112 (1.9); 132.1294 (0.4); 131.8822 (1.1); 131.6300 (1.3); 131.3774 (0.4); 123.7094 (0.6); 121.9132 (1.1); 120.1175 (1.7); 118.3239 (0.5); 112.1814 (0.8); 112.1590 (1.8); 112.1388 (1.5); 77.2257 (76.2); 77.0145 (82.0); 76.8021 (79.5); 62.3316 (15.0); 14.1876 (12.9); −0.0093 (1.0) |

TABLE A-(II)-continued

| NMR peak lists of compounds according to formula (II) |
|---|
| II.083: $^{13}$C-NMR (150.9 MHz, $d_6$-DMSO):<br>δ = 159.4809 (15.0); 142.3013 (1.9); 132.8869 (8.8); 115.3685 (14.0); 115.1782 (8.1); 112.8310 (12.0); 40.5248 (4.2); 40.4074 (106.9); 40.2683 (321.3); 40.1288 (636.8); 39.9896 (758.1); 39.8506 (649.4); 39.7118 (324.9); 39.5728 (104.5) |
| II.084: $^{13}$C-NMR (150.9 MHz, $d_6$-DMSO):<br>δ = 159.7336 (2.4); 159.7083 (2.4); 156.0529 (1.9); 154.2358 (2.0); 141.6558 (3.1); 141.6338 (3.6); 109.4306 (2.0); 109.3639 (1.8); 101.4119 (2.9); 101.2425 (2.5); 52.9262 (15.0); 40.5309 (1.0); 40.4121 (27.9); 40.2730 (86.8); 40.1341 (175.1); 39.9952 (206.8); 39.8563 (175.0); 39.7172 (86.6); 39.5776 (28.1); 16.1942 (11.9) |
| II.085: $^{13}$C-NMR (150.9 MHz, CDCl3):<br>δ = 158.5311 (4.6); 136.6160 (3.5); 132.5220 (2.7); 127.7766 (3.4); 114.6006 (2.7); 110.9947 (5.3); 77.2416 (48.4); 77.0299 (52.0); 76.8175 (49.9); 53.5835 (15.0); 29.7070 (0.7); −0.0038 (1.0) |
| II.086: $^{13}$C-NMR (150.9 MHz, $d_6$-DMSO):<br>δ = 163.5502 (2.5); 161.5963 (2.8); 159.9702 (3.0); 159.9568 (3.1); 118.3427 (4.5); 117.1624 (3.8); 101.0574 (2.1); 100.9601 (3.0); 53.3781 (15.0); 40.5339 (0.8); 40.4144 (19.6); 40.2752 (59.3); 40.1358 (119.4); 39.9967 (142.2); 39.8578 (121.7); 39.7189 (60.8); 39.5799 (19.5) |
| II.087: $^{13}$C-NMR (150.9 MHz, $d_6$-DMSO):<br>δ = 159.9106 (15.0); 134.7528 (7.4); 130.3190 (7.7); 125.4625 (10.0); 112.8415 (10.3); 111.5279 (8.9); 40.5153 (1.3); 40.3983 (22.5); 40.2588 (68.0); 40.1197 (136.8); 39.9808 (161.8); 39.8419 (137.6); 39.7029 (68.8); 39.5638 (22.4); 0.5615 (0.5) |
| II.088: $^{13}$C-NMR (150.9 MHz, $d_6$-DMSO):<br>δ = 159.9877 (15.0); 135.5135 (11.7); 134.5952 (8.9); 128.0842 (9.7); 111.8149 (11.6); 109.3664 (8.2); 40.5140 (1.1); 40.3937 (22.4); 40.2550 (67.6); 40.1160 (133.1); 39.9767 (154.3); 39.8372 (132.0); 39.6981 (66.8); 39.5592 (21.7); 1.6267 (0.4); 0.5543 (0.5) |
| II.090: $^{13}$C-NMR (151.0 MHz, $d_6$-DMSO):<br>δ = 159.4832 (2.5); 145.2818 (2.0); 134.3074 (6.3); 132.6453 (2.1); 112.4169 (2.3); 111.5649 (2.4); 62.3153 (6.3); 40.2350 (2.3); 40.1152 (8.8); 39.9767 (26.1); 39.8380 (50.9); 39.6990 (59.5); 39.5600 (50.4); 39.4209 (25.2); 39.2818 (8.2); 23.7902 (0.3); 14.1553 (7.0); 0.2484 (0.2) |
| II.091: $^{13}$C-NMR (150.9 MHz, $d_6$-DMSO):<br>δ = 158.3654 (4.5); 130.7803 (5.4); 130.6577 (5.2); 128.7798 (4.3); 116.7682 (3.6); 112.3757 (4.7); 62.7960 (12.2); 40.5352 (0.6); 40.4150 (17.5); 40.2759 (52.8); 40.1364 (105.4); 39.9972 (125.7); 39.8583 (107.9); 39.7194 (54.0); 39.5805 (17.5); 14.4025 (15.0) |
| II.092: $^{13}$C-NMR (150.9 MHz, $d_6$-DMSO):<br>δ = 158.7003 (6.3); 137.9743 (4.0); 134.3028 (4.5); 117.6204 (5.7); 111.7527 (5.5); 110.3972 (5.3); 63.1582 (13.5); 40.5327 (0.7); 40.4151 (16.8); 40.2760 (50.8); 40.1366 (100.5); 39.9973 (119.8); 39.8584 (102.7); 39.7195 (51.4); 39.5805 (16.6); 14.3725 (15.0) |
| II.093: $^{13}$C-NMR (150.9 MHz, $d_6$-DMSO):<br>δ = 158.6468 (5.6); 145.8232 (4.0); 127.8682 (3.2); 117.3143 (4.8); 116.3557 (3.7); 112.1748 (4.7); 62.8677 (13.0); 40.5334 (0.8); 40.4151 (17.7); 40.2759 (53.4); 40.1365 (106.2); 39.9973 (126.6); 39.8583 (108.5); 39.7194 (54.4); 39.5804 (17.5); 25.9563 (0.3); 14.4037 (15.0) |
| II.094: $^{13}$C-NMR (150.9 MHz, $d_6$-DMSO):<br>δ = 163.1586 (8.0); 161.2120 (9.7); 161.0887 (14.0); 161.0751 (15.0); 119.0984 (13.2); 117.1606 (14.8); 100.6621 (7.9); 100.5680 (7.9); 40.5248 (4.4); 40.4064 (110.7); 40.2670 (335.4); 40.1277 (677.4); 39.9887 (804.4); 39.8498 (685.3); 39.7109 (341.6); 39.5718 (110.1) |
| II.095: $^{13}$C-NMR (125.8 MHz, CDCl3):<br>δ = 159.0451 (5.5); 145.5447 (4.4); 127.1993 (4.6); 117.1821 (6.6); 116.9052 (4.9); 111.1575 (7.9); 77.2847 (184.2); 77.0303 (181.4); 76.7759 (182.4); 53.1125 (15.0) |
| II.096: $^{13}$C-NMR (125.8 MHz, CDCl3):<br>δ = 158.9440 (3.8); 138.4776 (5.0); 132.8416 (4.4); 118.1883 (5.2); 110.7824 (6.5); 110.2676 (5.5); 77.2847 (138.2); 77.0304 (137.2); 76.7758 (138.9); 53.3653 (15.0) |
| II.097: $^{13}$C-NMR (125.8 MHz, $d_6$-DMSO):<br>δ = 160.1481 (15.0); 137.7552 (9.0); 136.3604 (10.2); 116.7227 (11.2); 111.8664 (12.7); 109.7781 (11.2); 40.4893 (16.2); 40.3222 (50.1); 40.1552 (99.3); 39.9886 (116.5); 39.8217 (99.5); 39.6547 (50.0); 39.4876 (16.4) |
| II.098: $^{13}$C-NMR (125.8 MHz, $d_6$-DMSO):<br>δ = 160.1618 (7.5); 145.1222 (6.0); 129.8365 (4.8); 116.2635 (5.3); 116.2376 (5.3); 112.2551 (6.4); 40.4985 (15.0); 40.3318 (45.8); 40.1652 (91.8); 39.9983 (108.9); 39.8312 (92.8); 39.6641 (46.4); 39.4971 (15.0) |
| II.099: $^{13}$C-NMR (125.7 MHz, $d_6$-DMSO):<br>δ = 161.0507 (12.9); 138.5850 (1.9); 136.2360 (1.8); 136.0439 (4.6); 135.8530 (2.1); 119.8143 (8.0); 113.5728 (15.0); 110.6789 (5.2); 110.5424 (1.1); 108.8008 (10.1); 106.9245 (5.0); 40.4903 (45.8); 40.4152 (6.2); 40.3231 (140.9); 40.2458 (12.1); 40.1560 (280.9); 39.9891 (328.1); 39.8223 (279.2); 39.6554 (140.8); 39.4882 (45.8) |
| II.100: $^{13}$C-NMR (125.8 MHz, $d_6$-DMSO):<br>δ = 161.2520 (8.3); 137.7818 (4.8); 134.8242 (12.1); 130.5419 (4.5); 114.8172 (6.3); 113.9267 (5.1); 40.4996 (15.0); 40.3328 (45.0); 40.1661 (89.3); 39.9991 (104.9); 39.8320 (89.0); 39.6649 (44.0); 39.4978 (13.9) |
| II.101: $^{13}$C-NMR (125.8 MHz, $d_6$-DMSO):<br>δ = 163.0633 (6.0); 163.0435 (5.4); 161.5563 (3.9); 159.2320 (4.0); 140.6381 (4.9); 116.3428 (4.3); 110.2064 (3.2); 110.1231 (3.3); 40.4752 (9.0); 40.3081 (27.4); 40.1415 (54.6); 39.9746 (64.6); 39.8076 (55.2); 39.6406 (27.7); 39.4734 (9.1); 14.1391 (15.0) |
| II.102: $^{13}$C-NMR (125.8 MHz, $d_6$-DMSO):<br>δ = 163.0772 (4.5); 163.0555 (5.1); 162.7106 (3.1); 160.4021 (2.9); 141.9891 (5.0); 117.3356 (4.1); 98.4609 (3.2); 98.3571 (2.5); 40.4986 (15.0); 40.3317 (45.6); 40.1650 (92.4); 39.9982 (109.4); 39.8311 (93.6); 39.6640 (46.8); 39.4971 (15.1); 15.6789 (12.4) |
| II.103: $^{13}$C-NMR (125.8 MHz, $d_6$-DMSO):<br>δ = 170.7858 (0.4); 159.5143 (5.8); 140.4690 (1.6); 131.1048 (5.1); 126.6859 (5.8); 113.1024 (4.1); 111.9436 (5.6); 60.2114 (1.2); 40.4981 (15.0); 40.4229 (1.9); 40.3312 (45.8); 40.2560 (3.4); 40.1645 (91.2); 39.9977 (108.1); 39.8307 (92.5); 39.6636 (46.4); 39.4965 (15.0); 21.2258 (1.2); 14.5513 (1.4) |
| II.104: $^{13}$C-NMR (125.8 MHz, $d_6$-DMSO):<br>δ = 159.4631 (3.5); 144.8184 (0.8); 119.4689 (2.7); 118.3196 (3.6); 115.6975 (2.7); 112.7882 (3.1); 40.5024 (15.0); 40.3354 (46.3); 40.2598 (3.5); 40.1683 (92.5); 40.0013 (108.5); 39.8343 (91.8); 39.6677 (45.9); 39.5008 (15.0) |

Biological Data—Compounds According to Formula (I)

Example A described below show the induction of defence gene expression in *Arabidopsis thaliana* by compounds according to formula (I), specifically the stimulation of the salicylic acid pathway. Therefore, these compounds could induce host defences and thus protect plants against a wide range of pathogens including bacteria and fungi.

Examples B, C, D, E and F described below show the in vivo activity of compounds in planta according to formula (I) by stimulating the plant defense against various pathogens infecting plants including bacteria and fungi.

Examples G, H, I and J described below show the in vitro cell test direct inactivity of compounds according to formula (I) against various pathogens including bacteria and fungi, thus illustrating the mode of action of compounds according to formula (I) as plant host defence inducers.

Example A: Induction of Defense Gene Expression in *Arabidopsis thaliana*

*Arabidopsis thaliana* reporter plants containing the coding sequence of a green fluorescent protein (GFP) linked to the salicylate responsive promoter sequence of the PR1 (pathogenesis-related protein I) gene (AT2G14610) were grown for five days and then sprayed with compounds. On the 3rd day after spraying, plant fluorescence was assessed with a MacroFluo instrument from Leica Microsystems (Wetzlar, Germany). Fluorescences were quantified with the Meta-Morph Microscopy Automation & Image Analysis Software (Molecular Devices, Sunnyvale, Calif., United States).

Background fluorescence in mock treated leaves was set as 1.00. Salicylic acid treatment (300 ppm) resulted in a relative fluorescence value of 2.70, proving the validity of the test system.

In this test, the following compounds according to the invention showed a relative fluorescence value at least above 2 at a concentration of 300 ppm of compound: I.0003; I.0004; I.0005; I.0006; I.0012; I.0014; I.0016; I.0017; I.0018; I.0019; I.0021; I.0022; I.0023; I.0024; I.0026; I.0027; I.0029; 1.0034; I.0035; I.0036; I.0038; I.0039; I.0041; I.0042; I.0043; I.0045; I.0046; I.0047; I.0048; 1.0050; I.0052; I.0053; I.0054; I.0055; I.0059; I.0060; I.0062; I.0063; I.0064; I.0065; I.0066; I.0067; I.0068; I.0069; I.0070; I.0072; I.0073; I.0074; I.0075; I.0076; I.0077; I.0078; I.0079; I.0081; I.0083; I.0084; I.0085; I.0086; I.0087; I.0088; I.0089; I.0090; I.0091; I.0092; I.0093; I.0094; I.0096; I.0097; I.0098; I.0099; I.0100; I.0101; I.0102; I.0103; I.0105; I.0109; I.0113; I.0119; I.0120; I.0121; I.0122; I.0123; I.0124; I.0125; I.0126; I.0127; I.0128; I.0130; I.0131; I.0132; I.0133; I.0134; I.0135; I.0136; I.0137; I.0138; I.0140; I.0141; I.0142; I.0143; I.0144; I.0145; I.0146; I.0147; I.0148; I.0149; I.0150; I.0151; I.0152; I.0154; I.0155; I.0157; I.0159; I.0162; I.0163; I.0164; I.0165; I.0166; I.0168; I.0169; I.0170; I.0172; I.0173; I.0175; I.0176; I.0177; I.0178; I.0179; I.0180; I.0181; I.0182; I.0183; I.0184; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0206; I.0207; I.0208; I.0209; I.0210; I.0211; I.0212; I.0213; I.0214; I.0215; I.0216; I.0217; I.0220; I.0221; I.0224; I.0226; I.0227; I.0228; I.0229; I.0230; I.0231; I.0232; I.0233; I.0234; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0270; I.0271; I.0272; I.0273; I.0274; I.0276; I.0277; I.0278; I.0279; I.0280; I.0281; I.0282; I.0283; I.0284; I.0285; I.0286; I.0287; I.0290; I.0291; I.0292; I.0293; I.0294; I.0295; I.0297; I.0301; I.0302; I.0303; I.0304; I.0305; I.0306; I.0308; I.0309; I.0310; I.0311; I.0313; I.0316; I.0317; I.0319; I.0322; I.0323; I.0324; I.0325; I.0327; I.0328; I.0330; I.0332; I.0333; I.0334; I.0335; I.0336; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0369; I.0371; I.0373; I.0374; I.0375; I.0376; I.0377; I.0378; I.0379; I.0385; I.0386; I.0387; I.0388; I.0389; I.0390; I.0391; I.0413; I.0414; I.0415; I.0416; I.0417; I.0418; I.0419; I.0420; I.0422; I.0423; I.0424; I.0425; I.0426; I.0427; I.0428; I.0429; I.0430; I.0431; I.0432; I.0433; I.0435; I.0436; I.0437; I.0438; I.0439; I.0440; I.0441; I.0442; I.0443; I.0444; I.0445; I.0448; I.0450; I.0451; I.0452; I.0453; I.0454; I.0455; I.0456; I.0457; I.0458; I.0459; I.0460; I.0461; I.0462; I.0467; I.0468; I.0469; I.0472; I.0473; I.0475; I.0476; I.0477; I.0478; I.0480; I.0482; I.0483; I.0484; I.0485; I.0486; I.0487; I.0488; I.0489; I.0490; I.0491; I.0492; I.0495; I.0498; I.0499; I.0500; I.0501; I.0502; I.0503; I.0504; I.0505; I.0506; I.0507; I.0508; I.0510; I.0511; I.0515; I.0516; I.0518; I.0520; I.0522; I.0523; I.0524; I.0525; I.0526; I.0527; I.0528; I.0529; I.0530; I.0531; I.0532; I.0533; I.0535; I.0536; I.0537; I.0539; I.0540; I.0541; I.0542; I.0543; I.0544; I.0545; I.0546; I.0547; I.0548; I.0549; I.0550; I.0551; I.0552; I.0553; I.0554; I.0555; I.0556; I.0557; I.0558; I.0559; I.0561; I.0562; I.0563; I.0565; I.0566; I.0567; I.0568; I.0569; I.0570; I.0571; I.0572; I.0573; I.0574; I.0575; I.0576; I.0577; I.0578; I.0579; I.0580; I.0581; I.0582; I.0583; I.0584; I.0586; I.0587; I.0588; I.0589; I.0590; I.0591; I.0592; I.0593; I.0594; I.0595; I.0596; I.0597; I.0598; I.0599; I.0601; I.0602; I.0603; I.0604; I.0605; I.0606; I.0607; I.0609; I.0610; I.0625; I.0628; I.0633; I.0634; I.0635; I.0636; I.0637; I.0639; I.0640; I.0641; I.0642; I.0643; I.0644; I.0645; I.0646; I.0647; I.0648; I.0649; I.0650; I.0651; I.0664; I.0665; I.0666; I.0667; I.0668; I.0669; I.0670; I.0671; I.0672; I.0678; I.0679; I.0680; I.0681; I.0683; I.0685; I.0686; I.0695; I.0696; I.0698; I.0700; I.0701; I.0702; I.0703; I.0704; I.0705; I.0710; I.0715; I.0716; I.0717; I.0718; I.0719; I.0720; I.0721; I.0722; I.0723; I.0724; I.0725; I.0726; I.0849; I.0850; I.0851; I.0852; I.0853; I.0854; I.0855; I.0856; I.0857; I.0858; I.0859; I.0860; I.0861; I.0862; I.0863; I.0864; I.0865; I.0866; I.0867; I.0876; I.0878; I.0879; I.0880; I.0881; I.0883; I.0884; I.0886; I.0887; I.0888; I.0889; I.0890; I.0894; I.0895; I.0896; I.0898; I.0900; I.0902; I.0903; I.0904; I.0905; I.0906; I.0907; I.0908; I.0909; I.0910; I.0911; I.0912; I.0913; I.0917; I.0918; I.0919; I.0921; I.0922; I.0923; I.0924; I.0926; I.0927; I.0928; I.0929; I.0930; I.0931; I.0932; I.0933; I.0934; I.0935; I.0936; I.0937; I.0939; I.0940; I.0942; I.0943; I.0944; I.0945; I.0946; I.0947; I.0949; I.0950; I.0951; I.0952; I.0953; I.0955; I.0956; I.0957; I.0958; I.0959; I.0960; I.0961; I.0962; I.0963; I.0964; I.0965 I.0966; I.0967; I.0968; I.0969; I.0970; I.0971; I.0972; I.0973; I.0974; I.0975; I.0977; I.0978; I.0979; I.0980; I.0981; I.0982; I.0983; I.0984; I.0985; I.0986; I.0987; I.0988; I.0989 I.0990; I.0991; I.0992; I.0993; I.0994; I.0995; I.0996; I.0997; I.0998; I.0999; I.1000; I.1001; I.1003; I.1004; I.1005; I.1007; I.1008; I.1010; I.1011; I.1013; I.1014; I.1017; I.1018; I.1019; I.1020; I.1022; I.1023; I.1024;

I.1025; I.1026; I.1027; I.1028; I.1029; I.1030; I.1031; I.1032; I.1033; I.1034; I.1035.

In this test, the following compounds according to the invention showed a relative fluorescence value at least above 2 at a concentration of 75 ppm of compound: I.0003; I.0004; I.0005; I.0006; I.0014; I.0016; I.0017; I.0021; I.0023; I.0024; I.0025; I.0026; I.0027; I.0029; I.0033; I.0034; I.0035; I.0036; I.0038; I.0041; I.0042; I.0043; I.0045; I.0046; I.0047; I.0048; I.0050; I.0052; I.0053; I.0054; I.0059; I.0060; I.0062; I.0063; I.0065; I.0066; I.0067; I.0068; I.0069; I.0070; I.0074; I.0075; I.0077; I.0078; I.0079; I.0091; I.0092; I.0093; I.0094; I.0096; I.0098; I.0102; I.0104; I.0119; I.0120; I.0121; I.0122; I.0123; I.0124; I.0125; I.0127; I.0129; I.0130; I.0133; I.0135; I.0136; I.0138; I.0140; I.0141; I.0142; I.0144; I.0145; I.0146; I.0147; I.0148; I.0149; I.0151; I.0154; I.0155; I.0157; I.0158; I.0159; I.0162; I.0164; I.0165; I.0168; I.0169; I.0170; I.0172; I.0175; I.0176; I.0177; I.0178; I.0179; I.0180; I.0181; I.0182; I.0183; I.0184; I.0185; I.0186; I.0187; I.0190; I.0192; I.0193; I.0194; I.0195; I.0197; I.0198; I.0199; I.0200; I.0201; I.0202; I.0203; I.0204; I.0206; I.0207; I.0208; I.0210; I.0211; I.0212; I.0213; I.0214; I.0215; I.0216; I.0217; I.0220; I.0227; I.0228; I.0230; I.0231; I.0233; I.0234; I.0236; I.0237; I.0238; I.0239; I.0240; I.0241; I.0243; I.0244; I.0247; I.0248; I.0249; I.0250; I.0252; I.0253; I.0254; I.0255; I.0256; I.0257; I.0260; I.0262; I.0263; I.0264; I.0265; I.0267; I.0268; I.0270; I.0272; I.0274; I.0276; I.0279; I.0281; I.0282; I.0283; I.0284; I.0285; I.0287; I.0292; I.0293; I.0294; I.0302; I.0303; I.0304; I.0322; I.0323; I.0324; I.0325; I.0327; I.0328; I.0330; I.0332; I.0333; I.0339; I.0340; I.0341; I.0342; I.0343; I.0344; I.0345; I.0346; I.0348; I.0350; I.0351; I.0352; I.0353; I.0354; I.0355; I.0356; I.0357; I.0358; I.0360; I.0361; I.0362; I.0363; I.0364; I.0385; I.0386; I.0388; I.0414; I.0415; I.0416; I.0417; I.0418; I.0419; I.0420; I.0422; I.0424; I.0425; I.0426; I.0431; I.0435; I.0436; I.0438; I.0439; I.0441; I.0442; I.0443; I.0444; I.0452; I.0453; I.0454; I.0455; I.0456; I.0457; I.0458; I.0459; I.0460; I.0461; I.0462; I.0467; I.0482; I.0485; I.0486; I.0488; I.0489; I.0490; I.0491; I.0492; I.0495; I.0498; I.0500; I.0503; I.0504; I.0523; I.0524; I.0525; I.0526; I.0527; I.0528; I.0529; I.0530; I.0531; I.0532; I.0533; I.0535; I.0536; I.0537; I.0541; I.0543; I.0545; I.0546; I.0547; I.0548; I.0549; I.0550; I.0551; I.0552; I.0553; I.0555; I.0556; I.0557; I.0558; I.0559; I.0562; I.0563; I.0565; I.0566; I.0567; I.0568; I.0570; I.0571; I.0572; I.0573; I.0575; I.0576; I.0577; I.0578; I.0579; I.0580; I.0581; I.0583; I.0586; I.0587; I.0588; I.0590; I.0591; I.0592; I.0593; I.0594; I.0595; I.0596; I.0597; I.0598; I.0599; I.0601; I.0602; I.0603; I.0604; I.0605; I.0606; I.0607; I.0625; I.0634; I.0635; I.0636; I.0639; I.0640; I.0641; I.0642; I.0643; I.0644; I.0645; I.0646; I.0647; I.0648; I.0649; I.0650; I.0651; I.0664; I.0665; I.0666; I.0667; I.0671; I.0672; I.0678; I.0679; I.0680; I.0681; I.0695; I.0700; I.0702; I.0703; I.0705; I.0715; I.0716; I.0717; I.0718; I.0719; I.0720; I.0721; I.0722; I.0723; I.0724; I.0725; I.0726; I.0849; I.0850; I.0851; I.0852; I.0853; I.0854; I.0855; I.0856; I.0857; I.0858; I.0859; I.0860; I.0861; I.0863; I.0864; I.0867; I.0872; I.0878; I.0879; I.0880; I.0883; I.0886; I.0887; I.0888; I.0903; I.0904; I.0905; I.0907; I.0908; I.0909; I.0911; I.0912; I.0917; I.0918; I.0922; I.0923; I.0924; I.0926; I.0927; I.0928; I.0930; I.0931; I.0932; I.0933; I.0934; I.0940; I.0942; I.0943; I.0946; I.0947; I.0949; I.0952; I.0953; I.0955; I.0959; I.0960; I.0961; I.0962; I.0963; I.0964; I.0965; I.0966; I.0967; I.0968; I.0969; I.0972; I.0973; I.0981; I.0982; I.0983; I.0984; I.0985; I.0986; I.0987; I.0988; I.0989; I.0990; I.0991; I.0992; I.0993; I.0994; I.0995; I.0996; I.0997; I.0998; I.1000; I.1001; I.1003; I.1005; I.1007; I.1008; I.1011; I.1018; I.1019; I.1022; I.1023; I.1025; I.1026; I.1027; I.1028; I.1029; I.1031; I.1032; I.1033; I.1034; I.1035.

Salicylate is a major defence hormone against plant pathogens. All the compounds described above stimulate the salicylic acid pathway and therefore could protect plants against a wide range of pathogens.

Example B: In Vivo Preventive Test on *Peronospora parasitica* (Crucifer Downy Mildew)

The tested active ingredients were prepared by homogenization in a mixture of acetone/Dimethyl sulfoxide/Tween®, and then diluted with water to obtain the desired active material concentration.

The young plants of cabbage were treated by spraying the active ingredient prepared as described above. Control plants were treated only with an aqueous solution of acetone/Dimethyl sulfoxide/Tween®.

After 72 hours, the plants were contaminated by spraying the leaves with an aqueous suspension of *Peronospora parasitica* spores. The contaminated cabbage plants were incubated for 5 days at 20° C. and at 100% relative humidity.

The test was evaluated 5 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I.0047; I.0131; I.0139; I.0601; I.0935.

In this test the following compounds according to the invention showed efficacy between 80% and 89% at a concentration of 500 ppm of active ingredient: I.0004; I.0025; I.0039; I.0051; I.0053; I.0059; I.0079; I.0136; I.0258; I.0277; I.0281; I.0282; I.0308; I.0435; I.0937.

In this test the following compounds according to the invention showed efficacy between 90% and 100% at a concentration of 500 ppm of active ingredient: I.0003; I.0006; I.0017; I.0018; I.0019; I.0021; I.0022; I.0024; I.0026; I.0027; I.0032; I.0034; I.0036; I.0041; I.0042; I.0043; I.0046; I.0048; I.0050; I.0052; I.0055; I.0062; I.0063; I.0065; I.0066; I.0067; I.0068; I.0069; I.0070; I.0072; I.0075; I.0078; I.0086; I.0087; I.0091; I.0092; I.0093; I.0096; I.0105; I.0119; I.0121; I.0122; I.0123; I.0124; I.0125; I.0126; I.0127; I.0129; I.0130; I.0132; I.0133; I.0138; I.0140; I.0142; I.0145; I.0163; I.0165; I.0167; I.0168; I.0170; I.0172; I.0178; I.0179; I.0180; I.0183; I.0184; I.0186; I.0187; I.0193; I.0194; I.0195; I.0197; I.0200; I.0201; I.0203; I.0208; I.0210; I.0213; I.0247; I.0248; I.0249; I.0250; I.0252; I.0253; I.0254; I.0255; I.0257; I.0260; I.0266; I.0267; I.0268; I.0270; I.0271; I.0272; I.0273; I.0274; I.0285; I.0290; I.0293; I.0294; I.0303; I.0309; I.0322; I.0327; I.0328; I.0434; I.0436; I.0437; I.0438; I.0439; I.0440; I.0441; I.0442; I.0443; I.0444; I.0449; I.0450; I.0451; I.0452; I.0453; I.0454; I.0456; I.0457; I.0459; I.0460; I.0461; I.0462; I.0467; I.0468; I.0472; I.0473; I.0476; I.0477; I.0590; I.0594; I.0595; I.0596; I.0597; I.0598; I.0599; I.0607; I.0625; I.0651; I.0705; I.0725; I.0919.

In this test the following compounds according to the invention showed efficacy between 70% and 79% at a concentration of 31 ppm of active ingredient: I.0038; I.0045; I.0055; I.0096; I.0136; I.0212; I.0252; I.0254; I.0257;

I.0260; I.0270; I.0366; I.0428; I.0453; I.0455; I.0467; I.0469; I.0477; I.0483; I.0861; I.0951; I.0954; I.0998; I.1017; I.1027.

In this test the following compounds according to the invention showed efficacy between 80% and 89% at a concentration of 31 ppm of active ingredient: I.0016; I.0026; I.0035; I.0043; I.0068; I.0075; I.0099; I.0119; I.0126; I.0129; I.0138; I.0163; I.0190; I.0193; I.0285; I.0303; I.0311; I.0322; I.0341; I.0347; I.0356; I.0440; I.0456; I.0460; I.0533; I.0535; I.0556; I.0558; I.0596; I.0597; I.0607; I.0647; I.0725; I.0851; I.0854; I.1000; I.1001; I.1004; I.1019; I.1022.

In this test the following compounds according to the invention showed efficacy between 90% and 100% at a concentration of 31 ppm of active ingredient: I.0005; I.0006; I.0017; I.0019; I.0021; I.0022; I.0024; I.0027; I.0034; I.0036; I.0041; I.0051; I.0059; I.0060; I.0062; I.0063; I.0066; I.0067; I.0069; I.0070; I.0072; I.0078; I.0085; I.0086; I.0087; I.0090; I.0091; I.0092; I.0093; I.0094; I.0120; I.0121; I.0122; I.0123; I.0125; I.0127; I.0133; I.0140; I.0141; I.0142; I.0144; I.0145; I.0154; I.0165; I.0168; I.0170; I.0172; I.0176; I.0177; I.0178; I.0180; I.0181; I.0182; I.0183; I.0184; I.0185; I.0186; I.0187; I.0194; I.0195; I.0197; I.0198; I.0199; I.0200; I.0201; I.0202; I.0203; I.0204; I.0205; I.0206; I.0207; I.0208; I.0210; I.0213; I.0227; I.0241; I.0243; I.0244; I.0247; I.0248; I.0253; I.0255; I.0258; I.0264; I.0265; I.0266; I.0267; I.0268; I.0272; I.0286; I.0287; I.0290; I.0291; I.0292; I.0293; I.0294; I.0302; I.0324; I.0327; I.0338; I.0343; I.0344; I.0354; I.0355; I.0414; I.0415; I.0416; I.0422; I.0423; I.0436; I.0437; I.0438; I.0439; I.0441; I.0442; I.0444; I.0449; I.0450; I.0452; I.0454; I.0457; I.0461; I.0462; I.0472; I.0473; I.0484; I.0485; I.0491; I.0492; I.0500; I.0523; I.0525; I.0527; I.0529; I.0530; I.0531; I.0543; I.0547; I.0550; I.0553; I.0555; I.0557; I.0559; I.0561; I.0590; I.0595; I.0598; I.0599; I.0604; I.0605; I.0634; I.0635; I.0646; I.0855; I.0856; I.0857; I.0858; I.0859; I.0860; I.0862; I.0931; I.0932; I.0933; I.0950; I.0952; I.0953; I.0955; I.0958; I.0997; I.1003; I.1007; I.1008; I.1018; I.1025; I.1026; I.1031; I.1032; I.1033; I.1034.

In this test the following compounds according to the invention showed efficacy between 70% and 79% at a concentration of 125 ppm of active ingredient: I.0043; I.0099; I.0199; I.0273; I.0424; I.0476; I.0533; I.0535; I.0570; I.0573; I.0594; I.0596; I.0625; I.0636; I.0937; I.0950; I.1023.

In this test the following compounds according to the invention showed efficacy between 80% and 89% at a concentration of 125 ppm of active ingredient: I.0038; I.0055; I.0094; I.0120; I.0129; I.0163; I.0167; I.0192; I.0193; I.0258; I.0271; I.0272; I.0274; I.0277; I.0282; I.0356; I.0359; I.0428; I.0435; I.0455; I.0460; I.0477; I.0540; I.0541; I.0571; I.0601; I.0919; I.0933; I.1019.

In this test the following compounds according to the invention showed efficacy between 90% and 100% at a concentration of 125 ppm of active ingredient: I.0004; I.0005; I.0006; I.0017; I.0019; I.0021; I.0022; I.0024; I.0026; I.0027; I.0034; I.0035; I.0036; I.0041; I.0042; I.0048; I.0050; I.0051; I.0059; I.0060; I.0062; I.0063; I.0066; I.0067; I.0068; I.0069; I.0070; I.0072; I.0075; I.0078; I.0085; I.0086; I.0087; I.0090; I.0091; I.0092; I.0093; I.0096; I.0105; I.0119; I.0121; I.0122; I.0123; I.0124; I.0125; I.0126; I.0127; I.0133; I.0136; I.0138; I.0140; I.0141; I.0142; I.0144; I.0145; I.0154; I.0165; I.0168; I.0170; I.0172; I.0176; I.0177; I.0178; I.0179; I.0180; I.0181; I.0182; I.0183; I.0184; I.0185; I.0186; I.0187; I.0188; I.0190; I.0194; I.0195; I.0197; I.0200; I.0201; I.0202; I.0203; I.0204; I.0205; I.0206; I.0207; I.0208; I.0210; I.0212; I.0213; I.0227; I.0241; I.0243; I.0244; I.0247; I.0248; I.0249; I.0252; I.0253; I.0254; I.0255; I.0257; I.0260; I.0264; I.0265; I.0266; I.0267; I.0268; I.0285; I.0286; I.0287; I.0290; I.0291; I.0293; I.0294; I.0302; I.0303; I.0322; I.0324; I.0327; I.0329; I.0338; I.0341; I.0343; I.0344; I.0347; I.0354; I.0355; I.0366; I.0367; I.0414; I.0415; I.0416; I.0422; I.0423; I.0434; I.0436; I.0437; I.0438; I.0439; I.0440; I.0441; I.0442; I.0443; I.0444; I.0449; I.0450; I.0451; I.0452; I.0453; I.0454; I.0456; I.0457; I.0459; I.0461; I.0462; I.0467; I.0469; I.0472; I.0473; I.0483; I.0484; I.0485; I.0491; I.0492; I.0500; I.0523; I.0525; I.0527; I.0529; I.0530; I.0531; I.0542; I.0543; I.0547; I.0550; I.0553; I.0554; I.0555; I.0556; I.0557; I.0558; I.0559; I.0561; I.0590; I.0595; I.0597; I.0598; I.0599; I.0602; I.0604; I.0605; I.0606; I.0607; I.0634; I.0635; I.0646; I.0647; I.0705; I.0725; I.0851; I.0852; I.0854; I.0855; I.0856; I.0857; I.0858; I.0859; I.0860; I.0861; I.0862; I.0931; I.0932; I.0952; I.0953; I.0955; I.0958; I.0997; I.0998; I.1000; I.1001; I.1003; I.1004; I.1007; I.1008; I.1017; I.1018; I.1020; I.1022; I.1025; I.1026; I.1027; I.1031; I.1032; I.1033; I.1034; I.1035.

Example C: In Vivo Preventive Test on *Pseudomonas syringae* pv. Tomato (Bacterial Speck on Tomato)

The tested active ingredients were prepared by homogenization in a mixture of acetone/Dimethyl sulfoxide/Tween®, and then diluted with water to obtain the desired active material concentration.

The young plants of tomato were treated by spraying the active ingredient prepared as described above. Control plants were treated only with an aqueous solution of acetone/Dimethyl sulfoxide/Tween®.

After 72 hours, the plants were contaminated by spraying the leaves with an aqueous bacteria suspension of *Pseudomonas syringae* pv. tomato. The contaminated tomato plants were incubated for 4 days in saturated atmosphere at 22° C. day/20° C. night—70% HR and then for 1 or 2 days at 22° C. day/20° C. night at 70-80% relative humidity.

The test was evaluated 5 or 6 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I.0004; I.0019; I.0047; I.0054; I.0059; I.0070; I.0072; I.0075; I.0078; I.0100; I.0122; I.0127; I.0167; I.0168; I.0171; I.0194; I.0197; I.0254; I.0258; I.0270; I.0273; I.0274; I.0276; I.0301; I.0306; I.0444; I.0461; I.0462; I.0467; I.0472; I.0590; I.0625.

In this test the following compounds according to the invention showed efficacy between 80% and 89% at a concentration of 500 ppm of active ingredient: I.0021; I.0024; I.0034; I.0041; I.0046; I.0052; I.0063; I.0067; I.0087; I.0091; I.0138; I.0163; I.0165; I.0170; I.0172; I.0186; I.0200; I.0201; I.0203; I.0208; I.0210; I.0247; I.0249; I.0253; I.0255; I.0267; I.0268; I.0281; I.0282; I.0285; I.0303; I.0305; I.0308; I.0322; I.0328; I.0436; I.0437; I.0438; I.0451; I.0452; I.0453; I.0454; I.0457; I.0460; I.0597; I.0598; I.065I.

In this test the following compounds according to the invention showed efficacy between 90% and 100% at a concentration of 500 ppm of active ingredient: I.0025; I.0036; I.0051; I.0053; I.0066; I.0068; I.0069; I.0086; I.0119; I.0121; I.0140; I.0142; I.0145; I.0178; I.0180; I.0183; I.0184; I.0187; I.0195; I.0213; I.0250; I.0257; I.0260; I.0266; I.0293; I.0294; I.0304; I.0324; I.0325; I.0327; I.0434; I.0445; I.0456; I.0591; I.0592; I.0595; I.0596; I.0599; I.0607.

In this test the following compounds according to the invention showed efficacy between 70% and 79% at a concentration of 31 ppm of active ingredient: I.0022; I.0063; I.0066; I.0072; I.0085; I.0086; I.0178; I.0194; I.0195; I.0199; I.0200; I.0201; I.0208; I.0264; I.0272; I.0285; I.0286; I.0324; I.0341; I.0366; I.0385; I.0428; I.0438; I.0456; I.0457; I.0467; I.0529; I.0531; I.0533; I.0541; I.0547; I.0553; I.0595; I.0597; I.0605; I.0646; I.0862; I.1027.

In this test the following compounds according to the invention showed efficacy between 80% and 89% at a concentration of 31 ppm of active ingredient: I.0019; I.0021; I.0036; I.0069; I.0142; I.0145; I.0177; I.0180; I.0182; I.0186; I.0187; I.0213; I.0306; I.0327; I.0343; I.0344; I.0422; I.0423; I.0424; I.0426; I.0461; I.0591; I.0855; I.0859; I.0933; I.1007; I.1008.

In this test the following compounds according to the invention showed efficacy between 90% and 100% at a concentration of 31 ppm of active ingredient: I.0068; I.0075; I.0181; I.0183; I.0184; I.0241; I.0415; I.0416; I.0439; I.0492; I.0527; I.0634; I.0635; I.0636; I.0857; I.1003.

In this test the following compounds according to the invention showed efficacy between 70% and 79% at a concentration of 125 ppm of active ingredient: I.0019; I.0022; I.0034; I.0047; I.0066; I.0067; I.0072; I.0078; I.0091; I.0100; I.0119; I.0120; I.0122; I.0135; I.0136; I.0140; I.0168; I.0172; I.0176; I.0179; I.0190; I.0194; I.0200; I.0210; I.0243; I.0257; I.0258; I.0266; I.0285; I.0286; I.0304; I.0308; I.0341; I.0356; I.0366; I.0385; I.0442; I.0460; I.0461; I.0467; I.0472; I.0491; I.0553; I.0556; I.0557; I.0583; I.0601; I.0852; I.1000; I.1025; I.1031; I.1035.

In this test the following compounds according to the invention showed efficacy between 80% and 89% at a concentration of 125 ppm of active ingredient: I.0025; I.0036; I.0053; I.0063; I.0075; I.0127; I.0133; I.0138; I.0141; I.0142; I.0144; I.0145; I.0163; I.0180; I.0184; I.0187; I.0198; I.0199; I.0201; I.0202; I.0205; I.0227; I.0247; I.0253; I.0255; I.0260; I.0291; I.0306; I.0324; I.0327; I.0344; I.0347; I.0355; I.0386; I.0426; I.0434; I.0435; I.0436; I.0438; I.0439; I.0451; I.0453; I.0454; I.0457; I.0523; I.0530; I.0531; I.0540; I.0547; I.0555; I.0596; I.0599; I.0605; I.0606; I.0932; I.0933; I.0953; I.1007; I.1020; I.1026.

In this test the following compounds according to the invention showed efficacy between 90% and 100% at a concentration of 125 ppm of active ingredient: I.0021; I.0027; I.0051; I.0068; I.0069; I.0085; I.0086; I.0154; I.0165; I.0177; I.0178; I.0181; I.0182; I.0183; I.0186; I.0195; I.0213; I.0236; I.0241; I.0244; I.0264; I.0287; I.0343; I.0414; I.0415; I.0416; I.0422; I.0423; I.0424; I.0428; I.0456; I.0492; I.0500; I.0527; I.0541; I.0542; I.0559; I.0570; I.0591; I.0595; I.0602; I.0604; I.0634; I.0635; I.0636; I.0646; I.0647; I.0855; I.0856; I.0857; I.0858; I.0859; I.0860; I.0862; I.0958; I.0997; I.0998; I.1003; I.1004; I.1008; I.1018; I.1027.

Example D: In Vivo Preventive Test on *Xanthomonas campestris* pv. *Campestris* (Black Rot on Cabbage)

The tested active ingredients were prepared by homogenization in a mixture of acetone/Dimethyl sulfoxide/Tween®, and then diluted with water to obtain the desired active material concentration.

The young plants of cabbage were treated by spraying the active ingredient prepared as described above. Control plants were treated only with an aqueous solution of acetone/Dimethyl sulfoxide/Tween®.

After 72 hours, the plants were contaminated by spraying the leaves with an aqueous bacteria suspension of *Xanthomonas campestris* pv. *campestris*. The contaminated cabbage plants were incubated for 8 or 10 days at 27° C. at 95% relative humidity.

The test was evaluated 8 or 10 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I.0004; I.0032; I.0051; I.0052; I.0059; I.0068; I.0069; I.0077; I.0078; I.0087; I.0092; I.0132; I.0133; I.0138; I.0170; I.0197; I.0249; I.0252; I.0253; I.0306; I.0323; I.0435; I.0598.

In this test the following compounds according to the invention showed efficacy between 80% and 89% at a concentration of 500 ppm of active ingredient: I.0017; I.0025; I.0070; I.0086; I.0119; I.0121; I.0123; I.0125; I.0126; I.0127; I.0130; I.0131; I.0145; I.0200; I.0210; I.0250; I.0272; I.0277; I.0285; I.0290; I.0293; I.0303; I.0309; I.0311; I.0322; I.0325; I.0441; I.0445; I.0449; I.0592; I.0594.

In this test the following compounds according to the invention showed efficacy between 90% and 100% at a concentration of 500 ppm of active ingredient: I.0019; I.0021; I.0022; I.0024; I.0027; I.0036; I.0041; I.0062; I.0075; I.0091; I.0122; I.0129; I.0172; I.0180; I.0251; I.0255; I.0266; I.0267; I.0268; I.0294; I.0304; I.0305; I.0434; I.0472; I.0590; I.0591; I.0593; I.0705.

In this test the following compounds according to the invention showed efficacy between 70% and 79% at a concentration of 31 ppm of active ingredient: I.0041; I.0053; I.0062; I.0066; I.0105; I.0119; I.0120; I.0122; I.0126; I.0130; I.0132; I.0139; I.0140; I.0145; I.0154; I.0163; I.0199; I.0200; I.0201; I.0203; I.0204; I.0227; I.0253; I.0258; I.0379; I.0380; I.0426; I.0436; I.0437; I.0439; I.0449; I.0457; I.0472; I.0511; I.0585; I.0596; I.0704; I.0857; I.0858; I.0997; I.1003; I.1022; I.1031.

In this test the following compounds according to the invention showed efficacy between 80% and 89% at a concentration of 31 ppm of active ingredient: I.0022; I.0027; I.0034; I.0051; I.0059; I.0063; I.0068; I.0069; I.0082; I.0087; I.0091; I.0093; I.0125; I.0127; I.0129; I.0133; I.0138; I.0141; I.0142; I.0172; I.0181; I.0187; I.0195; I.0208; I.0210; I.0213; I.0243; I.0244; I.0266; I.0267; I.0285; I.0290; I.0324; I.0359; I.0367; I.0372; I.0378; I.0385; I.0400; I.0401; I.0415; I.0428; I.0438; I.0444; I.0529; I.0531; I.0543; I.0554; I.0584; I.0590; I.0592; I.0595; I.0598; I.0601; I.0856; I.0860; I.0954; I.0998; I.1008.

In this test the following compounds according to the invention showed efficacy between 90% and 100% at a concentration of 31 ppm of active ingredient: I.0006; I.0019;

I.0021; I.0024; I.0070; I.0085; I.0086; I.0183; I.0184; I.0185; I.0186; I.0194; I.0202; I.0247; I.0248; I.0249; I.0250; I.0251; I.0264; I.0287; I.0291; I.0293; I.0304; I.0325; I.0341; I.0356; I.0366; I.0414; I.0416; I.0422; I.0423; I.0424; I.0461; I.0462; I.0530; I.0533; I.0547; I.0553; I.0555; I.0556; I.0557; I.0558; I.0559; I.0591; I.0593; I.0594; I.0599; I.0855; I.0862; I.0953; I.0955.

In this test the following compounds according to the invention showed efficacy between 70% and 79% at a concentration of 125 ppm of active ingredient: I.0003; I.0017; I.0038; I.0078; I.0090; I.0092; I.0105; I.0121; I.0135; I.0136; I.0140; I.0170; I.0190; I.0200; I.0210; I.0243; I.0252; I.0323; I.0324; I.0368; I.0379; I.0401; I.0406; I.0422; I.0424; I.0426; I.0461; I.0531; I.0543; I.0547; I.0599; I.0651; I.0705; I.0955; I.0998; I.1003; I.1004; I.1008.

In this test the following compounds according to the invention showed efficacy between 80% and 89% at a concentration of 125 ppm of active ingredient: I.0005; I.0006; I.0016; I.0036; I.0042; I.0051; I.0052; I.0059; I.0060; I.0066; I.0068; I.0070; I.0086; I.0091; I.0093; I.0096; I.0122; I.0123; I.0125; I.0126; I.0129; I.0130; I.0133; I.0138; I.0141; I.0145; I.0154; I.0184; I.0187; I.0194; I.0195; I.0199; I.0201; I.0208; I.0213; I.0244; I.0251; I.0255; I.0264; I.0268; I.0277; I.0305; I.0322; I.0325; I.0338; I.0372; I.0378; I.0380; I.0400; I.0437; I.0438; I.0441; I.0444; I.0452; I.0456; I.0457; I.0460; I.0462; I.0467; I.0472; I.0529; I.0530; I.0550; I.0553; I.0557; I.0559; I.0585; I.0601; I.0954; I.0997.

In this test the following compounds according to the invention showed efficacy between 90% and 100% at a concentration of 125 ppm of active ingredient: I.0019; I.0021; I.0022; I.0024; I.0027; I.0034; I.0041; I.0062; I.0063; I.0069; I.0075; I.0082; I.0085; I.0087; I.0119; I.0120; I.0127; I.0131; I.0172; I.0186; I.0198; I.0202; I.0203; I.0204; I.0247; I.0248; I.0249; I.0250; I.0266; I.0267; I.0285; I.0291; I.0293; I.0294; I.0304; I.0306; I.0334; I.0341; I.0356; I.0359; I.0366; I.0367; I.0385; I.0386; I.0414; I.0428; I.0442; I.0445; I.0533; I.0554; I.0555; I.0556; I.0591; I.0592; I.0593; I.0594; I.0598.

Example E: In Vivo Preventive Test on *Colletotrichum lindemuthianum* (Antrachnose on Bean)

The tested active ingredients were prepared by homogenization in a mixture of acetone/Dimethyl sulfoxide/Tween®, and then diluted with water to obtain the desired active material concentration.

The young plants of bean were treated by spraying the active ingredient prepared as described above. Control plants were treated only with an aqueous solution of acetone/Dimethyl sulfoxide/Tween®.

After 72 hours, the plants were contaminated by spraying the leaves with an aqueous suspension of *Colletotrichum lindemuthianum* spores. The contaminated bean plants were incubated for 24 hours at 20° C. and at 100% relative humidity and then for 5 days at 20° C. and at 90% relative humidity.

The test was evaluated 6 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I.0006; I.0025; I.0036; I.0067; I.0069; I.0076; I.0089; I.0136; I.0172; I.0250; I.0305; I.0443; I.0454; I.0456; I.0458; I.0476; I.0597; I.0599; I.0607; I.0919 In this test the following compounds according to the invention showed efficacy between 80% and 89% at a concentration of 500 ppm of active ingredient: I.0003; I.0004; I.0022; I.0027; I.0033; I.0034; I.0051; I.0052; I.0075; I.0091; I.0092; I.0093; I.0105; I.0123; I.0125; I.0126; I.0127; I.0129; I.0131; I.0180; I.0193; I.0197; I.0203; I.0208; I.0210; I.0249; I.0253; I.0257; I.0260; I.0267; I.0268; I.0272; I.0285; I.0294; I.0303; I.0323; I.0328; I.0439; I.0440; I.0450; I.0452; I.0453; I.0460; I.0477; I.0594; I.0595; I.0725; I.0938.

In this test the following compounds according to the invention showed efficacy between 90% and 100% at a concentration of 500 ppm of active ingredient: I.0019; I.0021; I.0024; I.0041; I.0046; I.0047; I.0048; I.0062; I.0063; I.0070; I.0072; I.0073; I.0078; I.0079; I.0086; I.0100; I.0119; I.0121; I.0122; I.0124; I.0133; I.0140; I.0142; I.0145; I.0170; I.0178; I.0179; I.0183; I.0184; I.0186; I.0187; I.0194; I.0195; I.0200; I.0201; I.0213; I.0247; I.0255; I.0266; I.0293; I.0322; I.0324; I.0325; I.0327; I.0434; I.0436; I.0437; I.0438; I.0441; I.0442; I.0444; I.0445; I.0449; I.0451; I.0457; I.0461; I.0462; I.0467; I.0472; I.0473; I.0478; I.0596.

In this test the following compounds according to the invention showed efficacy between 70% and 79% at a concentration of 31 ppm of active ingredient: I.0006; I.0017; I.0034; I.0052; I.0062; I.0069; I.0072; I.0086; I.0089; I.0100; I.0145; I.0154; I.0172; I.0175; I.0183; I.0197; I.0198; I.0199; I.0200; I.0202; I.0210; I.0248; I.0260; I.0293; I.0415; I.0449; I.0452; I.0457; I.0492; I.0500; I.0523; I.0531; I.0856; I.0857; I.1004; I.1023.

In this test the following compounds according to the invention showed efficacy between 80% and 89% at a concentration of 31 ppm of active ingredient: I.0142; I.0177; I.0178; I.0179; I.0182; I.0184; I.0194; I.0195; I.0201; I.0203; I.0204; I.0207; I.0324; I.0423; I.0439; I.0561; I.0931; I.0933; I.1003.

In this test the following compounds according to the invention showed efficacy between 90% and 100% at a concentration of 31 ppm of active ingredient: I.0185; I.0187; I.0208; I.0213; I.0438; I.0550; I.0855.

In this test the following compounds according to the invention showed efficacy between 70% and 79% at a concentration of 125 ppm of active ingredient: I.0005; I.0017; I.0027; I.0051; I.0062; I.0067; I.0082; I.0088; I.0091; I.0092; I.0100; I.0105; I.0119; I.0120; I.0121; I.0136; I.0154; I.0175; I.0180; I.0188; I.0190; I.0244; I.0253; I.0255; I.0264; I.0268; I.0323; I.0333; I.0341; I.0414; I.0428; I.0439; I.0442; I.0445; I.0450; I.0452; I.0478; I.0484; I.0485; I.0491; I.0492; I.0525; I.0529; I.0530; I.0535; I.0541; I.0570; I.0605; I.0856; I.0859; I.1008; I.1017; I.1019; I.1020; I.1026; I.1030.

In this test the following compounds according to the invention showed efficacy between 80% and 89% at a concentration of 125 ppm of active ingredient: I.0006; I.0024; I.0047; I.0068; I.0087; I.0093; I.0124; I.0125; I.0127; I.0133; I.0141; I.0172; I.0176; I.0182; I.0194; I.0198; I.0200; I.0204; I.0210; I.0212; I.0213; I.0247; I.0248; I.0260; I.0287; I.0293; I.0322; I.0325; I.0327; I.0338; I.0354; I.0355; I.0415; I.0422; I.0423; I.0434; I.0436; I.0437; I.0438; I.0441; I.0444; I.0451; I.0457; I.0458; I.0461; I.0462; I.0483; I.0523; I.0527; I.0531; I.0543; I.0550; I.0553; I.0555; I.0558; I.0559; I.0561; I.0635; I.0858; I.0860; I.0862; I.0932; I.0933; I.0997; I.0998; I.1004; I.1022; I.1023; I.1025; I.1027.

In this test the following compounds according to the invention showed efficacy between 90% and 100% at a concentration of 125 ppm of active ingredient: I.0046; I.0048; I.0052; I.0063; I.0066; I.0069; I.0085; I.0086; I.0142; I.0144; I.0145; I.0177; I.0178; I.0179; I.0181; I.0183; I.0184; I.0185; I.0186; I.0187; I.0199; I.0201; I.0202; I.0206; I.0207; I.0208; I.0265; I.0286; I.0324; I.0416; I.0449; I.0472; I.0473; I.0500; I.0557; I.0855; I.0857; I.0931; I.0953; I.1003; I.1007; I.1018.

Example F: In Vivo Preventive Test on *Uromyces appendiculatus* (Bean Rust)

The tested active ingredients were prepared by homogenization in a mixture of acetone/Dimethyl sulfoxide/Tween®, and then diluted with water to obtain the desired active material concentration.

The young plants of bean were treated by spraying the active ingredient prepared as described above. Control plants were treated only with an aqueous solution of acetone/Dimethyl sulfoxide/Tween®.

After 72 hours, the plants were contaminated by spraying the leaves with an aqueous suspension of *Uromyces appendiculatus* spores. The contaminated bean plants were incubated for 24 hours at 20° C. and at 100% relative humidity and then for 9 days at 20° C. and at 70-80% relative humidity.

The test was evaluated 10 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: I.0270; I.0310; I.0449; I.0453; I.0473; I.0919.

In this test the following compounds according to the invention showed efficacy between 80% and 89% at a concentration of 500 ppm of active ingredient: I.0041; I.0072; I.0087; I.0105; I.0123; I.0126; I.0168; I.0180; I.0183; I.0273; I.0292; I.0322; I.0437; I.0440; I.0454; I.0591; I.0596; I.0598.

In this test the following compounds according to the invention showed efficacy between 90% and 100% at a concentration of 500 ppm of active ingredient: I.0006; I.0019; I.0021; I.0022; I.0024; I.0027; I.0032; I.0034; I.0046; I.0047; I.0048; I.0050; I.0051; I.0059; I.0062; I.0066; I.0067; I.0068; I.0069; I.0070; I.0075; I.0078; I.0086; I.0091; I.0092; I.0093; I.0119; I.0121; I.0122; I.0125; I.0127; I.0129; I.0130; I.0133; I.0138; I.0140; I.0142; I.0145; I.0170; I.0172; I.0178; I.0179; I.0184; I.0187; I.0193; I.0194; I.0195; I.0200; I.0201; I.0203; I.0208; I.0210; I.0213; I.0247; I.0248; I.0249; I.0250; I.0251; I.0253; I.0254; I.0255; I.0257; I.0258; I.0266; I.0267; I.0268; I.0272; I.0274; I.0285; I.0293; I.0294; I.0306; I.0323; I.0324; I.0325; I.0327; I.0434; I.0436; I.0438; I.0441; I.0442; I.0444; I.0445; I.0450; I.0451; I.0457; I.0459; I.0461; I.0462; I.0472; I.0594; I.0595; I.0597; I.0599; I.0607; I.0625; I.0651; I.0704; I.0705; I.0725; I.0935; I.0937; I.0938.

In this test the following compounds according to the invention showed efficacy between 70% and 79% at a concentration of 31 ppm of active ingredient: I.0069; I.0086; I.0196; I.0200; I.0201; I.0202; I.0205; I.0227; I.0232; I.0241; I.0258; I.0323; I.0529; I.0535; I.0547; I.0561; I.0604; I.1000; I.1002; I.1008.

In this test the following compounds according to the invention showed efficacy between 80% and 89% at a concentration of 31 ppm of active ingredient: I.0019; I.0048; I.0051; I.0090; I.0093; I.0121; I.0140; I.0142; I.0145; I.0178; I.0179; I.0194; I.0203; I.0206; I.0244; I.0247; I.0423; I.0457; I.0500; I.0540; I.0635; I.0859; I.0997; I.0998; I.1017.

In this test the following compounds according to the invention showed efficacy between 90% and 100% at a concentration of 31 ppm of active ingredient: I.0006; I.0022; I.0046; I.0050; I.0062; I.0066; I.0127; I.0144; I.0176; I.0177; I.0181; I.0182; I.0184; I.0185; I.0186; I.0187; I.0198; I.0204; I.0207; I.0208; I.0210; I.0212; I.0248; I.0250; I.0251; I.0264; I.0265; I.0285; I.0324; I.0325; I.0354; I.0355; I.0415; I.0416; I.0422; I.0426; I.0434; I.0436; I.0483; I.0484; I.0485; I.0491; I.0492; I.0523; I.0525; I.0541; I.0542; I.0550; I.0558; I.0559; I.0590; I.0634; I.0705; I.0725; I.0852; I.0855; I.0856; I.0857; I.0858; I.0860; I.0862; I.0931; I.0932; I.0933; I.0935; I.0938; I.0950; I.0952; I.0953; I.0955; I.0958; I.1003; I.1004; I.1007; I.1018; I.1019; I.1020; I.1022; I.1023; I.1025; I.1026; I.1027.

In this test the following compounds according to the invention showed efficacy between 70% and 79% at a concentration of 125 ppm of active ingredient: I.0035; I.0068; I.0072; I.0120; I.0130; I.0154; I.0193; I.0250; I.0255; I.0287; I.0331; I.0366; I.0529; I.0531; I.0570; I.0601; I.0648; I.0851; I.0853; I.0861; I.1021.

In this test the following compounds according to the invention showed efficacy between 80% and 89% at a concentration of 125 ppm of active ingredient: I.0034; I.0047; I.0059; I.0070; I.0087; I.0099; I.0117; I.0133; I.0138; I.0170; I.0202; I.0236; I.0272; I.0334; I.0440; I.0442; I.0451; I.0472; I.0530; I.0590; I.0646; I.0647; I.0999; I.1002; I.1034.

In this test the following compounds according to the invention showed efficacy between 90% and 100% at a concentration of 125 ppm of active ingredient: I.0006; I.0019; I.0021; I.0022; I.0024; I.0027; I.0046; I.0048; I.0050; I.0051; I.0062; I.0063; I.0066; I.0067; I.0069; I.0086; I.0088; I.0090; I.0091; I.0092; I.0093; I.0121; I.0122; I.0125; I.0136; I.0140; I.0141; I.0142; I.0144; I.0145; I.0172; I.0176; I.0177; I.0178; I.0179; I.0181; I.0182; I.0183; I.0184; I.0185; I.0186; I.0187; I.0194; I.0195; I.0196; I.0198; I.0199; I.0200; I.0201; I.0203; I.0204; I.0205; I.0206; I.0207; I.0208; I.0210; I.0212; I.0227; I.0232; I.0241; I.0244; I.0247; I.0248; I.0249; I.0251; I.0260; I.0264; I.0265; I.0266; I.0268; I.0285; I.0293; I.0294; I.0302; I.0303; I.0314; I.0323; I.0324; I.0325; I.0327; I.0329; I.0338; I.0343; I.0344; I.0354; I.0355; I.0415; I.0416; I.0422; I.0423; I.0428; I.0434; I.0436; I.0437; I.0438; I.0445; I.0457; I.0461; I.0483; I.0484; I.0485; I.0491; I.0492; I.0500; I.0523; I.0525; I.0527; I.0540; I.0541; I.0542; I.0543; I.0547; I.0550; I.0555; I.0556; I.0557; I.0558; I.0559; I.0561; I.0595; I.0596; I.0604; I.0605; I.0634; I.0635; I.0705; I.0725; I.0852; I.0854; I.0855; I.0856; I.0857; I.0858; I.0859; I.0860; I.0862; I.0931; I.0932; I.0933; I.0935; I.0938; I.0950; I.0952; I.0953; I.0958; I.0997; I.0998; I.1000; I.1001; I.1003; I.1004; I.1007; I.1008; I.1017; I.1018; I.1019; I.1020; I.1022; I.1023; I.1024; I.1025; I.1026; I.1027; I.1031; I.1033.

Example G: *Alternaria alternata* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spores suspension Fungicides were solubilized in DMSO and the solution used to prepare the required range of concentrations. The final concentration of DMSO used in the assay was ≤□1%.

A spore suspension of *A. alternata* was prepared and diluted to the desired spore density.

Fungicides were evaluated for their ability to inhibit spore germination and mycelium growth in liquid culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test, the following compounds according to the invention showed no direct activity (efficacy lower than or equal to 30%) at a concentration of 20 ppm of active ingredient: I.0001; I.0002; I.0003; I.0004; I.0005; I.0008; I.0009; I.0010; I.0011; I.0012; I.0013; I.0014; I.0015; I.0018; I.0019; I.0020; I.0021; I.0022; I.0023; I.0024; I.0025; I.0026; I.0027; I.0032; I.0034; I.0036; I.0038; I.0041; I.0043; I.0044; I.0045; I.0046; I.0047; I.0048; I.0049; I.0050; I.0051; I.0052; I.0053; I.0054; I.0057; I.0058; I.0059; I.0060; I.0061; I.0062; I.0063; I.0064; I.0065; I.0066; I.0067; I.0068; I.0069; I.0070; I.0071; I.0072; I.0073; I.0074; I.0075; I.0076; I.0077; I.0078; I.0079; I.0080; I.0081; I.0082; I.0083; I.0084; I.0085; I.0086; I.0087; I.0088; I.0089; I.0090; I.0091; I.0092; I.0093; I.0094; I.0095; I.0096; I.0097; I.0098; I.0099; I.0100; I.0101; I.0102; I.0103; I.0104; I.0105; I.0106; I.0108; I.0109; I.0110; I.0111; I.0112; I.0113; I.0114; I.0115; I.0119; I.0120; I.0121; I.0122; I.0125; I.0126; I.0133; I.0135; I.0138; I.0139; I.0140; I.0142; I.0144; I.0145; I.0146; I.0147; I.0148; I.0149; I.0151; I.0152; I.0154; I.0155; I.0156; I.0157; I.0158; I.0159; I.0160; I.0161; I.0162; I.0163; I.0165; I.0166; I.0167; I.0168; I.0169; I.0170; I.0171; I.0172; I.0173; I.0174; I.0175; I.0177; I.0178; I.0179; I.0180; I.0181; I.0182; I.0183; I.0184; I.0185; I.0186; I.0187; I.0189; I.0190; I.0191; I.0192; I.0196; I.0198; I.0199; I.0200; I.0201; I.0202; I.0203; I.0204; I.0205; I.0207; I.0208; I.0209; I.0211; I.0212; I.0213; I.0214; I.0215; I.0216; I.0217; I.0218; I.0219; I.0220; I.0221; I.0222; I.0223; I.0224; I.0225; I.0227; I.0228; I.0229; I.0230; I.0231; I.0232; I.0233; I.0234; I.0235; I.0236; I.0237; I.0238; I.0240; I.0241; I.0243; I.0244; I.0245; I.0246; I.0247; I.0248; I.0249; I.0250; I.0251; I.0253; I.0254; I.0255; I.0256; I.0257; I.0258; I.0259; I.0261; I.0262; I.0263; I.0264; I.0265; I.0266; I.0267; I.0268; I.0269; I.0270; I.0272; I.0273; I.0274; I.0275; I.0276; I.0277; I.0279; I.0280; I.0281; I.0282; I.0283; I.0284; I.0285; I.0286; I.0287; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0317; I.0318; I.0319; I.0320; I.0321; I.0324; I.0327; I.0329; I.0330; I.0331; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0373; I.0374; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0414; I.0415; I.0416; I.0417; I.0418; I.0419; I.0420; I.0421; I.0422; I.0423; I.0424; I.0425; I.0426; I.0427; I.0428; I.0429; I.0430; I.0431; I.0432; I.0433; I.0434; I.0435; I.0436; I.0437; I.0438; I.0439; I.0440; I.0442; I.0444; I.0446; I.0447; I.0448; I.0451; I.0452; I.0453; I.0455; I.0456; I.0458; I.0459; I.0460; I.0463; I.0464; I.0465; I.0467; I.0469; I.0470; I.0471; I.0472; I.0473; I.0476; I.0478; I.0481; I.0482; I.0484; I.0485; I.0486; I.0487; I.0488; I.0489; I.0490; I.0492; I.0493; I.0494; I.0495; I.0497; I.0498; I.0499; I.0501; I.0523; I.0524; I.0527; I.0528; I.0529; I.0532; I.0533; I.0535; I.0537; I.0538; I.0539; I.0540; I.0541; I.0543; I.0545; I.0546; I.0548; I.0549; I.0550; I.0551; I.0552; I.0553; I.0554; I.0555; I.0556; I.0557; I.0558; I.0559; I.0562; I.0652; I.0653; I.0657; I.0660; I.0661; I.0662; I.0663; I.0665; I.0666; I.0667; I.0668; I.0669; I.0670; I.0671; I.0672; I.0673; I.0676; I.0678; I.0679; I.0680; I.0681; I.0683; I.0684; I.0685; I.0686; I.0687; I.0690; I.0693; I.0694; I.0695; I.0696; I.0697; I.0698; I.0706; I.0708; I.0709; I.0710; I.0711; I.0712; I.0713; I.0718; I.0719; I.0720; I.0721; I.0723; I.0726; I.0849; I.0850; I.0851; I.0852; I.0853; I.0855; I.0856; I.0858; I.0859; I.0860; I.0862; I.0863; I.0866; I.0867; I.0868; I.0870; I.0871; I.0872; I.0874; I.0931; I.0932; I.0940; I.0941; I.0942; I.0943; I.0944; I.0946; I.0950; I.0951; I.0952; I.0953; I.0955; I.0956; I.0958; I.0959; I.0960; I.0963; I.0964; I.0967; I.0968; I.0974; I.0976; I.0977; I.0979; I.0980; I.0981; I.0982; I.0987; I.0989; I.0990; I.0991; I.0992; I.0993; I.0994; I.0995; I.0996; I.0997; I.0998; I.0999; I.1002; I.1004; I.1005; I.1007; I.1008; I.1010; I.1011; I.1013; I.1014; I.1015; I.1016; I.1017; I.1018; I.1019; I.1020; I.1021; I.1023; I.1024; I.1025; I.1028; I.1034.

In this test, the following compounds according to the invention showed no direct activity (efficacy lower than or equal to 30%) at a concentration of 10 ppm of active ingredient: I.0001; I.0002; I.0003; I.0004; I.0005; I.0006; I.0007; I.0008; I.0009; I.0010; I.0011; I.0012; I.0013; I.0014; I.0015; I.0016; I.0017; I.0018; I.0019; I.0020; I.0021; I.0022; I.0024; I.0025; I.0026; I.0027; I.0031; I.0032; I.0033; I.0034; I.0035; I.0036; I.0037; I.0038; I.0039; I.0040; I.0041; I.0042; I.0043; I.0044; I.0045; I.0046; I.0047; I.0048; I.0049; I.0050; I.0051; I.0052; I.0053; I.0054; I.0055; I.0056; I.0057; I.0058; I.0059; I.0060; I.0061; I.0062; I.0063; I.0064; I.0065; I.0066; I.0067; I.0068; I.0069; I.0070; I.0071; I.0072; I.0073; I.0074; I.0075; I.0076; I.0077; I.0078; I.0079; I.0080; I.0081; I.0082; I.0083; I.0084; I.0085; I.0086; I.0087; I.0088; I.0089; I.0090; I.0091; I.0092; I.0093; I.0094; I.0095; I.0096; I.0097; I.0098; I.0099; I.0100; I.0101; I.0102; I.0103; I.0104; I.0105; I.0106; I.0108; I.0109; I.0110; I.0111; I.0112; I.0113; I.0114; I.0115; I.0119; I.0120; I.0121; I.0122; I.0124; I.0125; I.0126; I.0129; I.0130; I.0133; I.0134; I.0135; I.0136; I.0137; I.0138; I.0139; I.0140; I.0141; I.0142; I.0143; I.0144; I.0145; I.0146; I.0147; I.0148; I.0149; I.0151; I.0152; I.0154; I.0155; I.0156; I.0157; I.0158; I.0159; I.0160; I.0161; I.0162; I.0163; I.0164; I.0165; I.0166; I.0167; I.0168; I.0169; I.0170; I.0171; I.0172; I.0173; I.0174; I.0175; I.0176; I.0177; I.0178; I.0179; I.0180; I.0181; I.0182; I.0183; I.0184; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0206; I.0207; I.0208; I.0209; I.0210; I.0211; I.0212; I.0213; I.0214; I.0215; I.0216; I.0217; I.0218; I.0219; I.0220; I.0221; I.0222; I.0223; I.0224; I.0225; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0253; I.0254; I.0255; I.0256; I.0257; I.0258; I.0259; I.0260; I.0261; I.0262; I.0263; I.0264; I.0265; I.0266; I.0267; I.0268; I.0269; I.0270; I.0272; I.0273; I.0274; I.0275; I.0276; I.0277;

I.0278; I.0279; I.0280; I.0281; I.0282; I.0283; I.0284; I.0285; I.0286; I.0287; I.0290; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0317; I.0318; I.0319; I.0320; I.0321; I.0324; I.0325; I.0327; I.0328; I.0329; I.0330; I.0331; I.0335; I.0336; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0373; I.0374; I.0375; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0417; I.0418; I.0419; I.0420; I.0421; I.0422; I.0423; I.0424; I.0425; I.0426; I.0427; I.0428; I.0429; I.0430; I.0431; I.0432; I.0433; I.0434; I.0435; I.0436; I.0437; I.0438; I.0439; I.0440; I.0441; I.0442; I.0444; I.0446; I.0447; I.0448; I.0449; I.0452; I.0453; I.0454; I.0455; I.0456; I.0457; I.0458; I.0459; I.0460; I.0462; I.0463; I.0464; I.0465; I.0466; I.0467; I.0470; I.0471; I.0472; I.0473; I.0477; I.0481; I.0482; I.0483; I.0484; I.0485; I.0486; I.0487; I.0488; I.0489; I.0490; I.0491; I.0492; I.0493; I.0494; I.0495; I.0496; I.0497; I.0498; I.0499; I.0500; I.0501; I.0523; I.0524; I.0525; I.0526; I.0527; I.0528; I.0529; I.0530; I.0531; I.0532; I.0533; I.0535; I.0536; I.0537; I.0538; I.0539; I.0540; I.0541; I.0542; I.0543; I.0544; I.0545; I.0546; I.0547; I.0548; I.0549; I.0550; I.0551; I.0552; I.0553; I.0554; I.0555; I.0556; I.0557; I.0558; I.0559; I.0561; I.0562; I.0652; I.0653; I.0654; I.0656; I.0657; I.0658; I.0659; I.0660; I.0661; I.0662; I.0663; I.0664; I.0665; I.0666; I.0667; I.0668; I.0669; I.0670; I.0671; I.0672; I.0673; I.0674; I.0675; I.0676; I.0677; I.0678; I.0679; I.0680; I.0681; I.0682; I.0683; I.0684; I.0685; I.0686; I.0687; I.0689; I.0690; I.0692; I.0693; I.0694; I.0695; I.0696; I.0697; I.0698; I.0706; I.0707; I.0708; I.0709; I.0710; I.0711; I.0712; I.0713; I.0714; I.0716; I.0717; I.0718; I.0719; I.0720; I.0721; I.0722; I.0723; I.0724; I.0726; I.0849; I.0850; I.0851; I.0852; I.0853; I.0854; I.0855; I.0856; I.0857; I.0858; I.0859; I.0860; I.0861; I.0862; I.0863; I.0864; I.0865; I.0866; I.0868; I.0870; I.0871; I.0872; I.0873; I.0874; I.0931; I.0932; I.0934; I.0940; I.0941; I.0942; I.0943; I.0944; I.0946; I.0948; I.0950; I.0951; I.0952; I.0953; I.0954; I.0955; I.0956; I.0958; I.0959; I.0960; I.0961; I.0962; I.0963; I.0964; I.0965; I.0966; I.0967; I.0968; I.0969; I.0970; I.0971; I.0972; I.0973; I.0974; I.0976; I.0977; I.0979; I.0980; I.0981; I.0982; I.0983; I.0984; I.0985; I.0987; I.0988; I.0989; I.0990; I.0991; I.0992; I.0993; I.0994; I.0995; I.0996; I.0997; I.0998; I.0999; I.1002; I.1003; I.1004; I.1005; I.1007; I.1008; I.1010; I.1011; I.1013; I.1014; I.1015; I.1016; I.1017; I.1018; I.1019; I.1020; I.1021; I.1023; I.1024; I.1025; I.1026; I.1028; I.1033; I.1034.

Example H: *Colletotrichum lindemuthianum* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spores suspension Fungicides were solubilized in DMSO and the solution used to prepare the required range of concentrations. The final concentration of DMSO used in the assay was ≤□1%.

A spore suspension of *C. lindemuthianum* was prepared and diluted to the desired spore density.

Fungicides were evaluated for their ability to inhibit spores germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test, the following compounds according to the invention showed no direct activity (efficacy lower than or equal to 30%) at a concentration of 20 ppm of active ingredient: I.0001; I.0004; I.0005; I.0009; I.0011; I.0015; I.0018; I.0019; I.0020; I.0021; I.0022; I.0024; I.0025; I.0026; I.0032; I.0035; I.0036; I.0038; I.0039; I.0041; I.0042; I.0043; I.0045; I.0046; I.0048; I.0049; I.0050; I.0051; I.0052; I.0053; I.0054; I.0058; I.0059; I.0060; I.0061; I.0062; I.0069; I.0070; I.0071; I.0078; I.0079; I.0080; I.0083; I.0084; I.0093; I.0094; I.0095; I.0102; I.0103; I.0104; I.0110; I.0113; I.0114; I.0124; I.0126; I.0127; I.0129; I.0130; I.0131; I.0133; I.0134; I.0135; I.0136; I.0140; I.0142; I.0143; I.0147; I.0148; I.0149; I.0151; I.0152; I.0153; I.0154; I.0155; I.0156; I.0157; I.0158; I.0159; I.0160; I.0161; I.0162; I.0164; I.0168; I.0169; I.0170; I.0171; I.0172; I.0173; I.0174; I.0175; I.0185; I.0186; I.0187; I.0189; I.0190; I.0191; I.0192; I.0193; I.0194; I.0195; I.0196; I.0197; I.0198; I.0199; I.0200; I.0201; I.0202; I.0203; I.0204; I.0205; I.0207; I.0208; I.0215; I.0216; I.0217; I.0218; I.0219; I.0220; I.0221; I.0222; I.0223; I.0224; I.0225; I.0226; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0270; I.0273; I.0274; I.0275; I.0276; I.0277; I.0279; I.0281; I.0282; I.0283; I.0284; I.0285; I.0286; I.0287; I.0291; I.0292; I.0293; I.0294; I.0295; I.0296; I.0297; I.0298; I.0301; I.0302; I.0303; I.0304; I.0305; I.0306; I.0308; I.0309; I.0310; I.0311; I.0312; I.0313; I.0314; I.0315; I.0316; I.0318; I.0319; I.0320; I.0321; I.0322; I.0324; I.0327; I.0329; I.0330; I.0335; I.0337; I.0338; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0374; I.0375; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0394; I.0395; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0418; I.0419; I.0420; I.0421; I.0422; I.0423; I.0424; I.0425; I.0426; I.0427; I.0428; I.0429; I.0430; I.0431; I.0432; I.0433; I.0435; I.0436; I.0438; I.0442; I.0444; I.0447; I.0449; I.0453; I.0455; I.0456; I.0457; I.0460; I.0461; I.0462; I.0463; I.0464; I.0465; I.0466; I.0467; I.0469; I.0470; I.0471; I.0472; I.0473; I.0475; I.0476; I.0478; I.0480; I.0482; I.0484; I.0486; I.0487; I.0488; I.0489; I.0490; I.0492; I.0493; I.0494; I.0497; I.0498; I.0499; I.0501; I.0523; I.0526; I.0527; I.0528; I.0530; I.0532; I.0535; I.0536; I.0537; I.0539; I.0540; I.0541; I.0542; I.0543; I.0545; I.0548; I.0549; I.0550; I.0553; I.0554; I.0556; I.0557;

I.0558; I.0559; I.0562; I.0652; I.0653; I.0654; I.0656; I.0657; I.0658; I.0659; I.0660; I.0661; I.0662; I.0663; I.0664; I.0665; I.0666; I.0667; I.0668; I.0670; I.0671; I.0672; I.0673; I.0674; I.0675; I.0676; I.0677; I.0678; I.0679; I.0680; I.0681; I.0682; I.0683; I.0684; I.0685; I.0686; I.0687; I.0689; I.0690; I.0691; I.0692; I.0693; I.0694; I.0695; I.0696; I.0698; I.0706; I.0707; I.0708; I.0709; I.0710; I.0711; I.0712; I.0713; I.0715; I.0716; I.0717; I.0718; I.0719; I.0720; I.0721; I.0722; I.0723; I.0724; I.0726; I.0849; I.0852; I.0853; I.0855; I.0856; I.0857; I.0858; I.0859; I.0860; I.0862; I.0863; I.0865; I.0866; I.0867; I.0868; I.0870; I.0871; I.0931; I.0934; I.0940; I.0941; I.0942; I.0943; I.0944; I.0946; I.0948; I.0950; I.0951; I.0952; I.0954; I.0955; I.0957; I.0958; I.0959; I.0960; I.0961; I.0962; I.0963; I.0964; I.0965; I.0966; I.0967; I.0971; I.0972; I.0973; I.0974; I.0975; I.0976; I.0977; I.0979; I.0980; I.0981; I.0982; I.0983; I.0984; I.0985; I.0987; I.0988; I.0989; I.0990; I.0992; I.0993; I.0994; I.0995; I.0996; I.0997; I.0998; I.0999; I.1000; I.1001; I.1002; I.1007; I.1008; I.1011; I.1015; I.1016; I.1017; I.1018; I.1021; I.1023; I.1024; I.1025; I.1026; I.1027; I.1028; I.1033; I.1034.

In this test, the following compounds according to the invention showed no direct activity (efficacy lower than or equal to 30%) at a concentration of 10 ppm of active ingredient: I.0001; I.0002; I.0004; I.0005; I.0008; I.0009; I.0011; I.0012; I.0013; I.0015; I.0018; I.0019; I.0020; I.0021; I.0022; I.0024; I.0025; I.0026; I.0027; I.0032; I.0034; I.0035; I.0036; I.0038; I.0039; I.0041; I.0042; I.0043; I.0045; I.0046; I.0047; I.0048; I.0049; I.0050; I.0051; I.0052; I.0053; I.0054; I.0058; I.0059; I.0060; I.0061; I.0062; I.0066; I.0069; I.0070; I.0071; I.0074; I.0075; I.0078; I.0079; I.0080; I.0081; I.0082; I.0083; I.0084; I.0085; I.0089; I.0093; I.0094; I.0095; I.0097; I.0102; I.0103; I.0104; I.0106; I.0109; I.0110; I.0111; I.0112; I.0113; I.0114; I.0115; I.0119; I.0120; I.0121; I.0122; I.0123; I.0124; I.0125; I.0126; I.0127; I.0129; I.0130; I.0131; I.0132; I.0133; I.0134; I.0135; I.0136; I.0138; I.0139; I.0140; I.0142; I.0143; I.0144; I.0145; I.0147; I.0148; I.0149; I.0151; I.0152; I.0153; I.0154; I.0155; I.0156; I.0157; I.0158; I.0159; I.0160; I.0161; I.0162; I.0163; I.0164; I.0165; I.0166; I.0167; I.0168; I.0169; I.0170; I.0171; I.0172; I.0173; I.0174; I.0175; I.0176; I.0177; I.0178; I.0179; I.0183; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0206; I.0207; I.0208; I.0209; I.0211; I.0212; I.0213; I.0214; I.0215; I.0216; I.0217; I.0218; I.0219; I.0220; I.0221; I.0222; I.0223; I.0224; I.0225; I.0226; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0269; I.0270; I.0271; I.0272; I.0273; I.0274; I.0275; I.0276; I.0277; I.0278; I.0279; I.0280; I.0281; I.0282; I.0283; I.0284; I.0285; I.0286; I.0287; I.0290; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0318; I.0319; I.0320; I.0321; I.0322; I.0324; I.0325; I.0327; I.0329; I.0330; I.0332; I.0334; I.0335; I.0336; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0373; I.0374; I.0375; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0394; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0417; I.0418; I.0419; I.0420; I.0421; I.0422; I.0423; I.0424; I.0425; I.0426; I.0427; I.0428; I.0429; I.0430; I.0431; I.0432; I.0433; I.0434; I.0435; I.0436; I.0438; I.0442; I.0444; I.0447; I.0448; I.0449; I.0452; I.0453; I.0454; I.0455; I.0456; I.0457; I.0458; I.0459; I.0460; I.0461; I.0462; I.0463; I.0464; I.0465; I.0466; I.0467; I.0470; I.0471; I.0472; I.0473; I.0477; I.0481; I.0482; I.0483; I.0484; I.0485; I.0486; I.0487; I.0488; I.0489; I.0490; I.0491; I.0492; I.0493; I.0494; I.0495; I.0496; I.0497; I.0498; I.0499; I.0500; I.0501; I.0523; I.0524; I.0526; I.0527; I.0528; I.0529; I.0530; I.0531; I.0532; I.0533; I.0535; I.0536; I.0537; I.0538; I.0539; I.0540; I.0541; I.0542; I.0543; I.0544; I.0545; I.0546; I.0547; I.0548; I.0549; I.0550; I.0551; I.0552; I.0553; I.0554; I.0556; I.0557; I.0558; I.0559; I.0561; I.0562; I.0652; I.0653; I.0654; I.0655; I.0656; I.0657; I.0658; I.0659; I.0660; I.0661; I.0662; I.0663; I.0664; I.0665; I.0666; I.0667; I.0668; I.0669; I.0670; I.0671; I.0672; I.0673; I.0674; I.0675; I.0676; I.0677; I.0678; I.0679; I.0680; I.0681; I.0682; I.0683; I.0684; I.0685; I.0686; I.0687; I.0689; I.0690; I.0691; I.0692; I.0693; I.0694; I.0695; I.0696; I.0697; I.0698; I.0706; I.0707; I.0708; I.0709; I.0710; I.0711; I.0712; I.0713; I.0714; I.0715; I.0716; I.0717; I.0718; I.0719; I.0720; I.0721; I.0722; I.0723; I.0724; I.0726; I.0849; I.0850; I.0851; I.0852; I.0853; I.0854; I.0855; I.0856; I.0857; I.0858; I.0859; I.0860; I.0861; I.0862; I.0863; I.0864; I.0865; I.0866; I.0867; I.0868; I.0870; I.0871; I.0876; I.0878; I.0931; I.0932; I.0934; I.0940; I.0941; I.0942; I.0943; I.0944; I.0945; I.0946; I.0948; I.0950; I.0951; I.0952; I.0953; I.0954; I.0955; I.0956; I.0957; I.0958; I.0959; I.0960; I.0961; I.0962; I.0963; I.0964; I.0965; I.0966; I.0967; I.0968; I.0969; I.0970; I.0971; I.0972; I.0973; I.0974; I.0975; I.0976; I.0977; I.0978; I.0979; I.0980; I.0981; I.0982; I.0983; I.0984; I.0985; I.0986; I.0987; I.0988; I.0989; I.0990; I.0991; I.0992; I.0993; I.0994; I.0995; I.0996; I.0997; I.0998; I.0999; I.1000; I.1001; I.1002; I.1003; I.1004; I.1007; I.1008; I.1011; I.1014; I.1015; I.1016; I.1017; I.1018; I.1019; I.1020; I.1021; I.1023; I.1024; I.1025; I.1026; I.1027; I.1028; I.1033; I.1034.

Example I: *Xanthomonas campestris* pv. *Campestris* In Vitro Cell Test

Solvent: DMSO

Culture medium: LB broth medium (Luria Broth Miller) Sigma

Inoculum: bacteria suspension

Compounds were solubilized in DMSO and the solution used to prepare the required range of concentrations. The final concentration of DMSO used in the assay was ≤1%.

Inoculum was prepared from a pre-culture of bacteria grown in liquid medium and diluted to the desired optical density (OD).

Compounds were evaluated for their ability to inhibit bacteria growth in liquid culture assay. The compounds were added in the desired concentrations to culture medium containing the bacteria suspension. After 24 h of incubation, the efficacy of compounds was determined by spectrometric measurement of bacteria growth. Inhibition was determined by comparing the absorbance values in wells containing the compounds with the absorbance in control wells without active ingredients.

In this test, the following compounds according to the invention showed no direct activity (efficacy lower than or equal to 30%) at a concentration of 20 ppm of active ingredient: I.0001; I.0002; I.0003; I.0004; I.0005; I.0006; I.0007; I.0008; I.0009; I.0010; I.0011; I.0012; I.0013; I.0014; I.0015; I.0016; I.0017; I.0018; I.0019; I.0020; I.0021; I.0022; I.0023; I.0024; I.0025; I.0026; I.0027; I.0028; I.0029; I.0030; I.0031; I.0032; I.0034; I.0035; I.0036; I.0038; I.0039; I.0041; I.0042; I.0043; I.0045; I.0046; I.0047; I.0048; I.0049; I.0050; I.0051; I.0052; I.0053; I.0054; I.0055; I.0056; I.0057; I.0058; I.0059; I.0060; I.0061; I.0063; I.0064; I.0065; I.0066; I.0067; I.0068; I.0069; I.0070; I.0071; I.0072; I.0073; I.0074; I.0075; I.0076; I.0077; I.0078; I.0079; I.0080; I.0081; I.0082; I.0083; I.0084; I.0085; I.0086; I.0087; I.0088; I.0089; I.0090; I.0091; I.0092; I.0093; I.0094; I.0095; I.0096; I.0097; I.0098; I.0099; I.0101; I.0102; I.0103; I.0104; I.0106; I.0109; I.0110; I.0111; I.0112; I.0113; I.0114; I.0115; I.0117; I.0118; I.0119; I.0120; I.0121; I.0122; I.0123; I.0124; I.0125; I.0126; I.0127; I.0128; I.0129; I.0130; I.0131; I.0132; I.0133; I.0134; I.0135; I.0136; I.0137; I.0138; I.0139; I.0140; I.0141; I.0142; I.0143; I.0144; I.0145; I.0146; I.0147; I.0148; I.0149; I.0150; I.0151; I.0152; I.0153; I.0154; I.0155; I.0156; I.0157; I.0158; I.0159; I.0160; I.0161; I.0162; I.0163; I.0164; I.0165; I.0166; I.0167; I.0168; I.0169; I.0170; I.0171; I.0172; I.0173; I.0174; I.0175; I.0176; I.0177; I.0178; I.0179; I.0180; I.0181; I.0182; I.0183; I.0184; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0206; I.0207; I.0208; I.0209; I.0210; I.0211; I.0212; I.0213; I.0214; I.0215; I.0216; I.0217; I.0218; I.0219; I.0220; I.0221; I.0222; I.0223; I.0224; I.0225; I.0226; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0269; I.0270; I.0271; I.0272; I.0273; I.0274; I.0275; I.0276; I.0277; I.0278; I.0279; I.0280; I.0281; I.0282; I.0283; I.0284; I.0285; I.0286; I.0287; I.0290; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0317; I.0318; I.0319; I.0320; I.0321; I.0322; I.0323; I.0324; I.0325; I.0327; I.0328; I.0329; I.0330; I.0331; I.0332; I.0333; I.0334; I.0335; I.0336; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0373; I.0374; I.0375; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0394; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0417; I.0418; I.0419; I.0420; I.0422; I.0423; I.0424; I.0425; I.0426; I.0427; I.0428; I.0429; I.0430; I.0431; I.0432; I.0433; I.0434; I.0435; I.0436; I.0437; I.0438; I.0439; I.0440; I.0441; I.0442; I.0443; I.0444; I.0446; I.0447; I.0448; I.0449; I.0450; I.0451; I.0452; I.0453; I.0454; I.0455; I.0456; I.0457; I.0458; I.0459; I.0460; I.0461; I.0462; I.0463; I.0464; I.0465; I.0466; I.0467; I.0468; I.0469; I.0470; I.0471; I.0472; I.0473; I.0475; I.0476; I.0477; I.0478; I.0479; I.0480; I.0481; I.0482; I.0483; I.0484; I.0485; I.0486; I.0487; I.0488; I.0489; I.0490; I.0491; I.0492; I.0493; I.0494; I.0495; I.0496; I.0497; I.0498; I.0499; I.0500; I.0501; I.0523; I.0524; I.0525; I.0526; I.0527; I.0528; I.0529; I.0530; I.0531; I.0532; I.0533; I.0536; I.0537; I.0538; I.0539; I.0540; I.0541; I.0542; I.0543; I.0544; I.0545; I.0546; I.0547; I.0548; I.0549; I.0550; I.0551; I.0552; I.0553; I.0554; I.0555; I.0556; I.0557; I.0558; I.0559; I.0561; I.0562; I.0652; I.0653; I.0654; I.0655; I.0657; I.0658; I.0659; I.0660; I.0661; I.0662; I.0663; I.0665; I.0666; I.0667; I.0668; I.0669; I.0670; I.0671; I.0673; I.0674; I.0675; I.0677; I.0678; I.0679; I.0680; I.0681; I.0682; I.0683; I.0684; I.0685; I.0686; I.0687; I.0689; I.0690; I.0691; I.0692; I.0693; I.0694; I.0695; I.0696; I.0697; I.0698; I.0706; I.0707; I.0708; I.0709; I.0710; I.0711; I.0712; I.0713; I.0714; I.0715; I.0716; I.0717; I.0718; I.0719; I.0720; I.0721; I.0722; I.0723; I.0726; I.0849; I.0850; I.0851; I.0852; I.0853; I.0854; I.0855; I.0856; I.0857; I.0858; I.0859; I.0860; I.0861; I.0862; I.0863; I.0864; I.0865; I.0866; I.0867; I.0868; I.0870; I.0871; I.0872; I.0873; I.0874; I.0876; I.0931; I.0932; I.0934; I.0940; I.0941; I.0942; I.0943; I.0944; I.0945; I.0946; I.0947; I.0948; I.0950; I.0951; I.0952; I.0953; I.0954; I.0955; I.0956; I.0957; I.0958; I.0959; I.0960; I.0961; I.0962; I.0963; I.0964; I.0965; I.0966; I.0967; I.0968; I.0969; I.0970; I.0971; I.0972; I.0973; I.0974; I.0975; I.0976; I.0977; I.0978; I.0979; I.0980; I.0981; I.0982; I.0983; I.0984; I.0985; I.0986; I.0987; I.0988; I.0989; I.0990; I.0991; I.0992; I.0993; I.0994; I.0995; I.0996; I.0997; I.0998; I.0999; I.1000; I.1001; I.1002; I.1003; I.1004; I.1005; I.1007; I.1008; I.1010; I.1011; I.1013; I.1014; I.1015; I.1016; I.1017; I.1018; I.1019; I.1020; I.1021; I.1022; I.1023; I.1024; I.1025; I.1026; I.1027; I.1028; I.1033; I.1034.

In this test, the following compounds according to the invention showed no direct activity (efficacy lower than or equal to 30%) at a concentration of 10 ppm of active ingredient: I.0001; I.0002; I.0003; I.0004; I.0005; I.0006; I.0007; I.0008; I.0009; I.0010; I.0011; I.0012; I.0013; I.0014; I.0015; I.0016; I.0017; I.0018; I.0019; I.0020; I.0021; I.0022; I.0023; I.0024; I.0025; I.0026; I.0027; I.0028; I.0029; I.0030; I.0031; I.0032; I.0033; I.0034; I.0035; I.0036; I.0037; I.0038; I.0039; I.0040; I.0041; I.0042; I.0043; I.0044; I.0045; I.0046; I.0047; I.0048; I.0049; I.0050; I.0051; I.0052; I.0053; I.0054; I.0055; I.0056; I.0057; I.0058; I.0059; I.0060; I.0061; I.0062; I.0063; I.0064; I.0065; I.0066; I.0067; I.0068; I.0069; I.0070; I.0071; I.0072; I.0073; I.0074; I.0075; I.0076; I.0077; I.0078; I.0079; I.0080; I.0081; I.0082; I.0083; I.0084; I.0085; I.0086; I.0087; I.0088; I.0089; I.0090; I.0091; I.0092; I.0093; I.0094; I.0095; I.0096; I.0097; I.0098; I.0099; I.0100; I.0101; I.0102; I.0103; I.0104; I.0105; I.0106; I.0108; I.0109; I.0110; I.0111; I.0112; I.0113; I.0114; I.0115; I.0117; I.0118; I.0119; I.0120; I.0121; I.0122; I.0123; I.0124; I.0125; I.0126; I.0127; I.0128; I.0129; I.0130; I.0131; I.0132; I.0133; I.0134; I.0135; I.0136; I.0137; I.0138; I.0139; I.0140; I.0141; I.0142; I.0143; I.0144; I.0145; I.0146; I.0147; I.0148; I.0149; I.0150; I.0151; I.0152; I.0153; I.0154; I.0155; I.0156; I.0157; I.0158; I.0159; I.0160; I.0161; I.0162;

I.0163; I.0164; I.0165; I.0166; I.0167; I.0168; I.0169; I.0170; I.0171; I.0172; I.0173; I.0174; I.0175; I.0176; I.0177; I.0178; I.0179; I.0180; I.0181; I.0182; I.0183; I.0184; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0206; I.0207; I.0208; I.0209; I.0210; I.0211; I.0212; I.0213; I.0214; I.0215; I.0216; I.0217; I.0218; I.0219; I.0220; I.0221; I.0222; I.0223; I.0224; I.0225; I.0226; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0269; I.0270; I.0271; I.0272; I.0273; I.0274; I.0275; I.0276; I.0277; I.0278; I.0279; I.0280; I.0281; I.0282; I.0283; I.0284; I.0285; I.0286; I.0287; I.0290; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0317; I.0318; I.0319; I.0320; I.0321; I.0322; I.0323; I.0324; I.0325; I.0327; I.0328; I.0329; I.0330; I.0331; I.0332; I.0333; I.0334; I.0335; I.0336; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0373; I.0374; I.0375; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0394; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0417; I.0418; I.0419; I.0420; I.0421; I.0422; I.0423; I.0424; I.0425; I.0426; I.0427; I.0428; I.0429; I.0430; I.0431; I.0432; I.0433; I.0434; I.0435; I.0436; I.0437; I.0438; I.0439; I.0440; I.0441; I.0442; I.0443; I.0444; I.0445; I.0446; I.0447; I.0448; I.0449; I.0450; I.0451; I.0452; I.0453; I.0454; I.0455; I.0456; I.0457; I.0458; I.0459; I.0460; I.0461; I.0462; I.0463; I.0464; I.0465; I.0466; I.0467; I.0468; I.0469; I.0470; I.0471; I.0472; I.0473; I.0475; I.0476; I.0477; I.0478; I.0479; I.0480; I.0481; I.0482; I.0483; I.0484; I.0485; I.0486; I.0487; I.0488; I.0489; I.0490; I.0491; I.0492; I.0493; I.0494; I.0495; I.0496; I.0498; I.0499; I.0500; I.0501; I.0523; I.0524; I.0525; I.0526; I.0527; I.0528; I.0529; I.0530; I.0531; I.0532; I.0533; I.0535; I.0537; I.0538; I.0539; I.0540; I.0541; I.0542; I.0543; I.0544; I.0545; I.0546; I.0547; I.0548; I.0549; I.0550; I.0551; I.0553; I.0554; I.0555; I.0556; I.0557; I.0558; I.0559; I.0561; I.0562; I.0652; I.0653; I.0654; I.0655; I.0658; I.0659; I.0660; I.0661; I.0662; I.0663; I.0666; I.0667; I.0668; I.0669; I.0670; I.0671; I.0672; I.0673; I.0674; I.0675; I.0677; I.0678; I.0679; I.0680; I.0681; I.0682; I.0684; I.0685; I.0686; I.0687; I.0689; I.0690; I.0691; I.0692; I.0693; I.0694; I.0695; I.0697; I.0698; I.0706; I.0707; I.0708; I.0709; I.0711; I.0712; I.0713; I.0714; I.0715; I.0716; I.0718; I.0719; I.0720; I.0721; I.0722; I.0726; I.0849; I.0850; I.0851; I.0852; I.0853; I.0854; I.0855; I.0856; I.0857; I.0858; I.0859; I.0860; I.0861; I.0862; I.0863; I.0864; I.0865; I.0866; I.0867; I.0868; I.0870; I.0871; I.0872; I.0873; I.0874; I.0876; I.0878; I.0931; I.0932; I.0940; I.0941; I.0942; I.0943; I.0944; I.0945; I.0946; I.0947; I.0948; I.0950; I.0951; I.0952; I.0953; I.0954; I.0955; I.0956; I.0957; I.0958; I.0959; I.0960; I.0961; I.0962; I.0963; I.0964; I.0965; I.0966; I.0967; I.0968; I.0969; I.0970; I.0971; I.0972; I.0973; I.0974; I.0975; I.0976; I.0977; I.0978; I.0979; I.0980; I.0981; I.0982; I.0983; I.0984; I.0985; I.0986; I.0987; I.0988; I.0989; I.0990; I.0991; I.0992; I.0993; I.0994; I.0995; I.0996; I.0997; I.0998; I.0999; I.1000; I.1001; I.1002; I.1003; I.1004; I.1005; I.1007; I.1008; I.1010; I.1013; I.1014; I.1015; I.1016; I.1017; I.1018; I.1019; I.1020; I.1021; I.1022; I.1023; I.1024; I.1025; I.1026; I.1027; I.1028; I.1033; I.1034.

Example J: *Pseudomonas syringae* pv. Tomato In Vitro Cell Test

Solvent: DMSO

Culture medium: LB broth medium (Luria Broth Miller) Sigma

Inoculum: bacteria suspension

Compounds were solubilized in DMSO and the solution used to prepare the required range of concentrations. The final concentration of DMSO used in the assay was ≤1%.

Inoculum was prepared from a pre-culture of bacteria grown in liquid medium and diluted to the desired optical density (OD).

Compounds were evaluated for their ability to inhibit bacteria growth in liquid culture assay. The compounds were added in the desired concentrations to culture medium containing the bacteria suspension. After 24 h of incubation, the efficacy of compounds was determined by spectrometric measurement of bacteria growth. Inhibition was determined by comparing the absorbance values in wells containing the compounds with the absorbance in control wells without active ingredients.

In this test, the following compounds according to the invention showed no direct activity (efficacy lower than or equal to 30%) at a concentration of 20 ppm of active ingredient: I.0001; I.0002; I.0003; I.0004; I.0005; I.0006; I.0007; I.0008; I.0009; I.0010; I.0011; I.0012; I.0013; I.0014; I.0015; I.0016; I.0017; I.0018; I.0019; I.0020; I.0021; I.0022; I.0023; I.0024; I.0025; I.0026; I.0027; I.0028; I.0029; I.0030; I.0031; I.0032; I.0033; I.0034; I.0035; I.0036; I.0037; I.0038; I.0039; I.0040; I.0041; I.0042; I.0043; I.0044; I.0045; I.0046; I.0047; I.0048; I.0049; I.0050; I.0051; I.0052; I.0053; I.0054; I.0055; I.0056; I.0057; I.0058; I.0059; I.0060; I.0061; I.0062; I.0063; I.0064; I.0065; I.0066; I.0067; I.0068; I.0069; I.0070; I.0071; I.0072; I.0073; I.0074; I.0075; I.0076; I.0077; I.0078; I.0079; I.0080; I.0081; I.0082; I.0083; I.0084; I.0085; I.0086; I.0087; I.0088; I.0089; I.0090; I.0091; I.0092; I.0093; I.0094; I.0095; I.0096; I.0097; I.0098; I.0099; I.0100; I.0101; I.0102; I.0103; I.0104; I.0105; I.0106; I.0108; I.0109; I.0110; I.0111; I.0112; I.0113; I.0114; I.0115; I.0117; I.0118; I.0119; I.0120; I.0121; I.0122; I.0123; I.0124; I.0125; I.0126; I.0127; I.0128; I.0129; I.0130; I.0131; I.0132; I.0133; I.0134; I.0135; I.0136; I.0137; I.0138; I.0139; I.0140; I.0141; I.0142; I.0143; I.0144; I.0145; I.0146; I.0147; I.0148; I.0149; I.0150; I.0151; I.0152; I.0153; I.0154; I.0155; I.0156; I.0157; I.0158; I.0159; I.0160; I.0161; I.0162; I.0163; I.0164; I.0165; I.0166; I.0167; I.0168; I.0169; I.0170; I.0171; I.0172; I.0173; I.0174; I.0175; I.0176; I.0177; I.0178; I.0179; I.0180; I.0181; I.0182; I.0183; I.0184; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0207; I.0209; I.0210; I.0211; I.0212; I.0213; I.0214; I.0215; I.0216; I.0217; I.0218; I.0219; I.0220;

I.0221; I.0222; I.0223; I.0224; I.0225; I.0226; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0269; I.0270; I.0271; I.0272; I.0273; I.0274; I.0275; I.0276; I.0277; I.0278; I.0279; I.0280; I.0281; I.0282; I.0283; I.0284; I.0285; I.0286; I.0287; I.0290; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0317; I.0318; I.0319; I.0320; I.0321; I.0322; I.0323; I.0324; I.0325; I.0327; I.0328; I.0329; I.0330; I.0331; I.0332; I.0333; I.0335; I.0336; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0357; I.0358; I.0359; I.0360; I.0361; I.0362; I.0363; I.0364; I.0365; I.0366; I.0367; I.0368; I.0369; I.0371; I.0373; I.0374; I.0375; I.0376; I.0377; I.0380; I.0381; I.0382; I.0383; I.0384; I.0385; I.0386; I.0387; I.0388; I.0389; I.0390; I.0391; I.0392; I.0393; I.0394; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0417; I.0418; I.0419; I.0420; I.0421; I.0422; I.0423; I.0424; I.0425; I.0426; I.0427; I.0428; I.0429; I.0430; I.0431; I.0432; I.0433; I.0434; I.0435; I.0436; I.0437; I.0438; I.0439; I.0440; I.0441; I.0442; I.0443; I.0444; I.0445; I.0446; I.0447; I.0448; I.0449; I.0450; I.0451; I.0452; I.0453; I.0454; I.0455; I.0456; I.0457; I.0458; I.0459; I.0460; I.0461; I.0462; I.0463; I.0464; I.0465; I.0466; I.0467; I.0468; I.0469; I.0470; I.0471; I.0473; I.0475; I.0476; I.0477; I.0478; I.0479; I.0480; I.0481; I.0482; I.0483; I.0484; I.0485; I.0486; I.0487; I.0488; I.0489; I.0490; I.0491; I.0492; I.0493; I.0494; I.0495; I.0496; I.0497; I.0498; I.0499; I.0500; I.0501; I.0523; I.0524; I.0525; I.0526; I.0527; I.0528; I.0529; I.0530; I.0531; I.0532; I.0533; I.0535; I.0536; I.0537; I.0538; I.0539; I.0540; I.0541; I.0542; I.0543; I.0544; I.0545; I.0546; I.0547; I.0548; I.0549; I.0550; I.0551; I.0552; I.0553; I.0554; I.0555; I.0556; I.0557; I.0558; I.0559; I.0561; I.0562; I.0652; I.0653; I.0654; I.0655; I.0656; I.0657; I.0658; I.0659; I.0660; I.0661; I.0662; I.0663; I.0664; I.0665; I.0666; I.0667; I.0668; I.0669; I.0670; I.0671; I.0672; I.0673; I.0674; I.0675; I.0676; I.0677; I.0678; I.0679; I.0680; I.0681; I.0682; I.0683; I.0684; I.0685; I.0686; I.0687; I.0689; I.0690; I.0691; I.0692; I.0693; I.0694; I.0695; I.0696; I.0697; I.0698; I.0706; I.0707; I.0708; I.0709; I.0710; I.0711; I.0712; I.0713; I.0714; I.0715; I.0716; I.0717; I.0718; I.0719; I.0720; I.0721; I.0722; I.0723; I.0724; I.0726; I.0849; I.0850; I.0851; I.0852; I.0853; I.0854; I.0855; I.0856; I.0857; I.0858; I.0859; I.0860; I.0861; I.0862; I.0864; I.0865; I.0866; I.0867; I.0868; I.0870; I.0871; I.0872; I.0873; I.0874; I.0876; I.0878; I.0931; I.0932; I.0934; I.0940; I.0941; I.0942; I.0943; I.0944; I.0945; I.0946; I.0947; I.0948; I.0950; I.0951; I.0952; I.0953; I.0954; I.0955; I.0956; I.0957; I.0958; I.0959; I.0960; I.0961; I.0962; I.0963; I.0964; I.0965; I.0966; I.0967; I.0968; I.0969; I.0970; I.0971; I.0972; I.0973; I.0974; I.0975; I.0976; I.0977; I.0978; I.0979; I.0980; I.0981; I.0982; I.0983; I.0984; I.0985; I.0986; I.0987; I.0988; I.0989; I.0990; I.0991; I.0992; I.0993; I.0994; I.0995; I.0996; I.0997; I.0998; I.0999; I.1000; I.1002; I.1003; I.1004; I.1005; I.1010; I.1011; I.1013; I.1014; I.1015; I.1016; I.1017; I.1018; I.1019; I.1020; I.1021; I.1022; I.1023; I.1024; I.1025; I.1026; I.1027; I.1028; I.1033; I.1034.

In this test, the following compounds according to the invention showed no direct activity (efficacy lower than or equal to 30%) at a concentration of 10 ppm of active ingredient: I.0001; I.0002; I.0003; I.0004; I.0005; I.0006; I.0007; I.0008; I.0009; I.0010; I.0011; I.0012; I.0013; I.0014; I.0015; I.0016; I.0017; I.0018; I.0019; I.0020; I.0021; I.0022; I.0023; I.0024; I.0025; I.0026; I.0027; I.0028; I.0029; I.0030; I.0031; I.0032; I.0033; I.0034; I.0035; I.0036; I.0037; I.0038; I.0039; I.0040; I.0041; I.0042; I.0043; I.0044; I.0045; I.0046; I.0047; I.0048; I.0049; I.0050; I.0051; I.0052; I.0053; I.0054; I.0055; I.0056; I.0057; I.0058; I.0059; I.0060; I.0061; I.0062; I.0063; I.0064; I.0065; I.0066; I.0067; I.0068; I.0069; I.0070; I.0071; I.0072; I.0073; I.0074; I.0075; I.0076; I.0077; I.0078; I.0079; I.0080; I.0081; I.0082; I.0083; I.0084; I.0085; I.0086; I.0087; I.0088; I.0089; I.0090; I.0091; I.0092; I.0093; I.0094; I.0095; I.0096; I.0097; I.0098; I.0099; I.0100; I.0101; I.0102; I.0103; I.0104; I.0105; I.0106; I.0108; I.0109; I.0110; I.0111; I.0112; I.0113; I.0114; I.0115; I.0117; I.0118; I.0119; I.0120; I.0121; I.0122; I.0123; I.0124; I.0125; I.0126; I.0127; I.0128; I.0129; I.0130; I.0131; I.0132; I.0133; I.0134; I.0135; I.0136; I.0137; I.0138; I.0139; I.0140; I.0141; I.0142; I.0143; I.0144; I.0145; I.0146; I.0147; I.0148; I.0149; I.0150; I.0151; I.0152; I.0153; I.0154; I.0155; I.0156; I.0157; I.0158; I.0159; I.0160; I.0161; I.0162; I.0163; I.0164; I.0165; I.0166; I.0167; I.0168; I.0169; I.0170; I.0171; I.0172; I.0173; I.0174; I.0175; I.0176; I.0177; I.0178; I.0179; I.0180; I.0181; I.0182; I.0183; I.0184; I.0185; I.0186; I.0187; I.0188; I.0189; I.0190; I.0191; I.0192; I.0193; I.0194; I.0195; I.0196; I.0197; I.0198; I.0199; I.0200; I.0201; I.0202; I.0203; I.0204; I.0205; I.0206; I.0207; I.0208; I.0209; I.0210; I.0211; I.0212; I.0213; I.0214; I.0215; I.0216; I.0217; I.0218; I.0219; I.0220; I.0221; I.0222; I.0223; I.0224; I.0225; I.0226; I.0227; I.0228; I.0229; I.0230; I.0231; I.0232; I.0233; I.0234; I.0235; I.0236; I.0237; I.0238; I.0239; I.0240; I.0241; I.0242; I.0243; I.0244; I.0245; I.0246; I.0247; I.0248; I.0249; I.0250; I.0251; I.0252; I.0253; I.0254; I.0255; I.0256; I.0257; I.0258; I.0259; I.0260; I.0261; I.0262; I.0263; I.0264; I.0265; I.0266; I.0267; I.0268; I.0269; I.0270; I.0271; I.0272; I.0273; I.0274; I.0275; I.0276; I.0277; I.0278; I.0279; I.0280; I.0281; I.0282; I.0283; I.0284; I.0285; I.0286; I.0287; I.0290; I.0291; I.0292; I.0293; I.0294; I.0295; I.0296; I.0297; I.0298; I.0299; I.0300; I.0301; I.0302; I.0303; I.0304; I.0305; I.0306; I.0308; I.0309; I.0310; I.0311; I.0312; I.0313; I.0314; I.0315; I.0316; I.0317; I.0318; I.0319; I.0320; I.0321; I.0322; I.0323; I.0324; I.0325; I.0327; I.0328; I.0329; I.0330; I.0331; I.0332; I.0333; I.0334; I.0335; I.0336; I.0337; I.0338; I.0339; I.0340; I.0341; I.0342; I.0343; I.0344; I.0345; I.0346; I.0347; I.0348; I.0349; I.0350; I.0351; I.0352; I.0353; I.0354; I.0355; I.0356; I.0357; I.0358; I.0359; I.0360; I.0361; I.0362; I.0363; I.0364; I.0365; I.0366; I.0367; I.0368; I.0369; I.0370; I.0371; I.0372; I.0373; I.0374; I.0375; I.0376; I.0377; I.0378; I.0379; I.0380; I.0381; I.0382; I.0383; I.0384; I.0385; I.0386; I.0387; I.0388; I.0389; I.0390; I.0391; I.0392; I.0393; I.0394; I.0395; I.0396; I.0397; I.0398; I.0399; I.0400; I.0401; I.0402; I.0403; I.0404; I.0405; I.0406; I.0407; I.0408; I.0409; I.0410; I.0411; I.0412; I.0413; I.0414; I.0415; I.0416; I.0417; I.0418; I.0419; I.0420; I.0421; I.0422; I.0423; I.0424; I.0425; I.0426; I.0427; I.0428; I.0429; I.0430; I.0431; I.0432;

I.0433; I.0434; I.0435; I.0436; I.0437; I.0438; I.0439; I.0440; I.0441; I.0442; I.0443; I.0444; I.0445; I.0446; I.0447; I.0448; I.0449; I.0450; I.0451; I.0452; I.0453; I.0454; I.0455; I.0456; I.0457; I.0458; I.0459; I.0460; I.0461; I.0462; I.0463; I.0464; I.0465; I.0466; I.0467; I.0468; I.0469; I.0470; I.0471; I.0473; I.0475; I.0476; I.0477; I.0478; I.0479; I.0480; I.0481; I.0482; I.0483; I.0484; I.0485; I.0486; I.0487; I.0488; I.0489; I.0490; I.0491; I.0492; I.0493; I.0494; I.0495; I.0496; I.0497; I.0498; I.0499; I.0500; I.0501; I.0523; I.0524; I.0525; I.0526; I.0527; I.0528; I.0529; I.0530; I.0531; I.0532; I.0533; I.0535; I.0536; I.0537; I.0538; I.0539; I.0540; I.0541; I.0542; I.0543; I.0544; I.0545; I.0546; I.0547; I.0548; I.0549; I.0550; I.0551; I.0552; I.0553; I.0554; I.0555; I.0556; I.0557; I.0558; I.0559; I.0561; I.0562; I.0652; I.0653; I.0654; I.0655; I.0656; I.0657; I.0658; I.0659; I.0660; I.0661; I.0662; I.0663; I.0664; I.0665; I.0666; I.0667; I.0668; I.0669; I.0670; I.0671; I.0672; I.0673; I.0674; I.0675; I.0676; I.0677; I.0678; I.0679; I.0680; I.0681; I.0682; I.0683; I.0684; I.0685; I.0686; I.0687; I.0690; I.0691; I.0692; I.0693; I.0694; I.0695; I.0696; I.0697; I.0698; I.0706; I.0707; I.0708; I.0709; I.0710; I.0711; I.0712; I.0713; I.0714; I.0715; I.0716; I.0717; I.0718; I.0719; I.0720; I.0721; I.0722; I.0723; I.0724; I.0726; I.0849; I.0850; I.0851; I.0852; I.0853; I.0854; I.0855; I.0856; I.0857; I.0858; I.0859; I.0860; I.0861; I.0862; I.0864; I.0865; I.0866; I.0867; I.0868; I.0870; I.0871; I.0872; I.0873; I.0874; I.0876; I.0878; I.0931; I.0932; I.0934; I.0940; I.0941; I.0942; I.0943; I.0944; I.0945; I.0946; I.0947; I.0948; I.0950; I.0951; I.0952; I.0953; I.0954; I.0955; I.0956; I.0957; I.0958; I.0959; I.0960; I.0961; I.0962; I.0963; I.0964; I.0965; I.0966; I.0967; I.0968; I.0969; I.0970; I.0971; I.0972; I.0973; I.0974; I.0975; I.0976; I.0977; I.0978; I.0979; I.0980; I.0981; I.0982; I.0983; I.0984; I.0985; I.0986; I.0987; I.0988; I.0989; I.0990; I.0991; I.0992; I.0993; I.0994; I.0995; I.0996; I.0997; I.0998; I.0999; I.1000; I.1002; I.1003; I.1004; I.1005; I.1008; I.1010; I.1011; I.1013; I.1014; I.1015; I.1016; I.1017; I.1018; I.1019; I.1020; I.1021; I.1022; I.1023; I.1024; I.1025; I.1026; I.1027; I.1028; I.1034.

Biological Data—Compounds According to Formula (II)

Example K described below show the induction of defence gene expression in *Arabidopsis thaliana* by compounds according to formula (II), specifically the stimulation of the salicylic acid pathway. Therefore, these compounds could induce host defences and thus protect plants against a wide range of pathogens including bacteria and fungi.

Examples L, M and N described below show the in vivo activity of compounds in planta according to formula (II) by stimulating the plant defense against various pathogens infecting plants including bacteria and fungi.

Examples O and P described below show the in vitro cell test direct inactivity of compounds according to formula (II) against various pathogens including bacteria and fungi, thus illustrating the mode of action of compounds according to formula (II) as plant host defence inducers.

Example K: Induction of Defense Gene Expression in *Arabidopsis thaliana*

*Arabidopsis thaliana* reporter plants containing the coding sequence of a green fluorescent protein (GFP) linked to the salicylate responsive promoter sequence of the PR1 (pathogenesis-related protein I) gene (AT2G14610) were grown for five days and then sprayed with compounds. On the 3rd day after spraying, plant fluorescence was assessed with a MacroFluo instrument from Leica Microsystems (Wetzlar, Germany). Fluorescences were quantified with the Meta-Morph Microscopy Automation & Image Analysis Software (Molecular Devices, Sunnyvale, Calif., United States).

Background fluorescence in mock treated leaves was set as 1.00. Salicylic acid treatment (300 ppm) resulted in a relative fluorescence value of 2.70, proving the validity of the test system.

In this test, the following compounds according to the invention showed a relative fluorescence value at least above 2 at a concentration of 300 ppm of compound: II.001; II.003; II.004; II.005; II.006; II.007; II.009; II.010; II.011; II.012; II.014; II.015; II.016; II.017; II.018; II.019; II.020; II.022; II.023; II.025; II.026; II.027; II.029; II.030; II.031; II.032; II.033; II.034; II.036; II.037; II.039; II.040; II.042; II.043; II.045; II.046; II.047; II.048; II.050; II.051; II.052; II.060; II.061; II.064; II.066; II.067; II.068; II.069; II.071; II.074; II.075; II.077; II.078; II.079; II.080; II.083; II.084; II.085; II.087; II.088; II.091; II.092; II.093; II.099; II.104.

In this test, the following compounds according to the invention showed a relative fluorescence value at least above 2 at a concentration of 75 ppm of compound: II.003; II.004; II.005; II.006; II.009; II.010; II.011; II.012; II.014; II.015; II.016; II.017; II.018; II.019; II.020; II.023; II.025; II.026; II.027; II.031; II.036; II.037; II.039; II.042; II.050; II.051; II.052; II.061; II.067; II.068; II.069; II.071; II.075; II.077; II.078; II.079; II.080; II.083; II.085; II.087; II.088; II.092; II.099; II.104.

Salicylate is a major defense hormone against plant pathogens. All the compounds described above stimulate the salicylic acid pathway and therefore could protect plants against a wide range of pathogens.

Example L: In Vivo Preventive Test on *Peronospora parasitica* (Crucifer Downy Mildew)

The tested active ingredients were prepared by homogenization in a mixture of acetone/Dimethyl sulfoxide/Tween®, and then diluted with water to obtain the desired active material concentration.

The young plants of cabbage were treated by spraying the active ingredient prepared as described above. Control plants were treated only with an aqueous solution of acetone/Dimethyl sulfoxide/Tween®.

After 72 hours, the plants were contaminated by spraying the leaves with an aqueous suspension of *Peronospora parasitica* spores. The contaminated cabbage plants were incubated for 5 days at 20° C. and at 100% relative humidity.

The test was evaluated 5 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: II.083.

In this test the following compounds according to the invention showed efficacy between 80% and 89% at a concentration of 500 ppm of active ingredient: II.032; II.033.

In this test the following compounds according to the invention showed efficacy between 90% and 100% at a concentration of 500 ppm of active ingredient: II.014; II.015; II.017; II.018; II.025; II.026; II.027; II.036; II.039; II.040; II.048; II.050; II.051; II.052; II.078; II.087; II.088; II.099.

In this test the following compounds according to the invention showed efficacy between 70% and 79% at a concentration of 125 ppm of active ingredient: 11.052; 11.083.

In this test the following compounds according to the invention showed efficacy between 80% and 89% at a concentration of 125 ppm of active ingredient: 11.017; 11.036; 11.040.

In this test the following compounds according to the invention showed efficacy between 90% and 100% at a concentration of 125 ppm of active ingredient: II.005; II.014; II.015; II.016; II.018; II.025; II.026; II.027; II.030; II.039; II.042; II.043; II.048; II.050; II.051; II.075; II.077; II.078; II.080; II.087; II.099.

Example M: In Vivo Preventive Test on *Xanthomonas campestris* pv. *Campestris* (Black Rot on Cabbage)

The tested active ingredients were prepared by homogenization in a mixture of acetone/Dimethyl sulfoxide/Tween®, and then diluted with water to obtain the desired active material concentration.

The young plants of cabbage were treated by spraying the active ingredient prepared as described above. Control plants were treated only with an aqueous solution of acetone/Dimethyl sulfoxide/Tween®.

After 72 hours, the plants were contaminated by spraying the leaves with an aqueous bacteria suspension of *Xanthomonas campestris* pv. *campestris*. The contaminated cabbage plants were incubated for 8 or 10 days at 27° C. at 95% relative humidity.

The test was evaluated 8 or 10 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: II.028; II.050; II.083.

In this test the following compounds according to the invention showed efficacy between 80% and 89% at a concentration of 500 ppm of active ingredient: II.017.

In this test the following compounds according to the invention showed efficacy between 90% and 100% at a concentration of 500 ppm of active ingredient: II.018; II.025; II.026; II.051.

Example N: In Vivo Preventive Test on *Uromyces appendiculatus* (Bean Rust)

The tested active ingredients were prepared by homogenization in a mixture of acetone/Dimethyl sulfoxide/Tween®, and then diluted with water to obtain the desired active material concentration.

The young plants of bean were treated by spraying the active ingredient prepared as described above. Control plants were treated only with an aqueous solution of acetone/Dimethyl sulfoxide/Tween®.

After 72 hours, the plants were contaminated by spraying the leaves with an aqueous suspension of *Uromyces appendiculatus* spores. The contaminated bean plants were incubated for 24 hours at 20° C. and at 100% relative humidity and then for 9 days at 20° C. and at 70-80% relative humidity.

The test was evaluated 10 days after the inoculation. 0% means an efficacy which corresponds to that of the control plants while an efficacy of 100% means that no disease was observed.

In this test the following compounds according to the invention showed efficacy between 70% and 79% at a concentration of 125 ppm of active ingredient: II.077; II.078.

In this test the following compounds according to the invention showed efficacy between 80% and 89% at a concentration of 125 ppm of active ingredient: II.015; II.037; II.079; II.080; II.088.

In this test the following compounds according to the invention showed efficacy between 90% and 100% at a concentration of 125 ppm of active ingredient: II.017; II.018; II.027; II.042; II.051; II.075; II.087.

Example O: *Colletotrichum lindemuthianum* In Vitro Cell Test

Solvent: DMSO

Culture medium: 14.6 g anhydrous D-glucose (VWR), 7.1 g Mycological Peptone (Oxoid), 1.4 g granulated Yeast Extract (Merck), QSP 1 liter Inoculum: spores suspension Fungicides were solubilized in DMSO and the solution used to prepare the required range of concentrations. The final concentration of DMSO used in the assay was: ≤□1%.

A spore suspension of *C. lindemuthianum* was prepared and diluted to the desired spore density.

Fungicides were evaluated for their ability to inhibit spores germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test, the following compounds according to the invention showed no direct activity (efficacy lower than or equal to 30%) at a concentration of 20 ppm of active ingredient: II.001; II.002; II.003; II.004; II.005; II.006; II.007; II.008; II.009; II.010; II.011; II.012; II.013; II.016; II.019; II.020; II.023; II.024; II.025; II.026; II.027; II.028; II.029; II.031; II.032; II.033; II.034; II.035; II.036; II.037; II.038; II.039; II.040; II.041; II.042; II.043; II.044; II.045; II.046; II.047; II.048; II.049; II.050; II.051; II.052; II.073; II.074; II.078; II.079; II.080; II.083; II.084; II.085; II.086; II.087; II.088; II.090; II.092; II.099.

In this test, the following compounds according to the invention showed no direct activity (efficacy lower than or equal to 30%) at a concentration of 10 ppm of active ingredient: II.001; II.002; II.003; II.004; II.005; II.006; II.007; II.008; II.009; II.010; II.011; II.012; II.013; II.016; II.019; II.020; II.023; II.024; II.025; II.026; II.027; II.028; II.029; II.030; II.031; II.032; II.033; II.034; II.035; II.036; II.037; II.038; II.039; II.040; II.041; II.042; II.043; II.044; II.045; II.046; II.048; II.049; II.050; II.051; II.052; II.073; II.074; II.077; II.078; II.079; II.080; II.083; II.084; II.085; II.086; II.087; II.088; II.090; II.092; II.099.

Example P: *Xanthomonas campestris* pv. *Campestris* In Vitro Cell Test

Solvent: DMSO
Culture medium: LB broth medium (Luria Broth Miller) Sigma
Inoculum: bacteria suspension Compounds were solubilized in DMSO and the solution used to prepare the required range of concentrations. The final concentration of DMSO used in the assay was ≤1%.

Inoculum was prepared from a pre-culture of bacteria grown in liquid medium and diluted to the desired optical density (OD).

Compounds were evaluated for their ability to inhibit bacteria growth in liquid culture assay. The compounds were added in the desired concentrations to culture medium containing the bacteria suspension. After 24 h of incubation, the efficacy of compounds was determined by spectrometric measurement of bacteria growth. Inhibition was determined by comparing the absorbance values in wells containing the compounds with the absorbance in control wells without active ingredients.

In this test, the following compounds according to the invention showed no direct activity (efficacy lower than or equal to 30%) at a concentration of 20 ppm of active ingredient: II.001; II.002; II.003; II.004; II.005; II.006; II.007; II.008; II.009; II.010; II.011; II.012; II.013; II.014; II.015; II.016; II.017; II.018; II.019; II.020; II.021; II.022; II.023; II.024; II.025; II.026; II.027; II.028; II.029; II.030; II.031; II.032; II.033; II.034; II.035; II.036; II.037; II.038; II.039; II.040; II.041; II.042; II.043; II.044; II.045; II.046; II.048; II.049; II.050; II.051; II.052; II.073; II.074; II.077; II.078; II.079; II.080; II.083; II.084; II.085; II.086; II.087; II.088; II.090; II.091; II.092; II.093; II.099.

The invention claimed is:

1. A compound of formula (I):

(I)

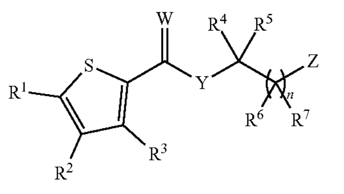

wherein:

$R^1$ and $R^2$ are selected independently from one another from the group consisting of halogen, cyano, $C_1$-$C_6$-alkyl and $C_1$-$C_6$-haloalkyl, wherein at least one of $R^1$ and $R^2$ is halogen;

$R^3$ is selected from the group consisting of cyano and $C_1$-$C_6$-haloalkyl;

$R^4$ and $R^5$ are selected independently from one another from the group consisting of hydrogen, halogen, cyano, hydroxyl, $C_1$-$C_6$-alkyl, $C_1$-$C_6$-hydroxyalkyl, $C_1$-$C_6$-alkoxy, $C_1$-$C_6$-haloalkyl, —O—C(═O)—$C_1$-$C_6$-alkyl, $C_3$-$C_6$-carbocycle, 4-, 5- or 6-membered non-aromatic heterocyclyl, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, aryl, 5- to 9-membered heteroaryl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-4-, 5- or 6-membered non-aromatic heterocyclyl, —$C_1$-$C_6$-alkyl-aryl, —$C_1$-$C_6$-alkyl-hydroxyaryl, —$C_1$-$C_6$-alkyl-5- to 9-membered heteroaryl, —$C_1$-$C_6$-alkyl-S—$C_1$-$C_6$-alkyl, —$C_1$-$C_6$-alkyl-S—C(═O)—$C_1$-$C_6$-alkyl, —$C_1$-$C_6$-alkyl-O—(C═O)—$C_1$-$C_6$-alkyl, —$C_1$-$C_6$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—OH, —$C_1$-$C_6$-alkyl-C(═O)—O—$C_1$-$C_6$-alkyl, —$C_1$-$C_6$-alkyl-NH—C(═NH)—$NH_2$, —S—$C_1$-$C_6$-alkyl, —S—C(═O)—$C_1$-$C_6$-alkyl, —S—C(═O)—O—$C_1$-$C_6$-alkyl, —S—C(═S)—O—$C_1$-$C_6$-alkyl, —S—C(═O)—S—$C_1$-$C_6$-alkyl, —S—C(═O)—$NH_2$, —S—C(═O)—NH($C_1$-$C_6$-alkyl), —S—C(═O)—NH($C_1$-$C_6$-alkyl)$_2$, —S—C(═S)—$NH_2$, —S—C(═S)—NH($C_1$-$C_6$-alkyl), —S—C(═S)—NH($C_1$-$C_6$-alkyl)$_2$, —$C_1$-$C_6$-alkyl-S—C(═O)—O—$C_1$-$C_6$-alkyl, —$C_1$-$C_6$-alkyl-S—C(═O)—S—$C_1$-$C_6$-alkyl, —$C_1$-$C_6$-alkyl-S—C(═O)—$NH_2$, —$C_1$-$C_6$-alkyl-S—C(═O)—NH($C_1$-$C_6$-alkyl), —$C_1$-$C_6$-alkyl-S—C(═O)—NH($C_1$-$C_6$-alkyl)$_2$, —$C_1$-$C_6$-alkyl-S—C(═S)—$NH_2$, —$C_1$-$C_6$-alkyl-S—C(═S)—NH($C_1$-$C_6$-alkyl), and —$C_1$-$C_6$-alkyl-S—C(═S)—NH($C_1$-$C_6$-alkyl)$_2$, wherein acyclic $R_4$, $R_5$ radicals may be substituted with one or more $R^w$ substituents, wherein cyclic $R_4$, $R_5$ radicals may be substituted with one or more $R^x$ substituents, wherein at least one of $R^4$ and $R^5$ is hydrogen, $C_1$-$C_6$-alkyl or $C_3$-$C_6$-carbocycle, or $R^4$ and $R^5$ are taken together with the carbon atom to which they are attached to form a $C_3$-$C_6$-carbocycle or a 3- to 6-membered heterocycle, wherein said $C_3$-$C_6$-carbocycle and 3- to 6-membered heterocycle may be substituted with one or more $R^x$ substituents, wherein $R^w$ is independently selected from the group consisting of nitro, hydroxyl, cyano, carboxyl, amino, sulfanyl, pentafluoro-$\lambda^6$-sulfanyl, formyl, carbamoyl, carbamate, $C_3$-$C_7$-cycloalkyl, $C_3$-$C_7$-halogenocycloalkyl having 1 to 5 halogen atoms, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_8$-alkylsulfamoyl and di-$C_1$-$C_8$-alkylsulfamoyl, wherein $R^x$ is independently selected from the group consisting of halogen, nitro, hydroxyl, cyano, carboxyl, amino, sulfanyl, pentafluoro-$\lambda^6$-sulfanyl, formyl, carbamoyl, carbamate, $C_1$-$C_8$-alkyl, $C_3$-$C_7$-cycloalkyl, $C_1$-$C_8$-halogenoalkyl having 1 to 5 halogen atoms, $C_3$-$C_7$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_6$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_6$-alkylcarbamoyl, di-$C_1$-$C_8$-alkylcarbamoyl, $C_1$-$C_8$- alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl, $C_1$-$C_8$-halogenoalkylsulfonyl having 1 to 5 halogen atoms; $C_1$-$C_8$-alkylsulfonylamino, $C_1$-$C_8$-halogenoalkylsulfonylamino having 1 to 5 halogen atoms; sulfamoyl; $C_1$-$C_6$-alkylsulfamoyl and di-$C_1$-$C_8$-alkylsulfamoyl;

$R^6$ and $R^7$ are independently selected from the group consisting of hydrogen, $C_1$-$C_6$-alkyl, and $C_3$-$C_6$-carbocycle, or $R^6$ and $R^7$ are taken together with the carbon atom to which they are attached to form a $C_3$-$C_6$-carbocycle or a 3- to 6-membered heterocycle;

n is 0 or 1;

W is oxygen or sulfur;

Y is $NR^8$, wherein $R^8$ is selected from the group consisting of hydrogen, $C_1$-$C_6$-alkyl, $C_1$-$C_6$-haloalkyl, $C_1$-$C_6$-cyanoalkyl, hydroxy, $C_1$-$C_6$-alkoxy and $C_3$-$C_6$-carbocycle;

Z is selected from the group consisting of cyano, —C(═O)—$OR^a$, —C(═O)—$SR^a$, —C(═O)—$NR^bR^c$, —C(═S)—$NR^bR^c$ and —C(═O)—NH—$CR^dR^e$—C(═O)—$OR^a$, wherein $R^a$ is selected from the group consisting of hydrogen, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered non-aromatic heterocyclyl, —$C_1$-$C_6$-alkyl-Si($C_1$-$C_6$-alkyl)$_3$, —$C_1$-$C_6$-alkyl-$C_3$-$C_8$-cycloalkyl, 5- to 9-membered heteroaryl and —$C_1$-$C_6$-alkyl-5- to 9-membered heteroaryl, or $R^a$ is taken together with $R_4$ and with the atoms to which they are attached to form a 4- to 7-membered heterocycle, wherein $R^b$ and $R^c$ are independently selected from the group consisting of hydrogen, $C_1$-$C_6$-alkyl, hydroxyl, $C_1$-$C_6$-alkoxy, cyano, $C_1$-$C_6$-cyanoalkyl, or $R^b$ can form together with $R_4$ and with the atoms to which they are attached, a 4- to 7-membered heterocycle, wherein $R^d$ and $R^e$ are independently selected from the group consisting of hydrogen, cyano, hydroxyl, $C_1$-$C_6$-alkyl, $C_1$-$C_6$-hydroxyalkyl, $C_1$-$C_6$-alkoxy, —O—C(═O)—$C_1$-$C_6$-alkyl, $C_3$-$C_6$-carbocycle, —C(═O)—$NH_2$, —C(═O)—NH($C_1$-$C_6$-alkyl), —C(═O)—N($C_1$-$C_6$-alkyl)$_2$, —C(═O)—OH, —C(═O)—O—$C_1$-$C_6$-alkyl, aryl, 5- to 9-membered heteroaryl, —$C_1$-$C_6$-alkyl-$C_1$-$C_6$-alkoxy, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-5- to 9-membered heteroaryl, —$C_1$-$C_6$-alkyl-S—$C_1$-$C_6$-alkyl, —$C_1$-$C_6$-alkyl-S—C(═O)—$C_1$-$C_6$-alkyl, —$C_1$-$C_6$-alkyl-O—(C═O)—$C_1$-$C_6$-alkyl, —$C_1$-$C_6$-alkyl-C(═O)—$NH_2$, —$C_1$-$C_6$-alkyl-C(═O)—NH($C_1$-$C_6$-alkyl), —$C_1$-$C_6$-alkyl-C(═O)—N($C_1$-$C_6$-alkyl)$_2$, —$C_1$-$C_6$-alkyl-C(═O)—OH, —$C_1$-$C_6$-alkyl-C(═O)—O—$C_1$-$C_6$-alkyl, and —$C_1$-$C_6$-alkyl-NH—C(═NH)—$NH_2$, wherein at least one of $R^d$ and $R^e$ is hydrogen, $C_1$-$C_6$-alkyl or $C_3$-$C_6$-carbocycle, or $R^d$ and $R^e$ are taken together with the carbon atom to which they are attached to form a carbonyl, $C_3$-$C_6$-carbocycle, or a 3- to 6-membered heterocycle.

2. The compound according to claim 1, provided that if $R^1$ is $C_1$-$C_6$-haloalkyl or $R^2$ is $C_1$-$C_6$-haloalkyl and $R^4$ is selected from the group consisting of hydrogen and $C_1$-$C_6$-alkyl and $R^5$ is selected from the group consisting of hydrogen and $C_1$-$C_6$-alkyl, and n is 0, and W is oxygen, then Z is selected from the group consisting of cyano, —C(═O)—$SR^a$, —C(═O)—$NR^bR^c$, —C(═S)—$NR^bR^c$ and —C(═O)—NH—$CR^dR^e$—C(═O)—$OR^a$.

3. The compound according to claim 1, provided that if $R^4$ and $R^5$ are selected independently from one another from the group consisting of hydrogen, $C_1$-$C_6$-alkyl, $C_1$-$C_6$-hydroxyalkyl, $C_3$-$C_6$-carbocycle, aryl, —$C_1$-$C_6$-alkyl-$C_1$-$C_6$-alkoxy, —$C_1$-$C_6$-alkyl-$C_3$-$C_6$-carbocycle, $C_1$-$C_6$-alkyl-O—(C═O)—$C_1$-$C_6$-alkyl, —$C_1$-$C_6$-alkyl-C(═O)—OH; —$C_1$-$C_6$-alkyl-aryl and —$C_1$-$C_6$-alkyl-S—$C_1$-$C_6$-alkyl, wherein at least one of $R^4$ and $R^5$ is hydrogen, $C_1$-$C_6$-alkyl or $C_3$-$C_6$-carbocycle, and n is 0 and W is oxygen, and Y is $NR^8$, wherein $R^8$ is selected from the group consisting of hydrogen and $C_1$-$C_6$-alkyl, then Z is selected from the group consisting of cyano, —C(═O)—$SR^a$, —C(═S)—$NR^bR^c$ and —C(═O)—NH—$CR^dR^e$—C(═O)—$OR^a$.

4. The compound according to claim 1, wherein $R^1$ and $R^2$ are selected independently from one another from the group consisting of F, Cl, Br, I, cyano, and $CH_3$.

5. The compound according to claim 1, wherein $R^3$ is selected from the group consisting of cyano, $CHF_2$, and $CF_3$.

6. The compound according to claim 1, with the following combinations of $R^1$, $R^2$ and $R^3$

| $R^1$ | $R^2$ | $R^3$ |
|---|---|---|
| Halogen | Halogen | $CF_3$ or $CHF_2$. |

7. The compound according to claim 1, wherein $R^4$ is selected from the group consisting of hydrogen, $C_1$-$C_6$-alkyl, $C_1$-$C_6$-hydroxyalkyl, $C_3$-$C_6$-carbocycle, C(═O)—OH, —C(═O)—O—$C_1$-$C_6$-alkyl, —$C_1$-$C_6$-alkyl-$C_1$-$C_6$-alkoxy, —$C_1$-$C_6$-alkyl-$C_1$-$C_6$-haloalkyl, —$C_1$-$C_6$-alkyl-$C_3$-$C_6$-carbocycle, —$C_1$-$C_6$-alkyl-aryl, —$C_1$-$C_6$-alkyl-hydroxyaryl, —$C_1$-$C_6$-alkyl-S—$C_1$-$C_6$-alkyl-, —$C_1$-$C_6$-alkyl-C(═O)—$NH_2$, —$C_1$-$C_6$-alkyl-C(═O)—OH, and —$C_1$-$C_6$-alkyl-C(═O)—O—$C_1$-$C_6$-alkyl, and $R_5$ is selected from the group consisting of hydrogen, $C_1$-$C_6$-alkyl and $C_3$-$C_6$-carbocycle; or $R^4$ and $R^5$ are together with the carbon atom to which they are attached to form a $C_3$-$C_6$-carbocycle.

8. The compound according to claim 1, wherein $R^6$ and $R^7$ are independently selected from the group consisting of hydrogen, $C_1$-$C_3$-alkyl, and $C_3$-$C_6$-carbocycle.

9. The compound according to claim 1, wherein n is 0.

10. The compound according to claim 1, wherein W is oxygen.

11. The compound according to claim 1, wherein Y is selected from the group consisting of NH, N—$OCH_3$, and N—OH.

12. The compound according to claim 1, wherein Z is selected from the group consisting of cyano, —C(═O)—$SR^a$, —C(═O)—$NR^bR^c$, —C(═S)—$NR^bR^c$ and —C(═O)—NH—$CR^dR^e$—C(═O)—$OR^a$.

13. A composition comprising at least one compound of formula (I) according to claim 1, and at least one agriculturally suitable auxiliary.

14. A method for controlling bacterial and/or fungal diseases in plants, comprising applying at least one compound of formula (I) according to claim 1 to the plants, plant parts, seeds, fruits or to the soil in which the plants grow.

15. A method for controlling bacterial and/or fungal diseases in plants, comprising applying a composition according to claim 13 to the plants, plant parts, seeds, fruits or to the soil in which the plants grow.

* * * * *